US012540337B2

(12) United States Patent
Delagrave et al.

(10) Patent No.: US 12,540,337 B2

(45) Date of Patent: Feb. 3, 2026

(54) SURFACE-MODIFIED VIRAL PARTICLES AND MODULAR VIRAL PARTICLES

(71) Applicant: FLAGSHIP PIONEERING INNOVATIONS V, INC., Cambridge, MA (US)

(72) Inventors: Simon Delagrave, Sudbury, MA (US); Kurt Adam Swanson, West Newton, MA (US); Noah Robert Cohen, Ashland, MA (US); Shu-Hao Liou, Cambridge, MA (US); Amir Khan, Brookline, MA (US)

(73) Assignee: FLAGSHIP PIONEERING INNOVATIONS V, INC., Cambridge, MA (US)

( * ) Notice: Subject to any disclaimer, the term of this patent is extended or adjusted under 35 U.S.C. 154(b) by 0 days.

(21) Appl. No.: 19/046,064

(22) Filed: Feb. 5, 2025

(65) Prior Publication Data

US 2025/0171807 A1 May 29, 2025

Related U.S. Application Data

(63) Continuation of application No. 18/719,065, filed as application No. PCT/US2022/081572 on Dec. 14, 2022, now abandoned.

(60) Provisional application No. 63/344,029, filed on May 19, 2022, provisional application No. 63/289,967, filed on Dec. 15, 2021, provisional application No. 63/289,975, filed on Dec. 15, 2021.

(51) Int. Cl.

| | |
|---|---|
| ***C12N 15/86*** | (2006.01) |
| ***C07K 14/005*** | (2006.01) |
| ***C12N 7/00*** | (2006.01) |

(52) U.S. Cl.

CPC ............ *C12N 15/86* (2013.01); *C07K 14/005* (2013.01); *C12N 7/00* (2013.01); *C12N 2750/00022* (2013.01); *C12N 2750/00023* (2013.01); *C12N 2750/00043* (2013.01); *C12N 2750/00051* (2013.01)

(58) Field of Classification Search

None

See application file for complete search history.

(56) References Cited

U.S. PATENT DOCUMENTS

| | | | |
|---|---|---|---|
| 2020/0048649 | A1 | 2/2020 | Muyldermans et al. |
| 2022/0372519 | A1 | 11/2022 | Hajjar et al. |
| 2023/0340527 | A1 | 10/2023 | Delagrave et al. |
| 2025/0059559 | A1 | 2/2025 | Delagrave et al. |

FOREIGN PATENT DOCUMENTS

| | | | | |
|---|---|---|---|---|
| WO | WO-2010044889 | A2 * | 4/2010 | ......... A61K 31/7052 |
| WO | 2020123753 | A2 | 6/2020 | |
| WO | 2022140560 | A1 | 6/2022 | |

OTHER PUBLICATIONS

Hallsworth, et al. Appl Environ Microbiol. Dec. 2003;69(12):7032-4. doi: 10.1128/AEM.69.12.7032-7034.2003. PMID: 14660346. (Year: 2003).*

Spandole, et al. Arch Virol. Apr. 2015;160(4):893-908. doi: 10.1007/s00705-015-2363-9. Epub Feb. 15, 2015. PMID: 25680568. (Year: 2015).*

Liou, et al. Nat Commun. Aug. 22, 2024;15(1):7219. doi: 10.1038/s41467-024-51064-8. PMID: 39174507. (Year: 2024).*

International Search Report and Written Opinion in International Patent Application No. PCT/US2022/081572 mailed May 30, 2023, 19 pages.

Liou et al. "Anellovirus Structure Reveals a Mechanism for Immune Evasion." bioRxiv preprint, version posted Jul. 2, 2022 [online].

* cited by examiner

*Primary Examiner* — Benjamin P Blumel

*Assistant Examiner* — Jeffrey Mark Sifford

(74) *Attorney, Agent, or Firm* — K&L Gates LLP

(57) ABSTRACT

This invention relates generally to anellovectors, anelloVLPs, and compositions and uses thereof.

12 Claims, 61 Drawing Sheets

Specification includes a Sequence Listing.

| Construct Name | Description |
|---|---|
| pRTx - 7062<br>CS - Cterm | 184 C-Terminal residues of CS protein<br>for 293 expression |
| pRTx - 7063<br>CS - CTerm - CTC | 184 C-Terminal residues of CS protein<br>with additional C-Terminal Cysteine for conjugation |

| Construct Name | Description |
|---|---|
| CS - Ring10-ORF1 Fusion | 184 C-Terminal residues of CS protein fused into ORF1 replacing HVRs (251-383) |

| Strain | Genus | Tissue of origin | Sf9 Expression | ORF1(Da) | ORF1 (# residues) | Genome Size (bp) |
|---|---|---|---|---|---|---|
| Ring1 | α | spleen | - | 87961 | 743 | 3753 |
| Ring2 | β | lung | +++ | 78696 | 666 | 2975 |
| Ring3 | γ | CD8 | + | 80593 | 677 | 3264 |
| Ring4 | γ | CD8 | ++ | 78835 | 662 | 3174 |
| Ring5 | α | pan | + | 87304 | 728 | 3696 |
| Ring6 | α | pan | + | 90194 | 767 | 3828 |
| Ring7 | α | pan | – | 90605 | 766 | 3815 |
| Ring9 | β | blood | +++ | 79700 | 673 | 2845 |
| Ring10 | β | lung | +++ | 81700 | 689 | 2912 |
| Ring20 | α | serum | - | 90022 | 769 | 3853 |

FIG. 4A

VLPs from several Ring strains have been observed by EM
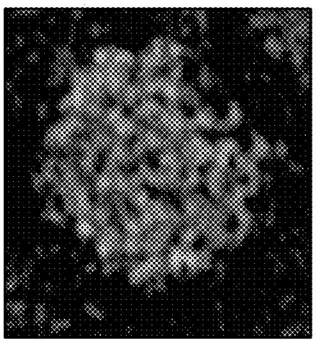
Ring 2 VLP
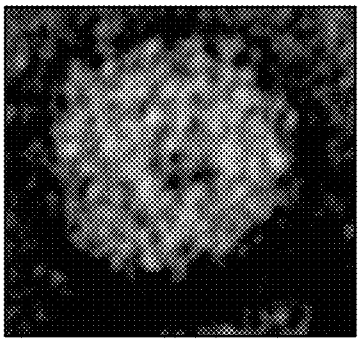
Ring 10 VLP
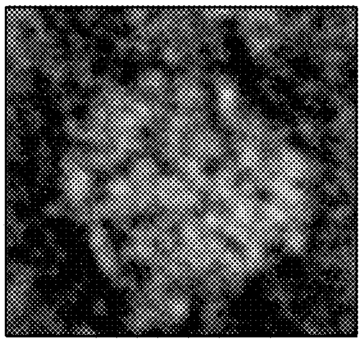
CAV VLP
FIG. 4B Disassemble with 2 M urea →

| | |
|---|---|
| 1 | SmSc Ring 2 N-HIS #2-1-1 cells |
| 2 | SmSc Ring 2 N-HIS #2-2-1 cells |
| 3 | SmSc Ring 2 N-HIS (PS) #4-1-1 cells |
| 6 | 10L Ring2-6xHIS P2 #4-1- cells |
| 7 | SmSc EmptyBV #3 cells |
| 8 | See Blue Plus2 Marker 3ul |
| 9 | SmSc Ring 2 N-HIS #2-1-1 UC |
| 10 | SmSc Ring 2 N-HIs #2-2-1 UC |
| 11 | SmSc Ring 2 N-HIs (PS) #4-1-1 UC |
| 14 | 10L Ring2-6xHIS P2 #4-1 cells |
| 15 | SmSc EmptyBV #3 UC |

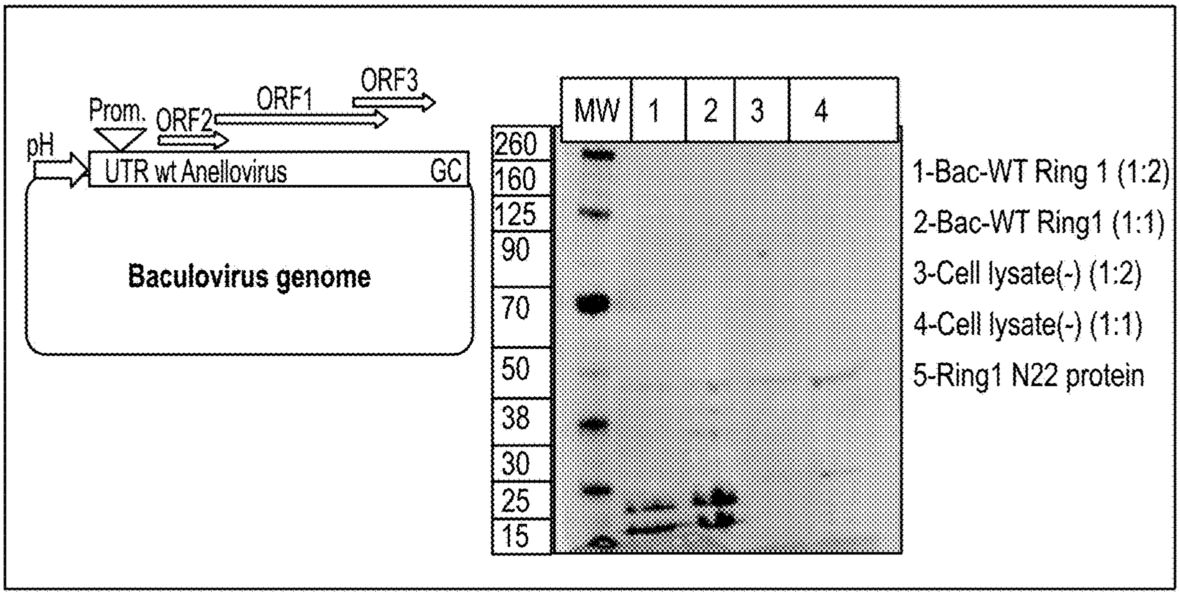
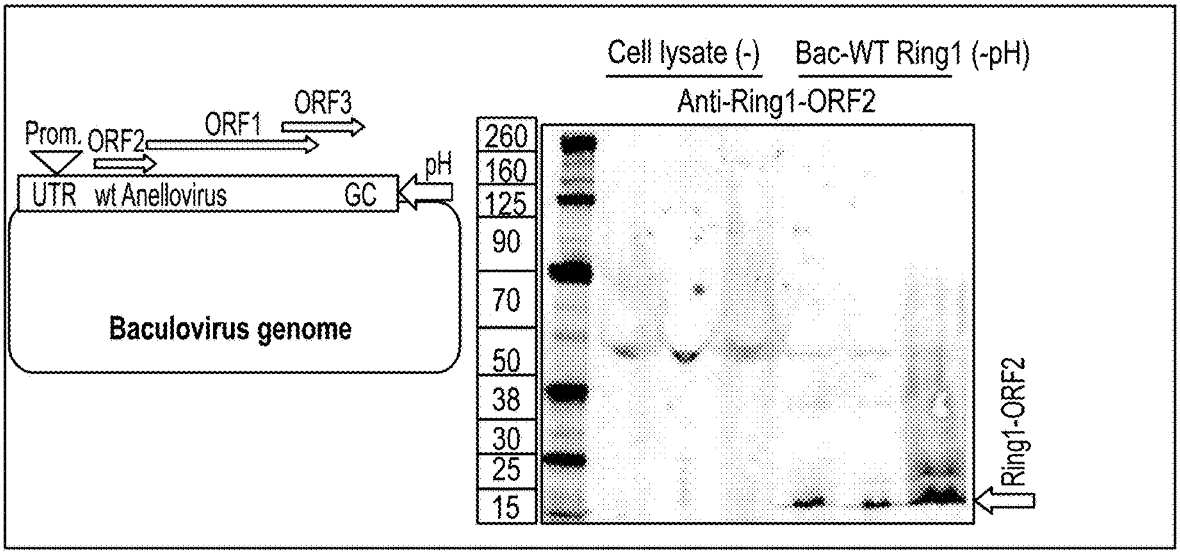
FIG. 16

Target1: TTMV. Target 2: TTV.

```
Density not observed                       K48                JR B  αBC 1  αBC 2
           10        20        30        40                 50        60        70        80        90        100
LY1 (β)   MPW-WYR--RRSYNPWRRRNWFRR--PRKTIYRRYRRRRRWVRRKPFYKR--------------KIKRLNIVEWQPKSIRKCRIKGMLCLFQTTEDRLSYNFDMYEESIIPEKLPGGGG
LY2 (β)   MPY-YYR--RRRYN-YRRPRWYGRGWIRRPFRRRFRRKRRV---RPTY------------------TTIPLKQWQPPYKRTCYIKGQDCLIYYSNLRLGNNSTMYEKSIVPVHWPGGGS
SAf1A (γ) MPF-WWRR-RRKFWTNNRFNYTKRRRYRKRWPRRRRRRRPYRRPIRRRRRKLRK-V------KRKKKSLIVRQWQPDSIRTCKIIGQSAIVVGAEGKQMYCYTVNKLINVPPKTPYGGG
JA20 (α) MAYGWWRRRRRRWRRWRRPWRRRWRTRRRRPARRRGRRRNVRRRRRGRWRRRYRRWKRKGRRRRKAKIIIRQWQPNYRRRCNIVGYLPILICGGNTVSRNYATHSDD-TNYPGPFGGG
          Mpϕ WWR  RRϕ    R RR RR    RR ϕRRR RRRRR RR  Y  KR             KYKRL ϕYQWQP  IRKCYI Gϕ  Lϕ      Y   NYT      ϕϕP Y PGGGG

JR C  αCD  βCD      JR D       JR E     ϕEF 1  οEF2  JR F     JR G       JR H
            110       120       130       140       150       160       170       180       190       200       210       220       230
LY1 (β)   FSIKNISLYALYQEHIHARNIFTHTNTDRPLARYTGCSLKFYQSKDIDYVVTYSTSLPLRSSMGMYNSMQPSIHLMQQNKLIVPSKQTQKRRKPYIKKHISPPTQMKSQWYFQHNIANIPLLMIRTTA
LY2 (β)   FSVSMLTLDALYDIHKLCRNWWTSTNQDLPLVRYKGCKITFYQSTFTDYIVRIHTELPANSNKLTYPNTHPLMMMMSKYKHIIPSRQTRRKKKPYTKIFVKPPPQFENKWYFATDLYKIPLLQIHCTA
SAf1A (Y) FGVDQYTLKYLYEEYRFAQNIWTQSNVLKDLCRYINVKLIFYRDNKTDFVLSYDRNPPFQLTKFTYPGAHPQQIMLQKHHKFILSQMTKPNGRLTKKLKIKPPKQMLSKWFFSKQFCKYPLLSLKASA
JA20 (α) MTTDKFSLRILYDEYKRFMNYWTASNEDLDLCRYLGCTFYFFRHPEVDFIIKINTMPPFLDTTITAPSIHPGLMALDKRARWIPSLKNRPGKKHYIKIRVGAPKMFTDKWYPQTDLCDMTLLTIYATA
          F    ϕSL  LY EH     NϕWT SN  LDL RY GC ϕ FYR    ϕDFIV Y    PPF    MYTYP ϕHP  ϕϕL KγKIϕIPS  TγPYYK   KϕYIYPPKQϕ  KWγFQ  ϕ    PLL L  TA

JR I                  V562          Density not observed
              540       550       560       570       580       590       600       610       620       630
LY1 (β)   EAKVKYS--FNFKWGGDLPPMSTITNPTDQPTYVVPNNFNETTSLQNPT-TRPEHFLYSFDERRGQLTEKATKRLLKD-WETKETSLLSTEYRFAEPTQTQAPQ
LY2 (β)   NISMFYK--FYFKWGGSPPKAINVENPAHQIQYPIPRNEHETTSLQSPG-EAPESILYSFDYRHGNYTTTALSRISQD-WALKDTVSKITEPDRQQLLKQALEC
SAf1A (Y) NWELKYKYIFTFKWGGPQFHEPEIADPSKQEQYDVPDTFYQTIQIEDPEGQDPRSLIHDWDYRHGFVKERSLKRMSTY-FSTHTDQQATSEEDIPKKKKRIGPQ
JA20 (α)  SLGIKYR--FKWIWGGNPVRQQVVRNPCKEP-HSSGNRVPRSIQIVDPRYNSPELTIHAWDFRRGFFGPKAIQRMQQQPTATEFFSAGRKRPRRDTEVYQSDQE
          L ϕKY   F FKWGG  ϕ     V NP   Q   Y ϕP       ϕQϕ DP     P   ϕϕH WDϕRRGϕϕT γALKRM      ϕ      ϕ

                      Density not observed
                                                   640       650       660       670
LY1 (β)   EDP------------------------------SSEEEEESNLFERLLRQRTKQLQLKRRIIQTLKDLQKLE
LY2 (β)   LQ-------------------------------ISEETQEKKEKEVQQLISNLRQQQQLYRERIISLLKDQ
SAf1A (Y) LTVF-----------------------------QQKEEETLSCLLSLCKKDTFQETETQEDLQQLIKQQQEQQLLLKRNILQLIHKLKENQQMLQLHTGMLP
JA20 (α)  KEQKESSLFPPVKLLRRVPPWEDSEQEQSGSQSSEEETATLSQQLKQQLQQQRVLGVKLRLLFNQVQKIQQNQDINPTLLPRGGDLVSFFQAVP
```

FIG. 32D

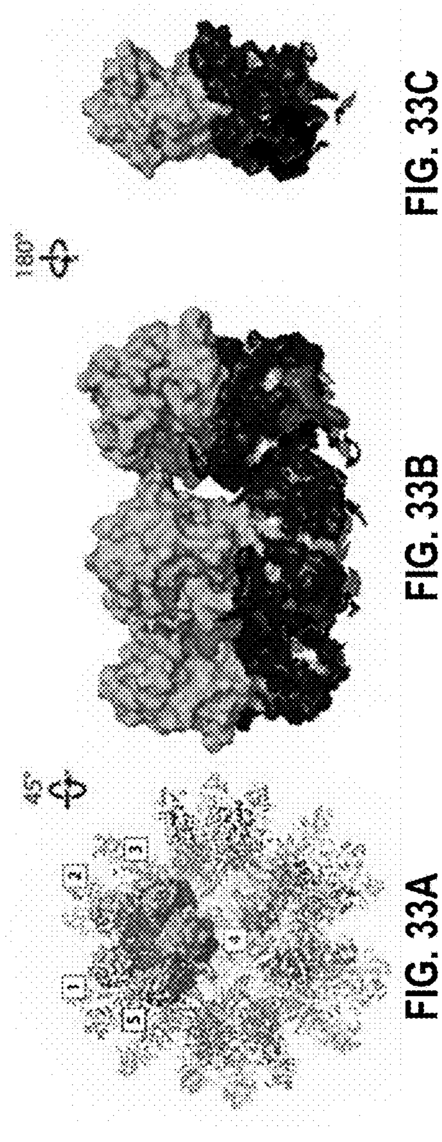
FIG. 33A
FIG. 33B
FIG. 33C
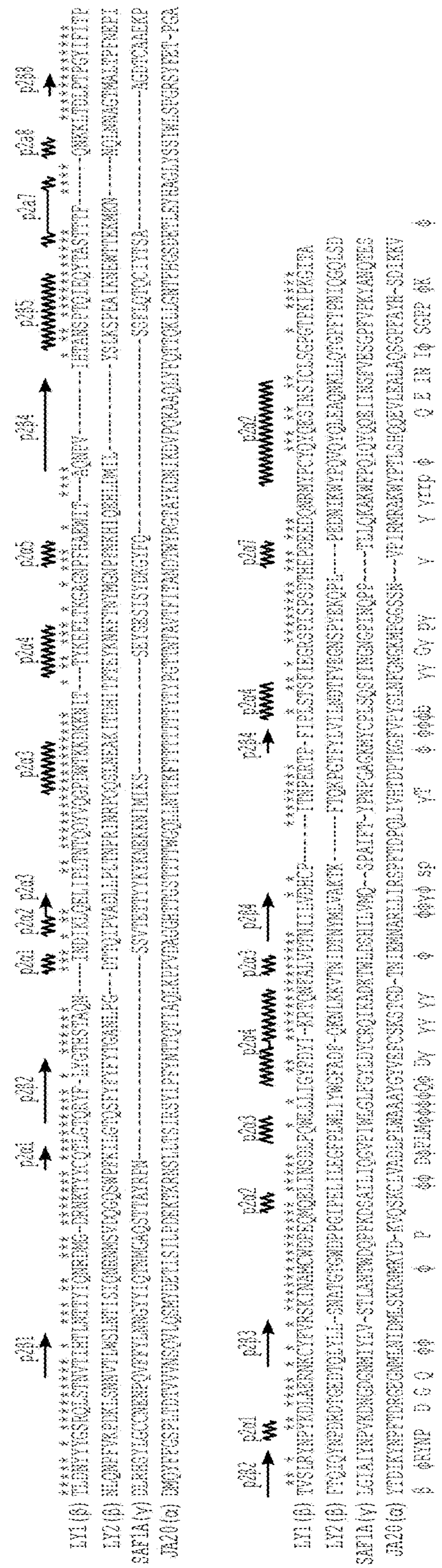
FIG. 33D

Ly1 Full-Length

Ly1 ΔARM

Ly1 ΔARM ΔC-Term

| | α-helix | β-sheet | Turns | Unordered |
|---|---|---|---|---|
| SELCON | 60.1% | 4.4% | 14.6% | 21.6% |
| CONTILL | 70.2% | 2.2% | 7.9% | 19.8% |
| CDSSTR | 87.7% | 2.2% | 3.8% | 5.5% |
| average | 72.7% | 2.8% | 8.8% | 15.6% |

```
                            10        20                            30                          40        50        60        70        80        90        100
LY1(β)         MPW--WYRRR---SYNPWRRRNWFR------R----PRKTI----YRRYRRRRR---WVRR-----------KPFYKRKIKRLNIVEWQPKSIRKCRIKGMLCLFQTTEDRLSYNFDMYEESIIPEKLPGGGG
LY2(β)         MPY--YYRRR---RYNYRRP---RW------Y----GRGWI----RRPFRRRF------RR-----------KRRVRPTYTTIPLKQWQPPYKRTCYIKGQDCLIYYSNLRLGMNSTMYEKSIVPVHWPGGGS
MN773391.1(β)  MPP--FRRNW---WSNYYKPK-WRR------RRFPARRRRF----TTTFRKRRRRTKKVKRH----F----YSKKYKRKLKKIILRQWQPSTIKRCKIEGYLCLFQAGKGRFSFNYASYKESFCPEHEFGGGG
MN769198.1(β)  MPW--YNY-----WPRRRRLRRYWR------R----PRKTL----RRRYWRRPR---WVRR-----------P--YKRKLRKIVLTQFQPKTIRKSKIKGPICLFQTTNKRLVNNFDMYETSEVPEHQPGGGG
MN774797.1(β)  MPW--R-RRR---YFRRYRYRPRRW------R----PRKTF----RTRYYRRRH---WVRK-----------KRL-RKKLKKLHITEYQPSSIRKCKVKGILCLFQTSIERICYNFDMYEESIVPDRLPGGGG
JA20(α)        MAYGWWRRRRRR-W-RRWRRRPWRRR--W-RTR---RRRPARRRGRRRNVRRRRRGRWRRR-----YRRWKR-KGRRRRKAKIIIRQWQPNYRRRCNIVGYLPILICGGNTVSRNYATHSDDTNY-PGPFGGG
MN766736.1(α)  MPW--WRWRRG--W--RWPRRRWRTYRRRRRLPRRRPRRAVRRPRRRRVRRRRGRGWYRGRRYSRRLYR-RRYV--RRKRKTLIWRQWQPQNIRKCRIRGIIPMIICGHLRSNRNYALHSDDIVEQNTPFGGA
MN765841.1(α)  MAWRWWWRRRRP-W--PYRRRRWRTIRTR------RPRRPVRRRRRRRRVRRRRWGRRRGR---RTYYR-RRFRKKKRKRKKLVLKQWNPSTIRRCTITGMIPLIVCGHTSAGRNYALRSDDFIPQSQPFGGS
MN765788.1(α)  MAWRWWWNRRPR-R--RWTRRRWRRLRTR------RPRRPVRRRRRRRRVRRRRWGRRRGR---RTFYR-RRFKKRRRRRRKLTLKQWNPSTIRKCSIRGTVALVMCGHTKAGRNYALHSEDYVPSLISMGGS
MN765502.1(α)  MAYWWWRRRRR---------RPWRRRRRW-RLRRPRRRRATYRRRRGRRRVRKRRGRWRRT-----YRRWRRRKGRRRHKKKIIMKQWQPNFIRHCFIVGEMPLIFCGBNTTSQNFATHSDDLVA-KGPYGGG
SAf1A(γ)       MPF--WWRRRRKFWTNNRFNYTKRRRYRKRWPRRRRRRRPY----RRPIRR-RR-----RK----------LRKV-KRKKKSLIVRQWQPDSIRTCKIIGQSAIVVGABGKQMYCYTVNKLINVPPKTPYGGG
MN777719.1(γ)  MPF--WWGRRNRFWYKNNYRRRAYRRKRKRWPKRR--RRNF----RRPTRRRRR-----RR----------RKQKVRKKKQTLTLKVWQPDTIRKCRIKGTGIHIVGGNGTQYRCFTANRFDWTPPLMPGGGG
MN776710.1(γ)  MPF--WWRRRRKPWYGKWRFRRRRRYNAPRRKRKFYQRRRY----RRTNRR--------RR----------KYKVRRKKRKTIAIRQWQPESITKCKIIGFSNLVLGABGTQYLCWTSQQEDYTQPKAFGGGG
MN778499.1(γ)  MPF--WWPRRRRWWATTRFKRRKPRYPKRR--RRRRYKRKY----RRAPRR-RR-----RR----------RRKV-RRKKPNLIVRQWQPDSIVLCKIKLFGSLVLGABGTQYLCYTNEKGAWTPPQQPGGGG
MN777204.1(γ)  MPF--WWRRRRKFWRGRRRPFYKRTTKRRR--RRVRYRQRF----RRPYRRRRR-----RR----------KHKV-RRKRQKLPIYQWQPDSIRKCKIKGVGTLILGAHGKQFVCYTDVQKKAPPPKAPGGGG
               MP   WWRRR   W    R RR RR              RR       RRR RRRRR     RR                KRK KRL   QWQP  IRKC I G   L           NYT        P   PGGGG
               ϕ ϕ  ϕ YYY   ϕ    Y YY YY              YY ϕ     YYY YYYYY     YY          Y     YYYYY ϕ  ϕY ϕ ϕ  ϕYY Yϕ  ϕ  ϕϕ          ϕ         ϕϕp Y
```

FIG. 38

```
                 110       120       130       140       150       160       170       180       190       200
LY1(β)        FSIKNISLYALYQEHIHAHNIFTHTNTDRPLARYTGCSLKFYQSKDIDYVVTYSTSLPLRSSMGMYNSMQPSIHLM-QQNKLIVPSKQTQ-KRRKPYIKKHI
LY2(β)        FSVSMLTLDALYDIHKLCRNWWTSTNQDLPLVRYKGCKITFYQSTFTDYIVRIHTELPANSNKLTYPNTHPLMMMM-SKYKHIIPSRQTR-RKKKPYTKIFV
MN773391.1(β) WGLQQLSLSNLYSQNCDLMNWWTKSNNHLNLCRYMGCEITLFRQDTVDYVFTYFDEQPKNVSKYYYATFHPTKLML-YNRKIVVPSFASQPHKRKPYKRKFI
MN769198.1(β) WGIKVFTLEGLYSBHIYGRNIWTVTNQDLPLVRYLGCSIRFYQSEYTDYVATYSNQLPLQSSLGMYNAMQPNIHLL-LKNKITMPGLKTY-KRRVPYKKVFV
MN774797.1(β) FSIKNLSLQSLYLEHTHGHNIFTSTNBPYPLMRYTGCTIRLYRSADVDYIVSYDNQWPLKSTMkMYNSMQPQIHYL-LRHRlIVTSKKTNPNKRKLYKKVFI
JA20(α)       MTTDKFSLRILYDEYKRFMNYWTASNBDLDLCRYLGCTFYFFRBPEVDFIIKINTMPPFLDTTITAPSIHPGLMAL-DKRARWIPSLKNR-PGKKHYIKIRV
MN766736.1(α) LSTTSWSLKVLYDQHQRGLNRWSSSNEMLDLARYNGCRFTFYRDKVTDFIVTYDISAPYKLDKYSSPSYHPGMMMLKTKNKILIPSFNTK-PKGRSTVSVKI
MN765841.1(α) FSTTTWNLNVLYDBHLKFHNKWSYPNTQLDLARYLGAYFYFYRDPKTDFIVTYNTVPPFKIDKYSSPMLHPGMLMQ-RKKRILIPSFETR-PKGKRRIRVKI
MN765788.1(α) FSTTTWSLKALYDEFQKFHNRWSYPNTQLDLARFKGSKWTFYRDPKVDYIVTYYTVPPFKLNKLSSPFLHPGMMMQ-YKKKILVPSYQTK-PKGKGKVSIWI
MN765502.1(α) MTTTKFTLRILYDBHLRFMNFWTVSNEDLDLCRYLGVKLTFYRHPTVDFMVQIHTQPPFLDTELTGPSIHPGMMIL-NKKKIFVPSLKTR-PNRKHKVRVKI
SAf1A(γ)      FGVDQYTLKYLYEEYRFAQNIWTQSNVLKDLCRYINVKLIFYRDNKTDFVLSYDRNPPFQLTKFTYPGAHPQQIML-QKHHKFILSQMTK-PNGRLTKKLKI
MN777719.1(γ) FGVEKFTLQHLYNEHLLSNNIWTQSNKMLDLVRYTGCRIKFYRHETIDFIASYNRNLPFNLEKYTYADSHPNSLLH-SRHKKLIPSLKTR-RSGKRYITMKI
MN776710.1(γ) FGCELINLDWLYSEWVKHNNIWTKTNTNKDHLVRYTGAYIYFLRPTIDFVIAYSLQPPFBLTKFTYPDIQPQNLLL-RKRKRIILSLASK-PBGKRFVKVKI
MN778499.1(γ) FGIETYSLSYLYDQYLLRRCIWTKSNDYKDLCRYLRCKITFFRHPKIDFVVNYARQPPFLLEKPTYMHCHPIALLL-SQHKRVILSKRSD-PKAKNRVTLII
MN777204.1(γ) FACEQFSLGGLYEQYKFRNNIWTASNINMDLCRYLGVRMIFYRHPDIDFILNYDRQPPFVLDQLTYPLCHPQNLLL-GKHKILLLSKATK-PNGKLRKKVFI
              F     SL  LY EH    N WT SN  LDL RY GC   FYR    DFIV Y    PPF    MYTYP  HP    L  K KI IPS   T  P GK    K  I
              ϕ     ϕ ϕ  ϕϕ         ϕϕ         ϕ γϕ    ϕ ϕϕγ   ϕ ϕϕϕ ϕ    ϕϕϕ    γϕ ϕ   ϕ ϕ   ϕϕϕ  γγγ ϕϕϕ     γ  γγγ    γϕγϕ
```

FIG. 38 continued

```
                210       220       230       240       250       260                 270       280        290                  300
Y1(β)           SPPTQMKSQWYFQHNIANIPLLMIRTTALTLDNYYIGSRQLSTNVTIHTLNTTYIQNRDWG~DRN------KTYYCQTL~GTQRYFLYGTHSTAQN----INDIKLQE------------LIPL
LY2(β)          KPPPQFENKWYFATDLYKIPLLQIHCTACNLQNPFVKPDKLSNNVTLWSLNTISIQNRNMSVDQG------QSWPFKILGTQSFYFYFYTGANLPG---DTTQIPVAD------------LLPL
MN773391.1(β)   RAPKLMKNQWYFQQQLAPYPLLQFAATAVSLNKMFGSSKALNNNCTVYCLNTDFFRHPHFQY-SA-------QPFTP-DG-GNQPTYIYTIQRGE----PPITAYKYFN------------LTFL
MN769198.1(β)   PPPTQLENKWYFQQNIAKTPLLMTRVTACSLNKFYIDPDHINTNLTITSLNVSLFSNRQFQD-AT--------DYHPKTV-GTINYYLYSTTQNP----PYNGPLKLKM------------LIPL
MN774797.1(β)   PPPTQMKNQWYFQSTLANIPLFMLRTSATSLDHWFIGTRDKSTNITILTLNTSVIFHRNWDK-GT-------QPYYANVV-GTQKVWLYATDQSAS----PIFNEIKLKN------------LIFL
JA20(α)         GAPKMFTDKWYPQTDLCDMTLLTIYATAADMQYPFGSPLTDTVVVNSQVLQSMYDETISILPDEK------TKRNSLLTSIRSYIPFYNTTQTIAQLKPFVDAGGHTT------------GSTT
MN766736.1(α)   KPPKLFLDKWYTQEDLCTVNLVTFAVSAASFTHPFCPPQTDNPCCTFQVLKDFYYPIIGYSAAE-------TKVSSVFSNILYKHCTYYQSFLTQQFIGKIVKLPDGTL------------VSSL
MN765841.1(α)   KPPTLFEDKWYTQSDLCSVNLLSLAVSAASFKHPFCPPQTENICITFQVLRDFYYTQMNVTDTKGTDIS-DKDKAIFDNHLYKFANYYQTVHTLGQLNPTQ---------------------
MN765788.1(α)   KPPVLFEDKWYTQQDLCPVNLLSLAVSAASFLHPFCPPESDNMCITFQVLQDFYYTQMGVTQMTGTTLT-EADNNIFKNHLYKQASYYQSLHTTGQLNATQ---------------------
MN765502.1(α)   GPPRLYEDKWYPQSELCDTTLLTVYATACDLQFPFGSPLTDNPCVNFQVLGSAYKKHLSILSTND-----SKNLTHYETALFSKTAYYNTFETIAQLKPTGQTTG-----------------
SAf1A(γ)        KPPKQMLSKWFFSKQFCKYPLLSLKASALDLRHSYLGCCNENPQVEFYYLNHGYYIQTNWGAQST-------TAYRPN-----------------------SSVTETT------------YYKY
MN777719.1(γ)   KPPKPVSNKWFFQETFSSTPLFKLTTSIIDLRYPHISQIGSNELVSLFCLNTDFYANAGWGNVHPPGTHS-KWYVPY-----------------------HNIAAIT------------TVVI
MN776710.1(γ)   RPPKQMITKWFFQHQFSGYGLVQLSAAAATFRHPNIGPKSQNQMVTIYFLDTTIFNRPNWAQAQE------DAWTPA-----------------------GTH-RTWTFEYQVKGQTQPKTVQ
MN778499.1(γ)   KPPKQMITKWFFTKQFALFDLLQIQAAACTLNYPKLGCCNENLIISIFYLNPQFFQDSQWAQYTT------SPYKPY-----------------------QTIDTQLTYHYKIGNQTGQYK--
MN777204.1(γ)   KPPKQMLNKWFFQEQFQSAPLLSIRASICSLQYPHIGCCMPNRTVTFFALNPGFYQQGNWAYDGGE---T-NPYKPW-----------------------PBIPKKLYF-WDVATIPASWMEQ
                 PPKQ   KWYFQ  L   PLL L  TA SL  PF      N  VT   LN        W
                γϕϕγ ϕ  γϕϕϕ   ϕ    ϕϕ        ϕ  ϕϕϕ       ϕ ϕ  ϕ    ϕϕ    ϕ                ϕ           ϕ ϕ
```

FIG. 38 continued

```
                        310        320                 330       340                       350       360                 370       380       390       400
          LY1(β)   T----NTQDYVQGFDWTEKDKHNIT-------TYKEF---LTKGAGNPFHAEWIT---AQNPV-----------IHTANSPTQIEQIYTASTTTF-----QNKKLTDLPTPGYIFITPTVSLRYNPYKDLAER
          LY2(β)   T----NPRINRPGQSLNEAKITDHI-------TFTEYKNKFTNYWGNPFNKHIQEHLDMIL--------------YSLKSPEAIKNEWTTENMKW-----NQLNNAGTMALTPFNEPIFTQIQYNPDRDTGED
   MN773391.1(β)   G----QTMTNDPGIPLSNNNN------------------YTKNEWGNVFFYKYLNNDEL--------------TYVSKETIDQVKQK---------------KNQQITSGFTLKDQPYYYTLKYNPYKDKGKG
   MN769198.1(β)   T----DTMIYKPGINYEEYKRNNTTK--G----WNDWKTEYTIYSGNPFHANYLSVGEP--------------VFLIGKKPSDLFSSE------------------EGETSDYTTAELTKTIRYNPYNDQGQT
   MN774797.1(β)   G----NTQHNTQGYSYAEYLTHYHKT--HSSTTVEEWQ--KSANWGNPFYKDYLTNPSN--------------DHQVFASYTDILQFANK-LKTS-----QD-TTIKESTFSFTPIEMTKRLRYNPYKDNGVN
         JA20(α)   T----TWGQLLNTTKFTTTTTTTYTYPG----TTNTA---VTFITANDTWYRGTAYKDNIKDVPQKAAQLYF---QTTQKLLGNTFHGSDETLEYHAGLYSSIWLSPGRSYFET-PGAYTDIKYNPFTDRGEG
   MN766736.1(α)   ASGPSSYPEGSNINKNSIEQ--YNTWLS-------------QFNTGANQHYNFCNYKPDYSKLEWLRKYYFEWETYKKASIPPDHLTPSVNWYEYHIGLFSPIFLSPFRSSSLEFPRAYQDVTYNPLVDKGVG
   MN765841.1(α)   --QPALFSD---RQNQGIPE--KDSYLS-----GIGP---NKLQTGNNSIYGQPNYNPDIEKLHKIRKWFFKQETTANT-IHGQYGHPQNDAVDYHIGKYSPIFLSPYRT-NLQFPTAYVDVTYNPLVDKGLG
   MN765788.1(α)   --KPANYST---NDK---IP--QETWLS-----TTGP---AGFKTGNNSIYGVPNYKPDYTKLEEIRKWFFKQETTDNA-IHGSYGKPVYNAVDYHIGKYSPIFLSPYRT-NTQFSTAYRDITYNPNTDKGKG
   MN765502.1(α)   P----TWQDVQNTTNLDSS-----------------G---TNQATSNDTWYYGNTYKDNIKDLTKKARDRYLAAT---QKAFPAYATLQSPLYEYHGGCYSSIFLSAGRA-YFETLGAYSDIIYNPFVDKGIG
        SAf1A(γ)   K----NEKKNIHIKS------------------SEYS---ESISYDKGYFQ---------------------------SSFLQTQCIYTSA-----------------AGDTCAAEKPLGIAIYNPVKDNGDG
   MN777719.1(γ)   K----GRDTQITVDG------------------SDYK---KSVSYETGYFQ---------------------------PKLLQAEKIKN---------------------TAMENIPIQASRYNPTKDDGVG
   MN776710.1(γ)   M----PPSTPQDPYK------------------TKYA---TSISRDYGWWQ---------------------------KAILNSTKVTIDGT--------------------MYSNRTVYSARYNPNEDTGQG
   MN778499.1(γ)   ------PEFLNKTGQ------------------QAYY---ESISLDKGWFS---------------------------PKIMNTQYITQSGS------------------ETHLAAIPVGAARYNPEIDDGKG
   MN777204.1(γ)   E----KAKHRVEIDL------------------STYS---QSIDYQKGYFT---------------------------SKVLQAKLVTQDST-----------------GTSTIANTPLNIARYNPAIDTGKG
                                                                                                                                          RYNP  D G G
                                                 ϕ  ϕ        ϕ   ϕ   ϕ                              ϕ  ϕϕ                                ϕϕ  ϕ
```

FIG. 38 continued

```
                       410          420        430         440          450         460                   470         480         490       500
      LY1(β) NKCYFVRS-KINAHGWDPEQHQELINSDLPQWLLLFGYPDYIKRTQNFA-LVDTNYILVDHCPYT-----N--PEKTPFIPLSTSFIEGRSPYSPSDTHEPDEEDQNRW
      LY2(β) TQLYLLSN--ATGTGWDPPGIPELILEGFPLWLIYWGFADFQKNLKKVT-NIDTNYMLVAKTKFTQ----K--PGTFYLVILNDTFVEGNSPYEKQPL----PEDNIRW
MN773391.1(β) NQAYWVSNIEATKQNWEPPNDPDLIISDFPFWIMLWGWEDMTKRIGKCR-NLDNDWILVLRTQYF----S--DKMTAYVPLSEAFIHGQGPYFVDR-SEIKGQDYABW
MN769198.1(β) NICYFKAN-FKSETTWQPPDNPDLTNENLPFWLLLWGFSDWHKKIKKHL-HIDSSYILVMRHIPL-----A--LNTEYIVPLSDSFLQGKSPFSPEE--QPIGADRTTW
MN774797.1(β) NLCYFLNCKEVNGLSWDQPHNPDLTNENLPLWILLFGFSDFQKKLAKLK-RIDTDYTFVIKSTYT-----E--PTHLYIVPINISMSEGHSPYEDQA----NFVDDDRW
     JA20(α) NMLWIDWL-SKKNMKYD-KVQSKCLVADLPLWAAAYGYVEFCSKSTGDT-NIHMNARLLIRSPFTDPQLIVHTDPTKGFVPYSLNFGNGKMPGGSSN---VPIRMRAKW
MN766736.1(α) NVIWFQYN-TKADTQLT-LPSCKCVIEDIPLWAAFYGYSDFVQQEIGPYTDAESVGLVCVICPYTKPPMKNPDNPMMGYVFYDSNFGAGKWIDGSGF---VPLYWQTRW
MN765841.1(α) NKMWIQSV-TKSDTQFN-ELNCKCVLQDIPIWAMATGYAEFIESELGLQEEVYSVYIICVICPYTQPKMYSDTNVNTGYVFYDSLFGDGKMPSGTGL---VPFYYQSRW
MN765788.1(α) NHIWIQSV-TKTNTTLN--SQCRCHIQDIPIWAAVTGYAEFCESELN--SEVHNLYICCIICPYTKPKLYNNTDPTQGYVFYDTLFGDGKMPTGTGL---VPVWLQSRW
MN765502.1(α) NMVWIDYL-SKEDAVYT-PRTSKCLIRDQPLWASFNGYSEFCSKSTGDG-AVNINTRVVIKCPYTTPMLADNSNENQGFVPYSLNFGKGKMKGGSSQ---VPLSWRCRW
     SAf1A(γ) NMIYLVST--LANTWDQPPKDSAILIQGVPIWLGLFGYLDYCRQIKADKTWLDSHILVMQ-SPAIFTYPNP--GAGKWYCPLSQSFINGNGPFNQPP----TLLQKARW
MN777719.1(γ) NKLWLVNV--LNYSFAPPKTDADLYIENLPLWQLVWGFTDFVKQTKKDS-TFLNTYYAAFESKYLEPAVS----TSKIYIPIDMSFIQGKGPYDSYV----SNYRKQNW
MN776710.1(γ) NAVYLVSL--LQSKWTAPSDDR-LVIVGQPLWMCMYGLYSYYQDLLKDK-NFNTHYMFVVRSPAIKPITVS---RQDFYPFIDWDFINGVLPWEEYL----SEKIKATW
MN778499.1(γ) NEIYLVSV--TTGHYTKPSEDN-LVFRGLPLWLMFFGLYSFIKKIKTA--SFLPLHMFVVKSEYILPKPKD--PQKQYFPFVDLNFINGKNPYNSYI----SSTQRQTW
MN777204.1(γ) NTIWLHSN--LTTAYTKPAVDKTVILEGLPLWMMLFGWLSWVQHVKGAP-DFYLSYTLCVESPAIEIATKG--ETINPVIPLDASFINGNAPYNQTI----SQKDLTHW
             N              P     L   DPLW    G DF             Y  V SPYT             VP D F  G  PY      V      W
               ϕϕϕ        ϕ       ϕϕϕ ϕϕϕϕϕϕϕϕ ϕ  ϕ γγ γ    ϕ  ϕϕϕϕϕ   ϕ           ϕϕϕϕϕ  ϕϕ  ϕ ϕϕ      ϕ    γ γ
```

FIG. 38 continued

```
                      510       520        530       540       550       560           570        580       590       600
LY1(β)          YPCYQYQQESINSICLSGPGTPKIPKGIT--AEAKVKYSFNFKWGGDLPPMSTITNPTDQPT----YVVPNNFNETTSLQNPT-TRPEHFLYSFDERRGQLTEKATK
LY2(β)          YPQVQYQLEAQNKLLQTGPFTPNIQGQLS--DNISMFYKFYFKWGGSPPKAINVENPAHQIQ----YPIPRNEHETTSLQSPG-EAPESILYSFDYRHGNYTTTALS
MN773391.1(β)   YPRYRYQREAIENILMTGPMVCRADNINN--IQSLIKYKFFFKWGGTPATMENVYDPMSQPI----TPSPNNLISTNEIINPE-TSIDNYIYKWDTRRDILTQKATD
MN769198.1(β)   HPQFQHQAEAINTICSSGPGTTKIPDNYS--VQGLMKYSFYFKWGGSPPPMSTIEDPIQQPT----YPVPHNFNLTTSLQNPE-TDPASILWSFDQRRHTLTKKAIE
MN774797.1(β)   FPSFQFQQEAYTDICLSGPGTARIPKGDT--AEAKMHYTFHFKWGGELPDMEQIADPSEKPT----YPIPNNFLSTTSLQNPT-QAPETYLYKFDQRGDYITKTAAK
JA20(α)         YPTLSHQQEVLEALAQSGPFAYHSDIK---KVSLGIKYRFKWIWGGNPVRQQVVRNPCKEP-----HSSGNRVPRSIQIVDPRYNSPELTIHAWDFRRGFFGPKAIQ
MN766736.1(α)   RPETLFQESTMRDITMTGPFSYKDELK---NTVLTAKYKFNFRWGGNLLHEQTIRNPCPTNAH----PSTGRQPRDVQVVDPITVGPRFVFBSWDWRRGFLSEAAIK
MN765841.1(α)   YPRLRFQLQVLHDMYICGPFSYKDDLK---STVLTAEYKFRFLWGGNMIPEQVIRNPCKAEGAGSGYTYPDRLPRDLQIADPQTMGPEWAFHTWDWRHGLFGKGALK
MN765788.1(α)   YPRLIFQAQVLHDLYLTGPFSYKDDLK---SFTISAKYNFKFLWGGTIIPEQVIKNPCKEQD--SPFTFTGRQPRDLQVTDPQTMGPEWVFHTWDWRRGLFGENAIK
MN765502.1(α)   YVMMYHQQEFMEAIVQSGPWAYKGDEK---SAVLAMKYVFNWKWGGNPISGQVVRNPCKTSS-------SSREPRSIQAVDPKRVAPPLVFHSWDYRRGLFGHASIK
SAf1A(γ)        FPQIQYQQEIINSFVESGPFVPKYANQTESNWELKYKYIFTFKWGGPQFHEPEIADPSKQEQ----YDVPDTFYQTIQIEDPEGQDPRSLIHDWDYRRGFVKERSLK
MN777719.1(γ)   YPTLNAQLKTLNAIAQAGPFVPKLDNIFLSSWELYSNYTFYFKFGGSELPEPDTVNPQDQGT----YVIPTNIQKAIQVSNPQKQSPYTTLHSWDYRRGLITSSAFK
MN776710.1(γ)   YPQATFQTTTINALVESGPFVPRLTNIPDSTWELVYKYKFFFKWGGPQTHDDHVQDPKHQPD----YDTPDTLHQTIQIGDPKKQTPESIIHEWDYRRGFITQTALK
MN778499.1(γ)   YPTCEHQVETINAFVKCGPFVPKLDNDRDSTWELPFKSTFYFKWGGPQMPNQNVSDPKDKTS----YIVPDTVQEGLQITNPLKQKAESLLHEWDYRRGLIKTKAFK
MN777204.1(γ)   YPDIYNQTEIINSIVTSGPYIPKLDNIKNSTWELHYYYQFFFKWGGPEITDQPVADPSKQPV----YDALDKQQQGIQVRNPAKQKYATLMHPWDIRRGIITNKALK
                YP    Q E IN I  SGPF  K          L  KY F FKWGG      V NP  Q      Y  P        Q  DP     P    H WD RRG  T  ALK
                ϕϕ ϕ         ϕϕ   ϕϕ ϕγ          ϕ  ϕ ϕγϕ ϕ ϕγϕ     ϕ    ϕ  ϕ      ϕ ϕϕ       ϕ ϕ  ϕ          ϕϕ  ϕ ϕγγ ϕϕ   γ ϕγ
```

FIG. 38 continued

```
                         610        620        630                                    640        650        660        670
       LY1(β)   RLLKD-WETKETSL-LSTEYRFAEPTQTQAP--QEDP-----------------------------SSEEEEESNLFERLLRQRTKQLQLKRRIIQTLKDLQKLE
       LY2(β)   RISQD-WALKDTVS-KITEPDRQQLLKQALE--CLQ------------------------------ISEETQEKKEKEVQQLISNLRQQQQLYRERIISLLKDQ
 MN773391.1(β)   RITKS-STYDSNVF-TDGRETSTDIPLFQTT--QKA-----------------------------PQEET-PETQAETLLLQLHQLQQFNLQLQQRFNNLKQLMQNI
 MN769198.1(β)   RLQKD-TGIKTITV-TGGSHFDPTFTISQEE--T-------------------------------SEESS-EEEKETSLLEKLQQQRQQRRLKLRIMKTLLKIQQLE
 MN774797.1(β)   RIRKD-WSTKTDSL-SITAPRFAEAAQTQDT--S-------------------------------TETTS-EEEEEEDLFQQLNQQRLKQQRLKQRIKLIILQKLQTT
      JA20(α)   RMQQQPTATEFFSA-GRKRPRRDTEVYQSDQ--EKEQKESSLFPPVKLLRRVPPWEDSEQEQSGSQSSEEETATLSQQLKQQLQQQRVLGVKLRLLFNQVQKIQQNQDINPTLLPRGGDLVSFFQAVP
 MN766736.1(α)   RIRDQPLDYEAYSF-MPKRPRFFPP-TTGGEQLPGEQEESSSS-----------AEE-NNLISFEEGQEPKAQAVHKQLLKHLRKQRVLGQRLRALYQNLQKTQAGLHINPLLFSQA
 MN765841.1(α)   RVSEKPDYDADYYV-LPKKPRFFPP-TDGSQGQEKDSDLQEISLPF-------PFEE----TLSKSQEEVQTQQQQRDLHLRLAQQQRLGQQLKHLYTQILKTQAGLHINPLLYNHV
 MN765788.1(α)   RVSEQPSHDADYYA-PPKKPRLFPP-TDLQEQES-AFDFTPQELKI-------LSEA-PQQSEEEENQEEEQQLQQRELQLRLQEQFRIRHQLQHLFVQVLKTQAGLHINPLFLNPV
 MN765502.1(α)   RMSEESATPTLFTGPAGKRPRRDTS-VQQAEE-DQ-QKESSS---FRVQRQLQPWIHSSQETQSSQEEMQAQGTVQEQLIQQLGEQRALRKQLEFLASQVLKVQAGQHIHPLLSSQA
     SAf1A(γ)   RMSTY-FSTHTDQQ-ATSEEDIPKKKKR--IGPQ-LTVP---------------------------QQKEEETLSCLLSLCKKDTFQETETQEDLQQLIKQQQEQQLLLKRNILQLIHKLKENQQMLQLHTGMLP
 MN777719.1(γ)   RMCEN-QTTDTEFE-PDTE-TIPKKKKKIQHGNQ-LQRA---------------------------EEETQEIQNCLLSLCEENTFQETP-QTSLLELIQQQQQQQQLKHNLLKLLSDLKLKQRSLQLQTGLIH
 MN776710.1(γ)   RMSEN-IQTDTDFQ-SDDS-ASPRKKRK--VTKK-MPIT---------------------------SQKEENIKKCLLSLCQEETQ---ETPENLQDLIQQQQQQQHLLKRNLLQLLTHLKQQQRYLSLQTGILD
 MN778499.1(γ)   RMLEN-LSIESDVY-PSA--ETPRKRQR---VENS-LHYQ--------------------------EEENQEIKTCLLSLCESSSSEKEEEEKNLLHLIQQQQQQQKQLKLQLLTLIKDLKEKQNALQLQTGVI
 MN777204.1(γ)   RMQQN-LSIDSTFE-AGS---TPAKKPRI--TGPC-FTAL--------------------------QEIHQEERSCLQTLCKESTSQEAQEETDIQLLIAQQQQKQRELKYNLLKLISYMKEQQNMLKLHTGMLN
                RM                                                                 E        L         QQ
                γϕ    ϕ     ϕ
```

FIG. 38 continued

*0.5% Dextran added in the buffer for the specific prep

Primary Ab- R19 HVR3
Secondary Ab- Goat anti Rabbit

AB- Streptavidin CV 800

| Lane | Sample |
|---|---|
| 1 | Ladder |
| 2 | RBD-DBCO |
| 3 | RBD-CalFluor 488 |
| 4 | RBD-Azide |
| 5 | RBD-Alexa488 |

| Lane | Sample |
| --- | --- |
| 1 | Ladder |
| 2 | pRTx-2652 post SE-FPLC dialyzed |
| 3 | FlowThru 1 |
| 4 | FlowThru 2 |
| 5 | FlowThru 3 |
| 6 | pRTx-2652 concentrated |

RBD (26kDa) + ORF1
(~62 kDa) = ~90 kDa band

| Lane | Sample |
| --- | --- |
| 1 | Ladder |
| 2 | pRTx-2652 (R2 ORF1 Cterm 611) |
| 6 | 0.5 mg/ml RBD |
| 7 | pRTx-2652 + 0.5 mg/ml RBD |

SURFACE-MODIFIED VIRAL PARTICLES AND MODULAR VIRAL PARTICLES

CROSS REFERENCE TO RELATED APPLICATIONS

This application is a Continuation of U.S. patent application Ser. No. 18/719,065, filed Jun. 12, 2024, which is a U.S. National Phase Application under 35 U.S.C. § 371 of International Application No. PCT/US2022/081572 filed Dec. 14, 2022, which claims the benefit of U.S. Provisional Application No. 63/289,967, filed Dec. 15, 2021, U.S. Provisional Application No. 63/289,975, filed Dec. 15, 2021, and U.S. Provisional Application No. 63/344,029, filed May 19, 2022. The contents of the aforesaid applications are hereby incorporated by reference in their entirety.

SEQUENCE LISTING

The instant application contains a Sequence Listing which has been submitted electronically in XML format and is hereby incorporated by reference in its entirety. Said XML copy, created on Feb. 4, 2025, is named V2057-702020FT_SL.xml and is 1,080,562 bytes in size.

BACKGROUND

There is an ongoing need to develop suitable vectors to deliver therapeutic agents to patients.

SUMMARY

The present disclosure provides an anellovector, e.g., a synthetic anellovector, which can be used as a delivery vehicle, e.g., for delivering genetic material, for delivering an effector, e.g., a payload, or for delivering a therapeutic agent or a therapeutic effector to a eukaryotic cell (e.g., a human cell or a human tissue). The anellovector generally comprises on its exterior surface (e.g., attached to a proteinaceous exterior) a surface moiety as described herein. In some embodiments, an anellovector (e.g., particle, e.g., a viral particle, e.g., an Anellovirus particle) comprises a genetic element (e.g., a genetic element comprising a therapeutic DNA sequence) encapsulated in a proteinaceous exterior (e.g., a proteinaceous exterior comprising an Anellovirus capsid protein, e.g., an Anellovirus ORF1 molecule or a polypeptide encoded by an Anellovirus ORF1 nucleic acid, e.g., as described herein), which is capable of introducing the genetic element into a cell (e.g., a mammalian cell, e.g., a human cell). In some embodiments, the anellovector is a particle comprising a proteinaceous exterior comprising a polypeptide encoded by an Anellovirus ORF1 nucleic acid (e.g., an ORF1 nucleic acid of Betatorquevirus, e.g., as described herein). The genetic element of an anellovector of the present disclosure is typically a circular and/or single-stranded DNA molecule (e.g., circular and single stranded), and generally includes a protein binding sequence that binds to the proteinaceous exterior enclosing it, or a polypeptide attached thereto, which may facilitate enclosure of the genetic element within the proteinaceous exterior and/or enrichment of the genetic element, relative to other nucleic acids, within the proteinaceous exterior. In some instances, the genetic element is circular or linear. In some instances, the genetic element comprises or encodes an effector (e.g., a nucleic acid effector, such as a non-coding RNA, or a polypeptide effector, e.g., a protein), e.g., which can be expressed in the cell. In some embodiments, the effector is a therapeutic agent or a therapeutic effector, e.g., as described herein. In some instances, the effector is an endogenous effector or an exogenous effector, e.g., to a wild-type Anellovirus or a target cell. In some embodiments, the effector is exogenous to a wild-type Anellovirus or a target cell. In some embodiments, the anellovector can deliver an effector into a cell by contacting the cell and introducing a genetic element encoding the effector into the cell, such that the effector is made or expressed by the cell. In certain instances, the effector is an endogenous effector (e.g., endogenous to the target cell but, e.g., provided in increased amounts by the anellovector). In other instances, the effector is an exogenous effector. The effector can, in some instances, modulate a function of the cell or modulate an activity or level of a target molecule in the cell. For example, the effector can decrease levels of a target protein in the cell. In another example, the anellovector can deliver and express an effector, e.g., an exogenous protein, in vivo. Anellovectors can be used, for example, to deliver genetic material to a target cell, tissue or subject; to deliver an effector to a target cell, tissue or subject; or for treatment of diseases and disorders, e.g., by delivering an effector that can operate as a therapeutic agent to a desired cell, tissue, or subject. In some instances, the anellovector is made by in vitro assembly. In vitro assembly of an anellovector generally involves the formation of a proteinaceous exterior enclosing a genetic element, which occurs outside of a host cell (e.g., in a cell-free suspension, lysate, or supernatant). In vitro assembly may, in some instances, utilize components generated in a host cell but does not generally require a host cell for particle assembly.

The present disclosure provides an anelloVLP, e.g., a synthetic anelloVLP, which can be used as a delivery vehicle, e.g., for delivering genetic material, for delivering an effector, e.g., a payload, or for delivering a therapeutic agent or a therapeutic effector to a eukaryotic cell (e.g., a human cell or a human tissue). The anelloVLP generally comprises on its exterior surface (e.g., attached to a proteinaceous exterior) a surface moiety as described herein. In some embodiments, the surface moiety comprises the effector. In some embodiments, the surface moiety comprises a targeting agent (e.g., an agent that targets the anelloVLP to a target cell or tissue). In some embodiments, an anelloVLP (e.g., particle, e.g., a viral particle, e.g., an Anellovirus particle) comprises a proteinaceous exterior (e.g., a proteinaceous exterior comprising an Anellovirus capsid protein, e.g., an Anellovirus ORF1 molecule or a polypeptide encoded by an Anellovirus ORF1 nucleic acid, e.g., as described herein). In some embodiments, the anelloVLP is a particle comprising a proteinaceous exterior comprising a polypeptide encoded by an Anellovirus ORF1 nucleic acid (e.g., an ORF1 nucleic acid of Betatorquevirus, e.g., as described herein). In some embodiments, the proteinaceous exterior encloses an effector. In some embodiments, the effector is a therapeutic agent or a therapeutic effector, e.g., as described herein. In some instances, the effector is an endogenous effector or an exogenous effector, e.g., to a wild-type Anellovirus or a target cell. In some embodiments, the effector is exogenous to a wild-type Anellovirus or a target cell. In some embodiments, the anelloVLP can deliver an effector into a cell by contacting the cell and introducing the effector into the cell. In certain instances, the effector is an endogenous effector (e.g., endogenous to the target cell but, e.g., provided in increased amounts by the anelloVLP). In other instances, the effector is an exogenous effector. The effector can, in some instances, modulate a function of the cell or modulate an activity or level of a target molecule in the cell. For example, the effector can decrease levels of a target protein in the cell. In another example, the anelloVLP can deliver an effector, e.g., an exogenous protein, in vivo. AnelloVLPs can be used, for example, to deliver an effector to a target cell, tissue or subject; or for treatment of diseases and disorders, e.g., by delivering an effector that can operate as a therapeutic agent to a desired cell, tissue, or subject. In some instances, the anelloVLP is made by in vitro assembly. In vitro assembly of an anelloVLP generally involves the formation of a proteinaceous exterior in connection with an effector (e.g., the proteinaceous exterior enclosing the effector), which occurs outside of a host cell (e.g., in a cell-free suspension, lysate, or supernatant). In vitro assembly of an anelloVLP may, in some instances, utilize components generated in a host cell but does not generally require a host cell for particle assembly.

The invention further provides synthetic anellovectors and synthetic anelloVLPs. A synthetic anellovector or synthetic anelloVLP has at least one structural difference compared to a wild-type virus (e.g., a wild-type Anellovirus, e.g., a described herein), e.g., a deletion, insertion, substitution, modification (e.g., enzymatic modification), relative to the wild-type virus. Generally, synthetic anellovectors and synthetic anelloVLPs include a proteinaceous exterior, which can be used for delivering an effector (e.g., an exogenous effector or an endogenous effector) into eukaryotic (e.g., human) cells. In some embodiments, the anellovector or anelloVLP does not cause a detectable and/or an unwanted immune or inflammatory response, e.g., does not cause more than a 1%, 5%, 10%, 15% increase in a molecular marker(s) of inflammation, e.g., TNF-alpha, IL-6, IL-12, IFN, as well as B-cell response e.g. reactive or neutralizing antibodies, e.g., the anellovector or anelloVLP may be substantially non-immunogenic to the target cell, tissue or subject.

In an aspect, the invention features an anellovector comprising: (i) a genetic element comprising a promoter element and a sequence encoding an effector (e.g., an endogenous or exogenous effector), and a protein binding sequence (e.g., an exterior protein binding sequence, e.g., a packaging signal); and (ii) a proteinaceous exterior; wherein the genetic element is enclosed within the proteinaceous exterior (e.g., a capsid); and wherein the anellovector is capable of delivering the genetic element into a eukaryotic (e.g., mammalian, e.g., human) cell. In some embodiments, the anellovector comprises a surface moiety (e.g., a surface moiety having effector and/or targeting function), e.g., displayed on the exterior surface of the anellovector (e.g., as described herein). In some embodiments, the surface moiety comprises the effector.

In some embodiments, the genetic element is a single-stranded and/or circular DNA. Alternatively or in combination, the genetic element has one, two, three, or all of the following properties: is circular, is single-stranded, it integrates into the genome of a cell at a frequency of less than about 0.0001%, 0.001%, 0.005%, 0.01%, 0.05%, 0.1%, 0.5%, 1%, 1.5%, or 2% of the genetic element that enters the cell, and/or it integrates into the genome of a target cell at less than 1, 2, 3, 4, 5, 6, 7, 8, 9, 10, 15, 20, 25, or 30 copies per genome. In some embodiments, integration frequency is determined as described in Wang et al. (2004, *Gene Therapy* 11: 711-721, incorporated herein by reference in its entirety). In some embodiments, the genetic element is enclosed within the proteinaceous exterior. In some embodiments, the anellovector is capable of delivering the genetic element into a eukaryotic cell. In some embodiments, the genetic element comprises a nucleic acid sequence (e.g., a nucleic acid sequence of between 300-4000 nucleotides, e.g., between 300-3500 nucleotides, between 300-3000 nucleotides, between 300-2500 nucleotides, between 300-2000 nucleotides, between 300-1500 nucleotides) having at least 75% (e.g., at least 75, 76, 77, 78, 79, 80, 90, 91, 92, 93, 94, 95, 96, 97, 98, 99, or 100%) sequence identity to a sequence of a wild-type Anellovirus (e.g., a wild-type Torque Teno virus (TTV), Torque Teno mini virus (TTMV), or TTMDV sequence, e.g., a wild-type Anellovirus sequence as listed in any one of Tables A1-A25 or N1-N25). In some embodiments, the genetic element comprises a nucleic acid sequence (e.g., a nucleic acid sequence of at least 300 nucleotides, 500 nucleotides, 1000 nucleotides, 1500 nucleotides, 2000 nucleotides, 2500 nucleotides, 3000 nucleotides or more) having at least 75% (e.g., at least 75, 76, 77, 78, 79, 80, 90, 91, 92, 93, 94, 95, 96, 97, 98, 99, or 100%) sequence identity to a sequence of a wild-type Anellovirus (e.g., a wild-type Anellovirus sequence as described herein, e.g., as listed in any one of Tables A1-A25 or N1-N25). In some embodiments, the nucleic acid sequence is codon-optimized, e.g., for expression in a mammalian (e.g., human) cell. In some embodiments, at least 50%, 60%, 70%, 80%, 90%, 95%, 96%, 97%, 98%, 99%, or 100% of the codons in the nucleic acid sequence are codon-optimized, e.g., for expression in a mammalian (e.g., human) cell.

In an aspect, the invention features an anelloVLP comprising a proteinaceous exterior (e.g., a capsid) and an effector; wherein the anelloVLP is capable of delivering the effector into a eukaryotic (e.g., mammalian, e.g., human) cell. In some embodiments, the effector is comprised in a surface moiety, e.g., displayed on the exterior surface of the anelloVLP (e.g., as described herein).

In an aspect, the invention features an infectious (to a human cell) particle comprising an Anellovirus capsid (e.g., a capsid comprising an Anellovirus ORF, e.g., ORF1, polypeptide). In some embodiments, the infectious particle encapsulates a genetic element comprising a protein binding sequence that binds to the capsid and a heterologous (to the Anellovirus) sequence encoding a therapeutic effector. In some embodiments, the particle is capable of delivering the genetic element into a mammalian, e.g., human, cell. In some embodiments, the genetic element has less than about 6% (e.g., less than 6%, 5.5%, 5%, 4.5%, 4%, 3.5%, 3%, 2.5%, 2%, 1.5%, or less) identity to a wild type Anellovirus. In some embodiments, the genetic element has no more than 1.5%, 2%, 2.5%, 3%, 3.5%, 4%, 4.5%, 5%, 5.5% or 6% identity to a wild type Anellovirus. In some embodiments, the genetic element has at least about 2% to at least about 5.5% (e.g., 2 to 5%, 3% to 5%, 4% to 5%) identity to a wild type Anellovirus. In some embodiments, the genetic element has greater than about 2000, 3000, 4000, 4500, or 5000 nucleotides of non-viral sequence (e.g., non Anellovirus genome sequence). In some embodiments, the genetic element has greater than about 2000 to 5000, 2500 to 4500, 3000 to 4500, 2500 to 4500, 3500, or 4000, 4500 (e.g., between about 3000 to 4500) nucleotides of non-viral sequence (e.g., non Anellovirus genome sequence). In some embodiments, the genetic element is a single-stranded, circular DNA. Alternatively or in combination, the genetic element has one, two or 3 of the following properties: is circular, is single stranded, it integrates into the genome of a cell at a frequency of less than about 0.001%, 0.005%, 0.01%, 0.05%, 0.1%, 0.5%, 1%, 1.5%, or 2% of the genetic element that enters the cell, it integrates into the genome of a target cell at less than 1, 2, 3, 4, 5, 6, 7, 8, 9, 10, 15, 20, 25, or 30 copies per genome or integrates at a frequency of less than about 0.0001%, 0.001%, 0.005%, 0.01%, 0.05%, 0.1%, 0.5%, 1%, 1.5%, or 2% of the genetic element that enters the cell. In some embodiments, integration frequency is determined as described in Wang et al. (2004, *Gene Therapy* 11: 711-721, incorporated herein by reference in its entirety).

Also described herein are viral vectors and viral particles based on Anelloviruses, which can be used to deliver an agent (e.g., an exogenous effector or an endogenous effector, e.g., a therapeutic effector) to a cell (e.g., a cell in a subject to be treated therapeutically). In some embodiments, Anelloviruses can be used as effective delivery vehicles for introducing an agent, such as an effector described herein, to a target cell, e.g., a target cell in a subject to be treated therapeutically or prophylactically.

In an aspect, the invention features a polypeptide (e.g., a synthetic polypeptide, e.g., an ORF1 molecule) comprising (e.g., in series):

(i) a first region comprising an arginine-rich region, e.g., amino acid sequence having at least 70% (e.g., at least about 70, 80, 90, 95, 96, 97, 98, 99, or 100%) sequence identity to an arginine-rich region sequence described herein or a sequence of at least about 40 amino acids comprising at least 60%, 70%, or 80% basic residues (e.g., arginine, lysine, or a combination thereof), (ii) a second region comprising a jelly-roll domain, e.g., an amino acid sequence having at least 30% (e.g., at least about 30, 35, 40, 50, 60, 70, 80, 90, 95, 96, 97, 98, 99, or 100%) sequence identity to a jelly-roll region sequence described herein or a sequence comprising at least 6 beta strands, (iii) a third region comprising an amino acid sequence having at least 30% (e.g., at least about 30, 35, 40, 50, 60, 70, 80, 90, 95, 96, 97, 98, 99, or 100%) sequence identity to an N22 domain sequence described herein, (iv) a fourth region comprising an amino acid sequence having at least 70% (e.g., at least about 70, 80, 90, 95, 96, 97, 98, 99, or 100%) sequence identity to an Anellovirus ORF1 C-terminal domain (CTD) sequence described herein, and (v) optionally wherein the polypeptide has an amino acid sequence having less than 100%, 99%, 98%, 95%, 90%, 85%, 80% sequence identity to a wild type Anellovirus ORF1 protein described herein.

In some embodiments, the polypeptide comprises at least about 70, 80, 90, 95, 96, 97, 98, 99, or 100% sequence identity to an Anellovirus ORF1 molecule as described herein (e.g., as listed in any one of Tables A1-A25). In some embodiments, the polypeptide comprises at least about 70, 80, 90, 95, 96, 97, 98, 99, or 100% sequence identity to a subsequence (e.g., an arginine (Arg)-rich domain, a jelly-roll domain, a hypervariable region (HVR), an N22 domain, or a C-terminal domain (CTD)) of an Anellovirus ORF1 molecule as described herein (e.g., as listed in any one of Tables A1-A25). In one embodiment, the amino acid sequences of the (i), (ii), (iii), and (iv) region have at least 90% sequence identity to their respective references and wherein the polypeptide has an amino acid sequence having less than 100%, 99%, 98%, 95%, 90%, 85%, 80% sequence identity to a wild type Anellovirus ORF1 protein described herein.

In an aspect, the invention features a complex comprising a polypeptide as described herein (e.g., an Anellovirus ORF1 molecule as described herein) and a genetic element comprising a promoter element and a nucleic acid sequence (e.g., a DNA sequence) encoding an effector (e.g., an exogenous effector or an endogenous effector), and a protein binding sequence.

The present disclosure further provides nucleic acid molecules (e.g., a nucleic acid molecule that includes a genetic element as described herein, or a nucleic acid molecule that includes a sequence encoding a proteinaceous exterior protein as described herein). A nucleic acid molecule of the invention may include one or both of (a) a genetic element as described herein, and (b) a nucleic acid sequence encoding a proteinaceous exterior protein as described herein.

In an aspect, the invention features an isolated nucleic acid molecule comprising a genetic element comprising a promoter element operably linked to a sequence encoding an effector, e.g., a payload, and an exterior protein binding sequence. In some embodiments, the exterior protein binding sequence includes a sequence at least 75% (at least 80%, 85%, 90%, 95%, 97%, 100%) identical to a 5'UTR sequence of an Anellovirus, as disclosed herein. In some embodiments, the genetic element is a single-stranded DNA, is circular, integrates at a frequency of less than about 0.001%, 0.005%, 0.01%, 0.05%, 0.1%, 0.5%, 1%, 1.5%, or 2% of the genetic element that enters the cell, and/or integrates into the genome of a target cell at less than 1, 2, 3, 4, 5, 6, 7, 8, 9, 10, 15, 20, 25, or 30 copies per genome or integrates at a frequency of less than about 0.001%, 0.005%, 0.01%, 0.05%, 0.1%, 0.5%, 1%, 1.5%, or 2% of the genetic element that enters the cell. In some embodiments, integration frequency is determined as described in Wang et al. (2004, *Gene Therapy* 11: 711-721, incorporated herein by reference in its entirety). In embodiments, the effector does not originate from TTV and is not an SV40-miR-S1. In embodiments, the nucleic acid molecule does not comprise the polynucleotide sequence of TTMV-LY2. In embodiments, the promoter element is capable of directing expression of the effector in a eukaryotic (e.g., mammalian, e.g., human) cell.

In some embodiments, the nucleic acid molecule is circular. In some embodiments, the nucleic acid molecule is linear. In some embodiments, a nucleic acid molecule described herein comprises one or more modified nucleotides (e.g., a base modification, sugar modification, or backbone modification).

In some embodiments, the nucleic acid molecule comprises a sequence encoding an ORF1 molecule (e.g., an Anellovirus ORF1 protein, e.g., as described herein). In some embodiments, the nucleic acid molecule comprises a sequence encoding an ORF2 molecule (e.g., an Anellovirus ORF2 protein, e.g., as described herein). In some embodiments, the nucleic acid molecule comprises a sequence encoding an ORF3 molecule (e.g., an Anellovirus ORF3 protein, e.g., as described herein). In an aspect, the invention features a genetic element comprising one, two, or three of: (i) a promoter element and a sequence encoding an effector, e.g., an exogenous or endogenous effector; (ii) at least 72 contiguous nucleotides (e.g., at least 72, 73, 74, 75, 76, 77, 78, 79, 80, 90, 100, or 150 nucleotides) having at least 75% (e.g., at least 75, 76, 77, 78, 79, 80, 90, 91, 92, 93, 94, 95, 96, 97, 98, 99, or 100%) sequence identity to a wild-type Anellovirus sequence; or at least 100 (e.g., at least 300, 500, 1000, 1500) contiguous nucleotides having at least 72% (e.g., at least 72, 73, 74, 75, 76, 77, 78, 79, 80, 90, 91, 92, 93, 94, 95, 96, 97, 98, 99, or 100%) sequence identity to a wild-type Anellovirus sequence; and (iii) a protein binding sequence, e.g., an exterior protein binding sequence, and wherein the nucleic acid construct is a single-stranded DNA; and wherein the nucleic acid construct is circular, integrates at a frequency of less than about 0.001%, 0.005%, 0.01%, 0.05%, 0.1%, 0.5%, 1%, 1.5%, or 2% of the genetic element that enters the cell, and/or integrates into the genome of a target cell at less than 1, 2, 3, 4, 5, 6, 7, 8, 9, 10, 15, 20, 25, or 30 copies per genome In some embodiments, a genetic element encoding an effector (e.g., an exogenous or endogenous effector, e.g., as described herein) is codon optimized. In some embodiments, the genetic element is circular. In some embodiments, the genetic element is linear. In some embodiments, the genetic element comprises an anellovector, e.g., as described herein. In some embodiments, a genetic element described herein comprises one or more modified nucleotides (e.g., a base modification, sugar modification, or backbone modification). In some embodiments, the genetic element comprises a sequence encoding an ORF1 molecule (e.g., an Anellovirus ORF1 protein, e.g., as described herein). In some embodiments, the genetic element comprises a sequence encoding an ORF2 molecule (e.g., an Anellovirus ORF2 protein, e.g., as described herein). In some embodiments, the genetic element comprises a sequence encoding an ORF3 molecule (e.g., an Anellovirus ORF3 protein, e.g., as described herein).

In an aspect, the invention features a host cell or helper cell comprising: (a) a nucleic acid comprising a sequence encoding one or more of an ORF1 molecule, an ORF2 molecule, or an ORF3 molecule (e.g, a sequence encoding an Anellovirus ORF1 polypeptide described herein), wherein the nucleic acid is a plasmid, is a viral nucleic acid, or is integrated into a helper cell chromosome; and (b) a genetic element, wherein the genetic element comprises (i) a promoter element operably linked to a nucleic acid sequence (e.g., a DNA sequence) encoding an effector (e.g., an exogenous effector or an endogenous effector) and (ii) a protein binding sequence that binds the polypeptide of (a), wherein optionally the genetic element does not encode an ORF1 polypeptide (e.g., an ORF1 protein). For example, the host cell or helper cell comprises (a) and (b) either in cis (both part of the same nucleic acid molecule) or in trans (each part of a different nucleic acid molecule). In embodiments, the genetic element of (b) is circular, single-stranded DNA. In some embodiments, the host cell is a manufacturing cell line. In some embodiments, the host cell or helper cell is adherent or in suspension, or both. In some embodiments, the host cell or helper cell is grown in a microcarrier. In some embodiments, the host cell or helper cell is compatible with cGMP manufacturing practices. In some embodiments, the host cell or helper cell is grown in a medium suitable for promoting cell growth. In certain embodiments, once the host cell or helper cell has grown sufficiently (e.g., to an appropriate cell density), the medium may be exchanged with a medium suitable for production of anellovectors by the host cell or helper cell.

In an aspect, the invention features a pharmaceutical composition comprising an anellovector (e.g., a synthetic anellovector) as described herein. In embodiments, the pharmaceutical composition further comprises a pharmaceutically acceptable carrier or excipient. In embodiments, the pharmaceutical composition comprises a unit dose comprising about $10^5$-$10^{14}$ genome equivalents of the anellovector per kilogram of a target subject. In some embodiments, the pharmaceutical composition comprising the preparation will be stable over an acceptable period of time and temperature, and/or be compatible with the desired route of administration and/or any devices this route of administration will require, e.g., needles or syringes. In some embodiments, the pharmaceutical composition is formulated for administration as a single dose or multiple doses. In some embodiments, the pharmaceutical composition is formulated at the site of administration, e.g., by a healthcare professional. In some embodiments, the pharmaceutical composition comprises a desired concentration of anellovector genomes or genomic equivalents (e.g., as defined by number of genomes per volume).

In an aspect, the invention features a method of treating a disease or disorder in a subject, the method comprising administering to the subject an anellovector, e.g., a synthetic anellovector, e.g., as described herein.

In an aspect, the invention features a method of delivering an effector or payload (e.g., an endogenous or exogenous effector) to a cell, tissue or subject, the method comprising administering to the subject an anellovector, e.g., a synthetic anellovector, e.g., as described herein, wherein the anellovector comprises a nucleic acid sequence encoding the effector. In embodiments, the payload is a nucleic acid. In embodiments, the payload is a polypeptide.

In an aspect, the invention features a method of delivering an anellovector to a cell, comprising contacting the anellovector, e.g., a synthetic anellovector, e.g., as described herein, with a cell, e.g., a eukaryotic cell, e.g., a mammalian cell, e.g., in vivo or ex vivo.

In an aspect, the invention features a method of treating a disease or disorder in a subject, the method comprising administering to the subject an anelloVLP, e.g., a synthetic anelloVLP, e.g., as described herein.

In an aspect, the invention features a method of delivering an effector or payload (e.g., an endogenous or exogenous effector) to a cell, tissue or subject, the method comprising administering to the subject an anelloVLP, e.g., a synthetic anelloVLP, e.g., as described herein, wherein the anelloVLP comprises the effector (e.g., wherein the proteinaceous exterior of the anelloVLP encapsulates the effector). In embodiments, the payload is a nucleic acid. In embodiments, the payload is a polypeptide (e.g., a protein).

In an aspect, the invention features a method of delivering an anelloVLP to a cell, comprising contacting the anelloVLP, e.g., a synthetic anelloVLP, e.g., as described herein, with a cell, e.g., a eukaryotic cell, e.g., a mammalian cell, e.g., in vivo or ex vivo.

In an aspect, the invention features a method of making an anellovector, e.g., a synthetic anellovector. The method includes:

a) providing a host cell comprising:

(i) a first nucleic acid molecule comprising the nucleic acid sequence of a genetic element of an anellovector, e.g., a synthetic anellovector, as described herein, and (ii) the first nucleic acid or a second nucleic acid molecule encoding one or more of an amino acid sequence chosen from ORF1, ORF2, ORF2/2, ORF2/3, ORF1/1, or ORF1/2, e.g., as listed in any one of Tables A1-A25, or an amino acid sequence having at least 70% (e.g., at least 70%, 75%, 80%, 85%, 90%, 95%, 96%, 97%, 98%, 99%, or 100%) sequence identity thereto; and b) incubating the host cell under conditions suitable to make the anellovector.

In some embodiments, the method further includes, prior to step (a), introducing the first nucleic acid molecule and/or the second nucleic acid molecule into the host cell. In some embodiments, the second nucleic acid molecule is introduced into the host cell prior to, concurrently with, or after the first nucleic acid molecule. In other embodiments, the second nucleic acid molecule is integrated into the genome of the host cell. In some embodiments, the second nucleic acid molecule is a helper (e.g., a helper plasmid or the genome of a helper virus).

In another aspect, the invention features a method of manufacturing an anellovector composition, comprising:

a) providing a host cell comprising, e.g., expressing one or more components (e.g., all of the components) of an anellovector, e.g., a synthetic anellovector, e.g., as described herein. For example, the host cell comprises (a) a nucleic acid comprising a sequence encoding an Anellovirus ORF1 polypeptide described herein, wherein the nucleic acid is a plasmid, is a viral nucleic acid, or is integrated into a helper cell chromosome; and (b) a genetic element, wherein the genetic element comprises (i) a promoter element operably linked to a nucleic acid sequence (e.g., a DNA sequence) encoding an effector (e.g., an exogenous effector or an endogenous effector) and (i) a protein binding sequence (e.g, packaging sequence) that binds the polypeptide of (a), wherein the host cell or helper cell comprises (a) and (b) either in cis or in trans. In embodiments, the genetic element of (b) is circular, single-stranded DNA. In some embodiments, the host cell is a manufacturing cell line;

b) culturing the host cell under conditions suitable for producing a preparation of anellovectors from the host cell, wherein the anellovectors of the preparation comprise a proteinaceous exterior (e.g., comprising an ORF1 molecule) encapsulating the genetic element (e.g., as described herein), thereby making a preparation of anellovectors; and optionally, c) formulating the preparation of anellovectors, e.g., as a pharmaceutical composition suitable for administration to a subject.

In some embodiments, the components of the anellovector are introduced into the host cell at the time of production (e.g., by transient transfection). In some embodiments, the host cell stably expresses the components of the anellovector (e.g., wherein one or more nucleic acids encoding the components of the anellovector are introduced into the host cell, or a progenitor thereof, e.g., by stable transfection).

In some embodiments, the method further comprises one or more purification steps (e.g., purification by sedimentation, chromatography, and/or ultrafiltration). In some embodiments, the purification steps comprise removing one or more of serum, host cell DNA, host cell proteins, particles lacking the genetic element, and/or phenol red from the preparation. In some embodiments, the resultant preparation or a pharmaceutical composition comprising the preparation will be stable over an acceptable period of time and temperature, and/or be compatible with the desired route of administration and/or any devices this route of administration will require, e.g., needles or syringes.

In an aspect, the invention features a method of manufacturing an anellovector composition, comprising: a) providing a plurality of anellovectors described herein, or a preparation of anellovectors described herein; and b) formulating the anellovectors or preparation thereof, e.g., as a pharmaceutical composition suitable for administration to a subject.

In an aspect, the invention features a method of manufacturing an anelloVLP composition, comprising: a) providing a plurality of anelloVLPs described herein, or a preparation of anelloVLPs described herein; and b) formulating the anelloVLPs or preparation thereof, e.g., as a pharmaceutical composition suitable for administration to a subject.

In an aspect, the invention features a method of making a host cell, e.g., a first host cell or a producer cell (e.g., as shown in FIG. 20), e.g., a population of first host cells, comprising an anellovector, the method comprising introducing a genetic element, e.g., as described herein, to a host cell and culturing the host cell under conditions suitable for production of the anellovector. In some embodiments, the method further comprises introducing a helper, e.g., a helper virus, to the host cell. In some embodiments, the introducing comprises transfection (e.g., chemical transfection) or electroporation of the host cell with the anellovector.

In an aspect, the invention features a method of making an anellovector, comprising providing a host cell, e.g., a first host cell or producer cell (e.g., as shown in FIG. 20), comprising an anellovector, e.g., as described herein, and purifying the anellovector from the host cell. In some embodiments, the method further comprises, prior to the providing step, contacting the host cell with an anellovector, e.g., as described herein, and incubating the host cell under conditions suitable for production of the anellovector. In some embodiments, the host cell is the first host cell or producer cell described in the above method of making a host cell. In some embodiments, purifying the anellovector from the host cell comprises lysing the host cell.

In some embodiments, the method further comprises a second step of contacting the anellovector produced by the first host cell or producer cell with a second host cell, e.g., a permissive cell (e.g., as shown in FIG. 20), e.g., a population of second host cells. In some embodiments, the method further comprises incubating the second host cell inder conditions suitable for production of the anellovector. In some embodiments, the method further comprises purifying an anellovector from the second host cell, e.g., thereby producing an anellovector seed population. In some embodiments, at least about 2-100-fold more of the anellovector is produced from the population of second host cells than from the population of first host cells. In some embodiments, purifying the anellovector from the second host cell comprises lysing the second host cell. In some embodiments, the method further comprises a second step of contacting the anellovector produced by the second host cell with a third host cell, e.g., permissive cells (e.g., as shown in FIG. 20), e.g., a population of third host cells. In some embodiments, the method further comprises incubating the third host cell inder conditions suitable for production of the anellovector. In some embodiments, the method further comprises purifying an anellovector from the third host cell, e.g., thereby producing an anellovector stock population. In some embodiments, purifying the anellovector from the third host cell comprises lysing the third host cell. In some embodiments, at least about 2-100-fold more of the anellovector is produced from the population of third host cells than from the population of second host cells.

In some embodiments, the host cell is grown in a medium suitable for promoting cell growth. In certain embodiments, once the host cell has grown sufficiently (e.g., to an appropriate cell density), the medium may be exchanged with a medium suitable for production of anellovectors by the host cell. In some embodiments, anellovectors produced by a host cell separated from the host cell (e.g., by lysing the host cell) prior to contact with a second host cell. In some embodiments, anellovectors produced by a host cell are contacted with a second host cell without an intervening purification step.

In an aspect, the invention features a method of making a pharmaceutical anellovector preparation. The method comprises (a) making an anellovector preparation as described herein, (b) evaluating the preparation (e.g., a pharmaceutical anellovector preparation, anellovector seed population or the anellovector stock population) for one or more pharmaceutical quality control parameters, e.g., identity, purity, titer, potency (e.g., in genomic equivalents per anellovector particle), and/or the nucleic acid sequence, e.g., from the genetic element comprised by the anellovector, and (c) formulating the preparation for pharmaceutical use of the evaluation meets a predetermined criterion, e.g, meets a pharmaceutical specification. In some embodiments, evaluating identity comprises evaluating (e.g., confirming) the sequence of the genetic element of the anellovector, e.g., the sequence encoding the effector. In some embodiments, evaluating purity comprises evaluating the amount of an impurity, e.g., *mycoplasma*, endotoxin, host cell nucleic acids (e.g., host cell DNA and/or host cell RNA), animal-derived process impurities (e.g., serum albumin or trypsin), replication-competent agents (RCA), e.g., replication-competent virus or unwanted anellovectors (e.g., an anellovector other than the desired anellovector, e.g., a synthetic anellovector as described herein), free viral capsid protein, adventitious agents, and aggregates. In some embodiments, evaluating titer comprises evaluating the ratio of functional versus non-functional (e.g., infectious vs non-infectious) anellovectors in the preparation (e.g., as evaluated by HPLC). In some embodiments, evaluating potency comprises evaluating the level of anellovector function (e.g., expression and/or function of an effector encoded therein or genomic equivalents) detectable in the preparation. In some embodiments, the impurities comprise residual denaturant (e.g., urea) or cellular substituents (e.g., proteasomes or ferritin).

In some embodiments, the formulated preparation is substantially free of pathogens, host cell contaminants or impurities; has a predetermined level of non-infectious particles or a predetermined ratio of particles:infectious units (e.g., <300:1, <200:1, <100:1, or <50:1). In some embodiments, multiple anellovectors can be produced in a single batch. In some embodiments, the levels of the anellovectors produced in the batch can be evaluated (e.g., individually or together).

In an aspect, the invention features a method of making a pharmaceutical anelloVLP preparation. The method comprises (a) making an anelloVLP preparation as described herein, (b) evaluating the preparation (e.g., a pharmaceutical anelloVLP preparation, anelloVLP seed population or the anelloVLP stock population) for one or more pharmaceutical quality control parameters, e.g., identity, purity, titer, potency, and (c) formulating the preparation for pharmaceutical use of the evaluation meets a predetermined criterion, e.g, meets a pharmaceutical specification. In some embodiments, evaluating purity comprises evaluating the amount of an impurity, e.g., *mycoplasma*, endotoxin, host cell nucleic acids (e.g., host cell DNA and/or host cell RNA), animal-derived process impurities (e.g., serum albumin or trypsin), replication-competent agents (RCA), e.g., replication-competent virus or unwanted VLPs (e.g., an anelloVLP other than the desired anelloVLP, e.g., a synthetic anelloVLP as described herein), free viral capsid protein, adventitious agents, and aggregates. In some embodiments, evalating titer comprises evaluating the ratio of functional versus non-functional (e.g., infectious vs non-infectious) anelloVLPs in the preparation (e.g., as evaluated by HPLC). In some embodiments, evaluating potency comprises evaluating the level of anelloVLP function (e.g., expression and/or function of an effector encoded therein or genomic equivalents) detectable in the preparation. In some embodiments, the impurities comprise residual denaturant (e.g., urea) or cellular substituents (e.g., proteasomes or ferritin).

In some embodiments, the formulated preparation is substantially free of pathogens, host cell contaminants or impurities; has a predetermined level of non-infectious particles or a predetermined ratio of particles:infectious units (e.g., <300:1, <200:1, <100:1, or <50:1). In some embodiments, multiple anelloVLPs can be produced in a single batch. In some embodiments, the levels of the anelloVLPs produced in the batch can be evaluated (e.g., individually or together).

In an aspect, the invention features a host cell comprising:

(i) a first nucleic acid molecule comprising the nucleic acid sequence of a genetic element of an anellovector as described herein, and (ii) optionally, a second nucleic acid molecule encoding one or more of an amino acid sequence chosen from ORF1, ORF2, ORF2/2, ORF2/3, ORF1/1, or ORF1/2 as listed in any one of Tables A1-A25, or an amino acid sequence having at least about 70% (e.g., at least about 70, 80, 90, 95, 96, 97, 98, 99, or 100%) sequence identity thereto.

In an aspect, the invention features a reaction mixture comprising an anellovector described herein and a helper virus, wherein the helper virus comprises a polynucleotide, e.g., a polynucleotide encoding an exterior protein, (e.g., an exterior protein capable of binding to the exterior protein binding sequence and, optionally, a lipid envelope), a polynucleotide encoding a replication protein (e.g., a polymerase), or any combination thereof.

In some embodiments, an anellovector (e.g., a synthetic anellovector) is isolated, e.g., isolated from a host cell and/or isolated from other constituents in a solution (e.g., a supernatant). In some embodiments, an anellovector (e.g., a synthetic anellovector) is purified, e.g., from a solution (e.g., a supernatant). In some embodiments, an anellovector is enriched in a solution relative to other constituents in the solution.

In some embodiments of any of the aforesaid anellovectors, compositions or methods, providing an anellovector comprises separating (e.g., harvesting) an anellovector from a composition comprising an anellovector-producing cell, e.g., as described herein. In other embodiments, providing an anellovector comprises obtaining an anellovector or a preparation thereof, e.g., from a third party.

In some embodiments of any of the aforesaid anellovectors, anellovectors, compositions or methods, the genetic element comprises an anellovector genome, e.g., as identified according to the method described in Example 9. In embodiments, the anellovector genome is an anellovector genome capable of self-replication and/or self-amplification. In some embodiments, the anellovector genome is not capable of self-replication and/or self-amplification. In some embodiments, the anellovector genome is capable of replicating and/or being amplified in trans, e.g., in the presence of a helper, e.g., a helper virus.

Additional features of any of the aforesaid anellovectors, anelloVLPs, compositions or methods include one or more of the following enumerated embodiments.

Those skilled in the art will recognize, or be able to ascertain using no more than routine experimentation, many equivalents to the specific embodiments of the invention described herein. Such equivalents are intended to be encompassed by the following enumerated embodiments.

Enumerated Embodiments

1. A particle comprising:

a proteinaceous exterior comprising about 40-80 (e.g., about 60), 100-140 (e.g., about 120), or 160-200 (e.g., about 180) copies of an Anellovirus ORF1 molecule, wherein the particle:

(i) does not comprise (e.g., does not enclose) a polynucleotide (e.g., as determined using a nuclease protection assay as described herein), (ii) does not comprise (e.g., does not enclose) a polynucleotide of greater than 1000, 500, 200, or 100 nucleotides in length, or (iii) comprises less than about 1, 2, 3, 4, 5, 6, 7, 8, 9, 10, 15, 20, 25, 30, 40, 50, 60, 70, 80, 90, 100, 150, 200, 250, 300, 400, 500, 600, 700, 800, 900, or 1000 nucleotides.

2. The particle of embodiment 1, wherein the Anellovirus ORF1 molecule comprises an ORF1 domain and an exogenous surface moiety.

3. The particle of embodiment 1, wherein the Anellovirus ORF1 molecule is bound to an exogenous surface moiety via a noncovalent integration or a covalent bond other than a peptide bond.

4. The particle of embodiment 1, wherein the Anellovirus ORF1 molecule does not comprise an arginine-rich domain.

5. The particle of embodiment 1, wherein the particle is a virus-like particle (VLP).

6. A particle comprising:

(a) a proteinaceous exterior comprising about 40-80 (e.g., about 60), 100-140 (e.g., about 120), or 160-200 (e.g., about 180) copies of an Anellovirus ORF1 molecule and an exogenous surface moiety, and (b) a genetic element comprising a heterologous nucleic acid sequence encoding an exogenous effector.

7. A particle comprising:

a proteinaceous exterior comprising an Anellovirus ORF1 molecule, wherein the ORF1 molecule comprises an ORF1 domain and an exogenous surface moiety;

wherein one or more of:

a) the exogenous surface moiety is chosen from a receptor, a ligand, an antibody molecule (e.g., scFv), an antigen (e.g., a viral antigen, a bacterial antigen, a fungal antigen, or a parasite antigen) an adjuvant (e.g., TLR agonist, e.g., bacterial flagellin);

b) wherein the ORF1 molecule comprises a hypervariable region (HVR);

c) wherein the particle comprises a genetic element that encodes a peptide or polypeptide that boosts an immune response (e.g. an adjuvant, a TCR agonist (e.g., a bacterial flagellin));

d) wherein the exogenos surface moiety is between 1-5, 5-10, 10-20, 20-50, 50-100, 100-200, 200-500, or 500-1000 amino acids in length;

e) wherein a polypeptide linker region is situated between the exogenous surface moiety and the ORF1 molecule, f) wherein the particle comprises 1-2, 2-5, 5-10, 10-20, 20-40, 40-60, 60-80, 80-100, 100-125, 125-150, 150-175, 175-200, 200-225, 225-250, 250-275, or 275-300 copies of the exogenous surface moiety;

g) wherein the proteinaceous exterior comprises (i) a plurality of ORF1 molecules lacking the exogenous surface moiety (e.g., a wild-type ORF1 molecule) and (ii) a plurality of ORF1 molecules that comprise the exogenous surface moiety, wherein optionally the ratio of (i): (ii) is between 10:1-5:1, 5:1-2:1, 2:1-1:2, 1:2-1:5, or 1:5-1:10; and/or h) wherein the particle further comprises a second exogenous surface moiety.

8. The particle of embodiment 7, wherein the exogenous surface moiety is situated at an insertion point between an N-terminal portion of the ORF1 domain and a C-terminal portion of the ORF1 domain.

9. The particle of embodiment 8, wherein the insertion point is in the HVR.

10. The particle of any of embodiments 7-9, further comprising a genetic element comprising a heterologous nucleic acid sequence encoding an exogenous effector.

11. The particle of any of embodiments 7-10, wherein the particle does not comprise (e.g., does not enclose) a polynucleotide, or does not comprise (e.g., does not enclose) a polynucleotide of greater than 1000, 500, 200, or 100 nucleotides in length, or comprises less than about 1, 2, 3, 4, 5, 6, 7, 8, 9, 10, 15, 20, 25, 30, 40, 50, 60, 70, 80, 90, 100, 150, 200, 250, 300, 400, 500, 600, 700, 800, 900, or 1000 nucleotides.

12. A particle comprising:

a proteinaceous exterior comprising an Anellovirus ORF1 molecule, and an exogenous surface moiety, wherein the exogenous surface moiety is covalently bound to the ORF1 molecule using a bond other than a peptide bond.

13. The particle of embodiment 12, wherein the exogenous surface moiety is attached to an NHS moiety, and the exogenous surface moiety is bound to the ORF1 molecule via the NHS moiety.

14. The particle of embodiment 12 or 13, wherein a non-polypeptide linker is situated between the exogenous surface moiety and the ORF1 molecule.

15. The particle of embodiment 14, wherein the non-polypeptide linker comprises a click linkage.

16. The particle of embodiment 14, wherein the non-polypeptide linker is produced by a click reaction between a DBCO moiety and an azide moiety.

17. The particle of embodiment 16, wherein, prior to the click reaction, the DBCO moiety is attached to the Anellovirus ORF1 molecule via an NHS moiety.

18. The particle of embodiment 16 or 17, wherein, prior to the click reaction, the azide moiety is attached to the exogenous surface moiety via an NHS moiety.

19. The particle of embodiment 17 or 18, wherein the NHS moiety of the DBCO moiety is attached to a lysine residue on the surface of the Anellovirus ORF1 molecule.

20. The particle of any of embodiments 17-19, wherein the NHS moiety of the azide moiety is attached to a lysine residue on the surface of the exogenous surface moiety.

21. The particle of embodiment 16, wherein, prior to the click reaction, the DBCO moiety is attached to the exogenous surface moiety via an NHS moiety.

22. The particle of embodiment 16 or 21, wherein, prior to the click reaction, the azide moiety is attached to the Anellovirus ORF1 molecule via an NHS moiety.

23. The particle of embodiment 21 or 22, wherein the NHS moiety of the DBCO moiety is attached to a lysine residue on the surface of the exogenous surface moiety.

24. The particle of any of embodiments 21-23, wherein the NHS moiety of the azide moiety is attached to a lysine residue on the surface of the Anellovirus ORF1 molecule.

25. A particle comprising:

a proteinaceous exterior comprising an Anellovirus ORF1 molecule, and an exogenous surface moiety, wherein the exogenous surface moiety is non-covalently bound to the ORF1 molecule.

26. The particle of embodiment 25, wherein the ORF1 molecule comprises an exogenous binding domain (e.g., MS2 coat protein or avidin), and the exogenous surface moiety comprises a cognate binding moiety (e.g., MS2 hairpin or biotin) that binds the exogenous binding domain.

27. The particle of any of embodiments 12-26, wherein the exogenous surface moiety comprises a polypeptide.

28. The particle of any of embodiments 12-27, wherein the exogenous surface moiety comprises a small molecule or nucleic acid molecule (e.g., polynucleotide).

29. The particle of any of the preceding, wherein the ratio of ORF1 molecule to exogenous surface moiety is between about 60:1-30:1, 30:1-20:1, 20:1-10:1, or 10:1-1:1.

30. The particle of any of the preceding embodiments, wherein the antibody molecule is a bispecific antibody molecule.

31. The particle of embodiment 30, wherein the bispecific antibody molecule comprises: a first antigen-binding domain that binds a first antigen on a first type of host cell, and a second antigen-binding domain that binds a second antigen on a second type of host cell.

32. The particle of any of the preceding embodiments, which is capable of entering a target cell, e.g., by endocytosis.

33. The particle of embodiment 32, wherein the exogenous surface moiety binds to a cognate moiety in the target cell.

34. The particle of embodiment 32, wherein the particle comprises a genetic element encoding an exogenous effector to be delivered to the interior of the target cell.

35. The particle of any of the preceding embodiments, wherein a genetic element is enclosed within the proteinaceous exterior.

36. The particle of any of the preceding embodiments, which particle does not comprise a polynucleotide, or does not comprise a polynucleotide of greater than 1000, 500, 200, or 100 nucleotides in length.

37. The particle of any of the preceding embodiments, wherein the Anellovirus ORF1 molecule comprises:

(b) a first region comprising an Anellovirus ORF1 jelly-roll region, e.g., an amino acid sequence having at least 30% (e.g., at least about 30, 35, 40, 50, 60, 70, 80, 90, 95, 96, 97, 98, 99, or 100%) sequence identity to a Anellovirus ORF1 jelly-roll region sequence described herein or a sequence comprising at least 6 beta strands;

(c) a second region comprising an Anellovirus ORF1 N22 domain, e.g., an amino acid sequence having at least 30% (e.g., at least about 30, 35, 40, 50, 60, 70, 80, 90, 95, 96, 97, 98, 99, or 100%) sequence identity to an Anellovirus ORF1 N22 domain sequence described herein; and (d) a third region comprising an Anellovirus ORF1 C-terminal domain (CTD), e.g., an amino acid sequence having at least 30% (e.g., at least about 30, 35, 40, 50, 60, 70, 80, 90, 95, 96, 97, 98, 99, or 100%) sequence identity to an Anellovirus ORF1 CTD sequence described herein; and wherein the Anellovirus ORF1 molecule does not comprise an Anellovirus ORF1 arginine-rich region, e.g., a sequence of at least about 40 amino acids comprising at least 60%, 70%, or 80% basic residues (e.g., arginine, lysine, or a combination thereof).

38. A preparation comprising the particle of any of the preceding embodiments.

39. The preparation of embodiment 38, wherein the preparation comprises less than $10^{10}$-$10^{14}$ (e.g., less than $10^{10}$-$10^{11}$, $10^{11}$-$10^{12}$, $10^{12}$-$10^{13}$, or $10^{13}$-$10^{14}$) viral genome equivalents of nucleic acid molecules (e.g., genetic elements, e.g., of an anellovector as described herein) per kilogram of a subject to be administered the composition (e.g., as determined by qPCR or by measuring optical density).

40. A polypeptide, e.g., an Anellovirus ORF1 molecule, comprising:

(b) a first region comprising an Anellovirus ORF1 jelly-roll region, e.g., an amino acid sequence having at least 30% (e.g., at least about 30, 35, 40, 50, 60, 70, 80, 90, 95, 96, 97, 98, 99, or 100%) sequence identity to a Anellovirus ORF1 jelly-roll region sequence described herein or a sequence comprising at least 6 beta strands;

(c) a second region comprising an Anellovirus ORF1 N22 domain, e.g., an amino acid sequence having at least 30% (e.g., at least about 30, 35, 40, 50, 60, 70, 80, 90, 95, 96, 97, 98, 99, or 100%) sequence identity to an Anellovirus ORF1 N22 domain sequence described herein; and (d) a third region comprising an Anellovirus ORF1 C-terminal domain (CTD), e.g., an amino acid sequence having at least 30% (e.g., at least about 30, 35, 40, 50, 60, 70, 80, 90, 95, 96, 97, 98, 99, or 100%) sequence identity to an Anellovirus ORF1 CTD sequence described herein; and wherein the polypeptide does not comprise an Anellovirus ORF1 arginine-rich region, e.g., a sequence of at least about 40 amino acids comprising at least 60%, 70%, or 80% basic residues (e.g., arginine, lysine, or a combination thereof).

41. A nucleic acid molecule encoding a polypeptide of embodiment 40. 42. A particle comprising a proteinaceous exterior comprising an Anellovirus ORF1 molecule, wherein the ORF1 molecule comprises an ORF1 domain and an exogenous surface domain;

wherein the particle is made by contacting a plurality of Anellovirus ORF1 molecules in a cell-free solution under conditions suitable to form a proteinaceous exterior comprising the plurality of Anellovirus ORF1 molecules.

43. The particle of embodiment 42, wherein the particle does not comprise (e.g., does not enclose) a polynucleotide, or does not comprise (e.g., does not enclose) a polynucleotide of greater than 1000, 500, 200, or 100 nucleotides in length.

44. A method of making a particle, the method comprising:

contacting a plurality of Anellovirus ORF1 molecules in a cell-free solution under conditions suitable to form a proteinaceous exterior comprising the plurality of Anellovirus ORF1 molecules;

thereby making a particle.

45. A method of modulating a biological activity in a cell, the method comprising:

contacting the cell with a particle of any of the proceeding embodiments;

wherein the cell comprises a moiety on its surface that binds to the exogenous surface moiety of the particle.

46. A method of targeting a particle to a cell, the method comprising:

contacting the cell with a particle of any of the proceeding embodiments;

wherein the cell comprises a moiety on its surface that binds to the exogenous surface moiety of the particle.

47. The polypeptide, particle, nucleic acid molecule, or method of any of the preceding embodiments, wherein the exogenous surface moiety is fused to the N-terminus of the Anellovirus ORF1 molecule.

48. The polypeptide, particle, nucleic acid molecule, or method of any of the preceding embodiments, wherein the exogenous surface moiety is fused to the C-terminus of the Anellovirus ORF1 molecule.

49. The polypeptide, particle, nucleic acid molecule, or method of any of the preceding embodiments, wherein the exogenous surface moiety is inserted within the amino acid sequence of the Anellovirus ORF1 molecule.

50. An ORF1 molecule comprising an exogenous surface moiety, wherein the exogenous surface moiety is fused to, replaces, and/or is situated within an insertion point of an ORF1 domain (e.g., within an HVR or P2).

51. An ORF1 molecule comprising an exogenous surface moiety, wherein the exogenous surface moiety is fused to, replaces, and/or is situated at an insertion point between residues corresponding to positions 284-285 of Ring 10 ORF1, e.g., in an ORF1 domain (e.g., within the HVR).

52. An ORF1 molecule comprising an exogenous surface moiety, wherein the exogenous surface moiety is fused to, replaces, and/or is situated at an insertion point between residues corresponding to positions 328-329 of Ring 10 ORF1, e.g., in an ORF1 domain (e.g., within the HVR).

53. An ORF1 molecule comprising an exogenous surface moiety, wherein the exogenous surface moiety is fused to, replaces, and/or is situated at an insertion point between residues corresponding to positions 256-383 of Ring 10 ORF1, e.g., in an ORF1 domain (e.g., within the HVR).

54. An ORF1 molecule comprising an exogenous surface moiety, wherein the exogenous surface moiety is fused to, replaces, and/or is situated at an insertion point between residues corresponding to positions 251-383 of Ring 10 ORF1, e.g., in an ORF1 domain (e.g., within the HVR).

55. An ORF1 molecule comprising an exogenous surface moiety, wherein the exogenous surface moiety is fused to, replaces, and/or is situated at an insertion point between residues corresponding to positions 251-384 of Ring 10 ORF1, e.g., in an ORF1 domain (e.g., within the HVR).

56. An ORF1 molecule comprising an exogenous surface moiety, wherein the exogenous surface moiety is attached to (e.g., conjugated to) the amino acid residue (e.g., a cysteine residue) corresponding to position 254, 263, 264, 265, 272, 273, 274, 276, 283, 284, 285, 287, 288, 290, 291, 308, 311, 312, 313, 314, 316, 317, 318, 319, 321, 324, 328, 329, 341, 343, 354, 358, 361, 362, 363, 364, 365, 368, 369, 371, 374, 376, 378, 380, or 381 of Ring 10 ORF1, e.g., in an ORF1 domain (e.g., within the HVR).

57. The ORF1 molecule of any of embodiments 51-56, wherein the exogenous surface moiety forms a pentamer when the ORF1 molecule is complexed with four other ORF1 molecules (e.g., four other copies of the ORF1 molecule).

58. The ORF1 molecule of any of embodiments 51-56, wherein the exogenous surface moiety forms a trimer when the ORF1 molecule is complexed with four other ORF1 molecules (e.g., four other copies of the ORF1 molecule).

59. The ORF1 molecule of any of embodiments 51-56, wherein the exogenous surface moiety forms a dimer when the ORF1 molecule is complexed with four other ORF1 molecules (e.g., four other copies of the ORF1 molecule).

60. A protein complex comprising five ORF1 molecules, wherein each of the ORF1 molecules comprises:

(i) an ORF1 domain, and (ii) an exogenous surface moiety;

wherein the exogenous surface moieties of the five ORF1 molecules forms a pentamer.

61. The protein complex of embodiment 60, wherein each of the exogenous surface moieties is fused to, replaces, and/or is situated within an insertion point of an ORF1 domain (e.g., within an HVR) of the corresponding ORF1 molecule.

62. The protein complex of embodiment 60, wherein each of the exogenous surface moieties is fused to, replaces, and/or is situated within an insertion point between residues corresponding to positions 284-285 in an ORF1 domain (e.g., within the HVR) of Ring 10 ORF1.

63. The protein complex of embodiment 60, wherein each of the exogenous surface moieties is fused to, replaces, and/or is situated within an insertion point between residues corresponding to positions 328-329 in an ORF1 domain (e.g., within the HVR) of Ring 10 ORF1.

64. The protein complex of embodiment 60, wherein each of the exogenous surface moieties is fused to, replaces, and/or is situated within an insertion point between residues corresponding to positions 256-383 in an ORF1 domain (e.g., within the HVR) of Ring 10 ORF1.

65. The protein complex of embodiment 60, wherein each of the exogenous surface moieties is fused to, replaces, and/or is situated within an insertion point between residues corresponding to positions 251-383 in an ORF1 domain (e.g., within the HVR) of Ring 10 ORF1.

66. The protein complex of embodiment 60, wherein each of the exogenous surface moieties is fused to, replaces, and/or is situated within an insertion point between residues corresponding to positions 251-384 in an ORF1 domain (e.g., within the HVR) of Ring 10 ORF1.

67. The protein complex of embodiment 60, wherein each of the exogenous surface moieties is attached to (e.g., conjugated to) the amino acid residue (e.g., a cysteine residue) corresponding to position 254, 263, 264, 265, 272, 273, 274, 276, 283, 284, 285, 287, 288, 290, 291, 308, 311, 312, 313, 314, 316, 317, 318, 319, 321, 324, 328, 329, 341, 343, 354, 358, 361, 362, 363, 364, 365, 368, 369, 371, 374, 376, 378, 380, or 381 of Ring 10 ORF1, e.g., in an ORF1 domain (e.g., within the HVR).

68. The protein complex of any of embodiments 60-67, wherein the exogenous surface moieties of the ORF1 molecules have the same amino acid sequences.

69. The protein complex of any of embodiments 60-67, wherein at least two (e.g., at least 2, 3, 4, or 5) of the exogenous surface moieties of the ORF1 molecules have different amino acid sequences.

70. A protein complex comprising three ORF1 molecules, wherein each of the ORF1 molecules comprises:

(i) an ORF1 domain, and (ii) an exogenous surface moiety;

wherein the exogenous surface moieties of the three ORF1 molecules forms atrimer.

71. The protein complex of embodiment 70, wherein each of the exogenous surface moieties is fused to, replaces, and/or is situated within an insertion point of an ORF1 domain (e.g., within an HVR) of the corresponding ORF1 molecule.

72. The protein complex of embodiment 70, wherein each of the exogenous surface moieties is fused to, replaces, and/or is situated within an insertion point between positions 284-285 in an ORF1 domain (e.g., within the HVR) of the corresponding ORF1 molecule.

73. The protein complex of embodiment 70, wherein each of the exogenous surface moieties is fused to, replaces, and/or is situated within an insertion point between positions 328-329 in an ORF1 domain (e.g., within the HVR) of the corresponding ORF1 molecule.

74. The protein complex of embodiment 70, wherein each of the exogenous surface moieties is fused to, replaces, and/or is situated within an insertion point between positions 256-383 in an ORF1 domain (e.g., within the HVR) of the corresponding ORF1 molecule.

75. The protein complex of embodiment 70, wherein each of the exogenous surface moieties is fused to, replaces, and/or is situated within an insertion point between positions 251-383 in an ORF1 domain (e.g., within the HVR) of the corresponding ORF1 molecule.

76. The protein complex of embodiment 70, wherein each of the exogenous surface moieties is fused to, replaces, and/or is situated within an insertion point between positions 251-384 in an ORF1 domain (e.g., within the HVR) of the corresponding ORF1 molecule.

77. The protein complex of embodiment 70, wherein each of the exogenous surface moieties is attached to (e.g., conjugated to) the amino acid residue (e.g., a cysteine residue) at position 254, 263, 264, 265, 272, 273, 274, 276, 283, 284, 285, 287, 288, 290, 291, 308, 311, 312, 313, 314, 316, 317, 318, 319, 321, 324, 328, 329, 341, 343, 354, 358, 361, 362, 363, 364, 365, 368, 369, 371, 374, 376, 378, 380, or 381 of the corresponding ORF1 molecule, e.g., in an ORF1 domain (e.g., within the HVR).

78. The protein complex of any of embodiments 70-77, wherein the exogenous surface moieties of the ORF1 molecules have the same amino acid sequences.

79. The protein complex of any of embodiments 70-78, wherein at least two (e.g., at least 2 or 3) of the exogenous surface moieties of the ORF1 molecules have different amino acid sequences.

80. A protein complex comprising two ORF1 molecules, wherein each of the ORF1 molecules comprises:

(i) an ORF1 domain, and (ii) an exogenous surface moiety;

wherein the exogenous surface moieties of the two ORF1 molecules forms a dimer.

81. The protein complex of embodiment 80, wherein each of the exogenous surface moieties is fused to, replaces, and/or is situated within an insertion point of an ORF1 domain (e.g., within an HVR) of the corresponding ORF1 molecule.

82. The protein complex of embodiment 80, wherein each of the exogenous surface moieties is fused to, replaces, and/or is situated within an insertion point between residues corresponding to positions 284-285 in an ORF1 domain (e.g., within the HVR) of Ring 10 ORF1.

83. The protein complex of embodiment 80, wherein each of the exogenous surface moieties is fused to, replaces, and/or is situated within an insertion point between residues corresponding to positions 328-329 in an ORF1 domain (e.g., within the HVR) of Ring 10 ORF1.

84. The protein complex of embodiment 80, wherein each of the exogenous surface moieties is fused to, replaces, and/or is situated within an insertion point between residues corresponding to positions 256-383 in an ORF1 domain (e.g., within the HVR) of Ring 10 ORF1.

85. The protein complex of embodiment 80, wherein each of the exogenous surface moieties is fused to, replaces, and/or is situated within an insertion point between residues corresponding to positions 251-383 in an ORF1 domain (e.g., within the HVR) of Ring 10 ORF1.

86. The protein complex of embodiment 80, wherein each of the exogenous surface moieties is fused to, replaces, and/or is situated within an insertion point between residues corresponding to positions 251-384 in an ORF1 domain (e.g., within the HVR) of Ring 10 ORF1.

87. The protein complex of embodiment 80, wherein each of the exogenous surface moieties is attached to (e.g., conjugated to) the amino acid residue (e.g., a cysteine residue) corresponding to position 254, 263, 264, 265, 272, 273, 274, 276, 283, 284, 285, 287, 288, 290, 291, 308, 311, 312, 313, 314, 316, 317, 318, 319, 321, 324, 328, 329, 341, 343, 354, 358, 361, 362, 363, 364, 365, 368, 369, 371, 374, 376, 378, 380, or 381 of Ring 10 ORF1, e.g., in an ORF1 domain (e.g., within the HVR).

88. The protein complex of any of embodiments 80-87, wherein the exogenous surface moieties of the two ORF1 molecules have the same amino acid sequences.

89. The protein complex of any of embodiments 80-87, wherein the exogenous surface moieties of the two ORF1 molecules have different amino acid sequences.

90. The polypeptide, particle, nucleic acid molecule, method, or protein complex of any of the preceding embodiments, wherein the polypeptide or ORF1 molecule comprises one or more substitutions of a cysteine residues (e.g., one or more cysteine to alanine substitutions or one or more cysteine to serine substitutions).

91. The polypeptide, particle, nucleic acid molecule, method, or protein complex of any of the preceding embodiments, wherein the polypeptide or ORF1 molecule comprises a cysteine to serine mutation at one or more (e.g., 1, 2, 3, 4, 5, 6, 7, or 8) residues corresponding to position 63, 70, 137, 269, 403, 460, 503, and/or 515 of a Ring 10 ORF1 protein (e.g., as described herein).

92. The polypeptide, particle, nucleic acid molecule, method, or protein complex of any of the preceding embodiments, wherein the polypeptide or ORF1 molecule comprises a cysteine to alanine mutation at one or more (e.g., 1, 2, 3, 4, 5, 6, or 7) residues corresponding to position 63, 137, 269, 403, 460, 503, and/or 515 of a Ring 10 ORF1 protein (e.g., as described herein).

93. The polypeptide, particle, nucleic acid molecule, method, or protein complex of any of the preceding embodiments, wherein the polypeptide or ORF1 molecule comprises a cysteine to serine mutation at the residue corresponding to position 70 of a Ring 10 ORF1 protein (e.g., as described herein).

94. The polypeptide, particle, nucleic acid molecule, method, or protein complex of any of the preceding embodiments, wherein the polypeptide or ORF1 molecule comprises a substitution of an amino acid residue (e.g., a threonine, serine, asparagine, alanine, glutamine, or lysine residue) to cysteine.

95. The polypeptide, particle, nucleic acid molecule, method, or protein complex of embodiment 94, wherein the polypeptide or ORF1 molecule comprises a threonine to cysteine substitution, e.g., at the position corresponding to position 365 of a Ring 10 ORF1 protein (e.g., as described herein).

96. The polypeptide, particle, nucleic acid molecule, method, or protein complex of embodiment 94, wherein the polypeptide or ORF1 molecule comprises a serine to cysteine substitution, e.g., at the position corresponding to position 284 of a Ring 10 ORF1 protein (e.g., as described herein).

97. The polypeptide, particle, nucleic acid molecule, method, or protein complex of embodiment 94, wherein the polypeptide or ORF1 molecule comprises an asparagine to cysteine substitution, e.g., at the position corresponding to position 290 of a Ring 10 ORF1 protein (e.g., as described herein).

98. The polypeptide, particle, nucleic acid molecule, method, or protein complex of embodiment 94, wherein the polypeptide or ORF1 molecule comprises a lysine to cysteine substitution, e.g., at the position corresponding to position 317 of a Ring 10 ORF1 protein (e.g., as described herein).

99. The polypeptide, particle, nucleic acid molecule, method, or protein complex of embodiment 94, wherein the polypeptide or ORF1 molecule comprises a lysine to cysteine substitution, e.g., at the position corresponding to position 324 of a Ring 10 ORF1 protein (e.g., as described herein).

100. The polypeptide, particle, nucleic acid molecule, method, or protein complex of embodiment 94, wherein the polypeptide or ORF1 molecule comprises an alanine to cysteine substitution, e.g., at the position corresponding to position 362 of a Ring 10 ORF1 protein (e.g., as described herein).

101. The polypeptide, particle, nucleic acid molecule, method, or protein complex of embodiment 94, wherein the polypeptide or ORF1 molecule comprises a serine to cysteine substitution, e.g., at the position corresponding to position 363 of a Ring 10 ORF1 protein (e.g., as described herein).

102. The polypeptide, particle, nucleic acid molecule, method, or protein complex of embodiment 94, wherein the polypeptide or ORF1 molecule comprises an asparagine to cysteine substitution, e.g., at the position corresponding to position 369 of a Ring 10 ORF1 protein (e.g., as described herein).

103. The polypeptide, particle, nucleic acid molecule, method, or protein complex of embodiment 94, wherein the polypeptide or ORF1 molecule comprises a lysine to cysteine substitution, e.g., at the position corresponding to position 371 of a Ring 10 ORF1 protein (e.g., as described herein).

104. The polypeptide, particle, nucleic acid molecule, method, or protein complex of embodiment 94, wherein the polypeptide or ORF1 molecule comprises a glutamine to cysteine substitution, e.g., at the position corresponding to position 287 of a Ring 10 ORF1 protein (e.g., as described herein).

105. The polypeptide, particle, nucleic acid molecule, method, or protein complex of embodiment 94, wherein the polypeptide or ORF1 molecule comprises one or more substitutions to cysteine at one or more positions corresponding to Y254, R263, N264, K265, L272, G273, T274, R276, H283, T285, N288, D291, Q308, D311, W312, T313, E314, D316, H318, N319, T321, T328, K329, T341, Q343, T354, Q358, T361, T364, Q368, D374, P376, P378, Y380, and/or 1381 of a Ring 10 ORF1 protein (e.g., as described herein).

106. A particle comprising:
- (a) a proteinaceous exterior comprising an ORF1 molecule; and
- (b) a genetic element comprising a heterologous nucleic acid sequence encoding an exogenous effector;

wherein the genetic element is enclosed within the proteinaceous exterior; and wherein the particle has one or more of the following characteristics:
- (i) the genetic element (e.g., a DNA genetic element) does not comprise an Anellovirus 5' UTR or an origin of replication;
- (ii) the sequence encoding the exogenous effector takes up at least 90%, 95%, 96%, 97%, 98%, 99% or 100% of the genetic element (e.g., a DNA genetic element);
- (iii) the heterologous nucleic acid sequence takes up at least 90%, 95%, 96%, 97%, 98%, 99% or 100% of the genetic element (e.g., a DNA genetic element);
- (iv) the particle does not comprise a detectable amount of (e.g., any) polypeptides from a host cell, or comprises less than 5, 10, 15, 20, 25, 30, 40, or 50 copies of a polypeptide from a host cell;
- (v) the particle does not comprise a detectable amount of (e.g., any) nucleic acid molecules from a host cell, or comprises less than 2, 3, 4, or 5 copies of a nucleic acid molecule from a host cell;
- (vi) the particle comprises a denaturant in a concentration of less than about 0.01M, 0.1M, 0.2M, 0.3M, 0.4M, 0.5M, 0.6M, 0.7M, 0.8M, 0.9M, 1M, LIM, 1.2M, 1.3M, 1.5M, 1.5M, 1.6M, 1.7M, 1.8M, 1.9M, or 2M;
- (vii) does not substantially replicate when introduced into a cell (e.g., a human cell); and/or
- (viii) has a symmetrical morphology.

107. The particle of embodiment 106, wherein the heterologous nucleic acid sequence is about 60-100, 100-200, 200-300, 300-400, 400-500, 500-600, 600-700, 700-800, 800-900, 900-1000, 1000-1500, or 1500-2000, 2000-3000, 3000-4000, or 4000-5000 nucleotides in length.

108. A population of the particles of embodiment 106, wherein at least 75%, 80%, 90%, 95%, 96%, 97%, 98%, 99%, or 100% of the particles in the population comprise at least 50, 55, or 60 copies of an Anellovirus ORF1 molecule.

109. A population of the particles of embodiment 106, wherein at least 90% of the particles in the population have a diameter of at least 30, 31, 32, 33, 34, or 35 nm.

110. A population of the particles of embodiment 106, wherein at least 90%, 95%, 96%, 97%, 98%, 99%, or 100% of the particles have a symmetrical morphology.

111. A population of the particles of embodiment 106, wherein the population does not comprise a detectable amount of polypeptides from a host cell, or comprises less than 1, 2, 3, 4, 5, 10, 15, 20, 25, 30, 40, or 50 copies per particle of a polypeptide from a host cell.

112. A population of the particles of embodiment 106, wherein the population does not comprise a detectable amount of nucleic acid molecules from a host cell, or comprises less than 1, 2, 3, 4, 5, 10, 15, 20, 25, 30, 40, or 50 copies per particle of a nucleic acid molecule from a host cell.

113. A population of the particles of embodiment 106, wherein the population comprises less than 10 ng of nucleic acids.

114. A population of the particles of embodiment 106, wherein the population does not comprise a detectable amount of nucleic acid molecules from a host cell, or comprises less than 1, 2, 3, 4, 5, 10, 15, 20, 25, 30, 40, or 50 copies per particle of a nucleic acid molecule having a length of 200 bp or less from a host cell.

115. A particle comprising:

a proteinaceous exterior comprising about 40-80 (e.g., about 60) copies of an ORF1 molecule; and wherein the particle:
- (i) does not comprise (e.g., does not enclose) a polynucleotide,
- (ii) does not comprise (e.g., does not enclose) detectable levels of polynucleotides,
- (iii) does not comprise (e.g., does not enclose) a polynucleotide of greater than 1000, 500, 200, or 100 nucleotides in length,
- (iv) does not comprise (e.g., does not enclose) a polynucleotide comprising any contiguous nucleic acid sequences of at least 50, 100, 150, 200, 300, 400, 500, 600, 700, 800, 900, or 1000 nucleotides in length having least 75%, 80%, 85%, 90%, 95%, 96%, 97%, 98%, 99%, or 100% sequence identity to contiguous sequence in a wild-type Anellovirus genome (e.g., as described herein), and/or
- (v) does not comprise a polynucleotide comprising an Anellovirus 5' UTR or an origin of replication.

116. The particle of embodiment 115, further comprising an exogenous effector.

117. The particle of embodiment 116, wherein the exogenous effector is enclosed within the proteinaceous exterior.

118. The particle of embodiment 115 or 116, wherein the exogenous effector is a polypeptide.

119. The particle of any of embodiments 115-118, wherein the exogenous effector is a small molecule.

120. A composition comprising a plurality of particles, the particles comprising a proteinaceous exterior comprising about 40-80 (e.g., about 60) copies of an ORF1 molecule;

wherein at least 50%, 60%, 70%, 75%, 80%, 85%, 90%, 95%, 96%, 97%, 98%, 99%, 99.5%, or 99.9% of the particles do not comprise (e.g., do not enclose):
- (i) a polynucleotide,
- (ii) a nucleic acid molecule of greater than 1000, 500, 200, or 100 nucleotides in length,
- (iii) a plurality of polynucleotides,
- (iv) a circular nucleic acid molecule,
- (v) a single-stranded nucleic acid molecule, and/or
- (vi) a genetic element (e.g., a genetic element of an anellovector), e.g., as described herein; or wherein the composition comprises less than $10^{10}$-$10^{14}$ (e.g., less than $10^{10}$-$10^{11}$, $10^{11}$-$10^{12}$, $10^{12}$-$10^{13}$, or $10^{13}$-$10^{14}$) viral genome equivalents of nucleic acid molecules (e.g., genetic elements, e.g., of an anellovector as described herein) per kilogram of a subject to be administered the composition (e.g., as determined by qPCR or by measuring optical density).

121. The composition of embodiment 120, further comprising a denaturant (e.g., urea), e.g., in concentration of less than about 0.01M, 0.1M, 0.2M, 0.3M, 0.4M, 0.5M, 0.6M, 0.7M, 0.8M, 0.9M, 1M, 1.1M, 1.2M, 1.3M, 1.5M, 1.5M, 1.6M, 1.7M, 1.8M, 1.9M, or 2M; proteasomes; or ferritin.

122. The composition of embodiment 120 or 121, wherein the composition comprises 0.01-100 mg of the particles (e.g., 0.01-1, 1-10, 10-20, 20-30, 30-40, 40-50, 50-60, 60-70, 70-80, 80-90, or 90-100 mg of the particles).

123. A method of disassembling a particle, the method comprising:
- (a) providing a mixture comprising a particle and a denaturant, wherein the particle comprises:
  - (i) a proteinaceous exterior comprising a plurality of Anellovirus ORF1 molecules, and
  - (ii) a nucleic acid molecule (e.g., a nucleic acid endogenous to a host cell or a nucleic acid exogenous to a host cell, e.g., an anellovirus genome); and
- (b) incubating the mixture under conditions suitable for: disassembly of the proteinaceous exterior, and dissociation of the nucleic acid molecule from the proteinaceous exterior.

124. The method of embodiment 123, wherein the Anellovirus ORF1 molecules were made in mammalian cells.

125. The method of embodiment 123 or 124, wherein the conditions suitable for disassembly of the proteinaceous exterior comprises one or more of: a predetermined conductivity, a detergent (e.g., SDS (e.g., 0.1% SDS), Tween, or Triton), a chaotropic agent (e.g, urea), a high salt solution (e.g., a solution comprising NaCl, e.g., at a concentration of at least about 1M, e.g., at least about 0.5, 0.6, 0.7, 0.8, 0.9, 1.0, 1.1, 1.2, 1.3, 1.4, 1.5, 2, 3, 4, or 5M), or conditions involving a predetermined temperature.

126. The method of any of embodiments 123-125, wherein the mixture comprises a population of the particles.

127. The method of any of embodiments 123-126, wherein the incubating of (b) results in at least 50%, 60% . . . 95%, or 100% of the population of particles being disassembled.

128. The method of any of embodiments 123-127, further comprising a step of (c) removing (partially or completely) the nucleic acid molecule from the mixture, e.g., by washing.

129. The method of any of embodiments 123-128, wherein the host cell is a human cell.

130. A method of making an anellovector, the method comprising:
- (a) providing a mixture comprising a plurality of Anellovirus ORF1 molecules, wherein at least 75%, 80%, 90%, 95%, 96%, 97%, 98%, 99%, or 100% of the plurality of ORF1 molecules are not comprised in a particle comprising about 40-80 (e.g., about 60) copies of an ORF1 molecule;
- (b) subjecting the mixture to conditions suitable for in vitro assembly of the Anellovirus ORF1 molecules; and
- (c) incubating the Anellovirus ORF1 molecules with a plurality of genetic elements, under conditions suitable for assembly of the Anellovirus ORF1 molecules into one or more anellovectors each enclosing one or more of the genetic elements.

131. The method of embodiment 130, wherein the mixture provided in (a) is under denaturing conditions, e.g., wherein the mixture comprises a denaturant at a level sufficient to disassemble a complex (e.g., a proteinaceous exterior) comprising at least about 20, 30, 40, 50, or 60 copies, or 20-30, 30-40, 40-50, or 50-60 copies, of the Anellovirus ORF1 molecule.

132. The method of embodiment 130 or 131, wherein the conditions suitable for in vitro assembly comprise reducing the concentration of a denaturant or removing the mixture from denaturing conditions.

133. A method of making an anellovector, the method comprising:
- (a) providing a mixture comprising a plurality of Anellovirus ORF1 molecules and subjecting the mixture to denaturing conditions (e.g., providing a denaturant as part of the mixture, e.g., contacting the mixture with a denaturant), wherein at least 75%, 80%, 90%, 95%, 96%, 97%, 98%, 99%, or 100% of the plurality of ORF1 molecules are not comprised in a particle comprising about 40-80 (e.g., about 60) copies of an ORF1 molecule;
- (b) subjecting the mixture to non-denaturing conditions (e.g., reducing the concentration of the denaturant to a level) suitable for in vitro assembly of the Anellovirus ORF1 molecules (e.g., by dialysis); and
- (c) incubating the Anellovirus ORF1 molecules with a plurality of genetic elements, under conditions suitable for assembly of the Anellovirus ORF1 molecules into one or more anellovectors each enclosing one or more of the genetic elements.

134. The method of embodiment 133, wherein (b) and (c) are performed concurrently.

135. The method of embodiment 133, wherein (b) is performed prior to (c).

136. The method of any of embodiments 133-135, wherein the genetic elements are introduced into a mixture comprising the Anellovirus ORF1 molecules prior to, concurrently with, or after (b).

137. The method of any of embodiments 133-136, wherein at least 75%, 80%, 90%, 95%, 96%, 97%, 98%, 99%, or 100% of the plurality of ORF1 molecules in the mixture of (a) are comprised in capsomers (e.g., decamers or particles of 25-40 nm in diameter, e.g., 25-30, 30-32, 32-35, or 35-40 nm in diameter or about 25, 26, 27, 28, 29, 30, 31, 32, 33, 34, 35, 36, 37, 38, 39, or 40 nm).

138. The method of any of embodiments 133-137, wherein the ratio of ORF1 molecules in the mixture of (a) comprised in capsomers (e.g., decamers) compared to ORF1 molecules in the mixture of (a) comprised in particles is at least 2:1, 3:1, 4:1, 5:1, 10:1, 50:1, 100:1, 500:1, 1000:1, 5000:1, or 10,000:1.

139. The method of any of embodiments 133-138, wherein at least 75%, 80%, 90%, 95%, 96%, 97%, 98%, 99%, or 100% of the plurality of ORF1 molecules after the incubating of (c) are comprised in anellovectors (e.g., 60mers or particles of at least 30, 31, 32, 33, 34, or 35 nm in diameter).

140. The method of any of embodiments 133-139, wherein the genetic element encodes an exogenous effector.

141. The method of any of embodiments 133-140, wherein the genetic element is an oligonucleotide.

142. The method of any of embodiments 133-141, wherein the genetic element does not encode a polypeptide or functional nucleic acid.

143. The method of any of embodiments 133-142, wherein the concentration of the denaturant after step (b) is no more than about 0.01M, 0.1M, 0.2M, 0.3M, 0.4M, 0.5M, 0.6M, 0.7M, 0.8M, 0.9M, 1M, 1.1M, 1.2M, 1.3M, 1.5M, 1.5M, 1.6M, 1.7M, 1.8M, 1.9M, or 2M.

144. The method of any of embodiments 133-143, wherein, after the incubating of (c), at least 75%, 80%, 90%, 95%, 96%, 97%, 98%, 99%, or 100% of the particles in the mixture comprise at least 50, 55, or 60 copies of an Anellovirus ORF1 molecule.

145. The method of any of embodiments 133-144, wherein, after the incubating of (c), at least 90% of the particles in the mixture have a diameter of at least 30, 31, 32, 33, 34, or 35 nm.

146. The method of any of embodiments 133-145, wherein, after the incubating of (c), at least 90%, 95%, 96%, 97%, 98%, 99%, or 100% of the particles in the mixture have a symmetrical morphology.

147. The method of any of embodiments 133-146, wherein the denaturant is selected from a chaotropic agent (e.g., urea), heat (e.g., temperature above about 85, 86, 87, 88, 89, 90, 91, 92, 93, 94, or 95° C.), or pH (e.g., acidic pH or basic pH).

148. A method of making an anelloVLP, the method comprising:

(a) providing a mixture comprising a plurality of Anellovirus ORF1 molecules, wherein at least 75%, 80%, 90%, 95%, 96%, 97%, 98%, 99%, or 100% of the plurality of ORF1 molecules are not comprised in a particle comprising about 40-80 (e.g., about 60) copies of an ORF1 molecule;

(b) subjecting the mixture to conditions suitable for in vitro assembly of the Anellovirus ORF1 molecules; and (c) incubating the Anellovirus ORF1 molecules with a plurality of effectors (e.g., exogenous effectors), under conditions suitable for assembly of the Anellovirus ORF1 molecules into one or more anelloVLPs each enclosing one or more of the effectors.

149. The method of embodiment 148, wherein the mixture provided in (a) is under denaturing conditions, e.g., wherein the mixture comprises a denaturant at a level sufficient to disassemble a complex (e.g., a proteinaceous exterior) comprising at least about 20, 30, 40, 50, or 60 copies, or 20-30, 30-40, 40-50, or 50-60 copies, of the Anellovirus ORF1 molecule.

150. The method of embodiment 148 or 149, wherein the conditions suitable for in vitro assembly comprise reducing the concentration of a denaturant or removing the mixture from denaturing conditions. 151. A method of making an anelloVLP, the method comprising:

(a) providing a mixture comprising a plurality of Anellovirus ORF1 molecules and a denaturant, wherein at least 75%, 80%, 90%, 95%, 96%, 97%, 98%, 99%, or 100% of the plurality of ORF1 molecules are not comprised in a particle comprising about 40-80 (e.g., about 60) copies of an ORF1 molecule;

(b) reducing the concentration of the denaturant to a level suitable for in vitro assembly of the Anellovirus ORF1 molecules; and (c) incubating the Anellovirus ORF1 molecules with a plurality of effectors (e.g., exogenous effectors), under conditions suitable for in vitro assembly of the Anellovirus ORF1 molecules into one or more anelloVLPs each enclosing one or more of the effectors.

152. The method of embodiment 151, wherein the effectors are introduced into a mixture comprising the Anellovirus ORF1 molecules prior to, concurrently with, or after (b).

153. The method of embodiment 151 or 152, wherein at least 75%, 80%, 90%, 95%, 96%, 97%, 98%, 99%, or 100% of the plurality of ORF1 molecules in the mixture of (a) are comprised in capsomers (e.g., decamers or particles of at most 25-40 nm in diameter, e.g., 25-30, 30-32, 32-35, or 35-40 nm in diameter or about 25, 26, 27, 28, 29, 30, 31, 32, 33, 34, 35, 36, 37, 38, 39, or 40 nm).

154. The method of any of embodiments 151-153, wherein the ratio of ORF1 molecules in the mixture of (a) comprised in capsomers (e.g., decamers) compared to ORF1 molecules in the mixture of (a) comprised in particles is at least 2:1, 3:1, 4:1, 5:1, 10:1, 50:1, 100:1, 500:1, 1000:1, 5000:1, or 10,000:1.

155. The method of any of embodiments 151-154, wherein at least 75%, 80%, 90%, 95%, 96%, 97%, 98%, 99%, or 100% of the plurality of ORF1 molecules after the incubating of (c) are comprised in anelloVLPs (e.g., 60mers or particles of at least 30, 31, 32, 33, 34, or 35 nm in diameter).

156. The method of any of embodiments 151-155, wherein the anelloVLP has one or more of the following characteristics:

(i) does not comprise (e.g., does not enclose) a polynucleotide, (ii) does not comprise (e.g., does not enclose) detectable levels of polynucleotides, (iii) does not comprise (e.g., does not enclose) a polynucleotide of greater than 1000, 500, 200, or 100 nucleotides in length, (iv) does not comprise (e.g., does not enclose) a polynucleotide comprising any contiguous nucleic acid sequences of at least 50, 100, 150, 200, 300, 400, 500, 600, 700, 800, 900, or 1000 nucleotides in length having least 75%, 80%, 85%, 90%, 95%, 96%, 97%, 98%, 99%, or 100% sequence identity to contiguous sequence in a wild-type Anellovirus genome (e.g., as described herein), and/or (v) does not comprise a polynucleotide comprising an Anellovirus 5' UTR or an origin of replication.

157. The method of any of embodiments 151-156, wherein the concentration of the denaturant after step (b) is no more than about 0.01M, 0.1M, 0.2M, 0.3M, 0.4M, 0.5M, 0.6M, 0.7M, 0.8M, 0.9M, 1M, 1.1M, 1.2M, 1.3M, 1.5M, 1.5M, 1.6M, 1.7M, 1.8M, 1.9M, or 2M.

158. The method of any of embodiments 151-157, wherein, after the incubating of (c), at least 75%, 80%, 90%, 95%, 96%, 97%, 98%, 99%, or 100% of the particles in the mixture comprise at least 50, 55, or 60 copies of an Anellovirus ORF1 molecule.

159. The method of any of embodiments 151-158, wherein, after the incubating of (c), at least 90% of the particles in the mixture have a diameter of at least 30, 31, 32, 33, 34, or 35 nm.

160. The method of any of embodiments 151-159, wherein, after the incubating of (c), at least 90%, 95%, 96%, 97%, 98%, 99%, or 100% of the particles in the mixture have a symmetrical morphology.

161. The method of any of embodiments 151-160, wherein the denaturant is selected from a chaotropic agent (e.g., urea), heat (e.g., temperature above about 85, 86, 87, 88, 89, 90, 91, 92, 93, 94, or 95° C.), or pH (e.g., acidic pH or basic pH).

162. A method of making an anelloVLP, the method comprising:

(a) providing a mixture comprising a particle and a denaturant, wherein the particle comprises:
  (i) a proteinaceous exterior comprising a plurality of Anellovirus ORF1 molecules, and
  (ii) a nucleic acid molecule (e.g., a host cell nucleic acid molecule); and
(b) incubating the mixture under conditions suitable for: disassembly of the proteinaceous exterior, and dissociation of the nucleic acid molecule from the proteinaceous exterior;
(c) providing a mixture comprising a plurality of Anellovirus ORF1 molecules and a denaturant, wherein at least 75%, 80%, 90%, 95%, 96%, 97%, 98%, 99%, or 100% of the plurality of ORF1 molecules are not comprised in a particle comprising about 40-80 (e.g., about 60) copies of an ORF1 molecule;
(d) reducing the concentration of the denaturant to a level suitable for in vitro assembly of the Anellovirus ORF1 molecules; and
(e) incubating the Anellovirus ORF1 molecules with a plurality of effectors (e.g., exogenous effectors), under conditions suitable for assembly of the Anellovirus ORF1 molecules into one or more anelloVLPs each enclosing one or more of the effectors.

163. A polypeptide, e.g., an ORF1 molecule, comprising one or more of:

(a) a first region comprising an amino acid sequence having at least 70% (e.g., at least about 70, 80, 90, 95, 96, 97, 98, 99, or 100%) sequence identity to an arginine-rich region sequence described herein (e.g., MPYYYRRRRYNYRRPRWYGRGWIRRPFRRRFRRKRRVR (SEQ ID NO: 216) or MAWGWWKRRRRWWFRKRWTRGRLRRRWPRSARRRPRRRRVRRRRRWRRGRRKTRTYRRRRRFRRRGRK (SEQ ID NO: 186), or as listed in any one of Tables A1-A25) or a sequence of at least about 40 amino acids comprising at least 60%, 70%, or 80% basic residues (e.g., arginine, lysine, or a combination thereof),
(b) a second region comprising an amino acid sequence having at least 30% (e.g., at least about 30, 35, 40, 50, 60, 70, 80, 90, 95, 96, 97, 98, 99, or 100%) sequence identity to a jelly-roll region sequence described herein (e.g., PTYTTIPLKQWQPPYKRTCYIKGQDCLIYYSNLRLGMNSTMYEKSIVPVHWPGGGSFSVSMLTLD ALYDIHKLCRNWWTSTNQDLPLVRYKGCKITFYQSTFTDYI VRIHTELPANSNKLTYPNTHPLM MMMSKYKHIIPSRQTRRKKKPYTKIFVKPPPQFENKWYFATDLYKIPLLQIHCTACNLQNPFVKP DKLSNNVTLWSLNT (SEQ ID NO: 217), or as listed in any of any one of Tables A1-A25) or a sequence comprising at least 6 (e.g., at least 6, 7, 8, 9, 10, 11, or 12) beta strands;
(c) a third region comprising an amino acid sequence having at least 30% (e.g., at least about 30, 35, 40, 50, 60, 70, 80, 90, 95, 96, 97, 98, 99, or 100%) sequence identity to an N22 domain sequence described herein (e.g., TMALTPFNEPIFTQIQYNPDRDTGEDTQLYLLSNATGTGWDPPGIPELILEGFPLWLIYWGFADFQ KNLKKVTNIDTNYMLVAKTKFTQKPGTFYLVILNDTFVEGNSPYEKQPL PEDNIKWYPQVQYQL EAQNKLLQTGPFTPNIQGQLSDNISMFYKFYFK (SEQ ID NO: 219), or as listed in any of any one of Tables A1-A25); and
(d) a fourth region comprising an amino acid sequence having at least 30% (e.g., at least about 30, 35, 40, 50, 60, 70, 80, 90, 95, 96, 97, 98, 99, or 100%) sequence identity to an Anellovirus ORF1 C-terminal domain (CTD) sequence described herein (e.g., WGGSPPKAINVENPAHQIQYPIPRNEHETTSLQSPGEAPESILYSFDYRHGNYTTTALSRISQDWA LKDTVSKITEPDRQQLLKQALECLQISEETQEKKEKEVQ QLISNLRQQQQLYRERIISLLKDQ (SEQ ID NO: 220), or as listed in any of any one of Tables A1-A25);

wherein the ORF1 molecule comprises at least one difference (e.g., a mutation, chemical modification, or epigenetic alteration) relative to a wild-type ORF1 protein (e.g., as described herein), e.g., an insertion, substitution, chemical or enzymatic modification, and/or deletion, e.g., a deletion of a domain (e.g., one or more of an arginine-rich region, jelly-roll domain, HVR, N22, or CTD, e.g., as described herein).

164. The polypeptide of embodiment 163, wherein the amino acid sequences of the region of (a), (b), (c), and (d) have at least 90% sequence identity to their respective references.

165. The polypeptide of embodiment 163, wherein the polypeptide comprises:

(i) the first region and the second region;
(ii) the first region and the third region;
(iii) the first region and the fourth region;
(iv) the second region and the third region;
(v) the second region and the fourth region;
(vi) the third region and the fourth region;
(vii) the first region, the second region, and the third region;
(viii) the first region, the second region, and the fourth region;
(ix) the first region, the third region, and the fourth region; or
(x) the second region, the third region, and the fourth region.

166. The polypeptide of any of embodiments 163-165, wherein:

the first region comprises an amino acid sequence having at least 70% (e.g., at least about 70, 80, 90, 95, 96, 97, 98, 99, or 100%) sequence identity to an arginine-rich region sequence as listed in any one of Tables A1-A25;
the second region comprises an amino acid sequence having at least 70% (e.g., at least about 70, 80, 90, 95, 96, 97, 98, 99, or 100%) sequence identity to a jelly-roll region sequence as listed in any one of Tables A1-A25;

the third region comprises an amino acid sequence having at least 70% (e.g., at least about 70, 80, 90, 95, 96, 97, 98, 99, or 100%) sequence identity to an N22 domain sequence as listed in any one of Tables A1-A25; and/or the fourth region comprises an amino acid sequence having at least 70% (e.g., at least about 70, 80, 90, 95, 96, 97, 98, 99, or 100%) sequence identity to a CTD sequence as listed in any one of Tables A1-A25.

167. The polypeptide according to embodiment 166, wherein the amino acid sequences of the first, second, third and fourth region have at least 90% sequence identity to their respective references.

168. The polypeptide of any of the preceding embodiments, wherein the polypeptide comprises, in N-terminal to C-terminal order, the first region, the second region, the third region, and the fourth region.

169. The polypeptide of any of the preceding embodiments, wherein the at least one difference comprises at least one difference in the first region relative to the arginine-rich region of a wild-type ORF1 protein.

170. The polypeptide of any of the preceding embodiments, wherein the first region comprises an arginine-rich region from the ORF1 protein of an Anellovirus other than the wild-type Anellovirus to which the polypeptide, or the portion thereof excluding the first region, has greatest sequence identity.

171. The polypeptide of any of the preceding embodiments, wherein the first region comprises an amino acid sequence having at least 70% sequence identity to the arginine-rich region from an Anellovirus other than the wild-type Anellovirus to which the polypeptide has greatest sequence identity.

172. The polypeptide of any of the preceding embodiments, wherein the second region comprises a jelly-roll region from the ORF1 protein of an Anellovirus other than the wild-type Anellovirus to which the polypeptide, or the portion thereof excluding the second region, has greatest sequence identity.

173. The polypeptide of any of the preceding embodiments, wherein the second region comprises an amino acid sequence having at least 70% sequence identity to the jelly-roll region from an Anellovirus other than the wild-type Anellovirus to which the polypeptide has greatest sequence identity.

174. The polypeptide of any of the preceding embodiments, wherein the third region comprises an N22 domain from the ORF1 protein of an Anellovirus other than the wild-type Anellovirus to which the polypeptide, or the portion thereof excluding the third region, has greatest sequence identity.

175. The polypeptide of any of the preceding embodiments, wherein the third region comprises an amino acid sequence having at least 70% sequence identity to the N22 region from an Anellovirus other than the wild-type Anellovirus to which the polypeptide has greatest sequence identity.

176. The polypeptide of any of the preceding embodiments, wherein the fourth region comprises a CTD domain from the ORF1 protein of an Anellovirus other than the wild-type Anellovirus to which the polypeptide, or the portion thereof excluding the fourth region, has greatest sequence identity.

177. The polypeptide of any of the preceding embodiments, wherein the fourth region comprises an amino acid sequence having at least 70% sequence identity to the CTD region from an Anellovirus other than the wild-type Anellovirus to which the polypeptide has greatest sequence identity.

178. The polypeptide of any of embodiments 163-177, wherein the HVR sequence is positioned between the second region and the third region.

179. The polypeptide of embodiment 178, wherein the HVR sequence comprises an amino acid sequence having at least 70% (e.g., at least about 70, 80, 90, 95, 96, 97, 98, 99, or 100%) sequence identity to the HVR from an Anellovirus other than the wild-type Anellovirus to which the ORF1 protein has greatest sequence identity.

180. The polypeptide of any of embodiment 178 or 179, wherein the HVR sequence is heterologous relative to one or more of the first region, second region, third region, and/or fourth region.

181. The polypeptide of any of embodiments 178-180, wherein the HVR sequence comprises an HVR from the ORF1 protein of an Anellovirus other than the wild-type Anellovirus to which the polypeptide, or the portion thereof excluding the HVR sequence, has greatest sequence identity.

182. The polypeptide of any of embodiments 178-181, wherein the HVR sequence comprises an amino acid sequence having at least 70% sequence identity to the HVR from an Anellovirus other than the wild-type Anellovirus to which the polypeptide has greatest sequence identity.

183. The anellovector of any of the preceding embodiments, wherein the proteinaceous exterior comprises a polypeptide of any of embodiments 58-77.

184. The particle of any of the preceding embodiments, wherein the proteinaceous exterior comprises a polypeptide of any of embodiments 58-77.

185. The anelloVLP of any of the preceding embodiments, wherein the proteinaceous exterior comprises a polypeptide of any of embodiments 58-77.

186. A method of making two or more different Anellovirus ORF molecules, the method comprising:

(i) providing an insect cell comprising a nucleic acid construct encoding two or more different Anellovirus ORF molecules (e.g., two or more of an ORF1, ORF2, ORF2/2, ORF2/3, ORF1/1, and/or ORF1/2 molecule);

(ii) incubating the insect cell under conditions suitable for expression of the two or more different Anellovirus ORF molecules.

187. The method of embodiment 186, wherein the nucleic acid construct comprises sequences encoding all of an ORF1, ORF2, ORF2/2, ORF2/3, ORF1/1, and/or ORF1/2 molecule.

188. The method of embodiment 186, further comprising incubating the insect cell under conditions suitable for secretion of the Anellovirus ORF molecule.

189. The method of embodiment 186, further isolating the Anellovirus ORF molecule from the insect cell.

190. The method of embodiment 189, wherein the isolating step comprises lysing the insect cell.

191. The method of any of embodiments 186-190, wherein the Anellovirus ORF comprises an Anellovirus ORF1 molecule.

192. A method of making an Anellovirus ORF1 molecule, the method comprising:

(i) providing an insect cell comprising a nucleic acid construct encoding an Anellovirus ORF1 molecule, wherein:

(a) the Anellovirus ORF1 molecule has a molecular weight of at least 101 kDa, (b) the Anellovirus ORF1 molecule is a full-length Anellovirus ORF1 protein, (c) a plurality of the Anellovirus ORF1 molecules, when in the presence of an Anellovirus genetic element, enclose the Anellovirus genetic element, (d) the Anellovirus ORF1 molecule is not a TTV ORF1 protein, (e) the Anellovirus ORF1 molecule is a Betatorquevirus or Gammatorquevirus ORF1 molecule; or (f) the Anellovirus ORF1 molecule comprises an Anellovirus ORF1 Arginine-rich region and an Anellovirus C-terminal domain;

(ii) incubating the insect cell under conditions suitable for expression of the Anellovirus ORF1 molecule.

193. The method of embodiment 192, further comprising incubating the insect cell under conditions suitable for secretion of the Anellovirus ORF1 molecule.

194. The method of embodiment 192, further isolating the Anellovirus ORF1 molecule from the insect cell.

195. The method of embodiment 194, wherein the isolating step comprises lysing the insect cell.

196. The method of any of the preceding embodiments, wherein the incubation step produces an amount of the Anellovirus ORF1 molecule detectable by Western blot, e.g., as described herein.

197. A method of making an Anellovirus ORF molecule (e.g., an ORF1, ORF2, ORF2/2, ORF2/3, ORF1/1, and/or ORF1/2 molecule), the method comprising:

(i) providing an insect cell (e.g., an Sf9 cell) comprising a nucleic acid construct encoding the Anellovirus ORF molecule;

(ii) incubating the insect cell under conditions suitable for expression of a plurality of the Anellovirus ORF molecules; and (iii) optionally isolating, purifying, and/or enriching the plurality of Anellovirus ORF molecules from the insect cell or other components or constituents thereof;

thereby making the Anellovirus ORF molecule.

198. The method of embodiment 197, wherein the Anellovirus ORF molecule is fused to a marker (e.g., a His tag), e.g., at its N-terminal end or at its C-terminal end (e.g., as described in Table E1 and/or Example 9).

199. The method of embodiment 197 or 198, wherein the insect cell further comprises a nucleic acid construct encoding one or more additional Anellovirus ORF molecules (e.g., one or more of an ORF1, ORF2, ORF2/2, ORF2/3, ORF1/1, and/or ORF1/2 molecule), and wherein the method further comprises:

incubating the insect cell under conditions suitable for expression of a plurality of the one or more additional Anellovirus ORF molecules, e.g., prior to, concurrently with, or subsequent to step (ii); and optionally isolating, purifying, and/or enriching the plurality of the one or more additional Anellovirus ORF molecules from the insect cell or other components or constituents thereof, e.g., prior to, concurrently with, or subsequent to step (iii).

200. The method of embodiment 199, wherein the nucleic acid construct encoding the one or more additional Anellovirus ORF molecules is the same as the nucleic acid construct of (i).

201. The method of embodiment 200, wherein the nucleic acid construct of (i) comprises sequences encoding 2, 3, 4, 5, or all 6 of an Anellovirus ORF1, ORF2, ORF2/2, ORF2/3, ORF1/1, and/or ORF1/2 molecule.

202. The method of embodiment 200, wherein the nucleic acid construct of (i) encodes an Anellovirus ORF1, ORF2, ORF2/2, ORF2/3, ORF1/1, and ORF1/2 molecule.

203. The method of embodiment 200, wherein the nucleic acid construct of (i) comprises the full open reading frame region of an Anellovirus genome.

204. The method of embodiment 199, wherein the nucleic acid construct encoding the one or more additional Anellovirus ORF molecules is different from the nucleic acid construct of (i).

205. The method of any of embodiments 199-204, wherein the Anellovirus ORF molecules are from the same Anellovirus genome.

206. The method of any of embodiments 199-204, wherein the Anellovirus ORF molecules are from a plurality of Anellovirus genomes (e.g., wherein the ORF1 molecule is from one Anellovirus genome and the ORF2 molecule is from a different Anellovirus genome).

207. The method of any of embodiments 199-206, wherein one or more of the Anellovirus ORF molecules are from an Alphatorquevirus (e.g., as listed in Table E2).

208. The method of any of embodiments 199-207, wherein one or more of the Anellovirus ORF molecules are from a Betatorquevirus (e.g., as listed in Table E2).

209. The method of any of embodiments 199-208, wherein one or more of the Anellovirus ORF molecules are from a Gammatorquevirus (e.g., as listed in Table E2).

210. The method of any of embodiments 199-209, wherein the nucleic acid construct or constructs each comprises a promoter (e.g., a promoter controlling expression of one or more of the Anellovirus ORF molecules, e.g., a baculovirus polyhedron promoter).

211. The method of any of embodiments 199-210, further comprising incubating the insect cell under conditions suitable for secretion of the Anellovirus ORF molecules.

212. The method of any of embodiments 199-211, wherein the isolating step comprises lysing the insect cell.

213. The method of any of embodiments 199-212, wherein the incubation step produces an amount of the Anellovirus ORF molecule (e.g., ORF1 molecule) detectable by Western blot, e.g., as described herein.

214. The method of any of embodiments 199-213, wherein the incubation step produces at least 1, 2, 3, 4, 5, or 6 mg of the Anellovirus ORF1 molecule per 1 L of cell culture (e.g., Sf9 culture).

215. The method of any of the preceding embodiments, wherein the Anellovirus ORF molecules are isolated, purified, or enriched by isopycnic centrifugation.

216. The method of any of the preceding embodiments, wherein the Anellovirus ORF molecule is an Anellovirus ORF1 molecule, and wherein the method further comprises:

contacting, in vitro, the isolated, purified, or enriched Anellovirus ORF1 molecule with a genetic element under conditions suitable for enclosure of the genetic element by a proteinaceous exterior comprising the Anellovirus ORF1 molecule, e.g., as described herein.

Other features, objects, and advantages of the invention will be apparent from the description and drawings, and from the claims.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In addition, the materials, methods, and examples are illustrative only and not intended to be limiting.

BRIEF DESCRIPTION OF THE DRAWINGS

The following detailed description of the embodiments of the invention will be better understood when read in conjunction with the appended drawings. For the purpose of illustrating the invention, there are shown in the drawings embodiments that are presently exemplified. It should be understood, however, that the invention is not limited to the precise arrangement and instrumentalities of the embodiments shown in the drawings.

FIGS. 4A and 4B are a series of diagrams showing successful expression of Anellovirus ORF1 molecules in cells. (A) Anellovirus strains for which ORF1 expression was detected from Sf9 cells included Ring2, Ring3, Ring4, Ring5, Ring6, Ring9, and Ring10 (e.g., as described herein). (B) Virus-like particles (VLPs) were observed by electron microscopy after production of Anellovirus ORF1 proteins for Ring2 and Ring10, as well as for chicken anemia virus (CAV) VP1.

FIG. 16 shows that expression of Ring1 ORF2 is independent of the polyhedron promoter (arrow labeled pH) in Sf9 cells.

FIG. 32D depicts the structural arginine-rich region, JR, and structural C-terminal domains of Ring 10 aligned with corresponding ORF1 sequences from different anellovirus genera (indicated in parentheses). Basic residues of Ring 10 positioned to potentially contact the viral genome are indicated with asterisks.

FIG. 33A depicts the anellovirus particle structure as shown as a surface rendering. The particle is shown with 5 spikes forming a crown structure, numbered for clarity. The spike domains extend from the core on the 5-fold axis.

FIG. 33B depicts the exterior of the crown structure as shown from the side with five spike domains. The hydrophobic and hydrophilic conserved residues are shown.

FIG. 33C depicts the same spike domain from FIG. 33B rotated to view residues on the interior of the crown structure.

FIG. 33D depicts the spike domain of Ring 10 aligned with ORF1 sequences representative of different anellovirus genera (indicated in parentheses). Asterisks indicate the surface-exposed residues of the P1 domain and P2 domain. Below the alignment are >30% consensus residues, or Ø or γ indicating the residues are >70% hydrophobic or >60% hydrophilic, respectively.

FIG. 37A is a table showing averages of secondary structure fractions estimated by different packages of CDPro. α-helix dominates the secondary structure assignment from the CD spectrum. FIG. 37B shows an experimental spectrum of the C-terminal peptide overlaid with the calculated and averaged reference set spectra from three different packages (SELCON3, CDSSTR, and CONTINLL).

FIG. 38 depicts sequence alignment of 15 known anelloviruses within different genera indicated in parentheses. The conserved amino acids are shown in the first row underneath the sequence. The top row underneath the sequence alignment indicates the homology sequence if the conservation is larger than 30%. The bottom row shows either hydrophobic (o, within 70% similarity) or 60% positive charged (y, within 60% similarity) of amino acids, respectively. The alignment was done by Geneious-implemented Clustal Omega.

FIG. 39A depicts the sphere representation of Ring 10 spike (identical to FIG. 33C). FIGS. 39B and 39C are the spike representations for alpha-fold predicted JA20 and MN779270.1, respectively. P1 and P2 domains are demonstrated. FIG. 39D shows the sequence alignment between Ring 10, JA20, and MN779210.1.

DETAILED DESCRIPTION OF CERTAIN EMBODIMENTS

Definitions

Figure 1:
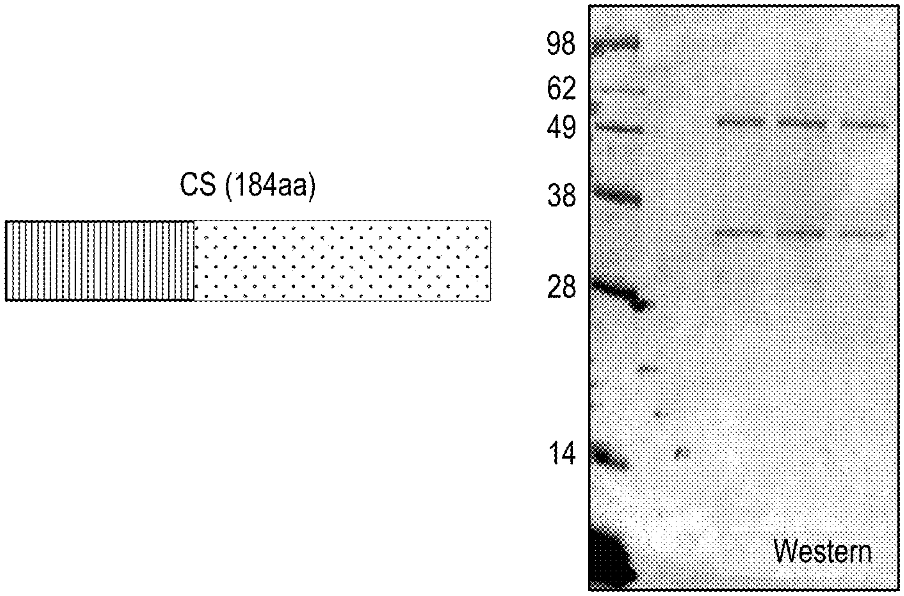
FIG. 1 is a series of diagrams showing production of exemplary malaria peptide conjugation constructs comprising the C-terminal region of a CS protein.

The present invention will be described with respect to particular embodiments and with reference to certain figures, but the invention is not limited thereto but only by the claims. Terms as set forth hereinafter are generally to be understood in their common sense unless indicated otherwise.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is to be understood to preferably also disclose a group which consists only of these embodiments.

Where an indefinite or definite article is used when referring to a singular noun, e.g. "a", "an" or "the", this includes a plural of that noun unless something else is specifically stated.

The wording "compound, composition, product, etc. for treating, modulating, etc." is to be understood to refer a compound, composition, product, etc. per se which is suitable for the indicated purposes of treating, modulating, etc. The wording "compound, composition, product, etc. for treating, modulating, etc." additionally discloses that, as an embodiment, such compound, composition, product, etc. is for use in treating, modulating, etc.

The wording "compound, composition, product, etc. for use in . . . ", "use of a compound, composition, product, etc in the manufacture of a medicament, pharmaceutical composition, veterinary composition, diagnostic composition, etc. for . . . ", or "compound, composition, product, etc. for use as a medicament . . . " indicates that such compounds, compositions, products, etc. are to be used in therapeutic methods which may be practiced on the human or animal body. They are considered as an equivalent disclosure of embodiments and claims pertaining to methods of treatment, etc. If an embodiment or a claim thus refers to "a compound for use in treating a human or animal being suspected to suffer from a disease", this is considered to be also a disclosure of a "use of a compound in the manufacture of a medicament for treating a human or animal being suspected to suffer from a disease" or a "method of treatment by administering a compound to a human or animal being suspected to suffer from a disease". The wording "compound, composition, product, etc. for treating, modulating, etc." is to be understood to refer a compound, composition, product, etc. per se which is suitable for the indicated purposes of treating, modulating, etc.

If hereinafter examples of a term, value, number, etc. are provided in parentheses, this is to be understood as an indication that the examples mentioned in the parentheses can constitute an embodiment. For example, if it is stated that "in embodiments, the nucleic acid molecule comprises a nucleic acid sequence having at least about 70%, 75%, 80%, 85%, 90%, 95%, 96%, 97%, 98%, 99%, or 100% sequence identity to the Anellovirus ORF1-encoding nucleotide sequence of Table 1 (e.g., nucleotides 571-2613 of the nucleic acid sequence of Table 1)", then some embodiments relate to nucleic acid molecules comprising a nucleic acid sequence having at least about 70%, 75%, 80%, 85%, 90%, 95%, 96%, 97%, 98%, 99%, or 100% sequence identity to nucleotides 571-2613 of the nucleic acid sequence of Table 1.

As used herein, the term "anellovector" refers to a vehicle comprising a genetic element, e.g., an episome, e.g., circular DNA, enclosed in a proteinaceous exterior. A "synthetic anellovector," as used herein, generally refers to an anellovector that is not naturally occurring, e.g., has a sequence that is different relative to a wild-type virus (e.g., a wild-type Anellovirus as described herein). In some embodiments, the proteinaceous exterior comprises an ORF1 molecule (e.g., an Anellovirus ORF1 protein), e.g., as described herein. In some embodiments, the proteinaceous exterior comprises a plurality of ORF1 molecules (e.g., an Anellovirus ORF1 protein), e.g., at least about 40, 45, 50, 55, 60, 65, or 70 ORF1 molecules. In some embodiments, the synthetic anellovector is engineered or recombinant, e.g., comprises a genetic element that comprises a difference or modification relative to a wild-type viral genome (e.g., a wild-type Anellovirus genome as described herein). In some embodiments, enclosed within a proteinaceous exterior encompasses 100% coverage by a proteinaceous exterior, as well as less than 100% coverage, e.g., 95%, 90%, 85%, 80%, 70%, 60%, 50% or less. For example, gaps or discontinuities (e.g., that render the proteinaceous exterior permeable to water, ions, peptides, or small molecules) may be present in the proteinaceous exterior, so long as the genetic element is retained in the proteinaceous exterior, e.g., prior to entry into a host cell. In some embodiments, the anellovector is purified, e.g., it is separated from its original source and/or substantially free (>50%, >60%, >70%, >80%, >90%) of other components.

An anellovector may, in some embodiments, comprise a nucleic acid vector that comprises sufficient nucleic acid sequence derived from or highly similar to (e.g., at least 85%, 90%, 95%, 96%, 97%, 98%, 99%, or 100% identical to) an Anellovirus genome sequence or a contiguous portion thereof to allow packaging into a proteinaceous exterior (e.g., a capsid), and further comprises a heterologous sequence. In some embodiments, the anellovector is a viral vector or a naked nucleic acid. In some embodiments, the anellovector comprises at least about 50, 60, 70, 71, 72, 73, 74, 75, 80, 90, 100, 150, 200, 300, 400, 500, 600, 700, 800, 900, 1000, 1100, 1200, 1300, 1400, 1500, 1600, 1700, 1800, 1900, 2000, 2500, 3000, or 3500 consecutive nucleotides of a native Anellovirus sequence or a sequence highly similar (e.g., at least 85%, 90%, 95%, 96%, 97%, 98%, 99%, or 100% identical) thereto. In some embodiments, the anellovector further comprises one or more of an Anellovirus ORF1, ORF2, or ORF3. In some embodiments, the heterologous sequence comprises a multiple cloning site, comprises a heterologous promoter, comprises a coding region for a therapeutic protein, or encodes a therapeutic nucleic acid. In some embodiments, the capsid is a wild-type Anellovirus capsid. In embodiments, an anellovector comprises a genetic element described herein, e.g., comprises a genetic element comprising a promoter, a sequence encoding a therapeutic effector, and a capsid binding sequence.

As used herein, the term "anelloVLP" refers to a vehicle (e.g., a virus-like particle) comprising a proteinaceous exterior and an effector (e.g., an exogenous effector). In some instances, an anelloVLP does not comprise a substantial amount of a nucleic acid. In some embodiments, the proteinaceous exterior comprises an ORF1 molecule (e.g., an Anellovirus ORF1 protein), e.g., as described herein. In some embodiments, the proteinaceous exterior comprises a plurality of ORF1 molecules (e.g., an Anellovirus ORF1 protein), e.g., at least about 40, 45, 50, 55, 60, 65, or 70 ORF1 molecules. In some embodiments, the effector is enclosed in the proteinaceous exterior. In some embodiments, the effector is on the surface of the proteinaceous exterior (e.g., comprised in a surface moiety as described herein). In some embodiments, the anelloVLP does not comprise a polynucleotide of greater than 50, 100, 150, 200, 300, 400, 500, 600, 700, 800, 900, 1000, 1100, 1200, 1300, 1400, 1500, 1600, 1700, 1800, 1900, or 2000 nucleotides in length. In some embodiments, the anelloVLP does not comprise a polynucleotide comprising an Anellovirus 5' UTR or Anellovirus origin of replication. In some embodiments, the anelloVLP does not comprise a polynucleotide comprising any contiguous nucleic acid sequences of at least 50, 100, 150, 200, 300, 400, 500, 600, 700, 800, 900, or 1000 nucleotides in length having least 75%, 80%, 85%, 90%, 95%, 96%, 97%, 98%, 99%, or 100% sequence identity to contiguous sequence in a wild-type Anellovirus genome (e.g., as described herein).

As used herein, the term "antibody molecule" refers to a protein, e.g., an immunoglobulin chain or fragment thereof, comprising at least one immunoglobulin variable domain sequence. The term "antibody molecule" encompasses full-length antibodies and antibody fragments (e.g., scFvs). In some embodiments, an antibody molecule is a multispecific antibody molecule, e.g., the antibody molecule comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In embodiments, the multispecific antibody molecule is a bispecific antibody molecule. A bispecific antibody molecule is generally characterized by a first immunoglobulin variable domain sequence which has binding specificity for a first epitope and a second immunoglobulin variable domain sequence that has binding specificity for a second epitope.

The term "disassembly," as used herein with respect to a particle, such as a virus-like particle (VLP), or a proteinaceous exterior, refers to disassociating one or more components of the particle (e.g., a capsid protein, e.g., an ORF1 molecule as described herein) from the remainder of the particle. In some instances, disassembly of a particle (e.g., a VLP) comprises separating enough of the ORF1 molecules from each other that they no longer form a proteinaceous exterior. In some instances, a ORF1 molecules separated from each other via disassembly of a particle form capsomers (e.g., decameric capsomers), e.g., as described herein. In some embodiments, disassembly reduces the particle to individual monomers. In some embodiments, after disassembly, multimers, e.g., decamers, monomers, and/or pentamers remain.

In some instances, disassembly comprises denaturation of protein complexes of the particle (e.g., breaking noncovalent bounds between ORF1 molecules in the proteinaceous exterior). In some instances, disassembly is driven by a denaturant as described herein The term "in vitro assembly," as used herein with respect to an anellovector or an anelloVLP, refers to the formation of a proteinaceous exterior comprising an ORF1 molecule, wherein the formation does not take place inside of a cell (e.g., takes place in a cell-free system such as a cell-free suspension, a lysate, or a supernatant). In some instances, in vitro assembly of an anellovector comprises enclosure, outside of a cell, of a genetic element (e.g., as described herein) within the proteinaceous exterior. In some instances, in vitro assembly of an anelloVLP comprises association, outside of a cell, of an effector (e.g., an exogenous effector, e.g., as described herein) with the proteinaceous exterior (e.g., enclosed within the proteinaceous exterior). In vitro assembly of a proteinaceous exterior may occur, in some instances, under conditions suitable for multimerization of a plurality of ORF1 molecules (e.g., nondenaturing conditions), e.g., to form a multimer of more than 10, 11, 12, 13, 14, 15, 16, 17, 18, 19, or 20 ORF1 molecules. In some instances, in vitro assembly results in the formation of a proteinaceous exterior comprising at least about 20, 30, 40, 50, or 60 ORF1 molecules, or about 20-30, 30-40, 40-50, 50-60, or 60-70 ORF1 molecules). In some instances, the proteinaceous exterior is formed from ORF1 molecules that were produced in a cell and then purified therefrom. In some instances, the in vitro assembly takes place in a solution free of cells or constituents thereof. In other instances, the in vitro assembly takes place in a solution comprising cell debris (e.g., from lysed cells). In some instances, the in vitro assembly takes place in a solution substantially free of cellular nucleic acid molecules (e.g., genomic DNA, mitochondrial DNA, mRNA, and/or noncoding RNA from a cell). As used herein, a nucleic acid "encoding" refers to a nucleic acid sequence encoding an amino acid sequence or a functional polynucleotide (e.g., a non-coding RNA, e.g., an siRNA or miRNA).

An "exogenous" agent (e.g., an effector, a nucleic acid (e.g., RNA), a gene, payload, protein) as used herein refers to an agent that is either not comprised by, or not encoded by, a corresponding wild-type virus, e.g., an Anellovirus as described herein. In some embodiments, the exogenous agent does not naturally exist, such as a protein or nucleic acid that has a sequence that is altered (e.g., by insertion, deletion, or substitution) relative to a naturally occurring protein or nucleic acid. In some embodiments, the exogenous agent does not naturally exist in the host cell. In some embodiments, the exogenous agent exists naturally in the host cell but is exogenous to the virus. In some embodiments, the exogenous agent exists naturally in the host cell, but is not present at a desired level or at a desired time.

A "heterologous" agent or element (e.g., an effector, a nucleic acid sequence, an amino acid sequence), as used herein with respect to another agent or element (e.g., an effector, a nucleic acid sequence, an amino acid sequence), refers to agents or elements that are not naturally found together, e.g., in a wild-type virus, e.g., an Anellovirus. In some embodiments, a heterologous nucleic acid sequence may be present in the same nucleic acid as a naturally occurring nucleic acid sequence (e.g., a sequence that is naturally occurring in the Anellovirus). In some embodiments, a heterologous agent or element is exogenous relative to an Anellovirus from which other (e.g., the remainder of) elements of the anellovector are based.

As used herein, the term "genetic element" refers to a nucleic acid sequence, generally in an anellovector. It is understood that the genetic element can be produced as naked DNA and optionally further assembled into a proteinaceous exterior. It is also understood that an anellovector can insert its genetic element into a cell, resulting in the genetic element being present in the cell and the proteinaceous exterior not necessarily entering the cell.

As used herein, the term "ORF1 molecule" refers to a polypeptide having an activity and/or a structural feature of an Anellovirus ORF1 protein (e.g., an Anellovirus ORF1 protein as described herein, e.g., as listed in any one of Tables A1-A25), or a functional fragment thereof. An ORF1 molecule may, in some instances, comprise one or more of (e.g., 1, 2, 3 or 4 of): a first region comprising at least 60% basic residues (e.g., at least 60% arginine residues), a second region comprising at least about six beta strands (e.g., at least 4, 5, 6, 7, 8, 9, 10, 11, or 12 beta strands), a third region comprising a structure or an activity of an Anellovirus N22 domain (e.g., as described herein, e.g., an N22 domain from an Anellovirus ORF1 protein as described herein), and/or a fourth region comprising a structure or an activity of an Anellovirus C-terminal domain (CTD) (e.g., as described herein, e.g., a CTD from an Anellovirus ORF1 protein as described herein). In some instances, the ORF1 molecule comprises, in N-terminal to C-terminal order, the first, second, third, and fourth regions. In some instances, an anellovector comprises an ORF1 molecule comprising, in N-terminal to C-terminal order, the first, second, third, and fourth regions. An ORF1 molecule may, in some instances, comprise a polypeptide encoded by an Anellovirus ORF1 nucleic acid (e.g., as listed in any one of Tables N1-N25). An ORF1 molecule may, in some instances, further comprise a heterologous sequence, e.g., a hypervariable region (HVR), e.g., an HVR from an Anellovirus ORF1 protein, e.g., as described herein. An "Anellovirus ORF1 protein," as used herein, refers to an ORF1 protein encoded by an Anellovirus genome (e.g., a wild-type Anellovirus genome, e.g., as described herein), e.g., an ORF1 protein having the amino acid sequence as listed in any one of Tables A1-A25, or as encoded by the ORF1 gene as listed in any one of Tables N1-N25.

The term "ORF1 domain," as used herein with respect to an ORF1 molecule, refers to the portion of the ORF1 molecule having the structure or function of an Anellovirus ORF1 protein. The ORF1 domain is generally capable of forming a multimer with other copies of the ORF1 domain (e.g., in other ORF1 molecules), or with other ORF1 molecules, e.g., to form a proteinaceous exterior (e.g., of an anellovector or anelloVLP as described herein). In some instances, the ORF1 molecule may comprise one or more additional domains other than the ORF1 domain (for example, a domain comprising or attached to a surface effector, e.g., as described herein). In some instances, the amino acid sequence of an ORF1 domain comprises an insertion (e.g., an insertion encoding a surface moiety or a domain capable of binding to a surface moiety), e.g., between the N-terminal end and C-terminal end of the ORF1 domain. In certain instances, the insertion does not substantially disrupt the structure and/or function of the ORF1 domain, e.g., such that the ORF1 domain remains capable of forming a multimer with other ORF1 domains or ORF1 molecules. The position within the ORF1 domain sequence into which the insertion is made is referred to herein as the "insertion point." An insertion can be made into an ORF1 domain by any genetic or polypeptide engineering method known in the art. In some embodiments, an ORF1 molecule consists of an ORF1 domain. In other embodiments, an ORF1 molecule comprises an ORF1 domain and a heterologous domain (e.g., a surface moiety as described herein). In some embodiments, an ORF1 domain is connected to a surface moiety by a polypeptide linker region.

As used herein, the term "ORF2 molecule" refers to a polypeptide having an activity and/or a structural feature of an Anellovirus ORF2 protein (e.g., an Anellovirus ORF2 protein as described herein, e.g., as listed in any one of Tables A1-A25), or a functional fragment thereof. An "Anellovirus ORF2 protein," as used herein, refers to an ORF2 protein encoded by an Anellovirus genome (e.g., a wild-type Anellovirus genome, e.g., as described herein), e.g., an ORF2 protein having the amino acid sequence as listed in any one of Tables A1-A25, or as encoded by the ORF2 gene as listed in any one of Tables N1-N25.

As used herein, the term "particle" refers to a vehicle having a diameter of less than 100 nm (e.g., about 20-25, 25-30, 30-35, or 35-40 nm) comprising a proteinaceous exterior. In some instances, the particle comprises a plurality of ORF1 molecules. The proteinaceous exterior of the particle generally forms an enclosure capable of limiting or preventing movement of certain molecules between the inside and outside of the proteinaceous exterior. In some embodiments, gaps or discontinuities (e.g., that render the proteinaceous exterior permeable to water, ions, peptides, or small molecules) may be present in the proteinaceous exterior. In certain embodiments, the gaps or discontinuities are of a sufficiently small size (e.g., diameter) that the proteinaceous exterior limits or prevents one or more large macromolecules (e.g., peptides, polypeptides, polynucleotides, lipids, or polysaccharides) from passing through the proteinaceous exterior.

As used herein, the term "proteinaceous exterior" refers to an exterior component that is predominantly (e.g., >50%, >60%, >70%, >80%, >90%) protein.

As used herein, the term "regulatory nucleic acid" refers to a nucleic acid sequence that modifies expression, e.g., transcription and/or translation, of a DNA sequence that encodes an expression product. In embodiments, the expression product comprises RNA or protein.

As used herein, the term "regulatory sequence" refers to a nucleic acid sequence that modifies transcription of a target gene product. In some embodiments, the regulatory sequence is a promoter or an enhancer.

As used herein, the term "replication protein" refers to a protein, e.g., a viral protein, that is utilized during infection, viral genome replication/expression, viral protein synthesis, and/or assembly of the viral components.

Figure 7A:
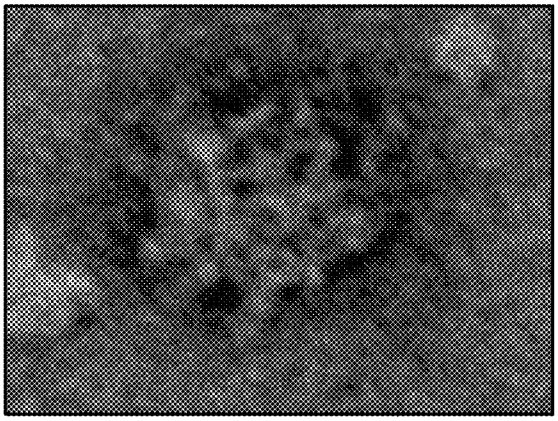
FIGS. 7A-7B are a series of electron micrographs showing exemplary symmetrical (A) and asymmetrical (B) particle morphologies.
Figure 7B:
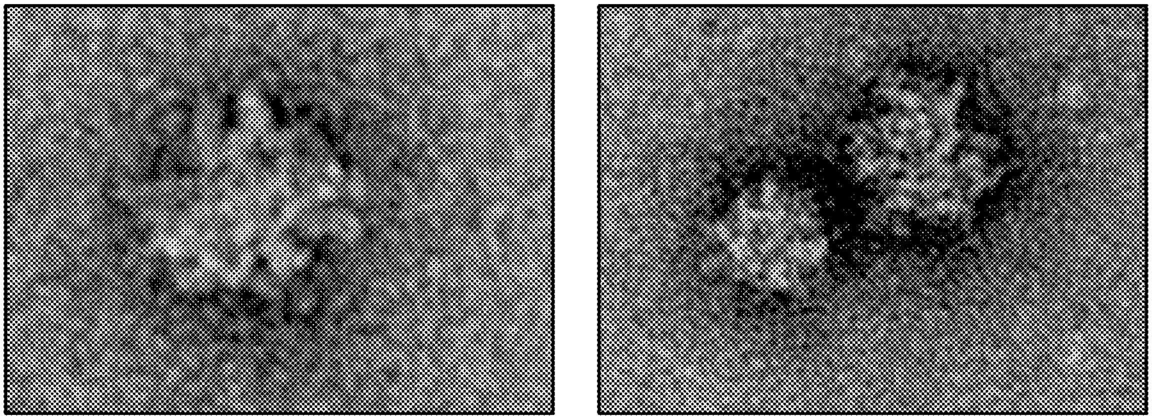

When viewed by electron microscopy, anellovector or anelloVLP particles typically adopt one of two conformations: a symmetrical morphology (e.g., as exemplified in FIG. 7A) and an asymmetrical, or less symmetrical, morphology (e.g., as exemplified in FIG. 7B). Accordingly, the term "symmetrical morphology," as used herein with respect to anellovector or anelloVLP particle morphology, refers to a particle having a shape that is predominantly symmetrical. The particle having symmetrical morphology may, in some instances, be approximately round. The particle having symmetrical morphology may, in some instances, not be perfectly circular or spherical (e.g., may be ovoid). In some instances, the particle having symmetrical morphology may include one or more deviations from a circular or spherical shape (e.g., one or more protrusions or indentations from its surface).

As used herein, a "substantially non-pathogenic" organism, particle, or component, refers to an organism, particle (e.g., a virus or an anellovector, e.g., as described herein), or component thereof that does not cause or induce a detectable disease or pathogenic condition, e.g., in a host organism, e.g., a mammal, e.g., a human. In some embodiments, administration of an anellovector to a subject can result in minor reactions or side effects that are acceptable as part of standard of care.

As used herein, the term "non-pathogenic" refers to an organism or component thereof that does not cause or induce a detectable disease or pathogenic condition, e.g., in a host organism, e.g., a mammal, e.g., a human.

As used herein, a "substantially non-integrating" genetic element refers to a genetic element, e.g., a genetic element in a virus or anellovector, e.g., as described herein, wherein less than about 0.01%, 0.05%, 0.1%, 0.5%, or 1% of the genetic element that enter into a host cell (e.g., a eukaryotic cell) or organism (e.g., a mammal, e.g., a human) integrate into the genome. In some embodiments the genetic element does not detectably integrate into the genome of, e.g., a host cell. In some embodiments, integration of the genetic element into the genome can be detected using techniques as described herein, e.g., nucleic acid sequencing, PCR detection and/or nucleic acid hybridization.

As used herein, a "substantially non-immunogenic" organism, particle, or component, refers to an organism, particle (e.g., a virus or anellovector, e.g., as described herein), or component thereof, that does not cause or induce an undesired or untargeted immune response, e.g., in a host tissue or organism (e.g., a mammal, e.g., a human). In some embodiments, the substantially non-immunogenic organism, particle, or component does not produce a detectable immune response. In some embodiments, the substantially non-immunogenic anellovector does not produce a detectable immune response against a protein comprising an amino acid sequence or encoded by a nucleic acid sequence shown in any one of Tables N1-N25. In some embodiments, an immune response (e.g., an undesired or untargeted immune response) is detected by assaying antibody presence or level (e.g., presence or level of an anti-anellovector antibody, e.g., presence or level of an antibody against an anellovector as described herein) in a subject, e.g., according to the anti-TTV antibody detection method described in Tsuda et al. (1999; *J Virol. Methods* 77: 199-206; incorporated herein by reference) and/or the method for determining anti-TTV IgG levels described in Kakkola et al. (2008; *Virology* 382: 182-189; incorporated herein by reference). Antibodies against an Anellovirus or an anellovector based thereon can also be detected by methods in the art for detecting anti-viral antibodies, e.g., methods of detecting anti-AAV antibodies, e.g., as described in Calcedo et al. (2013; Front. Immunol. 4(341): 1-7; incorporated herein by reference).

A "subsequence" as used herein refers to a nucleic acid sequence or an amino acid sequence that is comprised in a larger nucleic acid sequence or amino acid sequence, respectively. In some instances, a subsequence may comprise a domain or functional fragment of the larger sequence. In some instances, the subsequence may comprise a fragment of the larger sequence capable of forming secondary and/or tertiary structures when isolated from the larger sequence similar to the secondary and/or tertiary structures formed by the subsequence when present with the remainder of the larger sequence. In some instances, a subsequence can be replaced by another sequence (e.g., a subseqence comprising an exogenous sequence or a sequence heterologous to the remainder of the larger sequence, e.g., a corresponding subsequence from a different Anellovirus).

As used herein, the term "surface moiety" refers to a moiety for which at least a portion is exposed on the exterior surface of a particle (e.g., exposed to the solution surrounding the particle). The surface moiety is generally attached, directly or indirectly, to a component of the proteinaceous exterior of the particle (e.g., an ORF1 molecule). In some instances, the surface moiety is covalently attached to the component of the proteinaceous exterior of the particle (e.g., the ORF1 molecule). In some instances, the surface moiety is noncovalently attached to the component of the proteinaceous exterior of the particle (e.g., the ORF1 molecule). In some instances, the surface moiety is bound to a binding moiety that is in turn attached (e.g., covalently or noncovalently) to the component of the proteinaceous exterior of the particle (e.g., the ORF1 molecule). In some instances, the surface moiety is comprised in an ORF1 molecule (e.g., is a heterologous domain of an ORF1 molecule). In some instances, a surface moiety is exogenous relative to an Anellovirus (e.g., the Anellovirus from which the ORF1 molecule was derived and/or an Anellovirus for which the ORF1 protein has at least 50%, 60%, 70%, 75%, 80%, 85%, 90%, 95%, 96%, 97%, 98%, 99%, or 100% sequence identity to the ORF1 molecule). In some instances, a surface moiety is exogenous relative a target cell (e.g., a mammalian cell, e.g., a human cell) to be infected by the particle.

As used herein, "treatment", "treating" and cognates thereof refer to the medical management of a subject with the intent to improve, ameliorate, stabilize, prevent or cure a disease, pathological condition, or disorder. This term includes active treatment (treatment directed to improve the disease, pathological condition, or disorder), causal treatment (treatment directed to the cause of the associated disease, pathological condition, or disorder), palliative treatment (treatment designed for the relief of symptoms), preventative treatment (treatment directed to preventing, minimizing or partially or completely inhibiting the development of the associated disease, pathological condition, or disorder); and supportive treatment (treatment employed to supplement another therapy).

As used herein, the term "virome" refers to viruses in a particular environment, e.g., a part of a body, e.g., in an organism, e.g. in a cell, e.g. in a tissue.

This invention relates generally to anellovectors, e.g., synthetic anellovectors, and uses thereof. The present disclosure provides anellovectors, compositions comprising anellovectors, and methods of making or using anellovectors. Anellovectors are generally useful as delivery vehicles, e.g., for delivering a therapeutic agent to a eukaryotic cell. Generally, an anellovector will include a genetic element comprising a nucleic acid sequence (e.g., encoding an effector, e.g., an exogenous effector or an endogenous effector) enclosed within a proteinaceous exterior. An anellovector may include one or more deletions of sequences (e.g., regions or domains as described herein) relative to an Anellovirus sequence (e.g., as described herein). Anellovectors can be used as a substantially non-immunogenic vehicle for delivering the genetic element, or an effector encoded therein (e.g., a polypeptide or nucleic acid effector, e.g., as described herein), into eukaryotic cells, e.g., to treat a disease or disorder in a subject comprising the cells.

TABLE OF CONTENTS

I. Anellovectors and AnelloVLPs
A. Anelloviruses
B. ORF1 molecules
C. ORF2 molecules
D. Genetic elements
E. Protein binding sequences
F. 5' UTR Regions
G. GC-rich regions
H. Effectors
I. Proteinaceous exterior
J. Surface moieties
i. Click chemistry
(a) Exemplary click chemistries
(b) Mutations of surface lysines
(c) Mutations of surface cysteines
ii. Genetic grafting
iii. X-fold symmetry
II. Compositions and Methods for Making Anellovectors and AnelloVLPs
A. Components and Assembly of Anellovectors and AnelloVLPs
i. ORF1 molecules for assembly of anellovectors and anelloVLPs
ii. ORF2 molecules for assembly of anellovectors and anelloVLPs
iii. Production of protein components
(a) Baculovirus expression systems
(b) Insect cell systems
(c) Mammalian cell systems
B. Genetic Element Constructs
i. Plasmids
ii. Circular nucleic acid constructs
iii. In vitro circularization
iv. Tandem constructs
v. Cis/trans constructs
vi. Expression cassettes
vii. Design and production of a genetic element construct
C. Effectors
D. Host Cells
i. Introduction of genetic elements into host cells
ii. Methods for providing protein(s) in cis or trans
iii. Exemplary cell types
E. Culture Conditions
F. Harvest
G. In vitro assembly methods for anellovectors
H. In vitro assembly for anelloVLPs
I. Enrichment and Purification
III. Vectors
IV. Compositions
V. Host cells -continued

TABLE OF CONTENTS

VI. Methods of use
VII. Methods of production
VIII. Administration/Delivery

I. Anellovectors and AnelloVLPs

In some aspects, the invention described herein comprises compositions and methods of using and making an anellovector, anellovector preparations, anelloVLPs, anelloVLP preparations, and therapeutic compositions.

Anellovectors

In some embodiments, the anellovector has a sequence, structure, and/or function that is based on an Anellovirus (e.g., an Anellovirus as described herein, e.g., an Anellovirus comprising a nucleic acid or polypeptide comprising a sequence as shown in any one of Tables A1-A25 or N1-N25), or fragments or portions thereof, or other substantially non-pathogenic virus, e.g., a symbiotic virus, commensal virus, native virus. In some embodiments, an Anellovirus-based anellovector comprises at least one element exogenous to that Anellovirus, e.g., an exogenous effector or a nucleic acid sequence encoding an exogenous effector disposed within a genetic element of the anellovector. In some embodiments, an Anellovirus-based anellovector comprises at least one element heterologous to another element from that Anellovirus, e.g., an effector-encoding nucleic acid sequence that is heterologous to another linked nucleic acid sequence, such as a promoter element. In some embodiments, an anellovector comprises a genetic element (e.g., circular DNA, e.g., single stranded DNA), which comprise at least one element that is heterologous relative to the remainder of the genetic element and/or the proteinaceous exterior (e.g., an exogenous element encoding an effector, e.g., as described herein). An anellovector may be a delivery vehicle (e.g., a substantially non-pathogenic delivery vehicle) for a payload into a host, e.g., a human. In some embodiments, the anellovector is capable of replicating in a eukaryotic cell, e.g., a mammalian cell, e.g., a human cell. In some embodiments, the anellovector is substantially non-pathogenic and/or substantially non-integrating in the mammalian (e.g., human) cell. In some embodiments, the anellovector is substantially non-immunogenic in a mammal, e.g., a human. In some embodiments, the anellovector is replication-deficient. In some embodiments, the anellovector is replication-competent.

In some embodiments the anellovector comprises a curon, or a component thereof (e.g., a genetic element, e.g., comprising a sequence encoding an effector, and/or a proteinaceous exterior), e.g., as described in PCT Application No. PCT/US2018/037379, which is incorporated herein by reference in its entirety.

In an aspect, the invention includes an anellovector comprising (i) a genetic element comprising a promoter element, a sequence encoding an effector, (e.g., an endogenous effector or an exogenous effector, e.g., a payload), and a protein binding sequence (e.g., an exterior protein binding sequence, e.g., a packaging signal), wherein the genetic element is a single-stranded DNA, and has one or both of the following properties: is circular and/or integrates into the genome of a eukaryotic cell at a frequency of less than about 0.001%, 0.005%, 0.01%, 0.05%, 0.1%, 0.5%, 1%, 1.5%, or 2% of the genetic element that enters the cell; and (ii) a proteinaceous exterior; wherein the genetic element is enclosed within the proteinaceous exterior; and wherein the anellovector is capable of delivering the genetic element into a eukaryotic cell.

In some embodiments of the anellovector described herein, the genetic element integrates at a frequency of less than about 0.001%, 0.005%, 0.01%, 0.05%, 0.1%, 0.5%, 1%, 1.5%, or 2% of the genetic element that enters a cell. In some embodiments, less than about 0.01%, 0.05%, 0.1%, 0.5%, 1%, 2%, 3%, 4%, or 5% of the genetic elements from a plurality of the anellovectors administered to a subject will integrate into the genome of one or more host cells in the subject. In some embodiments, the genetic elements of a population of anellovectors, e.g., as described herein, integrate into the genome of a host cell at a frequency less than that of a comparable population of AAV viruses, e.g., at about a 50%, 60%, 70%, 75%, 80%, 85%, 90%, 95%, 100%, or more lower frequency than the comparable population of AAV viruses.

In an aspect, the invention includes an anellovector comprising: (i) a genetic element comprising a promoter element and a sequence encoding an effector (e.g., an endogenous effector or an exogenous effector, e.g., a payload), and a protein binding sequence (e.g., an exterior protein binding sequence), wherein the genetic element has at least 75% (e.g., at least 75, 76, 77, 78, 79, 80, 90, 91, 92, 93, 94, 95, 96, 97, 98, 99, or 100%) sequence identity to a wild-type Anellovirus sequence (e.g., a wild-type Torque Teno virus (TTV), Torque Teno mini virus (TTMV), or TTMDV sequence, e.g., a wild-type Anellovirus sequence as listed in any one of Tables N1-N25); and (ii) a proteinaceous exterior; wherein the genetic element is enclosed within the proteinaceous exterior; and wherein the anellovector is capable of delivering the genetic element into a eukaryotic cell.

In one aspect, the invention includes an anellovector comprising:

a) a genetic element comprising (i) a sequence encoding an exterior protein (e.g., a non-pathogenic exterior protein), (ii) an exterior protein binding sequence that binds the genetic element to the non-pathogenic exterior protein, and (iii) a sequence encoding an effector (e.g., an endogenous or exogenous effector); and
b) a proteinaceous exterior that is associated with, e.g., envelops or encloses, the genetic element.

In some embodiments, the anellovector includes sequences or expression products from (or having >70%, 75%, 80%, 85%, 90%, 95%, 97%, 98%, 99%, 100% homology to) a non-enveloped, circular, single-stranded DNA virus. Animal circular single-stranded DNA viruses generally refer to a subgroup of single strand DNA (ssDNA) viruses, which infect eukaryotic non-plant hosts, and have a circular genome. Thus, animal circular ssDNA viruses are distinguishable from ssDNA viruses that infect prokaryotes (i.e. Microviridae and Inoviridae) and from ssDNA viruses that infect plants (i.e. Geminiviridae and Nanoviridae). They are also distinguishable from linear ssDNA viruses that infect non-plant eukaryotes (i.e. Parvoviridiae).

In some embodiments, the anellovector modulates a host cellular function, e.g., transiently or long term. In certain embodiments, the cellular function is stably altered, such as a modulation that persists for at least about 1 hr to about 30 days, or at least about 2 hrs, 6 hrs, 12 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or longer or any time therebetween. In certain embodiments, the cellular function is transiently altered, e.g., such as a modulation that persists for no more than about 30 mins to about 7 days, or no more than about 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 24 hrs, 36 hrs, 48 hrs, 60 hrs, 72 hrs, 4 days, 5 days, 6 days, 7 days, or any time therebetween.

In some embodiments, the genetic element comprises a promoter element. In some embodiments, the promoter element is selected from an RNA polymerase II-dependent promoter, an RNA polymerase III-dependent promoter, a PGK promoter, a CMV promoter, an EF-1α promoter, an SV40 promoter, a CAGG promoter, or a UBC promoter, TTV viral promoters, Tissue specific, U6 (pollIII), minimal CMV promoter with upstream DNA binding sites for activator proteins (TetR-VP16, Gal4-VP16, dCas9-VP16, etc). In some embodiments, the promoter element comprises a TATA box. In some embodiments, the promoter element is endogenous to a wild-type Anellovirus, e.g., as described herein.

In some embodiments, the genetic element comprises one or more of the following characteristics: single-stranded, circular, negative strand, and/or DNA. In some embodiments, the genetic element comprises an episome. In some embodiments, the portions of the genetic element excluding the effector have a combined size of about 2.5-5 kb (e.g., about 2.8-4kb, about 2.8-3.2kb, about 3.6-3.9kb, or about 2.8-2.9kb), less than about 5kb (e.g., less than about 2.9kb, 3.2 kb, 3.6kb, 3.9kb, or 4kb), or at least 100 nucleotides (e.g., at least 1kb).

The anellovectors, compositions comprising anellovectors, methods using such anellovectors, etc., as described herein are, in some instances, based in part on the examples which illustrate how different effectors, for example miRNAs (e.g. against IFN or miR-625), shRNA, etc and protein binding sequences, for example DNA sequences that bind to capsid protein such as Q99153, are combined with proteinaceious exteriors, for example a capsid disclosed in Arch Virol (2007) 152: 1961-1975, to produce anellovectors which can then be used to deliver an effector to cells (e.g., animal cells, e.g., human cells or non-human animal cells such as pig or mouse cells). In embodiments, the effector can silence expression of a factor such as an interferon. The examples further describe how anellovectors can be made by inserting effectors into sequences derived, e.g., from an Anellovirus. It is on the basis of these examples that the description hereinafter contemplates various variations of the specific findings and combinations considered in the examples. For example, the skilled person will understand from the examples that the specific miRNAs are used just as an example of an effector and that other effectors may be, e.g., other regulatory nucleic acids or therapeutic peptides. Similarly, the specific capsids used in the examples may be replaced by substantially non-pathogenic proteins described hereinafter. The specific Anellovirus sequences described in the examples may also be replaced by the Anellovirus sequences described hereinafter. These considerations similarly apply to protein binding sequences, regulatory sequences such as promoters, and the like. Independent thereof, the person skilled in the art will in particular consider such embodiments which are closely related to the examples.

In some embodiments, an anellovector, or the genetic element comprised in the anellovector, is introduced into a cell (e.g., a human cell). In some embodiments, the effector (e.g., an RNA, e.g., an miRNA), e.g., encoded by the genetic element of an anellovector, is expressed in a cell (e.g., a human cell), e.g., once the anellovector or the genetic element has been introduced into the cell. In some embodiments, introduction of the anellovector, or genetic element comprised therein, into a cell modulates (e.g., increases or decreases) the level of a target molecule (e.g., a target nucleic acid, e.g., RNA, or a target polypeptide) in the cell, e.g., by altering the expression level of the target molecule by the cell. In some embodiments, introduction of the anellovector, or genetic element comprised therein, decreases level of interferon produced by the cell. In some embodiments, introduction of the anellovector, or genetic element comprised therein, into a cell modulates (e.g., increases or decreases) a function of the cell. In some embodiments, introduction of the anellovector, or genetic element comprised therein, into a cell modulates (e.g., increases or decreases) the viability of the cell. In some embodiments, introduction of the anellovector, or genetic element comprised therein, into a cell decreases viability of a cell (e.g., a cancer cell).

In some embodiments, an anellovector (e.g., a synthetic anellovector) described herein induces an antibody prevalence of less than 70% (e.g., less than about 60%, 50%, 40%, 30%, 20%, or 10% antibody prevalence). In some embodiments, antibody prevalence is determined according to methods known in the art. In some embodiments, antibody prevalence is determined by detecting antibodies against an Anellovirus (e.g., as described herein), or an anellovector based thereon, in a biological sample, e.g., according to the anti-TTV antibody detection method described in Tsuda et al. (1999; J Virol. Methods 77: 199-206; incorporated herein by reference) and/or the method for determining anti-TTV IgG seroprevalence described in Kakkola et al. (2008; *Virology* 382: 182-189; incorporated herein by reference). Antibodies against an Anellovirus or an anellovector based thereon can also be detected by methods in the art for detecting anti-viral antibodies, e.g., methods of detecting anti-AAV antibodies, e.g., as described in Calcedo et al. (2013; Front. Immunol. 4(341): 1-7; incorporated herein by reference).

In some embodiments, a replication deficient, replication defective, or replication incompetent genetic element does not encode all of the necessary machinery or components required for replication of the genetic element. In some embodiments, a replication defective genetic element does not encode a replication factor. In some embodiments, a replication defective genetic element does not encode one or more ORFs (e.g., ORF1, ORF1/1, ORF1/2, ORF2, ORF2/2, ORF2/3, and/or ORF2t/3, e.g., as described herein). In some embodiments, the machinery or components not encoded by the genetic element may be provided in trans (e.g., using a helper, e.g., a helper virus or helper plasmid, or encoded in a nucleic acid comprised by the host cell, e.g., integrated into the genome of the host cell), e.g., such that the genetic element can undergo replication in the presence of the machinery or components provided in trans.

In some embodiments, a packaging deficient, packaging defective, or packaging incompetent genetic element cannot be packaged into a proteinaceous exterior (e.g., wherein the proteinaceous exterior comprises a capsid or a portion thereof, e.g., comprising a polypeptide encoded by an ORF1 nucleic acid, e.g., as described herein). In some embodiments, a packaging deficient genetic element is packaged into a proteinaceous exterior at an efficiency less than 10% (e.g., less than 10%, 9%, 8%, 7%, 6%, 5%, 4%, 3%, 2%, 1%, 0.5%, 0.1%, 0.01%, or 0.001%) compared to a wild-type Anellovirus (e.g., as described herein). In some embodiments, the packaging defective genetic element cannot be packaged into a proteinaceous exterior even in the presence of factors (e.g., ORF1, ORF1/1, ORF1/2, ORF2, ORF2/2, ORF2/3, or ORF2t/3) that would permit packaging of the genetic element of a wild-type Anellovirus (e.g., as described herein). In some embodiments, a packaging deficient genetic element is packaged into a proteinaceous exterior at an efficiency less than 10% (e.g., less than 10%, 9%, 8%, 7%, 6%, 5%, 4%, 3%, 2%, 1%, 0.5%, 0.1%, 0.01%, or 0.001%) compared to a wild-type Anellovirus (e.g., as described herein), even in the presence of factors (e.g., ORF1, ORF1/1, ORF1/2, ORF2, ORF2/2, ORF2/3, or ORF2t/3) that would permit packaging of the genetic element of a wild-type Anellovirus (e.g., as described herein).

In some embodiments, a packaging competent genetic element can be packaged into a proteinaceous exterior (e.g., wherein the proteinaceous exterior comprises a capsid or a portion thereof, e.g., comprising a polypeptide encoded by an ORF1 nucleic acid, e.g., as described herein). In some embodiments, a packaging competent genetic element is packaged into a proteinaceous exterior at an efficiency of at least 20% (e.g., at least 20%, 30%, 40%, 50%, 60%, 70%, 80%, 85%, 90%, 95%, 96%, 97%, 98%, 99%, 100%, or higher) compared to a wild-type Anellovirus (e.g., as described herein). In some embodiments, the packaging competent genetic element can be packaged into a proteinaceous exterior in the presence of factors (e.g., ORF1, ORF1/1, ORF1/2, ORF2, ORF2/2, ORF2/3, or ORF2t/3) that would permit packaging of the genetic element of a wild-type Anellovirus (e.g., as described herein). In some embodiments, a packaging competent genetic element is packaged into a proteinaceous exterior at an efficiency of at least 20% (e.g., at least 20%, 30%, 40%, 50%, 60%, 70%, 80%, 85%, 90%, 95%, 96%, 97%, 98%, 99%, 100%, or higher) compared to a wild-type Anellovirus (e.g., as described herein) in the presence of factors (e.g., ORF1, ORF1/1, ORF1/2, ORF2, ORF2/2, ORF2/3, or ORF2t/3) that would permit packaging of the genetic element of a wild-type Anellovirus (e.g., as described herein).

AnelloVLPs

In some embodiments, the anelloVLP has a sequence, structure, and/or function that is based on an Anellovirus (e.g., an Anellovirus as described herein, e.g., an Anellovirus comprising a nucleic acid or polypeptide comprising a sequence as shown in any one of Tables A1-A25), or fragments or portions thereof, or other substantially non-pathogenic virus, e.g., a symbiotic virus, commensal virus, native virus. In some embodiments, an Anellovirus-based anelloVLP comprises at least one element exogenous to that Anellovirus, e.g., an exogenous effector or a nucleic acid sequence encoding an exogenous effector. In some embodiments, the anelloVLP comprises a surface moiety comprising the exogenous effector. In some embodiments, an Anellovirus-based anelloVLP comprises at least one element heterologous to another element from that Anellovirus, e.g., an effector-encoding nucleic acid sequence that is heterologous to another linked nucleic acid sequence, such as a promoter element. An anelloVLP may be a delivery vehicle (e.g., a substantially non-pathogenic delivery vehicle) for a payload into a host, e.g., a human. In some embodiments, the anelloVLP is not capable of replicating in a eukaryotic cell, e.g., a mammalian cell, e.g., a human cell. In some embodiments, the anelloVLP is substantially non-pathogenic and/or substantially non-integrating in the mammalian (e.g., human) cell. In some embodiments, the anelloVLP is substantially non-immunogenic in a mammal, e.g., a human.

In an aspect, the invention includes an anelloVLP comprising a proteinaceous exterior and an effector (e.g., an exogenous effector); wherein the anelloVLP is capable of delivering the exogenous effector into a eukaryotic cell. In some embodiments, the exogenous effector is enclosed within the proteinaceous exterior. In some embodiments, the exogenous effector is comprised in a surface moiety on the surface of the anelloVLP (e.g., as described herein). In some embodiments, the proteinaceous exterior comprises one or more ORF1 molecules (e.g., an Anellovirus ORF1 protein, e.g., as described herein, or a polypeptide having at least 50%, 60%, 70%, 75%, 80%, 85%, 90%, 95%, 96%, 97%, 98%, or 99% sequence identity thereto).

In some embodiments, the anelloVLP includes sequences or expression products from (or having >70%, 75%, 80%, 85%, 90%, 95%, 97%, 98%, 99%, 100% homology to) a non-enveloped, circular, single-stranded DNA virus. Animal circular single-stranded DNA viruses generally refer to a subgroup of single strand DNA (ssDNA) viruses, which infect eukaryotic non-plant hosts, and have a circular genome. Thus, animal circular ssDNA viruses are distinguishable from ssDNA viruses that infect prokaryotes (i.e. Microviridae and Inoviridae) and from ssDNA viruses that infect plants (i.e. Geminiviridae and Nanoviridae). They are also distinguishable from linear ssDNA viruses that infect non-plant eukaryotes (i.e. Parvoviridiae).

In some embodiments, the anelloVLP modulates a host cellular function, e.g., transiently or long term. In certain embodiments, the cellular function is stably altered, such as a modulation that persists for at least about 1 hr to about 30 days, or at least about 2 hrs, 6 hrs, 12 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or longer or any time therebetween. In certain embodiments, the cellular function is transiently altered, e.g., such as a modulation that persists for no more than about 30 mins to about 7 days, or no more than about 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 24 hrs, 36 hrs, 48 hrs, 60 hrs, 72 hrs, 4 days, 5 days, 6 days, 7 days, or any time therebetween.

The anelloVLPs, compositions comprising anelloVLPs, methods using such anelloVLPs, etc., as described herein are, in some instances, based in part on the examples which illustrate how different effectors, for example miRNAs (e.g. against IFN or miR-625), shRNA, etc and protein binding sequences, for example DNA sequences that bind to capsid protein such as Q99153, are combined with proteinaceious exteriors, for example a capsid disclosed in Arch Virol (2007) 152: 1961-1975, to produce anelloVLPs which can then be used to deliver an effector to cells (e.g., animal cells, e.g., human cells or non-human animal cells such as pig or mouse cells). In embodiments, the effector can silence expression of a factor such as an interferon. The examples further describe how anelloVLPs can be made by inserting effectors into sequences derived, e.g., from an Anellovirus. It is on the basis of these examples that the description hereinafter contemplates various variations of the specific findings and combinations considered in the examples. For example, the skilled person will understand from the examples that the specific miRNAs are used just as an example of an effector and that other effectors may be, e.g., other regulatory nucleic acids or therapeutic peptides. Similarly, the specific capsids used in the examples may be replaced by substantially non-pathogenic proteins described hereinafter. The specific Anellovirus sequences described in the examples may also be replaced by the Anellovirus sequences described hereinafter. These considerations similarly apply to protein binding sequences, regulatory sequences such as promoters, and the like. Independent thereof, the person skilled in the art will in particular consider such embodiments which are closely related to the examples.

In some embodiments, an anelloVLP is introduced into a cell (e.g., a human cell). In some embodiments, the exogenous effector is delivered to the cell. In some embodiments, delivery of the exogenous effector to a cell modulates (e.g., increases or decreases) the level of a target molecule (e.g., a target nucleic acid, e.g., RNA, or a target polypeptide) in the cell, e.g., by altering the expression level of the target molecule by the cell. In some embodiments, delivery of the exogenous effector to a cell modulates (e.g., increases or decreases) a function of the cell. In some embodiments, delivery of the exogenous effector to a cell modulates (e.g., increases or decreases) the viability of the cell. In some embodiments, delivery of the exogenous effector to a cell decreases viability of a cell (e.g., a cancer cell).

In some embodiments, an anelloVLP (e.g., a synthetic anelloVLP) described herein induces an antibody prevalence of less than 70% (e.g., less than about 60%, 50%, 40%, 30%, 20%, or 10% antibody prevalence). In some embodiments, antibody prevalence is determined according to methods known in the art. In some embodiments, antibody prevalence is determined by detecting antibodies against an Anellovirus (e.g., as described herein), or an anelloVLP based thereon, in a biological sample, e.g., according to the anti-TTV antibody detection method described in Tsuda et al. (1999; *J. Virol. Methods* 77: 199-206; incorporated herein by reference) and/or the method for determining anti-TTV IgG seroprevalence described in Kakkola et al. (2008; *Virology* 382: 182-189; incorporated herein by reference). Antibodies against an Anellovirus or an anelloVLP based thereon can also be detected by methods in the art for detecting anti-viral antibodies, e.g., methods of detecting anti-AAV antibodies, e.g., as described in Calcedo et al. (2013; *Front. Immunol.* 4(341): 1-7; incorporated herein by reference).

Anelloviruses

In some embodiments, an anellovector or anelloVLP, e.g., as described herein, comprises sequences or expression products derived from an Anellovirus. In some embodiments, an anellovector or anelloVLP includes one or more sequences or expression products that are exogenous relative to the Anellovirus. In some embodiments, an anellovector or anelloVLP includes one or more sequences or expression products that are endogenous relative to the Anellovirus. In some embodiments, an anellovector or anelloVLP includes one or more sequences or expression products that are heterologous relative to one or more other sequences or expression products in the anellovector. Anelloviruses generally have single-stranded circular DNA genomes with negative polarity. Anelloviruses have not generally been linked to any human disease. However, attempts to link Anellovirus infection with human disease are confounded by the high incidence of asymptomatic Anellovirus viremia in control cohort population(s), the remarkable genomic diversity within the anellovirus viral family, the historical inability to propagate the agent in vitro, and the lack of animal model(s) of Anellovirus disease (Yzebe et al., Panminerva Med. (2002) 44:167-177; Biagini, P., Vet. Microbiol. (2004) 98:95-101).

Anelloviruses are generally transmitted by oronasal or fecal-oral infection, mother-to-infant and/or in utero transmission (Gerner et al., Ped. Infect. Dis. J. (2000) 19:1074-

1077). Infected persons can, in some instances, be characterized by a prolonged (months to years) Anellovirus viremia. Humans may be co-infected with more than one genogroup or strain (Saback, et al., Scad. J. Infect. Dis. (2001) 33:121-125). There is a suggestion that these genogroups can recombine within infected humans (Rey et al., Infect. (2003) 31:226-233). The double stranded isoform (replicative) intermediates have been found in several tissues, such as liver, peripheral blood mononuclear cells and bone marrow (Kikuchi et al., J. Med. Virol. (2000) 61:165-170; Okamoto et al., Biochem. Biophys. Res. Commun. (2002) 270:657-662; Rodriguez-lnigo et al., Am. J. Pathol. (2000) 156:1227-1234).

In some embodiments, an anellovector or anelloVLP as described herein comprises one or more polypeptides (e.g., ORF1 molecules) comprising an amino acid sequence having at least about 50%, 60%, 70%, 75%, 80%, 85%, 90%, 95%, 96%, 97%, 98%, 99%, or 100% sequence identity to an Anellovirus sequence, e.g., as described herein, or a fragment thereof. In embodiments, the polypeptide comprises an amino acid sequence encoded by a nucleic acid sequence selected from a sequence as shown in any one of Tables N1-N25, or a sequence having at least 70%, 75%, 80%, 85%, 90%, 95%, 96%, 97%, 98%, 99%, or 100% sequence identity thereto. In embodiments, the polypeptide comprises a sequence as shown in any one of Tables A1-A25, or a sequence having at least 70%, 75%, 80%, 85%, 90%, 95%, 96%, 97%, 98%, 99%, or 100% sequence identity thereto.

In some embodiments, the genetic element comprises a nucleotide sequence encoding an amino acid sequence or a functional fragment thereof or a sequence having at least about 60%, 70% 80%, 85%, 90% 95%, 96%, 97%, 98%, 99%, or 100% sequence identity to any one of the amino acid sequences described herein, e.g., an Anellovirus amino acid sequence.

In some embodiments, an anellovector as described herein comprises one or more nucleic acid molecules (e.g., a genetic element as described herein) comprising a sequence having at least about 70%, 75%, 80%, 85%, 90%, 95%, 96%, 97%, 98%, 99%, or 100% sequence identity to an Anellovirus sequence, e.g., as described herein, or a fragment thereof. In embodiments, the anellovector comprises a nucleic acid sequence selected from a sequence as shown in any one of Tables N1-N25, or a sequence having at least 70%, 75%, 80%, 85%, 90%, 95%, 96%, 97%, 98%, 99%, or 100% sequence identity thereto. In embodiments, the anellovector comprises a polypeptide comprising a sequence as shown in any one of Tables A1-A25, or a sequence having at least 70%, 75%, 80%, 85%, 90%, 95%, 96%, 97%, 98%, 99%, or 100% sequence identity thereto.

In some embodiments, an anellovector as described herein comprises one or more nucleic acid molecules (e.g., a genetic element as described herein) comprising a sequence having at least about 70%, 75%, 80%, 85%, 90%, 95%, 96%, 97%, 98%, 99%, or 100% sequence identity to one or more of a TATA box, cap site, initiator element, transcriptional start site, 5' UTR conserved domain, ORF1, ORF1/1, ORF1/2, ORF2, ORF2/2, ORF2/3, ORF2t/3, three open-reading frame region, poly(A) signal, GC-rich region, or any combination thereof, of any of the Anelloviruses described herein (e.g., an Anellovirus sequence as annotated, or as encoded by a sequence listed, in any one of Tables N1-N25. In some embodiments, the nucleic acid molecule comprises a sequence encoding a capsid protein, e.g., an ORF1, ORF1/1, ORF1/2, ORF2, ORF2/2, ORF2/3, ORF2t/3 sequence of any of the Anelloviruses described herein (e.g., an Anellovirus sequence as annotated, or as encoded by a sequence listed, in any one of Tables N1-N25). In some embodiments, the nucleic acid molecule comprises a sequence encoding a capsid protein comprising an amino acid sequence having at least about 70%, 75%, 80%, 85%, 90%, 95%, 96%, 97%, 98%, 99%, or 100% sequence identity to an Anellovirus ORF1 or ORF2 protein (e.g., an ORF1 or ORF2 amino acid sequence as shown in any one of Tables A1-A25, or an ORF1 or ORF2 amino acid sequence encoded by a nucleic acid sequence as shown in any one of Tables N1-N25). In embodiments, the nucleic acid molecule comprises a sequence encoding a capsid protein comprising an amino acid sequence having at least about 70%, 75%, 80%, 85%, 90%, 95%, 96%, 97%, 98%, 99%, or 100% sequence identity to an Anellovirus ORF1 protein (e.g., an ORF1 amino acid sequence as shown in any one of Tables A1-A25, or an ORF1 amino acid sequence encoded by a nucleic acid sequence as shown in any one of Tables N1-N25).

Nucleic Acid Sequences

In some embodiments, the nucleic acid molecule comprises a nucleic acid sequence having at least about 70%, 75%, 80%, 85%, 90%, 95%, 96%, 97%, 98%, 99%, or 100% sequence identity to the Anellovirus ORF1 nucleotide sequence of any one of Tables N1-N25. In some embodiments, the nucleic acid molecule comprises a nucleic acid sequence having at least about 70%, 75%, 80%, 85%, 90%, 95%, 96%, 97%, 98%, 99%, or 100% sequence identity to the Anellovirus ORF2 nucleotide sequence of any one of Tables N1-N25. In some embodiments, the nucleic acid molecule comprises a nucleic acid sequence having at least about 70%, 75%, 80%, 85%, 90%, 95%, 96%, 97%, 98%, 99%, or 100% sequence identity to the Anellovirus ORF3 nucleotide sequence of any one of Tables N1-N25. In some embodiments, the nucleic acid molecule comprises a nucleic acid sequence having at least about 70%, 75%, 80%, 85%, 90%, 95%, 96%, 97%, 98%, 99%, or 100% sequence identity to the Anellovirus GC-rich region nucleotide sequence of any one of Tables N1-N25. In some embodiments, the nucleic acid molecule comprises a nucleic acid sequence having at least about 70%, 75%, 80%, 85%, 90%, 95%, 96%, 97%, 98%, 99%, or 100% sequence identity to the Anellovirus 5' UTR conserved domain nucleotide sequence of any one of Tables N1-N25.

Amino Acid Sequences Encoded by Nucleic Acid Sequences

In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the Anellovirus ORF1 amino acid sequence of any one of Tables A1-A25. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the Anellovirus ORF2 amino acid sequence of any one of Tables A1-A25. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the Anellovirus ORF3 amino acid sequence of any one of Tables A1-A25.

Proteins Comprising Amino Acid Sequences

In embodiments, the anellovector described herein comprises a protein having an amino acid sequence having at least about 70%, 75%, 80%, 85%, 90%, 95%, 96%, 97%, 98%, 99%, or 100% sequence identity to the Anellovirus ORF1 amino acid sequence of any one of Tables A1-A25. In embodiments, the anellovector described herein comprises a protein having an amino acid sequence having at least about 70%, 75%, 80%, 85%, 90%, 95%, 96%, 97%, 98%, 99%, or 100% sequence identity to the Anellovirus ORF2 amino acid sequence of any one of Tables A1-A25. In embodiments, the anellovector described herein comprises a protein having an amino acid sequence having at least about 70%, 75%, 80%, 85%, 90%, 95%, 96%, 97%, 98%, 99%, or 100% sequence identity to the Anellovirus ORF3 amino acid sequence of any one of Tables A1-A25. In some embodiments, the ORF1 molecule (e.g., comprised in the anellovector) comprises an Anellovirus ORF1 protein of any one of Tables A1-A25 or a splice variant or post-translationally processed (e.g., proteolytically processed) variant thereof. In some embodiments, the ORF2 molecule (e.g., comprised in the anellovector) comprises an Anellovirus ORF2 protein of any one of Tables A1-A25 or a splice variant or post-translationally processed (e.g., proteolytically processed) variant thereof. In some embodiments, the ORF3 molecule (e.g., comprised in the anellovector) comprises an Anellovirus ORF3 protein of any one of Tables A1-A25 or a splice variant or post-translationally processed (e.g., proteolytically processed) variant thereof.

Polypeptides Comprising Amino Acid Sequences

In some embodiments, the polypeptide described herein comprises an amino acid sequence having at least about 70%, 75%, 80%, 85%, 90%, 95%, 96%, 97%, 98%, 99%, or 100% sequence identity to an Anellovirus ORF1 amino acid sequence described herein. In embodiments, the polypeptide described herein comprises an amino acid sequence having at least about 70%, 75%, 80%, 85%, 90%, 95%, 96%, 97%, 98%, 99%, or 100% sequence identity to the Anellovirus ORF1 amino acid sequence of any one of Tables A1-A25.

In some embodiments, the polypeptide described herein comprises an amino acid sequence having at least about 70%, 75%, 80%, 85%, 90%, 95%, 96%, 97%, 98%, 99%, or 100% sequence identity to an ORF1 molecule encoded by an Anellovirus ORF1 nucleic acid described herein. In some embodiments, the polypeptide described herein comprises an amino acid sequence having at least about 70%, 75%, 80%, 85%, 90%, 95%, 96%, 97%, 98%, 99%, or 100% sequence identity to an ORF1 molecule encoded by an Anellovirus ORF1 nucleic acid as listed in any one of Tables A1-A25.

In some embodiments, the polypeptide described herein comprises an amino acid sequence having at least about 70%, 75%, 80%, 85%, 90%, 95%, 96%, 97%, 98%, 99%, or 100% sequence identity to an Anellovirus ORF2 amino acid sequence described herein. In embodiments, the polypeptide described herein comprises an amino acid sequence having at least about 70%, 75%, 80%, 85%, 90%, 95%, 96%, 97%, 98%, 99%, or 100% sequence identity to the Anellovirus ORF2 amino acid sequence of any one of Tables A1-A25.

In some embodiments, the polypeptide described herein comprises an amino acid sequence having at least about 70%, 75%, 80%, 85%, 90%, 95%, 96%, 97%, 98%, 99%, or 100% sequence identity to an ORF2 molecule encoded by an Anellovirus ORF2 nucleic acid described herein. In some embodiments, the polypeptide described herein comprises an amino acid sequence having at least about 70%, 75%, 80%, 85%, 90%, 95%, 96%, 97%, 98%, 99%, or 100% sequence identity to an ORF2 molecule encoded by an Anellovirus ORF2 nucleic acid as listed in any one of Tables A1-A25.

In some embodiments, the polypeptide described herein comprises an amino acid sequence having at least about 70%, 75%, 80%, 85%, 90%, 95%, 96%, 97%, 98%, 99%, or 100% sequence identity to an Anellovirus ORF3 amino acid sequence described herein. In embodiments, the polypeptide described herein comprises an amino acid sequence having at least about 70%, 75%, 80%, 85%, 90%, 95%, 96%, 97%, 98%, 99%, or 100% sequence identity to the Anellovirus ORF3 amino acid sequence of any one of Tables A1-A25.

In some embodiments, the polypeptide described herein comprises an amino acid sequence having at least about 70%, 75%, 80%, 85%, 90%, 95%, 96%, 97%, 98%, 99%, or 100% sequence identity to an ORF3 molecule encoded by an Anellovirus ORF3 nucleic acid described herein. In some embodiments, the polypeptide described herein comprises an amino acid sequence having at least about 70%, 75%, 80%, 85%, 90%, 95%, 96%, 97%, 98%, 99%, or 100% sequence identity to an ORF3 molecule encoded by an Anellovirus ORF3 nucleic acid as listed in any one of Tables A1-A25.

In some embodiments, the polypeptide comprises an amino acid sequence (e.g., an ORF1, ORF1/1, ORF1/2, ORF2, ORF2/2, ORF2/3, or ORF2t/3 sequence) as shown in any one of Tables A1-A25, or a sequence having at least 70%, 75%, 80%, 85%, 90%, 95%, 96%, 97%, 98%, 99%, or 100% sequence identity thereto.

TABLE N1

Novel *Anellovirus* nucleic acid sequence (*Alphatorquevirus*)

| | |
|---|---|
| Name | TTV-RTx1 |
| Genus/Clade | *Alphatorquevirus*, Clade 6 |
| Accession Number | SRR2167793 |
| Full Sequence: 3648 bp | |

```
1        10        20        30        40        50
|        |         |         |         |         |
CGTCACTAACCACGTGACTCCCACAGGCCAACCACAGTGTACGTGATTCA
CTTCCTGGGAGTGGTTTACATTATAATATAAGCAACTGCACTTCCGAATG
GCTGAGTTTTCCACGCCCGTCCGCAGCGAGAACACCACGGAGGGGAGTCC
GCGCGTCCCGTGGGCGGGTGCCGAAGGTGAGTTTACACACCGCAGTCAAG
GGGCAATTCGGGCACGGGACTGGCCGGGCTATGGGCAAGGCTCTTAAAAA
GCTATGTTTCTTGGTAGGCCGTACCGAAAGAAAAGGAAACTGCTACTGCT
ACCACTGCATTCTACACCGAAAACTAGCCGGGTTATGAGCTGGTCTAGGC
CTGTACATAATGCCACAGGCATTGAAAGAAACTGGTGGGAGTCCTGTCTT
AGATCCCACGCAAGTTCTTGTGGCTGCGGTAATTTTGTTAATCATATTAA
TGTACTGGCTAATCGGTATGGCTTTGCTGGTTCCACGGAGACGCCGGGTA
ATCCTCGGCCGAGGCCCCCGGTACTGAGCTCCACCACCAGCACTCCTACC
GATCAATCCAGACCAGCTCTACCATGGCATGGGGATACTGGTGGAGAAGG
CGCTTCTGGAGACCCCGCAGGAGATGGAGAACGTGGCGCCGCAGAAGGAG
ACTACGGCCCAGAAGATCTAGACGCACTTTTCGACGCACTCGACGAAGAG
```

TABLE N1-continued

| Novel *Anellovirus* nucleic acid sequence (*Alphatorquevirus*) |
|---|
| TAAGGAGGCGACGGTGGGGGAGGCGTGCACGCAGGCGGGGATGGCGACGC<br>AGGACTTATATTAGAGCCAGGCGACGCAGGAGACGAAAAAGACTTGTACT<br>GACTCAGTGGCATCCCGCAGTTAGAAGAAAATGTAAAATTACAGGCTACA<br>TGCCTATAGTATACTGTGGACATGGCAGAGCTAGTTTTAACTATGCCTGG<br>CACTCTGATGACTGTATAAAACAACCACTACCCTTTGGAGGCTCACTATC<br>TACAGTGTCCTTCAACCTAAAAGTACTATTTGACGAAAACCAAAGAGGAC<br>TAAACAAATGGAGCTACCCAAATGACCAACTAGACCTCGCCAGATACAAA<br>GGCTGTAGACTAACATTTTACAGAAAAAAAAACACAGACTACATAGCTCA<br>ATATGACATATCAGAACCTTATCAACTAGACAAATATAGCTGTGCAAACT<br>ATCACCCCTCAAAAATGATGTTTGCAAAAAACAAAATTTTAATTCCTAGC<br>TATGATACAAAACCTAGAGGCAGACAAAGAGTTAGAGTTAGAATAGGGCC<br>CCCTAAACTATTTACAGACAAGTGGTACAGTCAATCAGACTTATGCAAGG<br>TAAACCTTGTGTCACTTGCGGTTTCTGCGGCTTCCTTTCTCCACCCATTC<br>GGCTCACCACAAACTGCCAACTTTTGTGCAACCTTCCAGGTGCTGCAACC<br>GTTCTACTACCAGGCTATAGGCATTAGTTCTACAAAACACTCAGAAGTTA<br>TAGACATTTTATATAAGAAAAATACATACTGGCAAAGCAACATTACCTCT<br>TGGTTTTTAACTAATGTTAAAAACCCAAAAAATATGTCCACAAAAAATGTT<br>TGAGGACATTAATGTTAAATCAAACAAAGACAGTAATTATGACTGGTTTC<br>CATTTACCCCATACACTACAGAAAACTATTCAAAAATTCAAAATGCAGCT<br>CAAGAATACTGGAAATATTTAACTAGTGACCACCCACAAGCTACTAATAG<br>CAATGAAGGCCTAGTACAACCATGGACTAATGCCACTATAAAACAATATG<br>AATACCACCTCGGTATGTTTAGTCCTATATTTATAGGACCTACCAGAGCT<br>AAAACTAAATTTAAAACAGCATACTTTGACTGCACTTATAACCCACTACT<br>AGACAAAGGAATGGGAAACAGAATATGGTATCAATACGCAACCAAAGCTG<br>ACACACAAATATCAAAAACAGGGTGCTACTGCATGTTAGAAGACATTCCA<br>ATATATGCAGCATTTTATGGATACGTAGACTTTATAGAAATGGAAATAGG<br>TAAAGGACAAGACATTAAAGAGAACGGACTTATTTGCTGCATATGTAGAT<br>ACACAGACCCCCCAATGTACAATGAACAACATCCAGACATGGGATTTGTA<br>TTTTATAACACTAACTTTGGAAATGGAAAATGGATAGATGGACGGGGCGA<br>CATACCTACTTACTGGATGCAAAGATGGAGACCTGTTGTATTATTTCAAA<br>CTGATGTTATTAGAGACTTAGTAGAAACTGGACCTTTTAGTTACAAAGAT<br>GACCTAGCAAATACCTCACTGACTATGAAATATGAATTCTATTTTACCTG<br>GGGCGGAAACCAGGCGTACCACCAGACAATCAAAAACCCTTGTAAAGACG<br>AAGGTACCGGACCCCATAGACAGCCTAGAGACGTACAAGTTACGGACCCG<br>ACAACCGTGGGACCTGAATATGTGTTCCACGCGTGGGACTGGAGACGGGG<br>CTTCCTTAGCGAGCGAGCTCTCAGACGCATGTTCGAAAAACCTCTCAACT<br>ATGATGAGTATTCTAAAAAACCAAAAAGACCTAGAATATTTCCTCCAACA<br>GAAACAGAGTCCCGAAACCAAGAGCTCGAAGAAAGCTCGCTTTCAGAGGA<br>AGAAAAGTCGCTACTCTCCACAGAAGAGATCCAGAAAGAGGAGATACAGC<br>GACAGTTCAAGCGACAGCTCAAGCGACAGCTGCGCCTCGGGCAGCAGCTC<br>AAACTCCTCCAACAACAACTCCTCAAGACGCAAGCGGGCCTGCACCTAAA<br>CCCCCTTTCATATTTCCCGCAATAAATAAAGTGTACCTGTTCCCAGACAG<br>AGCTCCAAAACCTAAACCCACCTCTGGAGACTGGGAAACAGAGTATGCAG<br>CTTGCAGTGCCTTTGACAGACCCGCTAGAACCAACCTTAGCTCACCCCCT<br>TACTACCCAGGAGTACCTACTCCCTGGCAAGTAAAATTCAGCCTTAAATT<br>TCAATAAAGTGCATTTTTACTACAGCTGGGCCGTGGGAGTTTCACTTGTC<br>GGTGTCTACCTCTTAAGGTCACTAAGCACTCCGAGCGCAGCGAGGAGTGC<br>GACCCTTAACCCTGGGTCAACGCCTTCGGAGCCGCGCGCTACGCCTTCGG<br>CTGCGCGCGGCACCTCAGACCCCCGCTCGTGCTGACGCGCTTGCGCGCGT<br>CAGACCACTTCGGGCTCGCGGGGGTCGGGAACTTTGCTAACAGACTCCGA<br>GGTGCCATTGGACACAGAGTGGGCGTTCAGCAACGAAAGTGAGTGGGGCC<br>AGACTTCGCCATAAGGCCTTTATCTTCTTGCCATTTGTCAGTATAAGGGG<br>TTGCCATAGGCTTCGGCCTCAATTTTAGGCCTTCCGGACTACCAAAATGG<br>CCGATTTAGTGACGTCACGGCGGCCATTTTAAGTAAGGCGGAAGTAACTC<br>CACTATTTACAAAATGGCGGCGGAGCACTTCCGGCTTGCCCAAAATGGCG<br>GCAAAAAACATCCGGGTCAAAGGTCGTTACCACGTCACAAGTCACGTGGG<br>AGGGTGGTGCTGTAAACCCGGAAGCAATCCTCTCACGTGGCTAGTCACGT<br>GACTAACACGTCACACCCGCCATTTTGTTTTACAAAATGGCCGACTTCCT<br>TCCGCTTTTTTAAAAATAACGGCTCAGCGGCGGCGCGCGCGCTACGCG<br>(SEQ ID NO: 830) |

Annotations:

| Putative Domain | Base range |
|---|---|
| TATA Box | 77-81 |
| Initiator Element | 95-110 |
| Transcriptional Start Site | 105 |
| 5' UTR Conserved Domain | 165-235 |
| ORF2 | 335-703 |
| ORF2/2 | 335-699; 2326-2759 |
| ORF2/3 | 335-699; 2552-2957 |

TABLE N1-continued

| Novel *Anellovirus* nucleic acid sequence (*Alphatorquevirus*) | |
|---|---|
| ORF2t/3 | 335-465; 2552-2957 |
| ORF1 | 574-2775 |
| ORF1/1 | 574-699; 2326-2775 |
| ORF1/2 | 574-699; 2552-2759 |
| Three open-reading frame region | 2535-2746 |
| Poly(A) Signal | 2953-2958 |
| GC-rich region ** | 3620-3648 |

TABLE A1

| Novel *Anellovirus* amino acid sequences (*Alphatorquevirus*, Clade 6)<br>TTV-RTx1 (*Alphatorquevirus* Clade 6) | |
|---|---|
| ORF2 | MSWSRPVHNATGIERNWWESCLRSHASSCGCGNFVNHINVLANRYGFAGS<br>TETPGNPRPRPPVLSSTTSTPTDQSRPALPWHGDTGGEGASGDPAGDGERGA<br>AEGDYGPEDLDALFDALDEE (SEQ ID NO: 831) |
| ORF2/2 | MSWSRPVHNATGIERNWWESCLRSHASSCGCGNFVNHINVLANRYGFAGS<br>TETPGNPRPRPPVLSSTTSTPTDQSRPALPWHGDTGGEGASGDPAGDGERGA<br>AEGDYGPEDLDALFDALDEEQSKTLVKTKVPDPIDSLETYKLRTRQPWDLN<br>MCSTRGTGDGASLASELSDACSKNLSTMMSILKNQKDLEYFLQQKQSPETK<br>SSKKARFQRKKSRYSPQKRSRKRRYSDSSSDSSSDSCASGSSSNSSNNNSSRR<br>KRACT (SEQ ID NO: 832) |
| ORF2/3 | MSWSRPVHNATGIERNWWESCLRSHASSCGCGNFVNHINVLANRYGFAGS<br>TETPGNPRPRPPVLSSTTSTPTDQSRPALPWHGDTGGEGASGDPAGDGERGA<br>AEGDYGPEDLDALFDALDEENRVPKPRARRKLAFRGRKVATLHRRDPERG<br>DTATVQATAQATAAPRAAAQTPPTTTPQDASGPAPKPPFIFPAINKVYLFPD<br>RAPKPKPTSGDWETEYAACSAFDRPARTNLSSPPYYPGVPTPWQVKFSLKF<br>Q (SEQ ID NO: 833) |
| ORF2t/3 | MSWSRPVHNATGIERNWWESCLRSHASSCGCGNFVNHINVLANRNRVPKP<br>RARRKLAFRGRKVATLHRRDPERGDTATVQATAQATAAPRAAAQTPPTTTP<br>QDASGPAPKPPFIFPAINKVYLFPDRAPKPKPTSGDWETEYAACSAFDRPART<br>NLSSPPYYPGVPTPWQVKFSLKFQ (SEQ ID NO: 834) |
| ORF1 | MAWGYWWRRRFWRPRRRWRTWRRRRRLRPRRSRRTFRRTRRRVRRRRW<br>GRRARRRGWRRRTYIRARRRRRRKRLVLTQWHPAVRRKCKITGYMPIVYC<br>GHGRASFNYAWHSDDCIKQPLPFGGSLSTVSFNLKVLFDENQRGLNKWSYP<br>NDQLDLARYKGCRLTFYRKKNTDYIAQYDISEPYQLDKYSCANYHPSKMM<br>FAKNKILIPSYDTKPRGRQRVRVRIGPPKLFTDKWYSQSDLCKVNLVSLAVS<br>AASFLHPFGSPQTANFCATFQVLQPFYYQAIGISSTKHSEVIDILYKKNTYWQ<br>SNITSWFLTNVKNPKNMSTKMFEDINVKSNKDSNYDWFPFTPYTTENYSKIQ<br>NAAQEYWKYLTSDHPQATNSNEGLVQPWTNATIKQYEYHLGMFSPIFIGPT<br>RAKTKFKTAYFDCTYNPLLDKGMGNRIWYQYATKADTQISKTGCYCMLED<br>IPIYAAFYGYVDFIEMEIGKGQDIKENGLICCICRYTDPPMYNEQHPDMGFVF<br>YNTNFGNGKWIDGRGDIPTYWMQRWRPVVLFQTDVIRDLVETGPFSYKDD<br>LANTSLTMKYEFYFTWGGNQAYHQTIKNPCKDEGTGPHRQPRDVQVTDPT<br>TVGPEYVFHAWDWRRGFLSERALRRMFEKPLNYDEYSKKPKRPRIFPPTET<br>ESRNQELEESSLSEEEKSLLSTEEIQKEEIQRQFKRQLKRQLRLGQQLKLLQQ<br>QLLKTQAGLHLNPLSYFPQ (SEQ ID NO: 835) |
| ORF1/1 | MAWGYWWRRRFWRPRRRWRTWRRRRRLRPRRSRRTFRRTRRRTIKNPCK<br>DEGTGPHRQPRDVQVTDPTTVGPEYVFHAWDWRRGFLSERALRRMFEKPL<br>NYDEYSKKPKRPRIFPPTETESRNQELEESSLSEEEKSLLSTEEIQKEEIQRQFK<br>RQLKRQLRLGQQLKLLQQQLLKTQAGLHLNPLSYFPQ (SEQ ID NO: 836) |
| ORF1/2 | MAWGYWWRRRFWRPRRRWRTWRRRRRLRPRRSRRTFRRTRRRKQSPETK<br>SSKKARFQRKKSRYSPQKRSRKRRYSDSSSDSSSDSCASGSSSNSSNNNSSRR<br>KRACT (SEQ ID NO: 837) |

TABLE N2

| Novel *Anellovirus* nucleic acid sequence (*Alphatorquevirus*) | |
|---|---|
| Name | TTV-RTx2 |
| Genus/Clade | *Alphatorquevirus*, Clade 6 |
| Accession Number | SRR3479021 |
| Full Sequence: 3704 bp | |

```
1        10         20         30         40         50
|         |          |          |          |          |
CCCCGAAGTCCGTCACTAACCACGTGACTCCCACAGGCCAATCAGATGCT
ATGTCGTGCACTTCCTGGGCTGTGTCTACGTCCTCATATAAGTAACTGCA
CTTCCGAATGGCTGAGTTTTCCACGCCCGTCCGCAGCGGCAGCACCACGG
AGGGTGATCCCCGCGTCCCGTGGGCGGGTGCCGGAGGTGAGTTTACACAC
CGCAGTCAAGGGGCAATTCGGGCACGGGACTGGCCGGGCTATGGGCAAGG
CTCTTAAAAAGCTATGTTCTTCGGTAGGTGCTGGAGAAAGAAAAGGAAAG
TGCTTCTGCAAGATCTGTCAACTCCACCGAAAAAACCTGCTATGAGTGTG
TGGCTTCCTCCCATAGACAATGTTACCGAGCGTGAGAGGAGCTGGCTCTC
TAGCATTCTTCAGTCTCACAGAGCTTTTTGTGGGTGCCATGATGCTATCT
ATCATCTTAGCAGTCTGGCTGCTCGCTTTAATATGCAACCAGGGCCGTCG
CCGGGTGGTGATTCTAGGCCGCCGCGACCGCCACTAAGACGCCTGCCCGC
GCTCCCGGGTCCCAGAGACCCCCCTAGCGACACCAACAACCGCAGGTCAT
GGCCTACTGGGGATGGTGGAGACGGAGGCGCTGGCCAAGGCGCAGGTGGA
GGCGCTACCGCTACCGAAGAAGACTACCGCGCCGAAGACCTAGACGAGCT
GTACGCCGCCCTCGAAGGAGACGAGTAAGGAGGCGCCGCGGTAGGGGGTG
GTACAGAGGGCGACGCTACTCCCGCAGACGGTACAGACGTAGATATGTGA
GGCGAAAGAGAAAGACTCTAGTTTGGAGACAGTGGCAGCCTCAAAATATC
AGAAAATGCAGGATCAGGGGCATAATTCCCATCCTGATATGCGGACACGG
GAGGGGGGCCAGAAACTATGCGCTCCACAGCGACGACATAACCCCCCAGA
ACACCCCCTTCGGGGGAGGACTGAGCACCACCTCCTGGAGCCTAAAAGTG
CTATATGACCAGCACACCAGGGGACTCAACAGGTGGTCTGCCAGTAACGA
GAGCCTAGACCTTGCCAGATACAATGGCTGTAGTTTCACTTTCTACAGAG
ACAAAAAGACTGACTTTATAGTGACCTATGACACCTCTGCTCCCTACAAA
CTAGACAAATACAGCTCCCCCAGCTACCACCCAGGGTCCATGATGCTCAT
GACAAAACACAAAATCCTGATCCCCAGTTTTGACACAAAACCCAAAGGTC
CTGCCAAAATTAGAGTCAGAATCAAGCCCCCCAAAATGTTCTTAGATAAA
TGGTACACTCAAGACGACCTCTGTTCCGTTAATCTTGTGTCACTTGCGGT
TAGCGCAGCTTCCTTTACACATCCGTTCTGCCCACCACTAACTGACACTC
CTTGTGTAACGCTGCAGGTGTTGAAAGACTTCTACTACACAACCATAGGC
TACTCCTCTAATGCAGACAAAGTAGAGTCTGTATTCACTAACACTCTCTA
CAAACACTGCTGCTACTATCAGTCCTTTCTCACCACTCAATTTATAGCCA
AAATCACTCGCACACCAGATGGACAACCAGTAGCCACATTCTCTCCTCCT
ACCTCTTTCCCTGGCACAACTGTAACAAAAAGTTCCATAGAATCATTTAA
CCAATGGGTAACTTCCACAGGTACAAGTGGCTGGCTAACAAATGCAAACC
AACACTTTCATTTCTGTAACTATAAACCAGATGCCACAAAGCTAAAATGG
CTCAGACAGTACTACTTTGACTGGGAAACATACAAATTAGCAGATGTAAA
GCCAGACGGCCTTACACCCTCAGTAAACTGGTATGAGTACAGAATAGGCC
TCTTTAGTCCTATTTTCCTGAGCCCCTTCAGATCTAGCAGTCTAGACTTT
CCCAGAGCCTACCAGGATGTGAACTACAACCCCCTGGTAGACAAAGGAGT
GGGCAACATCATATGGTTCCAATACAACACAAAACCAGACACACAGCTGT
CAGTACCCAGCTGCAAGTGTGTCATAGAAGACAAACCCCTATGGGCAGCC
TTCTATGGCTACAGTGACTTTGTACAACAAGAGATAGGAGACTACACAGA
CGCAGAGGCCGTGGGCTTCGTCTGTGTCATCTGTCCATACACCAAACCCC
CTCTAAAAAACCCAGACAACCCCATGCAAGGGTTCATATTCTATGACAGC
CTTTTTGGCAATGGCAAGTGGATAGATGGCACGGGGCACGTCCCCCTTTA
CTGGCAGAGCAGGTGGAGGCCAGAGATGCTCTTCCAAGAAAACACCATGA
GAGACATCACACTATCTGGGCCCTTCAGCTACAAGGACGACTATAAGAAC
TGTGTACTGACTTGCAAATACAAATTTAACTTTCGATTCGGGGGCAATCT
TCTCCACGAACAGACGATCAGAAACCCATGCCCCACGGACGGACATCCCA
GTACCGGTAGACAGCCTAGAGACGTACAAGTGGTTGACCCGATCAAAGTG
GGCCCCCGGTTCGTGTTCCACTCCTGGGACTGGCGCAGAGGCTACCTTAG
CCCAGCAGCTCTCAAAAGAATTGGAGAGCAACCGCTCGATTATGAAGCTT
ATTCGTACCGCCCAAAGAGACCTAGAATCTTTCCTCCCACAGAAGGAGAC
CAGCTCGCCCGAAGTCGAGAAGAAGACTCATTTTCAGAGGAAGAAAGTCC
CCATATCTCGTTCGAAGAGGGGCAGGAACCGAAAGCCCAGGCGGTACAGC
AGCACCTCCTCCGACACCTCAGAAAGCAGCGAGAACTCCGAAAGCGACTC
CGAGCCCTGTTCCAAAGCCTCCAAAAGACGCAGGCGGGTCTCCACGTAAA
TCCATTATTATTCAACCAGCCTGCAATCAGGTTCTGATGTTCCCAGAGAT
GGGGCCTAAGCCAGCTCCCACTGCCCAAGACTGGCAGTGCGAATACGAGA
CATGTAAGCACTGGGATAGACCCCCCAGAAAGTTTCTCACAGACCCCCCT
TTCTATCCCTGGGCCCCTACTACTTACAATGTATCTTTCAAGCTAAACTT
CAAATAAACTAGGCCGTGGGAGTCTCACTTGTCGGTGTCTACCTCTTAAG
GTCACTAAGCACTCCGAGCGTCAGCGAGGAGTGCGACCCCTTCCCCCTGGT
GCAACGCCCTCGGCGGCCGCGCGCTACGCCTTCGGCTGCGCGCGGCACCT
CGGACCCCCGCTCGTGCTGACGCGCTCGCGCGCGTCAGACCACTTCGGGC
TCGCGGGGGTCGGGAAATTTGCTAAACAGACTCCGAGTTGCCATTGGACA
CAGGAGCTGTGAATCAGTAACGAAAGTGAGTGGGGCCAGACTTCGCCATA
AGGCCTTTATCTTCTTGCCATTTGTCCGTGAGGAGGGGTCGCCAAGACGC
GGACCCCGTTTTCGGACCTTCCGAACTACCAAAATGGCCGATTCAGTGAC
GTCACGGCAGCCATTTTGTGTAAGCACCGCCCAGGACAGACGTCACAGTT
CAAAGGTCATCCTCGAGCGGAACTTACAGAAAATGGCGGTCAATTGCTTC
```

TABLE N2-continued

| Novel *Anellovirus* nucleic acid sequence (*Alphatorquevirus*) |
|---|
| CGGGTCAAAGGTCACGCCTACGTCATAAGTCACGTGGTGGAGGCTACTGC<br>GCATACACGGAAGTAGGCCCCGCCACGTGACCGACCACGTGGGTGCTGCG<br>TCACGGCCGCCATTTTGTATCACAAAATGGCCGACTTCCTTCCTCTTTTT<br>CAAA (SEQ ID NO: 838) |

Annotations:

| Putative Domain | Base range |
|---|---|
| TATA Box | 87-91 |
| Initiator Element | 105-120 |
| Transcriptional Start Site | 115 |
| 5' UTR Conserved Domain | 175-245 |
| ORF2 | 342-728 |
| ORF2/2 | 342-724; 2414-2849 |
| ORF2/3 | 342-724; 2643-3057 |
| ORF1 | 599-2887 |
| ORF1/1 | 599-724; 2414-2887 |
| ORF1/2 | 599-724; 2643-2849 |
| Three open-reading frame region | 2626-2846 |
| Poly(A) Signal | 3052-3058 |

TABLE A2

Novel *Anellovirus* amino acid sequences (*Alphatorquevirus*, Clade 6)
TTV-RTx2 (*Alphatorquevirus* Clade 6)

| | |
|---|---|
| ORF2 | MSVWLPPIDNVTERERSWLSSILQSHRAFCGCHDAIYHLSSLAARFNMQPGP<br>SPGGDSRPPRPPLRRLPALPGPRDPPSDTNNRRSWPTGDGGDGGAGQGAGG<br>GATATEEDYRAEDLDELYAALEGDE (SEQ ID NO: 839) |
| ORF2/2 | MSVWLPPIDNVTERERSWLSSILQSHRAFCGCHDAIYHLSSLAARFNMQPGP<br>SPGGDSRPPRPPLRRLPALPGPRDPPSDTNNRRSWPTGDGGDGGAGQGAGG<br>GATATEEDYRAEDLDELYAALEGDERSETHAPRTDIPVPVDSLETYKWLTR<br>SKWAPGSCSTPGTGAEATLAQQLSKELESNRSIMKLIRTAQRDLESFLPQKE<br>TSSPEVEKKTHFQRKKVPISRSKRGRNRKPRRYSSTSSDTSESSENSESDSEPC<br>SKASKRRRRVST (SEQ ID NO: 840) |
| ORF2/3 | MSVWLPPIDNVTERERSWLSSILQSHRAFCGCHDAIYHLSSLAARFNMQPGP<br>SPGGDSRPPRPPLRRLPALPGPRDPPSDTNNRRSWPTGDGGDGGAGQGAGG<br>GATATEEDYRAEDLDELYAALEGDERRPARPKSRRRLIFRGRKSPYLVRRG<br>AGTESPGGTAAPPPTPQKAARTPKATPSPVPKPPKDAGGSPRKSIIIQPACNQ<br>VLMFPEMGPKPAPTAQDWQCEYETCKHWDRPPRKFLTDPPFYPWAPTTYN<br>VSFKLNFK (SEQ ID NO: 841) |
| ORF1 | MAYWGWWRRRRWPRRRWRRYRYRRRLPRRRPRRAVRRPRRRRVRRRRG<br>RGWYRGRRYSRRRYRRRYVRRKRKTLVWRQWQPQNIRKCRIRGIIPILICGH<br>GRGARNYALHSDDITPQNTPFGGGLSTTSWSLKVLYDQHTRGLNRWSASNE<br>SLDLARYNGCSFTFYRDKKTDFIVTYDTSAPYKLDKYSSPSYHPGSMMLMT<br>KHKILIPSFDTKPKGPAKIRVRIKPPKMFLDKWYTQDDLCSVNLVSLAVSAA<br>SFTHPFCPPLTDTPCVTLQVLKDFYYTTIGYSSNADKVESVFTNTLYKHCCY<br>YQSFLTTQFIAKITRTPDGQPVATFSPPTSFPGTTVTKSSIESFNQWVTSTGTS<br>GWLTNANQHFHFCNYKPDATKLKWLRQYYFDWETYKLADVKPDGLTPSV<br>NWYEYRIGLFSPIFLSPFRSSSLDFPRAYQDVNYNPLVDKGVGNIIWFQYNTK<br>PDTQLSVPSCKCVIEDKPLWAAFYGYSDFVQQEIGDYTDAEAVGFVCVICPY<br>TKPPLKNPDNPMQGFIFYDSLFGNGKWIDGTGHVPLYWQSRWRPEMLFQE<br>NTMRDITLSGPFSYKDDYKNCVLTCKYKFNFRFGGNLLHEQTIRNPCPTDGH<br>PSTGRQPRDVQVVDPIKVGPRFVFHSWDWRRGYLSPAALKRIGEQPLDYEA<br>YSYRPKRPRIFPPTEGDQLARSREEDSFSEEESPHISFEEGQEPKAQAVQQHLL<br>RHLRKQRELRKRLRALFQSLQKTQAGLHVNPLLFNQPAIRF (SEQ ID NO:<br>842) |

TABLE A2-continued

| Novel *Anellovirus* amino acid sequences (*Alphatorquevirus*, Clade 6) TTV-RTx2 (*Alphatorquevirus* Clade 6) | |
|---|---|
| ORF1/1 | MAYWGWWRRRRWPRRRWRRYRYRRRLPRRRPRRAVRRPRRRRTIRNPCP TDGHPSTGRQPRDVQVVDPIKVGPRFVFHSWDWRRGYLSPAALKRIGEQPL DYEAYSYRPKRPRIFPPTEGDQLARSREEDSFSEEESPHISFEEGQEPKAQAV QQHLLRHLRKQRELRKRLRALFQSLQKTQAGLHVNPLLFNQPAIRF (SEQ ID NO: 843) |
| ORF1/2 | MAYWGWWRRRRWPRRRWRRYRYRRRLPRRRPRRAVRRPRRRRKETSSPE VEKKTHFQRKKVPISRSKRGRNRKPRRYSSTSSDTSESSENSESDSEPCSKAS KRRRRVST (SEQ ID NO: 844) |

TABLE N3

| Novel *Anellovirus* nucleic acid sequence (*Alphatorquevirus*) | |
|---|---|
| Name | TTV-RTx3 |
| Genus/Clade | *Alphatorquevirus*, Clade 4 |
| Accession Number | SRR3479781 |
| Full Sequence: 3653 bp | |

```
1         10         20         30         40         50
|         |          |          |          |          |
CCAACCAGAGTCTATGTCGTGCACTTCCTGGGCATGGTCTACGTAATAAT
ATAAAGCGGTGCACTTCCGAATGGCTGAGTTTTCCACGCCCGTCCGCAGC
GAGATCGCGACGGAGGAGCGATCGAGCGTCCCGAGGGCGGGTGCCGGAGG
TGAGTTTACACACCGCAGTCAAGGGGCAATTCGGGCTCGGGACTGGCCGG
GCTATGGGCAAGGCTCTTAAAAAGCCATGTTTCTCGGTAAACTTTACAGG
CAGAAAAGGAAACTGCTACTGCAGCCTGTGCGTGCTCCACAGACGCCATC
TTCCATGAGCTCTACCTGGCGAGTGCCCCGCGGCGATGTCTCCGCCCGCG
AGCTATGTTGGTACCGCTCAGTTCGAGAGAGCCACGATGCTTTTTGTGGC
TGTCGTGATCCTGTTTTTCATCTTTCTCGTCTGGCTGCACGTTCTAACCA
TCAGGGACCTCCGACGCCCCCCACGGACGAGCGCCCGTCGGCGTCTACCC
CAGTGAGGCGCCTGCTGCCGCTGCCCTCCTACCCCGGCGAGGGTCCCCAG
GCTAGATGGCCTGGTGGGGATGGAGAAGGCGCTGGTGGCGCCCGCGGAGG
CGCTGGAGATGGCGGCGCCCGCGCAGGCGAAGAAGAGTACCGGCCCGAAG
ACCTCGACGAGCTGTTCGACGCTATCGAACAAGAACAGTAAGGAGACGGA
GGCGAGGGTGGCGGAGGGGCTACAGGCGCCGTTACAGACTGAGACGCTAC
CGTAGAAGGGGCAGGCGACGCAAAAAAATAGTACTGACTCAGTGGAACCC
CCAGACTGTCAGAAAGTGCTTTATCAGAGGACTGATGCCAGTACTATGGG
CGGGCATGGGCACGGGGGGCCACAACTACGCCGTCCGCTCAGATGACTTT
GTGGTAGACAGAGGCTTCGGGGGCTCCTTCGCCACAGAAACTTTCTCCCT
GAGGGTCCTCTTTGACCAGTACCAGAGAGGATTTAATAGGTGGTCTCACA
CCAACGAAGACCTAGACCTGGCCCGCTACACGGGCTGCAAATGGACATTT
TACAGACACCAAGACACAGACTTTATAGTGTACTTTACAAACAATCCCCC
CATGAAAACCAACCAGCACACAGCCCCTCTCACAACTCCAGGCATGCTCA
TGAGGAGCAAGTATAAAATACTAGTGCCCAGTTTTAAAACAAGACCAAAG
GGCAGAAAAACAGTGTCAGTGAGAGTTAGACCCCCCAAACTGTTTCAGGA
CAAATGGTATACTCAACAGGACCTCTGTCCAGTACCCCTCGTCCAACTGA
ACGTGACCGCAGCGGATTTCACACATCCGTTCGGCTCACCACTAACTGAC
ACGCCTTGCATAAGATTCCAAGTTTTAGGGAACTTATACAACAAGTGCCT
AAATATAGATCTTCCGCAATTTGATGAGGACGGTGAGATACTCACTTCAA
CACCTTATAACAGAGAAAACAAAGAAGATCTTAAAAAGCTTTATAAAACT
CTATTTGTAGATGAACACGCAGGCAATTATTGGCAGACATTCTTAACCAA
CACAATGGTAAAGTCACACATAGATGCAAACCAAGCAAAGACATACGATC
AAGAAAAAACTGCTGCAGAACAAGGTAAAGACCCCTTCCCAACAAACCCA
CCAAAAGACCAATTCACTACCTGGAACAAGAAACTAGTAGACCCTAGAGA
CAGCAACTTTCTCTTTGCCACATATCACCCAAAAAACATTAAAAAAGCTA
TAAAAACCATGAGAGACAACAACTTTGCTCTCACCACAGGCAAAAATGAC
ATATATGGAGACTACACCGCGGCCTACACCAGAAACACCCACATGCTAGA
CTACTACCTAGGCTTTTATAGCCCCATATTTCTTTCCAGCGGTAGGTCCA
ACACAGAGTTCTGGACCGCCTACAGAGACATAGTATATAATCCCCTCTTA
GACAAAGGCACAGGCAACATGATCTGGTTCCAATATCACACAAAAACAGA
CAATATATACAAAAAACCAGAGTGCCACTGGGAGATACTAGACATGCCCC
TGTGGGCCCTCTGCAACGGGTATGTAGAGTACCTAGAGAGCCAAATAAAG
TACGGGGACATCCTAGTAGAGGGCAAAGTCCTCATCAGATGCCCCTACAC
CAAACCCGCACTGGTAGACCCCAATAACAGCCTAGCTGGTTACGTGGTAT
TCAACACCACCTTCGGCCAGGGAAAATGGATAGATGGCAAAGGCTACATC
CCCCTACACGAGAGGAGCAAGTGGTACGTCATGCTCAGATACCAGACCGA
CGTACTCCATGACATAGTGACTTGTGGACCCTGGCAGTACAGAGACGATA
ACAAAAACTCTCAGCTAATAGCCAAGTACAGATTCAAGTTCTACTGGGGA
GGTAACATGGTACATTCTCAGGTCATCAGAAACCCGTGCAAAGACACCCA
AGTATCCGGACCCCGTCGACAGCCTCGCGAAGTACAAGTCGTTGACCCGC
AACTCATTACGCCGCCGTGGGTCCTCCACTCGTTCGACCAGAGACGAGGA
ATGTTTACTGCAGGAGCTATCAAACGTCTGCTCAAGCAACCAATACCTGG
```

TABLE N3-continued

| Novel *Anellovirus* nucleic acid sequence (*Alphatorquevirus*) |
|---|
| CGAGTATGCTCCTACACCACTCAGGGTCCCGCTCCTCTTTCCCTCCTCAG<br>AGTTCCAGCGAGAGGGAGAAGATGCAGAAAGCGGCTCAGGTTCACCACCC<br>AAGAGACCGCGACTCTGGCAGGAAGAGGCCAACCAGACGCAAACGGAGTC<br>CTCGGAGGGGCCGGCGGAGACGACGAGGGAGCTCCTCGAGCGAAAGCTCA<br>GAGAGCAGCGAGTCCTCAACCTCCAACTCCAGCATGTCGCAGTACAACTC<br>GCCAAAACCCAAGCGAACCTCCACATAAACCCCCTATTATACTCCCAGCC<br>TTAAACAAAGTGTATCTATTCCCCCCTGACAAGCCCACTCCCATACAGNN<br>NNNNNNNNNNNNNNNNAACACAGAGTTCGAAGCCTGCCAGGCCTTCGACA<br>GACCACCTAGAAAATACCTCTCAGACACACCTACCTACCCTTGGCTCCCC<br>GTCCCCAATCCTGAAATAAAGGTCAGCTTTAAGCTCGGTTTCAAATCTTA<br>CAAGGCCGTGGGAGTTTCACTGGTCGGTGTCTACCTCTTAAGGTCACTAA<br>GCACTCCGAGCGTCAGCGAGGAGTGCGACCCTTCCCCCTGGTGCAACGCC<br>CTCGGCGGCCGCGCGCTACGCCTTCGGCTGCGCGCGGCACCTCGGACCCC<br>CGCTCGTGCTGACGCGCTCGCGCGCGTCAGACCACTTCGGGCTCGCGGGG<br>GTCGGGAATTTTGCTAAACAGACTCCGAGTTGCCATTGGACACTGTAGCT<br>GTGAATCAGTAACGAAAGTGAGTGGGGCCAGACTTCGCCATAAGGCCTTT<br>ATCTTCTTGCCATTGGTCCGTGTAGGGGGTCGCCATAGGCTTCGGGTTCG<br>GTTTTAGGCCTTCCGGACTACAAAAATGGCGGATTTAGTGACGTCACGGC<br>CGCCATTTTAAGTAGGTGCCGTCCAGGACTGCTGTTCCGGGTCACAGGGC<br>ATCCTCGGCGGAACTTACACAAAATGGCGGTCAAAAACATCCGGGTCAAA<br>GGTCGCAGCTACGTCATAAGTCACGTGCAGGGGTCCTGCTGCGTCATATG<br>CGG (SEQ ID NO: 845) |

Annotations:

| Putative Domain | Base range |
|---|---|
| TATA Box | 50-55 |
| Initiator Element | 68-83 |
| Transcriptional Start Site | 78 |
| 5' UTR Conserved Domain | 138-208 |
| ORF2 | 305-691 |
| ORF2/2 | 305-687; 2422-2878 |
| ORF2/3 | 305-687; 2564-3317 |
| ORF2t/3 | 305-360; 2564-3317 |
| ORF1 | 556-2904 |
| ORF1/1 | 556-687; 2422-2904 |
| ORF1/2 | 556-687; 2564-2878 |
| Three open-reading frame region | 2626-2846 |
| Poly(A) Signal | 3316-3319 |

TABLE A3

| Novel *Anellovirus* amino acid sequences (*Alphatorquevirus*, Clade 4)<br>TTV-RTx3 (*Alphatorquevirus* Clade 4) | |
|---|---|
| ORF2 | MSSTWRVPRGDVSARELCWYRSVRESHDAFCGCRDPVFHLSRLAARSNHQ<br>GPPTPPTDERPSASTPVRRLLPLPSYPGEGPQARWPGGDGEGAGGARGGAG<br>DGGARAGEEEYRPEDLDELFDAIEQEQ (SEQ ID NO: 846) |
| ORF2/2 | MSSTWRVPRGDVSARELCWYRSVRESHDAFCGCRDPVFHLSRLAARSNHQ<br>GPPTPPTDERPSASTPVRRLLPLPSYPGEGPQARWPGGDGEGAGGARGGAG<br>DGGARAGEEEYRPEDLDELFDAIEQEQSSETRAKTPKYPDPVDSLAKYKSLT<br>RNSLRRRGSSTRSTRDEECLLQELSNVCSSNQYLASMLLHHSGSRSSFPPQSS<br>SEREKMQKAAQVHHPRDRDSGRKRPTRRKRSPRRGRRRRRGSSSSESSESSE<br>SSTSNSSMSQYNSPKPKRTST (SEQ ID NO: 847) |
| ORF2/3 | MSSTWRVPRGDVSARELCWYRSVRESHDAFCGCRDPVFHLSRLAARSNHQ<br>GPPTPPTDERPSASTPVRRLLPLPSYPGEGPQARWPGGDGEGAGGARGGAG<br>DGGARAGEEEYRPEDLDELFDAIEQEQSYQTSAQATNTWRVCSYTTQGPAP<br>LSLLRVPARGRRCRKRLRFTTQETATLAGRGQPDANGVLGGAGGDDEGAP<br>RAKAQRAASPQPPTPACRSTTRQNPSEPPHKPPIILPALNKVYLFPPDKPTPIQ<br>XXXXXXNTEFEACQAFDRPPRKYLSDTPTYPWLPVPNPEIKVSFKLGFKSYK |

TABLE A3-continued

| Novel *Anellovirus* amino acid sequences (*Alphatorquevirus*, Clade 4) TTV-RTx3 (*Alphatorquevirus* Clade 4) | |
|---|---|
| | AVGVSLVGVYLLRSLSTPSVSEECDPSPWCNALGGRALRLRLRAAPRTPAR ADALARVRPLRARGGREFC (SEQ ID NO: 848) |
| ORF2t/3 | MSSTWRVPRGDVSARELCWSYQTSAQATNTWRVCSYTTQGPAPLSLLRVP ARGRRCRKRLRFTTQETATLAGRGQPDANGVLGGAGGDDEGAPRAKAQR AASPQPPTPACRSTTRQNPSEPPHKPPIILPALNKVYLFPPDKPTPIQXXXXXX NTEFEACQAFDRPPRKYLSDTPTYPWLPVPNPEIKVSFKLGFKSYKAVGVSL VGVYLLRSLSTPSVSEECDPSPWCNALGGRALRLRLRAAPRTPARADALAR VRPLRARGGREFC (SEQ ID NO: 849) |
| ORF1 | MAWWGWRRRWWRPRRRWRWRRPRRRRRVPARRPRRAVRRYRTRTVRR RRRGWRRGYRRRYRLRRYRRRGRRRKKIVLTQWNPQTVRKCFIRGLMPVL WAGMGTGGHNYAVRSDDFVVDRGFGGSFATETFSLRVLFDQYQRGFNRW SHTNEDLDLARYTGCKWTFYRHQDTDFIVYFTNNPPMKTNQHTAPLTTPG MLMRSKYKILVPSFKTRPKGRKTVSVRVRPPKLFQDKWYTQQDLCPVPLVQ LNVTAADFTHPFGSPLTDTPCIRFQVLGNLYNKCLNIDLPQFDEDGEILTSTP YNRENKEDLKKLYKTLFVDEHAGNYWQTFLTNTMVKSHIDANQAKTYDQ EKTAAEQGKDPFPTNPPKDQFTTWNKKLVDPRDSNFLFATYHPKNIKKAIKT MRDNNFALTTGKNDIYGDYTAAYTRNTHMLDYYLGFYSPIFLSSGRSNTEF WTAYRDIVYNPLLDKGTGNMIWFQYHTKTDNIYKKPECHWEILDMPLWAL CNGYVEYLESQIKYGDILVEGKVLIRCPYTKPALVDPNNSLAGYVVFNTTFG QGKWIDGKGYIPLHERSKWYVMLRYQTDVLHDIVTCGPWQYRDDNKNSQ LIAKYRFKFYWGGNMVHSQVIRNPCKDTQVSGPRRQPREVQVVDPQLITPP WVLHSFDQRRGMFTAGAIKRLLKQPIPGEYAPTPLRVPLLFPSSEFQREGED AESGSGSPPKRPRLWQEEANQTQTESSEGPAETTRELLERKLREQRVLNLQL QHVAVQLAKTQANLHINPLLYSQP (SEQ ID NO: 850) |
| ORF1/1 | MAWWGWRRRWWRPRRRWRWRRPRRRRRVPARRPRRAVRRYRTRTVIRN PCKDTQVSGPRRQPREVQVVDPQLITPPWVLHSFDQRRGMFTAGAIKRLLK QPIPGEYAPTPLRVPLLFPSSEFQREGEDAESGSGSPPKRPRLWQEEANQTQT ESSEGPAETTRELLERKLREQRVLNLQLQHVAVQLAKTQANLHINPLLYSQP (SEQ ID NO: 852) |
| ORF1/2 | MAWWGWRRRWWRPRRRWRWRRPRRRRRVPARRPRRAVRRYRTRTELSN VCSSNQYLASMLLHHSGSRSSFPPQSSSEREKMQKAAQVHHPRDRDSGRKR PTRRKRSPRRGRRRRRGSSSSESSESSESSTSNSSMSQYNSPKPKRTST (SEQ ID NO: 853) |

TABLE N4

| Novel *Anellovirus* nucleic acid sequence (*Alphatorquevirus*) | |
|---|---|
| Name | TTV-RTx4 |
| Genus/Clade | *Alphatorquevirus*, Clade 4 |
| Accession Number | SRR3481579 |
| Full Sequence: 3742 bp | |

```
1        10        20        30        40        50
|         |         |         |         |         |
AAAGTGCTACGTCACTAACCACGTGACACCCACAGGCCAACCGAATGCTA
TGTCGTGCACTTCCTGGGCCGGGTCTACGTCCTCATATAACTACCTGCAC
TTCCGAATGGCTGAGTTTTCCACGCCCGTCCGCAGCGGTGAAGCCACGGA
GGGAGATCAGCGCGTCCCGAGGGCGGGTGCCGAAGGTGAGTTTACACACC
GAAGTCAAGGGGCAATTCGGGCTCGGGACTGGCCGGGCTATGGGCAAGGC
TCTGAAAAAAGCATGTTTATTGGCAGGCATTACAGAAAGAAAAGGGCGCT
GCCACTGTGTGCTGTGCGATCAACAAAGAAGGCTTGCAAACTACTAATAG
TAATGTGGACCCCACCTCGCAATGACCAACAGTACCTTAACTGGCAATGG
TACTCAAGTATACTTAGCTCCCACGCTGCTATGTGCGGGTGTCCCGACGT
TGTTGCTCATTTTAATCATCTTGCTTCTGTGCTTCGCGCCCCGCAAAATC
CACCCCCACCCGGTCCCCAGCGAAACCTGCCCCTCCGACGGCTGCCGGCT
CTCCCGGCTGCGCCAGAGGCGCCCGGAGATAGAGCACCATGGCCTATGGC
TGGTGGCGCCGGAGGAGAAGACGGTGGCGCAGGTGGAGACGCAGACCATG
GAGGCGCCGCTGGAGGACCAGAAGACGCAGACCTGTTAGACGCCGTGGCC
GCCGCAGAAACGTAAGGAGACGCCGCAGAGGAGGGAGGTGGAGGAGGAGG
TACAGGAGATGGAAAAGAAAGGGCAGACGCAGAAAAAAAGCTAAAATAAT
AATAAGACAATGGCAACCTAACTACAGAAGGAGATGTAACATAGTAGGCT
ATATTCCTGTACTGATATGTGGCGAAAATACTGTCAGCAGAAACTATGCC
ACACACTCAGACGATACTAACTACCCAGGACCCTTTGGGGGGGGTATGAC
TACAGACAAATTTACCTTAAGAATTCTGTATGACGAGTACAAAAGGTTTA
TGAACTATTGGACAGCATCTAATGAAGACCTAGACCTCTGTAGATATCTA
GGAGTAAACCTGTACTTTTTTAGACACCCAGAAGTAGACTTTATTATAAA
AATAAATACCATGCCCCCTTTTCTAGACACAGAACTAACAGCTCCTAGCA
TACACCCAGGAATGCTAGCCTTAGACAAAAGAGCAAGATGGATACCTAGC
TTAAAATCTAGACCAGGAAAAAAACACTATATTAAAATAAGAGTAGGGGC
```

TABLE N4-continued

| Novel *Anellovirus* nucleic acid sequence (*Alphatorquevirus*) |
| --- |
| GCCTAAAATGTTCACAGATAAATGGTACCCCCAAACAGATCTTTGTGACA<br>TGGTGCTGCTAACTGTCTATGCAACCGCAGCGGATATGCAATATCCGTTC<br>GGCTCACCACTAACTGACTCTGTGGTTGTGAACTTCCAGGTTCTGCAATC<br>CATGTATGATGAAACCATTAGCATATTACCAGATCAAAAGGAGAAAAGAA<br>TAACGCTGCTCACTAGTATAGCCTTTTATAACACCACACAAACTATAGCC<br>CAATTAAAGCCATTTATAGATGCAGGCAATATGACTTCAACTACAACAGC<br>AACAACATGGGGATCATACATAAACACAACCAAATTTAATACAGCAGCCA<br>CTACAACATACACATACCCAGGCAGTACTACAACTACAGTAACTATGTTA<br>ACTTGTAATGACTCCTGGTACAGAGGAACAGTATATAACGACCAAATTAA<br>AAATTTACCAAAGGAAGCAGCTCAATTATACTTAAAAGCAACAAAAACCT<br>TACTAGGAAACACCTTCACAAATGACGACCACACACTAGAATACCATGGA<br>GGACTGTACAGCTCAATTTGGCTGTCCCCCGGCAGATCTTACTTTGAAAC<br>ACCAGGAGCATACACAGACATAAAATACAACCCATTTACAGACAGAGGAG<br>AAGGAAACATGCTATGGATAGACTGGCTAAGCAAAAAAAATATGAACTAT<br>GACAAACTACAAAGTAAATGTTTAATATCAGACCTACCTTTATGGGCAGC<br>AGCATATGGATATTTAGAATTTTGTGCAAAAAGTACAGGAGACCAAAATA<br>TACACATGAATGCCAGACTACTAATAAGAAGTCCCTTTACAGACCCCCAA<br>CTACTAGTACACACAAACCCCACAAAAGGCTTTGTTCCCTACTCTTTAAA<br>CTTTGGAAATGGTAAAATGCCAGGAGGTAGTAGTAATGTTCCTATTAGAA<br>TGAGAGCTAAATGGTATCCAACATTGTTTCACCAGCAAGAAGTACTAGAG<br>GCCTTAGCACAGTCAGGCCCCTTTGCATACCACTCAGACATTAAAAAAGT<br>ATCTCTGGGTATGAAATACCGTTTTAAGTGGATCTGGGGTGGAAACCCCG<br>TTCGCCAACAGGTTGTTAGAAATCCCTGCAAAGACTCCCACTCCTCGGTC<br>AATAGAGTCCCTAGAAGCTTACAAATCGTTGACCCGAAATACAACTCACC<br>GGAACTCACATTCCATACGTGGGACTTCAGACGTGGCCTCTTTGGCCAGA<br>AAGCTATTGAGAGAATGCAACAACAACCAACAACTACTGACATTTTTTCA<br>GCAGGCCGCAAGAGACCCAGGAGGGACACCGAGGTGTACCACTCCAGCCA<br>AGAAGGGGAGCAAAAAGAAAGCTTACTTTTCCCCCCAGTCAAGCTCCTCA<br>GACGAGTCCCCCCGTGGGAAGACTCGCAGCAGGAGGAAAGCGGGTCGCAA<br>AGCTCAGAGGAAGAGACGCAGACCGTCTCCCAGCAGCTCAAGCAGCAGCT<br>GCAGCAACAGCGAATCCTGGGAGTCAAACTCATACTCCTGTTCAACCAAG<br>TCCAAAAAATCCAACAAAATCAAGATATCAACCCTACCTTGTTACCAAGG<br>GGGGGGGATCTAGCATCCTTATTTCAAATAGCACCATAAACATGTTTGGA<br>GACCCCAAACCTTACAACCCTTCCAGTAATGACTGGAAAGAGGAGTATGA<br>GGCCTGTAGAATATGGGACAGACCCCCAAGAGGCAATCTAAGAGACACCC<br>CCTTTTACCCCTGGGCCCCCAAAGAAAACCAGTACCGTGTAAACTTTAAA<br>CTTGGATTTCAATAAAGCTAGGCCGTGGGACTTTCACTTGTCGGTGTCTG<br>CTTATAAAAGTAACCAAGCACTCCGAGCGAAGCGAGGAGTGCGACCCTTG<br>GGGGCTCAACGACTTCGGAGCCGCGCGTTAAGCCTTCGGCTGCGCGCGGC<br>ACCTCAGACCCCCGCTCGTGCTGACACGCTTGCGCGTGTCAGACCACTTC<br>GGGCTCGCGGGGGTCGGGAAATTTATTAAACAGACTCCGAGTTGCCATTG<br>GACACAGTAGTCTATGAACAGCAACGAAAGTGAGTGGGGCCAGACTTCGC<br>CATAAGGCCTTTATCTTCTTGCCATTTGTCAGTATAGAGGGTCGCCATAG<br>GCTTCGGTCTCCATTTTAACCTGTAAAAACTACCAAAATGGCCGTTCCAG<br>TGACGTGACAGCCGCCATTTTAAGTAGCTGACGTCAAGGATTGACGTAAA<br>GGTTAAAGGTCATCCTCGGCGGAAGCTACACAAAATGGTGGACAACATCT<br>TCCGGGTCAAAGGTCGTGCACACGTCAAAAGTCACGTGGTGGGGACCCGC<br>TGTAACCCGGAAGTAGGCCCCGTCACGTGATTTGTCACGTGTGTACACGT<br>CACAGCCGCCATTTTGTTTTACAAAATGGCTGACTTCCTTCCTCTTTTTT<br>GAAAAAAGGCGCCAAAAAAGGCTCCGCCCCCCGGCCCCCCCC (SEQ ID NO: 854) |

Annotations:

| Putative Domain | Base range |
| --- | --- |
| TATA Box | 86-90 |
| Initiator Element | 104-119 |
| Transcriptional Start Site | 114 |
| 5' UTR Conserved Domain | 174-244 |
| ORF2 | 353-715 |
| ORF2/2 | 353-711; 2362-2863 |
| ORF2/3 | 353-711; 2555-3065 |
| ORF2t/3 | 353-432; 2555-3065 |
| ORF1 | 589-2889 |
| ORF1/1 | 589-711; 2362-2889 |
| ORF1/2 | 589-711; 2555-2863 |

TABLE N4-continued

| Novel *Anellovirus* nucleic acid sequence (*Alphatorquevirus*) | |
|---|---|
| Three open-reading frame region | 2555-2863 |
| Poly(A) Signal | 3062-3066 |
| GC-rich region, or a portion thereof** | 3720-3742 |

TABLE A4

| Novel *Anellovirus* amino acid sequences (*Alphatorquevirus*, Clade 4) TTV-RTx4 (*Alphatorquevirus* Clade 4) | |
|---|---|
| ORF2 | MWTPPRNDQQYLNWQWYSSILSSHAAMCGCPDVVAHFNHLASVLRAPQN PPPPGPQRNLPLRRLPALPAAPEAPGDRAPWPMAGGAGGEDGGAGGDADH GGAAGGPEDADLLDAVAAAET (SEQ ID NO: 855) |
| ORF2/2 | MWTPPRNDQQYLNWQWYSSILSSHAAMCGCPDVVAHFNHLASVLRAPQN PPPPGPQRNLPLRRLPALPAAPEAPGDRAPWPMAGGAGGEDGGAGGDADH GGAAGGPEDADLLDAVAAAETLLEIPAKTPTPRSIESLEAYKSLTRNTTHRN SHSIRGTSDVASLARKLLRECNNNQQLLTFFQQAARDPGGTPRCTTPAKKGS KKKAYFSPQSSSSDESPRGKTRSRRKAGRKAQRKRRPSPSSSSSSCSNSESW ESNSYSCSTKSKKSNKIKISTLPCYQGGGI (SEQ ID NO: 856) |
| ORF2/3 | MWTPPRNDQQYLNWQWYSSILSSHAAMCGCPDVVAHFNHLASVLRAPQN PPPPGPQRNLPLRRLPALPAAPEAPGDRAPWPMAGGAGGEDGGAGGDADH GGAAGGPEDADLLDAVAAAETPQETQEGHRGVPLQPRRGAKRKLTFPPSQ APQTSPPVGRLAAGGKRVAKLRGRDADRLPAAQAAAAATANPGSQTHTPV QPSPKNPTKSRYQPYLVTKGGGSSILISNSTINMFGDPKPYNPSSNDWKEEYE ACRIWDRPPRGNLRDTPFYPWAPKENQYRVNFKLGFQ (SEQ ID NO: 857) |
| ORF2t/3 | MWTPPRNDQQYLNWQWYSSILSSHAAMPQETQEGHRGVPLQPRRGAKRK LTFPPSQAPQTSPPVGRLAAGGKRVAKLRGRDADRLPAAQAAAAATANPGS QTHTPVQPSPKNPTKSRYQPYLVTKGGGSSILISNSTINMFGDPKPYNPSSND WKEEYEACRIWDRPPRGNLRDTPFYPWAPKENQYRVNFKLGFQ (SEQ ID NO: 858) |
| ORF1 | MAYGWWRRRRRRWRRWRRRPWRRRWRTRRRRPVRRRGRRRNVRRRRR GGRWRRRYRRWKRKGRRRKKAKIIIRQWQPNYRRRCNIVGYIPVLICGENT VSRNYATHSDDTNYPGPFGGGMTTDKFTLRILYDEYKRFMNYWTASNEDL DLCRYLGVNLYFFRHPEVDFIIKINTMPPFLDTELTAPSIHPGMLALDKRARW IPSLKSRPGKKHYIKIRVGAPKMFTDKWYPQTDLCDMVLLTVYATAADMQ YPFGSPLTDSVVVNFQVLQSMYDETISILPDQKEKRITLLTSIAFYNTTQTIAQ LKPFIDAGNMTSTTTATTWGSYINTTKFNTAATTTYTYPGSTTTTVTMLTCN DSWYRGTVYNDQIKNLPKEAAQLYLKATKTLLGNTFINDDHTLEYHGGLY SSIWLSPGRSYFETPGAYTDIKYNPFTDRGEGNMLWIDWLSKKNMNYDKLQ SKCLISDLPLWAAAYGYLEFCAKSTGDQNIHMNARLLIRSPFTDPQLLVHTN PTKGFVPYSLNFGNGKMPGGSSNVPIRMRAKWYPTLFHQQEVLEALAQSGP FAYHSDIKKVSLGMKYRFKWIWGGNPVRQQVVRNPCKDSHSSVNRVPRSL QIVDPKYNSPELTFHTWDFRRGLFGQKAIERMQQQPTTTDIFSAGRKRPRRD TEVYHSSQEGEQKESLLFPPVKLLRRVPPWEDSQQEESGSQSSEEETQTVSQ QLKQQLQQQRILGVKLILLFNQVQKIQQNQDINPTLLPRGGDLASLFQIAP (SEQ ID NO: 859) |
| ORF1/1 | MAYGWWRRRRRRWRRWRRRPWRRRWRTRRRRPVRRRGRRRNVVRNPC KDSHSSVNRVPRSLQIVDPKYNSPELTFHTWDFRRGLFGQKAIERMQQQPTT TDIFSAGRKRPRRDTEVYHSSQEGEQKESLLFPPVKLLRRVPPWEDSQQEES GSQSSEEETQTVSQQLKQQLQQQRILGVKLILLFNQVQKIQQNQDINPTLLPR GGDLASLFQIAP (SEQ ID NO: 860) |
| ORF1/2 | MAYGWWRRRRRRWRRWRRRPWRRRWRTRRRRPVRRRGRRRNAARDPG GTPRCTTPAKKGSKKKAYFSPQSSSSDESPRGKTRSRRKAGRKAQRKRRPS PSSSSSSCSNSESWESNSYSCSTKSKKSNKIKISTLPCYQGGGI (SEQ ID NO: 861) |

TABLE N5

| Novel *Anellovirus* nucleic acid sequence (*Alphatorquevirus*) | |
|---|---|
| Name | TTV-RTx5b |
| Genus/Clade | *Alphatorquevirus*, Clade 5 |
| Accession Number | SRR3481639 |
| Full Sequence: 3553 bp | |

TABLE N5-continued

Novel *Anellovirus* nucleic acid sequence (*Alphatorquevirus*)

```
1         10         20         30         40         50
|         |          |          |          |          |
ATACCTCATCATATAAAGCGGCGCACTTCCGAATGGCTGAGTTTTCCACG
CCCGTCCGCAGCGAGATCGCGACGGAGGAGCGATCGAGCGTCCCGAGGGC
GGGTGCCGGAGGTGAGTTTACACACCGCAGTCAAGGGGCAATTCGGGCTC
GGGACTGGCCGGGCTATGGGGCAAGACTCTTAAAAAAGCCATGTTTCTCG
GTAAACTTTACAGAAAGAAAAGGGCACTGTCACTGCTACGCGTGCGAGCT
CCAGAGGCGAAACCACCTGCTATGAGTTGGAGACCCCCGGTGCACAACCC
CAATGGGATCGAGAGAAACCTGTGGGAGGCATTCTTTCGCATGCATGCTT
CAGCTTGTGGTTGTGGCGATCTTGTTGGCCATCTTACTGTACTGGCTGGT
CGGTATGGTGCTCCTCCTCGTCCCCCGGCCCCCGGCGCTCCCAGACCACC
GCTGATACGCCAGCTGGCCCTTCCGGCGCCCCCCGCCGATCCTCAACAGG
CTAACCCACAATGGCCTGGTGGGGACGGTGGAGAAGATGGCGCTGGAGGC
CCCGCCGCTGGCGGCGCCGTCGCAGACGCCGAGTACCAAGAAGACGAGCT
CAACGCCCTGTTCGACGCCGTCGAGCAAGAAGAGTAAGGAGGAGGCGATG
GGGGAGGCGGAGGTGGAGACGGGGGTACAGACGCAGACTGAGACTAAGAC
GCAGACGCAGACGAAAGCGAAAGATAGTACTAACTCAGTGGAATCCCGCC
AAAGTGCGGAGGTGTACTATTAAGGGAGTTCTGCCCATGATCCTGTGCGG
GGCCGGGCGCTCGGGGITTAACTACGGACTGCACAGCGACGACTACACTG
TACAGAAGCCCCTTGGCCAGAACCCCCACGGGGGCGGCATGAGTACAGTG
ACTTTTAGCCTACAGGTGCTCTATGACCAGTACCAGAGGTTTATGAACAA
GTGGTCGTACTCCAACGACCAGCTAGACCTCGCCAGGTACTTTGGCTGCA
CCTTCTGGTTCTACAGACACCCAGAGGTGGACTTTGTAGCTCAGTTTGAC
AACGTTCCCCCCATGAAAATGGACGAGAACACAGCCCCAAACACTCATCC
CTCTTTCTTACTACAGAACAAACACAAGGTTAAAATTCCCAGCTTTAAAA
CAAAGCCTTTTGGTAAAAAAAGAGTTAGAGTTACAGTAGGGCCCCCCAAA
CTGTTTGAAGATAAGTGGTACAGCCAACATGACTTGTGTAAGGTGCCCCT
AGTCAGTTGGCGGTTAACCGCAGCTGACTTCAGGTTTCCGTTCTGCTCAC
CACAAACTGACAACCCTTGCTACACCTTCCAGGTATTGCATGAAGAGTAT
TACCCAGTAATAGGCACTTCTGCTTTAGAAAACGGCAGTAACTACAATAG
CTCAGCTATAACAGCCTTAGAAAAATTCTTATATGAAAAATGCACACACT
ATCAAACATTTGCCACAGACACCAGACTTAATCCTCAGCGACCAGTGTCA
TCTACAAATGCAAACAAAACATACACCCCCTCAGGCTCCCAAGAAACAAT
AGTGTGGGGGCAGTCAGATTTTAATTTATTTAAAAAGCACACAGACAGCA
ACTATGGCTACTGCACCTACTGTCCTACCAATGACTTAGCTACAAAAATT
AAAAAGTACAGAGACAAAAGATTCGACTGGCTAACAAACATGCCAGTAAC
AAACACCTGCCACATAAATGCCACCTTCGCCCGAGGCAAAATTAAAGAAT
GGGAGTACCACCTAGGGTGGTTCTCAAACATCTTTATAGGCAACCTGAGA
CACAACCTAGCATTCCGGGCCGCATACATAGACATCACCTANACAGACAA
GGGAGAAGGCAACATTATCTGGTTCCAGTACCTCACTAAACCCACCACAG
AGTACATAGAAGCCCAAGCAAAGTGCTCCATCACAAACATACCCCTGTAT
GCTGCTTTTTATGGCTACGAAGACTACCTCCAGAGAACACTAGGCCCCTA
CCAAGATGTAGAAACCCTAGGTATAATCTGTGTTAAATGTCCCTACACAG
ATCCCCCTCTAGITCACAAGTCTACAGATAAAAAGAACTGGGGCTACGTG
TTCTACGACGTGCACTTTGGCAACGGAAAGACCCCAGAGGGACTGGGCCA
GGTGCACCCTTACTGGATGCAGAGGTGGAGACCCTACGTACAGTTTCAGA
AAGACACTATGAACAAAATAGCCAGGACGGGACCGTTCAGCTACAGAGAC
GAGACGCCTTCCATCACCCTGACCGCCGGGTACAAGTTTCATTTTAACTG
GGGGGGCGACTCTATATTTCCACAGATTATTAAAAACCCCTGCCCAGACA
GCGGGGTACGACCTTCATCCAGTAGAGAGCGTCGCTCAGTACAAGTCGTT
AGCCCGCTCACAATGGGGCCAGAGTACATATTCCACCGGTGGGACTGGCG
ACGGGGGTTCTTTAATCAAAAAGCTCTCAAAAGAATGCTTGAAAAATCAA
TTAATGATGGAGAGTATCCAACAGGCCCAAAGGTCCCTCGATGGTTTCCC
CCACTCGACAACCAAGAGCAAGAAGGCGCCTCAGGTTCAGAGGAGACAAG
GTCGCAGTCCTCGCAAGAAGAAGCCGCTCAAGAAGCCCTCCAAGAAGTCC
AAGAGGCGTCGCTACAGCAGCACCTCCTCCAGCAGTACCGAGAGCAGCGA
CGGATCGGAAAGCAACTCCAACTCGTCATGCTGCAGCTCACCAAGACGCA
GAGCAACCTGCACATAAACCCCCGTGTTCTTGGCCATGCATAAATAAAGT
CTACATGTTTCCCCCCGACAAGCCCATGCCCATACACGGGTACCACGGGT
GGGAGACGGAGTACCAGGCCTGCAAGGCCTTCAACAGGCCCCCCAGAAAC
TACCTTTCAGACAAACCCATCTACCCTTGGCTCCCTCGCCCCGAACCCGA
AATAATAGTGAGCTTTAGGTTCGGTTTCAAATAAACAAGGCCGCAAATAA
ACAAGGCCGTGGGAGTTTCACTGGTCGGTGTCTACCTCTTAAGGTCACTA
AGCACTCCGAGCGTTAGCGAGGAGTGCGACCCTTCCCCCTGGTGCCACGC
CCTCGGCGGCCGCGCGCTACGCCTNNNNNNNNNNNNNNNNNNNNNNNNNN
NNNNNNNNNNNNNNNNNNNNNNNNNNTGAATCAGTAACGAAAGTGAGTGG
GGCCAGACTTCGCCATAAGGCCTTTATCTTCTTGCCATTGGTCCGTGTGG
GGAGTCGCCATAGGCTTCGGGCTCGGTTTTAGGCCTTCCGGACTACAAAA
ACCGCCATTTTAGTGACGTCACGGCGGCCATTTTAAGTAAGCATGGCGGG
CGGTGACGTACAAGTTGAAAGGTCACCGCGCTTCCGTGTTTACTCAAAAT
GGTGGCCAACTGCTTCCGGGTCAAAGGTCGGCGGCCACGTCATAAGTCAC
GTGGGAGGGCTGCGTCACAAACACGGAAGTGGCTGTCCCACGTGACTTGT
CACGTGATTGCTACGTCACGGCCGCCATTTTAGTTCACAAAATGGCGGAC
TTC (SEQ ID NO: 862)
```

TABLE N5-continued

| Novel *Anellovirus* nucleic acid sequence (*Alphatorquevirus*) | |
|---|---|
| Annotations: | |
| Putative Domain | Base range |
| TATA Box | 12-17 |
| Initiator Element | 30-45 |
| Transcriptional Start Site | 40 |
| 5' UTR Conserved Domain | 100-171 |
| ORF2 | 272-637 |
| ORF2/2 | 272-633; 2326-2767 |
| ORF2/3 | 272-633; 2525-2984 |
| ORF2t/3 | 272-633; 2525-2984 |
| ORF1 | 511-2793 |
| ORF1/1 | 511-711; 2326-2793 |
| ORF1/2 | 511-711; 2525-2767 |
| Three open-reading frame region | 2525-2767 |
| Poly(A) Signal | 2981-2985 |
| Unknown sequence | 3125-3176 |

*Note:
Modifications made to maintain reading frames:
-"C" inserted into ORF2 430
-"N" inserted into ORF1 1842

TABLE A5

| Novel *Anellovirus* amino acid sequences (*Alphatorquevirus*, Clade 5) TTV-RTx5b (*Alphatorquevirus* Clade 5) | |
|---|---|
| ORF2 | MSWRPPVHNPNGIERNLWEAFFRMHASACGCGDLVGHLTVLAGRYGAPPR PPAPGAPRPPLIRQLALPAPPADPQQANPQWPGGDGGEDGAGGPAAGGAVA DAEYQEDELNALFDAVEQEE (SEQ ID NO: 863) |
| ORF2/2 | MSWRPPVHNPNGIERNLWEAFFRMHASACGCGDLVGHLTVLAGRYGAPPR PPAPGAPRPPLIRQLALPAPPADPQQANPQWPGGDGGEDGAGGPAAGGAVA DAEYQEDELNALFDAVEQEELLKTPAQTAGYDLHPVESVAQYKSLARSQW GQSTYSTGGTGDGGSLIKKLSKECLKNQLMMESIQQAQRSLDGFPHSTTKSK KAPQVQRRQGRSPRKKKPLKKPSKKSKRRRYSSTSSSSTESSDGSESNSNSSC CSSPRRRATCT (SEQ ID NO: 864) |
| ORF2/3 | MSWRPPVHNPNGIERNLWEAFFRMHASACGCGDLVGHLTVLAGRYGAPPR PPAPGAPRPPLIRQLALPAPPADPQQANPQWPGGDGGEDGAGGPAAGGAVA DAEYQEDELNALFDAVEQEEPKGPSMVSPTRQPRARRRLRFRGDKVAVLAR RSRSRSPPRSPRGVATAAPPPAVPRAATDRKATPTRHAAAHQDAEQPAHKP PCSWPCINKVYMFPPDKPMPIHGYHGWETEYQACKAFNRPPRNYLSDKPIY PWLPRPEPEIIVSFRFGFK (SEQ ID NO: 865) |
| ORF2t/3 | MSWRPPVHNPNGIERNLWEAFFRMHASACGCGDLVGHLTVLAGRPKGPSM VSPTRQPRARRRLRFRGDKVAVLARRSRSRSPPRSPRGVATAAPPPAVPRAA TDRKATPTRHAAAHQDAEQPAHKPPCSWPCINKVYMFPPDKPMPIHGYHG WETEYQACKAFNRPPRNYLSDKPIYPWLPRPEPEIIVSFRFGFK (SEQ ID NO: 866) |
| ORF1 | MAWWGRWRRWRWRPRRWRRRRRRRVPRRRAQRPVRRRRARRVRRRRW GRRRWRRGYRRRLRLRRRRRRKRKIVLTQWNPAKVRRCTIKGVLPMILCG AGRSGFNYGLHSDDYTVQKPLGQNPHGGGMSTVTFSLQVLYDQYQRFMN KWSYSNDQLDLARYFGCTFWFYRHPEVDFVAQFDNVPPMKMDENTAPNT HPSFLLQNKHKVKIPSFKTKPFGKKRVRVTVGPPKLFEDKWYSQHDLCKVP LVSWRLTAADFRFPFCSPQTDNPCYTFQVLHEEYYPVIGTSALENGSNYNSS AITALEKFLYEKCTHYQTFATDTRLNPQRPVSSTNANKTYTPSGSQETIVWG QSDFNLFKKHTDSNYGYCTYCPTNDLATKIKKYRDKRFDWLTNMPVTNTC HINATFARGKIKEWEYHLGWFSNIFIGNLRHNLAFRAAYIDITXTDKGEGNII WFQYLTKPTTEYIEAQAKCSITNIPLYAAFYGYEDYLQRTLGPYQDVETLGII |

TABLE A5-continued

| Novel *Anellovirus* amino acid sequences (*Alphatorquevirus*, Clade 5)<br>TTV-RTx5b (*Alphatorquevirus* Clade 5) | |
|---|---|
| | CVKCPYTDPPLVHKSTDKKNWGYVFYDVHFGNGKTPEGLGQVHPYWMQR WRPYVQFQKDTMNKIARTGPFSYRDETPSITLTAGYKFHFNWGGDSIFPQIIK NPCPDSGVRPSSSRERRSVQVVSPLTMGPEYIFHRWDWRRGFFNQKALKRM LEKSINDGEYPTGPKVPRWFPPLDNQEQEGASGSEETRSQSSQEEAAQEALQ EVQEASLQQHLLQQYREQRRIGKQLQLVMLQLTKTQSNLHINPRVLGHA (SEQ ID NO: 867) |
| ORF1/1 | MAWWGRWRRWRWRPRRWRRRRRRRVPRRRAQRPVRRRRARRIIKNPCPD SGVRPSSSRERRSVQVVSPLTMGPEYIFHRWDWRRGFFNQKALKRMLEKSI NDGEYPTGPKVPRWFPPLDNQEQEGASGSEETRSQSSQEEAAQEALQEVQE ASLQQHLLQQYREQRRIGKQLQLVMLQLTKTQSNLHINPRVLGHA (SEQ ID NO: 868) |
| ORF1/2 | MAWWGRWRRWRWRPRRWRRRRRRRVPRRRAQRPVRRRRARRAQRSLDG FPHSTTKSKKAPQVQRRQGRSPRKKKPLKKPSKKSKRRRYSSTSSSSTESSD GSESNSNSSCCSSPRRRATCT (SEQ ID NO: 869) |

TABLE N6

Novel *Anellovirus* nucleic acid sequence (*Alphatorquevirus*)

| | |
|---|---|
| Name | TTV-RTx6 |
| Genus/Clade | *Alphatorquevirus*, Clade 5 |
| Accession Number | SRR3438066 |
| Full Sequence: 3896 bp | |

```
1        10        20        30        40        50
|         |         |         |         |         |
TAAACTTCCTCTTTTAATAGGAAACCACAAAATTTGCATTGCCGACCACA
AACGCATATGCAAATTTACTTCCCCAAAAACTCAACCACAAAATTTGCAT
TGCCGCCCACAAACGTCTACTTTAACCACATCCTCTAACATGTTAGAAAC
TCCACCCAACTACTTCATTAGTATACAGCATCACAAGGGAGGAGCCAAAC
AACTATATAACCAAGTGTACTTCCGAATGGCTGAGTTTATGCCGCCAGAC
GGAGACGGGATCGCGACGGAGGAGCGATCGAGCGTCCCGAGGGCGGGTGC
CGGAGGTGAGTTTACACACCGCAGTCAAGGGGCAATTCGGGCTCGGGACT
GGCCGGGCTATGGGCAAGGCTCTTAAAAAAGCCATGTTTCTCGGTCGACC
TTACAGAAAGAAAAGGGCACTGTCACTGCTACGCGTGCGAGCTCCAGAGG
CGAAACCACCTGCTATGAGCTGGAGGCCCCCGGTGCACAACCCTAATGGG
ATCCAGAGAAACCTGTGGGAGGCATTCTTTCGCATGCATGCTGCAGCTTG
TGGTTGTGGCGATCTTGTTGGCCATATTACTGTACTGGCTGGTCGGTATG
GTGCTCCTCCTCGTCCCCCGGCCCCCGGGGCTCCCAGACCACCGCTGATA
CGCCAGCTGGCCCTTCCGGCGCCCCCCGCCGATCCTCAACAGGCTAACCC
ACAATGGCCTGGTGGGGACGGTGGAGAAGATGGCGCTGGAGGCCCCGCCG
CTGGCGGCGCCGTCGCAGACGCCGAGTACCAAGAAGACGAGCTCAACGCC
CTGTTCGACGCCGTCGAGCAAGAAGAGTAAGGAGGAGGCGATGGGGGAGG
CGGAGGTGGAGACGGGGGTACAGACGCAGACTAAGACTGAGACGCAGACG
CAGACGAAAGAAAATAAGACTGACTCAGTGGAACCCAGCCAAAGTCAGGA
GATGTACTATTAAGGGGGTGCTACCCATGATCTTATGCGGCGCCGGCCGC
TCGGGGTTTAACTATGGACTGCACAGCGACGACTACACGGTGCAGAAACC
CCTGGGGCAGAACCCCCACGGGGGCGGCATGAGCACAGTAACTTTTAGCC
TACAAGTACTATTTGACCAGTACCAGAGGTTTATGAACCGGTGGTCGTAC
TCCAACGACCAGCTAGACCTCGCCAGGTACTTTGGCTGCACCTTCTACTT
TTACAGACACCCTGAAATTGACTTTGTAGCTCAGTATGACAATGTACCCC
CAATGAAAATGGACGAGAACACGGCNCCTAACACTCACCCCTCTTTTCTA
CTACAAAACAAACGCAAAATTAAAATCCCCAGCTTTAAAACCAAGCCATT
TGGCAGAAAAAGAGTAAAAGTAACAGTGGGGCCCCCCAAACTGTTTGAAG
ATAAATGGTACAGCCAGCATGACTTGTGTAAGGTGCCCCTAGTCAGTTGG
CGGTTAACCGCATGTGACTTCAGGTTTCCGTTCTGCTCACCACTAACTGA
CAACCCTTGCTACACCTTCCAGGTATTGCATGAAAACTATTACCCAGTCA
TAGGCACTTCCTCTTTAGAAAACGGTACAAACTACAATAACACTGCTATA
ACTACCCTTGAGACATGGCTATATGGAAAATGCACACACTATCAAACATT
TGCCACAGACACCAGACTTAATCCACAGAGACCTGTATCTTCAAGTAATG
CAAATGAAACTTATACTCCTAGTGGTTCTAAAGAATCAATAATATGGGGA
CAGTCTGACTGGGCAAACTTTAAAAAGAACACAGACAGCAACTATGGCTA
CTGTTCCTACTGCCCCTCAAATGGCACTAACGGAACAGTAGATAAAATTA
AAAAATACAGAGACCAAAGATTTAGATGGCTTACAGAAATGCCAGTACCT
AACACCTGTCACATACATGCCACCTTCGCCCGAGGCACTATTAAATACTG
GGAGTACCACCTAGGCTGGTACTCAAACATATTTATTGGCAACCTCAGAC
ACAACTTAGCCTTCAGACCAGCCTACATAGACATTACCTACAATCCCATC
ACTGACAAAGGAGAGGGCAACATTATCTGGTTCCAGTACCTCACTAAGCC
CACCACAGAATACATAGAAACCCAGGCAAAATGCACCATTACTAACATTC
CCCTTTATGCTGCTTTCTATGGCTACGAAGACTACCTCCAGAGAACACTA
GGCCCCTACCAAGATGTAGAAACCCTAGGCATAATCTGTGTTAAATGTCC
CTACACAGATCCCCCTCTAGTTCACAAAGACAAAAGTAAAACCAACTGGG
```

TABLE N6-continued

| Novel *Anellovirus* nucleic acid sequence (*Alphatorquevirus*) |
|---|
| GCTACGTATTCTACGACGCCCACTTTGGCAACGGAAAGACCCCAGAGGGA<br>CTAGGCCAAGTACACCCTTACTGGATGCAGAGATGGAGACCCTATGTACA<br>GTTTCAAAAAGACACCATGCACAAAATATCCAGAACGGGACCCTTCAGCT<br>ACAGAGACGACACGCCTTCCATCACCCTCACTGCCGAATACAAGTTTCGT<br>TTTAACTGGGGGGGCGACTCTATATTTCCACAGATTATTAAAAACCCCTG<br>CCCAGACACCGGGGTTCGACCTTCAACCGGTAGAGACCGTCGCTCAGTAC<br>AAGTCGTTAGCCCGCTCACAATGGGACCCCAGTTTATATTCCACTCATGG<br>GACTGGAGACGGGGGTTCTTTAATCAAAAAACTCTCAAAAGAATGCTTGA<br>AAAACCAGTTAATGATGGAGAATATCCAACAGGCCCAAAGGTGCCTCGAT<br>GGTTTCCCCCACTCGACAACCAAGAGCAAGAAGGCGTCTCAGATACAGAG<br>ACGACAACCTCGCAGTCCTCGCAAGAAGAAGCCGCTCAAGAAGCCCTCCA<br>AGAAGTCCAAGAGGCGTCGCTACAGCAGCACCTCCTCCAGCAGTACCGAG<br>AGCAGCGAAGAATCGGAAAGCAACTCCAACTCGTCATGCTCCAACTCACC<br>AAGACGCAGAGCAACCTGCACATAAATCCCCGTGTCCTTGGCCATGCATA<br>AATAAAGTGTACATGTTTCCCCCCGAAAAGCCAATGCCCATACACGGCTA<br>CCACGGGTGGGAGACAGAGTATCAGGCCTGCAAGGCCTTTGACAGGCCCC<br>CTAGAAACTACCTATCAGACAAACCCATCTACCCCTGGCTTCCCCGCTCC<br>CAACCAGAATTTAAAGTGAGTTTAAGCTTGGCTGTCAATAAACAAGNNN<br>NNNNNNNNNNNNNNNNNNNNNNNNNNNNNNNNNNNNNNNNNNNNNNNNNN<br>NNNNNNNNNNNNNNNNNNNNNNNNNNNNNNNNNNNNNNNNNNNNNNNNNN<br>NNNNNNNNNNNNNNNNNNNNNNNNNNNNNNNNNNNNNNNNNNNNNNNNNN<br>NNNNNNNNNNNNNNNNNNNNNNNNNNNNNNNNNNNNNNNNNNNNNNNNNN<br>NNNNNNNNNNNNNNNNNNNNNNNNNNNNNNNNNNNNNNNNNNNNNNNNNN<br>NNNNNNNNNNNNNNNNNNNNNNNNNNNNNNNNNNNNNNNNNNNNNNNNNN<br>NNNNNNNNNNNNNNNNNNNNNNNNNNNNNNNNNNNNNNNNNNNNNNNNNN<br>NNNNNNNNNNNNNNNNNNNNNNNNNNNNNNNNNNNNNNNNNNNNNNNNNN<br>NNNNNNNNNNNNNNNNNNNNNNNNNNNNNNNNNNNNNNNNNNNNNNNNNN<br>NNNNNGTTTACACAAAATGGTGGCCAAGTCCTTCCGGGTGAAAGGTCGGC<br>GCCTACGTCATAAGTCACGTGGGGAGGGCTGCGTCACAACCAGGAAGCAA<br>TCCTCACCACGTGATTTGTCACGTGATCGCTACGTCACGGCCGCCATTTT<br>AGTTTACAAAATGGCGGACTTCCTTCCTCTTTTTCAAAAATAACGGCCCT<br>GCGGCGGCGCGCGCGCTGCGCGCGCGCGCCGGGGGCTGCCGCCCCA (SEQ ID NO: 870) |

Annotations:

| Putative Domain | Base range |
|---|---|
| TATA Box | 206-210 |
| Initiator Element | 224-239 |
| Transcriptional Start Site | 234 |
| 5' UTR Conserved Domain | 294-364 |
| ORF2 | 465-830 |
| ORF2/2 | 465-826; 2534-2975 |
| ORF2/3 | 465-826; 2721-3192 |
| ORF2t/3 | 465-595; 2721-3192 |
| ORF1 | 704-3001 |
| ORF1/1 | 704-826; 2534-3001 |
| ORF1/2 | 704-826; 2721-2975 |
| Three open-reading frame region | 2721-2975 |
| Poly(A) Signal | 3189-3193 |
| Unknown sequence | 3198-3655 |
| GC-rich region, or a portion thereof** | 3844-3895 |

TABLE A6

| Novel *Anellovirus* amino acid sequences (*Alphatorquevirus*, Clade 5)<br>TTV-RTx6 (*Alphatorquevirus* Clade 5) | |
|---|---|
| ORF2 | MSWRPPVHNPNGIQRNLWEAFFRMHAAACGCGDLVGHITVLAGRYGAPPR<br>PPAPGAPRPPLIRQLALPAPPADPQQANPQWPGGDGGEDGAGGPAAGGAVA<br>DAEYQEDELNALFDAVEQEE (SEQ ID NO: 871) |

TABLE A6-continued

| Novel *Anellovirus* amino acid sequences (*Alphatorquevirus*, Clade 5) TTV-RTx6 (*Alphatorquevirus* Clade 5) | |
|---|---|
| ORF2/2 | MSWRPPVHNPNGIQRNLWEAFFRMHAAACGCGDLVGHITVLAGRYGAPPR PPAPGAPRPPLIRQLALPAPPADPQQANPQWPGGDGGEDGAGGPAAGGAVA DAEYQEDELNALFDAVEQEELLKTPAQTPGFDLQPVETVAQYKSLARSQW DPSLYSTHGTGDGGSLIKKLSKECLKNQLMMENIQQAQRCLDGFPHSTTKS KKASQIQRRQPRSPRKKKPLKKPSKKSKRRRYSSTSSSSTESSEESESNSNSSC SNSPRRRATCT (SEQ ID NO: 872) |
| ORF2/3 | MSWRPPVHNPNGIQRNLWEAFFRMHAAACGCGDLVGHITVLAGRYGAPPR PPAPGAPRPPLIRQLALPAPPADPQQANPQWPGGDGGEDGAGGPAAGGAVA DAEYQEDELNALFDAVEQEEISNRPKGASMVSPTRQPRARRRLRYRDDNLA VLARRSRSRSPPRSPRGVATAAPPPAVPRAAKNRKATPTRHAPTHQDAEQP AHKSPCPWPCINKVYMFPPEKPMPIHGYHGWETEYQACKAFDRPPRNYLSD KPIYPWLPRSQPEFKVSFKLGCQ (SEQ ID NO: 873) |
| ORF2t/3 | MSWRPPVHNPNGIQRNLWEAFFRMHAAACGCGDLVGHITVLAGRISNRPK GASMVSPTRQPRARRRLRYRDDNLAVLARRSRSRSPPRSPRGVATAAPPPA VPRAAKNRKATPTRHAPTHQDAEQPAHKSPCPWPCINKVYMFPPEKPMPIH GYHGWETEYQACKAFDRPPRNYLSDKPIYPWLPRSQPEFKVSFKLGCQ (SEQ ID NO: 874) |
| ORF1 | MAWWGRWRRWRWRPRRWRRRRRRRVPRRRAQRPVRRRRARRVRRRRW GRRRWRRGYRRRLRLRRRRRRKKIRLTQWNPAKVRRCTIKGVLPMILCGA GRSGFNYGLHSDDYTVQKPLGQNPHGGGMSTVTFSLQVLFDQYQRFMNR WSYSNDQLDLARYFGCTFYFYRHPEIDFVAQYDNVPPMKMDENTAPNTHP SFLLQNKRKIKIPSFKTKPFGRKRVKVTVGPPKLFEDKWYSQHDLCKVPLVS WRLTACDFRFPFCSPLTDNPCYTFQVLHENYYPVIGTSSLENGTNYNNTAIT TLETWLYGKCTHYQTFATDTRLNPQRPVSSSNANETYTPSGSKESIIWGQSD WANFKKNTDSNYGYCSYCPSNGTNGTVDKIKKYRDQRFRWLTEMPVPNTC HIHATFARGTIKYWEYHLGWYSNIFIGNLRHNLAFRPAYIDITYNPITDKGEG NIIWFQYLTKPTTEYIETQAKCTITNIPLYAAFYGYEDYLQRTLGPYQDVETL GIICVKCPYTDPPLVHKDKSKTNWGYVFYDAHFGNGKTPEGLGQVHPYWM QRWRPYVQFQKDTMHKISRTGPFSYRDDTPSITLTAEYKFRFNWGGDSIFPQ IIKNPCPDTGVRPSTGRDRRSVQVVSPLTMGPQFIFHSWDWRRGFFNQKTLK RMLEKPVNDGEYPTGPKVPRWFPPLDNQEQEGVSDTETTTSQSSQEEAAQE ALQEVQEASLQQHLLQQYREQRRIGKQLQLVMLQLTKTQSNLHINPRVLGH A (SEQ ID NO: 875) |
| ORF1/1 | MAWWGRWRRWRWRPRRWRRRRRRRVPRRRAQRPVRRRRARRIIKNPCPD TGVRPSTGRDRRSVQVVSPLTMGPQFIFHSWDWRRGFFNQKTLKRMLEKPV NDGEYPTGPKVPRWFPPLDNQEQEGVSDTETTTSQSSQEEAAQEALQEVQE ASLQQHLLQQYREQRRIGKQLQLVMLQLTKTQSNLHINPRVLGHA (SEQ ID NO: 876) |
| ORF1/2 | MAWWGRWRRWRWRPRRWRRRRRRRVPRRRAQRPVRRRRARRNIQQAQR CLDGFPHSTTKSKKASQIQRRQPRSPRKKKPLKKPSKKSKRRRYSSTSSSSTE SSEESESNSNSSCSNSPRRRATCT (SEQ ID NO: 877) |

TABLE N7

Exemplary *Anellovirus* nucleic acid sequence (*Alphatorquevirus*, Clade 1)

| | |
|---|---|
| Name | TTV-CT30F |
| Genus/Clade | *Alphatorquevirus*, Clade 1 |
| Accession Number | AB064597.1 |
| Full Sequence: 3570 bp | |

```
1         10         20         30         40         50
|         |          |          |          |          |
ATTTTGTGCAGCCCGCCAATTCTCGTTCAAACAGGCCAATCAGGAGGCTC
TACGTACACTTCCTGGGGTGTGTCTTCGAAGAGTATATAAGCAGAGGCGG
TGACGAATGGTAGAGTTTTTCCTGGCCCGTCCGCGGCGAGAGCGCGAGCG
GAGCGAGCGATCGAGCGTCCCGTGGGCGGGTGCCGTAGGTGAGTTTACAC
ACCGCAGTCAAGGGGCAATTCGGGCTCGGGACTGGCCGGGCTATGGGCAA
GATTCTTAAAAAATTCCCCCGATCCCTCTGTCGCCAGGACATAAAAACAT
GCCGTGGAGACCGCCGGTGCATAGTGTCCAGGGGCGAGAGGATCAGTGGT
TCGCGAGCTTTTTTCACGGCCACGCTTCATTTTGCGGTTGCGGTGACGCT
GTTGGCCATCTTAATAGCATTGCTCCTCGCTTTCCTCGCGCCGGTCCACC
AAGGCCCCCTCCGGGGCTAGAGCAGCCTAACCCCCCGCAGCAGGGCCCGG
CCGGGCCCGGAGGGCCGCCCGCCATCTTGGCGCTGCCGGCTCCGCCCGCG
GAGCCTGACGACCCGCAGCCACGGCGTGGTGGTGGGGACGGTGGCGCCGC
CGCTGGCGCCGCAGGCGACCGTGGAGACCGAGACTACGACGAAGAAGAGC
TAGACGAGCTTTTCCGCGCCGCCGCCGAAGACGATTTGTAAGTAGGAGAT
GGCGCCGGCCTTACAGGCGCAGGAGGAGACGCGGGCGACGCAGACGCAGA
```

TABLE N7-continued

| Exemplary *Anellovirus* nucleic acid sequence (*Alphatorquevirus*, Clade 1) |
|---|
| CGCAGACGCAGACATAAGCCCACCCTAGTACTCAGACAGTGGCAACCTGA<br>CGTTATCAGACACTGTAAGATAACAGGACGGATGCCCCTCATTATCTGTG<br>GAAAGGGGTCCACCCAGTTCAACTACATCACCCACGCGGACGACATCACC<br>CCCAGGGGAGCCTCCTACGGGGGCAACTTCACAAACATGACTTTCTCCCT<br>GGAGGCAATATACGAACAGTTTCTGTACCACAGAAACAGGTGGTCAGCCT<br>CCAACCACGACCTCGAACTCTGCAGATACAAGGGTACCACCCTAAAACTG<br>TACAGGCACCCAGATGTAGACTACATAGTCACCTACAGCAGAACGGGACC<br>CTTTGAGATCAGCCACATGACCTACCTCAGCACTCACCCCCTTCTCATGC<br>TGCTAAACAAACACCACATAGTGGTGCCCAGCCTAAAGACTAAGCCCAGG<br>GGCAGAAAGGCCATAAAAGTCAGAATAAGACCCCCCAAACTCATGAACAA<br>CAAGTGGTACTTCACCAGAGACTTCTGTAACATAGGCCTCTTCCAGCTCT<br>GGGCCACAGGCTTAGAACTCAGAAACCCCTGGCTCAGAATGAGCACCCTG<br>AGCCCCTGCATAGGCTTCAATGTCCTTAAAAACAGCATTTACACAAACCT<br>CAGCAACCTACCTCAGCACAGAGAAGACAGACTTAACATTATTAACAACA<br>CATTACACCCACATGACATAACAGGACCAAACAATAAAAAATGGCAGTAC<br>ACATATACCAAACTCATGGCCCCCATTTACTATTCAGCAAACAGGGCCAG<br>CACCTATGACTTACTACGAGAGTATGGCCTCTACAGTCCATACTACCTAA<br>ACCCCACAAGGATAAACCTTGACTGGATGACCCCCTACACACACGTCAGG<br>TACAATCCACTAGTAGACAAGGGCTTCGGAAACAGAATATACATACAGTG<br>GTGCTCAGAGGCAGATGTAAGCTACAACAGGACTAAATCCAAGTGTCTCT<br>TACAAGACATGCCCCTGTTTTTCATGTGCTATGGCTACATAGACTGGGCA<br>ATTAAAAACACAGGGGTCTCCTCACTAGCGAGAGACGCCAGAATCTGCAT<br>CAGGTGTCCCTACACAGAGCCACAGCTGGTGGGCTCCACAGAAGACATAG<br>GGTTCGTACCCATCACAGAGACCTTCATGAGGGGCGACATGCCGGTACTT<br>GCACCATACATACCGTTGAGCTGGTTTTGCAAGTGGTATCCCAACATAGC<br>TCACCAGAAGGAAGTACTTGAGGCAATCATTTCCTGCAGCCCCTTCATGC<br>CCCGTGACCAGGGCATGAACGGTTGGGATATTACAATAGGTTACAAAATG<br>GACTTCTTATGGGGCGGTTCCCCTCTCCCCTCACAGCCAATCGACGACCC<br>CTGCCAGCAGGGAACCCACCCGATTCCCGACCCCGATAAGCACCCTCGCC<br>TCCTACAAGTGTCGAACCCGAAACTGCTCGGACCGAGGACAGTGTTCCAC<br>AAGTGGGACATCAGACGTGGGCAGTTTAGCAAAAGAAGTATTAAAAGAGT<br>GTCAGAATACTCATCGGATGATGAATCTCTTGCGCCAGGTCTCCCATCAA<br>AGCGAAACAAGCTCGACTCGGCCTTCAGAGGAGAAAACCCAGAGCAAAAA<br>GAATGCTATTCTCTCCTCAAAGCACTCGAGGAAGAAGAGACCCCAGAAGA<br>AGAAGAACCAGCACCCCAAGAAAAAGCCCAGAAAGAGGAGCTACTCCACC<br>AGCTCCAGCTCCAGAGACGCCACCAGCGAGTCCTCAGACGAGGGCTCAAG<br>CTCGTCTTTACAGACATCCTCCGACTCCGCCAGGGAGTCCACTGGAACCC<br>CGAGCTCACATAGAGCCCCCACCTTACATACCAGACCTACTTTTTCCCAA<br>TACTGGTAAAAAAAAAAAATTCTCTCCCTTCGACTGGGAAACGGAGGCCC<br>AGCTAGCAGGGATATTCAAGCGTCCTATGCGCTTCTATCCCTCAGACACC<br>CCTCACTACCCGTGGTTACCCCCCAAGCGCGATATCCCGAAAATATGTAA<br>CATAAACTTCAAAATAAAGCTGCAAGAGTGAGTGATTCGAGGCCCTCCTC<br>TGTTCACTTAGCGGTGTCTACCTCTTAAAGTCACCAAGCACTCCGAGCGT<br>CAGCGAGGAGTGCGACCCTCCACCAAGGGGCAACTTCCTCGGGGTCCGGC<br>GCTACGCGCTTCGCGCTGCGCCGGACGCCTCGGACCCCCCCCCGACCCGA<br>ATCGCTCGCGCGATTCGGACCTGCGGCCTCGGGGGGGGTCGGGGGCTTTA<br>CTAAACAGACTCCGAGTTGCCACTGGACTCAGGAGCTGTGAATCAGTAAC<br>GAAAGTGAGTGGGGCCAGACTTCGCCATAGGGCCTTTAACTTGGGGTCGT<br>CTGTCGGTGGCTTCCGGGTCCGCCTGGGCGCCGCCATTTTAGCTTTAGAC<br>GCCATTTTAGGCCCTCGCGGGCACCCGTAGGCGCGTTTTAATGACGTCAC<br>GGCAGCCATTTTGTCGTGACGTTTGAGACACGTGATGGGGGCGTGCCTAA<br>ACCCGGAAGCATCCCTGGTCACGTGACTCTGACGTCACGGCGGCCATTTT<br>GTGCTGTCCGCCATCTTGTGACTTCCTTCCGCTTTTTCAAAAAAAAAGAG<br>GAAGTATGACAGTAGCGGCGGGGGGGCGGCCGCGTTCGCGCGCCGCCCAC<br>CAGGGGGTGCTGCGCGCCCCCCCCGCGCATGCGCGGGGCCCCCCCCCGG<br>GGGGGCTCCGCCCCCCCGGCCCCCCCCCCGTGCTAAACCCACCGCGCATGC<br>GCGACCACGCCCCCGCCGCC (SEQ ID NO: 1) |

Annotations:

| Putative Domain | Base range |
|---|---|
| TATA Box | 84-90 |
| Cap Site | 107-114 |
| Transcriptional Start Site | 114 |
| 5' UTR Conserved Domain | 177-247 |
| ORF2 | 299-691 |
| ORF2/2 | 299-687; 2137-2659 |
| ORF2/3 | 299-687; 2339-2831 |
| ORF2t/3 | 299-348; 2339-2831 |

TABLE N7-continued

| Exemplary *Anellovirus* nucleic acid sequence (*Alphatorquevirus*, Clade 1) | |
|---|---|
| ORF1 | 571-2613 |
| ORF1/1 | 571-687; 2137-2613 |
| ORF1/2 | 571-687; 2339-2659 |
| Three open-reading frame region | 2325-2610 |
| Poly(A) Signal | 2813-2818 |
| GC-rich region | 3415-3570 |

TABLE A7

| Exemplary *Anellovirus* amino acid sequences (*Alphatorquevirus*, Clade 1) TTV-CT30F (*Alphatorquevirus* Clade 1) | |
|---|---|
| ORF2 | MPWRPPVHSVQGREDQWFASFFHGHASFCGCGDAVGHLNSIAPRFPRAGPPRPPPG LEQPNPPQQGPAGPGGPPAILALPAPPAEPDDPQPRRGGGDGGAAAGAAGDRGDRD YDEEELDELFRAAAEDDL (SEQ ID NO: 2) |
| ORF2/2 | MPWRPPVHSVQGREDQWFASFFHGHASFCGCGDAVGHLNSIAPRFPRAGPPRPPPG LEQPNPPQQGPAGPGGPPAILALPAPPAEPDDPQPRRGGGDGGAAAGAAGDRGDRD YDEEELDELFRAAAEDDFQSTTPASREPTRFPTPISTLASYKCRTRNCSDRGQCSTSG TSDVGSLAKEVLKECQNTHRMMNLLRQVSHQSETSSTRPSEEKTQSKKNAILSSKH SRKKRPQKKKNQHPKKKPRKRSYSTSSSSRDATSESSDEGSSSSLQTSSDSARESTGT PSSHRAPTLHTRPTFSQYW (SEQ ID NO: 3) |
| ORF2/3 | MPWRPPVHSVQGREDQWFASFFHGHASFCGCGDAVGHLNSIAPRFPRAGPPRPPPG LEQPNPPQQGPAGPGGPPAILALPAPPAEPDDPQPRRGGGDGGAAAGAAGDRGDRD YDEEELDELFRAAAEDDLSPIKAKQARLGLQRRKPRAKRMLFSPQSTRGRRDPRRR RTSTPRKSPERGATPPAPAPETPPASPQTRAQARLYRHPPTPPGSPLEPRAHIEPPPYIP DLLFPNTGKKKKFSPFDWETEAQLAGIFKRPMRFYPSDTPHYPWLPPKRDIPKICNIN FKIKLQE (SEQ ID NO: 4) |
| ORF2t/3 | MPWRPPVHSVQGREDQWSPIKAKQARLGLQRRKPRAKRMLFSPQSTRGRRDPRRR RTSTPRKSPERGATPPAPAPETPPASPQTRAQARLYRHPPTPPGSPLEPRAHIEPPPYIP DLLFPNTGKKKKFSPFDWETEAQLAGIFKRPMRFYPSDTPHYPWLPPKRDIPKICNIN FKIKLQE (SEQ ID NO: 5) |
| ORF1 | TAWWWGRWRRRWRRRRPWRPRLRRRRARRAFPRRRRRRFVSRRWRRPYRRRRR RGRRRRRRRRRHKPTLVLRQWQPDVIRHCKITGRMPLIICGKGSTQFNYITHADDIT PRGASYGGNFTNMTFSLEAIYEQFLYHRNRWSASNHDLELCRYKGTTLKLYRHPD VDYIVTYSRTGPFEISHMTYLSTHPLLMLLNKHHIVVPSLKTKPRGRKAIKVRIRPPK LMNNKWYFTRDFCNIGLFQLWATGLELRNPWLRMSTLSPCIGENVLKNSIYTNLSN LPQHREDRLNIINNTLHPHDITGPNNKKWQYTYTKLMAPIYYSANRASTYDLLREY GLYSPYYLNPTRINLDWMTPYTHVRYNPLVDKGFGNRIYIQWCSEADVSYNRTKSK CLLQDMPLFFMCYGYIDWAIKNTGVSSLARDARICIRCPYTEPQLVGSTEDIGFVPIT ETFMRGDMPVLAPYIPLSWFCKWYPNIAHQKEVLEAIISCSPFMPRDQGMNGWDITI GYKMDFLWGGSPLPSQPIDDPCQQGTHPIPDPDKHPRLLQVSNPKLLGPRTVFHKW DIRRGQFSKRSIKRVSEYSSDDESLAPGLPSKRNKLDSAFRGENPEQKECYSLLKALE EEETPEEEEPAPQEKAQKEELLHQLQLQRRHQRVLRRGLKLVFTDILRLRQGVHWN PELT (SEQ ID NO: 6) |
| ORF1/1 | TAWWWGRWRRRWRRRRPWRPRLRRRRARRAFPRRRRRRFPIDDPCQQGTHPIPDP DKHPRLLQVSNPKLLGPRTVFHKWDIRRGQFSKRSIKRVSEYSSDDESLAPGLPSKR NKLDSAFRGENPEQKECYSLLKALEEEETPEEEEPAPQEKAQKEELLHQLQLQRRH QRVLRRGLKLVFTDILRLRQGVHWNPELT (SEQ ID NO: 7) |
| ORF1/2 | TAWWWGRWRRRWRRRRPWRPRLRRRRARRAFPRRRRRRFVSHQSETSSTRPSEE KTQSKKNAILSSKHSRKKRPQKKKNQHPKKKPRKRSYSTSSSSRDATSESSDEGSSS SLQTSSDSARESTGTPSSHRAPTLHTRPTFSQYW (SEQ ID NO: 8) |

TABLE N8

Exemplary *Anellovirus* nucleic acid sequence (*Alphatorquevirus*, Clade 2)

| | |
|---|---|
| Name | TTV-P13-1 |
| Genus/Clade | *Alphatorquevirus*, Clade 2 |
| Accession Number | KT163896.1 |
| Full Sequence: 3451 bp | |

```
1        10         20         30         40         50
|         |          |          |          |          |
AATTTTGCTAAACAGACTCCGAGGTGCTCTTGGACACTGAGTGGGCGTAC
AGCAACGAAAGTGAGTGGGGCCAGACTTCGCCATAAGGCCTTTATCTTCG
GGTCTACATCATAATATAAAGATGTGCACTTCCGAATGGCTGAGTTTTTC
ACGCCATTCCGCAGCGGTGGAGCAGCGCAGCCACGACCCCCGCGTCCCGA
GGGCGGGTGCCGGAGGTGAGTTTACACACCGCAGTCAAGGGGCAATTCGG
GCTCGGGACTGGCCGGGCCCGGGCAAGGCTCTTAAAGCGAAACCATGTTC
CTCGGCAGGCCCTACCGCCACAGAAAGCGGCACCAGGCCGGCAAGAAAGG
GCCACTGCCACTGCCAAATCTGCAACCTGCACAGGAGAAACGGGCTGGTG
GTCCGTCCTTGATGGCCTCCGGACGCAGGGGATGGATGCCCCCGGACCTG
ACGGTCCAGGAGAGGGAGGATGCCTGGTGGACCAGCTTCTGCGCTAGCCA
CCGCAGCTTTTGTAGCTGCGACGATCCTGTGGGCCATATTAATACTCTCG
CCCGCGATAATAGTCCTCTGGCCCAGACTCCTACTACAACTTCAGGCCAG
GGGCCGCCGCCGCCGCCTACGCCTCCGCGGACGCCGGGGCCGCGCCCTGG
GTCTGCTCCGGACCAGGGGGGAAGGATCAGGGCCTCCTGGACCTACCCCC
TAGCCCCCGGAGGTCCCGGTAGCACGCCATGGCCTACTGGTGGGGCCGGA
GACGCCGGTGGCGCCGCTGGAGGAGGCGCCGGCGTCCTCTCCGCCGCCGC
CGGCGGTGGCGGAGAAGGCGACGCTGGCCCAGAAGGCGCCGGTGGAGGCG
AAGGAGACGACGTGCGAGACCTGCTCGCCGCTATCGAAGGAGACGTGGGC
GCAGACGGGTAAGGAGACGCCGTCGCCCCCAGAAACTAGTACTGACTCAG
TGGAATCCCCAGACTGTGAGAAAGTGTGTTATTAGGGGGTTTCTGCCCCT
GTTCTTCTGCGGACAGGGGGCCTACCACAGAAACTTTACAGACCACTATG
ACGATGTGTTCCCCAAGGGACCCAGCGGAGGTGGGCACGGGAGCATGGTG
TTCAACCTGTCCTTTCTGTACCAAGAGTTTAAGAAGCACCACAATAAGTG
GTCGCGCAGCAACCTGGACTTTGACTTAGTGAGATACAAGGGCACAGTGA
TAAAGCTGTACAGACACCAGGACTTTGACTACATAGTGTGGATAAGCAGG
ACCCCTCCCTTCCAGGAGAGCCTGCTCACAGTAATGACCCACCAGCCCAG
CGTCATGCTGCAGGCAAAAAAGTGCATAATAGTAAAGAGCTACAGGACCC
ACCCGGGGGGCAAACCCTATGTAACTGCAAAAGTTAGGCCCCCCAGACTC
CTAACTGACAAGTGGTACTTCCAGTCAGACTTCTGCAACGTTCCGCTTTT
TAGCCTACAGTTTGCCCTTGCGGAACTGCGGTTTCCGATCTGCTCACCAC
AAACTGACACCAATTGCATTAACTTCCTGGTGTTAGATGACATCTACTAC
AAGTTTCTAGATAATAAGCCTAAACAGAGTTCAGACCCTAATGACGAAAA
CAGAATAAAATTCTGGCACGGCCTATGGTCCACTATGAGATATTTAAACA
CCACCTACATAAACACACTGTTTCCAGGCACAGACAGTCTAGTGGCCGCC
AAAGATACTGACAATAGTGTAAATAAATACCCCAGCACAGCCACTAAACA
GCCCTACAAAGACAGTCAGTACATGCAAAATATATGGAATACATCAAAAA
TACATGCCTTATATACGTGGGTAGCAGAGACAAACTACAAAAGACTGCAG
GCCTACTACACACAGACCTACGGAGGCTACCAGAGACAATTTTTCACAGG
AAAACAGTACTGGGACTACAGAGTAGGCATGTTTAGTCCAGCCTTCCTGA
GTCCCAGCAGACTAAATCCCCAGAACCCAGGGGCATACACAGAGGTCTCC
TACAACCCCTGGACAGACGAGGGCACGGGCAACGTAGTGTGCCTGCAGTA
TCTGACTAAAGAGACCTCAGACTACAAACCAGGTGGTGGGAGCAAGTTCT
GCATAGAAGGTGTGCCTCTATGGGCAGCGCTGGTGGGATACGTAGACATG
TGTAAAAAAGAGGGCAAGGACCCGGGCATCAGACTAAACTGTCTCCTGTT
AGTCAAGTGTCCCTATACAAAGCCTCAGCTGTATGACAAAAAAAACCCCG
AGAAACTGTTTGTACCTTACTCCTATAACTTTGGGCACGGCAAGATGCCG
GGGGGAGACAAATACATACCCATAGAGTTCAAAGACAGGTGGTACCCCTG
CCTGCTCCACCAAGAGGAGTGGATAGAGGACATTGTCAGGTCGGGACCCT
TCGTTCCAAAAGACATGCCCAGCAGCGTCACCTGCATGATGAGGTACAGC
TCTCTTTTTAACTGGGGCGGTAATATAATCCAAGAACAGGCCGTGGAAGA
CCCCTGTAAGAAAGGCACCTTCGTCGTTCCCGGAACCAGTGGCATCGCTC
GCATACTACAAGTCAGCAACCCGGCCAAGCAGACCCCCACGACAACCTGG
CACTCGTGGGACTGGAGACGATCCCTCTTTACAGAGACGGGTCTTAAAAG
AATGCGCGAACAACAACCATATGATGAACTGTCTTATACGGGCCCTAAAA
AGCCAAAACTGTCCCTTCCCGCAGGGCCCGCCGTCCCCGGTGCCGCCGTC
GCCTCCTCCTGGTGGGAAACAAAACAGGTCACCTCGCCAGACGTCAGCGA
GACGGAGACCGAAGCAGAAGCCCACCAAGAGGAAGAGACGGAGCCGGAGG
AGGGAGTCCAGCTCCAGCAGCTGTGGGAGCAGCAACTCCTGCAAAAGCGA
CAGCTGGGAGTCGTGTTCCAGCAACTCCTCCGACTCAGACAGGGGGCGGA
GATCCACCCGGGCCTCGTATAATTCCTGGGCCCCAGAACCCGTACCTGCT
TTTCCCGGAGCAGGCCCCTCCAAAAGTGCCTATTTTTGACCCCTTTGGTC
AGAAAACAGAGCTAGAGCTGTGCGGCTGCTTCGACAGGCCGCCCAGGAAC
AACCCCTACGACCACCCCTTCTACCCCTGGCTGCCCAAAGAGCCTCCCTC
CTACTACCAGGGCTACAAAGTGTCTTTCAAACTAGGGTTCCACCCAGACA
AGCATGTGTGAACCCCGCCAATAAACCACTGCTGCTACACTGATTCTTAG
GCCGTGGGAGTCTCACTGGTCGGTGTCTACCTCTTAAGGTCACTAAGCAC
TCCGAGCGTTAGCGAGGAGTGCGACCCTACCCCCTGGGCCCACTTCTTCG
GAGCCGCGCGCTACGCCTTCGGCTGCGCGCGGCACCTCAGACCCCCGCTC
GTGCTGACACGCTTGCGCGTGTCAGACCACTTCGGGCTCGCGGGGGTCGG
G (SEQ ID NO: 9)
```

TABLE N8-continued

| Exemplary *Anellovirus* nucleic acid sequence (*Alphatorquevirus*, Clade 2) | |
|---|---|
| Annotations: | |
| Putative Domain | Base range |
| TATA Box | 112-119 |
| Initiator Element | 128-148 |
| Transcriptional Start Site | 148 |
| 5' UTR Conserved Domain | 204-273 |
| ORF2 | 412-912 |
| ORF2/2 | 412-908; 2490-3039 |
| ORF2/3 | 412-908; 2725-3208 |
| ORF1 | 729-2972 |
| ORF1/1 | 729-908; 2490-2972 |
| ORF1/2 | 729-908; 2725-3039 |
| Three open-reading frame region | 2699-2969 |
| Poly(A) Signal | 3220-3225 |
| GC-rich region | 3302-3541 |

TABLE A8

| Exemplary *Anellovirus* amino acid sequences (*Alphatorquevirus*, Clade 2) TTV-P13-1 (*Alphatorquevirus* Clade 2) | |
|---|---|
| ORF2 | MASGRRGWMPPDLTVQEREDAWWTSFCASHRSFCSCDDPVGHINTLARDN SPLAQTPTTTSGQGPPPPPTPPRTPGPRPGSAPDQGGRIRASWTYPLAPGGPG STPWPTGGAGDAGGAAGGGAGVLSAAAGGGGEGDAGPEGAGGGEGDDV RDLLAAIEGDVGADG (SEQ ID NO: 10) |
| ORF2/2 | MASGRRGWMPPDLTVQEREDAWWTSFCASHRSFCSCDDPVGHINTLARDN SPLAQTPTTTSGQGPPPPPTPPRTPGPRPGSAPDQGGRIRASWTYPLAPGGPG STPWPTGGAGDAGGAAGGGAGVLSAAAGGGGEGDAGPEGAGGGEGDDV RDLLAAIEGDVGADGPWKTPVRKAPSSFPEPVASLAYYKSATRPSRPPRQPG TRGTGDDPSLQRRVLKECANNNHMMNCLIRALKSQNCPFPQGPPSPVPPSPP PGGKQNRSPRQTSARRRPKQKPTKRKRRSRRRESSSSSCGSSNSCKSDSWES CSSNSSDSDRGRRSTRASYNSWAPEPVPAFPGAGPSKSAYF (SEQ ID NO: 11) |
| ORF2/3 | MASGRRGWMPPDLTVQEREDAWWTSFCASHRSFCSCDDPVGHINTLARDN SPLAQTPTTTSGQGPPPPPTPPRTPGPRPGSAPDQGGRIRASWTYPLAPGGPG STPWPTGGAGDAGGAAGGGAGVLSAAAGGGGEGDAGPEGAGGGEGDDV RDLLAAIEGDVGADGARRPRCRRLLLVGNKTGHLARRQRDGDRSRSPPRG RDGAGGGSPAPAAVGAATPAKATAGSRVPATPPTQTGGGDPPGPRIIPGPQN PYLLFPEQAPPKVPIFDPFGQKTELELCGCFDRPPRNNPYDHPFYPWLPKEPP SYYQGYKVSFKLGFHPDKHV (SEQ ID NO: 12) |
| ORF1 | MAYWWGRRRRWRRWRRRRRPLRRRRRWRRRRRWPRRRRWRRRRRRARP ARRYRRRRGRRRVRRRRRPQKLVLTQWNPQTVRKCVIRGFLPLFFCGQGAY HRNFTDHYDDVFPKGPSGGGHGSMVFNLSFLYQEFKKHHNKWSRSNLDFD LVRYKGTVIKLYRHQDFDYIVWISRTPPFQESLLTVMTHQPSVMLQAKKCII VKSYRTHPGGKPYVTAKVRPPRLLTDKWYFQSDFCNVPLFSLQFALAELRF PICSPQTDTNCINFLVLDDIYYKFLDNKPKQSSDPNDENRIKFWHGLWSTMR YLNTTYINTLFPGTDSLVAAKDTDNSVNKYPSTATKQPYKDSQYMQNIWNT SKIHALYTWVAETNYKRLQAYYTQTYGGYQRQFFTGKQYWDYRVGMFSP AFLSPSRLNPQNPGAYTEVSYNPWTDEGTGNVVCLQYLTKETSDYKPGGGS KFCIEGVPLWAALVGYVDMCKKEGKDPGIRLNCLLLVKCPYTKPQLYDKK NPEKLFVPYSYNFGHGKMPGGDKYIPIEFKDRWYPCLLHQEEWIEDIVRSGP FVPKDMPSSVTCMMRYSSLFNWGGNIIQEQAVEDPCKKGTFVVPGTSGIARI LQVSNPAKQTPTTTWHSWDWRRSLFTETGLKRMREQQPYDELSYTGPKKP KLSLPAGPAVPGAAVASSWWETKQVTSPDVSETETEAEAHQEEETEPEEGV QLQQLWEQQLLQKRQLGVVFQQLLRLRQGAEIHPGLV (SEQ ID NO: 13) |
| ORF1/1 | MAYWWGRRRRWRRWRRRRRPLRRRRRWRRRRRWPRRRRWRRRRRRARP ARRYRRRRGRRRAVEDPCKKGTFVVPGTSGIARILQVSNPAKQTPTTTWHS |

TABLE A8-continued

| Exemplary *Anellovirus* amino acid sequences (*Alphatorquevirus*, Clade 2)<br>TTV-P13-1 (*Alphatorquevirus* Clade 2) | |
|---|---|
| | WDWRRSLFTETGLKRMREQQPYDELSYTGPKKPKLSLPAGPAVPGAAVASS<br>WWETKQVTSPDVSETETEAEAHQEEETEPEEGVQLQQLWEQQLLQKRQLG<br>VVFQQLLRLRQGAEIHPGLV (SEQ ID NO: 14) |
| ORF1/2 | MAYWWGRRRRWRRWRRRRRPLRRRRRWRRRRRWPRRRRWRRRRRRARP<br>ARRYRRRRGRRRGPPSPVPPSPPPGGKQNRSPRQTSARRRPKQKPTKRKRRS<br>RRRESSSSSCGSSNSCKSDSWESCSSNSSDSDRGRRSTRASYNSWAPEPVPAF<br>PGAGPSKSAYF (SEQ ID NO: 15) |

TABLE N9

Exemplary *Anellovirus* nucleic acid sequence (*Alphatorquevirus*, Clade 3)

| | |
|---|---|
| Name | Ring1 |
| Genus/Clade | *Alphatorquevirus*, Clade 3 |
| Accession Number | AJ620231.1 |
| Full Sequence: 3753 bp | |

```
1        10         20         30         40         50
|         |          |          |          |          |
TGCTACGTCACTAACCCACGTGTCCTCTACAGGCCAATCGCAGTCTATGT
CGTGCACTTCCTGGGCATGGTCTACATAATTATATAAATGCTTGCACTTC
CGAATGGCTGAGTTTTTGCTGCCCGTCCGCGGAGAGGAGCCACGGCAGGG
GATCCGAACGTCCTGAGGGCGGGTGCCGGAGGTGAGTTTACACACCGAAG
TCAAGGGGCAATTCGGGCTCAGGACTGGCCGGGCTTTGGGCAAGGCTCTT
AAAAATGCACTTTTCTCGAATAAGCAGAAAGAAAAGGAAAGTGCTACTGC
TTTGCGTGCCAGCAGCTAAGAAAAAACCAACTGCTATGAGCTTCTGGAAA
CCTCCGGTACACAATGTCACGGGGATCCAACGCATGTGGTATGAGTCCTT
TCACCGTGGCCACGCTTCTTTTTGTGGTTGTGGGAATCCTATACTTCACA
TTACTGCACTTGCTGAAACATATGGCCATCCAACAGGCCCGAGACCTTCT
GGGCCACCGGGAGTAGACCCCAACCCCCACATCCGTAGAGCCAGGCCTGC
CCCGGCCGCTCCGGAGCCCTCACAGGTTGATTCGAGACCAGCCCTGACAT
GGCATGGGGATGGTGGAAGCGACGGAGGCGCTGGTGGTTCCGGAAGCGGT
GGACCCGTGGCAGACTTCGCAGACGATGGCCTCGATCAGCTCGTCGCCGC
CCTAGACGACGAAGAGTAAGGAGGCGCAGACGGTGGAGGAGGGGGAGACG
AAAAACAAGGACTTACAGACGCAGGAGACGCTTTAGACGCAGGGGACGAA
AAGCAAAACTTATAATAAAACTGTGGCAACCTGCAGTAATTAAAAGATGC
AGAATAAAGGGATACATACCACTGATTATAAGTGGGAACGGTACCTTTGC
CACAAACTTTACCAGTCACATAAATGACAGAATAATGAAAGGCCCCTTCG
GGGGAGGACACAGCACTATGAGGTTCAGCCTCTACATTTTGTTTGAGGAG
CACCTCAGACACATGAACTTCTGGACCAGAAGCAACGATAACCTAGAGCT
AACCAGATACTTGGGGGCTTCAGTAAAAATATACAGGCACCCAGACCAAG
ACTTTATAGTAATATACAACAGAAGAACCCCTCTAGGAGGCAACATCTAC
ACAGCACCCTCTCTACACCCAGGCAATGCCATTTTAGCAAAACACAAAAT
ATTAGTACCAAGTTTACAGACAAGACCAAAGGGTAGAAAAGCAATTAGAC
TAAGAATAGCACCCCCCACACTCTTTACAGACAAGTGGTACTTTCAAAAG
GACATAGCCGACCTCACCCTTTTCAACATCATGGCAGTTGAGGCTGACTT
GCGGTTTCCGTTCTGCTCACCACAAACTGACAACACTTGCATCAGCTTCC
AGGTCCTTAGTTCCGTTTACAACAACTACCTCAGTATTAATACCTTTAAT
AATGACAACTCAGACTCAAAGTTAAAAGAATTTTTAAATAAAGCATTTCC
AACAACAGGCACAAAAGGAACAAGTTTAAATGCACTAAATACATTTAGAA
CAGAAGGATGCATAAGTCACCCACAACTAAAAAAACCAAACCCACAAATA
AACAAACCATTAGAGTCACAATACTTTGCACCTTTAGATGCCCTCTGGGG
AGACCCCATATACTATAATGATCTAAATGAAAACAAAAGTTTGAACGATA
TCATTGAGAAAATACTAATAAAAAACATGATTACATACCATGCAAAACTA
AGAGAATTTCCAAATTCATACCAAGGAAACAAGGCCTTTTGCCACCTAAC
AGGCATATACAGCCCACCATACCTAAACCAAGGCAGAATATCTCCAGAAA
TATTTGGACTGTACACAGAAATAATTTACAACCCTTACACAGACAAAGGA
ACTGGAAACAAAGTATGGATGGACCCACTAACTAAAGAGAACAACATATA
TAAAGAAGGACAGAGCAAATGCCTACTGACTGACATGCCCCTATGGACTT
TACTTTTTGGATATACAGACTGGTGTAAAAAGGACACTAATAACTGGGAC
TTACCACTAAACTACAGACTAGTACTAATATGCCCTTATACCTTTCCAAA
ATTGTACAATGAAAAAGTAAAAGACTATGGGTACATCCCGTACTCCTACA
AATTCGGAGCGGGTCAGATGCCAGACGGCAGCAACTACATACCCTTTCAG
TTTAGAGCAAAGTGGTACCCCACAGTACTACACCAGCAACAGGTAATGGA
GGACATAAGCAGGAGCGGGCCCTTTGCACCTAAGGTAGAAAAACCAAGCA
CTCAGCTGGTAATGAAGTACTGTTTTAACTTTAACTGGGGCGGTAACCCT
ATCATTGAACAGATTGTTAAAGACCCCAGCTTCCAGCCCACCTATGAAAT
ACCCGGTACCGGTAACATCCCTAGAAGAATACAAGTCATCGACCCGCGGG
TCCTGGGACCGCACTACTCGTTCCGGTCATGGGACATGCGCAGACACACA
TTTAGCAGAGCAAGTATTAAGAGAGTGTCAGAACAACAAGAAACTTCTGA
CCTTGTATTCTCAGGCCCAAAAAAGCCTCGGGTCGACATCCCAAAACAAG
AAACCCAAGAAGAAAGCTCACATTCACTCCAAAGAGAATCGAGACCGTGG
GAGACCGAGGAAGAAAGCGAGACAGAAGCCCTCTCGCAAGAGAGCCAAGA
```

TABLE N9-continued

| Exemplary *Anellovirus* nucleic acid sequence (*Alphatorquevirus*, Clade 3) |
|---|
| GGTCCCCTTCCAACAGCAGTTGCAGCAGCAGTACCAAGAGCAGCTCAAGC<br>TCAGACAGGGAATCAAAGTCCTCTTCGAGCAGCTCATAAGGACCCAACAA<br>GGGGTCCATGTAAACCCATGCCTACGGTAGGTCCCAGGCAGTGGCTGTTT<br>CCAGAGAGAAAGCCAGCCCCAGCTCCTAGCAGTGGAGACTGGGCCATGGA<br>GTTTCTCGCAGCAAAAATATTTGATAGGCCAGTTAGAAGCAACCTTAAAG<br>ATACCCCTTACTACCCATATGTTAAAAACCAATACAATGTCTACTTTGAC<br>CTTAAATTTGAATAAACAGCAGCTTCAAACTTGCAAGGCCGTGGGAGTTT<br>CACTGGTCGGTGTCTACCTCTAAAGGTCACTAAGCACTCCGAGCGTAAGC<br>GAGGAGTGCGACCCTCCCCCCTGGAACAACTTCTTCGGAGTCCGGCGCTA<br>CGCCTTCGGCTGCGCCGGACACCTCAGACCCCCCCTCCACCCGAAACGCT<br>TGCGCGTTTCGGACCTTCGGCGTCGGGGGGGTCGGGAGCTTTATTAAACG<br>GACTCCGAAGTGCTCTTGGACACTGAGGGGGTGAACAGCAACGAAAGTGA<br>GTGGGGCCAGACTTCGCCATAAGGCCTTTATCTTCTTGCCATTTGTCAGT<br>GTCCGGGGTCGCCATAGGCTTCGGGCTCGTTTTTAGGCCTTCCGGACTAC<br>AAAAATCGCCATTTTGGTGACGTCACGGCCGCCATCTTAAGTAGTTGAGG<br>CGGACGGTGGCGTGAGTTCAAAGGTCACCATCAGCCACACCTACTCAAAA<br>TGGTGGACAATTTCTTCCGGGTCAAAGGTTACAGCCGCCATGTTAAAACA<br>CGTGACGTATGACGTCACGGCCGCCATTTTGTGACACAAGATGGCCGACT<br>TCCTTCCTCTTTTTCAAAAAAAAGCGGAAGTGCCGCCGCGGCGGCGGGGG<br>GCGGCGCGCTGCGCGCGCCGCCCAGTAGGGGGAGCCATGCGCCCCCCCCC<br>GCGCATGCGCGGGGCCCCCCCCCGCGGGGGGCTCCGCCCCCCGGCCCCCC<br>CCG (SEQ ID NO: 16) |

Annotations:

| Putative Domain | Base range |
|---|---|
| TATA Box | 83-88 |
| Cap Site | 104-111 |
| Transcriptional Start Site | 111 |
| 5' UTR Conserved Domain | 170-240 |
| ORF2 | 336-719 |
| ORF2/2 | 336-715; 2363-2789 |
| ORF2/3 | 336-715; 2565-3015 |
| ORF2t/3 | 336-388; 2565-3015 |
| ORF1 | 599-2830 |
| ORF1/1 | 599-715; 2363-2830 |
| ORF1/2 | 599-715; 2565-2789 |
| Three open-reading frame region | 2551-2786 |
| Poly(A) Signal | 3011-3016 |
| GC-rich region | 3632-3753 |

TABLE A9

| Exemplary *Anellovirus* amino acid sequences (*Alphatorquevirus*, Clade 3)<br>Ring1 (*Alphatorquevirus* Clade 3) | |
|---|---|
| ORF2 | MSFWKPPVHNVTGIQRMWYESFHRGHASFCGCGNPILHITALAETYGHPTGPRPSG<br>PPGVDPNPHIRRARPAPAAPEPSQVDSRPALTWHGDGGSDGGAGGSGSGGPVADFA<br>DDGLDQLVAALDDEE (SEQ ID NO: 17) |
| ORF2/2 | MSFWKPPVHNVTGIQRMWYESFHRGHASFCGCGNPILHITALAETYGHPTGPRPSG<br>PPGVDPNPHIRRARPAPAAPEPSQVDSRPALTWHGDGGSDGGAGGSGSGGPVADFA<br>DDGLDQLVAALDDEELLKTPASSPPMKYPVPVTSLEEYKSSTRGSWDRTTRSGHGT<br>CADTHLAEQVLRECQNNKKLLTLYSQAQKSLGSTSQNKKPKKKAHIHSKENRDRG<br>RPRKKARQKPSRKRAKRSPSNSSCSSSTKSSSSSDRESKSSSSSS (SEQ ID NO: 18) |
| ORF2/3 | MSFWKPPVHNVTGIQRMWYESFHRGHASFCGCGNPILHITALAETYGHPTGPRPSG<br>PPGVDPNPHIRRARPAPAAPEPSQVDSRPALTWHGDGGSDGGAGGSGSGGPVADFA<br>DDGLDQLVAALDDEEPKKASGRHPKTRNPRRKLTFTPKRIETVGDRGRKRDRSPLA<br>REPRGPLPTAVAAAVPRAAQAQTGNQSPLRAAHKDPTRGPCKPMPTVGPRQWLFP |

TABLE A9-continued

| Exemplary *Anellovirus* amino acid sequences (*Alphatorquevirus*, Clade 3) Ring1 (*Alphatorquevirus* Clade 3) | |
|---|---|
| | ERKPAPAPSSGDWAMEFLAAKIFDRPVRSNLKDTPYYPYVKNQYNVYFDLKFE (SEQ ID NO: 19) |
| ORF2t/3 | MSFWKPPVHNVTGIQRMWPKKASGRHPKTRNPRRKLTFTPKRIETVGDRGRKRDR SPLAREPRGPLPTAVAAAVPRAAQAQTGNQSPLRAAHKDPTRGPCKPMPTVGPRQ WLFPERKPAPAPSSGDWAMEFLAAKIFDRPVRSNLKDTPYYPYVKNQYNVYFDLK FE (SEQ ID NO: 20) |
| ORF1 | MAWGWWKRRRRWWFRKRWTRGRLRRRWPRSARRRPRRRRVRRRRRWRRGRRK TRTYRRRRRFRRRGRKAKLIIKLWQPAVIKRCRIKGYIPLIISGNGTFATNFTSHINDR IMKGPFGGGHSTMRFSLYILFEEHLRHMNFWTRSNDNLELTRYLGASVKIYRHPDQ DFIVIYNRRTPLGGNIYTAPSLHPGNAILAKHKILVPSLQTRPKGRKAIRLRIAPPTLFT DKWYFQKDIADLTLFNIMAVEADLRFPFCSPQTDNTCISFQVLSSVYNNYLSINTEN NDNSDSKLKEFLNKAFPTTGTKGTSLNALNTFRTEGCISHPQLKKPNPQINKPLESQ YFAPLDALWGDPIYYNDLNENKSLNDIIEKILIKNMITYHAKLREFPNSYQGNKAFC HLTGIYSPPYLNQGRISPEIFGLYTEIIYNPYTDKGTGNKVWMDPLTKENNIYKEGQS KCLLTDMPLWTLLFGYTDWCKKDTNNWDLPLNYRLVLICPYTFPKLYNEKVKDY GYIPYSYKFGAGQMPDGSNYIPFQFRAKWYPTVLHQQQVMEDISRSGPFAPKVEKP STQLVMKYCFNFNWGGNPIIEQIVKDPSFQPTYEIPGTGNIPRRIQVIDPRVLGPHYSF RSWDMRRHTFSRASIKRVSEQQETSDLVFSGPKKPRVDIPKQETQEESSHSLQRESR PWETEEESETEALSQESQEVPFQQQLQQQYQEQLKLRQGIKVLFEQLIRTQQGVHV NPCLR (SEQ ID NO: 21) |
| ORF1/1 | MAWGWWKRRRRWWFRKRWTRGRLRRRWPRSARRRPRRRRIVKDPSFQPTYEIPG TGNIPRRIQVIDPRVLGPHYSFRSWDMRRHTFSRASIKRVSEQQETSDLVFSGPKKPR VDIPKQETQEESSHSLQRESRPWETEEESETEALSQESQEVPFQQQLQQQYQEQLKL RQGIKVLFEQLIRTQQGVHVNPCLR (SEQ ID NO: 22) |
| ORF1/2 | MAWGWWKRRRRWWFRKRWTRGRLRRRWPRSARRRPRRRRAQKSLGSTSQNKK PKKKAHIHSKENRDRGRPRKKARQKPSRKRAKRSPSNSSCSSSTKSSSSSDRESKSSS SSS (SEQ ID NO: 23) |

TABLE N10

Exemplary *Anellovirus* nucleic acid sequence (*Alphatorquevirus*, Clade 4)

| | |
|---|---|
| Name | TTV-HD20a |
| Genus/Clade | *Alphatorquevirus*, Clade 4 |
| Accession Number | FR751492.1 |
| Full Sequence 3878 bp | |

```
1         10         20         30         40         50
|         |          |          |          |          |
AAATACGTCACTAACCACGTGACTCCCACAGGCCAACCACAGTCTATGTC
GTGCACTTCCTGGGCATGGTCTACGTGATAATATAAAGCGGTGCACTTCC
GAATGGCTGAGTTTTCCACGCCCGTCCGCAGCGAGATCGCGACGTAGGAG
CGATCGAGCGTCCCGAGGGCGGGTGCCGGAGGTGAGTTTACACACCGCAG
TCAAGGGGCAATTCGGGCTCGGGAGGCCGGGCCATGGGCAAGGCTCTTAA
AAAGCTATGTTTCTCGGTAAAATCTACAGGAAGAAAAGGAAACTGCTTCT
GCAGGCTGTGCGTGCTCCGCAGACGCCATCTTCCATGAGCCGCTGCTGGT
GTCCCCCTCGGGGTGATGTCTCCTCCCGCGAGTCTCGATGGTACGAGGCG
GTTCGAGGAAGCCACGATGCTTTTTGTGGCTGTAGTGATCCTATTCTTCA
TCTTTCTCGTCTGGCTGCACGTTTTAACCATCAGGGACCTCCGACGCCCC
CCACGGACGACCGTGCGCCGCAGAATACCCCAGTGAGACGCCTGCTGCCT
CTCCCCAGCTACCCCGGCGAGGGTCCCCAGGCTAGATGGCCTGGTGGGGA
TGGAGGCGCCGCTGGTGGCGACCGAAGAGAAGGTGGAGATGGCGGCGCGC
GCGCCGCCGAAGACGAGTACCAGCCCGAAGACCTAGACGAGCTTTTCGGC
GCTATCGAACAAGAACAGTAAGGAGGAGGCGAAGGGGGAGGCGGAGGGGC
TACCGGCGCCGTTACAGACTGAGACGCTATGCCAGACGCAGGTTCCGACG
CAAAAAGATAGTACTGACTCAGTGGAACCCCCAGACTACCAGAAAATGTA
TAATAAGGGGCATGATGCCAGTACTGTGGGCCGGCATGGGTACGGGGGGC
AGAAACTATGCAGTGAGGTCAGATGACTATGTGGTGAACAAAGGGTTCGG
GGGCTCCTTCGCCACGGAGACCTTCTCCCTGAAGGTTCTCTATGACCAGT
TTCAAAGGGGCTTCAACAGGTGGTCCCACACTAACGAGGACCTAGACCTG
GCCCGCTACAGGGGCTGCAGGTGGACTTTTTACAGACATAAAGACACAGA
CTTTATAGTGTACTTTACAAACAATCCTCCCATGAAGACCAACCAGTTCT
CCGCGCCCCTGACGACCCCCGGCATGCTCATGCGCAGTAAATACAAAGTC
CTCATTCCCAGCTTCCAGACCAGACCCAAGGGTCGCAAAACAGTAACCGT
TAAAATAAGACCCCCCAAACTATTTCAAGACAAGTGGTACACCCAGCAGG
ACCTGTGTTCAGTTCCTCTTGTCCAACTGAACGTGACCGCAGCTGATTTC
ACACATCCGTTCGGCTCACCACTAACTGAAACTCCTTGCGTAGAGTTCCA
GGTGCTGGGTGACTTGTACAATACATGTCTCAATATCGACCTTCCGCAAT
TTAGTGAATTAGGAGAAATAACTAGTGCCTACTCAAAACCAAACTCAAAT
AACCTAAAAGAATTATACAAAGAATTGTTCACAAAAGCCACATCAGGACA
```

TABLE N10-continued

| Exemplary *Anellovirus* nucleic acid sequence (*Alphatorquevirus*, Clade 4) |
|---|
| CTACTGGCAGACATTCATAACCAACAGCATGGTCAGAGCACACATAGATG<br>CAGACAAAGCTAAAGAAGCACAAAGAGCATCCACCACACCCTCATACAAC<br>AATGACCCCTTCCCCACAATACCTGTTAAATCAGAGTTTGCACAGTGGAA<br>AAAGAAATTCACAGACACTAGAGACAGCCCCTTTCTTTTTGCCACTTACC<br>ATCCCGAAGCTATAAAAGACACAATTATGAAAATGAGAGAGAACAACTTT<br>AAGCTAGAGACAGGACCCAATGACAAGTATGGAGACTACACAGCACAGTA<br>CCAAGGAAACACACACATGCTAGACTACTACCTTGGCTTTTACAGCCCCA<br>TATTCCTCTCAGATGGAAGGTCTAACGTAGAATTCTTCACTGCCTACAGA<br>GACATAGTATACAATCCCTTCTTAGACAAGGCCCAGGGCAACATGGTGTG<br>GTTTCAGTACCACACAAAGACAGACAACAAGTTTAAAAAACCAGAGTGCC<br>ACTGGGAAATCAAAGACATGCCCCTGTGGGCCCTCCTAAACGGATATGTA<br>GACTACTTAGAGACTCAAATACAGTATGGTGACCTCAGTAAAGAAGGGAA<br>AGTCCTCATCAGGTGTCCCTACACCAAGCCAGCACTAGTAGACCCCAGAG<br>ACGACACTGCAGGATATGTAGTCTACAACAGAAACTTTGGCAGAGGCAAG<br>TGGATAGACGGAGGGGGCTACATCCCCCTGCACGAGAGGACAAAATGGTA<br>CGTGATGCTCAGATACCAGACGGACGTCTTCCATGACATAGTGACCTGTG<br>GGCCCTGGCAGTACAGAGACGACAACAAAAACAGCCAGCTAGTGGCCAAA<br>TACCGCTTCAGCTTTATATGGGGAGGTAACACTGTCCACTCTCAGGTCAT<br>CAGAAACCCGTGCAAAGACAACCAAGTATCCGGTCCCCGTCGACAGCCTA<br>GGGATATACAAGTCGTTGACCCGCAACGCATCACGCCGCCGTGGGTCCTC<br>CACAGCTTCGACCAGCGAAGAGGCCTCTTTACTGAAACAGCTCTCAGGCG<br>CCTGCTCCAGGAACCACTACCTGGCGAGTATGCTGTTAGCACCCTCAGGA<br>CACCCCTCCTCTTTCTACCCTCAGAATACCAGCGAGAAGACGGCGCTGCA<br>GAAAGCGCCTCAGGTTCACCGGCCAAAAGACCCCGTATCTGGTCAGAAGA<br>GAGTCAGACGGAGACGATCTCCTCGGAGGAGAACCCGGCGGAGACGACGA<br>GGGAGCTCCTCCAGCGAAAGCTCCGAGAGCAGCGAGCACTCCAGTTCCAA<br>CTCCAGCACTTCGCGGTCCAACTCGCCAAGACCCAGGCGAATCTCCACGT<br>AAACCCCCTGTTATCTTTCCCGCAATGAATAAGGTCTTTCTGTTTCCCCC<br>AGAGGGTCCCAAGCCCATCCTGGGCAAAGAGGCCTGGCAGGACGAGTACG<br>AGACCTGCAGGGTCTGGAACAGACCTGCCAGAACCCACCACACAGACACC<br>CCCTTCTATCCCTGGGCCCCCCACAAGTTCCATGTAAGCTTCAAACTTGG<br>CTTCCAATAAAATTACTAGGCCGTGGAACTCTCACTGGTCGGTGTCTACC<br>TCTTAAGGTCACTAAGCACTCCGAGCGTCAGCGAGGAGTGCGACCCTCTA<br>CCCTGGTGCAACGCCCTCGGCGGCCGCGCGCTACGCCTTCGGCTGCGCGC<br>GGCACCTCGGACCCCCGCTCGTGCTGACGCGCTCGCGCGCGTCAGACCAC<br>TTCGGGCTCGCGGGGGTCGGGAATTTTGCTAAACAGACTCCGAGTTGCCA<br>TTGGACACTGTAGCTGTGAATCAGTAACGAAAGTGAGTGGGGCCAGACTT<br>CGCCATAGGGCCTTTATCTTCTTGCCATTGGTCCGTGTAGGGGGTCGCCA<br>TAGGCTTCGACCTCCCTTTTAGGCCTTCCGGACTACAAAAATGGCGGATT<br>CAGTGACGTCACGGCCGCCATTTTAAGTAGGTGCCGTCCAGGACTGCAGT<br>TCCGGGTCAGAGTGCATCCTCGGCGGAACCTGCACAAAATGGCGGTCAAT<br>ATCTTCCGGGTCAAAGGTCACACCTACGTCATAAGTCACGTGACTGGGTC<br>CTGCTACGTCATATGCGGAAGTAGGCCCCGCCACGTGACTCGTCACGTGG<br>GCGCTGCGTCACGGCGGCCATTTTGTATCACAAAATGGCGGACTTCCTTC<br>CTCTTTTTTAAAAATAACGGCCCAGCGGCGGCGCGCGCGCTTCGCGCGCG<br>CGCCGGGGGGCTCCGCCCCCCCCCGCGCATGCGCGGGGCCCCCCCCCGCG<br>GGGGGCTCCGCCCCCCGGTCCCCCCCCG (SEQ ID NO: 24) |

Annotations:

| Putative Domain | Base range |
|---|---|
| TATA Box | 82-87 |
| Initiator Element | 95-115 |
| Transcriptional Start Site | 115 |
| 5' UTR Conserved Domain | 170-238 |
| ORF2 | 335-721 |
| ORF2/2 | 335-717; 2446-2902 |
| ORF2/3 | 335-717; 2675-3109 |
| ORF1 | 586-2928 |
| ORF1/1 | 586-717; 2446-2928 |
| ORF1/2 | 586-717; 2675-2902 |
| Three open-reading frame region | 2640-2899 |
| Poly(A) Signal | 3106-3114 |
| GC-rich region | 3768-3878 |

TABLE A10

| Exemplary *Anellovirus* amino acid sequences (*Alphatorquevirus*, Clade 4) TTV-HD20a (*Alphatorquevirus* Clade 4) | |
|---|---|
| ORF2 | MSRCWCPPRGDVSSRESRWYEAVRGSHDAFCGCSDPILHLSRLAARFNHQG PPTPPTDDRAPQNTPVRRLLPLPSYPGEGPQARWPGGDGGAAGGDRREGGD GGARAAEDEYQPEDLDELFGAIEQEQ (SEQ ID NO: 25) |
| ORF2/2 | MSRCWCPPRGDVSSRESRWYEAVRGSHDAFCGCSDPILHLSRLAARFNHQG PPTPPTDDRAPQNTPVRRLLPLPSYPGEGPQARWPGGDGGAAGGDRREGGD GGARAAEDEYQPEDLDELFGAIEQEQSSETRAKTTKYPVPVDSLGIYKSLTR NASRRRGSSTASTSEEASLLKQLSGACSRNHYLASMLLAPSGHPSSFYPQNT SEKTALQKAPQVHRPKDPVSGQKRVRRRRSPRRRTRRRRRGSSSSESSESSE HSSSNSSTSRSNSPRPRRIST (SEQ ID NO: 26) |
| ORF2/3 | MSRCWCPPRGDVSSRESRWYEAVRGSHDAFCGCSDPILHLSRLAARFNHQG PPTPPTDDRAPQNTPVRRLLPLPSYPGEGPQARWPGGDGGAAGGDRREGGD GGARAAEDEYQPEDLDELFGAIEQEQIPARRRRCRKRLRFTGQKTPYLVRRE SDGDDLLGGEPGGDDEGAPPAKAPRAASTPVPTPALRGPTRQDPGESPRKPP VIFPPAMNKVFLFPPEGPKPILGKEAWQDEYETCRVWNRPARTHHTDTPFYP WAPHKFHVSFKLGFQ (SEQ ID NO: 27) |
| ORF1 | MAWWGWRRRWWRPKRRWRWRRARRRRRVPARRPRRAFRRYRTRTVRR RRRGRRRGYRRRYRLRRYARRRFRRKKIVLTQWNPQTTRKCIIRGMMPVL WAGMGTGGRNYAVRSDDYVVNKGFGGSFATETFSLKVLYDQFQRGFNRW SHTNEDLDLARYRGCRWTFYRHKDTDFIVYFTNNPPMKTNQFSAPLTTPGM LMRSKYKVLIPSFQTRPKGRKTVTVKIRPPKLFQDKWYTQQDLCSVPLVQL NVTAADFTHPFGSPLTETPCVEFQVLGDLYNTCLNIDLPQFSELGEITSAYSK PNSNNLKELYKELFTKATSGHYWQTFITNSMVRAHIDADKAKEAQRASTTP SYNNDPFPTIPVKSEFAQWKKKFTDTRDSPFLFATYHPEAIKDTIMKMRENN FKLETGPNDKYGDYTAQYQGNTHMLDYYLGFYSPIFLSDGRSNVEFFTAYR DIVYNPFLDKAQGNMVWFQYHTKTDNKFKKPECHWEIKDMPLWALLNGY VDYLETQIQYGDLSKEGKVLIRCPYTKPALVDPRDDTAGYVVYNRNFGRGK WIDGGGYIPLHERTKWYVMLRYQTDVFHDIVTCGPWQYRDDNKNSQLVA KYRFSFIWGGNTVHSQVIRNPCKDNQVSGPRRQPRDIQVVDPQRITPPWVLH SFDQRRGLFTETALRRLLQEPLPGEYAVSTLRTPLLFLPSEYQREDGAAESAS GSPAKRPRIWSEESQTETISSEENPAETTRELLQRKLREQRALQFQLQHFAVQ LAKTQANLHVNPLLSFPQ (SEQ ID NO: 28) |
| ORF1/1 | MAWWGWRRRWWRPKRRWRWRRARRRRRVPARRPRRAFRRYRTRTVIRN PCKDNQVSGPRRQPRDIQVVDPQRITPPWVLHSFDQRRGLFTETALRRLLQE PLPGEYAVSTLRTPLLFLPSEYQREDGAAESASGSPAKRPRIWSEESQTETISS EENPAETTRELLQRKLREQRALQFQLQHFAVQLAKTQANLHVNPLLSFPQ (SEQ ID NO: 29) |
| ORF1/2 | MAWWGWRRRWWRPKRRWRWRRARRRRRVPARRPRRAFRRYRTRTNTSE KTALQKAPQVHRPKDPVSGQKRVRRRRSPRRRTRRRRRGSSSSESSESSEHS SSNSSTSRSNSPRPRRIST (SEQ ID NO: 30) |

TABLE N11

Exemplary *Anellovirus* nucleic acid sequence (*Alphatorquevirus*, Clade 5)

| | |
|---|---|
| Name | TTV-16 (TUS01) |
| Genus/Clade | *Alphatorquevirus*, Clade 5 |
| Accession Number | AB017613.1 |
| full Sequence: 3818 bp | |

```
1         10         20         30         40         50
|         |          |          |          |          |
AAGTCCGCCACTAACCACGTGACTCCCGCAGGCCAACCCAGTACTATGTC
GTCCACTTCCTGGGACGAGTCTACGTCCTGATATAAGTAAGTGCACTTCC
GAATGGCTGAGTTTTCCACGCCCGTCCGCAGCGAGAACGCCACGGAGGGG
AGTCCGCGCGTCCCGAGGGCGGGTGCCGGAGGTGAGTTTACACACCGCAG
TCAAGGGGCAATTCGGGCTCGGGACTGGCCGGGCCCCGGGCAAGGCTCTT
AAAAAATGCACTTTCGCAGAGTGCGAGCGAAAAGGAAACTGCTACTGCAA
GCTGTGCGAGCTCCACCGAAGGCACCTGCCATGAGCTTCACCACACCTAC
TATTAATGCCGGGATCCGAGAGCAGCAATGGTTCGAGTCCACCCTTAGAT
CCCACCACTCGTTCTGTGGCTGTGGTGATCCCGTGCTTCATTTTACTAAC
CTTGCTACTCGCTTTAACTATCTGCCTGCTACCTCTTCGCCTCTGGACCC
TCCCGGCCCAGCGCCGCGAGGCCGCCCGGCGCTCCGCCGCCTCCCGGCAC
TCCCTTCAGCCCCCGCGACCCCTTCTAGAGAACTAGCATGGCCTACTGGT
TCAGAAGGTGGGGCTGGAGGCCGAGGCGCCGGTGGAGAAGGTGGCGCCGC
CGTCGAAGGAGACTACCGAGAAGAAGAACTAGACGAGCTGTTCGCGGCCT
TGGAAGAAGACGCAAACCAAGGGTAAGGAGGCGCCGCAGAACTCGCAGAC
GTACCTACAGACGGGGGTGGAGACGCAGGAGGTACATAAGACGGGGGCGA
CGCAAAAAGAAACTCATACTGACTCAGTGGAACCCGGCAATAGTTAAGAG
GTGCAACATTAAGGGCGGACTTCCAATAATTATATGCGGAGAGCCCAGGG
```

TABLE N11-continued

| Exemplary *Anellovirus* nucleic acid sequence (*Alphatorquevirus*, Clade 5) |
|---|
| CAGCCTTTAACTATGGCTACCACATGGAGGACTACACTCCTCAACCTTTC<br>CCCTTCGGAGGGGGAATGAGCACAGTGACTTTCTCTCTGAAAGCCTTGTA<br>TGACCAGTACCTAAAACACCAAAACAGGTGGACTTTCTCAAACGACCAGC<br>TAGACCTCGCCAGATACAGGGGCTGTAAACTAAGGTTCTACAGAAGCCCC<br>GTCTGTGACTTTATAGTACACTACAACCTAATACCTCCACTAAAAATGAA<br>CCAGTTCACAAGTCCCAACACGCACCCGGGACTACTCATGCTCAGCAAAC<br>ACAAGATAATAATTCCCAGCTTTCAAACAAGACCTGGGGGCAGACGCTTT<br>GTTAAAATAAGACTTAATCCCCCCAAACTATTTGAAGACAAGTGGTACAC<br>TCAGCAAGACCTGTGCAAGGTTCCGCTCGTTAGTATTACAGCAACTGCGG<br>CTGACTTGCGGTATCCGTTCTGCTCACCACAAACGAACAACCCCTTGCACC<br>ACCTTCCAGGTACTGCGCAAGAACTACAATACAGTTATAGGAACTTCCGT<br>AAAAGACCAAGAGTCCACACAAGACTTTGAAAATTGGCTTTATAAAACAG<br>ACTCACACTATCAAACATTTGCCACAGAGGCTCAACTAGGCAGAATTCCT<br>GCATTTAATCCTGATGGCACTAAAAACACTAAACAGCAGTCGTGGCAAGA<br>TAACTGGAGCAAAAAAAATTCACCATGGACAGGTAACTCAGGTACATACC<br>CACAAACAACCAGTGAAATGTACAAAATTCCATATGACAGTAACTTCGGC<br>TTTCCCACATACAGAGCCCAAAAAGACTACATTTTAGAAAGAAGACAGTG<br>CAACTTTAACTATGAAGTTAATAATCCAGTTAGCAAAAAAGTATGGCCAC<br>AACCTAGTACAACAACACCCACAGTAGACTACTATGAATACCACTGTGGA<br>TGGTTCAGCAACATATTCATAGGCCCCAACAGATACAACCTACAGTTTCA<br>AACAGCATATGTAGACACCACATACAACCCACTAATGGACAAGGGCAAAG<br>GCAACAAAATATGGTTTCAATATCTGTCTAAAAAGGGCACAGACTACAAT<br>GAAAAACAATGCTACTGCACCCTAGAAGACATGCCCCTATGGGCAATATG<br>CTTTGGATACACTGACTATGTAGAGACTCAACTAGGACCCAATGTGGACC<br>ATGAAACAGCAGGCTTAATAATTATGATCTGTCCATACACTCAACCACCT<br>ATGTATGACAAAAACAGACCTAACTGGGGATACGTAGTCTATGACACAAA<br>CTTTGGCAATGGAAAAATGCCCTCAGGAAGTGGCCAAGTCCCAGTATACT<br>GGCAATGCCGATGGAGGCCCATGCTGTGGTTCCAACAACAAGTACTCAAT<br>GACATCTCAAAGACTGGACCGTACGCCTACAGAGACGAATATAAAAATGT<br>ACAACTGACTCTCTACTACAACTTTATTTTTAACTGGGGGGGCGACATGT<br>ATTACCCACAGGTCGTTAAAAACCCCTGTGGAGACTCCGGAATCGTTCCC<br>GGTTCCGGTAGATTCACTCGAGAAGTACAAGTCGTTAGCCCGCTTTCCAT<br>GGGACCGGCCTACATCTTCCACTACTTCGACTCCAGACGCGGGTTCTTTA<br>GTGAAAAAGCTCTTAAAAGAATGCAACAACAACAAGAATTTGATGAATCT<br>TTTACATTCAAACCTAAGAGACCCAAACTTTCTACAGCAGCCGCAGAAAT<br>CCTCCAGCTCGAAGAAGACTCGACTTCAGGGGAAGGAAAATCGCCACTAC<br>AGCAAGAAGAGAAAGAAGTCGAAGTCCTCCAAACGCCGACAGTACAGCTC<br>CAGCTCCAGCGAAACATCCAGGAGCAGCTCGCAATCAAGCAGCAGCTCCA<br>ATTCCTCTTGCTCCAACTCCTCAAAACCCAATCCAATTTGCATTTAAACC<br>CACAATTTTTAAGCCCTTCATAAAATATGACATGTTTGGGGACCCCCTTC<br>CTCACCCCCCAACAGCCGAAGAGTGGGAAACAGAGTACCAGTGCTGTAAG<br>GCCTTTAACAGACCACCTAGAACCAACCTAAAAGACACCCCCTTCTACCC<br>CTGGGTACCTAAACCTAAACCTCAATTCCGTGTATCTTTTAAACTTGGTT<br>TTCAATAAACAAGGCCGTGGGAGTTTCACTTGTCGGTGTCAACCTCTTAA<br>GGTCACTAAGCACTCCGAGCGTAAGCGAGGAGTGCGACCCTCCCCCCTGG<br>GGCAACTCCCTCGAAGTCCGGCGCTACGCGCTTCGCGCTGCGCCGGACAT<br>CTCGGACCCCCCCTCCACCCGAAACGCTTGCGCGTTTCGGACCTTCGGCG<br>TCGGGGGGGTCGGGGGCTTTACTAAACAGACTCCGAGGTGCCATTGGACA<br>CTGAGGGGATGAACAGCAACGAAAGTGAGTGGGGCCAGACTTCGCCATAA<br>GGCCTTTATCTTCTTGCCATTTGTCAGTATAGAGGGTCGCCATAGGCTTC<br>GGCCTCCATTTTAACCTCTAAAAACTACCAAAATGGCCGTTCCAGTGACG<br>TCACAGCCGCCATTTTAAGTAGCTGACGTCAAGGATTGACGTGAAGGTTA<br>AAGGTCATCCTCGGCGGAAGCTACACAAAATGGTGGACAACATCTTCCGG<br>GTCAAAGGTCGTGCACACGTCATAAGTCACGTGGTGGGGACCCGCTGTAA<br>CCCGGAAGTAGGCCCCGTCACGTGATTTGTCACGTGTGTACACGTCACAA<br>CCGCCATTTTGTTTTACAAAATGGCTGACTTCCTTCCTCTTTTTTAAAAA<br>AAACGGCCGTGCGGCGGCGCGCGCGCTTCGCGCGCGCGCCGGGGGCTGCC<br>GCCCCCCCCCGCGCATGCGCGCGGGGCCCCCCCCCGCGGGGGGCTCCGCC<br>CCCCGGCCCCCCCCCCCG (SEQ ID NO: 31) |

Annotations:

| Putative Domain | Base range |
|---|---|
| TATA Box | 82-86 |
| Initiator Element | 100-115 |
| Transcriptional Start Site | 115 |
| 5' UTR Conserved Domain | 170-240 |
| ORF2 | 331-726 |
| ORF2/2 | 331-722; 2412-2847 |
| ORF2/3 | 331-722; 2638-3058 |

TABLE N11-continued

| Exemplary *Anellovirus* nucleic acid sequence (*Alphatorquevirus*, Clade 5) | |
|---|---|
| ORF2t/3 | 331-380; 2638-3058 |
| ORF1 | 588-2873 |
| ORF1/1 | 588-722; 2412-2873 |
| ORF1/2 | 588-722; 2638-2847 |
| Three open-reading frame region | 2699-2969 |
| Poly(A) Signal | 3220-3225 |
| GC-rich region | 3302-3541 |

TABLE A11

| Exemplary *Anellovirus* amino acid sequences (*Alphatorquevirus*, Clade 5) TTV-16-TUS01 (*Alphatorquevirus* Clade 5) | |
|---|---|
| ORF2 | MSFTTPTINAGIREQQWFESTLRSHHSFCGCGDPVLHFTNLATRFNYLPATSS PLDPPGPAPRGRPALRRLPALPSAPATPSRELAWPTGSEGGAGGRGAGGEGG AAVEGDYREEELDELFAALEEDANQG (SEQ ID NO: 32) |
| ORF2/2 | MSFTTPTINAGIREQQWFESTLRSHHSFCGCGDPVLHFTNLATRENYLPATSS PLDPPGPAPRGRPALRRLPALPSAPATPSRELAWPTGSEGGAGGRGAGGEGG AAVEGDYREEELDELFAALEEDANQGSLKTPVETPESFPVPVDSLEKYKSLA RFPWDRPTSSTTSTPDAGSLVKKLLKECNNNKNLMNLLHSNLRDPNFLQQP QKSSSSKKTRLQGKENRHYSKKRKKSKSSKRRQYSSSSSETSRSSSQSSSSSN SSCSNSSKPNPICI (SEQ ID NO: 33) |
| ORF2/3 | MSFTTPTINAGIREQQWFESTLRSHHSFCGCGDPVLHFTNLATRENYLPATSS PLDPPGPAPRGRPALRRLPALPSAPATPSRELAWPTGSEGGAGGRGAGGEGG AAVEGDYREEELDELFAALEEDANQGSRRNPPARRRLDFRGRKIATTARRE RSRSPPNADSTAPAPAKHPGAARNQAAAPIPLAPTPQNPIQFAFKPTIFKPFIK YDMFGDPLPHPPTAEEWETEYQCCKAFNRPPRTNLKDTPFYPWVPKPKPQF RVSFKLGFQ (SEQ ID NO: 34) |
| ORF2t/3 | MSFTTPTINAGIREQQCSRRNPPARRRLDFRGRKIATTARRERSRSPPNADST APAPAKHPGAARNQAAAPIPLAPTPQNPIQFAFKPTIFKPFIKYDMFGDPLPH PPTAEEWETEYQCCKAFNRPPRTNLKDTPFYPWVPKPKPQFRVSFKLGFQ (SEQ ID NO: 35) |
| ORF1 | MAYWFRRWGWRPRRRWRRWRRRRRRLPRRRTRRAVRGLGRRRKPRVRR RRRTRRRTYRRGWRRRRYIRRGRRKKKLILTQWNPAIVKRCNIKGGLPIIICG EPRAAFNYGYHMEDYTPQPFPFGGMSTVTFSLKALYDQYLKHQNRWTFS NDQLDLARYRGCKLRFYRSPVCDFIVHYNLIPPLKMNQFTSPNTHPGLLMLS KHKIIIPSFQTRPGGRRFVKIRLNPPKLFEDKWYTQQDLCKVPLVSITATAAD LRYPFCSPQTNNPCTTFQVLRKNYNTVIGTSVKDQESTQDFENWLYKTDSH YQTFATEAQLGRIPAFNPDGTKNTKQQSWQDNWSKKNSPWTGNSGTYPQT TSEMYKIPYDSNFGFPTYRAQKDYILERRQCNFNYEVNNPVSKKVWPQPST TTPTVDYYEYHCGWFSNIFIGPNRYNLQFQTAYVDTTYNPLMDKGKGNKIW FQYLSKKGTDYNEKQCYCTLEDMPLWAICFGYTDYVETQLGPNVDHETAG LIIMICPYTQPPMYDKNRPNWGYVVYDTNFGNGKMPSGSGQVPVYWQCR WRPMLWFQQQVLNDISKTGPYAYRDEYKNVQLTLYYNFIFNWGGDMYYP QVVKNPCGDSGIVPGSGRFTREVQVVSPLSMGPAYIFHYFDSRRGFFSEKAL KRMQQQQEFDESFTFKPKRPKLSTAAAEILQLEEDSTSGEGKSPLQQEEKEV EVLQTPTVQLQLQRNIQEQLAIKQQLQFLLLQLLKTQSNLHLNPQFLSPS (SEQ ID NO: 36) |
| ORF1/1 | MAYWFRRWGWRPRRRWRRWRRRRRRLPRRRTRRAVRGLGRRRKPRVVK NPCGDSGIVPGSGRFTREVQVVSPLSMGPAYIFHYFDSRRGFFSEKALKRMQ QQQEFDESFTFKPKRPKLSTAAAEILQLEEDSTSGEGKSPLQQEEKEVEVLQT PTVQLQLQRNIQEQLAIKQQLQFLLLQLLKTQSNLHLNPQFLSPS (SEQ ID NO: 37) |
| ORF1/2 | MAYWFRRWGWRPRRRWRRWRRRRRRLPRRRTRRAVRGLGRRRKPRQPQ KSSSSKKTRLQGKENRHYSKKRKKSKSSKRRQYSSSSSETSRSSSQSSSSSNS SCSNSSKPNPICI (SEQ ID NO: 38) |

TABLE N12

| Exemplary *Anellovirus* nucleic acid sequence (*Alphatorquevirus*, Clade 6) | |
|---|---|
| Name | TTV-TJN02 |
| Genus/Clade | *Alphatorquevirus*, Clade 6 |
| Accession Number | AB028669.1 |
| Full Sequence: 3794 bp | |

```
1         10         20         30         40         50
|         |          |          |          |          |
CCCGAAGTCCGTCACTAACCACGTGACTCCTGTCGCCCAATCAGAGTGTA
TGTCGTGCATTTCCTGGGCATGGTCTACATCCTGATATAACTAAGTGCAC
TTCCGAATGGCTGAGTTTTCCACGCCCGTCCGCAGCGAGGGAGCGACGGA
GGAGCTCCCGAGCGTCCCGAGGGCGGGTGCCGGAGGTGAGTTTACACACC
GCAGTCAAGGGGCAATTCGGGCTCGGGACTGGCCGGGCTATGGGCAAGGC
TCTTAGGGTCTTCATTCTTAATATGTTTCTTGGCAGAGTTTACCGCCACA
AGAAAAGGAAAGTGCTACTGTCCACACTGCGAGCTCCACAGGCGTCTCGC
AGGGCTATGAGTTGGCGACCCCCGGTACACGATGCACCCGGCATCGAGCG
CAATTGGTACGAGGCCTGTTTCAGAGCCCACGCTGGAGCTTGTGGCTGTG
GCAATTTTATTATGCACCTTAATCTTTTGGCTGGGCGTTATGGTTTTACT
CCGGGGTCAGCGCCGCCAGGTGGTCCTCCTCCGGGCACCCCGCAGATAAG
GAGAGCCAGGCCTAGTCCCGCCGCACCAGAGCAGCCCGCTGCCCTACCAT
GGCATGGGGATGGTGGAGATGGCGGCGCCGCTGGCCCGCCAGACGCTGGA
GGAGACGCCGTCGCCGGCGCCCCGTACGGAGAACAAGAGCTCGCCGACCT
GCTCGACGCTATAGAAGACGACGAACAGTAAGAACCAGGCGAAGGCGGTG
GGGGCGCAGACGGTACAGACGGGGCTGGAGACGCAGGACTTATGTGAGAA
AGGGGCGACACAGAAAAAAGAAAAAGAGACTGATACTGAGACAGTGGCAA
CCAGCCACAAGACGCAGATGTACCATAACTGGGTACCTGCCCATAGTGTT
CTGCGGCCACACTAGGGGCAATAAAAACTATGCACTACACTCTGACGACT
ACACCCCCCAAGGACAACCATTIGGAGGGGCTCTAAGCACTACCTCATTC
TCTTTAAAAGTACTATTTGACCAGCATCAGAGAGGACTAAACAAGTGGTC
TTTTCCAAACGACCAACTAGACCTCGCCAGATATAGAGGCTGCAAATTTA
TATTTTATAGAACAAAACAAACTGACTGGGTGGGCCAGTATGACATATCA
GAACCCTACAAGCTAGACAAATACAGCTGCCCCAACTATCACCCTGGAAA
CATGATTAAGGCAAAGCACAAATTTTTAATACCAAGCTATGACACTAATC
CTAGAGGCAGACAAAAAATTATAGTTAAAATTCCCCCCCCAGACCTCTTT
GTAGACAAGTGGTACACTCAAGAGGATCTGTGTTCCGTTAATCTTGTGTC
ACTTGCGGTTTCTGCGGCTTCCTTTCTCCACCCATTCGGCTCACCACAAA
CTGACAACCCTTGCTACACCTTCCAGGTGTTGAAAGAGTTCTACTATCAG
GCAATAGGCTTCTCTGCAAGCACACAAGCAATGACATCAGTATTAGACAC
GCTATACACACAAAACAGTTATTGGGAATCTAATCTAACTCAGTTTTATG
TACTTAATGCAAAAAAAGGCAGTGATACAACACAGCCTTTAACTAGCAAT
ATGCCAACTCGTGAAGAGTTTATGGCAAAAAAAAATACCAATTACAACTG
GTATACATACAAGGCCGCGTCAGTAAAAAATAAACTACATCAAATGAGAC
AAACCTATTTTGAGGAGTTAACCTCTAAGGGGCCACAAACAACAAAAAGT
GAGGAAGGCTACAGTCAGCACTGGACCACCCCCTCCACAAACGCCTACGA
ATATCACTTAGGAATGTTTAGTGCAATATTTCTAGCCCCAGACAGGCCAG
TACCTAGATTTCCATGCGCCTACCAAGATGTAACTTACAACCCCTTAATG
GACAAAGGGGTGGGAAACCACATTTGGTTTCAGTACAACACAAAGGCAGA
CACTCAGCTAATAGTCACAGGAGGGTCCTGCAAAGCACACATACAAGACA
TACCACTGTGGGCGGCCTTCTATGGATACAGTGACTTTATAGAGTCAGAA
CTAGGCCCCTTTGTAGATGCAGAGACGGTAGGCTTAGTGTGTGTAATATG
CCCTTATACAAAACCCCCCATGTACAACAAGACAAACCCCGCCATGGGCT
ACGTGTTCTATGACAGAAACTTTGGTGACGGAAAATGGACTGACGGACGG
GGCAAAATAGAGCCCTACTGGCAAGTTAGGTGGAGGCCCGAAATGCTTTT
CCAAGAAACTGTAATGGCAGACCTAGTTCAGACTGGGCCCTTTAGCTACA
AAGACGAACTTAAAAACAGCACCCTAGTGTGCAAGTACAAATTCTATTTC
ACCTGGGGAGGTAACATGATGTTCCAACAGACGATCAAAAACCCGTGCAA
GACGGACGGACAACCCACCGACTCCAGTAGACACCCTAGAGGAATACAAG
TGGCGGACCCGGAACAAATGGGACCCCGCTGGGTGTTCCACTCCTTTGAC
TGGCGAAGGGGCTATCTTAGCGAGAAAGCTCTCAAACGCCTGCAAGAAAA
ACCTCTTGACTATGACGAATATTTTACACAACCAAAAAGACCTAGAATCT
TTCCTCCAACAGAATCAGCAGAGGGAGAGTTCCGAGAGCCCGAAAAAGGC
TCGTATTCAGAGGAAGAAAGGTCGCAAGCCTCTGCCGAAGAGCAGACGCA
GGAGGCGACAGTACTCCTCCTCAAGCGACGACTCAGAGAGCAACAGCAGC
TCCAGCAGCAGCTCCAATTCCTCACCCGAGAAATGTTCAAAACGCAAGCG
GGTCTCCACCTAAACCCTATGTTATTAAACCAGCGATAAACCAAGTGTAC
CTGTTTCCAGAGAGGGCCCCAAAACCCCCTCCTAGCAGCCAAGACTGGCA
GCAGGAGTACGAGGCCTGCGCAGCCTGGGACAGGCCCCCTAGATACAATC
TGTCCTCTCCTCCTTTCTACCCCAGCTGCCCTTCAAAATTCTGTGTAAAA
TTCAGCCTTGGCTTTAAATAAATGGCAACTTTACTGTGCAAGGCCGTGGG
AGTTTCACTGGTCGGTGTCTACCTCTAAAGGTCACTAAGCACTCCGAGCG
TTAGCGAGGAGTGCGACCCTTCCCCCTGACTCAACTTCTTCGGAGCCGCG
CGCTACGCCTTCGGCTGCGCGCGGCACCTCAGACCCCCGCTCGTGCTGAC
ACGCTCGCGCGTGTCAGACCACTTCGGGCTCGCGGGGGTCGGGAATTTTG
CTAAACAGACTCCGAGTTGCTCTTGGACACTGAGGGGGCATATCAGTAAC
GAAAGTGAGTGGGGCCAGACTTCGCCATAAGGCCTTTATCTTCTTGCCAT
TGGATAGTATCGAGGGTTGCCATAGGCTTCGACCTCCATTTTAGGCCTTC
CGGACTACAAAAATGGCCGTTTTAGTGACGTCACGGCCGCCATTTTAAGT
AAGGCGGAAGCAGCTCGGCGTACACAAAATGGCGGCGGAGCACTTCCGGC
TTGCCCAAAATGGTGGGCAACTTCTTCCGGGTCAAAGGTCACAGCTACGT
```

TABLE N12-continued

| Exemplary *Anellovirus* nucleic acid sequence (*Alphatorquevirus*, Clade 6) |
|---|
| CACAAGTCACGTGGGGAGGGTTGGCGTTTAACCCGGAAGCCAATCCTCTT<br>ACGTGGCCTGTCACGTGACTTGTACGTCACGACCACCATTTTGTTTTACA<br>AAATGGCCGACTTCCTTCCTCTTTTTTAAAAATAACGGTTCGGCGGCGGC<br>GCGCGCGCTACGCGCGCGCGCCGGGGGGCTGCCGCCCCCCCCCCGCGCAT<br>GCGCGGGGCCCCCCCCCGCGGGGGGCTCCGCCCCCCGGCCCCCC (SEQ ID NO: 39) |

Annotations:

| Putative Domain | Base range |
|---|---|
| TATA Box | 89-90 |
| Cap Site | 107-114 |
| Transcriptional Start Site | 114 |
| 5' UTR Conserved Domain | 174-244 |
| ORF2 | 357-731 |
| ORF2/2 | 357-727; 2381-2813 |
| ORF2/3 | 357-727; 2619-3021 |
| ORF2t/3 | 357-406; 2619-3021 |
| ORF1 | 599-2839 |
| ORF1/1 | 599-727; 2381-2839 |
| ORF1/2 | 599-727; 2619-2813 |
| Three open-reading frame region | 2596-2810 |
| Poly(A) Signal | 3017-3022 |
| GC-rich region | 3691-3794 |

TABLE A12

| Exemplary *Anellovirus* amino acid sequences (*Alphatorquevirus*, Clade 6)<br>TTV-TJN02 (*Alphatorquevirus* Clade 6) | |
|---|---|
| ORF2 | MSWRPPVHDAPGIERNWYEACFRAHAGACGCGNFIMHLNLLAGRYGFTPGSAPPG<br>GPPPGTPQIRRARPSPAAPEQPAALPWHGDGGDGGAAGPPDAGGDAVAGAPYGEQ<br>ELADLLDAIEDDEQ (SEQ ID NO: 40) |
| ORF2/2 | MSWRPPVHDAPGIERNWYEACFRAHAGACGCGNFIMHLNLLAGRYGFTPGSAPPG<br>GPPPGTPQIRRARPSPAAPEQPAALPWHGDGGDGGAAGPPDAGGDAVAGAPYGEQ<br>ELADLLDAIEDDEQRSKTRARRTDNPPTPVDTLEEYKWRTRNKWDPAGCSTPLTGE<br>GAILARKLSNACKKNLLTMTNILHNQKDLESFLQQNQQRESSESPKKARIQRKKGR<br>KPLPKSRRRRRQYSSSSDDSESNSSSSSSSNSSPEKCSKRKRVST (SEQ ID NO: 41) |
| ORF2/3 | MSWRPPVHDAPGIERNWYEACFRAHAGACGCGNFIMHLNLLAGRYGFTPGSAPPG<br>GPPPGTPQIRRARPSPAAPEQPAALPWHGDGGDGGAAGPPDAGGDAVAGAPYGEQ<br>ELADLLDAIEDDEHRGRVPRARKRLVFRGRKVASLCRRADAGGDSTPPQATTQRAT<br>AAPAAAPIPHPRNVQNASGSPPKPYVIKPAINQVYLFPERAPKPPPSSQDWQQEYEA<br>CAAWDRPPRYNLSSPPFYPSCPSKFCVKFSLGFK (SEQ ID NO: 42) |
| ORF2t/3 | MSWRPPVHDAPGIERNCRGRVPRARKRLVFRGRKVASLCRRADAGGDSTPPQATT<br>QRATAAPAAAPIPHPRNVQNASGSPPKPYVIKPAINQVYLFPERAPKPPPSSQDWQQ<br>EYEACAAWDRPPRYNLSSPPFYPSCPSKFCVKFSLGFK (SEQ ID NO: 43) |
| ORF1 | MAWGWWRWRRRWPARRWRRRRRRRPVRRTRARRPARRYRRRRTVRTRRRRWG<br>RRRYRRGWRRRTYVRKGRHRKKKKRLILRQWQPATRRRCTITGYLPIVFCGHTRG<br>NKNYALHSDDYTPQGQPFGGALSTTSFSLKVLFDQHQRGLNKWSFPNDQLDLARY<br>RGCKFIFYRTKQTDWVGQYDISEPYKLDKYSCPNYHPGNMIKAKHKFLIPSYDTNP<br>RGRQKIIVKIPPPDLFVDKWYTQEDLCSVNLVSLAVSAASFLHPFGSPQTDNPCYTF<br>QVLKEFYYQAIGFSASTQAMTSVLDTLYTQNSYWESNLTQFYVLNAKKGSDTTQPL<br>TSNMPTREEFMAKKNTNYNWYTYKAASVKNKLHQMRQTYFEELTSKGPQTTKSE<br>EGYSQHWTTPSTNAYEYHLGMFSAIFLAPDRPVPRFPCAYQDVTYNPLMDKGVGN<br>HIWFQYNTKADTQLIVTGGSCKAHIQDIPLWAAFYGYSDFIESELGPFVDAETVGLV<br>CVICPYTKPPMYNKTNPAMGYVFYDRNFGDGKWTDGRGKIEPYWQVRWRPEMLF<br>QETVMADLVQTGPFSYKDELKNSTLVCKYKFYFTWGGNMMFQQTIKNPCKTDGQ |

TABLE A12-continued

| Exemplary *Anellovirus* amino acid sequences (*Alphatorquevirus*, Clade 6) TTV-TJN02 (*Alphatorquevirus* Clade 6) | |
|---|---|
| | PTDSSRHPRGIQVADPEQMGPRWVFHSFDWRRGYLSEKALKRLQEKPLDYDEYFT QPKRPRIFPPTESAEGEFREPEKGSYSEEERSQASAEEQTQEATVLLLKRRLREQQQL QQQLQFLTREMFKTQAGLHLNPMLLNQR (SEQ ID NO: 44) |
| ORF1/1 | MAWGWWRWRRRWPARRWRRRRRRRPVRRTRARRPARRYRRRRTTIKNPCKTDG QPTDSSRHPRGIQVADPEQMGPRWVFHSFDWRRGYLSEKALKRLQEKPLDYDEYF TQPKRPRIFPPTESAEGEFREPEKGSYSEEERSQASAEEQTQEATVLLLKRRLREQQQ LQQQLQFLTREMFKTQAGLHLNPMLLNQR (SEQ ID NO: 45) |
| ORF1/2 | MAWGWWRWRRRWPARRWRRRRRRRPVRRTRARRPARRYRRRRTQRESSESPKK ARIQRKKGRKPLPKSRRRRRQYSSSSDDSESNSSSSSSSNSSPEKCSKRKRVST (SEQ ID NO: 46) |

TABLE N13

Exemplary *Anellovirus* nucleic acid sequence (*Alphatorquevirus*, Clade 7)

| | |
|---|---|
| Name | TTV-HD16d |
| Genus/Clade | *Alphatorquevirus*, Clade 7 |
| Accession Number | FR751479.1 |
| Full Sequence: 3866 bp | |

```
1        10         20         30         40         50
|         |          |          |          |          |
AAGTCCGTCACTAACCACGTGACTCCCGCAGGCCAATCAGAGTCTATGTC
GTGCACTTCCTGGGCATGGTCTACGTTCTCATATAACTAACTGCACTTCC
GAATGGCTGAGTTTTCCACGCCCGTCCGCAGCGGCAGCACCACGGAGGGT
GATCCCCGCGTCCCGAGGGCGGGTGCCGAAGGTGAGTTTACACACCGCAG
TCAAGGGGCAATTCGGGCTCGGGACTGGCCGGGCTATGGGCAAGGCTCTT
AGGGCTTTCATTGTTAAAAATGTTTCTCGGCAGGCCTTACAGGAGAAAGA
AAAGGGCGCTGTCACTGCCTGGCGTGCGAGCTGCACAGGCGAAACAACCT
GGTGATATGAGCTGGAGCCGTCCAGTACATAATGCCGCCGGGATCGAAAG
GCAGTGGTTCGAATCCACCTTTAGATCCCACGCTAGTTGCTGTGGCTGCG
GCAATTTTGTTAATCATATTAATGTACTGGCTGCTCGCTACGGCTTTACT
GGGGGGCCGACGCCGCCAGGTGGTCCTGGGCCGCGTCCACAACTGAGGCC
CGCGCTTCCCGCGCCGGACCCCGACCCCCAGGCGCCCAACCGTGAGCCAT
GGCGTGGAGCTGGTGGTGGCAACGATGGAGAAGGCGCCGCTGGAAACCCA
GGAGGCGCCGCTGGAGACGTCTACGATGGAGAAGACCTAGACGCGCTGTT
CGCCGCCGTCGTCGAGGACGTAGAGTAAGGAGGCGGAGGTGGGCGCGTAG
ACGGGGGCGACGCAGACGGTACGCCACCAGACGAAAGAGACGTTATAGGG
GTCGCCGCTTTAAAAAGAAACTAGTACTGACTCAGTGGCACCCTAATACC
ATGAGACGCTGCTTAATCAAGGGCATAGTCCCCCTGGTAATATGCGGCCA
CACCAGGTGGAACTACAACTACGCCCTCCATAGCAAGGACTACACAGAGG
AGGGTCGCTACCCTCACGGGGGGGCCCTCAGCACCACTACGTGGTCCCTT
AAGGTGCTGTATGACGAGCACCTCAAACACCACGACTTCTGGGGCTATCC
CAACAACCAGCTAGACCTGGCCAGGTACAAGGGGGCCAAGTTCACCTTCT
ACAGACACAAAAAGACTGACTTTATAATATTCTTTAACAGAAAGCCTCCC
TTTAAGCTAAACAAGTACAGCTGTGCCTCCTATCACCCAGGCATGCTGAT
GCAGCAGAGACACAAGATCCTGCTACCCAGCTACGAAACTAAACCCAAGG
GCAGGCCAAAGATAACAGTTAGAATAAAGCCCCCCACTCTGTTAGAGGAC
AAGTGGTACACCCAGCAGGACCTGTGCGACGTTAACCTGTTGCAACTTGT
GGTCACTGCGGCTGACTTTCGACATCCACTCTGCTCACCACAAACGAACA
CTCCAACCACAACCTTCCAGGTGTTGAAAGACATCTATTATGACACTATG
AGCATATCTGAACCCACAGACTCCTACACTAGTGTTAACAATAAAAGTAC
AACACAAACTTTTACTAACTACTCAAACACCTTAGAAAACATTCTGTACA
CACGAGCCTCCTACTGGAACTCGTTCCACGCCACTGAATACCTAAACCCC
AACATCATATACAAAAACGGTGAAAAACTATTCAAAGAACATGAAGACTT
AATAACCTGGATGACCCAAACTAACAATACCGGGTTTCTAACTAAAAACA
ACACAGCTTTTGGCAACAACAGCTACAGGCCCAATGCAGACAAAATTAAA
AAAGCCAGAAAGACATACTGGAACGCCCTAATAGGCACCAACGACCTGGC
CACTAATATAGGCCAGGCCAGAGCAGAAAGGTTCGAGTACCACCTAGGCT
GGTACTCCCCCATATTTCTCAGCAGACACAGGAGCAACATGAACTTTGCC
AGGGCCTACCAAGACGTCACATACAACCCCAACTGTGACAGGGGAGTTAA
CAACAGGGTGTGGGTTCAGCCTCTAACTAAACCCACCACAGAGTTCGACG
AGAAAAGGTGTAAGTGCGTAGTGCAGCACCTGCCTCTGTGGGCGGCTCTG
TACTGCTACCAAGACTTTGTAGAGGAGGAGCTGGGGTCCTCCTCAGAGAT
ATTAAATTCATGCCTACTGGTATTACAGTGCCCTTACACCTTTCCCCCAA
TGTATGACAAAAAGCTACCAGACAAGGGATTCGTGTTTTATGACTCCCTT
TTTGGAGACGGCAAAATGTCTGACGGACGCGGACAGGTGGACATTTTCTG
GCAACAGCGATGGTACCCTCGCTTAGCCACTCAGATGCAAGTCATGCACG
ACATCACCATGACGGGCCCCTTCTCCTACCGAGACGAGCTAGTTAGCACC
CAACTGACTGCCAAGTACACCTTTGACTTTATGTGGGGCGGAAATATGAT
CTCCACACAGATCATCAAGAACCCCTGCAAAGACAGTGGACTGGAACCCG
CCTACCCCGGTAGACAGCGTCGCGACTTACAAATTGTTGACCCATACTCC
```

TABLE N13-continued

| Exemplary *Anellovirus* nucleic acid sequence (*Alphatorquevirus*, Clade 7) |
|---|
| ATGGGCCCCCAATTCTCGTTCCACAACTGGGACTACAGACATGGCCTTTT<br>TGGCCAAGACGCTATCGACAGAGTGTCTAAACAACCAAAAGATGATGCAG<br>ACTATCCTAACCCATACAAAAGGCCTAGATATTTTCCACCCACAGACCAA<br>GCCGCCCAAGAGCAAGAAAAAGACTTCAGTTTCCTCAAAACAGCACCGTC<br>GAACTCAGAAGAGAGCGATCAAGAAGTCCTCCAAGAAACGCAAGTACTCC<br>GATTCCAGCCAGAGCAGCACAAGCAACTCCACCTGCAGCTCGCAGAGCGG<br>CAGCGAATCGGAGAGCAACTCCGATACCTACTCCAACAGATGTTCAAAAC<br>TCAGGCCAATCTCCACCTAAACCCATATACATTTACCCAGCTGTAAAGCA<br>GGTGTTTATGTTTGACCCCCCGGGCCCTAAGGCTATCTCGGGCGCCAAGG<br>CCTGGGAGGACGAGTTCCTCACCGCAAAAGTGTGGAACCGCCCGGTACGC<br>AAGTACTACTCAGACACCCCCTACTACCCCTGGGCCCCCAAACCCCAGTA<br>CTCTGTCAGTTTCAAACTCGGCTGGAAATAAAAAAAGCCTGCTCCACTGT<br>ACTAGGCCGTGGGAGTTTCACTCGTCGGTGTCTACCTCTTAAGGTCACCA<br>AGCACTCCGAGCGTCAGCGAGGAGTGCGACCCTTGGGGTGGGGTGCAACG<br>CCCTCGGCGGCCGCGCGCTACGCCTTCGGCTGCGCGCGGCACCTCGGACC<br>CCCGCTCGTGCTGACGCGCTTGCGCGCGTCAGACCACTTCGGGCTCGCGG<br>GGGTCGGAAATTTTGCTAAACAGACTCCGAGTTGCCATTGGACACTGGAG<br>CCGTGAATCAGTAACGAAAGTGAGTGGGGCCAGACTTCGCCATAAGGCCT<br>TTATCTTTTTGCCATTTGTCCGTGGGGAAGGGTCGCTGCAAGCGCGGACC<br>CCGTTTTCACCCCTTCCGGACTACAAAAATAGCGCATTAGTGACGTCACG<br>GCCGCCATTTTAAGTAAGGCGGAAGCAACTCCACTTTCTCACAAAATGGC<br>GGCGGAGCACTTCCGGCTTGCCCAAAATGGCCGCCAAAAACATCCGGGTC<br>AAAGTTCGCCGCTACGTCATAAGTCACGTGACTGGGGAGGTACTTAAACA<br>CGGAAGTATCCTCAACCACGTAACTGGTCACGTGGTGCGCACGTCACGGC<br>AACCATTTTGTTTTACAAAATGGCGCATTTCCTTCCTCTTTTTTAAAAAT<br>TAACCGTTGGCGGCGGCGCGCGCGCTACGCGCGCGCGCCGGGGAGCTCTG<br>CCCCCCCCCGCGCATGCGCGCGGGTCCCCCCCCCGCGGGGGGCTCCGCCC<br>CCCGGTCCCCCCCCCG (SEQ ID NO: 47) |

Annotations:

| Putative Domain | Base range |
|---|---|
| TATA Box | 82-86 |
| Initiator Element | 94-115 |
| Transcriptional Start Site | 115 |
| 5' UTR Conserved Domain | 170-240 |
| ORF2 | 357-728 |
| ORF2/2 | 357-724; 2411-2870 |
| ORF2/3 | 357-724; 2646-3081 |
| ORF1 | 599-2896 |
| ORF1/1 | 599-724; 2411-2896 |
| ORF1/2 | 599-724; 2646-2870 |
| Three open-reading frame region | 2629-2867 |
| Poly(A) Signal | 3076-3086 |
| GC-rich region | 3759-3866 |

TABLE A13

| Exemplary *Anellovirus* amino acid sequences (*Alphatorquevirus*, Clade 7)<br>TTV-HD16d (*Alphatorquevirus* Clade 7) | |
|---|---|
| ORF2 | MSWSRPVHNAAGIERQWFESTFRSHASCCGCGNFVNHINVLAARYGFTGGP<br>TPPGGPGPRPQLRPALPAPDPDPQAPNREPWRGAGGGNDGEGAAGNPGGA<br>AGDVYDGEDLDALFAAVVEDVE (SEQ ID NO: 48) |
| ORF2/2 | MSWSRPVHNAAGIERQWFESTFRSHASCCGCGNFVNHINVLAARYGFTGGP<br>TPPGGPGPRPQLRPALPAPDPDPQAPNREPWRGAGGGNDGEGAAGNPGGA<br>AGDVYDGEDLDALFAAVVEDVESSRTPAKTVDWNPPTPVDSVATYKLLTH<br>TPWAPNSRSTTGTTDMAFLAKTLSTECLNNQKMMQTILTHTKGLDIFHPQT<br>KPPKSKKKTSVSSKQHRRTQKRAIKKSSKKRKYSDSSQSSTSNSTCSSQSGSE<br>SESNSDTYSNRCSKLRPIST (SEQ ID NO: 49) |

TABLE A13-continued

| Exemplary *Anellovirus* amino acid sequences (*Alphatorquevirus*, Clade 7) TTV-HD16d (*Alphatorquevirus* Clade 7) | |
|---|---|
| ORF2/3 | MSWSRPVHNAAGIERQWFESTFRSHASCCGCGNFVNHINVLAARYGFTGGP TPPGGPGPRPQLRPALPAPDPDPQAPNREPWRGAGGGNDGEGAAGNPGGA AGDVYDGEDLDALFAAVVEDVEPSRPRARKRLQFPQNSTVELRRERSRSPP RNASTPIPARAAQATPPAARRAAANRRATPIPTPTDVQNSGQSPPKPIYIYPA VKQVFMFDPPGPKAISGAKAWEDEFLTAKVWNRPVRKYYSDTPYYPWAPK PQYSVSFKLGWK (SEQ ID NO: 50) |
| ORF1 | MAWSWWWQRWRRRRWKPRRRRWRRLRWRRPRRAVRRRRRGRRVRRRR WARRRGRRRRYATRRKRRYRGRRFKKKLVLTQWHPNTMRRCLIKGIVPLV ICGHTRWNYNYALHSKDYTEEGRYPHGGALSTTTWSLKVLYDEHLKHHDF WGYPNNQLDLARYKGAKFTFYRHKKTDFIIFFNRKPPFKLNKYSCASYHPG MLMQQRHKILLPSYETKPKGRPKITVRIKPPTLLEDKWYTQQDLCDVNLLQ LVVTAADFRHPLCSPQTNTPTTTFQVLKDIYYDTMSISEPTDSYTSVNNKSTT QTFTNYSNTLENILYTRASYWNSFHATEYLNPNIIYKNGEKLFKEHEDLITW MTQTNNTGFLTKNNTAFGNNSYRPNADKIKKARKTYWNALIGTNDLATNI GQARAERFEYHLGWYSPIFLSRHRSNMNFARAYQDVTYNPNCDRGVNNRV WVQPLTKPTTEFDEKRCKCVVQHLPLWAALYCYQDFVEEELGSSSEILNSC LLVLQCPYTFPPMYDKKLPDKGFVFYDSLFGDGKMSDGRGQVDIFWQQRW YPRLATQMQVMHDITMTGPFSYRDELVSTQLTAKYTFDFMWGGNMISTQII KNPCKDSGLEPAYPGRQRRDLQIVDPYSMGPQFSFHNWDYRHGLFGQDAID RVSKQPKDDADYPNPYKRPRYFPPTDQAAQEQEKDFSFLKTAPSNSEESDQE VLQETQVLRFQPEQHKQLHLQLAERQRIGEQLRYLLQQMFKTQANLHLNPY TFTQL (SEQ ID NO: 51) |
| ORF1/1 | MAWSWWWQRWRRRRWKPRRRRWRRLRWRRPRRAVRRRRRGRRIIKNPC KDSGLEPAYPGRQRRDLQIVDPYSMGPQFSFHNWDYRHGLFGQDAIDRVSK QPKDDADYPNPYKRPRYFPPTDQAAQEQEKDFSFLKTAPSNSEESDQEVLQE TQVLRFQPEQHKQLHLQLAERQRIGEQLRYLLQQMFKTQANLHLNPYTFTQ L (SEQ ID NO: 52) |
| ORF1/2 | MAWSWWWQRWRRRRWKPRRRRWRRLRWRRPRRAVRRRRRGRRTKPPK SKKKTSVSSKQHRRTQKRAIKKSSKKRKYSDSSQSSTSNSTCSSQSGSESESN SDTYSNRCSKLRPIST (SEQ ID NO: 53) |

TABLE N14

Exemplary *Anellovirus* nucleic acid sequence (*Betatorquevirus*)

| | |
|---|---|
| Name | Ring2 |
| Genus/Clade | *Betatorquevirus* |
| Accession Number | JX134045.1 |
| Full Sequence: 2797 bp | |

```
1         10         20         30         40         50
|         |          |          |          |          |
TAATAAATATTCAACAGGAAAACCACCTAATTTAAATTGCCGACCACAAA
CCGTCACTTAGTTCCCCTTTTTGCAACAACTTCTGCTTTTTTCCAACTGC
CGGAAAACCACATAATTTGCATGGCTAACCACAAACTGATATGCTAATTA
ACTTCCACAAAACAACTTCCCCTTTTAAAACCACACCTACAAATTAATTA
TTAAACACAGTCACATCCTGGGAGGTACTACCACACTATAATACCAAGTG
CACTTCCGAATGGCTGAGTTTATGCCGCTAGACGGAGAACGCATCAGTTA
CTGACTGCGGACTGAACTTGGGCGGGTGCCGAAGGTGAGTGAAACCACCG
AAGTCAAGGGGCAATTCGGGCTAGTTCAGTCTAGCGGAACGGGCAAGAAA
CTTAAAATTATTTTATTTTTCAGATGAGCGACTGCTTTAAACCAACATGC
TACAACAACAAAACAAAGCAAACTCACTGGATTAATAACCTGCATTTAAC
CCACGACCTGATCTGCTTCTGCCCAACACCAACTAGACACTTATTACTAG
CTTTAGCAGAACAACAAGAAACAATTGAAGTGTCTAAACAAGAAAAAGAA
AAAATAACAAGATGCCTTATTACTACAGAAGAAGACGGTACAACTACAGA
CGTCCTAGATGGTATGGACGAGGTTGGATTAGACGCCCTTTTCGCAGAAG
ATTTCGAAGAAAAAGAAGGGTAAGACCTACTTATACTACTATTCCTCTAA
AGCAATGGCAACCGCCATATAAAAGAACATGCTATATAAAAGGACAAGAC
TGTTTAATATACTATAGCAACTTAAGACTGGGAATGAATAGTACAATGTA
TGAAAAAAGTATTGTACCTGTACATTGGCCGGGAGGGGGTTCTTTTTCTG
TAAGCATGTTAACTTTAGATGCCTTGTATGATATACATAAACTTTGTAGA
AACTGGTGGACATCCACAAACCAAGACTTACCACTAGTAAGATATAAAGG
ATGCAAAATAACATTTTATCAAAGCACATTTACAGACTACATAGTAAGAA
TACATACAGAACTACCAGCTAACAGTAACAAACTAACATACCCAAACACA
CATCCACTAATGATGATGATGTCTAAGTACAAACACATTATACCTAGTAG
ACAAACAAGAAGAAAAAAGAAACCATACACAAAAATATTTGTAAAACCAC
CTCCGCAATTTGAAAACAAATGGTACTTTGCTACAGACCTCTACAAAATT
CCATTACTACAAATACACTGCACAGCATGCAACTTACAAAACCCATTTGT
AAAACCAGACAAATTATCAAACAATGTTACATTATGGTCACTAAACACCA
TAAGCATACAAAATAGAAACATGTCAGTGGATCAAGGACAATCATGGCCA
```

TABLE N14-continued

| Exemplary *Anellovirus* nucleic acid sequence (*Betatorquevirus*) |
| --- |
| TTTAAAATACTAGGAACACAAAGCTTTTATTTTTACTTTTACACCGGAGC<br>AAACCTACCAGGTGACACAACACAAATACCAGTAGCAGACCTATTACCAC<br>TAACAAACCCAAGAATAAACAGACCAGGACAATCACTAAATGAGGCAAAA<br>ATTACAGACCATATTACTTTCACAGAATACAAAAACAAATTTACAAATTA<br>TTGGGGTAACCCATTTAATAAACACATTCAAGAACACCTAGATATGATAC<br>TATACTCACTAAAAAGTCCAGAAGCAATAAAAAACGAATGGACAACAGAA<br>AACATGAAATGGAACCAATTAAACAATGCAGGAACAATGGCATTAACACC<br>ATTTAACGAGCCAATATTCACACAAATACAATATAACCCAGATAGAGACA<br>CAGGAGAAGACACTCAATTATACCTACTCTCTAACGCTACAGGAACAGGA<br>TGGGACCCACCAGGAATTCCAGAATTAATACTAGAAGGATTTCCACTATG<br>GTTAATATATTGGGGATTTGCAGACTTTCAAAAAAACCTAAAAAAAGTAA<br>CAAACATAGACACAAATTACATGTTAGTAGCAAAAACAAAATTTACACAA<br>AAACCTGGCACATTCTACTTAGTAATACTAAATGACACCTTTGTAGAAGG<br>CAATAGCCCATATGAAAAACAACCTTTACCTGAAGACAACATTAAATGGT<br>ACCCACAAGTACAATACCAATTAGAAGCACAAAACAAACTACTACAAACT<br>GGGCCATTTACACCAAACATACAAGGACAACTATCAGACAATATATCAAT<br>GTTTTATAAATTTTACTTTAAATGGGGAGGAAGCCCACCAAAAGCAATTA<br>ATGTTGAAAATCCTGCCCACCAGATTCAATATCCCATACCCCGTAACGAG<br>CATGAAACAACTTCGTTACAGAGTCCAGGGGAAGCCCCAGAATCCATCTT<br>ATACTCCTTCGACTATAGACACGGGAACTACACAACAACAGCTTTGTCAC<br>GAATTAGCCAAGACTGGGCACTTAAAGACACTGTTTCTAAAATTACAGAG<br>CCAGATCGACAGCAACTGCTCAAACAAGCCCTCGAATGCCTGCAAATCTC<br>GGAAGAAACGCAGGAGAAAAAAGAAAAAGAAGTACAGCAGCTCATCAGCA<br>ACCTCAGACAGCAGCAGCAGCTGTACAGAGAGCGAATAATATCATTATTA<br>AAGGACCAATAACTTTTAACTGTGTAAAAAAGGTGAAATTGTTTGATGAT<br>AAACCAAAAAACCGTAGATTTACACCTGAGGAATTTGAAACTGAGTTACA<br>AATAGCAAAATGGTTAAAGAGACCCCCAAGATCCTTTGTAAATGATCCTC<br>CCTTTTACCCATGGTTACCACCTGAACCTGTTGTAAACTTTAAGCTTAAT<br>TTTACTGAATAAAGGCCAGCATTAATTCACTTAAGGAGTCTGTTTATTTA<br>AGTTAAACCTTAATAAACGGTCACCGCCTCCCTAATACGCAGGCGCAGAA<br>AGGGGGCTCCGCCCCCTTTAACCCCCAGGGGGCTCCGCCCCCTGAAACCC<br>CCAAGGGGGCTACGCCCCCTTACACCCCC (SEQ ID NO: 54) |

Annotations:

| Putative Domain | Base range |
| --- | --- |
| TATA Box | 237-243 |
| Cap Site | 260-267 |
| Transcriptional Start Site | 267 |
| 5' UTR Conserved Domain | 323-393 |
| ORF2 | 424-723 |
| ORF2/2 | 424-719; 2274-2589 |
| ORF2/3 | 424-719; 2449-2812 |
| ORF1 | 612- 2612 |
| ORF1/1 | 612-719; 2274-2612 |
| ORF1/2 | 612-719; 2449-2589 |
| Three open-reading frame region | 2441-2586 |
| Poly(A) Signal | 2808-2813 |
| GC-rich region | 2868-2929 |

TABLE A14

| Exemplary *Anellovirus* amino acid sequences (*Betatorquevirus*) Ring2 (*Betatorquevirus*) | |
|---|---|
| ORF2 | MSDCFKPTCYNNKTKQTHWINNLHLTHDLICFCPTPTRHLLLALAEQQETIEVSKQE KEKITRCLITTEEDGTTTDVLDGMDEVGLDALFAEDFEEKEG (SEQ ID NO: 55) |
| ORF2/2 | MSDCFKPTCYNNKTKQTHWINNLHLTHDLICFCPTPTRHLLLALAEQQETIEVSKQE KEKITRCLITTEEDGTTTDVLDGMDEVGLDALFAEDFEEKEGFNIPYPVTSMKQLRY RVQGKPQNPSYTPSTIDTGTTQQQLCHELAKTGHLKTLFLKLQSQIDSNCSNKPSNA CKSRKKRRRKKKKKYSSSSATSDSSSSCTESE (SEQ ID NO: 56) |
| ORF2/3 | MSDCFKPTCYNNKTKQTHWINNLHLTHDLICFCPTPTRHLLLALAEQQETIEVSKQE KEKITRCLITTEEDGTTTDVLDGMDEVGLDALFAEDFEEKEGARSTATAQTSPRMP ANLGRNAGEKRKRSTAAHQQPQTAAAAVQRANNIIIKGPITFNCVKKVKLFDDKPK NRRFTPEEFETELQIAKWLKRPPRSFVNDPPFYPWLPPEPVVNFKLNFTE (SEQ ID NO: 57) |
| ORF1 | MPYYYRRRRYNYRRPRWYGRGWIRRPFRRRFRRKRRVRPTYTTIPLKQWQPPYKR TCYIKGQDCLIYYSNLRLGMNSTMYEKSIVPVHWPGGGSFSVSMLTLDALYDIHKL CRNWWTSTNQDLPLVRYKGCKITFYQSTFTDYIVRIHTELPANSNKLTYPNTHPLM MMMSKYKHIIPSRQTRRKKKPYTKIFVKPPPQFENKWYFATDLYKIPLLQIHCTACN LQNPFVKPDKLSNNVTLWSLNTISIQNRNMSVDQGQSWPFKILGTQSFYFYFYTGA NLPGDTTQIPVADLLPLTNPRINRPGQSLNEAKITDHITFTEYKNKFTNYWGNPFNK HIQEHLDMILYSLKSPEAIKNEWTTENMKWNQLNNAGTMALTPFNEPIFTQIQYNP DRDTGEDTQLYLLSNATGTGWDPPGIPELILEGFPLWLIYWGFADFQKNLKKVTNID TNYMLVAKTKFTQKPGTFYLVILNDTFVEGNSPYEKQPLPEDNIKWYPQVQYQLEA QNKLLQTGPFTPNIQGQLSDNISMFYKFYFKWGGSPPKAINVENPAHQIQYPIPRNE HETTSLQSPGEAPESILYSFDYRHGNYTTTALSRISQDWALKDTVSKITEPDRQQLLK QALECLQISEETQEKKEKEVQQLISNLRQQQQLYRERIISLLKDQ (SEQ ID NO: 58) |
| ORF1/1 | MPYYYRRRRYNYRRPRWYGRGWIRRPFRRRFRRKRRIQYPIPRNEHETTSLQSPGE APESILYSFDYRHGNYTTTALSRISQDWALKDTVSKITEPDRQQLLKQALECLQISEE TQEKKEKEVQQLISNLRQQQQLYRERIISLLKDQ (SEQ ID NO: 59) |
| ORF1/2 | MPYYYRRRRYNYRRPRWYGRGWIRRPFRRRFRRKRRSQIDSNCSNKPSNACKSRK KRRRKKKKKYSSSSATSDSSSSCTESE (SEQ ID NO: 60) |

TABLE N15

Exemplary *Anellovirus* nucleic acid sequence (*Gammatorquevirus*)

| | |
|---|---|
| Name | TTMDV-MD1-073 |
| Genus/Clade | *Gammatorquevirus* |
| Accession Number | AB290918.1 |
| Full Sequence: 3242 bp | |

```
1         10         20         30         40         50
|         |          |          |          |          |
AGGTGGAGACTCTTAAGCTATATAACCAAGTGGGGTGGCGAATGGCTGAG
TTTACCCCGCTAGACGGTGCAGGGACCGGATCGAGCGCAGCGAGGAGGTC
CCCGGCTGCCCGTGGGCGGGAGCCCGAGGTGAGTGAAACCACCGAGGTCT
AGGGGCAATTCGGGCTAGGGCAGTCTAGCGGAACGGGCAAGAAACTTAAA
AATATTTCTTTTACAGATGCAAAACCTATCAGCCAAAGACTTCTACAAAC
CATGCAGATACAACTGTGAAACTAAAAACCAAATGTGGATGTCTGGCATT
GCTGACTCCCATGACAGTTGGTGTGACTGTGATACTCCTTTTGCTCACCT
CCTGGCTAGTATTTTTCCTCCTGGTCACACAGATCGCACACGAACCATCC
AAGAAATACTTACCAGAGATTTTAGGAAAACATGCCTTTCTGGTGGGGCC
GACGCAACAAATTCTGGTATGGCCGAAACTATAGAAGAAAAAAGAGAAGA
TTTCCAAAAAGAAGAAAAAGAAGATTTTACAGAAGAACAAAATATAGAAG
ACCTGCTCGCCGCCGTCGCAGACGCAGAAGGAAGGTAAGAAGAAAAAAAA
AAACTCTTATAGTAAGACAATGGCAGCCAGACTCTATTGTACTCTGTAAA
ATTAAAGGGTATGACTCTATAATATGGGGAGCTGAAGGCACACAGTTTCA
ATGTTCTACACATGAAATGTATGAATATACAAGACAAAAGTACCCTGGGG
GAGGAGGATTTGGTGTACAACTTTACAGCTTAGAGTATTTGTATGACCAA
TGGAAACTTAGAAATAATATATGGACTAAAACAAATCAACTCAAAGATTT
GTGTAGATACTTAAAATGTGTTATGACCTTTTACAGACACCAACACATAG
ATTTTGTAATTGTATATGAAAGACAACCCCCATTTGAAATAGATAAACTA
ACATACATGAAATATCATCCATATATGTTATTACAAAGAAAGCATAAAAT
AATTTTACCTAGTCAAACAACTAATCCTAGAGGTAAATTAAAAAAAAAGA
AAACTATTAAACCTCCCAAACAAATGCTCAGCAAATGGTTTTTTCAACAA
CAATTTGCTAAATATGATCTACTACTTATTGCTGCAGCAGCATGTAGTTT
AAGATACCCTAGAATAGGCTGCTGCAATGAAAATAGAATGATAACCTTAT
ACTGTTTAAATACTAAATTTTATCAAGATACAGAATGGGGAACTACAAAA
CAGGCCCCCCACTACTTTAAACCATATGCAACAATTAATAAATCCATGAT
ATTTGTCTCTAACTATGGAGGTAAAAAAACAGAATATAACATAGGCCAAT
GGATAGAAACAGATATACCTGGAGAAGGTAATCTAGCAAGATACTACAGA
TCAATAAGTAAAGAAGGAGGTTACTTTTCACCTAAAATACTGCAAGCATA
```

TABLE N15-continued

| Exemplary *Anellovirus* nucleic acid sequence (*Gammatorquevirus*) |
|---|
| TCAAACAAAAGTAAAGTCTGTAGACTACAAACCTTTACCAATTGTTTTAG<br>GTAGATATAACCCAGCAATAGATGATGGAAAAGGCAACAAAATTTACTTA<br>CAAACTATAATGAATGGCCATTGGGGCCTACCTCAAAAAACACCAGATTA<br>TATAATAGAAGAGGTCCCTCTTTGGCTAGGCTTCTGGGGATACTATAACT<br>ACTTAAAACAAACAAGAACTGAAGCTATATTTCCACTACACATGTTTGTA<br>GTGCAAAGCAAATACATTCAAACACAACAAACAGAAACACCTAACAATTT<br>TTGGGCATTTATAGACAACAGCTTTATACAGGGCAAAAACCCATGGGACT<br>CAGTTATTACTTACTCAGAACAAAAGCTATGGTTTCCTACAGTTGCATGG<br>CAACTAAAAACCATAAATGCTATTTGTGAAAGTGGACCATATGTACCTAA<br>ACTAGACAATCAAACATATAGTACCTGGGAACTAGCAACTCATTACTCAT<br>TTCACTTTAAATGGGGTGGTCCACAGATATCAGACCAACCAGTTGAAGAC<br>CCAGGAAACAAAAACAAATATGATGTGCCCGATACAATCAAAGAAGCATT<br>ACAAATTGTTAACCCAGCAAAAAACATTGCTGCCACGATGTTCCATGACT<br>GGGACTACAGACGGGGTTGCATTACATCAACAGCTATTAAAAGAATGCAA<br>CAAAACCTCCCAACTGATTCATCTCTCGAATCTGATTCAGACTCAGAACC<br>AGCACCCAAGAAAAAAAGACTACTACCAGTCCTCCACGACCCACAAAAGA<br>AAACGGAAAAGATCAACCAATGTCTCCTCTCTCTCTGCGAAGAAAGTACA<br>TGCCAGGAGCAGGAAACGGAGGAAAACATCCTCAAGCTCATCCAGCAGCA<br>GCAGCAGCAGCAGCAGAAACTCAAGCACAACCTCTTAGTACTAATCAAGG<br>ACTTAAAAGTGAAACAAAGATTATTACAACTACAAACGGGGGTACTAGAA<br>TAACCCTTACCAGATTTAAACCAGGATTTGAGCAAGAAACTGAAAAAGAG<br>TTAGCACAAGCATTTAACAGACCCCCTAGACTGTTCAAAGAAGATAAACC<br>CTTTTACCCCTGGCTACCCAGATTTACACCCCTTGTAAACTTTCACCTTA<br>ATTTTAAAGGCTAGGCCTACACTGCTCACTTAGTGGTGTATGTTTATTAA<br>AGTTTGCACCCCAGAAAAATTGTAAAATAAAAAAAAAAAAAAAAAAATAAA<br>AAATTGCAAAAATTCGGCGCTCGCGCGCGCTGCGCGCGCGAGCGCCGTCA<br>CGCGCCGGCGCTCGCGCGCCGCGCGTATGTGCTAACACACCACGCACCTA<br>GATTGGGGTGCGCGCGTAGCGCGCGCACCCCAATGCGCCCCGCCCTCGTT<br>CCGACCCGCTTGCGCGGGTCGGACCACTTCGGGCTCGGGGGGGCGCGCCT<br>GCGGCGCTTATTTACTAAACAGACTCCGAGTCGCCATTGGGCCCCCCCTA<br>AGCTCCGCCCCCCTCATGAATATTCATAAAGGAAACCACAAAATTAGAAT<br>TGCCGACCACAAACTGCCATATGCTAATTAGTTCCCCTTTTACACAGTAA<br>AAAGGGGAAGTGGGGGGGCAGAGCCCCCCCACACCCCCCGCGGGGGGGGC<br>AGAGCCCCCCCCGCACCCCCCCTACGTCACAGGCCACGCCCCCGCCGCCA<br>TCTTGGGTGCGGCAGGGCGGGGACTAAAATGGCGGGACCCAATCATTTTA<br>TACTTTCACTTTCCAATTAAAACCCGCCACGTCACACAAAAG (SEQ ID NO: 61) |

Annotations:

| Putative Domain | Base range |
|---|---|
| TATA Box | 21-25 |
| Cap Site | 42-49 |
| Transcriptional Start Site | 49 |
| 5' UTR Conserved Domain | 117-187 |
| ORF2 | 283-588 |
| ORF2/2 | 283-584; 1977-2388 |
| ORF2/3 | 283-584; 2197-2614 |
| ORF1 | 432-2453 |
| ORF1/1 | 432-584; 1977-2453 |
| ORF1/2 | 432-584; 2197-2388 |
| Three open-reading frame region | 2186-2385 |
| Poly(A) Signal | 2676-2681 |
| GC-rich region | 3054-3172 |

TABLE A15

| Exemplary *Anellovirus* amino acid sequences (*Gammatorquevirus*) TTMDV-MD1-073 (*Gammatorquevirus*) | |
|---|---|
| ORF2 | MWMSGIADSHDSWCDCDTPFAHLLASIFPPGHTDRTRTIQEILTRDFRKTCLSGGAD ATNSGMAETIEEKREDFQKEEKEDFTEEQNIEDLLAAVADAEGR (SEQ ID NO: 62) |
| ORF2/2 | MWMSGIADSHDSWCDCDTPFAHLLASIFPPGHTDRTRTIQEILTRDFRKTCLSGGAD ATNSGMAETIEEKREDFQKEEKEDFTEEQNIEDLLAAVADAEGRYQTNQLKTQETK TNMMCPIQSKKHYKLLTQQKTLLPRCSMTGTTDGVALHQQLLKECNKTSQLIHLSN LIQTQNQHPRKKDYYQSSTTHKRKRKRSTNVSSLSAKKVHARSRKRRKTSSSSSSS SSSSRNSSTTS (SEQ ID NO: 63) |
| ORF2/3 | MWMSGIADSHDSWCDCDTPFAHLLASIFPPGHTDRTRTIQEILTRDFRKTCLSGGAD ATNSGMAETIEEKREDFQKEEKEDFTEEQNIEDLLAAVADAEGRTSTQEKKTTTSPP RPTKENGKDQPMSPLSLRRKYMPGAGNGGKHPQAHPAAAAAAAETQAQPLSTNQ GLKSETKIITTTNGGTRITLTRFKPGFEQETEKELAQAFNRPPRLFKEDKPFYPWLPRF TPLVNFHLNFKG (SEQ ID NO: 64) |
| ORF1 | MPFWWGRRNKFWYGRNYRRKKRRFPKRRKRRFYRRTKYRRPARRRRRRRKVR RKKKTLIVRQWQPDSIVLCKIKGYDSIIWGAEGTQFQCSTHEMYEYTRQKYPGGGG FGVQLYSLEYLYDQWKLRNNIWTKTNQLKDLCRYLKCVMTFYRHQHIDFVIVYER QPPFEIDKLTYMKYHPYMLLQRKHKIILPSQTTNPRGKLKKKTIKPPKQMLSKWFF QQQFAKYDLLLIAAAACSLRYPRIGCCNENRMITLYCLNTKFYQDTEWGTTKQAPH YFKPYATINKSMIFVSNYGGKKTEYNIGQWIETDIPGEGNLARYYRSISKEGGYFSPK ILQAYQTKVKSVDYKPLPIVLGRYNPAIDDGKGNKIYLQTIMNGHWGLPQKTPDYII EEVPLWLGFWGYYNYLKQTRTEAIFPLHMFVVQSKYIQTQQTETPNNFWAFIDNSFI QGKNPWDSVITYSEQKLWFPTVAWQLKTINAICESGPYVPKLDNQTYSTWELATH YSFHFKWGGPQISDQPVEDPGNKNKYDVPDTIKEALQIVNPAKNIAATMFHDWDY RRGCITSTAIKRMQQNLPTDSSLESDSDSEPAPKKKRLLPVLHDPQKKTEKINQCLLS LCEESTCQEQETEENILKLIQQQQQQQQKLKHNLLVLIKDLKVKQRLLQLQTGVLE (SEQ ID NO: 65) |
| ORF1/1 | MPFWWGRRNKFWYGRNYRRKKRRFPKRRKRRFYRRTKYRRPARRRRRRRKISD QPVEDPGNKNKYDVPDTIKEALQIVNPAKNIAATMFHDWDYRRGCITSTAIKRMQQ NLPTDSSLESDSDSEPAPKKKRLLPVLHDPQKKTEKINQCLLSLCEESTCQEQETEEN ILKLIQQQQQQQQKLKHNLLVLIKDLKVKQRLLQLQTGVLE (SEQ ID NO: 66) |
| ORF1/2 | MPFWWGRRNKFWYGRNYRRKKRRFPKRRKRRFYRRTKYRRPARRRRRRRKISD QPVEDPGNKNKYDVPDTIKEALQIVNPAKNIAATMFHDWDYRRGCITSTAIKRMQQ NLPTDSSLESDSDSEPAPKKKRLLPVLHDPQKKTEKINQCLLSLCEESTCQEQETEEN ILKLIQQQQQQQQKLKHNLLVLIKDLKVKQRLLQLQTGVLE (SEQ ID NO: 67) |

TABLE N16

Exemplary *Anellovirus* nucleic acid sequence (*Gammatorquevirus*)

| | |
|---|---|
| Name | Ring3.1 |
| Genus/Clade | *Gammatorquevirus* |
| Accession Number | |
| Full Sequence: 3264 bp | |

```
1         10         20         30         40         50
|         |          |          |          |          |
TAAAATGGCGGCAACCAATCATTTTATACTTTCACTTTCCAATTACAAGC
CGCCACGTCACAGAACAGGGGTGGAGACTTTAAAACTATATAACCAAGTG
ATGTGACGAATGGCTGAGTTTACCCCGCTAGACGGTGCAGGGACCGGATC
GAGCGCAGCGAGGAGGTCCCCGGCTGCCCGTGGGCGGGAGCCCGAGGTGA
GTGAAACCACCGAGGTCTAGGGGCAATTCGGGCTAGGGCAGTCTAGCGGA
ACGGGCAAGAAACTTAAAATATGTTTTGTTTCAGATGCAGACACCTGCTT
CACAGATAAGCTCAGACGACTTCTTTGTACACACTCCATTTAATGCAGTA
ACTAAACAGCAAATATGGATGTCTCAAATTGCTGATGGACATGACAACAT
TTGTCACTGCCACCGTCCTTTTGCTCACCTGCTTGCTAATATTTTTCCTC
CTGGTCATAAAGACAGGGATCTTACCATTAATCAAATACTTGCTAGAGAT
CTTACAGAAACATGCCATTCTGGTGGAGACGAAGGAACAAGCGGTGGTGG
GGTCGCCGCTTCCGCTACCGCCGCTACAACAAATATAAAACCAGAAGGAG
ACGCAGAATACCCAGAAGACGAAATAGAAGATTTACTAAGACACGCAGGA
GAAGAAAAAGAAAGAAGGTAAGAAGAAAACTTAAAAAAATTACTATTAAA
CAATGGCAGCCAGATTCAGTGAAAAAATGTAAAATTAAAGGATATAGTAC
TTTAGTTATGGGTGCACAAGGAAAACAATACAACTGTTACACAAACCAAG
CAAGTGACTATGTTCAGCCTAAAGCACCACAAGGTGGGGGCTTTGGCTGT
GAAGTATTTAATTTAAAATGGCTATACCAAGAATATACTGCACACAGAAA
TATTTGGACAAAAACAAATGAATATACAGACCTTTGTAGATACACTGGAG
CTCAAATAATTTTATACAGGCACCCAGATGTTGATTTTATAGTCAGCTGG
GACAATCAGCCACCTTTTTTACTTAACAAATATACATATCCAGAACTGCA
ACCACAAAACCTTTTACTAGCTAGAAGGAAAAGAATTATTCTTAGTCAAA
AATCAAACCCCAAAGGAAAACTAAGAATTAAACTAAGAATACCACCACCA
```

TABLE N16-continued

| Exemplary *Anellovirus* nucleic acid sequence (*Gammatorquevirus*) |
|---|
| AAACAAATGATAACAAAATGGTTTTTTCAAAGAGACTTTTGTGATGTGAA<br>TCTGTTTAAACTATGTGCTTCTGCTGCTTCTTTCCGCTACCCAGGTATCA<br>GTCATGGAGCTCAAAGTACTATTTTTTCTGCATATGCTTTAAACACTGAC<br>TTTTATCAATGCAGTGACTGGTGCCAAACTAACACAGAAACTGGCTACCT<br>AAACATTAAAACACAACAAATGCCACTATGGTTTCATTACAGAGAGGGTG<br>GCAAAGAGAAATGGTATAAATACACCAACAAAGAACACAGACCATATACA<br>AATACATATCTTAAAAGTATTAGCTATAATGATGGATTGTTTTCTCCTAA<br>AGCCATGTTTGCATTTGAAGTAAAAGCGGGGGGTGAAGGAACAACAGAAC<br>CACCACAAGGCGCCCAATTAATTGCTAACCTTCCACTCATTGCACTAAGA<br>TATAATCCACATGAAGACACAGGCCATGGCAATGAAATTTACCTTACATC<br>AACTTTTAAAGGTACATATGACAAACCTAAAGTTACTGATGCTCTATACT<br>TTAACAATGTACCCCTGTGGATGGGATTTTATGGCTACTGGGACTTTATA<br>TTACAAGAAACAAAAAACAAAGGTGTCTTTGATCAACATATGTTTGTTGT<br>TAAATGTCCTGCCTTAAGGCCCATATCACAAGTCACAAAACAAGTATACT<br>ACCCACTTGTAGACATGGACTTTTGTTCAGGGAGACTGCCATTTGATGAA<br>TATTTATCCAAAGACATTAAAAGTCATTGGTATCCCACTGCAGAAAGACA<br>AACAGTTACAATAAATAATTTTGTTACAGCAGGTCCATACATGCCTAAAT<br>TTGAACCCACAGACAAAGACAGTACATGGCAATTAAACTATCACTATAAA<br>TTTTTTTTTAAGTGGGGTGGTCCACAAGTCACAGACCCAACTGTTGAAGA<br>CCCATGCAGCAGAAACAAATATCCTGTCCCCGATACAATGCAACAAACAA<br>TACAAATTAAAAACCCTGAAAAGCTGCACCCAGCAACCCTCTTCCATGAC<br>TGGGACCTTAGAAGGGGCTTCATTACACAAGCAGCTATTAAAAGAATGTC<br>AGAAAACCTCCAAATTGATTCATCTTTCGAATCTGATGGCACAGAATCAC<br>CCAAAAAAAAGAAAAGATGCACCAAAGAAATCCCAACACAAAACCAAAAG<br>CAAGAAGAGATCCAAGAATGTCTCCTCTCACTCTGCGAAGAGCCTACATG<br>CCAAGAAGAAACAGAGGACCTCCAGCTCTTCATCCAGCAGCAGCAGCAGC<br>AGCAGTACAAGCTCAGAAAAAACCTCTTCAAACTCCTCACTCACCTGAAA<br>AAAGGACAGAGAATAAGTCAACTACAAACGGGACTTTTAGAGTAATACCA<br>TTTAAACCAGGTTTTGAACAAGAAACAGAAAAAGAACTTGCCATAGCTTT<br>CTGCAGACCACCTAGAAAATATAAAAATGATCCCCCTTTTTATCCCTGGT<br>TACCATGGACACCCCTTGTACACTTTAACCTTAATTACAAAGGCTAGGCC<br>AACACTGTTCACTTAGTGGTGTATGTTTAATAAAGTTTCACCCCCAAAAA<br>AAAAAAAAAAAAAAAAAAAAAAAAAAAAAAATAAAAAATTGCAAAAATTCG<br>GCGCTCGCGCGCGCTGCGCGCGCGCGAGCGCCGTCACGCGCCGGCGCTCG<br>CGCGCCGCGCGTATGTGCTAACACACCACGCACCTAGATTGGGGTGCGCG<br>CGCTAGCGCGCGCACCCCAATGCGCCCCGCCCTCGTTCCGACCCGCTTGC<br>GCGGGTCGGACCACTTCGGGCTCGGGGGGGCGCGCCTGCGGCGCTTTTTT<br>ACTAAACAGACTCCGAGCCGCCATTTGGCCCCCCCTAAGCTCCGCCCCCC<br>TCATGAATATTCATAAAGGAAACCACATAATTAGAATTGCCGACCACAAA<br>CTGCCATATGCTAATTAGTTCCCCTTTTACACAGTAAAAAGGGGAAGTGG<br>GGGGGCATAGCCCCCCCACACCCCCCGCGGGGGGGGCAGAGCCCCCCCCC<br>GCACCCCCCCCCTACGTCACAATCCACGCCCCCGCCGCCATCTTGGGTGC<br>GGCAGGGCGGGGGC (SEQ ID NO: 878) |

Annotations:

| Putative Domain | Base range |
|---|---|
| TATA Box | 87-93 |
| Cap Site | 110-117 |
| Transcriptional Start Site | 117 |
| 5' UTR Conserved Domain | 185-255 |
| ORF2 | 285-671 |
| ORF2/2 | 285-667; 2063-2498 |
| ORF2/3 | 285-667; 2295-2697 |
| TAIP | 385-585 |
| ORF1 | 512-2545 |
| ORF1/1 | 512-667; 2063-2545 |
| ORF1/2 | 512-667; 2295-2498 |
| Three open-reading frame region | 2295-2495 |
| Poly(A) Signal | 2729-2734 |
| GC-rich region | 3141-3264 |

TABLE A16

| Exemplary *Anellovirus* amino acid sequences (*Gammatorquevirus*) Ring 3.1 (*Gammatorquevirus*) | |
|---|---|
| ORF2 | MQTPASQISSDDFFVHTPFNAVTKQQIWMSQIADGHDNICHCHRPFAHLLAN IFPPGHKDRDLTINQ ILARDLTETCHSGGDEGTSGGGVAASATAATTNIKPEGDAEYPEDEIEDLLR HAGEEKERR (SEQ ID NO: 879) |
| ORF2/2 | MQTPASQISSDDFFVHTPFNAVTKQQIWMSQIADGHDNICHCHRPFAHLLAN IFPPGHKDRDLTINQ ILARDLTETCHSGGDEGTSGGGVAASATAATTNIKPEGDAEYPEDEIEDLLR HAGEEKERSGVVHKSQTQLLKTHAAETNILSPIQCNKQYKLKTLKSCTQQPS SMTGTLEGASLHKQLLKECQKTSKLIHLSNLMAQNHPKKRKDAPKKSQHK TKSKKRSKNVSSHSAKSLHAKKKQRTSSSSSSSSSSSTSSEKTSSNSSLT (SEQ ID NO: 880) |
| ORF2/3 | MQTPASQISSDDFFVHTPFNAVTKQQIWMSQIADGHDNICHCHRPFAHLLAN IFPPGHKDRDLTINQ ILARDLTETCHSGGDEGTSGGGVAASATAATTNIKPEGDAEYPEDEIEDLLR HAGEEKERRITQKKEKMHQRNPNTKPKARRDPRMSPLTLRRAYMPRRNRG PPALHPAAAAAAVQAQKKPLQTPHSPEKRTENKSTTNGTFRVIPFKPGFEQE TEKELAIAFCRPPRKYKNDPPFYPWLPWTPLVHFNLNYKG (SEQ ID NO: 881) |
| TAIP | MDMTTFVTATVLLLTCLLIFFLLVIKTGILPLIKYLLEILQKHAILVETKEQAV VGSPLPLPPLQQI (SEQ ID NO: 882) |
| ORF1 | MPFWWRRRNKRWWGRRFRYRRYNKYKTRRRRRIPRRRNRRFTKTRRRRK RKKVRRKLKKITIKQWQP DSVKKCKIKGYSTLVMGAQGKQYNCYTNQASDYVQPKAPQGGGFGCEVF NLKWLYQEYTAHRNIWTKTNEYTDLCRYTGAQIILYRHPDVDFIVSWDNQP PFLLNKYTYPELQPQNLLLARRKRIILSQKSNPKGKLRIKLRIPPPKQMITKWF FQRDFCDVNLFKLCASAASFRYPGISHGAQSTIFSAYALNTDFYQCSDWCQT NTETGYLNIKTQQMPLWFHYREGGKEKWYKYTNKEHRPYTNTYLKSISYN DGLFSPKAMFAFEVKAGGEGTTEPPQGAQLIANLPLIALRYNPHEDTGHGNE IYLTSTFKGTYDKPKVTDALYFNNVPLWMGFYGYWDFILQETKNKGVFDQ HMFVVKCPALRPISQVTKQVYYPLVDMDFCSGRLPFDEYLSKDIKSHWYPT AERQTVTINNFVTAGPYMPKFEPTDKDSTWQLNYHYKFFFKWGGPQVTDP TVEDPCSRNKYPVPDTMQQTIQIKNPEKLHPATLFHDWDLRRGFITQAAIKR MSENLQIDSSFESDGTESPKKKKRCTKEIPTQNQKQEEIQECLLSLCEEPTCQ EETEDLQLFIQQQQQQQYKLRKNLFKLLTHLKKGQRISQLQTGLLE (SEQ ID NO: 883) |
| ORF1/1 | MPFWWRRRNKRWWGRRFRYRRYNKYKTRRRRRIPRRRNRRFTKTRRRRK RKKWGGPQVTDPTVEDPCSRNKYPVPDTMQQTIQIKNPEKLHPATLFHDWD LRRGFITQAAIKRMSENLQIDSSFESDGTESPKKKKRCTKEIPTQNQKQEEIQE CLLSLCEEPTCQEETEDLQLFIQQQQQQQYKLRKNLFKLLTHLKKGQRISQL QTGLLE (SEQ ID NO: 884) |
| ORF1/2 | MPFWWRRRNKRWWGRRFRYRRYNKYKTRRRRRIPRRRNRRFTKTRRRRK RKKNHPKKRKDAPKKSQHKTKSKKRSKNVSSHSAKSLHAKKKQRTSSSSSS SSSSSSTSSEKTSSNSSLT (SEQ ID NO: 885) |

TABLE N17

Exemplary *Anellovirus* nucleic acid sequence (*Gammatorquevirus*)

| | |
|---|---|
| Name | Ring4 |
| Genus/Clade | *Gammatorquevirus* |
| Accession Number | |
| Full Sequence: 3176 bp | |

```
1         10         20         30         40         50
|         |          |          |          |          |
TAAAATGGCGGGAGCCAATCATTTTATACTTTCACTTTCCAATTAAAAAT
GGCCACGTCACAAACAAGGGGTGGAGCCATTTAAACTATATAACTAAGTG
GGGTGGCGAATGGCTGAGTTTACCCCGCTAGACGGTGCAGGGACCGGATC
GAGCGCAGCGAGGAGGTCCCCGGCTGCCCATGGGCGGGAGCCGAGGTGAG
TGAAACCACCGAGGTCTAGGGGCAATTCGGGCTAGGGCAGTCTAGCGGAA
CGGGCAAGAAACTTAAAACAATATTTGTTTTACAGATGGTTAGTATATCC
TCAAGTGATTTTTTTAAGAAAACGAAATTTAATGAGGAGACGCAGAACCA
AGTATGGATGTCTCAAATTGCTGACTCTCATGATAATATCTGCAGTTGCT
GGCATCCATTTGCTCACCTTCTTGCTTCCATATTTCCTCCTGGCCACAAA
GATCGTGATCTTACTATTAACCAAATTCTTCTAAGAGATTATAAAGAAAA
ATGCCATTCTGGTGGAGAAGAAGGAGAAAATTCTGGACCAACAACAGGTT
TAATTACACCAAAAGAAGAAGATATAGAAAAAGATGGCCCAGAAGGCGCC
GCAGAAGAAGACCATACAGACGCCCTGTTCGCCGCCGCCGTAGAAAACTT
```

TABLE N17-continued

| Exemplary *Anellovirus* nucleic acid sequence (*Gammatorquevirus*) |
|---|
| CGAAAGGTAAAGAGAAAAAAAAAATCTTTAATTGTTAGACAATGGCAACC<br>AGACAGTATAAGAACTTGTAAAATTATAGGACAGTCAGCTATAGTTGTTG<br>GGGCTGAAGGAAAGCAAATGTACTGTTATACTGTCAATAAGTTAATTAAT<br>GTGCCCCCAAAAACACCATATGGGGGAGGCTTTGGAGTAGACCAATACAC<br>ACTGAAATACTTATATGAAGAATACAGATTTGCACAAAACATTTGGACAC<br>AATCTAATGTACTGAAAGACTTATGCAGATACATAAATGTTAAGCTAATA<br>TTCTACAGAGACAACAAAACAGACTTTGTCCTTTCCTATGACAGAAACCC<br>ACCTTTTCAACTAACAAAATTTACATACCCAGGAGCACACCCACAACAAA<br>TCATGCTTCAAAAACACCACAAATTCATACTATCACAAATGACAAAGCCT<br>AATGGAAGACTAACAAAAAAACTCAAAATTAAACCTCCTAAACAAATGCT<br>TTCTAAATGGTTCTTTTCAAAACAATTCTGTAAATACCCTTTACTATCTC<br>TTAAAGCTTCTGCACTAGACCTTAGGCACTCTTACCTAGGCTGCTGTAAT<br>GAAAATCCACAGGTATTTTTTTATTATTTAAACCATGGATACTACACAAT<br>AACAAACTGGGGAGCACAATCCTCAACAGCATACAGACCTAACTCCAAGG<br>TGACAGACACAACATACTACAGATACAAAAATGACAGAAAAAATATTAAC<br>ATTAAAAGCCATGAATACGAAAAAAGTATATCATATGAAAACGGTTATTT<br>TCAATCTAGTTTCTTACAAACACAGTGCATATATACCAGTGAGCGTGGTG<br>AAGCCTGTATAGCAGAAAAACCACTAGGAATAGCTATTTACAATCCAGTA<br>AAAGACAATGGAGATGGTAATATGATATACCTTGTAAGCACTCTAGCAAA<br>CACTTGGGACCAGCCTCCAAAAGACAGTGCTATTTTAATACAAGGAGTAC<br>CCATATGGCTAGGCTTATTTGGATATTTAGACTACTGTAGACAAATTAAA<br>GCTGACAAAACATGGCTAGACAGTCATGTACTAGTAATTCAAAGTCCTGC<br>TATTTTTACTTACCCAAATCCAGGAGCAGGCAAATGGTATTGTCCACTAT<br>CACAAAGTTTTATAAATGGCAATGGTCCGTTTAATCAACCACCTACACTG<br>CTACAAAAAGCAAAGTGGTTTCCACAAATACAATACCAACAAGAAATTAT<br>TAATAGCTTTGTAGAATCAGGACCATTTGTTCCCAAATATGCAAATCAAA<br>CTGAAAGCAACTGGGAACTAAAATATAAATATGTTTTTACATTTAAGTGG<br>GGTGGACCACAATTCCATGAACCAGAAATTGCTGACCCTAGCAAACAAGA<br>GCAGTATGATGTCCCCGATACTTTCTACCAAACAATACAAATTGAAGATC<br>CAGAAGGACAAGACCCCAGATCTCTCATCCATGATTGGGACTACAGACGA<br>GGCTTTATTAAAGAAAGATCTCTTAAAAGAATGTCAACTTACTTCTCAAC<br>TCATACAGATCAGCAAGCAACTTCAGAGGAAGACATTCCCAAAAAGAAAA<br>AGAGAATTGGACCCCAACTCACAGTCCCACAACAAAAAGAAGAGGAGACA<br>CTGTCATGTCTCCTCTCTCTCTGCAAAAAAGATACCTTCCAAGAAACAGA<br>GACACAAGAAGACCTCCAGCAGCTCATCAAGCAGCAGCAGGAGCAGCAGC<br>TCCTCCTCAAGAGAAACATCCTCCAGCTCATCCACAAACTAAAAGAGAAT<br>CAACAAATGCTTCAGCTTCACACAGGCATGTTACCTTAACCAGATTTAAA<br>CCTGGATTTGAAGAGCAAACAGAGAGAGAATTAGCAATTATATTTCATAG<br>GCCCCCTAGAACCTACAAAGAGGACCTTCCATTCTATCCCTGGCTACCAC<br>CTGCACCCCTTGTACAATTTAACCTTAACTTCAAAGGCTAGGCCAACAAT<br>GTACACTTAGTAAAGCATGTTTATTAAAGCACAACCCCCAAAATAAATGT<br>AAAAATAAAAAAAAAAAAAAAAAAATAAAAAATTGCAAAAATTCGGCGCT<br>CGCGCGCATGTGCGCCTCTGGCGCAAATCACGCAACGCTCGCGCGCCCGC<br>GTATGTCTCTTTACCACGCACCTAGATTGGGGTGCGCGCGCTAGCGCGCG<br>CACCCCAATGCGCCCCGCCCTCGTTCCGACCCGCTTGCGCGGGTCGGACC<br>ACTTCGGGCTCGGGGGGGCGCGCCTGCGGCGCTTTTTTACTAAACAGACT<br>CCGAGCCGCCATTTGGCCCCCTAAGCTCCGCCCCCCTCATGAATATTCAT<br>AAAGGAAACCACATAATTAGAATTGCCGACCACAAACTGCCATATGCTAA<br>TTAGTTCCCCTTTTACAAAGTAAAAGGGGAAGTGAACATAGCCCCACACC<br>CGCAGGGGCAAGGCCCCGCACCCCTACGTCACTAACCACGCCCCCGCCGC<br>CATCTTGGGTGCGGCAGGGGGGGGC (SEQ ID NO: 886) |

Annotations:

| Putative Domain | Base range |
|---|---|
| TATA Box | 87-93 |
| Cap Site | 110-117 |
| Transcriptional Start Site | 117 |
| 5' UTR Conserved Domain | 185-254 |
| ORF2 | 286-660 |
| ORF2/2 | 286-656; 1998-2442 |
| ORF2/3 | 286-656; 2209-2641 |
| TAIP | 385-484 |
| ORF1 | 501-2489 |
| ORF1/1 | 501-656; 1998-2489 |
| ORF1/2 | 501-656; 2209-2442 |

TABLE N17-continued

| Exemplary *Anellovirus* nucleic acid sequence (*Gammatorquevirus*) | |
|---|---|
| Three open-reading frame region | 2209-2439 |
| Poly(A) Signal | 2672-2678 |
| GC-rich region | 3076-3176 |

TABLE A17

| Exemplary *Anellovirus* amino acid sequences (*Gammatorquevirus*) Ring 4 (*Gammatorquevirus*) | |
|---|---|
| ORF2 | MVSISSSDFFKKTKFNEETQNQVWMSQIADSHDNICSCWHPFAHLLASIFPP GHKDRDLTINQILLR DYKEKCHSGGEEGENSGPTTGLITPKEEDIEKDGPEGAAEEDHTDALFAAAV ENFER (SEQ ID NO: 887) |
| ORF2/2 | MVSISSSDFFKKTKFNEETQNQVWMSQIADSHDNICSCWHPFAHLLASIFPP GHKDRDLTINQILLRDYKEKCHSGGEEGENSGPTTGLITPKEEDIEKDGPEGA AEEDHTDALFAAAVENFESGVDHNSMNQKLLTLANKSSMMSPILSTKQYKL KIQKDKTPDLSSMIGTTDEALLKKDLLKECQLTSQLIQISKQLQRKTFPKRKR ELDPNSQSHNKKKRRHCHVSSLSAKKIPSKKQRHKKTSSSSSSSSRSSSSSSR ETSSSSSTN (SEQ ID NO: 888) |
| ORF2/3 | MVSISSSDFFKKTKFNEETQNQVWMSQIADSHDNICSCWHPFAHLLASIFPP GHKDRDLTINQILLRDYKEKCHSGGEEGENSGPTTGLITPKEEDIEKDGPEGA AEEDHTDALFAAAVENFERSASNFRGRHSQKEKENWTPTHSPTTKRRGDTV MSPLSLQKRYLPRNRDTRRPPAAHQAAAGAAAPPQEKHPPAHPQTKRESTN ASASHRHVTLTRFKPGFEEQTERELAIIFHRPPRTYKEDLPFYPWLPPAPLVQ FNLNFKG (SEQ ID NO: 889) |
| TAIP | MRRRRTKYGCLKLLTLMIISAVAGIHLLTFLLPYFLLATKIVILLLTKFF (SEQ ID NO: 890) |
| ORF1 | MPFWWRRRRKFWTNNRFNYTKRRRYRKRWPRRRRRRRPYRRPVRRRRRK LRKVKRKKKSLIVRQWQPDSIRTCKIIGQSAIVVGAEGKQMYCYTVNKLINV PPKTPYGGGFGVDQYTLKYLYEEYRFAQNIWTQSNVLKDLCRYINVKLIFY RDNKTDFVLSYDRNPPFQLTKFTYPGAHPQQIMLQKHHKFILSQMTKPNGR LTKKLKIKPPKQMLSKWFFSKQFCKYPLLSLKASALDLRHSYLGCCNENPQ VFFYYLNHGYYTITNWGAQSSTAYRPNSKVTDTTYYRYKNDRKNINIKSHE YEKSISYENGYFQSSFLQTQCIYTSERGEACIAEKPLGIAIYNPVKDNGDGNM IYLVSTLANTWDQPPKDSAILIQGVPIWLGLFGYLDYCRQIKADKTWLDSHV LVIQSPAIFTYPNPGAGKWYCPLSQSFINGNGPFNQPPTLLQKAKWFPQIQYQ QEIINSFVESGPFVPKYANQTESNWELKYKYVFTFKWGGPQFHEPEIADPSK QEQYDVPDTFYQTIQIEDPEGQDPRSLIHDWDYRRGFIKERSLKRMSTYFST HTDQQATSEEDIPKKKKRIGPQLTVPQQKEEETLSCLLSLCKKDTFQETETQE DLQQLIKQQQEQQLLLKRNILQLIHKLKENQQMLQLHTGMLP (SEQ ID NO: 891) |
| ORF1/1 | MPFWWRRRRKFWTNNRFNYTKRRRYRKRWPRRRRRRRPYRRPVRRRRRK LRKWGGPQFHEPEIADPSKQEQYDVPDTFYQTIQIEDPEGQDPRSLIHDWDY RRGFIKERSLKRMSTYFSTHTDQQATSEEDIPKKKKRIGPQLTVPQQKEEETL SCLLSLCKKDTFQETETQEDLQQLIKQQQEQQLLLKRNILQLIHKLKENQQM LQLHTGMLP (SEQ ID NO: 892) |
| ORF1/2 | MPFWWRRRRKFWTNNRFNYTKRRRYRKRWPRRRRRRRPYRRPVRRRRRK LRKISKQLQRKTFPKRKR ELDPNSQSHNKKKRRHCHVSSLSAKKIPSKKQRHKKTSSSSSSSSRSSSSSSR ETSSSSSTN (SEQ ID NO: 893) |

TABLE N18

| Exemplary *Anellovirus* nucleic acid sequence (*Alphatorquevirus*)- Clade 1 | |
|---|---|
| Name | Ring5.2 |
| Genus/Clade | *Alphaatorquevirus* Clade 1 |
| Accession Number | |
| Full Sequence: 3696 bp | |

```
1        10         20         30         40         50
|         |          |          |          |          |
ATTTTGTTCAGCCCGCCAATTTCTCTTTCAAACAGGCCAATCAGCTACTA
CTTCGTGCACTTCCTGGGGCGTGTCCTGCCGCTCTATATAAGCAGAGGCG
GTGACGAATGGTAGAGTTTTTCTTGGCCCGTCCGCGGCGAGAGCGCGAGC
GAAGCGAGCGATCGAGCGTCCCGAGGGCGGGTGCCGGAGGTGAGTTTACA
CACCGCAGTCAAGGGGCAATTCGGGCTCGGGACTGGCCGGGCTATGGGCA
AGATTCTTAAAAAATTCCCCCGATCCCTTTGCCGCCAGGACATAAAAACA
TGCCGTGGAGACCGCCGGTCCATAGTGTCCAGGGGCGAGAGGATCAGTGG
TTCGCAAGCTTTTTTCACGGCCACGATTCGTTTTGCGGCTGCGGTGACCC
TCTTGGCCATATTAATAGCATTGCTCATCGCTTTCCTCGCGCCGGTCCAC
CAAGGCCCCCTCCGGGGCTAGATCAGCCTAACCCCCGGGAGCAGGGCCCG
GCCGGACCCGGAGGGCCGCCCGCCATCTTGGCCCTGCCGGCTCCGCCCGC
GGAGCCTGACGACCCGCAGCCACGGCGTGGTGGTGGGGACGGTGGCGCCG
CCGCTGGCGCCGCAGACGACCATACACAACGAGACTACGACGAAGAAGAG
CTAGACGAGCTTTTCCGCGCCGCCGCCGAAGACGATTTGTAAGTAGGAGA
TGGCGCCGGCCTTACAGGCGCAGGAGGAGACGCGGGCGACGCAGACGCAG
ACGCAGACGCAGACATAAGCCCACCCTAATACTCAGACAGTGGCAACCTG
ACTGTATCAGACACTGTAAAATAACAGGATGGATGCCCCTCATTATCTGT
GGAAAGGGGTCCACCCAGTTCAACTACATCACCCACGCGGACGATATCAC
CCCCAGGGGAGCCTCCTACGGAGGCAATTTCACAAACATGACTTTCTCCC
TGGAGGCCATATATGAACAGTTCCTATACCACAGAAACAGGTGGTCGGCC
TCTAACCACGACCTAGAACTGTGCAGATACAAGGGGACCACCTTAAAACT
CTACAGACACCCAGAAGTAGACTACATAGTTACCTACAGCAGAACAGGAC
CCTTTGAAATCAGCCACATGACCTACCTCAGCACTCACCCCATGCTAATG
CTGCTAAACAAGCACCACATTGTGGTGCCCAGCTTAAAGACTAAGCCCAG
AGGCAGAAAGGCCATAAAAGTCAGGATAAGGCCCCCAAAACTCATGAACA
ACAAGTGGTACTTCACCAGAGACTTCTGTAACATAGGCCTCTTCCAGCTC
TGGGCCACAGGCTTAGAACTCAGAAACCCCTGGCTCAGAATGAGCACCCT
GAGCCCCTGCATAGGCTTTAATGTCCTCAAAAACAGCATTTACACAAACC
TCAGCAACCTGCCACAATACAAAAACGAAAGACTAAACATCATTAACAAC
ATACTTCACCCACAAGAAATTACAGGTACAAACAACAAAAAGTGGCAGTA
CACATACACCAAACTCATGGCCCCTATTTACTATTCAGCAAACAGGGCCA
GCACCTATGACTGGGAAAATTACAGCAAAGAAACAAACTACAATAATACA
TATGTTAAATTTACCCAGAAAAGACAGGAAAAACTAACTAAAATTAGAAA
AGAGTGGCAGATGCTTTATCCACAACAACCCACAGCACTGCCAGACTCCT
ATGACCTCCTACAAGAGTATGGCCTCTACAGTCCATACTACCTAAACCCC
ACAAGAATAAACCTAGACTGGATGACCCCATACACACACGTCAGATACAA
TCCCCTAGTAGACAAGGGCTTTGGAAACAGAATATACATCCAGTGGTGCT
CAGAAGCAGATGTTAGCTACAACAGGACAAAATCCAAGTGTCTGCTACAA
GACATGCCCCTGTTTTTCATGTGCTATGGCTACATAGACTGGGCAATAAA
AAACACTGGAGTGTCATCTCTAGTGAAGGACGCCAGAATCTGCATCAGGT
GTCCCTACACAGAGCCACAACTAGTTGGCTCCACAGAAGACATAGGCTTT
GTACCCATCTCAGAAACCTTCATGAGGGGCGACATGCCGGTACTTGCACC
ATACATACCGTTAAGCTGGTTTTGCAAGTGGTATCCCAACATAGCTCACC
AAAAGGAAGTCCTTGAGTCAATCATTTCCTGCAGCCCCTTCATGCCCCGT
GACCAAGACATGAACGGTTGGGATATCACAATCGGTTACAAAATGGACTT
CTTATGGGGCGGTTCCCCTCTCCCCTCACAGCCAATCGACGACCCCTGCC
AGCAGGGAACCCACCCGATTCCCGACCCCGATAAACACCCTCGCCTCCTA
CAAGTCTCGAACCCGAAACTACTCGGACCGAGGACAGTGTTCCACAAGTG
GGACATCAGACGTGGGCAGTTTAGCAAAAGAAGTATTAAGAGAGTGTCAG
AATACTCAAGCGATGATGAATCTCTTGCGCCAGGTCTCCCATCAAAGCGA
AACAAGCTCGACTCGGCGTTCCGAGGAGAAAATCGAGAGCAAAAAGAATG
CTATTCTCTCCTCAAAGCGCTCGAGGAAGAAGAGACCCCAGAAGAAGAAG
AACCAGCACCCCAAGAAAAAGCCCAGAAAGAGGAGCTACTCCACCAGCTC
CAGCTCCAGAGACGCCACCAGCGAGTCCTCAGACGAGGGCTCAAGCTCGT
CTTTACAGACATCCTCCGACTCCGCCAGGGAGTCCACTGGAACCCGGAGC
TCACATAGCGCCCCCACCTTACATACCAGACCTGCTTTTTCCCAATACTG
GTAAAAAAAAAAAATTCTCTCCCTTCGATTGGGAGACAGAGGCGCAAATA
GCGGGGTGGATGCGGCGGCCCATGCGCTTCTATCCCTCAGACACCCCTCA
CTACCCGTGGCTACCCCCCGAGCGAGATATCCCGAAAATATGTAACATAA
ACTTCAAAATAAAGCTTCAAGAGTGAGTGATTCGAGGCCCTCCTCTGTTC
ACTTAGCGGTGTCTACCTCTTAAGGTCACTAAGCACTCCGAGCGTAAGCG
AGGAGTGCGACCCTCTACCAAGGGGCAACTTCCTCGGGGTCCGGCGCTAC
GCGCTTCGCGCTGCGCCGGACATCTCGGACCCCTCGACCCGAATCGCTTG
CGCGATTCGGACCTGCGGCCTCGGGGGGGTCGGGGGCTTTACTAAACAGA
CTCCGAGGTGCCATTGGACACTGTAGGGGGTGAACAGCAACGAAAGTGAG
TGGGGCCAGACTTCGCCATAAGGCCTTTATCTTCTTGCCATTGGATAGTG
ACTTCCGGGTCCGCCTGGGGGCCGCCATTTTAGCTTCGGCCGCCATTTTA
GGCCCTCGCGGGCCTCCGTAGGCGCGCTTTAGTGACGTCACGGCAGCCAT
TTTGTCGTGACGTTTGAGACACGTGATGGGGGCGTGCCTAAACCCGGAAG
CATCCCTGGTCACGTGACTCTGACGTCACGGCGGCCATCTTGTGCTGTCC
```

TABLE N18-continued

| Exemplary *Anellovirus* nucleic acid sequence (*Alphatorquevirus*)-Clade 1 |
|---|
| GCCATCTTGTAACTTCCTTCCGCTTTTTCAAAAAAAAAGAGGAAGTGTGA<br>CGTAGCGGCGGGGGGGCGGCGCGCTTCGCGCGCCGCCCACCAGGGGGCGC<br>TGCGCGCCCCCCCGCGCATGCGCAGGGGCCTCTCGAGGGGCTCCGCCCCCC<br>CCCCGTGCTAAATTTACCGCGCATGCGCGACCACGCCCCCGCCGCC (SEQ ID NO: 894) |

Annotations:

| Putative Domain | Base range |
|---|---|
| TATA Box | 85-91 |
| Cap Site | 108-115 |
| Transcriptional Start Site | 115 |
| 5' UTR Conserved Domain | 178-248 |
| ORF2 | 300-692 |
| ORF2/2 | 300-688; 2282-2804 |
| ORF2/3 | 300-688; 2484-2976 |
| ORF2t/3 | 300-349: 2484-2976 |
| TAIP | 322-471 |
| ORF1 | 572 -2758 |
| ORF1/1 | 572-688; 2282-2758 |
| ORF1/2 | 572-688; 2484-2804 |
| Three open-reading frame region | 2484-2755 |
| Poly(A) Signal | 3018-3023 |
| GC-rich region | 3555-3696 |

TABLE A18

| Exemplary *Anellovirus* amino acid sequences (*Alphatorquevirus*) Clade 1 Ring 5.2 (*Alphaatorquevirus*) Clade 1 | |
|---|---|
| ORF2 | MPWRPPVHSVQGREDQWFASFFHGHDSFCGCGDPLGHINSIAHRFPRAGPP RPPPGLDQPNPREQGPAGPGGPPAILALPAPPAEPDDPQPRRGGGDGGAAAG AADDHTQRDYDEEELDELFRAAAEDDL (SEQ ID NO: 895) |
| ORF2/2 | MPWRPPVHSVQGREDQWFASFFHGHDSFCGCGDPLGHINSIAHRFPRAGPP RPPPGLDQPNPREQGPAGPGGPPAILALPAPPAEPDDPQPRRGGGDGGAAAG AADDHTQRDYDEEELDELFRAAAEDDFQSTTPASREPTRFPTPINTLASYKS RTRNYSDRGQCSTSGTSDVGSLAKEVLRECQNTQAMMNLLRQVSHQSETSS TRRSEEKIESKKNAILSSKRSRKKRPQKKKNQHPKKKPRKRSYSTSSSSRDAT SESSDEGSSSSLQTSSDSARESTGTRSSHSAPTLHTRPAFSQYW (SEQ ID NO: 896) |
| ORF2/3 | MPWRPPVHSVQGREDQWFASFFHGHDSFCGCGDPLGHINSIAHRFPRAGPP RPPPGLDQPNPREQGPAGPGGPPAILALPAPPAEPDDPQPRRGGGDGGAAAG AADDHTQRDYDEEELDELFRAAAEDDLSPIKAKQARLGVPRRKSRAKRMLF SPQSARGRRDPRRRRTSTPRKSPERGATPPAPAPETPPASPQTRAQARLYRHP PTPPGSPLEPGAHIAPPPYIPDLLFPNTGKKKKFSPFDWETEAQIAGWMRRPM RFYPSDTPHYPWLPPERDIPKICNINFKIKLQ (SEQ ID NO: 897) |
| ORF2t/3 | MPWRPPVHSVQGREDQWSPIKAKQARLGVPRRKSRAKRMLFSPQSARGRR DPRRRRTSTPRKSPERGATPPAPAPETPPASPQTRAQARLYRHPPTPPGSPLEP GAHIAPPPYIPDLLFPNTGKKKKFSPFDWETEAQIAGWMRRPMRFYPSDTPH YPWLPPERDIPKICNINFKIKLQE (SEQ ID NO: 898) |
| TAIP | IVSRGERISGSQAFFTATIRFAAAVTLLAILIALLIAFLAPVHQGPLRG (SEQ ID NO: 899) |
| ORF1 | TAWWWGRWRRRWRRRRPYTTRLRRRRARRAFPRRRRRRFVSRRWRRPYR RRRRRGRRRRRRRRRHKPTLILRQWQPDCIRHCKITGWMPLIICGKGSTQFN YITHADDITPRGASYGGNFTNMTFSLEAIYEQFLYHRNRWSASNHDLELCRY |

TABLE A18-continued

| Exemplary *Anellovirus* amino acid sequences (*Alphatorquevirus*) Clade 1<br>Ring 5.2 (*Alphaatorquevirus*) Clade 1 | |
|---|---|
| | KGTTLKLYRHPEVDYIVTYSRTGPFEISHMTYLSTHPMLMLLNKHHIVVPSL<br>KTKPRGRKAIKVRIRPPKLMNNKWYFTRDFCNIGLFQLWATGLELRNPWLR<br>MSTLSPCIGFNVLKNSIYTNLSNLPQYKNERLNIINNILHPQEITGTNNKKWQ<br>YTYTKLMAPIYYSANRASTYDWENYSKETNYNNTYVKFTQKRQEKLTKIR<br>KEWQMLYPQQPTALPDSYDLLQEYGLYSPYYLNPTRINLDWMTPYTHVRY<br>NPLVDKGFGNRIYIQWCSEADVSYNRTKSKCLLQDMPLFFMCYGYIDWAIK<br>NTGVSSLVKDARICIRCPYTEPQLVGSTEDIGFVPISETFMRGDMPVLAPYIPL<br>SWFCKWYPNIAHQKEVLESIISCSPFMPRDQDMNGWDITIGYKMDFLWGGS<br>PLPSQPIDDPCQQGTHPIPDPDKHPRLLQVSNPKLLGPRTVFHKWDIRRGQFS<br>KRSIKRVSEYSSDDESLAPGLPSKRNKLDSAFRGENREQKECYSLLKALEEE<br>ETPEEEEPAPQEKAQKEELLHQLQLQRRHQRVLRRGLKLVFTDILRLRQGVH<br>WNPELT (SEQ ID NO: 900) |
| ORF1/1 | TAWWWGRWRRRWRRRRPYTTRLRRRRARRAFPRRRRRRFPIDDPCQQGT<br>HPIPDPDKHPRLLQVSNPKLLGPRTVFHKWDIRRGQFSKRSIKRVSEYSSDDE<br>SLAPGLPSKRNKLDSAFRGENREQKECYSLLKALEEEETPEEEEPAPQEKAQ<br>KEELLHQLQLQRRHQRVLRRGLKLVFTDILRLRQGVHWNPELT (SEQ ID<br>NO: 901) |
| ORF1/2 | TAWWWGRWRRRWRRRRPYTTRLRRRRARRAFPRRRRRRFVSHQSETSSTR<br>RSEEKIESKKNAILSSK<br>RSRKKRPQKKKNQHPKKKPRKRSYSTSSSSRDATSESSDEGSSSSLQTSSDSA<br>RESTGTRSSHSAPTLHTRPAFSQYW (SEQ ID NO: 902) |

TABLE N19

| Exemplary *Anellovirus* nucleic acid sequence (*Alphatorquevirus*)-<br>Clade 3 | |
|---|---|
| Name | Ring 6.0 |
| Genus/Clade | *Alphatorquevirus*-Clade 3 |
| Accession Number | |
| Full Sequence: 3828 bp | |

```
1         10         20         30         40         50
|         |          |          |          |          |
GTGCTACGTCACTAACCTACGTGTCCGTCTCCCATAGGCCGGACACCGTA
TACGTCATACACTTCCTGGGCATGGTCTACGTGATAATATAAGTGGCTGC
ACTTCCGAATGGCTGAGTTTTCCACGCCCGTCCGCAGCGAGGACGCCACG
GAGGGGGATCCGCGCGTCCCGAGGGCGGGTGCCGGAGGTGAGTTTACACA
CCGCAGTCAAGGGGCAATTCGGGCTCGGGACTGGCCGGGCTATGGGCAAG
GCTCTTAAAAATGCACTTTTCTAGGTGCAGTAGAAAGAAAAGGACATTGT
CACTGCTACCACTGTACCATTCACAGAAAGCTAGGCCATCTGTGACAGGT
ATGTGGAGACCCCCGACTCGAAATGCGTTCAATATTCAACGTGACTGGTT
CTACAGTTGCTTTCACTCCCACGCTTCTATGTGCGGCTGTGCTGATTTTA
TTGGTCATTTCAATCATATCGCTGCTATGCTCGGCCGTCCGGAAGACCAG
AACCCTCCTCCGCCACCCGGGGCTCTGAGACCCCTACCCGCTCTCCCGGC
CTCTTCCGAGGCACCCGGTGATCGAGCGCCATGGCCTATGGGTGGTGGCG
GAGGCGACGGAGGCGCCCGTGGTGGAGGAGGAGATGGCGCCGCTGGAGAC
GCCGTCGGAGACCCCGCAGACGCCGACCTCGTCGCCGCTATCGACGCCGC
AGAACAGTAAGGAGGCGCGGCAGGGGGAGGTGGACTAGAGCACACAGGAG
ATGGCGCCGCAAGGGAAAACGCAGTCGCAAAAAAAAGATTATTATAAGAC
AATGGCAGCCCAACTACACTCGCAGATGCAACATAGTGGGCTACATGCCT
CTACTAATATGTGGGGAAAATACTGTTGCTACAAACTATGCCACCCACTC
AGACGACAGCTACTACCCCGGACCCTTTGGGGGGGAATGACTACAGACA
AATTTACTCTAAGAATACTGTATGATGAGTACAAAAGGTTCATGAACTAC
TGGACCTCTTCAAACGAGGACCTAGACCTATGTAGATACCTGGGATGCAC
TCTATATGTGTTTAGACACCCAGAAGTAGACTTTATAATCATTATAAATA
CCTCTCCTCCATTCCTAGACACAGAAATAACAGGGCCTAGCATACACCCA
GGTATGATGGCCCTTAACAAAAGAAGCAGATGGATACCTAGCATAAAAAA
CAGACCAGGCAGAAAGCACTATATAAAGATTAAAGTAGGAGCCCCCCGAA
TGTTCACAGATAAGTGGTACCCCCAAACAGACCTCTGTGACATGACACTC
CTAACGATCTTTGCCAGTGCGGCGGATATGCAATATCCGTTCGGCTCACC
ACTAACTGACACCATAGTTGTGTCATTCCAAGTTCTGCAATCCATGTACA
ACGACTGCCTGAGTGTACTTCCTGATAATTTTGCAGAGACATCAGGCAAA
GGCACCCAACTACATGAGAACATAATACAACATCTGCCCTACTACAACAC
CACACAAACACAAGCACAATTTAAAAGATTTATAGAAAACATGAATGCAA
CAAATGGAGACAATATATGGGCAAGCTACATAAACACAACCAAGTTCTCA
TCCGCAAACACTCCAAAGAATGACACAGGCATAGGAGGCCCTTACACTAC
ATATTCAGACTCATGGTACAAAGGCACAGTATACAATGACAAAATTAAAA
CCATACCAATAAAAGCAAGCAAGTTATACTACGAGCAAACCAAAAACCTC
ATTGGCATTACATTCACTGGATCCACACACAGACTCCATTACTGTGGAGG
CCTATACTCCTCCGTATGGCTATCAGCAGGTAGATCCTACTTTGAAACCA
AAGGCCCATACACAGACATAACTTACAACCCCTTTTCAGACAGAGGAGAG
```

TABLE N19-continued

| Exemplary *Anellovirus* nucleic acid sequence (*Alphatorquevirus*)-Clade 3 |
|---|
| GGTAACATGCTATGGATAGACTGGCTAACTAAAAATGACTCAGTGTACTC<br>AAAAACAAGTAGCAAGTGTCTTATAGAAAACCTGCCCCTGTGGGCCTCAG<br>TATACGGATATAAAGAATACTGCAGCAAGGTAACAGGAGACACAAACATA<br>GAACACAACTGTAGATGTGTTATCAGAAGCCCCTACACAGTACCACAACT<br>GTTAGACCACAACAATCCCTTCAGAGGATACGTGCCTTATAGCTTCAACT<br>TTGGAAATGGTAAAATGCCAGGCGGTAGCAGCCTAGTGCCCATTAGAATG<br>AGAGCCAAGTGGTACCCCACTCTGTTCCACCAAAAAGAAGTTCTAGAAGC<br>CATAGCACAGGCGGGCCCCTTCGCATACCACTCAGATATTAAAAAAGTGT<br>CCCTGGGCATAAAGTACAGATTTAAGTGGGTGTGGGGTGGCAACCCCGTG<br>TCCCAACAGGTTGTTAGAAACCCCTGCAAGACCACCCAAGGTTCCTCGGG<br>CAATAGAGTGCCTCGATCAATACAAGTCGTTGACCCGCGGTACAACACGC<br>CAGAACTCACCATACACGCGTGGGACTTCAGACATGGGTTCTTTGGCAGA<br>AAAGCTATTAAGAGAATGCAAGAACAACCAATACCTCATGACACTTTTTC<br>AGCAGGGTTCAAGCGCAGTCGCCGAGATACAGAAGCACTCCAATGCAGCC<br>AAGAAGAGCAACAAAAAGAAAACTTACTTTTCCCAGTCCAGCAGCTCAAG<br>CGAGTCCCCCCGTGGGAGACCTCGCAAGAGAGCCAAAGCGAGGAAGAAAA<br>CTCGCAAAAACAGGAGACCCTCTCCCAGCAACTCAGAGACCAGCTGCACA<br>AGCAGCGGCTCATGGGAGAGCAACTCCGATCGCTCCTCTACCAAATGCAG<br>AGGGTCCAACAAAATCAACACATAAACCCTATGTTATTGCCAAAGGGTCT<br>GGCATTAACTTCTATTTCTCACAATGTAATATAGATATGTTTGGTGACCC<br>CAAACCCTACAAGCCCTCCTCCAATGACTGGAAGGAGGAGTACGAGGCCG<br>CAAAGTACTGGGACAGACCCCCCAGACGCGACCTGAGGAGCACCCCCTTC<br>TACCCCTGGGCCCCCACCCCCAAACCATACAATGTCAACTTTGCCCTCAA<br>CTACAAATAAACGGTGGCCGTGGGAGTTTCACTTGTCGGTGTCTACCTCT<br>TAAGGTCACTAAGCACTCCGAGCGTAAGCGAGGAGTGCGACCCTTCACCA<br>AGGGCAACTCCCTCGAAGTCCGGCGCTACGCGCTTCGCGCTGCGCCGGAC<br>ATCTCGGACCCCCCCTCGACCCGAATCGCTTGCGCGATTCGGACCTGCGG<br>CCTCGGGGGGGTCGGGGGCTTTACTAAACAGACTCCGAGGTGCCATTGGA<br>CACTGAGGGGGTGAACAGCAACGAAAGTGAGTGGGGCCAGACTTCGCCAT<br>AAGGCCTTTATCTTCTTGCCATTTGTCCGCGACCGGGGGTCGCTCCTAGG<br>CGCGGACCCCGTTTCGGGGTCCTTCCGGGTTCATCGGCGCCGTTCCAGTG<br>ACGTCACGGGCGCCATGTTAAGTGGCTGTCGCCGAGGATTGACGTCACAG<br>TTCAAAGGTCATCCTCGGCGGTAACCGCAAACATGGCGGTCAATCTCTTC<br>CGGGTCAAAGGTCGTGCATACGTCATAAGTCACATGACAGGGGTCCACTT<br>AAACACGGAAGTAGGCCCCGACATGTGACTCGTCACGTGTGTACACGTCA<br>CGGCCGCCATTTTGTTTTACAAAATGGCCGACTTCCTTCCTGTTTTTTAA<br>AAAAAGGCGCGAAAAAACCGTCGGCGGGGGCCGCGCGCTGCGCGCGCGGG<br>AGGCAATGCCTCCCCCCCCCCGCGCGCATGCGCGCGGGTCCCCCCCCCTC<br>CGGGGGGCTCCGCCCCCCGGCCCCCCCC (SEQ ID NO: 903) |

Annotations:

| Putative Domain | Base range |
|---|---|
| TATA Box | 85-92 |
| Cap Site | 109-116 |
| Transcriptional Start Site | 116 |
| 5' UTR Conserved Domain | 176-246 |
| ORF2 | 351-710 |
| ORF2/2 | 351-706; 2360-2825 |
| ORF2/3 | 351-706; 2556-3060 |
| TAIP | 373-528 |
| ORF1 | 581-2884 |
| ORF1/1 | 581-706; 2360-2884 |
| ORF1/2 | 581-706; 2556-2825 |
| Three open-reading frame region | 2556-2821 |
| Poly(A) Signal | 3055-3061 |
| GC-rich region | 3720-3828 |

TABLE A19

| Exemplary *Anellovirus* amino acid sequences (*Alphatorquevirus*)-Clade 3 Ring 6.0 (*Alphatorquevirus*) | |
|---|---|
| ORF2 | MWRPPTRNAFNIQRDWFYSCFHSHASMCGCADFIGHFNHIAAMLGRPEDQ NPPPPPGALRPLPALPASSEAPGDRAPWPMGGGGGDGGARGGGGDGAAGD AVGDPADADLVAAIDAAEQ (SEQ ID NO: 904) |
| ORF2/2 | MWRPPTRNAFNIQRDWFYSCFHSHASMCGCADFIGHFNHIAAMLGRPEDQ NPPPPPGALRPLPALPASSEAPGDRAPWPMGGGGGDGGARGGGGDGAAGD AVGDPADADLVAAIDAAEQLLETPARPPKVPRAIECLDQYKSLTRGTTRQNS PYTRGTSDMGSLAEKLLRECKNNQYLMTLFQQGSSAVAEIQKHSNAAKKS NKKKTYFSQSSSSSESPRGRPRKRAKARKKTRKNRRPSPSNSETSCTSSGSW ESNSDRSSTKCRGSNKINT (SEQ ID NO: 905) |
| ORF2/3 | MWRPPTRNAFNIQRDWFYSCFHSHASMCGCADFIGHFNHIAAMLGRPEDQ NPPPPPGALRPLPALPASSEAPGDRAPWPMGGGGGDGGARGGGGDGAAGD AVGDPADADLVAAIDAAEQVQAQSPRYRSTPMQPRRATKRKLTFPSPAAQA SPPVGDLAREPKRGRKLAKTGDPLPATQRPAAQAAAHGRATPIAPLPNAEG PTKSTHKPYVIAKGSGINFYFSQCNIDMFGDPKPYKPSSNDWKEEYEAAKY WDRPPRRDLRSTPFYPWAPTPKPYNVNFALNYK (SEQ ID NO: 906) |
| TAIP | MRSIFNVTGSTVAFTPTLLCAAVLILLVISIISLLCSAVRKTRTLLRHPGL (SEQ ID NO: 907) |
| ORF1 | MAYGWWRRRRRRPWWRRRWRRWRRRRRPRRRRPRRRYRRRRTVRRRGR GRWTRAHRRWRRKGKRSRKKKIIRQWQPNYTRRCNIVGYMPLLICGENTV ATNYATHSDDSYYPGPFGGGMTTDKFTLRILYDEYKRFMNYWTSSNEDLD LCRYLGCTLYVFRHPEVDFIIIINTSPPFLDTEITGPSIHPGMMALNKRSRWIPS IKNRPGRKHYIKIKVGAPRMFTDKWYPQTDLCDMTLLTIFASAADMQYPFG SPLTDTIVVSFQVLQSMYNDCLSVLPDNFAETSGKGTQLHENIIQHLPYYNTT QTQAQFKRFIENMNATNGDNIWASYINTTKFSSANTPKNDTGIGGPYTTYSD SWYKGTVYNDKIKTIPIKASKLYYEQTKNLIGITFTGSTHRLHYCGGLYSSV WLSAGRSYFETKGPYTDITYNPFSDRGEGNMLWIDWLTKNDSVYSKTSSKC LIENLPLWASVYGYKEYCSKVTGDTNIEHNCRCVIRSPYTVPQLLDHNNPFR GYVPYSFNFGNGKMPGGSSLVPIRMRAKWYPTLFHQKEVLEAIAQAGPFAY HSDIKKVSLGIKYRFKWVWGGNPVSQQVVRNPCKTTQGSSGNRVPRSIQVV DPRYNTPELTIHAWDFRHGFFGRKAIKRMQEQPIPHDTFSAGFKRSRRDTEA LQCSQEEQQKENLLFPVQQLKRVPPWETSQESQSEEENSQKQETLSQQLRD QLHKQRLMGEQLRSLLYQMQRVQQNQHINPMLLPKGLALTSISHNVI (SEQ ID NO: 908) |
| ORF1/1 | MAYGWWRRRRRRPWWRRRWRRWRRRRRPRRRRPRRRYRRRRTVVRNPC KTTQGSSGNRVPRSIQVVDPRYNTPELTIHAWDFRHGFFGRKAIKRMQEQPI PHDTFSAGFKRSRRDTEALQCSQEEQQKENLLFPVQQLKRVPPWETSQESQS EEENSQKQETLSQQLRDQLHKQRLMGEQLRSLLYQMQRVQQNQHINPMLL PKGLALTSISHNVI (SEQ ID NO: 909) |
| ORF1/2 | MAYGWWRRRRRRPWWRRRWRRWRRRRRPRRRRPRRRYRRRRTGSSAVA EIQKHSNAAKKSNKKKTYFSQSSSSSESPRGRPRKRAKARKKTRKNRRPSPS NSETSCTSSGSWESNSDRSSTKCRGSNKINT (SEQ ID NO: 910) |

TABLE N20

| Exemplary *Anellovirus* nucleic acid sequence (*Alphatorquevirus*)-Clade 7 | |
|---|---|
| Name | Ring7 |
| Genus/Clade | *Alphatorquevirus*-Clade 7 |
| Accession Number | |
| Full Sequence: 3815 bp | |

```
1         10         20         30         40         50
|         |          |          |          |          |
AAGATCGTCACTAACCACGTGACTCCTCTCGCCCAATCAGTGTCTACGTC
GTCCATTTCCTGGGCATGGTCTACATCCTGATATAAAGCGATGCACTTCC
GAATGGCTGAGTTTTCCACGCCCGTCCGCGGCGAGATCGCGACGGAGGAG
CGATCGAGCGTCCCGAGGGCGGGTGCCGGAGGTGAGTTTACACACCGCAG
TCAAGGGGCAATTCGGGCTCGGGACTGGCCGGGCTATGGGCAAGGCTCTT
AAAGCGTACGTCCCCCGCTATGTTTCTCGGCAGGGTGTGGAGGAAACAGA
AAAGGAAAGTGCTTCTGCTGGCTGTGCGAGCTACACAGAAAACATCTTCC
ATGAGTATCTGGCGTCCCCCCCTTGGGAATGTCTCCTACAGGGAGAGAAA
TTGGCTTCAGGCCGTCGAAACATCCCACAGTTCTTTTTGTGGCTGTGGTG
ATTTTATTCTTCATCTTACTAATTTGGCTGCACGCTTTGCTCTCCAGGGG
CCCCCGCCAGAGGGTGGTCCACCTCGGCCGAGGCCGCCGCTCCTGAGAGC
GCTGCCGGCCCCCGAGGTCCGCAGGGAGACGCGCACAGAGAACCGGGGCG
CCTCCGGTGAGCCATGGCCTGGCGATGGTGGTGGCAGAGACGATGGCGCC
```

TABLE N20-continued

Exemplary *Anellovirus* nucleic acid sequence (*Alphatorquevirus*)-
Clade 7

GCCGCCGGTGGCCCCGCAGACGGTGGAGACGCCTACGACGCCGGAGACCT
AGACGACCTGTTCGCCGCCGTCGAAGAAGAACAACAGTAAGGAGGCGGAG
GTGGAGGGGCAGACGTGGGCGACGCACATACACCCGACGCGCGGTCAGAC
GCAGACGCAGACCCAGAAAGAGACTTGTACTGACTCAGTGGAGCCCCCAG
ACAGTCAGAAACTGCTCAATAAGGGGCATAGTGCCCATGGTAATATGCGG
ACACACAAAAGCAGGTAGAAACTATGCTATTCATAGCGAGGACTTCACCA
CACAGATACAACCCTTCGGGGGCAGTTTCAGCACGACCACCTGGTCCCTA
AAAGTGCTGTGGGACGAGCACCAGAAATTCCAGAACAGATGGTCCTACCC
AAACACACAACTAGACCTGGCCAGATACAGAGGGGTCACCTTCTGGTTCT
ACAGAGACCAGAAAACAGACTATATAGTACAGTGGAGTAGGAATCCCCCT
TTTAAACTCAATAAATACAGCAGTGCCATGTACCACCCGGGCATGATGAT
GCAGGCCAAAAGGAAACTAGTTGTACCTAGTTTCCAGACCAGACCCAAAG
GCAAGAAGAGATACAGAGTCACAATAAAACCCCCTAACATGTTTGCTGAC
AAGTGGTACACTCAAGAGGACCTGTGTCCGGTACCTCTTGTGCAAATTGT
GGTTTCTGCGGCGAGCCTGCTACATCCGTTCTGCCCACCACAAACGAACA
ACCCTTGCATCACCTTCCAGGTTTTGAAAGACATATATGATGAATGCATA
GGAGTTAACGAAACTATGAAAGATAAGTATAAGAAATTACAAACAACACT
ATACACCACTTGCACATACTATCAAACAACACAAGTACTGGCACAGCTAT
CTCCTGCCTTTCAACCTGCTATGAAACCTACTACTACACAATCAGCAGCT
ACAGCGACAACACTAGGAAACTATGTACCAGAGTTAAAGTACAACAATGG
CTCTTTTCACACAGGACAAAACGCAGTATTCGGCATGTGCTCATACAAAC
CAACAGACAGCATAATGACAAAAGCTAATGGCTGGTTTTGGCAAAACCTA
ATGGTAGACAACAACCTACATAGTTCTTATGGCAAGGCAACATTAGAATG
CATGGAGTATCACACAGGCATATACAGCTCTATATTTCTAAGTCCACAAA
GATCTTTAGAATTCCCAGCAGCATACCAAGACGTTACATACAACCCTAAC
TGTGATAGAGCAGTTGGAAACGTAGTTTGGTTTCAGTACAGCACTAAAAT
GGATACAAATTTTGATGAAACAAAATGTAAATGTGTCCTTAAAAACATTC
CACTGTGGGCGGCCTTCAATGGCTACTCAGACTTTATAATGCAAGAACTC
AGCATAAGTACAGAAATCCACAACTTTGGCATAGTGTGCTTTCAGTGCCC
GTACACTTTTCCCCCCTGTTTCAATAAAAACAAACCCCTAAAGGGGTACG
TGTTCTATGACACCACCTTTGGTAATGGAAAAATGCCAGACGGATCGGGG
CACGTACCCATCTACTGGCAGCAGAGATGGTGGATCAGACTAGCCTTCCA
GGTCCAGGTCATGCATGACTTTGTACTAACAGGCCCCTTTAGCTACAAAG
ATGACCTAGCAAACACCACACTCACAGCCAGATACAAATTTAAATTCAAA
TGGGGCGGCAATATCATCCCTGAACAGATTATCAAGAACCCGTGTCACAG
AGAGCAGTCCCTCGCTTCCTATCCCGATAGACAACGTCGCGACCTACAAG
TTGTTGACCCATCAACCATGGGCCCGATCTACACCTTCCACACATGGGAC
TGGCGACGGGGGCTTTTTGGTGCAGATGCTATCCAGAGAGTGTCACAAAA
ACCGGGAGATGCTCTCCGCTTTACAAACCCTTTCAAGAGACCCAGATATC
TTCCCCCGACAGACAGAGAAGACTACCGACAAGAAGAAGACTTCGCTTTA
CAGGAAAAAAGACGGCGCACATCCACAGAAGAAGCCCAGGACGAGGAGAG
CCCCCCGGAAAGCGCGCCGCTCCTACAGCAGCAGCAGCAGCAGCGGCAGC
TCTCAGTCCACCTCGCGGAGCAGCAGCGACTCGGAGTCCAACTCCGATAC
ATCCTCCAAGAAGTCCTCAAAACGCAAGCGGGTCTCCACCTAAACCCCCT
ATTATTAGGCCCGCCACAAACAAGGTCTATCTCTTTGAGCCCTCCAAAGG
CCTACTCCCCATAGTAGGAAAAGAGGCCTGGGAGGACGAGTACTGCACCT
GCAAGTACTGGGATCGCCCTCCCAGAACCAACCACCTAGACATCCCCACT
TATCCCTGGATGCCCACAAACTTCAAAGTCAGCTTCAAACTTGGATTTAA
ACCCTAAATAAAAATACAAGGCCGTACACTGTTCACTTGTCGGTGTCTAC
CTCTATAAGTCACTAAGCACTCCGAGCGCAGCGAGGAGTGCGACCCTCAG
CGGTGGGTGCAACGCCCTCGGCGGCCGCGCGCTACGCCTTCGGCTGCGCG
CGGCACCTCGGACCCCCGCTCGTGCTGACACGCTCGCGCGTGTCAGACCA
CTTCGGGCTCGCGGGGGTCGGGAATTTTGCTAAACAGACTCCGAGTTGCT
CTTGGACACTGTAGCTGTGAATCAGTAACGAAAGTGAGTGGGGCCAGACT
TCGCCATAAGGCCTTTATCTTCTTGCCATTGGTCCGTCTCGGGGGTCGCC
ATAGGCTTCGGGCTCGGTTTTAGGCCTTCCGGACTACCAAAATGGCGGAT
TCCGTGACGTCATGGCCGCCATTTTAAGTAAGGCGGAACAGGCTGTCACC
CCGTGTCAAAGTTCAGGGGTCAGCCTTCCGCTTTACACAAAATGGAGGTC
AATATCTTCCGGGTCAAAGGTCGCTACCGCGTCATAAGTCACGTGGGGAA
GGCTGCTGTGAATCCGGAAGTAGCTGACCCACGTGACTTGTCACGTGACT
AGCACGTCACGGCAGCCATTTTGAATCACAAAATGGCCGACTTCCTTCCT
CTTTTTTAAAAATAACGGCCCGGCGGCGGCGCGCGCGCTTCGCGCCGCTC
CGCCCCCCCCGCGCATGCGCGGACCCCCCCCCGCGGGGGGCTCCGCCCC
CCGGTCCCCCCCCCG (SEQ ID NO: 911)

Annotations:

| Putative Domain | Base range |
| --- | --- |
| TATA Box | 82-87 |
| Cap Site | 103-110 |
| Transcriptional Start Site | 110 |
| 5' UTR Conserved Domain | 170-240 |

TABLE N20-continued

| Exemplary *Anellovirus* nucleic acid sequence (*Alphatorquevirus*)-Clade 7 | |
|---|---|
| ORF2 | 351-740 |
| ORF2/2 | 351-737; 2378-2843 |
| ORF2/3 | 351-737; 2526-3057 |
| TAIP | 379-543 |
| ORF1 | 614 -2911 |
| ORF1/1 | 614-737; 2378-2911 |
| ORF1/2 | 614-737; 2526-2843 |
| Three open-reading frame region | 2526-2840 |
| Poly(A) Signal | 3056-3062 |
| GC-rich region | 3716-3815 |

TABLE A20

| Exemplary *Anellovirus* amino acid sequences (*Alphatorquevirus*)-Clade 7 Ring7.0 (*Alphatorquevirus*) | |
|---|---|
| ORF2 | MSIWRPPLGNVSYRERNWLQAVETSHSSFCGCGDFILHLTNLAARFALQGPP PEGGPPRPRPPLLRA LPAPEVRRETRTENRGASGEPWPGDGGGRDDGAAAGGPADGGDAYDAGD LDDLFAAVEEEQQ (SEQ ID NO: 912) |
| ORF2/2 | MSIWRPPLGNVSYRERNWLQAVETSHSSFCGCGDFILHLTNLAARFALQGPP PEGGPPRPRPPLLRA LPAPEVRRETRTENRGASGEPWPGDGGGRDDGAAAGGPADGGDAYDAGD LDDLFAAVEEEQQLSRTRVTESSPSLPIPIDNVATYKLLTHQPWARSTPSTHG TGDGGFLVQMLSRECHKNREMLSALQTLSRDPDIFPRQTEKTTDKKKTSLY RKKDGAHPQKKPRTRRAPRKARRSYSSSSSSGSSQSTSRSSSDSESNSDTSSK KSSKRKRVST (SEQ ID NO: 913) |
| ORF2/3 | MSIWRPPLGNVSYRERNWLQAVETSHSSFCGCGDFILHLTNLAARFALQGPP PEGGPPRPRPPLLRA LPAPEVRRETRTENRGASGEPWPGDGGGRDDGAAAGGPADGGDAYDAGD LDDLFAAVEEEQQCYPESVTKTGRCSPLYKPFQETQISSPDRQRRLPTRRRLR FTGKKTAHIHRRSPGRGEPPGKRAAPTAAAAAAAALSPPRGAAATRSPTPIH PPRSPQNASGSPPKPPIIRPATNKVYLFEPSKGLLPIVGKEAWEDEYCTCKYW DRPPRTNHLDIPTYPWMPTNFKVSFKLGFKP (SEQ ID NO: 914) |
| TAIP | MSPTGREIGFRPSKHPTVLFVAVVILFFILLIWLHALLSRGPRQRVVHLGRGR RS (SEQ ID NO: 915) |
| ORF1 | MAWRWWWQRRWRRRRWPRRRWRRLRRRRPRRPVRRRRRRTTVRRRRW RGRRGRRRTYTRRAVRRRRRPRKRLVLTQWSPQTVRNCSIRGIVPMVICGHT KAGRNYAIHSEDFTTQIQPFGGSFSTTTWSLKVLWDEHQKFQNRWSYPNTQ LDLARYRGVTFWFYRDQKTDYIVQWSRNPPFKLNKYSSAMYHPGMMMQA KRKLVVPSFQTRPKGKKRYRVTIKPPNMFADKWYTQEDLCPVPLVQIVVSA ASLLHPFCPPQTNNPCITFQVLKDIYDECIGVNETMKDKYKKLQTTLYTTCT YYQTTQVLAQLSPAFQPAMKPTTTQSAATATTLGNYVPELKYNNGSFHTGQ NAVFGMCSYKPTDSIMTKANGWFWQNLMVDNNLHSSYGKATLECMEYHT GIYSSIFLSPQRSLEFPAAYQDVTYNPNCDRAVGNVVWFQYSTKMDTNFDE TKCKCVLKNIPLWAAFNGYSDFIMQELSISTEIHNFGIVCFQCPYTFPPCENK NKPLKGYVFYDTTFGNGKMPDGSGHVPIYWQQRWWIRLAFQVQVMHDFV LTGPFSYKDDLANTTLTARYKFKFKWGGNIIPEQIIKNPCHREQSLASYPDRQ RRDLQVVDPSTMGPIYTFHTWDWRRGLFGADAIQRVSQKPGDALRFTNPFK RPRYLPPTDREDYRQEEDFALQEKRRRTSTEEAQDEESPPESAPLLQQQQQQ RQLSVHLAEQQRLGVQLRYILQEVLKTQAGLHLNPLLLGPPQTRSISLSPPKA YSP (SEQ ID NO: 916) |
| ORF1/1 | MAWRWWWQRRWRRRRWPRRRWRRLRRRRPRRPVRRRRRRTTIIKNPCHR EQSLASYPDRQRRDLQVVDPSTMGPIYTFHTWDWRRGLFGADAIQRVSQKP GDALRFTNPFKRPRYLPPTDREDYRQEEDFALQEKRRRTSTEEAQDEESPPE SAPLLQQQQQQRQLSVHLAEQQRLGVQLRYILQEVLKTQAGLHLNPLLLGP PQTRSISLSPPKAYSP (SEQ ID NO: 917) |

TABLE A20-continued

| Exemplary *Anellovirus* amino acid sequences (*Alphatorquevirus*)-Clade 7 Ring7.0 (*Alphatorquevirus*) | |
|---|---|
| ORF1/2 | MAWRWWWQRRWRRRRWPRRRWRRLRRRRPRRPVRRRRRRTTMLSRECH KNREMLSALQTLSRDPDIFPRQTEKTTDKKKTSLYRKKDGAHPQKKPRTRR APRKARRSYSSSSSSGSSQSTSRSSSDSESNSDTSSKKSSKRKRVST (SEQ ID NO: 918) |

TABLE N21

| Exemplary *Anellovirus* nucleic acid sequence (*Betatorquevirus*) | |
|---|---|
| Name | Ring9 |
| Genus/Clade | *Betatorquevirus* |
| Accession Number | MH649263.1 |
| Full Sequence: 2845 bp | |

```
1         10         20         30         40         50
|         |          |          |          |          |
TTATTAATATTCAACAGGAAAACCACCTAATTTAAATTGCCGACCACAAA
CCGTCACTAACTTCCTTATTTAACATTACTTCCCTTTTAACCAATGAATA
TTCATACAACACATCACACTTCCTGGGAGGAGACATAAAACTATATAACT
AACTACACAGACGAATGGCTGAGTTTATGCCGCTAGACGGAGGACGCACA
GCTACTGCTGCGACCTGAACTTGGGCGGGTGCCGAAGGTGAGTGTAACCA
CCGTAGTCAAGGGGCAATTCGGGCTAGTTCAGTCTAGCGGAACGGGCAAG
ATTATTAATACAAACTTATTTTTACAGATGAGCAAACAACTAAAACCAAC
TTTATACAAAGACAAATCATTGGAATTACAATGGCTAAACAACATTTTTA
GCTCTCACGACCTGTGCTGCGGCTGCAACGATCCAGTTTTACATTTACTG
ATTTTAATTAACAAAACCGGAGAAGCACCTAAACCAGAAGAAGACATTAA
AAATATAAAATGCCTCCTTACTGGCGCCAAAAATACTACCGAAGAAGATA
TAGACCTTTCTCCTGGAGAACTAGAAGAATTATTCAAAGAAGAAAAAGAT
GGAGATACCGCAAACCAAGAAAAACATACTGGAGAAGAAAACTGCGGGTA
AGAAAACGTTTTTATAAAAGAAAGTTAAAAAAAATTGTACTTAAACAGTT
TCAACCAAAAATTATTAGAAGATGTACAATATTTGGAACAATCTGCCTAT
TTCAAGGCTCTCCAGAAAGAGCCAACAATAATTATATTCAAACAATCTAC
TCCTACGTACCAGATAAAGAACCAGGAGGAGGGGGATGGACTTTAATAAC
TGAAAGCTTAAGTAGTTTATGGGAAGACTGGGAACATTTAAAAAATGTAT
GGACTCAAAGTAACGCTGGTTTACCACTTGTAAGATACGGGGGAGTAACA
TTATACTTTTATCAATCTGCCTATACTGACTATATTGCTCAAGTTTTCAA
CTGTTATCCTATGACAGACACAAAATACACACATGCAGACTCAGCACCAA
ACAGAATGTTATTAAAAAAACATGTAATAAGAGTACCTAGCAGAGAAACA
CGCAAAAAAAGAAAGCCATACAAAAGAGTTAGAGTAGGACCTCCTTCTCA
AATGCAAAACAAATGGTACTTTCAAAGAGACATATGTGAAATACCATTAA
TAATGATTGCAGCCACAGCCGTTGACTTTAGATATCCCTTTTGTGCAAGC
GACTGTGCTAGTAACAACTTAACTCTAACATGTTTAAACCCACTATTGTT
TCAAAACCAAGACTTTGACCACCCATCCGATACACAAGGCTACTTTCCAA
AACCTGGAGTATATCTATACTCAACACAAAGAAGTAACAAGCCAAGTTCT
TCAGACTGTATATACTTAGGAAACACAAAAGACAATCAAGAAGGTAAATC
TGCAAGTAGTCTAATGACTCTAAAAACACAAAAAATAACAGATTGGGGAA
ATCCATTTTGGCATTATTATATAGACGGTTCTAAAAAAATATTTTCTTAC
TTTAAACCCCCATCACAATTAGACAGCAGCGACTTTGAACACATGACAGA
ATTAGCAGAACCAATGTTTATACAAGTTAGATACAACCCAGAAAGAGACA
CAGGACAAGGAAACTTAATATACGTAACAGAAAACTTTAGAGGACAACAC
TGGGACCCTCCATCTAGTGACAACCTAAAATTAGATGGATTTCCCTTATA
TGACATGTGCTGGGGTTTCATAGACTGGATAGAAAAAGTTCATGAAACAG
AAAACTTACTTACCAACTACTGCTTCTGTATTAGAAGCAGCGCTTTCAAT
GAAAAAAAAACAGTTTTTATACCTGTAGATCATTCATTTTTAACAGGTTT
TAGCCCATATGAAACTCCAGTTAAATCATCAGACCAAGCTCACTGGCACC
CACAAATAAGATTTCAAACAAAATCAATAAATGACATTTGTTTAACAGGC
CCCGGTTGTGCTAGGTCCCCATATGGCAATTACATGCAGGCAAAAATGAG
TTATAAATTTCATGTAAAATGGGGAGGATGTCCAAAAACTTATGAAAAAC
CATATGATCCTTGTTCACAGCCCAATTGGACTATTCCCCATAACCTCAAT
GAAACAATACAAATCCAGAATCCAAACACATGCCCACAAACAGAACTCCA
AGAATGGGACTGGCGACGTGATATTGTTACAAAAAAAGCTATCGAAAGAA
TTAGACAACACACGGAACCTCATGAAACTTTGCAAATCTCTACAGGTTCC
AAACACAACCCACCAGTACACAGACAAACATCACCGTGGACGGACTCAGA
AACGGACTCGGAAGAGGAAAAAGACCAAACACAAGAGATCCAGATCCAGC
TCAACAAGCTCAGAAAGCATCAACAGCATCTCAAGCAGCAGCTCAAGCAG
TACCTGAAACCCCAAAATATAGAATAGTTGCAAGCAACATAAAAGTTGAA
CTTTTTCCTACTAAAAAACCTTTTAAAAACAGACGCTTTACTCCTTCTGA
AAGAGAAACAGAAAGACAATGTGCTAAAGCTTTTTGTAGACCAGAAAGAC
ATTTCTTTTATGATCCTCCTTTTTACCCTTACTGTGTACCTGAACCTATT
GTAAACTTTGCTTTGGGATATAAAATTTAAGGCCAACAAATTTCACTTAG
```

TABLE N21-continued

| Exemplary *Anellovirus* nucleic acid sequence (*Betatorquevirus*) |
| --- |
| TGGTGTCTGTTTATTAAAGTTTAACCTTAATAAGCATACTCCGCCTCCCT ACATTAAGGCGCCAAAAGGGGGCTCCGCCCCCTTAAACCCCAAGGGGGCT CCGCCCCCTTAAACCCCCAAGGGGGCTCCGCCCCCTTACACCCCC (SEQ ID NO: 1001) |

Annotations:

| Putative Domain | Base range |
| --- | --- |
| TATA Box | 142-148 |
| Initiation Element | 162-177 |
| Transcriptional Start Site | 172 |
| 5' UTR Conserved Domain | 226-296 |
| ORF2 | 328-651 |
| ORF2/2 | 328-647; 2121-2457 |
| ORF2/3 | 328-647; 2296-2680 |
| ORF1 | 510-2477 |
| ORF1/1 | 510-647; 2121-2477 |
| ORF1/2 | 510-647; 2296-2457 |
| Three open-reading frame region | 2296-2454 |
| GC-rich region | 2734-2845 |

TABLE A21

| Exemplary *Anellovirus* amino acid sequences (*Betatorquevirus*) Ring9 (*Betatorquevirus*) | |
| --- | --- |
| ORF2 | MSKQLKPTLYKDKSLELQWLNNIFSSHDLCCGCNDPVLHLLILINKTGEAPK PEEDIKNIKCLLTGAKNTTEEDIDLSPGELEELFKEEKDGDTANQEKHTGEE NCG (SEQ ID NO: 1002) |
| ORF2/2 | MSKQLKPTLYKDKSLELQWLNNIFSSHDLCCGCNDPVLHLLILINKTGEAPK PEEDIKNIKCLLTGAKNTTEEDIDLSPGELEELFKEEKDGDTANQEKHTGEE NCGPIGLFPITSMKQYKSRIQTHAHKQNSKNGTGDVILLQKKLSKELDNTRN LMKLCKSLQVPNTTHQYTDKHHRGRTQKRTRKRKKTKHKRSRSSSTSSESIN SISSSSSSST (SEQ ID NO: 1003) |
| ORF2/3 | MSKQLKPTLYKDKSLELQWLNNIFSSHDLCCGCNDPVLHLLILINKTGEAPK PEEDIKNIKCLLTGAKNTTEEDIDLSPGELEELFKEEKDGDTANQEKHTGEE NCGFQTQPTSTQTNITVDGLRNGLGRGKRPNTRDPDPAQQAQKASTASQAAA QAVPETPKYRIVASNIKVELFPTKKPFKNRRFTPSERETERQCAKAFCRPER HFFYDPPFYPYCVPEPIVNFALGYKI (SEQ ID NO: 1004) |
| ORF1 | MPPYWRQKYYRRRYRPFSWRTRRIIQRRKRWRYRKPRKTYWRRKLRVRKRFY KRKLKKIVLKQFQPKIIRRCTIFGTICLFQGSPERANNNYIQTIYSYVPDKE PGGGGWTLITESLSSLWEDWEHLKNVWTQSNAGLPLVRYGGVTLYFYQSAYT DYIAQVENCYPMTDTKYTHADSAPNRMLLKKHVIRVPSRETRKKRKPYKRVR VGPPSQMQNKWYFORDICEIPLIMIAATAVDFRYPFCASDCASNNLTLTCLN PLLFQNQDFDHPSDTQGYFPKPGVYLYSTQRSNKPSSSDCIYLGNTKDNQEG KSASSLMTLKTQKITDWGNPFWHYYIDGSKKIFSYFKPPSQLDSSDFEHMTE LAEPMFIQVRYNPERDTGQGNLIYVTENFRGQHWDPPSSDNLKLDGFPLYDM CWGFIDWIEKVHETENLLTNYCFCIRSSAFNEKKTVFIPVDHSFLTGFSPYE TPVKSSDQAHWHPQIRFQTKSINDICLTGPGCARSPYGNYMQAKMSYKFHVK WGGCPKTYEKPYDPCSQPNWTIPHNLNETIQIQNPNTCPQTELQEWDWRRDI VTKKAIERIRQHTEPHETLQISTGSKHNPPVHRQTSPWTDSETDSEEEKDQT QEIQIQLNKLRKHQQHLKQQLKQYLKPQNIE (SEQ ID NO: 1005) |
| ORF1/1 | MPPYWRQKYYRRRYRPFSWRTRRIIQRRKRWRYRKPRKTYWRRKLRPNWTIP HNLNETIQIQNPNTCPQTELQEWDWRRDIVTKKAIERIRQHTEPHETLQIST GSKHNPPVHRQTSPWTDSETDSEEEKDQTQEIQIQLNKLRKHQQHLKQQLKQ YLKPQNIE (SEQ ID NO: 1006) |

TABLE A21-continued

| Exemplary *Anellovirus* amino acid sequences (*Betatorquevirus*) Ring9 (*Betatorquevirus*) | |
|---|---|
| ORF1/2 | MPPYWRQKYYRRRYRPFSWRTRRIIQRRKRWRYRKPRKTYWRRKLRVPNTTH QYTDKHHRGRTQKRTRKRKKTKHKRSRSSSTSSESINSISSSSSSST (SEQ ID NO: 1007) |

TABLE N22

| Exemplary *Anellovirus* nucleic acid sequence (*Betatorquevirus*) | |
|---|---|
| Name | Ring10 |
| Genus/Clade | *Betatorquevirus* |
| Accession Number | JX134044.1 |
| Full Sequence: 2912 bp | |

```
1         10         20         30         40         50
|         |          |          |          |          |
TAATAAATATTCAACAGGAAAACCACCTAATTTAAATTGCCGACCACAAA
CCGTCACTTAGTTCCTCTTTTTCCACAACTTCCTCTTTTACTAATGAATA
TTCATGTAATTAATTAATAATCACCGTAATTCCGGGGAGGAGCCTTTAAA
CTATAAAACTAACTACACATTCGAATGGCTGAGTTTATGCCGCCAGACGG
AGACGGGATCACTTCAGTGACTCCAGGCTGATCAAGGGCGGGTGCCGAAG
GTGAGTGAAACCACCGTAGTCAAGGGGCAATTCGGGCTAGATCAGTCTGG
CGGAACGGGCAAGAAACTTAAAATGTACTTTATTTTACAGAAATGTTCAA
ATCTCCAACATACTTAACAACTAAAGGCAAAAACAATGCCTTAATCAACT
GCTTCGTTGGAGACCACGATCTTCTGTGCAGCTGTAACAATCCTGCCTAC
CATTGCCTCCAAATACTTGCAACTACCTTAGCACCTCAACTAAAACAAGA
AGAAAAACAACAAATAATACAATGCCTTGGTGGTACAGACGCCGTAGCTA
CAACCCGTGGAGACGAAGAAATTGGTTTAGAAGACCTAGAAAAACTATTT
ACAGAAGATACAGAAGAAGACGCCGCTGGGTAAGAAGAAAACCTTTTTAC
AAACGTAAAATTAAGAGACTAAATATAGTAGAATGGCAACCTAAATCAAT
TAGAAAATGTAGAATAAAAGGAATGCTATGCTTGTTTCAAACGACAGAAG
ACAGACTGTCATATAACTTTGATATGTATGAAGAGTCTATTATACCAGAA
AAACTGCCGGGAGGGGGGGGATTTAGCATTAAGAATATAAGCTTATATGC
CTTATACCAAGAACACATACATGCACACAACATATTTACACACACAAACA
CAGACAGACCACTAGCAAGATACACAGGCTGTTCTTTAAAATTCTACCAA
AGCAAAGACATAGACTACGTAGTAACATATTCTACATCACTCCCACTAAG
AAGCTCAATGGGAATGTACAACTCCATGCAACCATCCATACATCTAATGC
AACAAAACAAACTAATTGTACCAAGCAAACAAACACAAAAAAGAAGAAAA
CCATATATTAAAAAACATATATCACCACCAACACAAATGAAATCTCAATG
GTACTTTCAACATAACATTGCAAACATACCGCTACTAATGATAAGAACCA
CAGCATTAACATTAGATAATTACTATATAGGAAGCAGACAATTAAGTACA
AATGTCACTATACATACACTTAACACAACATACATCCAAAACAGAGACTG
GGGAGACAGAAATAAAACTTACTACTGCCAAACATTAGGAACACAAAGAT
ACTTCCTATATGGAACACATTCAACTGCACAAAATATTAATGACATAAAG
CTACAAGAACTAATACCTTTAACAAACACACAAGACTATGTACAAGGCTT
TGATTGGACAGAAAAAGACAAACATAACATAACAACCTACAAAGAATTCT
TAACTAAAGGAGCAGGAAATCCATTTCACGCAGAATGGATAACAGCACAA
AACCCAGTAATACACACAGCAAACAGTCCTACACAAATAGAACAAATATA
CACCGCTTCAACAACAACATTCCAAAACAAAAAACTAACAGACCTACCAA
CGCCAGGATATATATTTATAACTCCAACAGTAAGCTTAAGATACAACCCA
TACAAAGACCTAGCAGAAAGAAACAAATGCTACTTTGTAAGAAGCAAAAT
AAATGCACACGGGTGGGACCCAGAACAACACCAAGAATTAATAAACAGTG
ACCTACCACAATGGTTACTATTATTTGGCTACCCAGACTACATAAAAAGA
ACACAAAACTTTGCATTAGTAGACACAAATTACATACTAGTAGACCACTG
CCCATACACAAATCCAGAAAAAACACCATTTATACCTTTAAGCACATCAT
TTATAGAAGGTAGAAGCCCATACAGTCCTTCAGACACACATGAACCAGAT
GAAGAAGACCAAAACAGGTGGTACCCATGCTACCAATATCAACAAGAATC
AATAAATTCAATATGTCTTAGCGGTCCAGGCACACCAAAAATACCAAAAG
GAATAACAGCAGAAGCAAAAGTAAAATATTCCTTTAATTTTAAGTGGGGT
GGTGACCTACCACCAATGTCTACAATTACAAACCCGACAGACCAGCCAAC
ATATGTTGTTCCCAATAACTTCAATGAAACAACTTCGTTACAGAATCCAA
CCACCAGACCAGAGCACTTCTTGTACTCCTTTGACGAAAGGAGGGGACAA
CTTACAGAAAAAGCTACAAAACGCTTGCTTAAAGACTGGGAAACTAAAGA
AACTTCTTTATTGTCTACAGAATACAGATTCGCGGAGCCAACACAAACAC
AAGCCCCACAAGAGGACCCGTCCTCGGAAGAAGAAGAAGAGAGCAACCTC
TTCGAGCGACTCCTCCGACAGCGAACCAAGCAGCTCCAGCTCAAGCGCAG
AATAATACAAACATTGAAAGACCTACAAAAATTAGAATAACTAACAGCAA
AAACACCGTTTACCTATTTCCACCTGAACAAAAGAACAGAAGACTAACAC
CATGGGAAATACAAGAAGACAAAGAAATAGCCAATTTATTTGGCAGACCA
CATAGATACTTTTTAAAAGACATTCCTTTCTATTGGGATATACCCCCAGA
GCCTAAAGTAAACTTTGATTTAAATTTTCAATAAAGAAATAAAGGGCAAG
GCCCCATTAACTCAAAGTCGGTGTCTACCTCTTTAAGTTTAACTTTACTA
```

TABLE N22-continued

| Exemplary *Anellovirus* nucleic acid sequence (*Betatorquevirus*) |
|---|
| AACGGACTCCGCCTCCCTAAATTTGGGCGCCAAAAGGGGGCTCCGCCCCC<br>TTAAACCCCAGGGGGCTCCGCCCCCTAAAACCCCCAAGGGGGCTACGCCC<br>CCTTACACCCCC (SEQ ID NO: 1008) |

Annotations:

| Putative Domain | Base range |
|---|---|
| TATA Box | 152-158 |
| Initiation Element | 172-187 |
| Transcriptional Start Site | 182 |
| 5' UTR Conserved Domain | 239-309 |
| ORF2 | 343-633 |
| ORF2/2 | 343-629; 2196-2505 |
| ORF2/3 | 343-629; 2371-2734 |
| ORF1 | 522-2540 |
| ORF1/1 | 522-629; 2196-2540 |
| ORF1/2 | 522-629; 2371-2505 |
| Three open-reading frame region | 2276-2502 |
| GC-rich region | 2803-2912 |

TABLE A22

| Exemplary *Anellovirus* amino acid sequences (*Betatorquevirus*) Ring10 (*Betatorquevirus*) | |
|---|---|
| ORF2 | MFKSPTYLTTKGKNNALINCFVGDHDLLCSCNNPAYHCLQILATTLAPQLKQ EEKQQIIQCLGGTDAVATTRGDEEIGLEDLEKLFTEDTEEDAAG (SEQ ID NO: 1009) |
| ORF2/2 | MFKSPTYLTTKGKNNALINCFVGDHDLLCSCNNPAYHCLQILATTLAPQLKQ EEKQQIIQCLGGTDAVATTRGDEEIGLEDLEKLFTEDTEEDAAGQHMLFPIT SMKQLRYRIQPPDQSTSCTPLTKGGDNLQKKLQNACLKTGKLKKLLYCLQNT DSRSQHKHKPHKRTRPRKKKKRATSSSDSSDSEPSSSSSSAE (SEQ ID NO: 1010) |
| ORF2/3 | MFKSPTYLTTKGKNNALINCFVGDHDLLCSCNNPAYHCLQILATTLAPQLKQ EEKQQIIQCLGGTDAVATTRGDEEIGLEDLEKLFTEDTEEDAAGIQIRGANT NTSPTRGPVLGRRRREQPLRATPPTANQAAPAQAQNNTNIERPTKIRITNSK NTVYLFPPEQKNRRLTPWEIQEDKEIANLFGRPHRYFLKDIPFYWDIPPEPK VNFDLNFQ (SEQ ID NO: 1011) |
| ORF1 | MPWWYRRRSYNPWRRRNWFRRPRKTIYRRYRRRRRWVRRKPFYKRKIKRLNI VEWQPKSIRKCRIKGMLCLFQTTEDRLSYNFDMYEESIIPEKLPGGGGFSIK NISLYALYQEHIHAHNIFTHTNTDRPLARYTGCSLKFYQSKDIDYVVTYSTS LPLRSSMGMYNSMQPSIHLMQQNKLIVPSKQTQKRRKPYIKKHISPPTQMKS QWYFQHNIANIPLLMIRTTALTLDNYYIGSRQLSTNVTIHTLNTTYIQNRDW GDRNKTYYCQTLGTQRYFLYGTHSTAQNINDIKLQELIPLTNTQDYVQGFDW TEKDKHNITTYKEFLTKGAGNPFHAEWITAQNPVIHTANSPTQIEQIYTAST TTFQNKKLTDLPTPGYIFITPTVSLRYNPYKDLAERNKCYFVRSKINAHGWD PEQHQELINSDLPQWLLLFGYPDYIKRTQNFALVDTNYILVDHCPYTNPEKT PFIPLSTSFIEGRSPYSPSDTHEPDEEDQNRWYPCYQYQQESINSICLSGPG TPKIPKGITAEAKVKYSFNFKWGGDLPPMSTITNPTDQPTYVVPNNFNETTS LQNPTTRPEHFLYSFDERRGQLTEKATKRLLKDWETKETSLLSTEYRFAEPT QTQAPQEDPSSEEEEESNLFERLLRQRTKQLQLKRRIIQTLKDLQKLE (SEQ ID NO: 1012) |

TABLE A22-continued

| Exemplary *Anellovirus* amino acid sequences (*Betatorquevirus*) Ring10 (*Betatorquevirus*) | |
|---|---|
| ORF1/1 | MPWWYRRRSYNPWRRRNWFRRPRKTIYRRYRRRRRWPTYVVPNNFNETTSLQ NPTTRPEHFLYSFDERRGQLTEKATKRLLKDWETKETSLLSTEYRFAEPTQT QAPQEDPSSEEEEESNLFERLLRQRTKQLQLKRRIIQTLKDLQKLE |
| ORF1/2 | MPWWYRRRSYNPWRRRNWFRRPRKTIYRRYRRRRRWNTDSRSQHKHKPHKRT RPRKKKKRATSSSDSSDSEPSSSSSSAE (SEQ ID NO: 1013) |

TABLE N23

Exemplary *Anellovirus* nucleic acid sequence (*Alphatorquevirus*, Clade 4)

| | |
|---|---|
| Name | Ring20 |
| Genus/Clade | *Alphatorquevirus* Clade 4 |
| Accession Number | AF122914.3 |
| Full Sequence: 3853 bp | |

```
1         10        20        30        40        50
|         |         |         |         |         |
GGCTTAGTGCGTCACCACCCACGTGACCCGCCTCCGCCAATTAACAGGTA
CTTCGTACACTTCCTGGGCGGGCTTATAAGACTAATATAAGTAGCTGCAC
TTCCGAATGGCTGAGTTTTCCACGCCCGTCCGCAGCGGTGAAGCCACGGA
GGGAGCTCAGCGCGTCCCGAGGGCGGGTGCCGGAGGTGAGTTTACACACC
GCAGTCAAGGGGCAATTCGGGCTCGGGACTGGCCGGGCTTTGGGCAAGGC
TCTTAAAAAAGCTATGTTTATTGGCAGGCACTACCGAAAGAAAAGGGCGC
TGCTACTGCTATCTGTGCATTCTACAAAGACAAAAGGGAAACTTCTAATA
GCTATGTGGACTCCCCCACGCAATGATCAACAATACCTTAACTGGCAATG
GTACACTTCTGTACTTAGCTCCCACTCTGCTATGTGCGGGTGTTCCGACG
CTATCGCTCATCTTAATCATCTTGCTAATCTGCTTCGTGCCCCGCAAAAT
CCGCCCCCGCCTGATAATCCAAGACCCCTACCCGTGCGAGCACTGCCTGC
TCCCCCGGCTGCCCACGAGGCAGCCGGTGATCGAGCACCATGGCCTATGG
GTGGTGGAGGAGACGCCGGAGGCGCTGGCGCAGGTGGAGACGCCGACCAT
GGAGGCGCCGCTGGAGGACCCGCAGACGCAGACCTGCTAGACGCCGTGGC
CGCCGCAGAAACGTAAGGAGACGGCGCAGAGGGAGGTGGAGAAGGAGGTA
CAGGAGGTGGAAAAGAAAGGGCAGACGTAGAAGAAAAGCAAAAATAATAA
TAAGACAGTGGCAGCCAAACTACAGAAGAAGATGTAATATAGTGGGCTAC
CTCCCTATACTTATCTGTGGTGGAAATACTGTTTCTAGAAACTATGCCAC
ACACTCAGACGATACTAACTATCCAGGACCCTTTGGGGGAGGCATGACCA
CAGACAAATTCAGCCTTAGAATACTATATGATGAATACAAAAGATTTATG
AACTACTGGACAGCCTCAAATGAGGACCTAGATCTCTGTAGATATCTAGG
ATGCACTTTTTACTTCTTTAGACACCCTGAAGTAGACTTTATTATAAAAA
TAAACACCATGCCCCCATTCTTAGATACAACCATAACAGCACCTAGCATA
CACCCAGGCCTCATGGCCCTAGACAAAAGAGCCAGATGGATTCCTTCTCT
TAAAAATAGACCAGGTAAAAAACACTATATAAAAATTAGAGTAGGGGCTC
CTAAAATGTTCACAGATAAATGGTACCCTCAAACAGACCTCTGTGACATG
ACACTGCTAACTATCTATGCAACCGCAGCGGATATGCAATATCCGTTCGG
CTCACCACTAACTGACACTGTGGTTGTTAACTCCCAAGTTCTGCAATCCA
TGTATGATGAAACAATTAGCATATTACCTGATGAAAAAACTAAAAGAAAT
AGCCTTCTTACTTCTATAAGAAGCTACATACCTTTTTATAATACTACACA
AACAATAGCTCAATTAAAACCATTTGTAGATGCAGGAGGACACACAACAG
GCTCAACAACAACTACATGGGGACAACTATTAAACACAACTAAATTTACC
ACTACCACAACAACCACATACACATACCCTGGCACCACAAATACAGCAGT
AACATTTATAACAGCCAATGATACCTGGTACAGGGGAACAGCATATAAAG
ATAACATTAAAGATGTACCACAAAAAGCAGCACAATTATACTTTCAAACA
ACACAAAAACTACTAGGAAACACATTCCATGGCTCAGATGAAACACTTGA
ATACCATGCAGGCCTATACAGCTCTATCTGGCTATCACCAGGTAGATCCT
ACTTTGAAACACCAGGTGCATACACAGACATTAAATATAACCCTTTTACA
GACAGAGGAGAAGGCAACATGCTGTGGATAGACTGGCTAAGTAAAAAAAA
CATGAAATATGACAAAGTGCAAAGTAAGTGCCTAGTAGCAGACCTACCAC
TGTGGGCAGCAGCATATGGTTATGTAGAATTCTGCTCTAAAAGCACAGGA
GACACAAACATACACATGAATGCCAGACTACTAATAAGAAGTCCTTTTAC
AGACCCCCAGCTAATAGTACACACAGACCCCACTAAAGGCTTTGTACCCT
ATTCTTTAAACTTTGGAAATGGTAAAATGCCAGGAGGTAGCAGCAATGTT
CCCATAAGAATGAGAGCTAAGTGGTACCCCACTTTATCCCACCAACAAGA
AGTTCTAGAGGCCTTAGCACAGTCAGGACCCTTTGCTTATCACTCAGACA
TTAAAAAAGTATCTCTAGGCATAAAATACCGTTTTAAGTGGATCTGGGGT
GGAAACCCCGTTCGCCAACAGGTTGTTAGAAATCCCTGCAAGGAACCCCA
CTCCTCGGGCAATAGAGTCCCTAGAAGCATACAAATCGTTGACCCGAGAT
ACAACTCACCGGAACTTACCATCCATGCCTGGGACTTCAGACGTGGCTTC
TTTGGCCCGAAAGCTATTCAAAGAATGCAACAACAACCAACTGCTACTGA
ATTTTTTTCAGCAGGCCGCAAGAGACCCAGAAGGGACACAGAAGTGTATC
AGTCCGACCAAGAAAAGGAGCAAAAAGAAAGCTCGCTTTTCCCCCCAGTC
```

TABLE N23-continued

Exemplary *Anellovirus* nucleic acid sequence (*Alphatorquevirus*, Clade 4)

```
AAGCTCCTCCGAAGAGTCCCCCCGTGGGAGGACTCGGAACAGGAGCAAAG
CGGGTCGCAAAGCTCAGAGGAAGAGACGGCGACCCTCTCCCAGCAGCTCA
AACAGCAGCTGCAGCAGCAGCGAGTCTTGGGAGTCAAACTCAGACTCCTG
TTCAACCAAGTCCAAAAAATCCAACAAAATCAAGATATCAACCCTACCTT
GTTACCAAGGGGGGGGGATCTAGTATCCTTCTTTCAGGCTGTACCATAAA
TATGTTTCCAGACCCTAAACCTTACTGCCCCTCCAGCAATGACTGGAAAG
AAGAGTATGAGGCCTGTAAATATTGGGATAGACCTCCCAGACACAACCTT
AGAGACCCCCCCTTTTACCCCTGGGCCCCTAAAAACAATCCTTGCAATGT
AAGCTTTAAACTTGGCTTCAAATAAACTAGGCCGTGGGAGTTTCACTTGT
CGGTGTCTACCTCTATAAGTCACTAAGCACTCCGAGCGCAGCGAGGAGTG
CGACCCTTCCCCCTGGTGCAACGCCCTCGGCGGCCGCGCGCTACGCCTTC
GGCTGCGCGCGGCACCTCGGACCCCCGCTCGTGCTGACACGCTTGCGCGT
GTCAGACCACTTCGGGCTCGCGGGGGTCGGGAAATTTGCTAAACAGACTC
CGAGTTGCCATTGGACACTGTAGCTATGAATCAGTAACGAAAGTGAGTGG
GGCCAGACTTCGCCATAAGGCCTTTATCTTCTTGCCATTTGTCAGTATTG
GGGGTCGCCATAAACTTTGGGCTCCATTTTAGGCCTTCCGGACTACAAAA
ATCGCCATATTTGTGACGTCAGAGCCGCCATTTTAAGTCAGCTCTGGGGA
GGCGTGACTTCCAGTTCAAAGGTCATCCTCACCATAACTGGCACAAAATG
GCCGCCAACTTCTTCCGGGTCAAAGGTCACTGCTACGTCATAGGTGACGT
GGGGGGGGACCTACTTAAACACGGAAGTAGGCCCCGACACGTCACTGTCA
CGTGACAGTACGTCACAGCCGCCATTTTGTTTTACAAAATAGCCGACTTC
CTTCCTCTTTTTTAAAAAAAGGCGCCAAAAAAACCGTCGGCGGGGGGGCCG
CGCGCTGCGCGCGCGGCCCCCGGGGGAGGCACAGCCTCCCCCCCCCGCGC
GCATGCGCGCGGGTCCCCCCCCCTCCGGGGGGCTCCGCCCCCCGGCCCCC
CCC (SEQ ID NO: 1014)
```

Annotations:

| Putative Domain | Base range |
|---|---|
| TATA Box | 86-90 |
| Initiation Element | 104-119 |
| Transcriptional Start Site | 114 |
| 5' UTR Conserved Domain | 174-244 |
| ORF2 | 354-716 |
| ORF2/2 | 354-712; 2372-2873 |
| ORF2/3 | 354-712; 2565-3075 |
| ORF2t/3 | 354-400; 2565-3075 |
| TAIP | 373-690 |
| ORF1 | 590-2899 |
| ORF1/1 | 590-712; 2372-2899 |
| ORF1/2 | 590-712; 2565-2873 |

TABLE N23-continued

| Exemplary *Anellovirus* nucleic acid sequence (*Alphatorquevirus*, Clade 4) | |
|---|---|
| Three open-reading frame region | 2551-2870 |
| Poly(A)-Signal | 3071-3076 |
| GC-rich region | 3733-3853 |

TABLE A23

| Exemplary *Anellovirus* amino acid sequences (*Alphatorquevirus*) Ring20 (*Alphatorquevirus* Clade 4) | |
|---|---|
| ORF2 | MWTPPRNDQQYLNWQWYTSVLSSHSAMCGCSDAIAHLNHLANLLRAPQNPPPPDNPRPLPVRALPAPPAAHEAAGDRAPWPMGGGGDAGGAGAGGDADHGGAAGGPADADLLDAVAAAET (SEQ ID NO: 1015) |
| ORF2/2 | MWTPPRNDQQYLNWQWYTSVLSSHSAMCGCSDAIAHLNHLANLLRAPQNPPPPDNPRPLPVRALPAPPAAHEAAGDRAPWPMGGGGDAGGAGAGGDADHGGAAGGPADADLLDAVAAAETLLEIPARNPTPRAIESLEAYKSLTRDTTHRNLPSMPGTSDVASLARKLFKECNNNQLLLNFFQQAARDPEGTQKCISPTKKRSKKKARFSPQSSSSEESPRGRTRNRSKAGRKAQRKRRRPSPSSSNSSCSSSESWESNSDSCSTKSKKSNKIKISTLPCYQGGGI (SEQ ID NO: 1016) |
| ORF2/3 | MWTPPRNDQQYLNWQWYTSVLSSHSAMCGCSDAIAHLNHLANLLRAPQNPPPPDNPRPLPVRALPAPPAAHEAAGDRAPWPMGGGGDAGGAGAGGDADHGGAAGGPADADLLDAVAAAETPQETQKGHRSVSVRPRKGAKRKLAFPPSQAPPKSPPVGGLGTGAKRVAKLRGRDGDPLPAAQTAAAAAASLGSQTQTPVQPSPKNPTKSRYQPYLVTKGGGSSILLSGCTINMFPDPKPYCPSSNDWKEEYEACKYWDRPPRHNLRDPPFYPWAPKNNPCNVSFKLGFK (SEQ ID NO: 1017) |
| ORF2t/3 | MWTPPRNDQQYLNWQWPQETQKGHRSVSVRPRKGAKRKLAFPPSQAPPKSPPVGGLGTGAKRVAKLRGRDGDPLPAAQTAAAAAASLGSQTQTPVQPSPKNPTKSRYQPYLVTKGGGSSILLSGCTINMFPDPKPYCPSSNDWKEEYEACKYWDRPPRHNLRDPPFYPWAPKNNPCNVSFKLGFK (SEQ ID NO: 1018) |
| TAIP | MINNTLTGNGTLLYLAPTLLCAGVPTLSLILIILLICFVPRKIRPRLIIQDPYPCEHCLLPRLPTRQPVIEHHGLWVVEETPEALAQVETPTMEAPLEDPQTQTC (SEQ ID NO: 1019) |
| ORF1 | MAYGWWRRRRRRWRRWRRRPWRRRWRTRRRRPARRRGRRRNVRRRRRGRWRRRYRRWKRKGRRRRKAKIIIRQWQPNYRRRCNIVGYLPILICGGNTVSRNYATHSDDTNYPGPFGGGMTTDKFSLRILYDEYKRFMNYWTASNEDLDLCRYLGCTFYFFRHPEVDFIIKINTMPPFLDTTITAPSIHPGLMALDKRARWIPSLKNRPGKKHYIKIRVGAPKMFTDKWYPQTDLCDMTLLTIYATAADMQYPFGSPLTDTVVVNSQVLQSMYDETISILPDEKTKRNSLLTSIRSYIPFYNTTQTIAQLKPFVDAGGHTTGSTTTTWGQLLNTTKFTTTTTTTYTYPGTTNTAVTFITANDTWYRGTAYKDNIKDVPQKAAQLYFQTTQKLLGNTFHGSDETLEYHAGLYSSIWLSPGRSYFETPGAYTDIKYNPFTDRGEGNMLWIDWLSKKNMKYDKVQSKCLVADLPLWAAAYGYVEFCSKSTGDTNIHMNARLLIRSPFTDPQLIVHTDPTKGFVPYSLNFGNGKMPGGSSNVPIRMRAKWYPTLSHQQEVLEALAQSGPFAYHSDIKKVSLGIKYRFKWIWGGNPVRQQVVRNPCKEPHSSGNRVPRSIQIVDPRYNSPELTIHAWDFRRGFFGPKAIQRMQQQPTATEFFSAGRKRPRRDTEVYQSDQEKEQKESSLFPPVKLLRRVPPWEDSEQEQSGSQSSEEETATLSQQLKQQLQQQRVLGVKLRLLFNQVQKIQQNQDINPTLLPRGGDLVSFFQAVP (SEQ ID NO: 1020) |
| ORF1/1 | MAYGWWRRRRRRWRRWRRRPWRRRWRTRRRRPARRRGRRRNVVRNPCKEPHSSGNRVPRSIQIVDPRYNSPELTIHAWDFRRGFFGPKAIQRMQQQPTATEFFSAGRKRPRRDTEVYQSDQEKEQKESSLFPPVKLLRRVPPWEDSEQEQSGSQSSEEETATLSQQLKQQLQQQRVLGVKLRLLFNQVQKIQQNQDINPTLLPRGGDLVSFFQAVP (SEQ ID NO: 1021) |
| ORF1/2 | MAYGWWRRRRRRWRRWRRRPWRRRWRTRRRRPARRRGRRRNAARDPEGTQKCISPTKKRSKKKARFSPQSSSSEESPRGRTRNRSKAGRKAQRKRRRPSPSSSNSSCSSSESWESNSDSCSTKSKKSNKIKISTLPCYQGGGI (SEQ ID NO: 1022) |

TABLE N24

| Novel *Anellovirus* nucleic acid sequence (*Betatorquevirus*) | |
|---|---|
| Name | RING 19 |
| Genus/Clade | *Betatorquevirus* |
| Accession | N/A |
| Full Sequence: 2876 bp | |

```
1          10        20         30          40          50
|          |         |          |           |           |
CGGGAGCCGAAGGTGAGTGCAACCACCGTAGTCTAGGGGCAATTCGGGCT
AGTTCAGTATGGCGGAACGGGCAAGAAACTTAAATATTATTATTTTACAG
ATGCAAATACAACCACCTATTAGAACCTTCAAACAAACAATTTCAGATTG
GAAAAACTTAATTGTCCACGTTCACGACAACATTTGCAACTGCAATAAAC
CATTAGAACACACTATTGATACCTGTATCACCAATCCAGATGAATTAAGA
TTAAACAAATCTACTAAACAACAACTACAAAAATGCCTTGGTACCCCAGA
AGAAGATACCCAAGAAGACGTTATCGATGGCTTCGCAGATGGAGAGCTAG
ACGCCCTTTTCGCCCAAGATACAGAAGAAGATACTGGGTAAGAAACTATT
CTCGAAAGAGAAAACTATTTAAAATAACAACCAAAGAATGGCAACCAAAA
GTTATAAGAAAGACTCATGTAAAGGGCACCTATCCTTTGTTTCTTTGTAC
AAAGCACAGAATTAACAATAATATGATACAATATTTAGACTCTATAGCTC
CAGAACACTATTACGGAGGAGGAGGATTTTCAATAATGCAATTTTCCTTA
CAAGCCTTATATGAAGAATTTATAAAAGCAAAAAACTGGTGGACTAATAC
AAACTGCTTTTTACCACTTGTAAGATATATGGGTTGCTCATTCAAATTTT
ATAAAACTGAATTTTATGATTATATTGTACTAATTGAAAGATGTTATCCA
CTTGCTTGTACTGATGAAATGTACTTATCTACTCAACCTAGTATTATGAT
GCTTACAAGAAAATGTATTTTTGTACCATGCAAACAAAACAGCAAAGGTA
AAAAACCTTACAAAAAAGTTAGAGTAAGACCACCTTCACAAATGACTACA
GGATGGCATTTCTCACAAGACTTAGCAAACATGCCACTTGTAGTACTAAA
AACTTCAGTATGCAGCTTTGACAGATATTACACAGACAGTACAGCTAAAT
CAACCACAATAGGCTTTAAAACACTTAACACACAAACATTTAGATATCAT
GACTGGCAGGAACCACCTACAACAGGATACAAACCACAAAACCTACTATG
GTTTTATGGAGCAGAAAACGGATCACCAGTAGACCCCAACAACACAATAG
TATCAAACCTAATATACTTAGGAGGCACAGGACCTTATGAAAAAGGCACA
CCAATAAAAACAAACATAAGCAATTACTTTTCAGAGCCTAAACTGTGGGG
AAATATATTTCACGATGATTATACATCAGGAACATCACCCGTGTTTGTTA
CAAACAAATCACCATCAGAAATTAAAACCGCATGGAACACTATAAAAGAC
TTAACTGTTAAAGCTAGCGGTGTATTTACATTAAGAACAATTCCACTATG
GCTACCTTGCAGATACAACCCATTTGCAGACAAAGCAACCAACAACAAAA
TATGGCTAGTTTCTATACATTCAGACCACACAGAATGGAAACCAATAGAC
AATCCATTACTACAACGAACAGACCTTCCTTTATGGTTACTTGTATGGGG
TTGGCAAGATTGGCAGAAAAAAAACCAACAAACTTCACAACCTGATATTA
ATTATTTAACAGTAATATCTTCACCATATATATCATGCTACCCAAAATTA
GATTACTATGTGTTACTAGATGAAGGATTTTGGGAGGGTCACTCAACATA
CATAGAGTCAATTACAGACTCAGACAAAAAACACTGGTACCCTAAAAATA
GATTTCAAATAGAAACACTTAATCTAATAGCTAACACAGGTCCAGGAACT
GTAAAACTAAGAGAAAACCAAGCAGCAGAAGGTCACATGGTATATCGCTT
TAATTTTAAGCTTGGAGGATGTCCCGCACCGATGGAAAAAATATGTGACC
CTAGCAAACAATCCAAATATCCTATTCCCAATAACCAGCAACAAACAACT
TCGTTGCAGAGTCCAGAAAACCCAATTCAAACCTATCTCTACGACTTCGA
CGAAAGGAGGGGCCTACTTACAGAAAGAGCTACAAAAAGAATCAAACAAG
ATCACACATCTGAAAAAACTGTTTTGCCATTTACAGGAGCAGCAACAGAC
CTCCCCATACTCCAAACAACATCACAGGAGGAAAGCTCCTCGGAAGAAGA
AGAAGAGCAACAAGCGGAGAAGAAACTACTCCAGCTCCGAAGAAAGCAGC
ACCGACTCCGGGAGCGAATCCTCCAGCTATTAGACATACAAAATACATAA
TAAAACAAAGTACTGTAAAAATTGATATGTTTGGAGATACTCATGTACCT
AACCGTAGAATGACCCCAGAAGAATTTGAACAAGAACTAATTGTCGCTGG
TGTTTTTCGCAGACCTCCTTGTTACTATATAAAAGATAGACCTACTTATC
CTTATGTACCAAAACCTACTGATGAAAAATGTATGGTAAACTTTGACTTA
AACTTTCCTTAATAAACTACGCCTGCAAACTTTCACTCTCGGTGTCCATT
TATATAAGATAAAACTTAAATAAACATCCACCACTCTCCCAAATACGCAG
GCGCACAAGGGGGCTCCGCCCCCTTAAACCCCCAAGGGGGCTCCGCCCCC
TTAAACCCCCAAGGGGGCTCCGCCCCCTTACACCCCCTAATAAATATTCA
ACAGGAAAACCACCTAATTAGAATTGCCGACCACAAACCGTCACTTACTT
CTCCTTTTTGCACTTACTTCCTCTTTTACTTATTATTATTCATTACATTA
ATTAATAATCACTGTAATTCCGGGGAGGAGCTAACAATCTATATAACTAA
CTACACTTCCGAATGGCTGAGTTTATGCCGCCAGACGGAGACGGGATCAC
TTCAGTGACTCCAGGCTGAACTTGGG (SEQ ID NO: 1023)
```

Annotations:

| Putative Domain | Base range |
|---|---|
| ORF1 | 283-2250 |
| ORF2 | 59-391 |
| ORF3 | 2277-2462 |

TABLE N24-continued

| Novel *Anellovirus* nucleic acid sequence (*Betatorquevirus*) | |
|---|---|
| GC-rich region, or a portion thereof | 2515-2615 |
| 5' UTR Conserved Domain, or a portion thereof | 1-71 |

TABLE A24

Novel *Anellovirus* amino acid sequence (*Betatorquevirus*)
RING 19 (*Betatorquevirus*)

| | |
|---|---|
| ORF1 | MPWYPRRRYPRRRYRWLRRWRARRPFRPRYRRRYWVRNYSRKR KLFKITTKEWQPKVIRKTHVKGTYPLFLCTKHRINNNMIQYLD SIAPEHYYGGGGFSIMQFSLQALYEEFIKAKNWWTNTNCFLPL VRYMGCSFKFYKTEFYDYIVLIERCYPLACTDEMYLSTQPSIM MLTRKCIFVPCKQNSKGKKPYKKVRVRPPSQMTTGWHFSQDLA NMPLVVLKTSVCSFDRYYTDSTAKSTTIGFKTLNTQTFRYHDW QEPPTTGYKPQNLLWFYGAENGSPVDPNNTIVSNLIYLGGTGP YEKGTPIKTNISNYFSEPKLWGNIFHDDYTSGTSPVFVINKSP SEIKTAWNTIKDLTVKASGVFTLRTIPLWLPCRYNPFADKATN NKIWLVSIHSDHTEWKPIDNPLLQRTDLPLWLLVWGWQDWQKK NQQTSQPDINYLTVISSPYISCYPKLDYYVLLDEGFWEGHSTY IESITDSDKKHWYPKNRFQIETLNLIANTGPGTVKLRENQAAE GHMVYRFNFKLGGCPAPMEKICDPSKQSKYPIPNNQQQTTSLQ SPENPIQTYLYDFDERRGLLTERATKRIKQDHTSEKTVLPFTG AATDLPILQTTSQEESSSEEEEEQQAEKKLLQLRRKQHRLRER ILQLLDIQNT (SEQ ID NO: 1024) |
| ORF2 | MAERARNLNIIILQMQIQPPIRTFKQTISDWKNLIVHVHDNIC NCNKPLEHTIDTCITNPDELRLNKSTKQQLQKCLGTPEEDTQE DVIDGFADGELDALFAQDTEEDTG (SEQ ID NO: 1025) |
| ORF3 | MFGDTHVPNRRMTPEEFEQELIVAGVFRRPPCYYIKDRPTYPY VPKPTDEKCMVNFDLNFP (SEQ ID NO: 1026) |

TABLE N25

| Novel *Anellovirus* nucleic acid sequence (*Betatorquevirus*) | |
|---|---|
| Name | RING 19 alternate |
| Genus/Clade | *Betatorquevirus* |
| Accession | N/A |
| Full Sequence: 2876 bp | |

```
1          10        20         30          40          50
|          |         |          |           |           |
CGGGAGCCGAAGGTGAGTGCAACCACCGTAGTCTAGGGGCAATTCGGGCT
AGTTCAGTATGGCGGAACGGGCAAGAAACTTAAATATTATTATTTTACAG
ATGCAAATACAACCACCTATTAGAACCTTCAAACAAACAATTTCAGATTG
GAAAAACTTAATTGTCCACGTTCACGACAACATTTGCAACTGCAATAAAC
CATTAGAACACACTATTGATACCTGTATCACCAATCCAGATGAATTAAGA
TTAAACAAATCTACTAAACAACAACTACAAAAATGCCTTGGTACCCCAGA
AGAAGATACCCAAGAAGACGTTATCGATGGCTTCGCAGATGGAGAGCTAG
ACGCCCTTTTCGCCCAAGATACAGAAGAAGATACTGGGTAAGAAACTATT
CTCGAAAGAGAAAACTATTTAAAATAACAACCAAAGAATGGCAACCAAAA
GTTATAAGAAAGACTCATGTAAAGGGCACCTATCCTTTGTTTCTTTGTAC
AAAGCACAGAATTAACAATAATATGATACAATATTTAGACTCTATAGCTC
CAGAACACTATTACGGAGGAGGAGGATTTTCAATAATGCAATTTTCCTTA
CAAGCCTTATATGAAGAATTTATAAAAGCAAAAAACTGGTGGACTAATAC
AAACTGCTTTTTACCACTTGTAAGATATATGGGTTGCTCATTCAAATTTT
ATAAAACTGAATTTTATGATTATATTGTACTAATTGAAAGATGTTATCCA
CTTGCTTGTACTGATGAAATGTACTTATCTACTCAACCTAGTATTATGAT
GCTTACAAGAAAATGTATTTTTGTACCATGCAAACAAAACAGCAAAGGTA
AAAAACCTTACAAAAAAGTTAGAGTAAGACCACCTTCACAAATGACTACA
GGATGGCATTTCTCACAAGACTTAGCAAACATGCCACTTGTAGTACTAAA
AACTTCAGTATGCAGCTTTGACAGATATTACACAGACAGTACAGCTAAAT
CAACCACAATAGGCTTTAAAACACTTAACACACAAACATTTAGATATCAT
GACTGGCAGGAACCACCTACAACAGGATACAAACCACAAAACCTACTATG
GTTTTATGGAGCAGAAAACGGATCACCAGTAGACCCCAACAACACAATAG
```

TABLE N25-continued

| Novel *Anellovirus* nucleic acid sequence (*Betatorquevirus*) |
|---|
| TATCAAACCTAATATACTTAGGAGGCACAGGACCTTATGAAAAAGGCACA<br>CCAATAAAAACAAACATAAGCAATTACTTTTCAGAGCCTAAACTGTGGGG<br>AAATATATTTCACGATGATTATACATCAGGAACATCACCCGTGTTTGTTA<br>CAAACAAATCACCATCAGAAATTAAAACCGCATGGAACACTATAAAAGAC<br>TTAACTGTTAAAGCTAGCGGTGTATTTACATTAAGAACAATTCCACTATG<br>GCTACCTTGCAGATACAACCCATTTGCAGACAAAGCAACCAACAACAAAA<br>TATGGCTAGTTTCTATACATTCAGACCACACAGAATGGAAACCAATAGAC<br>AATCCATTACTACAACGAACAGACCTTCCTTTATGGTTACTTGTATGGGG<br>TTGGCAAGATTGGCAGAAAAAAAACCAACAAACTTCACAACCTGATATTA<br>ATTATTTAACAGTAATATCTTCACCATATATATCATGCTACCCAAAATTA<br>GATTACTATGTGTTACTAGATGAAGGATTTTGGGAGGGTCACTCAACATA<br>CATAGAGTCAATTACAGACTCAGACAAAAAACACTGGTACCCTAAAAATA<br>GATTTCAAATAGAAACACTTAATCTAATAGCTAACACAGGTCCAGGAACT<br>GTAAAACTAAGAGAAAACCAAGCAGCAGAAGGTCACATGGTATATCGCTT<br>TAATTTTAAGCTTGGAGGATGTCCCGCACCGATGGAAAAAATATGTGACC<br>CTAGCAAACAATCCAAATATCCTATTCCCAATAACCAGCAACAAACAACT<br>TCGTTGCAGAGTCCAGAAAACCCAATTCAAACCTATCTCTACGACTTCGA<br>CGAAAGGAGGGGCCTACTTACAGAAAGAGCTACAAAAAGAATCAAACAAG<br>ATCACACATCTGAAAAAACTGTTTTGCCATTTACAGGAGCAGCAACAGAC<br>CTCCCCATACTCCAAACAACATCACAGGAGGAAAGCTCCTCGGAAGAAGA<br>AGAAGAGCAACAAGCGGAGAAGAAACTACTCCAGCTCCGAAGAAAGCAGC<br>ACCGACTCCGGGAGCGAATCCTCCAGCTATTAGACATACAAAATACATAA<br>TAAAACAAAGTACTGTAAAAATTGATATGTTTGGAGATACTCATGTACCT<br>AACCGTAGAATGACCCCAGAAGAATTTGAACAAGAACTAATTGTCGCTGG<br>TGTTTTTCGCAGACCTCCTTGTTACTATATAAAAGATAGACCTACTTATC<br>CTTATGTACCAAAACCTACTGATGAAAAATGTATGGTAAACTTTGACTTA<br>AACTTTCCTTAATAAACTACGCCTGCAAACTTTCACTCTCGGTGTCCATT<br>TATATAAGATAAAACTTAAATAAACATCCACCACTCTCCCAAATACGCAG<br>GCGCACAAGGGGGCTCCGCCCCCTTAAACCCCCAAGGGGGCTCCGCCCCC<br>TTAAACCCCCAAGGGGGCTCCGCCCCCTTACACCCCCTAATAAATATTCA<br>ACAGGAAAACCACCTAATTAGAATTGCCGACCACAAACCGTCACTTACTT<br>CTCCTTTTTGCACTTACTTCCTCTTTTACTTATTATTATTCATTACATTA<br>ATTAATAATCACTGTAATTCCGGGGAGGAGCTAACAATCTATATAACTAA<br>CTACACTTCCGAATGGCTGAGTTTATGCCGCCAGACGGAGACGGGATCAC<br>TTCAGTGACTCCAGGCTGAACTTGGG (SEQ ID NO: 1027) |

| Annotations: | |
|---|---|
| Putative Domain | Base range |
| ORF1 | 283-2250 |
| ORF2 | 101-391 |
| ORF3 | 2277-2462 |
| GC-rich region, or a portion thereof | 2515-2615 |
| 5' UTR Conserved Domain, or a portion thereof | 1-71 |

TABLE A25

| Novel *Anellovirus* amino acid sequence (*Betatorquevirus*) RING 19 (*Betatorquevirus*) | |
|---|---|
| ORF1 | MPWYPRRRYPRRRYRWLRRWRARRPFRPRYRRRYWVRNYSRKR<br>KLFKITTKEWQPKVIRKTHVKGTYPLFLCTKHRINNNMIQYLD<br>SIAPEHYYGGGGFSIMQFSLQALYEEFIKAKNWWTNTNCFLPL<br>VRYMGCSFKFYKTEFYDYIVLIERCYPLACTDEMYLSTQPSIM<br>MLTRKCIFVPCKQNSKGKKPYKKVRVRPPSQMTTGWHFSQDLA<br>NMPLVVLKTSVCSFDRYYTDSTAKSTTIGFKTLNTQTFRYHDW<br>QEPPTTGYKPQNLLWFYGAENGSPVDPNNTIVSNLIYLGGTGP<br>YEKGTPIKTNISNYFSEPKLWGNIFHDDYTSGTSPVFVINKSP<br>SEIKTAWNTIKDLTVKASGVFTLRTIPLWLPCRYNPFADKATN<br>NKIWLVSIHSDHTEWKPIDNPLLQRTDLPLWLLVWGWQDWQKK<br>NQQTSQPDINYLTVISSPYISCYPKLDYYVLLDEGFWEGHSTY<br>IESITDSDKKHWYPKNRFQIETLNLIANTGPGTVKLRENQAAE<br>GHMVYRFNFKLGGCPAPMEKICDPSKQSKYPIPNNQQQTTSLQ<br>SPENPIQTYLYDFDERRGLLTERATKRIKQDHTSEKTVLPFTG<br>AATDLPILQTTSQEESSSEEEEEQQAEKKLLQLRRKQHRLRER<br>ILQLLDIQNT (SEQ ID NO: 1028) |

TABLE A25-continued

| Novel *Anellovirus* amino acid sequence (*Betatorquevirus*) RING 19 (*Betatorquevirus*) | |
|---|---|
| ORF2 | MQIQPPIRTFKQTISDWKNLIVHVHDNICNCNKPLEHTIDTCI<br>TNPDELRLNKSTKQQLQKCLGTPEEDTQEDVIDGFADGELDAL<br>FAQDTEEDTG (SEQ ID NO: 1029) |
| ORF3 | MFGDTHVPNRRMTPEEFEQELIVAGVFRRPPCYYIKDRPTYPY<br>VPKPTDEKCMVNFDLNFP (SEQ ID NO: 1030) |

In some embodiments, an anellovector or anelloVLP as described herein is a chimeric anellovector or anelloVLP. In some embodiments, a chimeric anellovector or anelloVLP further comprises one or more elements, polypeptides, or nucleic acids from a virus other than an Anellovirus.

In some embodiments, the chimeric anellovector or anelloVLP comprises a plurality of polypeptides (e.g., Anellovirus ORF1, ORF1/1, ORF1/2, ORF2, ORF2/2, ORF2/3, and/or ORF2t/3) comprising sequences from a plurality of different Anelloviruses (e.g., as described herein).

In some embodiments, the anellovector or anelloVLP comprises a chimeric polypeptide (e.g., Anellovirus ORF1, ORF1/1, ORF1/2, ORF2, ORF2/2, ORF2/3, and/or ORF2t/3), e.g., comprising at least one portion from an Anellovirus (e.g., as described herein) and at least one portion from a different virus (e.g., as described herein).

In some embodiments, the anellovector or anelloVLP comprises a chimeric polypeptide (e.g., Anellovirus ORF1, ORF1/l, ORF1/2, ORF2, ORF2/2, ORF2/3, and/or ORF2t/3), e.g., comprising at least one portion from one Anellovirus (e.g., as described herein) and at least one portion from a different Anellovirus (e.g., as described herein). In some embodiments, the anellovector or anelloVLP comprises a chimeric ORF1 molecule comprising at least one portion of an ORF1 molecule from one Anellovirus (e.g., as described herein), or an ORF1 molecule having at least 75%, 80%, 85%, 90%, 95%, 96%, 97%, 98%, or 99% amino acid sequence identity thereto, and at least one portion of an ORF1 molecule from a different Anellovirus (e.g., as described herein), or an ORF1 molecule having at least 75%, 80%, 85%, 90%, 95%, 96%, 97%, 98%, or 99% amino acid sequence identity thereto. In some embodiments, the chimeric ORF1 molecule comprises an ORF1 jelly-roll domain from one Anellovirus, or a sequence having at least 75%, 80%, 85%, 90%, 95%, 96%, 97%, 98%, or 99% sequence identity thereto, and an ORF1 amino acid subsequence (e.g., as described herein) from a different Anellovirus, or a sequence having at least 75%, 80%, 85%, 90%, 95%, 96%, 97%, 98%, or 99% sequence identity thereto. In some embodiments, the chimeric ORF1 molecule comprises an ORF1 arginine-rich region from one Anellovirus, or a sequence having at least 75%, 80%, 85%, 90%, 95%, 96%, 97%, 98%, or 99% sequence identity thereto, and an ORF1 amino acid subsequence (e.g., as described herein) from a different Anellovirus, or a sequence having at least 75%, 80%, 85%, 90%, 95%, 96%, 97%, 98%, or 99% sequence identity thereto. In some embodiments, the chimeric ORF1 molecule comprises an ORF1 hypervariable domain from one Anellovirus, or a sequence having at least 75%, 80%, 85%, 90%, 95%, 96%, 97%, 98%, or 99% sequence identity thereto, and an ORF1 amino acid subsequence (e.g., as described herein) from a different Anellovirus, or a sequence having at least 75%, 80%, 85%, 90%, 95%, 96%, 97%, 98%, or 99% sequence identity thereto. In some embodiments, the chimeric ORF1 molecule comprises an ORF1 N22 domain from one Anellovirus, or a sequence having at least 75%, 80%, 85%, 90%, 95%, 96%, 97%, 98%, or 99% sequence identity thereto, and an ORF1 amino acid subsequence (e.g., as described herein) from a different Anellovirus, or a sequence having at least 75%, 80%, 85%, 90%, 95%, 96%, 97%, 98%, or 99% sequence identity thereto. In some embodiments, the chimeric ORF1 molecule comprises an ORF1 C-terminal domain from one Anellovirus, or a sequence having at least 75%, 80%, 85%, 90%, 95%, 96%, 97%, 98%, or 99% sequence identity thereto, and an ORF1 amino acid subsequence (e.g., as described herein) from a different Anellovirus, or a sequence having at least 75%, 80%, 85%, 90%, 95%, 96%, 97%, 98%, or 99% sequence identity thereto.

In some embodiments, the anellovector or anelloVLP comprises a chimeric ORF1/1 molecule comprising at least one portion of an ORF1/1 molecule from one Anellovirus (e.g., as described herein), or an ORF1/1 molecule having at least 75%, 80%, 85%, 90%, 95%, 96%, 97%, 98%, or 99% amino acid sequence identity thereto, and at least one portion of an ORF1/1 molecule from a different Anellovirus (e.g., as described herein), or an ORF1/1 molecule having at least 75%, 80%, 85%, 90%, 95%, 96%, 97%, 98%, or 99% amino acid sequence identity thereto. In some embodiments, the anellovector or anelloVLP comprises a chimeric ORF1/2 molecule comprising at least one portion of an ORF1/2 molecule from one Anellovirus (e.g., as described herein), or an ORF1/2 molecule having at least 75%, 80%, 85%, 90%, 95%, 96%, 97%, 98%, or 99% amino acid sequence identity thereto, and at least one portion of an ORF1/2 molecule from a different Anellovirus (e.g., as described herein), or an ORF1/2 molecule having at least 75%, 80%, 85%, 90%, 95%, 96%, 97%, 98%, or 99% amino acid sequence identity thereto. In some embodiments, the anellovector or anelloVLP comprises a chimeric ORF2 molecule comprising at least one portion of an ORF2 molecule from one Anellovirus (e.g., as described herein), or an ORF2 molecule having at least 75%, 80%, 85%, 90%, 95%, 96%, 97%, 98%, or 99% amino acid sequence identity thereto, and at least one portion of an ORF2 molecule from a different Anellovirus (e.g., as described herein), or an ORF2 molecule having at least 75%, 80%, 85%, 90%, 95%, 96%, 97%, 98%, or 99% amino acid sequence identity thereto. In some embodiments, the anellovector or anelloVLP comprises a chimeric ORF2/2 molecule comprising at least one portion of an ORF2/2 molecule from one Anellovirus (e.g., as described herein), or an ORF2/2 molecule having at least 75%, 80%, 85%, 90%, 95%, 96%, 97%, 98%, or 99% amino acid sequence identity thereto, and at least one portion of an ORF2/2 molecule from a different Anellovirus (e.g., as described herein), or an ORF2/2 molecule having at least 75%, 80%, 85%, 90%, 95%, 96%, 97%, 98%, or 99% amino acid sequence identity thereto. In some embodiments, the anellovector or anelloVLP comprises a chimeric ORF2/3 molecule comprising at least one portion of an ORF2/3 molecule from one Anellovirus (e.g., as described herein), or an ORF2/3 molecule having at least 75%, 80%, 85%, 90%, 95%, 96%, 97%, 98%, or 99% amino acid sequence identity thereto, and at least one portion of an ORF2/3 molecule from a different Anellovirus (e.g., as described herein), or an ORF2/3 molecule having at least 75%, 80%, 85%, 90%, 95%, 96%, 97%, 98%, or 99% amino acid sequence identity thereto. In some embodiments, the anellovector or anelloVLP comprises a chimeric ORF2T/3 molecule comprising at least one portion of an ORF2T/3 molecule from one Anellovirus (e.g., as described herein), or an ORF2T/3 molecule having at least 75%, 80%, 85%, 90%, 95%, 96%, 97%, 98%, or 99% amino acid sequence identity thereto, and at least one portion of an ORF2T/3 molecule from a different Anellovirus (e.g., as described herein), or an ORF2T/3 molecule having at least 75%, 80%, 85%, 90%, 95%, 96%, 97%, 98%, or 99% amino acid sequence identity thereto.

In some embodiments, an anellovector comprises a nucleic acid comprising a sequence listed in PCT Application No. PCT/US2018/037379, incorporated herein by reference in its entirety. In some embodiments, an anellovector or anelloVLP comprises a polypeptide comprising a sequence listed in PCT Application No. PCT/US2018/037379, incorporated herein by reference in its entirety.

In some embodiments, an anellovector comprises an Anellovirus genome, e.g., as identified according to the method described in Example 9 of PCT Publication No. WO 2020/123816, incorporated by reference herein in its entirety. In some embodiments, an anellovector or anelloVLP comprises an Anellovirus sequence, or a portion thereof, as described in Example 30.

In some embodiments, an anellovector comprises a genetic element comprising a consensus Anellovirus motif, e.g., as shown in Table 19. In some embodiments, an anellovector comprises a genetic element comprising a consensus Anellovirus ORF1 motif, e.g., as shown in Table 19. In some embodiments, an anellovector comprises a genetic element comprising a consensus Anellovirus ORF1/1 motif, e.g., as shown in Table 19. In some embodiments, an anellovector comprises a genetic element comprising a consensus Anellovirus ORF1/2 motif, e.g., as shown in Table 19. In some embodiments, an anellovector comprises a genetic element comprising a consensus Anellovirus ORF2/2 motif, e.g., as shown in Table 19. In some embodiments, an anellovector comprises a genetic element comprising a consensus Anellovirus ORP2/3 motif, e.g., as shown in Table 19. In some embodiments, an anellovector comprises a genetic element comprising a consensus Anellovirus ORF2t/3 motif, e.g., as shown in Table 19. In some embodiments, X, as shown in Table 19, indicates any amino acid. In some embodiments, Z, as shown in Table 19, indicates glutamic acid or glutamine. In some embodiments, B, as shown in Table 19, indicates aspartic acid or asparagine. In some embodiments, J, as shown in Table 19, indicates leucine or isoleucine.

TABLE 19

Consensus motifs in open reading frames (ORFs) of *Anelloviruses*

| Consensus Threshold | Open Reading Frame | Position | Motif | SEQ ID NO: |
|---|---|---|---|---|
| 50 | ORF1 | 79 | LIJRQWQPXXIRRCXIXG YXPLIXC | 68 |
| 50 | ORF1 | 111 | NYXXHXD | 69 |
| 50 | ORF1 | 135 | FSLXXLYDZ | 70 |
| 50 | ORF1 | 149 | NXWTXSNXDLDLCRYXGC | 71 |
| 50 | ORF1 | 194 | TXPSXHPGXMXLXKHK | 72 |
| 50 | ORF1 | 212 | IPSLXTRPXG | 73 |
| 50 | ORF1 | 228 | RIXPPXLFXDKWYFQXDL | 74 |
| 50 | ORF1 | 250 | LLXIXATA | 75 |

TABLE 19-continued

Consensus motifs in open reading frames (ORFs) of *Anelloviruses*

| Consensus Threshold | Open Reading Frame | Position | Motif | SEQ ID NO: |
|---|---|---|---|---|
| 50 | ORF1 | 260 | LXXPFXSPXTD | 76 |
| 50 | ORF1 | 448 | YNPXXDKGXGNXIW | 77 |
| 50 | ORF1 | 519 | CPYTZPXL | 78 |
| 50 | ORF1 | 542 | XFGXGXMP | 79 |
| 50 | ORF1 | 569 | HQXEVXEX | 80 |
| 50 | ORF1 | 600 | KYXFXFXWGGNP | 81 |
| 50 | ORF1 | 653 | HSWDXRRG | 82 |
| 50 | ORF1 | 666 | AIKRXQQ | 83 |
| 50 | ORF1 | 750 | XQZQXXLR | 84 |
| 50 | ORF1/1 | 73 | PRXJQXXDP | 85 |
| 50 | ORF1/1 | 91 | HSWDXRRG | 86 |
| 50 | ORF1/1 | 105 | AIKRXQQ | 87 |
| 50 | ORF1/1 | 187 | QZQXXLR | 88 |
| 50 | ORF1/2 | 97 | KXKRRRR | 89 |
| 50 | ORF2/2 | 158 | PIXSLXXYKXXTR | 90 |
| 50 | ORF2/2 | 189 | LAXQLLKECXKN | 91 |
| 50 | ORF2/3 | 39 | HLNXLA | 92 |
| 50 | ORF2/3 | 272 | DRPPR | 93 |
| 50 | ORF2/3 | 281 | DXPFYPWXP | 94 |
| 50 | ORF2/3 | 300 | VXFKLXF | 95 |
| 50 | ORF2t/3 | 4 | WXPPVHBVXGIERXW | 96 |
| 50 | ORF2t/3 | 37 | AKRKLX | 97 |
| 50 | ORF2t/3 | 140 | PSSXDWXXEY | 98 |
| 50 | ORF2t/3 | 156 | DRPPR | 99 |
| 50 | ORF2t/3 | 167 | PFYPW | 100 |
| 50 | ORF2t/3 | 183 | NVXFKLXF | 101 |
| 50 | ORF1 | 84 | JXXXXWQPXXXXXCXIXG XXXJWQP | 102 |
| 50 | ORF1 | 149 | NXWXXXNXXXXLXRY | 103 |
| 50 | ORF1 | 448 | YNPXXDXG | 104 |

ORF1 Molecules

In some embodiments, the anellovector or anelloVLP comprises an ORF1 molecule and/or a nucleic acid encoding an ORF1 molecule. Generally, an ORF1 molecule comprises a polypeptide having the structural features and/or activity of an Anellovirus ORF1 protein (e.g., an Anellovirus ORF1 protein as described herein, e.g., as listed in any one of Tables A1-A25), or a functional fragment thereof. In some embodiments, the ORF 1 molecule comprises a truncation relative to an Anellovirus ORF 1 protein (e.g., an Anellovirus ORF1 protein as described herein, e.g., as listed in any one of Tables A1-A25). In some embodiments, the ORF1 molecule is truncated by at least 10, 20, 30, 40, 50, 60, 70, 80, 90, 100, 150, 200, 250, 300, 350, 400, 450, 500, 550, 600, 650, or 700 amino acids of the Anellovirus ORF1 protein. In some embodiments, an ORF1 molecule comprises an amino acid sequence having at least 70%, 75%, 80%, 85%, 90%, 95%, 96%, 97%, 98%, 99%, or 10000 sequence identity to an Anellovirus ORF1 protein sequence as shown in any one of Tables A1-A25. In some embodiments, an ORF1 molecule comprises an amino acid sequence having at least 75%, 80%, 85%, 90%, 95%, 96%, 97%, 98%, or 99% sequence identity to an Betatorquevirus ORF1 protein, e.g., as described herein. An ORF1 molecule can generally bind to a nucleic acid molecule, such as DNA (e.g., a genetic element, e.g., as described herein). In some embodiments, an ORF1 molecule localizes to the nucleus of a cell. In certain embodiments, an ORF1 molecule localizes to the nucleolus of a cell.

In some embodiments, an ORF1 molecule as described herein comprises an amino acid sequence (e.g., an ORF1 sequence, or an arginine-rich region, jelly-roll domain, HVR, N22, or C-terminal domain sequence) as listed in any of Tables A2, A4, A6, A8, A10, A12, C1-C5, 2, 4, 6, 8, 10, 12, 14, 16, 18, 20-37, or D1-D10 of PCT Publication No. WO2020/123816 (incorporated herein by reference in its entirety), or a sequence having at least 70% 80%, 85%, 90% 95%, 96%, 97%, 98% and 99% nucleotide sequence identity thereto.

Without wishing to be bound by theory, an ORF1 molecule may be capable of binding to other ORF1 molecules, e.g., to form a proteinaceous exterior (e.g., as described herein). Such an ORF1 molecule may be described as having the capacity to form a capsid. In some embodiments, the proteinaceous exterior may encapsidate a nucleic acid molecule (e.g., a genetic element as described herein). In some embodiments, a plurality of ORF1 molecules may form a multimer, e.g., to produce a proteinaceous exterior. In some embodiments, the multimer may be a homomultimer. In other embodiments, the multimer may be a heteromultimer (e.g., comprising a plurality of distinct ORF1 molecules). It is also contemplated that an ORF1 molecule may have replicase activity.

An ORF1 molecule may, in some embodiments, comprise one or more of: a first region comprising an arginine rich region, e.g., a region having at least 60% basic residues (e.g., at least 60%, 65%, 70%, 75%, 80%, 85%, 90%, 95%, or 100% basic residues; e.g., between 60%-90%, 60%-80%, 70%-90%, or 70-80% basic residues), and a second region comprising jelly-roll domain, e.g., at least six beta strands (e.g., 4, 5, 6, 7, 8, 9, 10, 11, or 12 beta strands).

Arginine-Rich Region

An arginine rich region has at least 70% (e.g., at least about 70, 80, 90, 95, 96, 97, 98, 99, or 100%) sequence identity to an arginine-rich region sequence described herein or a sequence of at least about 40 amino acids comprising at least 60%, 70%, or 80% basic residues (e.g., arginine, lysine, or a combination thereof).

Jelly Roll Domain

A jelly-roll domain or region comprises (e.g., consists of) a polypeptide (e.g., a domain or region comprised in a larger polypeptide) comprising one or more (e.g., 1, 2, or 3) of the following characteristics:

(i) at least 30% (e.g., at least 30%, 35%, 40%, 45%, 50%, 55%, 60%, 65%, 70%, 75%, 80%, 90%, or more) of the amino acids of the jelly-roll domain are part of one or more β-sheets;

(ii) the secondary structure of the jelly-roll domain comprises at least four (e.g., at least 4, 5, 6, 7, 8, 9, 10, 11, or 12) β-strands; and/or (iii) the tertiary structure of the jelly-roll domain comprises at least two (e.g., at least 2, 3, or 4) β-sheets; and/or (iv) the jelly-roll domain comprises a ratio of β-sheets to α-helices of at least 2:1, 3:1, 4:1, 5:1, 6:1, 7:1, 8:1, 9:1, or 10:1.

In certain embodiments, a jelly-roll domain comprises two β-sheets.

In certain embodiments, one or more (e.g., 1, 2, 3, 4, 5, 6, 7, 8, 9, or 10) of the β-sheets comprises about eight (e.g., 4, 5, 6, 7, 8, 9, 10, 11, or 12) β-strands. In certain embodiments, one or more (e.g., 1, 2, 3, 4, 5, 6, 7, 8, 9, or 10) of the β-sheets comprises eight β-strands. In certain embodiments, one or more (e.g., 1, 2, 3, 4, 5, 6, 7, 8, 9, or 10) of the β-sheets comprises seven β-strands. In certain embodiments, one or more (e.g., 1, 2, 3, 4, 5, 6, 7, 8, 9, or 10) of the β-sheets comprises six β-strands. In certain embodiments, one or more (e.g., 1, 2, 3, 4, 5, 6, 7, 8, 9, or 10) of the β-sheets comprises five β-strands. In certain embodiments, one or more (e.g., 1, 2, 3, 4, 5, 6, 7, 8, 9, or 10) of the β-sheets comprises four β-strands.

In some embodiments, the jelly-roll domain comprises a first 1-sheet in antiparallel orientation to a second β-sheet. In certain embodiments, the first 1-sheet comprises about four (e.g., 3, 4, 5, or 6) β-strands. In certain embodiments, the second 1-sheet comprises about four (e.g., 3, 4, 5, or 6) β-strands. In embodiments, the first and second 1-sheet comprise, in total, about eight (e.g., 6, 7, 8, 9, 10, 11, or 12) β-strands.

In certain embodiments, a jelly-roll domain is a component of a capsid protein (e.g., an ORF1 molecule as described herein). In certain embodiments, a jelly-roll domain has self-assembly activity. In some embodiments, a polypeptide comprising a jelly-roll domain binds to another copy of the polypeptide comprising the jelly-roll domain. In some embodiments, a jelly-roll domain of a first polypeptide binds to a jelly-roll domain of a second copy of the polypeptide.

An ORF1 molecule may also include a third region comprising the structure or activity of an Anellovirus N22 domain (e.g., as described herein, e.g., an N22 domain from an Anellovirus ORF1 protein as described herein), and/or a fourth region comprising the structure or activity of an Anellovirus C-terminal domain (CTD) (e.g., as described herein, e.g., a CTD from an Anellovirus ORF1 protein as described herein). In some embodiments, the ORF1 molecule comprises, in N-terminal to C-terminal order, the first, second, third, and fourth regions.

The ORF1 molecule may, in some embodiments, further comprise a hypervariable region (HVR), e.g., an HVR from an Anellovirus ORF1 protein, e.g., as described herein. In some embodiments, the HVR is positioned between the second region and the third region. In some embodiments, the HVR comprises comprises at least about 55 (e.g., at least about 45, 50, 51, 52, 53, 54, 55, 56, 57, 58, 59, 60, or 65) amino acids (e.g., about 45-160, 50-160, 55-160, 60-160, 45-150, 50-150, 55-150, 60-150, 45-140, 50-140, 55-140, or 60-140 amino acids).

In some embodiments, the first region can bind to a nucleic acid molecule (e.g., DNA). In some embodiments, the basic residues are selected from arginine, histidine, or lysine, or a combination thereof. In some embodiments, the first region comprises at least 60%, 65%, 70%, 75%, 80%, 85%, 90%, 95%, or 100% arginine residues (e.g., between 60%-90%, 60%-80%, 70%-90%, or 70-80% arginine residues). In some embodiments, the first region comprises about 30-120 amino acids (e.g., about 40-120, 40-100, 40-90, 40-80, 40-70, 50-100, 50-90, 50-80, 50-70, 60-100, 60-90, or 60-80 amino acids). In some embodiments, the first region comprises the structure or activity of a viral ORF1 arginine-rich region (e.g., an arginine-rich region from an Anellovirus ORF1 protein, e.g., as described herein). In some embodiments, the first region comprises a nuclear localization sigal.

In some embodiments, the second region comprises a jelly-roll domain, e.g., the structure or activity of a viral ORF1 jelly-roll domain (e.g., a jelly-roll domain from an Anellovirus ORF1 protein, e.g., as described herein). In some embodiments, the second region is capable of binding to the second region of another ORF1 molecule, e.g., to form a proteinaceous exterior (e.g., capsid) or a portion thereof.

In some embodiments, the fourth region is exposed on the surface of a proteinaceous exterior (e.g., a proteinaceous exterior comprising a multimer of ORF1 molecules, e.g., as described herein).

In some embodiments, the first region, second region, third region, fourth region, and/or HVR each comprise fewer than four (e.g., 0, 1, 2, or 3) beta sheets.

In some embodiments, one or more of the first region, second region, third region, fourth region, and/or HVR may be replaced by a heterologous amino acid sequence (e.g., the corresponding region from a heterologous ORF1 molecule). In some embodiments, the heterologous amino acid sequence has a desired functionality, e.g., as described herein.

In some embodiments, the ORF1 molecule comprises a plurality of conserved motifs (e.g., motifs comprising about 5, 6, 7, 8, 9, 10, 11, 12, 13, 14, 15, 16, 17, 18, 19, 20, 25, 30, 35, 40, 45, 50, 60, 70, 80, 90, 100, or more amino acids) (e.g., as shown in FIG. 34 of PCT Publication No. WO2020/123816). In some embodiments, the conserved motifs may show 60, 70, 80, 85, 90, 95, or 100% sequence identity to an ORF1 protein of one or more wild-type Anellovirus clades (e.g., Betatorquevirus). In some embodiments, the conserved motifs each have a length between 1-1000 (e.g., between 5-10, 5-15, 5-20, 10-15, 10-20, 15-20, 5-50, 5-100, 10-50, 10-100, 10-1000, 50-100, 50-1000, or 100-1000) amino acids. In certain embodiments, the conserved motifs consist of about 2-4% (e.g., about 1-8%, 1-6%, 1-5%, 1-4%, 2-8%, 2-6%, 2-5%, or 2-4%) of the sequence of the ORF1 molecule, and each show 100% sequence identity to the corresponding motifs in an ORF1 protein of the wild-type Anellovirus clade. In certain embodiments, the conserved motifs consist of about 5-10% (e.g., about 1-20%, 1-10%, 5-20%, or 5-10%) of the sequence of the ORF1 molecule, and each show 80% sequence identity to the corresponding motifs in an ORF1 protein of the wild-type Anellovirus clade. In certain embodiments, the conserved motifs consist of about 10-50% (e.g., about 10-20%, 10-30%, 10-40%, 10-50%, 20-40%, 20-50%, or 30-50%) of the sequence of the ORF1 molecule, and each show 60% sequence identity to the corresponding motifs in an ORF1 protein of the wild-type Anellovirus clade. In some embodiments, the conserved motifs comprise one or more amino acid sequences as listed in Table 19.

In some embodiments, an ORF1 molecule comprises at least one difference (e.g., a mutation, chemical modification, or epigenetic alteration) relative to a wild-type ORF1 protein, e.g., as described herein (e.g., as shown in any one of Tables A1-A25).

Conserved ORF1 Motif in N22 Domain

In some embodiments, a polypeptide (e.g., an ORF1 molecule) described herein comprises the amino acid sequence $YNPX^2DXGX^2N$ (SEQ ID NO: 829), wherein $X^n$ is a contiguous sequence of any n amino acids. For example, $X^2$ indicates a contiguous sequence of any two amino acids. In some embodiments, the $YNPX^2DXGX^2N$ (SEQ ID NO: 829) is comprised within the N22 domain of an ORF1 molecule, e.g., as described herein. In some embodiments, a genetic element described herein comprises a nucleic acid sequence (e.g., a nucleic acid sequence encoding an ORF1 molecule, e.g., as described herein) encoding the amino acid sequence $YNPX^2DXGX^2N$ (SEQ ID NO: 829), wherein $X^n$ is a contiguous sequence of any n amino acids.

In some embodiments, a polypeptide (e.g., an ORF1 molecule) comprises a conserved secondary structure, e.g., flanking and/or comprising a portion of the $YNPX^2DXGX^2N$ (SEQ ID NO: 829) motif, e.g., in an N22 domain. In some embodiments, the conserved secondary structure comprises a first beta strand and/or a second beta strand. In some embodiments, the first beta strand is about 5-6 (e.g., 3, 4, 5, 6, 7, or 8) amino acids in length. In some embodiments, the first beta strand comprises the tyrosine (Y) residue at the N-terminal end of the $YNPX^2DXGX^2N$ (SEQ ID NO: 829) motif. In some embodiments, the $YNPX^2DXGX^2N$ (SEQ ID NO: 829) motif comprises a random coil (e.g., about 8-9 amino acids of random coil). In some embodiments, the second beta strand is about 7-8 (e.g., 5, 6, 7, 8, 9, or 10) amino acids in length. In some embodiments, the second beta strand comprises the asparagine (N) residue at the C-terminal end of the $YNPX^2DXGX^2N$ (SEQ ID NO: 829) motif.

Figure 48:
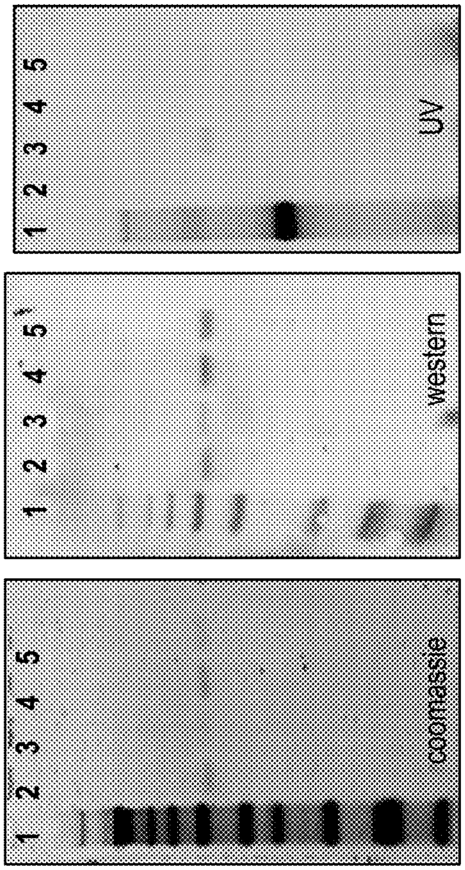
FIG. 48 is a diagram showing Coomassie staining, Western blot, and UV labeling for SARS-CoV-2 receptor binding domains (RBD) attached to DBCO, CalFluor 488, Azide, or Alexa488, as shown.

Exemplary $YNPX^2DXGX^2N$ (SEQ ID NO: 829) motif-flanking secondary structures are described in Example 47 and FIG. 48 of PCT Publication No. WO 2020/123816, incorporated by reference herein in its entirety. In some embodiments, an ORF1 molecule comprises a region comprising one or more (e.g., 1, 2, 3, 4, 5, 6, 7, 8, 9, 10, or all) of the secondary structural elements (e.g., beta strands) shown in FIG. 48 of PCT Publication No. WO 2020/123816. In some embodiments, an ORF1 molecule comprises a region comprising one or more (e.g., 1, 2, 3, 4, 5, 6, 7, 8, 9, 10, or all) of the secondary structural elements (e.g., beta strands) shown in FIG. 48 of PCT Publication No. WO 2020/123816, incorporated by reference herein in its entirety, flanking a $YNPX^2DXGX^2N$ (SEQ ID NO: 829) motif (e.g., as described herein).

Conserved Secondary Structural Motif in ORF1 Jelly-Roll Domain

In some embodiments, a polypeptide (e.g., an ORF1 molecule) described herein comprises one or more secondary structural elements comprised by an Anellovirus ORF1 protein (e.g., as described herein). In some embodiments, an ORF1 molecule comprises one or more secondary structural elements comprised by the jelly-roll domain of an Anellovius ORF1 protein (e.g., as described herein). Generally, an ORF1 jelly-roll domain comprises a secondary structure comprising, in order in the N-terminal to C-terminal direction, a first beta strand, a second beta strand, a first alpha helix, a third beta strand, a fourth beta strand, a fifth beta strand, a second alpha helix, a sixth beta strand, a seventh beta strand, an eighth beta strand, and a ninth beta strand. In some embodiments, an ORF1 molecule comprises a secondary structure comprising, in order in the N-terminal to C-terminal direction, a first beta strand, a second beta strand, a first alpha helix, a third beta strand, a fourth beta strand, a fifth beta strand, a second alpha helix, a sixth beta strand, a seventh beta strand, an eighth beta strand, and/or a ninth beta strand.

In some embodiments, a pair of the conserved secondary structural elements (i.e., the beta strands and/or alpha helices) are separated by an interstitial amino acid sequence, e.g., comprising a random coil sequence, a beta strand, or an alpha helix, or a combination thereof. Interstitial amino acid sequences between the conserved secondary structural elements may comprise, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more amino acids. In some embodiments, an ORF1 molecule may further comprise one or more additional beta strands and/or alpha helices (e.g., in the jelly-roll domain). In some embodiments, consecutive beta strands or consecutive alpha helices may be combined. In some embodiments, the first beta strand and the second beta strand are comprised in a larger beta strand. In some embodiments, the third beta strand and the fourth beta strand are comprised in a larger beta strand. In some embodiments, the fourth beta strand and the fifth beta strand are comprised in a larger beta strand. In some embodiments, the sixth beta strand and the seventh beta strand are comprised in a larger beta strand. In some embodiments, the seventh beta strand and the eighth beta strand are comprised in a larger beta strand. In some embodiments, the eighth beta strand and the ninth beta strand are comprised in a larger beta strand.

In some embodiments, the first beta strand is about 5-7 (e.g., 3, 4, 5, 6, 7, 8, 9, or 10) amino acids in length. In some embodiments, the second beta strand is about 15-16 (e.g., 13, 14, 15, 16, 17, 18, or 19) amino acids in length. In some embodiments, the first alpha helix is about 15-17 (e.g., 13, 14, 15, 16, 17, 18, 19, or 20) amino acids in length. In some embodiments, the third beta strand is about 3-4 (e.g., 1, 2, 3, 4, 5, or 6) amino acids in length. In some embodiments, the fourth beta strand is about 10-11 (e.g., 8, 9, 10, 11, 12, or 13) amino acids in length. In some embodiments, the fifth beta strand is about 6-7 (e.g., 4, 5, 6, 7, 8, 9, or 10) amino acids in length. In some embodiments, the second alpha helix is about 8-14 (e.g., 5, 6, 7, 8, 9, 10, 11, 12, 13, 14, 15, 16, or 17) amino acids in length. In some embodiments, the second alpha helix may be broken up into two smaller alpha helices (e.g., separated by a random coil sequence). In some embodiments, each of the two smaller alpha helices are about 4-6 (e.g., 2, 3, 4, 5, 6, 7, or 8) amino acids in length. In some embodiments, the sixth beta strand is about 4-5 (e.g., 2, 3, 4, 5, 6, or 7) amino acids in length. In some embodiments, the seventh beta strand is about 5-6 (e.g., 3, 4, 5, 6, 7, 8, or 9) amino acids in length. In some embodiments, the eighth beta strand is about 7-9 (e.g., 5, 6, 7, 8, 9, 10, 11, 12, or 13) amino acids in length. In some embodiments, the ninth beta strand is about 5-7 (e.g., 3, 4, 5, 6, 7, 8, 9, or 10) amino acids in length.

Figure 47:
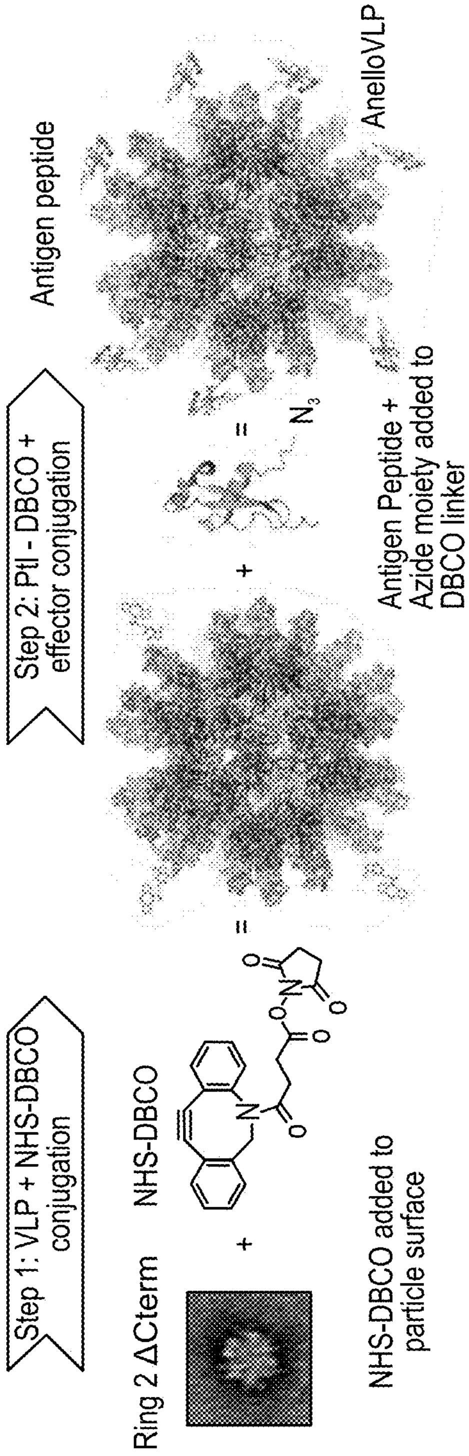
FIG. 47 is a diagram showing an exemplary two-step process for conjugating a surface effector moiety to the surface of an anelloVLP.

Exemplary jelly-roll domain secondary structures are described in Example 47 and FIG. 47 of PCT Publication No. WO 2020/123816, incorporated by reference herein in its entirety. In some embodiments, an ORF1 molecule comprises a region comprising one or more (e.g., 1, 2, 3, 4, 5, 6, 7, 8, 9, 10, or all) of the secondary structural elements (e.g., beta strands and/or alpha helices) of any of the jelly-roll domain secondary structures shown in FIG. 47 of PCT Publication No. WO 2020/123816, incorporated by reference herein in its entirety.

Exemplary ORF7 Sequences

In some embodiments, a polypeptide (e.g., an ORF1 molecule) described herein comprises an amino acid sequence having at least about 70%, 75%, 80%, 85%, 90%, 95%, 96%, 97%, 98%, 99%, or 100% sequence identity to one or more Anellovirus ORF1 subsequences, e.g., as described herein). In some embodiments, an anellovector or anelloVLP described herein comprises an ORF1 molecule comprising an amino acid sequence having at least about 70%, 75%, 80%, 85%, 90%, 95%, 96%, 97%, 98%, 99%, or 100% sequence identity to one or more Anellovirus ORF1 subsequences, e.g., as described herein. In some embodiments, an anellovector or anelloVLP described herein comprises a nucleic acid molecule (e.g., a genetic element) encoding an ORF1 molecule comprising an amino acid sequence having at least about 70%, 75%, 80%, 85%, 90%, 95%, 96%, 97%, 98%, 99%, or 100% sequence identity to one or more Anellovirus ORF1 subsequences, e.g., as described herein.

In some embodiments, the one or more Anellovirus ORF1 subsequences comprises one or more of an arginine (Arg)-rich domain, a jelly-roll domain, a hypervariable region (HVR), an N22 domain, or a C-terminal domain (CTD) (e.g., as listed herein), or sequences having at least about 70%, 75%, 80%, 85%, 90%, 95%, 96%, 97%, 98%, 99%, or 100% sequence identity thereto. In some embodiments, the ORF1 molecule comprises a plurality of subsequences from different Anelloviruses. In some embodiments, the ORF1 molecule comprises one or more of an Arg-rich domain, a jelly-roll domain, an N22 domain, and a CTD from one Anellovirus, and an HVR from another. In some embodiments, the ORF1 molecule comprises one or more of a jelly-roll domain, an HVR, an N22 domain, and a CTD from one Anellovirus, and an Arg-rich domain from another. In some embodiments, the ORF1 molecule comprises one or more of an Arg-rich domain, an HVR, an N22 domain, and a CTD from one Anellovirus, and a jelly-roll domain from another. In some embodiments, the ORF1 molecule comprises one or more of an Arg-rich domain, a jelly-roll domain, an HVR, and a CTD from one Anellovirus, and an N22 domain from another. In some embodiments, the ORF1 molecule comprises one or more of an Arg-rich domain, a jelly-roll domain, an HVR, and an N22 domain from one Anellovirus, and a CTD from another.

In some embodiments, the one or more Anellovirus ORF1 subsequences comprises one or more of an arginine (Arg)-rich domain, a jelly-roll domain, a hypervariable region (HVR), an N22 domain, or a C-terminal domain (CTD) as described in PCT Publication No. WO2020/123816 (incorporated herein by reference in entirety).

In some embodiments, a polypeptide (e.g., an ORF1 molecule) described herein comprises an amino acid sequence having at least about 70%, 75%, 80%, 85%, 90%, 95%, 96%, 97%, 98%, 99%, or 100% sequence identity to one or more Anellovirus ORF1 subsequences, e.g., as described in any of Tables 20-37, or D1-D11). In some embodiments, an anellosome described herein comprises an ORF1 molecule comprising an amino acid sequence having at least about 70%, 75%, 80%, 85%, 90%, 95%, 96%, 97%, 98%, 99%, or 100% sequence identity to one or more Anellovirus ORF1 subsequences, e.g., as described in any of Tables 20-37, or D1-D11. In some embodiments, an anellosome described herein comprises a nucleic acid molecule (e.g., a genetic element) encoding an ORF1 molecule comprising an amino acid sequence having at least about 70%, 75%, 80%, 85%, 90%, 95%, 96%, 97%, 98%, 99%, or 100% sequence identity to one or more Anellovirus ORF1 subsequences, e.g., as described in any of Tables 20-37, or D1-D11.

In some embodiments, the one or more Anellovirus ORF1 subsequences comprises one or more of an arginine (Arg)-rich domain, a jelly-roll domain, a hypervariable region (HVR), an N22 domain, or a C-terminal domain (CTD) (e.g., as listed in any of Tables 20-37, or D1-D11), or sequences having at least about 70%, 75%, 80%, 85%, 90%, 95%, 96%, 97%, 98%, 99%, or 100% sequence identity thereto. In some embodiments, the ORF1 molecule comprises a plurality of subsequences from different Anelloviruses (e.g., any combination of ORF1 subsequences selected from the Alphatorquevirus Clade 1-7 subsequences listed in Tables 20-37, or D1-D11). In embodiments, the ORF1 molecule comprises one or more of an Arg-rich domain, a jelly-roll domain, an N22 domain, and a CTD from one Anellovirus, and an HVR from another. In embodiments, the ORF1 molecule comprises one or more of a jelly-roll domain, an HVR, an N22 domain, and a CTD from one Anellovirus, and an Arg-rich domain from another. In embodiments, the ORF1 molecule comprises one or more of an Arg-rich domain, an HVR, an N22 domain, and a CTD from one Anellovirus, and a jelly-roll domain from another. In embodiments, the ORF1 molecule comprises one or more of an Arg-rich domain, a jelly-roll domain, an HVR, and a CTD from one Anellovirus, and an N22 domain from another. In embodiments, the ORF1 molecule comprises one or more of an Arg-rich domain, a jelly-roll domain, an HVR, and an N22 domain from one Anellovirus, and a CTD from another.

TABLE 20

Exemplary *Anellovirus* ORF1 amino acid subsequence (*Alphatorquevirus*, Clade 1)

| | |
|---|---|
| Name | CT30F |
| Genus/Clade | *Alphatorquevirus*, Clade 1 |
| Strain Accesion Number | AB064597.1 |
| Protein Accession Number | ANQ39351.1 |
| Full Sequence: 680 AA | |

```
1         10        20        30        40        50
|         |         |         |         |         |
TAWWWGRWRRRWRRRRPWRPRLRRRRARRAFPRRRRRRFVSRRWRRPYRR
RRRRGRRRRRRRRRHKPTLVLRQWQPDVIRHCKITGRMPLIICGKGSTQF
NYITHADDITPRGASYGGNFTNMTFSLEAIYEQFLYHRNRWSASNHDLEL
CRYKGTTLKLYRHPDVDYIVTYSRTGPFEISHMTYLSTHPLLMLLNKHHI
VVPSLKTKPRGRKAIKVRIRPPKLMNNKWYFTRDFCNIGLFQLWATGLEL
RNPWLRMSTLSPCIGENVLKNSIYTNLSNLPQHREDRLNIINNTLHPHDI
TGPNNKKWQYTYTKLMAPIYYSANRASTYDLLREYGLYSPYYLNPTRINL
DWMTPYTHVRYNPLVDKGFGNRIYIQWCSEADVSYNRTKSKCLLQDMPLF
FMCYGYIDWAIKNTGVSSLARDARICIRCPYTEPQLVGSTEDIGFVPITE
TFMRGDMPVLAPYIPLSWFCKWYPNIAHQKEVLEAIISCSPFMPRDQGMN
GWDITIGYKMDFLWGGSPLPSQPIDDPCQQGTHPIPDPDKHPRLLQVSNP
KLLGPRTVFHKWDIRRGQFSKRSIKRVSEYSSDDESLAPGLPSKRNKLDS
AFRGENPEQKECYSLLKALEEEETPEEEEPAPQEKAQKEELLHQLQLQRR
HQRVLRRGLKLVFTDILRLRQGVHWNPELT (SEQ ID NO: 173)
```

Annotations:

| Putative Domain | AA range |
|---|---|
| Arg-Rich Region | 1-66 |
| Jelly-roll domain | 67-277 |
| Hypervariable Region | 278-347 |
| N22 | 348-513 |
| C-terminal Domain | 513-680 |

TABLE 21

| Exemplary *Anellovirus* ORF1 amino acid subsequence (*Alphatorquevirus*, Clade 1) TTV-CT30F-ORF1 (*Alphatorquevirus* Clade 1) | |
|---|---|
| Arg-Rich Region | TAWWWGRWRRRWRRRRPWRPRLRRRRARRAFPRRRRRRFVSRRWRRPYRRRRRRGRRRRRRRRRHK (SEQ ID NO: 174) |
| Jelly-roll Domain | PTLVLRQWQPDVIRHCKITGRMPLIICGKGSTQFNYITHADDITPRGASYGGNFTNMTFSLEAIYEQFLYHRNRWSASNHDLELCRYKGTTLKLYRHPDVDYIVTYSRTGPFEISHMTYLSTHPLLMLLNKHHIVVPSLKTKPRGRKAIKVRIRPPKLMNNKWYFTRDFCNIGLFQLWATGLELRNPWLRMSTLSPCIGFNVLKNSIYTNL (SEQ ID NO: 175) |
| Hyper-variable domain | SNLPQHREDRLNIINNTLHPHDITGPNNKKWQYTYTKLMAPIYYSANRASTYDLLREYGLYSPYYLNPTR (SEQ ID NO: 176) |
| N22 | INLDWMTPYTHVRYNPLVDKGFGNRIYIQWCSEADVSYNRTKSKCLLQDMPLFFMCYGYIDWAIKNTGVSSLARDARICIRCPYTEPQLVGSTEDIGFVPITETFMRGDMPVLAPYIPLSWFCKWYPNIAHQKEVLEAIISCSPFMPRDQGMNGWDITIGYKMDFL (SEQ ID NO: 177) |
| C-terminal domain | WGGSPLPSQPIDDPCQQGTHPIPDPDKHPRLLQVSNPKLLGPRTVFHKWDIRRGQFSKRSIKRVSEYSSDDESLAPGLPSKRNKLDSAFRGENPEQKECYSLLKALEEEETPEEEEPAPQEKAQKEELLHQLQLQRRHQRVLRRGLKLVFTDILRLRQGVHWNPELT (SEQ ID NO: 178) |

TABLE 22

Exemplary *Anellovirus* ORF1 amino acid subsequence (*Alphatorquevirus*, Clade 2)

| | |
|---|---|
| Name | TTV-P13-1 |
| Genus/Clade | *Alphatorquevirus*, Clade 2 |
| Accession Number | KT163896.1 |
| Protein Accession Number | ANQ39351.1 |

Full Sequence: 747 AA

```
1         10         20         30         40         50
|         |          |          |          |          |
MAYWWGRRRRWRRWRRRRRPLRRRRRWRRRRRWPRRRRWRRRRRRARPAR
RYRRRRGRRRVRRRRRPQKLVLTQWNPQTVRKCVIRGFLPLFFCGQGAYH
RNFTDHYDDVFPKGPSGGGHGSMVENLSFLYQEFKKHHNKWSRSNLDEDL
VRYKGTVIKLYRHQDFDYIVWISRTPPFQESLLTVMTHQPSVMLQAKKCI
IVKSYRTHPGGKPYVTAKVRPPRLLTDKWYFQSDFCNVPLFSLQFALAEL
RFPICSPQTDTNCINFLVLDDIYYKFLDNKPKQSSDPNDENRIKFWHGLW
STMRYLNTTYINTLFPGTDSLVAAKDTDNSVNKYPSTATKQPYKDSQYMQ
NIWNTSKIHALYTWVAETNYKRLQAYYTQTYGGYQRQFFTGKQYWDYRVG
MFSPAFLSPSRLNPQNPGAYTEVSYNPWTDEGTGNVVCLQYLTKETSDYK
PGGGSKFCIEGVPLWAALVGYVDMCKKEGKDPGIRLNCLLLVKCPYTKPQ
LYDKKNPEKLFVPYSYNFGHGKMPGGDKYIPIEFKDRWYPCLLHQEEWIE
DIVRSGPFVPKDMPSSVTCMMRYSSLFNWGGNIIQEQAVEDPCKKGTFVV
PGTSGIARILQVSNPAKQTPTTTWHSWDWRRSLFTETGLKRMREQQPYDE
LSYTGPKKPKLSLPAGPAVPGAAVASSWWETKQVTSPDVSETETEAEAHQ
EEETEPEEGVQLQQLWEQQLLQKRQLGVVFQQLLRLRQGAEIHPGLV
(SEQ ID NO: 179)
```

Annotations:

| Putative Domain | AA range |
|---|---|
| Arg-Rich Region | 1-69 |
| Jelly-roll domain | 70-279 |
| Hypervariable Region | 280-411 |
| N22 | 412-578 |
| C-terminal Domain | 579-747 |

TABLE 23

| Exemplary *Anellovirus* ORF1 amino acid subsequence (*Alphatorquevirus*, Clade 2) TTV-P13-1-ORF1 (*Alphatorquevirus* Clade 2) | |
|---|---|
| Arg-Rich Region | MAYWWGRRRRWRRWRRRRRPLRRRRRWRRRRRWPRRRRWRRRRRRARPARRYRRRRGRRRVRRRRRPQK (SEQ ID NO: 180) |
| Jelly-roll Domain | LVLTQWNPQTVRKCVIRGFLPLFFCGQGAYHRNFTDHYDDVFPKGPSGGGHGSMVFNLSFLYQEFKKHHNKWSRSNLDFDLVRYKGTVIKLYRHQDFDYIVWISRTPPFQESLLTVMTHQPSVMLQAKKCIIVKSYRTHPGGKPYVTAKVRPPRLLTDKWYFQSDFCNVPLFSLQFALAELRFPICSPQTDTNCINFLVLDDIYYKFLDN (SEQ ID NO: 181) |
| Hyper-variable domain | KPKQSSDPNDENRIKFWHGLWSTMRYLNTTYINTLFPGTDSLVAAKDTDNSVNKYPSTATKQPYKDSQYMQNIWNTSKIHALYTWVAETNYKRLQAYYTQTYGGYQRQFFTGKQYWDYRVGMFSPAFLSPSR (SEQ ID NO:182) |
| N22 | LNPQNPGAYTEVSYNPWTDEGTGNVVCLQYLTKETSDYKPGGGSKFCIEGVPLWAALVGYVDMCKKEGKDPGIRLNCLLLVKCPYTKPQLYDKKNPEKLFVPYSYNFGHGKMPGGDKYIPIEFKDRWYPCLLHQEEWIEDIVRSGPFVPKDMPSSVTCMMRYSSLFN (SEQ ID NO: 183) |
| C-terminal domain | WGGNIIQEQAVEDPCKKGTFVVPGTSGIARILQVSNPAKQTPTTTWHSWDWRRSLFTETGLKRMREQQPYDELSYTGPKKPKLSLPAGPAVPGAAVASSWWETKQVTSPDVSETETEAEAHQEEETEPEEGVQLQQLWEQQLLQKRQLGVVFQQLLRLRQGAEIHPGLV (SEQ ID NO: 184) |

TABLE 24

Exemplary *Anellovirus* ORF1 amino acid subsequence (*Alphatorquevirus*, Clade 3)

| | |
|---|---|
| Name | Ring1 |
| Genus/Clade | *Alphatorquevirus*, Clade 3 |
| Accession Number | AJ620231.1 |
| Protein Accession Number | CAF05750.1 |

Full Sequence: 743 AA

```
1         10         20         30         40         50
|         |          |          |          |          |
MAWGWWKRRRRWWFRKRWTRGRLRRRWPRSARRRPRRRRVRRRRRWRRGR
RKTRTYRRRRRFRRRGRKAKLIIKLWQPAVIKRCRIKGYIPLIISGNGTF
ATNFTSHINDRIMKGPFGGGHSTMRFSLYILFEEHLRHMNFWTRSNDNLE
LTRYLGASVKIYRHPDQDFIVIYNRRTPLGGNIYTAPSLHPGNAILAKHK
ILVPSLQTRPKGRKAIRLRIAPPTLFTDKWYFQKDIADLTLFNIMAVEAD
LRFPFCSPQTDNTCISFQVLSSVYNNYLSINTENNDNSDSKLKEFLNKAF
PTTGTKGTSLNALNTFRTEGCISHPQLKKPNPQINKPLESQYFAPLDALW
GDPIYYNDLNENKSLNDIIEKILIKNMITYHAKLREFPNSYQGNKAFCHL
TGIYSPPYLNQGRISPEIFGLYTEIIYNPYTDKGTGNKVWMDPLTKENNI
YKEGQSKCLLTDMPLWTLLFGYTDWCKKDTNNWDLPLNYRLVLICPYTFP
KLYNEKVKDYGYIPYSYKFGAGQMPDGSNYIPFQFRAKWYPTVLHQQQVM
EDISRSGPFAPKVEKPSTQLVMKYCFNFNWGGNPIIEQIVKDPSFQPTYE
IPGTGNIPRRIQVIDPRVLGPHYSFRSWDMRRHTFSRASIKRVSEQQETS
DLVFSGPKKPRVDIPKQETQEESSHSLQRESRPWETEEESETEALSQESQ
EVPFQQQLQQQYQEQLKLRQGIKVLFEQLIRTQQGVHVNPCLR (SEQ
ID NO: 185)
```

Annotations:

| Putative Domain | AA range |
|---|---|
| Arg-Rich Region | 1-68 |
| Jelly-roll domain | 69-280 |
| Hypervariable Region | 281-413 |
| N22 | 414-579 |
| C-terminal Domain | 580-743 |

TABLE 25

| Exemplary *Anellovirus* ORF1 amino acid subsequence (*Alphatorquevirus*, Clade 3) Ring1 ORF1 (*Alphatorquevirus* Clade 3) | |
|---|---|
| Arg-Rich Region | MAWGWWKRRRRWWFRKRWTRGRLRRRWPRSARRRPRRRRVRRRRRWRRGRRKTRTYRRRRRFRRRGRK (SEQ ID NO: 186) |
| Jelly-roll Domain | AKLIIKLWQPAVIKRCRIKGYIPLIISGNGTFATNFTSHINDRIMKGPFGGGHSTMRFSLYILFEEHLRHMNFWTRSNDNLELTRYLGASVKIYRHPDQDFIVIYNRRTPLGGNIYTAPSLHPGNAILAKHKILVPSLQTRPKGRKAIRLRIAPPTLFTDKWYFQKDIADLTLFNIMAVEADLRFPFCSPQTDNTCISFQVLSSVYNNYLSI (SEQ ID NO: 187) |
| Hyper-variable domain | NTFNNDNSDSKLKEFLNKAFPTTGTKGTSLNALNTFRTEGCISHPQLKKPNPQINKPLESQYFAPLDALWGDPIYYNDLNENKSLNDIIEKILIKNMITYHAKLREFPNSYQGNKAFCHLTGIYSPPYLNQGR (SEQ ID NO: 188) |
| N22 | ISPEIFGLYTEIIYNPYTDKGTGNKVWMDPLTKENNIYKEGQSKCLLTDMPLWTLLFGYTDWCKKDTNNWDLPLNYRLVLICPYTFPKLYNEKVKDYGYIPYSYKFGAGQMPDGSNYIPFQFRAKWYPTVLHQQQVMEDISRSGPFAPKVEKPSTQLVMKYCFNFN (SEQ ID NO: 189) |
| C-terminal domain | WGGNPIEQIVKDPSFQPTYEIPGTGNIPRRIQVIDPRVLGPHYSFRSWDMRRHTFSRASIKRVSEQQETSDLVFSGPKKPRVDIPKQETQEESSHSLQRESRPWETEEESETEALSQESQEVPFQQQLQQQYQEQLKLRQGIKVLFEQLIRTQQGVHVNPCLR (SEQ ID NO: 190) |

TABLE 26

Exemplary *Anellovirus* ORF1 amino acid subsequence (*Alphatorquevirus*, Clade 4)

| | |
|---|---|
| Name | TTV-HD20a |
| Genus/Clade | *Alphatorquevirus*, Clade 4 |
| Accession Number | FR751492.1 |
| Protein Accession Number | NA |
| Full Sequence: 780 AA | |

```
1         10        20        30        40        50
|         |         |         |         |         |
MAWWGWRRRWWRPKRRWRWRRARRRRRVPARRPRRAFRRYRTRTVRRRRR
GRRRGYRRRYRLRRYARRRFRRKKIVLTQWNPQTTRKCIIRGMMPVLWAG
MGTGGRNYAVRSDDYVVNKGFGGSFATETFSLKVLYDQFORGENRWSHIN
EDLDLARYRGCRWTFYRHKDTDFIVYFTNNPPMKTNQFSAPLTTPGMLMR
SKYKVLIPSFQTRPKGRKTVTVKIRPPKLFQDKWYTQQDLCSVPLVQLNV
TAADFTHPFGSPLTETPCVEFQVLGDLYNTCLNIDLPQFSELGEITSAYS
KPNSNNLKELYKELFTKATSGHYWQTFITNSMVRAHIDADKAKEAQRAST
TPSYNNDPFPTIPVKSEFAQWKKKFTDTRDSPFLFATYHPEAIKDTIMKM
RENNFKLETGPNDKYGDYTAQYQGNTHMLDYYLGFYSPIFLSDGRSNVEF
FTAYRDIVYNPFLDKAQGNMVWFQYHTKTDNKFKKPECHWEIKDMPLWAL
LNGYVDYLETQIQYGDLSKEGKVLIRCPYTKPALVDPRDDTAGYVVYNRN
FGRGKWIDGGGYIPLHERTKWYVMLRYQTDVFHDIVTCGPWQYRDDNKNS
QLVAKYRFSFIWGGNTVHSQVIRNPCKDNQVSGPRRQPRDIQVVDPQRIT
PPWVLHSFDQRRGLFTETALRRLLQEPLPGEYAVSTLRTPLLFLPSEYQR
EDGAAESASGSPAKRPRIWSEESQTETISSEENPAETTRELLQRKLREQR
ALQFQLQHFAVQLAKTQANLHVNPLLSFPQ (SEQ ID NO: 191)
```

Annotations:

| Putative Domain | AA range |
|---|---|
| Arg-Rich Region | 1-74 |
| Jelly-roll domain | 75-284 |
| Hypervariable Region | 285-445 |
| N22 | 446-611 |
| C-terminal Domain | 612-780 |

TABLE 27

| Exemplary *Anellovirus* ORF1 amino acid subsequence (*Alphatorquevirus*, Clade 4) TTV-HD20a-ORF1 (*Alphatorquevirus* Clade 4) | |
|---|---|
| Arg-Rich Region | MAWWGWRRRWWRPKRRWRWRRARRRRRVPARRPRRAFRRYRTRTVRRRRRGRRRGYRRRYRLRRYARRRFRRKK (SEQ ID NO: 192) |
| Jelly-roll Domain | IVLTQWNPQTTRKCIIRGMMPVLWAGMGTGGRNYAVRSDDYVVNKGFGGSFATETFSLKVLYDQFQRGFNRWSHTNEDLDLARYRGCRWTFYRHKDTDFIVYFTNNPPMKTNQFSAPLTTPGMLMRSKYKVLIPSFQTRPKGRKTVTVKIRPPKLFQDKWYTQQDLCSVPLVQLNVTAADFTHPFGSPLTETPCVEFQVLGDLYNTCLNI (SEQ ID NO: 193) |
| Hyper-variable domain | DLPQFSELGEITSAYSKPNSNNLKELYKELFTKATSGHYWQTFITNSMVRAHIDADKAKEAQRASTTPSYNNDPFPTIPVKSEFAQWKKKFTDTRDSPFLFATYHPEAIKDTIMKMRENNFKLETGPNDKYGDYTAQYQGNTHMLDYYLGFYSPIFLSDGR (SEQ ID NO: 194) |
| N22 | SNVEFFTAYRDIVYNPFLDKAQGNMVWFQYHTKTDNKFKKPECHWEIKDMPLWALLNGYVDYLETQIQYGDLSKEGKVLIRCPYTKPALVDPRDDTAGYVVYNRNFGRGKWIDGGGYIPLHERTKWYVMLRYQTDVFHDIVTCGPWQYRDDNKNSQLVAKYRFSFI (SEQ ID NO: 195) |
| C-terminal domain | WGGNTVHSQVIRNPCKDNQVSGPRRQPRDIQVVDPQRITPPWVLHSFDQRRGLFTETALRRLLQEPLPGEYAVSTLRTPLLFLPSEYQREDGAAESASGSPAKRPRIWSEESQTETISSEENPAETTRELLQRKLREQRALQFQLQHFAVQLAKTQANLHVNPLLSFPQ (SEQ ID NO: 196) |

TABLE 28

Exemplary *Anellovirus* ORF1 amino acid subsequence (*Alphatorquevirus*, Clade 5)

| | |
|---|---|
| Name | TTV-16 (TUS01) |
| Genus/Clade | *Alphatorquevirus*, Clade 5 |
| Accession Number | AB017613.1 |
| Protein Accession Number | BAA82454.1 |
| Full Sequence: 761 AA | |

```
1         10        20        30        40        50
|         |         |         |         |         |
MAYWFRRWGWRPRRRWRRWRRRRRRLPRRRTRRAVRGLGRRRKPRVRRRR
RTRRRTYRRGWRRRRYIRRGRRKKKLILTQWNPAIVKRCNIKGGLPIIIC
GEPRAAFNYGYHMEDYTPQPFPFGGGMSTVTFSLKALYDQYLKHQNRWTF
SNDQLDLARYRGCKLRFYRSPVCDFIVHYNLIPPLKMNQFTSPNTHPGLL
MLSKHKIIIPSFQTRPGGRRFVKIRLNPPKLFEDKWYTQQDLCKVPLVSI
TATAADLRYPFCSPQTNNPCTTFQVLRKNYNTVIGTSVKDQESTQDFENW
LYKTDSHYQTFATEAQLGRIPAFNPDGTKNTKQQSWQDNWSKKNSPWTGN
SGTYPQTTSEMYKIPYDSNFGFPTYRAQKDYILERRQCNFNYEVNNPVSK
KVWPQPSTTTPTVDYYEYHCGWFSNIFIGPNRYNLQFQTAYVDTTYNPLM
DKGKGNKIWFQYLSKKGTDYNEKQCYCTLEDMPLWAICFGYTDYVETQLG
PNVDHETAGLIIMICPYTQPPMYDKNRPNWGYVVYDTNFGNGKMPSGSGQ
VPVYWQCRWRPMLWFQQQVLNDISKTGPYAYRDEYKNVQLTLYYNFIENW
GGDMYYPQVVKNPCGDSGIVPGSGRFTREVQVVSPLSMGPAYIFHYFDSR
RGFFSEKALKRMQQQQEFDESFTFKPKRPKLSTAAAEILQLEEDSTSGEG
KSPLQQEEKEVEVLQTPTVQLQLQRNIQEQLAIKQQLQFLLLQLLKTQSN
LHLNPQFLSPS (SEQ ID NO: 197)
```

Annotations:

| Putative Domain | AA range |
|---|---|
| Arg-Rich Region | 1-75 |
| Jelly-roll domain | 75-284 |
| Hypervariable Region | 285-432 |
| N22 | 433-599 |
| C-terminal Domain | 600-780 |

TABLE 29

| Exemplary *Anellovirus* ORF1 amino acid subsequence (*Alphatorquevirus*, Clade 5) TTV-16(TUS01)-ORF1 (*Alphatorquevirus* Clade 5) | |
|---|---|
| Arg-Rich Region | MAYWFRRWGWRPRRRWRRWRRRRRRLPRRRTRRAVRGLG<br>RRRKPRVRRRRRRRRTYRRGWRRRRYIRRGRRKKK<br>(SEQ ID NO: 198) |
| Jelly-roll Domain | LILTQWNPAIVKRCNIKGGLPIIICGEPRAAFNYGYHME<br>DYTPQPFPFGGGMSTVTFSLKALYDQYLKHQNRWTFSND<br>QLDLARYRGCKLRFYRSPVCDFIVHYNLIPPLKMNQFTS<br>PNTHPGLLMLSKHKIIIPSFQTRPGGRRFVKIRLNPPKL<br>FEDKWYTQQDLCKVPLVSITATAADLRYPFCSPQTNNPC<br>TTFQVLRKNYNTVI (SEQ ID NO: 199) |
| Hyper-variable domain | GTSVKDQESTQDFENWLYKTDSHYQTFATEAQLGRIPAF<br>NPDGTKNTKQQSWQDNWSKKNSPWTGNSGTYPQTTSEMY<br>KIPYDSNFGFPTYRAQKDYILERRQCNFNYEVNNPVSKK<br>VWPQPSTTTPTVDYYEYHCGWFSNIFIGPNR (SEQ ID<br>NO: 200) |
| N22 | YNLQFQTAYVDTTYNPLMDKGKGNKIWFQYLSKKGTDYN<br>EKQCYCTLEDMPLWAICFGYTDYVETQLGPNVDHETAGL<br>IIMICPYTQPPMYDKNRPNWGYVVYDTNFGNGKMPSGSG<br>QVPVYWQCRWRPMLWFQQQVLNDISKTGPYAYRDEYKNV<br>QLTLYYNFIFN (SEQ ID NO: 201) |
| C-terminal domain | WGGDMYYPQVVKNPCGDSGIVPGSGRFTREVQVVSPLSM<br>GPAYIFHYFDSRRGFFSEKALKRMQQQQEFDESFTFKPK<br>RPKLSTAAAEILQLEEDSTSGEGKSPLQQEEKEVEVLQT<br>PTVQLQLQRNIQEQLAIKQQLQFLLLQLLKTQSNLHLNP<br>QFLSPS (SEQ ID NO: 202) |

TABLE 30

Exemplary *Anellovirus* ORF1 amino acid subsequence (*Alphatorquevirus*, Clade 6)

| | |
|---|---|
| Name | TTV-TJN02 |
| Genus/Clade | *Alphatorquevirus*, Clade 6 |
| Accession Number | AB028669.1 |
| Protein Accession Number | BAA94878.1 |
| Full Sequence: 746 AA | |

1 10 20 30 40 50

MAWGWWRWRRRWPARRWRRRRRRRPVRRTRARRPARRYRRRRTVRTRRRR
WGRRRYRRGWRRRTYVRKGRHRKKKKRLILRQWQPATRRRCTITGYLPIV
FCGHTRGNKNYALHSDDYTPQGQPFGGALSTTSFSLKVLFDQHORGLNKW
SFPNDQLDLARYRGCKFIFYRTKQTDWVGQYDISEPYKLDKYSCPNYHPG
NMIKAKHKFLIPSYDTNPRGRQKIIVKIPPPDLFVDKWYTQEDLCSVNLV
SLAVSAASFLHPFGSPQTDNPCYTFQVLKEFYYQAIGFSASTQAMTSVLD
TLYTQNSYWESNLTQFYVLNAKKGSDTTQPLTSNMPTREEFMAKKNTNYN
WYTYKAASVKNKLHQMRQTYFEELTSKGPQTTKSEEGYSQHWTTPSTNAY
EYHLGMFSAIFLAPDRPVPRFPCAYQDVTYNPLMDKGVGNHIWFQYNTKA
DTQLIVTGGSCKAHIQDIPLWAAFYGYSDFIESELGPFVDAETVGLVCVI
CPYTKPPMYNKTNPAMGYVFYDRNFGDGKWTDGRGKIEPYWQVRWRPEML
FQETVMADLVQTGPFSYKDELKNSTLVCKYKFYFTWGGNMMFQQTIKNPC
KTDGQPTDSSRHPRGIQVADPEQMGPRWVFHSFDWRRGYLSEKALKRLQE
KPLDYDEYFTQPKRPRIFPPTESAEGEFREPEKGSYSEEERSQASAEEQT
QEATVLLLKRRLREQQQLQQQLQFLTREMFKTQAGLHLNPMLLNQR
(SEQ ID NO: 203)

Annotations:

| Putative Domain | AA range |
|---|---|
| Arg-Rich Region | 1-77 |
| Jelly-roll domain | 78-286 |
| Hypervariable Region | 287-416 |
| N22 | 417-585 |
| C-terminal Domain | 586-746 |

TABLE 31

| Exemplary *Anellovirus* ORF1 amino acid subsequence (*Alphatorquevirus*, Clade 6) TTV-TJN02-ORF1 (*Alphatorquevirus* Clade 6) | |
|---|---|
| Arg-Rich Region | MAWGWWRWRRRWPARRWRRRRRRRPVRRTRARRPARRYR<br>RRRTVRTRRRRWGRRRYRRGWRRRTYVRKGRHRKKKKR<br>(SEQ ID NO: 204) |
| Jelly-roll Domain | LILRQWQPATRRRCTITGYLPIVFCGHTRGNKNYALHSD<br>DYTPQGQPFGGALSTTSFSLKVLFDQHQRGLNKWSFPND<br>QLDLARYRGCKFIFYRTKQTDWVGQYDISEPYKLDKYSC<br>PNYHPGNMIKAKHKFLIPSYDTNPRGRQKIIVKIPPPDL<br>FVDKWYTQEDLCSVNLVSLAVSAASFLHPFGSPQTDNPC<br>YTFQVLKEFYYQAI (SEQ ID NO: 205) |
| Hyper-variable domain | GFSASTQAMTSVLDTLYTQNSYWESNLTQFYVLNAKKGS<br>DTTQPLTSNMPTREEFMAKKNTNYNWYTYKAASVKNKLH<br>QMRQTYFEELTSKGPQTTKSEEGYSQHWTTPSTNAYEYH<br>LGMFSAIFLAPDR (SEQ ID NO: 206) |
| N22 | PVPRFPCAYQDVTYNPLMDKGVGNHIWFQYNTKADTQLI<br>VTGGSCKAHIQDIPLWAAFYGYSDFIESELGPFVDAETV<br>GLVCVICPYTKPPMYNKTNPAMGYVFYDRNFGDGKWTDG<br>RGKIEPYWQVRWRPEMLFQETVMADLVQTGPFSYKDELK<br>NSTLVCKYKFYFT (SEQ ID NO: 207) |
| C-terminal domain | WGGNMMFQQTIKNPCKTDGQPTDSSRHPRGIQVADPEQM<br>GPRWVFHSFDWRRGYLSEKALKRLQEKPLDYDEYFTQPK<br>RPRIFPPTESAEGEFREPEKGSYSEEERSQASAEEQTQE<br>ATVLLLKRRLREQQQLQQQLQFLTREMFKTQAGLHLNPM<br>LLNQR (SEQ ID NO: 208) |

TABLE 32

Exemplary *Anellovirus* ORF1 amino acid subsequence (*Alphatorquevirus*, Clade 7)

| | |
|---|---|
| Name | TTV-HD16d |
| Genus/Clade | *Alphatorquevirus*, Clade 7 |
| Accession Number | FR751479.1 |
| Protein Accession Number | NA |
| Full Sequence: 765 AA | |

1 10 20 30 40 50

MAWSWWWQRWRRRRWKPRRRRWRRLRWRRPRRAVRRRRRGRRVRRRRWAR
RRGRRRRYATRRKRRYRGRRFKKKLVLTQWHPNTMRRCLIKGIVPLVICG
HTRWNYNYALHSKDYTEEGRYPHGGALSTTTWSLKVLYDEHLKHHDFWGY
PNNQLDLARYKGAKFTFYRHKKTDFIIFFNRKPPFKLNKYSCASYHPGML
MQQRHKILLPSYETKPKGRPKITVRIKPPTLLEDKWYTQQDLCDVNLLQL
VVTAADFRHPLCSPQTNTPTTTFQVLKDIYYDTMSISEPTDSYTSVNNKS
TTQTFTNYSNTLENILYTRASYWNSFHATEYLNPNIIYKNGEKLFKEHED
LITWMTQTNNTGFLTKNNTAFGNNSYRPNADKIKKARKTYWNALIGTNDL
ATNIGQARAERFEYHLGWYSPIFLSRHRSNMNFARAYQDVTYNPNCDRGV
NNRVWVQPLTKPTTEFDEKRCKCVVQHLPLWAALYCYQDFVEEELGSSSE
ILNSCLLVLQCPYTFPPMYDKKLPDKGFVFYDSLFGDGKMSDGRGQVDIF
WQQRWYPRLATQMQVMHDITMTGPFSYRDELVSTQLTAKYTFDEMWGGNM
ISTQIIKNPCKDSGLEPAYPGRQRRDLQIVDPYSMGPQFSFHNWDYRHGL
FGQDAIDRVSKQPKDDADYPNPYKRPRYFPPTDQAAQEQEKDFSFLKTAP
SNSEESDQEVLQETQVLRFQPEQHKQLHLQLAERQRIGEQLRYLLQQMFK
TQANLHLNPYTFTQL (SEQ ID NO: 209)

Annotations:

| Putative Domain | AA range |
|---|---|
| Arg-Rich Region | 1-74 |
| Jelly-roll domain | 75-286 |
| Hypervariable Region | 287-428 |
| N22 | 429-595 |
| C-terminal Domain | 596-765 |

TABLE 33

| Exemplary *Anellovirus* ORF1 amino acid subsequence (*Alphatorquevirus*, Clade 7) TTV-HD16d-ORF1 (*Alphatorquevirus* Clade 7) | |
|---|---|
| Arg-Rich Region | MAWSWWWQRWRRRRWKPRRRRWRRLRWRRPRRAVRRRRR GRRVRRRRWARRRGRRRRYATRRKRRYRGRRFKKK (SEQ ID NO: 210) |
| Jelly-roll Domain | LVLTQWHPNTMRRCLIKGIVPLVICGHTRWNYNYALHSK DYTEEGRYPHGGALSTTTWSLKVLYDEHLKHHDFWGYPN NQLDLARYKGAKFTFYRHKKTDFIIFFNRKPPFKLNKYS CASYHPGMLMQQRHKILLPSYETKPKGRPKITVRIKPPT LLEDKWYTQQDLCDVNLLQLVVTAADFRHPLCSPQTNTP TTTFQVLKDIYYDTMSI (SEQ ID NO: 211) |
| Hyper-variable domain | SEPTDSYTSVNNKSTTQTFTNYSNTLENILYTRASYWNS FHATEYLNPNIIYKNGEKLFKEHEDLITWMTQTNNTGFL TKNNTAFGNNSYRPNADKIKKARKTYWNALIGTNDLATN IGQARAERFEYHLGWYSPIFLSRHR (SEQ ID NO: 212) |
| N22 | SNMNFARAYQDVTYNPNCDRGVNNRVWVQPLTKPTTEFD EKRCKCVVQHLPLWAALYCYQDFVEEELGSSSEILNSCL LVLQCPYTFPPMYDKKLPDKGFVFYDSLFGDGKMSDGRG QVDIFWQQRWYPRLATQMQVMHDITMTGPFSYRDELVST QLTAKYTFDFM (SEQ ID NO: 213) |
| C-terminal domain | WGGNMISTQIIKNPCKDSGLEPAYPGRQRRDLQIVDPYS MGPQFSFHNWDYRHGLFGQDAIDRVSKQPKDDADYPNPY KRPRYFPPTDQAAQEQEKDFSFLKTAPSNSEESDQEVLQ ETQVLRFQPEQHKQLHLQLAERQRIGEQLRYLLQQMFKT QANLHLNPYTFTQL (SEQ ID NO: 214) |

TABLE 34

Exemplary *Anellovirus* ORF1 amino acid subsequence (*Betatorquevirus*)

| | |
|---|---|
| Name | Ring2 |
| Genus/Clade | *Betatorquevirus* |
| Accession Number | JX134045.1 |
| Protein Accession Number | AGG91484.1 |
| Full Sequence: 666 AA | |

```
1         10        20        30        40        50
|         |         |         |         |         |
MPYYYRRRRYNYRRPRWYGRGWIRRPFRRRFRRKRRVRPTYTTIPLKQWQ
PPYKRTCYIKGQDCLIYYSNLRLGMNSTMYEKSIVPVHWPGGGSFSVSML
TLDALYDIHKLCRNWWTSTNQDLPLVRYKGCKITFYQSTFTDYIVRIHTE
LPANSNKLTYPNTHPLMMMMSKYKHIIPSRQTRRKKKPYTKIFVKPPPQF
ENKWYFATDLYKIPLLQIHCTACNLQNPFVKPDKLSNNVTLWSLNTISIQ
NRNMSVDQGQSWPFKILGTQSFYFYFYTGANLPGDTTQIPVADLLPLINP
RINRPGQSLNEAKITDHITFTEYKNKFTNYWGNPENKHIQEHLDMILYSL
KSPEAIKNEWTTENMKWNQLNNAGTMALTPFNEPIFTQIQYNPDRDTGED
TQLYLLSNATGTGWDPPGIPELILEGFPLWLIYWGFADFQKNLKKVTNID
TNYMLVAKTKFTQKPGTFYLVILNDTFVEGNSPYEKQPLPEDNIKWYPQV
QYQLEAQNKLLQTGPFTPNIQGQLSDNISMFYKFYFKWGGSPPKAINVEN
PAHQIQYPIPRNEHETTSLQSPGEAPESILYSFDYRHGNYTTTALSRISQ
DWALKDTVSKITEPDRQQLLKQALECLQISEETQEKKEKEVQQLISNLRQ
QQQLYRERIISLLKDQ (SEQ ID NO: 215)
```

Annotations:

| Putative Domain | AA range |
|---|---|
| Arg-Rich Region | 1-38 |
| Jelly-roll domain | 39-246 |
| Hypervariable Region | 247-374 |
| N22 | 375-537 |
| C-terminal Domain | 538-666 |

TABLE 35

| Exemplary *Anellovirus* ORF1 amino acid subsequence (*Betatorquevirus*) Ring2 ORF1 (*Betatorquevirus*) | |
|---|---|
| Arg-Rich Region | MPYYYRRRRYNYRRPRWYGRGWIRRPFRRRFRRKRRVR (SEQ ID NO: 216) |
| Jelly-roll Domain | PTYTTIPLKQWQPPYKRTCYIKGQDCLIYYSNLRLGMNS TMYEKSIVPVHWPGGGSFSVSMLTLDALYDIHKLCRNWW TSTNQDLPLVRYKGCKITFYQSTFTDYIVRIHTELPANS NKLTYPNTHPLMMMMSKYKHIIPSRQTRRKKKPYTKIFV KPPPQFENKWYFATDLYKIPLLQIHCTACNLQNPFVKPD KLSNNVTLWSLNT (SEQ ID NO: 217) |
| Hyper-variable domain | ISIQNRNMSVDQGQSWPFKILGTQSFYFYFYTGANLPGD TTQIPVADLLPLTNPRINRPGQSLNEAKITDHITFTEYK NKFTNYWGNPFNKHIQEHLDMILYSLKSPEAIKNEWTTE NMKWNQLNNAG (SEQ ID NO: 218) |
| N22 | TMALTPFNEPIFTQIQYNPDRDTGEDTQLYLLSNATGTG WDPPGIPELILEGFPLWLIYWGFADFQKNLKKVTNIDTN YMLVAKTKFTQKPGTFYLVILNDTFVEGNSPYEKQPLPE DNIKWYPQVQYQLEAQNKLLQTGPFTPNIQGQLSDNISM FYKFYFK (SEQ ID NO: 219) |
| C-terminal domain | WGGSPPKAINVENPAHQIQYPIPRNEHETTSLOSPGEAP ESILYSFDYRHGNYTTTALSRISQDWALKDTVSKITEPD RQQLLKQALECLQISEETQEKKEKEVQQLISNLRQQQQL YRERIISLLKDQ (SEQ ID NO: 220) |

TABLE 36

Exemplary *Anellovirus* ORF1 amino acid subsequence (*Gammatorquevirus*)

| | |
|---|---|
| Name | TTMDV-MD1-073 |
| Genus/Clade | *Gammatorquevirus* |
| Accession Number | AB290918.1 |
| Protein Accession Number | BAG49427.1 |
| Full Sequence: 673 AA | |

```
1         10        20        30        40        50
|         |         |         |         |         |
MPFWWGRRNKFWYGRNYRRKKRRFPKRRKRRFYRRTKYRRPARRRRRRRR
KVRRKKKTLIVRQWQPDSIVLCKIKGYDSIIWGAEGTQFQCSTHEMYEYT
RQKYPGGGGFGVQLYSLEYLYDQWKLRNNIWTKTNQLKDLCRYLKCVMTF
YRHQHIDFVIVYERQPPFEIDKLTYMKYHPYMLLQRKHKIILPSQTTNPR
GKLKKKKTIKPPKQMLSKWFFQQQFAKYDLLLIAAAACSLRYPRIGCCNE
NRMITLYCLNTKFYQDTEWGTTKQAPHYFKPYATINKSMIFVSNYGGKKT
EYNIGQWIETDIPGEGNLARYYRSISKEGGYFSPKILQAYQTKVKSVDYK
PLPIVLGRYNPAIDDGKGNKIYLQTIMNGHWGLPQKTPDYIIEEVPLWLG
FWGYYNYLKQTRTEAIFPLHMFVVQSKYIQTQQTETPNNFWAFIDNSFIQ
GKNPWDSVITYSEQKLWFPTVAWQLKTINAICESGPYVPKLDNQTYSTWE
LATHYSFHFKWGGPQISDQPVEDPGNKNKYDVPDTIKEALQIVNPAKNIA
ATMFHDWDYRRGCITSTAIKRMQQNLPTDSSLESDSDSEPAPKKKRLLPV
LHDPQKKTEKINQCLLSLCEESTCQEQETEENILKLIQQQQQQQKLKHN
LLVLIKDLKVKQRLLQLQTGVLE (SEQ ID NO: 221)
```

Annotations:

| Putative Domain | AA range |
|---|---|
| Arg-Rich Region | 1-57 |
| Jelly-roll domain | 58-259 |
| Hypervariable Region | 260-351 |
| N22 | 352-510 |
| C-terminal Domain | 511-673 |

TABLE 37

Exemplary *Anellovirus* ORF1 amino acid subsequence (*Gammatorquevirus*)
TTV-HD16d-ORF1 (*Gammatorquevirus*)

| | |
|---|---|
| Arg-Rich Region | MPFWWGRRNKFWYGRNYRRKKRRFPKRRKRRFYRRTKYR RPARRRRRRRRKVRRKKK (SEQ ID NO: 222) |
| Jelly-roll Domain | TLIVRQWQPDSIVLCKIKGYDSIIWGAEGTQFQCSTHEM YEYTRQKYPGGGGFGVQLYSLEYLYDQWKLRNNIWTKTN QLKDLCRYLKCVMTFYRHQHIDFVIVYERQPPFEIDKLT YMKYHPYMLLQRKHKIILPSQTTNPRGKLKKKKTIKPPK QMLSKWFFQQQFAKYDLLLIAAAACSLRYPRIGCCNENR MITLYCL (SEQ ID NO: 223) |
| Hyper-variable domain | NTKFYQDTEWGTTKQAPHYFKPYATINKSMIFVSNYGGK KTEYNIGQWIETDIPGEGNLARYYRSISKEGGYFSPKIL QAYQTKVKSVDYKP (SEQ ID NO: 224) |
| N22 | LPIVLGRYNPAIDDGKGNKIYLQTIMNGHWGLPQKTPDY IIEEVPLWLGFWGYYNYLKQTRTEAIFPLHMFVVQSKYI QTQQTETPNNFWAFIDNSFIQGKNPWDSVITYSEQKLWF PTVAWQLKTINAICESGPYVPKLDNQTYSTWELATHYSF HFK (SEQ ID NO: 225) |
| C-terminal domain | WGGPQISDQPVEDPGNKNKYDVPDTIKEALQIVNPAKNI AATMFHDWDYRRGCITSTAIKRMQQNLPTDSSLESDSDS EPAPKKKRLLPVLHDPQKKTEKINQCLLSLCEESTCQEQ ETEENILKLIQQQQQQQKLKHNLLVLIKDLKVKQRLLQ LQTGVLE (SEQ ID NO: 226) |

TABLE D1

Exemplary *Anellovirus* ORF1 amino acid subsequence (*Gammatorquevirus*)

| | |
|---|---|
| Name | Ring 3.1 |
| Genus/Clade | *Gammatorquevirus* |

TABLE D1-continued

Exemplary *Anellovirus* ORF1 amino acid subsequence (*Gammatorquevirus*)

Accession Number
Protein Accession Number
Full Sequence: 677 AA

```
1         10        20        30        40        50
|         |         |         |         |         |
MPFWWRRRNKRWWGRRFRYRRYNKYKTRRRRRIPRRRNRRFTKTRRRRKR
KKVRRKLKKITIKQWQPDSVKKCKIKGYSTLVMGAQGKQYNCYTNQASDY
VQPKAPQGGGFGCEVFNLKWLYQEYTAHRNIWTKTNEYTDLCRYTGAQII
LYRHPDVDFIVSWDNQPPFLLNKYTYPELQPQNLLLARRKRIILSQKSNP
KGKLRIKLRIPPPKQMITKWFFQRDFCDVNLFKLCASAASFRYPGISHGA
QSTIFSAYALNTDFYQCSDWCQTNTETGYLNIKTQQMPLWFHYREGGKEK
WYKYTNKEHRPYTNTYLKSISYNDGLFSPKAMFAFEVKAGGEGTTEPPQG
AQLIANLPLIALRYNPHEDTGHGNEIYLTSTFKGTYDKPKVTDALYENNV
PLWMGFYGYWDFILQETKNKGVFDQHMFVVKCPALRPISQVTKQVYYPLV
DMDFCSGRLPFDEYLSKDIKSHWYPTAERQTVTINNFVTAGPYMPKFEPT
DKDSTWQLNYHYKFFFKWGGPQVTDPTVEDPCSRNKYPVPDTMQQTIQIK
NPEKLHPATLFHDWDLRRGFITQAAIKRMSENLQIDSSFESDGTESPKKK
KRCTKEIPTQNQKQEEIQECLLSLCEEPTCQEETEDLQLFIQQQQQQYK
LRKNLFKLLTHLKKGQRISQLQTGLLE (SEQ ID NO: 919)
```

Annotations:

| Putative Domain | AA range |
|---|---|
| Arg-Rich Region | 1-59 |
| Jelly-roll domain | 60-260 |
| Hypervariable Region | 261-356 |
| N22 | 357-517 |
| C-terminal Domain | 518-677 |

TABLE D2

Exemplary *Anellovirus* ORF1 amino acid subsequence (*Gammatorquevirus*)
Ring3.1 (*Gammatorquevirus*)

| | |
|---|---|
| Arg-Rich Region | MPFWWRRRNKRWWGRRFRYRRYNKYKTRRRRRIPRRRNRRFTKTRR RRKRKKVRRKLKK (SEQ ID NO: 920) |
| Jelly-roll Domain | ITIKQWQPDSVKKCKIKGYSTLVMGAQGKQYNCYTNQASDYVQPKAP QGGGFGCEVFNLKWLYQEYTAHRNIWTKTNEYTDLCRYTGAQIILYR HPDVDFIVSWDNQPPFLLNKYTYPELQPQNLLLARRKRIILSQKSNPKG KLRIKLRIPPPKQMITKWFFQRDFCDVNLFKLCASAASFRYPGISHGAQS TIFSAYAL (SEQ ID NO: 921) |
| Hypervariable domain | NTDFYQCSDWCQTNTETGYLNIKTQQMPLWFHYREGGKEKWYKYTN KEHRPYTNTYLKSISYNDGLFSPKAMFAFEVKAGGEGTTEPPQGAQLIA N (SEQ ID NO: 922) |
| N22 | LPLIALRYNPHEDTGHGNEIYLTSTFKGTYDKPKVTDALYFNNVPLWM GFYGYWDFILQETKNKGVFDQHMFVVKCPALRPISQVTKQVYYPLVD MDFCSGRLPFDEYLSKDIKSHWYPTAERQTVTINNFVTAGPYMPKFEPT DKDSTWQLNYHYKFFFK (SEQ ID NO: 923) |
| C-terminal domain | WGGPQVTDPTVEDPCSRNKYPVPDTMQQTIQIKNPEKLHPATLFHDWD LRRGFITQAAIKRMSENLQIDSSFESDGTESPKKKKRCTKEIPTQNQKQE EIQECLLSLCEEPTCQEETEDLQLFIQQQQQQYKLRKNLFKLLTHLKK GQRISQLQTGLLE (SEQ ID NO: 924) |

TABLE D3

| Exemplary *Anellovirus* ORF1 amino acid subsequence (*Gammatorquevirus*) | |
|---|---|
| Name | Ring 4 |
| Genus/Clade | *Gammatorquevirus* |
| Accession Number | |
| Protein Accession Number | |
| Full Sequence: 662 AA | |

```
1         10         20         30         40         50
|         |          |          |          |          |
MPFWWRRRRKFWTNNRFNYTKRRRYRKRWPRRRRRRRPYRRPVRRRRRKL
RKVKRKKKSLIVRQWQPDSIRTCKIIGQSAIVVGAEGKQMYCYTVNKLIN
VPPKTPYGGGFGVDQYTLKYLYEEYRFAQNIWTQSNVLKDLCRYINVKLI
FYRDNKTDFVLSYDRNPPFQLTKFTYPGAHPQQIMLQKHHKFILSQMTKP
NGRLTKKLKIKPPKQMLSKWFFSKQFCKYPLLSLKASALDLRHSYLGCCN
ENPQVFFYYLNHGYYTITNWGAQSSTAYRPNSKVIDTTYYRYKNDRKNIN
IKSHEYEKSISYENGYFQSSFLQTQCIYTSERGEACIAEKPLGIAIYNPV
KDNGDGNMIYLVSTLANTWDQPPKDSAILIQGVPIWLGLFGYLDYCRQIK
ADKTWLDSHVLVIQSPAIFTYPNPGAGKWYCPLSQSFINGNGPFNQPPTL
LQKAKWFPQIQYQQEIINSFVESGPFVPKYANQTESNWELKYKYVFTFKW
GGPQFHEPEIADPSKQEQYDVPDTFYQTIQIEDPEGQDPRSLIHDWDYRR
GFIKERSLKRMSTYFSTHTDQQATSEEDIPKKKKRIGPQLTVPQQKEEET
LSCLLSLCKKDTFQETETQEDLQQLIKQQQEQQLLLKRNILQLIHKLKEN
QQMLQLHTGMLP(SEQ ID NO: 925)
```

Annotations:

| Putative Domain | AA range |
|---|---|
| Arg-Rich Region | 1-58 |
| Jelly-roll domain | 59-260 |
| Hypervariable Region | 261-339 |
| N22 | 340-499 |
| C-terminal Domain | 500-662 |

TABLE D4

Exemplary *Anellovirus* ORF1 amino acid subsequence (*Gammatorquevirus*)
Ring4 (*Gammatorquevirus*)

| | |
|---|---|
| Arg-Rich Region | MPFWWRRRRKFWTNNRFNYTKRRRYRKRWPRRRRRRRPYRRPVRRR RRKLRKVKRKKK (SEQ ID NO: 926) |
| Jelly-roll Domain | SLIVRQWQPDSIRTCKIIGQSAIVVGAEGKQMYCYTVNKLINVPPKTPY GGGFGVDQYTLKYLYEEYRFAQNIWTQSNVLKDLCRYINVKLIFYRDN KTDFVLSYDRNPPFQLTKFTYPGAHPQQIMLQKHHKFILSQMTKPNGR LTKKLKIKPPKQMLSKWFFSKQFCKYPLLSLKASALDLRHSYLGCCNE NPQVFFYYL (SEQ ID NO: 927) |
| Hypervariable domain | NHGYYTITNWGAQSSTAYRPNSKVTDTTYYRYKNDRKNINIKSHEYEK SISYENGYFQSSFLQTQCIYTSERGEACIAE (SEQ ID NO: 928) |
| N22 | KPLGIAIYNPVKDNGDGNMIYLVSTLANTWDQPPKDSAILIQGVPIWLG LFGYLDYCRQIKADKTWLDSHVLVIQSPAIFTYPNPGAGKWYCPLSQSF INGNGPFNQPPTLLQKAKWFPQIQYQQEIINSFVESGPFVPKYANQTESN WELKYKYVFTFK (SEQ ID NO: 929) |
| C-terminal domain | WGGPQFHEPEIADPSKQEQYDVPDTFYQTIQIEDPEGQDPRSLIHDWDY RRGFIKERSLKRMSTYFSTHTDQQATSEEDIPKKKKRIGPQLTVPQQKE EETLSCLLSLCKKDTFQETETQEDLQQLIKQQQEQQLLLKRNILQLIHKL KENQQMLQLHTGMLP (SEQ ID NO: 930) |

TABLE D5

Exemplary *Anellovirus* ORF1 amino acid subsequence (*Alphatorquevirus*) Clade 1

| | |
|---|---|
| Name | Ring 5.2 |
| Genus/Clade | *Alphatorquevirus* Clade 1 |
| Accession Number | |
| Protein Accession Number | |
| Full Sequence: 728 AA | |

```
1         10         20         30         40         50
|         |          |          |          |          |
TAWWWGRWRRRWRRRRPYTTRLRRRRARRAFPRRRRRRFVSRRWRRPYRR
RRRRGRRRRRRRRRHKPTLILRQWQPDCIRHCKITGWMPLIICGKGSTQF
NYITHADDITPRGASYGGNFTNMTFSLEAIYEQFLYHRNRWSASNHDLEL
CRYKGTTLKLYRHPEVDYIVTYSRTGPFEISHMTYLSTHPMLMLLNKHHI
VVPSLKTKPRGRKAIKVRIRPPKLMNNKWYFTRDFCNIGLFQLWATGLEL
RNPWLRMSTLSPCIGENVLKNSIYTNLSNLPQYKNERLNIINNILHPQEI
TGTNNKKWQYTYTKLMAPIYYSANRASTYDWENYSKETNYNNTYVKFTQK
RQEKLTKIRKEWQMLYPQQPTALPDSYDLLQEYGLYSPYYLNPTRINLDW
MTPYTHVRYNPLVDKGFGNRIYIQWCSEADVSYNRTKSKCLLQDMPLFFM
CYGYIDWAIKNTGVSSLVKDARICIRCPYTEPQLVGSTEDIGFVPISETF
MRGDMPVLAPYIPLSWFCKWYPNIAHQKEVLESIISCSPFMPRDQDMNGW
DITIGYKMDFLWGGSPLPSQPIDDPCQQGTHPIPDPDKHPRLLQVSNPKL
LGPRTVFHKWDIRRGQFSKRSIKRVSEYSSDDESLAPGLPSKRNKLDSAF
RGENREQKECYSLLKALEEEETPEEEEPAPQEKAQKEELLHQLQLQRRHQ
RVLRRGLKLVFTDILRLRQGVHWNPELT (SEQ ID NO: 931)
```

Annotations:

| Putative Domain | AA range |
|---|---|
| Arg-Rich Region | 1-66 |
| Jelly-roll domain | 67-277 |
| Hypervariable Region | 278-395 |
| N22 | 396-561 |
| C-terminal Domain | 562-728 |

TABLE D6

Exemplary *Anellovirus* ORF1 amino acid subsequence (*Alphatorquevirus*) Clade 1 Ring5.2 (*Alphatorquevirus*) Clade 1

| | |
|---|---|
| Arg-Rich Region | TAWWWGRWRRRWRRRRPYTTRLRRRRARRAFPRRRRRRFVSRRWRR PYRRRRRRGRRRRRRRRRHK (SEQ ID NO: 932) |
| Jelly-roll Domain | PTLILRQWQPDCIRHCKITGWMPLIICGKGSTQFNYITHADDITPRGASY GGNFTNMTFSLEAIYEQFLYHRNRWSASNHDLELCRYKGTTLKLYRHP EVDYIVTYSRTGPFEISHMTYLSTHPMLMLLNKHHIVVPSLKTKPRGRK AIKVRIRPPKLMNNKWYFTRDFCNIGLFQLWATGLELRNPWLRMSTLS PCIGFNVLKNSIYTNL (SEQ ID NO: 933) |
| Hypervariable domain | SNLPQYKNERLNIINNILHPQEITGTNNKKWQYTYTKLMAPIYYSANRA STYDWENYSKETNYNNTYVKFTQKRQEKLTKIRKEWQMLYPQQPTAL PDSYDLLQEYGLYSPYYLNPTR (SEQ ID NO: 934) |
| N22 | INLDWMTPYTHVRYNPLVDKGFGNRIYIQWCSEADVSYNRTKSKCLL QDMPLFFMCYGYIDWAIKNTGVSSLVKDARICIRCPYTEPQLVGSTEDI GFVPISETFMRGDMPVLAPYIPLSWFCKWYPNIAHQKEVLESIISCSPFM PRDQDMNGWDITIGYKMDFL (SEQ ID NO: 935) |
| C-terminal domain | WGGSPLPSQPIDDPCQQGTHPIPDPDKHPRLLQVSNPKLLGPRTVFHKW DIRRGQFSKRSIKRVSEYSSDDESLAPGLPSKRNKLDSAFRGENREQKE CYSLLKALEEEETPEEEEPAPQEKAQKEELLHQLQLQRRHQRVLRRGL KLVFTDILRLRQGVHWNPELT (SEQ ID NO: 936) |

TABLE D7

| Exemplary *Anellovirus* ORF1 amino acid subsequence (*Alphatorquevirus*)-Clade 3 | |
|---|---|
| Name | Ring6.0 |
| Genus/Clade | *Alphatorquevirus* Clade 3 |
| Accession Number | |
| Protein Accession Number | |
| Full Sequence: 767 AA | |

```
1         10        20        30        40        50
|         |         |         |         |         |
MAYGWWRRRRRRPWWRRRWRRWRRRRRPRRRRPRRRYRRRRTVRRRGRGR
WTRAHRRWRRKGKRSRKKKIIIRQWQPNYTRRCNIVGYMPLLICGENTVA
TNYATHSDDSYYPGPFGGGMTTDKFTLRILYDEYKREMNYWTSSNEDLDL
CRYLGCTLYVFRHPEVDFIIIINTSPPFLDTEITGPSIHPGMMALNKRSR
WIPSIKNRPGRKHYIKIKVGAPRMFTDKWYPQTDLCDMTLLTIFASAADM
QYPFGSPLTDTIVVSFQVLQSMYNDCLSVLPDNFAETSGKGTQLHENIIQ
HLPYYNTTQTQAQFKRFIENMNATNGDNIWASYINTTKFSSANTPKNDTG
IGGPYTTYSDSWYKGTVYNDKIKTIPIKASKLYYEQTKNLIGITFTGSTH
RLHYCGGLYSSVWLSAGRSYFETKGPYTDITYNPFSDRGEGNMLWIDWLT
KNDSVYSKTSSKCLIENLPLWASVYGYKEYCSKVTGDTNIEHNCRCVIRS
PYTVPQLLDHNNPFRGYVPYSFNFGNGKMPGGSSLVPIRMRAKWYPTLFH
QKEVLEAIAQAGPFAYHSDIKKVSLGIKYRFKWVWGGNPVSQQVVRNPCK
TTQGSSGNRVPRSIQVVDPRYNTPELTIHAWDFRHGFFGRKAIKRMQEQP
IPHDTFSAGFKRSRRDTEALQCSQEEQQKENLLFPVQQLKRVPPWETSQE
SQSEEENSQKQETLSQQLRDQLHKQRLMGEQLRSLLYQMQRVQQNQHINP
MLLPKGLALTSISHNVI (SEQ ID NO: 937)
```

Annotations:

| Putative Domain | AA range |
|---|---|
| Arg-Rich Region | 1-69 |
| Jelly-roll domain | 70-269 |
| Hypervariable Region | 270-424 |
| N22 | 425-584 |
| C-terminal Domain | 585-767 |

TABLE D8

| Exemplary *Anellovirus* ORF1 amino acid subsequence (*Alphatorquevirus*)-Clade 3 Ring6.0 (*Alphatorquevirus*) | |
|---|---|
| Arg-Rich Region | MAYGWWRRRRRRPWWRRRWRRWRRRRRPRRRRPRRRYRRRRTVRR RGRGRWTRAHRRWRRKGKRSRKKK (SEQ ID NO: 938) |
| Jelly-roll Domain | IIIRQWQPNYTRRCNIVGYMPLLICGENTVATNYATHSDDSYYPGPFGG GMTTDKFTLRILYDEYKRFMNYWTSSNEDLDLCRYLGCTLYVFRHPE VDFIIIINTSPPFLDTEITGPSIHPGMMALNKRSRWIPSIKNRPGRKHYIKI KVGAPRMFTDKWYPQTDLCDMTLLTIFASAADMQYPFGSPLTDTIVVS FQVL (SEQ ID NO: 939) |
| Hypervariable domain | QSMYNDCLSVLPDNFAETSGKGTQLHENIIQHLPYYNTTQTQAQFKRFI ENMNATNGDNIWASYINTTKFSSANTPKNDTGIGGPYTTYSDSWYKGT VYNDKIKTIPIKASKLYYEQTKNLIGITFTGSTHRLHYCGGLYSSVWLSA GRSYFETK (SEQ ID NO: 940) |
| N22 | GPYTDITYNPFSDRGEGNMLWIDWLTKNDSVYSKTSSKCLIENLPLWA SVYGYKEYCSKVTGDTNIEHNCRCVIRSPYTVPQLLDHNNPFRGYVPY SFNFGNGKMPGGSSLVPIRMRAKWYPTLFHQKEVLEAIAQAGPFAYHS DIKKVSLGIKYRFKWV (SEQ ID NO: 941) |
| C-terminal domain | WGGNPVSQQVVRNPCKTTQGSSGNRVPRSIQVVDPRYNTPELTIHAWD FRHGFFGRKAIKRMQEQPIPHDTFSAGFKRSRRDTEALQCSQEEQQKEN LLFPVQQLKRVPPWETSQESQSEEENSQKQETLSQQLRDQLHKQRLMG EQLRSLLYQMQRVQQNQHINPMLLPKGLALTSISHNVI (SEQ ID NO: 942) |

TABLE D9

| Exemplary *Anellovirus* ORF1 amino acid subsequence (*Alphatorquevirus*)-Clade 7 | |
|---|---|
| Name | Ring 7.0 |
| Genus/Clade | *Alphatorquevirus*-Clade 7 |
| Accession Number | |
| Protein Accession Number | |
| Full Sequence: 766 AA | |

```
1         10         20         30         40         50
|         |          |          |          |          |
MAWRWWWQRRWRRRRWPRRRWRRLRRRRPRRPVRRRRRRTTVRRRRWRGR
RGRRTYTRRAVRRRRRPRKRLVLTQWSPQTVRNCSIRGIVPMVICGHTKA
GRNYAIHSEDFTTQIQPFGGSFSTTTWSLKVLWDEHQKFQNRWSYPNTQL
DLARYRGVTFWFYRDQKTDYIVQWSRNPPFKLNKYSSAMYHPGMMMQAKR
KLVVPSFQTRPKGKKRYRVTIKPPNMFADKWYTQEDLCPVPLVQIVVSAA
SLLHPFCPPQTNNPCITFQVLKDIYDECIGVNETMKDKYKKLQTTLYTTC
TYYQTTQVLAQLSPAFQPAMKPTTTQSAATATTLGNYVPELKYNNGSFHT
GQNAVFGMCSYKPTDSIMTKANGWFWQNLMVDNNLHSSYGKATLECMEYH
TGIYSSIFLSPQRSLEFPAAYQDVTYNPNCDRAVGNVVWFQYSTKMDTNF
DETKCKCVLKNIPLWAAFNGYSDFIMQELSISTEIHNFGIVCFQCPYTFP
PCFNKNKPLKGYVFYDTTFGNGKMPDGSGHVPIYWQQRWWIRLAFQVQVM
HDFVLTGPFSYKDDLANTTLTARYKFKFKWGGNIIPEQIIKNPCHREQSL
ASYPDRQRRDLQVVDPSTMGPIYTFHTWDWRRGLFGADAIQRVSQKPGDA
LRFTNPFKRPRYLPPTDREDYRQEEDFALQEKRRRTSTEEAQDEESPPES
APLLQQQQQQRQLSVHLAEQQRLGVQLRYILQEVLKTQAGLHLNPLLLGP
PQTRSISLSPPKAYSP (SEQ ID NO: 943)
```

Annotations:

| Putative Domain | AA range |
|---|---|
| Arg-Rich Region | 1-70 |
| Jelly-roll domain | 71-271 |
| Hypervariable Region | 272-418 |
| N22 | 419-579 |
| C-terminal Domain | 580-766 |

TABLE D10

| Exemplary *Anellovirus* ORF1 amino acid subsequence (*Alphatorquevirus*)-Clade 7 Ring7.0 (*Alphatorquevirus*) | |
|---|---|
| Arg-Rich Region | MAWRWWWQRRWRRRRWPRRRWRRLRRRRPRRPVRRRRRRTTVRRRRWRGRRGRRTYTRRAVRRRRRPRKR (SEQ ID NO: 944) |
| Jelly-roll Domain | LVLTQWSPQTVRNCSIRGIVPMVICGHTKAGRNYAIHSEDFTTQIQPFGGSFSTTTWSLKVLWDEHQKFQNRWSYPNTQLDLARYRGVTFWFYRDQKTDYIVQWSRNPPFKLNKYSSAMYHPGMMMQAKRKLVVPSFQTRPKGKKRYRVTIKPPNMFADKWYTQEDLCPVPLVQIVVSAASLLHPFCPPQTNNPCITFQVL (SEQ ID NO: 945) |
| Hypervariable domain | KDIYDECIGVNETMKDKYKKLQTTLYTTCTYYQTTQVLAQLSPAFQPAMKPTTTQSAATATTLGNYVPELKYNNGSFHTGQNAVFGMCSYKPTDSIMTKANGWFWQNLMVDNNLHSSYGKATLECMEYHTGIYSSIFLSPQRSLEFP (SEQ ID NO: 946) |
| N22 | AAYQDVTYNPNCDRAVGNVVWFQYSTKMDTNFDETKCKCVLKNIPLWAAFNGYSDFIMQELSISTEIHNFGIVCFQCPYTFPPCFNKNKPLKGYVFYDTTFGNGKMPDGSGHVPIYWQQRWWIRLAFQVQVMHDFVLTGPFSYKDDLANTTLTARYKFKFK (SEQ ID NO: 947) |
| C-terminal domain | WGGNIIPEQIIKNPCHREQSLASYPDRQRRDLQVVDPSTMGPIYTFHTWDWRRGLFGADAIQRVSQKPGDALRFTNPFKRPRYLPPTDREDYRQEEDFALQEKRRRTSTEEAQDEESPPESAPLLQQQQQQRQLSVHLAEQQRLGVQLRYILQEVLKTQAGLHLNPLLLGPPQTRSISLSPPKAYSP (SEQ ID NO: 948) |

TABLE D11

| Ring10 ORF1 amino acid subsequence (*Betatorquevirus*) | |
|---|---|
| Arg-Rich Region (1-45) | MPWWYRRRSYNPWRRRNWFRRPRKTIYRRYRRRRRWVR RKPFYKR |
| Jelly-roll Domain (46-229) | KIKRLNIVEWQPKSIRKCRIKGMLCLFQTTEDRLSYNFDMY EESIIPEKLPGGGGFSIKNISLYALYQEHIHAHNIFTHTNTDR PLARYTGCSLKFYQSKDIDYVVTYSTSLPLRSSMGMYNSM QPSIHLMQQNKLIVPSKQTQKRRKPYIKKHISPPTQMKSQW YFQHNIANIPLLMIRTTAL |
| Hypervariable domain (230-385) | TLDNYYIGSRQLSTNVTIHTLNTTYIQNRDWGDRNKTYYC QTLGTQRYFLYGTHSTAQNINDIKLQELIPLTNTQDYVQGF DWTEKDKHNITTYKEFLTKGAGNPFHAEWITAQNPVIHTA NSPTQIEQIYTASTTTFQNKKLTDLPTPGYIFITP |
| N22 domain (386-543) | TVSLRYNPYKDLAERNKCYFVRSKINAHGWDPEQHQELIN SDLPQWLLLFGYPDYIKRTQNFALVDTNYILVDHCPYTNPE KTPFIPLSTSFIEGRSPYSPSDTHEPDEEDQNRWYPCYQYQQ ESINSICLSGPGTPKIPKGITAEAKVKYSFNFKWG |
| C-terminal domain (544-672) | GDLPPMSTITNPTDQPTYVVPNNFNETTSLQNPTTRPEHFLY SFDERRGQLTEKATKRLLKDWETKETSLLSTEYRFAEPTQT QAPQEDPSSEEEEESNLFERLLRQRTKQLQLKRRIIQTLKDL QKLE |

Consensus ORF7 Domain Sequences

In some embodiments, an ORF1 molecule, e.g., as described herein, comprises one or more of a jelly-roll domain, N22 domain, and/or C-terminal domain (CTD). In some embodiments, the jelly-roll domain comprises an amino acid sequence having a jelly-roll domain consensus sequence as described herein (e.g., as listed in any of Tables 37A-37C). In some embodiments, the N22 domain comprises an amino acid sequence having a N22 domain consensus sequence as described herein (e.g., as listed in any of Tables 37A-37C). In some embodiments, the CTD domain comprises an amino acid sequence having a CTD domain consensus sequence as described herein (e.g., as listed in any of Tables 37A-37C). In some embodiments, the amino acids listed in any of Tables 37A-37C in the format "($X_{a\_b}$)" comprise a contiguous series of amino acids, in which the series comprises at least a, and at most b, amino acids. In certain embodiments, all of the amino acids in the series are identical. In other embodiments, the series comprises at least two (e.g., at least 2, 3, 4, 5, 6, 7, 8, 9, 10, 11, 12, 13, 14, 15, 16, 17, 18, 19, 20, or 21) different amino acids.

TABLE 37A

Alphatorquevius ORF1 domain consensus sequences

| Domain | Sequence | SEQ ID NO: |
|---|---|---|
| Jelly-Roll | LVLTQWQPNTVRRCYIRGYLPLIICGEN($X_{0-3}$)TTSRNYA THSDDTIQKGPFGGGMSTTTFSLRVLYDEYQRFMNRW TYSNEDLDLARYLGCKFTFYRHPDXDFIVQYNTNPPFK DTKLTAPSIHP($X_{1-5}$)GMLMLSKRKILIPSLKTRPKGKHY VKVRIGPPKLFEDKWYTQSDLCDVPLVXLYATAADLQ HPFGSPQTDNPCVTFQVLGSXYNKHLSISP; wherein X = any amino acid. | 227 |
| N22 | SNFEFPGAYTDITYNPLTDKGVGNMVWIQYLTKPDTIX DKTQS($X_{0-3}$)KCLIEDLPLWAALYGYVDFCEKETGDSAII XNXGRVLIRCPYTKPPLYDKT($X_{0-4}$)NKGFVPYSTNFGN GKMPGGSGYVPIYWRARWYPTLFHQKEVLEDIVQSGP FAYKDEKPSTQLVMKYCFNFN; wherein X = any amino acid. | 228 |
| CTD | WGGNPISQQVVRNPCKDSG($X_{0-3}$)SGXGRQPRSVQVVD PKYMGPEYTFHSWDWRRGLFGEKAIKRMSEQPTDDEI FTGGXPKRPRRDPPTXQXPEE($X_{1-4}$)QKESSSFR($X_{2-14}$)PW ESSSQEXESESQEEEE($X_{0-30}$)EQTVQQQLRQQLREQRRL RVQLQLLFQQLLKT($X_{0-4}$)QAGLHINPLLLSQA($X_{0-40}$)*; wherein X = any amino acid. | 229 |

TABLE 37B

| *Betatorquevius* ORF1 domain consensus sequences | | |
|---|---|---|
| Domain | Sequence | SEQ ID NO: |
| Jelly-Roll | LKQWQPSTIRKCKIKGYLPLFQCGKGRISNNYTQYKESI VPHHEPGGGGWSIQQFTLGALYEEHLKLRNWWTKSN DGLPLVRYLGCTIKLYRSEDTDYIVTYQRCYPMTATKL TYLSTQPSRMLMNKHKIIVPSKXT($X_{1-4}$)NKKKKPYKKIF IKPPSQMQNKWYFQQDIANTPLLQLTXTACSLDRMYL SSDSISNNITFTSLNTNFFQNPNFQ; wherein X = any amino acid. | 230 |
| N22 | ($X_{4-10}$)TPLYFECRYNPFKDKGTGNKVYLVSNN($X_{1-8}$)TG WDPPTDPDLIIEGFPLWLLLWGWLDWQKKLGKIQNID TDYILVIQSXYYIPP($X_{1-3}$)KLPYYVPLDXD($X_{0-2}$)FLHGRS PY($X_{3-16}$)PSDKQHWHPKVRFQXETINNIALTGPGTPKLP NQKSIQAHMKYKFYFK; wherein X = any amino acid. | 231 |
| CTD | WGGCPAPMETITDPCKQPKYPIPNNLLQTTSLQXPTTPI ETYLYKFDERRGLLTKKAAKRIKKDXTTETTLFTDTGX XTSTTLPTXXQTETTQEEXTSEEE($X_{0-5}$)ETLLQQLQQLR RKQKQLRXRILQLLQLLXLL($X_{0-26}$)*; wherein X = any amino acid. | 232 |

TABLE 37C

| *Gammatorquevius* ORF1 domain consensus sequences | | |
|---|---|---|
| Domain | Sequence | SEQ ID NO: |
| Jelly-Roll | TIPLKQWQPESIRKCKIKGYGTLVLGAEGRQFYCYTNE KDEYTPPKAPGGGGFGVELFSLEYLYEQWKARNNIWT KSNXYKDLCRYTGCKITFYRHPTTDFIVXYSRQPPFEID KXTYMXXHPQXLLLRKHKKIILSKATNPKGKLKKKIKI KPPKQMLNKWFFQKQFAXYGLVQLQAAACBLRYPRL GCCNENRLITLYYLN; wherein X = any amino acid. | 233 |
| N22 | LPIVVARYNPAXDTGKGNKXWLXSTLNGSXWAPPTTD KDLIIEGLPLWLALYGYWSYJKKVKKDKGILQSHMFV VKSPAIQPLXTATTQXTFYPXIDNSFIQGKXPYDEPJTX NQKKLWYPTLEHQQETINAIVESGPYVPKLDNQKNST WELXYXYTFYFK; wherein X = any amino acid. | 234 |
| CTD | WGGPQIPDQPVEDPKXQGTYPVPDTXQQTIQIXNPLKQ KPETMFHDWDYRRGIITSTALKRMQENLETDSSFXSDS EETP($X_{0-2}$)KKKKRLTXELPXPQEETEEIQSCLLSLCEEST CQEE($X_{1-6}$)ENLQQLIHQQQQQQQLKHNILKLLSDLKZ KQRLLQLQTGILE($X_{1-10}$)* wherein X = any amino acid. | 235 |

In some embodiments, the jelly-roll domain comprises a jelly-roll domain amino acid sequence as listed in any of Tables 37A-37C, or an amino acid sequence having at least 70%, 75%, 80%, 8%, 90%, 95%, 96%, 97%, 98%, 99% or 100% sequence identity thereto. In some embodiments, the N22 domain comprises a N22 domain amino acid sequence as listed in any of Tables 37A-37C, or an amino acid sequence having at least 70%, 75%, 80%, 8%, 90%, 95%, 96%, 97%, 98%, 99%, or 100% sequence identity thereto. In some embodiments, the CTD domain comprises a CTD domain amino acid sequence as listed in any of Tables 37A-37C, or an amino acid sequence having at least 70%, 75%, 80%, 8%, 90%, 95%, 96%, 97%, 98%, 99% or 100% sequence identity thereto.

Exemplary ORF1 Variant Constructs

Provided in the table below are exemplary Anellovirus ORF1 mutant and variant sequences.

TABLE X1

Exemplary *Anellovirus* ORF1 variant constructs

| #ID | Sequence |
|---|---|
| Ring2<br>delCterm<br>(Δ611-666)<br>(7047) | MPYYYRRRRYNYRRPRWYGRGWIRRPFRRRFRRKRRVRPTYTTIPLKQ<br>WQPPYKRTCYIKGQDCLIYYSNLRLGMNSTMYEKSIVPVHWPGGGSFS<br>VSMLTLDALYDIHKLCRNWWTSTNQDLPLVRYKGCKITFYQSTFTDYI<br>VRIHTELPANSNKLTYPNTHPLMMMMSKYKHIIPSRQTRRKKKPYTKIF<br>VKPPPQFENKWYFATDLYKIPLLQIHCTACNLQNPFVKPDKLSNNVTL<br>WSLNTISIQNRNMSVDQGQSWPFKILGTQSFYFYFYTGANLPGDTTQIP<br>VADLLPLTNPRINRPGQSLNEAKITDHITFTEYKNKFTNYWGNPFNKHI<br>QEHLDMILYSLKSPEAIKNEWTTENMKWNQLNNAGTMALTPFNEPIFT<br>QIQYNPDRDTGEDTQLYLLSNATGTGWDPPGIPELILEGFPLWLIYWGF<br>ADFQKNLKKVTNIDTNYMLVAKTKFTQKPGTFYLVILNDTFVEGNSPY<br>EKQPLPEDNIKWYPQVQYQLEAQNKLLQTGPFTPNIQGQLSDNISMFYK<br>FYFKWGGSPPKAINVENPAHQIQYPIPRNEHETTSLQSPGEAPESILYSFD<br>YRHGNYTTTALSRISQDWALKDTVSK |
| Ring19<br>delCterm<br>(Δ600-655)<br>(7120) | MPWYPRRRYPRRRYRWLRRWRARRPFRPRYRRRYWVRNYSRKRKLF<br>KITTKEWQPKVIRKTHVKGTYPLFLCTKHRINNNMIQYLDSIAPEHYYG<br>GGGFSIMQFSLQALYEEFIKAKNWWTNTNCFLPLVRYMGCSFKFYKTE<br>FYDYIVLIERCYPLACTDEMYLSTQPSIMMLTRKCIFVPCKQNSKGKKP<br>YKKVRVRPPSQMTTGWHFSQDLANMPLVVLKTSVCSFDRYYTDSTAK<br>STTIGFKTLNTQTFRYHDWQEPPTTGYKPQNLLWFYGAENGSPVDPNN<br>TIVSNLIYLGGTGPYEKGTPIKTNISNYFSEPKLWGNIFHDDYTSGTSPVF<br>VTNKSPSEIKTAWNTIKDLTVKASGVFTLRTIPLWLPCRYNPFADKATN<br>NKIWLVSIHSDHTEWKPIDNPLLQRTDLPLWLLVWGWQDWQKKNQQT<br>SQPDINYLTVISSPYISCYPKLDYYVLLDEGFWEGHSTYIESITDSDKKH<br>WYPKNRFQIETLNLIANTGPGTVKLRENQAAEGHMVYRFNFKLGGCPA<br>PMEKICDPSKQSKYPIPNNQQQTTSLQSPENPIQTYLYDFDERRGLLTER<br>ATKRIKQDHTSEKTVLP |

Identification of ORF1 Protein Sequences

In some embodiments, an Anellovirus ORF1 protein sequence, or a nucleic acid sequence encoding an ORF1 protein, can be identified from the genome of an Anellovirus (e.g., a putative Anellovirus genome identified, for example, by nucleic acid sequencing techniques, e.g., deep sequencing techniques). In some embodiments, an ORF1 protein sequence is identified by one or more (e.g., 1, 2, or all 3) of the following selection criteria:

(i) Length Selection: Protein sequences (e.g., putative Anellovirus ORF1 sequences passing the criteria described in (ii) or (iii) below) may be size-selected for those greater than about 600 amino acid residues to identify putative Anellovirus ORF1 proteins. In some embodiments, an Anellovirus ORF1 protein sequence is at least about 600, 650, 700, 750, 800, 850, 900, 950, or 1000 amino acid residues in length. In some embodiments, an Alphatorquevirus ORF1 protein sequence is at least about 700, 710, 720, 730, 740, 750, 760, 770, 780, 790, 800, 900, or 1000 amino acid residues in length. In some embodiments, a Betatorquevirus ORF1 protein sequence is at least about 650, 660, 670, 680, 690, 700, 750, 800, 900, or 1000 amino acid residues in length. In some embodiments, a Gammatorquevirus ORF1 protein sequence is at least about 650, 660, 670, 680, 690, 700, 750, 800, 900, or 1000 amino acid residues in length. In some embodiments, a nucleic acid sequence encoding an Anellovirus ORF1 protein is at least about 1800, 1900, 2000, 2100, 2200, 2300, 2400, or 2500 nucleotides in length. In some embodiments, a nucleic acid sequence encoding an Alphatorquevirus ORF1 protein sequence is at least about 2100, 2150, 2200, 2250, 2300, 2400, or 2500 nucleotides in length. In some embodiments, a nucleic acid sequence encoding a Betatorquevirus ORF1 protein sequence is at least about 1900, 1950, 2000, 2500, 2100, 2150, 2200, 2250, 2300, 2400, or 2500 or 1000 nucleotides in length. In some embodiments, a nucleic acid sequence encoding a Gammatorquevirus ORF1 protein sequence is at least about 1900, 1950, 2000, 2500, 2100, 2150, 2200, 2250, 2300, 2400, or 2500 or 1000 nucleotides in length.

(ii) Presence of ORF1 motif: Protein sequences (e.g., putative Anellovirus ORF1 sequences passing the criteria described in (i) above or (iii) below) may be filtered to identify those that contain the conserved ORF1 motif in the N22 domain described above. In some embodiments, a putative Anellovirus ORF1 sequence comprises the sequence YNPXXDXGXXN. In some embodiments, a putative Anellovirus ORF1 sequence comprises the sequence Y[NCS]PXXDX[GASKR]XX[NTSVAK].

(iii) Presence of arginine-rich region: Protein sequences (e.g., putative Anellovirus ORF1 sequences passing the criteria described in (i) and/or (ii) above) may be filtered for those that include an arginine-rich region (e.g., as described herein). In some embodiments, a putative Anellovirus ORF1 sequence comprises a contiguous sequence of at least about 30, 35, 40, 45, 50, 55, 60, 65, or 70 amino acids that comprises at least 30% (e.g., at least about 20%, 25%, 30%, 35%, 40%, 45%, or 50%) arginine residues. In some embodiments, a putative Anellovirus ORF1 sequence comprises a contiguous sequence of about 35-40, 40-45, 45-50, 50-55, 55-60, 60-65, or 65-70 amino acids that comprises at least 30% (e.g., at least about 20%, 25%, 30%, 35%, 40%, 45%, or 50%) arginine residues. In some embodiments, the arginine-rich region is positioned at least about 30, 40, 50, 60, 70, or 80 amino acids downstream of the start codon of the putative Anellovirus ORF1 protein. In some embodiments, the arginine-rich region is positioned at least about 50 amino acids downstream of the start codon of the putative Anellovirus ORF1 protein.

In some embodiments, an ORF1 protein is identified in an Anellovirus genome sequence as described in Example 36 of PCT Publication No. WO2020/123816 (incorporated herein by reference in its entirety).

ORF2 Molecules

In some embodiments, the anellovector or anelloVLP comprises an ORF2 molecule and/or a nucleic acid encoding an ORF2 molecule. Generally, an ORF2 molecule comprises a polypeptide having the structural features and/or activity of an Anellovirus ORF2 protein (e.g., an Anellovirus ORF2 protein as described herein, e.g., as listed in any one of Tables A1-A25), or a functional fragment thereof. In some embodiments, an ORF2 molecule comprises an amino acid sequence having at least 70%, 75%, 80%, 85%, 90%, 95%, 96%, 97%, 98%, 99%, or 100% sequence identity to an Anellovirus ORF2 protein sequence as shown in any one of Tables A1-A25.

In some embodiments, an ORF2 molecule comprises an amino acid sequence having at least 75%, 80%, 85%, 90%, 95%, 96%, 97%, 98%, or 99% sequence identity to an Alphatorquevirus, Betatorquevirus, or Gammatorquevirus ORF2 protein. In some embodiments, an ORF2 molecule (e.g., an ORF2 molecule having at least 75%, 80%, 85%, 90%, 95%, 96%, 97%, 98%, or 99% sequence identity to an Alphatorquevirus ORF2 protein) has a length of 250 or fewer amino acids (e.g., about 150-200 amino acids). In some embodiments, an ORF2 molecule (e.g., an ORF2 molecule having at least 75%, 80%, 85%, 90%, 95%, 96%, 97%, 98%, or 99% sequence identity to a Betatorquevirus ORF2 protein) has a length of about 50-150 amino acids. In some embodiments, an ORF2 molecule (e.g., an ORF2 molecule having at least 75%, 80%, 85%, 90%, 95%, 96%, 97%, 98%, or 99% sequence identity to a Gammatorquevirus ORF2 protein) has a length of about 100-200 amino acids (e.g., about 100-150 amino acids). In some embodiments, the ORF2 molecule comprises a helix-turn-helix motif (e.g., a helix-turn-helix motif comprising two alpha helices flanking a turn region). In some embodiments, the ORF2 molecule does not comprise the amino acid sequence of the ORF2 protein of TTV isolate TA278 or TTV isolate SANBAN. In some embodiments, an ORF2 molecule has protein phosphatase activity. In some embodiments, an ORF2 molecule comprises at least one difference (e.g., a mutation, chemical modification, or epigenetic alteration) relative to a wild-type ORF2 protein, e.g., as described herein (e.g., as shown in any one of Tables A1-A25).

Conserved ORF2 Motif

In some embodiments, a polypeptide (e.g., an ORF2 molecule) described herein comprises the amino acid sequence [W/F]$X^7$H$X^3$C$X^1$C$X^5$H (SEQ ID NO: 949), wherein $X^n$ is a contiguous sequence of any n amino acids. In embodiments, $X^7$ indicates a contiguous sequence of any seven amino acids. In some embodiments, $X^3$ indicates a contiguous sequence of any three amino acids. In some embodiments, $X^1$ indicates any single amino acid. In some embodiments, $X^5$ indicates a contiguous sequence of any five amino acids. In some embodiments, the [W/F]can be either tryptophan or phenylalanine. In some embodiments, the [W/F]$X^7$H$X^3$C$X^1$C$X^5$H (SEQ ID NO: 949) is comprised within the N22 domain of an ORF2 molecule, e.g., as described herein. In some embodiments, a genetic element described herein comprises a nucleic acid sequence (e.g., a nucleic acid sequence encoding an ORF2 molecule, e.g., as described herein) encoding the amino acid sequence [W/F]$X^7$H$X^3$C$X^1$C$X^5$H (SEQ ID NO: 949), wherein $X^n$ is a contiguous sequence of any n amino acids.

Genetic Elements

In some embodiments, the anellovector comprises a genetic element. In some embodiments, the genetic element has one or more of the following characteristics: is substantially non-integrating with a host cell's genome, is an episomal nucleic acid, is a single stranded DNA, is circular, is about 1 to 10 kb, exists within the nucleus of the cell, can be bound by endogenous proteins, produces an effector, such as a polypeptide or nucleic acid (e.g., an RNA, iRNA, microRNA) that targets a gene, activity, or function of a host or target cell. In one embodiment, the genetic element is a substantially non-integrating DNA. In some embodiments, the genetic element comprises a packaging signal, e.g., a sequence that binds a capsid protein. In some embodiments, outside of the packaging or capsid-binding sequence, the genetic element has less than 70%, 60%, 50%, 40%, 30%, 20%, 10%, 5% sequence identity to a wild type Anellovirus nucleic acid sequence, e.g., has less than 70%, 60%, 50%, 40%, 30%, 20%, 10%, 5% sequence identity to an Anellovirus nucleic acid sequence, e.g., as described herein. In some embodiments, outside of the packaging or capsid-binding sequence, the genetic element has less than 500, 450, 400, 350, 300, 250, 200, 150, or 100 contiguous nucleotides that are at least 70%, 75%, 80%, 8%, 90%, 95%, 96%, 97%, 98%, 99%, or 100% identical to an Anellovirus nucleic acid sequence. In certain embodiments, the genetic element is a circular, single stranded DNA that comprises a promoter sequence, a sequence encoding a therapeutic effector, and a capsid binding protein.

In some embodiments, the genetic element has at least about 70%, 75%, 80%, 8%, 90%, 95%, 96%, 97%, 98%, 99%, or 100% sequence identity to an Anellovirus nucleic acid sequence, e.g., as described herein (e.g., as described in any one of Tables N1-N25), or a fragment thereof, or encodes an amino acid sequence having at least about 70%, 75%, 80%, 8%, 90%, 95%, 96%, 97%, 98%, 99%, or 100% sequence identity to an Anellovirus amino acid sequence (e.g., as described in any one of Tables A1-A25), or a fragment thereof. In some embodiments, the genetic element comprises a sequence encoding an effector (e.g., an endogenous effector or an exogenous effector, e.g., a payload), e.g., a polypeptide effector (e.g., a protein) or nucleic acid effector (e.g., a non-coding RNA, e.g., a miRNA, siRNA, mRNA, lncRNA, RNA, DNA, an antisense RNA, gRNA).

In some embodiments, the genetic element has a length less than 20kb (e.g., less than about 19kb, 18kb, 17kb, 16kb, 15kb, 14kb, 13kb, 12kb, 11kb, 10kb, 9kb, 8kb, 7kb, 6kb, 5kb, 4kb, 3kb, 2kb, 1kb, or less). In some embodiments, the genetic element has, independently or in addition to, a length greater than 1000b (e.g., at least about 1.1kb, 1.2kb, 1.3kb, 1.4kb, 1.5kb, 1.6kb, 1.7kb, 1.8kb, 1.9kb, 2kb, 2.1kb, 2.2kb, 2.3kb, 2.4kb, 2.5kb, 2.6kb, 2.7kb, 2.8kb, 2.9kb, 3kb, 3.1kb, 3.2kb, 3.3kb, 3.4kb, 3.5kb, 3.6kb, 3.7kb, 3.8kb, 3.9kb, 4kb, 4.1kb, 4.2kb, 4.3kb, 4.4kb, 4.5kb, 4.6kb, 4.7kb, 4.8kb, 4.9kb, 5kb, or greater). In some embodiments, the genetic element has a length of about 2.5-4.6, 2.8-4.0, 3.0-3.8, or 3.2-3.7 kb. In some embodiments, the genetic element has a length of about 1.5-2.0, 1.5-2.5, 1.5-3.0, 1.5-3.5, 1.5-3.8, 1.5-3.9, 1.5-4.0, 1.5-4.5, or 1.5-5.0 kb. In some embodiments, the genetic element has a length of about 2.0-2.5, 2.0-3.0, 2.0-3.5, 2.0-3.8, 2.0-3.9, 2.0-4.0, 2.0-4.5, or 2.0-5.0 kb. In some embodiments, the genetic element has a length of about 2.5-3.0, 2.5-3.5, 2.5-3.8, 2.5-3.9, 2.5-4.0, 2.5-4.5, or 2.5-5.0 kb. In some embodiments, the genetic element has a length of about 3.0-5.0, 3.5-5.0, 4.0-5.0, or 4.5-5.0 kb. In some embodiments, the genetic element has a length of about 1.5-2.0, 2.0-2.5, 2.5-3.0, 3.0-3.5, 3.1-3.6, 3.2-3.7, 3.3-3.8, 3.4-3.9, 3.5-4.0, 4.0-4.5, or 4.5-5.0 kb.

In some embodiments, the genetic element comprises one or more of the features described herein, e.g., a sequence encoding a substantially non-pathogenic protein, a protein binding sequence, one or more sequences encoding a regulatory nucleic acid, one or more regulatory sequences, one or more sequences encoding a replication protein, and other sequences. In some embodiments, the substantially non-pathogenic protein comprises an amino acid sequence or a functional fragment thereof or a sequence having at least about 60%, 65%, 70%, 75%, 80%, 85%, 90% 95%, 96%, 97%, 98%, 99%, or 100% sequence identity to any one of the amino acid sequences described herein, an Anellovirus amino acid sequence, e.g., as listed in any one of Tables A1-A25.

In some embodiments, the genetic element was produced from a double-stranded circular DNA (e.g., produced by in vitro circularization). In some embodiments, the genetic element was produced by rolling circle replication from the double-stranded circular DNA. In some embodiments, the rolling circle replication occurs in a cell (e.g., a host cell, e.g., a mammalian cell, e.g., a human cell, e.g., a HEK293T cell, an A549 cell, or a Jurkat cell). In some embodiments, the genetic element can be amplified exponentially by rolling circle replication in the cell. In some embodiments, the genetic element can be amplified linearly by rolling circle replication in the cell. In some embodiments, the double-stranded circular DNA or genetic element is capable of yielding at least 2, 4, 8, 16, 32, 64, 128, 256, 518, 1024 or more times the original quantity by rolling circle replication in the cell. In some embodiments, the double-stranded circular DNA was introduced into the cell, e.g., as described herein.

In some embodiments, the double-stranded circular DNA and/or the genetic element does not comprise one or more bacterial plasmid elements (e.g., a bacterial origin of replication or a selectable marker, e.g., a bacterial resistance gene). In some embodiments, the double-stranded circular DNA and/or the genetic element does not comprise a bacterial plasmid backbone.

In one embodiment, the invention includes a genetic element comprising a nucleic acid sequence (e.g., a DNA sequence) encoding (i) a substantially non-pathogenic exterior protein, (ii) an exterior protein binding sequence that binds the genetic element to the substantially non-pathogenic exterior protein, and (iii) a regulatory nucleic acid. In such an embodiment, the genetic element may comprise one or more sequences with at least about 60%, 70% 80%, 85%, 90% 95%, 96%, 97%, 98% and 99% nucleotide sequence identity to any one of the nucleotide sequences to a native viral sequence (e.g., a native Anellovirus sequence, e.g., as described herein).

In some embodiments, a genetic element as described herein comprises a sequence (e.g., a TATA box, cap site, transcriptional start site, 5' UTR, open reading frame (ORF), poly(A) signal, or GC-rich region sequence) as listed in any of Tables A1, A3, A5, A7, A9, A11, B1-B5, 1, 3, 5, 7, 9, 11, 13, 15, or 17 of PCT Publication No. WO2020/123816 (incorporated herein by reference in its entirety), or a sequence having at least 70% 80%, 85%, 90% 95%, 96%, 97%, 98% and 99% nucleotide sequence identity thereto.

In some embodiments, a genetic element comprises a sequence encoding an effector (e.g., an exogenous effector). In some embodiments, the effector-encoding sequence is inserted into an Anellovirus genome sequence (e.g., as described herein). In some embodiments, the effector-encoding sequence replaces a contiguous sequence (e.g., of at least 5, 10, 15, 20, 25, 30, 40, 50, 60, 70, 80, 90, 100, 200, 300, 400, 500, 600, 700, 800, 900, 1000, or more nucleotides) from the Anellovirus genome sequence. In some embodiments, the effector-encoding sequence replaces a TATA box, cap site, transcriptional start site, 5' UTR, open reading frame (ORF), poly(A) signal, or GC-rich region sequence, or a portion thereof (e.g., a portion consisting of at least 5, 10, 15, 20, 25, 30, 40, 50, 60, 70, 80, 90, 100, 200, 300, 400, 500, 600, 700, 800, 900, 1000, or more nucleotides) e.g., as listed in any of Tables A1, A3, A5, A7, A9, A11, B1-B5, 1, 3, 5, 7, 9, 11, 13, 15, or 17 of PCT Publication No. WO2020/123816 (incorporated herein by reference in its entirety), or a sequence having at least 70% 80%, 85%, 90% 95%, 96%, 97%, 98% and 99% nucleotide sequence identity thereto.

In some embodiments, the sequence of a first nucleic acid element comprised in a genetic element (e.g., a TATA box, cap site, transcriptional start site, 5' UTR, open reading frame (ORF), poly(A) signal, or GC-rich region) overlaps with the sequence of a second nucleic acid element (e.g., a TATA box, cap site, transcriptional start site, 5' UTR, open reading frame (ORF), poly(A) signal, or GC-rich region), e.g., by at least 5, 10, 15, 20, 25, 30, 40, 50, 60, 70, 80, 90, 100, 150, 200, 250, 300, 400, or 500 nucleotides. In some embodiments, the sequence of a first nucleic acid element comprised in a genetic element (e.g., a TATA box, cap site, transcriptional start site, 5' UTR, open reading frame (ORF), poly(A) signal, or GC-rich region) does not overlap with the sequence of a second nucleic acid element (e.g., a TATA box, cap site, transcriptional start site, 5' UTR, open reading frame (ORF), poly(A) signal, or GC-rich region).

Protein Binding Sequence

A strategy employed by many viruses is that the viral capsid protein recognizes a specific protein binding sequence in its genome. For example, in viruses with unsegmented genomes, such as the L-A virus of yeast, there is a secondary structure (stem-loop) and a specific sequence at the 5' end of the genome that are both used to bind the viral capsid protein. However, viruses with segmented genomes, such as Reoviridae, Orthomyxoviridae (influenza), Bunyaviruses and Arenaviruses, need to package each of the genomic segments. Some viruses utilize a complementarity region of the segments to aid the virus in including one of each of the genomic molecules. Other viruses have specific binding sites for each of the different segments. See for example, Curr Opin Struct Biol. 2010 February; 20(1): 114-120; and Journal of Virology (2003), 77(24), 13036-13041.

In some embodiments, the genetic element encodes a protein binding sequence that binds to the substantially non-pathogenic protein. In some embodiments, the protein binding sequence facilitates packaging the genetic element into the proteinaceous exterior. In some embodiments, the protein binding sequence specifically binds an arginine-rich region of the substantially non-pathogenic protein. In some embodiments, the genetic element comprises a protein binding sequence as described in Example 8 of PCT Publication No. WO 2020/123816, incorporated by reference herein in its entirety. In some embodiments, the genetic element comprises a protein binding sequence having at least 70%, 80%, 85%, 90%, 95%, 96%, 97%, 98%, 99%, or 100% sequence identity to a 5' UTR conserved domain or GC-rich domain of an Anellovirus sequence (e.g., as shown in any one of Tables N1-N25).

In embodiments, the protein binding sequence has at least about 70%, 75%, 80%, 85%, 90%, 95%, 96%, 97%, 98%, 99%, or 100% sequence identity to the Anellovirus 5' UTR conserved domain nucleotide sequence of any one of Tables N1-N25.

5' UTR Regions

Figure 20:
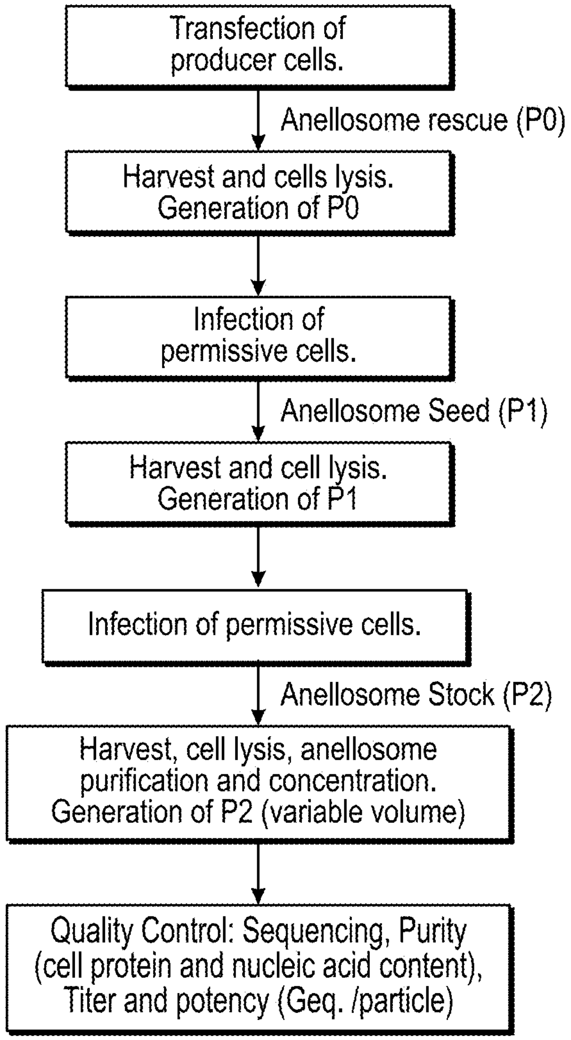
FIG. 20 is a schematic showing an exemplary workflow for production of anellovectors (e.g., replication-competent or replication-deficient anellovectors as described herein).

In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to a nucleic acid sequence shown in Table 38 and/or FIG. 20 of PCT Publication No. WO 2020/123816. In some embodiments, the genetic element (e.g., protein-binding sequence of the genetic element) comprises a nucleic acid sequence of the Consensus 5' UTR sequence shown in Table 38, wherein $X_1$, $X_2$, $X_3$, $X_4$, and $X_5$ are each independently any nucleotide, e.g., wherein $X_1$=G or T, $X_2$=C or A, $X_3$=G or A, $X_4$=T or C, and $X_5$=A, C, or T). In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the Consensus 5' UTR sequence shown in Table 38. In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the exemplary TTV 5' UTR sequence shown in Table 38. In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the TTV-CT30F 5' UTR sequence shown in Table 38. In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the TTV-HD23a 5' UTR sequence shown in Table 38. In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the TTV-JA20 5' UTR sequence shown in Table 38. In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the TTV-TJN02 5' UTR sequence shown in Table 38. In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the TTV-tth8 5' UTR sequence shown in Table 38.

In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the Alphatorquevirus Consensus 5' UTR sequence shown in Table 38. In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the Alphatorquevirus Clade 1 5' UTR sequence shown in Table 38. In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the Alphatorquevirus Clade 2 5' UTR sequence shown in Table 38. In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the Alphatorquevirus Clade 3 5' UTR sequence shown in Table 38. In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the Alphatorquevirus Clade 4 5' UTR sequence shown in Table 38. In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the Alphatorquevirus Clade 5 5' UTR sequence shown in Table 38. In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the Alphatorquevirus Clade 6 5' UTR sequence shown in Table 38. In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the Alphatorquevirus Clade 7 5' UTR sequence shown in Table 38.

In some embodiments, the genetic element comprises a nucleic acid sequence having at least about 70%, 75%, 80%, 85%, 90%, 95%, 96%, 97%, 98%, 99%, or 100% sequence identity to the Anellovirus 5' UTR conserved domain nucleotide sequence ofany one of Tables N1-N25.

In some embodiments, the genetic element comprises a nucleic acid sequence having at least about 70%, 75%, 80%, 85%, 90%, 95%, 96%, 97%, 98%, 99%, or 100% sequence identity to the Anellovirus 5' UTR conserved domain nucleotide sequence of any one of Tables N1-N25.

TABLE 38

| Exemplary 5' UTR sequences from Anelloviruses | | |
|---|---|---|
| Source | Sequence | SEQ ID NO: |
| Consensus | CGGGTGCCG$X_1$AGGTGAGTTTACACACCG$X_2$AGT CAAGGGGCAATTCGGGCTC$X_3$GGACTGGCCGGG C$X_4X_5$TGGG<br>$X_1$ = G or T<br>$X_2$ = C or A<br>$X_3$ = Gor A<br>$X_4$ = T or C<br>$X_5$ = A, C, or T | 105 |
| Exemplary TTV Sequence | CGGGTGCCGGAGGTGAGTTTACACACCGCAGTC AAGGGGCAATTCGGGCTCGGGACTGGCCGGGCT WTGGG | 106 |
| TTV-CT30F | CGGGTGCCGTAGGTGAGTTTACACACCGCAGTC AAGGGGCAATTCGGGCTCGGGACTGGCCGGGCT ATGGG | 107 |
| TTV-HD23a | CGGGTGCCGGAGGTGAGTTTACACACCGCAGTC AAGGGGCAATTCGGGCTCGGGACTGGCCGGGCC CTGGG | 108 |
| TTV-JA20 | CGGGTGCCGGAGGTGAGTTTACACACCGCAGTC AAGGGGCAATTCGGGCTCGGGACTGGCCGGGCT TTGGG | 109 |
| TTV-TJN02 | CGGGTGCCGGAGGTGAGTTTACACACCGCAGTC AAGGGGCAATTCGGGCTCGGGACTGGCCGGGCT ATGGG | 110 |
| TTV-tth8 | CGGGTGCCGGAGGTGAGTTTACACACCGAAGTC AAGGGGCAATTCGGGCTCAGGACTGGCCGGGCT TTGGG | 111 |
| *Alphatorquevirus* Consensus 5' UTR | CGGGTGCCGGAGGTGAGTTTACACACCGCAGTC AAGGGGCAATTCGGGCTCGGGACTGGCCGGGC $X_1X_2$TGGG; wherein $X_1$ comprises T or C, and wherein $X_2$ comprises A, C, or T. | 112 |
| *Alphatorquevirus* Clade 1 5' UTR (e.g., TTV-CT30F) | CGGGTGCCGTAGGTGAGTTTACACACCGCAGTC AAGGGGCAATTCGGGCTCGGGACTGGCCGGGCT ATGGG | 113 |
| *Alphatorquevirus* Clade 2 5' UTR (e.g., TTV-P13-1) | CGGGTGCCGGAGGTGAGTTTACACACCGCAGTC AAGGGGCAATTCGGGCTCGGGACTGGCCGGGCC CGGG | 114 |
| *Alphatorquevirus* Clade 3 5' UTR (e.g., TTV-tth8) | CGGGTGCCGGAGGTGAGTTTACACACCGAAGTC AAGGGGCAATTCGGGCTCAGGACTGGCCGGGCT TTGGG | 115 |
| *Alphatorquevirus* Clade 4 5' UTR (e.g., TTV-HD20a) | CGGGTGCCGGAGGTGAGTTTACACACCGCAGTC AAGGGGCAATTCGGGCTCGGGAGGCCGGGCCAT GGG | 116 |
| *Alphatorquevirus* Clade 5 5' UTR (e.g., TTV-16) | CGGGTGCCGGAGGTGAGTTTACACACCGCAGTC AAGGGGCAATTCGGGCTCGGGACTGGCCGGGCC CCGGG | 117 |
| *Alphatorquevirus* Clade 6 5' UTR (e.g., TTV-TJN02) | CGGGTGCCGGAGGTGAGTTTACACACCGCAGTC AAGGGGCAATTCGGGCTCGGGACTGGCCGGGCT ATGGG | 118 |
| *Alphatorquevirus* Clade 7 5' UTR (e.g., TTV-HD16d) | CGGGTGCCGAAGGTGAGTTTACACACCGCAGTC AAGGGGCAATTCGGGCTCGGGACTGGCCGGGCT ATGGG | 119 |

Identification of 5S' UTR Sequences

In some embodiments, an Anellovirus 5' UTR sequence can be identified within the genome of an Anellovirus (e.g., a putative Anellovirus genome identified, for example, by nucleic acid sequencing techniques, e.g., deep sequencing techniques). In some embodiments, an Anellovirus 5' UTR sequence is identified by one or both of the following steps:

(i) Identification of circularization junction point: In some embodiments, a 5' UTR will be positioned near a circularization junction point of a full-length, circularized Anellovirus genome. A circularization junction point can be identified, for example, by identifying overlapping regions of the sequence. In some embodiments, an overlapping region of the sequence can be trimmed from the sequence to produce a full-length Anellovirus genome sequence that has been circularized. In some embodiments, a genome sequence is circularized in this manner using software. Without wishing to be bound by theory, computationally circularizing a genome may result in the start position for the sequence being oriented in a non-biological. Landmarks within the sequence can be used to re-orient sequences in the proper direction. For example, landmark sequence may include sequences having substantial homology to one or more elements within an Anellovirus genome as described herein (e.g., one or more of a TATA box, cap site, initiator element, transcriptional start site, 5' UTR conserved domain, ORF1, ORF1/1, ORF1/2, ORF2, ORF2/2, ORF2/3, ORF2t/3, three open-reading frame region, poly(A) signal, or GC-rich region of an Anellovirus, e.g., as described herein).

(ii) Identification of 5' UTR sequence: Once a putative Anellovirus genome sequence has been obtained, the sequence (or portions thereof, e.g., having a length between about 40-50, 50-60, 60-70, 70-80, 80-90, or 90-100 nucleotides) can be compared to one or more Anellovirus 5' UTR sequences (e.g., as described herein) to identify sequences having substantial homology thereto. In some embodiments, a putative Anellovirus 5' UTR region has at least 50%, 60%, 70%, 75%, 80%, 85%, 90%, 95%, 96%, 97%, 98%, 99%, or 100% sequence identity to an Anellovirus 5' UTR sequence as described herein.

GC-Rich Regions

Figure 32A:
FIG. 32A depicts 60 Ring 10 structural jelly roll (JR) domains. Sixty Ring 10 structural jelly roll (JR) domains form the core of anellovirus particles.

In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to a nucleic acid sequence shown in any of Table 39 and/or FIGS. 20 and 32 of PCT Publication No. WO 2020/123816. In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to a GC-rich sequence shown in Table 39.

In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to a 36-nucleotide GC-rich sequence as shown in Table 39 (e.g., 36-nucleotide consensus GC-rich region sequence 1, 36-nucleotide consensus GC-rich region sequence 2, TTV Clade 1 36-nucleotide region, TTV Clade 3 36-nucleotide region, TTV Clade 3 isolate GH1 36-nucleotide region, TTV Clade 3 sle1932 36-nucleotide region, TTV Clade 4 ctdc002 36-nucleotide region, TTV Clade 5 36-nucleotide region, TTV Clade 6 36-nucleotide region, or TTV Clade 7 36-nucleotide region). In some embodiments, the genetic element (e.g., protein-binding sequence of the genetic element) comprises a nucleic acid sequence comprising at least 10, 15, 20, 25, 30, 31, 32, 33, 34, 35, or 36 consecutive nucleotides of a 36-nucleotide GC-rich sequence as shown in Table 39 (e.g., 36-nucleotide consensus GC-rich region sequence 1, 36-nucleotide consensus GC-rich region sequence 2, TTV Clade 1 36-nucleotide region, TTV Clade 3 36-nucleotide region, TTV Clade 3 isolate GH1 36-nucleotide region, TTV Clade 3 sle1932 36-nucleotide region, TTV Clade 4 ctdc002 36-nucleotide region, TTV Clade 5 36-nucleotide region, TTV Clade 6 36-nucleotide region, or TTV Clade 7 36-nucleotide region).

In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to an Alphatorquevirus GC-rich region sequence, e.g., selected from TTV-CT3OF, TTV-P13-1, TTV-tth8, TTV-HD20a, TTV-16, TTV-TJN02, or TTV-HD16d, e.g., as listed in Table 39. In some embodiments, the genetic element (e.g., protein-binding sequence of the genetic element) comprises a nucleic acid sequence comprising at least 10, 15, 20, 25, 30, 35, 40, 45, 50, 60, 70, 80, 90, 100, 104, 105, 108, 110, 111, 115, 120, 122, 130, 140, 145, 150, 155, or 156 consecutive nucleotides of an Alphatorquevirus GC-rich region sequence, e.g., selected from TTV-CT30F, TTV-P13-1, TTV-tth8, TTV-HD20a, TTV-16, TTV-TJN02, or TTV-HD16d, e.g., as listed in Table 39.

In some embodiments, the 36-nucleotide GC-rich sequence is selected from:

```
                                    (SEQ ID NO: 160)
(i) CGCGCTGCGCGCGCCGCCCAGTAGGGGGAGCCATGC,

                                    (SEQ ID NO: 164)
(ii) GCGCTX1CGCGCGCGCGCCGGGGGGCTGCGCCCCCCC,
wherein X1 is selected from T, G, or A;

                                    (SEQ ID NO: 165)
(iii) GCGCTTCGCGCGCCGCCCACTAGGGGGCGTTGCGCG;

                                    (SEQ ID NO: 166)
(iv) GCGCTGCGCGCGCCGCCCAGTAGGGGGCGCAATGCG;

                                    (SEQ ID NO: 167)
(v) GCGCTGCGCGCGCGGCCCCCGGGGGAGGCATTGCCT;

                                    (SEQ ID NO: 168)
(vi) GCGCTGCGCGCGCGCGCCGGGGGGGCGCCAGCGCCC;

                                    (SEQ ID NO: 169)
(vii) GCGCTTCGCGCGCGCGCCGGGGGGCTCCGCCCCCCC;

                                    (SEQ ID NO: 170)
(viii) GCGCTTCGCGCGCGCGCCGGGGGGCTGCGCCCCCCC;

                                    (SEQ ID NO: 171)
(ix) GCGCTACGCGCGCGCGCCGGGGGGCTGCGCCCCCCC;
or

                                    (SEQ ID NO: 172)
(x) GCGCTACGCGCGCGCGCCGGGGGGCTCTGCCCCCCC.
```

In some embodiments, the genetic element (e.g., protein-binding sequence of the genetic element) comprises the nucleic acid sequence CGCGCTGCGCGCGCCGCCCAGTAGGGGGAGCCATGC (SEQ ID NO: 160).

In some embodiments, the genetic element (e.g., protein-binding sequence of the genetic element) comprises a nucleic acid sequence of the Consensus GC-rich sequence shown in Table 39, wherein $X_1$, $X_4$, $X_5$, $X_6$, $X_7$, $X_{12}$, $X_{13}$, $X_{14}$, $X_{15}$, $X_{20}$, $X_{21}$, $X_{22}$, $X_{26}$, $X_{29}$, $X_{30}$, and $X_{33}$ are each independently any nucleotide and wherein $X_2$, $X_3$, $X_8$, $X_9$, $X_{10}$, $X_{11}$, $X_{16}$, $X_{17}$, $X_{18}$, $X_{19}$, $X_{23}$, $X_{24}$, $X_{25}$, $X_{27}$, $X_{28}$, $X_{31}$, $X_{32}$, and $X_{34}$ are each independently absent or any nucleotide. In some embodiments, one or more of (e.g., all of) $X_1$ through $X_{34}$ are each independently the nucleotide (or absent) specified in Table 39. In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to an exemplary TTV GC-rich sequence shown in Table 39 (e.g., the full sequence, Fragment 1, Fragment 2, Fragment 3, or any combination thereof, e.g., Fragments 1-3 in order). In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to a TTV-CT30F GC-rich sequence shown in Table 39 (e.g., the full sequence, Fragment 1, Fragment 2, Fragment 3, Fragment 4, Fragment 5, Fragment 6, Fragment 7, Fragment 8, or any combination thereof, e.g., Fragments 1-7 in order). In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to a TTV-HD23a GC-rich sequence shown in Table 39 (e.g., the full sequence, Fragment 1, Fragment 2, Fragment 3, Fragment 4, Fragment 5, Fragment 6, or any combination thereof, e.g., Fragments 1-6 in order). In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to a TTV-JA20 GC-rich sequence shown in Table 39 (e.g., the full sequence, Fragment 1, Fragment 2, or any combination thereof, e.g., Fragments 1 and 2 in order). In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to a TTV-TJN02 GC-rich sequence shown in Table 39 (e.g., the full sequence, Fragment 1, Fragment 2, Fragment 3, Fragment 4, Fragment 5, Fragment 6, Fragment 7, Fragment 8, or any combination thereof, e.g., Fragments 1-8 in order). In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to a TTV-tth8 GC-rich sequence shown in Table 39 (e.g., the full sequence, Fragment 1, Fragment 2, Fragment 3, Fragment 4, Fragment 5, Fragment 6, Fragment 7, Fragment 8, Fragment 9, or any combination thereof, e.g., Fragments 1-6 in order). In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to Fragment 7 shown in Table 39. In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to Fragment 8 shown in Table 39. In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to Fragment 9 shown in Table 39.

TABLE 39

Exemplary GC-rich sequences from Anelloviruses

| Source | Sequence | SEQ ID NO: |
|---|---|---|
| Consensus | $CGGCGGX_1GGX_2GX_3X_4X_5CGCGCTX_6CGCGC$<br>$GCX_7X_8X_9X_{10}CX_{11}X_{12}X_{13}X_{14}GGGGX_{15}X_{16}X_{17}X_{18}$<br>$X_{19}X_{20}X_{21}GCX_{22}X_{23}X_{24}X_{25}CCCCCCCX_{26}CGCGC$<br>$ATX_{27}X_{28}GCX_{29}CGGGX_{30}CCCCCCCCCX_{31}X_{32}X_{33}$<br>$GGGGGGCTCCGX_{34}CCCCCCGGCCCCCC$ | 120 |
| | $X_1$ = G or C | |
| | $X_2$ = G, C, or absent | |
| | $X_3$ = C or absent | |
| | $X_4$ = G or C | |
| | $X_5$ = G or C | |
| | $X_6$ = T, G, or A | |
| | $X_7$ = G or C | |
| | $X_8$ = G or absent | |
| | $X_9$ = C or absent | |
| | $X_{10}$ = C or absent | |
| | $X_{11}$ = G, A, or absent | |
| | $X_{12}$ = G or C | |
| | $X_{13}$ = C or T | |
| | $X_{14}$ = G or A | |
| | $X_{15}$ = G or A | |
| | $X_{16}$ = A, G, T, or absent | |
| | $X_{17}$ = G, C, or absent | |
| | $X_{18}$ = G, C, or absent | |
| | $X_{19}$ = C, A, or absent | |
| | $X_{20}$ = C or A | |
| | $X_{21}$ = T or A | |
| | $X_{22}$ = G or C | |
| | $X_{23}$ = G, T, or absent | |
| | $X_{24}$ = C or absent | |

TABLE 39-continued

| Exemplary GC-rich sequences from Anelloviruses | | | |
|---|---|---|---|
| Source | | Sequence | SEQ ID NO: |
| | | $X_{25}$ = G, C, or absent<br>$X_{26}$ = G or C<br>$X_{27}$ = G or absent<br>$X_{28}$ = C or absent<br>$X_{29}$ = G or A<br>$X_{30}$ = G or T<br>$X_{31}$ = C, T, or absent<br>$X_{32}$ = G, C, A, or absent<br>$X_{33}$ = G or C<br>$X_{34}$ = C or absent | |
| Exemplary TTV Sequence | Full sequence | GCCGCCGCGGCGGCGGSGGNGNSGCGCGCT<br>DCGCGCGCSNNNCRCCRGGGGGNNNNCWG<br>CSNCNCCCCCCCCCGCGCATGCGCGGGKCC<br>CCCCCCCNNCGGGGGGCTCCGCCCCCCGGC<br>CCCCCCCCGTGCTAAACCCACCGCGCATGC<br>GCGACCACGCCCCCGCCGCC | 121 |
| | Fragment 1 | GCCGCCGCGGCGGCGGSGGNGNSGCGCGCT<br>DCGCGCGCSNNNCRCCRGGGGGNNNNCWG<br>CSNCNCCCCCCCCCGCGCAT | 122 |
| | Fragment 2 | GCGCGGGKCCCCCCCCCNNCGGGGGGCTC<br>CG | 123 |
| | Fragment 3 | CCCCCCGGCCCCCCCCGTGCTAAACCCAC<br>CGCGCATGCGCGACCACGCCCCCGCCGCC | 124 |
| TTV-CT30F | Full sequence | GCGGCGG-GGGGGCG-GCCGCG-<br>TTCGCGCGCCGCCCACCAGGGGGTG--<br>CTGCG-CGCCCCCCCCCGCGCAT<br>GCGCGGGGCCCCCCCCC--<br>GGGGGGGCTCCGCCCCCCCGGCCCCCCCCC<br>GTGCTAAACCCACCGCGCATGCGCGACCAC<br>GCCCCCGCCGCC | 125 |
| | Fragment 1 | GCGGCGG | 126 |
| | Fragment 2 | GGGGGCG | 127 |
| | Fragment 3 | GCCGCG | 128 |
| | Fragment 4 | TTCGCGCGCCGCCCACCAGGGGGTG | 129 |
| | Fragment 5 | CTGCG | 130 |
| | Fragment 6 | CGCCCCCCCCCGCGCAT | 131 |
| | Fragment 7 | GCGCGGGGCCCCCCCCC | 132 |
| | Fragment 8 | GGGGGGGCTCCGCCCCCCCGGCCCCCCCCC<br>GTGCTAAACCCACCGCGCATGCGCGACCAC<br>GCCCCCGCCGCC | 133 |
| TTV-HD23a | Full sequence | CGGCGGCGGCGGCG-<br>CGCGCGCTGCGCGCGCG---<br>CGCCGGGGGGGCGCCAGCG-<br>CCCCCCCCCCCGCGCAT<br>GCACGGGTCCCCCCCCCCACGGGGGGCTCC<br>G CCCCCCGGCCCCCCCCC | 134 |
| | Fragment 1 | CGGCGGCGGCGGCG | 135 |
| | Fragment 2 | CGCGCGCTGCGCGCGCG | 136 |
| | Fragment 3 | CGCCGGGGGGGCGCCAGCG | 137 |
| | Fragment 4 | CCCCCCCCCCCGCGCAT | 138 |
| | Fragment 5 | GCACGGGTCCCCCCCCCCACGGGGGGCTCC<br>G | 139 |
| | Fragment 6 | CCCCCCGGCCCCCCCCC | 140 |
| TTV-JA20 | Full sequence | CCGTCGGCGGGGGGGCCGCGCGCTGCGCG<br>CGCGGCCC-<br>CCGGGGGAGGCACAGCCTCCCCCCCCCGCG<br>CGCATGCGCGCGGGTCCCCCCCCCTCCGGG<br>GGGCTCCGCCCCCCCGGCCCCCCCC | 141 |
| | Fragment 1 | CCGTCGGCGGGGGGGCCGCGCGCTGCGCG<br>CGCGGCCC | 142 |
| | Fragment 2 | CCGGGGGAGGCACAGCCTCCCCCCCCCGCG<br>CGCATGCGCGCGGGTCCCCCCCCCTCCGGG<br>GGGCTCCGCCCCCCCGGCCCCCCCC | 143 |
| TTV-TJN02 | Full sequence | CGGCGGCGGCG-CGCGCGCTACGCGCGCG--<br>-CGCCGGGGGG----CTGCCGC-<br>CCCCCCCCCGCGCAT<br>GCGCGGGGCCCCCCCCC-<br>GCGGGGGGCTCCG CCCCCCGGCCCCCC | 144 |
| | Fragment 1 | CGGCGGCGGCG | 145 |
| | Fragment 2 | CGCGCGCTACGCGCGCG | 146 |

TABLE 39-continued

| Exemplary GC-rich sequences from Anelloviruses | | | |
|---|---|---|---|
| Source | | Sequence | SEQ ID NO: |
| | Fragment 3 | CGCCGGGGGG | 147 |
| | Fragment 4 | CTGCCGC | 148 |
| | Fragment 5 | CCCCCCCCCGCGCAT | 149 |
| | Fragment 6 | GCGCGGGGCCCCCCCCC | 150 |
| | Fragment 7 | GCGGGGGGCTCCG | 151 |
| | Fragment 8 | CCCCCCGGCCCCCC | 152 |
| TTV-tth8 | Full sequence | GCCGCCGCGGCGGCGGGGG-GCGGCGCGCTGCGCGCGCCGCCCAGTAGG GGGAGCCATGCG---CCCCCCCCCGCGCAT GCGCGGGGCCCCCCCCC-GCGGGGGGCTCCG CCCCCCGGCCCCCCCCG | 153 |
| | Fragment 1 | GCCGCCGCGGCGGCGGGGG | 154 |
| | Fragment 2 | GCGGCGCGCTGCGCGCGCCGCCCAGTAGG GGGAGCCATGCG | 155 |
| | Fragment 3 | CCCCCCCCCGCGCAT | 156 |
| | Fragment 4 | GCGCGGGGCCCCCCCCC | 157 |
| | Fragment 5 | GCGGGGGGCTCCG | 158 |
| | Fragment 6 | CCCCCCGGCCCCCCCCG | 159 |
| | Fragment 7 | CGCGCTGCGCGCGCCGCCCAGTAGGGGGA GCCATGC | 160 |
| | Fragment 8 | CCGCCATCTTAAGTAGTTGAGGCGGACGGT GGCGTGAGTTCAAAGGTCACCATCAGCCAC ACCTACTCAAAATGGTGG | 161 |
| | Fragment 9 | CTTAAGTAGTTGAGGCGGACGGTGGCGTGA GTTCAAAGGTCACCATCAGCCACACCTACT CAAAATGGTGGACAATTTCTTCCGGGTCAA AGGTTACAGCCGCCATGTTAAAACACGTGA CGTATGACGTCACGGCCGCCATTTTGTGAC ACAAGATGGCCGACTTCCTTCC | 162 |
| Additional GC-rich Sequences (as shown in FIG. 32 of PCT Publication No. WO 2020/123816) | 36-nucleotide consensus GC-rich region sequence 1 | CGCGCTGCGCGCGCCGCCCAGTAGGGGGA GCCATGC | 163 |
| | 36-nucleotide region consensus sequence 2 | GCGCTX$_1$CGCGCGCGCGCCGGGGGGCTGCG CCCCCCC, wherein X$_1$ is selected from T, G, or A | 164 |
| | TTV Clade 1 36-nucleotide region | GCGCTTCGCGCGCCGCCCACTAGGGGGCGT TGCGCG | 165 |
| | TTV Clade 3 36-nucleotide region | GCGCTGCGCGCGCCGCCCAGTAGGGGGCG CAATGCG | 166 |
| | TTV Clade 3 isolate GH1 36-nucleotide region | GCGCTGCGCGCGCGGCCCCCGGGGGAGGC ATTGCCT | 167 |
| | TTV Clade 3 sle 1932 36-nucleotide region | GCGCTGCGCGCGCGCGCCGGGGGGGCGCC AGCGCCC | 168 |
| | TTV Clade 4 ctdc002 36-nucleotide region | GCGCTTCGCGCGCGCGCCGGGGGGCTCCGC CCCCCC | 169 |
| | TTV Clade 5 36-nucleotide region | GCGCTTCGCGCGCGCGCCGGGGGGCTGCGC CCCCCC | 170 |
| | TTV Clade 6 36-nucleotide region | GCGCTACGCGCGCGCGCCGGGGGGCTGCG CCCCCCC | 171 |
| | TTV Clade 7 36-nucleotide region | GCGCTACGCGCGCGCGCCGGGGGGCTCTGC CCCCCC | 172 |
| Additional Alphatorquevirus GC-rich region sequences | TTV-CT30F | GCGGCGGGGGGGCGGCCGCGTTCGCGCGC CGCCCACCAGGGGGTGCTGCGCGCCCCCCC CCGCGCATGCGCGGGGCCCCCCCCCGGGG GGGCTCCGCCCCCCCGGCCCCCCCCCGTGC TAAACCCACCGCGCATGCGCGACCACGCCC CCGCCGCC | 801 |

TABLE 39-continued

Exemplary GC-rich sequences from Anelloviruses

| Source | Sequence | SEQ ID NO: |
| --- | --- | --- |
| TTV-P13-1 | CCGAGCGTTAGCGAGGAGTGCGACCCTACC<br>CCCTGGGCCCACTTCTTCGGAGCCGCGCGC<br>TACGCCTTCGGCTGCGCGCGGCACCTCAGA<br>CCCCCGCTCGTGCTGACACGCTTGCGCGTG<br>TCAGACCACTTCGGGCTCGCGGGGGTCGGG | 802 |
| TTV-tth8 | GCCGCCGCGGCGGCGGGGGGCGGCGCGCT<br>GCGCGCGCCGCCCAGTAGGGGGAGCCATG<br>CGCCCCCCCCCGCGCATGCGCGGGGCCCCC<br>CCCCGCGGGGGGCTCCGCCCCCCGGCCCCC<br>CCCG | 803 |
| TTV-HD20a | CGGCCCAGCGGCGGCGCGCGCGCTTCGCGC<br>GCGCGCCGGGGGGCTCCGCCCCCCCCCGCG<br>CATGCGCGGGGCCCCCCCCCGCGGGGGGCT<br>CCGCCCCCCGGTCCCCCCCCG | 804 |
| TTV-16 | CGGCCGTGCGGCGGCGCGCGCGCTTCGCGC<br>GCGCGCCGGGGGCTGCCGCCCCCCCCCGCG<br>CATGCGCGCGGGGCCCCCCCCCGCGGGGG<br>GCTCCGCCCCCCGGCCCCCCCCCCCG | 805 |
| TTV-TJN02 | CGGCGGCGGCGCGCGCGCTACGCGCGCGC<br>GCCGGGGGGCTGCCGCCCCCCCCCCGCGCA<br>TGCGCGGGGCCCCCCCCCGCGGGGGGCTCC<br>GCCCCCCGGCCCCCC | 806 |
| TTV-HD16d | GGCGGCGGCGCGCGCGCTACGCGCGCGCG<br>CCGGGGAGCTCTGCCCCCCCCCGCGCATGC<br>GCGCGGGTCCCCCCCCCGCGGGGGGCTCCG<br>CCCCCCGGTCCCCCCCCCG | 807 |

In some embodiments, the genetic element comprises a nucleic acid sequence having at least about 70%, 75%, 80%, 85%, 90%, 95%, 96%, 97%, 98%, 99%, or 100% sequence identity to the Anellovirus GC-rich nucleotide sequence of any one of Tables N1-N25.

Effector

In some embodiments, the genetic element may include one or more sequences that encode a functional effector, e.g., an endogenous effector or an exogenous effector, e.g., a therapeutic polypeptide or nucleic acid, e.g., cytotoxic or cytolytic RNA or protein. In some embodiments, the functional nucleic acid is a non-coding RNA. In some embodiments, the functional nucleic acid is a coding RNA. The effector may modulate a biological activity, for example increasing or decreasing enzymatic activity, gene expression, cell signaling, and cellular or organ function. Effector activities may also include binding regulatory proteins to modulate activity of the regulator, such as transcription or translation. Effector activities also may include activator or inhibitor functions. For example, the effector may induce enzymatic activity by triggering increased substrate affinity in an enzyme, e.g., fructose 2,6-bisphosphate activates phosphofructokinase 1 and increases the rate of glycolysis in response to the insulin. In another example, the effector may inhibit substrate binding to a receptor and inhibit its activation, e.g., naltrexone and naloxone bind opioid receptors without activating them and block the receptors' ability to bind opioids. Effector activities may also include modulating protein stability/degradation and/or transcript stability/degradation. For example, proteins may be targeted for degradation by the polypeptide co-factor, ubiquitin, onto proteins to mark them for degradation. In another example, the effector inhibits enzymatic activity by blocking the enzyme's active site, e.g., methotrexate is a structural analog of tetrahydrofolate, a coenzyme for the enzyme dihydrofolate reductase that binds to dihydrofolate reductase 1000-fold more tightly than the natural substrate and inhibits nucleotide base synthesis.

In some embodiments, the sequence encoding an effector is part of the genetic element, e.g., it can be inserted at an insert site as described in Example 10, 12, or 22 of PCT Publication No. WO 2020/123816, incorporated by reference herein in its entirety, and Example 28 herein. In some embodiments, the sequence encoding an effector is inserted into the genetic element at a noncoding region, e.g., a noncoding region disposed 3' of the open reading frames and 5' of the GC-rich region of the genetic element, in the 5' noncoding region upstream of the TATA box, in the 5' UTR, in the 3' noncoding region downstream of the poly-A signal, or upstream of the GC-rich region. In some embodiments, the sequence encoding an effector is inserted into the genetic element at about nucleotide 3588 of a TTV-tth8 plasmid, e.g., as described herein or at about nucleotide 2843 of a TTMV-LY2 plasmid, e.g., as described herein. In some embodiments, the sequence encoding an effector is inserted into the genetic element at or within nucleotides 336-3015 of a TTV-tth8 plasmid, e.g., as described herein, or at or within nucleotides 242-2812 of a TTV-LY2 plasmid, e.g., as described herein. In some embodiments, the sequence encoding an effector replaces part or all of an open reading frame (e.g., an ORF as described herein, e.g., an ORF1, ORF1/1, ORF1/2, ORF2, ORF2/2, ORF2/3, and/or ORF2t/3 as shown in any one of Tables A1-A25 or N1-N25).

In some embodiments, the sequence encoding an effector comprises 100-2000, 100-1000, 100-500, 100-200, 200-2000, 200-1000, 200-500, 500-1000, 500-2000, or 1000-2000 nucleotides. In some embodiments, the effector is a nucleic acid or protein payload, e.g., as described in Example 28.

Regulatory Nucleic Acid

In some embodiments, the effector is a regulatory nucleic acid. Regulatory nucleic acids modify expression of an endogenous gene and/or an exogenous gene. In one embodiment, the regulatory nucleic acid targets a host gene. The regulatory nucleic acids may include, but are not limited to, a nucleic acid that hybridizes to an endogenous gene (e.g., miRNA, siRNA, mRNA, lncRNA, RNA, DNA, an antisense RNA, gRNA as described herein elsewhere), nucleic acid that hybridizes to an exogenous nucleic acid such as a viral DNA or RNA, nucleic acid that hybridizes to an RNA, nucleic acid that interferes with gene transcription, nucleic acid that interferes with RNA translation, nucleic acid that stabilizes RNA or destabilizes RNA such as through targeting for degradation, and nucleic acid that modulates a DNA or RNA binding factor. In some embodiments, the regulatory nucleic acid encodes an miRNA.

In some embodiments, the regulatory nucleic acid comprises RNA or RNA-like structures typically containing 5-500 base pairs (depending on the specific RNA structure, e.g., miRNA 5-30 bps, lncRNA 200-500 bps) and may have a nucleobase sequence identical (or complementary) or nearly identical (or substantially complementary) to a coding sequence in an expressed target gene within the cell, or a sequence encoding an expressed target gene within the cell.

In some embodiments, the regulatory nucleic acid comprises a nucleic acid sequence, e.g., a guide RNA (gRNA). In some embodiments, the DNA targeting moiety comprises a guide RNA or nucleic acid encoding the guide RNA. A gRNA short synthetic RNA can be composed of a "scaffold" sequence necessary for binding to the incomplete effector moiety and a user-defined ~20 nucleotide targeting sequence for a genomic target. In practice, guide RNA sequences are generally designed to have a length of between 17-24 nucleotides (e.g., 19, 20, or 21 nucleotides) and complementary to the targeted nucleic acid sequence. Custom gRNA generators and algorithms are available commercially for use in the design of effective guide RNAs. Gene editing has also been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing). Chemically modified sgRNAs have also been demonstrated to be effective in genome editing; see, for example, Hendel et al. (2015) Nature Biotechnol., 985-991.

The regulatory nucleic acid comprises a gRNA that recognizes specific DNA sequences (e.g., sequences adjacent to or within a promoter, enhancer, silencer, or repressor of a gene).

Certain regulatory nucleic acids can inhibit gene expression through the biological process of RNA interference (RNAi). RNAi molecules comprise RNA or RNA-like structures typically containing 15-50 base pairs (such as about 18-25 base pairs) and having a nucleobase sequence identical (complementary) or nearly identical (substantially complementary) to a coding sequence in an expressed target gene within the cell. RNAi molecules include, but are not limited to: short interfering RNAs (siRNAs), double-strand RNAs (dsRNA), micro RNAs (miRNAs), short hairpin RNAs (shRNA), meroduplexes, and dicer substrates (U.S. Pat. Nos. 8,084,599 8,349,809 and 8,513,207).

Long non-coding RNAs (lncRNA) are defined as non-protein coding transcripts longer than 100 nucleotides. This somewhat arbitrary limit distinguishes lncRNAs from small regulatory RNAs such as microRNAs (miRNAs), short interfering RNAs (siRNAs), and other short RNAs. In general, the majority (~78%) of lncRNAs are characterized as tissue-specific. Divergent lncRNAs that are transcribed in the opposite direction to nearby protein-coding genes (comprise a significant proportion ~20% of total lncRNAs in mammalian genomes) may possibly regulate the transcription of the nearby gene.

The genetic element may encode regulatory nucleic acids with a sequence substantially complementary, or fully complementary, to all or a fragment of an endogenous gene or gene product (e.g., mRNA). The regulatory nucleic acids may complement sequences at the boundary between introns and exons to prevent the maturation of newly-generated nuclear RNA transcripts of specific genes into mRNA for transcription. The regulatory nucleic acids that are complementary to specific genes can hybridize with the mRNA for that gene and prevent its translation. The antisense regulatory nucleic acid can be DNA, RNA, or a derivative or hybrid thereof.

The length of the regulatory nucleic acid that hybridizes to the transcript of interest may be between 5 to 30 nucleotides, between about 10 to 30 nucleotides, or about 11, 12, 13, 14, 15, 16, 17, 18, 19, 20, 21, 22, 23, 24, 25, 26, 27, 28, 29, 30 or more nucleotides. The degree of identity of the regulatory nucleic acid to the targeted transcript should be at least 75%, at least 80%, at least 85%, at least 90%, or at least 95%.

The genetic element may encode a regulatory nucleic acid, e.g., a micro RNA (miRNA) molecule identical to about 5 to about 25 contiguous nucleotides of a target gene. In some embodiments, the miRNA sequence targets a mRNA and commences with the dinucleotide AA, comprises a GC-content of about 30-70% (about 30-60%, about 40-60%, or about 45%-55%), and does not have a high percentage identity to any nucleotide sequence other than the target in the genome of the mammal in which it is to be introduced, for example as determined by standard BLAST search.

In some embodiments, the regulatory nucleic acid is at least one miRNA, e.g., 2, 3, 4, 5, 6, or more. In some embodiments, the genetic element comprises a sequence that encodes an miRNA at least about 75%, 80%, 85%, 90% 95%, 96%, 97%, 98%, 99% or 100% nucleotide sequence identity to any one of the nucleotide sequences or a sequence that is complementary to a sequence described herein.

siRNAs and shRNAs resemble intermediates in the processing pathway of the endogenous microRNA (miRNA) genes (Bartel, Cell 116:281-297, 2004). In some embodiments, siRNAs can function as miRNAs and vice versa (Zeng et al., Mol Cell 9:1327-1333, 2002; Doench et al., Genes Dev 17:438-442, 2003). MicroRNAs, like siRNAs, use RISC to downregulate target genes, but unlike siRNAs, most animal miRNAs do not cleave the mRNA. Instead, miRNAs reduce protein output through translational suppression or polyA removal and mRNA degradation (Wu et al., Proc Natl Acad Sci USA 103:4034-4039, 2006). Known miRNA binding sites are within mRNA 3' UTRs; miRNAs seem to target sites with near-perfect complementarity to nucleotides 2-8 from the miRNA's 5' end (Rajewsky, Nat Genet 38 Suppl:S8-13, 2006; Lim et al., Nature 433:769-773, 2005). This region is known as the seed region. Because siRNAs and miRNAs are interchangeable, exogenous siRNAs downregulate mRNAs with seed complementarity to the siRNA (Birmingham et al., Nat Methods 3:199-204, 2006. Multiple target sites within a 3' UTR give stronger downregulation (Doench et al., Genes Dev 17:438-442, 2003).

Lists of known miRNA sequences can be found in databases maintained by research organizations, such as Wellcome Trust Sanger Institute, Penn Center for Bioinformatics, Memorial Sloan Kettering Cancer Center, and European Molecule Biology Laboratory, among others. Known effective siRNA sequences and cognate binding sites are also well represented in the relevant literature. RNAi molecules are readily designed and produced by technologies known in the art. In addition, there are computational tools that increase the chance of finding effective and specific sequence motifs (Lagana et al., Methods Mol. Bio., 2015, 1269:393-412).

The regulatory nucleic acid may modulate expression of RNA encoded by a gene. Because multiple genes can share some degree of sequence homology with each other, in some embodiments, the regulatory nucleic acid can be designed to target a class of genes with sufficient sequence homology. In some embodiments, the regulatory nucleic acid can contain a sequence that has complementarity to sequences that are shared amongst different gene targets or are unique for a specific gene target. In some embodiments, the regulatory nucleic acid can be designed to target conserved regions of an RNA sequence having homology between several genes thereby targeting several genes in a gene family (e.g., different gene isoforms, splice variants, mutant genes, etc.). In some embodiments, the regulatory nucleic acid can be designed to target a sequence that is unique to a specific RNA sequence of a single gene.

In some embodiments, the genetic element may include one or more sequences that encode regulatory nucleic acids that modulate expression of one or more genes.

In one embodiment, the gRNA described elsewhere herein are used as part of a CRISPR system for gene editing. For the purposes of gene editing, the anellovector or anelloVLP may be designed to include one or multiple guide RNA sequences corresponding to a desired target DNA sequence; see, for example, Cong et al. (2013) Science, 339:819-823; Ran et al. (2013) Nature Protocols, 8:2281-2308. At least about 16 or 17 nucleotides of gRNA sequence generally allow for Cas9-mediated DNA cleavage to occur; for Cpf1 at least about 16 nucleotides of gRNA sequence is needed to achieve detectable DNA cleavage.

Therapeutic Effectors (e.g., Peptides or Polypeptides)

In some embodiments, the genetic element comprises a therapeutic expression sequence, e.g., a sequence that encodes a therapeutic peptide or polypeptide, e.g., an intracellular peptide or intracellular polypeptide, a secreted polypeptide, or a protein replacement therapeutic, e.g., a wild-type protein or a functional fragment or variant thereof. In some embodiments, the genetic element includes a sequence encoding a protein e.g., a therapeutic protein. Some examples of therapeutic proteins may include, but are not limited to, a hormone, a cytokine, an enzyme, an antibody (e.g., one or a plurality of polypeptides encoding at least a heavy chain or a light chain), a transcription factor, a receptor (e.g., a membrane receptor), a ligand, a membrane transporter, a secreted protein, a peptide, a carrier protein, a structural protein, a nuclease, or a component thereof.

In some embodiments, the genetic element includes a sequence encoding a peptide e.g., a therapeutic peptide. The peptides may be linear or branched. The peptide has a length from about 5 to about 500 amino acids, about 15 to about 400 amino acids, about 20 to about 325 amino acids, about 25 to about 250 amino acids, about 50 to about 200 amino acids, or any range there between.

In some embodiments, the polypeptide encoded by the therapeutic expression sequence may be a functional variant or fragment thereof of any of the above, e.g., a protein having at least 80%, 85%, 90%, 95%, $^{967}$%, 98%, 99% identity to a protein sequence which disclosed in a table herein by reference to its UniProt ID.

In some embodiments, the therapeutic expression sequence may encode an antibody or antibody fragment that binds any of the above, e.g., an antibody against a protein having at least 80%, 85%, 90%, 95%, 967%, 98%, 99% identity to a protein sequence which disclosed in a table herein by reference to its UniProt ID. The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An "antibody fragment" refers to a molecule that includes at least one heavy chain or light chain and binds an antigen. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments.

In some embodiments, an effector as described herein comprises a cytosolic polypeptide or cytosolic peptide, e.g., a wild-type protein or a functional fragment or variant thereof.

In some embodiments, the effector comprises a regulatory intracellular polypeptide, e.g., a wild-type protein or a functional fragment or variant thereof. In some embodiments, the regulatory intracellular polypeptide binds one or more molecule (e.g., protein or nucleic acid) endogenous to the target cell. In some embodiments, the regulatory intracellular polypeptide increases the level or activity of one or more molecule (e.g., protein or nucleic acid) endogenous to the target cell. In some embodiments, the regulatory intracellular polypeptide decreases the level or activity of one or more molecule (e.g., protein or nucleic acid) endogenous to the target cell.

In some embodiments, an effector as described herein comprises a secreted polypeptide effector, e.g., a wild-type protein or a functional fragment or variant thereof. Exemplary secreted therapeutics include cytokines and cytokine receptors.

Exemplary cytokines and cytokine receptors are described, e.g., in Akdis et al., "Interleukins (from IL-1 to IL-38), interferons, transforming growth factor β, and TNF-α: Receptors, functions, and roles in diseases" October 2016 Volume 138, Issue 4, Pages 984-1010.

Additional exemplary secreted therapeutics include polypeptide hormones and receptors, e.g., a wild-type protein or a functional fragment or variant thereof.

Additional exemplary secreted therapeutics include growth factors, e.g., a wild-type protein or a functional fragment or variant thereof. Exemplary growth factors and growth factor receptors are described, e.g., in Bafico et al., "Classification of Growth Factors and Their Receptors" Holland-Frei Cancer Medicine. 6th edition.

Additional exemplary secreted therapeutics include clotting-associated factors, e.g., a wild-type protein or a functional fragment or variant thereof.

In some embodiments, an effector described herein comprises a protein replacement therapeutic, e.g., a wild-type protein or a functional fragment or variant thereof. Exemplary protein replacement therapeutics are described herein.

In some embodiments, an effector described herein comprises an enzymatic effector, e.g., a wild-type protein or a functional fragment or variant thereof.

In some embodiments, an effector described herein comprises a non-enzymatic effector, e.g., a wild-type protein or a functional fragment or variant thereof.

In some embodiments, an effector described herein comprises a protein that, when mutated, causes a lysosomal storage disorder, e.g., a wild-type protein or a functional fragment or variant thereof. In some embodiments, an effector described herein comprises a transporter protein, e.g., a wild-type protein or a functional fragment or variant thereof.

In some embodiments, a functional variant of a wild-type protein comprises a protein that has one or more activities of the wild-type protein, e.g., the functional variant catalyzes the same reaction as the corresponding wild-type protein, e.g., at a rate no less than 10%, 20%, 30%, 40%, or 50% lower than the wild-type protein. In some embodiments, the functional variant binds to the same binding partner that is bound by the wild-type protein, e.g., with a Kd of no more than 10%, 20%, 30%, 40%, or 50% higher than the Kd of the corresponding wild-type protein for the same binding partner under the same conditions. In some embodiments, the functional variant has at a polyeptpide sequence at least 70%, 75%, 80%, 85%, 90%, 95%, 96%, 97%, 98%, or 99% identical to that of the wild-type polypeptide. In some embodiments, the functional variant comprises a homolog (e.g., ortholog or paralog) of the corresponding wild-type protein. In some embodiments, the functional variant is a fusion protein. In some embodiments, the fusion comprises a first region with at least 70%, 75%, 80%, 85%, 90%, 95%, 96%, 97%, 98%, or 99% identity to the corresponding wild-type protein, and a second, heterologous region. In some embodiments, the functional variant comprises or consists of a fragment of the corresponding wild-type protein.

In some embodiments, an effector as described herein comprises a transformation factor, e.g., a wild-type protein or a fragment or variant thereof. In embodiments, the transformation factor is a protein factor that transforms fibroblasts into differentiated cells. In some embodiments, an effector as described herein comprises a protein that stimulates cellular regeneration, e.g., a wild-type protein or a fragment or variant thereof.

In some embodiments, an effector as described herein modulates STING/cGAS signaling, e.g., a wild-type protein or a fragment or variant thereof. In some embodiments, the STING modulator is a polypeptide, e.g., a viral polypeptide or a functional variant thereof. For instance, the effector may comprise a STING modulator (e.g., inhibitor) described in Maringer et al. "Message in a bottle: lessons learned from antagonism of STING signalling during RNA virus infection" Cytokine & Growth Factor Reviews Volume 25, Issue 6, December 2014, Pages 669-679. Additional STING modulators (e.g., activators) are described, e.g., in Wang et al. "STING activator c-di-GMP enhances the anti-tumor effects of peptide vaccines in melanoma-bearing mice." Cancer Immunol Immunother. 2015 August; 64(8):1057-66. doi: 10.1007/s00262-015-1713-5. Epub 2015 May 19; Bose "cGAS/STING Pathway in Cancer: Jekyll and Hyde Story of Cancer Immune Response" Int J Mol Sci. 2017 November; 18(11): 2456; and Fu et al. "STING agonist formulated cancer vaccines can cure established tumors resistant to PD-1 blockade" Sci Transl Med. 2015 Apr. 15; 7(283): 283ra52. Some examples of peptides include, but are not limited to, fluorescent tag or marker, antigen, peptide therapeutic, synthetic or analog peptide from naturally-bioactive peptide, agonist or antagonist peptide, anti-microbial peptide, a targeting or cytotoxic peptide, a degradation or self-destruction peptide, and degradation or self-destruction peptides. Peptides useful in the invention described herein also include antigen-binding peptides, e.g., antigen binding antibody or antibody-like fragments, such as single chain antibodies, nanobodies (see, e.g., Steeland et al. 2016. Nanobodies as therapeutics: big opportunities for small antibodies. Drug Discov Today: 21(7):1076-113). Such antigen binding peptides may bind a cytosolic antigen, a nuclear antigen, or an intra-organellar antigen.

In some embodiments, the genetic element comprises a sequence that encodes small peptides, peptidomimetics (e.g., peptoids), amino acids, and amino acid analogs. Such therapeutics generally have a molecular weight less than about 5,000 grams per mole, a molecular weight less than about 2,000 grams per mole, a molecular weight less than about 1,000 grams per mole, a molecular weight less than about 500 grams per mole, and salts, esters, and other pharmaceutically acceptable forms of such compounds. Such therapeutics may include, but are not limited to, a neurotransmitter, a hormone, a drug, a toxin, a viral or microbial particle, a synthetic molecule, and agonists or antagonists thereof.

In some embodiments, the composition, anellovector, or anelloVLP described herein includes a polypeptide linked to a ligand that is capable of targeting a specific location, tissue, or cell.

Gene Editing Components

The genetic element of the anellovector may include one or more genes that encode a component of a gene editing system. Alternatively, an anellovector or anelloVLP as described herein may comprise a component of a gene editing system. Exemplary gene editing systems include the clustered regulatory interspaced short palindromic repeat (CRISPR) system, zinc finger nucleases (ZFNs), and Transcription Activator-Like Effector-based Nucleases (TALEN). ZFNs, TALENs, and CRISPR-based methods are described, e.g., in Gaj et al. Trends Biotechnol. 31.7(2013): 397-405; CRISPR methods of gene editing are described, e.g., in Guan et al., Application of CRISPR-Cas system in gene therapy: Pre-clinical progress in animal model. DNA Repair 2016 October; 46:1-8. doi: 10.1016/j.dnarep.2016.07.004; Zheng et al., Precise gene deletion and replacement using the CRISPR/Cas9 system in human cells. BioTechniques, Vol. 57, No. 3, September 2014, pp. 115-124.

CRISPR systems are adaptive defense systems originally discovered in bacteria and archaea. CRISPR systems use RNA-guided nucleases termed CRISPR-associated or "Cas" endonucleases (e. g., Cas9 or Cpf1) to cleave foreign DNA. In a typical CRISPR/Cas system, an endonuclease is directed to a target nucleotide sequence (e. g., a site in the genome that is to be sequence-edited) by sequence-specific, non-coding "guide RNAs" that target single- or double-stranded DNA sequences. Three classes (I-III) of CRISPR systems have been identified. The class II CRISPR systems use a single Cas endonuclease (rather than multiple Cas proteins). One class II CRISPR system includes a type II Cas endonuclease such as Cas9, a CRISPR RNA ("crRNA"), and a trans-activating crRNA ("tracrRNA"). The crRNA contains a "guide RNA", typically about 20-nucleotide RNA sequence that corresponds to a target DNA sequence. The crRNA also contains a region that binds to the tracrRNA to form a partially double-stranded structure which is cleaved by RNase III, resulting in a crRNA/tracrRNA hybrid. The crRNA/tracrRNA hybrid then directs the Cas9 endonuclease to recognize and cleave the target DNA sequence. The target DNA sequence must generally be adjacent to a "protospacer adjacent motif" ("PAM") that is specific for a given Cas endonuclease; however, PAM sequences appear throughout a given genome.

In some embodiments, the anellovector includes a gene for a CRISPR endonuclease. For example, some CRISPR endonucleases identified from various prokaryotic species have unique PAM sequence requirements; examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), and 5'-NNNGATT (*Neisseria meningitidis*). Some endonucleases, e. g., Cas9 endonucleases, are associated with G-rich PAM sites, e. g., 5'-NGG, and perform blunt-end cleaving of the target DNA at a location 3 nucleotides upstream from (5' from) the PAM site. Another class II CRISPR system includes the type V endonuclease Cpf1, which is smaller than Cas9; examples include AsCpf1 (from Acidaminococcus sp.) and LbCpf1 (from Lachnospiraceae sp.). Cpf1 endonucleases, are associated with T-rich PAM sites, e. g., 5'-TTN. Cpf1 can also recognize a 5'-CTA PAM motif. Cpf1 cleaves the target DNA by introducing an offset or staggered double-strand break with a 4- or 5-nucleotide 5' overhang, for example, cleaving a target DNA with a 5-nucleotide offset or staggered cut located 18 nucleotides downstream from (3' from) from the PAM site on the coding strand and 23 nucleotides downstream from the PAM site on the complimentary strand; the 5-nucleotide overhang that results from such offset cleavage allows more precise genome editing by DNA insertion by homologous recombination than by insertion at blunt-end cleaved DNA. See, e. g., Zetsche et al. (2015) Cell, 163:759-771.

A variety of CRISPR associated (Cas) genes may be included in the anellovector. Specific examples of genes are those that encode Cas proteins from class II systems including Cas1, Cas2, Cas3, Cas4, Cas5, Cas6, Cas7, Cas8, Cas9, Cas10, Cpf1, C2C1, or C2C3. In some embodiments, the anellovector includes a gene encoding a Cas protein, e.g., a Cas9 protein, may be from any of a variety of prokaryotic species. In some embodiments, the anellovector includes a gene encoding a particular Cas protein, e.g., a particular Cas9 protein, is selected to recognize a particular protospacer-adjacent motif (PAM) sequence. In some embodiments, the anellovector includes nucleic acids encoding two or more different Cas proteins, or two or more Cas proteins, may be introduced into a cell, zygote, embryo, or animal, e.g., to allow for recognition and modification of sites comprising the same, similar or different PAM motifs. In some embodiments, the anellovector includes a gene encoding a modified Cas protein with a deactivated nuclease, e.g., nuclease-deficient Cas9.

Whereas wild-type Cas9 protein generates double-strand breaks (DSBs) at specific DNA sequences targeted by a gRNA, a number of CRISPR endonucleases having modified functionalities are known, for example: a "nickase" version of Cas endonuclease (e.g., Cas9) generates only a single-strand break; a catalytically inactive Cas endonuclease, e.g., Cas9 ("dCas9") does not cut the target DNA. A gene encoding a dCas9 can be fused with a gene encoding an effector domain to repress (CRISPRi) or activate (CRISPRa) expression of a target gene. For example, the gene may encode a Cas9 fusion with a transcriptional silencer (e.g., a KRAB domain) or a transcriptional activator (e.g., a dCas9-VP64 fusion). A gene encoding a catalytically inactive Cas9 (dCas9) fused to FokI nuclease ("dCas9-FokI") can be included to generate DSBs at target sequences homologous to two gRNAs. See, e. g., the numerous CRISPR/Cas9 plasmids disclosed in and publicly available from the Addgene repository (Addgene, 75 Sidney St., Suite 550A, Cambridge, MA 02139; addgene.org/crispr/). A "double nickase" Cas9 that introduces two separate double-strand breaks, each directed by a separate guide RNA, is described as achieving more accurate genome editing by Ran et al. (2013) Cell, 154:1380-1389.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1.

In some embodiments, the anellovector comprises a gene encoding a polypeptide described herein, e.g., a targeted nuclease, e.g., a Cas9, e.g., a wild type Cas9, a nickase Cas9 (e.g., Cas9 D10A), a dead Cas9 (dCas9), eSpCas9, Cpf1, C2C1, or C2C3, and a gRNA. The choice of genes encoding the nuclease and gRNA(s) is determined by whether the targeted mutation is a deletion, substitution, or addition of nucleotides, e.g., a deletion, substitution, or addition of nucleotides to a targeted sequence. Genes that encode a catalytically inactive endonuclease e.g., a dead Cas9 (dCas9, e.g., D10A; H840A) tethered with all or a portion of (e.g., biologically active portion of) an (one or more) effector domain (e.g., VP64) create chimeric proteins that can modulate activity and/or expression of one or more target nucleic acids sequences.

In some embodiments, the anellovector includes a gene encoding a fusion of a dCas9 with all or a portion of one or more effector domains (e.g., a full-length wild-type effector domain, or a fragment or variant thereof, e.g., a biologically active portion thereof) to create a chimeric protein useful in the methods described herein. Accordingly, in some embodiments, the anellovector includes a gene encoding a dCas9-methylase fusion. In other some embodiments, the anellovector includes a gene encoding a dCas9-enzyme fusion with a site-specific gRNA to target an endogenous gene.

In other aspects, the anellovector includes a gene encoding 1, 2, 3, 4, 5, 6, 7, 8, 9, 10, 11, 12, 13, 14, 15, 16, 17, 18, 19, 20, or more effector domains (all or a biologically active portion) fused with dCas9.

Regulatory Sequences

In some embodiments, the genetic element comprises a regulatory sequence, e.g., a promoter or an enhancer, operably linked to the sequence encoding the effector.

In some embodiments, a promoter includes a DNA sequence that is located adjacent to a DNA sequence that encodes an expression product. A promoter may be linked operatively to the adjacent DNA sequence. A promoter typically increases an amount of product expressed from the DNA sequence as compared to an amount of the expressed product when no promoter exists. A promoter from one organism can be utilized to enhance product expression from the DNA sequence that originates from another organism. For example, a vertebrate promoter may be used for the expression of jellyfish GFP in vertebrates. In addition, one promoter element can increase an amount of products expressed for multiple DNA sequences attached in tandem. Hence, one promoter element can enhance the expression of one or more products. Multiple promoter elements are well-known to persons of ordinary skill in the art.

In one embodiment, high-level constitutive expression is desired. Examples of such promoters include, without limitation, the retroviral Rous sarcoma virus (RSV) long terminal repeat (LTR) promoter/enhancer, the cytomegalovirus (CMV) immediate early promoter/enhancer (see, e.g., Boshart et al, Cell, 41:521-530 (1985)), the SV40 promoter, the dihydrofolate reductase promoter, the cytoplasmic .beta.-actin promoter and the phosphoglycerol kinase (PGK) promoter.

In another embodiment, inducible promoters may be desired. Inducible promoters are those which are regulated by exogenously supplied compounds, either in cis or in trans, including without limitation, the zinc-inducible sheep metallothionine (MT) promoter; the dexamethasone (Dex)-inducible mouse mammary tumor virus (MMTV) promoter; the T7 polymerase promoter system (WO 98/10088); the tetracycline-repressible system (Gossen et al, Proc. Natl. Acad. Sci. USA, 89:5547-5551 (1992)); the tetracycline-inducible system (Gossen et al., Science, 268:1766-1769 (1995); see also Harvey et al., Curr. Opin. Chem. Biol., 2:512-518 (1998)); the RU486-inducible system (Wang et al., Nat. Biotech., 15:239-243 (1997) and Wang et al., Gene Ther., 4:432-441 (1997)]; and the rapamycin-inducible system (Magari et al., J. Clin. Invest., 100:2865-2872 (1997); Rivera et al., Nat. Medicine. 2:1028-1032 (1996)). Other types of inducible promoters which may be useful in this context are those which are regulated by a specific physiological state, e.g., temperature, acute phase, or in replicating cells only.

In some embodiments, a native promoter for a gene or nucleic acid sequence of interest is used. The native promoter may be used when it is desired that expression of the gene or the nucleic acid sequence should mimic the native expression. The native promoter may be used when expression of the gene or other nucleic acid sequence must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the genetic element comprises a gene operably linked to a tissue-specific promoter. For instance, if expression in skeletal muscle is desired, a promoter active in muscle may be used. These include the promoters from genes encoding skeletal α-actin, myosin light chain 2A, dystrophin, muscle creatine kinase, as well as synthetic muscle promoters with activities higher than naturally-occurring promoters. See Li et al., Nat. Biotech., 17:241-245 (1999). Examples of promoters that are tissue-specific are known for liver albumin, Miyatake et al. J. Virol., 71:5124-32 (1997); hepatitis B virus core promoter, Sandig et al., Gene Ther. 3:1002-9 (1996); alpha-fetoprotein (AFP), Arbuthnot et al., Hum. Gene Ther., 7:1503-14 (1996)], bone (osteocalcin, Stein et al., Mol. Biol. Rep., 24:185-96 (1997); bone sialoprotein, Chen et al., J. Bone Miner. Res. 11:654-64 (1996)), lymphocytes (CD2, Hansal et al., J. Immunol., 161:1063-8 (1998); immunoglobulin heavy chain; T cell receptor a chain), neuronal (neuron-specific enolase (NSE) promoter, Andersen et al. Cell. Mol. Neurobiol., 13:503-15 (1993); neurofilament light-chain gene, Piccioli et al., Proc. Natl. Acad. Sci. USA, 88:5611-5 (1991); the neuron-specific vgf gene, Piccioli et al., Neuron, 15:373-84 (1995)]; among others.

The genetic element may include an enhancer, e.g., a DNA sequence that is located adjacent to the DNA sequence that encodes a gene. Enhancer elements are typically located upstream of a promoter element or can be located downstream of or within a coding DNA sequence (e.g., a DNA sequence transcribed or translated into a product or products). Hence, an enhancer element can be located 100 base pairs, 200 base pairs, or 300 or more base pairs upstream or downstream of a DNA sequence that encodes the product. Enhancer elements can increase an amount of recombinant product expressed from a DNA sequence above increased expression afforded by a promoter element. Multiple enhancer elements are readily available to persons of ordinary skill in the art.

In some embodiments, the genetic element comprises one or more inverted terminal repeats (ITR) flanking the sequences encoding the expression products described herein. In some embodiments, the genetic element comprises one or more long terminal repeats (LTR) flanking the sequence encoding the expression products described herein. Examples of promoter sequences that may be used, include, but are not limited to, the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, and a Rous sarcoma virus promoter.

Replication Proteins

In some embodiments, the genetic element of the anellovector, e.g., synthetic anellovector, may include sequences that encode one or more replication proteins. In some embodiments, the anellovector may replicate by a rolling-circle replication method, e.g., synthesis of the leading strand and the lagging strand is uncoupled. In such embodiments, the anellovector comprises three elements additional elements: i) a gene encoding an initiator protein, ii) a double strand origin, and iii) a single strand origin. A rolling circle replication (RCR) protein complex comprising replication proteins binds to the leading strand and destabilizes the replication origin. The RCR complex cleaves the genome to generate a free 3'OH extremity. Cellular DNA polymerase initiates viral DNA replication from the free 3'OH extremity. After the genome has been replicated, the RCR complex closes the loop covalently. This leads to the release of a positive circular single-stranded parental DNA molecule and a circular double-stranded DNA molecule composed of the negative parental strand and the newly synthesized positive strand. The single-stranded DNA molecule can be either encapsidated or involved in a second round of replication. See for example, Virology Journal 2009, 6:60 doi:10.1186/1743-422X-6-60.

The genetic element may comprise a sequence encoding a polymerase, e.g., RNA polymerase or a DNA polymerase.

Other Sequences

In some embodiments, the genetic element further includes a nucleic acid encoding a product (e.g., a ribozyme, a therapeutic mRNA encoding a protein, an exogenous gene).

In some embodiments, the genetic element includes one or more sequences that affect species and/or tissue and/or cell tropism (e.g. capsid protein sequences), infectivity (e.g. capsid protein sequences), immunosuppression/activation (e.g. regulatory nucleic acids), viral genome binding and/or packaging, immune evasion (non-immunogenicity and/or tolerance), pharmacokinetics, endocytosis and/or cell attachment, nuclear entry, intracellular modulation and localization, exocytosis modulation, propagation, and nucleic acid protection of the anellovector in a host or host cell.

In some embodiments, the genetic element may comprise other sequences that include DNA, RNA, or artificial nucleic acids. The other sequences may include, but are not limited to, genomic DNA, cDNA, or sequences that encode tRNA, mRNA, rRNA, miRNA, gRNA, siRNA, or other RNAi molecules. In one embodiment, the genetic element includes a sequence encoding an siRNA to target a different loci of the same gene expression product as the regulatory nucleic acid. In one embodiment, the genetic element includes a sequence encoding an siRNA to target a different gene expression product as the regulatory nucleic acid.

In some embodiments, the genetic element further comprises one or more of the following sequences: a sequence that encodes one or more miRNAs, a sequence that encodes one or more replication proteins, a sequence that encodes an exogenous gene, a sequence that encodes a therapeutic, a regulatory sequence (e.g., a promoter, enhancer), a sequence that encodes one or more regulatory sequences that targets endogenous genes (siRNA, lncRNAs, shRNA), and a sequence that encodes a therapeutic mRNA or protein.

The other sequences may have a length from about 2 to about 5000 nts, about 10 to about 100 nts, about 50 to about 150 nts, about 100 to about 200 nts, about 150 to about 250 nts, about 200 to about 300 nts, about 250 to about 350 nts, about 300 to about 500 nts, about 10 to about 1000 nts, about 50 to about 1000 nts, about 100 to about 1000 nts, about 1000 to about 2000 nts, about 2000 to about 3000 nts, about 3000 to about 4000 nts, about 4000 to about 5000 nts, or any range therebetween.

Encoded Genes

For example, the genetic element may include a gene associated with a signaling biochemical pathway, e.g., a signaling biochemical pathway-associated gene or polynucleotide. Examples include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease.

Examples of disease-associated genes and polynucleotides are available from McKusick-Nathans Institute of Genetic Medicine, Johns Hopkins University (Baltimore, Md.) and National Center for Biotechnology Information, National Library of Medicine (Bethesda, Md.). Examples of disease-associated genes and polynucleotides are listed in Tables A and B of U.S. Pat. No. 8,697,359, which are herein incorporated by reference in their entirety. Disease specific information is available from McKusick-Nathans Institute of Genetic Medicine, Johns Hopkins University (Baltimore, Md.) and National Center for Biotechnology Information, National Library of Medicine (Bethesda, Md.). Examples of signaling biochemical pathway-associated genes and polynucleotides are listed in Tables A-C of U.S. Pat. No. 8,697,359, which are herein incorporated by reference in their entirety.

Moreover, the genetic elements can encode targeting moieties, as described elsewhere herein. This can be achieved, e.g., by inserting a polynucleotide encoding a sugar, a glycolipid, or a protein, such as an antibody. Those skilled in the art know additional methods for generating targeting moieties.

Viral Sequence

In some embodiments, the genetic element comprises at least one viral sequence. In some embodiments, the sequence has homology or identity to one or more sequence from a single stranded DNA virus, e.g., Anellovirus, Bidnavirus, Circovirus, Geminivirus, Genomovirus, Inovirus, Microvirus, Nanovirus, Parvovirus, and Spiravirus. In some embodiments, the sequence has homology or identity to one or more sequence from a double stranded DNA virus, e.g., Adenovirus, Ampullavirus, Ascovirus, Asfarvirus, Baculovirus, Fusellovirus, Globulovirus, Guttavirus, Hytrosavirus, Herpesvirus, Iridovirus, Lipothrixvirus, Nimavirus, and Poxvirus. In some embodiments, the sequence has homology or identity to one or more sequence from an RNA virus, e.g., Alphavirus, Furovirus, Hepatitis virus, Hordeivirus, Tobamovirus, Tobravirus, Tricornavirus, Rubivirus, Birnavirus, Cystovirus, Partitivirus, and Reovirus.

In some embodiments, the genetic element may comprise one or more sequences from a non-pathogenic virus, e.g., a symbiotic virus, e.g., a commensal virus, e.g., a native virus, e.g., an Anellovirus. Recent changes in nomenclature have classified the three Anelloviruses able to infect human cells into Alphatorquevirus (TT), Betatorquevirus (TTM), and Gammatorquevirus (TTMD) Genera of the Anelloviridae family of viruses. To date Anelloviruses have not been linked to any human disease. In some embodiments, the genetic element may comprise a sequence with homology or identity to a Torque Teno Virus (TT), a non-enveloped, single-stranded DNA virus with a circular, negative-sense genome. In some embodiments, the genetic element may comprise a sequence with homology or identity to a SEN virus, a Sentinel virus, a TTV-like mini virus, and a TT virus. Different types of TT viruses have been described including TT virus genotype 6, TT virus group, TTV-like virus DXL1, and TTV-like virus DXL2. In some embodiments, the genetic element may comprise a sequence with homology or identity to a smaller virus, Torque Teno-like Mini Virus (TTM), or a third virus with a genomic size in between that of TTV and TTMV, named Torque Teno-like Midi Virus (TTMD). In some embodiments, the genetic element may comprise one or more sequences or a fragment of a sequence from a non-pathogenic virus having at least about 60%, 70% 80%, 85%, 90% 95%, 96%, 97%, 98% and 99% nucleotide sequence identity to any one of the nucleotide sequences described herein.

In some embodiments, the genetic element comprises one or more sequences with homology or identity to one or more sequences from one or more non-Anelloviruses, e.g., adenovirus, herpes virus, pox virus, vaccinia virus, SV40, papilloma virus, an RNA virus such as a retrovirus, e.g., lentivirus, a single-stranded RNA virus, e.g., hepatitis virus, or a double-stranded RNA virus e.g., rotavirus. Since, in some embodiments, recombinant retroviruses are defective, assistance may be provided order to produce infectious particles. Such assistance can be provided, e.g., by using helper cell lines that contain plasmids encoding all of the structural genes of the retrovirus under the control of regulatory sequences within the LTR. Suitable cell lines for replicating the anellovectors described herein include cell lines known in the art, e.g., A549 cells, which can be modified as described herein. Said genetic element can additionally contain a gene encoding a selectable marker so that the desired genetic elements can be identified.

In some embodiments, the genetic element includes non-silent mutations, e.g., base substitutions, deletions, or additions resulting in amino acid differences in the encoded polypeptide, so long as the sequence remains at least about 70%, 75%, 80%, 85%, 90%, 95%, 96%, 97%, 98%, or 99% identical to the polypeptide encoded by the first nucleotide sequence or otherwise is useful for practicing the present invention. In this regard, certain conservative amino acid substitutions may be made which are generally recognized not to inactivate overall protein function: such as in regard of positively charged amino acids (and vice versa), lysine, arginine and histidine; in regard of negatively charged amino acids (and vice versa), aspartic acid and glutamic acid; and in regard of certain groups of neutrally charged amino acids (and in all cases, also vice versa), (1) alanine and serine, (2) asparagine, glutamine, and histidine, (3) cysteine and serine, (4) glycine and proline, (5) isoleucine, leucine and valine, (6) methionine, leucine and isoleucine, (7) phenylalanine, methionine, leucine, and tyrosine, (8) serine and threonine, (9) tryptophan and tyrosine, (10) and for example tyrosine, tryptophan and phenylalanine. Amino acids can be classified according to physical properties and contribution to secondary and tertiary protein structure. A conservative substitution is recognized in the art as a substitution of one amino acid for another amino acid that has similar properties.

Identity of two or more nucleic acid or polypeptide sequences having the same or a specified percentage of nucleotides or amino acid residues that are the same (e.g., about 60%, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) may be measured using a BLAST or BLAST 2.0 sequence comparison algorithms with default parameters described below, or by manual alignment and visual inspection (see, e.g., NCBI web site www_ncbi_nlm-_nih_gov/BLAST/or the like). Identity may also refer to, or may be applied to, the compliment of a test sequence. Identity also includes sequences that have deletions and/or additions, as well as those that have substitutions. As described herein, the algorithms account for gaps and the like. Identity may exist over a region that is at least about 10 amino acids or nucleotides in length, about 15 amino acids or nucleotides in length, about 20 amino acids or nucleotides in length, about 25 amino acids or nucleotides in length, about 30 amino acids or nucleotides in length, about 35 amino acids or nucleotides in length, about 40 amino acids or nucleotides in length, about 45 amino acids or nucleotides in length, about 50 amino acids or nucleotides in length, or more.

In some embodiments, the genetic element comprises a nucleotide sequence with at least about 75% nucleotide sequence identity, at least about 80%, 85%, 90% 95%, 96%, 97%, 98%, 99% or 100% nucleotide sequence identity to any one of the nucleotide sequences described herein, e.g., as listed in any one of Tables N1-N25. Since the genetic code is degenerate, a homologous nucleotide sequence can include any number of silent base changes, i.e., nucleotide substitutions that nonetheless encode the same amino acid.

Gene Editing Component

The genetic element of the anellovector may include one or more genes that encode a component of a gene editing system. Exemplary gene editing systems include the clustered regulatory interspaced short palindromic repeat (CRISPR) system, zinc finger nucleases (ZFNs), and Transcription Activator-Like Effector-based Nucleases (TALEN). ZFNs, TALENs, and CRISPR-based methods are described, e.g., in Gaj et al. Trends Biotechnol. 31.7(2013): 397-405; CRISPR methods of gene editing are described, e.g., in Guan et al., Application of CRISPR-Cas system in gene therapy: Pre-clinical progress in animal model. DNA Repair 2016 October; 46:1-8. doi: 10.1016/j.dnarep.2016.07.004; Zheng et al., Precise gene deletion and replacement using the CRISPR/Cas9 system in human cells. BioTechniques, Vol. 57, No. 3, September 2014, pp. 115-124.

CRISPR systems are adaptive defense systems originally discovered in bacteria and archaea. CRISPR systems use RNA-guided nucleases termed CRISPR-associated or "Cas" endonucleases (e. g., Cas9 or Cpf1) to cleave foreign DNA. In a typical CRISPR/Cas system, an endonuclease is directed to a target nucleotide sequence (e. g., a site in the genome that is to be sequence-edited) by sequence-specific, non-coding "guide RNAs" that target single- or double-stranded DNA sequences. Three classes (I-III) of CRISPR systems have been identified. The class II CRISPR systems use a single Cas endonuclease (rather than multiple Cas proteins). One class II CRISPR system includes a type II Cas endonuclease such as Cas9, a CRISPR RNA ("crRNA"), and a trans-activating crRNA ("tracrRNA"). The crRNA contains a "guide RNA", typically about 20-nucleotide RNA sequence that corresponds to a target DNA sequence. The crRNA also contains a region that binds to the tracrRNA to form a partially double-stranded structure which is cleaved by RNase III, resulting in a crRNA/tracrRNA hybrid. The crRNA/tracrRNA hybrid then directs the Cas9 endonuclease to recognize and cleave the target DNA sequence. The target DNA sequence must generally be adjacent to a "protospacer adjacent motif" ("PAM") that is specific for a given Cas endonuclease; however, PAM sequences appear throughout a given genome.

In some embodiments, the anellovector includes a gene for a CRISPR endonuclease. For example, some CRISPR endonucleases identified from various prokaryotic species have unique PAM sequence requirements; examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), and 5'-NNNGATT (*Neisseria meningitidis*). Some endonucleases, e. g., Cas9 endonucleases, are associated with G-rich PAM sites, e. g., 5'-NGG, and perform blunt-end cleaving of the target DNA at a location 3 nucleotides upstream from (5' from) the PAM site. Another class II CRISPR system includes the type V endonuclease Cpf1, which is smaller than Cas9; examples include AsCpf1 (from Acidaminococcus sp.) and LbCpf1 (from Lachnospiraceae sp.). Cpf1 endonucleases, are associated with T-rich PAM sites, e. g., 5'-TTN. Cpf1 can also recognize a 5'-CTA PAM motif. Cpf1 cleaves the target DNA by introducing an offset or staggered double-strand break with a 4- or 5-nucleotide 5' overhang, for example, cleaving a target DNA with a 5-nucleotide offset or staggered cut located 18 nucleotides downstream from (3' from) from the PAM site on the coding strand and 23 nucleotides downstream from the PAM site on the complimentary strand; the 5-nucleotide overhang that results from such offset cleavage allows more precise genome editing by DNA insertion by homologous recombination than by insertion at blunt-end cleaved DNA. See, e. g., Zetsche et al. (2015) Cell, 163:759-771.

A variety of CRISPR associated (Cas) genes may be included in the anellovector. Specific examples of genes are those that encode Cas proteins from class II systems including Cas1, Cas2, Cas3, Cas4, Cas5, Cas6, Cas7, Cas8, Cas9, Cas10, Cpf1, C2C1, or C2C3. In some embodiments, the anellovector includes a gene encoding a Cas protein, e.g., a Cas9 protein, may be from any of a variety of prokaryotic species. In some embodiments, the anellovector includes a gene encoding a particular Cas protein, e.g., a particular Cas9 protein, is selected to recognize a particular protospacer-adjacent motif (PAM) sequence. In some embodiments, the anellovector includes nucleic acids encoding two or more different Cas proteins, or two or more Cas proteins, may be introduced into a cell, zygote, embryo, or animal, e.g., to allow for recognition and modification of sites comprising the same, similar or different PAM motifs. In some embodiments, the anellovector includes a gene encoding a modified Cas protein with a deactivated nuclease, e.g., nuclease-deficient Cas9.

Whereas wild-type Cas9 protein generates double-strand breaks (DSBs) at specific DNA sequences targeted by a gRNA, a number of CRISPR endonucleases having modified functionalities are known, for example: a "nickase" version of Cas9 generates only a single-strand break; a catalytically inactive Cas9 ("dCas9") does not cut the target DNA. A gene encoding a dCas9 can be fused with a gene encoding an effector domain to repress (CRISPRi) or activate (CRISPRa) expression of a target gene. For example, the gene may encode a Cas9 fusion with a transcriptional silencer (e.g., a KRAB domain) or a transcriptional activator (e.g., a dCas9-VP64 fusion). A gene encoding a catalytically inactive Cas9 (dCas9) fused to FokI nuclease ("dCas9-FokI") can be included to generate DSBs at target sequences homologous to two gRNAs. See, e. g., the numerous CRISPR/Cas9 plasmids disclosed in and publicly available from the Addgene repository (Addgene, 75 Sidney St., Suite 550A, Cambridge, MA 02139; addgene.org/crispr/). A "double nickase" Cas9 that introduces two separate double-strand breaks, each directed by a separate guide RNA, is described as achieving more accurate genome editing by Ran et al. (2013) Cell, 154:1380-1389.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1.

In some embodiments, the anellovector comprises a gene encoding a polypeptide described herein, e.g., a targeted nuclease, e.g., a Cas9, e.g., a wild type Cas9, a nickase Cas9 (e.g., Cas9 D10A), a dead Cas9 (dCas9), eSpCas9, Cpf1, C2C1, or C2C3, and a gRNA. The choice of genes encoding the nuclease and gRNA(s) is determined by whether the targeted mutation is a deletion, substitution, or addition of nucleotides, e.g., a deletion, substitution, or addition of nucleotides to a targeted sequence. Genes that encode a catalytically inactive endonuclease e.g., a dead Cas9 (dCas9, e.g., D10A; H840A) tethered with all or a portion of (e.g., biologically active portion of) an (one or more) effector domain (e.g., VP64) create chimeric proteins that can modulate activity and/or expression of one or more target nucleic acids sequences.

As used herein, a "biologically active portion of an effector domain" is a portion that maintains the function (e.g. completely, partially, or minimally) of an effector domain (e.g., a "minimal" or "core" domain). In some embodiments, the anellovector includes a gene encoding a fusion of a dCas9 with all or a portion of one or more effector domains to create a chimeric protein useful in the methods described herein. Accordingly, in some embodiments, the anellovector includes a gene encoding a dCas9-methylase fusion. In other some embodiments, the anellovector includes a gene encoding a dCas9-enzyme fusion with a site-specific gRNA to target an endogenous gene.

In other aspects, the anellovector includes a gene encoding 1, 2, 3, 4, 5, 6, 7, 8, 9, 10, 11, 12, 13, 14, 15, 16, 17, 18, 19, 20, or more effector domains (all or a biologically active portion) fused with dCas9.

Proteinaceous Exterior

In some embodiments, the anellovector, e.g., synthetic anellovector, comprises a proteinaceous exterior that encloses the genetic element. In some embodiments, the anelloVLP, e.g., synthetic anelloVLP, comprises a proteinaceous exterior and an effector (e.g., an exogenous effector). The proteinaceous exterior can comprise a substantially non-pathogenic exterior protein that fails to elicit an unwanted immune response in a mammal. The proteinaceous exterior of the anellovectors or anelloVLPs typically comprises a substantially non-pathogenic protein that may self-assemble into an icosahedral formation that makes up the proteinaceous exterior.

In some embodiments, the proteinaceous exterior protein is encoded by a sequence of the genetic element of the anellovector (e.g., is in cis with the genetic element). In other embodiments, the proteinaceous exterior protein is encoded by a nucleic acid separate from the genetic element of the anellovector (e.g., is in trans with the genetic element).

In some embodiments, the protein, e.g., substantially non-pathogenic protein and/or proteinaceous exterior protein, comprises one or more glycosylated amino acids, e.g., 2, 3, 4, 5, 6, 7, 8, 9, 10, or more.

In some embodiments, the protein, e.g., substantially non-pathogenic protein and/or proteinaceous exterior protein comprises at least one hydrophilic DNA-binding region, an arginine-rich region, a threonine-rich region, a glutamine-rich region, a N-terminal polyarginine sequence, a variable region, a C-terminal polyglutamine/glutamate sequence, and one or more disulfide bridges.

In some embodiments, the protein is a capsid protein, e.g., has a sequence having at least about 60%, 65%, 70%, 75%, 80%, 85%, 90% 95%, 96%, 97%, 98%, 99%, or 100% sequence identity to a protein encoded by any one of the nucleotide sequences encoding a capsid protein described herein, e.g., an Anellovirus ORF1 sequence or a capsid protein sequence as listed in any one of Tables A1-A25. In some embodiments, the protein or a functional fragment of a capsid protein is encoded by a nucleotide sequence having at least about 60%, 70% 80%, 85%, 90% 95%, 96%, 97%, 98%, 99%, or 100% sequence identity to any one of the nucleotide sequences described herein, e.g., an Anellovirus capsid sequence or a capsid protein sequence as listed in any one of Tables A1-A25. In some embodiments, the protein comprises a capsid protein or a functional fragment of a capsid protein that is encoded by a capsid nucleotide sequence or a sequence having at least about 60%, 65%, 70%, 75%, 80%, 85%, 90% 95%, 96%, 97%, 98%, 99%, or 100% nucleotide sequence identity to any one of the nucleotide sequences described herein, e.g., an Anellovirus capsid sequence or a capsid protein sequence as listed in any one of Tables N1-N25.

In some embodiments, the anellovector comprises a nucleotide sequence encoding a capsid protein or a functional fragment of a capsid protein or a sequence having at least about 60%, 70% 80%, 85%, 90% 95%, 96%, 97%, 98%, 99%, or 100% sequence identity to any one of the amino acid sequences described herein, e.g., an Anellovirus capsid sequence or a capsid protein sequence in any one of Tables A1-A25. In some embodiments, the anellovector comprises a nucleotide sequence encoding a capsid protein or a functional fragment of a capsid protein or a sequence having at least about 60%, 65%, 70%, 75%, 80%, 85%, 90% 95%, 96%, 97%, 98%, 99%, or 100% sequence identity to any one of the amino acid sequences described herein, e.g., an Anellovirus capsid sequence or a capsid protein sequence in any one of Tables A1-A25.

In some embodiments, the anellovector comprises a nucleotide sequence encoding an amino acid sequence having about position 1 to about position 150 (e.g., or any subset of amino acids within each range, e.g., about position 20 to about position 35, about position 25 to about position 30, about position 26 to about 30), about position 150 to about position 390 (e.g., or any subset of amino acids within each range, e.g., about position 200 to about position 380, about position 205 to about position 375, about position 205 to about 371), about 390 to about position 525, about position 525 to about position 850 (e.g., or any subset of amino acids within each range, e.g., about position 530 to about position 840, about position 545 to about position 830, about position 550 to about 820), about 850 to about position 950 (e.g., or any subset of amino acids within each range, e.g., about position 860 to about position 940, about position 870 to about position 930, about position 880 to about 923) of the amino acid sequences described herein, an Anellovirus amino acid sequence, e.g., as listed in any one of Tables A1-A25, or a functional fragment thereof. In some embodiments, the protein comprises an amino acid sequence or a functional fragment thereof or a sequence having at least about 60%, 65%, 70%, 75%, 80%, 85%, 90% 95%, 96%, 97%, 98%, 99%, or 100% sequence identity to about position 1 to about position 150 (e.g., or any subset of amino acids within each range as described herein), about position 150 to about position 390, about position 390 to about position 525, about position 525 to about position 850, about position 850 to about position 950 of the amino acid sequences described herein, an Anellovirus amino acid sequence, e.g., as listed in any one of Tables A1-A25.

In some embodiments, the protein comprises an amino acid sequence or a functional fragment thereof or a sequence having at least about 60%, 65%, 70%, 75%, 80%, 85%, 90% 95%, 96%, 97%, 98%, 99%, or 100% sequence identity to any one of the amino acid sequences or ranges of amino acids described herein, an Anellovirus amino acid sequence, e.g., as listed in any one of Tables A1-A25. In some embodiments, the ranges of amino acids with less sequence identity may provide one or more of the properties described herein and differences in cell/tissue/species specificity (e.g. tropism).

In some embodiments, the anellovector or anelloVLP lacks lipids in the proteinaceous exterior. In some embodiments, the anellovector or anelloVLP lacks a lipid bilayer, e.g., a viral envelope. In some embodiments, the interior of the anellovector or anelloVLP is entirely covered (e.g., 100% coverage) by a proteinaceous exterior. In some embodiments, the interior of the anellovector or anelloVLP is less than 100% covered by the proteinaceous exterior, e.g., 95%, 90%, 85%, 80%, 70%, 60%, 50% or less coverage. In some embodiments, the proteinaceous exterior comprises gaps or discontinuities, e.g., permitting permeability to water, ions, peptides, or small molecules, e.g., so long as the genetic element is retained in the anellovector.

In some embodiments, the proteinaceous exterior comprises one or more proteins or polypeptides that specifically recognize and/or bind a host cell, e.g., a complementary protein or polypeptide, to mediate entry of the genetic element into the host cell.

In some embodiments, the proteinaceous exterior comprises one or more of the following: one or more glycosylated proteins, a hydrophilic DNA-binding region, an arginine-rich region, a threonine-rich region, a glutamine-rich region, a N-terminal polyarginine sequence, a variable region, a C-terminal polyglutamine/glutamate sequence, and one or more disulfide bridges. For example, the proteinaceous exterior comprises a protein encoded by an Anellovirus ORF1 described herein.

In some embodiments, the proteinaceous exterior comprises one or more of the following characteristics: an icosahedral symmetry, recognizes and/or binds a molecule that interacts with one or more host cell molecules to mediate entry into the host cell, lacks lipid molecules, lacks carbohydrates, is pH and temperature stable, is detergent resistant, and is substantially non-immunogenic or non-pathogenic in a host.

Surface Moieties

An anellovector or anelloVLP as described herein may, in some instances, include one or more moieties attached to its surface (e.g., a surface moiety that can act as an effector and/or a targeting agent). In some instances, an anellovector or anelloVLP comprises more than one distinct surface moiety (e.g., a first surface moiety having an effector function as described herein and a second surface moiety that targets the anellovector or anelloVLP to a cell or tissue of interest). In some instances, the surface moiety is covalently attached to the surface of the anellovector or anelloVLP. For example, the surface moiety may be covalently attached to the proteinaceous exterior or a component thereof (e.g., covalently attached to an ORF1 molecule of the proteinaceous exterior). In certain embodiments, the surface moiety is fused to an ORF1 molecule. In some instances, the surface moiety is noncovalently attached to the surface of the anellovector or anelloVLP. For example, the surface moiety may be noncovalently bound to the proteinaceous exterior or a component thereof (e.g., noncovalently bound to an ORF1 molecule of the proteinaceous exterior). In certain embodiments, the surface moiety comprises a region that specifically binds to a cognate moiety on or attached to the ORF1 molecule. In an embodiment, the ORF1 molecule comprises a binding moiety (e.g., an antibody molecule) that specifically recognizes an epitope on the region on the surface moiety. In an embodiment, the surface moiety comprises a binding moiety (e.g., an antibody molecule) that specifically recognizes an epitope on the ORF1 molecule. In an embodiment, the surface moiety comprises a streptavidin moiety that binds to a biotin moiety on the surface of the anellovector or anelloVLP (e.g., a biotin moiety attached to an ORF1 molecule of the proteinaceous exterior of the anellovector or anelloVLP). In an embodiment, the surface moiety comprises a biotin moiety that binds to a streptavidin moiety on the surface of the anellovector or anelloVLP (e.g., a streptavidin moiety attached to an ORF1 molecule of the proteinaceous exterior of the anellovector or anelloVLP).

In embodiments, all copies of an ORF1 molecule in the proteinaceous exterior of an anellovector or anelloVLP are attached to copies of the surface moiety. In embodiments, some copies of the ORF1 molecule in the proteinaceous exterior of an anellovector or anelloVLP are attached to copies of the surface moiety and some copies of the ORF1 molecule in the proteinaceous exterior of an anellovector or anelloVLP are not attached to copies of the surface moiety. In embodiments, some copies of the ORF1 molecule in the proteinaceous exterior of an anellovector or anelloVLP are attached to copies of a first surface moiety and some copies of the ORF1 molecule in the proteinaceous exterior of an anellovector or anelloVLP are attached to copies of a second surface moiety. In embodiments, some copies of the ORF1 molecule in the proteinaceous exterior of an anellovector or anelloVLP are attached to copies of a third surface moiety.

In some embodiments, all copies of an ORF1 molecule in the proteinaceous exterior of an anellovector or anelloVLP are attached at the same position (e.g., a lysine residue) of the ORF1 molecule to a copy of a surface moiety. In some embodiments, a first copy of an ORF1 molecule in the proteinaceous exterior of an anellovector or anelloVLP is attached at a first position (e.g., a first lysine residue) of the ORF1 molecule to a first copy of a surface moiety, and a second copy of an ORF1 molecule in the proteinaceous exterior of an anellovector or anelloVLP is attached at a second position (e.g., a second lysine residue) of the ORF1 molecule to a second of a surface moiety. In some embodiments, the proteinaceous exterior further comprises one or more copies of an ORF1 molecule having a surface moiety attached to a one or more additional positions (e.g., one or more additional lysine residues). In certain embodiments, the first lysine residue, the second lysine residue, and/or the one or more additional lysine residues are positioned on the surface of the proteinaceous exterior. In some embodiments, the surface moiety is attached to the ORF1 molecule via click chemistry or genetic grafting, e.g., as described herein.

In some instances, the surface moiety comprises an effector function (e.g., as described herein). For example, the surface moiety may modulate a biological activity, e.g., of a target cell or organ. In some instances, the surface moiety induces modulation of the biological activity via binding to a cognate moiety on a target cell. For example, the surface moiety may comprise a ligand that binds to a receptor on the surface of the target cell, e.g., wherein binding of the surface moiety to the receptor initiates a downstream signaling cascade of interest. In some instances, the effector activity comprises increasing or decreasing enzymatic activity, gene expression, cell signaling, and/or cellular or organ function within a target cell or organ. Effector activities may also include binding regulatory proteins to modulate activity of the regulator, such as transcription or translation. Effector activities also may include activator or inhibitor functions.

In some instances, the surface moiety can target the anellovector or anelloVLP to a target cell. For example, the surface moiety may specifically bind to a cognate moiety on the surface of the target cell. The cognate moiety on the surface of the target cell may be, for example, a molecule specifically expressed or preferentially expressed by the target cell. The cognate moiety may be, for example, a polypeptide, lipid, sugar, or small molecule. In certain embodiments, the cognate moiety is a transmembrane protein (e.g., comprising an extracellular domain that binds to the surface moiety of the anellovector or the anelloVLP). In certain embodiments, the cognate moiety is tethered to the surface of the cell (e.g., via a GPI anchor). In some instances, the surface moiety provides a tropism (e.g., to a target tissue or target cell type) for the anellovector or anelloVLP.

In some instances, the surface moiety comprises an effector function and a targeting function, e.g., as described herein. In some instances, the surface moiety comprises a domain having an effector function as described herein. In some instances, the surface moiety comprises a domain having a targeting function as described herein.

In some instances, the surface moiety binds specifically to one cognate moiety. In some embodiments, the surface moiety binds specifically to more than one cognate moiety. In some embodiments, the surface moiety comprises a plurality of binding regions, for example, each of which specifically binds to a different cognate moiety. For example, the surface moiety may be bispecific or trispecific. In some embodiments, the surface moiety comprises a plurality of binding regions, for example, each of which binds to the same cognate moiety or copies thereof (e.g., at different epitopes of the cognate moiety or the same epitope of the cognate moiety). In certain embodiments, the surface moiety having multiple binding regions that specifically bind to the same cognate moiety results in greater avidity for the target moiety.

Click Chemistry

In an aspect, the disclosure provides an ORF1 molecule comprising: (i) the amino acid sequence of an Anellovirus ORF1 protein, or an amino acid sequence having at least 75%, 80%, 85%, 90%, 95%, 96%, 97%, 98%, or 99% sequence identity thereto; and (ii) a click handle (e.g., an NHS click handle or a maleimide click handle, e.g., as described herein). In certain embodiments, the click handle is covalently attached to the ORF 1 molecule. In certain embodiments, the click handle is noncovalently attached to the ORF1 molecule. In certain embodiments, the click handle is used to attach the ORF1 molecule to a surface moiety, e.g., via a click reaction, e.g., as described herein.

A "click handle," as that term is used herein, refers to a chemical moiety that is capable of reacting with a second click handle in a click reaction. In some embodiments, a click handle comprises an NHS moiety and/or a maleimide moiety. In certain embodiments, a click handle comprises a DBCO moiety. In certain embodiments, a click handle comprises an azide moiety. In some embodiments, a click handle is attached to a polypeptide (e.g., an ORF1 molecule). In other embodiments, a click handle comprises a reactive group capable of forming a covalent bond with a polypeptide (e.g., an ORF1 molecule). A "click reaction", as that term is used herein, refers to a range of reactions used to covalently link a first and a second moiety, for convenient production of linked products. It typically has one or more of the following characteristics: it is fast, is specific, is high-yield, is efficient, is spontaneous, does not significantly alter biocompatibility of the linked entities, has a high reaction rate, produces a stable product, favors production of a single reaction product, has high atom economy, is chemoselective, is modular, is stereoselective, is insensitive to oxygen, is insensitive to water, is high purity, generates only inoffensive or relatively non-toxic byproducts that can be removed by nonchromatographic methods (e.g., crystallization or distillation), needs no solvent or can be performed in a solvent that is benign or physiologically compatible, e.g., water, stable under physiological conditions. Examples include an alkyne/azide reaction, a diene/dienophile reaction, or a thiol/alkene reaction. Other reactions can be used. In embodiments, a click reaction has a second order forward rate constant of 10-200 M-1s-1, 1-20 M-1s-1, or at least 1, 2, 3, 5, 10, 20, 50, 60, 100, 200, 500, 1E3, 2E3, 5E3, 1E4, 2E4, 5E4, 1E5, 2E5, 5E5, or 1E6 M-1s-1, e.g., at 20° C. in PBS. In some embodiments, a click reaction has at least 75%, 80%, 85%, 90%, 95%, 96%, 97%, 98%, or 99% yield, e.g., for a reaction time of 1 hour at 20° C. in PBS.

In some embodiments, a surface moiety is attached to a polypeptide by conjugation of a lysine residue on the surface of the polypeptide to an NHS click handle on the surface moiety (e.g., as described in Example 2 or 3 herein). In some embodiments, a surface moiety is attached to a polypeptide by conjugation of a lysine residue on the surface of the surface moiety to an NHS click handle on the polypeptide (e.g., as described in Example 2 or 3 herein).

In some embodiments, a surface moiety is attached to a polypeptide by conjugation of a cysteine residue on the surface of the polypeptide to a maleimide click handle on the surface moiety (e.g., as described in Example 4 herein). In some embodiments, a surface moiety is attached to a polypeptide by conjugation of a cysteine residue on the surface of the surface moiety to a maleimide click handle on the polypeptide (e.g., as described in Example 4 herein).

In an aspect, the disclosure provides an ORF1 molecule comprising a surface moiety, wherein the surface moiety was attached to the ORF1 molecule via a click reaction.

In an aspect, the disclosure provides a particle (e.g., an anellovector or anelloVLP) comprising: (i) a proteinaceous exterior comprising an ORF1 molecule; and (ii) a click handle (e.g., an NHS click handle and/or a maleimide click handle, e.g., as described herein). In certain embodiments, the click handle is covalently attached to the ORF1 molecule. In some embodiments, the particle is an anellovector comprising a genetic element enclosed in the proteinaceous exterior. In some embodiments, the particle is an anelloVLP comprising an effector (e.g., an exogenous effector), e.g., enclosed in the proteinaceous exterior.

Mutations of Surface Lysines

In an aspect, the disclosure provides an ORF1 molecule comprising the amino acid sequence of an Anellovirus ORF1 protein (or an amino acid sequence having at least 75%, 80%, 85%, 90%, 95%, 96%, 97%, 98%, or 99% sequence identity thereto), wherein at least 30%, 40%, 50%, 60%, 70%, 75%, 80%, 85%, 90%, 95%, 96%, 97%, 98%, 99%, or 100% of the lysine residues in the amino acid sequence of the Anellovirus ORF1 protein has been mutated (e.g., substituted with another amino acid, e.g., threonine, alanine, serine, asparagine, or glutamine). In some embodiments, all but one lysine residue of the Anellovirus ORF1 protein that are exposed from the surface of a proteinaceous exterior comprising the Anellovirus ORF1 protein are mutated (e.g., substituted with another amino acid, e.g., serine or alanine). In some embodiments, all lysine residues of the Anellovirus ORF1 protein that are exposed from the surface of a proteinaceous exterior comprising the Anellovirus ORF1 protein are mutated (e.g., substituted with another amino acid, e.g., serine or alanine). In some embodiments, all but one of the lysine residues of the Anellovirus ORF1 protein are mutated (e.g., substituted with another amino acid, e.g., serine or alanine). In certain embodiments, the one lysine residue not mutated is exposed on the surface of a proteinaceous exterior comprising the Anellovirus ORF1 protein.

In some embodiments, all lysine residues of the Anellovirus ORF1 protein are mutated (e.g., substituted with another amino acid, e.g., serine or alanine). In some embodiments, the ORF1 molecule further comprises a lysine residue not found in the amino acid sequence of the Anellovirus ORF1 protein (e.g., a lysine residue inserted or substituted into the Anellovirus ORF1 protein sequence, or a lysine residue attached to the N-terminal or C-terminal end of the Anellovirus ORF1 protein sequence).

Such mutated ORF1 molecules may be useful, for example, for controlling covalent attachment of a surface moiety to a lysine residue in the proteinaceous exterior (e.g., via a NHS click reaction as described herein, e.g., in Example 2 or 3).

Mutations of Surface Cysteines

In an aspect, the disclosure provides an ORF1 molecule comprising the amino acid sequence of an Anellovirus ORF1 protein (or an amino acid sequence having at least 75%, 80%, 85%, 90%, 95%, 96%, 97%, 98%, or 99% sequence identity thereto), wherein at least 30%, 40%, 50%, 60%, 70%, 75%, 80%, 85%, 90%, 95%, 96%, 97%, 98%, 99%, or 100% of the cysteine residues in the amino acid sequence of the Anellovirus ORF1 protein has been mutated (e.g., substituted with another amino acid, e.g., serine or alanine). In some embodiments, all but one cysteine residue of the Anellovirus ORF1 protein that are exposed from the surface of a proteinaceous exterior comprising the Anellovirus ORF1 protein are mutated (e.g., substituted with another amino acid, e.g., serine or alanine). In some embodiments, all cysteine residues of the Anellovirus ORF1 protein that are exposed from the surface of a proteinaceous exterior comprising the Anellovirus ORF1 protein are mutated (e.g., substituted with another amino acid, e.g., serine or alanine). In some embodiments, cysteine residues exposed on the surface of the ORF1 molecule are mutated to serine. In some embodiments, cysteine residues interior to the ORF1 molecule are mutated to alanine. In embodiments, one or more cysteine residues corresponding to positions 57, 64, 112, 131, 220, 223, 626 of Ring10 ORF1 are mutated (e.g., to serine or alanine).

In some embodiments, all but one of the cysteine residues of the Anellovirus ORF1 protein are mutated (e.g., substituted with another amino acid, e.g., serine or alanine). In certain embodiments, the one cysteine residue not mutated is exposed on the surface of a proteinaceous exterior comprising the Anellovirus ORF1 protein. In embodiments, the cysteine residue not mutated is selected from residues corresponding to positions 57, 64, 112, 131, 220, 223, 626 of Ring10 ORF1 protein.

In embodiments, the cysteine residue is located in the P2 domain of the ORF1 molecule (e.g., at a position corresponding to position 365 of Ring10 ORF1 protein, e.g., as described in Example 4). In embodiments, the cysteine residue is located in the HVR of the ORF1 molecule.

In some embodiments, all cysteine residues of the Anellovirus ORF1 protein are mutated (e.g., substituted with another amino acid, e.g., serine or alanine). In some embodiments, the ORF1 molecule further comprises a cysteine residue not found in the amino acid sequence of the Anellovirus ORF1 protein (e.g., a cysteine residue inserted or substituted into the Anellovirus ORF1 protein sequence, or a cysteine residue attached to the N-terminal or C-terminal end of the Anellovirus ORF1 protein sequence).

Such mutated ORF1 molecules may be useful, for example, for controlling covalent attachment of a surface moiety to a cysteine residue in the proteinaceous exterior (e.g., via a maleimide click reaction as described herein, e.g., in Example 4).

Polypeptides

The surface moiety can, in some instances, comprise a polypeptide. In some embodiments, the polypeptide is a about 5-10, 10-15, 15-20, 20-25, 25-30, 30-40, 40-50, 50-100, 100-150, 150-200, 200-250, 250-300, 300-400, 400-500, 500-600, 600-700, 700-800, 800-900, 900-1000, 1000-1500, 1500-2000, 2000-2500, 2500-3000, 3000-4000, or 4000-5000 amino acids in length). In some embodiments, the surface moiety is a polypeptide fused to a protein of the anellovector or anelloVLP (e.g., an ORF1 molecule of the anellovector or anelloVLP). In certain embodiments, the peptide is linear or branched.

In some embodiments, the surface moiety comprises an antibody molecule (e.g., an antibody or an antigen-binding fragment thereof). In certain embodiments, the surface moiety comprises an Fv, Fab, Fab', Fab'-SH, $F(ab')_2$, diabody, linear antibody, single-chain antibody molecule (e.g. scFv), or a multispecific antibody formed from antibody fragments. In certain embodiments, the surface moiety is a multispecific antibody molecule (e.g., a bispecific antibody molecule or a trispecific antibody molecule). In some embodiments, the surface moiety is selected from a hormone, cytokine, enzyme, transcription factor, receptor, ligand, transporter, secreted protein, carrier protein, structural protein, or a functional fragment thereof (e.g., as described herein). In some embodiments, the surface moiety comprises a polypeptide effector (e.g., as described herein). In certain embodiments, the surface moiety comprises a therapeutic effector (e.g., as described herein). In embodiments, the surface moiety comprises a regulatory intracellular polypeptide (e.g., as described herein). In embodiments, the surface moiety comprises a secreted polypeptide effector (e.g., as described herein). In embodiments, the surface moiety comprises a viral polypeptide or peptide. In embodiments, the surface moiety comprises a SARS-CoV-2 polypeptide or peptide (e.g., a receptor binding domain, e.g., of a spike protein, e.g., as described herein), or a polypeptide having at least 75%, 80%, 85%, 90%, 95%, 96%, 97%, 98%, or 99% sequence identity thereto. In embodiments, the surface moiety comprises a polypeptide having at least 75%, 80%, 85%, 90%, 95%, 96%, 97%, 98%, 99%, or 100% amino acid sequence identity to amino acids 319-541 from SARS-CoV-2 coronavirus spike protein (e.g., according to ThermoFisher Catalog #RP-87704). In some embodiments, the surface moiety comprises a binding moiety (e.g., a biotin moiety). In some embodiments, the surface moiety comprises a fluorophore (e.g., an Alexa Fluor moiety, e.g., Alexa Fluor 647).

In some embodiments, a polypeptide surface moiety is displayed on the surface of the anellovector or anelloVLP. In some embodiments, the surface moiety is covalently attached to the surface (e.g., proteinaceous exterior) of the anellovector or anelloVLP. In certain embodiments, the surface moiety is a polypeptide fused to an ORF1 molecule. In embodiments, the surface moiety is a heterologous domain of an ORF1 molecule. In embodiments, the surface moiety replaces a region (e.g., a subdomain as described herein, e.g., an HVR) of an ORF1 protein. In embodiments, all copies of the ORF1 molecule in the proteinaceous exterior of an anellovector or anelloVLP are fused to copies of the surface moiety. In embodiments, some copies of the ORF1 molecule in the proteinaceous exterior of an anellovector or anelloVLP are fused to copies of the surface moiety and some copies of the ORF1 molecule in the proteinaceous exterior of an anellovector or anelloVLP are not fused to copies of the surface moiety. In embodiments, some copies of the ORF1 molecule in the proteinaceous exterior of an anellovector or anelloVLP are fused to copies of a first surface moiety and some copies of the ORF1 molecule in the proteinaceous exterior of an anellovector or anelloVLP are fused to copies of a second surface moiety.

In some embodiments, the surface moiety is noncovalently attached to the surface (e.g., proteinaceous exterior) of the anellovector or anelloVLP. For example, the surface moiety may comprise a binding domain that binds to a region on the surface (e.g., proteinaceous exterior) of the anellovector or anelloVLP. In an embodiment, the surface moiety comprises an antibody molecule that specifically binds to an ORF1 molecule of the proteinaceous exterior of the anellovector or anelloVLP.

Genetic Grafting of ORF7 to a Surface Moiety

In some embodiments, an ORF1 molecule comprises the amino acid sequence of a surface moiety, e.g., as described herein. An ORF1 molecule may be fused (e.g., at the N-terminus or C-terminus) to the surface moiety. In some embodiments, a surface moiety is grafted into the sequence of the ORF1 molecule. For example, a surface moiety may be inserted within or between domains of the ORF1 molecule.

In certain embodiments, the surface moiety is grafted at or within 1-5, 5-10, 10-15, 15-20, 20-25, 25-30, 30-35, or 35-40 amino acid residues of a jelly-roll region as described herein.

In certain embodiments, the surface moiety is grafted at or within the HVR, or a portion thereof (e.g., a portion consisting of 5-10, 10-15, 15-20, 20-30, 30-40, 40-50, 50-60, 60-70, 70-80, 80-90, 90-100, 100-110, 110-120, 120-130, 130-140, or 140-150 amino acids thereof).

In certain embodiments, the surface moiety is grafted at or within 1-5, 5-10, 10-15, 15-20, 20-25, 25-30, 30-35, 35-40, 40-50, 50-60, 60-70, 70-80, 80-90, 90-100, 100-125, 125-150, 150-175, or 175-200 amino acid residues of the C-terminal end of a jelly-roll region as described herein. In certain embodiments, the surface moiety is grafted at or within 1-5, 5-10, 10-15, 15-20, 20-25, 25-30, 30-35, 35-40, 40-50, 50-60, 60-70, 70-80, 80-90, 90-100, 100-125, 125-150, 150-175, or 175-200 amino acid residues of the N-terminal end of an N22 domain or CTD as described herein.

Exemplary ORF7 Molecules Attached to Surface Moieties

In some embodiments, a surface moiety and ORF1 fusion protein comprises an amino acid sequence as listed in Table E1 below, or an amino acid sequence having at least 75%, 80%, 85%, 90%, 95%, 96%, 97%, 98%, or 99% sequence identity thereto. In some embodiments, a surface moiety comprises an amino acid sequence as listed in Table E1 below, or an amino acid sequence having at least 75%, 80%, 85%, 90%, 95%, 96%, 97%, 98%, or 99% sequence identity thereto. In some embodiments, a surface moiety comprises a CS protein, or a functional fragment thereof (e.g., a fragment comprising the 184 C-terminal residues of a CS protein). In some embodiments, a surface moiety comprises a hepatitis B virus surface antigen. In some embodiments, a surface moiety comprises one or more (e.g., 1, 2, 3, 4, 5, or 6) NANP peptides (e.g., NANP-2 peptides). In some embodiments, a surface moiety comprises a cysteine residue (e.g., a C-terminal cysteine residue). In some embodiments, a surface moiety comprises an NHS click handle (e.g., as described herein).

In an aspect, the disclosure provides a nucleic acid molecule encoding a fusion protein comprising a surface moiety and an ORF1 molecule (e.g., as described herein).

In an aspect, the disclosure provides a polypeptide comprising a CCN5 protein and a C-terminal cysteine residue. In some embodiments, the polypeptide comprises the amino acid sequence of CCN5 CTerMCys as listed in Table E1 below, or an amino acid sequence having at least 75%, 80%, 85%, 90%, 95%, 96%, 97%, 98%, or 99% sequence identity thereto. In an aspect, the disclosure provides a polypeptide comprising an aflibercept protein and a C-terminal cysteine residue. In some embodiments, the polypeptide comprises the amino acid sequence of aflibercept as listed in Table E1 below, or an amino acid sequence having at least 75%, 80%, 85%, 90%, 95%, 96%, 97%, 98%, or 99% sequence identity thereto. In an aspect, the disclosure provides a polypeptide comprising ranibizumab and a C-terminal cysteine residue. In some embodiments, the polypeptide comprises the amino acid sequence of ranibizumab HC malE_CTermCys as listed in Table E1 below, or an amino acid sequence having at least 75%, 80%, 85%, 90%, 95%, 96%, 97%, 98%, or 99% sequence identity thereto. In some embodiments, the polypeptide comprises the amino acid sequence of scFab RaniHC-link50-LC malE_CTermCys as listed in Table E1 below, or an amino acid sequence having at least 75%, 80%, 85%, 90%, 95%, 96%, 97%, 98%, or 99% sequence identity thereto. In an aspect, the disclosure provides a polypeptide comprising bevacizumab and a C-terminal cysteine residue.

In some embodiments, the polypeptide comprises the amino acid sequence of bevacizumab HC malE_CTermCys as listed in Table E1 below, or an amino acid sequence having at least 75%, 80%, 85%, 90%, 95%, 96%, 97%, 98%, or 99% sequence identity thereto.

X-Fold Symmetry

In some embodiments, an ORF1 molecule as described herein comprises a surface moiety situated at a position such that, when the ORF1 molecule is complexed with one or more additional copies of the ORF1 molecules (each attached to another surface moiety, e.g., copies of the same surface moiety or one or more different surface moieties), the surface moieties form a multimer. In certain embodiments, a complex of two such ORF1 molecules attached to surface moieties results in the formation of a dimer of the surface moieties. In certain embodiments, a complex of three such ORF1 molecules attached to surface moieties results in the formation of a trimer of the surface moieties. In certain embodiments, a complex of five such ORF1 molecules attached to surface moieties results in the formation of a pentamer of the surface moieties.

To form a multimer of surface moieties, the surface moieties are generally attached to the ORF1 molecule at a surface-exposed portion of the ORF1 molecule. In some embodiments, the surface-exposed portion of the ORF1 molecule is part of a hypervariable region (HVR) of the ORF1 molecule, e.g., as described herein. In certain embodiments, the surface moiety is fused to or is attached at or between residues of the ORF1 molecule corresponding to positions 284-285 of a Ring10 ORF1 protein. In certain embodiments, the surface moiety is fused to or is attached at or between residues of the ORF1 molecule corresponding to positions 328-329 of a Ring10 ORF1 protein. In certain embodiments, the surface moiety is fused to or is attached at or between residues of the ORF1 molecule corresponding to positions 256-383 of a Ring10 ORF1 protein. In certain embodiments, the surface moiety is fused to or is attached at or between residues of the ORF1 molecule corresponding to positions 251-383 of a Ring10 ORF1 protein. In certain embodiments, the surface moiety is fused to or is attached at or between residues of the ORF1 molecule corresponding to positions 251-384 of a Ring10 ORF1 protein. In certain embodiments, the surface moiety is attached at the amino acid residue (e.g., a cysteine residue) corresponding to position 254, 263, 264, 265, 272, 273, 274, 276, 283, 284, 285, 287, 288, 290, 291, 308, 311, 312, 313, 314, 316, 317, 318, 319, 321, 324, 328, 329, 341, 343, 354, 358, 361, 362, 363, 364, 365, 368, 369, 371, 374, 376, 378, 380, or 381 of Ring 10 ORF1, e.g., in an ORF1 domain (e.g., within the HVR or P2 domain).

In an aspect, the disclosure provides an ORF1 molecule comprising the amino acid sequence of an ORF1 protein comprising at least one mutation (e.g., deletion, substitution, addition, insertion, or frameshift) in a surface-exposed region relative to a wild-type ORF1 protein sequence (e.g., as described herein. In some embodiments, the surface-exposed region comprises the region corresponding amino acids 251-386 of the amino acid sequence of Ring 10 ORF1 (e.g., as described herein).

In an aspect, the disclosure provides an ORF1 molecule comprising the amino acid sequence of an ORF1 protein comprising at least one mutation (e.g., deletion, substitution, addition, insertion, or frameshift) in the HVR relative to a wild-type ORF1 protein sequence (e.g., as described herein).

In some embodiments, the glutamine residue corresponding to Q287 of Ring 10 (e.g., as described herein) has been mutated (e.g., substituted). In some embodiments, the glutamine residue corresponding to Q287 of Ring 10 has been mutated to a cysteine residue. In certain embodiments, the ORF1 molecule comprises the amino acid sequence of the Ring 10 ORF1 protein, or an amino acid sequence having at least 75%, 80%, 85%, 90%, 95%, 96%, 97%, 98%, or 99% sequence identity thereto, and a Q287C mutation.

In some embodiments, the threonine residue corresponding to T365 of Ring 10 (e.g., as described herein) has been mutated (e.g., substituted). In some embodiments, the threonine residue corresponding to T365 of Ring 10 has been mutated to a cysteine residue. In certain embodiments, the ORF1 molecule comprises the amino acid sequence of the Ring 10 ORF1 protein, or an amino acid sequence having at least 75%, 80%, 85%, 90%, 95%, 96%, 97%, 98%, or 99% sequence identity thereto, and a T365C mutation.

In an aspect, the disclosure provides a polypeptide comprising an amino acid sequence as listed in Table E1 below, or an amino acid sequence having at least 75%, 80%, 85%, 90%, 95%, 96%, 97%, 98%, or 99% sequence identity thereto. In some embodiments, the polypeptide further comprises the amino acid sequence of an ORF1 protein (e.g., as described herein), or an amino acid sequence having at least 75%, 80%, 85%, 90%, 95%, 96%, 97%, 98%, or 99% sequence identity thereto.

In an aspect, the disclosure provides a nucleic acid molecule encoding a polypeptide comprising an amino acid sequence as listed in Table E1 below, or an amino acid sequence having at least 75%, 80%, 85%, 90%, 95%, 96%, 97%, 98%, or 99% sequence identity thereto. In some embodiments, the polypeptide encoded by the nucleic acid molecule further comprises the amino acid sequence of an ORF1 protein (e.g., as described herein), or an amino acid sequence having at least 75%, 80%, 85%, 90%, 95%, 96%, 97%, 98%, or 99% sequence identity thereto. In some embodiments, an anellovector as described herein comprises a proteinaceous exterior comprising an ORF1 molecule as described above. In some embodiments, an anellovector as described herein comprises a proteinaceous exterior comprising an ORF1 molecule encoded by a nucleic acid molecule as described above. In some embodiments, an anelloVLP as described herein comprises a proteinaceous exterior comprising an ORF1 molecule as described above. In some embodiments, an anelloVLP as described herein comprises a proteinaceous exterior comprising an ORF1 molecule encoded by a nucleic acid molecule as described above.

Nucleic Acid Molecules

The surface moiety may, in some instances, comprise a nucleic acid molecule. In some embodiments, the surface moiety comprises DNA (e.g., single-stranded DNA or double-stranded DNA). In some embodiments, the surface moiety comprises RNA (e.g., single-stranded RNA or double-stranded RNA). In some embodiments, the surface moiety comprises DNA and RNA (e.g., a strand of DNA hybridized to a strand of RNA). In some embodiments, the surface moiety comprises an oligonucleotide (e.g., an oligonucleotide having a length of about 5-10, 10-15, 15-20, 20-25, 25-30, 30-35, 35-40, 40-45, 45-50, 50-60, 60-70, 70-80, 80-90, or 90-100 nucleotides). In some embodiments, the surface moiety comprises a functional nucleic acid molecule (e.g., a functional RNA). In certain embodiments, the surface moiety comprises an mRNA, siRNA, miRNA, or tRNA.

Small Molecules

The surface moiety may, in some instances, comprise a small molecule. In some embodiments, the small molecule has a molecular weight less than about 5,000 grams per mole, e.g., organic or inorganic compounds having a molecular weight less than about 2,000 grams per mole, e.g., organic or inorganic compounds having a molecular weight less than about 1,000 grams per mole, e.g., organic or inorganic compounds having a molecular weight less than about 500 grams per mole. In some embodiments, the small molecule is a salt, ester, or other pharmaceutically acceptable form of such compounds. Small molecules may include, but are not limited to, a neurotransmitter, a hormone, a drug, a toxin, a viral or microbial particle, a synthetic molecule, and an agonist or an antagonist. In some embodiments, the small molecule is a pharmaceutically active agent. In one embodiment, the small molecule is an inhibitor of a metabolic activity or component. Useful classes of pharmaceutically active agents include, but are not limited to, antibiotics, anti-inflammatory drugs, angiogenic or vasoactive agents, growth factors and chemotherapeutic (anti-neoplastic) agents (e.g., tumor suppressors). One or a combination of molecules from the categories and examples described herein or from Orme-Johnson 2007, Methods Cell Biol. 2007; 80:813-26 (incorporated by reference in its entirety) can be used. In one embodiment, the small molecule comprises an antibiotic, anti-inflammatory drug, angiogenic or vasoactive agent, growth factor or chemotherapeutic agent.

Examples of small molecules that can be used as surface moieties as described herein include, without limitation, those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference.

Vaccines Antigens

In some instances, a surface moiety comprises an antigen (e.g., an antigen recognized by the immune system of a subject to be delivered the anellovector or anelloVLP). In some embodiments, a surface moiety comprises a vaccine. In some embodiments, a surface moiety comprises an epitope from a bacterium, virus, fungus, or parasite. In some embodiments, a surface moiety comprises a vaccine for a pathogen (e.g., the surface moiety comprises an antigen of the pathogen). In certain embodiments, the surface moiety comprises one or more vaccine antigens as listed in Table V1 below. In embodiments, the surface moiety comprises one vaccine antigen listed in Table V1. In embodiments, the surface moiety comprises a plurality of distinct vaccine antigens listed in Table V1 (e.g., a plurality of distinct vaccine antigens listed in a single row of Table V1).

TABLE V1

| Exemplary vaccine antigens that can be included in a surface moiety of an anellovector or anelloVLP as described herein. |
|---|
| Ascomycota, e.g., Eurotiomycetes, e.g., Eurotiales, e.g., Trichocomaceae, e.g., *Aspergillus* species antigen (e.g., *Aspergillus versicolor* AVS) |
| Monodnaviria, e.g., Shotokuvirae, e.g., Cossaviricota, e.g., Papovaviricetes, e.g., Sepolyvirales, e.g., Polyomaviridae, e.g., Betapolyomavirus, e.g., BK Virus antigen |
| Proteobacteria, e.g., Betaproteobacteria, e.g., Burkholderiales, e.g., Alcaligenaceae, e.g., *Bordetella*, e.g., *Bordetella pertussis* antigen (e.g., pertussis toxin, filamentous haemagglutinin, pertactin) |
| Spirochaetes, e.g., Spirochaetales, e.g., Spriochaetaceae, e.g., *Borrelia*, e.g., *Borrelia burgdorferi* antigen |
| Proteobacteria, e.g., Betaproteobacteria, e.g., Burkholderiales, e.g., Burkholderiaceae, e.g., *Burkholderia*, e.g., *Burkholderia* species antigen (e.g., hydratase/aldolase PhnE) |
| Riboviria, e.g., Orthornavirae, e.g., Kitrinoviricota, e.g. Alsuviricetes, e.g., Martellivirales, e.g., Togaviridae, e.g., Alphavirus, e.g., Chikungunya virus (CHIKV) antigens |
| Chlamydiae, e.g., Chlamydiales, e.g., Chlamydiaceae, e.g., *Chlamydia*, e.g., *Chlamydia trachomatis* antigen |
| Proteobacteria, e.g., Gammaproteobacteria, e.g., Vibrionales, e.g., Vibrionaceae, e.g., *Vibrio*, e.g., *Vibrio cholerae*, e.g., Cholera antigen (e.g., cholera toxin B subunit) |
| "Firmicutes", e.g., Clostridia, e.g., Clostridiales, e.g., Peptostreptococcaceae, e.g., Clostridioides, e.g., *Clostridium*, e.g., *Clostridium difficile* antigen |
| Alveolata, e.g., Apicomplexa, e.g., Conoidasida, e.g., Eucoccidiorida, e.g., Eimeriorina, e.g., Cryoptosporidiidae, e.g., Cryptosporidium antigen |
| Duplodoaviria, e.g., Heunggongvirae, e.g., Peploviricota, e.g., Herviviricetes, e.g., Herpesvirales, e.g., Herpesviridae, e.g., Betaberpesvirinae, e.g., Cytomegalovirus (CMV) antigen |
| "Actinobacteria", e.g., Acintobacteria, e.g., Mycobacteriales, e.g., Corynebacteriaceae, e.g., *Corynebacterium*, Diphtheria antigen (e.g., diphtheria toxoid) |
| Amoebozoa, e.g., Entamoebidae, e.g., Entamoeba, e.g., Entamoeba histolytica antigen |
| Riboviria, e.g., Orthornavirae, e.g., Pisuviricota, e.g., Pisoniviricetes, e.g., Picornavirales, e.g., Picornaviridae, e.g., Enterovirus, e.g., Enterovirus 71 antigen (e,g., VP1) |
| Duplodnaviria, e.g., Heunggongvirae, e.g., Peploviricota, e.g., Herviviricetes, e.g., Herpesviridae, e.g., Lymphocryptovirus, e.g., Epstein-Barr virus antigen |
| Proteobacteria, e.g., Gammaproteobacteria, e.g., Enterobacterlaes, e.g., Enterobacteriaceae, e.g., *Escherichia*, e.g., *Escherichia coli* antigen (e.g., bifunctional penicillin-binding protein) |
| Riboviria, e.g., Orthornavirae, e.g., Kitrinoviricota, e.g., Flasuviricetes, e.g., Amarillovirales, *Flaviviridae* genus (Dengue Virus) antigen |
| Proteobacteria, e.g., Epsilonproteobacteria, e.g., Campylobacterales, e.g., Helicobacteraceae, e.g., *Helicobacter*, e.g., *Helicobacter pylori* antigen |
| Hepatitis antigen (e.g., hepatitis A (HAV), e.g., B (HBV), e.g., C (HCV), e.g., D (HDV) e.g., G (HGV) virus antigen) |
| Duplodnaviria, e.g., Heunggongvirae, e.g., Peploviricota, e.g., Herviviricetes, e.g., Herpesviridae, e.g., Alphaberpesvirinae, e.g., Simplexvirus, e.g., Herpes simplex antigen |
| Varidnaviria, e.g., Bamfordvirae, e.g., Preplasmiviricota, e.g., Tectiliviricetes, e.g., Rowavirales, e.g., Adenoviridae, e.g., Aviadenovirus, e.g., Ichtadenovirus, e..g, Testadenovirus, e.g., Atadenovirus, e.g., Mastadenovirus, e.g., Siadenovirus Human adenovirus antigen (e.g., type 34 hexon protein) |
| Riboviria, e.g., Pararnavirae, e.g., Artverviricota, e.g., Revtraviricetes, e.g., Ortervirales, e.g., Retroviridae, e.g., |

TABLE V1-continued

| Exemplary vaccine antigens that can be included in a surface moiety of an anellovector or anelloVLP as described herein. |
| --- |
| Orthoretrovirinae, e.g., Lentivirus, e.g., Human immunodeficiency virus (HIV) antigen (e.g., GP-120, GP-160) |
| Riboviria, e.g., Orthornavirae, e.g., Negarnaviricota, e.g., Monjiviricetes, e.g., Mononegavirales, e.g., Pneumoviridae, e.g., Metapneumovirus, e.g., Human metapneumovirus antigen |
| Monodoaviria, e.g., Shotokuvirae, e.g., Cossaviricota, e.g., Papovaviricetes, e.g., Zurhausenvirales, e.g., Papillomaviridae, e.g, Alphapapillomavirus, e.g., Betapapillomavirus, e.g., Chipapillomavirus, e.g., Deltapapillovirus, e.g., Dyochipapillomavirus, e.g., Dyodeltapapillomavirus, e.g., Dyoepsilonpapillomavirus, e.g., Dyoetapapillomavirus, e.g., Dyoiotapapillomavirus, e.g., Dyokappapapillomavirus, e.g., Dyolambdapapillomavirus, e.g., Dyomupapillomavirus, e.g., Dyonupapillomavirus, e.g., Dyoomegapapillomavirus, e.g., Dyoomikronpapillomavirus, e.g., Dyophipapillomavirus, e.g., Dyopipapillomavirus, e.g., Dyopsipapillomavirus, e.g., Dyorhopapillomavirus, e.g., Dyosigmapapillomavirus, e.g., Dyotaupapillomavirus, e.g., Dyothetapapillomavirus, e.g., Dyoupsilonpapillomavirus, e.g., Dyoxipapillomavirus, e.g., Dyozetapapillomavirus e.g., Gammapapillomavirus, e.g., Iotapapillomavirus, e.g., Kappapapillomavirus, e.g., Lambdapapillomavirus, e.g., Mupapillomavirus, e.g., Nupapillomavirus, e.g., Omegapapillomavirus, e.., Omikronpapillomavirus, e.g., Phipapillomavirus, e.g., Pipapillomavirus, e.g., Psipapillomavirus, e.g., Rhopapillomavirus, e.g., Sigmapapillomavirus, e.g., Taupapillomavirus, e.g., Tbetapapillomavirus, e.g., Treisdeltapapillomavirus, e.g., Treisepsiolonpapillomavirus, e.g., Treisetapapillomavirus, e.g., Treisiotapapillomavirus, e.g., Trieskappapapillomavirus, e.g., Treisthetapapillomavirus, e.g., Treiszetapapillomavirus, e.g., Upsilonpapillomavirus, e.g., Xipapillomavirus, e.g., Zetapapillomavirus, e.g., Alefpapillomavirus, e.g., Human papilloma virus (HPV) antigen (e.g., L1 major capsid protein) |
| Riboviria, e.g., Orthornavirae, e.g., Negarnaviricota, e.g., Insthoviricetes, e.g., Articulavirales, e.g., Orthomyxoviridae, e.g., Alphainfluenzavirus, e.g., Betainfluenzavirus, e.g., Gammainfluenzavirus, e.g., Deltainfluenzavirus, e.g., Influenza virus antigen (e.g., HA) |
| Monodnaviria, e.g., Shotokuvirae, e.g., Cossaviricota, e.g., Papovaviricetes, e.g., Sepolyvirales, e.g., Polyomaviridae, e.g., Betapolyomavirus, e.g., JC Virus/JC polyomavirus antigen |
| Proteobacteria, e.g., gammaproteobacteria, e.g., Enterobacterales, e.g., *Klebsiella*, e.g., *Klebsiella pneumoniae* antigen |
| Riboviria, e.g., Orthornavirae, e.g., Negarnaviricota, e.g., Ellioviricetes, e.g., Bunyavirales, e.g., Arenaviridae, e.g., Mammarenavirus, e.g., Lassa virus antigen |
| Euglenozoa, e.g., Kinetoplastea, e.g., Trypanosomatida, e.g., Leishmania promastigotes antigen |
| Spriochaetes, e.g., Spirochaetales, e.g., Leptospiraceae, e.g., *Leptospira*, e.g., *Leptospira interrogans* antigen |
| Proteobacteria, e.g., Betaproteobacteria, e.g., Neisseriales, e.g., Neisseriaceae, e.g., *Neisseria*, e.g., Meningococcal antigen (e.g., capsular polysaccharides of serogroup A, B, C, Y and W-135) |
| Actinobacteria, e.g., Corynebacteriales, e.g., Mycobacteriaceae, e.g., *Mycobacterium*, e.g., *Mycobacterium tuberculosis* antigen |
| Proteobacteria, e.g., etaproteobacteria, e.g., Neisseriales, e.g., Neisseriaceae, e.g., *Neisseria*, e.g., *N. meningitidis* antigen (e.g., type Y polysaccharide [MenY], type W polysaccharide [MenW]) |
| Proteobacteria, e.g., etaproteobacteria, e.g., Neisseriales, e.g., Neisseriaceae, e.g., *Neisseria*, e.g., *Neisseriea gonorrhea* antigen |
| Apicomplexa, e.g., Aconoidasida, e.g., Haemospororida, e.g., Plasmodiidae, e.g., Plasmodium, e.g., *Plasmodium* species antigen (e.g., HRPII, pLDH, pAldo) |
| "Firmicutes", e.g., Bacilli, e.g., Lactobacillies, e.g., Streptococcaceae, e.g., *Streptococcus*, e.g., Pneumococcal antigen (e.g., *Streptococcus pneumoniae* type 3 capsular polysaccharide) |
| Proteobacteria, e.g., Gammaproteobacteria, e.g., Pseudomonadales, e.g., Pseudomonadaceae, e.g., *Pseudomonas*, e.g., *Pseudomonas* species antigen (e.g., ferredoxin reductase component) |
| Riboviria, e.g., Orthornavirae, e.g., Negarnaviricota, e.g., Monjiviricetes, e.g., Mononegavirales, e.g., Rhabdoviridae, e.g., Lyssavirus, e.g., Rabies antigen |
| Riboviria, e.g., Orthornavirae, e.g., Negarnaviricota, e.g., Monjiviricetes, e.g., Mononegavirales, e.g., Pneumoviridae, e.g., Orthopneumovirus, e.g., Respiratory syncytial virus (RSV) antigen |
| Riboviria, e.g., Orthornavirae, e.g., Negarnaviricota, e.g., Ellioviricetes, e.g., Bunyavirales, e.g., Phenuviridae, e.g., Phlebovirus, e.g., Rift Valley fever Virus antigen |
| Riboviria, e.g., Orthornavirae, e.g., Duplornaviricota, e.g., Resentoviricetes, e.g., Reovirales, e.g., Reoviridae, e.g., Sedoreovirinae, e.g., Rotavirus, e.g., Rotavirus antigen (e.g., VP8, H1N1 M2, H7N9 F) |
| Proteobacteria, e.g., Gammaproteobacteria, e.g., Enterobacterales, e.g., Enterobacteriaceae, e.., *Salmonella*, e.g., *Salmonella typhi* antigen (e.g., Vi polysaccharide) |
| Platyhelminthes, e.g., Diplostomida, e.g., Schistosomatidae, e.g., Schistosomatinae, e.g., Schistosoma, e.g., *Schistosoma* species antigen |
| Proteobacteria, e.g., Gammaproteobacteria, e.g., Enterobacterales, e.g., Enterobacteriaceae, e.g., *Shigell*, e.g., *Shigella* antigen (e.g., *shigella* polysaccharides) |
| "Firmicutes", e.g., Bacilli, e.g., Bacillales, e.g., Staphylococcaceae, e.g., Staphylococcus, e.g., Staphylococcal antigen (e.g., staphylococcal enterotoxin B) |
| "Firmicutes", e.g., Bacilli, e.g., Lactobacillales, e.g. Streptococcaceae, e.g., *Streptococcus*, e.g., *Streptococcus agalactiae* antigen |
| "Firmicutes", e.g., Bacilli, e.g., Lactobacillales, e.g., Streptococcaceae, e.g., *Streptococcus*, e.g., *Streptococcus pyogenes* antigen |
| "Firmicutes", e.g., Clostridia, e.g., Clostridiales, e.g., Clostridiaceae, e.g., Clostridium, e.g., Tetanus antigen (e.g., tetanus toxoid) |
| Riboviria, e.g., Orthornavirae, e.g., Kitrinoviricota, e.g., Flasuviricetes, e.g., Amarillovirales, e.g., Flaviviridae, e.g., Flavivirus, e.g., Tick-borne encephalitis (TBE) antigen |
| Apicomplexa, e.g., Conoidasida, e.g., Eucoccidiorida, e.g., Sarcocystidae, e.g., Toxoplasmatinae, e.g., Toxoplasma, e.g., Toxoplasma gondii antigen |
| Spirochaetes, e.g., Spirochaetales, e.g., Spirochaetaceae, e.g., *Treponema*, e.g., *Treponema pallidum* antigen |
| "Actinobacteria", e.g., Actinobacteria, e.g., Mycobacteriales, e.g., Mycobacteriaceae, e.g., Mycobacterium, e.g., Tuberculosis antigen |
| Riboviria, e.g., Orthornavirae, e.g., Negarnaviricota, e.g., Monjiviricetes, e.g., Mononegavirales, e.g., Rhabdoviridae, e.g., Vesiculovirus, e.g., Vesicular stomatitis virus antigen (e.g., vesicular stomatitis virus glycoprotein) |
| Proteobacteria, e.g., Gammaproteobacteria, e.g., Vibrionales, e..g, Vibrionaceae, e.g., *Vibrio*, e.g., *Vibrio cholerae* antigen |
| Riboviria, e.g., Orthornavirae, e.g., Kitrinoviricota, e.g., Flasuviricetes, e.g., Amarillovirales, e.g., Flaviviridae, e.g., Flavivirus, e.g., West Nile virus (WNV) antigen |

TABLE V1-continued

| Exemplary vaccine antigens that can be included in a surface moiety of an anellovector or anelloVLP as described herein. |
| --- |
| Riboviria, e.g., Orthornavirae, e.g., Kitrinoviricota, e.g., Flasuviricetes, e.g., Amarillovirales, e.g., Flaviviridae, e.g., Flavivirus, e.g., Zika virus antigen |
| Apicomplexa, e.g., Aconoidasida, e.g., Haemospororida, e.g., Plasmodiidae, e.g., *Plasmodium*, e.g., *Plasmodium vivax*, *Plasmodium falciparum*, *Plasmodium malariae*, *Plasmodium ovale*, or *Plasmodium knowlesi*. |
| Riboviria, e.g., Orthornavirae, e.g., Pisuviricota, e.g., Pisoniviricetes, e.g., Nidovirales, e.g., Coronaviridae, e.g., Betacoronavirus, e.g., Sebacovirus, e.g., severe acute respiratory syndrome-related coronavirus, e.g., SARS-CoV-2, e.g., SARS-CoV-2 alpha variant, SARS-CoV-2 beta variant, SARS-CoV-2 gamma variant, SARS-CoV-2 delta variant, or SARS-CoV-2 omicron variant |

In some embodiments, a vaccine comprising an anellovector or anelloVLP as described herein is administered with an adjuvant. In certain embodiments, the adjuvant is an inorganic adjuvant (e.g., potassium alum, aluminium hydroxide, aluminium phosphate, or calcium phosphate hydroxide). In certain embodiments, the adjuvant is an oil-based adjuvant (e.g., paraffin oil). In certain embodiments, the adjuvant is a saponin. In certain embodiments, the adjuvant is a cytokine. In certain embodiments, the adjuvant is a squalene. In certain embodiments, the adjuvant is Freund's complete adjuvant.

In some embodiments, a vaccine as described herein is administered in a dose comprising about $10^{10}$ to $10^{14}$ viral genome equivalents of an anellovector as described herein. In some embodiments, a vaccine as described herein is administered as a dose comprising about $10^{10}$ to $10^{14}$ particles (e.g., anellovectors or anelloVLPs) as described herein.

Ligands

In some instances, a surface moiety as described herein comprises a ligand (e.g., a ligand that binds specifically to a receptor on a target cell). In some embodiments, the ligand is a growth factor. In certain embodiments, the ligand binds to a growth factor receptor on the surface of the target cell. In some embodiments, the ligand is a cytokine. In some embodiments, the ligand is a hormone.

II. Compositions and Methods for Making Anellovectors and AnelloVLPs

The present disclosure provides, in some aspects, anellovectors, anelloVLPs, and methods thereof for delivering effectors. In some embodiments, the anellovectors, anelloVLPs, or components thereof can be made as described below. In some embodiments, the compositions and methods described herein can be used to produce a genetic element or a genetic element construct. In some embodiments, the compositions and methods described herein can be used to produce one or more Anellovirus ORF molecules (e.g., an ORF1, ORF2, ORF2/2, ORF2/3, ORF1/1, or ORF1/2 molecule, or a functional fragment or splice variant thereof). In some embodiments, the compositions and methods described herein can be used to produce a proteinaceous exterior or a component thereof (e.g., an ORF1 molecule), e.g., in a host cell.

In some embodiments, the anellovectors, anelloVLPs, or components thereof can be made using a tandem construct, e.g., as described in PCT Application No. PCT/US2021/037091, which is incorporated herein by reference in its entirety.

The present disclosure provides, in some aspects, compositions (e.g., bacmids, donor vectors, baculovirus particles, and cells comprising same) and methods that can be used for producing anellovectors or anelloVLPs, e.g., as described herein. In some embodiments, the compositions and methods described herein can be used to produce a genetic element or a genetic element construct. In some embodiments, the compositions and methods described herein can be used to produce one or more Anellovirus ORF molecules (e.g., an ORF1, ORF2, ORF2/2, ORF2/3, ORF1/1, or ORF1/2 molecule, or a functional fragment or splice variant thereof). In some embodiments, the compositions and methods described herein can be used to produce a proteinaceous exterior or a component thereof (e.g., an ORF1 molecule). In some embodiments, the anellovectors, anelloVLPs, or components thereof can be made using a bacmid/insect cell system, e.g., as described as described in PCT Application No. PCT/US2021/037076, which is incorporated herein by reference in its entirety.

Without wishing to be bound by theory, rolling circle amplification may occur via Rep protein binding to a Rep binding site (e.g., comprising a 5' UTR, e.g., comprising a hairpin loop and/or an origin of replication, e.g., as described herein) positioned 5' relative to (or within the 5' region of) the genetic element region. The Rep protein may then proceed through the genetic element region, resulting in the synthesis of the genetic element. The genetic element may then be circularized and then enclosed within a proteinaceous exterior to form an anellovector.

Components and Assembly of Anellovectors and AnelloVLPs

The compositions and methods herein can be used to produce anellovectors and anelloVLPs. As described herein, an anellovector generally comprises a genetic element (e.g., a single-stranded, circular DNA molecule, e.g., comprising a 5' UTR region as described herein) enclosed within a proteinaceous exterior (e.g., comprising a polypeptide encoded by an Anellovirus ORF1 nucleic acid, e.g., as described herein). In some embodiments, the genetic element comprises one or more sequences encoding Anellovirus ORFs (e.g., one or more of an Anellovirus ORF1, ORF2, ORF2/2, ORF2/3, ORF1/1, or ORF1/2). As described herein, an anelloVLP generally comprises a proteinaceous exterior (e.g., comprising a polypeptide encoded by an Anellovirus ORF1 nucleic acid, e.g., as described herein) and an exogenous effector. As used herein, an Anellovirus ORF or ORF molecule (e.g., an Anellovirus ORF1, ORF2, ORF2/2, ORF2/3, ORF1/1, or ORF1/2) includes a polypeptide comprising an amino acid sequence having at least 70%, 75%, 80%, 85%, 90%, 95%, 96%, 97%, 98%, 99%, or 100% sequence identity to a corresponding Anellovirus ORF sequence, e.g., as described herein or as described in PCT/US2018/037379 or PCT/US19/65995 (each of which is incorporated by reference herein in their entirety). In embodiments, the genetic element comprises a sequence encoding an Anellovirus ORF1, or a splice variant or functional fragment thereof (e.g., a jelly-roll region, e.g., as described herein). In some embodiments, the proteinaceous exterior comprises a polypeptide encoded by an Anellovirus ORF1 nucleic acid (e.g., an Anellovirus ORF1 molecule or a splice variant or functional fragment thereof).

In some embodiments, an anellovector is assembled by enclosing a genetic element (e.g., as described herein) within a proteinaceous exterior (e.g., as described herein). In some embodiments, an anellovector is assembled by enclosing a genetic element (e.g., as described herein) within a proteinaceous exterior in vitro (e.g., as described herein) (e.g., wherein the enclosing occurs external to a host cell, e.g., in the absence of a host cell). In some embodiments, the genetic element is enclosed within the proteinaceous exterior in a host cell (e.g., as described herein). In some embodiments, a surface moiety is attached to the proteinaceous exterior (e.g., as described herein). In some embodiments, the proteinaceous exterior comprises an ORF1 molecule comprising a surface moiety (e.g., as described herein). In certain embodiments, the ORF1 molecule comprises a surface moiety fused to an ORF1 domain.

In some embodiments, an anelloVLP is assembled by enclosing an exogenous effector within a proteinaceous exterior (e.g., as described herein) in vitro (e.g., wherein the enclosing occurs external to a host cell, e.g., in the absence of a host cell). In some embodiments, an anelloVLP is assembled by contacting a plurality of ORF1 molecules (e.g., as described herein) with an effector in vitro (e.g., wherein the contacting occurs external to a host cell, e.g., in the absence of a host cell). In some embodiments, an anelloVLP is assembled by attaching an exogenous effector to the exterior surface of a proteinaceous exterior (e.g., as described herein) in vitro. In some embodiments, a surface moiety is attached to the proteinaceous exterior (e.g., as described herein). In some embodiments, the proteinaceous exterior comprises an ORF1 molecule comprising a surface moiety (e.g., as described herein). In certain embodiments, the ORF1 molecule comprises a surface moiety fused to an ORF1 domain.

In some embodiments, a host cell expresses one or more polypeptides comprised in the proteinaceous exterior (e.g., a polypeptide encoded by an Anellovirus ORF1 nucleic acid, e.g., an ORF1 molecule). For example, in some embodiments, the host cell comprises a nucleic acid sequence encoding an Anellovirus ORF1 molecule, e.g., a splice variant or a functional fragment of an Anellovirus ORF1 polypeptide (e.g., a wild-type Anellovirus ORF1 protein or a polypeptide encoded by a wild-type Anellovirus ORF1 nucleic acid, e.g., as described herein). In embodiments, the nucleic acid sequence encoding the Anellovirus ORF1 molecule is comprised in a nucleic acid construct (e.g., a plasmid, viral vector, virus, minicircle, bacmid, or artificial chromosome) comprised in the host cell. In embodiments, the nucleic acid sequence encoding the Anellovirus ORF1 molecule is integrated into the genome of the host cell.

In some embodiments, a host cell produces a genetic element from a nucleic acid construct comprising the sequence of the genetic element. In some embodiments, the nucleic acid construct is selected from a plasmid, in vitro circularized nucleic acid molecule, viral nucleic acid molecule, minicircle, bacmid, or artificial chromosome. In some embodiments, the genetic element is excised from the nucleic acid construct and, optionally, converted from a double-stranded form to a single-stranded form (e.g., by denaturation). In some embodiments, the genetic element is generated by a polymerase based on a template sequence in the nucleic acid construct. In some embodiments, the polymerase produces a single-stranded copy of the genetic element sequence, which can optionally be circularized to form a genetic element as described herein. In other embodiments, the nucleic acid construct is a double-stranded minicircle produced by circularizing the nucleic acid sequence of the genetic element in vitro. In embodiments, the in vitro-circularized (IVC) minicircle is introduced into the host cell, where it is converted to a single-stranded genetic element suitable for enclosure in a proteinaceous exterior, as described herein.

In some embodiments, the host cell comprises a genetic element construct (e.g., a bacmid, plasmid, or minicircle). In some embodiments, the host cell comprises a bacmid comprising one or more sequences encoding Anellovirus ORF molecules (e.g., ORF1, ORF2, ORF2/2, ORF2/3, ORF1/1, and/or ORF1/2 ORF molecules), or functional fragments thereof. In some embodiments, proteinaceous exterior proteins are expressed from the bacmid. In embodiments, the proteinaceous exterior proteins expressed from the bacmid enclose a genetic element, thereby forming an anellovector. In some embodiments, the bacmid comprises a backbone suitable for replication of the nucleic acid construct in insect cells (e.g., Sf9 cells), e.g., a baculovirus backbone region. In some embodiments, the bacmid comprises a backbone region suitable for replication of the genetic element construct in bacterial cells (e.g., *E. coli* cells, e.g., DH 10Bac cells). In some embodiments, the genetic element construct comprises a backbone suitable for replication of the nucleic acid construct in insect cells (e.g., Sf9 cells), e.g., a baculovirus backbone region. In some embodiments, the genetic element construct comprises a backbone region suitable for replication of the genetic element construct in bacterial cells (e.g., *E. coli* cells, e.g., DH 10Bac cells). In some embodiments, the bacmid is introduced into the host cell via a baculovirus particle. In embodiments, the bacmid is produced by a producer cell, e.g., an insect cell (e.g., an Sf9 cell) or a bacterial cell (e.g., an *E. coli* cell, e.g., a DH 10Bac cell). In embodiments, the producer cell comprises a bacmid and/or a donor vector, e.g., as described herein. In embodiments, the producer cell further comprises sufficient cellular machinery for replication of the bacmid and/or donor vector.

ORF1 Molecules, e.g., for Assembly of Anellovectors

An anellovector or anelloVLP as described herein generally comprises a proteinaceous exterior comprising a polypeptide encoded by an Anellovirus ORF1 nucleic acid (e.g., an Anellovirus ORF1 molecule or a splice variant or functional fragment thereof, e.g., as described herein). An ORF1 molecule may, in some embodiments, comprise one or more of: a first region comprising an arginine rich region, e.g., a region having at least 60% basic residues (e.g., at least 60%, 65%, 70%, 75%, 80%, 85%, 90%, 95%, or 100% basic residues; e.g., between 60%-90%, 60%-80%, 70%-90%, or 70-80% basic residues), and a second region comprising jelly-roll domain, e.g., at least six beta strands (e.g., 4, 5, 6, 7, 8, 9, 10, 11, or 12 beta strands). In embodiments, the proteinaceous exterior comprises one or more (e.g., 1, 2, 3, 4, or all 5) of an Anellovirus ORF1 arginine-rich region, jelly-roll region, N22 domain, hypervariable region, and/or C-terminal domain. In some embodiments, the proteinaceous exterior comprises an Anellovirus ORF1 jelly-roll region (e.g., as described herein). In some embodiments, the proteinaceous exterior comprises an Anellovirus ORF1 arginine-rich region (e.g., as described herein). In some embodiments, the proteinaceous exterior comprises an Anellovirus ORF1 N22 domain (e.g., as described herein). In some embodiments, the proteinaceous exterior comprises an Anellovirus hypervariable region (e.g., as described herein). In some embodiments, the proteinaceous exterior comprises an Anellovirus ORF1 C-terminal domain (e.g., as described herein).

In some embodiments, the anellovector comprises an ORF1 molecule and/or a nucleic acid encoding an ORF1 molecule. In some embodiments, the anelloVLP comprises an ORF1 molecule. Generally, an ORF1 molecule comprises a polypeptide having the structural features and/or activity of an Anellovirus ORF1 protein (e.g., an Anellovirus ORF1 protein as described herein), or a functional fragment thereof. In some embodiments, the ORF1 molecule comprises a truncation relative to an Anellovirus ORF1 protein (e.g., an Anellovirus ORF1 protein as described herein). In some embodiments, the ORF1 molecule is truncated by at least 10, 20, 30, 40, 50, 60, 70, 80, 90, 100, 150, 200, 250, 300, 350, 400, 450, 500, 550, 600, 650, or 700 amino acids of the Anellovirus ORF1 protein. In some embodiments, an ORF1 molecule comprises an amino acid sequence having at least 75%, 80%, 85%, 90%, 95%, 96%, 97%, 98%, or 99% sequence identity to a Betatorquevirus ORF1 protein, e.g., as described herein. An ORF1 molecule can generally bind to a nucleic acid molecule, such as DNA (e.g., a genetic element, e.g., as described herein). In some embodiments, an ORF1 molecule localizes to the nucleus of a cell. In certain embodiments, an ORF1 molecule localizes to the nucleolus of a cell.

Without wishing to be bound by theory, an ORF1 molecule may be capable of binding to other ORF1 molecules, e.g., to form a proteinaceous exterior (e.g., as described herein). Such an ORF1 molecule may be described as having the capacity to form a capsid. In some embodiments, the proteinaceous exterior may enclose a nucleic acid molecule (e.g., a genetic element as described herein, e.g., produced using a composition or construct as described herein) and/or an effector (e.g., an exogenous effector). In some embodiments, a plurality of ORF1 molecules may form a multimer, e.g., to produce a proteinaceous exterior. In some embodiments, the multimer may be a homomultimer. In other embodiments, the multimer may be a heteromultimer.

In some embodiments, a first plurality of anellovectors or anelloVLPs comprising an ORF1 molecule as described herein is administered to a subject. In some embodiments, a second plurality of anellovectors or anelloVLPs comprising an ORF1 molecule described herein, is subsequently administered to the subject following administration of the first plurality. In some embodiments the second plurality of anellovectors or anelloVLPs comprises an ORF1 molecule having the same amino acid sequence as the ORF1 molecule comprised by the anellovectors or anelloVLPs of the first plurality. In some embodiments the second plurality of anellovectors or anelloVLPs comprises an ORF1 molecule having at least 70%, 75%, 80%, 85%, 90%, 95%, 96%, 97%, 98%, 99%, or 100% amino acid sequence identity to the ORF1 molecule comprised by the anellovectors or anelloVLPs of the first plurality.

ORF2 Molecules, e.g., for Assembly of Anellovectors

Producing an anellovector or anelloVLP using the compositions or methods described herein may involve expression of an Anellovirus ORF2 molecule (e.g., as described herein), or a splice variant or functional fragment thereof. In some embodiments, the anellovector comprises an ORF2 molecule, or a splice variant or functional fragment thereof, and/or a nucleic acid encoding an ORF2 molecule, or a splice variant or functional fragment thereof. In some embodiments, the anellovector or anelloVLP does not comprise an ORF2 molecule, or a splice variant or functional fragment thereof, and/or a nucleic acid encoding an ORF2 molecule, or a splice variant or functional fragment thereof. In some embodiments, producing the anellovector or anelloVLP comprises expression of an ORF2 molecule, or a splice variant or functional fragment thereof, but the ORF2 molecule is not incorporated into the anellovector or anelloVLP.

Production of Protein Components

Protein components of an anellovector or anelloVLP, e.g., ORF1, can be produced in a variety of ways, e.g., as described herein. In some embodiments, one or more protein components of an anellovector or anelloVLP, including, e.g., the proteinaceous exterior, are produced in a host cell (e.g., the same host cell that packages the genetic elements into the proteinaceous exteriors, thereby producing the anellovectors). In some embodiments, one or more protein components of an anellovector or anelloVLP, including, e.g., the proteinaceous exterior, are produced in a cell that does not comprise a genetic element and/or a genetic element construct (e.g., as described herein). In some embodiments, one or more protein components of an anellovector or anelloVLP are produced and then secreted from a host cell. In some embodiments, one or more protein components of an anellovector or anelloVLP are produced and then isolated from a host cell (e.g., by lysing the host cell).

Baculovirus Expression Systems

A viral expression system, e.g., a baculovirus expression system, may be used to express proteins (e.g., for production of anellovectors or anelloVLPs), e.g., as described herein. Baculoviruses are rod-shaped viruses with a circular, supercoiled double-stranded DNA genome. Genera of baculoviruses include: Alphabaculovirus (nucleopolyhedroviruses (NPVs) isolated from *lepidoptera*), Betabaculoviruses (granuloviruses (GV) isolated from *lepidoptera*), Gammabaculoviruses (NPVs isolated from *hymenoptera*) and Deltabaculoviruses (NPVs isolated from Diptera). While GVs typically contain only one nucleocapsid per envelope, NPVs typically contain either single (SNPV) or multiple (MNPV) nucleocapsids per envelope. The enveloped virions are further occluded in granulin matrix in GVs and polyhedrin in NPVs. Baculoviruses typically have both lytic and occluded life cycles. In some embodiments, the lytic and occluded life cycles manifest independently throughout the three phases of virus replication: early, late, and very late phase. In some embodiments, during the early phase, viral DNA replication takes place following viral entry into the host cell, early viral gene expression and shut-off of the host gene expression machinery. In some embodiments, in the late phase late genes that code for viral DNA replication are expressed, viral particles are assembled, and extracellular virus (EV) is produced by the host cell. In some embodiments, in the very late phase the polyhedrin and p10 genes are expressed, occluded viruses (OV) are produced by the host cell, and the host cell is lysed. Since baculoviruses infect insect species, they can be used as biological agents to produce exogenous proteins in baculoviruses-permissive insect cells or larvae. Different isolates of baculovirus, such as *Autographa californica* multiple nuclear polyhedrosis virus (AcMNPV) and *Bombyx mori* (silkworm) nuclear polyhedrosis virus (BmNPV) may be used in exogenous protein expression. Various baculoviral expression systems are commercially available, e.g., from ThermoFisher.

In some embodiments, the proteins described herein (e.g., an Anellovirus ORF molecule, e.g., ORF1, ORF2, ORF2/2, ORF2/3, ORF1/1, or ORF1/2, or a functional fragment or splice variant thereof) may be expressed using a baculovirus expression vector (e.g., a bacmid) that comprises one or more components described herein. For example, a baculovirus expression vector may include one or more of (e.g., all of) a selectable marker (e.g., kanR), an origin of replication (e.g., one or both of a bacterial origin of replication and an insect cell origin of replication), a recombinase recognition site (e.g., an att site), and a promoter. In some embodiments, a baculovirus expression vector (e.g., a bacmid as described herein) can be produced by replacing the naturally occurring wild-type polyhedrin gene, which encodes for baculovirus occlusion bodies, with genes encoding the proteins described herein. In some embodiments, the genes encoding the proteins described herein are cloned into a baculovirus expression vector (e.g., a bacmid as described herein) containing a baculovirus promoter. In some embodiments, the baculovirual vector comprises one or more non-baculoviral promoters, e.g., a mammalian promoter or an Anellovirus promoter. In some embodiments, the genes encoding the proteins described herein are cloned into a donor vector (e.g., as described herein), which is then contacted with an empty baculovirus expression vector (e.g., an empty bacmid) such that the genes encoding the proteins described herein are transferred (e.g., by homologous recombination or transposase activity) from the donor vector into the baculovirus expression vector (e.g., bacmid). In some embodiments, the baculovirus promoter is flanked by baculovirus DNA from the nonessential polyhedrin gene locus. In some embodiments, a protein described herein is under the transcriptional control of the AcNPV polyhedrin promoter in the very late phase of viral replication. In some embodiments, a strong promoter suitable for use in baculoviral expression in insect cells include, but are not limited to, baculovirus p10 promoters, polyhedrin (polh) promoters, p6.9 promoters and capsid protein promoters. Weak promoters suitable for use in baculoviral expression in insect cells include ie1, ie2, ie0, et1, 39K (aka pp31) and gp64 promoters of baculoviruses.

In some embodiments, a recombinant baculovirus is produced by homologous recombination between a baculoviral genome (e.g., a wild-type or mutant baculoviral genome), and a transfer vector. In some embodiments, one or more genes encoding a protein described herein are cloned into the transfer vector. In some embodiments, the transfer vector further contains a baculovirus promoter flanked by DNA from a nonessential gene locus, e.g., polyhedrin gene. In some embodiments, one or more genes encoding a protein described herein are inserted into the baculoviral genome by homologous recombination between the baculoviral genome and the transfer vector. In some embodiments, the baculoviral genome is linearized at one or more unique sites. In some embodiments, the linearized sites are located near the target site for insertion of genes encoding the proteins described herein into the baculoviral genome. In some embodiments, a linearized baculoviral genome missing a fragment of the baculoviral genome downstream from a gene, e.g., polyhedrin gene, can be used for homologous recombination. In some embodiments, the baculoviral genome and transfer vector are co-transfected into insect cells. In some embodiments, the method of producing the recombinant baculovirus comprises the steps of preparing the baculoviral genome for performing homologous recombination with a transfer vector containing the genes encoding one or more protein described herein and co-transfecting the transfer vector and the baculoviral genome DNA into insect cells. In some embodiments, the baculoviral genome comprises a region homologous to a region of the transfer vector. These homologous regions may enhance the probability of recombination between the baculoviral genome and the transfer vector. In some embodiments, the homology region in the transfer vector is located upstream or downstream of the promoter. In some embodiments, to induce homologous recombination, the baculoviral genome, and transfer vector are mixed at a weight ratio of about 1:1 to 10:1.

In some embodiments, a recombinant baculovirus is generated by a method comprising site-specific transposition with Tn7, e.g., whereby the genes encoding the proteins described herein are inserted into bacmid DNA, e.g., propagated in bacteria, e.g., *E. coli* (e.g., DH 10Bac cells). In some embodiments, the genes encoding the proteins described herein are cloned into a pFASTBAC® vector and transformed into competent cells, e.g., DH10BAC® competent cells, containing the bacmid DNA with a mini-attTn7 target site. In some embodiments, the baculovirus expression vector, e.g., pFASTBAC® vector, may have a promoter, e.g., a dual promoter (e.g., polyhedrin promoter, p10 promoter). Commercially available pFASTBAC® donor plasmids include: pFASTBAC 1, pFASTBAC HT, and pFASTBAC DUAL. In some embodiments, recombinant bacmid DNA containing-colonies are identified and bacmid DNA is isolated to transfect insect cells.

In some embodiments, a baculoviral vector is introduced into an insect cell together with a helper nucleic acid. The introduction may be concurrent or sequential. In some embodiments, the helper nucleic acid provides one or more baculoviral proteins, e.g., to promote packaging of the baculoviral vector.

In some embodiments, recombinant baculovirus produced in insect cells (e.g., by homologous recombination) is expanded and used to infect insect cells (e.g., in the mid-logarithmic growth phase) for recombinant protein expression. In some embodiments, recombinant bacmid DNA produced by site-specific transposition in bacteria, e.g., *E. coli*, is used to transfect insect cells with a transfection agent, e.g., Cellfectin® II. Additional information on baculovirus expression systems is discussed in U.S. patent application Ser. Nos. 14/447,341, 14/277,892, and 12/278,916, which are hereby incorporated by reference.

Insect Cell Systems

The proteins described herein may be expressed in host cells (e.g., insect cells) infected or transfected with recombinant baculovirus or bacmid DNA, e.g., as described above. In some embodiments, the host or host cell is an insect cell (e.g., an Sf9 cell, Sf21 cell, or Hi5 cell). In some embodiments, the insect cell is derived from *Bombyx mori, Mamestra brassicae, Spodoptera frugiperda, Trichoplusia ni*, or *Drosophila melanogaster*. In some embodiments, the insect cell is selected from Sf9 and Sf21 cells derived from and Tn-368 and High Five™ BTI-TN-5B1-4 cells (also referred to as Hi5 cells) derived from *Trichoplusia ni*. In some embodiments, insect cell lines Sf21 and Sf9, derived from the ovaries of the pupal fall army worm *Spodoptera frugiperda*, can be used for the expression of recombinant proteins using the baculovirus expression system. In some embodiments, Sf21 and Sf9 insect cells may be cultured in commercially available serum-supplemented or serum-free media. Suitable media for culturing insect cells include: Grace's Supplemented (TNM-FH), IPL-41, TC-100, Schneider's Drosophila, SF-900 II SFM, and EXPRESS-FIVE™ SFM. In some embodiments, some serum-free media formulations utilize a phosphate buffer system to maintain a culture pH in the range of 6.0-6.4 (Licari et al. Insect cell hosts for baculovirus expression vectors contain endogenous exoglycosidase activity. Biotechnology Progress 9: 146-152 (1993) and Drugmand et al. Insect cells as factories for biomanufacturing. Biotechnology Advances 30:1140-1157 (2012)) for both cultivation and recombinant protein production. In some embodiments, a pH of 6.0-6.8 for cultivating various insect cell lines may be used. In some embodiments, insect cells are cultivated in suspension or as a monolayer at a temperature between 25° to 30° C. with aeration. Additional information on insect cells is discussed, for example, in U.S. patent application Ser. Nos. 14/564,512 and 14/775,154, each of which is hereby incorporated by reference.

Mammalian Cell Systems

In some embodiments, the proteins described herein may be expressed in vitro in animal cell lines infected or transfected with a vector encoding the protein, e.g., as described herein. Animal cell lines envisaged in the context of the present disclosure include porcine cell lines, e.g., immortalised porcine cell lines such as, but not limited to the porcine kidney epithelial cell lines PK-15 and SK, the monomyeloid cell line 3D4/31 and the testicular cell line ST. Also, other mammalian cells lines are included, such as CHO cells (Chinese hamster ovaries), MARC-145, MDBK, RK-13, EEL. Additionally or alternatively, particular embodiments of the methods of the invention make use of an animal cell line which is an epithelial cell line, i.e. a cell line of cells of epithelial lineage. Cell lines suitable for expressing the proteins described herein include, but are not limited to cell lines of human or primate origin, such as human or primate kidney carcinoma cell lines.

Genetic Element Constructs, e.g., for Assembly of Anellovectors

The genetic element of an anellovector as described herein may be produced from a genetic element construct that comprises a genetic element region and optionally other sequence such as vector backbone. Generally, the genetic element construct comprises an Anellovirus 5' UTR (e.g., as described herein). A genetic element construct may be any nucleic acid construct suitable for delivery of the sequence of the genetic element into a host cell in which the genetic element can be enclosed within a proteinaceous exterior. In some embodiments, the genetic element construct comprises a promoter. In some embodiments, the genetic element construct is a linear nucleic acid molecule. In some embodiments, the genetic element construct is a circular nucleic acid molecule (e.g., a plasmid, bacmid, or a minicircle, e.g., as described herein). The genetic element construct may, in some embodiments, be double-stranded. In other embodiments, the genetic element is single-stranded. In some embodiments, the genetic element construct comprises DNA. In some embodiments, the genetic element construct comprises RNA. In some embodiments, the genetic element construct comprises one or more modified nucleotides.

In some aspects, the present disclosure provides a method for replication and propagation of the anellovector as described herein (e.g., in a cell culture system), which may comprise one or more of the following steps: (a) introducing (e.g., transfecting) a genetic element (e.g., linearized) into a cell line sensitive to anellovector infection; (b) harvesting the cells and optionally isolating cells showing the presence of the genetic element; (c) culturing the cells obtained in step (b) (e.g., for at least three days, such as at least one week or longer), depending on experimental conditions and gene expression; and (d) harvesting the cells of step (c), e.g., as described herein.

Plasmids

In some embodiments, the genetic element construct is a plasmid. The plasmid will generally comprise the sequence of a genetic element as described herein as well as an origin of replication suitable for replication in a host cell (e.g., a bacterial origin of replication for replication in bacterial cells) and a selectable marker (e.g., an antibiotic resistance gene). In some embodiments, the sequence of the genetic element can be excised from the plasmid. In some embodiments, the plasmid is capable of replication in a bacterial cell. In some embodiments, the plasmid is capable of replication in a mammalian cell (e.g., a human cell). In some embodiments, a plasmid is at least 300, 400, 500, 600, 700, 800, 900, 1000, 2000, 3000, 4000, or 5000 bp in length. In some embodiments, the plasmid is less than 600, 700, 800, 900, 1000, 2000, 3000, 4000, 5000, 6000, 7000, 8000, 9000, or 10,000 bp in length. In some embodiments, the plasmid has a length between 300-400, 400-500, 500-600, 600-700, 700-800, 800-900, 900-1000, 1000-1500, 1500-2000, 2000-2500, 2500-3000, 3000-4000, or 4000-5000 bp. In some embodiments, the genetic element can be excised from a plasmid (e.g., by in vitro circularization), for example, to form a minicircle, e.g., as described herein. In embodiments, excision of the genetic element separates the genetic element sequence from the plasmid backbone (e.g., separates the genetic element from a bacterial backbone).

Small Circular Nucleic Acid Constructs

In some embodiments, the genetic element construct is a circular nucleic acid construct, e.g., lacking a backbone (e.g., lacking a bacterial origin of replication and/or selectable marker). In embodiments, the genetic element is a double-stranded circular nucleic acid construct. In embodiments, the double-stranded circular nucleic acid construct is produced by in vitro circularization (IVC), e.g., as described herein. In embodiments, the double-stranded circular nucleic acid construct can be introduced into a host cell, in which it can be converted into or used as a template for generating single-stranded circular genetic elements, e.g., as described herein. In some embodiments, the circular nucleic acid construct does not comprise a plasmid backbone or a functional fragment thereof. In some embodiments, the circular nucleic acid construct is at least 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, or 4500 bp in length. In some embodiments, the circular nucleic acid construct is less than 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5500, or 6000 bp in length. In some embodiments, the circular nucleic acid construct is between 2000-2100, 2100-2200, 2200-2300, 2300-2400, 2400-2500, 2500-2600, 2600-2700, 2700-2800, 2800-2900, 2900-3000, 3000-3100, 3100-3200, 3200-3300, 3300-3400, 3400-3500, 3500-3600, 3600-3700, 3700-3800, 3800-3900, 3900-4000, 4000-4100, 4100-4200, 4200-4300, 4300-4400, or 4400-4500 bp in length. In some embodiments, the circular nucleic acid construct is a minicircle.

In Vitro Circularization

In some instances, the genetic element to be packaged into a proteinaceous exterior is a single stranded circular DNA. The genetic element may, in some instances, be introduced into a host cell via a genetic element construct having a form other than a single stranded circular DNA. For example, the genetic element construct may be a double-stranded circular DNA. The double-stranded circular DNA may then be converted into a single-stranded circular DNA in the host cell (e.g., a host cell comprising a suitable enzyme for rolling circle replication, e.g., an Anellovirus Rep protein, e.g., Rep68/78, Rep60, RepA, RepB, Pre, MobM, TraX, TrwC, Mob02281, Mob02282, NikB, ORF50240, NikK, TecH, OrfJ, or TraI, e.g., as described in Wawrzyniak et al. 2017, *Front. Microbiol.* 8: 2353; incorporated herein by reference with respect to the listed enzymes). In some embodiments, the double-stranded circular DNA is produced by in vitro circularization (IVC), e.g., as described in Example 15 or PCT Publication No. WO 2020/123816, incorporated by reference herein in its entirety.

Generally, in vitro circularized DNA constructs can be produced by digesting a genetic element construct (e.g., a plasmid comprising the sequence of a genetic element) to be packaged, such that the genetic element sequence is excised as a linear DNA molecule. The resultant linear DNA can then be ligated, e.g., using a DNA ligase, to form a double-stranded circular DNA. In some instances, a double-stranded circular DNA produced by in vitro circularization can undergo rolling circle replication, e.g., as described herein. Without wishing to be bound by theory, it is contemplated that in vitro circularization results in a double-stranded DNA construct that can undergo rolling circle replication without further modification, thereby being capable of producing single-stranded circular DNA of a suitable size to be packaged into an anellovector, e.g., as described herein. In some embodiments, the double-stranded DNA construct is smaller than a plasmid (e.g., a bacterial plasmid). In some embodiments, the double-stranded DNA construct is excised from a plasmid (e.g., a bacterial plasmid) and then circularized, e.g., by in vitro circularization.

Tandem Constructs

In some embodiments, a genetic element construct comprises a first copy of a genetic element sequence (e.g., the nucleic acid sequence of a genetic element, e.g., as described herein) and at least a portion of a second copy of a genetic element sequence (e.g., the nucleic acid sequence of the same genetic element, or the nucleic acid sequence of a different genetic element), arranged in tandem. Genetic element constructs having such a structure are generally referred to herein as tandem constructs. Such tandem constructs are used for producing an anellovector genetic element. The first copy of the genetic element sequence and the second copy of the genetic element sequence may, in some instances, be immediately adjacent to each other on the genetic acid construct. In other instances, the first copy of the genetic element sequence and the second copy of the genetic element sequence may be separated, e.g., by a spacer sequence. In some embodiments, the second copy of the genetic element sequence, or the portion thereof, comprises an upstream replication-facilitating sequence (uRFS), e.g., as described herein. In some embodiments, the second copy of the genetic element sequence, or the portion thereof, comprises a downstream replication-facilitating sequence (dRFS), e.g., as described herein. In some embodiments, the uRFS and/or dRFS comprises an origin of replication (e.g., a mammalian origin of replication, an insect origin of replication, or a viral origin of replication, e.g., a non-Anellovirus origin of replication, e.g., as described herein) or portion thereof. In some embodiments, the uRFS and/or dRFS does not comprise an origin of replication. In some embodiments, the uRFS and/or dRFS comprises a hairpin loop (e.g., in the 5' UTR). In some embodiments, a tandem construct produces higher levels of a genetic element than an otherwise similar construct lacking the second copy of the genetic element or portion thereof. Without being bound by theory, a tandem construct described herein may, in some embodiments, replicate by rolling circle replication. In some embodiments, a tandem construct is a plasmid. In some embodiments, a tandem construct is circular. In some embodiments, a tandem construct is linear. In some embodiments, a tandem construct is single-stranded. In some embodiments, a tandem construct is double-stranded. In some embodiments, a tandem construct is DNA.

A tandem construct may, in some instances, include a first copy of the sequence of the genetic element and a second copy of the sequence of the genetic element, or a portion thereof. It is understood that the second copy can be an identical copy of the first copy or a portion thereof, or can comprise one or more sequence differences, e.g., substitutions, additions, or deletions. In some instances, the second copy of the genetic element sequence or portion thereof is positioned 5' relative to the first copy of the genetic element sequence. In some instances, the second copy of the genetic element sequence or portion thereof is positioned 3' relative to the first copy of the genetic element sequence. In some instances, the second copy of the genetic element sequence or portion thereof and the first copy of the genetic element sequence are adjacent to each other in the tandem construct. In some instances, the second copy of the genetic element sequence or portion thereof and the first copy of the genetic element sequence are separated, e.g., by a spacer sequence.

In some embodiments, the tandem constructs described herein can be used to produce the genetic element of a vector (e.g., anellovector), vehicle, or particle (e.g., viral particle) comprising a capsid (e.g., a capsid comprising an Anellovirus ORF, e.g., an ORF1 molecule, e.g., as described herein) encapsulating a genetic element comprising a protein binding sequence that binds to the capsid and a heterologous (e.g., relative to the Anellovirus from which the ORF1 molecule was derived) sequence encoding a therapeutic effector. In embodiments, the vector is capable of delivering the genetic element into a mammalian, e.g., human, cell. In some embodiments, the genetic element has less than about 50% (e.g., less than 50%, 40%, 30%, 25%, 20%, 15%, 10%, 9%, 8%, 7%, 6%, 5.5%, 5%, 4.5%, 4%, 3.5%, 3%, 2.5%, 2%, 1.5%, or less) identity to a wild type Anellovirus genome sequence. In some embodiments, the genetic element has no more than 1.5%, 2%, 2.5%, 3%, 3.5%, 4%, 4.5%, 5%, 5.5%, 6%, 7%, 8%, 9%, 10%, 15%, 20%, 25%, 30%, 40%, 50%, 60%, 70%, 75%, or 80% identity to a wild type Anellovirus genome sequence. In some embodiments, the genetic element has greater than about 2000, 3000, 4000, 4500, or 5000 contiguous nucleotides of non-Anellovirus genome sequence. In some embodiments, the genetic element has greater than about 2000 to 5000, 2500 to 4500, 3000 to 4500, 2500 to 4500, 3500, or 4000, 4500 (e.g., between about 3000 to 4500) nucleotides nucleotides of non-Anellovirus genome sequence.

In some embodiments of the systems and methods herein, a vector (e.g., an anellovector) is made by introducing into a cell a first nucleic acid molecule that is a genetic element or genetic element construct, e.g., a tandem construct, and a second nucleic acid molecule encoding one or more additional proteins (e.g., a Rep molecule and/or a capsid protein), e.g., as described herein. In some embodiments, the first nucleic acid molecule and the second nucleic acid molecule are attached to each other (e.g., in a genetic element construct described herein, e.g., in cis). In some embodiments, the first nucleic acid molecule and the second nucleic acid molecule are separate (e.g, in trans). In some embodiments, the first nucleic acid molecule is a plasmid, cosmid, bacmid, minicircle, or artificial chromosome. In some embodiments, the second nucleic acid molecule is a plasmid, cosmid, bacmid, minicircle, or artificial chromosome. In some embodiments, the second nucleic acid molecule is integrated into the genome of the host cell.

In some embodiments, the method further includes introducing the first nucleic acid molecule and/or the second nucleic acid molecule into the host cell. In some embodiments, the second nucleic acid molecule is introduced into the host cell prior to, concurrently with, or after the first nucleic acid molecule. In other embodiments, the second nucleic acid molecule is integrated into the genome of the host cell. In some embodiments, the second nucleic acid molecule is or comprises or is part of a helper construct, helper virus or other helper vector, e.g., as described herein.

Cis/Trans Constructs

In some embodiments, a genetic element construct as described herein comprises one or more sequences encoding one or more Anellovirus ORFs, e.g., proteinaceous exterior components (e.g., polypeptides encoded by an Anellovirus ORF1 nucleic acid, e.g., as described herein). For example, the genetic element construct may comprise a nucleic acid sequence encoding an Anellovirus ORF1 molecule. Such genetic element constructs can be suitable for introducing the genetic element and the Anellovirus ORF(s) into a host cell in cis. In other embodiments, a genetic element construct as described herein does not comprise sequences encoding one or more Anellovirus ORFs, e.g., proteinaceous exterior components (e.g., polypeptides encoded by an Anellovirus ORF1 nucleic acid, e.g., as described herein). For example, the genetic element construct may not comprise a nucleic acid sequence encoding an Anellovirus ORF1 molecule. Such genetic element constructs can be suitable for introducing the genetic element into a host cell, with the one or more Anellovirus ORFs to be provided in trans (e.g., via introduction of a second nucleic acid construct encoding one or more of the Anellovirus ORFs, or via an Anellovirus ORF cassette integrated into the genome of the host cell). In some embodiments, an ORF1 molecule is provided in trans, e.g., as described herein. In some embodiments, an ORF2 molecule is provided in trans, e.g., as described herein. In some embodiments, an ORF1 molecule and an ORF1 molecule are both provided in trans, e.g., as described herein.

In some embodiments, the genetic element construct comprises a sequence encoding an Anellovirus ORF1 molecule, or a splice variant or functional fragment thereof (e.g., a jelly-roll region, e.g., as described herein). In embodiments, the portion of the genetic element that does not comprise the sequence of the genetic element comprises the sequence encoding the Anellovirus ORF1 molecule, or splice variant or functional fragment thereof (e.g., in a cassette comprising a promoter and the sequence encoding the Anellovirus ORF1 molecule, or splice variant or functional fragment thereof). In further embodiments, the portion of the construct comprising the sequence of the genetic element comprises a sequence encoding an Anellovirus ORF1 molecule, or a splice variant or functional fragment thereof (e.g., a jelly-roll region, e.g., as described herein). In embodiments, enclosure of such a genetic element in a proteinaceous exterior (e.g., as described herein) produces a replication-component anellovector (e.g., an anellovector that upon infecting a cell, enables the cell to produce additional copies of the anellovector without introducing further nucleic acid constructs, e.g., encoding one or more Anellovirus ORFs as described herein, into the cell).

In other embodiments, the genetic element does not comprise a sequence encoding an Anellovirus ORF1 molecule, or a splice variant or functional fragment thereof (e.g., a jelly-roll region, e.g., as described herein). In embodiments, enclosure of such a genetic element in a proteinaceous exterior (e.g., as described herein) produces a replication-incompetent anellovector (e.g., an anellovector that, upon infecting a cell, does not enable the infected cell to produce additional anellovectors, e.g., in the absence of one or more additional constructs, e.g., encoding one or more Anellovirus ORFs as described herein).

Expression Cassettes

In some embodiments, a genetic element construct comprises one or more cassettes for expression of a polypeptide or noncoding RNA (e.g., a miRNA or an siRNA). In some embodiments, the genetic element construct comprises a cassette for expression of an effector (e.g., an exogenous or endogenous effector), e.g., a polypeptide or noncoding RNA, as described herein. In some embodiments, the genetic element construct comprises a cassette for expression of an Anellovirus protein (e.g., an Anellovirus ORF1, ORF2, ORF2/2, ORF2/3, ORF1/1, or ORF1/2, or a functional fragment thereof). The expression cassettes may, in some embodiments, be located within the genetic element sequence. In embodiments, an expression cassette for an effector is located within the genetic element sequence. In embodiments, an expression cassette for an Anellovirus protein is located within the genetic element sequence. In other embodiments, the expression cassettes are located at a position within the genetic element construct outside of the sequence of the genetic element (e.g., in the backbone). In embodiments, an expression cassette for an Anellovirus protein is located at a position within the genetic element construct outside of the sequence of the genetic element (e.g., in the backbone).

A polypeptide expression cassette generally comprises a promoter and a coding sequence encoding a polypeptide, e.g., an effector (e.g., an exogenous or endogenous effector as described herein) or an Anellovirus protein (e.g., a sequence encoding an Anellovirus ORF1, ORF2, ORF2/2, ORF2/3, ORF1/1, or ORF1/2, or a functional fragment thereof). Exemplary promoters that can be included in an polypeptide expression cassette (e.g., to drive expression of the polypeptide) include, without limitation, constitutive promoters (e.g., CMV, RSV, PGK, EF1a, or SV40), cell or tissue-specific promoters (e.g., skeletal α-actin promoter, myosin light chain 2A promoter, dystrophin promoter, muscle creatine kinase promoter, liver albumin promoter, hepatitis B virus core promoter, osteocalcin promoter, bone sialoprotein promoter, CD2 promoter, immunoglobulin heavy chain promoter, T cell receptor a chain promoter, neuron-specific enolase (NSE) promoter, or neurofilament light-chain promoter), and inducible promoters (e.g., zinc-inducible sheep metallothionine (MT) promoter; the dexamethasone (Dex)-inducible mouse mammary tumor virus (MMTV) promoter; the T7 polymerase promoter system, tetracycline-repressible system, tetracycline-inducible system, RU486-inducible system, rapamycin-inducible system), e.g., as described herein. In some embodiments, the expression cassette further comprises an enhancer, e.g., as described herein.

Design and Production of a Genetic Element Construct

Various methods are available for synthesizing a genetic element construct. For instance, the genetic element construct sequence may be divided into smaller overlapping pieces (e.g., in the range of about 100 bp to about 10 kb segments or individual ORFs) that are easier to synthesize. These DNA segments are synthesized from a set of overlapping single-stranded oligonucleotides. The resulting overlapping synthons are then assembled into larger pieces of DNA, e.g., the genetic element construct. The segments or ORFs may be assembled into the genetic element construct, e.g., by in vitro recombination or unique restriction sites at 5' and 3' ends to enable ligation.

The genetic element construct can be synthesized with a design algorithm that parses the construct sequence into oligo-length fragments, creating suitable design conditions for synthesis that take into account the complexity of the sequence space. Oligos are then chemically synthesized on semiconductor-based, high-density chips, where over 200,000 individual oligos are synthesized per chip. The oligos are assembled with an assembly techniques, such as BioFab®, to build longer DNA segments from the smaller oligos. This is done in a parallel fashion, so hundreds to thousands of synthetic DNA segments are built at one time.

Each genetic element construct or segment of the genetic element construct may be sequence verified. In some embodiments, high-throughput sequencing of RNA or DNA can take place using AnyDot.chips (Genovoxx, Germany), which allows for the monitoring of biological processes (e.g., miRNA expression or allele variability (SNP detection). Other high-throughput sequencing systems include those disclosed in Venter, J., et al. Science 16 Feb. 2001; Adams, M. et al, Science 24 Mar. 2000; and M. J, Levene, et al. Science 299:682-686, January 2003; as well as US Publication Application No. 20030044781 and 2006/0078937. Overall such systems involve sequencing a target nucleic acid molecule having a plurality of bases by the temporal addition of bases via a polymerization reaction that is measured on a molecule of nucleic acid, i.e., the activity of a nucleic acid polymerizing enzyme on the template nucleic acid molecule to be sequenced is followed in real time. In some embodiments, shotgun sequencing is performed.

A genetic element construct can be designed such that factors for replicating or packaging may be supplied in cis or in trans, relative to the genetic element. For example, when supplied in cis, the genetic element may comprise one or more genes encoding an Anellovirus ORF1, ORF1/1, ORF1/2, ORF2, ORF2/2, ORF2/3, or ORF2t/3, e.g., as described herein. In some embodiments, replication and/or packaging signals can be incorporated into a genetic element, for example, to induce amplification and/or encapsulation. In some embodiments, an effector is inserted into a specific site in the genome. In some embodiments, one or more viral ORFs are replaced with an effector.

In another example, when replication or packaging factors are supplied in trans, the genetic element may lack genes encoding one or more of an Anellovirus ORF1, ORF1/1, ORF1/2, ORF2, ORF2/2, ORF2/3, or ORF2t/3, e.g., as described herein; this protein or proteins may be supplied, e.g., by another nucleic acid, e.g., a helper nucleic acid. In some embodiments, minimal cis signals (e.g., 5' UTR and/or GC-rich region) are present in the genetic element. In some embodiments, the genetic element does not encode replication or packaging factors (e.g., replicase and/or capsid proteins). Such factors may, in some embodiments, be supplied by one or more helper nucleic acids (e.g., a helper viral nucleic acid, a helper plasmid, or a helper nucleic acid integrated into the host cell genome). In some embodiments, the helper nucleic acids express proteins and/or RNAs sufficient to induce amplification and/or packaging, but may lack their own packaging signals. In some embodiments, the genetic element and the helper nucleic acid are introduced into the host cell (e.g., concurrently or separately), resulting in amplification and/or packaging of the genetic element but not of the helper nucleic acid.

In some embodiments, the genetic element construct may be designed using computer-aided design tools.

General methods of making constructs are described in, for example, Khudyakov & Fields, *Artificial DNA: Methods and Applications*, CRC Press (2002); in Zhao, *Synthetic Biology: Tools and Applications*, (First Edition), Academic Press (2013); and Egli & Herdewijn, *Chemistry and Biology of Artificial Nucleic Acids*, (First Edition), Wiley-VCH (2012).

Effectors

The compositions and methods described herein can be used to produce a genetic element of an anellovector comprising a sequence encoding an effector (e.g., an exogenous effector or an endogenous effector), e.g., as described herein. The compositions and methods described herein can also be used to produce an anelloVLP comprising an effector (e.g., an exogenous effector or an endogenous effector), e.g., as described herein. The effector may be, in some instances, an endogenous effector or an exogenous effector. In some embodiments, the effector is a therapeutic effector. In some embodiments, the effector comprises a polypeptide (e.g., a therapeutic polypeptide or peptide, e.g., as described herein). In some embodiments, the effector comprises a non-coding RNA (e.g., an miRNA, siRNA, shRNA, mRNA, lncRNA, RNA, DNA, antisense RNA, or gRNA). In some embodiments, the effector comprises a regulatory nucleic acid, e.g., as described herein.

In some embodiments, the effector-encoding sequence may be inserted into the genetic element e.g., at a noncoding region, e.g., a noncoding region disposed 3' of the open reading frames and 5' of the GC-rich region of the genetic element, in the 5' noncoding region upstream of the TATA box, in the 5' UTR, in the 3' noncoding region downstream of the poly-A signal, or upstream of the GC-rich region. In some embodiments, the effector-encoding sequence may be inserted into the genetic element, e.g., in a coding sequence (e.g., in a sequence encoding an Anellovirus ORF1, ORF1/1, ORF1/2, ORF2, ORF2/2, ORF2/3, and/or ORF2t/3, e.g., as described herein). In some embodiments, the effector-encoding sequence replaces all or a part of the open reading frame. In some embodiments, the genetic element comprises a regulatory sequence (e.g., a promoter or enhancer, e.g., as described herein) operably linked to the effector-encoding sequence.

Host Cells

The anellovectors described herein can be produced, for example, in a host cell. Generally, a host cell is provided that comprises an anellovector genetic element and the components of an anellovector proteinaceous exterior (e.g., a polypeptide encoded by an Anellovirus ORF1 nucleic acid or an Anellovirus ORF1 molecule). The host cell is then incubated under conditions suitable for enclosure of the genetic element within the proteinaceous exterior (e.g., culture conditions as described herein). In some embodiments, the host cell is further incubated under conditions suitable for release of the anellovector from the host cell, e.g., into the surrounding supernatant. In some embodiments, the host cell is lysed for harvest of anellovectors from the cell lysate. In some embodiments, an anellovector may be introduced to a host cell line grown to a high cell density. In some embodiments, a host cell is an Expi-293 cell.

Introduction of Genetic Elements into Host Cells

The genetic element, or a nucleic acid construct comprising the sequence of a genetic element, may be introduced into a host cell. In some embodiments, the genetic element itself is introduced into the host cell. In some embodiments, a genetic element construct comprising the sequence of the genetic element (e.g., as described herein) is introduced into the host cell. A genetic element or genetic element construct can be introduced into a host cell, for example, using methods known in the art. For example, a genetic element or genetic element construct can be introduced into a host cell by transfection (e.g., stable transfection or transient transfection). In embodiments, the genetic element or genetic element construct is introduced into the host cell by lipofectamine transfection. In embodiments, the genetic element or genetic element construct is introduced into the host cell by calcium phosphate transfection. In some embodiments, the genetic element or genetic element construct is introduced into the host cell by electroporation. In some embodiments, the genetic element or genetic element construct is introduced into the host cell using a gene gun. In some embodiments, the genetic element or genetic element construct is introduced into the host cell by nucleofection. In some embodiments, the genetic element or genetic element construct is introduced into the host cell by PEI transfection. In some embodiments, the genetic element is introduced into the host cell by contacting the host cell with an anellovector comprising the genetic element In embodiments, the genetic element construct is capable of replication once introduced into the host cell. In embodiments, the genetic element can be produced from the genetic element construct once introduced into the host cell. In some embodiments, the genetic element is produced in the host cell by a polymerase, e.g., using the genetic element construct as a template.

In some embodiments, the genetic elements or vectors comprising the genetic elements are introduced (e.g., transfected) into cell lines that express a viral polymerase protein in order to achieve expression of the anellovector. To this end, cell lines that express an anellovector polymerase protein may be utilized as appropriate host cells. Host cells may be similarly engineered to provide other viral functions or additional functions.

To prepare the anellovector disclosed herein, a genetic element construct may be used to transfect cells that provide anellovector proteins and functions required for replication and production. Alternatively, cells may be transfected with a second construct (e.g., a virus) providing anellovector proteins and functions before, during, or after transfection by the genetic element or vector comprising the genetic element disclosed herein. In some embodiments, the second construct may be useful to complement production of an incomplete viral particle. The second construct (e.g., virus) may have a conditional growth defect, such as host range restriction or temperature sensitivity, e.g., which allows the subsequent selection of transfectant viruses. In some embodiments, the second construct may provide one or more replication proteins utilized by the host cells to achieve expression of the anellovector. In some embodiments, the host cells may be transfected with vectors encoding viral proteins such as the one or more replication proteins. In some embodiments, the second construct comprises an antiviral sensitivity.

The genetic element or vector comprising the genetic element disclosed herein can, in some instances, be replicated and produced into anellovectors using techniques known in the art. For example, various viral culture methods are described, e.g., in U.S. Pat. Nos. 4,650,764; 5,166,057; 5,854,037; European Patent Publication EP 0702085A1; U.S. patent application Ser. No. 09/152,845; International Patent Publications PCT WO97/12032; WO96/34625; European Patent Publication EP-A780475; WO 99/02657; WO 98/53078; WO 98/02530; WO 99/15672; WO 98/13501; WO 97/06270; and EPO 780 47SA1, each of which is incorporated by reference herein in its entirety.

Methods for Providing Protein(s) in Cis or Trans

In some embodiments (e.g., cis embodiments described herein), the genetic element construct further comprises one or more expression cassettes comprising a coding sequence for an Anellovirus ORF (e.g., an Anellovirus ORF1, ORF2, ORF2/2, ORF2/3, ORF1/1, or ORF1/2, or a functional fragment thereof). In embodiments, the genetic element construct comprises an expression cassette comprising a coding sequence for an Anellovirus ORF1, or a splice variant or functional fragment thereof. Such genetic element constructs, which comprise expression cassettes for the effector as well as the one or more Anellovirus ORFs, may be introduced into host cells. Host cells comprising such genetic element constructs may, in some instances, be capable of producing the genetic elements and components for proteinaceous exteriors, and for enclosure of the genetic elements within proteinaceous exteriors, without requiring additional nucleic acid constructs or integration of expression cassettes into the host cell genome. In other words, such genetic element constructs may be used for cis anellovector production methods in host cells, e.g., as described herein.

In some embodiments (e.g., trans embodiments described herein), the genetic element does not comprise an expression cassette comprising a coding sequence for one or more Anellovirus ORFs (e.g., an Anellovirus ORF1, ORF2, ORF2/2, ORF2/3, ORF1/1, or ORF1/2, or a functional fragment thereof). In embodiments, the genetic element construct does not comprise an expression cassette comprising a coding sequence for an Anellovirus ORF1, or a splice variant or functional fragment thereof. Such genetic element constructs, which comprise expression cassettes for the effector but lack expression cassettes for one or more Anellovirus ORFs (e.g., Anellovirus ORF1 or a splice variant or functional fragment thereof), may be introduced into host cells. Host cells comprising such genetic element constructs may, in some instances, require additional nucleic acid constructs or integration of expression cassettes into the host cell genome for production of one or more components of the anellovector (e.g., the proteinaceous exterior proteins). In some embodiments, host cells comprising such genetic element constructs are incapable of enclosure of the genetic elements within proteinaceous exteriors in the absence of an additional nucleic construct encoding an Anellovirus ORF1 molecule. In other words, such genetic element constructs may be used for trans anellovector production methods in host cells, e.g., as described herein.

In some embodiments (e.g., cis embodiments described herein), the genetic element construct further comprises one or more expression cassettes comprising a coding sequence for one or more non-Anellovirus ORF (e.g., a non-Anellovirus Rep molecule, e.g., an AAV Rep molecule, e.g., an AAV Rep protein, e.g., an AAV Rep2 protein). Such genetic element constructs, which comprise expression cassettes for the effector as well as the one or more non-Anellovirus ORFs, may be introduced into host cells. Host cells comprising such genetic element constructs may, in some instances, be capable of producing the genetic elements and components for proteinaceous exteriors, and for enclosure of the genetic elements within proteinaceous exteriors, without requiring additional nucleic acid constructs or integration of expression cassettes into the host cell genome. In other words, such genetic element constructs may be used for cis anellovector production methods in host cells, e.g., as described herein.

In some embodiments (e.g., trans embodiments described herein), the genetic element does not comprise an expression cassette comprising a coding sequence for one or more non-Anellovirus ORFs (e.g., a non-Anellovirus Rep molecule, e.g., an AAV Rep molecule, e.g., an AAV Rep protein, e.g., an AAV Rep2 protein). Such genetic element constructs, which comprise expression cassettes for the effector but lack expression cassettes for one or more non-Anellovirus ORFs (e.g., a non-Anellovirus Rep molecule, e.g., an AAV Rep molecule, e.g., an AAV Rep protein, e.g., an AAV Rep2 protein), may be introduced into host cells. Host cells comprising such genetic element constructs may, in some instances, require additional nucleic acid constructs or integration of expression cassettes into the host cell genome for production of one or more components of the anellovector (e.g., for replication of the genetic element). In some embodiments, host cells comprising such genetic element constructs are incapable of replicating the genetic elements in the absence of an additional nucleic construct, e.g., encoding a non-Anellovirus Rep molecule, e.g., an AAV Rep molecule, e.g., an AAV Rep protein, e.g., an AAV Rep2 protein. In other words, such genetic element constructs may be used for trans anellovector production methods in host cells, e.g., as described herein.

Exemplary Cell Types

Exemplary host cells suitable for production of anellovectors include, without limitation, mammalian cells, e.g., human cells and insect cells. In some embodiments, the host cell is a human cell or cell line. In some embodiments, the cell is an immune cell or cell line, e.g., a T cell or cell line, a cancer cell line, a hepatic cell or cell line, a neuron, a glial cell, a skin cell, an epithelial cell, a mesenchymal cell, a blood cell, an endothelial cell, a gastrointestinal cell, a progenitor cell, a precursor cell, a stem cell, a lung cell, a cardiac cell, or a muscle cell. In some embodiments, the host cell is an animal cell (e.g., a mouse cell, rat cell, rabbit cell, or hamster cell, or insect cell).

In some embodiments, the host cell is a lymphoid cell. In some embodiments, the host cell is a T cell or an immortalized T cell. In embodiments, the host cell is a Jurkat cell. In embodiments, the host cell is a MOLT cell (e.g., a MOLT-4 or a MOLT-3 cell). In embodiments, the host cell is a MOLT-4 cell. In embodiments, the host cell is a MOLT-3 cell. In some embodiments, the host cell is an acute lymphoblastic leukemia (ALL) cell, e.g., a MOLT cell, e.g., a MOLT-4 or MOLT-3 cell. In some embodiments, the host cell is a B cell or an immortalized B cell. In some embodiments, the host cell comprises a genetic element construct (e.g., as described herein).

In some embodiments, the host cell is a MOLT cell (e.g., a MOLT-4 or a MOLT-3 cell).

In some embodiments, the host cell is an acute lymphoblastic leukemia (ALL) cell, e.g., a MOLT cell, e.g., a MOLT-4 or MOLT-3 cell.

In some embodiments, the host cell is an Expi-293 cell. In some embodiments, the host cell is an Expi-293F cell.

In an aspect, the present disclosure provides a method of manufacturing an anellovector comprising a genetic element enclosed in a proteinaceous exterior, the method comprising providing a MOLT-4 cell comprising an anellovector genetic element, and incubating the MOLT-4 cell under conditions that allow the anellovector genetic element to become enclosed in a proteinaceous exterior in the MOLT-4 cell. In some embodiments, the MOLT-4 cell further comprises one or more Anellovirus proteins (e.g., an Anellovirus ORF1 molecule) that form part or all of the proteinaceous exterior. In some embodiments, the anellovector genetic element is produced in the MOLT-4 cell, e.g., from a genetic element construct (e.g., as described herein). In some embodiments, the method further comprises introducing the anellovector genetic element construct into the MOLT-4 cell.

In an aspect, the present disclosure provides a method of manufacturing an anellovector comprising a genetic element enclosed in a proteinaceous exterior, the method comprising providing a MOLT-3 cell comprising an anellovector genetic element, and incubating the MOLT-3 cell under conditions that allow the anellovector genetic element to become enclosed in a proteinaceous exterior in the MOLT-3 cell. In some embodiments, the MOLT-3 cell further comprises one or more Anellovirus proteins (e.g., an Anellovirus ORF1 molecule) that form part or all of the proteinaceous exterior. In some embodiments, the anellovector genetic element is produced in the MOLT-3 cell, e.g., from a genetic element construct (e.g., as described herein). In some embodiments, the method further comprises introducing the anellovector genetic element construct into the MOLT-3 cell.

In some embodiments, the host cell is a human cell. In embodiments, the host cell is a HEK293T cell, HEK293F cell, A549 cell, Jurkat cell, Raji cell, Chang cell, HeLa cell Phoenix cell, MRC-5 cell, NCI-H292 cell, or Wi38 cell. In some embodiments, the host cell is a non-human primate cell (e.g., a Vero cell, CV-1 cell, or LLCMK2 cell). In some embodiments, the host cell is a murine cell (e.g., a McCoy cell). In some embodiments, the host cell is a hamster cell (e.g., a CHO cell or BHK 21 cell). In some embodiments, the host cell is a MARC-145, MDBK, RK-13, or EEL cell. In some embodiments, the host cell is an epithelial cell (e.g., a cell line of epithelial lineage).

In some embodiments, the anellovector is cultivated in continuous animal cell line (e.g., immortalized cell lines that can be serially propagated). According to one embodiment of the invention, the cell lines may include porcine cell lines. The cell lines envisaged in the context of the present invention include immortalised porcine cell lines such as, but not limited to the porcine kidney epithelial cell lines PK-15 and SK, the monomyeloid cell line 3D4/31 and the testicular cell line ST.

Culture Conditions

Host cells comprising a genetic element and components of a proteinaceous exterior can be incubated under conditions suitable for enclosure of the genetic element within the proteinaceous exterior, thereby producing an anellovector. Suitable culture conditions include those described, e.g., in any of Examples 24, 25, 27, or 28. In some embodiments, the host cells are incubated in liquid media (e.g., Grace's Supplemented (TNM-FH), IPL-41, TC-100, Schneider's Drosophila, SF-900 II SFM, or and EXPRESS-FIVE™ SFM). In some embodiments, the host cells are incubated in adherent culture. In some embodiments, the host cells are incubated in suspension culture. In some embodiments, the host cells are incubated in a tube, bottle, microcarrier, or flask. In some embodiments, the host cells are incubated in a dish or well (e.g., a well on a plate). In some embodiments, the host cells are incubated under conditions suitable for proliferation of the host cells. In some embodiments, the host cells are incubated under conditions suitable for the host cells to release anellovectors produced therein into the surrounding supernatant.

The production of anellovector-containing cell cultures according to the present invention can be carried out in different scales (e.g., in flasks, roller bottles or bioreactors). The media used for the cultivation of the cells to be infected generally comprise the standard nutrients required for cell viability, but may also comprise additional nutrients dependent on the cell type. Optionally, the medium can be protein-free and/or serum-free. Depending on the cell type the cells can be cultured in suspension or on a substrate. In some embodiments, different media is used for growth of the host cells and for production of anellovectors.

Harvest

Anellovectors produced by host cells can be harvested, e.g., according to methods known in the art. For example, anellovectors released into the surrounding supernatant by host cells in culture can be harvested from the supernatant (e.g., as described in Example 24). In some embodiments, the supernatant is separated from the host cells to obtain the anellovectors. In some embodiments, the host cells are lysed before or during harvest. In some embodiments, the host cells are lysed in a detergent (e.g., Triton, e.g., 0.01%-0.1% Triton). In some embodiments, the anellovectors are harvested from the host cell lysates (e.g., as described in Example 10 of PCT Publication No. WO 2020/123816, incorporated by reference herein in its entirety). In some embodiments, the anellovectors are harvested from both the host cell lysates and the supernatant. In some embodiments, the purification and isolation of anellovectors is performed according to known methods in virus production, for example, as described in Rinaldi, et al., DNA Vaccines: Methods and Protocols (Methods in Molecular Biology), 3rd ed. 2014, Humana Press (incorporated herein by reference in its entirety). In some embodiments, the anellovector may be harvested and/or purified by separation of solutes based on biophysical properties, e.g., ion exchange chromatography or tangential flow filtration, prior to formulation with a pharmaceutical excipient.

In Vitro Assembly Methods for Anellovectors

An anellovector may be produced, e.g., by in vitro assembly, e.g., in the absence of a host cell, in a cell-free suspension, or in a supernatant. In some embodiments, the genetic element is contacted to an ORF1 molecule in vitro, e.g., under conditions that allow for assembly.

In an aspect, the present disclosure provides a particle (e.g., an anellovector as described herein) produced via in vitro assembly (e.g., as described herein). The particle may, in some instances, comprise a proteinaceous exterior comprising an ORF1 molecule and a genetic element encoding an exogenous effector, which is enclosed within the proteinaceous exterior. In some embodiments, a particle produced by in vitro assembly does not include a substantial (e.g., detectable) amount of one or more constituents (e.g., small molecules, peptides, polypeptides, nucleic acids, polynucleotides, lipids, sugars, and/or organelles) from a host cell (e.g., a host cell used to produce the ORF1 molecules and/or the genetic element). In some embodiments, the particle may have one or more (e.g., 1, 2, 3, 4, 5, 6, 7, 8, or all 9) of the following characteristics:

- (i) the genetic element (e.g., a DNA genetic element) does not comprise an Anellovirus 5' UTR and/or an Anellovirus origin of replication;
- (ii) the sequence encoding the exogenous effector takes up at least 90%, 95%, 96%, 97%, 98%, 99% or 100% of the genetic element (e.g., a DNA genetic element);
- (iii) the heterologous nucleic acid sequence takes up at least 90%, 95%, 96%, 97%, 98%, 99% or 100% of the genetic element (e.g., a DNA genetic element);
- (iv) the particle does not comprise a detectable amount of (e.g., any) polypeptides from a host cell, or comprises less than 5, 10, 15, 20, 25, 30, 40, or 50 copies of a polypeptide from a host cell;
- (v) the particle does not comprise a detectable amount of (e.g., any) nucleic acid molecules from a host cell other than the genetic element (or copies thereof), or comprises less than 2, 3, 4, or 5 copies of a nucleic acid molecule from a host cell;
- (vi) the particle comprises a denaturant in a concentration of less than about 0.01M, 0.1M, 0.2M, 0.3M, 0.4M, 0.5M, 0.6M, 0.7M, 0.8M, 0.9M, 1M, LIM, 1.2M, 1.3M, 1.5M, 1.5M, 1.6M, 1.7M, 1.8M, 1.9M, or 2M;
- (vii) does not substantially replicate when introduced into a cell (e.g., a human cell); and/or
- (viii) has a symmetrical morphology and/or a diameter of at least 30, 31, 32, 33, 34, or 35 nm.

In another aspect, the disclosure provides a population of the particles (e.g., the anellovectors).

In some embodiments, Anellovirus proteins to be used for in vitro assembly of a particle (e.g., an anellovector) as described herein are produced in a cell. In some embodiments, baculovirus constructs are used to produce Anellovirus proteins (e.g., one or more of an Anellovirus ORF1, ORF2, and/or ORF3 molecule, e.g., as described herein), for example, in insect cells (e.g., Sf9 cells). These proteins may then be used, e.g., for in vitro assembly to encapsidate a genetic element, e.g., a genetic element comprising RNA. In some embodiments, a polynucleotide encoding one or more Anellovirus proteins is fused to a promoter for expression in a host cell, e.g., an insect cell or an animal cell. In some embodiments, the polynucleotide is cloned into a baculovirus expression system. In some embodiments, a host cell, e.g., an insect cell, is infected with the baculovirus expression system and incubated for a period of time under conditions suitable for expression of the one or more Anellovirus proteins. In some embodiments, an infected cell is incubated for about 1, 2, 3, 4, 5, 10, 15, or 20 days. In some embodiments, an infected cell is lysed to recover the one or more Anellovirus proteins.

In some embodiments, an Anellovirus protein (e.g., an Anellovirus ORF1 molecule) is produced as described in Example 7. In some embodiments, an Anellovirus protein (e.g., an Anellovirus ORF1 molecule) is produced in insect cells as described in Example 8 or 10. In some embodiments, a plurality of Anellovirus ORF1 molecules has a propensity to self-assemble into a proteinaceous exterior, for example, to form a virus-like particle (VLP). In certain embodiments, the VLPs do not encapsulate a genetic element as described herein. In certain embodiments, the VLP comprises at least 40, 45, 50, 55, 60, 65, or 70 ORF1 molecules in its proteinaceous exterior.

In certain embodiments, a VLP comprising an Anellovirus ORF1 molecule can be denatured as described herein (e.g., using a chaotropic agent, such as urea). In embodiments, a VLP is denatured using one or more of: buffers of different pH, conditions of defined conductivity (salt content), a detergent (such as SDS (e.g., 0.1% SDS), Tween, Triton), a chaotropic agent (such as urea, e.g., as described herein), a high salt solution (e.g., a solution comprising NaCl, e.g., at a concentration of at least about 1M, e.g., at least about 0.5, 0.6, 0.7, 0.8, 0.9, 1.0, 1.1, 1.2, 1.3, 1.4, 1.5, 2, 3, 4, or 5M), or conditions involving defined temperature and time (reannealing temperatures), for example, as described in Example 12. In embodiments, a VLP is denatured using urea as described in Example 11. In embodiments, a VLP is denatured in urea at a concentration of about 1-10 M (e.g., about 1-2 M, 2-3 M, 3-4 M, 4-5 M, 5-6 M, 6-7 M, 7-8 M, 8-9 M, 9-10M, or 1-6 M). In embodiments, a VLP is denatured in urea at a concentration of about 1-10 M (e.g., about 1, 2, 3, 4, 5, 6, 7, 8, 9, or 10M). In an embodiment, a VLP is denatured in urea at a concentration of 2 M. In embodiments, a VLP is denatured under high salt conditions. In embodiments, denaturation of the VLP results in the ORF1 molecules forming capsomers (e.g., capsomeric decamers comprising about 10 copies of the ORF1 molecule).

In some embodiments, removing the capsomers from the presence of the chaotropic agent (e.g., by purifying the capsomers or removing the chaotropic agent, e.g., by dilution or dialysis) allows the ORF1 molecules to reform VLPs (e.g., VLPs comprising at least 40, 45, 50, 55, 60, 65, or 70 ORF1 molecules). In embodiments, VLPs are reformed by dialyzing out a chaotropic agent (e.g., urea) as described in Example 11. In some embodiments, VLPs are reformed in the presence of a cargo of interest, such as a genetic element (e.g., as described herein), under conditions suitable for enclosure of the cargo in the proteinaceous exterior of the VLP (e.g., as described in Example 12).In some embodiments, an isolated Anellovirus protein (e.g., an ORF1 molecule) is purified (e.g., from a cell). In some embodiments, an Anellovirus protein is purified using purification techniques including but not limited to chelating purification, heparin purification, gradient sedimentation purification, and/or SEC purification. In embodiments, an Anellovirus protein is purified as described in Example 7. In some embodiments, an Anellovirus protein (e.g., an Anellovirus ORF1 molecule) is purified from insect cells as described in Example 8 or 10. In some embodiments, a purified Anellovirus protein is mixed with a genetic element to encapsidate the genetic element, e.g., a genetic element comprising RNA. In some embodiments, a genetic element is encapisdated using an ORF1 protein, ORF2 protein, or modified version thereof. In some embodiments two nucleic acids are encapsidated. For instance, the first nucleic acid may be an mRNA e.g., chemically modified mRNA, and the second nucleic acid may be DNA.

In some embodiments, DNA encoding Anellovirus ORF1 (e.g., wildtype ORF1 protein, ORF1 proteins harboring mutations, e.g., to improve assembly efficiency, yield or stability, chimeric ORF1 protein, or fragments thereof) are expressed in insect cell lines (e.g., Sf9 and/or HighFive), animal cell lines (e.g., chicken cell lines (MDCC)), bacterial cells (e.g., *E. coli*) and/or mammalian cell lines (e.g., 293expi and/or MOLT4). In some embodiments, DNA encoding Anellovirus ORF1 may be untagged. In some embodiments, DNA encoding Anellovirus ORF1 may contain tags fused N-terminally and/or C-terminally. In some embodiments, DNA encoding Anellovirus ORF1 may harbor mutations, insertions or deletions within the ORF1 protein to introduce a tag, e.g., to aid in purification and/or identity determination, e.g., through immunostaining assays (including but not limited to ELISA or Western Blot). In some embodiments, DNA encoding Anellovirus ORF1 may be expressed alone or in combination with any number of helper proteins. In some embodiments, DNA encoding Anellovirus ORF1 is expressed in combination with Anellovirus ORF2 and/or ORF3 proteins.

In some embodiments, ORF1 proteins harboring mutations to improve assembly efficiency may include, but are not limited to, ORF1 proteins that harbor mutations introduced into the N-terminal Arginine Arm (ARG arm) to alter the pI of the ARG arm permitting pH sensitive nucleic acid binding to trigger particle assembly (SEQ ID 3-5). In some embodiments, ORF1 proteins harboring mutations that improve stability may include mutations to an interprotomer contacting beta strands F and G of the canonical jellyroll beta-barrel to alter hydrophobic state of the protomer surface and improve thermodynamic favorability of capsid formation.

In some embodiments, chimeric ORF1 proteins may include, but are not limited to, ORF1 proteins which have a portion or portions of their sequence replaced with comparable portions from another capsid protein, e.g., Beak and Feather Disease Virus (BFDV) capsid protein, or Hepatitis E capsid protein, e.g., ARG arm or F and G beta strands of Ring 9 ORF1 replaced with the comparable components from BFDV capsid protein. In some embodiments, chimeric ORF1 proteins may also include ORF1 proteins which have a portion or portions of their sequence replaced with comparable portions of another Anellovirus ORF1 protein (e.g., jellyroll fragments or the C-terminal portion of Ring 2 ORF1 replaced with comparable portions of Ring 9 ORF1.

In some embodiments, a genetic element to be used for in vitro assembly of a particle (e.g., an anellovector) as described herein are produced in a cell. In some embodiments, a cell is transfected with a construct (e.g., a plasmid, tandem construct, and/or an in vitro circularized nucleic acid molecule, e.g., as described herein) comprising the sequence of a genetic element. In embodiments, the cell is incubated under conditions suitable for replication of the construct. In embodiments, the cell is incubated under conditions suitable for production and/or replication of the genetic element (e.g., from the construct). In embodiments, the cell is lysed to recover the genetic element. In some embodiments, a genetic element to be used for in vitro assembly is a DNA, e.g., a single-stranded DNA (ssDNA). In embodiments, the genetic element is a negative sense ssDNA (e.g., generated as described in Example 6). In some embodiments, a genetic element to be used for in vitro assembly comprises RNA (e.g., an mRNA), for example, as described in Example 12. In some embodiments, a genetic element to be used for in vitro assembly comprises RNA (e.g., an mRNA) and the ORF1 molecule of the proteinaceous exterior comprises one or more contact residues that binds RNA (e.g., a domain from an RNA-binding protein, e.g., an mRNA-binding protein, e.g., MS2 coat protein), for example, as described in Example 12. In some embodiments, a genetic element to be used for in vitro assembly comprises RNA (e.g., an mRNA) and DNA (e.g., a DNA portion comprising a sequence that binds to an Anellovirus ORF1 molecule), for example, as described in Example 12. In certain embodiments, the RNA portion of the genetic element is covalently bound to the DNA portion of the genetic element. In certain embodiments, the RNA portion of the genetic element is hybridized to the DNA portion of the genetic element. In embodiments, the RNA portion of the genetic element comprises a region capable of hybridizing to (e.g., complementary to) at least a subsequence of the DNA portion of the genetic element.

In some embodiments, the present disclosure describes a method of making an anellovector, the method comprising: (a) providing a mixture comprising: (i) a genetic element (e.g., a genetic element comprising DNA and/or RNA), and (ii) an ORF1 molecule; and (b) incubating the mixture under conditions suitable for enclosing the genetic element within a proteinaceous exterior comprising the ORF1 molecule, thereby making an anellovector; wherein the mixture is not comprised in a cell. In some embodiments, the anellovector is assembled in vitro as described in Example 7. In some embodiments, the method further comprises, prior to the providing of (a), expressing the ORF1 molecule, e.g., in a host cell (e.g., an insect cell or a mammalian cell). In some embodiments, the expressing comprises incubating a host cell (e.g., an insect cell or a mammalian cell) comprising a nucleic acid molecule (e.g., a baculovirus expression vector) encoding the ORF1 molecule under conditions suitable for producing the ORF1 molecule. In some embodiments, the method further comprises, prior to the providing of (a), purifying the ORF1 molecule expressed by the host cell. In some embodiments, the method is performed in a cell-free system. In some embodiments, the present disclosure describes a method of manufacturing an anellovector composition, comprising: (a) providing a plurality of anellovectors or compositions according to any of the preceding embodiments; (b) optionally evaluating the plurality for one or more of: a contaminant described herein, an optical density measurement (e.g., OD 260), particle number (e.g., by HPLC), infectivity (e.g., particle:infectious unit ratio, e.g., as determined by fluorescence and/or ELISA); and (c) formulating the plurality of anellovectors, e.g., as a pharmaceutical composition suitable for administration to a subject, e.g., if one or more of the parameters of (b) meet a specified threshold.

In Vitro Assembly Methods for anelloVLPs

An anelloVLP as described herein may be produced, e.g., by in vitro assembly, e.g., in a cell-free suspension or in a supernatant. In some embodiments, the anelloVLP is produced by contacting a plurality of ORF1 molecules (e.g., in capsomers) to an effector (e.g., an exogenous effector) in vitro, e.g., under conditions that allow for assembly. In some embodiments, the plurality of ORF1 molecules enclose the effector in a proteinaceous exterior. In some embodiments, the effector is attached to the exterior surface of a proteinaceous exterior formed from the plurality of ORF1 molecules (e.g., as a surface moiety as described herein). In some embodiments, production of an anelloVLP comprises expressing a plurality of ORF1 molecules in a cell, purifying the plurality of ORF1 molecules, denaturing virus-like particles formed by the ORF1 molecules (e.g., as described herein), and then allowing the ORF1 molecules to reform virus-like particles in the presence of an effector (e.g., an exogenous effector), thereby forming anelloVLPs comprising the ORF1 molecules enclosing the effector.

In an aspect, the present disclosure provide a particle (e.g., an anelloVLP as described herein) produced via in vitro assembly (e.g., as described herein). The particle may, in some instances, comprise a proteinaceous exterior comprising an ORF1 molecule and an effector (e.g., an exogenous effector), e.g., as described herein. In some embodiments, the effector is enclosed within the proteinaceous exterior. In some embodiments, the effector is comprised in a surface moiety (e.g., as described herein) attached to the exterior surface of the proteinaceous exterior. In some embodiments, a particle produced by in vitro assembly does not include a substantial (e.g., detectable) amount of one or more constituents (e.g., small molecules, peptides, polypeptides, nucleic acids, polynucleotides, lipids, sugars, and/or organelles) from a host cell (e.g., a host cell used to produce the ORF1 molecules and/or the genetic element). In some embodiments, the particle may have one or more (e.g., 1, 2, 3, 4, or all 5) of the following characteristics:

(i) does not comprise (e.g., does not enclose) a polynucleotide, (ii) does not comprise (e.g., does not enclose) detectable levels of polynucleotides, (iii) does not comprise (e.g., does not enclose) a polynucleotide of greater than 1000, 500, 200, or 100 nucleotides in length, (iv) does not comprise (e.g., does not enclose) a polynucleotide comprising any contiguous nucleic acid sequences of at least 50, 100, 150, 200, 300, 400, 500, 600, 700, 800, 900, or 1000 nucleotides in length having least 75%, 80%, 85%, 90%, 95%, 96%, 97%, 98%, 99%, or 100% sequence identity to contiguous sequence in a wild-type Anellovirus genome (e.g., as described herein), and/or (v) does not comprise a polynucleotide comprising an Anellovirus 5' UTR or an origin of replication.

In another aspect, the disclosure provides a population of the particles (e.g., the anelloVLPs). In some embodiments, the population further comprises one or more anellovectors. In some embodiments, the population does not comprise anellovectors.

In some embodiments, Anellovirus proteins to be used for in vitro assembly of a particle (e.g., an anelloVLP) as described herein are produced in a cell. In some embodiments, baculovirus constructs are used to produce Anellovirus proteins (e.g., one or more of an Anellovirus ORF1, ORF2, and/or ORF3 molecule, e.g., as described herein), for example, in insect cells (e.g., Sf9 cells). These proteins may then be used, e.g., for in vitro assembly to form an anelloVLP, e.g., as described herein. In some embodiments, a polynucleotide encoding one or more Anellovirus proteins is fused to a promoter for expression in a host cell, e.g., an insect cell or an animal cell. In some embodiments, the polynucleotide is cloned into a baculovirus expression system. In some embodiments, a host cell, e.g., an insect cell, is infected with the baculovirus expression system and incubated for a period of time under conditions suitable for expression of the one or more Anellovirus proteins. In some embodiments, an infected cell is incubated for about 1, 2, 3, 4, 5, 10, 15, or 20 days. In some embodiments, an infected cell is lysed to recover the one or more Anellovirus proteins.

In some embodiments, an Anellovirus protein (e.g., an Anellovirus ORF1 molecule) is produced as described in Example 7. In some embodiments, an Anellovirus protein (e.g., an Anellovirus ORF1 molecule) is produced in insect cells as described in Example 8 or 10. In some embodiments, a plurality of Anellovirus ORF1 molecules has a propensity to self-assemble into a proteinaceous exterior, for example, to form a virus-like particle (VLP). In certain embodiments, the VLPs do not encapsulate a genetic element as described herein. In certain embodiments, the VLPs do not encapsulate an effector to be delivered to a target cell, e.g., as described herein. In certain embodiments, the VLP comprises at least 40, 45, 50, 55, 60, 65, or 70 ORF1 molecules in its proteinaceous exterior.

In certain embodiments, a VLP comprising an Anellovirus ORF1 molecule can be denatured as described herein (e.g., using a chaotropic agent, such as urea). In embodiments, a VLP is denatured using one or more of: buffers of different pH, conditions of defined conductivity (salt content), a detergent (such as SDS (e.g., 0.1% SDS), Tween, Triton), a chaotropic agent (such as urea, e.g., as described herein), a high salt solution (e.g., a solution comprising NaCl, e.g., at a concentration of at least about 1M, e.g., at least about 0.5, 0.6, 0.7, 0.8, 0.9, 1.0, 1.1, 1.2, 1.3, 1.4, 1.5, 2, 3, 4, or 5M), or conditions involving defined temperature and time (reannealing temperatures), for example, as described in Example 12. In embodiments, a VLP is denatured using urea as described in Example 11. In embodiments, a VLP is denatured in urea at a concentration of about 1-10 M (e.g., about 1-2 M, 2-3 M, 3-4 M, 4-5 M, 5-6 M, 6-7 M, 7-8 M, 8-9 M, 9-10M, or 1-6 M). In embodiments, a VLP is denatured in urea at a concentration of about 1-10 M (e.g., about 1, 2, 3, 4, 5, 6, 7, 8, 9, or 10M). In an embodiment, a VLP is denatured in urea at a concentration of 2 M. In embodiments, a VLP is denatured under high salt conditions. In embodiments, denaturation of the VLP results in the ORF1 molecules forming capsomers (e.g., capsomeric decamers comprising about 10 copies of the ORF1 molecule).

In some embodiments, removing the capsomers from the presence of the chaotropic agent (e.g., by purifying the capsomers or removing the chaotropic agent, e.g., by dilution or dialysis) allows the ORF1 molecules to reform VLPs (e.g., VLPs comprising at least 40, 45, 50, 55, 60, 65, or 70 ORF1 molecules). In embodiments, VLPs are reformed by dialyzing out a chaotropic agent (e.g., urea) as described in Example 11. In some embodiments, VLPs are reformed in the presence of a cargo of interest (e.g., an effector as described herein), for example, under conditions suitable for enclosure of the cargo in the proteinaceous exterior of the VLP (e.g., as described in Example 12). In some embodiments, an isolated Anellovirus protein (e.g., an ORF1 molecule) is purified (e.g., from a cell). In some embodiments, an Anellovirus protein is purified using purification techniques including but not limited to chelating purification, heparin purification, gradient sedimentation purification, and/or SEC purification. In embodiments, an Anellovirus protein is purified as described in Example 7. In some embodiments, an Anellovirus protein (e.g., an Anellovirus ORF1 molecule) is purified from insect cells as described in Example 8 or 10. In some embodiments, a plurality of purified Anellovirus proteins are mixed with an effector. In embodiments, the purified Anellovirus proteins encapsulated the effector. In some embodiments, the effector is encapsulated using an ORF1 protein, ORF2 protein, or modified version thereof.

In some embodiments, DNA encoding Anellovirus ORF1 (e.g., wildtype ORF1 protein, ORF1 proteins harboring mutations, e.g., to improve assembly efficiency, yield or stability, chimeric ORF1 protein, or fragments thereof) are expressed in insect cell lines (e.g., Sf9 and/or HighFive), animal cell lines (e.g., chicken cell lines (MDCC)), bacterial cells (e.g., *E. coli*) and/or mammalian cell lines (e.g., 293expi and/or MOLT4). In some embodiments, DNA encoding Anellovirus ORF1 may be untagged. In some embodiments, DNA encoding Anellovirus ORF1 may contain tags fused N-terminally and/or C-terminally. In some embodiments, DNA encoding Anellovirus ORF1 may harbor mutations, insertions or deletions within the ORF1 protein to introduce a tag, e.g., to aid in purification and/or identity determination, e.g., through immunostaining assays (including but not limited to ELISA or Western Blot). In some embodiments, DNA encoding Anellovirus ORF1 may be expressed alone or in combination with any number of helper proteins. In some embodiments, DNA encoding Anellovirus ORF1 is expressed in combination with Anellovirus ORF2 and/or ORF3 proteins.

In some embodiments, ORF1 proteins harboring mutations to improve assembly efficiency may include, but are not limited to, ORF1 proteins that harbor mutations introduced into the N-terminal Arginine Arm (ARG arm) to alter the pI of the ARG arm permitting pH sensitive nucleic acid binding to trigger particle assembly (SEQ ID 3-5). In some embodiments, ORF1 proteins harboring mutations that improve stability may include mutations to an interprotomer contacting beta strands F and G of the canonical jellyroll beta-barrel to alter hydrophobic state of the protomer surface and improve thermodynamic favorability of capsid formation.

In some embodiments, chimeric ORF1 proteins may include, but are not limited to, ORF1 proteins which have a portion or portions of their sequence replaced with comparable portions from another capsid protein, e.g., Beak and Feather Disease Virus (BFDV) capsid protein, or Hepatitis E capsid protein, e.g., ARG arm or F and G beta strands of Ring 9 ORF1 replaced with the comparable components from BFDV capsid protein. In some embodiments, chimeric ORF1 proteins may also include ORF1 proteins which have a portion or portions of their sequence replaced with comparable portions of another Anellovirus ORF1 protein (e.g., jellyroll fragments or the C-terminal portion of Ring 2 ORF1 replaced with comparable portions of Ring 9 ORF1.

In some embodiments, the present disclosure describes a method of making an anelloVLP, the method comprising: (a) providing a mixture comprising: (i) an effector (e.g., an exogenous effector), and (ii) an ORF1 molecule; and (b) incubating the mixture under conditions suitable for enclosing the effector within a proteinaceous exterior comprising the ORF1 molecule, thereby making an anelloVLP; wherein the mixture is not comprised in a cell. In some embodiments, the anelloVLP is assembled in vitro as described in Example 7. In some embodiments, the method further comprises, prior to the providing of (a), expressing the ORF1 molecule, e.g., in a host cell (e.g., an insect cell or a mammalian cell). In some embodiments, the expressing comprises incubating a host cell (e.g., an insect cell or a mammalian cell) comprising a nucleic acid molecule (e.g., a baculovirus expression vector) encoding the ORF1 molecule under conditions suitable for producing the ORF1 molecule. In some embodiments, the method further comprises, prior to the providing of (a), purifying the ORF1 molecule expressed by the host cell. In some embodiments, the method is performed in a cell-free system. In some embodiments, the present disclosure describes a method of manufacturing an anelloVLP composition, comprising: (a) providing a plurality of anelloVLPs or compositions according to any of the preceding embodiments; (b) optionally evaluating the plurality for one or more of: a contaminant described herein, an optical density measurement (e.g., OD 260), particle number (e.g., by HPLC), infectivity (e.g., particle:infectious unit ratio, e.g., as determined by fluorescence and/or ELISA); and (c) formulating the plurality of anelloVLPs, e.g., as a pharmaceutical composition suitable for administration to a subject, e.g., if one or more of the parameters of (b) meet a specified threshold.

Enrichment and Purification

Anellovectors or anelloVLPs produced as described herein can be further purified and/or enriched, e.g., to produce an anellovector preparation or an anelloVLP preparation, respectively. In some embodiments, the harvested anellovectors or anelloVLPs are isolated from other constituents or contaminants present in the harvest solution, e.g., using methods known in the art for purifying viral particles (e.g., purification by sedimentation, chromatography, and/or ultrafiltration). In some embodiments, the purification steps comprise removing one or more of serum, host cell DNA, host cell proteins, particles lacking the genetic element, and/or phenol red from the preparation. In some embodiments, the harvested anellovectors or anelloVLPs are enriched relative to other constituents or contaminants present in the harvest solution, e.g., using methods known in the art for enriching viral particles.

In some embodiments, the resultant preparation or a pharmaceutical composition comprising the preparation will be stable over an acceptable period of time and temperature, and/or be compatible with the desired route of administration and/or any devices this route of administration will require, e.g., needles or syringes.

III. Vectors

The genetic element described herein may be included in a vector. Suitable vectors as well as methods for their manufacture and their use are well known in the prior art.

In one aspect, the invention includes a vector comprising a genetic element comprising (i) a sequence encoding a non-pathogenic exterior protein, (ii) an exterior protein binding sequence that binds the genetic element to the non-pathogenic exterior protein, and (iii) a sequence encoding a regulatory nucleic acid.

The genetic element or any of the sequences within the genetic element can be obtained using any suitable method. Various recombinant methods are known in the art, such as, for example screening libraries from cells harboring viral sequences, deriving the sequences from a vector known to include the same, or isolating directly from cells and tissues containing the same, using standard techniques. Alternatively or in combination, part or all of the genetic element can be produced synthetically, rather than cloned.

In some embodiments, the vector includes regulatory elements, nucleic acid sequences homologous to target genes, and various reporter constructs for causing the expression of reporter molecules within a viable cell and/or when an intracellular molecule is present within a target cell.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some embodiments, the vector is substantially non-pathogenic and/or substantially non-integrating in a host cell or is substantially non-immunogenic in a host.

In some embodiments, the vector is in an amount sufficient to modulate one or more of phenotype, virus levels, gene expression, compete with other viruses, disease state, etc. at least about 5%, 10%, 15%, 20%, 25%, 30%, 35%, 40%, 45%, 50%, or more.

IV. Compositions

An anellovector or or anelloVLP described herein may also be included in pharmaceutical compositions with a pharmaceutical excipient, e.g., as described herein. In some embodiments, the pharmaceutical composition comprises at least $10^5$, $10^6$, $10^7$, $10^8$, $10^9$, $10^{10}$, $10^{11}$, $10^{12}$, $10^{13}$, $10^{14}$, or $10^{15}$ anellovectors or anelloVLPs. In some embodiments, the pharmaceutical composition comprises about $10^5$-$10^{15}$, $10^5$-$10^{10}$, or $10^{10}$-$10^{15}$ anellovectors or anelloVLPs. In some embodiments, the pharmaceutical composition comprises about $10^8$ (e.g., about $10^5$, $10^6$, $10^7$, $10^8$, $10^9$, or $10^{10}$) genomic equivalents/mL of the anellovector or anelloVLP. In some embodiments, the pharmaceutical composition comprises $10^5$-$10^{10}$, $10^6$-$10^{10}$, $10^7$-$10^{10}$, $10^8$-$10^{10}$, $10^9$-$10^{10}$, $10^5$-$10^6$, $10^5$-$10^7$, $10^5$-$10^8$, $10^5$-$10^9$, $10^5$-$10^{11}$, $10^5$-$10^{12}$, $10^5$-$10^{13}$, $10^5$-$10^{14}$, $10^5$-$10^5$, or $10^{10}$-$10^{15}$ genomic equivalents/mL of the anellovector or anelloVLP, e.g., as determined according to the method of Example 32. In some embodiments, the pharmaceutical composition comprises sufficient anellovectors or anelloVLPs to deliver at least 1, 2, 5, or 10, 100, 500, 1000, 2000, 5000, 8,000, $1\times10^4$, $\mathbf{1\times10^5}$, $\mathbf{1\times10^6}$, $1\times10^7$ or greater copies of a genetic element comprised in the anellovectors or anelloVLPs per cell to a population of the eukaryotic cells. In some embodiments, the pharmaceutical composition comprises sufficient anellovectors or anelloVLPs to deliver at least about $1\times10^4$, $\mathbf{1\times10^5}$, $\mathbf{1\times10^6}$, 1× or $10^7$, or about $1\times10^4$-$1\times10^5$, $\mathbf{1\times10^4}$-$1\times10^6$, $1\times10^4$-$1\times10^7$, $\mathbf{1\times10^5}$-$1\times10^6$, $1\times10^5$-$1\times10^7$, or $1\times10^6$-$1\times10^7$ copies of a genetic element comprised in the anellovectors or anelloVLPs per cell to a population of the eukaryotic cells.

In some embodiments, the pharmaceutical composition has one or more of the following characteristics: the pharmaceutical composition meets a pharmaceutical or good manufacturing practices (GMP) standard; the pharmaceutical composition was made according to good manufacturing practices (GMP); the pharmaceutical composition has a pathogen level below a predetermined reference value, e.g., is substantially free of pathogens; the pharmaceutical composition has a contaminant level below a predetermined reference value, e.g., is substantially free of contaminants; or the pharmaceutical composition has low immunogenicity or is substantially non-immunogenic, e.g., as described herein.

In some embodiments, the pharmaceutical composition comprises below a threshold amount of one or more contaminants. Exemplary contaminants that are desirably excluded or minimized in the pharmaceutical composition include, without limitation, host cell nucleic acids (e.g., host cell DNA and/or host cell RNA), animal-derived components (e.g., serum albumin or trypsin), replication-competent viruses, non-infectious particles, free viral capsid protein, adventitious agents, and aggregates. In embodiments, the contaminant is host cell DNA. In embodiments, the composition comprises less than about 10 ng of host cell DNA per dose. In embodiments, the level of host cell DNA in the composition is reduced by filtration and/or enzymatic degradation of host cell DNA. In embodiments, the pharmaceutical composition consists of less than 10% (e.g., less than about 10%, 5%, 4%, 3%, 2%, 1%, 0.5%, or 0.1%) contaminant by weight.

In one aspect, the invention described herein includes a pharmaceutical composition comprising:

a) an anellovector comprising a genetic element comprising (i) a sequence encoding a non-pathogenic exterior protein, (ii) an exterior protein binding sequence that binds the genetic element to the non-pathogenic exterior protein, and (iii) a sequence encoding a regulatory nucleic acid; and a proteinaceous exterior that is associated with, e.g., envelops or encloses, the genetic element; and b) a pharmaceutical excipient.

In one aspect, the invention described herein includes a pharmaceutical composition comprising:

a) an anelloVLP as described herein; and b) a pharmaceutical excipient.

Vesicles

In some embodiments, the composition further comprises a carrier component, e.g., a microparticle, liposome, vesicle, or exosome. In some embodiments, liposomes comprise spherical vesicle structures composed of a uni- or multilamellar lipid bilayer surrounding internal aqueous compartments and a relatively impermeable outer lipophilic phospholipid bilayer. Liposomes may be anionic, neutral or cationic. Liposomes are generally biocompatible, nontoxic, can deliver both hydrophilic and lipophilic drug molecules, protect their cargo from degradation by plasma enzymes, and transport their load across biological membranes (see, e.g., Spuch and Navarro, Journal of Drug Delivery, vol. 2011, Article ID 469679, 12 pages, 2011. doi:10.1155/2011/469679 for review).

Vesicles can be made from several different types of lipids; however, phospholipids are most commonly used to generate liposomes as drug carriers. Vesicles may comprise without limitation DOTMA, DOTAP, DOTIM, DDAB, alone or together with cholesterol to yield DOTMA and cholesterol, DOTAP and cholesterol, DOTIM and cholesterol, and DDAB and cholesterol. Methods for preparation of multilamellar vesicle lipids are known in the art (see for example U.S. Pat. No. 6,693,086, the teachings of which relating to multilamellar vesicle lipid preparation are incorporated herein by reference). Although vesicle formation can be spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi: 10.1155/2011/469679 for review). Extruded lipids can be prepared by extruding through filters of decreasing size, as described in Templeton et al., Nature Biotech, 15:647-652, 1997, the teachings of which relating to extruded lipid preparation are incorporated herein by reference.

As described herein, additives may be added to vesicles to modify their structure and/or properties. For example, either cholesterol or sphingomyelin may be added to the mixture to help stabilize the structure and to prevent the leakage of the inner cargo. Further, vesicles can be prepared from hydrogenated egg phosphatidylcholine or egg phosphatidylcholine, cholesterol, and dicetyl phosphate. (see, e.g., Spuch and Navarro, Journal of Drug Delivery, vol. 2011, Article ID 469679, 12 pages, 2011. doi:10.1155/2011/469679 for review). Also, vesicles may be surface modified during or after synthesis to include reactive groups complementary to the reactive groups on the recipient cells. Such reactive groups include without limitation maleimide groups. As an example, vesicles may be synthesized to include maleimide conjugated phospholipids such as without limitation DSPE-MaL-PEG2000.

A vesicle formulation may be mainly comprised of natural phospholipids and lipids such as 1,2-distearoryl-sn-glycero-3-phosphatidyl choline (DSPC), sphingomyelin, egg phosphatidylcholines and monosialoganglioside. Formulations made up of phospholipids only are less stable in plasma. However, manipulation of the lipid membrane with cholesterol reduces rapid release of the encapsulated cargo or 1,2-dioleoyl-sn-glycero-3-phosphoethanolamine (DOPE) increases stability (see, e.g., Spuch and Navarro, Journal of Drug Delivery, vol. 2011, Article ID 469679, 12 pages, 2011. doi:10.1155/2011/469679 for review).

In embodiments, lipids may be used to form lipid microparticles. Lipids include, but are not limited to, DLin-KC2-DMA4, C12-200 and colipids disteroylphosphatidyl choline, cholesterol, and PEG-DMG may be formulated (see, e.g., Novobrantseva, Molecular Therapy-Nucleic Acids (2012) 1, e4; doi:10.1038/mtna.2011.3) using a spontaneous vesicle formation procedure. The component molar ratio may be about 50/10/38.5/1.5 (DLin-KC2-DMA or C12-200/disteroylphosphatidyl choline/cholesterol/PEG-DMG). Tekmira has a portfolio of approximately 95 patent families, in the U.S. and abroad, that are directed to various aspects of lipid microparticles and lipid microparticles formulations (see, e.g., U.S. Pat. Nos. 7,982,027; 7,799,565; 8,058,069; 8,283,333; 7,901,708; 7,745,651; 7,803,397; 8,101,741; 8,188,263; 7,915,399; 8,236,943 and 7,838,658 and European Pat. Nos. 1766035; 1519714; 1781593 and 1664316), all of which may be used and/or adapted to the present invention.

In some embodiments, microparticles comprise one or more solidified polymer(s) that is arranged in a random manner. The microparticles may be biodegradable. Biodegradable microparticles may be synthesized, e.g., using methods known in the art including without limitation solvent evaporation, hot melt microencapsulation, solvent removal, and spray drying. Exemplary methods for synthesizing microparticles are described by Bershteyn et al., Soft Matter 4:1787-1787, 2008 and in US 2008/0014144 A1, the specific teachings of which relating to microparticle synthesis are incorporated herein by reference.

Exemplary synthetic polymers which can be used to form biodegradable microparticles include without limitation aliphatic polyesters, poly (lactic acid) (PLA), poly (glycolic acid) (PGA), co-polymers of lactic acid and glycolic acid (PLGA), polycarprolactone (PCL), polyanhydrides, poly (ortho)esters, polyurethanes, poly(butyric acid), poly(valeric acid), and poly(lactide-co-caprolactone), and natural polymers such as albumin, alginate and other polysaccharides including dextran and cellulose, collagen, chemical derivatives thereof, including substitutions, additions of chemical groups such as for example alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water, by surface or bulk erosion.

The microparticles' diameter ranges from 0.1-1000 micrometers (μm). In some embodiments, their diameter ranges in size from 1-750 μm, or from 50-500 μm, or from 100-250 μm. In some embodiments, their diameter ranges in size from 50-1000 μm, from 50-750 μm, from 50-500 μm, or from 50-250 μm. In some embodiments, their diameter ranges in size from 0.05-1000 μm, from 10-1000 μm, from 100-1000 μm, or from 500-1000 μm. In some embodiments, their diameter is about 0.5 μm, about 10 μm, about 50 μm, about 100 μm, about 200 μm, about 300 μm, about 350 μm, about 400 μm, about 450 μm, about 500 μm, about 550 μm, about 600 μm, about 650 μm, about 700 μm, about 750 μm, about 800 μm, about 850 μm, about 900 μm, about 950 μm, or about 1000 μm. As used in the context of microparticle diameters, the term "about" means+/−5% of the absolute value stated.

In some embodiments, a ligand is conjugated to the surface of the microparticle via a functional chemical group (carboxylic acids, aldehydes, amines, sulfhydryls and hydroxyls) present on the surface of the particle and present on the ligand to be attached. Functionality may be introduced into the microparticles by, for example, during the emulsion preparation of microparticles, incorporation of stabilizers with functional chemical groups.

Another example of introducing functional groups to the microparticle is during post-particle preparation, by direct crosslinking particles and ligands with homo- or heterobifunctional crosslinkers. This procedure may use a suitable chemistry and a class of crosslinkers (CDI, EDAC, glutaraldehydes, etc. as discussed in more detail below) or any other crosslinker that couples ligands to the particle surface via chemical modification of the particle surface after preparation. This also includes a process whereby amphiphilic molecules such as fatty acids, lipids or functional stabilizers may be passively adsorbed and adhered to the particle surface, thereby introducing functional end groups for tethering to ligands.

In some embodiments, the microparticles may be synthesized to comprise one or more targeting groups on their exterior surface to target a specific cell or tissue type (e.g., cardiomyocytes). These targeting groups include without limitation receptors, ligands, antibodies, and the like. These targeting groups bind their partner on the cells' surface. In some embodiments, the microparticles will integrate into a lipid bilayer that comprises the cell surface and the mitochondria are delivered to the cell.

The microparticles may also comprise a lipid bilayer on their outermost surface. This bilayer may be comprised of one or more lipids of the same or different type. Examples include without limitation phospholipids such as phosphocholines and phosphoinositols. Specific examples include without limitation DMPC, DOPC, DSPC, and various other lipids such as those described herein for liposomes.

In some embodiments, the carrier comprises nanoparticles, e.g., as described herein.

In some embodiments, the vesicles or microparticles described herein are functionalized with a diagnostic agent. Examples of diagnostic agents include, but are not limited to, commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium.

Carriers

A composition (e.g., pharmaceutical composition) described herein may comprise, be formulated with, and/or be delivered in, a carrier. In one aspect, the invention includes a composition, e.g., a pharmaceutical composition, comprising a carrier (e.g., a vesicle, a liposome, a lipid nanoparticle, an exosome, a red blood cell, an exosome (e.g., a mammalian or plant exosome), a fusosome) comprising (e.g., encapsulating) a composition described herein (e.g., an anellovector, anelloVLP, Anellovirus, or genetic element described herein).

In some embodiments, the compositions and systems described herein can be formulated in liposomes or other similar vesicles. Generally, liposomes are spherical vesicle structures composed of a uni- or multilamellar lipid bilayer surrounding internal aqueous compartments and a relatively impermeable outer lipophilic phospholipid bilayer. Liposomes may be anionic, neutral or cationic. Liposomes generally have one or more (e.g., all) of the following characteristics: biocompatibility, nontoxicity, can deliver both hydrophilic and lipophilic drug molecules, can protect their cargo from degradation by plasma enzymes, and can transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679; and Zylberberg & Matosevic. 2016. Drug Delivery, 23:9, 3319-3329, doi: 10.1080/10717544.2016.1177136).

Vesicles can be made from several different types of lipids; however, phospholipids are most commonly used to generate liposomes as drug carriers. Methods for preparation of multilamellar vesicle lipids are known (see, for example, U.S. Pat. No. 6,693,086, the teachings of which relating to multilamellar vesicle lipid preparation are incorporated herein by reference). Although vesicle formation can be spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review). Extruded lipids can be prepared by, e.g., extruding through filters of decreasing size, as described in Templeton et al., Nature Biotech, 15:647-652, 1997.

Lipid nanoparticles (LNPs) are another example of a carrier that provides a biocompatible and biodegradable delivery system for the pharmaceutical compositions described herein. See, e.g., Gordillo-Galeano et al. European Journal of Pharmaceutics and Biopharmaceutics. Volume 133, December 2018, Pages 285-308. Nanostructured lipid carriers (NLCs) are modified solid lipid nanoparticles (SLNs) that retain the characteristics of the SLN, improve drug stability and loading capacity, and prevent drug leakage. Polymer nanoparticles (PNPs) are an important component of drug delivery. These nanoparticles can effectively direct drug delivery to specific targets and improve drug stability and controlled drug release. Lipid-polymer nanoparticles (PLNs), a new type of carrier that combines liposomes and polymers, may also be employed. These nanoparticles possess the complementary advantages of PNPs and liposomes. A PLN is composed of a core-shell structure; the polymer core provides a stable structure, and the phospholipid shell offers good biocompatibility. As such, the two components increase the drug encapsulation efficiency rate, facilitate surface modification, and prevent leakage of water-soluble drugs. For a review, see, e.g., Li et al. 2017, Nanomaterials 7, 122; doi:10.3390/nano7060122.

Exosomes can also be used as drug delivery vehicles for the compositions and systems described herein. For a review, see Ha et al. July 2016. Acta Pharmaceutica Sinica B. Volume 6, Issue 4, Pages 287-296; doi.org/10.1016/j.apsb.2016.02.001.

Ex vivo differentiated red blood cells can also be used as a carrier for a composition described herein. See, e.g., WO2015073587; WO2017123646; WO2017123644; WO2018102740; WO2016183482; WO2015153102; WO2018151829; WO2018009838; Shi et al. 2014. Proc Natl Acad Sci USA. 111(28): 10131-10136; U.S. Pat. No. 9,644,180; Huang et al. 2017. Nature Communications 8: 423; Shi et al. 2014. Proc Natl Acad Sci USA. 111(28): 10131-10136.

Fusosome compositions, e.g., as described in WO2018208728, can also be used as carriers to deliver a composition described herein.

Membrane Penetrating Polypeptides

In some embodiments, the composition further comprises a membrane penetrating polypeptide (MPP) to carry the components into cells or across a membrane, e.g., cell or nuclear membrane. Membrane penetrating polypeptides that are capable of facilitating transport of substances across a membrane include, but are not limited to, cell-penetrating peptides (CPPs)(see, e.g., U.S. Pat. No. 8,603,966), fusion peptides for plant intracellular delivery (see, e.g., Ng et al., PLoS One, 2016, 11:e0154081), protein transduction domains, Trojan peptides, and membrane translocation signals (MTS) (see, e.g., Tung et al., Advanced Drug Delivery Reviews 55:281-294 (2003)). Some MPP are rich in amino acids, such as arginine, with positively charged side chains.

Membrane penetrating polypeptides have the ability of inducing membrane penetration of a component and allow macromolecular translocation within cells of multiple tissues in vivo upon systemic administration. A membrane penetrating polypeptide may also refer to a peptide which, when brought into contact with a cell under appropriate conditions, passes from the external environment in the intracellular environment, including the cytoplasm, organelles such as mitochondria, or the nucleus of the cell, in amounts significantly greater than would be reached with passive diffusion.

Components transported across a membrane may be reversibly or irreversibly linked to the membrane penetrating polypeptide. A linker may be a chemical bond, e.g., one or more covalent bonds or non-covalent bonds. In some embodiments, the linker is a peptide linker. Such a linker may be between 2-30 amino acids, or longer. The linker includes flexible, rigid or cleavable linkers.

Combinations

In one aspect, the anellovector, anelloVLP, or composition described herein may also include one or more heterologous moieties. In one aspect, the anellovector or composition comprising an anellovector or anelloVLP described herein may also include one or more heterologous moiety in a fusion. In some embodiments, a heterologous moiety may be linked with the genetic element. In some embodiments, a heterologous moiety may be enclosed in the proteinaceous exterior as part of the anellovector or anelloVLP. In some embodiments, a heterologous moiety may be administered with the anellovector or anelloVLP.

In one aspect, the invention includes a cell or tissue comprising any one of the anellovectors or anelloVLP and heterologous moieties described herein.

In another aspect, the invention includes a pharmaceutical composition comprising an anellovector or anelloVLP and the heterologous moiety described herein.

In some embodiments, the heterologous moiety may be a virus (e.g., an effector (e.g., a drug, small molecule), a targeting agent (e.g., a DNA targeting agent, antibody, receptor ligand), a tag (e.g., fluorophore, light sensitive agent such as KillerRed), or an editing or targeting moiety described herein. In some embodiments, a membrane translocating polypeptide described herein is linked to one or more heterologous moieties. In one embodiment, the heterologous moiety is a small molecule (e.g., a peptidomimetic or a small organic molecule with a molecular weight of less than 2000 daltons), a peptide or polypeptide (e.g., an antibody or antigen-binding fragment thereof), a nanoparticle, an aptamer, or pharmacoagent.

Viruses

In some embodiments, the composition may further comprise a virus as a heterologous moiety, e.g., a single stranded DNA virus, e.g., Anellovirus, Bidnavirus, Circovirus, Geminivirus, Genomovirus, Inovirus, Microvirus, Nanovirus, Parvovirus, and Spiravirus. In some embodiments, the composition may further comprise a double stranded DNA virus, e.g., Adenovirus, Ampullavirus, Ascovirus, Asfarvirus, Baculovirus, Fusellovirus, Globulovirus, Guttavirus, Hytrosavirus, Herpesvirus, Iridovirus, Lipothrixvirus, Nimavirus, and Poxvirus. In some embodiments, the composition may further comprise an RNA virus, e.g., Alphavirus, Furovirus, Hepatitis virus, Hordeivirus, Tobamovirus, Tobravirus, Tricornavirus, Rubivirus, Birnavirus, Cystovirus, Partitivirus, and Reovirus. In some embodiments, the anellovector or anelloVLP is administered with a virus as a heterologous moiety.

In some embodiments, the heterologous moiety may comprise a non-pathogenic, e.g., symbiotic, commensal, native, virus. In some embodiments, the non-pathogenic virus is one or more anelloviruses, e.g., Alphatorquevirus (TT), Betatorquevirus (TTM), and Gammatorquevirus (TTMD). In some embodiments, the anellovirus may include a Torque Teno Virus (TT), a SEN virus, a Sentinel virus, a TTV-like mini virus, a TT virus, a TT virus genotype 6, a TT virus group, a TTV-like virus DXL1, a TTV-like virus DXL2, a Torque Teno-like Mini Virus (TTM), or a Torque Teno-like Midi Virus (TTMD). In some embodiments, the non-pathogenic virus comprises one or more sequences having at least at least about 60%, 70% 80%, 85%, 90% 95%, 96%, 97%, 98% and 99% nucleotide sequence identity to any one of the nucleotide sequences described herein, e.g., as listed in any one of Tables N1-N25.

In some embodiments, the heterologous moiety may comprise one or more viruses that are identified as lacking in the subject. For example, a subject identified as having dyvirosis may be administered a composition comprising an anellovector and one or more viral components or viruses that are imbalanced in the subject or having a ratio that differs from a reference value, e.g., a healthy subject.

In some embodiments, the heterologous moiety may comprise one or more non-anelloviruses, e.g., adenovirus, herpes virus, pox virus, vaccinia virus, SV40, papilloma virus, an RNA virus such as a retrovirus, e.g., lenti virus, a single-stranded RNA virus, e.g., hepatitis virus, or a double-stranded RNA virus e.g., rotavirus. In some embodiments, the anellovector or the virus is defective, or requires assistance in order to produce infectious particles. Such assistance can be provided, e.g., by using helper cell lines that contain a nucleic acid, e.g., plasmids or DNA integrated into the genome, encoding one or more of (e.g., all of) the structural genes of the replication defective anellovector or virus under the control of regulatory sequences within the LTR. Suitable cell lines for replicating the anellovectors described herein include cell lines known in the art, e.g., A549 cells, which can be modified as described herein.

Targeting Moiety

In some embodiments, the composition, anellovector, or anelloVLP described herein may further comprise a targeting moiety, e.g., a targeting moiety that specifically binds to a molecule of interest present on a target cell. The targeting moiety may modulate a specific function of the molecule of interest or cell, modulate a specific molecule (e.g., enzyme, protein or nucleic acid), e.g., a specific molecule downstream of the molecule of interest in a pathway, or specifically bind to a target to localize the anellovector, or anelloVLP, or genetic element. For example, a targeting moiety may include a therapeutic that interacts with a specific molecule of interest to increase, decrease or otherwise modulate its function.

Tagging or Monitoring Moiety In some embodiments, the composition, anellovector, or anelloVLP described herein may further comprise a tag to label or monitor the anellovector, anelloVLP, or genetic element described herein. The tagging or monitoring moiety may be removable by chemical agents or enzymatic cleavage, such as proteolysis or intein splicing. An affinity tag may be useful to purify the tagged polypeptide using an affinity technique. Some examples include, chitin binding protein (CBP), maltose binding protein (MBP), glutathione-S-transferase (GST), and poly(His) tag. A solubilization tag may be useful to aid recombinant proteins expressed in chaperone-deficient species such as *E. coli* to assist in the proper folding in proteins and keep them from precipitating. Some examples include thioredoxin (TRX) and poly(NANP). The tagging or monitoring moiety may include a light sensitive tag, e.g., fluorescence. Fluorescent tags are useful for visualization. GFP and its variants are some examples commonly used as fluorescent tags. Protein tags may allow specific enzymatic modifications (such as biotinylation by biotin ligase) or chemical modifications (such as reaction with FlAsH-EDT2 for fluorescence imaging) to occur. Often tagging or monitoring moiety are combined, in order to connect proteins to multiple other components. The tagging or monitoring moiety may also be removed by specific proteolysis or enzymatic cleavage (e.g. by TEV protease, Thrombin, Factor Xa or Enteropeptidase).

Nanoparticles

In some embodiments, the composition, anellovector, or anelloVLP described herein may further comprise a nanoparticle. Nanoparticles include inorganic materials with a size between about 1 and about 1000 nanometers, between about 1 and about 500 nanometers in size, between about 1 and about 100 nm, between about 50 nm and about 300 nm, between about 75 nm and about 200 nm, between about 100 nm and about 200 nm, and any range therebetween. Nanoparticles generally have a composite structure of nanoscale dimensions. In some embodiments, nanoparticles are typically spherical although different morphologies are possible depending on the nanoparticle composition. The portion of the nanoparticle contacting an environment external to the nanoparticle is generally identified as the surface of the nanoparticle. In nanoparticles described herein, the size limitation can be restricted to two dimensions and so that nanoparticles include composite structure having a diameter from about 1 to about 1000 nm, where the specific diameter depends on the nanoparticle composition and on the intended use of the nanoparticle according to the experimental design. For example, nanoparticles used in therapeutic applications typically have a size of about 200 nm or below.

Additional desirable properties of the nanoparticle, such as surface charges and steric stabilization, can also vary in view of the specific application of interest. Exemplary properties that can be desirable in clinical applications such as cancer treatment are described in Davis et al, Nature 2008 vol. 7, pages 771-782; Duncan, Nature 2006 vol. 6, pages 688-701; and Allen, Nature 2002 vol. 2 pages 750-763, each incorporated herein by reference in its entirety. Additional properties are identifiable by a skilled person upon reading of the present disclosure. Nanoparticle dimensions and properties can be detected by techniques known in the art. Exemplary techniques to detect particles dimensions include but are not limited to dynamic light scattering (DLS) and a variety of microscopies such at transmission electron microscopy (TEM) and atomic force microscopy (AFM). Exemplary techniques to detect particle morphology include but are not limited to TEM and AFM. Exemplary techniques to detect surface charges of the nanoparticle include but are not limited to zeta potential method. Additional techniques suitable to detect other chemical properties comprise by $^{1}H$, $^{11}B$, and $^{13}C$ and $^{19}F$ NMR, UV/Vis and infrared/Raman spectroscopies and fluorescence spectroscopy (when nanoparticle is used in combination with fluorescent labels) and additional techniques identifiable by a skilled person.

Small Molecules

In some embodiments, the composition, anellovector, or anelloVLP described herein may further comprise a small molecule. Small molecule moieties include, but are not limited to, small peptides, peptidomimetics (e.g., peptoids), amino acids, amino acid analogs, synthetic polynucleotides, polynucleotide analogs, nucleotides, nucleotide analogs, organic and inorganic compounds (including heterorganic and organomettallic compounds) generally having a molecular weight less than about 5,000 grams per mole, e.g., organic or inorganic compounds having a molecular weight less than about 2,000 grams per mole, e.g., organic or inorganic compounds having a molecular weight less than about 1,000 grams per mole, e.g., organic or inorganic compounds having a molecular weight less than about 500 grams per mole, and salts, esters, and other pharmaceutically acceptable forms of such compounds. Small molecules may include, but are not limited to, a neurotransmitter, a hormone, a drug, a toxin, a viral or microbial particle, a synthetic molecule, and agonists or antagonists.

Examples of suitable small molecules include those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference. Some examples of small molecules include, but are not limited to, prion drugs such as tacrolimus, ubiquitin ligase or HECT ligase inhibitors such as heclin, histone modifying drugs such as sodium butyrate, enzymatic inhibitors such as 5-azacytidine, anthracyclines such as doxorubicin, beta-lactams such as penicillin, anti-bacterials, chemotherapy agents, anti-virals, modulators from other organisms such as VP64, and drugs with insufficient bioavailability such as chemotherapeutics with deficient pharmacokinetics.

In some embodiments, the small molecule is an epigenetic modifying agent, for example such as those described in de Groote et al. Nuc. Acids Res. (2012):1-18. Exemplary small molecule epigenetic modifying agents are described, e.g., in Lu et al. J. Biomolecular Screening 17.5(2012):555-71, e.g., at Table 1 or 2, incorporated herein by reference. In some embodiments, an epigenetic modifying agent comprises vorinostat or romidepsin. In some embodiments, an epigenetic modifying agent comprises an inhibitor of class I, II, III, and/or IV histone deacetylase (HDAC). In some embodiments, an epigenetic modifying agent comprises an activator of SirTI. In some embodiments, an epigenetic modifying agent comprises Garcinol, Lys-CoA, C646, (+)-JQI, I-BET, BICI, MS120, DZNep, UNC0321, EPZ004777, AZ505, AMI-I, pyrazole amide 7b, benzo[d]imidazole 17b, acylated dapsone derivative (e.e.g, PRMTI), methylstat, 4,4'-dicarboxy-2,2'-bipyridine, SID 85736331, hydroxamate analog 8, tanylcypromie, bisguanidine and biguanide polyamine analogs, UNC669, Vidaza, decitabine, sodium phenyl butyrate (SDB), lipoic acid (LA), quercetin, valproic acid, hydralazine, bactrim, green tea extract (e.g., epigallocatechin gallate (EGCG)), curcumin, sulforphane and/or allicin/diallyl disulfide. In some embodiments, an epigenetic modifying agent inhibits DNA methylation, e.g., is an inhibitor of DNA methyltransferase (e.g., is 5-azacitidine and/or decitabine). In some embodiments, an epigenetic modifying agent modifies histone modification, e.g., histone acetylation, histone methylation, histone sumoylation, and/or histone phosphorylation. In some embodiments, the epigenetic modifying agent is an inhibitor of a histone deacetylase (e.g., is vorinostat and/or trichostatin A).

In some embodiments, the small molecule is a pharmaceutically active agent. In one embodiment, the small molecule is an inhibitor of a metabolic activity or component. Useful classes of pharmaceutically active agents include, but are not limited to, antibiotics, anti-inflammatory drugs, angiogenic or vasoactive agents, growth factors and chemotherapeutic (anti-neoplastic) agents (e.g., tumour suppressers). One or a combination of molecules from the categories and examples described herein or from (Orme-Johnson 2007, Methods Cell Biol. 2007; 80:813-26) can be used. In one embodiment, the invention includes a composition comprising an antibiotic, anti-inflammatory drug, angiogenic or vasoactive agent, growth factor or chemotherapeutic agent.

Peptides or Proteins

In some embodiments, the composition, anellovector, or anelloVLP described herein may further comprise a peptide or protein. The peptide moieties may include, but are not limited to, a peptide ligand or antibody fragment (e.g., antibody fragment that binds a receptor such as an extracellular receptor), neuropeptide, hormone peptide, peptide drug, toxic peptide, viral or microbial peptide, synthetic peptide, and agonist or antagonist peptide.

Peptides moieties may be linear or branched. The peptide has a length from about 5 to about 200 amino acids, about 15 to about 150 amino acids, about 20 to about 125 amino acids, about 25 to about 100 amino acids, or any range therebetween.

Some examples of peptides include, but are not limited to, fluorescent tags or markers, antigens, antibodies, antibody fragments such as single domain antibodies, ligands and receptors such as glucagon-like peptide-1 (GLP-1), GLP-2 receptor 2, cholecystokinin B (CCKB) and somatostatin receptor, peptide therapeutics such as those that bind to specific cell surface receptors such as G protein-coupled receptors (GPCRs) or ion channels, synthetic or analog peptides from naturally-bioactive peptides, anti-microbial peptides, pore-forming peptides, tumor targeting or cytotoxic peptides, and degradation or self-destruction peptides such as an apoptosis-inducing peptide signal or photosensitizer peptide.

Peptides useful in the invention described herein also include small antigen-binding peptides, e.g., antigen binding antibody or antibody-like fragments, such as single chain antibodies, nanobodies (see, e.g., Steeland et al. 2016. Nanobodies as therapeutics: big opportunities for small antibodies. Drug Discov Today: 21(7):1076-113). Such small antigen binding peptides may bind a cytosolic antigen, a nuclear antigen, an intra-organellar antigen.

In some embodiments, the composition, anellovector, or anelloVLP described herein includes a polypeptide linked to a ligand that is capable of targeting a specific location, tissue, or cell.

Oligonucleotide Aptamers

In some embodiments, the composition, anellovector, or anelloVLP described herein may further comprise an oligonucleotide aptamer. Aptamer moieties are oligonucleotide or peptide aptamers. Oligonucleotide aptamers are single-stranded DNA or RNA (ssDNA or ssRNA) molecules that can bind to pre-selected targets including proteins and peptides with high affinity and specificity.

Oligonucleotide aptamers are nucleic acid species that may be engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers provide discriminate molecular recognition, and can be produced by chemical synthesis. In addition, aptamers may possess desirable storage properties, and elicit little or no immunogenicity in therapeutic applications.

Both DNA and RNA aptamers can show robust binding affinities for various targets. For example, DNA and RNA aptamers have been selected fort lysozyme, thrombin, human immunodeficiency virus trans-acting responsive element (HIV TAR)(see en.wikipedia.org/wiki/Aptamer-cite note-10), hemin, interferon γ, prostate specific antigen (PSA), dopamine, and the non-classical oncogene, heat shock factor 1 (HSF1).

Peptide Aptamers

In some embodiments, the composition, anellovector, or anelloVLP described herein may further comprise a peptide aptamer. Peptide aptamers have one (or more) short variable peptide domains, including peptides having low molecular weight, 12-14 kDa. Peptide aptamers may be designed to specifically bind to and interfere with protein-protein interactions inside cells.

Peptide aptamers are artificial proteins selected or engineered to bind specific target molecules. These proteins include of one or more peptide loops of variable sequence. They are typically isolated from combinatorial libraries and often subsequently improved by directed mutation or rounds of variable region mutagenesis and selection. In vivo, peptide aptamers can bind cellular protein targets and exert biological effects, including interference with the normal protein interactions of their targeted molecules with other proteins. In particular, a variable peptide aptamer loop attached to a transcription factor binding domain is screened against the target protein attached to a transcription factor activating domain. In vivo binding of the peptide aptamer to its target via this selection strategy is detected as expression of a downstream yeast marker gene. Such experiments identify particular proteins bound by the aptamers, and protein interactions that the aptamers disrupt, to cause the phenotype. In addition, peptide aptamers derivatized with appropriate functional moieties can cause specific post-translational modification of their target proteins, or change the subcellular localization of the targets Peptide aptamers can also recognize targets in vitro. They have found use in lieu of antibodies in biosensors and used to detect active isoforms of proteins from populations containing both inactive and active protein forms. Derivatives known as tadpoles, in which peptide aptamer "heads" are covalently linked to unique sequence double-stranded DNA "tails", allow quantification of scarce target molecules in mixtures by PCR (using, for example, the quantitative real-time polymerase chain reaction) of their DNA tails.

Peptide aptamer selection can be made using different systems, but the most used is currently the yeast two-hybrid system. Peptide aptamers can also be selected from combinatorial peptide libraries constructed by phage display and other surface display technologies such as mRNA display, ribosome display, bacterial display and yeast display. These experimental procedures are also known as biopannings. Among peptides obtained from biopannings, mimotopes can be considered as a kind of peptide aptamers. All the peptides panned from combinatorial peptide libraries have been stored in a special database with the name MimoDB.

V. Host Cells

The invention is further directed to a host or host cell comprising an anellovector or anelloVLP as described herein. In some embodiments, the host or host cell is a plant, insect, bacteria, fungus, vertebrate, mammal (e.g., human), or other organism or cell. In certain embodiments, as confirmed herein, provided anellovectors infect a range of different host cells. Target host cells include cells of mesodermal, endodermal, or ectodermal origin. Target host cells include, e.g., epithelial cells, muscle cells, white blood cells (e.g., lymphocytes), kidney tissue cells, lung tissue cells.

In some embodiments, the anellovector or anelloVLP is substantially non-immunogenic in the host. In certain embodiments, the anellovector or genetic element thereof, or the anelloVLP, fails to produce an undesired substantial response by the host's immune system. Some immune responses include, but are not limited to, humoral immune responses (e.g., production of antigen-specific antibodies) and cell-mediated immune responses (e.g., lymphocyte proliferation).

In some embodiments, a host or a host cell is contacted with (e.g., infected with) an anellovector or anelloVLP. In some embodiments, the host is a mammal, such as a human. The amount of the anellovector or anelloVLP in the host can be measured at any time after administration. In certain embodiments, a time course of anellovector growth in a culture is determined.

In some embodiments, the anellovector, e.g., an anellovector as described herein, is heritable. In some embodiments, the anellovector is transmitted linearly in fluids and/or cells from mother to child. In some embodiments, daughter cells from an original host cell comprise the anellovector. In some embodiments, a mother transmits the anellovector to child with an efficiency of at least 25%, 50%, 60%, 70%, 80%, 85%, 90%, 95%, or 99%, or a transmission efficiency from host cell to daughter cell at least 25%, 50%, 60%, 70%, 80%, 85%, 90%, 95%, or 99%. In some embodiments, the anellovector in a host cell has a transmission efficiency during meiosis of at 25%, 50%, 60%, 70%, 80%, 85%, 90%, 95%, or 99%. In some embodiments, the anellovector in a host cell has a transmission efficiency during mitosis of at least 25%, 50%, 60%, 70%, 80%, 85%, 90%, 95%, or 99%. In some embodiments, the anellovector in a cell has a transmission efficiency between about 10%-20%, 20%-30%, 30%-40%, 40%-50%, 50%-60%, 60%-70%, 70%-75%, 75%-80%, 80%-85%, 85%-90%, 90%-95%, 95%-99%, or any percentage therebetween.

In some embodiments, the anellovector, e.g., anellovector replicates within the host cell. In one embodiment, the anellovector is capable of replicating in a mammalian cell, e.g., human cell. In other embodiments, the anellovector is replication deficient or replication incompetent.

While in some embodiments the anellovector replicates in the host cell, the anellovector does not integrate into the genome of the host, e.g., with the host's chromosomes. In some embodiments, the anellovector has a negligible recombination frequency, e.g., with the host's chromosomes. In some embodiments, the anellovector has a recombination frequency, e.g., less than about 1.0 cM/Mb, 0.9 cM/Mb, 0.8 cM/Mb, 0.7 cM/Mb, 0.6 cM/Mb, 0.5 cM/Mb, 0.4 cM/Mb, 0.3 cM/Mb, 0.2 cM/Mb, 0.1 cM/Mb, or less, e.g., with the host's chromosomes.

VI. Methods of Use

The anellovectors and compositions comprising anellovectors or anelloVLPs described herein may be used in methods of treating a disease, disorder, or condition, e.g., in a subject (e.g., a mammalian subject, e.g., a human subject) in need thereof. Administration of a pharmaceutical composition described herein may be, for example, by way of parenteral (including intravenous, intratumoral, intraperitoneal, intramuscular, intracavity, and subcutaneous) administration. The anellovectors or anelloVLP may be administered alone or formulated as a pharmaceutical composition.

The anellovectors or anelloVLP may be administered in the form of a unit-dose composition, such as a unit dose parenteral composition. Such compositions are generally prepared by admixture and can be suitably adapted for parenteral administration. Such compositions may be, for example, in the form of injectable and infusable solutions or suspensions or suppositories or aerosols.

In some embodiments, administration of a anellovector or composition comprising same, e.g., as described herein, may result in delivery of a genetic element comprised by the anellovector to a target cell, e.g., in a subject.

An anellovector or anelloVLP, or composition thereof, described herein, e.g., comprising an effector (e.g., an endogenous or exogenous effector), may be used to deliver the effector to a cell, tissue, or subject. In some embodiments, the anellovector, or anelloVLP, or composition thereof is used to deliver the effector to bone marrow, blood, heart, GI or skin. Delivery of an effector by administration of an anellovector composition or anelloVLP composition described herein may modulate (e.g., increase or decrease) expression levels of a noncoding RNA or polypeptide in the cell, tissue, or subject. Modulation of expression level in this fashion may result in alteration of a functional activity in the cell to which the effector is delivered. In some embodiments, the modulated functional activity may be enzymatic, structural, or regulatory in nature.

In some embodiments, the anellovector or anelloVLP, or copies thereof, are detectable in a cell 24 hours (e.g., 1 day, 2 days, 3 days, 4 days, 5 days, 6 days, 1 week, 2 weeks, 3 weeks, 4 weeks, 30 days, or 1 month) after delivery into a cell. In embodiments, an anellovector, anelloVLP, or composition thereof mediates an effect on a target cell, and the effect lasts for at least 1, 2, 3, 4, 5, 6, or 7 days, 2, 3, or 4 weeks, or 1, 2, 3, 6, or 12 months. In some embodiments (e.g., wherein the anellovector or composition thereof comprises a genetic element encoding an exogenous protein), the effect lasts for less than 1, 2, 3, 4, 5, 6, or 7 days, 2, 3, or 4 weeks, or 1, 2, 3, 6, or 12 months.

Examples of diseases, disorders, and conditions that can be treated with an anellovector or anelloVLP described herein, or a composition comprising the anellovector or anelloVLP, include, without limitation: immune disorders, interferonopathies (e.g., Type I interferonopathies), infectious diseases, inflammatory disorders, autoimmune conditions, cancer (e.g., a solid tumor, e.g., lung cancer, non-small cell lung cancer, e.g., a tumor that expresses a gene responsive to mIR-625, e.g., caspase-3), and gastrointestinal disorders. In some embodiments, the anellovector or anelloVLP modulates (e.g., increases or decreases) an activity or function in a cell with which the anellovector is contacted. In some embodiments, the anellovector or anelloVLP modulates (e.g., increases or decreases) the level or activity of a molecule (e.g., a nucleic acid or a protein) in a cell with which the anellovector or anelloVLP is contacted. In some embodiments, the anellovector or anelloVLP decreases viability of a cell, e.g., a cancer cell, with which the anellovector or anelloVLP is contacted, e.g., by at least about 10%, 20%, 30%, 40%, 50%, 60%, 70%, 80%, 90%, 95%, 99%, or more. In some embodiments, the anellovector or anelloVLP comprises an effector, e.g., an miRNA, e.g., miR-625, that decreases viability of a cell, e.g., a cancer cell, with which the anellovector or anelloVLP is contacted, e.g., by at least about 10%, 20%, 30%, 40%, 50%, 60%, 70%, 80%, 90%, 95%, 99%, or more. In some embodiments, the anellovector or anelloVLP increases apoptosis of a cell, e.g., a cancer cell, e.g., by increasing caspase-3 activity, with which the anellovector is contacted, e.g., by at least about 10%, 20%, 30%, 40%, 50%, 60%, 70%, 80%, 90%, 95%, 99%, or more. In some embodiments, the anellovector or anelloVLP comprises an effector, e.g., an miRNA, e.g., miR-625, that increases apoptosis of a cell, e.g., a cancer cell, e.g., by increasing caspase-3 activity, with which the anellovector or anelloVLP is contacted, e.g., by at least about 10%, 20%, 30%, 40%, 50%, 60%, 70%, 80%, 90%, 95%, 99%, or more.

VII. Methods of Production

Producing the Genetic Element

Methods of making the genetic element of the anellovector are described in, for example, Khudyakov & Fields, *Artificial DNA: Methods and Applications*, CRC Press (2002); in Zhao, *Synthetic Biology: Tools and Applications*, (First Edition), Academic Press (2013); and Egli & Herdewijn, *Chemistry and Biology of Artificial Nucleic Acids*, (First Edition), Wiley-VCH (2012).

In some embodiments, the genetic element may be designed using computer-aided design tools. The anellovector may be divided into smaller overlapping pieces (e.g., in the range of about 100 bp to about 10 kb segments or individual ORFs) that are easier to synthesize. These DNA segments are synthesized from a set of overlapping single-stranded oligonucleotides. The resulting overlapping synthons are then assembled into larger pieces of DNA, e.g., the anellovector. The segments or ORFs may be assembled into the anellovector, e.g., in vitro recombination or unique restriction sites at 5' and 3' ends to enable ligation.

The genetic element can alternatively be synthesized with a design algorithm that parses the anellovector into oligo-length fragments, creating optimal design conditions for synthesis that take into account the complexity of the sequence space. Oligos are then chemically synthesized on semiconductor-based, high-density chips, where over 200,000 individual oligos are synthesized per chip. The oligos are assembled with an assembly techniques, such as BioFab®, to build longer DNA segments from the smaller oligos. This is done in a parallel fashion, so hundreds to thousands of synthetic DNA segments are built at one time.

Each genetic element or segment of the genetic element may be sequence verified. In some embodiments, high-throughput sequencing of RNA or DNA can take place using AnyDot.chips (Genovoxx, Germany), which allows for the monitoring of biological processes (e.g., miRNA expression or allele variability (SNP detection). In particular, the AnyDot-chips allow for 10×-50× enhancement of nucleotide fluorescence signal detection. AnyDot.chips and methods for using them are described in part in International Publication Application Nos. WO 02088382, WO 03020968, WO 0303 1947, WO 2005044836, PCTEP 05105657, PCMEP 05105655; and German Patent Application Nos. DE 101 49 786, DE 102 14 395, DE 103 56 837, DE 10 2004 009 704, DE 10 2004 025 696, DE 10 2004 025 746, DE 10 2004 025 694, DE 10 2004 025 695, DE 10 2004 025 744, DE 10 2004 025 745, and DE 10 2005 012301.

Other high-throughput sequencing systems include those disclosed in Venter, J., et al. Science 16 Feb. 2001; Adams, M. et al, Science 24 Mar. 2000; and M. J, Levene, et al. Science 299:682-686, January 2003; as well as US Publication Application No. 20030044781 and 2006/0078937. Overall such systems involve sequencing a target nucleic acid molecule having a plurality of bases by the temporal addition of bases via a polymerization reaction that is measured on a molecule of nucleic acid, i.e., the activity of a nucleic acid polymerizing enzyme on the template nucleic acid molecule to be sequenced is followed in real time. The sequence can then be deduced by identifying which base is being incorporated into the growing complementary strand of the target nucleic acid by the catalytic activity of the nucleic acid polymerizing enzyme at each step in the sequence of base additions. A polymerase on the target nucleic acid molecule complex is provided in a position suitable to move along the target nucleic acid molecule and extend the oligonucleotide primer at an active site. A plurality of labeled types of nucleotide analogs are provided proximate to the active site, with each distinguishably type of nucleotide analog being complementary to a different nucleotide in the target nucleic acid sequence. The growing nucleic acid strand is extended by using the polymerase to add a nucleotide analog to the nucleic acid strand at the active site, where the nucleotide analog being added is complementary to the nucleotide of the target nucleic acid at the active site. The nucleotide analog added to the oligonucleotide primer as a result of the polymerizing step is identified. The steps of providing labeled nucleotide analogs, polymerizing the growing nucleic acid strand, and identifying the added nucleotide analog are repeated so that the nucleic acid strand is further extended and the sequence of the target nucleic acid is determined.

In some embodiments, shotgun sequencing is performed. In shotgun sequencing, DNA is broken up randomly into numerous small segments, which are sequenced using the chain termination method to obtain reads. Multiple overlapping reads for the target DNA are obtained by performing several rounds of this fragmentation and sequencing. Computer programs then use the overlapping ends of different reads to assemble them into a continuous sequence.

In some embodiments, factors for replicating or packaging may be supplied in cis or in trans, relative to the genetic element. For example, when supplied in cis, the genetic element may comprise one or more genes encoding an Anellovirus ORF1, ORF1/1, ORF1/2, ORF2, ORF2/2, ORF2/3, or ORF2t/3, e.g., as described herein. In some embodiments, replication and/or packaging signals can be incorporated into a genetic element, for example, to induce amplification and/or encapsulation. In some embodiments, this is done both in context of larger regions of the anellovector genome (e.g., inserting effectors into a specific site in the genome, or replacing viral ORFs with effectors).

In another example, when supplied in trans, the genetic element may lack genes encoding one or more of an Anellovirus ORF1, ORF1/1, ORF1/2, ORF2, ORF2/2, ORF2/3, or ORF2t/3, e.g., as described herein; this protein or proteins may be supplied, e.g., by another nucleic acid, e.g., a helper nucleic acid. In some embodiments, minimal cis signals (e.g., 5' UTR and/or GC-rich region) are present in the genetic element. In some embodiments, the genetic element does not encode replication or packaging factors (e.g., replicase and/or capsid proteins). Such factors may, in some embodiments, be supplied by one or more helper nucleic acids (e.g., a helper viral nucleic acid, a helper plasmid, or a helper nucleic acid integrated into the host cell genome). In some embodiments, the helper nucleic acids express proteins and/or RNAs sufficient to induce amplification and/or packaging, but may lack their own packaging signals. In some embodiments, the genetic element and the helper nucleic acid are introduced into the host cell (e.g., concurrently or separately), resulting in amplification and/or packaging of the genetic element but not of the helper nucleic acid.

In Vitro Circularization

In some instances, the genetic element to be packaged into a proteinaceous exterior is a single stranded circular DNA. The genetic element may, in some instances, be introduced into a host cell in a form other than a single stranded circular DNA. For example, the genetic element may be introduced into the host cell as a double-stranded circular DNA. The double-stranded circular DNA may then be converted into a single-stranded circular DNA in the host cell (e.g., a host cell comprising a suitable enzyme for rolling circle replication, e.g., an Anellovirus Rep protein, e.g., Rep68/78, Rep60, RepA, RepB, Pre, MobM, TraX, TrwC, Mob02281, Mob02282, NikB, ORF50240, NikK, TecH, OrfJ, or TraI, e.g., as described in Wawrzyniak et al. 2017, *Front. Microbiol.* 8: 2353; incorporated herein by reference with respect to the listed enzymes). In some embodiments, the double-stranded circular DNA is produced by in vitro circularization, e.g., as described in Example 35 of PCT Publication No. WO 2020/123816, incorporated by reference herein in its entirety. Generally, in vitro circularized DNA constructs can be produced by digesting a plasmid comprising the sequence of a genetic element to be packaged, such that the genetic element sequence is excised as a linear DNA molecule. The resultant linear DNA can then be ligated, e.g., using a DNA ligase, to form a double-stranded circular DNA. In some instances, a double-stranded circular DNA produced by in vitro circularization can undergo rolling circle replication, e.g., as described herein. Without wishing to be bound by theory, it is contemplated that in vitro circularization results in a double-stranded DNA construct that can undergo rolling circle replication without further modification, thereby being capable of producing single-stranded circular DNA of a suitable size to be packaged into an anellovector, e.g., as described herein. In some embodiments, the double-stranded DNA construct is smaller than a plasmid (e.g., a bacterial plasmid). In some embodiments, the double-stranded DNA construct is excised from a plasmid (e.g., a bacterial plasmid) and then circularized, e.g., by in vitro circularization.

Producing the Anellovector

The genetic elements and vectors comprising the genetic elements prepared as described herein can be used in a variety of ways to express the anellovector in appropriate host cells. In some embodiments, the genetic element and vectors comprising the genetic element are transfected in appropriate host cells and the resulting RNA may direct the expression of the anellovector gene products, e.g., non-pathogenic protein and protein binding sequence, at high levels. Host cell systems which provide for high levels of expression include continuous cell lines that supply viral functions, such as cell lines superinfected with APV or MPV, respectively, cell lines engineered to complement APV or MPV functions, etc.

In some embodiments, the anellovector is produced as described in any of Examples 22, 25, or 26. In some embodiments, the anellovector is produced as described in any of Examples 1, 2, 5, 6, or 15-17 of PCT Publication No. WO 2020/123816, incorporated by reference herein in its entirety.

In some embodiments, the anellovector is cultivated in continuous animal cell lines in vitro. According to one embodiment of the invention, the cell lines may include porcine cell lines. The cell lines envisaged in the context of the present invention include immortalised porcine cell lines such as, but not limited to the porcine kidney epithelial cell lines PK-15 and SK, the monomyeloid cell line 3D4/31 and the testicular cell line ST. Also, other mammalian cells lines are included, such as CHO cells (Chinese hamster ovaries), MARC-145, MDBK, RK-13, EEL. Additionally or alternatively, particular embodiments of the methods of the invention make use of an animal cell line which is an epithelial cell line, i.e. a cell line of cells of epithelial lineage. Cell lines susceptible to infection with anellovectors include, but are not limited to cell lines of human or primate origin, such as human or primate kidney carcinoma cell lines.

In some embodiments, the genetic elements and vectors comprising the genetic elements are transfected into cell lines that express a viral polymerase protein in order to achieve expression of the anellovector. To this end, transformed cell lines that express an anellovector polymerase protein may be utilized as appropriate host cells. Host cells may be similarly engineered to provide other viral functions or additional functions.

To prepare the anellovector disclosed herein, a genetic element or vector comprising the genetic element disclosed herein may be used to transfect cells which provide anellovector proteins and functions required for replication and production. Alternatively, cells may be transfected with helper virus before, during, or after transfection by the genetic element or vector comprising the genetic element disclosed herein. In some embodiments, a helper virus may be useful to complement production of an incomplete viral particle. The helper virus may have a conditional growth defect, such as host range restriction or temperature sensitivity, which allows the subsequent selection of transfectant viruses. In some embodiments, a helper virus may provide one or more replication proteins utilized by the host cells to achieve expression of the anellovector. In some embodiments, the host cells may be transfected with vectors encoding viral proteins such as the one or more replication proteins. In some embodiments, a helper virus comprises an antiviral sensitivity.

The genetic element or vector comprising the genetic element disclosed herein can be replicated and produced into anellovector particles by any number of techniques known in the art, as described, e.g., in U.S. Pat. Nos. 4,650,764; 5,166,057; 5,854,037; European Patent Publication EP 0702085A1; U.S. patent application Ser. No. 09/152,845; International Patent Publications PCT WO97/12032; WO96/34625; European Patent Publication EP-A780475; WO 99/02657; WO 98/53078; WO 98/02530; WO 99/15672; WO 98/13501; WO 97/06270; and EPO 780 47SA1, each of which is incorporated by reference herein in its entirety.

The production of anellovector-containing cell cultures according to the present invention can be carried out in different scales, such as in flasks, roller bottles or bioreactors. The media used for the cultivation of the cells to be infected are known to the skilled person and can generally comprise the standard nutrients required for cell viability, but may also comprise additional nutrients dependent on the cell type. Optionally, the medium can be protein-free and/or serum-free. Depending on the cell type the cells can be cultured in suspension or on a substrate. In some embodiments, different media is used for growth of the host cells and for production of anellovectors.

The purification and isolation of anellovectors can be performed according to methods known by the skilled person in virus production and is described for example by Rinaldi, et al., DNA Vaccines: Methods and Protocols (Methods in Molecular Biology), 3rd ed. 2014, Humana Press.

In one aspect, the present invention includes a method for the in vitro replication and propagation of the anellovector as described herein, which may comprise the following steps: (a) transfecting a linearized genetic element into a cell line sensitive to anellovector infection; (b) harvesting the cells and isolating cells showing the presence of the genetic element; (c) culturing the cells obtained in step (b) for at least three days, such as at least one week or longer, depending on experimental conditions and gene expression; and (d) harvesting the cells of step (c).

In some embodiments, an anellovector may be introduced to a host cell line grown to a high cell density. In some embodiments, the anellovector may be harvested and/or purified by separation of solutes based on biophysical properties, e.g., ion exchange chromatography or tangential flow filtration, prior to formulation with a pharmaceutical excipient.

VIII. Administration/Delivery

The composition (e.g., a pharmaceutical composition comprising an anellovector or anelloVLP as described herein) may be formulated to include a pharmaceutically acceptable excipient. Pharmaceutical compositions may optionally comprise one or more additional active substances, e.g. therapeutically and/or prophylactically active substances. Pharmaceutical compositions of the present invention may be sterile and/or pyrogen-free. General considerations in the formulation and/or manufacture of pharmaceutical agents may be found, for example, in Remington: The Science and Practice of Pharmacy 21st ed., Lippincott Williams & Wilkins, 2005 (incorporated herein by reference).

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product.

In one aspect, the invention features a method of delivering an anellovector or anelloVLP to a subject. The method includes administering a pharmaceutical composition comprising an anellovector or anelloVLP as described herein to the subject. In some embodiments, the administered anellovector or anelloVLP replicates in the subject (e.g., becomes a part of the virome of the subject).

The pharmaceutical composition may include wild-type or native viral elements and/or modified viral elements. The anellovector may include one or more of the sequences (e.g., nucleic acid sequences or nucleic acid sequences encoding amino acid sequences thereof) in any one of Tables N1-N25 or a sequence with at least about 60%, 65%, 70%, 75%, 80%, 85%, 90% 95%, 96%, 97%, 98% and 99% nucleotide sequence identity to any one of the nucleotide sequences or a sequence that is complementary to the sequence in any one of Tables N1-N25. The anellovector may comprise a nucleic acid molecule comprising a nucleic acid sequence with at least about 60%, 65%, 70%, 75%, 80%, 85%, 90% 95%, 96%, 97%, 98% and 99% sequence identity to one or more of the sequences in any one of Tables N1-N25. The anellovector may comprise a nucleic acid molecule encoding an amino acid sequence with at least about 60%, 65%, 70%, 75%, 80%, 85%, 90% 95%, 96%, 97%, 98% and 99% sequence identity to any one of the amino acid sequences in any one of Tables A1-A25. The anellovector may comprise a polypeptide comprising an amino acid sequence with at least about 60%, 65%, 70%, 75%, 80%, 85%, 90% 95%, 96%, 97%, 98% and 99% sequence identity to any one of the amino acid sequences in any one of Tables A1-A25. The anellovector may include one or more of the sequences in any one of Tables A1-A25 or N1-N25, or a sequence with at least about 60%, 65%, 70%, 75%, 80%, 85%, 90% 95%, 96%, 97%, 98% and 99% nucleotide sequence identity to any one of the nucleotide sequences or a sequence that is complementary to the sequence in any one of Tables N1-N25.

In some embodiments, the anellovector or anelloVLP is sufficient to increase (stimulate) endogenous gene and protein expression, e.g., at least about 5%, 10%, 15%, 20%, 25%, 30%, 35%, 40%, 45%, 50%, or more as compared to a reference, e.g., a healthy control. In certain embodiments, the anellovector or anelloVLP is sufficient to decrease (inhibit) endogenous gene and protein expression, e.g., at least about 5%, 10%, 15%, 20%, 25%, 30%, 35%, 40%, 45%, 50%, or more as compared to a reference, e.g., a healthy control.

In some embodiments, the anellovector or anelloVLP inhibits/enhances one or more viral properties, e.g., tropism, infectivity, immunosuppression/activation, in a host or host cell, e.g., at least about 5%, 10%, 15%, 20%, 25%, 30%, 35%, 40%, 45%, 50%, or more as compared to a reference, e.g., a healthy control.

In some embodiments, the subject is administered the pharmaceutical composition further comprising one or more viral strains that are not represented in the viral genetic information.

In some embodiments, the pharmaceutical composition comprising an anellovector or anelloVLP described herein is administered in a dose and time sufficient to modulate a viral infection. Some non-limiting examples of viral infections include adeno-associated virus, Aichi virus, Australian bat lyssavirus, BK polyomavirus, Banna virus, Barmah forest virus, Bunyamwera virus, Bunyavirus La Crosse, Bunyavirus snowshoe hare, Cercopithecine herpesvirus, Chandipura virus, Chikungunya virus, Cosavirus A, Cowpox virus, Coxsackievirus, Crimean-Congo hemorrhagic fever virus, Dengue virus, Dhori virus, Dugbe virus, Duvenhage virus, Eastern equine encephalitis virus, Ebolavirus, Echovirus, Encephalomyocarditis virus, Epstein-Barr virus, European bat lyssavirus, GB virus C/Hepatitis G virus, Hantaan virus, Hendra virus, Hepatitis A virus, Hepatitis B virus, Hepatitis C virus, Hepatitis E virus, Hepatitis delta virus, Horsepox virus, Human adenovirus, Human astrovirus, Human coronavirus, Human cytomegalovirus, Human enterovirus 68, Human enterovirus 70, Human herpesvirus 1, Human herpesvirus 2, Human herpesvirus 6, Human herpesvirus 7, Human herpesvirus 8, Human immunodeficiency virus, Human papillomavirus 1, Human papillomavirus 2, Human papillomavirus 16, Human papillomavirus 18, Human parainfluenza, Human parvovirus B19, Human respiratory syncytial virus, Human rhinovirus, Human SARS coronavirus, Human spumaretrovirus, Human T-lymphotropic virus, Human torovirus, Influenza A virus, Influenza B virus, Influenza C virus, Isfahan virus, JC polyomavirus, Japanese encephalitis virus, Junin arenavirus, KI Polyomavirus, Kunjin virus, Lagos bat virus, Lake Victoria marburgvirus, Langat virus, Lassa virus, Lordsdale virus, Louping ill virus, Lymphocytic choriomeningitis virus, Machupo virus, Mayaro virus, MERS coronavirus, Measles virus, Mengo encephalomyocarditis virus, Merkel cell polyomavirus, Mokola virus, Molluscum contagiosum virus, Monkeypox virus, Mumps virus, Murray valley encephalitis virus, New York virus, Nipah virus, Norwalk virus, O'nyong-nyong virus, Orf virus, Oropouche virus, Pichinde virus, Poliovirus, Punta toro phlebovirus, Puumala virus, Rabies virus, Rift valley fever virus, Rosavirus A, Ross river virus, Rotavirus A, Rotavirus B, Rotavirus C, Rubella virus, Sagiyama virus, Salivirus A, Sandfly fever sicilian virus, Sapporo virus, Semliki forest virus, Seoul virus, Simian foamy virus, Simian virus 5, Sindbis virus, Southampton virus, St. louis encephalitis virus, Tick-borne powassan virus, Torque teno virus, Toscana virus, Uukuniemi virus, Vaccinia virus, Varicella-zoster virus, Variola virus, Venezuelan equine encephalitis virus, Vesicular stomatitis virus, Western equine encephalitis virus, WU polyomavirus, West Nile virus, Yaba monkey tumor virus, Yaba-like disease virus, Yellow fever virus, and Zika Virus. In certain embodiments, the anellovector or anelloVLP is sufficient to outcompete and/or displace a virus already present in the subject, e.g., at least about 5%, 10%, 15%, 20%, 25%, 30%, 35%, 40%, 45%, 50%, or more as compared to a reference. In certain embodiments, the anellovector or anelloVLP is sufficient to compete with chronic or acute viral infection. In certain embodiments, the anellovector or anelloVLP may be administered prophylactically to protect from viral infections (e.g. a provirotic). In some embodiments, the anellovector or anelloVLP is in an amount sufficient to modulate (e.g., phenotype, virus levels, gene expression, compete with other viruses, disease state, etc. at least about 5%, 10%, 15%, 20%, 25%, 30%, 35%, 40%, 45%, 50%, or more).

Redosing

The anellovectors or anelloVLPs described herein can, in some instances, be used as a delivery vehicle that can be administered in multiple doses (e.g., doses administered separately). While not wishing to be bound by theory, in some embodiments, an anellovector or anelloVLP (e.g., as described herein) induces a relatively low immune response (as measured, for example, as 50% GMT values, e.g., as observed in Example 29), e.g., allowing for repeated dosing of a subject with one or more anellovectors or anelloVLPs (e.g., multiple doses of the same anellovector or anelloVLP or different anellovectors or anelloVLPs). In an aspect, the invention provides a method of delivering an effector, comprising administering to a subject a first plurality of anellovectors or anelloVLPs and then a second plurality of anellovectors or anelloVLPs. In some embodiments, the second plurality of anellovectors or anelloVLPs comprise the same proteinaceous exterior as the anellovectors or anelloVLPs of the first plurality. In another aspect, the invention provides a method of selecting a subject (e.g., a human subject) to receive an effector, wherein the subject previously received, or was identified as having received, a first plurality of anellovectors or anelloVLPs comprising a genetic element encoding an effector, in which the method involves selecting the subject to receive a second plurality of anellovectors or anelloVLPs comprising a genetic element encoding an effector (e.g., the same effector as that encoded by the genetic element of the first plurality of anellovectors or anelloVLPs, or a different effector as that encoded by the genetic element of the first plurality of anellovectors or anelloVLPs). In another aspect, the invention provides a method of identifying a subject (e.g., a human subject) as suitable to receive a second plurality of anellovectors or anelloVLPs, the method comprising identifying the subject has having previously received a first plurality of anellovectors or anelloVLPs comprising a genetic element encoding an effector, wherein the subject being identified as having received the first plurality of anellovectors or anelloVLPs is indicative that the subject is suitable to receive the second plurality of anellovectors or anelloVLPs.

In some embodiments, the second plurality of anellovectors or anelloVLPs comprises a proteinaceous exterior with at least one surface epitope in common with the anellovectors or anelloVLPs of the first plurality of anellovectors or anelloVLPs. In some embodiments, the anellovectors or anelloVLPs of the first plurality and the anellovectors or anelloVLPs of the second plurality carry genetic elements encoding the same effector. In some embodiments, the anellovectors or anelloVLPs of the first plurality and the anellovectors or anelloVLPs of the second plurality carry genetic elements encoding different effectors.

In some embodiments, the second plurality comprises about the same quantity and/or concentration of anellovectors or anelloVLPs as the first plurality (e.g., when normalized to the body mass of the subject at the time of administration), e.g., the second plurality comprises 90-110%, e.g., 95-105% of the number of anellovectors or anelloVLPs in the first plurality when normalized to body mass of the subject at the time of administration. In some embodiments, wherein the first plurality comprises a greater dosage of anellovectors or anelloVLPs than the second plurality, e.g., wherein the first plurality comprises a greater quantity and/or concentration of anellovectors or anelloVLPs relative to the second plurality. In some embodiments, wherein the first plurality comprises a lower dosage of anellovectors or anelloVLPs than the second plurality, e.g., wherein the first plurality comprises a lower quantity and/or concentration of anellovectors or anelloVLPs relative to the second plurality.

In some embodiments, the subject is evaluated between the administration of the first and second pluralities of anellovectors or anelloVLPs, e.g., for the presence (e.g., persistence) of anellovectors or anelloVLPs from the first plurality, or progeny thereof. In some embodiments, the subject is administered the second plurality of anellovectors or anelloVLPs if the presence of anellovectors or anelloVLPs from the first plurality, or the progeny thereof, are not detected.

In some embodiments, the second plurality is administered to the subject at least 1, 2, 3, or 4 weeks, or 1, 2, 3, 4, 5, 6, 7, 8, 9, 10, 11, or 12 months, or 1, 2, 3, 4, 5, 10, or 20 years after the administration of the first plurality to the subject. In some embodiments, the second plurality is administered to the subject between 1-2 weeks, 2-3 weeks, 3-4 weeks, 1-2 months, 3-4 months, 4-5 months, 5-6 months, 6-7 months, 7-8 months, 8-9 months, 9-10 months, 10-11 months, 11-12 months, 1-2 years, 2-3 years, 3-4 years, 4-5 years, 5-10 years, or 10-20 years after the administration of the first plurality to the subject. In some embodiments, the method comprises administering a repeated dose of anellovectors or anelloVLPs over the course of at least 1, 2, 3, 4, or 5 years.

In some embodiments, the method further comprises assessing, after administration of the first plurality and before administration of the second plurality, one or more of:

a) the level or activity of the effector in the subject (e.g., by detecting a protein effector, e.g., by ELISA; by detecting a nucleic acid effector, e.g., by RT-PCR, or by detecting a downstream effect of the effector, e.g., level of an endogenous gene affected by the effector);

b) the level or activity of the anellovector or anelloVLP of the first plurality in the subject (e.g., by detecting the level of the VP1 of the anellovector or anelloVLP);
c) the presence, severity, progression, or a sign or symptom of a disease in the subject that the anellovector or anelloVLP was administered to treat; and/or
d) the presence or level of an immune response, e.g., neutralizing antibodies, against an anellovector or anelloVLP.

In some embodiments, the method further comprises administering to the subject a third, fourth, fifth, and/or further plurality of anellovectors or anelloVLPs, e.g., as described herein.

In some embodiments, the first plurality and the second plurality are administered via the same route of administration, e.g., intravenous administration. In some embodiments, the first plurality and the second plurality are administered via different routes of administration. In some embodiments, the first and the second pluralities are administered by the same entity (e.g., the same health care provider). In some embodiments, the first and the second pluralities are administered by different entities (e.g., different health care providers).

All references and publications cited herein are hereby incorporated by reference.

The following examples are provided to further illustrate some embodiments of the present invention, but are not intended to limit the scope of the invention; it will be understood by their exemplary nature that other procedures, methodologies, or techniques known to those skilled in the art may alternatively be used. Additional examples can be found, for example, in PCT Publication No. WO 2020/123816, incorporated by reference herein in its entirety.

EXAMPLES

Table of Contents

Example 1: Expression of ORF1 constructs for conjugation
Example 2: Conjugation of peptides via NHS click chemistry
Example 3: Conjugation of polypeptides via two-step click chemistry
Example 4: Conjugation of polypeptides via maleimide conjugation
Example 5: Genetic grafting of surface effector to the VLP surface
Example 6: Generation of circular ssDNA transgene for in vitro assembly of Anellovectors
Example 7: Anellovector ORF1 VLP expression in insect or mammalian cells and purification
Example 8: Expression of Ring2 and Ring10 Anellovirus ORF1s in insect cells
Example 9: Expression of CAV capsid protein VP1 in mammalian cells
Example 10: Expression of Ring2 ORF1 and ORF2 in insect cells
Example 11: Disassembly of Ring2 VLPs using urea
Example 12: Dissociation of Anellovirus VLPs and reassembly around nucleic acid cargoes
Example 13: Exemplary sequence s for ORF1 molecules
Example 14: Production of Anellovirus proteins in a baculovirus expression system
Example 15: Expression of Ring1 ORFs in Sf9 cells
Example 16: Expression of Ring2 ORFs in Sf9 cells
Example 17: Expression of all Ring2 ORFs simultaneously in Sf9 cells
Example 18: Co-delivery and independent expression of anellovirus genomes and recombinant Anellovirus ORFs in Sf9 cells
Example 19: Anellovirus ORF1 associates with DNA in Sf9 cells to form complexes isolated by isopycnic centrifugation
Example 20: Expression of ORF1 protein from a diverse array of Anelloviruses using baculovirus
Example 21: In vitro assembly of anellovectors using components produced via baculovirus system
Example 22: Identification and use of protein binding sequences: putative protein-binding sites in the Anellovirus genome
Example 23: Replication-deficient anellovectors and helper viruses
Example 24: Manufacturing process for replication-competent anellovectors
Example 25: Manufacturing process of replication-deficient anellovectors: recovery and scaling up of production of replication-deficient anellovectors
Example 26: Production of anellovectors using suspension cells: production of anellovectors in cells in suspension.
Example 27: Quantification of anellovector genome equivalents by qPCR: development of a hydrolysis probe-based quantitative PCR assay to quantify anellovectors
Example 28: Tandem copies of the Anellovirus genome
Example 29: In vitro circularized Anellovirus genomes: constructs comprising circular, double stranded Anelloviral genome DNA with minimal non-viral DNA
Example 30: Production of anellovectors containing chimeric ORF1 with hypervariable domains from different Torque Teno Virus strains
Example 31: Design of an anellovector harboring a DNA payload
Example 32: In vitro circularized genome as input material for producing anellovectors in vitro
Example 33: Antibody generation and western blot analysis
Example 34: Construct design, cell culture and protein expression/purification
Example 35: Negative-stained EM data collection and analysis
Example 36: Cryo-EM data collection and data analysis and molecular refinement
Example 37: Circular dichroism spectroscopy
Example 38: Anellovirus particle structure
Example 39: Anellovirus jelly roll domains
Example 40: Anellovirus spike domains
Example 41: Evasion of immune system
Example 42: Production and purification of AnelloVLPs
Example 43: Conjugation of AnelloVLPs
Example 44: VLP conjugation to SARS-CoV-2 RBD peptide

Example 1. Expression of ORF1 Constructs for Conjugation

In nature, Anelloviruses encapsidate circularized negative sense (ns) single stranded (ss) DNA genomes in part through interactions between the genome and the N-terminal arginine rich motif (ARM). UV absorption evidence suggests recombinant ORF1 containing the ARM forms virus like particles (VLPs) that are bound to nucleic acids, presumably non-specific host cell DNA fragments. To remove these potentially undesired host cell impurities, ORF1 constructs are generated in which the ARM is deleted.

Anellovirus ORF1 proteins, such as an ORF1 protein in which the ARM has been deleted, harbor a basic residue (lysine) on the particle surface which would be suitable for conjugating surface effectors including peptides, proteins such as antibodies, glycan groups or neuclic acid entities which are covalently bound to N-hydroxysuccinimide (NHS). NHS is a click-chemistry which binds to amino groups such as those located on lysine residues.

Example 2. Conjugation of Peptides Via NHS Click Chemistry

Based on the structural analysis described herein, basic residues (lysine residues) of Ring 10 ORF1 were identified as surface exposed on the VLP viral surface. Several surface effectors can be conjugated to the amine groups of lysine by adding the click-chemistry entity NHS. In one example, the short antigenic region of the malaria CS protein (for example, the NANP repeat region known to be immunogenic in the R21 malaria vaccine currently being evaluated in the clinic) can be synthesized with an NHS moiety. By mixing the NANP-NHS peptide with ORF1 VLPs, we can conjugate the antigenic region of the R21 vaccine candidate to the ORF1 VLP generating a novel malaria particle as a vaccine candidate. Conjugation of other entities to the surface lysines though NHS conjugation could also be generated such as anti-sense oligomers (ASOs) or glycans from other bacteria known to provide an immune response in vaccines (such as, for example, the glycans of Prevnar13).

Example 3. Conjugation of Polypeptides Via Two-Step Click Chemistry

As discussed in Example 2, surface exposed lysines are available for NHS conjugation. However, not every surface effector may be available for synthetic addition of NHS such as peptides, oligomers or glycans. In one example, larger surface effectors such as proteins (antibody fragments or larger vaccine antigens) could be generated with free cysteine, which can further be conjugated with click-chemistries, for example, by virtue of maleimide-click-chemistry linkers (maleimide being a click chemistry that binds thiols of free cysteine), which in turn can be added to paired chemistries on conjugated to free lysine on the VLP surface. In one example, a free cysteine could be engineered into a polypeptide encoding the C-terminal (immunogenic) portion of the malaria CS protein. This protein could then be conjugated by virtue of its free cysteine to a click chemistry moiety such as azide. The ORF1 VLP could be further conjugated by NHS-DBCO (DBCO being the click-chemistry partner of azide) by virtue of the surface lysines on ORF1. When the VLP-DBCO species is combined with the Azide-Malaria polypeptide species the DBCO-Azide conjugation would produce a covalently attached Malaria-VLP particle suitable as a malaria vaccine candidate. This two-step conjugation approach could be suitable for other larger surface effectors where direct synthesis with click-chemistry moieties is not available, including antibodies and larger nucleic acid oligomers.

Example 4. Conjugation of Polypeptides Via Maleimide Conjugation

In Examples 2 or 3 above, conjugation of surface effectors is done through conjugation of NHS moieties to surface lysines. This approach could have the added advantage of adding several surface effectors to the ORF1, depending on how many lysines are surface exposed in a given strain of ORF1. However, specific conjugation to ORF1 may be desired for some surface effectors to generate a more controlled product. In this example, a Ring 10 ORF1 structure (determined according to the structural analysis described herein) is used to define surface exposed regions of the VLP and introduce a free cysteine suitable for maleimide conjugation (maleimide being a click-chemistry that binds thiols in free cysteine residues), for example, at residues in the P2 domain of Ring10, such as Threonine 365. These engineered VLPs, perhaps in combination with deletion of the ARM as described in Example 1, would provide a cleaner, more controlled conjugation. By replacing the NHS species in Examples 2 and 3 with maleimide moieties, the conjugation of the surface effector, such as a maleimide malaria peptide, would be specifically targeted to a particular residue of interest, e.g., at a controlled stoichiometry.

To ensure only the desired target cysteines are available for modification with antigenic peptides or other surface effector molecules, the native cysteine residues of ORF1 (e.g., located at positions: 57, 64, 112, 131, 220, 223, 626) will also be replaced with either serine or alanine residues. When the residue to be mutated is on the surface of the molecule and the sidechain is exposed to solvent, replacing a cysteine with a serine is a conservative alteration as the two residues are isosteric and therefore should not disrupt the 3-dimensional structure of the protein. When the residue to be mutated is buried inside of the structure, alanine is a more conservative alteration as the polar side chain of serine is likely to destabilize the structure.

Example 5. Genetic Grafting of Surface Effector to the VLP Surface

Figure 2:
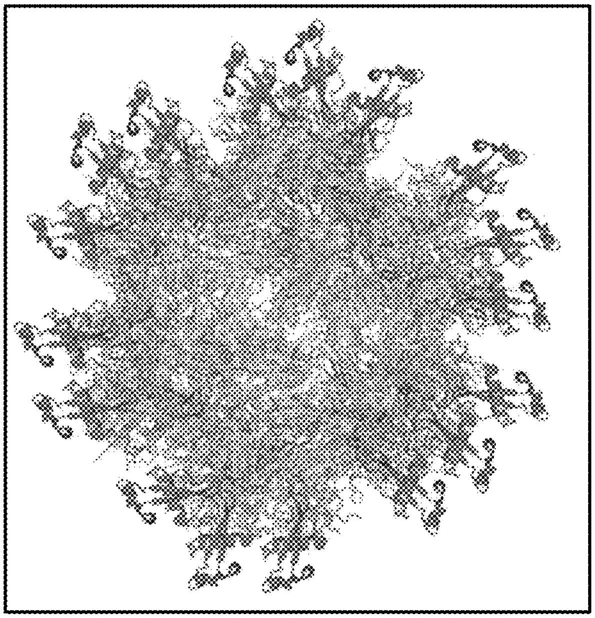
FIG. 2 is a series of diagrams showing the structure of an exemplary malaria peptide conjugation construct on the surface of an anellovector capsid.

Using a structure determined for Ring 10, the region of the VLP that is surface exposed can be identified, for example, such as an HVR region. In this example, a VLP construct is generated in which a surface effector coding sequence replaces or is inserted into the HVR region of ORF. One example could be the genetic fusion of the malaria CS immunogenic portion into the HVR region of ORF1 VLPs (FIG. 2). In these genetic fusions, the VLP does not require conjugation, but rather a fusion protein comprises an ORF1 portion and a surface effector portion, such that the surface effector portion is displayed on the outer surface of the VLP. The advantage of this approach would be alleviating the need to conjugate the VLP post purification, which may not be an efficient process. Another advantage would be that each copy of the ORF1 molecule would be known to contain one copy of the surface effector. In some iterations it may be advantageous to express ORF1 with and without surface effectors generating mixed VLPs with fewer surface effectors.

In an example, a surface effector and ORF1 fusion protein comprises an amino acid sequence as listed in Table E1 below.

TABLE E1

Exemplary ORF1-surface effector fusion protein amino acid sequences

| Construct Name | Amino Acid Sequence |
|---|---|
| R21 construct [184 C-Terminal residues of CS protein (CS-Cterm) fused to the Hepatitis B Virus Surface Antigen (HBsAg)] | ANPNANPNANPNANPNANPNANPNANPNANPNANPNANPNANPNANPN ANPNANPNANPNKNNQGNGQGHNMPNDPNRNVDENANANSAVKNNNNE EPSDKHIKEYLNKIQNSLSTEWSPCSVTCGNGIQVRIKPGSANKPKDE LDYANDIEKKICKMEKCSSVFNVVNSSIGLIMVLSFLFLNENTTSGFL GPLLVLQAGFFLLTRILTIPQSLDSWWTSLNFQGGAPTCPGQNSQSPT SNHSPTSCPPICPGYRWMCLRRFIIFLFILLLCLIFLLVLLDYQGMLP VCPLLPGTSTTGTGPCRTCTIPAQGTSMFPSCCCTKPSDGNCTCIPIP SSWAFARFLWEWASVRFSWLSLLVPFVQWFAGLSPTVWLSVIWMMWYR GPSLYNTLSPFLPLLPISFCLWVYI |
| R21 construct + C-Terminal Cysteine [184 C-Terminal residues of CS protein (CS-Cterm-184) fused to the Hepatitis B Virus Surface Antigen (HBsAg) with a Cysteine residue for conjugation] | ANPNANPNANPNANPNANPNANPNANPNANPNANPNANPNANPNANPN ANPNANPNANPNKNNQGNGQGHNMPNDPNRNVDENANANSAVKNNNNE EPSDKHIKEYLNKIQNSLSTEWSPCSVTCGNGIQVRIKPGSANKPKDE LDYANDIEKKICKMEKCSSVFNVVNSSIGLIMVLSFLFLNENTTSGFL GPLLVLQAGFFLLTRILTIPQSLDSWWTSLNFQGGAPTCPGQNSQSPT SNHSPTSCPPICPGYRWMCLRRFIIFLFILLLCLIFLLVLLDYQGMLP VCPLLPGTSTTGTGPCRTCTIPAQGTSMFPSCCCTKPSDGNCTCIPIP SSWAFARFLWEWASVRFSWLSLLVPFVQWFAGLSPTVWLSVIWMMWYR GPSLYNTLSPFLPLLPISFCLWVYIC |
| SB-7062 R21 CS C-Terminus [184 C-Terminal residues of CS protein for 293 expression] | MKIKTGARILALSALTTMMESASALAANPNANPNANPNANPNANPNAN PNANPNANPNANPNANPNANPNANPNANPNANPNANPNKNNQGNGQGH NMPNDPNRNVDENANANSAVKNNNNEEPSDKHIKEYLNKIQNSLSTEW SPCSVTCGNGIQVRIKPGSANKPKDELDYANDIEKKICKMEKCSSVFN VVNSSIGLIMVLSFLFLNPHHHHHHA |
| SB-7062 R21 CS C-Terminus + C-Terminal Cysteine [184 C-Terminal residues of CS protein with additional C-Terminal Cysteine for conjugation] | MKIKTGARILALSALTTMMFSASALAANPNANPNANPNANPNANPNAN PNANPNANPNANPNANPNANPNANPNANPNANPNANPNKNNQGNGQGH NMPNDPNRNVDENANANSAVKNNNNEEPSDKHIKEYLNKIQNSLSTEW SPCSVTCGNGIQVRIKPGSANKPKDELDYANDIEKKICKMEKCSSVFN VVNSSIGLIMVLSFLFLNPHHHHHHAC |
| R21 Peptide NANP$_{(6x)}$ [Peptide of N-Terminal residues of R21 6x(NANP) with NHS for conjugation] | NPNANPNANPNANPNANPNANPNA(K/Mal)-amide |
| R21 Peptide NANP-2 [Peptide of second segment of R21 with NHS for conjugation] | ANPNKNNQGNGQGHNMPNDPNRNVDENANANSAVKNNNNE(K/Mal)-amide |
| R21 Peptide Solved Structure [Structured portion of C-Terminal segment of R21] | EPSDKHIKEYLNKIQNSLSTEWSPSSVTSGNGIQVRIKPGSANKPKDE LDYANDIEKKISKMEKSS(K/Mal)-amide |
| Ring 10 (Ly1) Wt protein sequence | MPWWYRRRSYNPWRRRNWFRRPRKTIYRRYRRRRRWVRRKPFYK RKIKRLNIVEWQPKSIRKCRIKGMLCLFQTTEDRLSYNFDMYEE SIIPEKLPGGGGFSIKNISLYALYQEHIHAHNIFTHINTDRPLA RYTGCSLKFYQSKDIDYVVTYSTSLPLRSSMGMYNSMQPSIHLM QQNKLIVPSKQTQKRRKPYIKKHISPPTQMKSQWYFQHNIANIP LLMIRTTALTLDNYYIGSRQLSTNVTIHTLNTTYIQNRDWGDRN KTYYCQTLGTQRYFLYGTHSTAQNINDIKLQELIPLINTQDYVQ GFDWTEKDKHNITTYKEFLTKGAGNPFHAEWITAQNPVIHTANS PTQIEQIYTASTTTFQNKKLTDLPTPGYIFITPTVSLRYNPYKD LAERNKCYFVRSKINAHGWDPEQHQELINSDLPQWLLLFGYPDY IKRTQNFALVDTNYILVDHCPYTNPEKTPFIPLSTSFIEGRSPY SPSDTHEPDEEDQNRWYPCYQYQQESINSICLSGPGTPKIPKGI TAEAKVKYSFNFKWGGDLPPMSTITNPTDQPTYVVPNNFNETTS LQNPTTRPEHFLYSFDERRGQLTEKATKRLLKDWETKETSLLST EYRFAEPTQTQAPQEDPSSEEEEESNLFERLLRQRTKQLQLKRR IIQTLKDLQKLE |
| CCN5 CTermCys | MRGTPKTHLLAFSLLCLLSKVRTQLCPTPCTCPWPPPRCPLGVPLVLD GCGCCRVCARRLGEPCDQLHVCDASQGLVCQPGAGPGGRGALCLLAED DSSCEVNGRLYREGETFQPHCSIRCRCEDGGFTCVPLCSEDVRLPSWD CPHPRRVEVLGKCCPEWVCGQGGGLGTQPLPAQGPQFSGLVSSLPPGV PCPEWSTAWGPCSTTCGLGMATRVSNQNRFCRLETQRRLCLSRPCPPS RGRSPQNSAFGGGGSGGGGSGGGGSC* |
| Aflibercept malE_CTermCys | MKIKTGARILALSALTTMMFSASALASDTGRPFVEMYSEIPEIIHMTE GRELVIPCRVTSPNITVILKKFPLDTLIPDGKRIIWDSRKGFIISNAT YKEIGLLTCEATVNGHLYKTNYLTHRQTNTIIDVVLSPSHGIELSVGE KLVLNCTARTELNVGIDFNWEYPSSKHQHKKLVNRDLKTQSGSEMKKF LSTLTIDGVTRSDQGLYTCAASSGLMTKKNSTFVRVHEKDKTHTCPPC PAPELLGGPSVFLFPPKPKDTLMISRTPEVTCVVVDVSHEDPEVKFNW |

TABLE E1-continued

| Exemplary ORF1-surface effector fusion protein amino acid sequences | |
|---|---|
| Construct Name | Amino Acid Sequence |
| | YVDGVEVHNAKTKPREEQYNSTYRVVSVLTVLHQDWLNGKEYKCKVSN KALPAPIEKTISKAKGQPREPQVYTLPPSRDELTKNQVSLTCLVKGFY PSDIAVEWESNGQPENNYKTTPPVLDSDGSFFLYSKLTVDKSRWQQGN VFSCSVMHEALHNHYTQKSLSLSPGGGGSGGGGGGGGSGGGGSC |
| Aflib_D1-D2 malE_CTermCys | MKIKTGARILALSALTTMMFSASALASDTGRPFVEMYSEIPEIIHMTE GRELVIPCRVTSPNITVTLKKFPLDTLIPDGKRIIWDSRKGFIISNAT YKEIGLLTCEATVNGHLYKTNYLTHRQTNTIIDVVLSPSHGIELSVGE KLVLNCTARTELNVGIDFNWEYPSSKHQHKKLVNRDLKTQSGSEMKKF LSTLTIDGVTRSDQGLYTCAASSGLMTKKNSTFVRVHEKGGGGSGGGG SGGGGSC |
| Ranibizumab HC malE_CTermCys | MKIKTGARILALSALTTMMESASALAEVQLVESGGGLVQPGGSLRLSC AASGYDFTHYGMNWVRQAPGKGLEWVGWINTYTGEPTYAADFKRRFTF SLDTSKSTAYLQMNSLRAEDTAVYYCAKYPYYYGTSHWYFDVWGQGTL VTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSN TKVDKKVEPKSCDKTHLGGGGSGGGGSGGGGSC |
| Bevacizumab HC malE_CTermCys | MKIKTGARILALSALTTMMESASALAEVQLVESGGGLVQPGGSLRLSC AASGYTFTNYGMNWVRQAPGKGLEWVGWINTYTGEPTYAADFKRRFTF SLDTSKSTAYLQMNSLRAEDTAVYYCAKYPHYYGSSHWYFDVWGQGTL VTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSN TKVDKKVEPKSCDKTHTCPPCPAPELLGGPSVFLFPPKPKDTLMISRT PEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLP PSREEMTKNQVSLTCLVKGFYPSDIAVEWESNGQPENNYKTTPPVLDS DGSFFLYSKLTVDKSRWQQGNVFSCSVMHEALHNHYTQKSLSLSPGKK DELGGGGSGGGGSGGGGSC |
| scFab RaniHC-link50-LC malE_CTermCys | MKIKTGARILALSALTTMMESASALAEVQLVESGGGLVQPGGSLRLSC AASGYDFTHYGMNWVRQAPGKGLEWVGWINTYTGEPTYAADFKRRFTF SLDTSKSTAYLQMNSLRAEDTAVYYCAKYPYYYGTSHWYFDVWGQGTL VTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSN TKVDKKVEPKSCDKTHLGGSSGSGSGSTGTSSSGTGTSAGTTGTSAST SGSGSGGGGGSGGGGSAGGDIQLTQSPSSLSASVGDRVTITCSASQDI SNYLNWYQQKPGKAPKVLIYFTSSLHSGVPSRFSGSGSGTDFTLTISS LQPEDFATYYCQQYSTVPWTFGQGTKVEIKRTVAAPSVFIFPPSDEQL KSGTASVVCLLNNFYPREAKVQWKVDNALQSGNSQESVTEQDSKDSTY SLSSTLTLSKADYEKHKVYACEVTHQGLSSPVTKSFNRGECGGGGSGG GGSGGGGSC |

Figure 3:
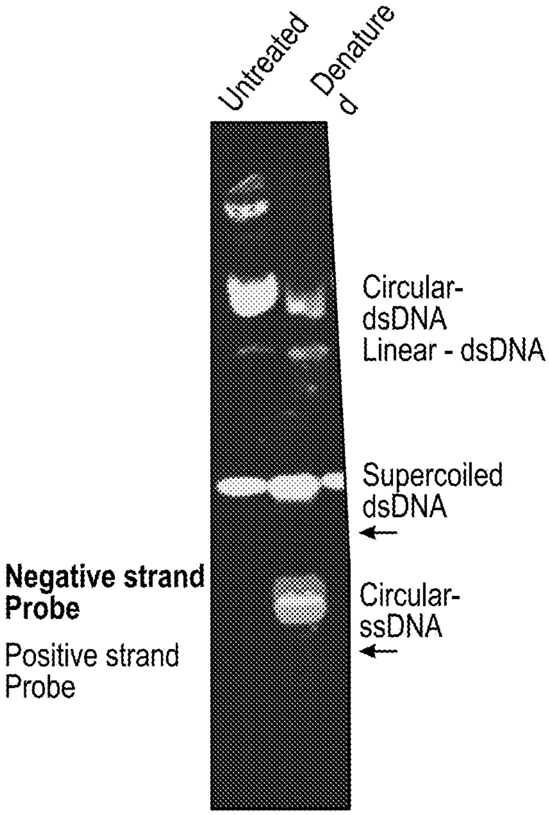
FIG. 3 is a diagram showing separation of in vitro circularized DNA into positive and negative sense circularized single-stranded DNA (ssDNA) after denaturation.

Example 6. Generation of Circular ssDNA Transgene for In Vitro Assembly of Anellovectors Anelloviruses encapsidate circularized negative sense (ns) single stranded (ss) DNA genomes. Described in this example is a method for generating circularized ns-ssDNA purified in vitro. First, the genome of an Anellovirus (e.g., the genome of strain Ring 2 as described herein) was generated in a plasmid for amplification. Next, the DNA encoding the viral genome was cut from the plasmid and re-ligated to form double-stranded in vitro circularized (IVC) DNA. The IVC DNA was denatured with heat by boiling at 80° C. for 5 minutes in the presence of urea and run on a denaturing gel overnight at 4° C. When the gel is stained with fluorescently-labeled primers from either the positive strand (to bind the negative-sense sequence) or the negative strand (to bind the positive-sense sequence) it was observed that the IVC DNA was separated into positive and negative sense circularized ssDNA (FIG. 3).

The ssDNA can be extracted from the gel using conventional DNA purification kits and used in anellovector in vitro encapsidation screening. Plasmids can also be cloned that encode viral genomes that also harbor reporter genes or therapeutic genes, for example, such that generation and encapsidation of the resulting circularized ssDNA would generate an anellovector that can transduce cells with the reporter or therapeutic gene.

Example 7. Anellovector ORF1 VLP Expression in Insect or Mammalian Cells and Purification Described in this example are expression and purification protocols for Anellovirus ORF1 recombinant proteins and variations that can be used, for example, in generating anellovector strains in vitro. Several Anellovirus ORF1 strains have been successfully expressed in insect (Sf9) and/or mammalian (293) cell lines (FIG. 4A). As described in Examples 8 and 9 below, several ORF1 proteins from different Anellovirus strains (as well as the related CAV Vp1 capsid protein) were shown to have a propensity to self-assemble into VLPs in vitro when observed by electron microscopy (FIG. 4B).

In one example, anellovectors can be produced in vitro by generating expression constructs for certain Anellovirus proteins (e.g., as described herein), such as an Anellovirus ORF1. Such expression constructs can be introduced into cells (e.g., mammalian cells or insect cells, e.g. Sf9 cells) to produce Anellovirus ORF1 proteins capable of forming capsids. Production of the ORF1 proteins can be done in the presence or absence of a suitable Anellovirus ORF2 protein. The expression constructs can also be engineered to attach (e.g., fuse) an affinity tag to the Anellovirus ORF1 protein. The ORF1 proteins can then be purified from the cells.

In some examples, a desired payload nucleic acid molecule (e.g., an engineered Anellovirus genome, a wild-type Anellovirus genome, an oligonucleotide, a single-stranded DNA, a double-stranded DNA, or an RNA, e.g., an mRNA) can be encapsulated by the ORF1 proteins in vitro, under conditions suitable for assembly of the ORF1 proteins into a proteinaceous exterior (e.g., a capsid). Such conditions may include, for example, a solution comprising one or more of: detergents, buffers, and/or reducing agents (e.g., as described herein), as well as incubation at a preselected temperature for a preselected time. This assembly can result in formation of particles (e.g., comprising assembled ORF1 proteins encapsulating the desired payload nucleic acid molecule). Particle formation can be assessed, for example, by co-migration of ssDNA in size exclusion chromatography and/or by detecting DNase-resistant payload nucleic acid molecules (e.g., by PCR), e.g., as described herein. In addition, particles can be assessed for their capacity to transduce target cells with the payload nucleic acid molecule (e.g., by detecting a gene product encoded by the payload nucleic acid molecule, e.g., a reporter).

In addition to exploring the purification and in vitro assembly of ORF1 from different strains, Anellovirus ORF1 fragments or chimeric molecules can be used to improve the efficiency of in vitro assembly. Such fragment or chimeric molecules include, but are not limited to, Anellovirus ORF1 proteins that harbor mutations introduced into the N-terminal Arginine-rich region (also referred to as the ARG arm) to alter the pI of the ARG arm, permitting pH sensitive nucleic acid binding to trigger particle assembly (SEQ ID NOs: 563-565). Anellovirus ORF1 mutations that improve stability include, for example, mutations to the interprotomer contacting beta strands F and G of the canonical jellyroll beta-barrel (F and G beta strands) to alter the hydrophobic state of the protomer surface to make capsid formation more thermodynamically favored.

Exemplary chimeric ORF1 proteins include, but are not limited to, Anellovirus ORF1 proteins which have a portion or portions of their sequence replaced with comparable portions from another capsid protein, such as BFDV, CAV capsid protein or Hepatitis E (such as the ARG arm or F and G beta strands of Ring 9 ORF1 replaced with the comparable components from BFDV capsid protein; SEQ ID NOs: 566-567). Chimeric ORF1 proteins may also include ORF1 proteins which have a portion or portions of their sequence replaced with comparable portions of another Anellovirus ORF1 protein (such as jellyroll fragments or the C-terminal portion of Ring 2 ORF1 replaced with comparable portions of Ring 9 ORF1; SEQ ID NOs: 568-575).

Proteins will be purified using purification techniques, including but not limited to chelating purification, heparin purification, gradient sedimentation purification and/or SEC purification.

Example 8. Expression of Ring2 and Ring10 Anellovirus ORF1s in Insect Cells

In this example, DNA sequences encoding Ring 2 ORF1 or Ring 10 ORF1, each fused to an N-terminal $HIS_6$-tag (HIS-ORF1), was codon optimized for insect expression and cloned into the baculovirus expression vector pFASTbac system according to the manufacture's method (ThermoFisher Scientific). Insect cells (Sf9 cells) were infected with Ring HIS-ORF1 baculovirus and the cells were harvested 3-days post-infection by centrifugation. The cells were lysed and the protein was purified using a chelating resin affinity column (HisTrap, GE Healthcare). The resulting material was purified again using a heparin affinity column (Heparin HiTrap, GE Healthcare) and fractions containing ORF1 were analyzed by negative staining electron microscopy. Both Ring 2 ORF1 and Ring 10 ORF1 exhibited an observed propensity to form ~35 nm virus-like particles (VLPs) in this in vitro setting (FIG. 4B).

Example 9. Expression of CAV Capsid Protein VP1 in Mammalian Cells

In this example, DNA sequences encoding CAV capsid protein (CAV Vp1), fused to an N-terminal $HIS_6$—Flag-tag (HIS-Flag-Vp1), and helper protein (Vp2) were codon optimized for mammalian expression and cloned into a mammalian expression vector including a CMV promoter. Mammalian cells (293expi cells) were transfected with CAV Vp1 and Vp2 expression vectors. The cells were harvested 3-days post-infection by centrifugation. The cells were lysed and the lysis was purified using chelation and heparin purification as described in Example 8. The elution fraction containing CAV Vp1 were analyzed by negative staining electron microscopy. As shown in FIG. 4B, CAV Vp1 virus-like particles were observed in this in vitro setting.

Example 10. Expression of Ring2 ORF1 and ORF2 in Insect Cells

Figure 5A:
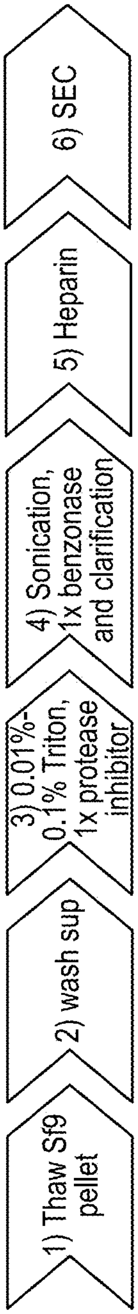
FIGS. 5A-5C are a series of diagrams showing successful expression and purification of Ring2 ORF1 and ORF2 proteins from Sf9 cells. (A) Exemplary workflow for purification of ORF1 and ORF2 proteins from Sf9 cells. (B) Western blot using anti-ORF1 antibody, showing detection of Ring2 ORF1 proteins produced in Sf9 cells as described. (C) Electron micrograph showing formation of virus-like particles (VLPs) from Ring2 ORF1 proteins produced in Sf9 cells as described.
Figure 5B:
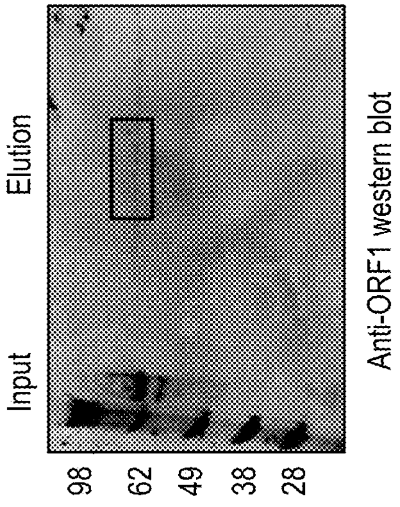
Figure 5C:
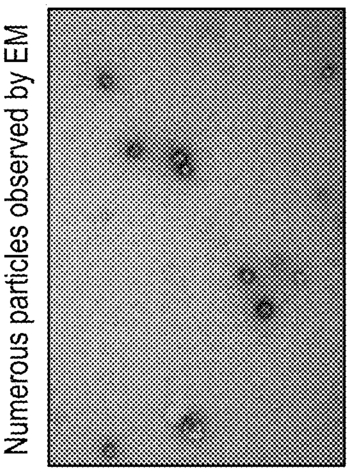

In this example, untagged Ring 2 ORF1 and ORF2 (a putative zinc-finger Ring 2 protein of unknown function) were cloned into a dual-expression baculovirus and co-expressed in Sf9 insect cells using a baculovirus system as described herein. Frozen pellet from a 1 L preparation of the Sf9 cells were resuspended in 60 mL cytosolic buffer (50 mM Tris pH 8, 50 mM NaCl, 1× protease inhibiter), vortexed, pipetted up-down and distributed into two 30 mL aliquotes in 50 mL conical tubes. The solutions were spun down for 20 min at 14,000 rpm using a fixed rotor centrifuge. The supernatant was collected into separate 50 mL conical tubes ("wash sup"). Each pellet was resuspended with 30 mL lysis buffer (50 mM Tris pH 8, 50 mM NaCl buffer, lx protease inhibitor, 0.01-0.1% Triton), vortexed, and sonicated with four cycles. 1× benzonase was added and the solutions were spun for 20 min at 14,000 rpm using a fixed rotor centrifuge. The lysate was incubated for about 30 minutes to allow the benzonase to react to remove host cell DNA. The ORF1 was purified from the lysates using an affinity purification step (heparin column pH=8 with a high salt gradient elution) and VLPs, partially formed VLPs, and ORF1 proteins (putative capsomers) were separated using size-exclusion purification (SEC; GE Healthcare Sephacryl S-500 column). The resulting material was analyzed by electron microscopy (FIG. 5A-5C). Approximately $10^{11}$ total VLP particles at approximately $10^{9}$-$10^{10}$ particles/ml concentration were purified, as determined by western blot analysis and electron microscopy. Such a high-titer VLP preparation can be used to define in vitro disassembly and re-assembly/encapsidation conditions for anellovector generation as described below.

Example 11. Disassembly of Ring2 VLPs Using Urea

Figure 6A:
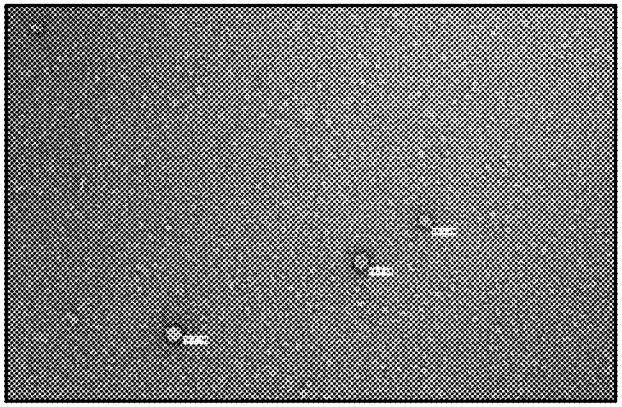
FIGS. 6A-6C are a series of diagrams showing disassembly of Ring2 VLPs using urea as a chaotropic denaturant. (A) Ring2 ORF1 protein was produced and purified from Sf9 cells as described, and VLPs were detected by electron microscopy. (B) After treatment with urea, VLPs are no longer observed, but instead the solution contains small ORF1 capsomers. (C) Expanded view of the boxed area shown in FIG. 6B, showing detail of the capsomers.
Figure 6B:
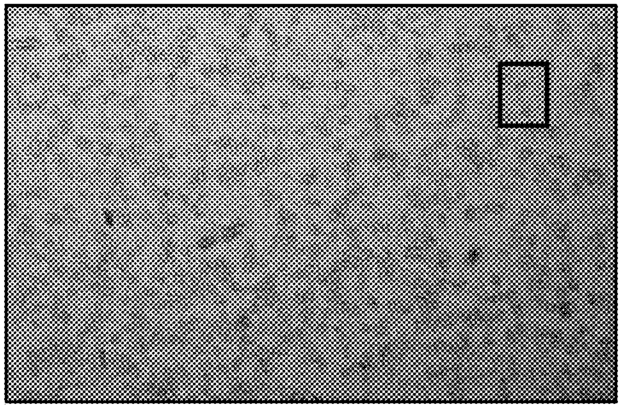
Figure 6C:
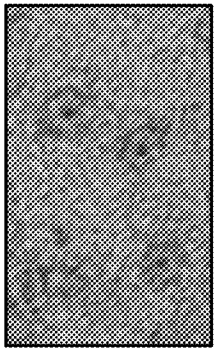

In this example, purified Ring2 VLPs were dissociated using a chaotropic agent. Briefly, purified Ring 2 VLPs were treated with urea at different concentrations, between 1 to 6 molar (M), to identify conditions sufficient to disassemble the particles. In one example, Ring 2 VLPs were treated with urea with a final concentration of 2M for approximately 10 minutes. The sample was observed by electron microscopy before (FIG. 6A) and after (FIG. 6B) urea treatment. Prior to treatment with urea, VLPs were observed with an estimated particle titer of $1\times10^9$ to $1\times10^{10}$ particles/ml. After treatment with urea, the VLPs were no longer observed. A new species, which appear to be hollow circles, like capsomers, was also observed (FIG. 6C).

In a further example, Ring 2 VLPs are dissociated with 2M urea, and the urea is dialyzed away in the absence or presence of mRNA encoding the mCherry reporter gene. In this example, mRNA is introduced at a molar concentration estimated to be approximately 5-times greater than the estimated number of VLPs prior to dissociation. The dissociated ORF1 and mRNA solution are incubated for approximately 30 minutes to allow complex formation before reassembly by dialysis. After the incubation period, disassembled ORF1 (i.e. VLPs treated with 2M urea) with or without mRNA are then dialyzed against 50 mM Tris pH 8.0 with 150 mM NaCl and 0.01% poloxamer to permit VLP reassembly. The initial VLPs, dissociated ORF1, reassembled ORF1 in the absence of nucleic acids, and reassembled ORF1 in the presence of nucleic acids are then screened by EM to confirm that the dissociation/re-assembly processes are successful as well as to estimate the amount of VLP recovered. It is contemplated that no VLPs will be observed for disassembled VLP or disassembled VLP dialyzed in the absence of mRNA. However, it is contemplated that VLPs prior to disassembly may be present at a particle titer of $1\times10^9$ to $1\times10^{10}$ particles/ml and the VLP formation observed after dialysis in the presence of mRNA may have a particle titer of $1\times10^7$ to $1\times10^8$ particles/ml. It is contemplated that VLP reassembly occurs when disassembled ORF1 is dialyzed/reassembled in the presence of mRNA, resulting in mRNA-encapsidated anellovectors.

Example 12. Dissociation of Anellovirus VLPs and Reassembly Around Nucleic Acid Cargoes In this example, Anellovirus ORF1 proteins produced and purified as described herein (e.g., wildtype ORF1 protein, chimeric ORF1 protein, or fragments thereof) will be disassembled and then reassembled in vitro. VLPs will be incubated under conditions sufficient to dissociate VLPs or viral capsids (e.g., as described herein), and then under conditions suitable enable reassembly, for example, around nucleic acid cargo (FIGS. 5A-5C). Exemplary nucleic acid cargo can include, without limitation, as double stranded DNA, single stranded DNA (ssDNA), or RNA that encodes a gene of interest to be delivered as a therapeutic agent. Exemplary conditions sufficient to dissociate VLPs or viral capsids include, but are not limited to, buffers of different pH, conditions of defined conductivity (salt content), conditions containing detergents (such as SDS, Tween, Triton), conditions containing chaotropic agents (such as Urea, e.g., as described herein) or conditions involving defined temperature and time (reannealing temperatures). Generally, nucleic acid cargo of defined concentration will be combined with Anellovirus ORF1 proteins of defined concentration and treated with conditions sufficient to permit nucleic acid encapsidation. The resulting particles can be subsequently purified using viral purification procedures in the art and/or as described herein.

Encapsidation of ssDNA Cargo

In this example, purified Anellovirus ORF1 proteins are treated with high salt in 2 M Urea to disassemble VLPs into dispersed protein or capsomers. The Anellovirus ORF1 proteins are then mixed with ssDNA and dialyzed against Tris pH 8.0 with 150 mM NaCl to permit VLP formation and ssDNA encapsidation. The subsequent complex is purified by SEC using to isolate anellovectors encapsidating ssDNA from non-encapsidated DNA. Anellovector assembly can be further evaluated by biophysical assessment such as DLS or electron microscopy, e.g., as described herein.

Encapsidation of mRNA Cargo with Wild-Type Anellovirus ORF7

In this example, purified Anellovirus ORF1 proteins are treated with 1 M NaCl with 0.1% SDS dissociate oligomers or VLPs into dispersed protein or capsomers. The Anellovirus ORF1 proteins are then mixed with mRNA, such as an mRNA that encodes a gene of interest (e.g., GFP, mCherry, or EPO), and dialyzed against Tris pH 8.0 with 150 mM NaCl to permit VLP formation. The subsequent complex is purified by SEC using Tris pH 8.0 buffer to isolate anellovectors encapsidating mRNA. Anellovector assembly can be further evaluated by in vitro or in vivo readout, for example, by transducing cells and observing the expression of a reporter gene (in the case of mCherry or GFP) or through expression of a gene of interest (such as using an ELISA to detect the expression of a gene such as EPO).

Encapsidation of mRNA Cargo with Modified ORF7 Having mRNA Binding Region

In this example, packaging of mRNA cargo by Anellovirus ORF1 proteins is improved by modifying the Anellovirus ORF1 protein to harbor contact residues known to bind mRNA. For example, the ssDNA contact residues and/or the jellyroll beta strands known to contact ssDNA and/or the N-terminal arginine ARM can be replaced with components of an mRNA binding viral protein (e.g., MS2 coat protein) or other mRNA-binding protein to permit efficient binding and packaging of mRNA. This mRNA-binding chimeric ORF1 could be then treated with 1 M NaCl with 0.1% SDS dissociate oligomers or VLPs into dispersed protein or capsomers. The chimeric ORF1 would then be mixed with mRNA, such as an mRNA that translate a gene of interest such as GFP, mCherry or EPO, and dialyzed against Tris pH 8.0 with 150 mM NaCl to permit VLP formation. The subsequent complex is purified by SEC using Tris pH 8.0 buffer to isolate anellovectors encapsidating mRNA. Anellovector assembly can be further evaluated by in vitro or in vivo readout, for example, by transducing cells and observing the expression of the reporter gene (in the case of mCherry or GFP) or through expression of a gene of interest (such as using an ELISA to detect the expression of a gene such as EPO).

Encapsidation of ssDNA-mRNA Hybrid Cargo with ORF1

In this example, packaging of mRNA cargo by Anellovirus ORF1 proteins is improved by binding the mRNA molecule to ssDNA or modifying the mRNA transgene in such a way that that a section of the backbone would permit binding to the ssDNA contact residues of wildtype Anellovirus ORF1. For example, modified ssDNA that can bind Anellovirus ORF1 by virtue of its sugar-chain backbone but pair with mRNA non-covalently is mixed with the mRNA to produce a synthetic mRNA complex. Alternatively, a synthetic mRNA transgene can be synthesized with a section or sections of the mRNA molecule harboring a DNA backbone permitting binding and encapsidation with Anellovirus ORF1, while retaining the portion of the mRNA that encodes the gene to be delivered. Anellovirus ORF1 could be then treated with 1 M NaCl with 0.1% SDS dissociate oligomers or VLPs into dispersed protein or capsomers. The Anellovirus ORF1 would then be mixed with the synthetic mRNA (complexes or molecules), such as an mRNA that translate a gene of interest such as GFP, mCherry or EPO, and dialyzed against Tris pH 8.0 with 150 mM NaCl to permit VLP formation. The subsequent particle is purified by SEC using Tris pH 8.0 buffer to isolate anellovectors encapsidating mRNA. Anellovector assembly can be further evaluated by in vitro or in vivo readout by transducing cells and observing the expression of the reporter gene (in the case of mCherry or GFP) or through expression of a gene of interest (such as using an ELISA to detect the expression of a gene such as EPO).

Example 13. Exemplary sequences for ORF1 molecules

| Sequence Name | Sequence | SEQ ID NO: |
|---|---|---|
| Ring 2 N-terminal HIS-FLAG-3CProtease-ORF1 | MGSSHHHHHHGSDYKDDDDKSGSLEVLFQGPSGMPYYYRRRRYNYRRPRWYGRGWIRRPFRRRFRRKRRVRPTYTTIPLKQWQPPYKRTCYIKGQDCLIYYSNLRLGMNSTMYEKSIVPVHWPGGGSFSVSMLTLDALYDIHKLCRNWWTSTNQDLPLVRYKGCKITFYQSTFTDYIVRIHTELPANSNKLTYPNTHPLMMMMSKYKHIIPSRQTRRKKKPYTKIFVKPPPQFENKWYFATDLYKIPLLQIHCTACNLQNPFVKPDKLSNNVTLWSLNTISIQNRNMSVDQGQSWPFKILGTQSFYFYFYTGANLPGDTTQIPVADLLPLINPRINRPGQSLNEAKITDHITFTEYKNKFTNYWGNPFNKHIQEHLDMILYSLKSPEAIKNEWTTENMKWNQLNNAGTMALTPFNEPIFTQIQYNPDRDTGEDTQLYLLSNATGTGWDPPGIPELILEGFPLWLIYWGFADFQKNLKKVINIDTNYMLVAKTKFTQKPGTFYLVILNDTFVEGNSPYEKQPLPEDNIKWYPQVQYQLEAQNKLLQTGPFTPNIQGQLSDNISMFYKFYFKWGGSPPKAINVENPAHQIQYPIPRNEHETTSLQSPGEAPESILYSFDYRHGNYTTTALSRISQDWALKDTVSKITEPDRQQLLKQALECLQISEETQEKKEKEVQQLISNLRQQQQLYRERIISLLKDQ | 561 |
| Ring 9 N-terminal HIS-FLAG-3CProtease-ORF1 | MGSSHHHHHHGSDYKDDDDKSGSLEVLFQGPSGMPPYWRQKYYRRRYRPFSWRTRRIIQRRKRWRYRKPRKTYWRRKLRVRKRFYKRKLKKIVLKQFQPKIIRRCTIFGTICLFQGSPERANNNYIQTIYSYVPDKEPGGGGWTLITESLSSLWEDWEHLKNVWTQSNAGLPLVRYGGVTLYFYQSAYTDYIAQVFNCYPMTDTKYTHADSAPNRMLLKKHVIRVPSRETRKKRKPYKRVRVGPPSQMQNKWYFQRDICEIPLIMIAATAVDFRYPFCASDCASNNLTLTCLNPLLFQNQDFDHPSDTQGYFPKPGVYLYSTQRSNKPSSSDCIYLGNTKDNQEGKSASSLMTLKTQKITDWGNPFWHYYIDGSKKIFSYFKPPSQLDSSDFEHMTELAEPMFIQVRYNPERDTGQGNLIYVTENFRGQHWDPPSSDNLKLDGFPLYDMCWGFIDWIEKVHETENLLTNYCFCIRSSAFNEKKTVFIPVDHSFLTGFSPYETPVKSSDQAHWHPQIRFQTKSINDICLTGPGCARSPYGNYMQAKMSYKFHVKWGGCPKTYEKPYDPCSQPNWTIPHNLNETIQIQNPNTCPQTELQEWDWRRDIVTKKAIERIRQHTEPHETLQISTGSKHNPPVHRQTSPWTDSETDSEEEKDQTQEIQIQLNKLRKHQQHLKQQLKQYLKPQNIE | 562 |
| Ring 2 ORF1 with ARG arm of Ring 9 (Ring 291) | MGSSHHHHHHGSDYKDDDDKSGSLEVLFQGPSGMPPYWRQKYYRRRYRPFSWRTRRIIQRRKRWRYRKPRKTYWRRKLRVRKRRVRPTYTTIPLKQWQPPYKRTCYIKGQDCLIYYSNLRLGMNSTMYEKSIVPVHWPGGGSFSVSMLTLDALYDIHKLCRNWWTSTNQDLPLVRYKGCKITFYQSTFTDYIVRIHTELPANSNKLTYPNTHPLMMMMSKYKHIIPSRQTRRKKKPYTKIFVKPPPQFENKWYFATDLYKIPLLQIHCTACNLQNPFVKPDKLSNNVTLWSLNTISIQNRNMSVDQGQSWPFKILGTQSFYFYFYTGANLPGDTTQIPVADLLPLINPRINRPGQSLNEAKITDHITFTEYKNKFTNYWGNPFNKHIQEHLDMILYSLKSPEAIKNEWTTENMKWNQLNNAGTMALTPFNEPIFTQIQYNPDRDTGEDTQLYLLSNATGTGWDPPGIPELILEGFPLWLIYWGFADFQKNLKKVTNIDTNYMLVAKTKFTQKPGTFYLVILNDTFVEGNSPYEKQPLPEDNIKWYPQVQYQLEAQNKLLQTGPFTPNIQGQLSDNISMFYKFYFKWGGSPPKAINVENPAHQIQYPIPRNEHETTSLQSPGEAPESILYSFDYRHGNYTTTALSRISQDWALKDTVSKITEPDRQQLLKQALECLQISEETQEKKEKEVQQLISNLRQQQQLYRERIISLLKDQ | 563 |
| Ring 2 ORF1 with ARG arm and Beta strands 1 + 2 722 epitope of Ring 9 (Ring 292) | MGSSHHHHHHGSDYKDDDDKSGSLEVLFQGPSGMPPYWRQKYYRRRYRPFSWRTRRIIQRRKRWRYRKPRKTYWRRKLRVRKRFYKRKLKKIVLKQFQPKIIRRCTIFGTICLFQGSNLRLGMNSTMYEKSIVPVHWPGGGSFSVSMLTLDALYDIHKLCRNWWTSTNQDLPLVRYKGCKITFYQSTFTDYIVRIHTELPANSNKLTYPNTHPLMMMMSKYKHIIPSRQTRRKKKPYTKIFVKPPPQFENKWYFATDLYKIPLLQIHCTACNLQNPFVKPDKLSNNVTLWSLNTISIQNRNMSVDQGQSWPFKILGTQSFYFYFYTGANLPGDTTQIPVADLLPLTNPRINRPGQSLNEAKITDHITFTEYKNKFTNYWGNPFNKHIQEHLDMILYSLKSPEAIKNEWTTENMKWNQLNNAGTMALTPFNEPIFTQIQYNPDRDTGEDTQLYLLSNATGTGWDPPGIPELILEGFPLWLIYWGFADFQKNLKKVTNIDTNYMLVAKTKFTQKPGTFYLVILNDTFVEGNSPYEKQPLPEDNIKWYPQVQYQLEAQNKLLQTGPFTPNIQGQLSDNISMFYKFYFKWGGSPPKAINVENPAHQIQYPIPRNEHETTSLQSPGEAPESILYSFDYRHGNYTTTALSRISQDWALKDTVSKITEPDRQQLLKQALECLQISEETQEKKEKEVQQLISNLRQQQQLYRERIISLLKDQ | 564 |

-continued

Example 13. Exemplary sequences for ORF1 molecules

| Sequence Name | Sequence | SEQ ID NO: |
|---|---|---|
| Ring 9 with LYS/HIS mutations in ARG arm and first beta strand | MGSSHHHHHHGSDYKDDDDKSGSLEVLFQGPSGMPPYWRQK<br>YYRRRYRPFSWRTRRIIQRRHRWRYRKPRHTYWRRHLRVRH<br>RFYHRHLHHIVLKQFQPKIIRRCTIFGTICLFQGSPERANN<br>NYIQTIYSYVPDKEPGGGGWTLITESLSSLWEDWEHLKNVW<br>TQSNAGLPLVRYGGVTLYFYQSAYTDYIAQVFNCYPMTDTK<br>YTHADSAPNRMLLKKHVIRVPSRETRKKRKPYKRVRVGPPS<br>QMQNKWYFQRDICEIPLIMIAATAVDFRYPFCASDCASNNL<br>TLTCLNPLLFQNQDFDHPSDTQGYFPKPGVYLYSTQRSNKP<br>SSSDCIYLGNTKDNQEGKSASSLMTLKTQKITDWGNPFWHY<br>YIDGSKKIFSYFKPPSQLDSSDFEHMTELAEPMFIQVRYNP<br>ERDTGQGNLIYVTENFRGQHWDPPSSDNLKLDGFPLYDMCW<br>GFIDWIEKVHETENLLTNYCFCIRSSAFNEKKTVFIPVDHS<br>FLTGFSPYETPVKSSDQAHWHPQIRFQTKSINDICLTGPGC<br>ARSPYGNYMQAKMSYKFHVKWGGCPKTYEKPYDPCSQPNWT<br>IPHNLNETIQIQNPNTCPQTELQEWDWRRDIVTKKAIERIR<br>QHTEPHETLQISTGSKHNPPVHRQTSPWTDSETDSEEEKDQ<br>TQEIQIQLNKLRKHQQHLKQQLKQYLKPQNIE | 565 |
| Ring 9 with ARG arm of BFDV | MGSSHHHHHHGSDYKDDDDKSGSLEVLFQGPSGMWGTSNCA<br>CAKFQIRRRYARPYRRRHIRRYRRRRRHFRRRRFTTNRRKR<br>FYKRKLKKIVLKQFQPKIIRRCTIFGTICLFQGSPERANNN<br>YIQTIYSYVPDKEPGGGGWTLITESLSSLWEDWEHLKNVWT<br>QSNAGLPLVRYGGVTLYFYQSAYTDYIAQVFNCYPMTDTKY<br>THADSAPNRMLLKKHVIRVPSRETRKKRKPYKRVRVGPPSQ<br>MQNKWYFQRDICEIPLIMIAATAVDFRYPFCASDCASNNLT<br>LTCLNPLLFQNQDFDHPSDTQGYFPKPGVYLYSTQRSNKPS<br>SSDCIYLGNTKDNQEGKSASSLMTLKTQKITDWGNPFWHYY<br>IDGSKKIFSYFKPPSQLDSSDFEHMTELAEPMFIQVRYNPE<br>RDTGQGNLIYVTENFRGQHWDPPSSDNLKLDGFPLYDMCWG<br>FIDWIEKVHETENLLTNYCFCIRSSAFNEKKTVFIPVDHSF<br>LTGFSPYETPVKSSDQAHWHPQIRFQTKSINDICLTGPGCA<br>RSPYGNYMQAKMSYKFHVKWGGCPKTYEKPYDPCSQPNWTI<br>PHNLNETIQIQNPNTCPQTELQEWDWRRDIVTKKAIERIRQ<br>HTEPHETLQISTGSKHNPPVHRQTSPWTDSETDSEEEKDQT<br>QEIQIQLNKLRKHQQHLKQQLKQYLKPQNIE | 566 |
| Ring 9 with beta strands Fand G of BFDV capsid protein | MGSSHHHHHHGSDYKDDDDKSGSLEVLFQGPSGMPPYWRQK<br>YYRRRYRPFSWRTRRIIQRRKRWRYRKPRKTYWRRKLRVRK<br>RFYKRKLKKIVLKQFQPKIIRRCTIFGTICLFQGSPERANN<br>NYIQTIYSYVPDKEPGGGGWTLITESLSSLWEDWEHLKNVW<br>TQSNAGLPLVRYGGVTLYFYQSAYTDYIAQVENCYPMTDTK<br>YTHADSAPNRMLLKKHAKKWFSRETRKKRKPGFKRLLGPPS<br>QMQNKWYFQRDICEIPLIMIAATAVDFRYPFCASDCASNNL<br>TLTCLNPLLFQNQDFDHPSDTQGYFPKPGVYLYSTQRSNKP<br>SSSDCIYLGNTKDNQEGKSASSLMTLKTQKITDWGNPFWHY<br>YIDGSKKIFSYFKPPSQLDSSDFEHMTELAEPMFIQVRYNP<br>ERDTGQGNLIYVTENFRGQHWDPPSSDNLKLDGFPLYDMCW<br>GFIDWIEKVHETENLLTNYCFCIRSSAFNEKKTVFIPVDHS<br>FLTGFSPYETPVKSSDQAHWHPQIRFQTKSINDICLTGPGC<br>ARSPYGNYMQAKMSYKFHVKWGGCPKTYEKPYDPCSQPNWT<br>IPHNLNETIQIQNPNTCPQTELQEWDWRRDIVTKKAIERIR<br>QHTEPHETLQISTGSKHNPPVHRQTSPWTDSETDSEEEKDQ<br>TQEIQIQLNKLRKHQQHLKQQLKQYLKPQNIE | 567 |
| Ring 2 with beta C of Ring 9 | MGSSHHHHHHGSDYKDDDDKSGSLEVLFQGPSGMPYYYRRR<br>RYNYRRPRWYGRGWIRRPFRRRFRRKRRVRPTYTTIPLKQW<br>QPPYKRRCTIFGTICLFQGSNLRLGMNSTMYEKSIVPVHWP<br>GGGSFSVSMLTLDALYDIHKLCRNWWTSTNQDLPLVRYKGC<br>KITFYQSTFTDYIVRIHTELPANSNKLTYPNTHPLMMMMSK<br>YKHIIPSRQTRRKKKPYTKIFVKPPPQFENKWYFATDLYKI<br>PLLQIHCTACNLQNPFVKPDKLSNNVTLWSLNTISIQNRNM<br>SVDQGQSWPFKILGTQSFYFYFYTGANLPGDTTQIPVADLL<br>PLINPRINRPGQSLNEAKITDHITFTEYKNKFTNYWGNPEN<br>KHIQEHLDMILYSLKSPEAIKNEWTTENMKWNQLNNAGTMA<br>LTPFNEPIFTQIQYNPDRDTGEDTQLYLLSNATGTGWDPPG<br>IPELILEGFPLWLIYWGFADFQKNLKKVTNIDTNYMLVAKT<br>KFTQKPGTFYLVILNDTFVEGNSPYEKQPLPEDNIKWYPQV<br>QYQLEAQNKLLQTGPFTPNIQGQLSDNISMFYKFYFKWGGS<br>PPKAINVENPAHQIQYPIPRNEHETTSLQSPGEAPESILYS<br>FDYRHGNYTTTALSRISQDWALKDTVSKITEPDRQQLLKQA<br>LECLQISEETQEKKEKEVQQLISNLRQQQQLYRERIISLLK<br>DQ | 568 |

-continued

| Example 13. Exemplary sequences for ORF1 molecules | | |
|---|---|---|
| Sequence Name | Sequence | SEQ ID NO: |
| Ring 2 with linker 1 of Ring 9 | MGSSHHHHHHGSDYKDDDDKSGSLEVLFQGPSGMPYYYRRR RYNYRRPRWYGRGWIRRPFRRRFRRKRRVRPTYTTIPLKQW QPPYKRTCYIKGQDCLIYYSPERANNNYIQTIYSYVPDKEP GGGGWTLITESLSSLWEDWEHLKNVWTQSNAGLPLVRYKGC KITFYQSTFTDYIVRIHTELPANSNKLTYPNTHPLMMMMSK YKHIIPSRQTRRKKKPYTKIFVKPPPQFENKWYFATDLYKI PLLQIHCTACNLQNPFVKPDKLSNNVTLWSLNTISIQNRNM SVDQGQSWPFKILGTQSFYFYFYTGANLPGDTTQIPVADLL PLINPRINRPGQSLNEAKITDHITFTEYKNKFTNYWGNPFN KHIQEHLDMILYSLKSPEAIKNEWTTENMKWNQLNNAGTMA LTPFNEPIFTQIQYNPDRDIGEDTQLYLLSNATGTGWDPPG IPELILEGFPLWLIYWGFADFQKNLKKVINIDTNYMLVAKT KFTQKPGTFYLVILNDTFVEGNSPYEKQPLPEDNIKWYPQV QYQLEAQNKLLQTGPFTPNIQGQLSDNISMFYKFYFKWGGS PPKAINVENPAHQIQYPIPRNEHETTSLQSPGEAPESILYS FDYRHGNYTTTALSRISQDWALKDTVSKITEPDRQQLLKQA LECLQISEETQEKKEKEVQQLISNLRQQQQLYRERIISLLK DQ | 569 |
| Ring 2 with beta strand D of Ring 9 | MGSSHHHHHHGSDYKDDDDKSGSLEVLFQGPSGMPYYYRRR RYNYRRPRWYGRGWIRRPFRRRFRRKRRVRPTYTTIPLKQW QPPYKRTCYIKGQDCLIYYSNLRLGMNSTMYEKSIVPVHWP GGGSFSVSMLTLDALYDIHKLCRNWWTSTNQDLPLVRYGGV TLYFYQSTFTDYIVRIHTELPANSNKLTYPNTHPLMMMMSK YKHIIPSRQTRRKKKPYTKIFVKPPPQFENKWYFATDLYKI PLLQIHCTACNLQNPFVKPDKLSNNVTLWSLNTISIQNRNM SVDQGQSWPFKILGTQSFYFYFYTGANLPGDTTQIPVADLL PLINPRINRPGQSLNEAKITDHITFTEYKNKFTNYWGNPFN KHIQEHLDMILYSLKSPEAIKNEWTTENMKWNQLNNAGTMA LTPFNEPIFTQIQYNPDRDTGEDTQLYLLSNATGTGWDPPG IPELILEGFPLWLIYWGFADFQKNLKKVTNIDTNYMLVAKT KFTQKPGTFYLVILNDTFVEGNSPYEKQPLPEDNIKWYPQV QYQLEAQNKLLQTGPFTPNIQGQLSDNISMFYKFYFKWGGS PPKAINVENPAHQIQYPIPRNEHETTSLQSPGEAPESILYS FDYRHGNYTTTALSRISQDWALKDTVSKITEPDRQQLLKQA LECLQISEETQEKKEKEVQQLISNLRQQQQLYRERIISLLK DQ | 570 |
| Ring 2 with linker 2 of Ring 9 | MGSSHHHHHHGSDYKDDDDKSGSLEVLFQGPSGMPYYYRRR RYNYRRPRWYGRGWIRRPFRRRFRRKRRVRPTYTTIPLKQW QPPYKRTCYIKGQDCLIYYSNLRLGMNSTMYEKSIVPVHWP GGGSFSVSMLTLDALYDIHKLCRNWWTSTNQDLPLVRYKGC KITFYQSTFTDYIVRIHNCYPMTDTKYTHADSAPNRMLLKK HKHIIPSRQTRRKKKPYTKIFVKPPPQFENKWYFATDLYKI PLLQIHCTACNLQNPFVKPDKLSNNVTLWSLNTISIQNRNM SVDQGQSWPFKILGTQSFYFYFYTGANLPGDTTQIPVADLL PLINPRINRPGQSLNEAKITDHITFTEYKNKFTNYWGNPFN KHIQEHLDMILYSLKSPEAIKNEWTTENMKWNQLNNAGTMA LTPFNEPIFTQIQYNPDRDTGEDTQLYLLSNATGTGWDPPG IPELILEGFPLWLIYWGFADFQKNLKKVINIDTNYMLVAKT KFTQKPGTFYLVILNDTFVEGNSPYEKQPLPEDNIKWYPQV QYQLEAQNKLLQTGPFTPNIQGQLSDNISMFYKFYFKWGGS PPKAINVENPAHQIQYPIPRNEHETTSLQSPGEAPESILYS FDYRHGNYTTTALSRISQDWALKDTVSKITEPDRQQLLKQA LECLQISEETQEKKEKEVQQLISNLRQQQQLYRERIISLLK DQ | 571 |
| Ring 2 with beta strand G DNA binding of Ring 9 | MGSSHHHHHHGSDYKDDDDKSGSLEVLFQGPSGMPYYYRRR RYNYRRPRWYGRGWIRRPFRRRFRRKRRVRPTYTTIPLKQW QPPYKRTCYIKGQDCLIYYSNLRLGMNSTMYEKSIVPVHWP GGGSFSVSMLTLDALYDIHKLCRNWWTSTNQDLPLVRYKGC KITFYQSTFTDYIVRIHTELPANSNKLTYPNTHPLMMMMSK YKHIIPSRQTRRKKKPYKRVRVKPPPQFENKWYFATDLYKI PLLQIHCTACNLQNPFVKPDKLSNNVTLWSLNTISIQNRNM SVDQGQSWPFKILGTQSFYFYFYTGANLPGDTTQIPVADLL PLTNPRINRPGQSLNEAKITDHITFTEYKNKFTNYWGNPFN KHIQEHLDMILYSLKSPEAIKNEWTTENMKWNQLNNAGTMA LTPFNEPIFTQIQYNPDRDIGEDTQLYLLSNATGTGWDPPG IPELILEGFPLWLIYWGFADFQKNLKKVINIDTNYMLVAKT KFTQKPGTFYLVILNDTFVEGNSPYEKQPLPEDNIKWYPQV QYQLEAQNKLLQTGPFTPNIQGQLSDNISMFYKFYFKWGGS PPKAINVENPAHQIQYPIPRNEHETTSLQSPGEAPESILYS | 572 |

-continued

| Example 13. Exemplary sequences for ORF1 molecules | | |
|---|---|---|
| Sequence Name | Sequence | SEQ ID NO: |
| | FDYRHGNYTTTALSRISQDWALKDTVSKITEPDRQQLLKQA LECLQISEETQEKKEKEVQQLISNLRQQQQLYRERIISLLK DQ | |
| Ring 2 with beta strand F interprotomer contact of Ring 9 | MGSSHHHHHHGSDYKDDDDKSGSLEVLFQGPSGMPYYYRRR RYNYRRPRWYGRGWIRRPFRRRFRRKRRVRPTYTTIPLKQW QPPYKRTCYIKGQDCLIYYSNLRLGMNSTMYEKSIVPVHWP GGGSFSVSMLTLDALYDIHKLCRNWWTSTNQDLPLVRYKGC KITFYQSTFTDYIVRIHTELPANSNKLTYPNTHPLMMMMSK HVIRVPSRQTRRKKKPYTKIFVKPPPQFENKWYFATDLYKI PLLQIHCTACNLQNPFVKPDKLSNNVTLWSLNTISIQNRNM SVDQGQSWPFKILGTQSFYFYFYTGANLPGDTTQIPVADLL PLINPRINRPGQSLNEAKITDHITFTEYKNKFTNYWGNPFN KHIQEHLDMILYSLKSPEAIKNEWTTENMKWNQLNNAGTMA LTPFNEPIFTQIQYNPDRDTGEDTQLYLLSNATGTGWDPPG IPELILEGFPLWLIYWGFADFQKNLKKVINIDTNYMLVAKT KFTQKPGTFYLVILNDTFVEGNSPYEKQPLPEDNIKWYPQV QYQLEAQNKLLQTGPFTPNIQGQLSDNISMFYKFYFKWGGS PPKAINVENPAHQIQYPIPRNEHETTSLQSPGEAPESILYS FDYRHGNYTTTALSRISQDWALKDTVSKITEPDRQQLLKQA LECLQISEETQEKKEKEVQQLISNLRQQQQLYRERIISLLK DQ | 573 |
| Ring 2 ORF1 with strand H and I with C-terminal fragment of Ring 9 | MGSSHHHHHHGSDYKDDDDKSGSLEVLFQGPSGMPYYYRRR RYNYRRPRWYGRGWIRRPFRRRFRRKRRVRPTYTTIPLKQW QPPYKRTCYIKGQDCLIYYSNLRLGMNSTMYEKSIVPVHWP GGGSFSVSMLTLDALYDIHKLCRNWWTSTNQDLPLVRYKGC KITFYQSTFTDYIVRIHTELPANSNKLTYPNTHPLMMMMSK YKHIIPSRQTRRKKKPYTKIFVKPPPQFENKWYFATDLYKI PLIMIAATAVDFRYPFCASDCASNNLTLTCLNPLLFQNQDE DHPSDTQGYFPKPGVYLYSTQRSNKPSSSDCIYLGNTKDNQ EGKSASSLMTLKTQKITDWGNPFWHYYIDGSKKIFSYFKPP SQLDSSDFEHMTELAEPMFIQVRYNPERDTGQGNLIYVTEN FRGQHWDPPSSDNLKLDGFPLYDMCWGFIDWIEKVHETENL LTNYCFCIRSSAFNEKKTVFIPVDHSFLTGFSPYETPVKSS DQAHWHPQIRFQTKSINDICLTGPGCARSPYGNYMQAKMSY KFHVKWGGCPKTYEKPYDPCSQPNWTIPHNLNETIQIQNPN TCPQTELQEWDWRRDIVTKKAIERIRQHTEPHETLQISTGS KHNPPVHRQTSPWTDSETDSEEEKDQTQEIQIQLNKLRKHQ QHLKQQLKQYLKPQNIE | 574 |
| Ring 2 ORF1 with strand I and C-terminal fragment of Ring 9 | MGSSHHHHHHGSDYKDDDDKSGSLEVLFQGPSGMPYYYRRR RYNYRRPRWYGRGWIRRPFRRRFRRKRRVRPTYTTIPLKQW QPPYKRTCYIKGQDCLIYYSNLRLGMNSTMYEKSIVPVHWP GGGSFSVSMLTLDALYDIHKLCRNWWTSTNQDLPLVRYKGC KITFYQSTFTDYIVRIHTELPANSNKLTYPNTHPLMMMMSK YKHIIPSRQTRRKKKPYTKIFVKPPPQFENKWYFATDLYKI PLLQIHCTACNLQNPFVKPDKLSNNLTLTCLNPLLFQNQDE DHPSDTQGYFPKPGVYLYSTQRSNKPSSSDCIYLGNTKDNQ EGKSASSLMTLKTQKITDWGNPFWHYYIDGSKKIFSYFKPP SQLDSSDFEHMTELAEPMFIQVRYNPERDIGQGNLIYVTEN FRGQHWDPPSSDNLKLDGFPLYDMCWGFIDWIEKVHETENL LTNYCFCIRSSAFNEKKTVFIPVDHSFLTGFSPYETPVKSS DQAHWHPQIRFQTKSINDICLTGPGCARSPYGNYMQAKMSY KFHVKWGGCPKTYEKPYDPCSQPNWTIPHNLNETIQIQNPN TCPQTELQEWDWRRDIVTKKAIERIRQHTEPHETLQISTGS KHNPPVHRQTSPWTDSETDSEEEKDQTQEIQIQLNKLRKHQ QHLKQQLKQYLKPQNIE | 575 |

Example 14: Production of Anellovirus Proteins in a Baculovirus Expression System In this example, a baculovirus expression system from Thermofisher Scientific (Cat. no. A38841) was adapted for expression of Anellovirus proteins. Briefly, a gene of interest (e.g., a gene encoding an Anellovirus ORF as described herein) was cloned into the pFastBac plasmid, which was then transformed into DH10Bac *E. coli* cells harboring a baculovirus genome. The transformants were grown on indicator plates according to the manufacturer's instructions and white colonies were selected for liquid culture and extraction of bacmid DNA. Recombination of the Anellovirus ORFs into the bacmids was validated by PCR.

Validated bacmid constructs showing successful recombination of the anellovirus ORF gene were then transfected into ExpiSf9 insect cells. The cells were incubated in a 27° C. non-humidified, non-$CO_2$ atmosphere incubator on an orbital shaker set at 125 rpm. After 72 hours post-transfection, Passage 0 stock (P0) recombinant baculovirus was harvested from the supernatant.

ExpiSf9 cells were infected using 25-100 μL of P0 baculovirus stock to make Passage 1 (P1) baculovirus for protein production. After 96 hours (approx. 4 days) post-infection, the supernatant was collected to obtain P1 baculovirus.

P1 recombinant baculovirus was titered by preparing five 10-fold serial dilutions of the test virus in fresh ExpiSf CD Medium in 1200 μL total volume. 800 μL of Expisf9 cells at $1.25\times10^6$ viable cells/mL were seeded in a deep well plate and 1000 μL of the different dilutions of the test virus were added to each well. One well was setup as a negative control. Plate was then incubated overnight at 27° C. in a non-humidified incubator on a shaking platform at 225±5 rpm. After approx. 14-16 hours of incubation, the plate was removed from the incubator and everything was transferred to microcentrifuge tubes and spun at 300×g for 5 minutes. Supernatant was aspirated and each cell pellet was resuspended in 100 μL of dilution buffer (PBS+2 Fetal Bovine Serum) containing Anti-Baculovirus Envelope gp64 APC antibody at a final concentration of 0.15 g/mL. Tubes were incubated for 30 mins at room temperature. Samples were then washed with 1 mL PBS followed by a 10 m centrifuge spin at 300×g. Supernatant was aspirated and cell pellet was resuspended in 1 mL Dilution Buffer. Samples were analyzed on a flow cytometer using the following parameters: red laser excitation: 633-647 nm; emission: 660 nm. Samples with different viral dilutions expressing percent positive gp64 were noted and used to calculate the viral titer.

For this and following examples, a series of recombinant bacmids and baculovirus vectors was produced for expression using the method described above. As shown in Table E2 below, various ORFs from LY2, tth8, and other anellovirus strains were cloned into bacmids. The ORFs were either tagged with an N-terminal His-tag with or without a human rhinovirus 3C (HRV 3C) proteolytic cleavage site, a C-terminal His-tag, or were left untagged, as indicated.

TABLE E2

Recombinant bacmid constructs produced.

| Construct #/name | Strain | Ring # | ORF | Tag type | Tag position | pFastBac | Bacmid | Baculovirus | Made |
|---|---|---|---|---|---|---|---|---|---|
| tth8 ORF1 | tth8 | Ring1 | ORF1 | no-tag | NA | Yes | Yes | No | in-house |
| tth8 ORF1 N-His | tth8 | Ring1 | ORF1 | 6xHis | N-ter | Yes | Yes | Yes | in-house |
| tth8 ORF1 C-His | tth8 | Ring1 | ORF1 | 6xHis | C-ter | Yes | Yes | Yes | in-house |
| tth8 ORF2 | tth8 | Ring1 | ORF2 | no-tag | NA | Yes | Yes | Yes | in-house |
| tth8 ORF2 C-His | tth8 | Ring1 | ORF2 | 6xHis | C-ter | Yes | Yes | Yes | in-house |
| tth8 ORF1/1 | tth8 | Ring1 | ORF1/1 | no-tag | NA | Yes | Yes | Yes | in-house |
| tth8 ORF1/1 C-His | tth8 | Ring1 | ORF1/1 | 6xHis | C-ter | Yes | Yes | Yes | in-house |
| tth8 ORF1/2 | tth8 | Ring1 | ORF1/2 | no-tag | NA | Yes | Yes | Yes | in-house |
| tth8 ORF1/2 C-His | tth8 | Ring1 | ORF1/2 | 6xHis | C-ter | Yes | Yes | Yes | in-house |
| tth8 ORF2/2 | tth8 | Ring1 | ORF2/2 | no-tag | NA | Yes | Yes | Yes | in-house |
| tth8 ORF2/2 C-His | tth8 | Ring1 | ORF2/2 | 6xHis | C-ter | Yes | Yes | Yes | in-house |
| tth8 ORF2/3 | tth8 | Ring1 | ORF2/3 | no-tag | NA | Yes | Yes | Yes | in-house |
| tth8 ORF2/3 C-His | tth8 | Ring1 | ORF2/3 | 6xHis | C-ter | Yes | Yes | Yes | in-house |
| tth8 FullORF | tth8 | Ring1 | FullORF | no-tag | NA | Yes | Yes | Yes | in-house |
| tth8 FullORF C-His | tth8 | Ring1 | FullORF | 6xHis | C-ter | Yes | Yes | Yes | in-house |
| tth8 ORF2 C-His | tth8 | Ring1 | ORF2/ORF1 | 6xHis | C-ter | Yes | Yes | Yes | in-house |
| Ring 3.1 ORF1 | 6B.CD8. contig3 | Ring3.1 | ORF1 | no-tag | NA | No | No | No | in-house |
| Ring 3.1 ORF1 C-His | 6B.CD8. contig3 | Ring3.1 | ORF1 | 6xHis | C-ter | Yes | Yes | Yes | in-house |
| Ring 3.1 ORF2 | 6B.CD8. contig3 | Ring3.1 | ORF2 | no-tag | NA | No | No | No | in-house |
| Ring 3.1 ORF2 C-His | 6B.CD8. contig3 | Ring3.1 | ORF2 | 6xHis | C-ter | Yes | Yes | Yes | in-house |
| Ring 3.1 ORF2/ORF1 C-His | 6B.CD8. contig3 | Ring3.1 | ORF2/ORF1 | 6xHis | C-ter | Yes | Yes | Yes | in-house |
| LY2 FullORF | LY2 | Ring2 | FullORF | no-tag | NA | Yes | Yes | No | in-house |
| LY2 FullORF N-His | LY2 | Ring2 | FullORF | 6xHis | N-ter | Yes | Yes | Yes | in-house |
| LY2 FullORF C-His | LY2 | Ring2 | FullORF | 6xHis | C-ter | Yes | Yes | Yes | in-house |
| LY2 ORF1 | LY2 | Ring2 | ORF1 | no-tag | NA | Yes | Yes | No | in-house |
| LY2 ORF1 N-His | LY2 | Ring2 | ORF1 | 6xHis | N-ter | Yes | Yes | Yes | in-house |
| LY2 ORF1 C-His | LY2 | Ring2 | ORF1 | 6xHis | C-ter | Yes | Yes | Yes | in-house |
| LY2 ORF1(dR) | LY2 | Ring2 | ORF1 (delta-arginine rich region) | no-tag | NA | Yes | No | No | in-house |
| LY2 ORF1(dR) N-His | LY2 | Ring2 | ORF1 (delta-arginine rich region) | 6xHis | N-ter | Yes | Yes | Yes | in-house |

TABLE E2-continued

Recombinant bacmid constructs produced.

| Construct #/name | Strain | Ring # | ORF | Tag type | Tag position | pFastBac | Bacmid | Baculovirus | Made |
|---|---|---|---|---|---|---|---|---|---|
| LY2 ORF1(dR) C-His | LY2 | Ring2 | ORF1 (delta-arginine rich region) | 6xHis | C-ter | Yes | Yes | Yes | in-house |
| LY2 ORF1/1 | LY2 | Ring2 | ORF1/1 | no-tag | NA | Yes | Yes | No | in-house |
| LY2 ORF1/1 N-His | LY2 | Ring2 | ORF1/1 | 6xHis | N-ter | Yes | Yes | Yes | in-house |
| LY2 ORF1/1 C-His | LY2 | Ring2 | ORF1/1 | 6xHis | C-ter | Yes | Yes | Yes | in-house |
| LY2 ORF1/2 | LY2 | Ring2 | ORF1/2 | no-tag | NA | Yes | Yes | No | in-house |
| LY2 ORF1/2 N-His | LY2 | Ring2 | ORF1/2 | 6xHis | N-ter | Yes | Yes | Yes | in-house |
| LY2 ORF1/2 C-His | LY2 | Ring2 | ORF1/2 | 6xHis | C-ter | Yes | Yes | Yes | in-house |
| LY2 ORF2 | LY2 | Ring2 | ORF2 | no-tag | NA | Yes | Yes | No | in-house |
| LY2 ORF2 N-His | LY2 | Ring2 | ORF2 | 6xHis | N-ter | Yes | Yes | Yes | in-house |
| LY2 ORF2 C-His | LY2 | Ring2 | ORF2 | 6xHis | C-ter | Yes | Yes | Yes | in-house |
| LY2 ORF2/2 | LY2 | Ring2 | ORF2/2 | no-tag | NA | Yes | Yes | No | in-house |
| LY2 ORF2/2 N-His | LY2 | Ring2 | ORF2/2 | 6xHis | N-ter | Yes | Yes | Yes | in-house |
| LY2 ORF2/2 C-His | LY2 | Ring2 | ORF2/2 | 6xHis | C-ter | Yes | Yes | Yes | in-house |
| LY2 ORF2/3 | LY2 | Ring2 | ORF2/3 | no-tag | NA | Yes | Yes | No | in-house |
| LY2 ORF2/3 N-His | LY2 | Ring2 | ORF2/3 | 6xHis | N-ter | Yes | Yes | Yes | in-house |
| LY2 ORF2/3 C-His | LY2 | Ring2 | ORF2/3 | 6xHis | C-ter | Yes | Yes | Yes | in-house |
| LY2 ORF2/ORF1 C-His | LY2 | Ring2 | ORF2/ORF1 | 6xHis | C-ter | Yes | Yes | Yes | in-house |
| LY2 ORF1 HisE354 | LY2 | Ring2 | ORF1 | 6xHis | After E354 | Yes | Yes | No | in-house |
| LY2 ORF1 HisN299 | LY2 | Ring2 | ORF1 | 6xHis | After N299 | Yes | Yes | No | in-house |
| LY2 ORF1 HisL267 | LY2 | Ring2 | ORF1 | 6xHis | After L267 | Yes | Yes | No | in-house |
| tth8 ORF1 (JA20 HVR) | tth8 | Ring1 | ORF1 (with JA20's hypervariable region) | 6xHis | C-ter | Yes | No | No | in-house |
| tth8 ORF1 (TJN02 HVR) | tth8 | Ring1 | ORF1 (with TJN02's hypervariable region) | 6xHis | C-ter | Yes | No | No | in-house |
| tth8 ORF1 (TTV16 (HVR) | tth8 | Ring1 | ORF1 (with TTV16's hypervariable region) | 6xHis | C-ter | Yes | No | No | in-house |
| Ring2 ORF1 (CodOpt) | LY2 | Ring2 | ORF1 (codon optimized) | no-tag | NA | Yes | Yes | Yes | Medigen |
| Ring2 ORF1 (CodOpt) HRV3C-6His | LY2 | Ring2 | ORF1 (codon optimized) | 6xHis | C-ter | Yes | Yes | Yes | Medigen |
| Ring4 ORF1 (CodOpt) | 6B.CD8. contig2 | Ring4 | ORF1 (codon optimized) | no-tag | NA | Yes | Yes | Yes | Medigen |
| RIng4 ORF1 (CodOpt) HRV3C-6His | 6B.CD8. contig2 | Ring4 | ORF1 (codon optimized) | 6xHis | C-ter | Yes | Yes | Yes | Medigen |
| RIng5.2 ORF1 (CodOpt) | CT30F | Ring5.2 | ORF1 (codon optimized) | no-tag | NA | Yes | Yes | Yes | Medigen |
| Ring5.2 ORF1 (CodOpt) HRV3C-6His | CT30F | RIng5.2 | ORF1 (codon optimized) | 6xHis | C-ter | Yes | Yes | Yes | Medigen |
| Ring6 ORF1 (CodOpt) | 190783.3 | Ring6 | ORF1 (codon optimized) | no-tag | NA | Yes | Yes | Yes | Medigen |
| Ring6 ORF1 (CodOpt) HRV3C-6His | 190783.3 | Ring6 | ORF1 (codon optimized) | 6xHis | C-ter | Yes | Yes | Yes | Medigen |
| Ring1 ORF1 (CosOpt) His | tth8 | Ring1 | ORF1 (codon optimized) | 6xHis | C-ter | Yes | Yes | Yes | Medigen |
| Rig3.1 ORF1 (CodOpt) His | 6B.CD8. contig3 | Ring3.1 | ORF1 (codon optimized) | 6xHis | C-ter | Yes | Yes | Yes | Medigen |
| Ring7 ORF1 (CodOpt) His | 190783.4 | Ring7 | ORF1 (codon optimized) | 6xHis | C-ter | Yes | Yes | Yes | Medigen |
| Ring2 (CodOpt) N-His | LY2 | Ring2 | ORF1 (codon optimized) | 6xHis | N-ter | Yes | Yes | Yes | Medigen |
| Ring2 (CodOpt) N-His (PS) | LY2 | Ring2 | ORF1 (codon optimized) | 6xHis-PreScision Protease recognition sequence) | N-ter | Yes | Yes | Yes | Medigen |
| Ring2 tandem | LY2 | Ring2 | 2x whole genome (without Polyhedrin promoter) | no-tag | NA | Yes | Yes | Yes | Medigen |

TABLE E2-continued

| Recombinant bacmid constructs produced. | | | | | | | | | |
|---|---|---|---|---|---|---|---|---|---|
| Construct #/name | Strain | Ring # | ORF | Tag type | Tag position | pFastBac | Bacmid | Baculovirus | Made |
| WTLY2 | LY2 | Ring2 | whole genome | no-tag | NA | Yes | Yes | Yes | in-house |
| WTtth8 | tth8 | Ring1 | whole genome | no-tag | NA | Yes | Yes | Yes | in-house |
| WTtth8 (Reverse) | tth8 | Ring1 | whole genome (with Reversed 5' Polyhedrin promoter) | no-tag | NA | Yes | Yes | Yes | in-house |
| LoxPWTLY2 | LY2 | Ring2 | LoxP-whole genome-LoxP | no-tag | NA | Yes | Yes | Yes | in-house |
| Cre-R | NA | NA | Cre recombinase | no-tag | NA | Yes | Yes | Yes | in-house |

"FullORF" = Full ORF-containing region, with noncoding regions removed; ORF2/3 tagged.

Figure 8:
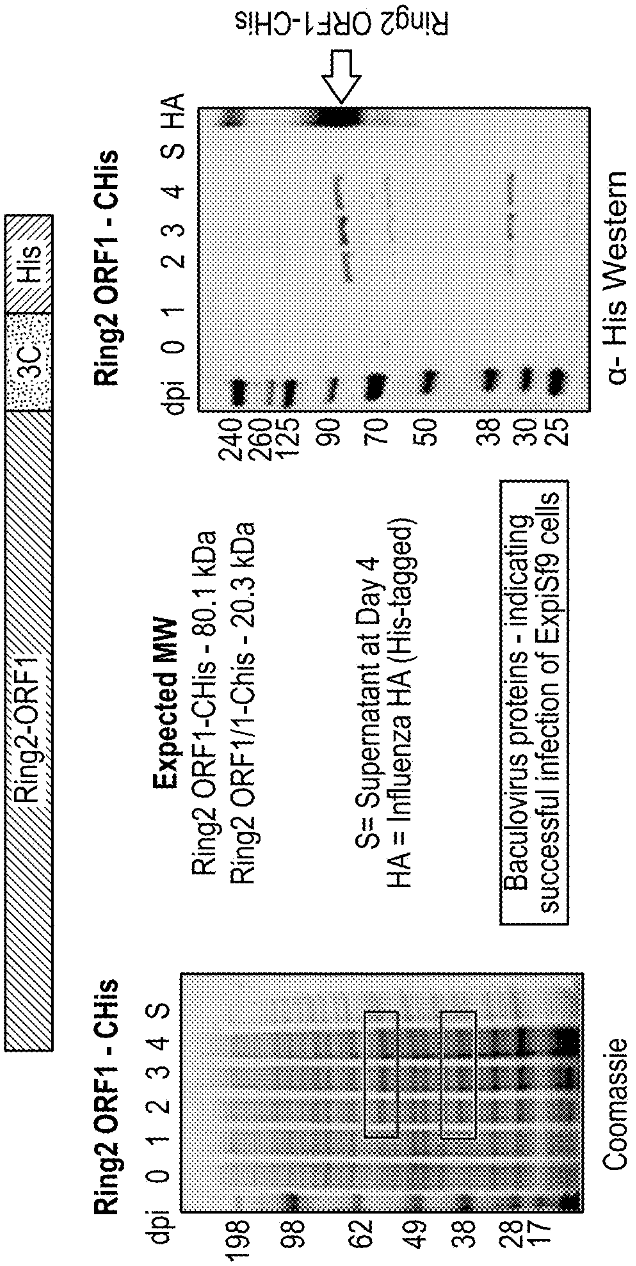
FIG. 8 depicts expression of Ring2 ORF1 with a C-terminal His tag in insect cells.

On the day before infection, ExpiSf9 cells were seeded at $5\times10^6$ cells/mi in 25 ml room temperature ExpiSf9 CD Medium in 125 ml Nalgene Single-Use PETG Erlenmeyer Plain Bottom Flask [Thermofisher Scientific Catalog no: 4115-0125]. The cell viability was monitored to ensure that it was maintained at or above 950%, 100 μL of ExpiSf Enhancer solution was added to the cells in a dropwise manner. Cells were incubated with shaking overnight in a 27° C. non-humidified, air-regulated, non-$CO_2$ atmosphere incubator using an orbital shaker at 125±5 rpm. On Day 1, approximately 18-24 hours after adding ExpiSf Enhancer, cells were infected with the indicated baculovirus at a multiplicity of infection (MOI) of 5 and incubated under the same conditions. Cells were harvested 72 hours post infection and viability was found to range between 60 and 800%. To analyze samples, cells were lysed by adding 1× Bolt LDS sample buffer [Invitrogen Catalog No.: B0007] and 1× Bolt reducing agent [Invitrogen Catalog No.: B0009] and sonicating for 2.5 minutes. As shown in FIG. 8, C-His-tagged LY2 ORF1 was successfully expressed in infected ExpiSf9 cells by day 2 post-infection as determined by western blotting using an anti-poly-histidine antibody. In addition, baculovirus proteins were detected by Coomassie staining, indicating a successful infection.

Figure 9:
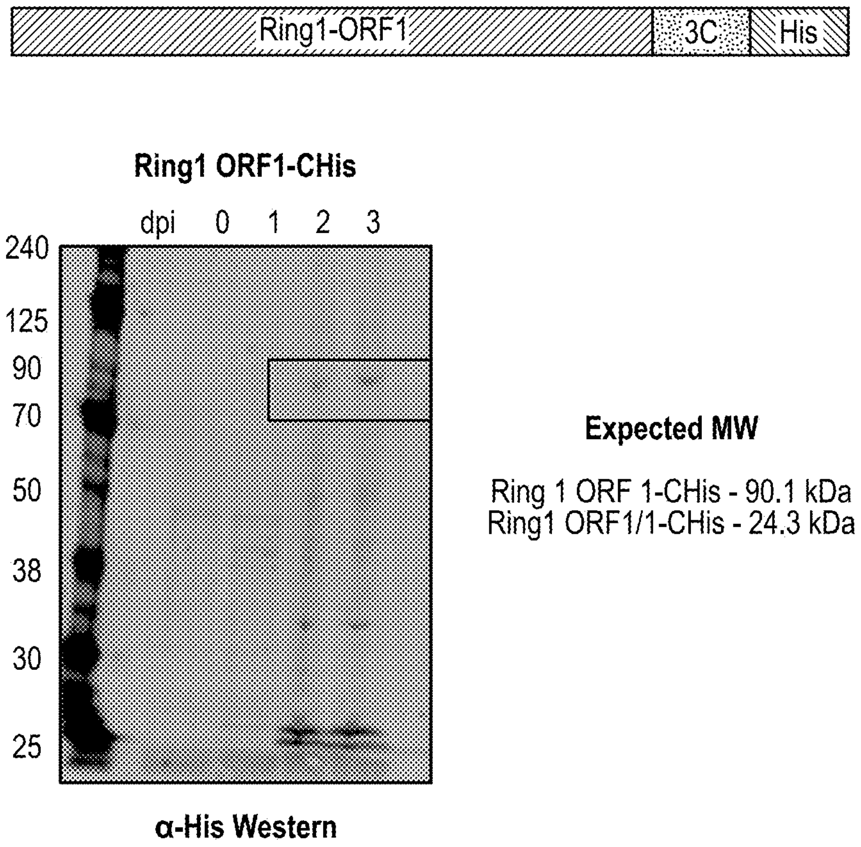
FIG. 9 depicts expression of Ring1 ORF1 and ORF1/1 with a C-terminal His tag in insect cells.

As shown in FIG. 9, C-His-tagged tth8 ORF1 and ORF1/1 were also successfully expressed in infected ExpiSf9 cells by day 2 post-infection.

Figure 10:
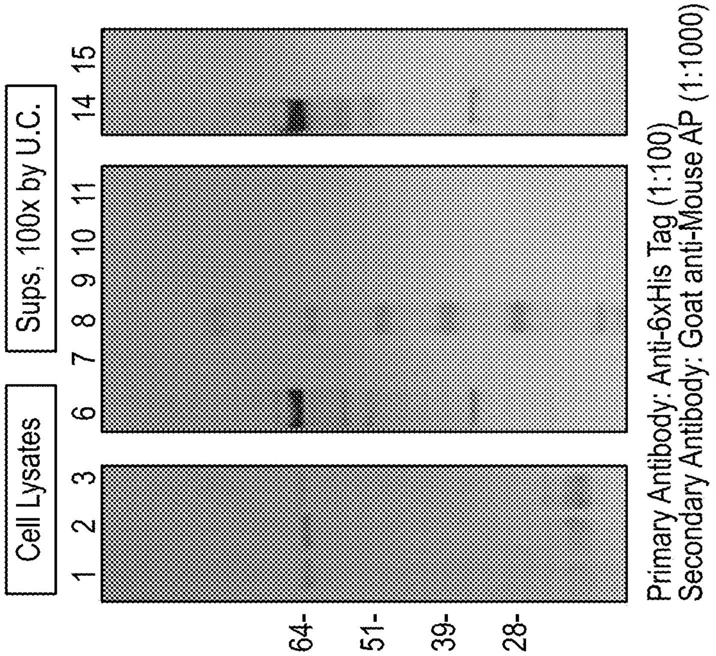
FIG. 10 depicts expression of Ring2 ORF1 with an N-terminal His-tag, with or without PreScission cleavage sequence, in insect cells.

N-terminally His-tagged LY2 ORF1 expression was also detected in infected ExpiSf9 cells (FIG. 10). Here, constructs either comprised an N-terminal His-tag which was immediately followed by the wildtype ORF1 sequence (lanes 1, 2, 9, 10, or 14), or an N-terminal His-tag which was followed by a rhinovirus 3C cleavage sequence (lanes 3, 11). Samples in lanes 1 to 7 are lysates loaded directly onto the gel, whereas samples in lanes 9-15 were prepared by first pelleting protein from conditioned medium via ultracentrifugation and resuspending the pellet in a 100-fold smaller volume. Samples shown in lanes 1-3 and 9-11 were grown at a small (5 mL) scale. Samples in lanes 6 and 14 were obtained from a 10L culture. Thus, this example shows that production of ORF1 from a plurality of strains with N or C terminal poly-histidine tags can be successfully carried out at a scale ranging from 5 mL to 10L, and that ORF1 can be found in Sf9 lysate or culture supernatant (conditioned medium).

Example 15: Expression of Ring1 ORFs in Sf9 Cells

Figure 11:
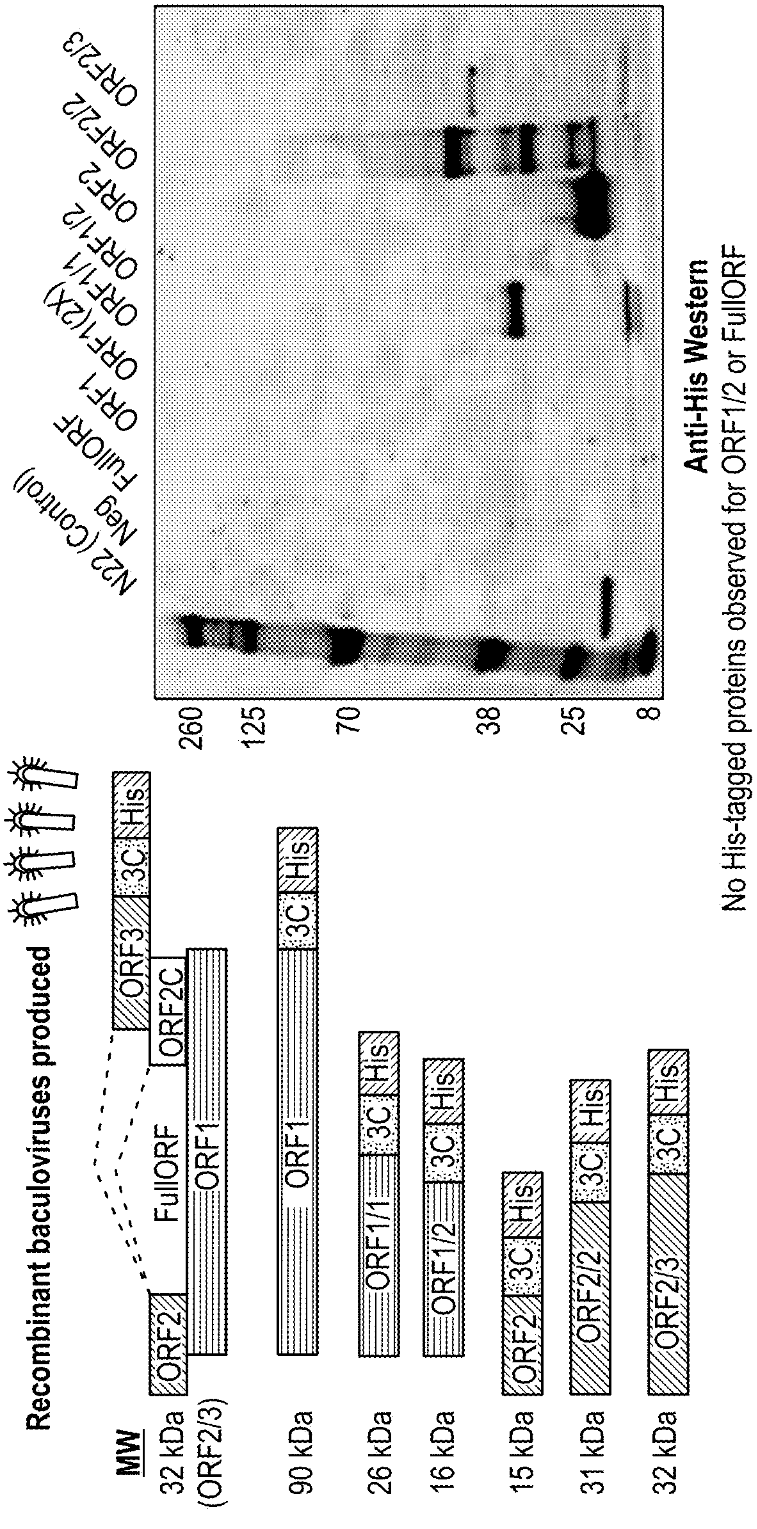
FIG. 11 depicts expression of Ring1 ORFs 1/1, 1/2, 2, 2/2, and 2/3 as C-terminal His-tagged recombinant proteins in insect cells.

In this example, a series of recombinant baculoviruses were produced with alternate arrangements of tth8 ORFs, each tagged with a C-terminal poly-histidine (FIG. 11). The recombinant baculovirus designs included one baculovirus construct for each of the tth8 ORF splice variants (i.e., ORF1, ORF1/1, ORF1/2, ORF2, ORF2/2, and ORF2/3), as well as a "FullORF" construct containing the full ORF region from tth8, driven by the baculovirus polyhedrin promoter. These baculoviruses were produced as described in Example 14.

Protein expression was then detected by western blot using anti-poly-histidine antibody. As shown in FIG. 11, His-tagged tth8 ORFs ORF1/1, ORF1/2, ORF2, ORF2/2 and ORF2/3 were detected.

Example 16: Expression of Ring2 ORFs in Sf9 Cells

Figure 12:
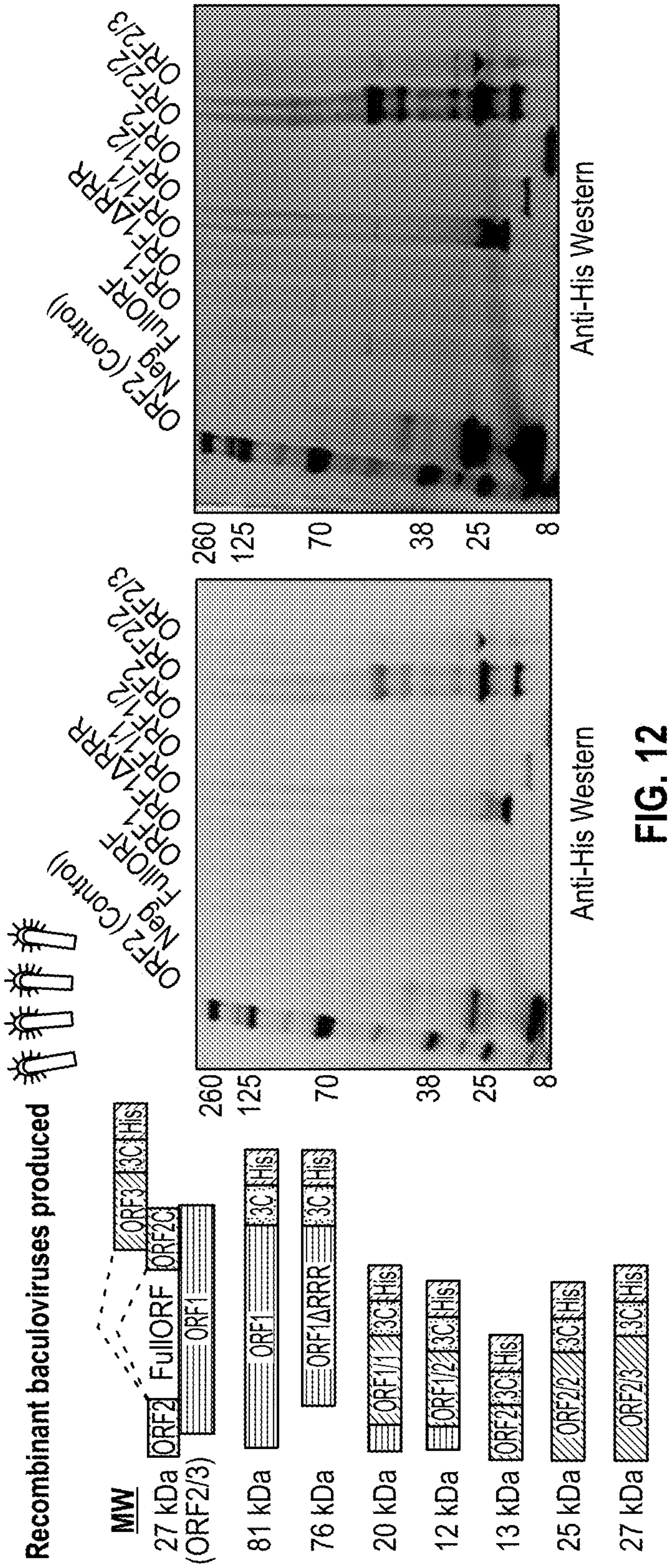
FIG. 12 depicts expression of individual Ring2 ORFs in insect cells. Two exposures of the same blot are shown in the middle and right panels. The left panel shows the structures of Ring2 constructs tested as indicated.

In one example, a series of recombinant baculoviruses were produced with alternate arrangements of Ring2 ORFs, each tagged with a poly-histidine tag at the C terminus (FIG. 12). The recombinant baculovirus designs included one baculovirus construct for each of the Ring2 ORF splice variants (i.e., ORF1, ORF1/1, ORF1/2, ORF2, ORF2/2, and ORF2/3), a variant in which the N-terminal arginine-rich region (RRR) is deleted (ORF1ΔRRR), as well as a "FullORF" construct containing the full ORF region from Ring2 driven by the baculovirus polyhedrin promoter. For each experimental condition, ExpiSf9 cells were infected with recombinant baculoviruses expressing individual Ring2 variants at an MOI of 5. The experimental conditions for this were as described in Examples 14 and 15.

Protein expression was then detected by western blot using anti-His. As shown in FIG. 12, His-tagged Ring2 ORFs ORF1, ORF1ΔRRR, ORF1/1, ORF1/2, ORF2, ORF2/2, and ORF2/3 were all detected.

In a further experiment as part of this example, recombinant baculoviruses comprising a Ring2 ORF1-encoding sequence and/or a Ring2 ORF2 splice variant-encoding sequence were used to infect Sf9 cells. The expression conditions tested included ORF1 alone, or co-infection of ORF1+"FullORF", ORF1+ORF2, ORF1+ORF2/2, and ORF1+ORF2/3, as well as a negative control labeled 'Neg'. ExpiSf9 cells were co-infected with baculoviruses at a MOI of 5 for each condition. Experimental conditions were as described in Examples 14 and 15. Protein expression of ORF1, ORF2, ORF2/2, and ORF2/3 was then assessed for each condition by western blot using either anti-His or anti-Ring2 N22. The latter is a monoclonal antibody that was obtained by immunizing mice with the N22 fragment of Ring2 ORF1 produced in *E. coli*, and then generating hybridomas.

Figure 13:
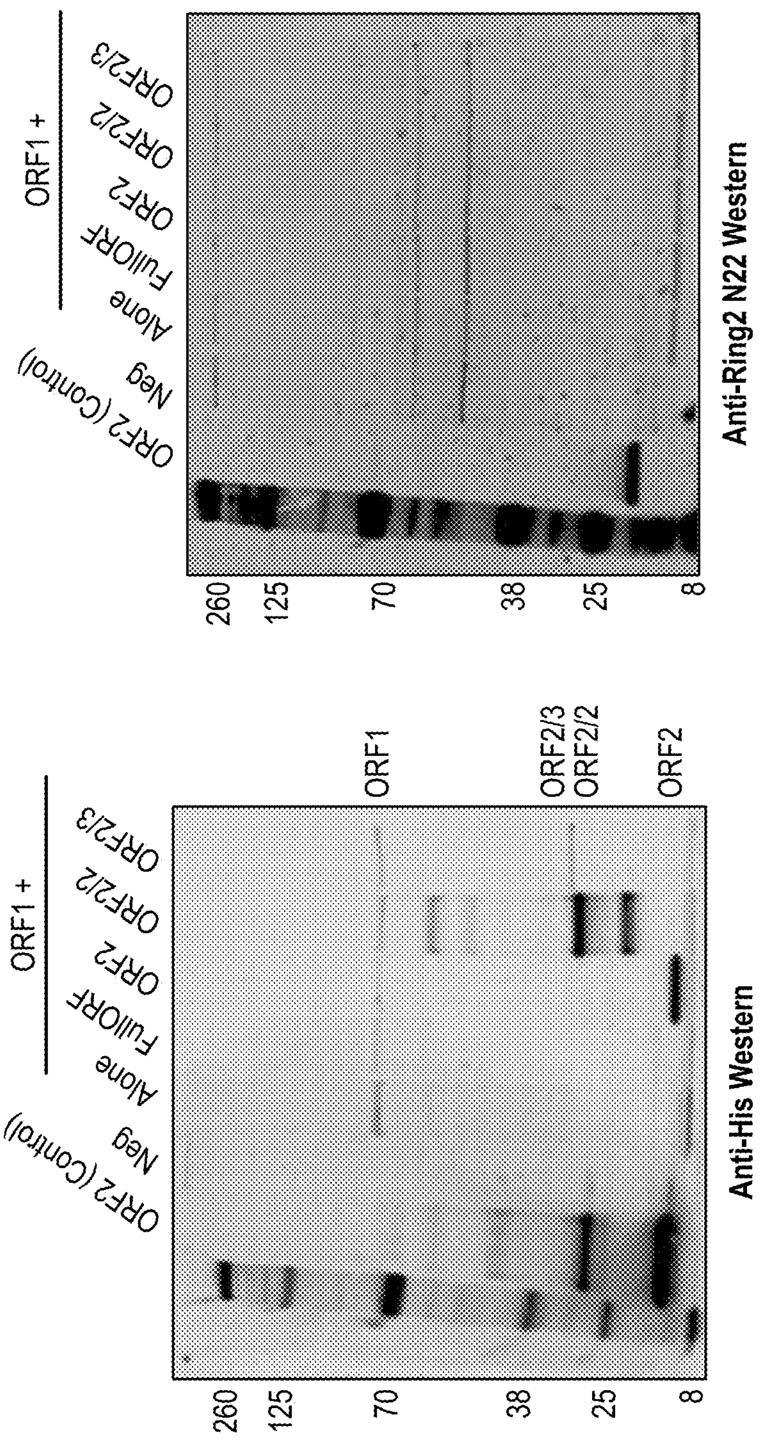
FIG. 13 depicts baculovirus-mediated co-expression of Ring2 ORF1+"FullORF", ORF1+ORF2, ORF1+ORF2/2, and ORF1+ORF2/3 in insect cells.

As shown in FIG. 13, both Westerns detected ORF1 as a band at ~81kD in each of the ORF1-infected conditions. The ORF1 band is highlighted by a dashed box in the anti-N22 Western, and is not visible in the negative control (Neg) sample. The lower molecular weight (~10 kD) band detected by both antibodies is thought to be a C-terminal fragment of ORF1. ORF2, ORF2/2, and ORF2/3 were also detected in the corresponding samples (anti-His blot). Thus, this example illustrates that both ORF1 and individual splice variants of ORF2 can be co-expressed in insect cells.

Example 17: Expression of all Ring2 ORFs Simultaneously in Sf9 Cells

Figure 14:
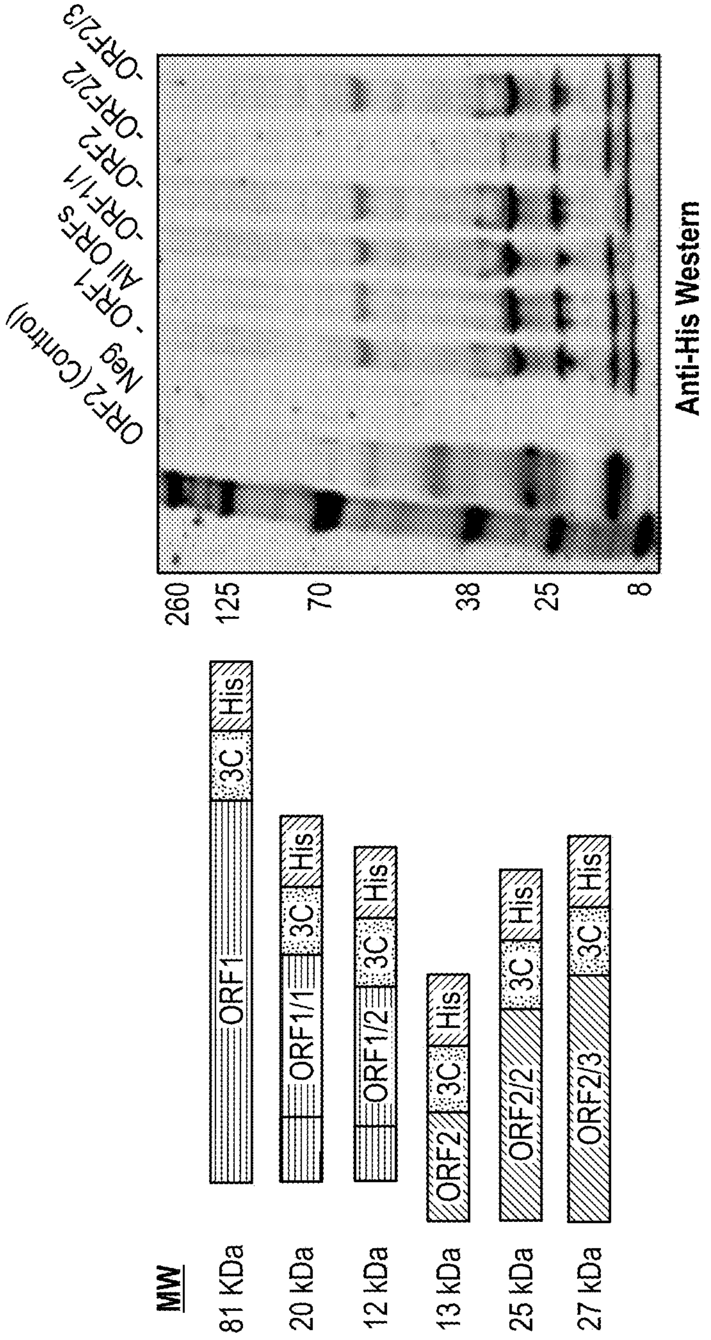
FIG. 14 depicts simultaneous co-expression of multiple Ring2 proteins in insect cells using baculovirus.

In one example, a series of six recombinant baculoviruses were produced, each designed to express a particular Ring2 ORF (i.e., ORF1, ORF1/1, ORF1/2, ORF2, ORF2/2, and ORF2/3), each tagged with a His tag (FIG. 14), as described in Example 16. Sf9 cells were infected with various combinations of the Ring2 ORF baculoviruses—specifically, each condition involved infecting cells with all but one ORF construct, as indicated in FIG. 14. Protein expression was then detected by western blot of whole cell suspension using anti-His. As shown in FIG. 14, His-tagged Ring2 ORFs were detected in the expected pattern. Either all ORFs were detected, or all except for the omitted one.

Figure 15:
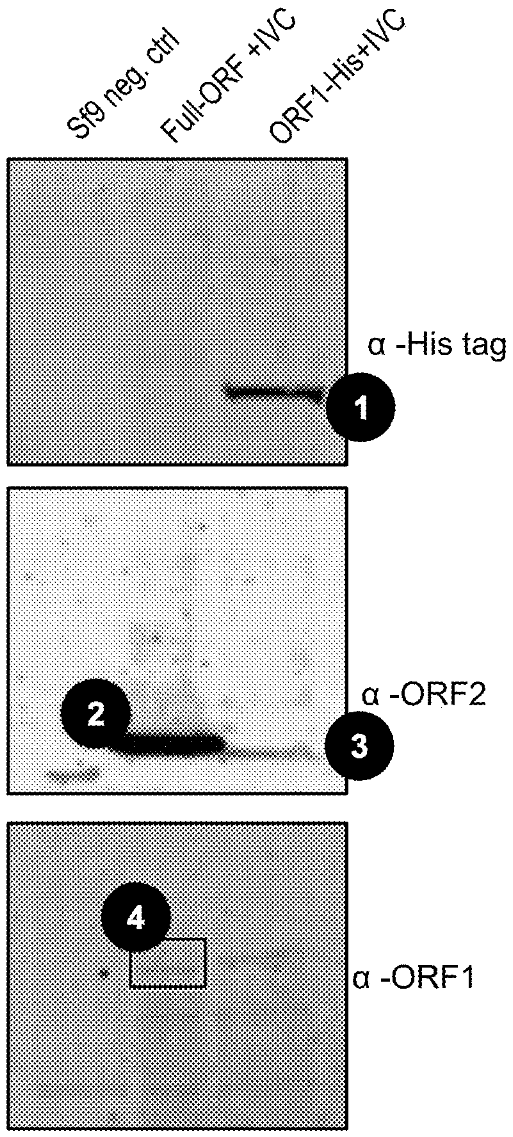
FIG. 15 depicts expression of ORFs from Anellovirus genome delivered into insect cells by baculovirus and by transfection.

Example 18: Co-Delivery and Independent Expression of Anellovirus Genomes and Recombinant Anellovirus ORFs in Sf9 Cells In this example, anellovirus ORFs and genomes were co-delivered in Sf9 cells by transfecting an in vitro circularized (IVC) anellovirus genome and infecting the cells with baculovirus encoding ORF1 tagged at its C-terminus with hexa-histidine (FIG. 15). Protein expression was then detected by western blot using anti-His, anti-ORF2, and anti-ORF1 monoclonal antibody targeting the N22 fragment. As shown (FIG. 15, bullet 1), His-tagged ORF1 was detected in this preparation showing successful recombinant ORF1 expression from the baculovirus vector. Consistent with this result, the same ORF1 protein was detected using the anti-ORF1 antibody (FIG. 15, bottom panel, right-most lane).

In the same sample of treated cells, the native anellovirus promoter was shown to be transcriptionally active in Sf9 cells because ORF2 expression was detected (FIG. 15, bullet 3) and could only have been produced by the IVC genome which was transfected into the cells.

In addition, Anellovirus ORFs were co-delivered and expressed in Sf9 cells using an in vitro circularized (IVC) construct and a FullORF baculovirus. Protein expression was then detected by western blot using anti-His, anti-Ring2 ORF2, and anti-Ring2 ORF1 N22. ORF1 protein was detected in the cells (FIG. 15, bullet 4) and could be the product of either the IVC or the FullORF baculovirus construct. Surprisingly, ORF2 protein was readily detected and its intensity suggests the expression is derived from the FullORF baculovirus construct (FIG. 15, bullet 2).

As a further test of the ability of the anellovirus genome to express its genes in insect cells, the tth8 anellovirus coding region was cloned into the pFastBac vector in both orientations. This yielded ‘FullORF’ tth8 baculovirus constructs in which the polyhedrin promoter was positioned upstream of either the sense or the anti-sense direction of the coding region. The latter configuration is highly unlikely to initiate transcription of the anellovirus genes. Consistent with our surprising observations in Ring2, expression of tth8 ORF2 was independent of the orientation of the coding region relative to the baculovirus polyhedrin promoter, suggesting that expression is driven by the anellovirus promoter (FIG. 16, bands at ~15 and 20 kDa).

This example shows that IVC transfections and baculovirus infections can co-deliver functional anellovirus genes to Sf9 insect cells and that the native anellovirus promoter is active in these cells.

Example 19: Anellovirus ORF1 Associates with DNA in Sf9 Cells to Form Complexes Isolated by Isopycnic Centrifugation In this example, Sf9 cells were transfected with IVC anellovirus genome LY2, infected with a baculovirus encoding LY2 ORF1 with a C-terminal poly-histidine tag, and then fractionated to determine whether ORF1 expressed using the baculoviral expression system forms protein-DNA complexes that can be isolated in vitro.

CsCl gradients were prepared by adding 8 ml of 1.2 g/ml CsCl solution (in TN buffer; 20 mM Tris pH 8.0, 140 mM NaCl) to ultracentrifuge tubes (Ultra-Clear 17 ml-Beckman #344061) for SW32.1 Ti rotor. Tubes were underlayed with 8 ml of 40% CsCl (in TN buffer), then capped with topper and run on Gradient Master program 5-50% for 13 minutes to prepare linear gradient. The caps were removed and the gradients overlayed with 0.5 ml-2 ml of Sf9 lysate to each tube and topped off to near the top with TN buffer containing 0.001% Poloxamer-188. Ultracentrifugation was for 18.5 hours at 22,500×RPM. Fractions were collected from the gradient by piercing the bottom of the tube and allowing ~600 ul fractions to flow into wells of a deep well block. The refractive index of each sample was measured to determine their density.

Anelloviral DNA content in the fractions was then determined by first extracting DNA from the fractions, and then by carrying out qPCR. Pure Link Viral DNA extraction Kit [Thermofisher Scientific Catalog no. 12280050] was used to purify viral DNA from 50 μL of the fractions. The samples were treated with Proteinase K and lysed using Lysis buffer by incubating at 56° C. for 15 min., washed with 99% ethanol, and transferred to a Viral Spin Column. Samples were centrifuged at 6800×g, washed twice with 500 uL Wash buffer provided with the kit and centrifuged again. 100 μL of RNase-free water was added to the column to elute the DNA.

For qPCR, 2× TaqMan Gene Expression Master Mix, 100 uM LY2 primers Forward (AGCAACAGGTAATGGAGGAC), 100 uM LY2 Reverse (TGAAGCTGGGGTCTTTAAC) along with 100 uM LY2 Probe (TCTACCTAGGTGCAAAGGGCC) were diluted in 5.83 uL Nuclease Free water for each reaction. The following conditions were used for each qPCR cycle: 50° C. hold for 2 minutes, 95° C. hold for 10 minutes followed by 40 cycles of 95° C. for 15 seconds and 60° C. for 1 minute on an Applied Biosystems Quant Studio 3 Real-Time PCR Machine. Each sample was run in triplicate and the entire assay was repeated thrice and used to plot the graph.

Figure 17:
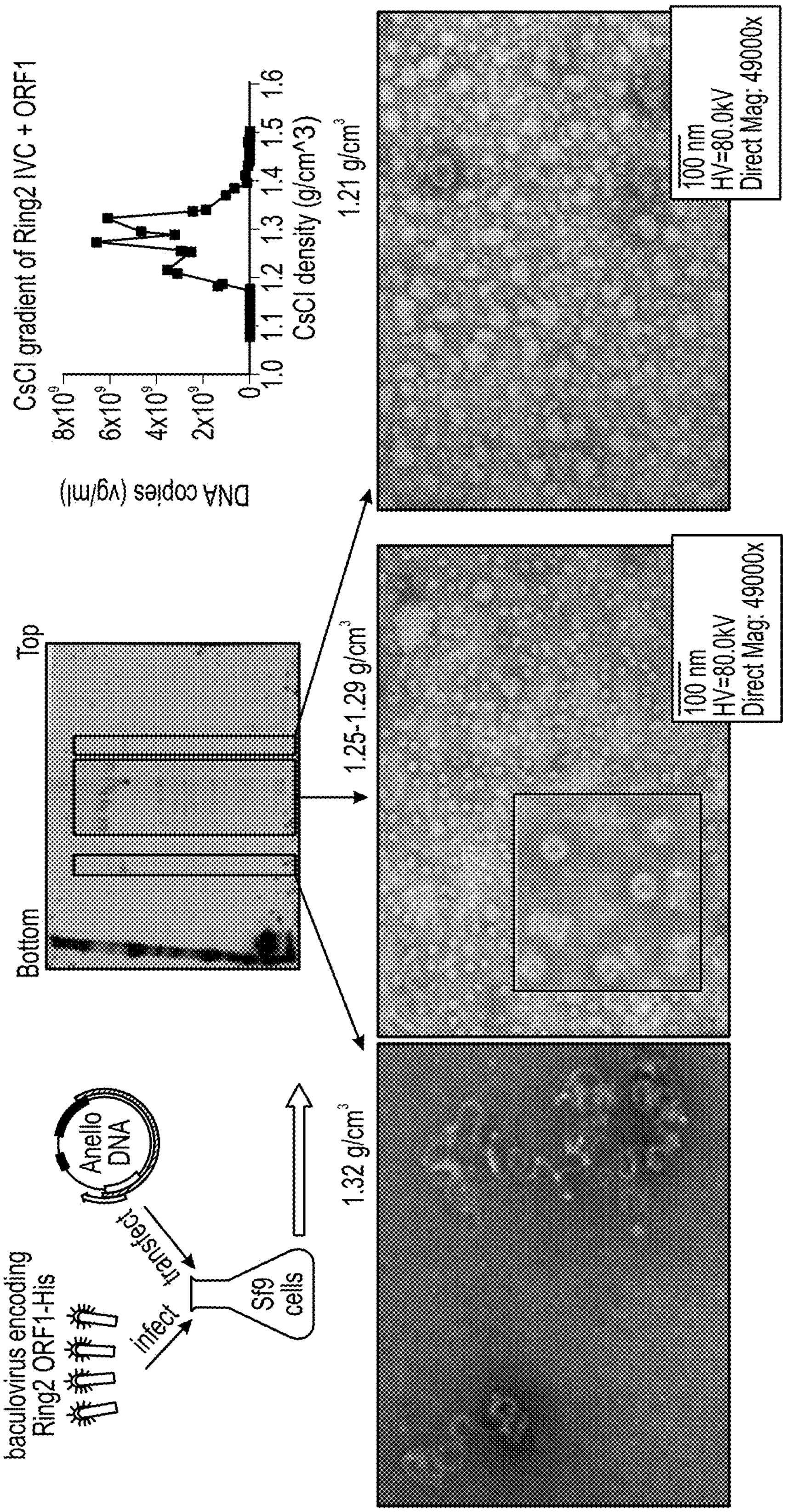
FIG. 17 depicts co-delivery of Ring2 ORF1-His and Ring2 genomic DNA into Sf9 cells, followed by incubation and fractionation on a CsCl linear density gradient. An anti-His tag Western blot of fractions is shown at the top of the figure, as well as a qPCR assay of each fraction. Bottom panels show transmission electron microscopy images of two individual fractions and a pool of fractions, as indicated by boxes on the Western blot. The inset in the middle panel is a zoomed-in view showing proteasome-like structures.

As shown in FIG. 17, isopycnic fractions were characterized by western blotting, quantitative PCR, and transmission electron microscopy. Anti-his western blotting of gradient fractions showed clear bands of the expected molecular weight for LY2 ORF1 in fractions having densities of 1.32 g/mL and 1.21 g/mL. In addition, fractions ranging from 1.25 to 1.29 g/mL had clear bands of higher and lower molecular weights than expected. Also, qPCR indicates the presence of LY2 genomic DNA in certain fractions, with peaks at approximately 1.21 g/mL, 1.29 g/mL, and 1.32 g/mL.

Negative stain transmission electron microscopy was carried out on the 1.32 g/mL and 1.21 g/mL fractions, as well as a pool of fractions ranging from 1.25 to 1.29 g/mL. The pool shows an abundance of particles, including several having the appearance of proteasomes. The presence of proteasomes may explain the western blot bands at low and high molecular weights. The former may be due to proteolytic degradation and the latter due to ubiquitylated ORF1, or ORF1 fragments covalently associated with proteasome proteins in the course of degradation. The 1.21 g/mL fraction shows particles of various sizes, including several which appear to be consistent with lipid-based particles. The 1.32 g/mL fraction shows remarkable DNA-like structures that stain differently than naked DNA, suggesting association with macromolecules such as protein.

Figure 18:
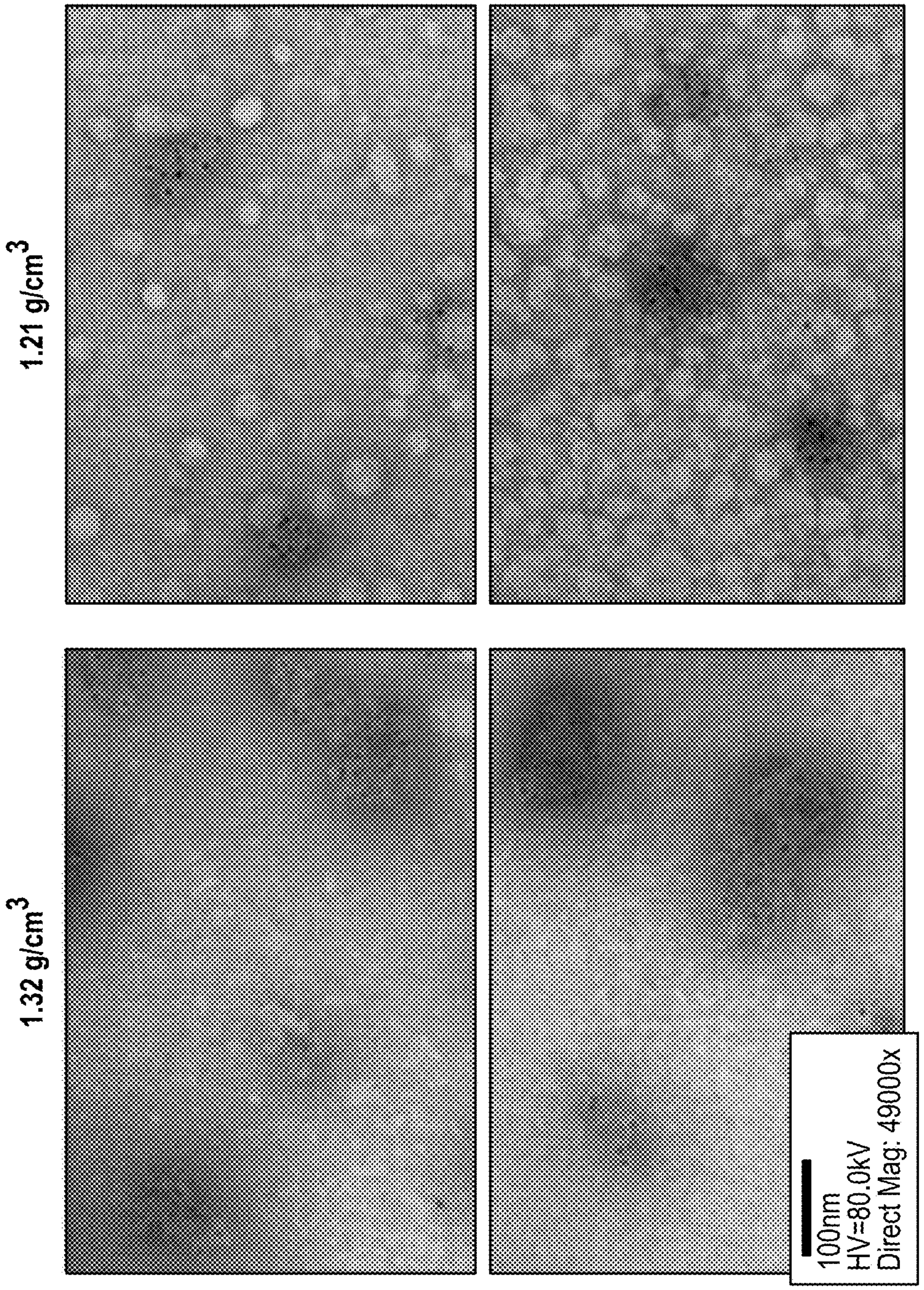
FIG. 18 depicts characterization of Sf9 isopycnic fractions by immunogold electron microscopy.

To determine if LY2 ORF1 is associated with the structures observed in the electron micrographs, immunogold detection using an anti-poly-histidine antibody was carried out. FIG. 18 shows gold label accumulating on the structures observed in the 1.32 and 1.21 g/mL fractions, consistent with the presence of ORF1-His in association with the DNA seen in the 1.32 g/mL fraction, and in the particles seen in the 1.21 g/mL fraction.

Taken together, these results show that ORF1 expressed in Sf9 cells can associate with DNA to form complexes having a density consistent with anellovirus particles.

Figure 19:
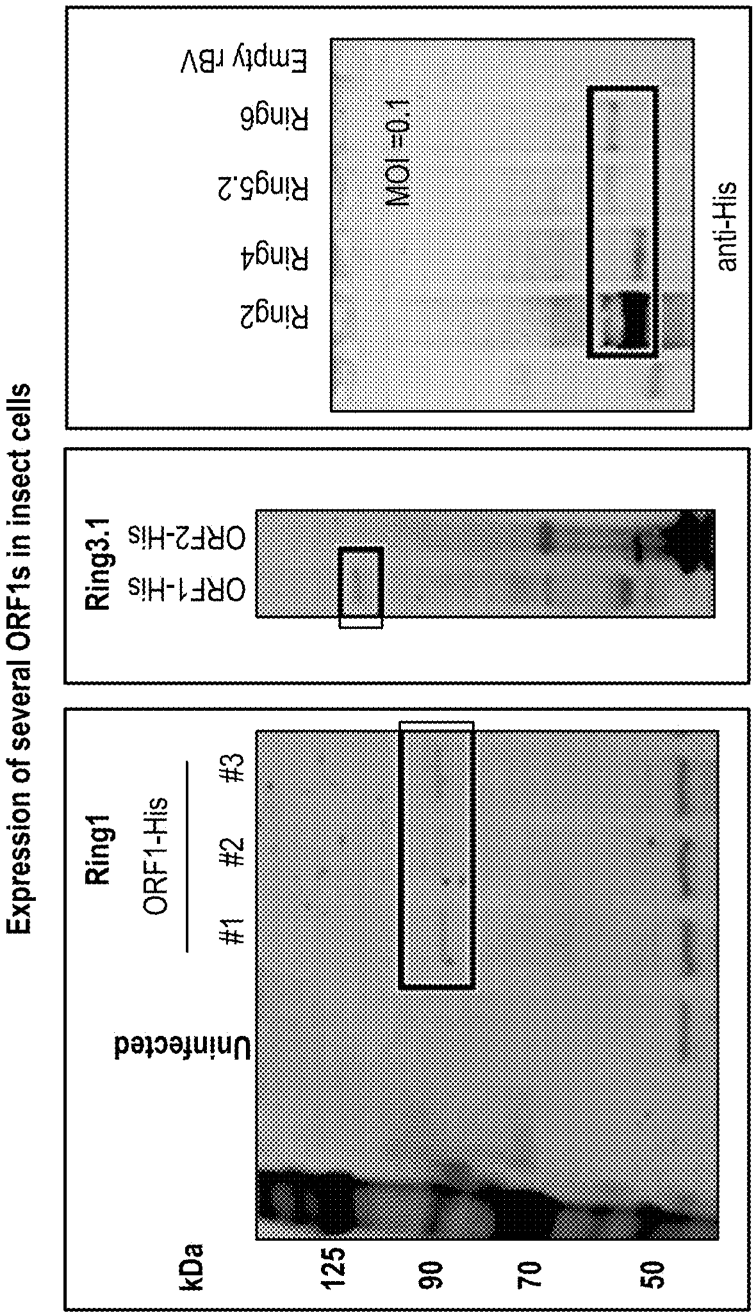
FIG. 19 depicts expression of ORF1 from additional Anellovirus strains.

Example 20: Expression of ORF1 Protein from a Diverse Array of Anelloviruses Using Baculovirus In this example, Sf9 cells were infected with baculoviruses engineered to express C-terminal His-tagged ORF1 proteins from anellovirus strains Ring3.1, Ring4, Ring5.2, Ring6, as well as Ring1 and Ring2. As shown in FIG. 19, ORF1 protein originating from each of the Anellovirus strains were successfully expressed in Sf9 cells. As shown in Table E3, Anellovirus ORF1 from the strains representing all three genera (Alphatorquevirus, Betatorquevirus, and Gammatorquevirus), were tested and their expression level is seen in FIGS. 3, 4, 5, and 19. In general, we find that the level of expression in this system is highest for ORF1 from Betatorqueviruses, intermediate from Gammatorqueviruses, and lowest from Alphatorqueviruses.

Example 21: In Vitro Assembly of Anellovectors Using Components Produced Via Baculovirus System In this example, baculovirus constructs suitable for expression of Anellovirus proteins (e.g., ORF1) are generated by in vitro assembly.

DNA encoding Anellovirus ORF1 (wildtype protein, chimeric protein or fragments thereof) which may be untagged or contain tags fused N-terminally, C-terminally, or harbor mutations within the ORF1 protein itself to introduce a tag to aid in purification and/or identity determination through immunostaining assays (such as, but not limited to, ELISA or Western Blot) is expressed in insect cell lines (Sf9 and/or HighFive). Anellovirus ORF1 may be expressed alone or in combination with any number of helper proteins including, but not limited to, Anellovirus ORF2 and/or ORF3 proteins.

Protein is purified using developed purification techniques potentially including but not limited to chelating purification, heparin purification, gradient sedimentation purification and/or size exclusion purification. ORF1 is evaluated for its ability to form capsomers or VLPs and used in subsequent steps for nucleic acid encapsidation.

In one example, DNA encoding Ring2 ORF1 fused to an N-terminal $HIS_6$-tag (HIS-ORF1) was codon optimized for insect expression and cloned into the baculovirus expression vector pFASTbac system to generate a baculovirus expressing Ring2 ORF-HIS recombinant protein using the Bac-to-BAC expression system according to manufacturer's method (ThermoFisher Scientific). 10 liters of insect cells (Sf9) were infected with Ring2 HIS-ORF1 baculovirus and the cells were harvested 3-days post-infection by centrifugation. The cells were lysed, and the lysate was purified using a chelating resin column using standard art in the field. The elution fraction containing HIS-ORF1 was dialyzed and treated with DNAse to digest host cell DNA. The resulting material was purified again using a chelating resin column and fractions containing ORF1 were retained for nucleic acid encapsidation and viral vector purification.

Nucleic acid encapsidation and viral vector purification: Ring ORF1 (wildtype protein, chimeric protein or fragments thereof) is treated with conditions sufficient to dissociate VLPs or viral capsids to enable reassembly with nucleic acid cargo. Nucleic acid cargo can be defined as double stranded DNA, single stranded DNA, or RNA which encodes a gene of interest that one wants to deliver as a therapeutic agent. Potential conditions sufficient to dissociate VLPs or viral capsids can, but are not limited to, buffers of different pH, conditions of defined conductivity (salt content), conditions containing detergents (such as SDS, Tween, Triton), conditions containing chaotropic agents (such as Urea) or conditions involving defined temperature and time (reannealing temperatures). Nucleic acid cargo of defined concentration is combined with Ring ORF1 of defined concentration and treated with conditions sufficient to permit nucleic acid encapsidation. The resulting particle, defined as viral vector, is subsequently purified, e.g., using developed standard viral purification procedures.

In one example, single stranded circular DNA of a GFP-expression plasmid is added to a solution of Ring 2 HIS-ORF1 and the resulting sample is treated with 0.1% SDS in 50 mM Tris pH 8 buffer at 37C for 30 minutes. The resulting solution is further purified using a heparin column and the viral vector eluted from the column using a gradient of increasing NaCl concentration. The integrity of the viral vector is tested by transducing the cell lines EKVX and HEK293, and observing GFP production in at least one of the cell lines by fluorescence microscopy, demonstrating encapsidation of the nucleic acid cargo by the ORF1 protein to form the viral vector.

TABLE E3

Strains for which recombinant ORF1 expression was successful

| Name | Genus |
|---|---|
| Ring1 | Alpha |
| Ring2 | Beta |
| Ring3.1 | Gamma |
| Ring4 | Gamma |
| Ring5.2 | Alpha |
| Ring6 | Alpha |
| HLH | Beta |
| ctgh3 | Beta |
| LY1 | Beta |

Example 22: Identification and Use of Protein Binding Sequences

This example describes putative protein-binding sites in the Anellovirus genome, which can be used for amplifying and packaging effectors, e.g., in an anellovector as described herein. In some instances, the protein-binding sites may be capable of binding to an exterior protein, such as a capsid protein.

Two conserved domains within the Anellovirus genome are putative origins of replication: the 5' UTR conserved domain (5CD) and the GC-rich domain (GCR) (de Villiers et al., Journal of Virology 2011; Okamoto et al., Virology 1999). In one example, in order to confirm whether these sequences act as DNA replication sites or as capsid packaging signals, deletions of each region are made in plasmids harboring an Anellovirus sequence. A539 cells are transfected with the deletion constructs. Transfected cells are incubated for four days, and then virus is isolated from supernatant and cell pellets. A549 cells are infected with virus, and after four days, virus is isolated from the supernatant and infected cell pellets. qPCR is performed to quantify viral genomes from the samples. Disruption of an origin of replication prevents viral replicase from amplifying viral DNA and results in reduced viral genomes isolated from transfected cell pellets compared to wild-type virus. A small amount of virus is still packaged and can be found in the transfected supernatant and infected cell pellets. In some embodiments, disruption of a packaging signal will prevent the viral DNA from being encapsulated by capsid proteins. Therefore, in embodiments, there will still be an amplification of viral genomes in the transfected cells, but no viral genomes are found in the supernatant or infected cell pellets.

In a further example, in order to characterize additional replication or packaging signals in the DNA, a series of deletions across the entire TTMV-LY2 genome is used. Deletions of 100 bp are made stepwise across the length of the sequence. Plasmids harboring Anellovirus genome deletions are transfected into A549 and tested as described above. In some embodiments, deletions that disrupt viral amplification or packaging will contain potential cis-regulatory domains.

Replication and packaging signals can be incorporated into effector-encoding DNA sequences (e.g., in a genetic element in an anellovector) to induce amplification and encapsulation. This is done both in context of larger regions of the anellovector genome (i.e., inserting effectors into a specific site in the genome, or replacing viral ORFs with effectors, etc.), or by incorporating minimal cis signals into the effector DNA. In cases where the anellovector lacks trans replication or packaging factors (e.g., replicase and capsid proteins, etc.), the trans factors are supplied by helper genes. The helper genes express all of the proteins and RNAs sufficient to induce amplification and packaging, but lack their own packaging signals. The anellovector DNA is co-transfected with helper genes, resulting in amplification and packaging of the effector but not of the helper genes.

Example 23: Replication-Deficient Anellovectors and Helper Viruses

For replication and packaging of an anellovector, some elements (e.g., an ORF1, ORF1/1, ORF1/2, ORF2, ORF2/2, ORF2/3, and/or ORF2t/3 molecule, or a nucleic acid sequence encoding same) can be provided in trans. These include proteins or non-coding RNAs that direct or support DNA replication or packaging. Trans elements can, in some instances, be provided from a source alternative to the anellovector, such as a helper virus, plasmid, or from the cellular genome.

Other elements are typically provided in cis (e.g., a TATA box, cap site, initiator element, transcriptional start site, 5' UTR conserved domain, three open-reading frame region, poly(A) signal, or GC-rich region). These elements can be, for example, sequences or structures in the anellovector DNA that act as origins of replication (e.g., to allow amplification of anellovector DNA) or packaging signals (e.g., to bind to proteins to load the genome into the capsid). Generally, a replication deficient virus or anellovector will be missing one or more of these elements, such that the DNA is unable to be packaged into an infectious virion or anellovector even if other elements are provided in trans.

Replication deficient viruses can be useful for controlling replication of an anellovector (e.g., a replication-deficient or packaging-deficient anellovector) in the same cell. In some instances, the virus will lack cis replication or packaging elements, but express trans elements such as proteins and non-coding RNAs. Generally, the therapeutic anellovector would lack some or all of these trans elements and would therefore be unable to replicate on its own, but would retain the cis elements. When co-transfected/infected into cells, the replication-deficient virus would drive the amplification and packaging of the anellovector. The packaged particles collected would thus be comprised solely of therapeutic anellovector, without contamination from the replication-deficient virus.

To develop a replication deficient anellovector, conserved elements in the non-coding regions of Anellovirus will be removed. In particular, deletions of the conserved 5' UTR domain and the GC-rich domain will be tested, both separately and together. Both elements are contemplated to be important for viral replication or packaging. Additionally, deletion series will be performed across the entire non-coding region to identify previously unknown regions of interest.

Successful deletion of a replication element will result in reduction of anellovector DNA amplification within the cell, e.g., as measured by qPCR, but will support some infectious anellovector production, e.g., as monitored by assays on infected cells that can include any or all of qPCR, western blots, fluorescence assays, or luminescence assays. Successful deletion of a packaging element will not disrupt anellovector DNA amplification, so an increase in anellovector DNA will be observed in transfected cells by qPCR. However, the anellovector genomes will not be encapsulated, so no infectious anellovector production will be observed.

Example 24: Manufacturing Process for Replication-Competent Anellovectors

This example describes a method for recovery and scaling up of production of replication-competent anellovectors. Anellovectors are replication competent when they encode in their genome all the required nucleic acid elements and ORFs necessary to replicate in cells. Since these anellovectors are not defective in their replication they do not need a complementing activity provided in trans. They might, however need helper activity, such as enhancers of transcriptions (e.g. sodium butyrate) or viral transcription factors (e.g. adenoviral E1, E2 E4, VA; HSV Vp16 and immediate early proteins).

In this example, double-stranded DNA encoding the full sequence of a synthetic anellovector either in its linear or circular form is introduced into 5E+05 adherent mammalian cells in a T75 flask by chemical transfection or into 5E+05 cells in suspension by electroporation. After an optimal period of time (e.g., 3-7 days post transfection), cells and supernatant are collected by scraping cells into the supernatant medium. A mild detergent, such as a biliary salt, is added to a final concentration of 0.5% and incubated at 37° C. for 30 minutes. Calcium and Magnesium Chloride is added to a final concentration of 0.5 mM and 2.5 mM, respectively. Endonuclease (e.g. DNAse I, Benzonase), is added and incubated at 25-37° C. for 0.5-4 hours. Anellovector suspension is centrifuged at 1000×g for 10 minutes at 4° C. The clarified supernatant is transferred to a new tube and diluted 1:1 with a cryoprotectant buffer (also known as stabilization buffer) and stored at −80° C. if desired. This produces passage 0 of the anellovector (P0). To bring the concentration of detergent below the safe limit to be used on cultured cells, this inoculum is diluted at least 100-fold or more in serum-free media (SFM) depending on the anellovector titer.

A fresh monolayer of mammalian cells in a T225 flask is overlaid with the minimum volume sufficient to cover the culture surface and incubated for 90 minutes at 37° C. and 5% carbon dioxide with gentle rocking. The mammalian cells used for this step may or may not be the same type of cells as used for the P0 recovery. After this incubation, the inoculum is replaced with 40 ml of serum-free, animal origin-free culture medium. Cells are incubated at 37° C. and 5% carbon dioxide for 3-7 days. 4 ml of a 10× solution of the same mild detergent previously utilized is added to achieve a final detergent concentration of 0.5%, and the mixture is then incubated at 37° C. for 30 minutes with gentle agitation. Endonuclease is added and incubated at 25-37° C. for 0.5-4 hours. The medium is then collected and centrifuged at 1000×g at 4° C. for 10 minutes. The clarified supernatant is mixed with 40 ml of stabilization buffer and stored at −80° C. This generates a seed stock, or passage 1 of anellovector (P1).

Depending on the titer of the stock, it is diluted no less than 100-fold in SFM and added to cells grown on multilayer flasks of the required size. Multiplicity of infection (MOI) and time of incubation is optimized at smaller scale to ensure maximal anellovector production. After harvest, anellovectors may then be purified and concentrated as needed. A schematic showing a workflow, e.g., as described in this example, is provided in FIG. 20.

Example 25: Manufacturing Process of Replication-Deficient Anellovectors

This example describes a method for recovery and scaling up of production of replication-deficient anellovectors.

Anellovectors can be rendered replication-deficient by deletion of one or more ORFs (e.g., ORF1, ORF1/1, ORF1/2, ORF2, ORF2/2, ORF2/3, and/or ORF2t/3) involved in replication. Replication-deficient anellovectors can be grown in a complementing cell line. Such cell line constitutively expresses components that promote anellovector growth but that are missing or nonfunctional in the genome of the anellovector.

In one example, the sequence(s) of any ORF(s) involved in anellovector propagation are cloned into a lentiviral expression system suitable for the generation of stable cell lines that encode a selection marker, and lentiviral vector is generated as described herein. A mammalian cell line capable of supporting anellovector propagation is infected with this lentiviral vector and subjected to selective pressure by the selection marker (e.g., puromycin or any other antibiotic) to select for cell populations that have stably integrated the cloned ORFs. Once this cell line is characterized and certified to complement the defect in the engineered anellovector, and hence to support growth and propagation of such anellovectors, it is expanded and banked in cryogenic storage. During expansion and maintenance of these cells, the selection antibiotic is added to the culture medium to maintain the selective pressure. Once anellovectors are introduced into these cells, the selection antibiotic may be withheld.

Once this cell line is established, growth and production of replication-deficient anellovectors is carried out, e.g., as described herein.

Example 26: Production of Anellovectors Using Suspension Cells

This example describes the production of anellovectors in cells in suspension.

In this example, an A549 or 293T producer cell line that is adapted to grow in suspension conditions is grown in animal component-free and antibiotic-free suspension medium (Thermo Fisher Scientific) in WAVE bioreactor bags at 37 degrees and 5% carbon dioxide. These cells, seeded at $1\times10^6$ viable cells/mL, are transfected using lipofectamine 2000 (Thermo Fisher Scientific) under current good manufacturing practices (cGMP), with a plasmid comprising anellovector sequences, along with any complementing plasmids suitable or required to package the anellovector (e.g., in the case of a replication-deficient anellovector, e.g., as described herein). The complementing plasmids can, in some instances, encode for viral proteins that have been deleted from the anellovector genome (e.g., an anellovector genome based on a viral genoe, e.g., an Anellovirus genome, e.g., as described herein) but are useful or required for replication and packaging of the anellovectors. Transfected cells are grown in the WAVE bioreactor bags and the supernatant is harvested at the following time points: 48, 72, and 96 hours post transfection. The supernatant is separated from the cell pellets for each sample using centrifugation. The packaged anellovector particles are then purified from the harvested supernatant and the lysed cell pellets using ion exchange chromatography.

The genome equivalents in the purified prep of the anellovectors can be determined, for example, by using a small aliquot of the purified prep to harvest the anellovector genome using a viral genome extraction kit (Qiagen), followed by qPCR using primers and probes targeted towards the anellovector DNA sequence, e.g., as described in Example 32.

The infectivity of the anellovectors in the purified prep can be quantified by making serial dilutions of the purified prep to infect new A549 cells. These cells are harvested 72 hours post transfection, followed by a qPCR assay on the genomic DNA using primers and probes that are specific to the anellovector DNA sequence.

Example 27: Quantification of Anellovector Genome Equivalents by qPCR

This example demonstrates the development of a hydrolysis probe-based quantitative PCR assay to quantify anellovectors. Sets of primers and probes are designed based on an Anellovirus genome sequence. using the software Geneious with a final user optimization. Exemplary primer sequences for TTV (Accession No. AJ620231.1) and TTMV (Accession No. JX134045.1) are shown in Table E4 below.

TABLE E4

Sequences of forward and reverse primers and hydrolysis probes used to quantify TTMV and TTV genome equivalents by quantitative PCR.

| TTMV | | SEQ ID NO: |
|---|---|---|
| Forward Primer | 5'-GAAGCCCACCAAAAGCAATT-3' | 697 |
| Reverse Primer | 5'-AGTTCCCGTGTCTATAGTCGA-3' | 698 |
| Probe | 5'-ACTTCGTTACAGAGTCCAGGGG-3' | 699 |
| TTV | | |
| Forward Primer | 5'-AGCAACAGGTAATGGAGGAC-3' | 700 |
| Reverse Primer | 5'-TGGAAGCTGGGGTCTTTAAC-3' | 701 |
| Probe | 5'-TCTACCTTAGGTGCAAAGGGCC-3' | 702 |

Figure 21:
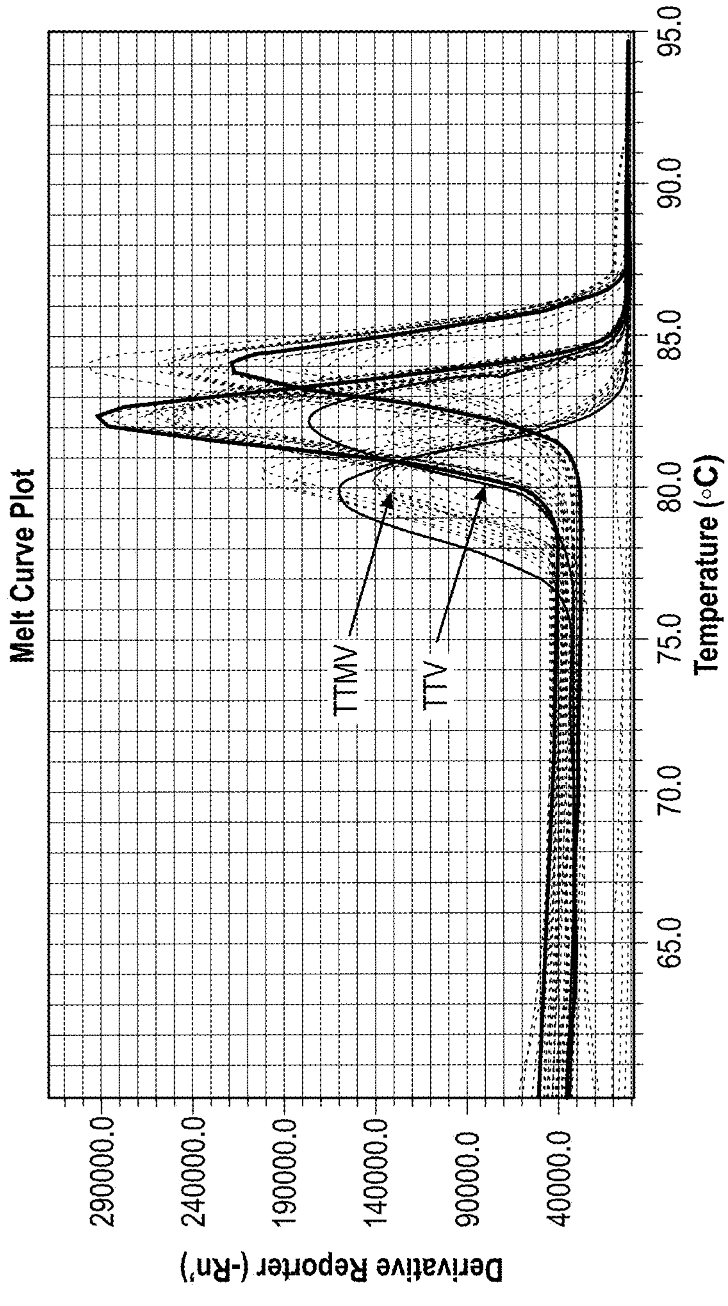
FIG. 21 is a graph showing primer specificity for primer sets designed for quantification of TTV and TTMV genomic equivalents. Quantitative PCR based on SYBR green chemistry shows one distinct peak for each of the amplification products using TTMV or TTV specific primer sets, as indicated, on plasmids encoding the respective genomes.

As a first step in the development process, qPCR is run using the Anellovirus primers with SYBR-green chemistry to check for primer specificity. FIG. 21 shows one distinct amplification peak for each primer pair.

Figure 22:
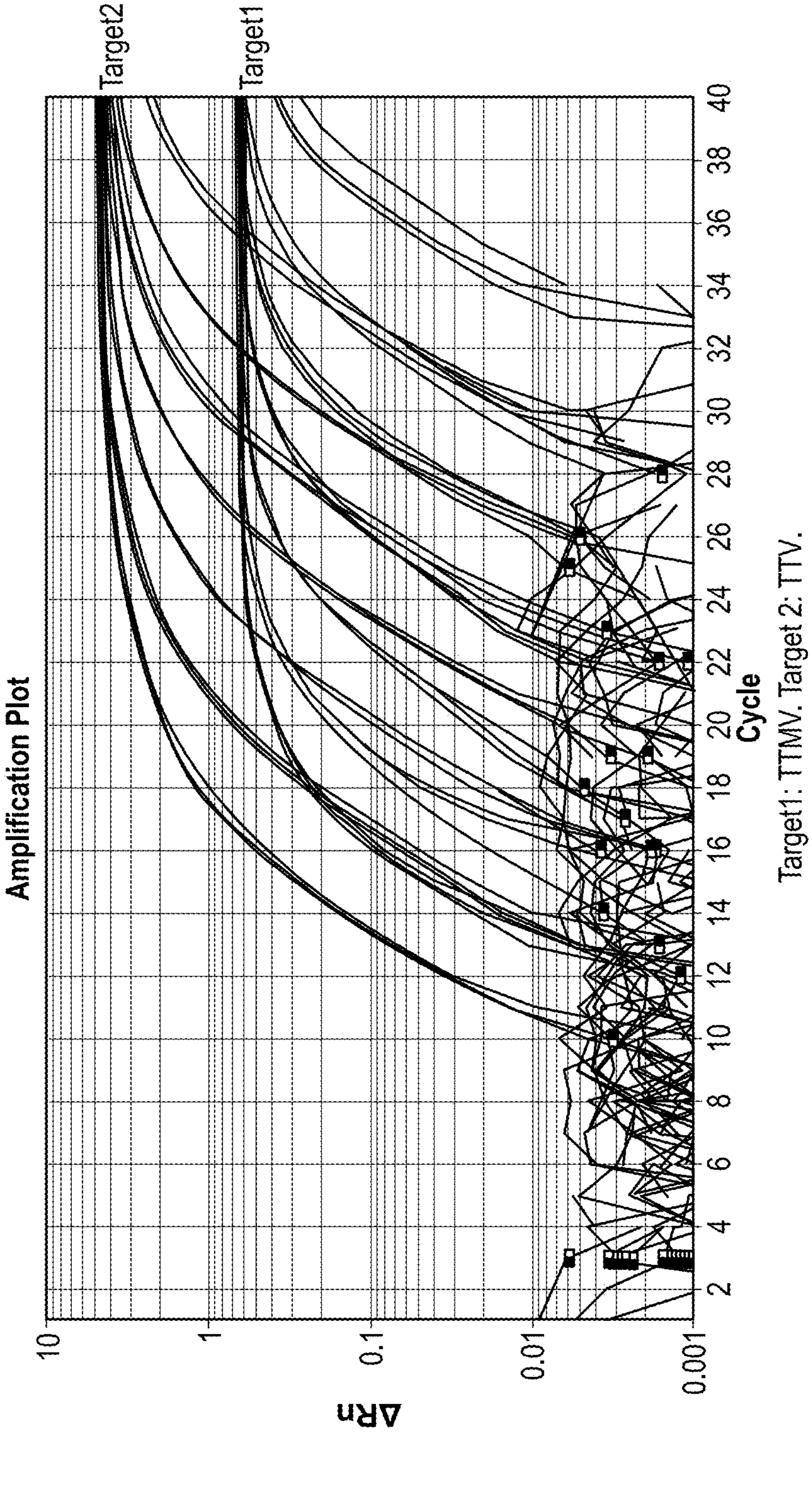
FIG. 22 is a graph showing an exemplary amplification plot for linear amplification of TTMV (Target 1) or TTV (Target 2) over a 7 log 10 of genome equivalent concentrations. Genome equivalents were quantified over 7 10-fold dilutions with high PCR efficiencies and linearity ($R^2$ TTMV: 0.996; $R^2$ TTV: 0.997).

Hydrolysis probes are ordered labeled with the fluorophore 6FAM at the 5' end and a minor groove binding, non-fluorescent quencher (MGBNFQ) at the 3' end. The PCR efficiency of the new primers and probes was evaluated using two different commercial master mixes using purified plasmid DNA as component of a standard curve and increasing concentrations of primers. The standard curve is set up by using purified plasmids containing the target sequences for the different sets of primers-probes. Seven tenfold serial dilutions are performed to achieve a linear range over 7 logs and a lower limit of quantification of 15 copies per 20ul reaction. All primers for qPCR are ordered from a commercial vendor such as IDT. Hydrolysis probes conjugated to the fluorophore 6FAM and a minor groove binding, non-fluorescent quencher (MGBNFQ) as well as all the qPCR master mixes are obtained from Thermo Fisher. An exemplary amplification plot is shown in FIG. 22.

Using these primer-probe sets and reagents, the genome equivalent (GEq)/ml in anellovector stocks is quantified. The linear range is then used to calculate the GEq/ml. Samples with higher concentrations than the linear range can be diluted as needed.

Example 28: Tandem Copies of the Anellovirus Genome

Figure 23A:
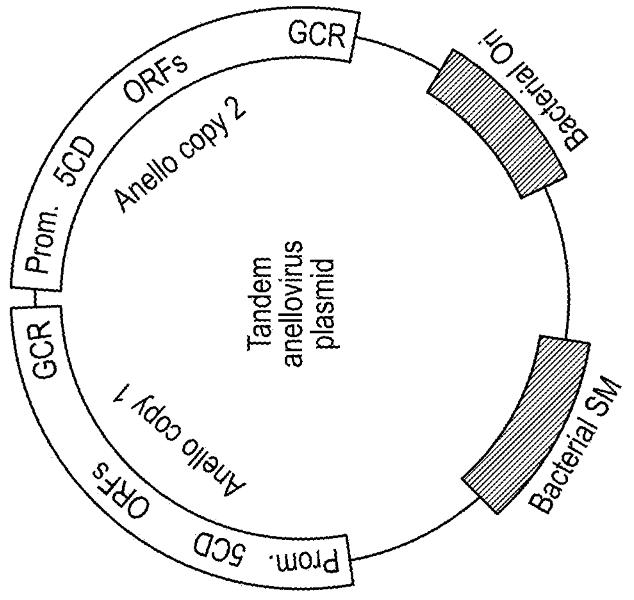
FIGS. 23A and 23B are a series of diagrams showing that a tandem Anellovirus plasmid can increase anellovirus or anellovector production. (A) Plasmid map for an exemplary tandem Anellovirus plasmid. (B) Transfection of HEK293T cells with a tandem Anellovirus plasmid resulted in production of four times the number of viral genomes compared to single-copy harboring plasmids.
Figure 23B:
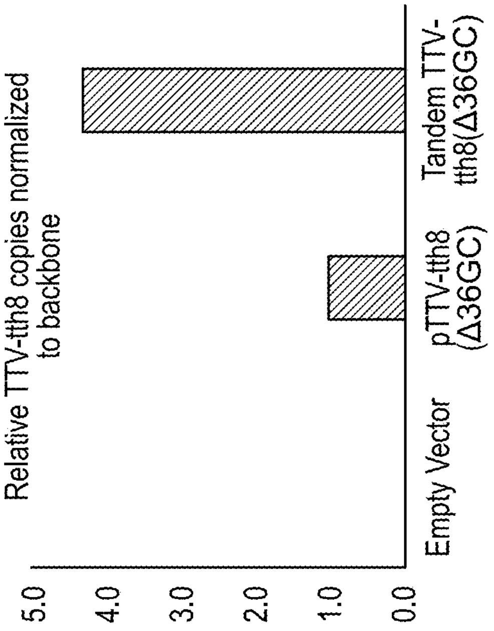
Figure 23C:
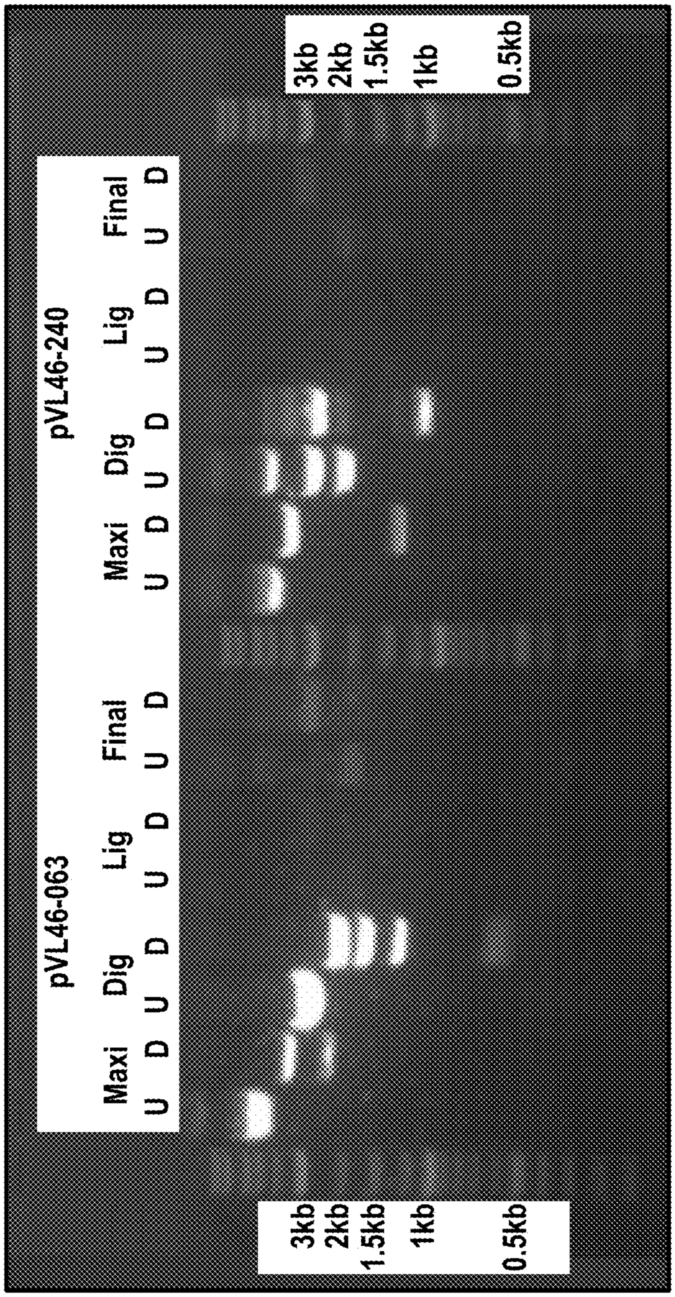
FIG. 23C is a gel electrophoresis image showing circularization of TTMV-LY2 plasmids pVL46-063 and pVL46-240.
Figure 23D:
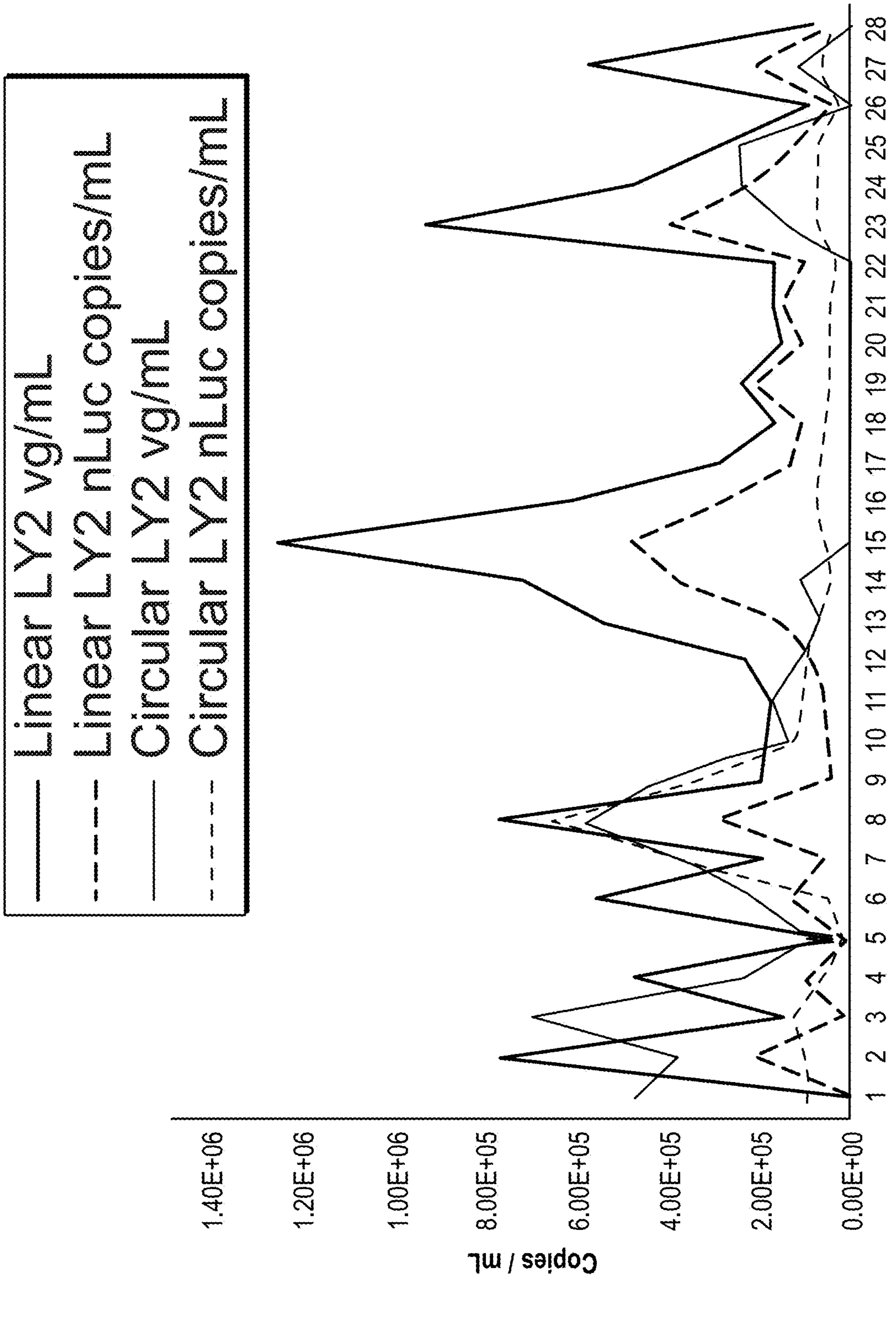
FIG. 23D is a chromatogram showing copy numbers for linear and circular TTMV-LY2 constructs, as determined by size exclusion chromatography (SEC).

This example describes plasmid-based expression vectors harboring two copies of a single anelloviral genome, arranged in tandem such that the GC-rich region of the upstream genome is near the 5' region of the downstream genome (FIG. 23A).

Anelloviruses replicate via rolling circle, in which a replicase (Rep) protein binds to the genome at an origin of replication and initiates DNA synthesis around the circle. For anellovirus genomes contained in plasmid backbones, this requires either replication of the full plasmid length, which is longer than the native viral genome, or recombination of the plasmid resulting in a smaller circle comprising the genome with minimal backbone. Therefore, viral replication off of a plasmid can be inefficient. To improve viral genome replication efficiency, plasmids are engineered with tandem copies of TTV-tth8 and TTMV-LY2. These plasmids present every possible circular permutation of the anelloviral genome: regardless of where the Rep protein binds, it will be able to drive replication of the viral genome from the upstream origin of replication to the downstream origin. A similar strategy has been used to produce porcine Anelloviruses (Huang et al., 2012, Journal of Virology 86 (11) 6042-6054).

Tandem anellovector can be assembled, for example, by sequentially cloning copies of the genome into a plasmid backbone, leaving 12 bp of non-viral DNA between the two sequences. Alternatively, tandem anellovector can be assembled via Golden-gate assembly, simultaneously incorporating two copies of the genome into a backbone and leaving no extra nucleotides between the genomes.

Plasmid harboring tandem copies of an anellovector genetic element sequence is transfected into HEK239T cells. Cells are incubated for five days, then lysed using 0.1% Triton X-100 and treated with nucleases to digest DNA not protected by viral capsids. qPCR is then performed using Tagman probes for the TTV-tth8 genome sequence and the plasmid backbone. TTV-tth8 genome copies are normalized to backbone copies.

Example 29: In Vitro Circularized Anellovirus Genomes

This example describes constructs comprising circular, double stranded Anelloviral genome DNA with minimal non-viral DNA. These circular viral genomes more closely match the double-stranded DNA intermediates found during wild-type Anellovirus replication. When introduced into a cell, such circular, double stranded Anelloviral genome DNA with minimal non-viral DNA can undergo rolling circle replication to produce, for example, a genetic element as described herein.

In one example, plasmids harboring an Anellovirus genome sequence are digested with restriction endonucleases recognizing sites flanking the genomic DNA. The resulting linearized genomes are then ligated to form circular DNA. These ligation reactions are done with varying DNA concentrations to optimize the intramolecular ligations. The ligated circles are either directly transfected into mammalian cells, or further processed to remove non-circular genome DNA by digesting with restriction endonucleases to cleave the plasmid backbone and exonucleases to degrade linear DNA. To demonstrate the improvements in Anellovirus production, circularized Anellovirus genome constructs are transfected into HEK293T cells. After 7 days of incubation, cells are lysed, and qPCR is performed to compare the levels of anellovirus genome between circularized and plasmid-based anelloviral genomes. Increased levels of Anelloviral genomes show that circularization of the viral DNA is a useful strategy for increasing Anellovirus production.

Digested plasmid can be purified on 1% agarose gels prior to electroelution or Qiagen column purification and ligation with T4 DNA Ligase. Circularized DNA is concentrated on a 100 kDa UF/DF membrane before transfection. Circularization is confirmed by gel electrophoresis. T-225 flasks are seeded with HEK293T at $3\times10^4$ cells/$cm^2$ one day prior to lipofection with Lipofectamine 2000. Nine micrograms of circularized Anellovirus DNA and 50 g of circularized Anellovirus-nLuc are co-transfected one day post flask seeding. As a comparison, an additional T-225 flask is co-transfected with 50 g of linearized Anellovirus and 50 g of linearized Anellovirus-nLuc.

Anellovector production proceeds for eight days prior to cell harvest in Triton X-100 harvest buffer. Generally, anellovectors can be enriched, e.g., by lysis of host cells, clarification of the lysate, filtration, and chromatography. In this example, harvested cells are nuclease treated prior to sodium chloride adjustment and 1.2 μm/0.45 μm normal flow filtration. Clarified harvest is concentrated and buffer exchanged into PBS on a 750 kDa MWCO mPES hollow fiber membrane. The TFF retentate is filtered with a 0.45 μm filter before loading on a Sephacryl S-500 HR SEC column pre-equilibrated in PBS. Anellovectors are processed across the SEC column at 30 cm/hr. Individual fractions are collected and assayed by qPCR for viral genome copy number and transgene copy number. Viral genomes and transgene copies are observed beginning at the void volume, Fraction 7, of the SEC chromatogram. Agreement between copy number for Anellovirus genomes and Anellovirus-nLuc transgene for Anellovectors produced using circularized input DNA at Fraction 7-Fraction 10 indicates packaged Anellovectors containing nLuc transgene. SEC fractions are pooled and concentrated using a 100 kDa MWCO PVDF membrane and then 0.2 m filtered prior to in vivo administration.

Example 30: Production of Anellovectors Containing Chimeric ORF1 with Hypervariable Domains from Different Torque Teno Virus Strains This example describes domain swapping of hypervariable regions of ORF1 to produce chimeric anellovectors containing the ORF1 arginine-rich region, jelly-roll domain, N22, and C-terminal domain of one TTV strain, and the hypervariable domain from an ORF1 protein of a different TTV strain.

Figure 24:
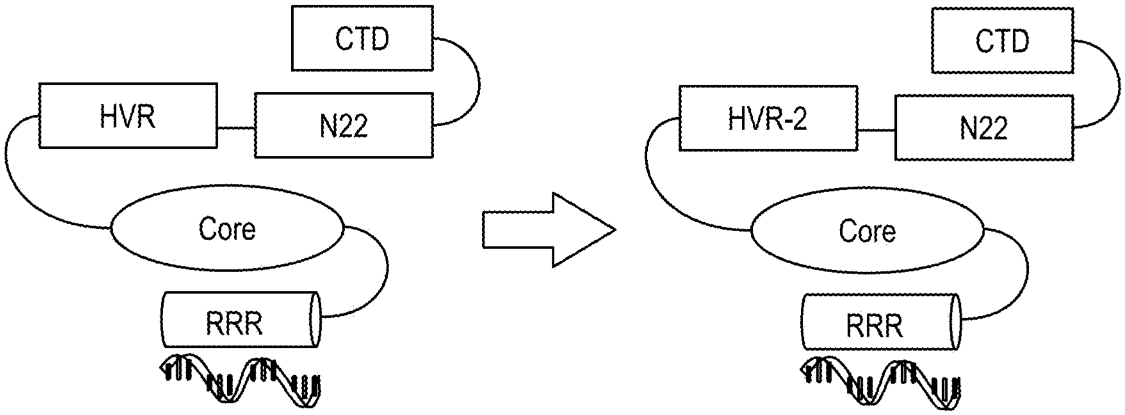
FIG. 24 is a schematic showing the domains of an Anellovirus ORF1 molecule and the hypervariable region to be replaced with a hypervariable domain from a different Anellovirus.
Figure 25:
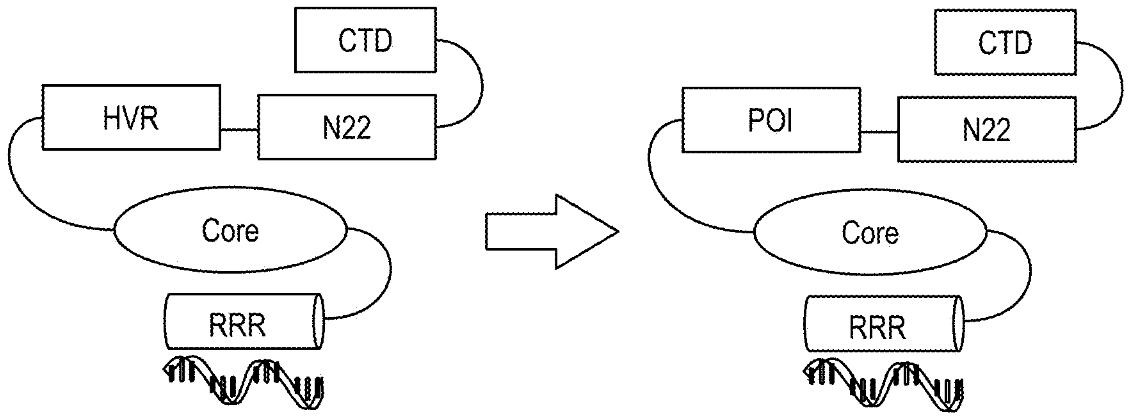
FIG. 25 is a schematic showing the domains of ORF1 and the hypervariable region that will be replaced with a protein or peptide of interest (POI) from a non-anellovirus source.

The full-length genome of a first Anellovirus is cloned into expression vectors for expression in mammalian cells. This genome is mutated to remove the hypervariable domain of the ORF1 coding sequence and replace it with the hypervariable domain of the ORF1 coding sequence from a second Anellovirus genome (FIG. 24). The plasmid containing the first Anellovirus genome with the swapped hypervariable domain is then linearized and circularized as described herein. HEK293T cells are transfected with the circularized genome and incubated for 5-7 days to allow anellovector production. After the incubation period anellovectors are purified from the supernatant and cell pellet of transfected cells by gradient ultracentrifugation.

To determine if the chimeric anellovectors are still infectious, the isolated viral particles are added to uninfected cells. The cells are incubated for 5-7 days to allow viral replication. After incubation the ability of the chimeric anellovectors to establish infection will be monitored by immunofluorescence, western blot, and qPCR. The structural integrity of the chimeric viruses is assessed by negative stain and cryo-electron microscopy. Chimeric anellovectors can further be tested for ability to infect cells in vivo. Establishment of the ability to produce functional chimeric anellovectors through hypervariable domain swapping could allow for engineering of viruses to alter tropism and potentially evade immune detection.

Example 31: Design of an Anellovector Harboring a Payload

This example describes the design of an exemplary anellovector genetic element harboring a trans gene. The genetic element is composed of the essential cis replication and packaging domains from an Anellovirus genome (e.g., as described herein) along with a non-Anellovirus payload, which may include, e.g., protein or non-coding RNA-expressing genes. The anellovector lacks essential trans protein elements for replication and packaging, and requires proteins provided by other sources (e.g., helpers, e.g., replicating viruses, expression plasmids, or genome integrations) for rolling circle replication and encapsidation.

Figure 26:
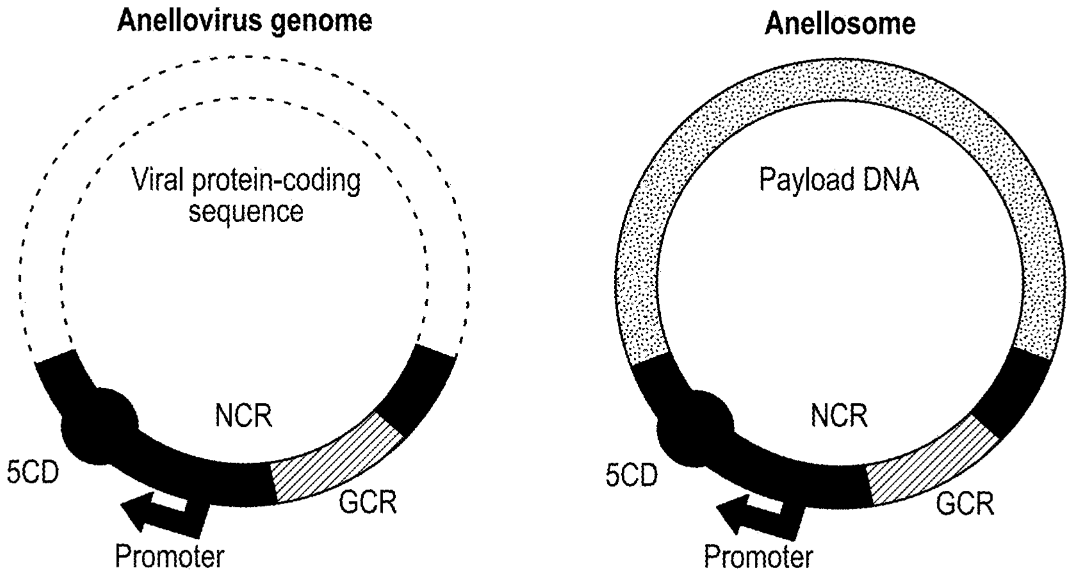
FIG. 26 is a series of diagrams showing the design of an exemplary anellovector genetic element based on an Anellovirus genome. The protein-coding region was deleted from the anellovirus genome (left), leaving the anelloviral non-coding region (NCR), including the viral promoter, 5'UTR conserved domain (5CD), and GC-rich region. Payload DNA was inserted into the non-coding region at the protein-coding locus (right). The resulting anellovector harbored the payload DNA (including open reading frames, genes, non-coding RNAs, etc.) and the essential anellovirus cis replication and packaging elements, but lacked the essential protein elements for replication and packaging.
Figure 27:
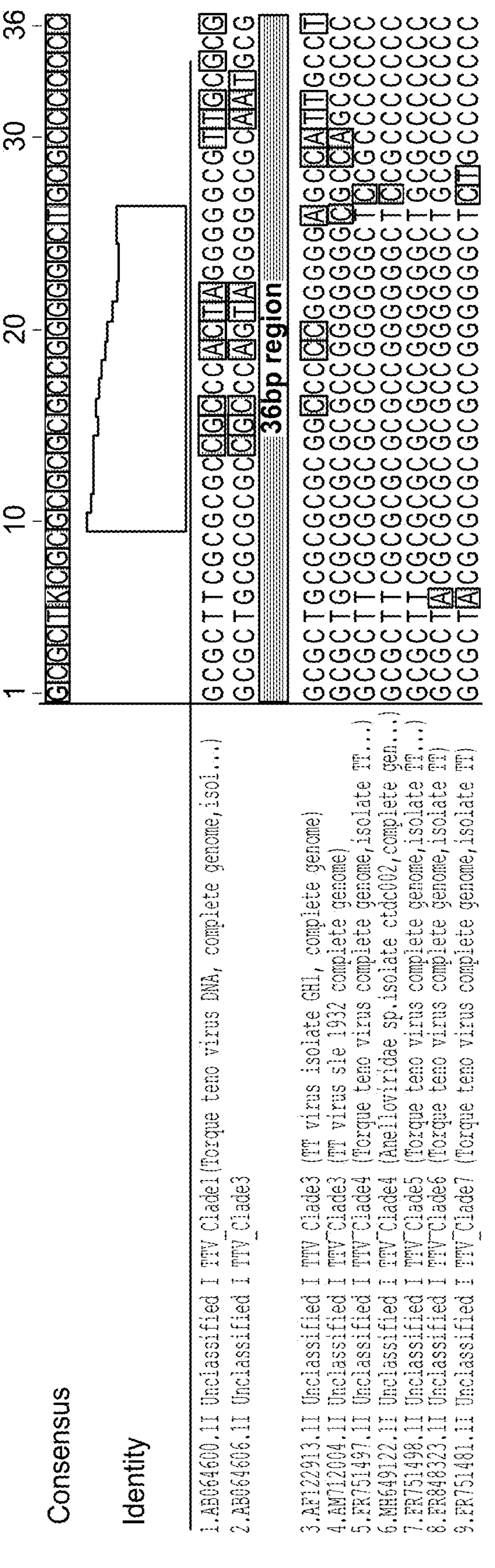
FIG. 27 is a diagram showing an alignment of 36-nucleotide GC-rich regions from nine Anellovirus genome sequences, and a consensus sequence based thereon (SEQ ID NOS 818-827, respectively, in order of appearance).
Figure 28:
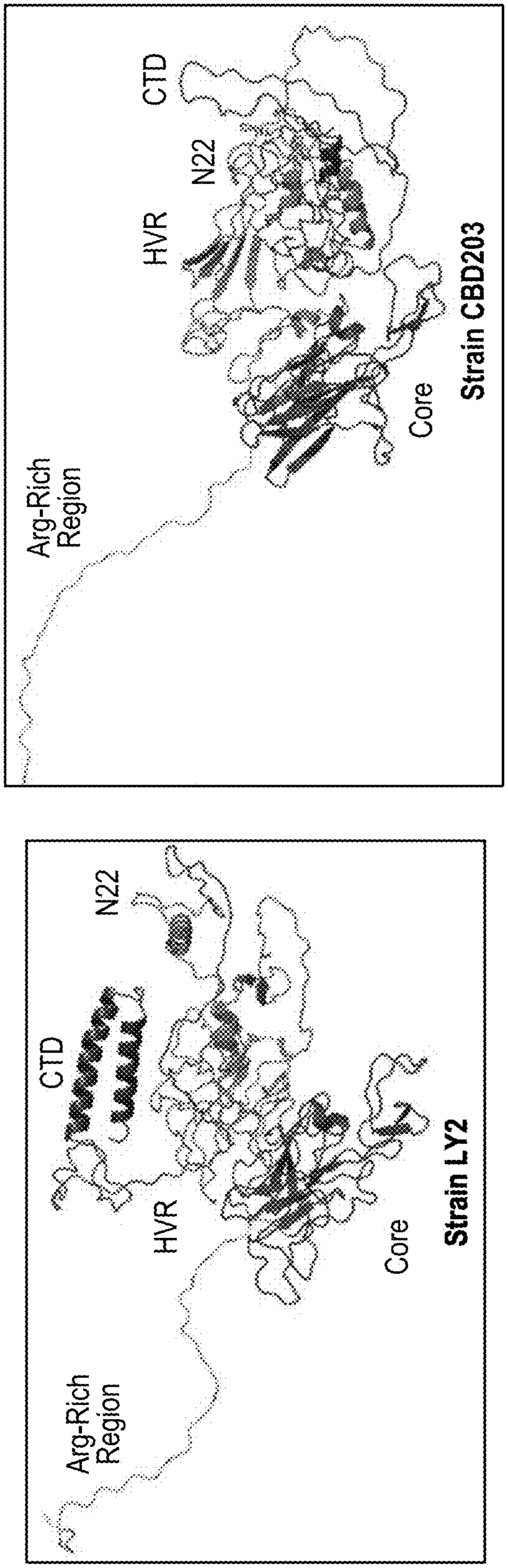
FIG. 28 is a series of diagrams showing ORF1 structures from Anellovirus strains LY2 and CBD203. Putative domains are labeled: arginine-rich region (arg-rich), core region comprising a jelly-roll domain, hypervariable region (HVR), N22 region, and C-terminal domain (CTD), as indicated.

In one set of examples, the entire protein-coding DNA sequence is deleted, from the first start codon to the last stop codon (FIG. 26). The resulting DNA retains the viral noncoding region (NCR), including the viral promoter, the 5' UTR conserved domain, the 3' UTR (which encodes miRNAs in some anellovirus strains), and the GC-rich region. The anellovector NCR harbors essential cis domains, including the viral origin of replication and capsid binding domains. However, lacking the anellovirus protein-coding open reading frames, the anellovector is unable to express essential protein factors required for DNA replication and encapsidation, and therefore cannot amplify or package unless these elements are provided in trans.

Payload DNA, including but not limited to protein-encoding sequences, full trans genes (including non-anelloviral promoter sequences), and non-coding RNA genes are incorporated into the anellovector genetic element by insertion into the site of the deleted anelloviral open reading frames (FIG. 26). Expression from protein-coding sequences can be driven, for example, by either the native viral promoter or a synthetic promoter incorporated as a trans gene.

Replication-deficient or incompetent anellovector genetic elements (e.g., as described herein) may lack the protein-coding sequences for viral replication and/or capsid factors. Therefore, packaged anellovectors are produced by co-transfecting cells with the anellovector DNA described in this example and viral-protein-encoding DNA. The viral proteins are expressed off of replication-competent wild-type viral genomes, non-replicating plasmids harboring the viral proteins under control of the viral promoter, or plasmids harboring the viral proteins under control of a strong constitutive promoter.

Example 32: In Vitro Circularized Genome as Input Material for Producing Anellovector Genetic Elements In Vitro This example demonstrates that in vitro circularized (IVC) double stranded anellovirus DNA, as source material for an anellovector genetic element as described herein, is more robust than an anellovirus genome DNA in a plasmid to yield packaged anellovector genomes of the expected density.

Figure 29:
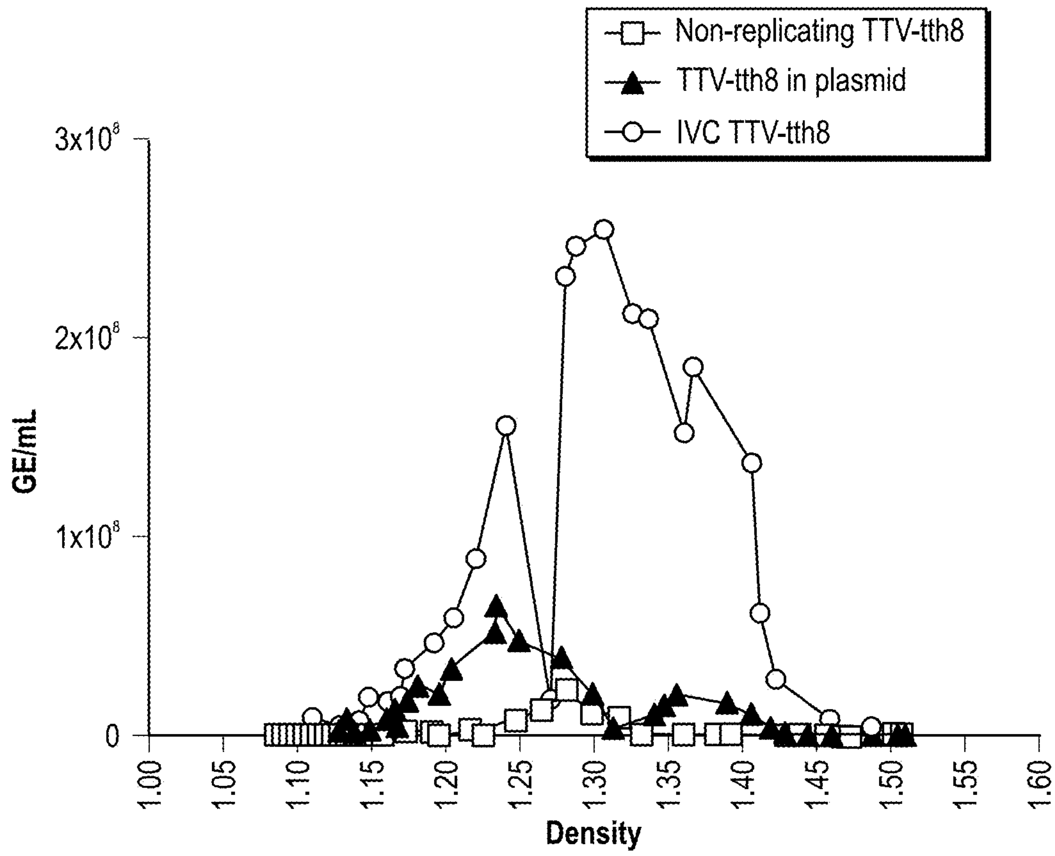
FIG. 29 is a graph showing the ability of an in vitro circularized (IVC) TTV-tth8 genome (IVC TTV-tth8) compared to a TTV-tth8 genome in a plasmid to yield TTV-tth8 genome copies at the expected density in HEK293T cells.

1.2E+07 HEK293T cells (human embryonic kidney cell line) in T75 flasks were transfected with 11.25 ug of either, (i) in vitro circularized double stranded TTV-tth8 genome (IVC TTV-tth8), (ii) TTV-tth8 genome in a plasmid backbone, or (iii) plasmid containing just the ORF1 sequence of TTV-tth8 (non-replicating TTV-tth8). Cells were harvested 7 days post transfection, lysed with 0.10% Triton, and treated with 100 units per ml of Benzonase. The lysates were used for cesium chloride density analysis; density was measured and TTV-tth8 copy quantification was performed for each fraction of the cesium chloride linear gradient. As shown in FIG. 29, IVC TTV-tth8 yielded dramatically more viral genome copies at the expected density of 1.33 as compared to TTV-tth8 plasmid.

Figure 30:
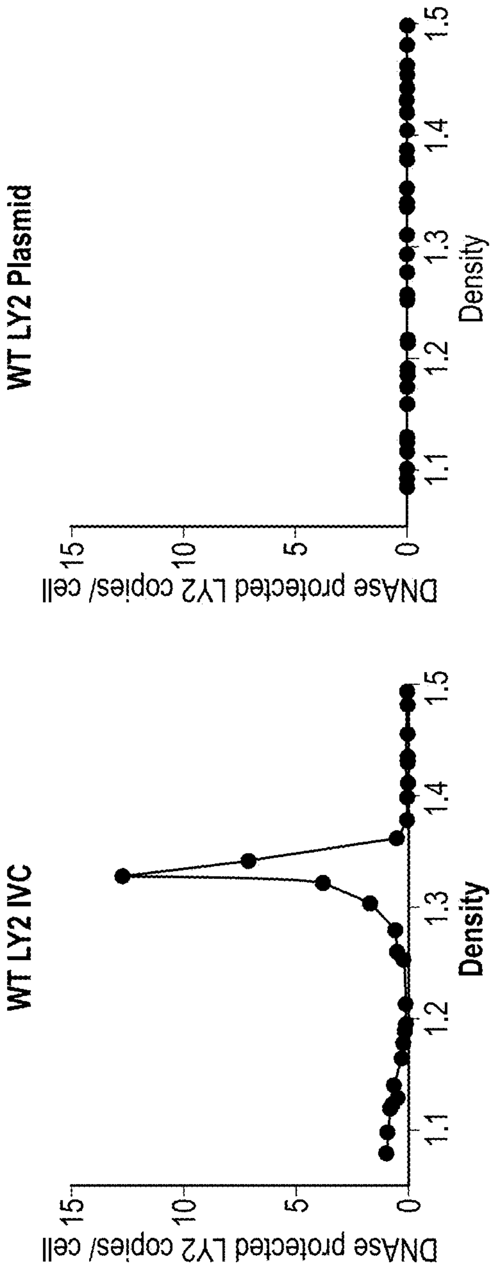
FIG. 30 is a series of graphs showing the ability of an in vitro circularized (IVC) LY2 genome (WT LY2 IVC) and a wild-type LY2 genome in plasmid (WT LY2 Plasmid) to yield LY2 genome copies at the expected density in Jurkat cells.

1E+07 Jurkat cells (human T lymphocyte cell line) were nucleofected with either in-vitro circularized LY2 genome (LY2 IVC) or LY2 genome in plasmid. Cells were harvested 4 days post transfection and lysed using a buffer containing 0.5% triton and 300 mM sodium chloride, followed by two rounds of instant freeze-thaw. The lysates were treated with 100 units/ml benzonase, followed by cesium chloride density analysis. Density measurement and LY2 genome quantification was performed on each fraction of the cesium chloride linear gradient. As shown in FIG. 30, transfection of in vitro circularized LY2 genome in Jurkat cells led to a sharp peak at the expected density, as compared to the transfection of plasmid containing the LY2 genome, which showed no detectable peak in FIG. 30.

In some embodiments, IVC anellovector genetic element constructs can be introduced into insect cells (e.g., Sf9 cells) and enclosed within proteinaceous exterior proteins expressed from a bacmid, e.g., as described herein.

Example 33: Antibody Generation and Western Blot Analysis

This example describes generation of Ring 10 (also referred to herein as Ly1) antibodies and western blot analysis for determining expression, e.g., of Ring 10 ORF1 proteins. Ring 10 antibodies were generated by immunizing rabbits with a synthetic peptide representing one of three portions of the ORF1 protein (jelly roll residues 46-58: KIKRLNIVEWQPK, spike domain residues 485-502: SPSDTHEPDEEDQNRWYP, C-terminal domain residues 635-672: SEEEEESNLFERLLRQRTKQLQLKRRIIQTLKDLQKLE) conjugated to a carrier protein by an engineered N-terminal cysteine. Rabbits were immunized twice, and polyclonal antibodies were purified from bleeds using protein A purification (Custom Antibody Production, Life Technologies corporation). Western blot analysis was performed using NUPAGE 4-12% gels (ThermoFisher) transferred to nitrocellulose membranes using the Transblot Turbo system (BioRad). Membranes were blocked with blocking buffer (Licor), probed ~16 hours with primary antibody, and detected using anti-rabbit IRDye infrared secondary antibodies and imaging system (Licor).

Example 34: Construct Design, Cell Culture and Protein Expression/Purification This example describes design of Ring 10 constructs, cell culture, and expression/purification of Ring 10 proteins. The Ring 10 ORF2 and ORF1 sequences were codon optimized for insect cells and with different ORF1 construct length variations (full-length ORF1, delARM with a deletion of residue 2-45, and delARM/delCTD with deletions of residues 2-45 and 552-672). The ORF2 and ORF1 constructs were cloned into the pFastBac Dual plasmid which was used to generate baculoviruses. To express the ORF1 proteins, Sf9 cells (Gibco™ 11496015) were infected by baculovirus with multiplicity of infection=1 and the cells were cultured for three days at 27° C. and harvested by centrifugation. The cells were lysed by treatment with 0.01% Triton X-100 (Sigma-Aldrich 11332481001), subjected to micro-fluidization, and treated with protease inhibitors (Thermo Scientific Halt Protease Inhibitor Cocktail, PI78438) and DNase (Benzonase®; Sigma). Cell lysate was subsequently purified using HiTrap Heparin affinity chromatography (Cytiva) followed by size-exclusion chromatography (HiPrep 16/60 Sephacryl S-500 HR; Cytiva).

Example 35: Negative-Stained EM Data Collection and Analysis

This example describes visualization of anellovirus particles using negative stain electron microscopy. Jeol 1200EX transmission electron microscope was used for screening different Ring 10 constructs. 10 μl of sample was blotted on 400 mesh carbon support film (cf400-cu, EMS) for 30 seconds. After washing by $ddH_2O$ for 30 seconds, the grid was stained by 0.75% of uranyl formate (UF) for 10 seconds before loading on the scope. Ring 10 delARM was further imaged at NanoImaging Service. 3 μl of 0.12 mg/ml was blotted to a continuous carbon grid and stained by 1% UF. Negative-stained electron microscopy was performed using a Thermo Fisher Scientific (Hillsboro, Oregon) Glacios Cryo Transmission Electron Microscope (cryo-TEM) operated at 200 kV and equipped with a TFS CETA-D 4×4 CMOS camera and a Falcon 4 direct electron detector.

Example 36: Cryo-EM Data Collection and Data Analysis and Molecular Refinement This example describes performing cryogenic electron microscopy (Cryo-EM) and data analysis, e.g., for determination of anellovirus particle structure. For the grid preparation, 3 μl of 0.3 mg/ml VLP sample was applied to a 1.2×1.3 graphene oxide grid. A total of 11,083 micrographs were collected from Glacios cryo-TEM (Thermo Fisher Scientific) operated at 200 kV with a Falcon 4 direct electron detector, at a nominal defocus range of −1.0-−2.5 μm and accumulated dose of 19.59 $e^-$/Å for a total of 15 frames in 3 minutes. The pixel size was 0.923 Å, with the magnification 150000×. Automated data-collection was carried out by Leginon software.

All micrographs were motion-corrected by Relion-4.0 implemented MotionCor2, and the contrast transfer function (CTF) parameters were estimated by Gctf. With manually picked particles from 20 micrographs to train the network, SPHIRE-crYOLO automatically picked 58,391 particles along with the PhosaurusNet network. All particles were extracted by Relion-4.0 and rescaled to 2-fold (pixel size 1.846 Å), followed by subsequence 2D classifications with 350 Å mask diameter to remove any junk particles. Two iterations of 2D classifications resulted in 11,185 particles, which were merged and reextracted to generate a de novo 3D initial model by Relion-4.0 with I1 symmetry. Notably, several similar initial models without symmetry imposed were obtained by Relion-4.0 and cisTEM. To obtain a better classification result, all particles were first subjected to a Refine3D with initial angular sampling 3.7° and local angular search 0.9° per step. The alignment parameters of each particle were transferred to a 3D classification with angular sampling interval 0.9° and local angular search 5° per step. 3D classification of the entire particle set attributed most of the particles into a single class. After CtfRefine and Bayesian polishing, the post-processing results in 3.98 Å resolution under the gold standard (with FSC=0.143).

The initial anellovirus TTMV-LY2 capsid monomer structure was predicted by TrRosetta, and Ring 10 structure was further predicted by RosettaCM. Structural refinement was performed by Rosetta and Phenix, and fine-adjusted by COOT. JA 20 and SAFIA structures are predicted by Alphafold.

Example 37: Circular Dichroism Spectroscopy

This example describes performing circular dichroism spectroscopy to determine secondary structure of, e.g., an anellovirus ORF1 protein. To determine the secondary structure of the Ring 10 C-terminal domain, the peptides used to generate C-terminal antibodies (residues 635-672) were analyzed at 25.8 μM in PBS on a Jasco J-815 circular dichroism spectropolarimeter using 2 mm path length cell at ambient temperature. Each data set is the average of three consecutive scans. The secondary structure was determined by using CDPro software package, compared with a reference set containing 56 proteins (IBasis=10). The final secondary structure fractions were averaged over the results from three programs (SELCON3, CDSSTR, CONTINLL) in CDPro.

Example 38: Anellovirus Particle Structure

This example describes determination of the particle structure of an exemplary Anellovirus.

Figure 31A:
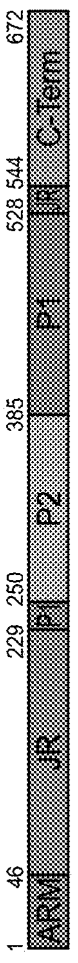
FIG. 31A is a schematic presentation of full-length Ring 10 ORF1 (also referred to herein as Ly1) labeled by domains: the structural arginine-rich motif (ARM), the structural jelly roll (JR) domain, the spike P1 domain, the spike P2 domain, and the C-terminal domain. Residue numbers beginning each domain and the structural C-terminal domain (also referred to as the C-terminus) are indicated above.
Figure 31B:
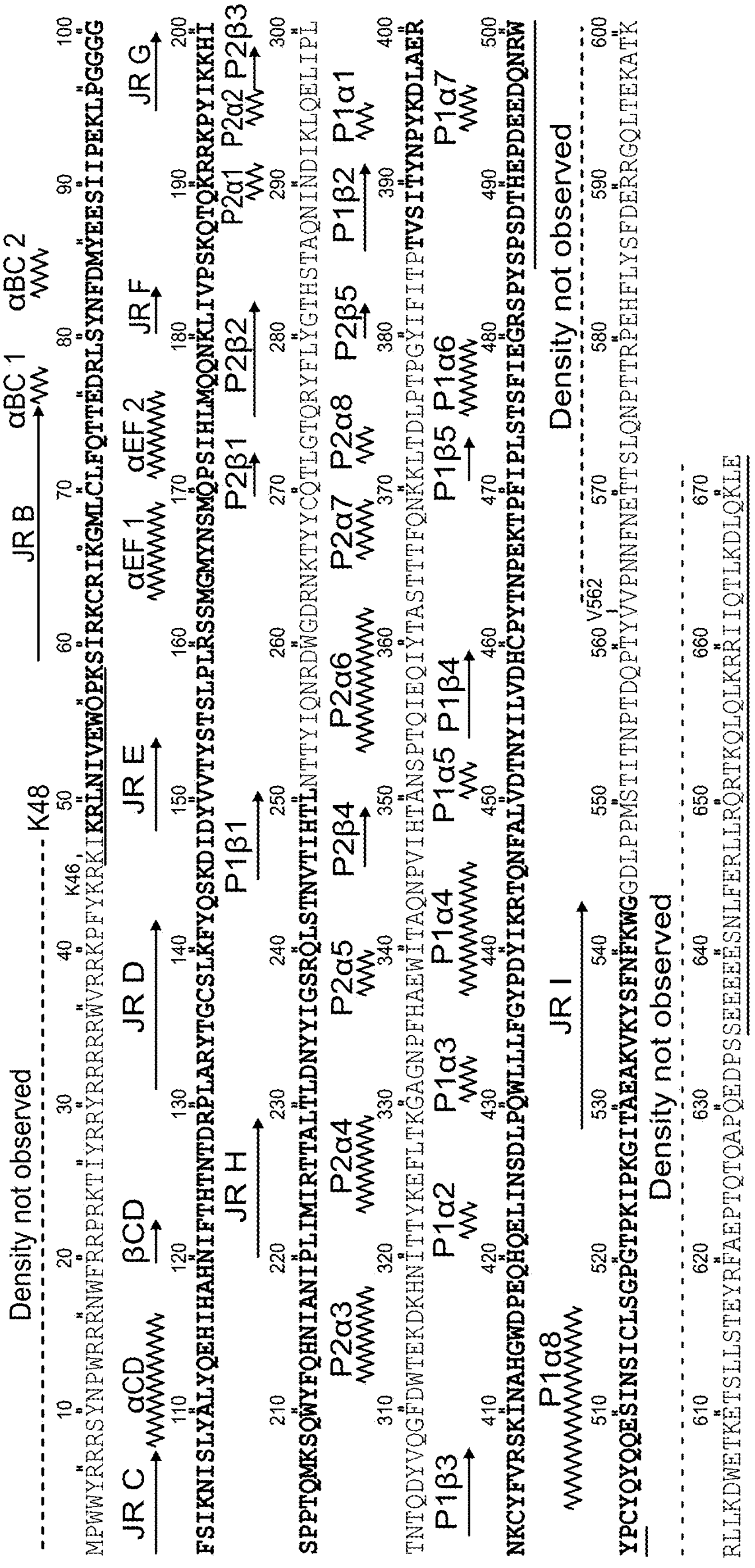
FIG. 31B is the sequence of full-length Ring 10 ORF1 with residue numbers indicated above. In bold are residues included in the Ring 10 delARM construct including the initial residue, K46, which is labeled. A dashed line above the sequence indicates residues not observed in the density. Secondary structure elements are indicated above with β-strands as arrows and α-helices as zig-zag lines. The JR β-strands are labeled B-I per convention while additional secondary structures are numbered by their domain. Three peptides used to generate polyclonal antibodies are underlined.
Figure 31C:
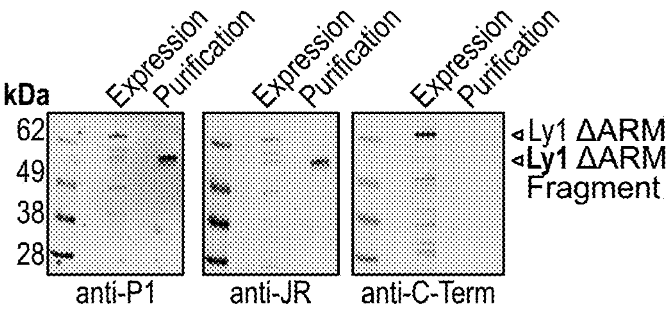
FIG. 31C shows western blot analysis of Ring 10 delARM after expression (Expression) and after purification and storage (Purification). A molecular weight marker is labeled to the left of the gels, while arrows on the right indicate the band of Ring 10 delARM before (Ring 10 delARM) and after proteolysis (Ring 10 delARM Fragment). Polyclonal antibodies used to probe the western blots are indicated below.
Figure 34A:
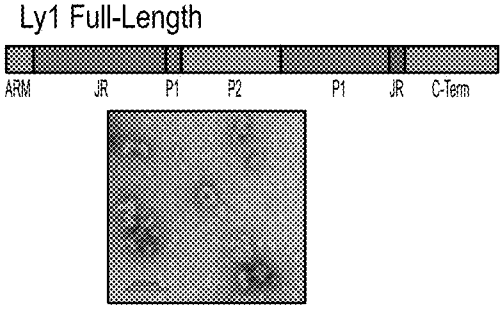
FIG. 34A is a schematic representation of full-length Ring 10 (top), which shows highly heterogeneous particles by negative-stained electron microscopy (bottom). Scale bar=100 nm.

Initial efforts to study the structure of a virus-like particle (VLP) derived from a TTMV isolate described herein as Ring 10, were done with the full-length ORF1 (residues 1-672) expressed in insect cells (Sf9). Full-length ORF1 was visualized by electron microscopy (as described in Example 35) and was observed to assemble into particles ~32 nm in diameter (FIG. 34A), similar to previously reported estimates of anellovirus size. However, full-length ORF1 particles lacked the homogeneous symmetry expected of viral particles (FIG. 34A). Genome packaging by ARM-containing viruses is believed to occur when the positive arginine residues bind a negatively charged genome, overcoming electrostatic repulsion of the ARM to permit ORF1 assembly. Therefore, Ring 10 delARM, an ORF1 construct wherein residues 2-45 are deleted, was designed as described in Example 34 (FIGS. 31A, 31B, and 34B) to facilitate more efficient ORF1 assembly in the absence of viral DNA. Ring 10 delARM expression was confirmed using a rabbit polyclonal antibody raised against a spike domain peptide (residues 485-502; FIG. 31B) as described in Example 33. A band consistent with Ring 10 delARM was observed by western blot analysis (expected mass of 73.3 kDa; FIG. 31C) performed as described in Example 33. Ring 10 delARM yielded an ORF1 band above the 62-kDa marker (FIG. 31C). The difference in apparent molecular weight of Ring 10 delARM ORF1 after initial expression and after purification suggested proteolysis. To identify the site of proteolysis, polyclonal antibodies to peptides from the extreme N- and C-termini of Ring 10 delARM (residues 46-58 and residues 635-672, respectively; FIG. 31B) were generated as described in Example 33, and the presence of the N-terminal peptide of Ring 10 delARM on the purified fragment and the absence of the C-terminal peptide were confirmed (FIG. 31C).

Figure 34B:
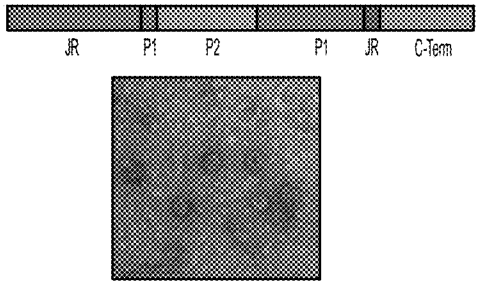
FIG. 34B is a schematic representation of Ring 10 delARM (arginine-rich motif; top), which demonstrates a structural homology virus-like particle (VLP) as shown by negative-stained electron microscopy (bottom). Scale bar=100 nm.
Figure 34C:
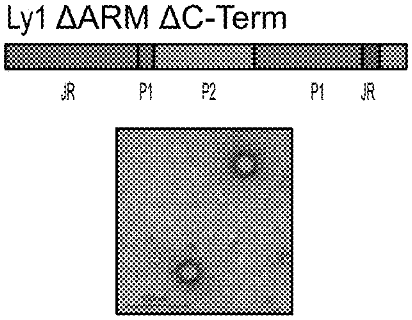
FIG. 34C is a schematic representation of Ring 10 delARM delCTD (top), wherein further truncation of the structural C-terminal domain (Δ552-672) preserves a structured VLP as shown by negative-stained electron microscopy (bottom). Scale bar=100 nm.
Figure 35:
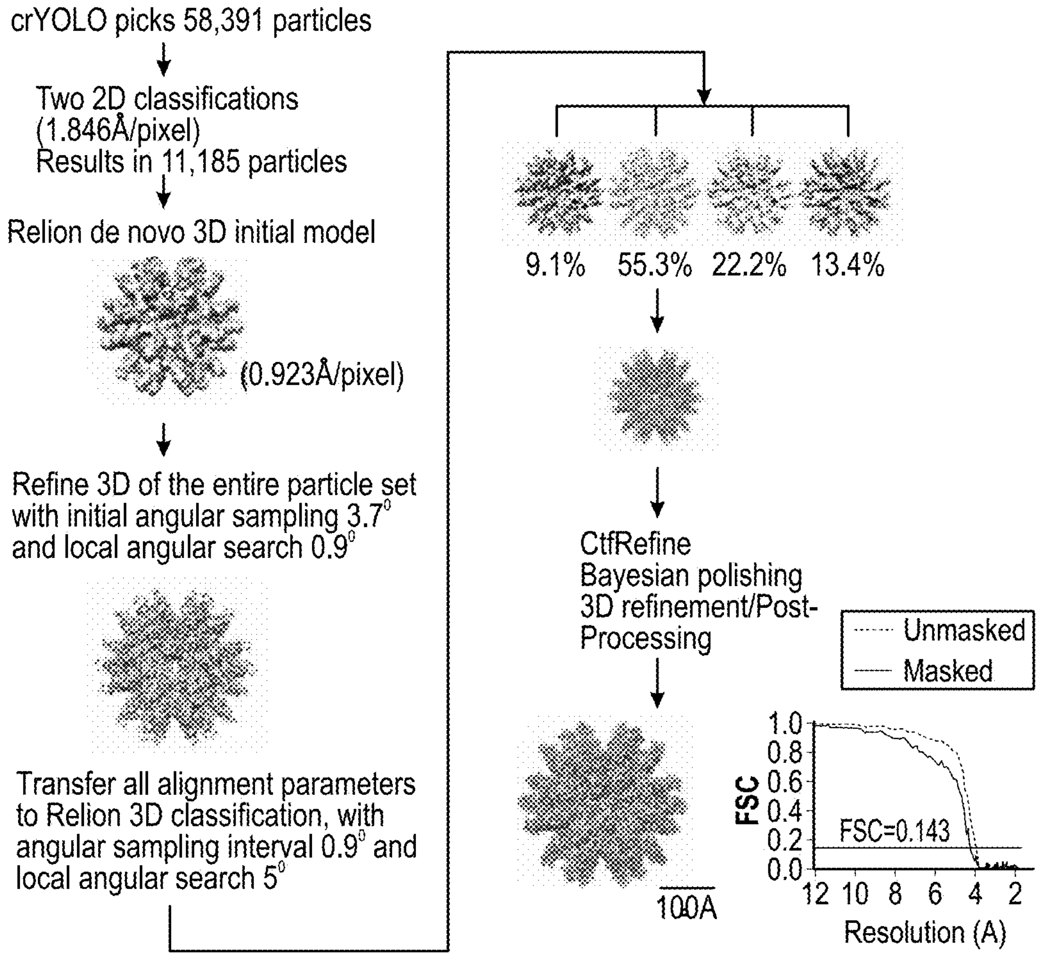
FIG. 35 depicts a data processing procedure of the Ring 10 delARM cryogenic electron microscopy (cryo-EM) reconstruction. In short, crYOLO picked 58,391 particles from 11,083 micrographs. Several rounds of 2D classification resulted in 11,185 particles. After Relion de novo initial model reconstruction, Relion 3D refinement was implemented to obtain the orientation parameters. All particles with parameters were fed in a 3D classification. The class with the most abundant particle population resulted in 3.98 Å resolution.
Figure 36A:
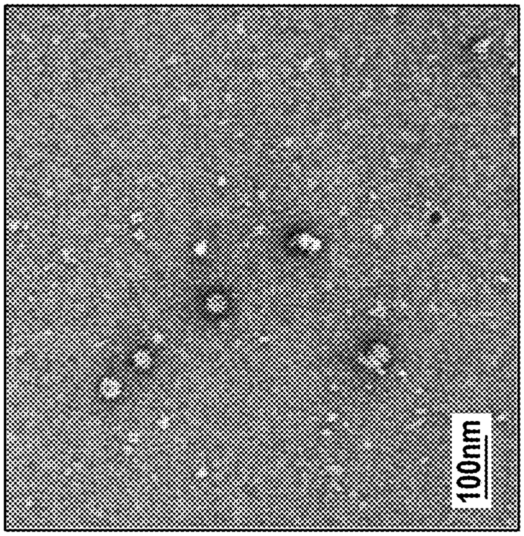
FIG. 36A is a representative negative-stained micrograph of Ring 10 delARM. The micrograph was imaged at NanoImaging Service.
Figure 36B:
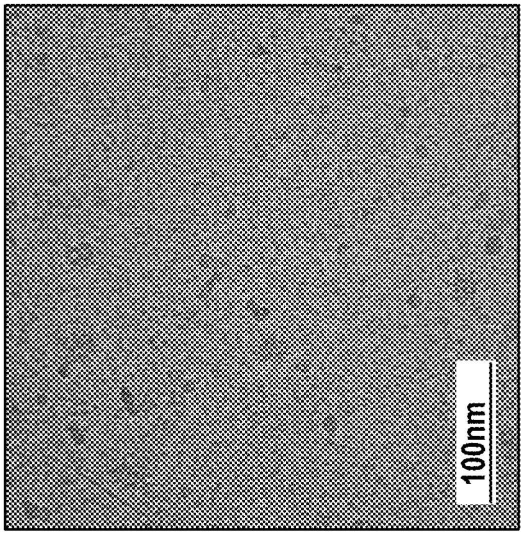
FIG. 36B is a representative cryo-EM micrograph of Ring 10 delARM. The micrograph was imaged at NanoImaging Service.

Electron microscopy (EM) analysis of the Ring 10 delARM fragment showed the VLPs formed were more homogeneous and symmetric in morphology relative to full-length ORF1 (FIGS. 34A and 34B). The formation of homogeneous VLPs following genetic removal of the N-terminus and proteolysis of the C-terminus has been observed in another JR-containing virus, hepatitis E (HEV). To determine if the C-terminus of Ring 10 ORF1 is required for particle formation, VLPs from construct Ring 10 ORF1 delARM delCTD (wherein residues 2-45 and 552-672 are deleted) were generated as described in Example 34. Ring 10 ORF1 delARM delCTD produced VLPs of similar symmetry to Ring 10 ORF1 delARM (FIGS. 34B and 34C). These results suggest that proteolysis of the ORF1 C-terminus may be a natural part of anellovirus formation. In light of recent evidence that the C-terminal region of ORF1 is the immunodominant region of anelloviruses, its excision from the mature particle would be consistent with the immune evasion properties of anelloviruses.

Figure 31D:
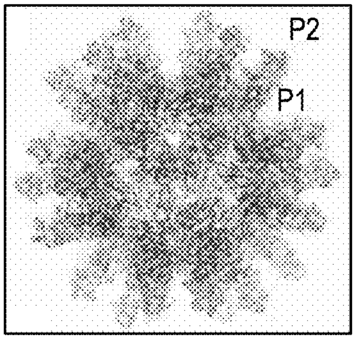
FIG. 31D is an overlay of the 3D reconstruction of Ring 10 delARM VLP electron density and 60-mer VLP molecular structure. The spike P1 and P2 domains are labeled.
Figure 31E:
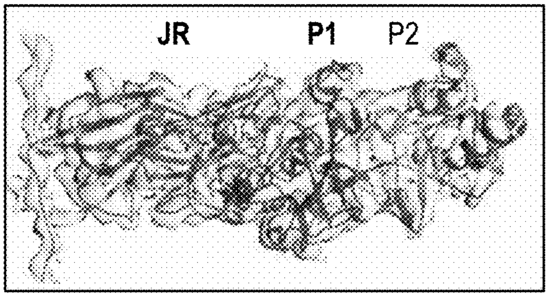
FIG. 31E depicts one ORF1 protomer, shown in its electron density with domains labeled.
Figure 31F:
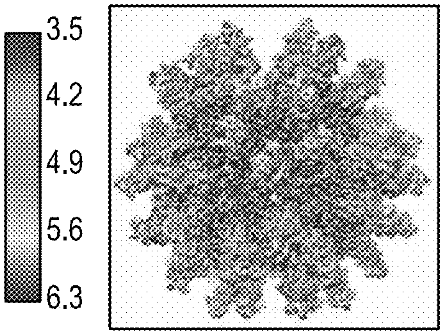
FIG. 31F depicts the electron density of Ring 10 delARM VLP indicated by its local resolution. The bar (left) indicates the resolution (unit in angstrom) scale. The particle (right) is oriented as in FIG. 31D.

The structure of the Ring 10 delARM particle was determined using cryo-EM to 3.98 Å resolution as described in Example 36 (FIGS. 31D-31F, 35, 36A, and 36B; Table S1). The anellovirus particle was shown to be formed by sixty ORF1 fragments organized in an icosahedral T=1 symmetry (FIG. 31D). Electron density for residues 48-562 was observed (FIG. 31B). The resulting mass of the observed Ring 10 fragment was calculated to be ~59.8 kDa. The N-terminal region (residues 46-228) forms part of the canonical 8-β-strand JR domain (β strands named B to H by convention). Unexpectedly, the eighth and final β-strand in the JR (strand I, residues 531-542) is located just prior to the C-terminal domain (FIG. 31B). The resulting fold of the ORF1 protomer has residues at the N- and C-termini generating the JR domain at the particle core while the intrastrand residues form the exterior of the particle surface. Intrastrand insertions forming the viral particle exterior can be found in other JR-containing viruses such as adeno-associated virus (AAV) and canine parvovirus (CPV). However, while the intrastrand insertions for AAV2 (228 residues) and CPV (227 residues) are between G and H β-strands, the 298-residue intrastrand insertion in Ring 10 is significantly larger and lies between β-strands H and I. The intrastrand region (residues 229-530) extends from the JR domain to form a structure herein referred to as a spike domain. The spike domain is formed by two globular domains: the spike P1 domain (residues 229-250 and 386-530) and the spike P2 domain (residues 25 1-385; FIG. 31B, 31E).

TABLE S1

Cryo-EM data collection, refinement and validation statistics of TTMV-Ring 10 delARM.

| | Ring 10 delARM |
|---|---|
| Data collection and processing | |
| Magnification | 150000x |
| Voltage (kV) | 200 |
| Electron exposure (e-/Å$^2$) | 1.31 |
| Defocus range (um) | −0.5~−2.5 |
| Pixel size (Å) | 0.923 |
| Symmetry imposed | I1 |
| Initial particle images (no.) | 58391 |
| Final particle images (no.) | 6271 |
| Map resolution (Å) | 3.98/0.143 |
| FSC threshold | |
| Map resolution range (Å) | 3.9-6 |
| Refinement | |
| Initial model used (PDB code) | |
| Model resolution (Å) | 3.98/0.143 |
| FSC threshold | |
| Model resolution range (Å) | 3.9-6 |
| Map sharpening B factor (Å$^2$) | −152.851 |
| Model composition | 253440/30900/0 |
| Non-hydrogen atoms | |
| Protein residues | |
| Ligands | |
| B factors (Å$^2$) | 30.00/243.72/133.17 |
| Protein | |
| Ligand | |
| R.m.s. deviations | 0.007/1.282 |
| Bond lengths (Å) | |
| Bond angles (°) | |
| Validation | 2.36/25.43/0 |
| MolProbity score | |
| Clashscore | |
| Poor rotamers (%) | |
| Ramachandran plot | 92.6/6.62/0.78 |
| Favored (%) | |
| Allowed (%) | |

TABLE S1-continued

| Cryo-EM data collection, refinement and validation statistics of TTMV-Ring 10 delARM. | |
|---|---|
| | Ring 10 delARM |
| Disallowed (%) | |
| CC (mask) | 0.81 |
| MolProbility | 2.36 |
| Clash Score | 25.43 |

Example 39: Anellovirus Structural Jelly Roll Domains

Figure 32B:
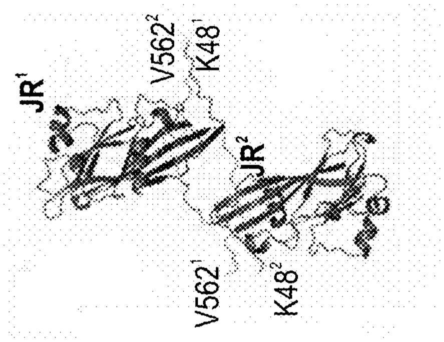
FIG. 32B depicts two JR domains, with the observed C-terminal domain backbone. The JR domains are arbitrarily labeled $JR^1$ and $JR^2$ with the first (K48) and last (V562) observed residues for each protomer labeled with the corresponding number for clarity.

This example describes the structure of anellovirus structural jelly roll (JR) domains. Sixty Ring 10 JR domains form the core of the virus particle (FIG. 32A-32D). The β-strands form β-sheets which are characterized by a C-H-E-F pattern on the core's exterior and B-I-D-G pattern on the core's interior. The N-terminus of strand B is oriented to place the ARM on the interior of the core, where it is positioned to bind the viral genome. The observed C-terminal residues (545-562) extend from the C-terminus of β-strand I on the interior of the particle and thread through JR domains on the 2-fold axis to contact the neighboring JR domain (FIG. 32B).

Figure 32C:
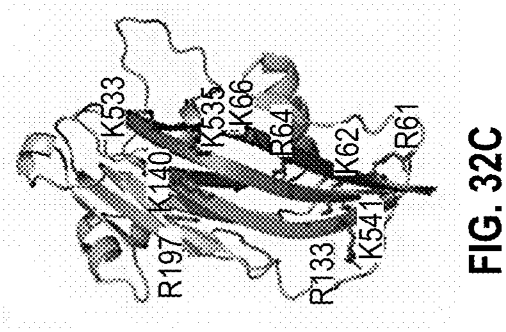
FIG. 32C depicts a single JR domain oriented to show the β-sheet on the interior of the particle core. Sidechains of basic residues in position to contact with the viral genome are shown and labeled.

In several JR-containing viruses, positively charged residues (arginine and lysine) oriented internally on strands B, I, D, and G are expected to bind the negatively charged viral genome (FIG. 32C). In Ring 10, basic residues Arg61, Lys62, Arg64, Lys66 (β-strand B), Lysl140 (β-strand D), Arg197 (β-strand G), Lys533, Lys535, and Lys541 (β-strand 1) are all oriented toward the particle interior and are likely responsible, together with the ARM/motif, for binding the negatively charged viral genome. Notably, density suggesting bound nucleic acid was not observed, possibly because the ARM deletion prevented nucleic acid binding or because any host cell nucleic acid encapsidated by the VLP would be too heterogeneous for detection. Alignment of anellovirus ORF1 sequences revealed that several of these putative DNA-binding residues are conserved across species, which supports their role in DNA-binding (FIG. 32D).

Example 40: Anellovirus Spike Domains

This example describes the structure of exemplary anellovirus spike domains, which include the P1 and P2 domains (e.g., as described herein). Residues 229 to 530 form the spike domain that extends ~6 nm from the JR core (FIG. 33A-33D). A β strand (residues 245-250) extending from JR β-strand H is the first component of the spike P1 domain and is N-terminal to the spike P2 domain (residues 251-385). The previously described hypervariable region (HVR) of ORF1 comprises the majority of the spike P2 domain. The remaining residues of the spike domain (residues 386-530) form five additional β-strands and eight helices, which, together with the residues 245-250 strand, fold into the spike P1 domain. The local resolution of P1 is only slightly lower than the JR domain (~4-4.5 Å), while the resolution of P2 is within 5-6 Å. This is likely a consequence of both being further from the radius of gyration and some flexibility of the HVR residues.

Neighboring spike domains pack together around the five-fold symmetry axis to form a ringed structure of 5 spike domains henceforth called the crown (FIG. 33A, 33B). A receptor for anelloviruses has not been identified to date. Given the diverse tropism of different anellovirus strains, it is possible that residues of the spike P2 HVR, which are the most surface-exposed, are involved in viral attachment and infection. However, the hypervariable sequence of the spike P2 domain may serve to aid in immune evasion rather than harboring a receptor-binding motif. If this is the case, a receptor-binding motif on the better conserved spike P1 domain, or even on the surface of the JR core, may exist.

Sequence alignment of the Ring 10 spike domain with other anelloviruses did not readily identify conserved spike surface residues (FIG. 33B-33D, FIG. 38; sequences reproduced below). In fact, the Ring 10 residues that are more conserved between other anelloviruses (e.g., Asp396, Pro429, Trp431, Gly437, Pro461, Phe477, Pro483, Trp500, Tyr501, Pro502, Gly518 and Pro519) are internal spike P1 residues supporting its globular fold. A few basic residues are semi-conserved on the spike P1 surface (e.g., Arg390, Arg481, Arg499, and Arg523) which could contribute to the particle's ability to bind heparin resin. A few semi-conserved hydrophobic or aromatic residues on spike P1 (e.g., Leu231, I1e236, Val245, Tyr404, Gly414, I1e424, Leu428, Leu432, Val450, I1e478, and Tyr484) are at least partially surface-exposed and could represent a conserved receptor binding surface (FIG. 33B-33D). If this is the case, then it is attractive to posit that anelloviruses have evolved their novel elongated H-I intrastrand spike domain to sterically hinder antibody binding to their cellular receptor-binding site present on the P1 surface using domain P2 which is able to tolerate highly diverse amino acid substitutions. This would allow diverse anelloviruses to repeatedly infect human hosts with minimal recognition and neutralization by the immune system.

Sequences included in sequence alignments (FIG. 38)

\>Ly1 (Ring10)_orf1
MPWWYRRRSYNPWRRRNWFRRPRKTIYRRYRRRRRWVRRKPFYKRKIKRLNIVEWQPKSIRKCRIKGMLCLFQT
TEDRLSYNFDMYEESIIPEKLPGGGGFSIKNISLYALYQEHIHAHNIFTHTNTDRPLARYTGCSLKFYQSKDID
YVVTYSTSLPLRSSMGMYNSMQPSIHLMQQNKLIVPSKQTQKRRKPYIKKHISPPTQMKSQWYFQHNIANIPLL
MIRTTALILDNYYIGSRQLSTNVTIHTLNTTYIQNRDWGDRNKTYYCQTLGTQRYFLYGTHSTAQNINDIKLQE
LIPLINTQDYVQGFDWTEKDKHNITTYKEFLTKGAGNPFHAEWITAQNPVIHTANSPTQIEQIYTASTTTFQNK
KLTDLPTPGYIFITPTVSLRYNPYKDLAERNKCYFVRSKINAHGWDPEQHQELINSDLPQWLLLFGYPDYIKRT
QNFALVDTNYILVDHCPYTNPEKTPFIPLSTSFIEGRSPYSPSDTHEPDEEDQNRWYPCYQYQQESINSICLSG
PGTPKIPKGITAEAKVKYSFNFKWGGDLPPMSTITNPTDQPTYVVPNNFNETTSLQNPTTRPEHFLYSFDERRG
QLTEKATKRLLKDWETKETSLLSTEYRFAEPTQTQAPQEDPSSEEEEESNLFERLLRQRTKQLQLKRRIIQTLK
DLQKLE \>Ly2 (Ring2)_orf1
MPYYYRRRRYNYRRPRWYGRGWIRRPFRRRFRRKRRVRPTYTTIPLKQWQPPYKRTCYIKGQDCLIYYSNLRLG
MNSTMYEKSIVPVHWPGGGSFSVSMLILDALYDIHKLCRNWWTSTNQDLPLVRYKGCKITFYQSTFTDYIVRIH
TELPANSNKLTYPNTHPLMMMMSKYKHIIPSRQTRRKKKPYTKIFVKPPPQFENKWYFATDLYKIPLLQIHCTA -continued Sequences included in sequence alignments (FIG. 38)

CNLQNPFVKPDKLSNNVTLWSLNTISIQNRNMSVDQGQSWPFKILGTQSFYFYFYTGANLPGDITQIPVADLLP
LINPRINRPGQSLNEAKITDHITFTEYKNKFTNYWGNPFNKHIQEHLDMILYSLKSPEAIKNEWTTENMKWNQL
NNAGTMALTPFNEPIFTQIQYNPDRDTGEDTQLYLLSNATGTGWDPPGIPELILEGFPLWLIYWGFADFQKNLK
KVTNIDTNYMLVAKTKFTQKPGTFYLVILNDTFVEGNSPYEKQPLPEDNIKWYPQVQYQLEAQNKLLQTGPFTP
NIQGQLSDNISMFYKFYFKWGGSPPKAINVENPAHQIQYPIPRNEHETTSLQSPGEAPESILYSFDYRHGNYTT
TALSRISQDWALKDTVSKITEPDRQQLLKQALECLQISEETQEKKEKEVQQLISNLRQQQQLYRERIISLLKDQ

>MN773391.1|Beta|245_2239_2_fow
MPPFRRNWWSNYYKPKWRRRRFPARRRRFTTTFRKRRRRTKKVKRHFYSKKYKRKLKKIILRQWQPSTIKRCKI
EGYLCLFQAGKGRFSFNYASYKESFCPEHEPGGGGWGLQQLSLSNLYSQNCDLMNWWTKSNNHLNLCRYMGCEI
TLFRQDTVDYVFTYFDEQPKNVSKYYYATFHPTKLMLYNRKIVVPSFASQPHKRKPYKRKFIRAPKLMKNQWYF
QQQLAPYPLLQFAATAVSLNKMFGSSKALNNNCTVYCLNTDFFRHPHFQYSAQPFTPDGGNQPTYIYTIQRGEP
PITAYKYFNLTFLGQTMINDPGIPLSNNNNYTKNEWGNVFFYKYLNNDELTYVSKETIDQVKQKKNQQITSGFT
LKDQPYYYTLKYNPYKDKGKGNQAYWVSNIEATKQNWEPPNDPDLIISDFPFWIMLWGWEDMTKRIGKCRNLDN
DWILVLRTQYFSDKMTAYVPLSEAFIHGQGPYFVDRSEIKGQDYAHWYPRYRYQREAIENILMTGPMVCRADNI
NNIQSLIKYKFFFKWGGTPATMENVYDPMSQPITPSPNNLISTNEIINPETSIDNYIYKWDTRRDILTQKATDR
ITKSSTYDSNVFTDGRETSTDIPLFQTTQKAPQEETPETQAETLLLQLHQLQQFNLQLQQRFNNLKQLMQNI >MN769198.1|Beta|265_2235_1_fow
MPWYNYWPRRRRLRRYWRRPRKTLRRRYWRRPRWVRRPYKRKLRKIVLTQFQPKTIRKSKIKGPICLFQTTNKR
LVNNFDMYETSEVPEHQPGGGGWGIKVFTLEGLYSEHIYGRNIWTVTNQDLPLVRYLGCSIRFYQSEYTDYVAT
YSNQLPLQSSLGMYNAMQPNIHLLLKNKITMPGLKTYKRRVPYKKVFVPPPTQLENKWYFQQNIAKTPLLMTRV
TACSLNKFYIDPDHINTNLTITSLNVSLFSNRQFQDATDYHPKTVGTINYYLYSTTQNPPYNGPLKLKMLIPLT
DTMIYKPGINYEEYKRNNTTKGWNDWKTEYTIYSGNPFHANYLSVGEPVFLIGKKPSDLFSSEEGETSDYTTAE
LIKTIRYNPYNDQGQTNICYFKANFKSETTWQPPDNPDLINENLPFWLLLWGFSDWHKKIKKHLHIDSSYILVM
RHIPLALNTEYIVPLSDSFLQGKSPFSPEEQPIGADRITWHPQFQHQAEAINTICSSGPGTTKIPDNYSVQGLM
KYSFYFKWGGSPPPMSTIEDPIQQPTYPVPHNFNLTTSLQNPETDPASILWSFDQRRHTLTKKAIERLQKDTGI
KTITVTGGSHFDPTPTISQEETSEESSEEEKETSLLEKLQQQQRQQRRLKLRIMKTLLKIQQLE >MN774797.1|Beta|244_2262_1_fow
MPWRRRRYFRRYRYRPRRWRPRKTFRTRYYRRRHWVRKKRLRKKLKKLHITEYQPSSIRKCKVKGILCLFQTSI
ERICYNFDMYEESIVPDRLPGGGGFSIKNLSLQSLYLEHTHGHNIFTSTNEPYPLMRYTGCTIRLYRSADVDYI
VSYDNQWPLKSTMKMYNSMQPQIHYLLRHRIIVTSKKTNPNKRKLYKKVFIPPPTQMKNQWYFQSTLANIPLFM
LRTSATSLDHWFIGTRDKSTNITILILNTSVIFHRNWDKGTQPYYANVVGTQKVWLYATDQSASPIFNEIKLKN
LIFLGNTQHNTQGYSYAEYLTHYHKTHSSTTVEEWQKSANWGNPFYKDYLTNPSNDHQVFASYTDILQFANKLK
TSQDTTIKESTFSFTPIEMTKRLRYNPYKDNGVNNLCYFLNCKEVNGLSWDQPHNPDLINENLPLWILLFGFSD
FQKKLAKLKRIDTDYTFVIKSTYTEPTHLYIVPINISMSEGHSPYEDQANFVDDDKWFPSFQFQQEAYTDICLS
GPGTARIPKGDTAEAKMHYTFHFKWGGELPDMEQIADPSEKPTYPIPNNFLSTTSLQNPTQAPETYLYKFDQRG
DYITKTAAKRIRKDWSTKTDSLSITAPRFAEAAQTQDTSTETTSEEEEEEDLFQQLNQQRLKQQRLKQRIKLIL
QKLQTT >AF122914.3|Alpha|417_2726_3_fow (JA20)
MAYGWWRRRRRRWRRWRRRPWRRRWRTRRRRPARRRGRRRNVRRRRRGRWRRRYRRWKRKGRRRRKAKIIIRQW
QPNYRRRCNIVGYLPILICGGNTVSRNYATHSDDTNYPGPFGGGMTTDKFSLRILYDEYKRFMNYWTASNEDLD
LCRYLGCTFYFFRHPEVDFIIKINTMPPFLDTTITAPSIHPGLMALDKRARWIPSLKNRPGKKHYIKIRVGAPK
MFTDKWYPQTDLCDMILLTIYATAADMQYPFGSPLTDTVVVNSQVLQSMYDETISILPDEKTKRNSLLTSIRSY
IPFYNTTQTIAQLKPFVDAGGHTTGSTTTTWGQLLNTTKFTTTTTTTYTYPGTTNTAVTFITANDTWYRGTAYK
DNIKDVPQKAAQLYFQTTQKLLGNTFHGSDETLEYHAGLYSSIWLSPGRSYFETPGAYTDIKYNPFTDRGEGNM
LWIDWLSKKNMKYDKVQSKCLVADLPLWAAAYGYVEFCSKSTGDINIHMNARLLIRSPFTDPQLIVHTDPTKGF
VPYSLNFGNGKMPGGSSNVPIRMRAKWYPTLSHQQEVLEALAQSGPFAYHSDIKKVSLGIKYRFKWIWGGNPVR
QQVVRNPCKEPHSSGNRVPRSIQIVDPRYNSPELTIHAWDFRRGFFGPKAIQRMQQQPTATEFFSAGRKRPRRD
TEVYQSDQEKEQKESSLFPPVKLLRRVPPWEDSEQEQSGSQSSEEETATLSQQLKQQLQQQRVLGVKLRLLFNQ
VQKIQQNQDINPTLLPRGGDLVSFFQAVP >MN766736.1|Alpha|422_2692_2_fow
MPWWRWRRGWRWPRRRWRTYRRRRRLPRRRPRRAVRRPRRRRVRRRRGRGWYRGRRYSRRLYRRRYVRRKRKTL
IWRQWQPQNIRKCRIRGIIPMIICGHLRSNRNYALHSDDIVEQNTPFGGALSTTSWSLKVLYDQHQRGLNRWSS
SNEMLDLARYNGCRFTFYRDKVTDFIVTYDISAPYKLDKYSSPSYHPGMMMLKTKNKILIPSENTKPKGRSTVS
VKIKPPKLFLDKWYTQEDLCTVNLVTFAVSAASFTHPFCPPQTDNPCCTFQVLKDFYYPIIGYSAAETKVSSVF
SNILYKHCTYYQSFLTQQFIGKIVKLPDGTLVSSLASGPSSYPEGSNINKNSIEQYNTWLSQFNTGANQHYNFC
NYKPDYSKLEWLRKYYFEWETYKKASIPPDHLTPSVNWYEYHIGLFSPIFLSPFRSSSLEFPRAYQDVTYNPLV
DKGVGNVIWFQYNTKADTQLTLPSCKCVIEDIPLWAAFYGYSDFVQQEIGPYTDAESVGLVCVICPYTKPPMKN
PDNPMMGYVFYDSNFGAGKWIDGSGFVPLYWQTRWRPETLFQESTMRDITMTGPFSYKDELKNTVLTAKYKFNF
RWGGNLLHEQTIRNPCPTNAHPSTGRQPRDVQVVDPITVGPRFVFHSWDWRRGFLSEAAIKRIRDQPLDYEAYS
FMPKRPRFFPPTTGGEQLPGEQEESSSSAEENNLISFEEGQEPKAQAVHKQLLKHLRKQRVLGQRLRALYQNLQ
KTQAGLHINPLLFSQA >MN765841.1|Alpha|389_2635_2_fow
MAWRWWWRRRRPWPYRRRRWRTIRTRRPRRPVRRRRRRRRVRRRRWGRRRGRRTYYRRRFRKKKRKRKKLVLKQ
WNPSTIRRCTITGMIPLIVCGHTSAGRNYALRSDDFIPQSQPFGGSFSTTTWNLNVLYDEHLKFHNKWSYPNTQ
LDLARYLGAYFYFYRDPKTDFIVTYNTVPPFKIDKYSSPMLHPGMLMQRKKRILIPSFETRPKGKRRIRVKIKP
PTLFEDKWYTQSDLCSVNLLSLAVSAASFKHPFCPPQTENICITFQVLRDFYYTQMNVTDTKGTDISDKDKAIF
DNHLYKFANYYQTVHTLGQLNPTQQPALFSDRQNQGIPEKDSYLSGIGPNKLQTGNNSIYGQPNYNPDIEKLHK
IRKWFFKQETTANTIHGQYGHPQNDAVDYHIGKYSPIFLSPYRTNLQFPTAYVDVTYNPLVDKGLGNKMWIQSV
TKSDTQFNELNCKCVLQDIPIWAMATGYAEFIESELGLQEEVYSVYIICVICPYTQPKMYSDTNVNTGYVFYDS
LFGDGKMPSGTGLVPFYYQSRWYPRLRFQLQVLHDMYICGPFSYKDDLKSTVLTAEYKFRFLWGGNMIPEQVIR
NPCKAEGAGSGYTYPDRLPRDLQIADPQTMGPEWAFHTWDWRHGLFGKGALKRVSEKPDYDADYYVLPKKPRFF -continued

| Sequences included in sequence alignments (FIG. 38) |
| --- |

PPTDGSQGQEKDSDLQEISLPFPFEETLSKSQEEVQTQQQRDLHLRLAQQQRLGQQLKHLYTQILKTQAGLHI
NPLLYNHV

>MN765502.1|Alpha|417_2624_3_fow
MAYWWWRRRRRRPWRRRRRWRLRRPRRRRATYRRRRGRRRVRKRRGRWRRTYRRWRRRKGRRRHKKKIIMKQWQ
PNFIRHCFIVGFMPLIFCGENTTSQNFATHSDDLVAKGPYGGGMTTTKFTLRILYDEHLRFMNFWTVSNEDLDL
CRYLGVKLTFYRHPTVDFMVQIHTQPPFLDTELTGPSIHPGMMILNKKKIFVPSLKTRPNRKHKVRVKIGPPRL
YEDKWYPQSELCDTTLLTVYATACDLQFPFGSPLTDNPCVNFQVLGSAYKKHLSILSINDSKNLTHYETALFSK
TAYYNTFETIAQLKPTGQTTGVTPTWQDVQNTTNLDSSGTNQATSNDTWYYGNTYKDNIKDLTKKARDRYLAAT
QKAFPAYATLQSPLYEYHGGCYSSIFLSAGRAYFETLGAYSDIIYNPFVDKGIGNMVWIDYLSKEDAVYTPRTS
KCLIRDQPLWASFNGYSEFCSKSTGDGAVNINTRVVIKCPYTTPMLADNSNENQGFVPYSLNFGKGKMKGGSSQ
VPLSWRCKWYVMMYHQQEFMEAIVQSGPWAYKGDEKSAVLAMKYVFNWKWGGNPISGQVVRNPCKTSSSSREPR
SIQAVDPKRVAPPLVFHSWDYRRGLFGHASIKRMSEESATPTLFTGPAGKRPRRDTSVQQAEEDQQKESSSFRV
QRQLQPWIHSSQETQSSQEEMQAQGTVQEQLIQQLGEQRALRKQLEFLASQVLKVQAGQHIHPLLSSQA >MN765788.1|Alpha|401_2629_2_fow
MAWRWWWNRRPRRRWTRRRWRRLRTRRPRRPVRRRRRRRRVRRRRWGRRRGRRTFYRRRFKKRRRRRRKLTLKQ
WNPSTIRKCSIRGTVALVMCGHTKAGRNYALHSEDYVPSLISMGGSFSTTTWSLKALYDEFQKFHNRWSYPNTQ
LDLARFKGSKWTFYRDPKVDYIVTYYTVPPFKLNKLSSPFLHPGMMMQYKKKILVPSYQTKPKGKGKVSIWIKP
PVLFEDKWYTQQDLCPVNLLSLAVSAASFLHPFCPPESDNMCITFQVLQDFYYTQMGVTQMTGTTLTEADNNIF
KNHLYKQASYYQSLHTTGQLNATQKPANYSTNDKIPQETWLSTTGPAGFKTGNNSIYGVPNYKPDYTKLEEIRK
WFFKQETTDNAIHGSYGKPVYNAVDYHIGKYSPIFLSPYRTNTQFSTAYRDITYNPNTDKGKGNHIWIQSVTKT
NTTLNSQCRCHIQDIPIWAAVTGYAEFCESELNSEVHNLYICCIICPYTKPKLYNNTDPTQGYVFYDTLFGDGK
MPTGTGLVPVWLQSRWYPRLIFQAQVLHDLYLTGPFSYKDDLKSFTISAKYNFKFLWGGTIIPEQVIKNPCKEQ
DSPFTFTGRQPRDLQVTDPQTMGPEWVFHTWDWRRGLFGENAIKRVSEQPSHDADYYAPPKKPRLFPPTDLQEQ
ESAFDFTPQELKILSEAPQQSEEEENQEEEQQLQQRELQLRLQEQFRIRHQLQHLFVQVLKTQAGLHINPLFLN
PV >MN779270.1|Gamma|312_2300_3_fow (SAfiA)
MPFWWRRRRKFWINNRFNYTKRRRYRKRWPRRRRRRRPYRRPIRRRRRKLRKVKRKKKSLIVRQWQPDSIRTCK
IIGQSAIVVGAEGKQMYCYTVNKLINVPPKTPYGGGFGVDQYTLKYLYEEYRFAQNIWTQSNVLKDLCRYINVK
LIFYRDNKTDFVLSYDRNPPFQLTKFTYPGAHPQQIMLQKHHKFILSQMTKPNGRLTKKLKIKPPKQMLSKWFF
SKQFCKYPLLSLKASALDLRHSYLGCCNENPQVFFYYLNHGYYIQTNWGAQSTTAYRPNSSVTETTYYKYKNEK
KNIHIKSSEYSESISYDKGYFQSSFLQTQCIYTSAAGDTCAAEKPLGIAIYNPVKDNGDGNMIYLVSTLANTWD
QPPKDSAILIQGVPIWLGLFGYLDYCRQIKADKTWLDSHILVMQSPAIFTYPNPGAGKWYCPLSQSFINGNGPF
NQPPTLLQKAKWFPQIQYQQEIINSFVESGPFVPKYANQTESNWELKYKYIFTFKWGGPQFHEPEIADPSKQEQ
YDVPDTFYQTIQIEDPEGQDPRSLIHDWDYRRGFVKERSLKRMSTYFSTHTDQQATSEEDIPKKKKRIGPQLTV
PQQKEEETLSCLLSLCKKDTFQETETQEDLQQLIKQQQEQQLLLKRNILQLIHKLKENQQMLQLHTGMLP >MN778499.1|Gamma|300_2288_3_fow
MPFWWPRRRRWWATTRFKRRKPRYPKRRRRRRYKRKYRRAPRRRRRRRRKVRRKKPNLIVRQWQPDSIVLCKIK
LFGSLVLGAEGTQYLCYTNEKGAWTPPQQPGGGGFGIETYSLSYLYDQYLLRRCIWTKSNDYKDLCRYLRCKIT
FFRHPKIDFVVNYARQPPFLLEKPTYMNCHPIALLLSQHKRVILSKRSDPKAKNRVTLIIKPPKQMITKWFFTK
QFALFDLLQIQAAACTLNYPKLGCCNENLIISIFYLNPQFFQDSQWAQYTTSPYKPYQTIDTQLTYHYKIGNQT
GQYKPEFLNKTGQQAYYESISLDKGWFSPKIMNTQYITQSGSETHLAAIPVGAARYNPEIDDGKGNEIYLVSVT
TGHYTKPSEDNLVFRGLPLWLMFFGLYSFIKKIKTASFLPLHMFVVKSEYILPKPKDPQKQYFPFVDLNFINGK
NPYNSYISSTQRQTWYPTCEHQVETINAFVKCGPFVPKLDNDRDSTWELPPKSTFYFKWGGPQMPNQNVSDPKD
KTSYIVPDTVQEGLQITNPLKQKAESLLHEWDYRRGLIKTKAFKRMLENLSIESDVYPSAETPRKRQRVENSLH
YQEEENQEIKTCLLSLCESSSSEKEEEEKNLLHLIQQQQQQQKQLKLQLLTLIKDLKEKQNALQLQTGVI >MN776710.1|Gamma|288_2279_3_fow
MPFWWRRRRKPWYGKWRFRRRRRYNAPRRKRKFYQRRRYRRINRRRRKYKVRRKKRKTIAIRQWQPESITKCKI
IGFSNLVLGAEGTQYLCWTSQQEDYTQPKAPGGGGFGCELINLDWLYSEWVKHNNIWTKININKDLVRYTGAYI
YFLRHPTIDFVIAYSLQPPFELTKFTYPDIQPQNLLLRKRKRIILSLASKPHGKRFVKVKIRPPKQMITKWFFQ
HQFSGYGLVQLSAAAATFRHPNIGPKSQNQMVTIYFLDITIFNRPNWAQAQEDAWTPAGTHRTWTFEYQVKGQT
QPKTVQMPPSTPQDPYKTKYATSISRDYGWWQKAILNSTKVTIDGTMYSNRTVYSARYNPNEDTGQGNAVYLVS
LLQSKWTAPSDDRLVIVGQPLWMCMYGLYSYYQDLLKDKNFNTHYMFVVRSPAIKPITVSRQDFYPFIDWDFIN
GVLPWEEYLSEKIKATWYPQATFQTTTINALVESGPFVPRLTNIPDSTWELVYKYKFFFKWGGPQTHDDHVQDP
KHQPDYDTPDTLHQTIQIGDPKKQTPESIIHEWDYRRGFITQTALKRMSENIQTDTDFQSDDSASPRKKRKVTK
KMPITSQKEENIKKCLLSLCQEETQETPENLQDLIQQQQQQQHLLKRNLLQLLTHLKQQQRYLSLQTGILD >MN777204.1|Gamma|313_2331_1_fow
MPFWWRRRRKFWRGRRRPFYKRTTKRRRRRVRYRQRFRRPYRRRRRRRKHKVRRKRQKLPIYQWQPDSIRKCKI
KGVGTLILGAHGKQFVCYTDVQKKAPPPKAPGGGGFACEQFSLGGLYEQYKFRNNIWTASNINMDLCRYLGVRM
IFYRHPDIDFILNYDRQPPFVLDQLTYPLCHPQNLLLGKHKILLLSKATKPNGKLRKKVFIKPPKQMLNKWFFQ
EQFQSAPLLSIRASICSLQYPHIGCCMPNRTVTFFALNPGFYQQGNWAYDGGETNPYKPWPHIPKKLYFWDVAT
IPASWMEQEKAKHRVEIDLSTYSQSIDYQKGYFTSKVLQAKLVTQDSTGISTIANTPLNIARYNPAIDTGKGNT
IWLHSNLTTAYTKPAVDKTVILEGLPLWMMLFGWLSWVQHVKGAPDFYLSYTLCVESPAIEIATKGETINPVIP
LDASFINGNAPYNQTISQKDLTHWYPDIYNQTEIINSIVTSGPYIPKLDNIKNSTWELHYYYQFFFKWGGPEIT
DQPVADPSKQPVYDALDKQQQGIQVRNPAKQKYATLMHPWDIRRGIITNKALKRMQQNLSIDSTFEAGSTPAKK
PRITGPCFTALQEIHQEERSCLQTLCKESTSQEAQEETDIQLLIAQQQQKQRELKYNLLKLISYMKEQQNMLKL
HTGMLN >MN777719.1|Gamma|319_2301_1_fow
MPFWWGRRNRFWYKNNYRRRAYRRKRKRWPKRRRRNFRRPTRRRRRRRRKQKVRKKKQTLTLKVWQPDTIRKCK
IKGTGIHIVGGNGTQYRCFTANRFDWTPPLMPGGGGFGVEKFTLQHLYNEHLLSNNIWTQSNKMLDLVRYTGCR
IKFYRHETIDFIASYNRNLPFNLEKYTYADSHPNSLLHSRHKKLIPSLKTRRSGKRYITMKIKPPKPVSNKWFF -continued

| Sequences included in sequence alignments (FIG. 38) |
|---|
| QETFSSTPLFKLITSIIDLRYPHISQIGSNELVSLFCLNTDFYANAGWGNVHPPGTHSKWYVPYHNIAAITTVV<br>IKGRDTQITVDGSDYKKSVSYETGYFQPKLLQAEKIKNTAMENIPIQASRYNPTKDDGVGNKLWLVNVLNYSFA<br>PPKIDADLYIENLPLWQLVWGFTDFVKQTKKDSTFLNTYYAAFESKYLEPAVSTSKIYIPIDMSFIQGKGPYDS<br>YVSNYRKQNWYPILNAQLKILNAIAQAGPFVPKLDNIFLSSWELYSNYTFYFKFGGSELPEPDTVNPQDQGTYV<br>IPTNIQKAIQVSNPQKQSPYTTLHSWDYRRGLITSSAFKRMCENQTTDTEFEPDTETIPKKKKKIQHGNQLQRA<br>EEETQEIQNCLLSLCEENTFQETPQTSLLELIQQQQQQQQLKHNLLKLLSDLKLKQRSLQLQTGLIH |

Example 41: Evasion of Immune System

Figures 37A, 37B:
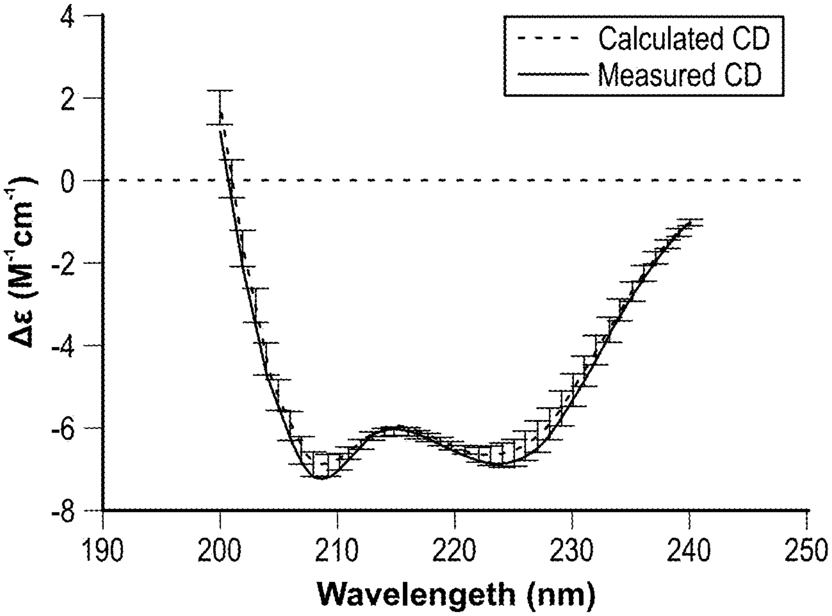
FIGS. 37A and 37B depict circular dichroism (CD) results of the TTMV-Ring 10 C-terminal peptide (CSEEEEESNLFERLLRQRTKQLQLKR-RIIQTLKDLQKLE, SEQ ID NO: 1047).
Figure 39A:
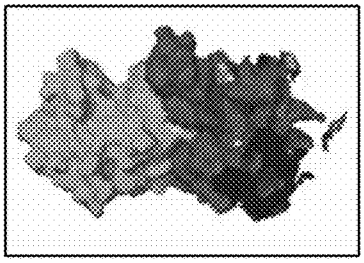
FIGS. 39A-39D depict the spikes of Ring 10 or alpha-fold predicted JA20 and MN779270.1.
Figure 39B:
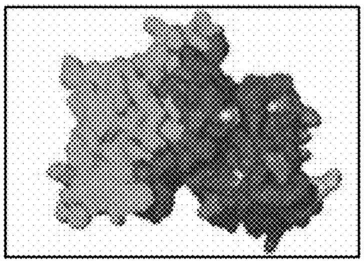
Figure 39C:
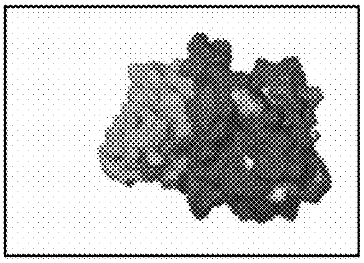
Figure 39D:
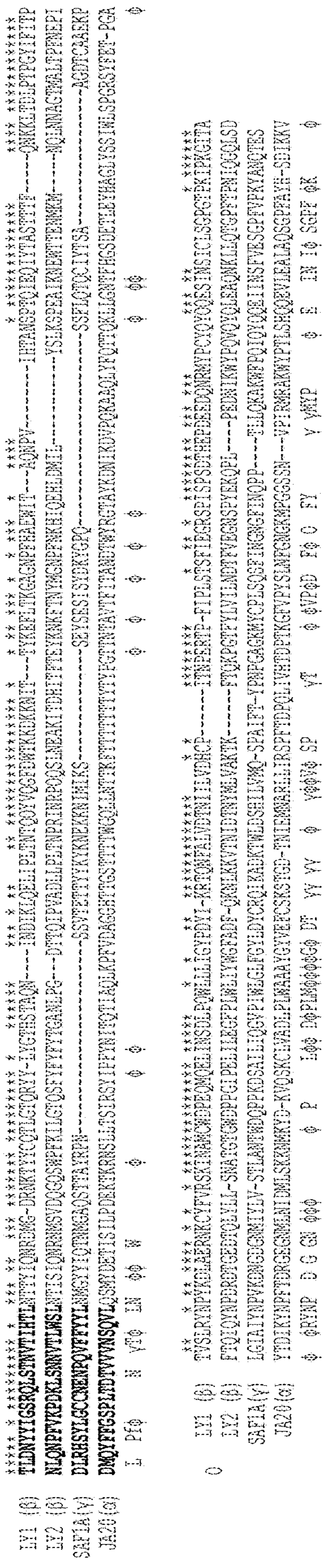

This Example describes the anellovirus C-terminal region and its relation to immune evasion. Absent from the Ring 10 structure is the majority of the C-terminal region (residues 545-672). Observed density for residues 545-562 showed that, were the C-terminal region present on the wild-type virus, the C-terminus would extend from the JR core toward the surface near the 3-fold axis between the spike domain crowns. The C-terminal region is semi-conserved between all anelloviruses, is predicted to be helical in nature, and has a glutamate-rich region (residues 636-640 on Ring 10) which could N-terminally cap a conserved helical motif. To determine if the C-terminal residues of Ring 10 would form a helical structure, circular dichroism experiments were performed, as described in Example 37, on the C-terminal peptides used to generate the aforementioned antibodies. Indeed, analysis with circular dichroism suggested that the C-terminal region (residues 635-672) is helical in solution, suggesting the C-terminal region would form a coiled-coil domain (FIGS. 37A and 37B), strongly suggesting a leucine-zipper like association of the helices perhaps due to the periodicity of hydrophobic residues. Electron microscopy of full-length Ring 10 ORF1 vs ORF1 which either had the C-terminus proteolytically removed or genetically removed suggested that particle formation is improved with the absence of the semi-conserved C-terminus (FIG. 34A-34C). Given that anelloviruses have evolved to evade the immune system, and that the C-terminal region is the immunodominant region of ORF1 and may be antagonistic to particle formation, the semi-conserved C-terminal region may be required for wild-type particle assembly but processed during viral particle maturation.

Despite anelloviruses constituting the majority of the human virome, their capsid structure was unknown. Determination of the Ring 10 structure as described by the examples included herein demonstrates that ORF1 encodes the capsid protein and that anelloviruses evolved a novel spike domain that extends around the 5-fold axis to form a crown structure. These crowns are capped with hypervariable P2 regions, which likely inhibits the development of antibodies against the better conserved spike P1 domain via steric hindrance. Analysis of the P1 surface revealed conserved residue patches that may have a receptor binding function.

The structure of the Ring 10 Betatorquevirus can be used to guide future anellovirus research. In particular, the diversity and immunological stealth of anelloviruses indicates that they could be used to deliver therapeutic genes to cell types not currently addressed by existing vectors, and that they may be less susceptible to pre-existing immunity or to the development of neutralizing antibodies following initial treatment. The availability of a capsid structure will help guide the design of anellovirus-based gene therapy vectors.

Example 42: Production and Purification of AnelloVLPs

Ring2 AnelloVLP:

A plasmid that encodes Ring2 ORF1 with a deletion of the C-terminus amino acids 611-666 (pRTx-2652; see also Table X1 construct listed as Ring2delCterm (Δ611-666) (7047)) was transfected into Expi293 cells. The cells were collected and resuspended in lysis buffer (50 mM Tris HCl, pH 8, 250 mM NaCl, 2 mM Magnesium Chloride). EDTA (0.5M) and protease inhibitor were added, and the cells were lysed using a microfluidizer. After lysing, protein inhibitor and triton X were added to the lysate and incubated for 30 minutes. The lysate was centrifuged at 12100 rpm and the supernatant was collected.

The lysate supernatant in 50 mM Tris HCl pH8, 250 mM NaCl was passed through a HiTrap heparin HP column (Cytiva) to separate 60mer VLPs from other smaller proteins from the mixture. The VLP fractions were dialyzed into Capto buffer (50 mM Tris HCl pH 8, 100 mM NaCl) overnight and incubated for 1.5 hrs with Capto400 resin at a 1:10 ratio of resin to protein. The preparation was spun down and supernatant collected.

Figure 40A:
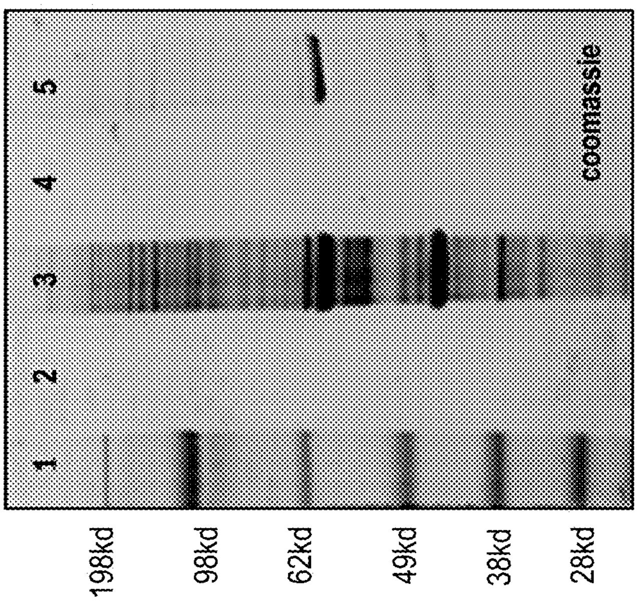
FIGS. 40A-40B are a series of diagrams showing a Coomassie stain (FIG. A1) and a Western blot (FIG. A2) for Ring2 virus-like particles (VLPs).
Figure 40B:
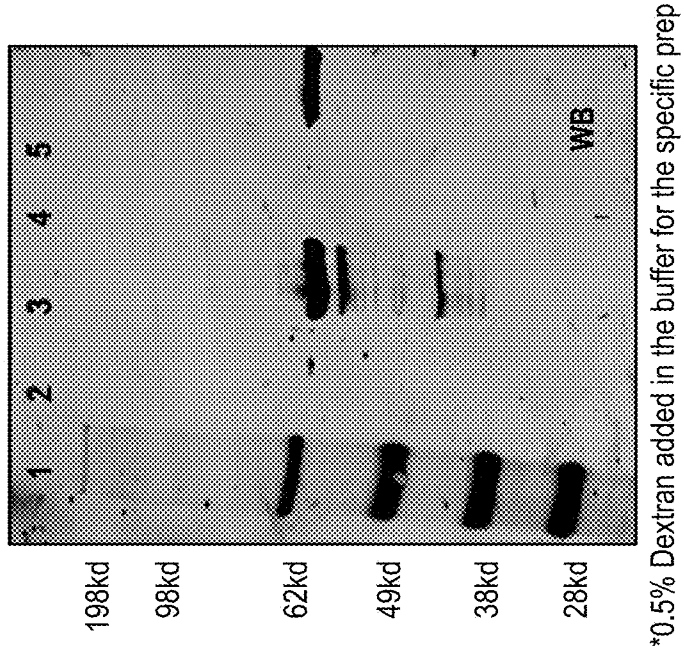

Samples were loaded onto a gel and Coomassie stained (FIG. 40A) or a Western blot was performed using a Ring2 HVR Linker primary antibody raised against amino acids 284-319 of the HVR region of Ring2 ORF1 and a goat-anti-rabbit secondary antibody (FIG. 40B). The lanes were as follows:

- Lane 1: Ladder
- Lane 2: Blank
- Land 3: 2652 unpurified material
- Lane 4: Blank
- Lane 5: Ring2 AnelloVLP 2652 after Capto400 purification Both gels show a relatively pure preparation of Ring2 VLPs after Capto400 purification (see lane 5).

Figure 41:
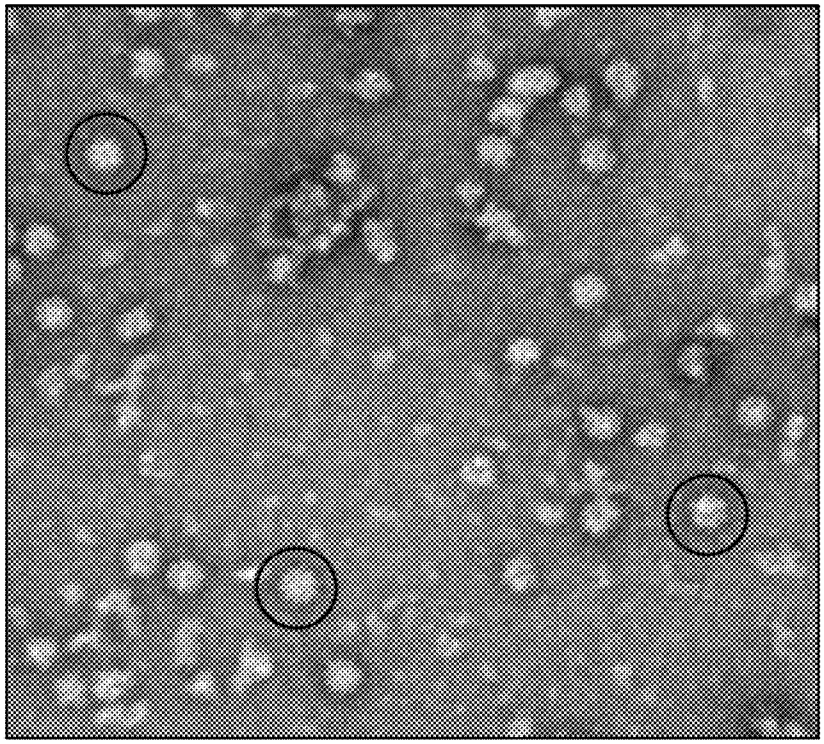
FIG. 41 is an electron micrograph showing Ring2 VLPs obtained after Capto400 purification.

Electron microscopy of the preparation obtained after Capto400 purification confirmed Ring2 VLP formation at 65000× magnification (FIG. 41).

Figure 42A:
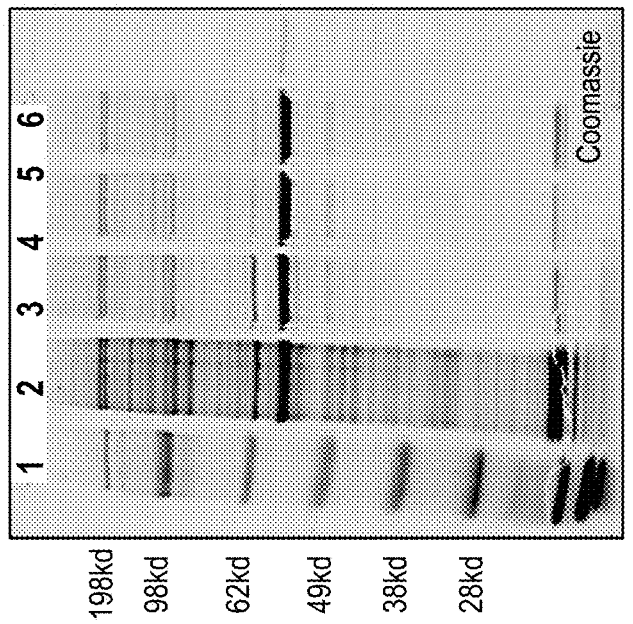
FIGS. 42A-42B are a series of diagrams showing a Coomassie stain (FIG. A4) and a Western blot (FIG. A5) for Ring19 VLPs.
Figure 42B:
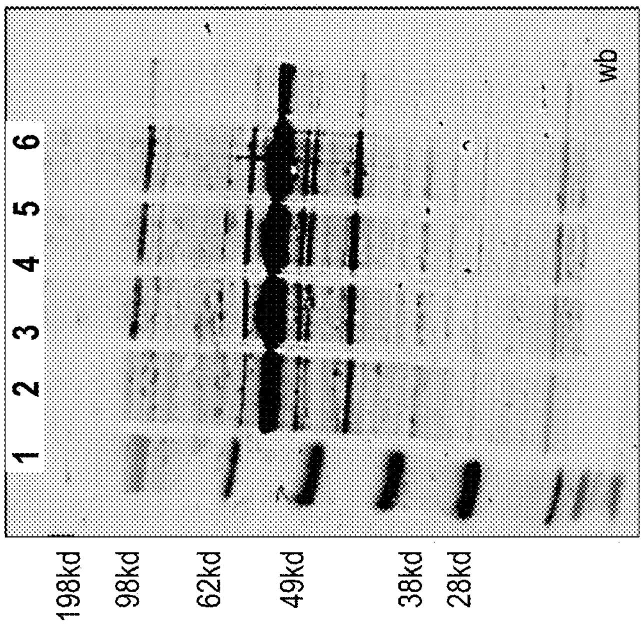

Ring19 AnelloVLP:

A plasmid that encodes Ring19 ORF1 with a deletion of the C-terminus amino acids 600-655 (pRTx-2814; see Table X1, construct Ring19delCterm (A600-655) (7120)) was similarly transfected as above into expi293 cells. The cells were collected and resuspended in lysis buffer (50 mM Tris HCl, pH 8, 250 mM NaCl, 2 mM Magnesium Chloride). EDTA (0.5M) and protease inhibitor were added, and the cells were lysed using a microfluidizer. After lysing, protein inhibitor and triton X were added to the lysate and incubated for 30 minutes. The lysate was centrifuged at 12100 rpm and the supernatant was collected. The supernatant was then purified through the HiTrap Heparin HP column and dialyzed into the Capto buffer as described above. The VLP preparation was then purified through a Capto400 column to further separate the VLPs from smaller proteins. Fractions "C12", "D1", and "D2" are different fractions collected during purification that showed peaks on the chromatogram. Samples from fractions C12, D1, and D2 were loaded onto a gel and Coomassie stained (FIG. 42A) or a Western blot was performed using a Ring19 HVR3 primary antibody that was raised against amino acids 342-352 of the Ring19 ORF1 HVR region (FIG. 42B). The lanes were as follows:

Lane 1: Ladder
Lane 2: Ring19 AnelloVLPs post heparin purification
Lane 3: Ring19 AnelloVLPs post dialysis
Lane 4: Ring19 AnelloVLPs capto400 C12 fraction
Lane 5: Ring19 AnelloVLPs capto400 D1 fraction
Lane 6: Ring19 AnelloVLPs capto400 D2 fraction Both gels show Ring19 VLPs after capto400 purification.

Figure 43:
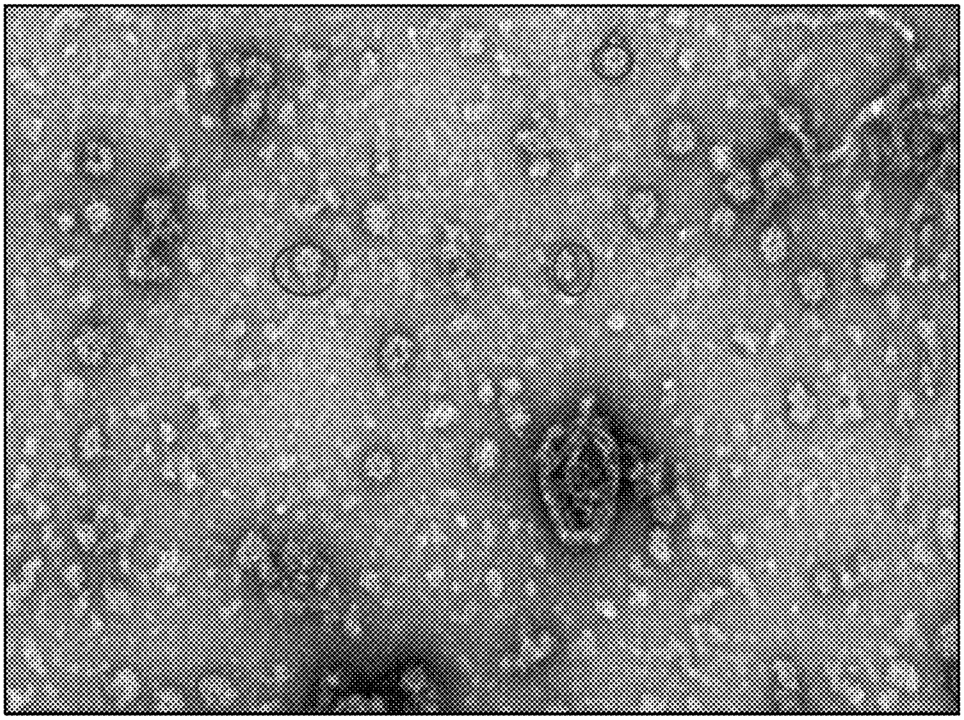
FIG. 43 is an electron micrograph showing Ring19 VLPs obtained after Capto400 purification.

Electron microscopy of the preparation obtained after Capto400 purification confirmed Ring19 VLP formation at 65000× magnification (FIG. 43).

Example 43: Conjugation of AnelloVLPs

Figure 44:
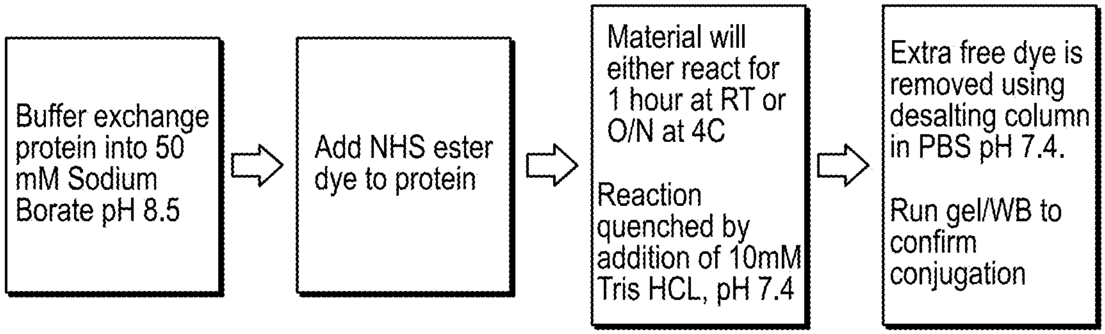
FIG. 44 is a diagram showing an exemplary workflow for conjugating NHS ester moieties to surface lysines of anelloVLPs using click chemistry.

In this example, NHS ester moieties were conjugated via click chemistry to the surface lysines of the AnelloVLPs prepared according to the example above. The conjugation workflow is shown in FIG. 44.

The preparations of the AnelloVLPs prepared above were buffer exchanged into 50 mM sodium borate pH8.5 overnight and NHS ester 647-Alexa Fluor™ ("NHS Ester 647") (Succinimidyl Ester), (ThermoFisher Catalog number: A20006) (for Ring2 AnelloVLPs) or EZ-Link™ NHS-Biotin ("NHS-Biotin") (ThermoFisher Catalog number: 20217) (for Ring19 AnelloVLPs) were added in varying VLP: NHS Ester molar ratios and reacted for 1 hr at room temperature or overnight at 4° C. The reactions were stopped by addition of 10 mM Tris HCl, pH7.4. The preparations were further desalted in PBS pH7.4 to remove extra free NHS ester moieties. Gels or Western blots were run to confirm conjugation.

Figure 45A:
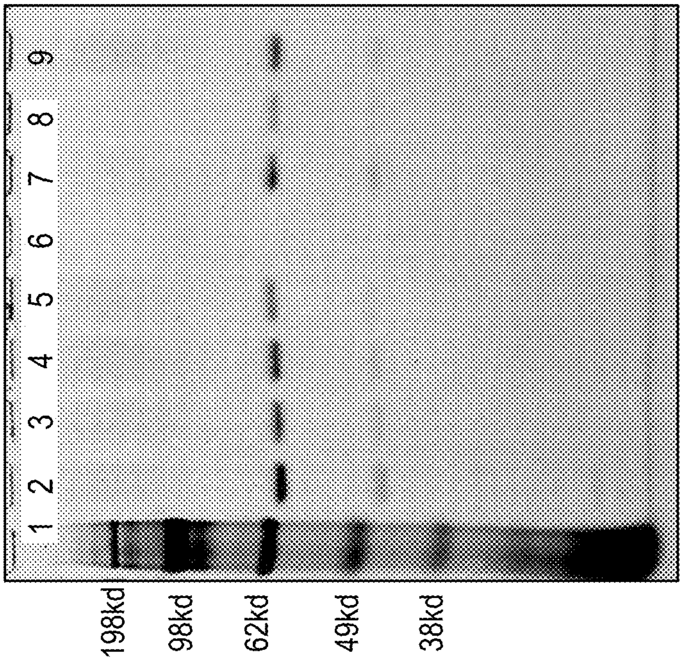
FIGS. 45A-45B are a series of diagrams showing a Coomassie stain (FIG. B2) and a Western blot (FIG. B3) for Ring2 VLPs conjugated with NHS Ester 647.
Figure 45B:
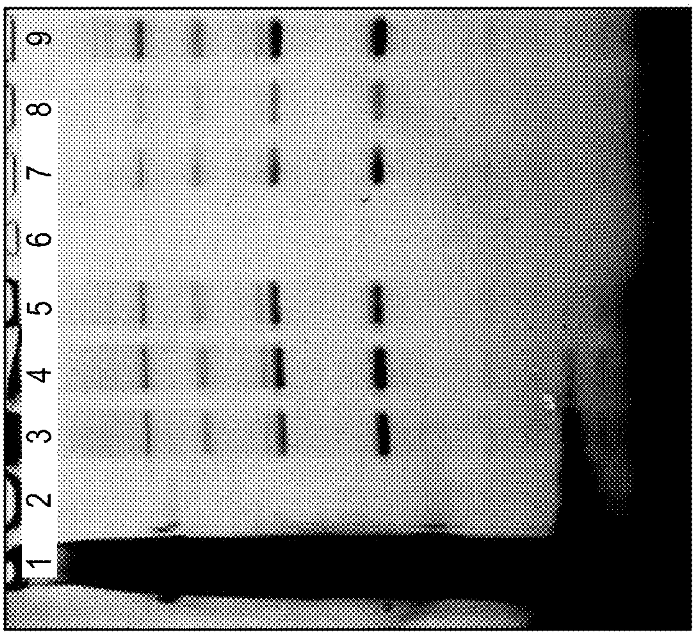

FIG. 45A shows a Coomassie stained gel and FIG. 45B shows a gel scanned under 520 nm of Ring2 AnelloVLP conjugated with NHS Ester 647. The lanes shown are as follows:

Lane 1: ladder
Lane 2: Ring2 AnelloVLP 2652 unlabeled
Lane 3: Ring2 AnelloVLP 2652 labeled at 1:5 VLP:NHS Ester 647 molar ratio, no desalt
Lane 4: Ring2 AnelloVLP 2652 labeled at 1:10 VLP:NHS Ester 647 molar ratio, no desalt
Lane 5: Ring2 AnelloVLP 2652 labeled at 1:20 VLP:NHS Ester 647 molar ratio, no desalt
Lane 6: Blank
Lane 7: Ring2 AnelloVLP 2652 labeled at 1:5 VLP:NHS Ester 647 molar ratio, desalted
Lane 8: Ring2 AnelloVLP 2652 labeled at 1:10 VLP:NHS Ester 647 molar ratio, desalted
Lane 9: Ring2 AnelloVLP 2652 labeled at 1:20 VLP:NHS Ester 647 molar ratio, desalted The Coomassie-stained gel shows Ring2 AnelloVLPs at around 62kD as expected in all protein-containing lanes. The gel scanned under 520 nm shows no visible band in lane 2 (unlabeled Ring2 AnelloVLP) while the other lanes containing labeled AnelloVPs show visible bands at about 62kD, confirming the conjugation of Ring2 AnelloVLPS with NHS Ester 647.

Figure 46B:
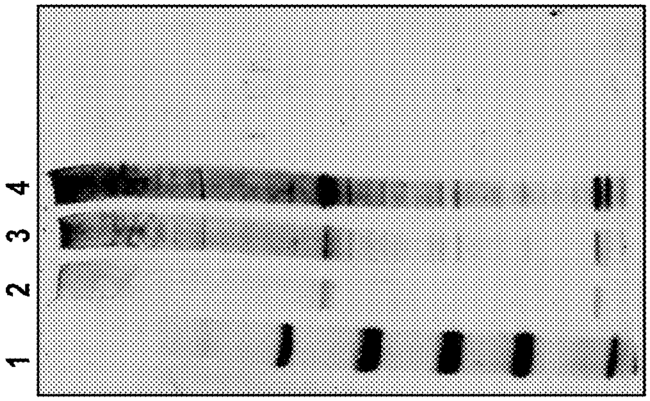
FIGS. 46A-46B are a series of diagrams showing Western blots for Ring2 anelloVLPs conjugated with NHS Ester biotin, labeled using a streptavidin CV 800 antibody (FIG. B4) or a Ring19 HVR3 primary antibody and a goat anti-rabbit secondary antibody (FIG. B5).
Figure 46A:
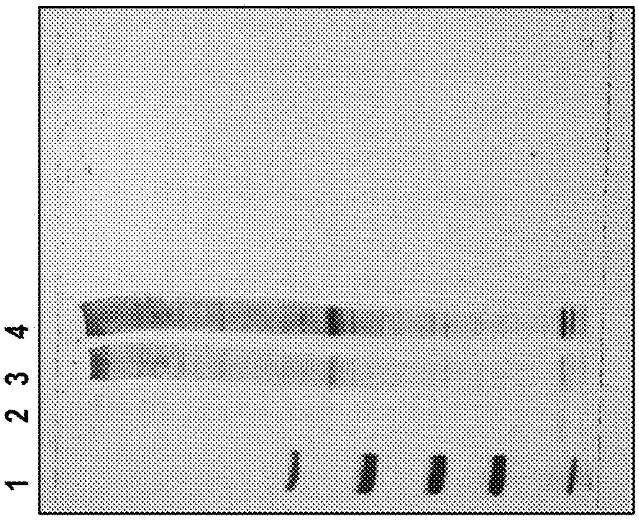

FIG. 46A shows a Western blot with a streptavidin CV 800 antibody [Licor Bioscience-Catalog number P/N: 926-32211] and FIG. 46B shows a Western blot with the R19 HVR3 primary antibody described above and a goat-anti rabbit secondary antibody. The lanes shown are as follows:

Lane 1: Ladder
Lane 2: Ring19 AnelloVLP unlabeled
Lane 3: Ring19 AnellovLP labeled at 1:5 VLP:NHS Ester biotin molar ratio [desalted]
Lane 4: Ring19 AnellovLP labeled at 1:10 VLP:NHS Ester biotin molar ratio [desalted]

The Western blot using the Ring19 specific antibody shows visible bands at around 62kD in both the unlabeled and labeled Ring19 AnelloVLP samples. The Western blot with streptavidin shows a band at around 62kD with Ring19 AnelloVLPs labeled with NHS Ester biotin while the unlabeled Ring19 AnelloVLP shows no visible band, confirming the conjugation of Ring19 AnelloVLPs with NHS Ester biotin.

Example 44: VLP Conjugation to SARS-CoV-2 RBD Peptide

In this Example, a His-Tag recombinant receptor binding domain (RBD) comprising amino acids 319-541 from SARS-CoV-2 coronavirus spike protein (ThermoFisher Catalog #RP-87704) (referred to in this example as RBD) was conjugated to the surface of AnelloVLPs. As shown in FIG. 47, the conjugation involved a first step of conjugating NHS-DBCO to the surface ORF1 of anelloVLPs. Azide-labeled RBD effectors were then conjugated to the anelloVLPs via the DBCO linker. This approach can be generalized to attach azide-labeled effectors (e.g., antigenic peptides and proteins) to anelloVLPs with DBCO linkers on their surfaces.

First, RBD was labeled with either DBCO or Azide to confirm that RBD could be labeled for future conjugation to AnelloVLPs. In brief, 100 μg of the His-tagged recombinant RBD (ThermoFisher Catalog #RP-87704) was resuspended in 1 ml of sodium borate buffer (pH=8.5) to final concentration of 0.1 mg/ml. The RBD amino acids from 319-541 contains 11 lysines that could potentially be labeled by NHS. Thus, in one condition, 2 μl of DBCO-PEG4-NHS 1 mg/ml was added to 200 μl of 0.1 mg/ml RBD and incubated overnight at 4° C. (2 μg DBCO-PEG4-NHS: 20 μg RBD). In a second condition, 2 μl of Azide-PEG4-NHS at 1 mg/ml was added to 200 μl of 0.1 mg/ml RBD and then incubated overnight at 4° C. (2 μg Azide-PEG4-NHS: 20 μg RBD). The next day, a zeba desalting column was prepared by opening the bottom of a column and placing it into a microfuge tube, spinning at 1500 g for 1 min at 4° C., adding 400 μl of Borate buffer (50 mM sodium borate) and spinning at 1500 g for one minute and then discarding the flow-through. This process is then repeated 3-4 times and the column is then placed into a fresh microfuge tube.

Unreacted DBCO/Azide was desalted out of the samples by running through a desalting column for two minutes at 1500 g and at 4° C. Samples were then split as follows:

a. 100 μl RBD-PEG4-DBCO
b. 100 μl RBD-PEG4-DBCO+CalFlour488
c. 100 μl RBD-PEG4-Azide
d. 100 μl RBD-PEG4-Azide+Alexa488 sDIBO RBD-PEG4-DBCO+CalFlour488 and RBD-PEG4-Azide+Alexa488 sDIBO were each made by adding 1 μl of CalFluor488 Azide/ClickIt Alexa488 sDIBO to the RBDs. The mixture was incubated for 30 minutes, and this process was then repeated three times. RBD-PEG4-DBCO+CalFlour488 and RBD-PEG4-Azide+Alexa488 sDIBO samples were then desalted as described. A western blot was then run to determine whether RBD labeling occurred. As shown in FIG. 48, labeling of RBD was confirmed with both DBCO and azide for future VLP conjugation. This demonstrated that a linker could be conjugated to the RBD.

Figure 49:
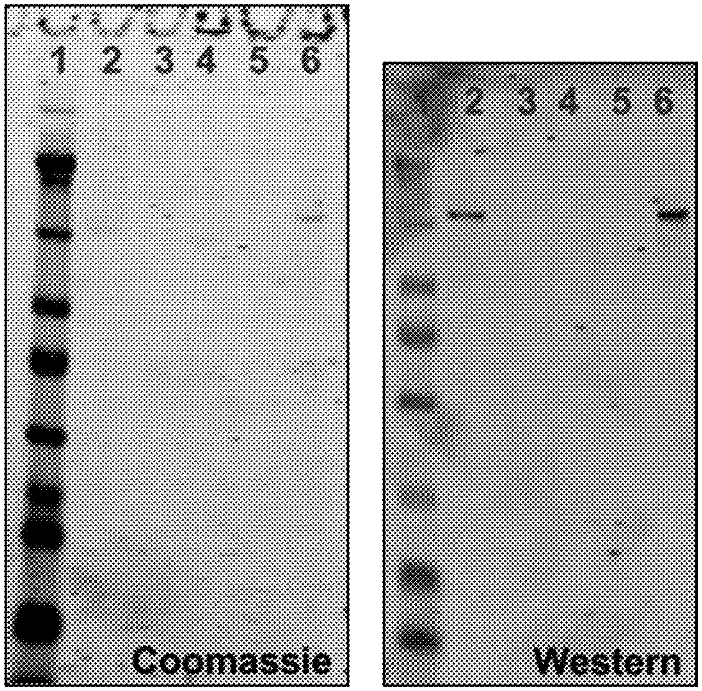
FIG. 49 is a diagram showing Coomassie staining and Western blot for pRTx-2652 (a Ring 2 ORF1 variant) produced using SE-FPLC.

To conjugate RBD to a Ring2 VLP, a fraction block of Ring2 ORF1 with a C-terminal deletion of amino acids 611-666 (pRTx-2652; corresponding to Ring2delCterm (A611-666) (7047) as listed in Table X1) in TBS was produced using SE-FPLC. Fractions were pooled and dialyzed into 2L of PBS+0.01% poloxamer at 4° C. After 3 hours, buffer was refreshed. This was then repeated twice more and left overnight at 4° C. Approximately 30 ml of the post-SE-FPLC solution was concentrated to approximately 1.5 ml final volume. A Western blot was run to confirm that the sample was retained (FIG. 49). The next day, approximately 1.5 ml of SE-FPLC pRTx-2652 was concentrated down to 220 μl.

1 μl NHS-PEG4-DBCO was added to 100 μl SE-FLPC pRTx-2652 samples generated as described above. The samples were then incubated for 1 hour at room temperature. 3 μl 1M Tris pH 8 was added, and the samples were desalted. RBD was labeled with NHS-PEG4-Azide by resuspending RBD in 200 μl borate buffer (0.5 mg/mL final) and 1 μl NHS-PEG4-Azide for 1 hour at room temperature. 3 μl 1M Tris pH 8 was then added and the RBD sample was desalted.

Figure 50:
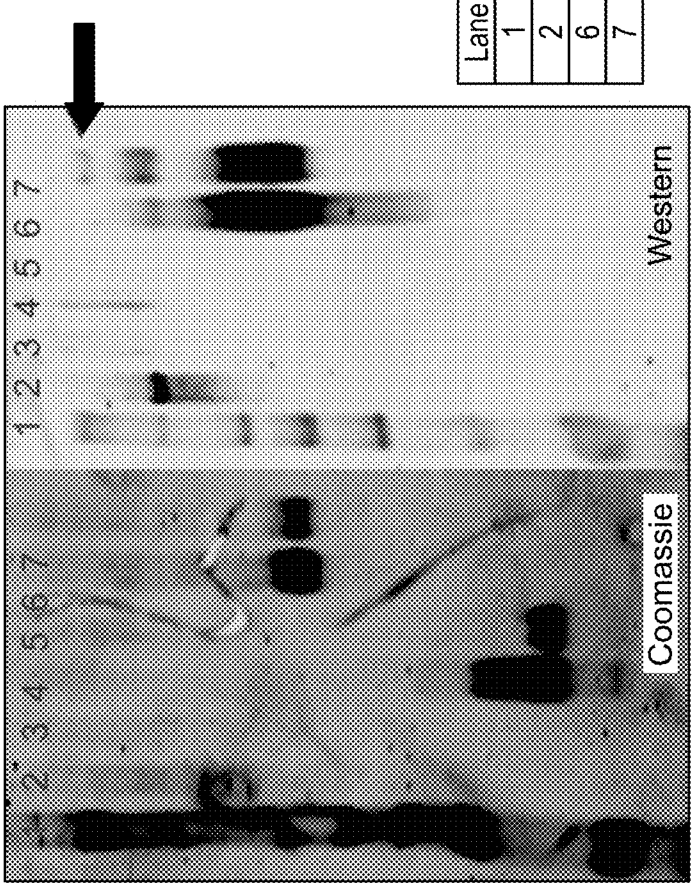
FIG. 50 is a diagram showing Coomassie staining and Western blot showing conjugation of RBD attached to an azide moiety to pRTx-2652 ORF1 polypeptide attached to DBCO, to produce RBD-pRTx-2652 conjugate anelloVLPs.

7.5 μl of the RBD peptide was then added to 30 μl of DBCO-2652 to produce a final peptide concentration 0.1 mg/ml. The sample was then incubated at 37° C. for 2.5 hours and conjugation was assessed by Coomassie staining and Western blot with an anti-Ring2 ORF1 antibody. As shown in FIG. 50, a 90 kDa band corresponding to the conjugation of RBD (26 kDa) to pRTx-2652 anelloVLPs (~62 kDa) was observed.

SEQUENCE LISTING

```
Sequence total quantity: 1075
SEQ ID NO: 1            moltype = DNA  length = 3570
FEATURE                 Location/Qualifiers
source                  1..3570
                        mol_type = genomic DNA
                        organism = Alphatorquevirus sp.
SEQUENCE: 1
atttgtgca gcccgccaat tctcgttcaa acaggccaat caggaggctc tacgtacact  60
tcctggggtg tgtcttcgaa gagtatataa gcagaggcgg tgacgaatgg tagagttttt  120
cctggcccgt ccgcggcgag agcgcgagcg gagcgagcga tcgagcgtcc cgtgggcggg  180
tgccgtaggt gagtttacac accgcagtca aggggcaatt cgggctcggg actggccggg  240
ctatgggcaa gattcttaaa aaattccccc gatccctctg tcgccaggac ataaaaacat  300
gccgtggaga ccgccggtgc atagtgtcca ggggcgagag gatcagtggt tcgcgagctt  360
ttttcacggc cacgcttcat tttgcggttg cggtgacgct gttggccatc ttaatagcat  420
tgctcctcgc tttcctcgcg ccggtccacc aaggcccccct ccggggctag agcagcctaa  480
ccccccgcag cagggcccgg ccgggcccgg agggccgccc gccatcttgg cgctgccggc  540
tccgcccgcg gagcctgacg acccgcagcc acggcgtggt ggtggggacg gtggcgccgc  600
cgctggcgcc gcaggcgacc gtggagaccg agactacgac gaagaagagc tagacgagct  660
tttccgcgcc gccgccgaag acgatttgta agtaggagat ggcgccggcc ttacaggcgc  720
aggaggagac gcgggcgacg cagacgcaga cgcagacgca gacataagcc caccctagta  780
ctcagacagt ggcaacctga cgttatcaga cactgtaaga taacaggacg gatgcccctc  840
attatctgtg gaaaggggtc cacccagttc aactacatca cccacgcgga cgacatcacc  900
cccaggggag cctcctacgg gggcaacttc acaaacatga ctttctccct ggaggcaata  960
tacgaacagt ttctgtacca cagaaacagg tggtcagcct ccaaccacga cctcgaactc  1020
tgcagataca agggtaccac cctaaaactg tacaggcacc cagatgtaga ctacatagtc  1080
acctacagca gaacgggacc ctttgagatc agccacatga cctacctcag cactcacccc  1140
cttctcatgc tgctaaacaa acaccacata gtggtgccca gcctaaagac taagcccagg  1200
ggcagaaagg ccataaaagt cagaataaga ccccccaaac tcatgaacaa caagtggtac  1260
ttcaccagag acttctgtaa cataggcctc ttccagctct gggccacagg cttagaactc  1320
agaaacccct ggctcagaat gagcaccctg agcccctgca taggcttcaa tgtccttaaa  1380
aacagcattt acacaaacct cagcaaccta cctcagcaca gagaagacag acttaacatt  1440
attaacaaca cattacaccc acatgacata acaggaccaa acaataaaaa atggcagtac  1500
acatatacca aactcatggc cccatttac tattcagcaa acagggccag cacctatgac  1560
ttactacgag agtatggcct ctacagtcca tactacctaa accccacaag gataaacctt  1620
gactggatga ccccctacac acacgtcagg tacaatccac tagtagacaa gggcttcgga  1680
aacagaatat acatacagtg gtgctcagag gcagatgtaa gctacaacag gactaaatcc  1740
aagtgtctct tacaagacat gcccctgttt ttcatgtgct atggctacat agactgggca  1800
attaaaaaca caggggtctc ctcactagcg agagacgcca gaatctgcat caggtgtccc  1860
tacacagagc cacagctggt gggctccaca gaagacatag ggttcgtacc catcacagag  1920
accttcatga ggggcgacat gccggtactt gcaccataca taccgttgag ctggttttgc  1980
aagtggtatc ccaacatagc tcaccagaag gaagtacttg aggcaatcat ttcctgcagc  2040
cccttcatgc cccgtgacca gggcatgaac ggttgggata ttacaatagg ttacaaaatg  2100
gacttcttat ggggcggttc ccctctcccc tcacagccaa tcgacgaccc ctgccagcag  2160
ggaacccacc cgattcccga ccccgataag caccctcgcc tcctacaagt gtcgaacccg  2220
aaactgctcg gaccgaggac agtgttccac aagtgggaca tcagacgtgg gcagtttagc  2280
aaaagaagta ttaaaagagt gtcagaatac tcatcggatg atgaatctct tgcgccaggt  2340
ctcccatcaa agcgaaacaa gctcgactcg gccttcagag gagaaaaccc agagcaaaaa  2400
gaatgctatt ctctcctcaa agcactcgag gaagaagaga ccccagaaga agaagaacca  2460
gcacccccaag aaaaagccca gaaagaggag ctactccacc agctccagct ccagagacgc  2520
caccagcgag tcctcagacg agggctcaag ctcgtcttta cagacatcct ccgactccgc  2580
cagggagtcc actggaaccc cgagctcaca tagagccccc accttacata ccagacctac  2640
tttttcccaa tactggtaaa aaaaaaaaat tctctccctt cgactgggaa acggaggccc  2700
agctagcagg gatattcaag cgtcctatgc gcttctatcc ctcagacacc cctcactacc  2760
cgtggttacc ccccaagcgc gatatcccga aaatatgtaa cataaacttc aaaataaagc  2820
tgcaagagtg agtgattcga ggccctcctc tgttcactta gcggtgtcta cctcttaaag  2880
tcaccaagca ctccgagcgt cagcgaggag tgcgaccctc caccaagggg caacttcctc  2940
ggggtccggc gctacgcgct tcgcgctgcg ccggacgcct cggacccccc cccgacccga  3000
```

```
atcgctcgcg cgattcggac ctgcggcctc ggggggggtc gggggcttta ctaaacagac  3060
tccgagttgc cactggactc aggagctgtg aatcagtaac gaaagtgagt ggggccagac  3120
ttcgccatag ggcctttaac ttggggtcgt ctgtcggtgg cttccgggtc cgcctgggcg  3180
ccgccatttt agctttagac gccattttag gccctcgcgg gcacccgtag gcgcgtttta  3240
atgacgtcac ggcagccatt ttgtcgtgac gtttgagaca cgtgatgggg gcgtgcctaa  3300
acccggaagc atccctggtc acgtgactct gacgtcacgg cggccatttt gtgctgtccg  3360
ccatcttgtg acttccttcc gctttttcaa aaaaaaagag gaagtatgac agtagcggcg  3420
ggggggcggc cgcgttcgcg cgccgcccac caggggggtgc tgcgcgcccc cccccgcgca  3480
tgcgcggggc cccccccggg gggggctccg cccccccggc cccccccgt gctaaaccca  3540
ccgcgcatgc gcgaccacgc ccccgccgcc                                    3570

SEQ ID NO: 2            moltype = AA  length = 130
FEATURE                 Location/Qualifiers
source                  1..130
                        mol_type = protein
                        organism = Alphatorquevirus sp.
SEQUENCE: 2
MPWRPPVHSV QGREDQWFAS FFHGHASFCG CGDAVGHLNS IAPRFPRAGP PRPPPGLEQP  60
NPPQQGPAGP GGPPAILALP APPAEPDDPQ PRRGGGDGGA AAGAAGDRGD RDYDEEELDE  120
LFRAAAEDDL                                                          130

SEQ ID NO: 3            moltype = AA  length = 303
FEATURE                 Location/Qualifiers
source                  1..303
                        mol_type = protein
                        organism = Alphatorquevirus sp.
SEQUENCE: 3
MPWRPPVHSV QGREDQWFAS FFHGHASFCG CGDAVGHLNS IAPRFPRAGP PRPPPGLEQP  60
NPPQQGPAGP GGPPAILALP APPAEPDDPQ PRRGGGDGGA AAGAAGDRGD RDYDEEELDE  120
LFRAAAEDDF QSTTPASREP TRFPTPISTL ASYKCRTRNC SDRGQCSTSG TSDVGSLAKE  180
VLKECQNTHR MMNLLRQVSH QSETSSTRPS EEKTQSKKNA ILSSKHSRKK RPQKKKNQHP  240
KKKPRKRSYS TSSSSRDATS ESSDEGSSSS LQTSSDSARE STGTPSSHRA PTLHTRPTFS  300
QYW                                                                 303

SEQ ID NO: 4            moltype = AA  length = 293
FEATURE                 Location/Qualifiers
source                  1..293
                        mol_type = protein
                        organism = Alphatorquevirus sp.
SEQUENCE: 4
MPWRPPVHSV QGREDQWFAS FFHGHASFCG CGDAVGHLNS IAPRFPRAGP PRPPPGLEQP  60
NPPQQGPAGP GGPPAILALP APPAEPDDPQ PRRGGGDGGA AAGAAGDRGD RDYDEEELDE  120
LFRAAAEDDL SPIKAKQARL GLQRRKPRAK RMLFSPQSTR GRRDPRRRRT STPRKSPERG  180
ATPPAPAPET PPASPQTRAQ ARLYRHPPTP PGSPLEPRAH IEPPPYIPDL LFPNTGKKKK  240
FSPFDWETEA QLAGIFKRPM RFYPSDTPHY PWLPPKRDIP KICNINFKIK LQE          293

SEQ ID NO: 5            moltype = AA  length = 180
FEATURE                 Location/Qualifiers
source                  1..180
                        mol_type = protein
                        organism = Alphatorquevirus sp.
SEQUENCE: 5
MPWRPPVHSV QGREDQWSPI KAKQARLGLQ RRKPRAKRML FSPQSTRGRR DPRRRRTSTP  60
RKSPERGATP PAPAPETPPA SPQTRAQARL YRHPPTPPGS PLEPRAHIEP PPYIPDLLFP  120
NTGKKKKFSP FDWETEAQLA GIFKRPMRFY PSDTPHYPWL PPKRDIPKIC NINFKIKLQE  180

SEQ ID NO: 6            moltype = AA  length = 680
FEATURE                 Location/Qualifiers
source                  1..680
                        mol_type = protein
                        organism = Alphatorquevirus sp.
SEQUENCE: 6
TAWWWGRWRR RWRRRRPWRP RLRRRRARRA FPRRRRRRFV SRRWRRPYRR RRRRGRRRRR  60
RRRRHKPTLV LRQWQPDVIR HCKITGRMPL IICGKGSTQF NYITHADDIT PRGASYGGNF  120
TNMTFSLEAI YEQFLYHRNR WSASNHDLEL CRYKGTTLKL YRHPDVDYIV TYSRTGPFEI  180
SHMTYLSTHP LLMLLNKHHI VVPSLKTKPR GRKAIKVRIR PPKLMNNKWY FTRDFCNIGL  240
FQLWATGLEL RNPWLRMSTL SPCIGFNVLK NSIYTNLSNL PQHREDRLNI INNTLHPHDI  300
TGPNNKKWQY TYTKLMAPIY YSANRASTYD LLREYGLYSP YYLNPTRINL DWMTPYTHVR  360
YNPLVDKGFG NRIYIQWCSE ADVSYNRTKS KCLLQDMPLF FMCYGYIDWA IKNTGVSSLA  420
RDARICIRCP YTEPQLVGST EDIGFVPITE TFMRGDMPVL APYIPLSWFC KWYPNIAHQK  480
EVLEAIISCS PFMPRDQGMN GWDITIGYKM DFLWGGSPLP SQPIDDPCQQ GTHPIPDPDK  540
HPRLLQVSNP KLLGPRTVFH KWDIRRGQFS KRSIKRVSEY SSDDESLAPG LPSKRNKLDS  600
AFRGENPEQK ECYSLLKALE EEETPEEEEP APQEKAQKEE LLHQLQLQRR HQRVLRRGLK  660
LVFTDILRLR QGVHWNPELT                                               680

SEQ ID NO: 7            moltype = AA  length = 197
FEATURE                 Location/Qualifiers
source                  1..197
                        mol_type = protein
```

```
                         organism = Alphatorquevirus sp.
SEQUENCE: 7
TAWWWGRWRR RWRRRRPWRP RLRRRRARRA FPRRRRRRFP IDDPCQQGTH PIPDPDKHPR  60
LLQVSNPKLL GPRTVFHKWD IRRGQFSKRS IKRVSEYSSD DESLAPGLPS KRNKLDSAFR  120
GENPEQKECY SLLKALEEEE TPEEEEPAPQ EKAQKEELLH QLQLQRRHQR VLRRGLKLVF  180
TDILRLRQGV HWNPELT                                                 197

SEQ ID NO: 8             moltype = AA  length = 145
FEATURE                  Location/Qualifiers
source                   1..145
                         mol_type = protein
                         organism = Alphatorquevirus sp.
SEQUENCE: 8
TAWWWGRWRR RWRRRRPWRP RLRRRRARRA FPRRRRRRFV SHQSETSSTR PSEEKTQSKK  60
NAILSSKHSR KKRPQKKKNQ HPKKKPRKRS YSTSSSSRDA TSESSDEGSS SSLQTSSDSA  120
RESTGTPSSH RAPTLHTRPT FSQYW                                        145

SEQ ID NO: 9             moltype = DNA  length = 3451
FEATURE                  Location/Qualifiers
source                   1..3451
                         mol_type = genomic DNA
                         organism = Alphatorquevirus sp.
SEQUENCE: 9
aattttgcta aacagactcc gaggtgctct tggacactga gtgggcgtac agcaacgaaa  60
gtgagtgggg ccagacttcg ccataaggcc tttatcttcg ggtctacatc ataatataaa  120
gatgtgcact tccgaatggc tgagtttttc acgccattcc gcagcggtgg agcagcgcag  180
ccacgacccc cgcgtcccga gggcgggtgc cggaggtgag tttacacacc gcagtcaagg  240
ggcaattcgg gctcgggact ggccgggccc gggcaaggct cttaaagcga aaccatgttc  300
ctcggcaggc cctaccgcca cagaaagcgg caccaggccg gcaagaaagg gccactgcca  360
ctgccaaatc tgcaacctgc acaggagaaa cgggctggtg gtccgtcctt gatggcctcc  420
ggacgcaggg gatggatgcc cccggacctg acggtccagg agagggagga tgcctggtgg  480
accagcttct gcgctagcca ccgcagcttt tgtagctgcg acgatcctgt gggccatatt  540
aatactctcg cccgcgataa tagtcctctg gcccagactc ctactacaac ttcaggccag  600
gggccgccgc cgccgcctac gcctccgcgg acgccggggc cgcgccctgg gtctgctccg  660
gaccaggggg gaaggatcag ggcctcctgg acctaccccc tagcccccgg aggtcccggt  720
agcacgccat ggcctactgg tggggccgga gacgccggtg gcgccgctgg aggaggcgcc  780
ggcgtcctct ccgccgccgc cggcggtggc ggagaaggcg acgctggccc agaaggcgcc  840
ggtggaggcg aaggagacga cgtgcgagac ctgctcgccg ctatcgaagg agacgtgggc  900
gcagacgggt aaggagacgc cgtcgccccc agaaactagt actgactcag tggaatcccc  960
agactgtgag aaagtgtgtt attagggggt ttctgcccct gttcttctgc ggacaggggg  1020
cctaccacag aaactttaca gaccactatg acgatgtgtt ccccaaggga cccagcggag  1080
gtgggcacgg gagcatggtg ttcaacctgt cctttctgta ccaagagttt aagaagcacc  1140
acaataagtg gtcgcgcagc aacctggact ttgacttagt gagatacaag ggcacagtga  1200
taaagctgta cagacaccag gactttgact acatagtgtg gataagcagg accccctccct  1260
tccaggagag cctgctcaca gtaatgaccc accagcccag cgtcatgctg caggcaaaaa  1320
agtgcataat agtaaagagc tacaggaccc acccgggggg caaaccctat gtaactgcaa  1380
aagttaggcc ccccagactc ctaactgaca agtggtactt ccagtcagac ttctgcaacg  1440
ttccgctttt tagcctacag tttgcccttg cggaactgcg gtttccgatc tgctcaccac  1500
aaactgacac caattgcatt aacttcctgg tgttagatga catctactac aagtttctag  1560
ataataagcc taaacagagt tcagacccta atgacgaaaa cagaataaaa ttctggcacg  1620
gcctatggtc cactatgaga tatttaaaca ccacctacat aaacacactg tttccaggca  1680
cagacagtct agtggccgcc aaagatactg acaatagtgt aaataaatac cccagcacag  1740
ccactaaaca gccctacaaa gacagtcagt acatgcaaaa tatatggaat acatcaaaaa  1800
tacatgcctt atatacgtgg gtagcagaga caaactacaa aagactgcag gcctactaca  1860
cacagaccta cggaggctac cagagacaat ttttcacagg aaaacagtac tgggactaca  1920
gagtaggcat gtttagtcca gccttcctga gtcccagcag actaaatccc cagaacccag  1980
gggcatacac agaggtctcc tacaacccct ggacagacga gggcacgggc aacgtagtgt  2040
gcctgcagta tctgactaaa gagacctcag actacaaacc aggtggtggg agcaagttct  2100
gcatagaagg tgtgcctcta tgggcagcgc tggtgggata cgtagacatg tgtaaaaaag  2160
agggcaagga cccgggcatc agactaaact gtctcctgtt agtcaagtgt ccctatacaa  2220
agcctcagct gtatgacaaa aaaaacccg agaaactgtt tgtaccttac tcctataact  2280
ttgggcacgg caagatgccg gggggagaca aatacatacc catagagttc aaagacaggt  2340
ggtacccctg cctgctccac caagaggagt ggatagagga cattgtcagg tcgggaccct  2400
tcgttccaaa agacatgccc agcagcgtca cctgcatgat gaggtacagc tctcttttta  2460
actggggcgg taatataatc caagaacagg ccgtggaaga cccctgtaag aaaggcacct  2520
tcgtcgttcc cggaaccagt ggcatcgctc gcatactaca agtcagcaac ccggccaagc  2580
agacccccac gacaacctgg cactcgtggg actggagacg atccctcttt acagagacgg  2640
gtcttaaaag aatgcgcgaa caacaaccat atgatgaact gtcttatacg ggccctaaaa  2700
agccaaaact gtcccttccc gcagggcccg ccgtccccgg tgccgccgtc gcctcctcct  2760
ggtgggaaac aaaacaggtc acctcgccag acgtcagcga gacggagacc gaagcagaag  2820
cccaccaaga ggaagagacg gagccggagg agggagtcca gctccagcag ctgtgggagc  2880
agcaactcct gcaaaagcga cagctgggag tcgtgttcca gcaactcctc cgactcagac  2940
agggggcgga gatccacccg ggcctcgtat aattcctggg ccccagaacc cgtacctgct  3000
tttcccggag caggcccctc caaaagtgcc tatttttgac ccctttggtc agaaaacaga  3060
gctagagctg tgcggctgct tcgacaggcc gcccaggaac aacccctacg accacccctt  3120
ctacccctgg ctgcccaaag agcctccctc ctactaccag ggctacaaag tgtctttcaa  3180
actagggttc cacccagaca agcatgtgtg aaccccgcca ataaaccact gctgctacac  3240
tgattcttag gccgtgggag tctcactggt cggtgtctac ctcttaaggt cactaagcac  3300
tccgagcgtt agcgaggagt gcgaccctac cccctgggcc cacttcttcg gagccgcgcg  3360
```

```
ctacgccttc ggctgcgcgc ggcacctcag acccccgctc gtgctgacac gcttgcgcgt  3420
gtcagaccac ttcgggctcg cgggggtcgg g                                  3451

SEQ ID NO: 10          moltype = AA  length = 166
FEATURE                Location/Qualifiers
source                 1..166
                       mol_type = protein
                       organism = Alphatorquevirus sp.
SEQUENCE: 10
MASGRRGWMP PDLTVQERED AWWTSFCASH RSFCSCDDPV GHINTLARDN SPLAQTPTTT  60
SGQGPPPPPT PPRTPGPRPG SAPDQGGRIR ASWTYPLAPG GPGSTPWPTG GAGDAGGAAG  120
GGAGVLSAAA GGGGEGDAGP EGAGGGEGDD VRDLLAAIEG DVGADG                 166

SEQ ID NO: 11          moltype = AA  length = 348
FEATURE                Location/Qualifiers
source                 1..348
                       mol_type = protein
                       organism = Alphatorquevirus sp.
SEQUENCE: 11
MASGRRGWMP PDLTVQERED AWWTSFCASH RSFCSCDDPV GHINTLARDN SPLAQTPTTT  60
SGQGPPPPPT PPRTPGPRPG SAPDQGGRIR ASWTYPLAPG GPGSTPWPTG GAGDAGGAAG  120
GGAGVLSAAA GGGGEGDAGP EGAGGGEGDD VRDLLAAIEG DVGADGPWKT PVRKAPSSFP  180
EPVASLAYYK SATRPSRPPR QPGTRGTGDD PSLQRRVLKE CANNNHMMNC LIRALKSQNC  240
PFPQGPPSPV PPSPPPGGKQ NRSPRQTSAR RRPKQKPTKR KRRSRRRESS SSSCGSSNSC  300
KSDSWESCSS NSSDSDRGRR STRASYNSWA PEPVPAFPGA GPSKSAYF                348

SEQ ID NO: 12          moltype = AA  length = 327
FEATURE                Location/Qualifiers
source                 1..327
                       mol_type = protein
                       organism = Alphatorquevirus sp.
SEQUENCE: 12
MASGRRGWMP PDLTVQERED AWWTSFCASH RSFCSCDDPV GHINTLARDN SPLAQTPTTT  60
SGQGPPPPPT PPRTPGPRPG SAPDQGGRIR ASWTYPLAPG GPGSTPWPTG GAGDAGGAAG  120
GGAGVLSAAA GGGGEGDAGP EGAGGGEGDD VRDLLAAIEG DVGADGARRP RCRRRLLLVG  180
NKTGHLARRQ RDGDRSRSPP RGRDGAGGGS PAPAAVGAAT PAKATAGSRV PATPPTQTGG  240
GDPPGPRIIP GPQNPYLLFP EQAPPKVPIF DPFGQKTELE LCGCFDRPPR NNPYDHPFYP  300
WLPKEPPSYY QGYKVSFKLG FHPDKHV                                       327

SEQ ID NO: 13          moltype = AA  length = 747
FEATURE                Location/Qualifiers
source                 1..747
                       mol_type = protein
                       organism = Alphatorquevirus sp.
SEQUENCE: 13
MAYWWGRRRR WRRWRRRRRP LRRRRRWRRR RRWPRRRRWR RRRRRARPAR RYRRRRGRRR  60
VRRRRRPQKL VLTQWNPQTV RKCVIRGFLP LFFCGQGAYH RNFTDHYDDV FPKGPSGGGH  120
GSMVFNLSFL YQEFKKHHNK WSRSNLDFDL VRYKGTVIKL YRHQDFDYIV WISRTPPFQE  180
SLLTVMTHQP SVMLQAKKCI IVKSYRTHPG GKPYVTAKVR PPRLLTDKWY FQSDFCNVPL  240
FSLQFALAEL RFPICSPQTD TNCINFLVLD DIYYKFLDNK PKQSSDPNDE NRIKFWHGLW  300
STMRYLNTTY INTLFPGTDS LVAAKDTDNS VNKYPSTATK QPYKDSQYMQ NIWNTSKIHA  360
LYTWVAETNY KRLQAYYTQT YGGYQRQFFT GKQYWDYRVG MFSPAFLSPS RLNPQNPGAY  420
TEVSYNPWTD EGTGNVVCLQ YLTKETSDYK PGGGSKFCIE GVPLWAALVG YVDMCKKEGK  480
DPGIRLNCLL LVKCPYTKPQ LYDKKNPEKL FVPYSYNFGH GKMPGGDKYI PIEFKDRWYP  540
CLLHQEEWIE DIVRSGPFVP KDMPSSVTCM MRYSSLFNWG GNIIQEQAVE DPCKKGTFVV  600
PGTSGIARIL QVSNPAKQTP TTTWHSWDWR RSLFTETGLK RMREQQPYDE LSYTGPKKPK  660
LSLPAGPAVP GAAVASSWWE TKQVTSPDVS ETETEAEAHQ EEETEPEEGV QLQQLWEQQL  720
LQKRQLGVVF QQLLRLRQGA EIHPGLV                                       747

SEQ ID NO: 14          moltype = AA  length = 220
FEATURE                Location/Qualifiers
source                 1..220
                       mol_type = protein
                       organism = Alphatorquevirus sp.
SEQUENCE: 14
MAYWWGRRRR WRRWRRRRRP LRRRRRWRRR RRWPRRRRWR RRRRRARPAR RYRRRRGRRR  60
AVEDPCKKGT FVVPGTSGIA RILQVSNPAK QTPTTTWHSW DWRRSLFTET GLKRMREQQP  120
YDELSYTGPK KPKLSLPAGP AVPGAAVASS WWETKQVTSP DVSETETEAE AHQEEETEPE  180
EGVQLQQLWE QQLLQKRQLG VVFQQLLRLR QGAEIHPGLV                         220

SEQ ID NO: 15          moltype = AA  length = 164
FEATURE                Location/Qualifiers
source                 1..164
                       mol_type = protein
                       organism = Alphatorquevirus sp.
SEQUENCE: 15
MAYWWGRRRR WRRWRRRRRP LRRRRRWRRR RRWPRRRRWR RRRRRARPAR RYRRRRGRRR  60
GPPSPVPPSP PPGGKQNRSP RQTSARRRPK QKPTKRKRRS RRRESSSSSC GSSNSCKSDS  120
WESCSSNSSD SDRGRRSTRA SYNSWAPEPV PAFPGAGPSK SAYF                    164
```

```
SEQ ID NO: 16          moltype = DNA  length = 3753
FEATURE                Location/Qualifiers
source                 1..3753
                       mol_type = genomic DNA
                       organism = Alphatorquevirus sp.
SEQUENCE: 16
tgctacgtca ctaacccacg tgtcctctac aggccaatcg cagtctatgt cgtgcacttc  60
ctgggcatgg tctacataat tatataaatg cttgcacttc cgaatggctg agtttttgct  120
gcccgtccgc ggagaggagc cacggcaggg gatccgaacg tcctgagggc gggtgccgga  180
ggtgagttta cacaccgaag tcaaggggca attcgggctc aggactggcc gggctttggg  240
caaggctctt aaaaatgcac ttttctcgaa taagcagaaa gaaaaggaaa gtgctactgc  300
tttgcgtgcc agcagctaag aaaaaaccaa ctgctatgag cttctggaaa cctccggtac  360
acaatgtcac ggggatccaa cgcatgtggt atgagtcctt tcaccgtggc cacgcttctt  420
tttgtggttg tgggaatcct atacttcaca ttactgcact tgctgaaaca tatggccatc  480
caacaggccc gagaccttct gggccaccgg gagtagaccc caacccccac atccgtagag  540
ccaggcctgc cccggccgct ccggagccct cacaggttga ttcgagacca gccctgacat  600
ggcatgggga tggtggaagc gacggaggcg ctggtggttc cggaagcggt ggacccgtgg  660
cagacttcgc agacgatggc ctcgatcagc tcgtcgccgc cctagacgac gaagagtaag  720
gaggcgcaga cggtggagga gggggagacg aaaaacaagg acttacagac gcaggagacg  780
ctttagacgc aggggacgaa aagcaaaact tataataaaa ctgtggcaac ctgcagtaat  840
taaaagatgc agaataaagg gatacatacc actgattata agtgggaacg gtacctttgc  900
cacaaacttt accagtcaca taaatgacag aataatgaaa ggccccttcg gggaggaca  960
cagcactatg aggttcagcc tctacatttt gtttgaggag cacctcagac acatgaactt  1020
ctggaccaga agcaacgata acctagagct aaccagatac ttgggggctt cagtaaaaat  1080
atacaggcac ccagaccaag actttatagt aatatacaac agaagaaccc ctctaggagg  1140
caacatctac acagcaccct ctctacaccc aggcaatgcc attttagcaa aacacaaaat  1200
attagtacca agtttacaga caagaccaaa gggtagaaaa gcaattagac taagaatagc  1260
accccccaca ctctttacag acaagtggta ctttcaaaag gacatagccg acctcaccct  1320
tttcaacatc atggcagttg aggctgactt gcggtttccg ttctgctcac cacaaactga  1380
caacacttgc atcagcttcc aggtccttag ttccgtttac aacaactacc tcagtattaa  1440
tacctttaat aatgacaact cagactcaaa gttaaaagaa tttttaaata aagcatttcc  1500
aacaacaggc acaaaaggaa caagtttaaa tgcactaaat acatttagaa cagaaggatg  1560
cataagtcac ccacaactaa aaaaaccaaa cccacaaata aacaaaccat tagagtcaca  1620
atactttgca cctttagatg ccctctgggg agaccccata tactataatg atctaaatga  1680
aaacaaaagt ttgaacgata tcattgagaa aatactaata aaaaacatga ttacatacca  1740
tgcaaaacta agagaatttc caaattcata ccaaggaaac aaggcctttt gccacctaac  1800
aggcatatac agcccaccat acctaaacca aggcagaata tctccagaaa tatttggact  1860
gtacacagaa ataatttaca acccttacac agacaaagga actggaaaca aagtatggat  1920
ggacccacta actaaagaga acaacatata taaagaagga cagagcaaat gcctactgac  1980
tgacatgccc ctatggactt tactttttgg atatacagac tggtgtaaaa aggacactaa  2040
taactgggac ttaccactaa actacagact agtactaata tgcccttata cctttccaaa  2100
attgtacaat gaaaaagtaa aagactatgg gtacatcccg tactcctaca aattcggagc  2160
gggtcagatg ccagacggca gcaactacat accctttcag tttagagcaa agtggtaccc  2220
cacagtacta caccagcaac aggtaatgga ggacataagc aggagcgggc cctttgcacc  2280
taaggtagaa aaaccaagca ctcagctggt aatgaagtac tgttttaact ttaactgggg  2340
cggtaaccct atcattgaac agattgttaa agaccccagc ttccagccca cctatgaaat  2400
acccggtacc ggtaacatcc ctagaagaat acaagtcatc gacccgcggg tcctgggacc  2460
gcactactcg ttccggtcat gggacatgcg cagacacaca tttagcagag caagtattaa  2520
gagagtgtca gaacaacaag aaacttctga ccttgtattc tcaggcccaa aaaagcctcg  2580
ggtcgacatc ccaaaacaag aaacccaaga agaaagctca cattcactcc aaagagaatc  2640
gagaccgtgg gagaccgagg aagaaagcga gacagaagcc ctctcgcaag agagccaaga  2700
ggtccccttc caacagcagt tgcagcagca gtaccaagag cagctcaagc tcagacaggg  2760
aatcaaagtc ctcttcgagc agctcataag gacccaacaa ggggtccatg taaacccatg  2820
cctacggtag gtcccaggca gtggctgttt ccagagagaa agccagcccc agctcctagc  2880
agtggagact gggccatgga gtttctcgca gcaaaaatat ttgataggcc agttagaagc  2940
aaccttaaag atacccctta ctacccatat gttaaaaacc aatacaatgt ctactttgac  3000
cttaaatttg aataaacagc agcttcaaac ttgcaaggcc gtgggagttt cactggtcgg  3060
tgtctacctc taaaggtcac taagcactcc gagcgtaagc gaggagtgcg accctccccc  3120
ctggaacaac ttcttcggag tccggcgcta cgccttcggc tgcgccggac acctcagacc  3180
cccctccac ccgaaacgct tgcgcgtttc ggaccttcgg cgtcgggggg gtcgggagct  3240
ttattaaacg gactccgaag tgctcttgga cactgagggg gtgaacagca acgaaagtga  3300
gtggggccag acttcgccat aaggccttta tcttcttgcc atttgtcagt gtccggggtc  3360
gccataggct tcgggctcgt ttttaggcct tccggactac aaaaatcgcc attttggtga  3420
cgtcacggcc gccatcttaa gtagttgagg cggacggtgg cgtgagttca aaggtcacca  3480
tcagccacac ctactcaaaa tggtggacaa tttcttccgg gtcaaaggtt acagccgcca  3540
tgttaaaaca cgtgacgtat gacgtcacgg ccgccatttt gtgacacaag atggccgact  3600
tccttcctct ttttcaaaaa aaagcggaag tgccgccgcg gcggcggggg gcggcgcgct  3660
gcgcgcgccg cccagtaggg ggagccatgc gcccccccc gcgcatgcgc ggggcccccc  3720
cccgcggggg gctccgcccc ccggcccccc ccg                              3753

SEQ ID NO: 17          moltype = AA  length = 127
FEATURE                Location/Qualifiers
source                 1..127
                       mol_type = protein
                       organism = Alphatorquevirus sp.
SEQUENCE: 17
MSFWKPPVHN VTGIQRMWYE SFHRGHASFC GCGNPILHIT ALAETYGHPT GPRPSGPPGV  60
DPNPHIRRAR PAPAAPEPSQ VDSRPALTWH GDGGSDGGAG GSGSGGPVAD FADDGLDQLV  120
```

```
AALDDEE                                                          127

SEQ ID NO: 18          moltype = AA  length = 268
FEATURE                Location/Qualifiers
source                 1..268
                       mol_type = protein
                       organism = Alphatorquevirus sp.
SEQUENCE: 18
MSFWKPPVHN VTGIQRMWYE SFHRGHASFC GCGNPILHIT ALAETYGHPT GPRPSGPPGV  60
DPNPHIRRAR PAPAAPEPSQ VDSRPALTWH GDGGSDGGAG GSGSGGPVAD FADDGLDQLV  120
AALDDEELLK TPASSPPMKY PVPVTSLEEY KSSTRGSWDR TTRSGHGTCA DTHLAEQVLR  180
ECQNNKKLLT LYSQAQKSLG STSQNKKPKK KAHIHSKENR DRGRPRKKAR QKPSRKRAKR  240
SPSNSSCSSS TKSSSSSDRE SKSSSSSS                                   268

SEQ ID NO: 19          moltype = AA  length = 276
FEATURE                Location/Qualifiers
source                 1..276
                       mol_type = protein
                       organism = Alphatorquevirus sp.
SEQUENCE: 19
MSFWKPPVHN VTGIQRMWYE SFHRGHASFC GCGNPILHIT ALAETYGHPT GPRPSGPPGV  60
DPNPHIRRAR PAPAAPEPSQ VDSRPALTWH GDGGSDGGAG GSGSGGPVAD FADDGLDQLV  120
AALDDEEPKK ASGRHPKTRN PRRKLTFTPK RIETVGDRGR KRDRSPLARE PRGPLPTAVA  180
AAVPRAAQAQ TGNQSPLRAA HKDPTRGPCK PMPTVGPRQW LFPERKPAPA PSSGDWAMEF  240
LAAKIFDRPV RSNLKDTPYY PYVKNQYNVY FDLKFE                           276

SEQ ID NO: 20          moltype = AA  length = 167
FEATURE                Location/Qualifiers
source                 1..167
                       mol_type = protein
                       organism = Alphatorquevirus sp.
SEQUENCE: 20
MSFWKPPVHN VTGIQRMWPK KASGRHPKTR NPRRKLTFTP KRIETVGDRG RKRDRSPLAR  60
EPRGPLPTAV AAAVPRAAQA QTGNQSPLRA AHKDPTRGPC KPMPTVGPRQ WLFPERKPAP  120
APSSGDWAME FLAAKIFDRP VRSNLKDTPY YPYVKNQYNV YFDLKFE                167

SEQ ID NO: 21          moltype = AA  length = 743
FEATURE                Location/Qualifiers
source                 1..743
                       mol_type = protein
                       organism = Alphatorquevirus sp.
SEQUENCE: 21
MAWGWWKRRR RWWFRKRWTR GRLRRRWPRS ARRRPRRRRV RRRRRWRRGR RKTRTYRRRR  60
RFRRRGRKAK LIIKLWQPAV IKRCRIKGYI PLIISGNGTF ATNFTSHIND RIMKGPFGGG  120
HSTMRFSLYI LFEEHLRHMN FWTRSNDNLE LTRYLGASVK IYRHPDQDFI VIYNRRTPLG  180
GNIYTAPSLH PGNAILAKHK ILVPSLQTRP KGRKAIRLRI APPTLFTDKW YFQKDIADLT  240
LFNIMAVEAD LRFPFCSPQT DNTCISFQVL SSVYNNYLSI NTFNNDNSDS KLKEFLNKAF  300
PTTGTKGTSL NALNTFRTEG CISHPQLKKP NPQINKPLES QYFAPLDALW GDPIYYNDLN  360
ENKSLNDIIE KILIKNMITY HAKLREFPNS YQGNKAFCHL TGIYSPPYLN QGRISPEIFG  420
LYTEIIYNPY TDKGTGNKVW MDPLTKENNI YKEGQSKCLL TDMPLWTLLF GYTDWCKKDT  480
NNWDLPLNYR LVLICPYTFP KLYNEKVKDY GYIPYSYKFG AGQMPDGSNY IPFQFRAKWY  540
PTVLHQQQVM EDISRSGPFA PKVEKPSTQL VMKYCFNFNW GGNPIIEQIV KDPSFQPTYE  600
IPGTGNIPRR IQVIDPRVLG PHYSFRSWDM RRHTFSRASI KRVSEQQETS DLVFSGPKKP  660
RVDIPKQETQ EESSHSLQRE SRPWETEEES ETEALSQESQ EVPFQQQLQQ QYQEQLKLRQ  720
GIKVLFEQLI RTQQGVHVNP CLR                                        743

SEQ ID NO: 22          moltype = AA  length = 194
FEATURE                Location/Qualifiers
source                 1..194
                       mol_type = protein
                       organism = Alphatorquevirus sp.
SEQUENCE: 22
MAWGWWKRRR RWWFRKRWTR GRLRRRWPRS ARRRPRRRRI VKDPSFQPTY EIPGTGNIPR  60
RIQVIDPRVL GPHYSFRSWD MRRHTFSRAS IKRVSEQQET SDLVFSGPKK PRVDIPKQET  120
QEESSHSLQR ESRPWETEEE SETEALSQES QEVPFQQQLQ QQYQEQLKLR QGIKVLFEQL  180
IRTQQGVHVN PCLR                                                  194

SEQ ID NO: 23          moltype = AA  length = 113
FEATURE                Location/Qualifiers
source                 1..113
                       mol_type = protein
                       organism = Alphatorquevirus sp.
SEQUENCE: 23
MAWGWWKRRR RWWFRKRWTR GRLRRRWPRS ARRRPRRRRA QKSLGSTSQN KKPKKKAHIH  60
SKENRDRGRP RKKARQKPSR KRAKRSPSNS SCSSSTKSSS SSDRESKSSS SSS          113

SEQ ID NO: 24          moltype = DNA  length = 3878
FEATURE                Location/Qualifiers
source                 1..3878
```

```
                         mol_type = genomic DNA
                         organism = Alphatorquevirus sp.
SEQUENCE: 24
aaatacgtca ctaaccacgt gactcccaca ggccaaccac agtctatgtc gtgcacttcc  60
tgggcatggt ctacgtgata atataaagcg gtgcacttcc gaatggctga gttttccacg  120
cccgtccgca gcgagatcgc gacgtaggag cgatcgagcg tcccgagggc gggtgccgga  180
ggtgagttta cacaccgcag tcaaggggca attcgggctc gggaggccgg gccatgggca  240
aggctcttaa aaagctatgt ttctcggtaa aatctacagg aagaaaagga aactgcttct  300
gcaggctgtg cgtgctccgc agacgccatc ttccatgagc cgctgctggt gtccccctcg  360
gggtgatgtc tcctcccgcg agtctcgatg gtacgaggcg gttcgaggaa gccacgatgc  420
tttttgtggc tgtagtgatc ctattcttca tctttctcgt ctggctgcac gttttaacca  480
tcagggacct ccgacgcccc ccacggacga ccgtgcgccg cagaataccc cagtgagacg  540
cctgctgcct ctccccagct accccggcga gggtccccag gctagatggc ctggtgggga  600
tggaggcgcc gctggtggcg accgaagaga aggtggagat ggcggcgcgc gcgccgccga  660
agacgagtac cagcccgaag acctagacga gcttttcggc gctatcgaac aagaacagta  720
aggaggaggc gaagggggag gcggaggggc taccggcgcc gttacagact gagacgctat  780
gccagacgca ggttccgacg caaaaagata gtactgactc agtggaaccc ccagactacc  840
agaaaatgta taataagggg catgatgcca gtactgtggg ccggcatggg tacggggggc  900
agaaactatg cagtgaggtc agatgactat gtggtgaaca aagggttcgg gggctccttc  960
gccacggaga ccttctccct gaaggttctc tatgaccagt ttcaaagggg cttcaacagg  1020
tggtcccaca ctaacgagga cctagacctg gcccgctaca ggggctgcag gtggactttt  1080
tacagacata aagacacaga ctttatagtg tactttacaa acaatcctcc catgaagacc  1140
aaccagttct ccgcgcccct gacgaccccc ggcatgctca tgcgcagtaa atacaaagtc  1200
ctcattccca gcttccagac cagacccaag ggtcgcaaaa cagtaaccgt taaaataaga  1260
ccccccaaac tatttcaaga caagtggtac acccagcagg acctgtgttc agttcctctt  1320
gtccaactga acgtgaccgc agctgatttc acacatccgt tcggctcacc actaactgaa  1380
actccttgcg tagagttcca ggtgctgggt gacttgtaca atacatgtct caatatcgac  1440
cttccgcaat ttagtgaatt aggagaaata actagtgcct actcaaaacc aaactcaaat  1500
aacctaaaag aattatacaa agaattgttc acaaaagcca catcaggaca ctactggcag  1560
acattcataa ccaacagcat ggtcagagca cacatagatg cagacaaagc taaagaagca  1620
caaagagcat ccaccacacc ctcatacaac aatgacccct tccccacaat acctgttaaa  1680
tcagagtttg cacagtggaa aaagaaattc acagacacta gagacagccc ctttcttttt  1740
gccacttacc atcccgaagc tataaaagac acaattatga aaatgagaga gaacaacttt  1800
aagctagaga caggacccaa tgacaagtat ggagactaca cagcacagta ccaaggaaac  1860
acacacatgc tagactacta ccttggcttt tacagcccca tattcctctc agatggaagg  1920
tctaacgtag aattcttcac tgcctacaga gacatagtat acaatccctt cttagacaag  1980
gcccagggca acatggtgtg gtttcagtac cacacaaaga cagacaacaa gtttaaaaaa  2040
ccagagtgcc actgggaaat caaagacatg cccctgtggg ccctcctaaa cggatatgta  2100
gactacttag agactcaaat acagtatggt gacctcagta aagaagggaa agtcctcatc  2160
aggtgtccct acaccaagcc agcactagta gaccccagag acgacactgc aggatatgta  2220
gtctacaaca gaaactttgg cagaggcaag tggatagacg gagggggcta catccccctg  2280
cacgagagga caaaatggta cgtgatgctc agataccaga cggacgtctt ccatgacata  2340
gtgacctgtg ggccctggca gtacagagac gacaacaaaa acagccagct agtggccaaa  2400
taccgcttca gctttatatg gggaggtaac actgtccact ctcaggtcat cagaaacccg  2460
tgcaaagaca accaagtatc cggtccccgt cgacagccta gggatataca agtcgttgac  2520
ccgcaacgca tcacgccgcc gtgggtcctc cacagcttcg accagcgaag aggcctcttt  2580
actgaaacag ctctcaggcg cctgctccag gaaccactac ctggcgagta tgctgttagc  2640
accctcagga cacccctcct ctttctaccc tcagaatacc agcgagaaga cggcgctgca  2700
gaaagcgcct caggttcacc ggccaaaaga ccccgtatct ggtcagaaga gagtcagacg  2760
gagacgatct cctcggagga gaacccggcg gagacgacga gggagctcct ccagcgaaag  2820
ctccgagagc agcgagcact ccagttccaa ctccagcact tcgcggtcca actcgccaag  2880
acccaggcga atctccacgt aaaccccctg ttatctttcc cgcaatgaat aaggtctttc  2940
tgtttccccc agagggtccc aagcccatcc tgggcaaaga ggcctggcag gacgagtacg  3000
agacctgcag ggtctggaac agacctgcca gaacccacca cacagacacc cccttctatc  3060
cctgggcccc ccacaagttc catgtaagct tcaaacttgg cttccaataa aattactagg  3120
ccgtggaact ctcactggtc ggtgtctacc tcttaaggtc actaagcact ccgagcgtca  3180
gcgaggagtg cgaccctcta ccctggtgca acgccctcgg cggccgcgcg ctacgccttc  3240
ggctgcgcgc ggcacctcgg acccccgctc gtgctgacgc gctcgcgcgc gtcagaccac  3300
ttcgggctcg cgggggtcgg gaattttgct aaacagactc cgagttgcca ttggacactg  3360
tagctgtgaa tcagtaacga aagtgagtgg ggccagactt cgccataggg cctttatctt  3420
cttgccattg gtccgtgtag gggtcgcca taggcttcga cctcccttt aggccttccg  3480
gactacaaaa atggcggatt cagtgacgtc acggccgcca ttttaagtag gtgccgtcca  3540
ggactgcagt tccgggtcag agtgcatcct cggcggaacc tgcacaaaat ggcggtcaat  3600
atcttccggg tcaaaggtca cacctacgtc ataagtcacg tgactgggtc ctgctacgtc  3660
atatgcggaa gtaggccccg ccacgtgact cgtcacgtgg gcgctgcgtc acggcggcca  3720
ttttgtatca caaaatggcg gacttccttc ctctttttta aaaataacgg cccagcggcg  3780
gcgcgcgcgc ttcgcgcgcg cgccgggggg ctccgccccc ccccgcgcat gcgcggggcc  3840
cccccccgcg gggggctccg ccccccggtc cccccccg                          3878

SEQ ID NO: 25            moltype = AA  length = 128
FEATURE                  Location/Qualifiers
source                   1..128
                         mol_type = protein
                         organism = Alphatorquevirus sp.
SEQUENCE: 25
MSRCWCPPRG DVSSRESRWY EAVRGSHDAF CGCSDPILHL SRLAARFNHQ GPPTPPTDDR  60
APQNTPVRRL LPLPSYPGEG PQARWPGGDG GAAGGDRREG GDGGARAAED EYQPEDLDEL  120
FGAIEQEQ                                                           128
```

```
SEQ ID NO: 26          moltype = AA  length = 279
FEATURE                Location/Qualifiers
source                 1..279
                       mol_type = protein
                       organism = Alphatorquevirus sp.
SEQUENCE: 26
MSRCWCPPRG DVSSRESRWY EAVRGSHDAF CGCSDPILHL SRLAARFNHQ GPPTPPTDDR  60
APQNTPVRRL LPLPSYPGEG PQARWPGGDG GAAGGDRREG GDGGARAAED EYQPEDLDEL  120
FGAIEQEQSS ETRAKTTKYP VPVDSLGIYK SLTRNASRRR GSSTASTSEE ASLLKQLSGA  180
CSRNHYLASM LLAPSGHPSS FYPQNTSEKT ALQKAPQVHR PKDPVSGQKR VRRRRSPRRR  240
TRRRRRGSSS SESSESSEHS SSNSSTSRSN SPRPRRIST                         279

SEQ ID NO: 27          moltype = AA  length = 272
FEATURE                Location/Qualifiers
source                 1..272
                       mol_type = protein
                       organism = Alphatorquevirus sp.
SEQUENCE: 27
MSRCWCPPRG DVSSRESRWY EAVRGSHDAF CGCSDPILHL SRLAARFNHQ GPPTPPTDDR  60
APQNTPVRRL LPLPSYPGEG PQARWPGGDG GAAGGDRREG GDGGARAAED EYQPEDLDEL  120
FGAIEQEQIP ARRRRCRKRL RFTGQKTPYL VRRESDGDDL LGGEPGGDDE GAPPAKAPRA  180
ASTPVPTPAL RGPTRQDPGE SPRKPPVIFP AMNKVFLFPP EGPKPILGKE AWQDEYETCR  240
VWNRPARTHH TDTPFYPWAP HKFHVSFKLG FQ                                272

SEQ ID NO: 28          moltype = AA  length = 780
FEATURE                Location/Qualifiers
source                 1..780
                       mol_type = protein
                       organism = Alphatorquevirus sp.
SEQUENCE: 28
MAWWGWRRRW WRPKRRWRWR RARRRRRVPA RRPRRAFRRY RTRTVRRRRR GRRRGYRRRY  60
RLRRYARRRF RRKKIVLTQW NPQTTRKCII RGMMPVLWAG MGTGGRNYAV RSDDYVVNKG  120
FGGSFATETF SLKVLYDQFQ RGFNRWSHTN EDLDLARYRG CRWTFYRHKD TDFIVYFTNN  180
PPMKTNQFSA PLTTPGMLMR SKYKVLIPSF QTRPKGRKTV TVKIRPPKLF QDKWYTQQDL  240
CSVPLVQLNV TAADFTHPFG SPLTETPCVE FQVLGDLYNT CLNIDLPQFS ELGEITSAYS  300
KPNSNNLKEL YKELFTKATS GHYWQTFITN SMVRAHIDAD KAKEAQRAST TPSYNNDPFP  360
TIPVKSEFAQ WKKKFTDTRD SPFLFATYHP EAIKDTIMKM RENNFKLETG PNDKYGDYTA  420
QYQGNTHMLD YYLGFYSPIF LSDGRSNVEF FTAYRDIVYN PFLDKAQGNM VWFQYHTKTD  480
NKFKKPECHW EIKDMPLWAL LNGYVDYLET QIQYGDLSKE GKVLIRCPYT KPALVDPRDD  540
TAGYVVYNRN FGRGKWIDGG GYIPLHERTK WYVMLRYQTD VFHDIVTCGP WQYRDDNKNS  600
QLVAKYRFSF IWGGNTVHSQ VIRNPCKDNQ VSGPRRQPRD IQVVDPQRIT PPWVLHSFDQ  660
RRGLFTETAL RRLLQEPLPG EYAVSTLRTP LLFLPSEYQR EDGAAESASG SPAKRPRIWS  720
EESQTETISS EENPAETTRE LLQRKLREQR ALQFQLQHFA VQLAKTQANL HVNPLLSFPQ  780

SEQ ID NO: 29          moltype = AA  length = 204
FEATURE                Location/Qualifiers
source                 1..204
                       mol_type = protein
                       organism = Alphatorquevirus sp.
SEQUENCE: 29
MAWWGWRRRW WRPKRRWRWR RARRRRRVPA RRPRRAFRRY RTRTVIRNPC KDNQVSGPRR  60
QPRDIQVVDP QRITPPWVLH SFDQRRGLFT ETALRRLLQE PLPGEYAVST LRTPLLFLPS  120
EYQREDGAAE SASGSPAKRP RIWSEESQTE TISSEENPAE TTRELLQRKL REQRALQFQL  180
QHFAVQLAKT QANLHVNPLL SFPQ                                         204

SEQ ID NO: 30          moltype = AA  length = 119
FEATURE                Location/Qualifiers
source                 1..119
                       mol_type = protein
                       organism = Alphatorquevirus sp.
SEQUENCE: 30
MAWWGWRRRW WRPKRRWRWR RARRRRRVPA RRPRRAFRRY RTRTNTSEKT ALQKAPQVHR  60
PKDPVSGQKR VRRRRSPRRR TRRRRRGSSS SESSESSEHS SSNSSTSRSN SPRPRRIST   119

SEQ ID NO: 31          moltype = DNA  length = 3818
FEATURE                Location/Qualifiers
source                 1..3818
                       mol_type = genomic DNA
                       organism = Alphatorquevirus sp.
SEQUENCE: 31
aagtccgcca ctaaccacgt gactcccgca ggccaaccca gtactatgtc gtccacttcc  60
tgggacgagt ctacgtcctg atataagtaa gtgcacttcc gaatggctga gttttccacg  120
cccgtccgca gcgagaacgc cacggagggg agtccgcgcg tcccgagggc gggtgccgga  180
ggtgagttta cacaccgcag tcaaggggca attcgggctc gggactggcc gggccccggg  240
caaggctctt aaaaaatgca ctttcgcaga gtgcgagcga aaaggaaact gctactgcaa  300
gctgtgcgag ctccaccgaa ggcacctgcc atgagcttca ccacacctac tattaatgcc  360
gggatccgag agcagcaatg gttcgagtcc acccttagat cccaccactc gttctgtggc  420
tgtggtgatc ccgtgcttca ttttactaac cttgctactc gctttaacta tctgcctgct  480
acctcttcgc ctctggaccc tcccggccca gcgccgcgag gccgcccggc gctccgccgc  540
```

```
ctcccggcac tcccttcagc ccccgcgacc ccttctagag aactagcatg gcctactggt  600
tcagaaggtg gggctggagg ccgaggcgcc ggtggagaag gtggcgccgc cgtcgaagga  660
gactaccgag aagaagaact agacgagctg ttcgcggcct tggaagaaga cgcaaaccaa  720
gggtaaggag gcgccgcaga actcgcagac gtacctacag acgggggtgg agacgcagga  780
ggtacataag acgggggcga cgcaaaaaga aactcatact gactcagtgg aacccggcaa  840
tagttaagag gtgcaacatt aagggcggac ttccaataat tatatgcgga gagcccaggg  900
cagcctttaa ctatggctac cacatggagg actacactcc tcaacctttc cccttcggag  960
ggggaatgag cacagtgact ttctctctga aagccttgta tgaccagtac ctaaaacacc  1020
aaaacaggtg gactttctca aacgaccagc tagacctcgc cagatacagg ggctgtaaac  1080
taaggttcta cagaagcccc gtctgtgact ttatagtaca ctacaaccta atacctccac  1140
taaaaatgaa ccagttcaca agtcccaaca cgcacccggg actactcatg ctcagcaaac  1200
acaagataat aattcccagc tttcaaacaa gacctggggg cagacgcttt gttaaaataa  1260
gacttaatcc ccccaaacta tttgaagaca agtggtacac tcagcaagac ctgtgcaagg  1320
ttccgctcgt tagtattaca gcaactgcgg ctgacttgcg gtatccgttc tgctcaccac  1380
aaacgaacaa cccttgcacc accttccagg tactgcgcaa gaactacaat acagttatag  1440
gaacttccgt aaaagaccaa gagtccacac aagactttga aaattggctt tataaaacag  1500
actcacacta tcaaacattt gccacagagg ctcaactagg cagaattcct gcatttaatc  1560
ctgatggcac taaaaacact aaacagcagt cgtggcaaga taactggagc aaaaaaaatt  1620
caccatggac aggtaactca ggtacatacc cacaaacaac cagtgaaatg tacaaaattc  1680
catatgacag taacttcggc tttcccacat acagagccca aaaagactac attttagaaa  1740
gaagacagtg caactttaac tatgaagtta ataatccagt tagcaaaaaa gtatggccac  1800
aacctagtac aacaacaccc acagtagact actatgaata ccactgtgga tggttcagca  1860
acatattcat aggccccaac agatacaacc tacagtttca aacagcatat gtagacacca  1920
catacaaccc actaatggac aagggcaaag gcaacaaaat atggtttcaa tatctgtcta  1980
aaaagggcac agactacaat gaaaaacaat gctactgcac cctagaagac atgcccctat  2040
gggcaatatg ctttggatac actgactatg tagagactca actaggaccc aatgtggacc  2100
atgaaacagc aggcttaata attatgatct gtccatacac tcaaccacct atgtatgaca  2160
aaaacagacc taactgggga tacgtagtct atgacacaaa ctttggcaat ggaaaaatgc  2220
cctcaggaag tggccaagtc ccagtatact ggcaatgccg atggaggccc atgctgtggt  2280
tccaacaaca agtactcaat gacatctcaa agactggacc gtacgcctac agagacgaat  2340
ataaaaatgt acaactgact ctctactaca actttatttt taactggggg ggcgacatgt  2400
attacccaca ggtcgttaaa aacccctgtg gagactccgg aatcgttccc ggttccggta  2460
gattcactcg agaagtacaa gtcgttagcc cgctttccat gggaccggcc tacatcttcc  2520
actacttcga ctccagacgc gggttcttta gtgaaaaagc tcttaaaaga atgcaacaac  2580
aacaagaatt tgatgaatct tttacattca aacctaagag acccaaactt tctacagcag  2640
ccgcagaaat cctccagctc gaagaagact cgacttcagg ggaaggaaaa tcgccactac  2700
agcaagaaga gaaagaagtc gaagtcctcc aaacgccgac agtacagctc cagctccagc  2760
gaaacatcca ggagcagctc gcaatcaagc agcagctcca attcctcttg ctccaactcc  2820
tcaaaaccca atccaatttg catttaaacc cacaattttt aagcccttca taaaatatga  2880
catgtttggg gaccccccttc ctcacccccc aacagccgaa gagtgggaaa cagagtacca  2940
gtgctgtaag gcctttaaca gaccacctag aaccaaccta aaagacaccc ccttctaccc  3000
ctgggtacct aaacctaaac ctcaattccg tgtatctttt aaacttggtt ttcaataaac  3060
aaggccgtgg gagtttcact tgtcggtgtc aacctcttaa ggtcactaag cactccgagc  3120
gtaagcgagg agtgcgaccc tccccccctgg ggcaactccc tcgaagtccg gcgctacgcg  3180
cttcgcgctg cgccggacat ctcggacccc ccctccaccc gaaacgcttg cgcgtttcgg  3240
accttcggcg tcgggggggt cgggggcttt actaaacaga ctccgaggtg ccattggaca  3300
ctgaggggat gaacagcaac gaaagtgagt ggggccagac ttcgccataa ggcctttatc  3360
ttcttgccat ttgtcagtat agagggtcgc cataggcttc ggcctccatt ttaacctcta  3420
aaaactacca aaatggccgt tccagtgacg tcacagccgc cattttaagt agctgacgtc  3480
aaggattgac gtgaaggtta aaggtcatcc tcggcggaag ctacacaaaa tggtggacaa  3540
catcttccgg gtcaaaggtc gtgcacacgt cataagtcac gtggtgggga cccgctgtaa  3600
cccggaagta ggcccccgtca cgtgatttgt cacgtgtgta cacgtcacaa ccgccatttt  3660
gttttacaaa atggctgact tccttcctct tttttaaaaa aaacggccgt gcggcggcgc  3720
gcgcgcttcg cgcgcgcgcc gggggctgcc gccccccccc gcgcatgcgc gcggggcccc  3780
cccccgcggg gggctccgcc ccccggcccc cccccccg                         3818
```

```
SEQ ID NO: 32          moltype = AA  length = 131
FEATURE                Location/Qualifiers
source                 1..131
                       mol_type = protein
                       organism = Alphatorquevirus sp.
SEQUENCE: 32
MSFTTPTINA GIREQQWFES TLRSHHSFCG CGDPVLHFTN LATRFNYLPA TSSPLDPPGP  60
APRGRPALRR LPALPSAPAT PSRELAWPTG SEGGAGGRGA GGEGGAAVEG DYREEELDEL  120
FAALEEDANQ G                                                     131

SEQ ID NO: 33          moltype = AA  length = 275
FEATURE                Location/Qualifiers
source                 1..275
                       mol_type = protein
                       organism = Alphatorquevirus sp.
SEQUENCE: 33
MSFTTPTINA GIREQQWFES TLRSHHSFCG CGDPVLHFTN LATRFNYLPA TSSPLDPPGP  60
APRGRPALRR LPALPSAPAT PSRELAWPTG SEGGAGGRGA GGEGGAAVEG DYREEELDEL  120
FAALEEDANQ GSLKTPVETP ESFPVPVDSL EKYKSLARFP WDRPTSSTTS TPDAGSLVKK  180
LLKECNNNKN LMNLLHSNLR DPNFLQQPQK SSSSKKTRLQ GKENRHYSKK RKKSKSSKRR  240
QYSSSSSETS RSSSQSSSSS NSSCSNSSKP NPICI                           275

SEQ ID NO: 34          moltype = AA  length = 270
```

```
FEATURE                Location/Qualifiers
source                 1..270
                       mol_type = protein
                       organism = Alphatorquevirus sp.
SEQUENCE: 34
MSFTTPTINA GIREQQWFES TLRSHHSFCG CGDPVLHFTN LATRFNYLPA TSSPLDPPGP  60
APRGRPALRR LPALPSAPAT PSRELAWPTG SEGGAGGRGA GGEGGAAVEG DYREEELDEL  120
FAALEEDANQ GSRRNPPARR RLDFRGRKIA TTARRERSRS PPNADSTAPA PAKHPGAARN  180
QAAAPIPLAP TPQNPIQFAF KPTIFKPFIK YDMFGDPLPH PPTAEEWETE YQCCKAFNRP  240
PRTNLKDTPF YPWVPKPKPQ FRVSFKLGFQ                                   270

SEQ ID NO: 35          moltype = AA  length = 156
FEATURE                Location/Qualifiers
source                 1..156
                       mol_type = protein
                       organism = Alphatorquevirus sp.
SEQUENCE: 35
MSFTTPTINA GIREQQCSRR NPPARRRLDF RGRKIATTAR RERSRSPPNA DSTAPAPAKH  60
PGAARNQAAA PIPLAPTPQN PIQFAFKPTI FKPFIKYDMF GDPLPHPPTA EEWETEYQCC  120
KAFNRPPRTN LKDTPFYPWV PKPKPQFRVS FKLGFQ                            156

SEQ ID NO: 36          moltype = AA  length = 761
FEATURE                Location/Qualifiers
source                 1..761
                       mol_type = protein
                       organism = Alphatorquevirus sp.
SEQUENCE: 36
MAYWFRRWGW RPRRRWRRWR RRRRRLPRRR TRRAVRGLGR RRKPRVRRRR RTRRRTYRRG  60
WRRRRYIRRG RRKKKLILTQ WNPAIVKRCN IKGGLPIIIC GEPRAAFNYG YHMEDYTPQP  120
FPFGGGMSTV TFSLKALYDQ YLKHQNRWTF SNDQLDLARY RGCKLRFYRS PVCDFIVHYN  180
LIPPLKMNQF TSPNTHPGLL MLSKHKIIIP SFQTRPGGRR FVKIRLNPPK LFEDKWYTQQ  240
DLCKVPLVSI TATAADLRYP FCSPQTNNPC TTFQVLRKNY NTVIGTSVKD QESTQDFENW  300
LYKTDSHYQT FATEAQLGRI PAFNPDGTKN TKQQSWQDNW SKKNSPWTGN SGTYPQTTSE  360
MYKIPYDSNF GFPTYRAQKD YILERRQCNF NYEVNNPVSK KVWPQPSTTT PTVDYYEYHC  420
GWFSNIFIGP NRYNLQFQTA YVDTTYNPLM DKGKGNKIWF QYLSKKGTDY NEKQCYCTLE  480
DMPLWAICFG YTDYVETQLG PNVDHETAGL IIMICPYTQP PMYDKNRPNW GYVVYDTNFG  540
NGKMPSGSGQ VPVYWQCRWR PMLWFQQQVL NDISKTGPYA YRDEYKNVQL TLYYNFIFNW  600
GGDMYYPQVV KNPCGDSGIV PGSGRFTREV QVVSPLSMGP AYIFHYFDSR RGFFSEKALK  660
RMQQQQEFDE SFTFKPKRPK LSTAAAEILQ LEEDSTSGEG KSPLQQEEKE VEVLQTPTVQ  720
LQLQRNIQEQ LAIKQQLQFL LLQLLKTQSN LHLNPQFLSP S                      761

SEQ ID NO: 37          moltype = AA  length = 198
FEATURE                Location/Qualifiers
source                 1..198
                       mol_type = protein
                       organism = Alphatorquevirus sp.
SEQUENCE: 37
MAYWFRRWGW RPRRRWRRWR RRRRRLPRRR TRRAVRGLGR RRKPRVVKNP CGDSGIVPGS  60
GRFTREVQVV SPLSMGPAYI FHYFDSRRGF FSEKALKRMQ QQQEFDESFT FKPKRPKLST  120
AAAEILQLEE DSTSGEGKSP LQQEEKEVEV LQTPTVQLQL QRNIQEQLAI KQQLQFLLLQ  180
LLKTQSNLHL NPQFLSPS                                                198

SEQ ID NO: 38          moltype = AA  length = 114
FEATURE                Location/Qualifiers
source                 1..114
                       mol_type = protein
                       organism = Alphatorquevirus sp.
SEQUENCE: 38
MAYWFRRWGW RPRRRWRRWR RRRRRLPRRR TRRAVRGLGR RRKPRQPQKS SSSKKTRLQG  60
KENRHYSKKR KKSKSSKRRQ YSSSSSETSR SSSQSSSSSN SSCSNSSKPN PICI        114

SEQ ID NO: 39          moltype = DNA  length = 3794
FEATURE                Location/Qualifiers
source                 1..3794
                       mol_type = genomic DNA
                       organism = Alphatorquevirus sp.
SEQUENCE: 39
cccgaagtcc gtcactaacc acgtgactcc tgtcgcccaa tcagagtgta tgtcgtgcat  60
ttcctgggca tggtctacat cctgatataa ctaagtgcac ttccgaatgg ctgagttttc  120
cacgcccgtc cgcagcgagg gagcgacgga ggagctcccg agcgtcccga gggcgggtgc  180
cggaggtgag tttacacacc gcagtcaagg ggcaattcgg gctcgggact ggccgggcta  240
tgggcaaggc tcttagggtc ttcattctta atatgtttct tggcagagtt taccgccaca  300
agaaaaggaa agtgctactg tccacactgc gagctccaca ggcgtctcgc agggctatga  360
gttggcgacc cccggtacac gatgcacccg gcatcgagcg caattggtac gaggcctgtt  420
tcagagccca cgctggagct tgtggctgtg gcaattttat tatgcacctt aatcttttgg  480
ctgggcgtta tggttttact ccggggtcag cgccgccagg tggtcctcct ccgggcaccc  540
cgcagataag gagagccagg cctagtcccg ccgcaccaga gcagcccgct gccctaccat  600
ggcatgggga tggtggagat ggcggcgccg ctggcccgcc agacgctgga ggagacgccg  660
tcgccggcgc cccgtacgga gaacaagagc tcgccgacct gctcgacgct atagaagacg  720
```

```
acgaacagta agaaccaggc gaaggcggtg ggggcgcaga cggtacagac ggggctggag  780
acgcaggact tatgtgagaa aggggcgaca cagaaaaaag aaaaagagac tgatactgag  840
acagtggcaa ccagccacaa gacgcagatg taccataact gggtacctgc ccatagtgtt  900
ctgcggccac actaggggca ataaaaacta tgcactacac tctgacgact acacccccca  960
aggacaacca tttggagggg ctctaagcac tacctcattc tctttaaaag tactatttga  1020
ccagcatcag agaggactaa acaagtggtc ttttccaaac gaccaactag acctcgccag  1080
atatagaggc tgcaaattta tattttatag aacaaaacaa actgactggg tgggccagta  1140
tgacatatca gaaccctaca agctagacaa atacagctgc ccaactatc accctggaaa  1200
catgattaag gcaaagcaca aatttttaat accaagctat gacactaatc ctagaggcag  1260
acaaaaaatt atagttaaaa ttcccccccc agacctcttt gtagacaagt ggtacactca  1320
agaggatctg tgttccgtta atcttgtgtc acttgcggtt tctgcggctt cctttctcca  1380
cccattcggc tcaccacaaa ctgacaaccc ttgctacacc ttccaggtgt tgaaagagtt  1440
ctactatcag gcaataggct tctctgcaag cacacaagca atgacatcag tattagacac  1500
gctatacaca caaaacagtt attgggaatc taatctaact cagttttatg tacttaatgc  1560
aaaaaaaggc agtgatacaa cacagccttt aactagcaat atgccaactc gtgaagagtt  1620
tatggcaaaa aaaaatacca attacaactg gtatacatac aaggccgcgt cagtaaaaaa  1680
taaactacat caaatgagac aaacctattt tgaggagtta acctctaagg ggccacaaac  1740
aacaaaaagt gaggaaggct acagtcagca ctggaccacc ccctccacaa acgcctacga  1800
atatcactta ggaatgttta gtgcaatatt tctagcccca gacaggccag tacctagatt  1860
tccatgcgcc taccaagatg taacttacaa ccccttaatg gacaaagggg tgggaaacca  1920
catttggttt cagtacaaca caaaggcaga cactcagcta atagtcacag gagggtcctg  1980
caaagcacac atacaagaca taccactgtg ggcggccttc tatggataca gtgactttat  2040
agagtcagaa ctaggcccct ttgtagatgc agagacggta ggcttagtgt gtgtaatatg  2100
cccttataca aaaccccccca tgtacaacaa gacaaacccc gccatgggct acgtgttcta  2160
tgacagaaac tttggtgacg gaaaatggac tgacggacgg ggcaaaatag agccctactg  2220
gcaagttagg tggaggcccg aaatgctttt ccaagaaact gtaatggcag acctagttca  2280
gactgggccc tttagctaca aagacgaact taaaaacagc accctagtgt gcaagtacaa  2340
attctatttc acctggggag gtaacatgat gttccaacag acgatcaaaa acccgtgcaa  2400
gacggacgga caacccaccg actccagtag acaccctaga ggaatacaag tggcggaccc  2460
ggaacaaatg ggacccgct gggtgttcca ctcctttgac tggcgaaggg gctatcttag  2520
cgagaaagct ctcaaacgcc tgcaagaaaa acctcttgac tatgacgaat attttacaca  2580
accaaaaaga cctagaatct ttcctccaac agaatcagca gagggagagt tccgagagcc  2640
cgaaaaaggc tcgtattcag aggaagaaag gtcgcaagcc tctgccgaag agcagacgca  2700
ggaggcgaca gtactcctcc tcaagcgacg actcagagag caacagcagc tccagcagca  2760
gctccaattc ctcacccgag aaatgttcaa aacgcaagcg ggtctccacc taaaccctat  2820
gttattaaac cagcgataaa ccaagtgtac ctgtttccag agagggcccc aaaacccccct  2880
cctagcagcc aagactggca gcaggagtac gaggcctgcg cagcctggga caggcccccct  2940
agatacaatc tgtcctctcc tcctttctac cccagctgcc cttcaaaatt ctgtgtaaaa  3000
ttcagccttg gctttaaata aatggcaact ttactgtgca aggccgtggg agtttcactg  3060
gtcggtgtct acctctaaag gtcactaagc actccgagcg ttagcgagga gtgcgaccct  3120
tccccctgac tcaacttctt cggagccgcg cgctacgcct tcggctgcgc gcggcacctc  3180
agacccccgc tcgtgctgac acgctcgcgc gtgtcagacc acttcgggct cgcgggggtc  3240
gggaattttg ctaaacagac tccgagttgc tcttggacac tgagggggca tatcagtaac  3300
gaaagtgagt ggggccagac ttcgccataa ggcctttatc ttcttgccat tggatagtat  3360
cgagggttgc cataggcttc gacctccatt ttaggccttc cggactacaa aaatggccgt  3420
tttagtgacg tcacggccgc cattttaagt aaggcggaag cagctcggcg tacacaaaat  3480
ggcggcggag cacttccggc ttgcccaaaa tggtgggcaa cttcttccgg gtcaaaggtc  3540
acagctacgt cacaagtcac gtggggaggg ttggcgttta acccggaagc caatcctctt  3600
acgtggcctg tcacgtgact tgtacgtcac gaccaccatt ttgttttaca aaatggccga  3660
cttccttcct ctttttaaa aataacggtt cggcggcggc gcgcgcgcta cgcgcgcgcg  3720
ccgggggggct gccgcccccc ccccgcgcat gcgcggggcc cccccccgcg gggggctccg  3780
ccccccggcc cccc                                                    3794
```

```
SEQ ID NO: 40          moltype = AA  length = 124
FEATURE                Location/Qualifiers
source                 1..124
                       mol_type = protein
                       organism = Alphatorquevirus sp.
SEQUENCE: 40
MSWRPPVHDA PGIERNWYEA CFRAHAGACG CGNFIMHLNL LAGRYGFTPG SAPPGGPPPG  60
TPQIRRARPS PAAPEQPAAL PWHGDGGDGG AAGPPDAGGD AVAGAPYGEQ ELADLLDAIE  120
DDEQ                                                               124

SEQ ID NO: 41          moltype = AA  length = 267
FEATURE                Location/Qualifiers
source                 1..267
                       mol_type = protein
                       organism = Alphatorquevirus sp.
SEQUENCE: 41
MSWRPPVHDA PGIERNWYEA CFRAHAGACG CGNFIMHLNL LAGRYGFTPG SAPPGGPPPG  60
TPQIRRARPS PAAPEQPAAL PWHGDGGDGG AAGPPDAGGD AVAGAPYGEQ ELADLLDAIE  120
DDEQRSKTRA RRTDNPPTPV DTLEEYKWRT RNKWDPAGCS TPLTGEGAIL ARKLSNACKK  180
NLLTMTNILH NQKDLESFLQ QNQQRESSES PKKARIQRKK GRKPLPKSRR RRRQYSSSSD  240
DSESNSSSSS SSNSSPEKCS KRKRVST                                       267

SEQ ID NO: 42          moltype = AA  length = 257
FEATURE                Location/Qualifiers
source                 1..257
                       mol_type = protein
```

```
                          organism = Alphatorquevirus sp.
SEQUENCE: 42
MSWRPPVHDA PGIERNWYEA CFRAHAGACG CGNFIMHLNL LAGRYGFTPG SAPPGGPPPG  60
TPQIRRARPS PAAPEQPAAL PWHGDGGDGG AAGPPDAGGD AVAGAPYGEQ ELADLLDAIE  120
DDEHRGRVPR ARKRLVFRGR KVASLCRRAD AGGDSTPPQA TTQRATAAPA AAPIPHPRNV  180
QNASGSPPKP YVIKPAINQV YLFPERAPKP PPSSQDWQQE YEACAAWDRP PRYNLSSPPF  240
YPSCPSKFCV KFSLGFK                                                257

SEQ ID NO: 43             moltype = AA  length = 150
FEATURE                   Location/Qualifiers
source                    1..150
                          mol_type = protein
                          organism = Alphatorquevirus sp.
SEQUENCE: 43
MSWRPPVHDA PGIERNCRGR VPRARKRLVF RGRKVASLCR RADAGGDSTP PQATTQRATA  60
APAAAPIPHP RNVQNASGSP PKPYVIKPAI NQVYLFPERA PKPPPSSQDW QQEYEACAAW  120
DRPPRYNLSS PPFYPSCPSK FCVKFSLGFK                                  150

SEQ ID NO: 44             moltype = AA  length = 746
FEATURE                   Location/Qualifiers
source                    1..746
                          mol_type = protein
                          organism = Alphatorquevirus sp.
SEQUENCE: 44
MAWGWWRWRR RWPARRWRRR RRRRPVRRTR ARRPARRYRR RRTVRTRRRR WGRRRYRRGW  60
RRRTYVRKGR HRKKKKRLIL RQWQPATRRR CTITGYLPIV FCGHTRGNKN YALHSDDYTP  120
QGQPFGGALS TTSFSLKVLF DQHQRGLNKW SFPNDQLDLA RYRGCKFIFY RTKQTDWVGQ  180
YDISEPYKLD KYSCPNYHPG NMIKAKHKFL IPSYDTNPRG RQKIIVKIPP PDLFVDKWYT  240
QEDLCSVNLV SLAVSAASFL HPFGSPQTDN PCYTFQVLKE FYYQAIGFSA STQAMTSVLD  300
TLYTQNSYWE SNLTQFYVLN AKKGSDTTQP LTSNMPTREE FMAKKNTNYN WYTYKAASVK  360
NKLHQMRQTY FEELTSKGPQ TTKSEEGYSQ HWTTPSTNAY EYHLGMFSAI FLAPDRPVPR  420
FPCAYQDVTY NPLMDKGVGN HIWFQYNTKA DTQLIVTGGS CKAHIQDIPL WAAFYGYSDF  480
IESELGPFVD AETVGLVCVI CPYTKPPMYN KTNPAMGYVF YDRNFGDGKW TDGRGKIEPY  540
WQVRWRPEML FQETVMADLV QTGPFSYKDE LKNSTLVCKY KFYFTWGGNM MFQQTIKNPC  600
KTDGQPTDSS RHPRGIQVAD PEQMGPRWVF HSFDWRRGYL SEKALKRLQE KPLDYDEYFT  660
QPKRPRIFPP TESAEGEFRE PEKGSYSEEE RSQASAEEQT QEATVLLLKR RLREQQQLQQ  720
QLQFLTREMF KTQAGLHLNP MLLNQR                                      746

SEQ ID NO: 45             moltype = AA  length = 195
FEATURE                   Location/Qualifiers
source                    1..195
                          mol_type = protein
                          organism = Alphatorquevirus sp.
SEQUENCE: 45
MAWGWWRWRR RWPARRWRRR RRRRPVRRTR ARRPARRYRR RRTTIKNPCK TDGQPTDSSR  60
HPRGIQVADP EQMGPRWVFH SFDWRRGYLS EKALKRLQEK PLDYDEYFTQ PKRPRIFPPT  120
ESAEGEFREP EKGSYSEEER SQASAEEQTQ EATVLLLKRR LREQQQLQQQ LQFLTREMFK  180
TQAGLHLNPM LLNQR                                                  195

SEQ ID NO: 46             moltype = AA  length = 107
FEATURE                   Location/Qualifiers
source                    1..107
                          mol_type = protein
                          organism = Alphatorquevirus sp.
SEQUENCE: 46
MAWGWWRWRR RWPARRWRRR RRRRPVRRTR ARRPARRYRR RRTQRESSES PKKARIQRKK  60
GRKPLPKSRR RRRQYSSSSD DSESNSSSSS SSNSSPEKCS KRKRVST                107

SEQ ID NO: 47             moltype = DNA  length = 3866
FEATURE                   Location/Qualifiers
source                    1..3866
                          mol_type = genomic DNA
                          organism = Alphatorquevirus sp.
SEQUENCE: 47
aagtccgtca ctaaccacgt gactcccgca ggccaatcag agtctatgtc gtgcacttcc  60
tgggcatggt ctacgttctc atataactaa ctgcacttcc gaatggctga gttttccacg  120
cccgtccgca gcggcagcac cacggagggt gatccccgcg tcccgagggc gggtgccgaa  180
ggtgagttta cacaccgcag tcaaggggca attcgggctc gggactggcc gggctatggg  240
caaggctctt agggctttca ttgttaaaaa tgtttctcgg caggccttac aggagaaaga  300
aaagggcgct gtcactgcct ggcgtgcgag ctgcacaggc gaaacaacct ggtgatatga  360
gctggagccg tccagtacat aatgccgccg ggatcgaaag gcagtggttc gaatccacct  420
ttagatccca cgctagttgc tgtggctgcg gcaattttgt taatcatatt aatgtactgg  480
ctgctcgcta cggctttact ggggggccga cgccgccagg tggtcctggg ccgcgtccac  540
aactgaggcc cgcgcttccc gcgccggacc ccgacccccca ggcgcccaac cgtgagccat  600
ggcgtggagc tggtggtggc aacgatggag aaggcgccgc tggaaaccca ggaggcgccg  660
ctggagacgt ctacgatgga gaagacctag acgcgctgtt cgccgccgtc gtcgaggacg  720
tagagtaagg aggcggaggt gggcgcgtag acgggggcga cgcagacggt acgccaccag  780
acgaaagaga cgttataggg gtcgccgctt taaaaagaaa ctagtactga ctcagtggca  840
ccctaatacc atgagacgct gcttaatcaa gggcatagtc cccctggtaa tatgcggcca  900
```

```
caccaggtgg aactacaact acgccctcca tagcaaggac tacacagagg agggtcgcta  960
ccctcacggg ggggccctca gcaccactac gtggtccctt aaggtgctgt atgacgagca  1020
cctcaaacac cacgacttct ggggctatcc caacaaccag ctagacctgg ccaggtacaa  1080
gggggccaag ttcaccttct acagacacaa aaagactgac tttataatat tctttaacag  1140
aaagcctccc tttaagctaa acaagtacag ctgtgcctcc tatcacccag gcatgctgat  1200
gcagcagaga cacaagatcc tgctacccag ctacgaaact aaacccaagg gcaggccaaa  1260
gataacagtt agaataaagc cccccactct gttagaggac aagtggtaca cccagcagga  1320
cctgtgcgac gttaacctgt tgcaacttgt ggtcactgcg gctgactttc gacatccact  1380
ctgctcacca caaacgaaca ctccaaccac aaccttccag gtgttgaaag acatctatta  1440
tgacactatg agcatatctg aacccacaga ctcctacact agtgttaaca ataaaagtac  1500
aacacaaact tttactaact actcaaacac cttagaaaac attctgtaca cacgagcctc  1560
ctactggaac tcgttccacg ccactgaata cctaaacccc aacatcatat acaaaaacgg  1620
tgaaaaacta ttcaaagaac atgaagactt aataacctgg atgacccaaa ctaacaatac  1680
cgggtttcta actaaaaaca acacagcttt tggcaacaac agctacaggc ccaatgcaga  1740
caaaattaaa aaagccagaa agacatactg gaacgcccta ataggcacca acgacctggc  1800
cactaatata ggccaggcca gagcagaaag gttcgagtac cacctaggct ggtactcccc  1860
catatttctc agcagacaca ggagcaacat gaactttgcc agggcctacc aagacgtcac  1920
atacaacccc aactgtgaca ggggagttaa caacagggtg tgggttcagc ctctaactaa  1980
acccaccaca gagttcgacg agaaaaggtg taagtgcgta gtgcagcacc tgcctctgtg  2040
ggcggctctg tactgctacc aagactttgt agaggaggag ctggggtcct cctcagagat  2100
attaaattca tgcctactgg tattacagtg cccttacacc tttcccccaa tgtatgacaa  2160
aaagctacca gacaagggat tcgtgtttta tgactccctt tttggagacg gcaaaatgtc  2220
tgacggacgc ggacaggtgg acattttctg gcaacagcga tggtaccctc gcttagccac  2280
tcagatgcaa gtcatgcacg acatcaccat gacgggcccc ttctcctacc gagacgagct  2340
agttagcacc caactgactg ccaagtacac ctttgacttt atgtggggcg gaaatatgat  2400
ctccacacag atcatcaaga acccctgcaa agacagtgga ctggaacccg cctaccccgg  2460
tagacagcgt cgcgacttac aaattgttga cccatactcc atgggccccc aattctcgtt  2520
ccacaactgg gactacagac atggcctttt tggccaagac gctatcgaca gagtgtctaa  2580
acaaccaaaa gatgatgcag actatcctaa cccatacaaa aggcctagat attttccacc  2640
cacagaccaa gccgcccaag agcaagaaaa agacttcagt ttcctcaaaa cagcaccgtc  2700
gaactcagaa gagagcgatc aagaagtcct ccaagaaacg caagtactcc gattccagcc  2760
agagcagcac aagcaactcc acctgcagct cgcagagcgg cagcgaatcg gagagcaact  2820
ccgataccta ctccaacaga tgttcaaaac tcaggccaat ctccacctaa acccatatac  2880
atttacccag ctgtaaagca ggtgtttatg tttgaccccc cgggccctaa ggctatctcg  2940
ggcgccaagg cctgggagga cgagttcctc accgcaaaag tgtggaaccg cccggtacgc  3000
aagtactact cagacacccc ctactacccc tgggccccca aaccccagta ctctgtcagt  3060
ttcaaactcg gctggaaata aaaaaagcct gctccactgt actaggccgt gggagtttca  3120
ctcgtcggtg tctacctctt aaggtcacca agcactccga gcgtcagcga ggagtgcgac  3180
ccttgggggt gggtgcaacg ccctcggcgg ccgcgcgcta cgccttcggc tgcgcgcggc  3240
acctcggacc cccgctcgtg ctgacgcgct tgcgcgcgtc agaccacttc gggctcgcgg  3300
gggtcggaaa ttttgctaaa cagactccga gttgccattg gacactggag ccgtgaatca  3360
gtaacgaaag tgagtggggc cagacttcgc cataaggcct ttatcttttt gccatttgtc  3420
cgtgggggaag ggtcgctgca agcgcggacc ccgttttcac cccttccgga ctacaaaaat  3480
agcgcattag tgacgtcacg gccgccattt taagtaaggc ggaagcaact ccactttctc  3540
acaaaatggc ggcggagcac ttccggcttg cccaaaatgg ccgccaaaaa catccgggtc  3600
aaagttcgcc gctacgtcat aagtcacgtg actggggagg tacttaaaca cggaagtatc  3660
ctcaaccacg taactggtca cgtggtgcgc acgtcacggc aaccattttg ttttacaaaa  3720
tggcgcattt ccttcctctt ttttaaaaat taaccgttgg cggcggcgcg cgcgctacgc  3780
gcgcgcgccg gggagctctg cccccccccg cgcatgcgcg cgggtccccc ccccgcgggg  3840
ggctccgccc cccggtcccc cccccg                                         3866
```

```
SEQ ID NO: 48          moltype = AA  length = 123
FEATURE                Location/Qualifiers
source                 1..123
                       mol_type = protein
                       organism = Alphatorquevirus sp.
SEQUENCE: 48
MSWSRPVHNA AGIERQWFES TFRSHASCCG CGNFVNHINV LAARYGFTGG PTPPGGPGPR  60
PQLRPALPAP DPDPQAPNRE PWRGAGGGND GEGAAGNPGG AAGDVYDGED LDALFAAVVE  120
DVE                                                                123
```

```
SEQ ID NO: 49          moltype = AA  length = 275
FEATURE                Location/Qualifiers
source                 1..275
                       mol_type = protein
                       organism = Alphatorquevirus sp.
SEQUENCE: 49
MSWSRPVHNA AGIERQWFES TFRSHASCCG CGNFVNHINV LAARYGFTGG PTPPGGPGPR  60
PQLRPALPAP DPDPQAPNRE PWRGAGGGND GEGAAGNPGG AAGDVYDGED LDALFAAVVE  120
DVESSRTPAK TVDWNPPTPV DSVATYKLLT HTPWAPNSRS TTGTTDMAFL AKTLSTECLN  180
NQKMMQTILT HTKGLDIFHP QTKPPKSKKK TSVSSKQHRR TQKRAIKKSS KKRKYSDSSQ  240
SSTSNSTCSS QSGSESESNS DTYSNRCSKL RPIST                             275
```

```
SEQ ID NO: 50          moltype = AA  length = 267
FEATURE                Location/Qualifiers
source                 1..267
                       mol_type = protein
                       organism = Alphatorquevirus sp.
SEQUENCE: 50
```

```
MSWSRPVHNA AGIERQWFES TFRSHASCCG CGNFVNHINV LAARYGFTGG PTPPGGPGPR  60
PQLRPALPAP DPDPQAPNRE PWRGAGGGND GEGAAGNPGG AAGDVYDGED LDALFAAVVE  120
DVEPSRPRAR KRLQFPQNST VELRRERSRS PPRNASTPIP ARAAQATPPA ARRAAANRRA  180
TPIPTPTDVQ NSGQSPPKPI YIYPAVKQVF MFDPPGPKAI SGAKAWEDEF LTAKVWNRPV  240
RKYYSDTPYY PWAPKPQYSV SFKLGWK                                      267

SEQ ID NO: 51          moltype = AA  length = 765
FEATURE                Location/Qualifiers
source                 1..765
                       mol_type = protein
                       organism = Alphatorquevirus sp.
SEQUENCE: 51
MAWSWWWQRW RRRRWKPRRR RWRRLRWRRP RRAVRRRRRG RRVRRRRWAR RRGRRRRYAT  60
RRKRRYRGRR FKKKLVLTQW HPNTMRRCLI KGIVPLVICG HTRWNYNYAL HSKDYTEEGR  120
YPHGGALSTT TWSLKVLYDE HLKHHDFWGY PNNQLDLARY KGAKFTFYRH KKTDFIIFFN  180
RKPPFKLNKY SCASYHPGML MQQRHKILLP SYETKPKGRP KITVRIKPPT LLEDKWYTQQ  240
DLCDVNLLQL VVTAADFRHP LCSPQTNTPT TTFQVLKDIY YDTMSISEPT DSYTSVNNKS  300
TTQTFTNYSN TLENILYTRA SYWNSFHATE YLNPNIIYKN GEKLFKEHED LITWMTQTNN  360
TGFLTKNNTA FGNNSYRPNA DKIKKARKTY WNALIGTNDL ATNIGQARAE RFEYHLGWYS  420
PIFLSRHRSN MNFARAYQDV TYNPNCDRGV NNRVWVQPLT KPTTEFDEKR CKCVVQHLPL  480
WAALYCYQDF VEEELGSSSE ILNSCLLVLQ CPYTFPPMYD KKLPDKGFVF YDSLFGDGKM  540
SDGRGQVDIF WQQRWYPRLA TQMQVMHDIT MTGPFSYRDE LVSTQLTAKY TFDFMWGGNM  600
ISTQIIKNPC KDSGLEPAYP GRQRRDLQIV DPYSMGPQFS FHNWDYRHGL FGQDAIDRVS  660
KQPKDDADYP NPYKRPRYFP PTDQAAQEQE KDFSFLKTAP SNSEESDQEV LQETQVLRFQ  720
PEQHKQLHLQ LAERQRIGEQ LRYLLQQMFK TQANLHLNPY TFTQL                  765

SEQ ID NO: 52          moltype = AA  length = 203
FEATURE                Location/Qualifiers
source                 1..203
                       mol_type = protein
                       organism = Alphatorquevirus sp.
SEQUENCE: 52
MAWSWWWQRW RRRRWKPRRR RWRRLRWRRP RRAVRRRRRG RRIIKNPCKD SGLEPAYPGR  60
QRRDLQIVDP YSMGPQFSFH NWDYRHGLFG QDAIDRVSKQ PKDDADYPNP YKRPRYFPPT  120
DQAAQEQEKD FSFLKTAPSN SEESDQEVLQ ETQVLRFQPE QHKQLHLQLA ERQRIGEQLR  180
YLLQQMFKTQ ANLHLNPYTF TQL                                          203

SEQ ID NO: 53          moltype = AA  length = 116
FEATURE                Location/Qualifiers
source                 1..116
                       mol_type = protein
                       organism = Alphatorquevirus sp.
SEQUENCE: 53
MAWSWWWQRW RRRRWKPRRR RWRRLRWRRP RRAVRRRRRG RRTKPPKSKK KTSVSSKQHR  60
RTQKRAIKKS SKKRKYSDSS QSSTSNSTCS SQSGSESESN SDTYSNRCSK LRPIST      116

SEQ ID NO: 54          moltype = DNA  length = 2979
FEATURE                Location/Qualifiers
source                 1..2979
                       mol_type = genomic DNA
                       organism = Betatorquevirus sp.
SEQUENCE: 54
taataaatat tcaacaggaa aaccacctaa tttaaattgc cgaccacaaa ccgtcactta  60
gttccccttt ttgcaacaac ttctgctttt ttccaactgc cggaaaacca cataatttgc  120
atggctaacc acaaactgat atgctaatta acttccacaa aacaacttcc ccttttaaaa  180
ccacacctac aaattaatta ttaaacacag tcacatcctg ggaggtacta ccacactata  240
ataccaagtg cacttccgaa tggctgagtt tatgccgcta gacggagaac gcatcagtta  300
ctgactgcgg actgaacttg ggcgggtgcc gaaggtgagt gaaaccaccg aagtcaaggg  360
gcaattcggg ctagttcagt ctagcggaac gggcaagaaa cttaaaatta ttttattttt  420
cagatgagcg actgctttaa accaacatgc tacaacaaca aaacaaagca aactcactgg  480
attaataacc tgcatttaac ccacgacctg atctgcttct gcccaacacc aactagacac  540
ttattactag ctttagcaga acaacaagaa acaattgaag tgtctaaaca agaaaaagaa  600
aaaataacaa gatgccttat tactacagaa gaagacggta caactacaga cgtcctagat  660
ggtatggacg aggttggatt agacgccctt ttcgcagaag atttcgaaga aaaagaaggg  720
taagacctac ttatactact attcctctaa agcaatggca accgccatat aaaagaacat  780
gctatataaa aggacaagac tgtttaatat actatagcaa cttaagactg ggaatgaata  840
gtacaatgta tgaaaaaagt attgtacctg tacattggcc gggagggggt tctttttctg  900
taagcatgtt aactttagat gccttgtatg atatacataa actttgtaga aactggtgga  960
catccacaaa ccaagactta ccactagtaa gatataaagg atgcaaaata acattttatc  1020
aaagcacatt tacagactac atagtaagaa tacatacaga actaccagct aacagtaaca  1080
aactaacata cccaaacaca catccactaa tgatgatgat gtctaagtac aaacacatta  1140
tacctagtag acaaacaaga agaaaaaaga aaccatacac aaaaatattt gtaaaaccac  1200
ctccgcaatt tgaaaacaaa tggtactttg ctacagacct ctacaaaatt ccattactac  1260
aaatacactg cacagcatgc aacttacaaa acccatttgt aaaaccagac aaattatcaa  1320
acaatgttac attatggtca ctaaacacca taagcataca aaatagaaac atgtcagtgg  1380
atcaaggaca atcatggcca tttaaaatac taggaacaca aagcttttat ttttactttt  1440
acaccggagc aaacctacca ggtgacacaa cacaaatacc agtagcagac ctattaccac  1500
taacaaaccc aagaataaac agaccaggac aatcactaaa tgaggcaaaa attacagacc  1560
atattacttt cacagaatac aaaaacaaat ttacaaatta ttggggtaac ccatttaata  1620
```

```
aacacattca agaacaccta gatatgatac tatactcact aaaaagtcca gaagcaataa  1680
aaaacgaatg gacaacagaa aacatgaaat ggaaccaatt aaacaatgca ggaacaatgg  1740
cattaacacc atttaacgag ccaatattca cacaaataca atataaccca gatagagaca  1800
caggagaaga cactcaatta tacctactct ctaacgctac aggaacagga tgggacccac  1860
caggaattcc agaattaata ctagaaggat ttccactatg gttaatatat tggggatttg  1920
cagactttca aaaaaaccta aaaaaagtaa caaacataga cacaaattac atgttagtag  1980
caaaaacaaa atttacacaa aaacctggca cattctactt agtaatacta aatgacacct  2040
ttgtagaagg caatagccca tatgaaaaac aacctttacc tgaagacaac attaaatggt  2100
acccacaagt acaataccaa ttagaagcac aaaacaaact actacaaact gggccattta  2160
caccaaacat acaaggacaa ctatcagaca atatatcaat gttttataaa ttttacttta  2220
aatggggagg aagcccacca aaagcaatta atgttgaaaa tcctgcccac cagattcaat  2280
atcccatacc ccgtaacgag catgaaacaa cttcgttaca gagtccaggg gaagccccag  2340
aatccatctt atactccttc gactatagac acgggaacta cacaacaaca gctttgtcac  2400
gaattagcca agactgggca cttaaagaca ctgtttctaa aattacagag ccagatcgac  2460
agcaactgct caaacaagcc ctcgaatgcc tgcaaatctc ggaagaaacg caggagaaaa  2520
aagaaaaaga agtacagcag ctcatcagca acctcagaca gcagcagcag ctgtacagag  2580
agcgaataat atcattatta aaggaccaat aacttttaac tgtgtaaaaa aggtgaaatt  2640
gtttgatgat aaaccaaaaa accgtagatt tacacctgag gaatttgaaa ctgagttaca  2700
aatagcaaaa tggttaaaga gacccccaag atcctttgta aatgatcctc ccttttaccc  2760
atggttacca cctgaacctg ttgtaaactt taagcttaat tttactgaat aaaggccagc  2820
attaattcac ttaaggagtc tgtttattta agttaaacct taataaacgg tcaccgcctc  2880
cctaatacgc aggcgcagaa agggggctcc gccccccttta acccccaggg ggctccgccc  2940
cctgaaaccc ccaagggggc tacgcccccct tacacccccc                        2979

SEQ ID NO: 55          moltype = AA  length = 99
FEATURE                Location/Qualifiers
source                 1..99
                       mol_type = protein
                       organism = Betatorquevirus sp.
SEQUENCE: 55
MSDCFKPTCY NNKTKQTHWI NNLHLTHDLI CFCPTPTRHL LLALAEQQET IEVSKQEKEK  60
ITRCLITTEE DGTTTDVLDG MDEVGLDALF AEDFEEKEG                         99

SEQ ID NO: 56          moltype = AA  length = 203
FEATURE                Location/Qualifiers
source                 1..203
                       mol_type = protein
                       organism = Betatorquevirus sp.
SEQUENCE: 56
MSDCFKPTCY NNKTKQTHWI NNLHLTHDLI CFCPTPTRHL LLALAEQQET IEVSKQEKEK  60
ITRCLITTEE DGTTTDVLDG MDEVGLDALF AEDFEEKEGF NIPYPVTSMK QLRYRVQGKP  120
QNPSYTPSTI DTGTTQQQLC HELAKTGHLK TLFLKLQSQI DSNCSNKPSN ACKSRKKRRR  180
KKKKKYSSSS ATSDSSSSCT ESE                                          203

SEQ ID NO: 57          moltype = AA  length = 219
FEATURE                Location/Qualifiers
source                 1..219
                       mol_type = protein
                       organism = Betatorquevirus sp.
SEQUENCE: 57
MSDCFKPTCY NNKTKQTHWI NNLHLTHDLI CFCPTPTRHL LLALAEQQET IEVSKQEKEK  60
ITRCLITTEE DGTTTDVLDG MDEVGLDALF AEDFEEKEGA RSTATAQTSP RMPANLGRNA  120
GEKRKRSTAA HQQPQTAAAA VQRANNIIIK GPITFNCVKK VKLFDDKPKN RRFTPEEFET  180
ELQIAKWLKR PPRSFVNDPP FYPWLPPEPV VNFKLNFTE                         219

SEQ ID NO: 58          moltype = AA  length = 666
FEATURE                Location/Qualifiers
source                 1..666
                       mol_type = protein
                       organism = Betatorquevirus sp.
SEQUENCE: 58
MPYYYRRRRY NYRRPRWYGR GWIRRPFRRR FRRKRRVRPT YTTIPLKQWQ PPYKRTCYIK  60
GQDCLIYYSN LRLGMNSTMY EKSIVPVHWP GGGSFSVSML TLDALYDIHK LCRNWWTSTN  120
QDLPLVRYKG CKITFYQSTF TDYIVRIHTE LPANSNKLTY PNTHPLMMMM SKYKHIIPSR  180
QTRRKKKPYT KIFVKPPPQF ENKWYFATDL YKIPLLQIHC TACNLQNPFV KPDKLSNNVT  240
LWSLNTISIQ NRNMSVDQGQ SWPFKILGTQ SFYFYFYTGA NLPGDTTQIP VADLLPLTNP  300
RINRPGQSLN EAKITDHITF TEYKNKFTNY WGNPFNKHIQ EHLDMILYSL KSPEAIKNEW  360
TTENMKWNQL NNAGTMALTP FNEPIFTQIQ YNPDRDTGED TQLYLLSNAT GTGWDPPGIP  420
ELILEGFPLW LIYWGFADFQ KNLKKVTNID TNYMLVAKTK FTQKPGTFYL VILNDTFVEG  480
NSPYEKQPLP EDNIKWYPQV QYQLEAQNKL LQTGPFTPNI QGQLSDNISM FYKFYFKWGG  540
SPPKAINVEN PAHQIQYPIP RNEHETTSLQ SPGEAPESIL YSFDYRHGNY TTTALSRISQ  600
DWALKDTVSK ITEPDRQQLL KQALECLQIS EETQEKKEKE VQQLISNLRQ QQQLYRERII  660
SLLKDQ                                                             666

SEQ ID NO: 59          moltype = AA  length = 148
FEATURE                Location/Qualifiers
source                 1..148
                       mol_type = protein
                       organism = Betatorquevirus sp.
```

```
SEQUENCE: 59
MPYYYRRRRY NYRRPRWYGR GWIRRPFRRR FRRKRRIQYP IPRNEHETTS LQSPGEAPES  60
ILYSFDYRHG NYTTTALSRI SQDWALKDTV SKITEPDRQQ LLKQALECLQ ISEETQEKKE  120
KEVQQLISNL RQQQQLYRER IISLLKDQ                                     148

SEQ ID NO: 60          moltype = AA  length = 82
FEATURE                Location/Qualifiers
source                 1..82
                       mol_type = protein
                       organism = Betatorquevirus sp.
SEQUENCE: 60
MPYYYRRRRY NYRRPRWYGR GWIRRPFRRR FRRKRRSQID SNCSNKPSNA CKSRKKRRRK  60
KKKKYSSSSA TSDSSSSCTE SE                                           82

SEQ ID NO: 61          moltype = DNA  length = 3242
FEATURE                Location/Qualifiers
source                 1..3242
                       mol_type = genomic DNA
                       organism = Gammatorquevirus sp.
SEQUENCE: 61
aggtggagac tcttaagcta tataaccaag tggggtggcg aatggctgag tttaccccgc  60
tagacggtgc agggaccgga tcgagcgcag cgaggaggtc cccggctgcc cgtgggcggg  120
agcccgaggt gagtgaaacc accgaggtct aggggcaatt cgggctaggg cagtctagcg  180
gaacgggcaa gaaacttaaa aatatttctt ttacagatgc aaaacctatc agccaaagac  240
ttctacaaac catgcagata caactgtgaa actaaaaacc aaatgtggat gtctggcatt  300
gctgactccc atgacagttg gtgtgactgt gatactcctt ttgctcacct cctggctagt  360
atttttcctc ctggtcacac agatcgcaca cgaaccatcc aagaaatact taccagagat  420
tttaggaaaa catgcctttc tggtggggcc gacgcaacaa attctggtat ggccgaaact  480
atagaagaaa aaagagaaga tttccaaaaa gaagaaaaag aagattttac agaagaacaa  540
aatatagaag acctgctcgc cgccgtcgca gacgcagaag gaaggtaaga agaaaaaaaa  600
aaactcttat agtaagacaa tggcagccag actctattgt actctgtaaa attaaagggt  660
atgactctat aatatgggga gctgaaggca cacagtttca atgttctaca catgaaatgt  720
atgaatatac aagacaaaag taccctgggg gaggaggatt tggtgtacaa ctttacagct  780
tagagtattt gtatgaccaa tggaaactta gaaataatat atggactaaa acaaatcaac  840
tcaaagattt gtgtagatac ttaaaatgtg ttatgacctt ttacagacac caacacatag  900
attttgtaat tgtatatgaa agacaacccc catttgaaat agataaacta acatacatga  960
aatatcatcc atatatgtta ttacaaagaa agcataaaat aattttacct agtcaaacaa  1020
ctaatcctag aggtaaatta aaaaaaaaga aaactattaa acctcccaaa caaatgctca  1080
gcaaatggtt ttttcaacaa caatttgcta aatatgatct actacttatt gctgcagcag  1140
catgtagttt aagataccct agaataggct gctgcaatga aaatagaggt ataaccttat  1200
actgtttaaa tactaaattt tatcaagata cagaatgggg aactacaaaa caggcccccc  1260
actactttaa accatatgca acaattaata aatccatgat atttgtctct aactatggag  1320
gtaaaaaaac agaatataac ataggccaat ggatagaaac agatatacct ggagaaggta  1380
atctagcaag atactacaga tcaataagta aagaaggagg ttacttttca cctaaaatac  1440
tgcaagcata tcaaacaaaa gtaaagtctg tagactacaa acctttacca attgttttag  1500
gtagatataa cccagcaata gatgatggaa aaggcaacaa aatttactta caaactataa  1560
tgaatggcca ttggggccta cctcaaaaaa caccagatta tataatagaa gaggtccctc  1620
tttggctagg cttctgggga tactataact acttaaaaca aacaagaact gaagctatat  1680
ttccactaca catgtttgta gtgcaaagca aatacattca aacacaacaa acagaaacac  1740
ctaacaattt ttgggcattt atagacaaca gctttataca gggcaaaaac ccatgggact  1800
cagttattac ttactcagaa caaaagctat ggtttcctac agttgcatgg caactaaaaa  1860
ccataaatgc tatttgtgaa agtggaccat atgtacctaa actagacaat caaacatata  1920
gtacctggga actagcaact cattactcat ttcactttaa atggggtggt ccacagatat  1980
cagaccaacc agttgaagac ccaggaaaca aaaacaaata tgatgtgccc gatacaatca  2040
aagaagcatt acaaattgtt aacccagcaa aaaacattgc tgccacgatg ttccatgact  2100
gggactacag acggggttgc attacatcaa cagctattaa aagaatgcaa caaaacctcc  2160
caactgattc atctctcgaa tctgattcag actcagaacc agcacccaag aaaaaaagac  2220
tactaccagt cctccacgac ccacaaaaga aaacggaaaa gatcaaccaa tgtctcctct  2280
ctctctgcga agaaagtaca tgccaggagc aggaaacgga ggaaaacatc ctcaagctca  2340
tccagcagca gcagcagcag cagcagaaac tcaagcacaa cctcttagta ctaatcaagg  2400
acttaaaagt gaaacaaaga ttattacaac tacaaacggg ggtactagaa taacccttac  2460
cagatttaaa ccaggatttg agcaagaaac tgaaaaagag ttagcacaag catttaacag  2520
acccccctaga ctgttcaaag aagataaacc cttttacccc tggctaccca gatttacacc  2580
ccttgtaaac tttcacctta attttaaagg ctaggcctac actgctcact tagtggtgta  2640
tgtttattaa agtttgcacc ccagaaaaat tgtaaaataa aaaaaaaaaa aaaaaataaa  2700
aaattgcaaa aattcggcgc tcgcgcgcgc tgcgcgcgcg agcgccgtca cgcgccggcg  2760
ctcgcgcgcc gcgcgtatgt gctaacacac cacgcaccta gattggggtg cgcgcgtagc  2820
gcgcgcaccc caatgcgccc cgccctcgtt ccgacccgct tgcgcgggtc ggaccacttc  2880
gggctcgggg gggcgcgcct gcggcgctta tttactaaac agactccgag tcgccattgg  2940
gcccccccta agctccgccc ccctcatgaa tattcataaa ggaaaccaca aaattagaat  3000
tgccgaccac aaactgccat atgctaatta gttccccttt tacacagtaa aaaggggaag  3060
tgggggggca gagccccccc acaccccccg cggggggggc agagccccccc ccgcaccccc  3120
cctacgtcac aggccacgcc cccgccgcca tcttgggtgc ggcagggcgg ggactaaaat  3180
ggcgggaccc aatcatttta tactttcact ttccaattaa aacccgccac gtcacacaaa  3240
ag                                                                 3242

SEQ ID NO: 62          moltype = AA  length = 101
FEATURE                Location/Qualifiers
source                 1..101
```

```
                        mol_type = protein
                        organism = Gammatorquevirus sp.
SEQUENCE: 62
MWMSGIADSH DSWCDCDTPF AHLLASIFPP GHTDRTRTIQ EILTRDFRKT CLSGGADATN  60
SGMAETIEEK REDFQKEEKE DFTEEQNIED LLAAVADAEG R                      101

SEQ ID NO: 63           moltype = AA  length = 237
FEATURE                 Location/Qualifiers
source                  1..237
                        mol_type = protein
                        organism = Gammatorquevirus sp.
SEQUENCE: 63
MWMSGIADSH DSWCDCDTPF AHLLASIFPP GHTDRTRTIQ EILTRDFRKT CLSGGADATN  60
SGMAETIEEK REDFQKEEKE DFTEEQNIED LLAAVADAEG RYQTNQLKTQ ETKTNMMCPI  120
QSKKHYKLLT QQKTLLPRCS MTGTTDGVAL HQQLLKECNK TSQLIHLSNL IQTQNQHPRK  180
KDYYQSSTTH KRKRKRSTNV SSLSAKKVHA RSRKRRKTSS SSSSSSSSS RNSSTTS      237

SEQ ID NO: 64           moltype = AA  length = 239
FEATURE                 Location/Qualifiers
source                  1..239
                        mol_type = protein
                        organism = Gammatorquevirus sp.
SEQUENCE: 64
MWMSGIADSH DSWCDCDTPF AHLLASIFPP GHTDRTRTIQ EILTRDFRKT CLSGGADATN  60
SGMAETIEEK REDFQKEEKE DFTEEQNIED LLAAVADAEG RTSTQEKKTT TSPPRPTKEN  120
GKDQPMSPLS LRRKYMPGAG NGGKHPQAHP AAAAAAAETQ AQPLSTNQGL KSETKIITTT  180
NGGTRITLTR FKPGFEQETE KELAQAFNRP PRLFKEDKPF YPWLPRFTPL VNFHLNFKG   239

SEQ ID NO: 65           moltype = AA  length = 673
FEATURE                 Location/Qualifiers
source                  1..673
                        mol_type = protein
                        organism = Gammatorquevirus sp.
SEQUENCE: 65
MPFWWGRRNK FWYGRNYRRK KRRFPKRRKR RFYRRTKYRR PARRRRRRRR KVRRKKKTLI  60
VRQWQPDSIV LCKIKGYDSI IWGAEGTQFQ CSTHEMYEYT RQKYPGGGGF GVQLYSLEYL  120
YDQWKLRNNI WTKTNQLKDL CRYLKCVMTF YRHQHIDFVI VYERQPPFEI DKLTYMKYHP  180
YMLLQRKHKI ILPSQTTNPR GKLKKKKTIK PPKQMLSKWF FQQQFAKYDL LLIAAAACSL  240
RYPRIGCCNE NRMITLYCLN TKFYQDTEWG TTKQAPHYFK PYATINKSMI FVSNYGGKKT  300
EYNIGQWIET DIPGEGNLAR YYRSISKEGG YFSPKILQAY QTKVKSVDYK PLPIVLGRYN  360
PAIDDGKGNK IYLQTIMNGH WGLPQKTPDY IIEEVPLWLG FWGYYNYLKQ TRTEAIFPLH  420
MFVVQSKYIQ TQQTETPNNF WAFIDNSFIQ GKNPWDSVIT YSEQKLWFPT VAWQLKTINA  480
ICESGPYVPK LDNQTYSTWE LATHYSFHFK WGGPQISDQP VEDPGNKNKY DVPDTIKEAL  540
QIVNPAKNIA ATMFHDWDYR RGCITSTAIK RMQQNLPTDS SLESDSDSEP APKKKRLLPV  600
LHDPQKKTEK INQCLLSLCE ESTCQEQETE ENILKLIQQQ QQQQQKLKHN LLVLIKDLKV  660
KQRLLQLQTG VLE                                                     673

SEQ ID NO: 66           moltype = AA  length = 209
FEATURE                 Location/Qualifiers
source                  1..209
                        mol_type = protein
                        organism = Gammatorquevirus sp.
SEQUENCE: 66
MPFWWGRRNK FWYGRNYRRK KRRFPKRRKR RFYRRTKYRR PARRRRRRRR KISDQPVEDP  60
GNKNKYDVPD TIKEALQIVN PAKNIAATMF HDWDYRRGCI TSTAIKRMQQ NLPTDSSLES  120
DSDSEPAPKK KRLLPVLHDP QKKTEKINQC LLSLCEESTC QEQETEENIL KLIQQQQQQQ  180
QKLKHNLLVL IKDLKVKQRL LQLQTGVLE                                    209

SEQ ID NO: 67           moltype = AA  length = 209
FEATURE                 Location/Qualifiers
source                  1..209
                        mol_type = protein
                        organism = Gammatorquevirus sp.
SEQUENCE: 67
MPFWWGRRNK FWYGRNYRRK KRRFPKRRKR RFYRRTKYRR PARRRRRRRR KISDQPVEDP  60
GNKNKYDVPD TIKEALQIVN PAKNIAATMF HDWDYRRGCI TSTAIKRMQQ NLPTDSSLES  120
DSDSEPAPKK KRLLPVLHDP QKKTEKINQC LLSLCEESTC QEQETEENIL KLIQQQQQQQ  180
QKLKHNLLVL IKDLKVKQRL LQLQTGVLE                                    209

SEQ ID NO: 68           moltype = AA  length = 25
FEATURE                 Location/Qualifiers
source                  1..25
                        mol_type = protein
                        organism = synthetic construct
VARIANT                 9
                        note = Any amino acid
VARIANT                 10
                        note = Any amino acid
VARIANT                 15
```

```
                        note = Any amino acid
VARIANT                 17
                        note = Any amino acid
VARIANT                 20
                        note = Any amino acid
VARIANT                 24
                        note = Any amino acid
SEQUENCE: 68
LIJRQWQPXX IRRCXIXGYX PLIXC                                     25

SEQ ID NO: 69           moltype = AA  length = 7
FEATURE                 Location/Qualifiers
source                  1..7
                        mol_type = protein
                        organism = synthetic construct
VARIANT                 3
                        note = Any amino acid
VARIANT                 4
                        note = Any amino acid
VARIANT                 6
                        note = Any amino acid
SEQUENCE: 69
NYXXHXD                                                         7

SEQ ID NO: 70           moltype = AA  length = 9
FEATURE                 Location/Qualifiers
source                  1..9
                        mol_type = protein
                        organism = synthetic construct
VARIANT                 4
                        note = Any amino acid
VARIANT                 5
                        note = Any amino acid
SEQUENCE: 70
FSLXXLYDZ                                                       9

SEQ ID NO: 71           moltype = AA  length = 18
FEATURE                 Location/Qualifiers
source                  1..18
                        mol_type = protein
                        organism = synthetic construct
VARIANT                 2
                        note = Any amino acid
VARIANT                 5
                        note = Any amino acid
VARIANT                 8
                        note = Any amino acid
VARIANT                 16
                        note = Any amino acid
SEQUENCE: 71
NXWTXSNXDL DLCRYXGC                                             18

SEQ ID NO: 72           moltype = AA  length = 16
FEATURE                 Location/Qualifiers
source                  1..16
                        mol_type = protein
                        organism = synthetic construct
VARIANT                 2
                        note = Any amino acid
VARIANT                 5
                        note = Any amino acid
VARIANT                 9
                        note = Any amino acid
VARIANT                 11
                        note = Any amino acid
VARIANT                 13
                        note = Any amino acid
SEQUENCE: 72
TXPSXHPGXM XLXKHK                                               16

SEQ ID NO: 73           moltype = AA  length = 10
FEATURE                 Location/Qualifiers
source                  1..10
                        mol_type = protein
                        organism = synthetic construct
VARIANT                 5
                        note = Any amino acid
VARIANT                 9
                        note = Any amino acid
```

```
SEQUENCE: 73
IPSLXTRPXG                                                    10

SEQ ID NO: 74          moltype = AA  length = 18
FEATURE                Location/Qualifiers
source                 1..18
                       mol_type = protein
                       organism = synthetic construct
VARIANT                3
                       note = Any amino acid
VARIANT                6
                       note = Any amino acid
VARIANT                9
                       note = Any amino acid
VARIANT                16
                       note = Any amino acid
SEQUENCE: 74
RIXPPXLFXD KWYFQXDL                                           18

SEQ ID NO: 75          moltype = AA  length = 8
FEATURE                Location/Qualifiers
source                 1..8
                       mol_type = protein
                       organism = synthetic construct
VARIANT                3
                       note = Any amino acid
VARIANT                5
                       note = Any amino acid
SEQUENCE: 75
LLXIXATA                                                      8

SEQ ID NO: 76          moltype = AA  length = 11
FEATURE                Location/Qualifiers
source                 1..11
                       mol_type = protein
                       organism = synthetic construct
VARIANT                2
                       note = Any amino acid
VARIANT                3
                       note = Any amino acid
VARIANT                6
                       note = Any amino acid
VARIANT                9
                       note = Any amino acid
SEQUENCE: 76
LXXPFXSPXT D                                                  11

SEQ ID NO: 77          moltype = AA  length = 14
FEATURE                Location/Qualifiers
source                 1..14
                       mol_type = protein
                       organism = synthetic construct
VARIANT                4
                       note = Any amino acid
VARIANT                5
                       note = Any amino acid
VARIANT                9
                       note = Any amino acid
VARIANT                12
                       note = Any amino acid
SEQUENCE: 77
YNPXXDKGXG NXIW                                               14

SEQ ID NO: 78          moltype = AA  length = 8
FEATURE                Location/Qualifiers
source                 1..8
                       mol_type = protein
                       organism = synthetic construct
VARIANT                7
                       note = Any amino acid
SEQUENCE: 78
CPYTZPXL                                                      8

SEQ ID NO: 79          moltype = AA  length = 8
FEATURE                Location/Qualifiers
source                 1..8
                       mol_type = protein
                       organism = synthetic construct
VARIANT                1
```

```
                        note = Any amino acid
VARIANT                 4
                        note = Any amino acid
VARIANT                 6
                        note = Any amino acid
SEQUENCE: 79
XFGXGXMP                                                                    8

SEQ ID NO: 80           moltype = AA  length = 8
FEATURE                 Location/Qualifiers
source                  1..8
                        mol_type = protein
                        organism = synthetic construct
VARIANT                 3
                        note = Any amino acid
VARIANT                 6
                        note = Any amino acid
VARIANT                 8
                        note = Any amino acid
SEQUENCE: 80
HQXEVXEX                                                                    8

SEQ ID NO: 81           moltype = AA  length = 12
FEATURE                 Location/Qualifiers
source                  1..12
                        mol_type = protein
                        organism = synthetic construct
VARIANT                 3
                        note = Any amino acid
VARIANT                 5
                        note = Any amino acid
VARIANT                 7
                        note = Any amino acid
SEQUENCE: 81
KYXFXFXWGG NP                                                               12

SEQ ID NO: 82           moltype = AA  length = 8
FEATURE                 Location/Qualifiers
source                  1..8
                        mol_type = protein
                        organism = synthetic construct
VARIANT                 5
                        note = Any amino acid
SEQUENCE: 82
HSWDXRRG                                                                    8

SEQ ID NO: 83           moltype = AA  length = 7
FEATURE                 Location/Qualifiers
source                  1..7
                        mol_type = protein
                        organism = synthetic construct
VARIANT                 5
                        note = Any amino acid
SEQUENCE: 83
AIKRXQQ                                                                     7

SEQ ID NO: 84           moltype = AA  length = 8
FEATURE                 Location/Qualifiers
source                  1..8
                        mol_type = protein
                        organism = synthetic construct
VARIANT                 1
                        note = Any amino acid
VARIANT                 5
                        note = Any amino acid
VARIANT                 6
                        note = Any amino acid
SEQUENCE: 84
XQZQXXLR                                                                    8

SEQ ID NO: 85           moltype = AA  length = 9
FEATURE                 Location/Qualifiers
source                  1..9
                        mol_type = protein
                        organism = synthetic construct
VARIANT                 3
                        note = Any amino acid
VARIANT                 6
                        note = Any amino acid
```

```
VARIANT                 7
                        note = Any amino acid
SEQUENCE: 85
PRXJQXXDP                                                                    9

SEQ ID NO: 86           moltype = AA  length = 8
FEATURE                 Location/Qualifiers
source                  1..8
                        mol_type = protein
                        organism = synthetic construct
VARIANT                 5
                        note = Any amino acid
SEQUENCE: 86
HSWDXRRG                                                                     8

SEQ ID NO: 87           moltype = AA  length = 7
FEATURE                 Location/Qualifiers
source                  1..7
                        mol_type = protein
                        organism = synthetic construct
VARIANT                 5
                        note = Any amino acid
SEQUENCE: 87
AIKRXQQ                                                                      7

SEQ ID NO: 88           moltype = AA  length = 7
FEATURE                 Location/Qualifiers
source                  1..7
                        mol_type = protein
                        organism = synthetic construct
VARIANT                 4
                        note = Any amino acid
VARIANT                 5
                        note = Any amino acid
SEQUENCE: 88
QZQXXLR                                                                      7

SEQ ID NO: 89           moltype = AA  length = 7
FEATURE                 Location/Qualifiers
source                  1..7
                        mol_type = protein
                        organism = synthetic construct
VARIANT                 2
                        note = Any amino acid
SEQUENCE: 89
KXKRRRR                                                                      7

SEQ ID NO: 90           moltype = AA  length = 13
FEATURE                 Location/Qualifiers
source                  1..13
                        mol_type = protein
                        organism = synthetic construct
VARIANT                 3
                        note = Any amino acid
VARIANT                 6
                        note = Any amino acid
VARIANT                 7
                        note = Any amino acid
VARIANT                 10
                        note = Any amino acid
VARIANT                 11
                        note = Any amino acid
SEQUENCE: 90
PIXSLXXYKX XTR                                                               13

SEQ ID NO: 91           moltype = AA  length = 12
FEATURE                 Location/Qualifiers
source                  1..12
                        mol_type = protein
                        organism = synthetic construct
VARIANT                 3
                        note = Any amino acid
VARIANT                 10
                        note = Any amino acid
SEQUENCE: 91
LAXQLLKECX KN                                                                12

SEQ ID NO: 92           moltype = AA  length = 6
FEATURE                 Location/Qualifiers
```

```
source                  1..6
                        mol_type = protein
                        organism = synthetic construct
VARIANT                 4
                        note = Any amino acid
SEQUENCE: 92
HLNXLA                                                                    6

SEQ ID NO: 93           moltype = AA  length = 5
FEATURE                 Location/Qualifiers
source                  1..5
                        mol_type = protein
                        organism = synthetic construct
SEQUENCE: 93
DRPPR                                                                     5

SEQ ID NO: 94           moltype = AA  length = 9
FEATURE                 Location/Qualifiers
source                  1..9
                        mol_type = protein
                        organism = synthetic construct
VARIANT                 2
                        note = Any amino acid
VARIANT                 8
                        note = Any amino acid
SEQUENCE: 94
DXPFYPWXP                                                                 9

SEQ ID NO: 95           moltype = AA  length = 7
FEATURE                 Location/Qualifiers
source                  1..7
                        mol_type = protein
                        organism = synthetic construct
VARIANT                 2
                        note = Any amino acid
VARIANT                 6
                        note = Any amino acid
SEQUENCE: 95
VXFKLXF                                                                   7

SEQ ID NO: 96           moltype = AA  length = 15
FEATURE                 Location/Qualifiers
source                  1..15
                        mol_type = protein
                        organism = synthetic construct
VARIANT                 2
                        note = Any amino acid
VARIANT                 9
                        note = Any amino acid
VARIANT                 14
                        note = Any amino acid
SEQUENCE: 96
WXPPVHBVXG IERXW                                                          15

SEQ ID NO: 97           moltype = AA  length = 6
FEATURE                 Location/Qualifiers
source                  1..6
                        mol_type = protein
                        organism = synthetic construct
VARIANT                 6
                        note = Any amino acid
SEQUENCE: 97
AKRKLX                                                                    6

SEQ ID NO: 98           moltype = AA  length = 10
FEATURE                 Location/Qualifiers
source                  1..10
                        mol_type = protein
                        organism = synthetic construct
VARIANT                 4
                        note = Any amino acid
VARIANT                 7
                        note = Any amino acid
VARIANT                 8
                        note = Any amino acid
SEQUENCE: 98
PSSXDWXXEY                                                                10

SEQ ID NO: 99           moltype = AA  length = 5
```

```
FEATURE                 Location/Qualifiers
source                  1..5
                        mol_type = protein
                        organism = synthetic construct
SEQUENCE: 99
DRPPR                                                                     5

SEQ ID NO: 100          moltype = AA  length = 5
FEATURE                 Location/Qualifiers
source                  1..5
                        mol_type = protein
                        organism = synthetic construct
SEQUENCE: 100
PFYPW                                                                     5

SEQ ID NO: 101          moltype = AA  length = 8
FEATURE                 Location/Qualifiers
source                  1..8
                        mol_type = protein
                        organism = synthetic construct
VARIANT                 3
                        note = Any amino acid
VARIANT                 7
                        note = Any amino acid
SEQUENCE: 101
NVXFKLXF                                                                  8

SEQ ID NO: 102          moltype = AA  length = 25
FEATURE                 Location/Qualifiers
source                  1..25
                        mol_type = protein
                        organism = synthetic construct
VARIANT                 2
                        note = Any amino acid
VARIANT                 3
                        note = Any amino acid
VARIANT                 4
                        note = Any amino acid
VARIANT                 5
                        note = Any amino acid
VARIANT                 9
                        note = Any amino acid
VARIANT                 10
                        note = Any amino acid
VARIANT                 11
                        note = Any amino acid
VARIANT                 12
                        note = Any amino acid
VARIANT                 13
                        note = Any amino acid
VARIANT                 15
                        note = Any amino acid
VARIANT                 17
                        note = Any amino acid
VARIANT                 19
                        note = Any amino acid
VARIANT                 20
                        note = Any amino acid
VARIANT                 21
                        note = Any amino acid
SEQUENCE: 102
JXXXXWQPXX XXXCXIXGXX XJWQP                                               25

SEQ ID NO: 103          moltype = AA  length = 15
FEATURE                 Location/Qualifiers
source                  1..15
                        mol_type = protein
                        organism = synthetic construct
VARIANT                 2
                        note = Any amino acid
VARIANT                 4
                        note = Any amino acid
VARIANT                 5
                        note = Any amino acid
VARIANT                 6
                        note = Any amino acid
VARIANT                 8
                        note = Any amino acid
VARIANT                 9
```

```
                        note = Any amino acid
VARIANT                 10
                        note = Any amino acid
VARIANT                 11
                        note = Any amino acid
VARIANT                 13
                        note = Any amino acid
SEQUENCE: 103
NXWXXXNXXX XLXRY                                                    15

SEQ ID NO: 104          moltype = AA  length = 8
FEATURE                 Location/Qualifiers
source                  1..8
                        mol_type = protein
                        organism = synthetic construct
VARIANT                 4
                        note = Any amino acid
VARIANT                 5
                        note = Any amino acid
VARIANT                 7
                        note = Any amino acid
SEQUENCE: 104
YNPXXDXG                                                            8

SEQ ID NO: 105          moltype = DNA  length = 71
FEATURE                 Location/Qualifiers
source                  1..71
                        mol_type = other DNA
                        organism = synthetic construct
SEQUENCE: 105
cgggtgccgk aggtgagttt acacaccgma gtcaaggggc aattcgggct crggactggc  60
cgggcyhtgg g                                                        71

SEQ ID NO: 106          moltype = DNA  length = 71
FEATURE                 Location/Qualifiers
source                  1..71
                        mol_type = other DNA
                        organism = synthetic construct
SEQUENCE: 106
cgggtgccgg aggtgagttt acacaccgca gtcaaggggc aattcgggct cgggactggc  60
cgggctwtgg g                                                        71

SEQ ID NO: 107          moltype = DNA  length = 71
FEATURE                 Location/Qualifiers
source                  1..71
                        mol_type = genomic DNA
                        organism = Torque teno virus
SEQUENCE: 107
cgggtgccgt aggtgagttt acacaccgca gtcaaggggc aattcgggct cgggactggc  60
cgggctatgg g                                                        71

SEQ ID NO: 108          moltype = DNA  length = 71
FEATURE                 Location/Qualifiers
source                  1..71
                        mol_type = genomic DNA
                        organism = Torque teno virus
SEQUENCE: 108
cgggtgccgg aggtgagttt acacaccgca gtcaaggggc aattcgggct cgggactggc  60
cgggccctgg g                                                        71

SEQ ID NO: 109          moltype = DNA  length = 71
FEATURE                 Location/Qualifiers
source                  1..71
                        mol_type = genomic DNA
                        organism = Torque teno virus
SEQUENCE: 109
cgggtgccgg aggtgagttt acacaccgca gtcaaggggc aattcgggct cgggactggc  60
cgggctttgg g                                                        71

SEQ ID NO: 110          moltype = DNA  length = 71
FEATURE                 Location/Qualifiers
source                  1..71
                        mol_type = genomic DNA
                        organism = Torque teno virus
SEQUENCE: 110
cgggtgccgg aggtgagttt acacaccgca gtcaaggggc aattcgggct cgggactggc  60
cgggctatgg g                                                        71

SEQ ID NO: 111          moltype = DNA  length = 71
```

```
FEATURE                 Location/Qualifiers
source                  1..71
                        mol_type = genomic DNA
                        organism = Torque teno virus
SEQUENCE: 111
cgggtgccgg aggtgagttt acacaccgaa gtcaaggggc aattcgggct caggactggc  60
cgggctttgg g                                                       71

SEQ ID NO: 112          moltype = DNA  length = 71
FEATURE                 Location/Qualifiers
source                  1..71
                        mol_type = other DNA
                        organism = synthetic construct
SEQUENCE: 112
cgggtgccgg aggtgagttt acacaccgca gtcaaggggc aattcgggct cgggactggc  60
cgggcyhtgg g                                                       71

SEQ ID NO: 113          moltype = DNA  length = 71
FEATURE                 Location/Qualifiers
source                  1..71
                        mol_type = genomic DNA
                        organism = Torque teno virus
SEQUENCE: 113
cgggtgccgt aggtgagttt acacaccgca gtcaaggggc aattcgggct cgggactggc  60
cgggctatgg g                                                       71

SEQ ID NO: 114          moltype = DNA  length = 70
FEATURE                 Location/Qualifiers
source                  1..70
                        mol_type = genomic DNA
                        organism = Torque teno virus
SEQUENCE: 114
cgggtgccgg aggtgagttt acacaccgca gtcaaggggc aattcgggct cgggactggc  60
cgggcccggg                                                         70

SEQ ID NO: 115          moltype = DNA  length = 71
FEATURE                 Location/Qualifiers
source                  1..71
                        mol_type = genomic DNA
                        organism = Torque teno virus
SEQUENCE: 115
cgggtgccgg aggtgagttt acacaccgaa gtcaaggggc aattcgggct caggactggc  60
cgggctttgg g                                                       71

SEQ ID NO: 116          moltype = DNA  length = 69
FEATURE                 Location/Qualifiers
source                  1..69
                        mol_type = genomic DNA
                        organism = Torque teno virus
SEQUENCE: 116
cgggtgccgg aggtgagttt acacaccgca gtcaaggggc aattcgggct cgggaggccg  60
ggccatggg                                                          69

SEQ ID NO: 117          moltype = DNA  length = 71
FEATURE                 Location/Qualifiers
source                  1..71
                        mol_type = genomic DNA
                        organism = Torque teno virus
SEQUENCE: 117
cgggtgccgg aggtgagttt acacaccgca gtcaaggggc aattcgggct cgggactggc  60
cgggccccgg g                                                       71

SEQ ID NO: 118          moltype = DNA  length = 71
FEATURE                 Location/Qualifiers
source                  1..71
                        mol_type = genomic DNA
                        organism = Torque teno virus
SEQUENCE: 118
cgggtgccgg aggtgagttt acacaccgca gtcaaggggc aattcgggct cgggactggc  60
cgggctatgg g                                                       71

SEQ ID NO: 119          moltype = DNA  length = 71
FEATURE                 Location/Qualifiers
source                  1..71
                        mol_type = genomic DNA
                        organism = Torque teno virus
SEQUENCE: 119
cgggtgccga aggtgagttt acacaccgca gtcaaggggc aattcgggct cgggactggc  60
cgggctatgg g                                                       71
```

```
SEQ ID NO: 120          moltype = DNA  length = 117
FEATURE                 Location/Qualifiers
source                  1..117
                        mol_type = other DNA
                        organism = synthetic construct
misc_difference         10
                        note = This base may be absent
misc_difference         12
                        note = This base may be absent
misc_difference         30
                        note = This base may be absent
misc_difference         31
                        note = This base may be absent
misc_difference         32
                        note = This base may be absent
misc_difference         34
                        note = This base may be absent
misc_difference         43
                        note = This base may be absent
misc_difference         44
                        note = This base may be absent
misc_difference         45
                        note = This base may be absent
misc_difference         46
                        note = This base may be absent
misc_difference         52
                        note = This base may be absent
misc_difference         53
                        note = This base may be absent
misc_difference         54
                        note = This base may be absent
misc_difference         70
                        note = This base may be absent
misc_difference         71
                        note = This base may be absent
misc_difference         89
                        note = This base may be absent
misc_difference         90
                        note = This base may be absent
misc_difference         103
                        note = This base may be absent
SEQUENCE: 120
cggcggsggs gcsscgcgct dcgcgcgcsg cccrsyrggg grdssmmwgc skcscccccc  60
cscgcgcatg cgcrcgggkc ccccccccyv sggggggctc cgccccccg gcccccc     117

SEQ ID NO: 121          moltype = DNA  length = 169
FEATURE                 Location/Qualifiers
source                  1..169
                        mol_type = other DNA
                        organism = synthetic construct
misc_difference         20
                        note = a, c, t, g, unknown or other
misc_difference         22
                        note = a, c, t, g, unknown or other
misc_difference         40
                        note = a, c, t, g, unknown or other
misc_difference         41
                        note = a, c, t, g, unknown or other
misc_difference         42
                        note = a, c, t, g, unknown or other
misc_difference         53
                        note = a, c, t, g, unknown or other
misc_difference         54
                        note = a, c, t, g, unknown or other
misc_difference         55
                        note = a, c, t, g, unknown or other
misc_difference         56
                        note = a, c, t, g, unknown or other
misc_difference         62
                        note = a, c, t, g, unknown or other
misc_difference         64
                        note = a, c, t, g, unknown or other
misc_difference         97
                        note = a, c, t, g, unknown or other
misc_difference         98
                        note = a, c, t, g, unknown or other
SEQUENCE: 121
gccgccgcgg cggcggsggn gnsgcgcgct dcgcgcgcsn nncrccrggg ggnnnncwgc  60
```

```
sncnccccc cccgcgcatg cgcgggkccc cccccnncg gggggctccg cccccggcc  120
ccccccgtg ctaaacccac cgcgcatgcg cgaccacgcc cccgccgcc            169

SEQ ID NO: 122         moltype = DNA  length = 79
FEATURE                Location/Qualifiers
source                 1..79
                       mol_type = other DNA
                       organism = synthetic construct
misc_difference        20
                       note = a, c, t, g, unknown or other
misc_difference        22
                       note = a, c, t, g, unknown or other
misc_difference        40
                       note = a, c, t, g, unknown or other
misc_difference        41
                       note = a, c, t, g, unknown or other
misc_difference        42
                       note = a, c, t, g, unknown or other
misc_difference        53
                       note = a, c, t, g, unknown or other
misc_difference        54
                       note = a, c, t, g, unknown or other
misc_difference        55
                       note = a, c, t, g, unknown or other
misc_difference        56
                       note = a, c, t, g, unknown or other
misc_difference        62
                       note = a, c, t, g, unknown or other
misc_difference        64
                       note = a, c, t, g, unknown or other
SEQUENCE: 122
gccgccgcgg cggcggsggn gnsgcgcgct dcgcgcgcsn nncrccrggg ggnnnncwgc  60
sncnccccc cccgcgcat                                               79

SEQ ID NO: 123         moltype = DNA  length = 31
FEATURE                Location/Qualifiers
source                 1..31
                       mol_type = other DNA
                       organism = synthetic construct
misc_difference        18
                       note = a, c, t, g, unknown or other
misc_difference        19
                       note = a, c, t, g, unknown or other
SEQUENCE: 123
gcgcgggkcc ccccccnnc ggggggctcc g                                 31

SEQ ID NO: 124         moltype = DNA  length = 59
FEATURE                Location/Qualifiers
source                 1..59
                       mol_type = other DNA
                       organism = synthetic construct
SEQUENCE: 124
cccccggcc ccccccgtg ctaaacccac cgcgcatgcg cgaccacgcc cccgccgcc   59

SEQ ID NO: 125         moltype = DNA  length = 156
FEATURE                Location/Qualifiers
source                 1..156
                       mol_type = genomic DNA
                       organism = Torque teno virus
SEQUENCE: 125
gcggcggggg ggcggccgcg ttcgcgcgcc gcccaccagg gggtgctgcg cgcccccccc  60
cgcgcatgcg cggggccccc ccccgggggg gctccgcccc cccggccccc ccccgtgcta  120
aacccaccgc gcatgcgcga ccacgccccc gccgcc                           156

SEQ ID NO: 126         moltype =   length =
SEQUENCE: 126
000

SEQ ID NO: 127         moltype =   length =
SEQUENCE: 127
000

SEQ ID NO: 128         moltype =   length =
SEQUENCE: 128
000

SEQ ID NO: 129         moltype = DNA  length = 25
FEATURE                Location/Qualifiers
source                 1..25
```

```
                        mol_type = genomic DNA
                        organism = Torque teno virus
SEQUENCE: 129
ttcgcgcgcc gcccaccagg gggtg                                          25

SEQ ID NO: 130          moltype =   length =
SEQUENCE: 130
000

SEQ ID NO: 131          moltype = DNA  length = 17
FEATURE                 Location/Qualifiers
source                  1..17
                        mol_type = genomic DNA
                        organism = Torque teno virus
SEQUENCE: 131
cgcccccccc cgcgcat                                                   17

SEQ ID NO: 132          moltype = DNA  length = 17
FEATURE                 Location/Qualifiers
source                  1..17
                        mol_type = genomic DNA
                        organism = Torque teno virus
SEQUENCE: 132
gcgcggggcc ccccccc                                                   17

SEQ ID NO: 133          moltype = DNA  length = 72
FEATURE                 Location/Qualifiers
source                  1..72
                        mol_type = genomic DNA
                        organism = Torque teno virus
SEQUENCE: 133
ggggggctc cgcccccccg gccccccccc gtgctaaacc caccgcgcat gcgcgaccac  60
gcccccgccg cc                                                        72

SEQ ID NO: 134          moltype = DNA  length = 115
FEATURE                 Location/Qualifiers
source                  1..115
                        mol_type = genomic DNA
                        organism = Torque teno virus
SEQUENCE: 134
cggcggcggc ggcgcgcgcg ctgcgcgcgc gcgccggggg ggcgccagcg cccccccccc  60
cgcgcatgca cgggtccccc cccccacggg gggctccgcc ccccggcccc ccccc       115

SEQ ID NO: 135          moltype = DNA  length = 14
FEATURE                 Location/Qualifiers
source                  1..14
                        mol_type = genomic DNA
                        organism = Torque teno virus
SEQUENCE: 135
cggcggcggc ggcg                                                      14

SEQ ID NO: 136          moltype = DNA  length = 17
FEATURE                 Location/Qualifiers
source                  1..17
                        mol_type = genomic DNA
                        organism = Torque teno virus
SEQUENCE: 136
cgcgcgctgc gcgcgcg                                                   17

SEQ ID NO: 137          moltype = DNA  length = 19
FEATURE                 Location/Qualifiers
source                  1..19
                        mol_type = genomic DNA
                        organism = Torque teno virus
SEQUENCE: 137
cgccgggggg gcgccagcg                                                 19

SEQ ID NO: 138          moltype = DNA  length = 17
FEATURE                 Location/Qualifiers
source                  1..17
                        mol_type = genomic DNA
                        organism = Torque teno virus
SEQUENCE: 138
cccccccccc cgcgcat                                                   17

SEQ ID NO: 139          moltype = DNA  length = 31
FEATURE                 Location/Qualifiers
source                  1..31
                        mol_type = genomic DNA
```

```
                        organism = Torque teno virus
SEQUENCE: 139
gcacgggtcc ccccccccac gggggctcc g                                31

SEQ ID NO: 140          moltype = DNA  length = 17
FEATURE                 Location/Qualifiers
source                  1..17
                        mol_type = genomic DNA
                        organism = Torque teno virus
SEQUENCE: 140
ccccccggcc ccccccc                                               17

SEQ ID NO: 141          moltype = DNA  length = 121
FEATURE                 Location/Qualifiers
source                  1..121
                        mol_type = genomic DNA
                        organism = Torque teno virus
SEQUENCE: 141
ccgtcggcgg gggggccgcg cgctgcgcgc gcggccccccg ggggaggcac agcctccccc  60
ccccgcgcgc atgcgcgcgg gtcccccccc ctccgggggg ctccgccccc cggccccccc  120
c                                                                121

SEQ ID NO: 142          moltype = DNA  length = 37
FEATURE                 Location/Qualifiers
source                  1..37
                        mol_type = genomic DNA
                        organism = Torque teno virus
SEQUENCE: 142
ccgtcggcgg gggggccgcg cgctgcgcgc gcggccc                        37

SEQ ID NO: 143          moltype = DNA  length = 84
FEATURE                 Location/Qualifiers
source                  1..84
                        mol_type = genomic DNA
                        organism = Torque teno virus
SEQUENCE: 143
ccgggggagg cacagcctcc ccccccccgcg cgcatgcgcg cgggtccccc cccctccggg  60
gggctccgcc ccccggcccc cccc                                       84

SEQ ID NO: 144          moltype = DNA  length = 104
FEATURE                 Location/Qualifiers
source                  1..104
                        mol_type = genomic DNA
                        organism = Torque teno virus
SEQUENCE: 144
cggcggcggc gcgcgcgcta cgcgcgcgcg ccgggggggct gccgcccccc ccccgcgcat  60
gcgcggggcc cccccccgcg gggggctccg ccccccggcc cccc                 104

SEQ ID NO: 145          moltype = DNA  length = 11
FEATURE                 Location/Qualifiers
source                  1..11
                        mol_type = genomic DNA
                        organism = Torque teno virus
SEQUENCE: 145
cggcggcggc g                                                     11

SEQ ID NO: 146          moltype = DNA  length = 17
FEATURE                 Location/Qualifiers
source                  1..17
                        mol_type = genomic DNA
                        organism = Torque teno virus
SEQUENCE: 146
cgcgcgctac gcgcgcg                                               17

SEQ ID NO: 147          moltype = DNA  length = 10
FEATURE                 Location/Qualifiers
source                  1..10
                        mol_type = genomic DNA
                        organism = Torque teno virus
SEQUENCE: 147
cgccgggggg                                                       10

SEQ ID NO: 148          moltype =   length =
SEQUENCE: 148
000

SEQ ID NO: 149          moltype = DNA  length = 15
FEATURE                 Location/Qualifiers
source                  1..15
```

```
                        mol_type = genomic DNA
                        organism = Torque teno virus
SEQUENCE: 149
cccccccccg cgcat                                               15

SEQ ID NO: 150          moltype = DNA  length = 17
FEATURE                 Location/Qualifiers
source                  1..17
                        mol_type = genomic DNA
                        organism = Torque teno virus
SEQUENCE: 150
gcgcggggcc ccccccc                                             17

SEQ ID NO: 151          moltype = DNA  length = 13
FEATURE                 Location/Qualifiers
source                  1..13
                        mol_type = genomic DNA
                        organism = Torque teno virus
SEQUENCE: 151
gcggggggct ccg                                                 13

SEQ ID NO: 152          moltype = DNA  length = 14
FEATURE                 Location/Qualifiers
source                  1..14
                        mol_type = genomic DNA
                        organism = Torque teno virus
SEQUENCE: 152
ccccccggcc cccc                                                14

SEQ ID NO: 153          moltype = DNA  length = 122
FEATURE                 Location/Qualifiers
source                  1..122
                        mol_type = genomic DNA
                        organism = Torque teno virus
SEQUENCE: 153
gccgccgcgg cggcgggggg cggcgcgctg cgcgcgccgc ccagtagggg gagccatgcg  60
cccccccccg cgcatgcgcg gggccccccc ccgcgggggg ctccgccccc cggccccccc  120
cg                                                             122

SEQ ID NO: 154          moltype = DNA  length = 19
FEATURE                 Location/Qualifiers
source                  1..19
                        mol_type = genomic DNA
                        organism = Torque teno virus
SEQUENCE: 154
gccgccgcgg cggcggggg                                           19

SEQ ID NO: 155          moltype = DNA  length = 41
FEATURE                 Location/Qualifiers
source                  1..41
                        mol_type = genomic DNA
                        organism = Torque teno virus
SEQUENCE: 155
gcggcgcgct gcgcgcgccg cccagtaggg ggagccatgc g                  41

SEQ ID NO: 156          moltype = DNA  length = 15
FEATURE                 Location/Qualifiers
source                  1..15
                        mol_type = genomic DNA
                        organism = Torque teno virus
SEQUENCE: 156
cccccccccg cgcat                                               15

SEQ ID NO: 157          moltype = DNA  length = 17
FEATURE                 Location/Qualifiers
source                  1..17
                        mol_type = genomic DNA
                        organism = Torque teno virus
SEQUENCE: 157
gcgcggggcc ccccccc                                             17

SEQ ID NO: 158          moltype = DNA  length = 13
FEATURE                 Location/Qualifiers
source                  1..13
                        mol_type = genomic DNA
                        organism = Torque teno virus
SEQUENCE: 158
gcggggggct ccg                                                 13
```

```
SEQ ID NO: 159          moltype = DNA  length = 17
FEATURE                 Location/Qualifiers
source                  1..17
                        mol_type = genomic DNA
                        organism = Torque teno virus
SEQUENCE: 159
ccccccggcc cccccg                                                   17

SEQ ID NO: 160          moltype = DNA  length = 36
FEATURE                 Location/Qualifiers
source                  1..36
                        mol_type = genomic DNA
                        organism = Torque teno virus
SEQUENCE: 160
cgcgctgcgc gcgccgccca gtagggggag ccatgc                             36

SEQ ID NO: 161          moltype = DNA  length = 78
FEATURE                 Location/Qualifiers
source                  1..78
                        mol_type = genomic DNA
                        organism = Torque teno virus
SEQUENCE: 161
ccgccatctt aagtagttga ggcggacggt ggcgtgagtt caaaggtcac catcagccac  60
acctactcaa aatggtgg                                                 78

SEQ ID NO: 162          moltype = DNA  length = 172
FEATURE                 Location/Qualifiers
source                  1..172
                        mol_type = genomic DNA
                        organism = Torque teno virus
SEQUENCE: 162
cttaagtagt tgaggcggac ggtggcgtga gttcaaaggt caccatcagc cacacctact  60
caaaatggtg gacaatttct tccgggtcaa aggttacagc cgccatgtta aaacacgtga  120
cgtatgacgt cacggccgcc attttgtgac acaagatggc cgacttcctt cc          172

SEQ ID NO: 163          moltype = DNA  length = 36
FEATURE                 Location/Qualifiers
source                  1..36
                        mol_type = other DNA
                        organism = synthetic construct
SEQUENCE: 163
cgcgctgcgc gcgccgccca gtagggggag ccatgc                             36

SEQ ID NO: 164          moltype = DNA  length = 36
FEATURE                 Location/Qualifiers
source                  1..36
                        mol_type = other DNA
                        organism = synthetic construct
SEQUENCE: 164
gcgctdcgcg cgcgcgccgg ggggctgcgc cccccc                             36

SEQ ID NO: 165          moltype = DNA  length = 36
FEATURE                 Location/Qualifiers
source                  1..36
                        mol_type = genomic DNA
                        organism = Torque teno virus
SEQUENCE: 165
gcgcttcgcg cgccgcccac tagggggcgt tgcgcg                             36

SEQ ID NO: 166          moltype = DNA  length = 36
FEATURE                 Location/Qualifiers
source                  1..36
                        mol_type = genomic DNA
                        organism = Torque teno virus
SEQUENCE: 166
gcgctgcgcg cgccgcccag tagggggcgc aatgcg                             36

SEQ ID NO: 167          moltype = DNA  length = 36
FEATURE                 Location/Qualifiers
source                  1..36
                        mol_type = genomic DNA
                        organism = Torque teno virus
SEQUENCE: 167
gcgctgcgcg cgcggccccc gggggaggca ttgcct                             36

SEQ ID NO: 168          moltype = DNA  length = 36
FEATURE                 Location/Qualifiers
source                  1..36
                        mol_type = genomic DNA
```

```
                         organism = Torque teno virus
SEQUENCE: 168
gcgctgcgcg cgcgcgccgg gggggcgcca gcgccc                          36

SEQ ID NO: 169           moltype = DNA  length = 36
FEATURE                  Location/Qualifiers
source                   1..36
                         mol_type = genomic DNA
                         organism = Torque teno virus
SEQUENCE: 169
gcgcttcgcg cgcgcgccgg ggggctccgc cccccc                          36

SEQ ID NO: 170           moltype = DNA  length = 36
FEATURE                  Location/Qualifiers
source                   1..36
                         mol_type = genomic DNA
                         organism = Torque teno virus
SEQUENCE: 170
gcgcttcgcg cgcgcgccgg ggggctgcgc cccccc                          36

SEQ ID NO: 171           moltype = DNA  length = 36
FEATURE                  Location/Qualifiers
source                   1..36
                         mol_type = genomic DNA
                         organism = Torque teno virus
SEQUENCE: 171
gcgctacgcg cgcgcgccgg ggggctgcgc cccccc                          36

SEQ ID NO: 172           moltype = DNA  length = 36
FEATURE                  Location/Qualifiers
source                   1..36
                         mol_type = genomic DNA
                         organism = Torque teno virus
SEQUENCE: 172
gcgctacgcg cgcgcgccgg ggggctctgc cccccc                          36

SEQ ID NO: 173           moltype = AA  length = 680
FEATURE                  Location/Qualifiers
source                   1..680
                         mol_type = protein
                         organism = Alphatorquevirus sp.
SEQUENCE: 173
TAWWWGRWRR RWRRRRPWRP RLRRRRARRA FPRRRRRRFV SRRWRRPYRR RRRRGRRRRR  60
RRRRHKPTLV LRQWQPDVIR HCKITGRMPL IICGKGSTQF NYITHADDIT PRGASYGGNF  120
TNMTFSLEAI YEQFLYHRNR WSASNHDLEL CRYKGTTLKL YRHPDVDYIV TYSRTGPFEI  180
SHMTYLSTHP LLMLLNKHHI VVPSLKTKPR GRKAIKVRIR PPKLMNNKWY FTRDFCNIGL  240
FQLWATGLEL RNPWLRMSTL SPCIGFNVLK NSIYTNLSNL PQHREDRLNI INNTLHPHDI  300
TGPNNKKWQY TYTKLMAPIY YSANRASTYD LLREYGLYSP YYLNPTRINL DWMTPYTHVR  360
YNPLVDKGFG NRIYIQWCSE ADVSYNRTKS KCLLQDMPLF FMCYGYIDWA IKNTGVSSLA  420
RDARICIRCP YTEPQLVGST EDIGFVPITE TFMRGDMPVL APYIPLSWFC KWYPNIAHQK  480
EVLEAIISCS PFMPRDQGMN GWDITIGYKM DFLWGGSPLP SQPIDDPCQQ GTHPIPDPDK  540
HPRLLQVSNP KLLGPRTVFH KWDIRRGQFS KRSIKRVSEY SSDDESLAPG LPSKRNKLDS  600
AFRGENPEQK ECYSLLKALE EEETPEEEEP APQEKAQKEE LLHQLQLQRR HQRVLRRGLK  660
LVFTDILRLR QGVHWNPELT                                              680

SEQ ID NO: 174           moltype = AA  length = 66
FEATURE                  Location/Qualifiers
source                   1..66
                         mol_type = protein
                         organism = Alphatorquevirus sp.
SEQUENCE: 174
TAWWWGRWRR RWRRRRPWRP RLRRRRARRA FPRRRRRRFV SRRWRRPYRR RRRRGRRRRR  60
RRRRHK                                                            66

SEQ ID NO: 175           moltype = AA  length = 211
FEATURE                  Location/Qualifiers
source                   1..211
                         mol_type = protein
                         organism = Alphatorquevirus sp.
SEQUENCE: 175
PTLVLRQWQP DVIRHCKITG RMPLIICGKG STQFNYITHA DDITPRGASY GGNFTNMTFS  60
LEAIYEQFLY HRNRWSASNH DLELCRYKGT TLKLYRHPDV DYIVTYSRTG PFEISHMTYL  120
STHPLLMLLN KHHIVVPSLK TKPRGRKAIK VRIRPPKLMN NKWYFTRDFC NIGLFQLWAT  180
GLELRNPWLR MSTLSPCIGF NVLKNSIYTN L                                 211

SEQ ID NO: 176           moltype = AA  length = 70
FEATURE                  Location/Qualifiers
source                   1..70
                         mol_type = protein
```

```
                          organism = Alphatorquevirus sp.
SEQUENCE: 176
SNLPQHREDR LNIINNTLHP HDITGPNNKK WQYTYTKLMA PIYYSANRAS TYDLLREYGL  60
YSPYYLNPTR                                                        70

SEQ ID NO: 177            moltype = AA  length = 166
FEATURE                   Location/Qualifiers
source                    1..166
                          mol_type = protein
                          organism = Alphatorquevirus sp.
SEQUENCE: 177
INLDWMTPYT HVRYNPLVDK GFGNRIYIQW CSEADVSYNR TKSKCLLQDM PLFFMCYGYI  60
DWAIKNTGVS SLARDARICI RCPYTEPQLV GSTEDIGFVP ITETFMRGDM PVLAPYIPLS  120
WFCKWYPNIA HQKEVLEAII SCSPFMPRDQ GMNGWDITIG YKMDFL                166

SEQ ID NO: 178            moltype = AA  length = 167
FEATURE                   Location/Qualifiers
source                    1..167
                          mol_type = protein
                          organism = Alphatorquevirus sp.
SEQUENCE: 178
WGGSPLPSQP IDDPCQQGTH PIPDPDKHPR LLQVSNPKLL GPRTVFHKWD IRRGQFSKRS  60
IKRVSEYSSD DESLAPGLPS KRNKLDSAFR GENPEQKECY SLLKALEEEE TPEEEEPAPQ  120
EKAQKEELLH QLQLQRRHQR VLRRGLKLVF TDILRLRQGV HWNPELT               167

SEQ ID NO: 179            moltype = AA  length = 747
FEATURE                   Location/Qualifiers
source                    1..747
                          mol_type = protein
                          organism = Alphatorquevirus sp.
SEQUENCE: 179
MAYWWGRRRR WRRWRRRRRP LRRRRRWRRR RRWPRRRRWR RRRRRARPAR RYRRRRGRRR  60
VRRRRRPQKL VLTQWNPQTV RKCVIRGFLP LFFCGQGAYH RNFTDHYDDV FPKGPSGGGH  120
GSMVFNLSFL YQEFKKHHNK WSRSNLDFDL VRYKGTVIKL YRHQDFDYIV WISRTPPFQE  180
SLLTVMTHQP SVMLQAKKCI IVKSYRTHPG GKPYVVTAKVR PPRLLTDKWY FQSDFCNVPL  240
FSLQFALAEL RFPICSPQTD TNCINFLVLD DIYYKFLDNK PKQSSDPNDE NRIKFWHGLW  300
STMRYLNTTY INTLFPGTDS LVAAKDTDNS VNKYPSTATK QPYKDSQYMQ NIWNTSKIHA  360
LYTWVAETNY KRLQAYYTQT YGGYQRQFFT GKQYWDYRVG MFSPAFLSPS RLNPQNPGAY  420
TEVSYNPWTD EGTGNVVCLQ YLTKETSDYK PGGGSKFCIE GVPLWAALVG YVDMCKKEGK  480
DPGIRLNCLL LVKCPYTKPQ LYDKKNPEKL FVPYSYNFGH GKMPGGDKYI PIEFKDRWYP  540
CLLHQEEWIE DIVRSGPFVP KDMPSSVTCM MRYSSLFNWG GNIIQEQAVE DPCKKGTFVV  600
PGTSGIARIL QVSNPAKQTP TTTWHSWDWR RSLFTETGLK RMREQQPYDE LSYTGPKKPK  660
LSLPAGPAVP GAAVASSWWE TKQVTSPDVS ETETEAEAHQ EEETEPEEGV QLQQLWEQQL  720
LQKRQLGVVF QQLLRLRQGA EIHPGLV                                     747

SEQ ID NO: 180            moltype = AA  length = 69
FEATURE                   Location/Qualifiers
source                    1..69
                          mol_type = protein
                          organism = Alphatorquevirus sp.
SEQUENCE: 180
MAYWWGRRRR WRRWRRRRRP LRRRRRWRRR RRWPRRRRWR RRRRRARPAR RYRRRRGRRR  60
VRRRRRPQK                                                         69

SEQ ID NO: 181            moltype = AA  length = 210
FEATURE                   Location/Qualifiers
source                    1..210
                          mol_type = protein
                          organism = Alphatorquevirus sp.
SEQUENCE: 181
LVLTQWNPQT VRKCVIRGFL PLFFCGQGAY HRNFTDHYDD VFPKGPSGGG HGSMVFNLSF  60
LYQEFKKHHN KWSRSNLDFD LVRYKGTVIK LYRHQDFDYI VWISRTPPFQ ESLLTVMTHQ  120
PSVMLQAKKC IIVKSYRTHP GGKPYVTAKV RPPRLLTDKW YFQSDFCNVP LFSLQFALAE  180
LRFPICSPQT DTNCINFLVL DDIYYKFLDN                                  210

SEQ ID NO: 182            moltype = AA  length = 132
FEATURE                   Location/Qualifiers
source                    1..132
                          mol_type = protein
                          organism = Alphatorquevirus sp.
SEQUENCE: 182
KPKQSSDPND ENRIKFWHGL WSTMRYLNTT YINTLFPGTD SLVAAKDTDN SVNKYPSTAT  60
KQPYKDSQYM QNIWNTSKIH ALYTWVAETN YKRLQAYYTQ TYGGYQRQFF TGKQYWDYRV  120
GMFSPAFLSP SR                                                     132

SEQ ID NO: 183            moltype = AA  length = 167
FEATURE                   Location/Qualifiers
source                    1..167
                          mol_type = protein
```

```
                         organism = Alphatorquevirus sp.
SEQUENCE: 183
LNPQNPGAYT EVSYNPWTDE GTGNVVCLQY LTKETSDYKP GGGSKFCIEG VPLWAALVGY  60
VDMCKKEGKD PGIRLNCLLL VKCPYTKPQL YDKKNPEKLF VPYSYNFGHG KMPGGDKYIP  120
IEFKDRWYPC LLHQEEWIED IVRSGPFVPK DMPSSVTCMM RYSSLFN                167

SEQ ID NO: 184           moltype = AA  length = 169
FEATURE                  Location/Qualifiers
source                   1..169
                         mol_type = protein
                         organism = Alphatorquevirus sp.
SEQUENCE: 184
WGGNIIQEQA VEDPCKKGTF VVPGTSGIAR ILQVSNPAKQ TPTTTWHSWD WRRSLFTETG  60
LKRMREQQPY DELSYTGPKK PKLSLPAGPA VPGAAVASSW WETKQVTSPD VSETETEAEA  120
HQEEETEPEE GVQLQQLWEQ QLLQKRQLGV VFQQLLRLRQ GAEIHPGLV              169

SEQ ID NO: 185           moltype = AA  length = 743
FEATURE                  Location/Qualifiers
source                   1..743
                         mol_type = protein
                         organism = Alphatorquevirus sp.
SEQUENCE: 185
MAWGWWKRRR RWWFRKRWTR GRLRRRWPRS ARRRPRRRRV RRRRRWRRGR RKTRTYRRRR  60
RFRRRGRKAK LIIKLWQPAV IKRCRIKGYI PLIISGNGTF ATNFTSHIND RIMKGPFGGG  120
HSTMRFSLYI LFEEHLRHMN FWTRSNDNLE LTRYLGASVK IYRHPDQDFI VIYNRRTPLG  180
GNIYTAPSLH PGNAILAKHK ILVPSLQTRP KGRKAIRLRI APPTLFTDKW YFQKDIADLT  240
LFNIMAVEAD LRFPFCSPQT DNTCISFQVL SSVYNNYLSI NTFNNDNSDS KLKEFLNKAF  300
PTTGTKGTSL NALNTFRTEG CISHPQLKKP NPQINKPLES QYFAPLDALW GDPIYYNDLN  360
ENKSLNDIIE KILIKNMITY HAKLREFPNS YQGNKAFCHL TGIYSPPYLN QGRISPEIFG  420
LYTEIIYNPY TDKGTGNKVW MDPLTKENNI YKEGQSKCLL TDMPLWTLLF GYTDWCKKDT  480
NNWDLPLNYR LVLICPYTFP KLYNEKVKDY GYIPYSYKFG AGQMPDGSNY IPFQFRAKWY  540
PTVLHQQQVM EDISRSGPFA PKVEKPSTQL VMKYCFNFNW GGNPIIEQIV KDPSFQPTYE  600
IPGTGNIPRR IQVIDPRVLG PHYSFRSWDM RRHTFSRASI KRVSEQQETS DLVFSGPKKP  660
RVDIPKQETQ EESSHSLQRE SRPWETEEES ETEALSQESQ EVPFQQQLQQ QYQEQLKLRQ  720
GIKVLFEQLI RTQQGVHVNP CLR                                          743

SEQ ID NO: 186           moltype = AA  length = 68
FEATURE                  Location/Qualifiers
source                   1..68
                         mol_type = protein
                         organism = Alphatorquevirus sp.
SEQUENCE: 186
MAWGWWKRRR RWWFRKRWTR GRLRRRWPRS ARRRPRRRRV RRRRRWRRGR RKTRTYRRRR  60
RFRRRGRK                                                          68

SEQ ID NO: 187           moltype = AA  length = 212
FEATURE                  Location/Qualifiers
source                   1..212
                         mol_type = protein
                         organism = Alphatorquevirus sp.
SEQUENCE: 187
AKLIIKLWQP AVIKRCRIKG YIPLIISGNG TFATNFTSHI NDRIMKGPFG GGHSTMRFSL  60
YILFEEHLRH MNFWTRSNDN LELTRYLGAS VKIYRHPDQD FIVIYNRRTP LGGNIYTAPS  120
LHPGNAILAK HKILVPSLQT RPKGRKAIRL RIAPPTLFTD KWYFQKDIAD LTLFNIMAVE  180
ADLRFPFCSP QTDNTCISFQ VLSSVYNNYL SI                                212

SEQ ID NO: 188           moltype = AA  length = 133
FEATURE                  Location/Qualifiers
source                   1..133
                         mol_type = protein
                         organism = Alphatorquevirus sp.
SEQUENCE: 188
NTFNNDNSDS KLKEFLNKAF PTTGTKGTSL NALNTFRTEG CISHPQLKKP NPQINKPLES  60
QYFAPLDALW GDPIYYNDLN ENKSLNDIIE KILIKNMITY HAKLREFPNS YQGNKAFCHL  120
TGIYSPPYLN QGR                                                     133

SEQ ID NO: 189           moltype = AA  length = 166
FEATURE                  Location/Qualifiers
source                   1..166
                         mol_type = protein
                         organism = Alphatorquevirus sp.
SEQUENCE: 189
ISPEIFGLYT EIIYNPYTDK GTGNKVWMDP LTKENNIYKE GQSKCLLTDM PLWTLLFGYT  60
DWCKKDTNNW DLPLNYRLVL ICPYTFPKLY NEKVKDYGYI PYSYKFGAGQ MPDGSNYIPF  120
QFRAKWYPTV LHQQQVMEDI SRSGPFAPKV EKPSTQLVMK YCFNFN                 166

SEQ ID NO: 190           moltype = AA  length = 164
FEATURE                  Location/Qualifiers
source                   1..164
```

```
                         mol_type = protein
                         organism = Alphatorquevirus sp.
SEQUENCE: 190
WGGNPIIEQI VKDPSFQPTY EIPGTGNIPR RIQVIDPRVL GPHYSFRSWD MRRHTFSRAS  60
IKRVSEQQET SDLVFSGPKK PRVDIPKQET QEESSHSLQR ESRPWETEEE SETEALSQES  120
QEVPFQQQLQ QQYQEQLKLR QGIKVLFEQL IRTQQGVHVN PCLR                  164

SEQ ID NO: 191           moltype = AA  length = 780
FEATURE                  Location/Qualifiers
source                   1..780
                         mol_type = protein
                         organism = Alphatorquevirus sp.
SEQUENCE: 191
MAWWGWRRRW WRPKRRWRWR RARRRRRVPA RRPRRAFRRY RTRTVRRRRR GRRRGYRRRY  60
RLRRYARRRF RRKKIVLTQW NPQTTRKCII RGMMPVLWAG MGTGGRNYAV RSDDYVVNKG  120
FGGSFATETF SLKVLYDQFQ RGFNRWSHTN EDLDLARYRG CRWTFYRHKD TDFIVYFTNN  180
PPMKTNQFSA PLTTPGMLMR SKYKVLIPSF QTRPKGRKTV TVKIRPPKLF QDKWYTQQDL  240
CSVPLVQLNV TAADFTHPFG SPLTETPCVE FQVLGDLYNT CLNIDLPQFS ELGEITSAYS  300
KPNSNNLKEL YKELFTKATS GHYWQTFITN SMVRAHIDAD KAKEAQRAST TPSYNNDPFP  360
TIPVKSEFAQ WKKKFTDTRD SPFLFATYHP EAIKDTIMKM RENNFKLETG PNDKYGDYTA  420
QYQGNTHMLD YYLGFYSPIF LSDGRSNVEF FTAYRDIVYN PFLDKAQGNM VWFQYHTKTD  480
NKFKKPECHW EIKDMPLWAL LNGYVDYLET QIQYGDLSKE GKVLIRCPYT KPALVDPRDD  540
TAGYVVYNRN FGRGKWIDGG GYIPLHERTK WYVMLRYQTD VFHDIVTCGP WQYRDDNKNS  600
QLVAKYRFSF IWGGNTVHSQ VIRNPCKDNQ VSGPRRQPRD IQVVDPQRIT PPWVLHSFDQ  660
RRGLFTETAL RRLLQEPLPG EYAVSTLRTP LLFLPSEYQR EDGAAESASG SPAKRPRIWS  720
EESQTETISS EENPAETTRE LLQRKLREQR ALQFQLQHFA VQLAKTQANL HVNPLLSFPQ  780

SEQ ID NO: 192           moltype = AA  length = 74
FEATURE                  Location/Qualifiers
source                   1..74
                         mol_type = protein
                         organism = Alphatorquevirus sp.
SEQUENCE: 192
MAWWGWRRRW WRPKRRWRWR RARRRRRVPA RRPRRAFRRY RTRTVRRRRR GRRRGYRRRY  60
RLRRYARRRF RRKK                                                   74

SEQ ID NO: 193           moltype = AA  length = 210
FEATURE                  Location/Qualifiers
source                   1..210
                         mol_type = protein
                         organism = Alphatorquevirus sp.
SEQUENCE: 193
IVLTQWNPQT TRKCIIRGMM PVLWAGMGTG GRNYAVRSDD YVVNKGFGGS FATETFSLKV  60
LYDQFQRGFN RWSHTNEDLD LARYRGCRWT FYRHKDTDFI VYFTNNPPMK TNQFSAPLTT  120
PGMLMRSKYK VLIPSFQTRP KGRKTVTVKI RPPKLFQDKW YTQQDLCSVP LVQLNVTAAD  180
FTHPFGSPLT ETPCVEFQVL GDLYNTCLNI                                  210

SEQ ID NO: 194           moltype = AA  length = 161
FEATURE                  Location/Qualifiers
source                   1..161
                         mol_type = protein
                         organism = Alphatorquevirus sp.
SEQUENCE: 194
DLPQFSELGE ITSAYSKPNS NNLKELYKEL FTKATSGHYW QTFITNSMVR AHIDADKAKE  60
AQRASTTPSY NNDPFPTIPV KSEFAQWKKK FTDTRDSPFL FATYHPEAIK DTIMKMRENN  120
FKLETGPNDK YGDYTAQYQG NTHMLDYYLG FYSPIFLSDG R                     161

SEQ ID NO: 195           moltype = AA  length = 166
FEATURE                  Location/Qualifiers
source                   1..166
                         mol_type = protein
                         organism = Alphatorquevirus sp.
SEQUENCE: 195
SNVEFFTAYR DIVYNPFLDK AQGNMVWFQY HTKTDNKFKK PECHWEIKDM PLWALLNGYV  60
DYLETQIQYG DLSKEGKVLI RCPYTKPALV DPRDDTAGYV VYNRNFGRGK WIDGGGYIPL  120
HERTKWYVML RYQTDVFHDI VTCGPWQYRD DNKNSQLVAK YRFSFI                166

SEQ ID NO: 196           moltype = AA  length = 169
FEATURE                  Location/Qualifiers
source                   1..169
                         mol_type = protein
                         organism = Alphatorquevirus sp.
SEQUENCE: 196
WGGNTVHSQV IRNPCKDNQV SGPRRQPRDI QVVDPQRITP PWVLHSFDQR RGLFTETALR  60
RLLQEPLPGE YAVSTLRTPL LFLPSEYQRE DGAAESASGS PAKRPRIWSE ESQTETISSE  120
ENPAETTREL LQRKLREQRA LQFQLQHFAV QLAKTQANLH VNPLLSFPQ              169

SEQ ID NO: 197           moltype = AA  length = 761
FEATURE                  Location/Qualifiers
```

```
source                  1..761
                        mol_type = protein
                        organism = Alphatorquevirus sp.
SEQUENCE: 197
MAYWFRRWGW RPRRRWRRWR RRRRRLPRRR TRRAVRGLGR RRKPRVRRRR RTRRRTYRRG  60
WRRRRYIRRG RRKKKLILTQ WNPAIVKRCN IKGGLPIIIC GEPRAAFNYG YHMEDYTPQP  120
FPFGGGMSTV TFSLKALYDQ YLKHQNRWTF SNDQLDLARY RGCKLRFYRS PVCDFIVHYN  180
LIPPLKMNQF TSPNTHPGLL MLSKHKIIIP SFQTRPGGRR FVKIRLNPPK LFEDKWYTQQ  240
DLCKVPLVSI TATAADLRYP FCSPQTNNPC TTFQVLRKNY NTVIGTSVKD QESTQDFENW  300
LYKTDSHYQT FATEAQLGRI PAFNPDGTKN TKQQSWQDNW SKKNSPWTGN SGTYPQTTSE  360
MYKIPYDSNF GFPTYRAQKD YILERRQCNF NYEVNNPVSK KVWPQPSTTT PTVDYYEYHC  420
GWFSNIFIGP NRYNLQFQTA YVDTTYNPLM DKGKGNKIWF QYLSKKGTDY NEKQCYCTLE  480
DMPLWAICFG YTDYVETQLG PNVDHETAGL IIMICPYTQP PMYDKNRPNW GYVVYDTNFG  540
NGKMPSGSGQ VPVYWQCRWR PMLWFQQQVL NDISKTGPYA YRDEYKNVQL TLYYNFIFNW  600
GGDMYYPQVV KNPCGDSGIV PGSGRFTREV QVVSPLSMGP AYIFHYFDSR RGFFSEKALK  660
RMQQQQEFDE SFTFKPKRPK LSTAAAEILQ LEEDSTSGEG KSPLQQEEKE VEVLQTPTVQ  720
LQLQRNIQEQ LAIKQQLQFL LLQLLKTQSN LHLNPQFLSP S                     761

SEQ ID NO: 198          moltype = AA  length = 75
FEATURE                 Location/Qualifiers
source                  1..75
                        mol_type = protein
                        organism = Alphatorquevirus sp.
SEQUENCE: 198
MAYWFRRWGW RPRRRWRRWR RRRRRLPRRR TRRAVRGLGR RRKPRVRRRR RTRRRTYRRG  60
WRRRRYIRRG RRKKK                                                  75

SEQ ID NO: 199          moltype = AA  length = 209
FEATURE                 Location/Qualifiers
source                  1..209
                        mol_type = protein
                        organism = Alphatorquevirus sp.
SEQUENCE: 199
LILTQWNPAI VKRCNIKGGL PIIICGEPRA AFNYGYHMED YTPQPFPFGG GMSTVTFSLK  60
ALYDQYLKHQ NRWTFSNDQL DLARYRGCKL RFYRSPVCDF IVHYNLIPPL KMNQFTSPNT  120
HPGLLMLSKH KIIIPSFQTR PGGRRFVKIR LNPPKLFEDK WYTQQDLCKV PLVSITATAA  180
DLRYPFCSPQ TNNPCTTFQV LRKNYNTVI                                   209

SEQ ID NO: 200          moltype = AA  length = 148
FEATURE                 Location/Qualifiers
source                  1..148
                        mol_type = protein
                        organism = Alphatorquevirus sp.
SEQUENCE: 200
GTSVKDQEST QDFENWLYKT DSHYQTFATE AQLGRIPAFN PDGTKNTKQQ SWQDNWSKKN  60
SPWTGNSGTY PQTTSEMYKI PYDSNFGFPT YRAQKDYILE RRQCNFNYEV NNPVSKKVWP  120
QPSTTTPTVD YYEYHCGWFS NIFIGPNR                                    148

SEQ ID NO: 201          moltype = AA  length = 167
FEATURE                 Location/Qualifiers
source                  1..167
                        mol_type = protein
                        organism = Alphatorquevirus sp.
SEQUENCE: 201
YNLQFQTAYV DTTYNPLMDK GKGNKIWFQY LSKKGTDYNE KQCYCTLEDM PLWAICFGYT  60
DYVETQLGPN VDHETAGLII MICPYTQPPM YDKNRPNWGY VVYDTNFGNG KMPSGSGQVP  120
VYWQCRWRPM LWFQQQVLND ISKTGPYAYR DEYKNVQLTL YYNFIFN               167

SEQ ID NO: 202          moltype = AA  length = 162
FEATURE                 Location/Qualifiers
source                  1..162
                        mol_type = protein
                        organism = Alphatorquevirus sp.
SEQUENCE: 202
WGGDMYYPQV VKNPCGDSGI VPGSGRFTRE VQVVSPLSMG PAYIFHYFDS RRGFFSEKAL  60
KRMQQQQEFD ESFTFKPKRP KLSTAAAEIL QLEEDSTSGE GKSPLQQEEK EVEVLQTPTV  120
QLQLQRNIQE QLAIKQQLQF LLLQLLKTQS NLHLNPQFLS PS                    162

SEQ ID NO: 203          moltype = AA  length = 746
FEATURE                 Location/Qualifiers
source                  1..746
                        mol_type = protein
                        organism = Alphatorquevirus sp.
SEQUENCE: 203
MAWGWWRWRR RWPARRWRRR RRRRPVRRTR ARRPARRYRR RRTVRTRRRR WGRRRYRRGW  60
RRRTYVRKGR HRKKKKRLIL RQWQPATRRR CTITGYLPIV FCGHTRGNKN YALHSDDYTP  120
QGQPFGGALS TTSFSLKVLF DQHQRGLNKW SFPNDQLDLA RYRGCKFIFY RTKQTDWVGQ  180
YDISEPYKLD KYSCPNYHPG NMIKAKHKFL IPSYDTNPRG RQKIIVKIPP PDLFVDKWYT  240
QEDLCSVNLV SLAVSAASFL HPFGSPQTDN PCYTFQVLKE FYYQAIGFSA STQAMTSVLD  300
```

```
TLYTQNSYWE SNLTQFYVLN AKKGSDTTQP LTSNMPTREE FMAKKNTNYN WYTYKAASVK  360
NKLHQMRQTY FEELTSKGPQ TTKSEEGYSQ HWTTPSTNAY EYHLGMFSAI FLAPDRPVPR  420
FPCAYQDVTY NPLMDKGVGN HIWFQYNTKA DTQLIVTGGS CKAHIQDIPL WAAFYGYSDF  480
IESELGPFVD AETVGLVCVI CPYTKPPMYN KTNPAMGYVF YDRNFGDGKW TDGRGKIEPY  540
WQVRWRPEML FQETVMADLV QTGPFSYKDE LKNSTLVCKY KFYFTWGGNM MFQQTIKNPC  600
KTDGQPTDSS RHPRGIQVAD PEQMGPRWVF HSFDWRRGYL SEKALKRLQE KPLDYDEYFT  660
QPKRPRIFPP TESAEGEFRE PEKGSYSEEE RSQASAEEQT QEATVLLLKR RLREQQQLQQ  720
QLQFLTREMF KTQAGLHLNP MLLNQR                                      746

SEQ ID NO: 204         moltype = AA  length = 77
FEATURE                Location/Qualifiers
source                 1..77
                       mol_type = protein
                       organism = Alphatorquevirus sp.
SEQUENCE: 204
MAWGWWRWRR RWPARRWRRR RRRRPVRRTR ARRPARRYRR RRTVRTRRRR WGRRRYRRGW  60
RRRTYVRKGR HRKKKKR                                                 77

SEQ ID NO: 205         moltype = AA  length = 209
FEATURE                Location/Qualifiers
source                 1..209
                       mol_type = protein
                       organism = Alphatorquevirus sp.
SEQUENCE: 205
LILRQWQPAT RRRCTITGYL PIVFCGHTRG NKNYALHSDD YTPQGQPFGG ALSTTSFSLK  60
VLFDQHQRGL NKWSFPNDQL DLARYRGCKF IFYRTKQTDW VGQYDISEPY KLDKYSCPNY  120
HPGNMIKAKH KFLIPSYDTN PRGRQKIIVK IPPPDLFVDK WYTQEDLCSV NLVSLAVSAA  180
SFLHPFGSPQ TDNPCYTFQV LKEFYYQAI                                   209

SEQ ID NO: 206         moltype = AA  length = 130
FEATURE                Location/Qualifiers
source                 1..130
                       mol_type = protein
                       organism = Alphatorquevirus sp.
SEQUENCE: 206
GFSASTQAMT SVLDTLYTQN SYWESNLTQF YVLNAKKGSD TTQPLTSNMP TREEFMAKKN  60
TNYNWYTYKA ASVKNKLHQM RQTYFEELTS KGPQTTKSEE GYSQHWTTPS TNAYEYHLGM  120
FSAIFLAPDR                                                        130

SEQ ID NO: 207         moltype = AA  length = 169
FEATURE                Location/Qualifiers
source                 1..169
                       mol_type = protein
                       organism = Alphatorquevirus sp.
SEQUENCE: 207
PVPRFPCAYQ DVTYNPLMDK GVGNHIWFQY NTKADTQLIV TGGSCKAHIQ DIPLWAAFYG  60
YSDFIESELG PFVDAETVGL VCVICPYTKP PMYNKTNPAM GYVFYDRNFG DGKWTDGRGK  120
IEPYWQVRWR PEMLFQETVM ADLVQTGPFS YKDELKNSTL VCKYKFYFT              169

SEQ ID NO: 208         moltype = AA  length = 161
FEATURE                Location/Qualifiers
source                 1..161
                       mol_type = protein
                       organism = Alphatorquevirus sp.
SEQUENCE: 208
WGGNMMFQQT IKNPCKTDGQ PTDSSRHPRG IQVADPEQMG PRWVFHSFDW RRGYLSEKAL  60
KRLQEKPLDY DEYFTQPKRP RIFPPTESAE GEFREPEKGS YSEEERSQAS AEEQTQEATV  120
LLLKRRLREQ QQLQQQLQFL TREMFKTQAG LHLNPMLLNQ R                      161

SEQ ID NO: 209         moltype = AA  length = 765
FEATURE                Location/Qualifiers
source                 1..765
                       mol_type = protein
                       organism = Alphatorquevirus sp.
SEQUENCE: 209
MAWSWWWQRW RRRRWKPRRR RWRRLRWRRP RRAVRRRRRG RRVRRRRWAR RRGRRRRYAT  60
RRKRRYRGRR FKKKLVLTQW HPNTMRRCLI KGIVPLVICG HTRWNYNYAL HSKDYTEEGR  120
YPHGGALSTT TWSLKVLYDE HLKHHDFWGY PNNQLDLARY KGAKFTFYRH KKTDFIIFFN  180
RKPPFKLNKY SCASYHPGML MQQRHKILLP SYETKPKGRP KITVRIKPPT LLEDKWYTQQ  240
DLCDVNLLQL VVTAADFRHP LCSPQTNTPT TTFQVLKDIY YDTMSISEPT DSYTSVNNKS  300
TTQTFTNYSN TLENILYTRA SYWNSFHATE YLNPNIIYKN GEKLFKEHED LITWMTQTNN  360
TGFLTKNNTA FGNNSYRPNA DKIKKARKTY WNALIGTNDL ATNIGQARAE RFEYHLGWYS  420
PIFLSRHRSN MNFARAYQDV TYNPNCDRGV NNRVWVQPLT KPTTEFDEKR CKCVVQHLPL  480
WAALYCYQDF VEEELGSSSE ILNSCLLVLQ CPYTFPPMYD KKLPDKGFVF YDSLFGDGKM  540
SDGRGQVDIF WQQRWYPRLA TQMQVMHDIT MTGPFSYRDE LVSTQLTAKY TFDFMWGGNM  600
ISTQIIKNPC KDSGLEPAYP GRQRRDLQIV DPYSMGPQFS FHNWDYRHGL FGQDAIDRVS  660
KQPKDDADYP NPYKRPRYFP PTDQAAQEQE KDFSFLKTAP SNSEESDQEV LQETQVLRFQ  720
PEQHKQLHLQ LAERQRIGEQ LRYLLQQMFK TQANLHLNPY TFTQL                 765
```

```
SEQ ID NO: 210         moltype = AA  length = 74
FEATURE                Location/Qualifiers
source                 1..74
                       mol_type = protein
                       organism = Alphatorquevirus sp.
SEQUENCE: 210
MAWSWWWQRW RRRRWKPRRR RWRRLRWRRP RRAVRRRRRG RRVRRRRWAR RRGRRRRYAT  60
RRKRRYRGRR FKKK                                                    74

SEQ ID NO: 211         moltype = AA  length = 212
FEATURE                Location/Qualifiers
source                 1..212
                       mol_type = protein
                       organism = Alphatorquevirus sp.
SEQUENCE: 211
LVLTQWHPNT MRRCLIKGIV PLVICGHTRW NYNYALHSKD YTEEGRYPHG GALSTTTWSL  60
KVLYDEHLKH HDFWGYPNNQ LDLARYKGAK FTFYRHKKTD FIIFFNRKPP FKLNKYSCAS  120
YHPGMLMQQR HKILLPSYET KPKGRPKITV RIKPPTLLED KWYTQQDLCD VNLLQLVVTA  180
ADFRHPLCSP QTNTPTTTFQ VLKDIYYDTM SI                                212

SEQ ID NO: 212         moltype = AA  length = 142
FEATURE                Location/Qualifiers
source                 1..142
                       mol_type = protein
                       organism = Alphatorquevirus sp.
SEQUENCE: 212
SEPTDSYTSV NNKSTTQTFT NYSNTLENIL YTRASYWNSF HATEYLNPNI IYKNGEKLFK  60
EHEDLITWMT QTNNTGFLTK NNTAFGNNSY RPNADKIKKA RKTYWNALIG TNDLATNIGQ  120
ARAERFEYHL GWYSPIFLSR HR                                           142

SEQ ID NO: 213         moltype = AA  length = 167
FEATURE                Location/Qualifiers
source                 1..167
                       mol_type = protein
                       organism = Alphatorquevirus sp.
SEQUENCE: 213
SNMNFARAYQ DVTYNPNCDR GVNNRVWVQP LTKPTTEFDE KRCKCVVQHL PLWAALYCYQ  60
DFVEEELGSS SEILNSCLLV LQCPYTFPPM YDKKLPDKGF VFYDSLFGDG KMSDGRGQVD  120
IFWQQRWYPR LATQMQVMHD ITMTGPFSYR DELVSTQLTA KYTFDFM                167

SEQ ID NO: 214         moltype = AA  length = 170
FEATURE                Location/Qualifiers
source                 1..170
                       mol_type = protein
                       organism = Alphatorquevirus sp.
SEQUENCE: 214
WGGNMISTQI IKNPCKDSGL EPAYPGRQRR DLQIVDPYSM GPQFSFHNWD YRHGLFGQDA  60
IDRVSKQPKD DADYPNPYKR PRYFPPTDQA AQEQEKDFSF LKTAPSNSEE SDQEVLQETQ  120
VLRFQPEQHK QLHLQLAERQ RIGEQLRYLL QQMFKTQANL HLNPYTFTQL             170

SEQ ID NO: 215         moltype = AA  length = 666
FEATURE                Location/Qualifiers
source                 1..666
                       mol_type = protein
                       organism = Betatorquevirus sp.
SEQUENCE: 215
MPYYYRRRRY NYRRPRWYGR GWIRRPFRRR FRRKRRVRPT YTTIPLKQWQ PPYKRTCYIK  60
GQDCLIYYSN LRLGMNSTMY EKSIVPVHWP GGGSFSVSML TLDALYDIHK LCRNWWTSTN  120
QDLPLVRYKG CKITFYQSTF TDYIVRIHTE LPANSNKLTY PNTHPLMMMM SKYKHIIPSR  180
QTRRKKKPYT KIFVKPPPQF ENKWYFATDL YKIPLLQIHC TACNLQNPFV KPDKLSNNVT  240
LWSLNTISIQ NRNMSVDQGQ SWPFKILGTQ SFYFYFYTGA NLPGDTTQIP VADLLPLTNP  300
RINRPGQSLN EAKITDHITF TEYKNKFTNY WGNPFNKHIQ EHLDMILYSL KSPEAIKNEW  360
TTENMKWNQL NNAGTMALTP FNEPIFTQIQ YNPDRDTGED TQLYLLSNAT GTGWDPPGIP  420
ELILEGFPLW LIYWGFADFQ KNLKKVTNID TNYMLVAKTK FTQKPGTFYL VILNDTFVEG  480
NSPYEKQPLP EDNIKWYPQV QYQLEAQNKL LQTGPFTPNI QGQLSDNISM FYKFYFKWGG  540
SPPKAINVEN PAHQIQYPIP RNEHETTSLQ SPGEAPESIL YSFDYRHGNY TTTALSRISQ  600
DWALKDTVSK ITEPDRQQLL KQALECLQIS EETQEKKEKE VQQLISNLRQ QQQLYRERII  660
SLLKDQ                                                             666

SEQ ID NO: 216         moltype = AA  length = 38
FEATURE                Location/Qualifiers
source                 1..38
                       mol_type = protein
                       organism = Betatorquevirus sp.
SEQUENCE: 216
MPYYYRRRRY NYRRPRWYGR GWIRRPFRRR FRRKRRVR                          38

SEQ ID NO: 217         moltype = AA  length = 208
FEATURE                Location/Qualifiers
```

```
source                  1..208
                        mol_type = protein
                        organism = Betatorquevirus sp.
SEQUENCE: 217
PTYTTIPLKQ WQPPYKRTCY IKGQDCLIYY SNLRLGMNST MYEKSIVPVH WPGGGSFSVS  60
MLTLDALYDI HKLCRNWWTS TNQDLPLVRY KGCKITFYQS TFTDYIVRIH TELPANSNKL  120
TYPNTHPLMM MMSKYKHIIP SRQTRRKKKP YTKIFVKPPP QFENKWYFAT DLYKIPLLQI  180
HCTACNLQNP FVKPDKLSNN VTLWSLNT                                    208

SEQ ID NO: 218          moltype = AA  length = 128
FEATURE                 Location/Qualifiers
source                  1..128
                        mol_type = protein
                        organism = Betatorquevirus sp.
SEQUENCE: 218
ISIQNRNMSV DQGQSWPFKI LGTQSFYFYF YTGANLPGDT TQIPVADLLP LTNPRINRPG  60
QSLNEAKITD HITFTEYKNK FTNYWGNPFN KHIQEHLDMI LYSLKSPEAI KNEWTTENMK  120
WNQLNNAG                                                          128

SEQ ID NO: 219          moltype = AA  length = 163
FEATURE                 Location/Qualifiers
source                  1..163
                        mol_type = protein
                        organism = Betatorquevirus sp.
SEQUENCE: 219
TMALTPFNEP IFTQIQYNPD RDTGEDTQLY LLSNATGTGW DPPGIPELIL EGFPLWLIYW  60
GFADFQKNLK KVTNIDTNYM LVAKTKFTQK PGTFYLVILN DTFVEGNSPY EKQPLPEDNI  120
KWYPQVQYQL EAQNKLLQTG PFTPNIQGQL SDNISMFYKF YFK                   163

SEQ ID NO: 220          moltype = AA  length = 129
FEATURE                 Location/Qualifiers
source                  1..129
                        mol_type = protein
                        organism = Betatorquevirus sp.
SEQUENCE: 220
WGGSPPKAIN VENPAHQIQY PIPRNEHETT SLQSPGEAPE SILYSFDYRH GNYTTTALSR  60
ISQDWALKDT VSKITEPDRQ QLLKQALECL QISEETQEKK EKEVQQLISN LRQQQQLYRE  120
RIISLLKDQ                                                         129

SEQ ID NO: 221          moltype = AA  length = 673
FEATURE                 Location/Qualifiers
source                  1..673
                        mol_type = protein
                        organism = Gammatorquevirus sp.
SEQUENCE: 221
MPFWWGRRNK FWYGRNYRRK KRRFPKRRKR RFYRRTKYRR PARRRRRRRR KVRRKKKTLI  60
VRQWQPDSIV LCKIKGYDSI IWGAEGTQFQ CSTHEMYEYT RQKYPGGGGF GVQLYSLEYL  120
YDQWKLRNNI WTKTNQLKDL CRYLKCVMTF YRHQHIDFVI VYERQPPFEI DKLTYMKYHP  180
YMLLQRKHKI ILPSQTTNPR GKLKKKKTIK PPKQMLSKWF FQQQFAKYDL LLIAAAACSL  240
RYPRIGCCNE NRMITLYCLN TKFYQDTEWG TTKQAPHYFK PYATINKSMI FVSNYGGKKT  300
EYNIGQWIET DIPGEGNLAR YYRSISKEGG YFSPKILQAY QTKVKSVDYK PLPIVLGRYN  360
PAIDDGKGNK IYLQTIMNGH WGLPQKTPDY IIEEVPLWLG FWGYYNYLKQ TRTEAIFPLH  420
MFVVQSKYIQ TQQTETPNNF WAFIDNSFIQ GKNPWDSVIT YSEQKLWFPT VAWQLKTINA  480
ICESGPYVPK LDNQTYSTWE LATHYSFHFK WGGPQISDQP VEDPGNKNKY DVPDTIKEAL  540
QIVNPAKNIA ATMFHDWDYR RGCITSTAIK RMQQNLPTDS SLESDSDSEP APKKKRLLPV  600
LHDPQKKTEK INQCLLSLCE ESTCQEQETE ENILKLIQQQ QQQQQKLKHN LLVLIKDLKV  660
KQRLLQLQTG VLE                                                    673

SEQ ID NO: 222          moltype = AA  length = 57
FEATURE                 Location/Qualifiers
source                  1..57
                        mol_type = protein
                        organism = Gammatorquevirus sp.
SEQUENCE: 222
MPFWWGRRNK FWYGRNYRRK KRRFPKRRKR RFYRRTKYRR PARRRRRRRR KVRRKKK    57

SEQ ID NO: 223          moltype = AA  length = 202
FEATURE                 Location/Qualifiers
source                  1..202
                        mol_type = protein
                        organism = Gammatorquevirus sp.
SEQUENCE: 223
TLIVRQWQPD SIVLCKIKGY DSIIWGAEGT QFQCSTHEMY EYTRQKYPGG GGFGVQLYSL  60
EYLYDQWKLR NNIWTKTNQL KDLCRYLKCV MTFYRHQHID FVIVYERQPP FEIDKLTYMK  120
YHPYMLLQRK HKIILPSQTT NPRGKLKKKK TIKPPKQMLS KWFFQQQFAK YDLLLIAAAA  180
CSLRYPRIGC CNENRMITLY CL                                          202

SEQ ID NO: 224          moltype = AA  length = 92
FEATURE                 Location/Qualifiers
```

```
source                  1..92
                        mol_type = protein
                        organism = Gammatorquevirus sp.
SEQUENCE: 224
NTKFYQDTEW GTTKQAPHYF KPYATINKSM IFVSNYGGKK TEYNIGQWIE TDIPGEGNLA  60
RYYRSISKEG GYFSPKILQA YQTKVKSVDY KP                                92

SEQ ID NO: 225          moltype = AA  length = 159
FEATURE                 Location/Qualifiers
source                  1..159
                        mol_type = protein
                        organism = Gammatorquevirus sp.
SEQUENCE: 225
LPIVLGRYNP AIDDGKGNKI YLQTIMNGHW GLPQKTPDYI IEEVPLWLGF WGYYNYLKQT  60
RTEAIFPLHM FVVQSKYIQT QQTETPNNFW AFIDNSFIQG KNPWDSVITY SEQKLWFPTV  120
AWQLKTINAI CESGPYVPKL DNQTYSTWEL ATHYSFHFK                         159

SEQ ID NO: 226          moltype = AA  length = 163
FEATURE                 Location/Qualifiers
source                  1..163
                        mol_type = protein
                        organism = Gammatorquevirus sp.
SEQUENCE: 226
WGGPQISDQP VEDPGNKNKY DVPDTIKEAL QIVNPAKNIA ATMFHDWDYR RGCITSTAIK  60
RMQQNLPTDS SLESDSDSEP APKKKRLLPV LHDPQKKTEK INQCLLSLCE ESTCQEQETE  120
ENILKLIQQQ QQQQQKLKHN LLVLIKDLKV KQRLLQLQTG VLE                   163

SEQ ID NO: 227          moltype = AA  length = 220
FEATURE                 Location/Qualifiers
source                  1..220
                        mol_type = protein
                        organism = synthetic construct
VARIANT                 29
                        note = Any amino acid
VARIANT                 30
                        note = Any amino acid
VARIANT                 31
                        note = Any amino acid
VARIANT                 29..31
                        note = This region may encompass 0-3 residues
VARIANT                 100
                        note = Any amino acid
VARIANT                 125
                        note = Any amino acid
VARIANT                 126
                        note = Any amino acid
VARIANT                 127
                        note = Any amino acid
VARIANT                 128
                        note = Any amino acid
VARIANT                 129
                        note = Any amino acid
VARIANT                 125..129
                        note = This region may encompass 1-5 residues
VARIANT                 181
                        note = Any amino acid
VARIANT                 211
                        note = Any amino acid
SEQUENCE: 227
LVLTQWQPNT VRRCYIRGYL PLIICGENXX XTTSRNYATH SDDTIQKGPF GGGMSTTTFS  60
LRVLYDEYQR FMNRWTYSNE DLDLARYLGC KFTFYRHPDX DFIVQYNTNP PFKDTKLTAP  120
SIHPXXXXXG MLMLSKRKIL IPSLKTRPKG KHYVKVRIGP PKLFEDKWYT QSDLCDVPLV  180
XLYATAADLQ HPFGSPQTDN PCVTFQVLGS XYNKHLSISP                        220

SEQ ID NO: 228          moltype = AA  length = 172
FEATURE                 Location/Qualifiers
source                  1..172
                        mol_type = protein
                        organism = synthetic construct
VARIANT                 38
                        note = Any amino acid
VARIANT                 44
                        note = Any amino acid
VARIANT                 45
                        note = Any amino acid
VARIANT                 46
                        note = Any amino acid
VARIANT                 44..46
                        note = This region may encompass 0-3 residues
```

```
VARIANT                 77
                        note = Any amino acid
VARIANT                 79
                        note = Any amino acid
VARIANT                 98
                        note = Any amino acid
VARIANT                 99
                        note = Any amino acid
VARIANT                 100
                        note = Any amino acid
VARIANT                 101
                        note = Any amino acid
VARIANT                 98..101
                        note = This region may encompass 0-4 residues
SEQUENCE: 228
SNFEFPGAYT DITYNPLTDK GVGNMVWIQY LTKPDTIXDK TQSXXXKCLI EDLPLWAALY  60
GYVDFCEKET GDSAIIXNXG RVLIRCPYTK PPLYDKTXXX XNKGFVPYST NFGNGKMPGG  120
SGYVPIYWRA RWYPTLFHQK EVLEDIVQSG PFAYKDEKPS TQLVMKYCFN FN          172

SEQ ID NO: 229          moltype = AA  length = 258
FEATURE                 Location/Qualifiers
source                  1..258
                        mol_type = protein
                        organism = synthetic construct
VARIANT                 20
                        note = Any amino acid
VARIANT                 21
                        note = Any amino acid
VARIANT                 22
                        note = Any amino acid
VARIANT                 20..22
                        note = This region may encompass 0-3 residues
VARIANT                 25
                        note = Any amino acid
VARIANT                 78
                        note = Any amino acid
VARIANT                 89
                        note = Any amino acid
VARIANT                 91
                        note = Any amino acid
VARIANT                 95
                        note = Any amino acid
VARIANT                 96
                        note = Any amino acid
VARIANT                 97
                        note = Any amino acid
VARIANT                 98
                        note = Any amino acid
VARIANT                 95..98
                        note = This region may encompass 1-4 residues
VARIANT                 107
                        note = Any amino acid
VARIANT                 108
                        note = Any amino acid
VARIANT                 109
                        note = Any amino acid
VARIANT                 110
                        note = Any amino acid
VARIANT                 111
                        note = Any amino acid
VARIANT                 112
                        note = Any amino acid
VARIANT                 113
                        note = Any amino acid
VARIANT                 114
                        note = Any amino acid
VARIANT                 115
                        note = Any amino acid
VARIANT                 116
                        note = Any amino acid
VARIANT                 117
                        note = Any amino acid
VARIANT                 118
                        note = Any amino acid
VARIANT                 119
                        note = Any amino acid
VARIANT                 120
                        note = Any amino acid
VARIANT                 107..120
```

```
                  note = This region may encompass 2-14 residues
VARIANT           129
                  note = Any amino acid
VARIANT           139
                  note = Any amino acid
VARIANT           140
                  note = Any amino acid
VARIANT           141
                  note = Any amino acid
VARIANT           142
                  note = Any amino acid
VARIANT           143
                  note = Any amino acid
VARIANT           144
                  note = Any amino acid
VARIANT           145
                  note = Any amino acid
VARIANT           146
                  note = Any amino acid
VARIANT           147
                  note = Any amino acid
VARIANT           148
                  note = Any amino acid
VARIANT           149
                  note = Any amino acid
VARIANT           150
                  note = Any amino acid
VARIANT           151
                  note = Any amino acid
VARIANT           152
                  note = Any amino acid
VARIANT           153
                  note = Any amino acid
VARIANT           154
                  note = Any amino acid
VARIANT           155
                  note = Any amino acid
VARIANT           156
                  note = Any amino acid
VARIANT           157
                  note = Any amino acid
VARIANT           158
                  note = Any amino acid
VARIANT           159
                  note = Any amino acid
VARIANT           160
                  note = Any amino acid
VARIANT           161
                  note = Any amino acid
VARIANT           162
                  note = Any amino acid
VARIANT           163
                  note = Any amino acid
VARIANT           164
                  note = Any amino acid
VARIANT           165
                  note = Any amino acid
VARIANT           166
                  note = Any amino acid
VARIANT           167
                  note = Any amino acid
VARIANT           168
                  note = Any amino acid
VARIANT           139..168
                  note = This region may encompass 0-30 residues
VARIANT           201
                  note = Any amino acid
VARIANT           202
                  note = Any amino acid
VARIANT           203
                  note = Any amino acid
VARIANT           204
                  note = Any amino acid
VARIANT           201..204
                  note = This region may encompass 0-4 residues
VARIANT           219
                  note = Any amino acid
VARIANT           220
                  note = Any amino acid
```

| | |
|---|---|
| VARIANT | 221<br>note = Any amino acid |
| VARIANT | 222<br>note = Any amino acid |
| VARIANT | 223<br>note = Any amino acid |
| VARIANT | 224<br>note = Any amino acid |
| VARIANT | 225<br>note = Any amino acid |
| VARIANT | 226<br>note = Any amino acid |
| VARIANT | 227<br>note = Any amino acid |
| VARIANT | 228<br>note = Any amino acid |
| VARIANT | 229<br>note = Any amino acid |
| VARIANT | 230<br>note = Any amino acid |
| VARIANT | 231<br>note = Any amino acid |
| VARIANT | 232<br>note = Any amino acid |
| VARIANT | 233<br>note = Any amino acid |
| VARIANT | 234<br>note = Any amino acid |
| VARIANT | 235<br>note = Any amino acid |
| VARIANT | 236<br>note = Any amino acid |
| VARIANT | 237<br>note = Any amino acid |
| VARIANT | 238<br>note = Any amino acid |
| VARIANT | 239<br>note = Any amino acid |
| VARIANT | 240<br>note = Any amino acid |
| VARIANT | 241<br>note = Any amino acid |
| VARIANT | 242<br>note = Any amino acid |
| VARIANT | 243<br>note = Any amino acid |
| VARIANT | 244<br>note = Any amino acid |
| VARIANT | 245<br>note = Any amino acid |
| VARIANT | 246<br>note = Any amino acid |
| VARIANT | 247<br>note = Any amino acid |
| VARIANT | 248<br>note = Any amino acid |
| VARIANT | 249<br>note = Any amino acid |
| VARIANT | 250<br>note = Any amino acid |
| VARIANT | 251<br>note = Any amino acid |
| VARIANT | 252<br>note = Any amino acid |
| VARIANT | 253<br>note = Any amino acid |
| VARIANT | 254<br>note = Any amino acid |
| VARIANT | 255<br>note = Any amino acid |
| VARIANT | 256<br>note = Any amino acid |
| VARIANT | 257<br>note = Any amino acid |
| VARIANT | 258<br>note = Any amino acid |
| VARIANT | 219..258<br>note = This region may encompass 0-40 residues |

SEQUENCE: 229

```
WGGNPISQQV VRNPCKDSGX XXSGXGRQPR SVQVVDPKYM GPEYTFHSWD WRRGLFGEKA  60
IKRMSEQPTD DEIFTGGXPK RPRRDPPTXQ XPEEXXXXQK ESSSFRXXXX XXXXXXXXXX  120
PWESSSQEXE SESQEEEEXX XXXXXXXXXX XXXXXXXXXX XXXXXXXXEQ TVQQQLRQQL  180
REQRRLRVQL QLLFQQLLKT XXXXQAGLHI NPLLLSQAXX XXXXXXXXXX XXXXXXXXXX  240
XXXXXXXXXX XXXXXXXX                                                258

SEQ ID NO: 230         moltype = AA  length = 214
FEATURE                Location/Qualifiers
source                 1..214
                       mol_type = protein
                       organism = synthetic construct
VARIANT                136
                       note = Any amino acid
VARIANT                138
                       note = Any amino acid
VARIANT                139
                       note = Any amino acid
VARIANT                140
                       note = Any amino acid
VARIANT                141
                       note = Any amino acid
VARIANT                138..141
                       note = This region may encompass 1-4 residues
VARIANT                179
                       note = Any amino acid
SEQUENCE: 230
LKQWQPSTIR KCKIKGYLPL FQCGKGRISN NYTQYKESIV PHHEPGGGGW SIQQFTLGAL  60
YEEHLKLRNW WTKSNDGLPL VRYLGCTIKL YRSEDTDYIV TYQRCYPMTA TKLTYLSTQP  120
SRMLMNKHKI IVPSKXTXXX XNKKKKPYKK IFIKPPSQMQ NKWYFQQDIA NTPLLQLTXT  180
ACSLDRMYLS SDSISNNITF TSLNTNFFQN PNFQ                              214

SEQ ID NO: 231         moltype = AA  length = 187
FEATURE                Location/Qualifiers
source                 1..187
                       mol_type = protein
                       organism = synthetic construct
VARIANT                1
                       note = Any amino acid
VARIANT                2
                       note = Any amino acid
VARIANT                3
                       note = Any amino acid
VARIANT                4
                       note = Any amino acid
VARIANT                5
                       note = Any amino acid
VARIANT                6
                       note = Any amino acid
VARIANT                7
                       note = Any amino acid
VARIANT                8
                       note = Any amino acid
VARIANT                9
                       note = Any amino acid
VARIANT                10
                       note = Any amino acid
VARIANT                1..10
                       note = This region may encompass 4-10 residues
VARIANT                38
                       note = Any amino acid
VARIANT                39
                       note = Any amino acid
VARIANT                40
                       note = Any amino acid
VARIANT                41
                       note = Any amino acid
VARIANT                42
                       note = Any amino acid
VARIANT                43
                       note = Any amino acid
VARIANT                44
                       note = Any amino acid
VARIANT                45
                       note = Any amino acid
VARIANT                38..45
                       note = This region may encompass 1-8 residues
VARIANT                94
                       note = Any amino acid
VARIANT                100
```

```
                        note = Any amino acid
VARIANT                 101
                        note = Any amino acid
VARIANT                 102
                        note = Any amino acid
VARIANT                 100..102
                        note = This region may encompass 1-3 residues
VARIANT                 112
                        note = Any amino acid
VARIANT                 114
                        note = Any amino acid
VARIANT                 115
                        note = Any amino acid
VARIANT                 114..115
                        note = This region may encompass 0-2 residues
VARIANT                 124
                        note = Any amino acid
VARIANT                 125
                        note = Any amino acid
VARIANT                 126
                        note = Any amino acid
VARIANT                 127
                        note = Any amino acid
VARIANT                 128
                        note = Any amino acid
VARIANT                 129
                        note = Any amino acid
VARIANT                 130
                        note = Any amino acid
VARIANT                 131
                        note = Any amino acid
VARIANT                 132
                        note = Any amino acid
VARIANT                 133
                        note = Any amino acid
VARIANT                 134
                        note = Any amino acid
VARIANT                 135
                        note = Any amino acid
VARIANT                 136
                        note = Any amino acid
VARIANT                 137
                        note = Any amino acid
VARIANT                 138
                        note = Any amino acid
VARIANT                 139
                        note = Any amino acid
VARIANT                 124..139
                        note = This region may encompass 3-16 residues
VARIANT                 154
                        note = Any amino acid
SEQUENCE: 231
XXXXXXXXXX TPLYFECRYN PFKDKGTGNK VYLVSNNXXX XXXXXTGWDP PTDPDLIIEG  60
FPLWLLLWGW LDWQKKLGKI QNIDTDYILV IQSXYYIPPX XXKLPYYVPL DXDXXFLHGR  120
SPYXXXXXXX XXXXXXXXXP SDKQHWHPKV RFQXETINNI ALTGPGTPKL PNQKSIQAHM  180
KYKFYFK                                                            187

SEQ ID NO: 232          moltype = AA  length = 163
FEATURE                 Location/Qualifiers
source                  1..163
                        mol_type = protein
                        organism = synthetic construct
VARIANT                 34
                        note = Any amino acid
VARIANT                 65
                        note = Any amino acid
VARIANT                 77
                        note = Any amino acid
VARIANT                 78
                        note = Any amino acid
VARIANT                 86
                        note = Any amino acid
VARIANT                 87
                        note = Any amino acid
VARIANT                 96
                        note = Any amino acid
VARIANT                 102
                        note = Any amino acid
VARIANT                 103
```

```
                          note = Any amino acid
VARIANT                   104
                          note = Any amino acid
VARIANT                   105
                          note = Any amino acid
VARIANT                   106
                          note = Any amino acid
VARIANT                   102..106
                          note = This region may encompass 0-5 residues
VARIANT                   125
                          note = Any amino acid
VARIANT                   135
                          note = Any amino acid
VARIANT                   138
                          note = Any amino acid
VARIANT                   139
                          note = Any amino acid
VARIANT                   140
                          note = Any amino acid
VARIANT                   141
                          note = Any amino acid
VARIANT                   142
                          note = Any amino acid
VARIANT                   143
                          note = Any amino acid
VARIANT                   144
                          note = Any amino acid
VARIANT                   145
                          note = Any amino acid
VARIANT                   146
                          note = Any amino acid
VARIANT                   147
                          note = Any amino acid
VARIANT                   148
                          note = Any amino acid
VARIANT                   149
                          note = Any amino acid
VARIANT                   150
                          note = Any amino acid
VARIANT                   151
                          note = Any amino acid
VARIANT                   152
                          note = Any amino acid
VARIANT                   153
                          note = Any amino acid
VARIANT                   154
                          note = Any amino acid
VARIANT                   155
                          note = Any amino acid
VARIANT                   156
                          note = Any amino acid
VARIANT                   157
                          note = Any amino acid
VARIANT                   158
                          note = Any amino acid
VARIANT                   159
                          note = Any amino acid
VARIANT                   160
                          note = Any amino acid
VARIANT                   161
                          note = Any amino acid
VARIANT                   162
                          note = Any amino acid
VARIANT                   163
                          note = Any amino acid
VARIANT                   138..163
                          note = This region may encompass 0-26 residues
SEQUENCE: 232
WGGCPAPMET ITDPCKQPKY PIPNNLLQTT SLQXPTTPIE TYLYKFDERR GLLTKKAAKR  60
IKKDXTTETT LFTDTGXXTS TTLPTXXQTE TTQEEXTSEE EXXXXXETLL QQLQQLRRKQ  120
KQLRXRILQL LQLLXLLXXX XXXXXXXXXX XXXXXXXXXX XXX                    163

SEQ ID NO: 233            moltype = AA  length = 203
FEATURE                   Location/Qualifiers
source                    1..203
                          mol_type = protein
                          organism = synthetic construct
VARIANT                   79
                          note = Any amino acid
```

```
VARIANT                 104
                        note = Any amino acid
VARIANT                 116
                        note = Any amino acid
VARIANT                 120
                        note = Any amino acid
VARIANT                 121
                        note = Any amino acid
VARIANT                 125
                        note = Any amino acid
VARIANT                 170
                        note = Any amino acid
SEQUENCE: 233
TIPLKQWQPE SIRKCKIKGY GTLVLGAEGR QFYCYTNEKD EYTPPKAPGG GGFGVELFSL  60
EYLYEQWKAR NNIWTKSNXY KDLCRYTGCK ITFYRHPTTD FIVXYSRQPP FEIDKXTYMX  120
XHPQXLLLRK HKKIILSKAT NPKGKLKKKI KIKPPKQMLN KWFFQKQFAX YGLVQLQAAA  180
CBLRYPRLGC CNENRLITLY YLN                                          203

SEQ ID NO: 234          moltype = AA  length = 162
FEATURE                 Location/Qualifiers
source                  1..162
                        mol_type = protein
                        organism = synthetic construct
VARIANT                 12
                        note = Any amino acid
VARIANT                 20
                        note = Any amino acid
VARIANT                 23
                        note = Any amino acid
VARIANT                 30
                        note = Any amino acid
VARIANT                 84
                        note = Any amino acid
VARIANT                 90
                        note = Any amino acid
VARIANT                 95
                        note = Any amino acid
VARIANT                 105
                        note = Any amino acid
VARIANT                 113
                        note = Any amino acid
VARIANT                 154
                        note = Any amino acid
VARIANT                 156
                        note = Any amino acid
SEQUENCE: 234
LPIVVARYNP AXDTGKGNKX WLXSTLNGSX WAPPTTDKDL IIEGLPLWLA LYGYWSYJKK  60
VKKDKGILQS HMFVVKSPAI QPLXTATTQX TFYPXIDNSF IQGKXPYDEP JTXNQKKLWY  120
PTLEHQQETI NAIVESGPYV PKLDNQKNST WELXYXYTFY FK                     162

SEQ ID NO: 235          moltype = AA  length = 177
FEATURE                 Location/Qualifiers
source                  1..177
                        mol_type = protein
                        organism = synthetic construct
VARIANT                 16
                        note = Any amino acid
VARIANT                 26
                        note = Any amino acid
VARIANT                 33
                        note = Any amino acid
VARIANT                 73
                        note = Any amino acid
VARIANT                 81
                        note = Any amino acid
VARIANT                 82
                        note = Any amino acid
VARIANT                 81..82
                        note = This region may encompass 0-2 residues
VARIANT                 90
                        note = Any amino acid
VARIANT                 94
                        note = Any amino acid
VARIANT                 119
                        note = Any amino acid
VARIANT                 120
                        note = Any amino acid
VARIANT                 121
                        note = Any amino acid
```

```
VARIANT                 122
                        note = Any amino acid
VARIANT                 123
                        note = Any amino acid
VARIANT                 124
                        note = Any amino acid
VARIANT                 119..124
                        note = This region may encompass 1-6 residues
VARIANT                 168
                        note = Any amino acid
VARIANT                 169
                        note = Any amino acid
VARIANT                 170
                        note = Any amino acid
VARIANT                 171
                        note = Any amino acid
VARIANT                 172
                        note = Any amino acid
VARIANT                 173
                        note = Any amino acid
VARIANT                 174
                        note = Any amino acid
VARIANT                 175
                        note = Any amino acid
VARIANT                 176
                        note = Any amino acid
VARIANT                 177
                        note = Any amino acid
VARIANT                 168..177
                        note = This region may encompass 1-10 residues
SEQUENCE: 235
WGGPQIPDQP VEDPKXQGTY PVPDTXQQTI QIXNPLKQKP ETMFHDWDYR RGIITSTALK  60
RMQENLETDS SFXSDSEETP XXKKKKRLTX ELPXPQEETE EIQSCLLSLC EESTCQEEXX  120
XXXXENLQQL IHQQQQQQQQ LKHNILKLLS DLKZKQRLLQ LQTGILEXXX XXXXXXX     177

SEQ ID NO: 236          moltype =   length =
SEQUENCE: 236
000

SEQ ID NO: 237          moltype =   length =
SEQUENCE: 237
000

SEQ ID NO: 238          moltype =   length =
SEQUENCE: 238
000

SEQ ID NO: 239          moltype =   length =
SEQUENCE: 239
000

SEQ ID NO: 240          moltype =   length =
SEQUENCE: 240
000

SEQ ID NO: 241          moltype =   length =
SEQUENCE: 241
000

SEQ ID NO: 242          moltype =   length =
SEQUENCE: 242
000

SEQ ID NO: 243          moltype =   length =
SEQUENCE: 243
000

SEQ ID NO: 244          moltype =   length =
SEQUENCE: 244
000

SEQ ID NO: 245          moltype =   length =
SEQUENCE: 245
000

SEQ ID NO: 246          moltype =   length =
SEQUENCE: 246
000
```

SEQ ID NO: 247 moltype = length =
SEQUENCE: 247
000

SEQ ID NO: 248 moltype = length =
SEQUENCE: 248
000

SEQ ID NO: 249 moltype = length =
SEQUENCE: 249
000

SEQ ID NO: 250 moltype = length =
SEQUENCE: 250
000

SEQ ID NO: 251 moltype = length =
SEQUENCE: 251
000

SEQ ID NO: 252 moltype = length =
SEQUENCE: 252
000

SEQ ID NO: 253 moltype = length =
SEQUENCE: 253
000

SEQ ID NO: 254 moltype = length =
SEQUENCE: 254
000

SEQ ID NO: 255 moltype = length =
SEQUENCE: 255
000

SEQ ID NO: 256 moltype = length =
SEQUENCE: 256
000

SEQ ID NO: 257 moltype = length =
SEQUENCE: 257
000

SEQ ID NO: 258 moltype = length =
SEQUENCE: 258
000

SEQ ID NO: 259 moltype = length =
SEQUENCE: 259
000

SEQ ID NO: 260 moltype = length =
SEQUENCE: 260
000

SEQ ID NO: 261 moltype = length =
SEQUENCE: 261
000

SEQ ID NO: 262 moltype = length =
SEQUENCE: 262
000

SEQ ID NO: 263 moltype = length =
SEQUENCE: 263
000

SEQ ID NO: 264 moltype = length =
SEQUENCE: 264
000

SEQ ID NO: 265 moltype = length =
SEQUENCE: 265
000

SEQ ID NO: 266 moltype = length =
SEQUENCE: 266
000

SEQ ID NO: 267 moltype = length =
SEQUENCE: 267
000

SEQ ID NO: 268 moltype = length =
SEQUENCE: 268
000

SEQ ID NO: 269 moltype = length =
SEQUENCE: 269
000

SEQ ID NO: 270 moltype = length =
SEQUENCE: 270
000

SEQ ID NO: 271 moltype = length =
SEQUENCE: 271
000

SEQ ID NO: 272 moltype = length =
SEQUENCE: 272
000

SEQ ID NO: 273 moltype = length =
SEQUENCE: 273
000

SEQ ID NO: 274 moltype = length =
SEQUENCE: 274
000

SEQ ID NO: 275 moltype = length =
SEQUENCE: 275
000

SEQ ID NO: 276 moltype = length =
SEQUENCE: 276
000

SEQ ID NO: 277 moltype = length =
SEQUENCE: 277
000

SEQ ID NO: 278 moltype = length =
SEQUENCE: 278
000

SEQ ID NO: 279 moltype = length =
SEQUENCE: 279
000

SEQ ID NO: 280 moltype = length =
SEQUENCE: 280
000

SEQ ID NO: 281 moltype = length =
SEQUENCE: 281
000

SEQ ID NO: 282 moltype = length =
SEQUENCE: 282
000

SEQ ID NO: 283 moltype = length =
SEQUENCE: 283
000

SEQ ID NO: 284 moltype = length =
SEQUENCE: 284
000

SEQ ID NO: 285 moltype = length =
SEQUENCE: 285
000

SEQ ID NO: 286 moltype = length =
SEQUENCE: 286

000

SEQ ID NO: 287 moltype = length =
SEQUENCE: 287
000

SEQ ID NO: 288 moltype = length =
SEQUENCE: 288
000

SEQ ID NO: 289 moltype = length =
SEQUENCE: 289
000

SEQ ID NO: 290 moltype = length =
SEQUENCE: 290
000

SEQ ID NO: 291 moltype = length =
SEQUENCE: 291
000

SEQ ID NO: 292 moltype = length =
SEQUENCE: 292
000

SEQ ID NO: 293 moltype = length =
SEQUENCE: 293
000

SEQ ID NO: 294 moltype = length =
SEQUENCE: 294
000

SEQ ID NO: 295 moltype = length =
SEQUENCE: 295
000

SEQ ID NO: 296 moltype = length =
SEQUENCE: 296
000

SEQ ID NO: 297 moltype = length =
SEQUENCE: 297
000

SEQ ID NO: 298 moltype = length =
SEQUENCE: 298
000

SEQ ID NO: 299 moltype = length =
SEQUENCE: 299
000

SEQ ID NO: 300 moltype = length =
SEQUENCE: 300
000

SEQ ID NO: 301 moltype = length =
SEQUENCE: 301
000

SEQ ID NO: 302 moltype = length =
SEQUENCE: 302
000

SEQ ID NO: 303 moltype = length =
SEQUENCE: 303
000

SEQ ID NO: 304 moltype = length =
SEQUENCE: 304
000

SEQ ID NO: 305 moltype = length =
SEQUENCE: 305
000

SEQ ID NO: 306 moltype = length =

SEQUENCE: 306
000

SEQ ID NO: 307 moltype = length =
SEQUENCE: 307
000

SEQ ID NO: 308 moltype = length =
SEQUENCE: 308
000

SEQ ID NO: 309 moltype = length =
SEQUENCE: 309
000

SEQ ID NO: 310 moltype = length =
SEQUENCE: 310
000

SEQ ID NO: 311 moltype = length =
SEQUENCE: 311
000

SEQ ID NO: 312 moltype = length =
SEQUENCE: 312
000

SEQ ID NO: 313 moltype = length =
SEQUENCE: 313
000

SEQ ID NO: 314 moltype = length =
SEQUENCE: 314
000

SEQ ID NO: 315 moltype = length =
SEQUENCE: 315
000

SEQ ID NO: 316 moltype = length =
SEQUENCE: 316
000

SEQ ID NO: 317 moltype = length =
SEQUENCE: 317
000

SEQ ID NO: 318 moltype = length =
SEQUENCE: 318
000

SEQ ID NO: 319 moltype = length =
SEQUENCE: 319
000

SEQ ID NO: 320 moltype = length =
SEQUENCE: 320
000

SEQ ID NO: 321 moltype = length =
SEQUENCE: 321
000

SEQ ID NO: 322 moltype = length =
SEQUENCE: 322
000

SEQ ID NO: 323 moltype = length =
SEQUENCE: 323
000

SEQ ID NO: 324 moltype = length =
SEQUENCE: 324
000

SEQ ID NO: 325 moltype = length =
SEQUENCE: 325
000

SEQ ID NO: 326 moltype = length =
SEQUENCE: 326
000

SEQ ID NO: 327 moltype = length =
SEQUENCE: 327
000

SEQ ID NO: 328 moltype = length =
SEQUENCE: 328
000

SEQ ID NO: 329 moltype = length =
SEQUENCE: 329
000

SEQ ID NO: 330 moltype = length =
SEQUENCE: 330
000

SEQ ID NO: 331 moltype = length =
SEQUENCE: 331
000

SEQ ID NO: 332 moltype = length =
SEQUENCE: 332
000

SEQ ID NO: 333 moltype = length =
SEQUENCE: 333
000

SEQ ID NO: 334 moltype = length =
SEQUENCE: 334
000

SEQ ID NO: 335 moltype = length =
SEQUENCE: 335
000

SEQ ID NO: 336 moltype = length =
SEQUENCE: 336
000

SEQ ID NO: 337 moltype = length =
SEQUENCE: 337
000

SEQ ID NO: 338 moltype = length =
SEQUENCE: 338
000

SEQ ID NO: 339 moltype = length =
SEQUENCE: 339
000

SEQ ID NO: 340 moltype = length =
SEQUENCE: 340
000

SEQ ID NO: 341 moltype = length =
SEQUENCE: 341
000

SEQ ID NO: 342 moltype = length =
SEQUENCE: 342
000

SEQ ID NO: 343 moltype = length =
SEQUENCE: 343
000

SEQ ID NO: 344 moltype = length =
SEQUENCE: 344
000

SEQ ID NO: 345 moltype = length =
SEQUENCE: 345
000

SEQ ID NO: 346 moltype = length =
SEQUENCE: 346
000

SEQ ID NO: 347 moltype = length =
SEQUENCE: 347
000

SEQ ID NO: 348 moltype = length =
SEQUENCE: 348
000

SEQ ID NO: 349 moltype = length =
SEQUENCE: 349
000

SEQ ID NO: 350 moltype = length =
SEQUENCE: 350
000

SEQ ID NO: 351 moltype = length =
SEQUENCE: 351
000

SEQ ID NO: 352 moltype = length =
SEQUENCE: 352
000

SEQ ID NO: 353 moltype = length =
SEQUENCE: 353
000

SEQ ID NO: 354 moltype = length =
SEQUENCE: 354
000

SEQ ID NO: 355 moltype = length =
SEQUENCE: 355
000

SEQ ID NO: 356 moltype = length =
SEQUENCE: 356
000

SEQ ID NO: 357 moltype = length =
SEQUENCE: 357
000

SEQ ID NO: 358 moltype = length =
SEQUENCE: 358
000

SEQ ID NO: 359 moltype = length =
SEQUENCE: 359
000

SEQ ID NO: 360 moltype = length =
SEQUENCE: 360
000

SEQ ID NO: 361 moltype = length =
SEQUENCE: 361
000

SEQ ID NO: 362 moltype = length =
SEQUENCE: 362
000

SEQ ID NO: 363 moltype = length =
SEQUENCE: 363
000

SEQ ID NO: 364 moltype = length =
SEQUENCE: 364
000

SEQ ID NO: 365 moltype = length =
SEQUENCE: 365

000

SEQ ID NO: 366 moltype = length =
SEQUENCE: 366
000

SEQ ID NO: 367 moltype = length =
SEQUENCE: 367
000

SEQ ID NO: 368 moltype = length =
SEQUENCE: 368
000

SEQ ID NO: 369 moltype = length =
SEQUENCE: 369
000

SEQ ID NO: 370 moltype = length =
SEQUENCE: 370
000

SEQ ID NO: 371 moltype = length =
SEQUENCE: 371
000

SEQ ID NO: 372 moltype = length =
SEQUENCE: 372
000

SEQ ID NO: 373 moltype = length =
SEQUENCE: 373
000

SEQ ID NO: 374 moltype = length =
SEQUENCE: 374
000

SEQ ID NO: 375 moltype = length =
SEQUENCE: 375
000

SEQ ID NO: 376 moltype = length =
SEQUENCE: 376
000

SEQ ID NO: 377 moltype = length =
SEQUENCE: 377
000

SEQ ID NO: 378 moltype = length =
SEQUENCE: 378
000

SEQ ID NO: 379 moltype = length =
SEQUENCE: 379
000

SEQ ID NO: 380 moltype = length =
SEQUENCE: 380
000

SEQ ID NO: 381 moltype = length =
SEQUENCE: 381
000

SEQ ID NO: 382 moltype = length =
SEQUENCE: 382
000

SEQ ID NO: 383 moltype = length =
SEQUENCE: 383
000

SEQ ID NO: 384 moltype = length =
SEQUENCE: 384
000

SEQ ID NO: 385 moltype = length =

SEQUENCE: 385
000

SEQ ID NO: 386 moltype = length =
SEQUENCE: 386
000

SEQ ID NO: 387 moltype = length =
SEQUENCE: 387
000

SEQ ID NO: 388 moltype = length =
SEQUENCE: 388
000

SEQ ID NO: 389 moltype = length =
SEQUENCE: 389
000

SEQ ID NO: 390 moltype = length =
SEQUENCE: 390
000

SEQ ID NO: 391 moltype = length =
SEQUENCE: 391
000

SEQ ID NO: 392 moltype = length =
SEQUENCE: 392
000

SEQ ID NO: 393 moltype = length =
SEQUENCE: 393
000

SEQ ID NO: 394 moltype = length =
SEQUENCE: 394
000

SEQ ID NO: 395 moltype = length =
SEQUENCE: 395
000

SEQ ID NO: 396 moltype = length =
SEQUENCE: 396
000

SEQ ID NO: 397 moltype = length =
SEQUENCE: 397
000

SEQ ID NO: 398 moltype = length =
SEQUENCE: 398
000

SEQ ID NO: 399 moltype = length =
SEQUENCE: 399
000

SEQ ID NO: 400 moltype = length =
SEQUENCE: 400
000

SEQ ID NO: 401 moltype = length =
SEQUENCE: 401
000

SEQ ID NO: 402 moltype = length =
SEQUENCE: 402
000

SEQ ID NO: 403 moltype = length =
SEQUENCE: 403
000

SEQ ID NO: 404 moltype = length =
SEQUENCE: 404
000

SEQ ID NO: 405 moltype = length =
SEQUENCE: 405
000

SEQ ID NO: 406 moltype = length =
SEQUENCE: 406
000

SEQ ID NO: 407 moltype = length =
SEQUENCE: 407
000

SEQ ID NO: 408 moltype = length =
SEQUENCE: 408
000

SEQ ID NO: 409 moltype = length =
SEQUENCE: 409
000

SEQ ID NO: 410 moltype = length =
SEQUENCE: 410
000

SEQ ID NO: 411 moltype = length =
SEQUENCE: 411
000

SEQ ID NO: 412 moltype = length =
SEQUENCE: 412
000

SEQ ID NO: 413 moltype = length =
SEQUENCE: 413
000

SEQ ID NO: 414 moltype = length =
SEQUENCE: 414
000

SEQ ID NO: 415 moltype = length =
SEQUENCE: 415
000

SEQ ID NO: 416 moltype = length =
SEQUENCE: 416
000

SEQ ID NO: 417 moltype = length =
SEQUENCE: 417
000

SEQ ID NO: 418 moltype = length =
SEQUENCE: 418
000

SEQ ID NO: 419 moltype = length =
SEQUENCE: 419
000

SEQ ID NO: 420 moltype = length =
SEQUENCE: 420
000

SEQ ID NO: 421 moltype = length =
SEQUENCE: 421
000

SEQ ID NO: 422 moltype = length =
SEQUENCE: 422
000

SEQ ID NO: 423 moltype = length =
SEQUENCE: 423
000

SEQ ID NO: 424 moltype = length =
SEQUENCE: 424
000

SEQ ID NO: 425 moltype = length =
SEQUENCE: 425
000

SEQ ID NO: 426 moltype = length =
SEQUENCE: 426
000

SEQ ID NO: 427 moltype = length =
SEQUENCE: 427
000

SEQ ID NO: 428 moltype = length =
SEQUENCE: 428
000

SEQ ID NO: 429 moltype = length =
SEQUENCE: 429
000

SEQ ID NO: 430 moltype = length =
SEQUENCE: 430
000

SEQ ID NO: 431 moltype = length =
SEQUENCE: 431
000

SEQ ID NO: 432 moltype = length =
SEQUENCE: 432
000

SEQ ID NO: 433 moltype = length =
SEQUENCE: 433
000

SEQ ID NO: 434 moltype = length =
SEQUENCE: 434
000

SEQ ID NO: 435 moltype = length =
SEQUENCE: 435
000

SEQ ID NO: 436 moltype = length =
SEQUENCE: 436
000

SEQ ID NO: 437 moltype = length =
SEQUENCE: 437
000

SEQ ID NO: 438 moltype = length =
SEQUENCE: 438
000

SEQ ID NO: 439 moltype = length =
SEQUENCE: 439
000

SEQ ID NO: 440 moltype = length =
SEQUENCE: 440
000

SEQ ID NO: 441 moltype = length =
SEQUENCE: 441
000

SEQ ID NO: 442 moltype = length =
SEQUENCE: 442
000

SEQ ID NO: 443 moltype = length =
SEQUENCE: 443
000

SEQ ID NO: 444 moltype = length =
SEQUENCE: 444

000

SEQ ID NO: 445 moltype = length =
SEQUENCE: 445
000

SEQ ID NO: 446 moltype = length =
SEQUENCE: 446
000

SEQ ID NO: 447 moltype = length =
SEQUENCE: 447
000

SEQ ID NO: 448 moltype = length =
SEQUENCE: 448
000

SEQ ID NO: 449 moltype = length =
SEQUENCE: 449
000

SEQ ID NO: 450 moltype = length =
SEQUENCE: 450
000

SEQ ID NO: 451 moltype = length =
SEQUENCE: 451
000

SEQ ID NO: 452 moltype = length =
SEQUENCE: 452
000

SEQ ID NO: 453 moltype = length =
SEQUENCE: 453
000

SEQ ID NO: 454 moltype = length =
SEQUENCE: 454
000

SEQ ID NO: 455 moltype = length =
SEQUENCE: 455
000

SEQ ID NO: 456 moltype = length =
SEQUENCE: 456
000

SEQ ID NO: 457 moltype = length =
SEQUENCE: 457
000

SEQ ID NO: 458 moltype = length =
SEQUENCE: 458
000

SEQ ID NO: 459 moltype = length =
SEQUENCE: 459
000

SEQ ID NO: 460 moltype = length =
SEQUENCE: 460
000

SEQ ID NO: 461 moltype = length =
SEQUENCE: 461
000

SEQ ID NO: 462 moltype = length =
SEQUENCE: 462
000

SEQ ID NO: 463 moltype = length =
SEQUENCE: 463
000

SEQ ID NO: 464 moltype = length =

SEQUENCE: 464
000

SEQ ID NO: 465 moltype = length =
SEQUENCE: 465
000

SEQ ID NO: 466 moltype = length =
SEQUENCE: 466
000

SEQ ID NO: 467 moltype = length =
SEQUENCE: 467
000

SEQ ID NO: 468 moltype = length =
SEQUENCE: 468
000

SEQ ID NO: 469 moltype = length =
SEQUENCE: 469
000

SEQ ID NO: 470 moltype = length =
SEQUENCE: 470
000

SEQ ID NO: 471 moltype = length =
SEQUENCE: 471
000

SEQ ID NO: 472 moltype = length =
SEQUENCE: 472
000

SEQ ID NO: 473 moltype = length =
SEQUENCE: 473
000

SEQ ID NO: 474 moltype = length =
SEQUENCE: 474
000

SEQ ID NO: 475 moltype = length =
SEQUENCE: 475
000

SEQ ID NO: 476 moltype = length =
SEQUENCE: 476
000

SEQ ID NO: 477 moltype = length =
SEQUENCE: 477
000

SEQ ID NO: 478 moltype = length =
SEQUENCE: 478
000

SEQ ID NO: 479 moltype = length =
SEQUENCE: 479
000

SEQ ID NO: 480 moltype = length =
SEQUENCE: 480
000

SEQ ID NO: 481 moltype = length =
SEQUENCE: 481
000

SEQ ID NO: 482 moltype = length =
SEQUENCE: 482
000

SEQ ID NO: 483 moltype = length =
SEQUENCE: 483
000

SEQ ID NO: 484 moltype = length =
SEQUENCE: 484
000

SEQ ID NO: 485 moltype = length =
SEQUENCE: 485
000

SEQ ID NO: 486 moltype = length =
SEQUENCE: 486
000

SEQ ID NO: 487 moltype = length =
SEQUENCE: 487
000

SEQ ID NO: 488 moltype = length =
SEQUENCE: 488
000

SEQ ID NO: 489 moltype = length =
SEQUENCE: 489
000

SEQ ID NO: 490 moltype = length =
SEQUENCE: 490
000

SEQ ID NO: 491 moltype = length =
SEQUENCE: 491
000

SEQ ID NO: 492 moltype = length =
SEQUENCE: 492
000

SEQ ID NO: 493 moltype = length =
SEQUENCE: 493
000

SEQ ID NO: 494 moltype = length =
SEQUENCE: 494
000

SEQ ID NO: 495 moltype = length =
SEQUENCE: 495
000

SEQ ID NO: 496 moltype = length =
SEQUENCE: 496
000

SEQ ID NO: 497 moltype = length =
SEQUENCE: 497
000

SEQ ID NO: 498 moltype = length =
SEQUENCE: 498
000

SEQ ID NO: 499 moltype = length =
SEQUENCE: 499
000

SEQ ID NO: 500 moltype = length =
SEQUENCE: 500
000

SEQ ID NO: 501 moltype = length =
SEQUENCE: 501
000

SEQ ID NO: 502 moltype = length =
SEQUENCE: 502
000

SEQ ID NO: 503 moltype = length =
SEQUENCE: 503
000

SEQ ID NO: 504 moltype = length =
SEQUENCE: 504
000

SEQ ID NO: 505 moltype = length =
SEQUENCE: 505
000

SEQ ID NO: 506 moltype = length =
SEQUENCE: 506
000

SEQ ID NO: 507 moltype = length =
SEQUENCE: 507
000

SEQ ID NO: 508 moltype = length =
SEQUENCE: 508
000

SEQ ID NO: 509 moltype = length =
SEQUENCE: 509
000

SEQ ID NO: 510 moltype = length =
SEQUENCE: 510
000

SEQ ID NO: 511 moltype = length =
SEQUENCE: 511
000

SEQ ID NO: 512 moltype = length =
SEQUENCE: 512
000

SEQ ID NO: 513 moltype = length =
SEQUENCE: 513
000

SEQ ID NO: 514 moltype = length =
SEQUENCE: 514
000

SEQ ID NO: 515 moltype = length =
SEQUENCE: 515
000

SEQ ID NO: 516 moltype = length =
SEQUENCE: 516
000

SEQ ID NO: 517 moltype = length =
SEQUENCE: 517
000

SEQ ID NO: 518 moltype = length =
SEQUENCE: 518
000

SEQ ID NO: 519 moltype = length =
SEQUENCE: 519
000

SEQ ID NO: 520 moltype = length =
SEQUENCE: 520
000

SEQ ID NO: 521 moltype = length =
SEQUENCE: 521
000

SEQ ID NO: 522 moltype = length =
SEQUENCE: 522
000

SEQ ID NO: 523 moltype = length =
SEQUENCE: 523

000

SEQ ID NO: 524 moltype = length =
SEQUENCE: 524
000

SEQ ID NO: 525 moltype = length =
SEQUENCE: 525
000

SEQ ID NO: 526 moltype = length =
SEQUENCE: 526
000

SEQ ID NO: 527 moltype = length =
SEQUENCE: 527
000

SEQ ID NO: 528 moltype = length =
SEQUENCE: 528
000

SEQ ID NO: 529 moltype = length =
SEQUENCE: 529
000

SEQ ID NO: 530 moltype = length =
SEQUENCE: 530
000

SEQ ID NO: 531 moltype = length =
SEQUENCE: 531
000

SEQ ID NO: 532 moltype = length =
SEQUENCE: 532
000

SEQ ID NO: 533 moltype = length =
SEQUENCE: 533
000

SEQ ID NO: 534 moltype = length =
SEQUENCE: 534
000

SEQ ID NO: 535 moltype = length =
SEQUENCE: 535
000

SEQ ID NO: 536 moltype = length =
SEQUENCE: 536
000

SEQ ID NO: 537 moltype = length =
SEQUENCE: 537
000

SEQ ID NO: 538 moltype = length =
SEQUENCE: 538
000

SEQ ID NO: 539 moltype = length =
SEQUENCE: 539
000

SEQ ID NO: 540 moltype = length =
SEQUENCE: 540
000

SEQ ID NO: 541 moltype = length =
SEQUENCE: 541
000

SEQ ID NO: 542 moltype = length =
SEQUENCE: 542
000

SEQ ID NO: 543 moltype = length =

SEQUENCE: 543
000

SEQ ID NO: 544 moltype = length =
SEQUENCE: 544
000

SEQ ID NO: 545 moltype = length =
SEQUENCE: 545
000

SEQ ID NO: 546 moltype = length =
SEQUENCE: 546
000

SEQ ID NO: 547 moltype = length =
SEQUENCE: 547
000

SEQ ID NO: 548 moltype = length =
SEQUENCE: 548
000

SEQ ID NO: 549 moltype = length =
SEQUENCE: 549
000

SEQ ID NO: 550 moltype = length =
SEQUENCE: 550
000

SEQ ID NO: 551 moltype = length =
SEQUENCE: 551
000

SEQ ID NO: 552 moltype = length =
SEQUENCE: 552
000

SEQ ID NO: 553 moltype = length =
SEQUENCE: 553
000

SEQ ID NO: 554 moltype = length =
SEQUENCE: 554
000

SEQ ID NO: 555 moltype = length =
SEQUENCE: 555
000

SEQ ID NO: 556 moltype = length =
SEQUENCE: 556
000

SEQ ID NO: 557 moltype = length =
SEQUENCE: 557
000

SEQ ID NO: 558 moltype = length =
SEQUENCE: 558
000

SEQ ID NO: 559 moltype = length =
SEQUENCE: 559
000

SEQ ID NO: 560 moltype = length =
SEQUENCE: 560
000

SEQ ID NO: 561 moltype = AA length = 699
FEATURE Location/Qualifiers
source 1..699
mol_type = protein
organism = synthetic construct
SEQUENCE: 561
MGSSHHHHHH GSDYKDDDDK SGSLEVLFQG PSGMPYYYRR RRYNYRRPRW YGRGWIRRPF 60
RRRFRRKRRV RPTYTTIPLK QWQPPYKRTC YIKGQDCLIY YSNLRLGMNS TMYEKSIVPV 120

```
HWPGGGSFSV SMLTLDALYD IHKLCRNWWT STNQDLPLVR YKGCKITFYQ STFTDYIVRI  180
HTELPANSNK LTYPNTHPLM MMMSKYKHII PSRQTRRKKK PYTKIFVKPP PQFENKWYFA  240
TDLYKIPLLQ IHCTACNLQN PFVKPDKLSN NVTLWSLNTI SIQNRNMSVD QGQSWPFKIL  300
GTQSFYFYFY TGANLPGDTT QIPVADLLPL TNPRINRPGQ SLNEAKITDH ITFTEYKNKF  360
TNYWGNPFNK HIQEHLDMIL YSLKSPEAIK NEWTTENMKW NQLNNAGTMA LTPFNEPIFT  420
QIQYNPDRDT GEDTQLYLLS NATGTGWDPP GIPELILEGF PLWLIYWGFA DFQKNLKKVT  480
NIDTNYMLVA KTKFTQKPGT FYLVILNDTF VEGNSPYEKQ PLPEDNIKWY PQVQYQLEAQ  540
NKLLQTGPFT PNIQGQLSDN ISMFYKFYFK WGGSPPKAIN VENPAHQIQY PIPRNEHETT  600
SLQSPGEAPE SILYSFDYRH GNYTTTALSR ISQDWALKDT VSKITEPDRQ QLLKQALECL  660
QISEETQEKK EKEVQQLISN LRQQQQLYRE RIISLLKDQ                         699

SEQ ID NO: 562          moltype = AA  length = 688
FEATURE                 Location/Qualifiers
source                  1..688
                        mol_type = protein
                        organism = synthetic construct
SEQUENCE: 562
MGSSHHHHHH GSDYKDDDDK SGSLEVLFQG PSGMPPYWRQ KYYRRRYRPF SWRTRRIIQR  60
RKRWRYRKPR KTYWRRKLRV RKRFYKRKLK KIVLKQFQPK IIRRCTIFGT ICLFQGSPER  120
ANNNYIQTIY SYVPDKEPGG GGWTLITESL SSLWEDWEHL KNVWTQSNAG LPLVRYGGVT  180
LYFYQSAYTD YIAQVFNCYP MTDTKYTHAD SAPNRMLLKK HVIRVPSRET RKKRKPYKRV  240
RVGPPSQMQN KWYFQRDICE IPLIMIAATA VDFRYPFCAS DCASNNLTLT CLNPLLFQNQ  300
DFDHPSDTQG YFPKPGVYLY STQRSNKPSS SDCIYLGNTK DNQEGKSASS LMTLKTQKIT  360
DWGNPFWHYY IDGSKKIFSY FKPPSQLDSS DFEHMTELAE PMFIQVRYNP ERDTGQGNLI  420
YVTENFRGQH WDPPSSDNLK LDGFPLYDMC WGFIDWIEKV HETENLLTNY CFCIRSSAFN  480
EKKTVFIPVD HSFLTGFSPY ETPVKSSDQA HWHPQIRFQT KSINDICLTG PGCARSPYGN  540
YMQAKMSYKF HVKWGGCPKT YEKPYDPCSQ PNWTIPHNLN ETIQIQNPNT CPQTELQEWD  600
WRRDIVTKKA IERIRQHTEP HETLQISTGS KHNPPVHRQT SPWTDSETDS EEEKDQTQEI  660
QIQLNKLRKH QQHLKQQLKQ YLKPQNIE                                    688

SEQ ID NO: 563          moltype = AA  length = 714
FEATURE                 Location/Qualifiers
source                  1..714
                        mol_type = protein
                        organism = synthetic construct
SEQUENCE: 563
MGSSHHHHHH GSDYKDDDDK SGSLEVLFQG PSGMPPYWRQ KYYRRRYRPF SWRTRRIIQR  60
RKRWRYRKPR KTYWRRKLRV RKRRVRPTYT TIPLKQWQPP YKRTCYIKGQ DCLIYYSNLR  120
LGMNSTMYEK SIVPVHWPGG GSFSVSMLTL DALYDIHKLC RNWWTSTNQD LPLVRYKGCK  180
ITFYQSTFTD YIVRIHTELP ANSNKLTYPN THPLMMMMSK YKHIIPSRQT RRKKKPYTKI  240
FVKPPPQFEN KWYFATDLYK IPLLQIHCTA CNLQNPFVKP DKLSNNVTLW SLNTISIQNR  300
NMSVDQGQSW PFKILGTQSF YFYFYTGANL PGDTTQIPVA DLLPLTNPRI NRPGQSLNEA  360
KITDHITFTE YKNKFTNYWG NPFNKHIQEH LDMILYSLKS PEAIKNEWTT ENMKWNQLNN  420
AGTMALTPFN EPIFTQIQYN PDRDTGEDTQ LYLLSNATGT GWDPPGIPEL ILEGFPLWLI  480
YWGFADFQKN LKKVTNIDTN YMLVAKTKFT QKPGTFYLVI LNDTFVEGNS PYEKQPLPED  540
NIKWYPQVQY QLEAQNKLLQ TGPFTPNIQG QLSDNISMFY KFYFKWGGSP PKAINVENPA  600
HQIQYPIPRN EHETTSLQSP GEAPESILYS FDYRHGNYTT TALSRISQDW ALKDTVSKIT  660
EPDRQQLLKQ ALECLQISEE TQEKKEKEVQ QLISNLRQQQ QLYRERIISL LKDQ        714

SEQ ID NO: 564          moltype = AA  length = 714
FEATURE                 Location/Qualifiers
source                  1..714
                        mol_type = protein
                        organism = synthetic construct
SEQUENCE: 564
MGSSHHHHHH GSDYKDDDDK SGSLEVLFQG PSGMPPYWRQ KYYRRRYRPF SWRTRRIIQR  60
RKRWRYRKPR KTYWRRKLRV RKRFYKRKLK KIVLKQFQPK IIRRCTIFGT ICLFQGSNLR  120
LGMNSTMYEK SIVPVHWPGG GSFSVSMLTL DALYDIHKLC RNWWTSTNQD LPLVRYKGCK  180
ITFYQSTFTD YIVRIHTELP ANSNKLTYPN THPLMMMMSK YKHIIPSRQT RRKKKPYTKI  240
FVKPPPQFEN KWYFATDLYK IPLLQIHCTA CNLQNPFVKP DKLSNNVTLW SLNTISIQNR  300
NMSVDQGQSW PFKILGTQSF YFYFYTGANL PGDTTQIPVA DLLPLTNPRI NRPGQSLNEA  360
KITDHITFTE YKNKFTNYWG NPFNKHIQEH LDMILYSLKS PEAIKNEWTT ENMKWNQLNN  420
AGTMALTPFN EPIFTQIQYN PDRDTGEDTQ LYLLSNATGT GWDPPGIPEL ILEGFPLWLI  480
YWGFADFQKN LKKVTNIDTN YMLVAKTKFT QKPGTFYLVI LNDTFVEGNS PYEKQPLPED  540
NIKWYPQVQY QLEAQNKLLQ TGPFTPNIQG QLSDNISMFY KFYFKWGGSP PKAINVENPA  600
HQIQYPIPRN EHETTSLQSP GEAPESILYS FDYRHGNYTT TALSRISQDW ALKDTVSKIT  660
EPDRQQLLKQ ALECLQISEE TQEKKEKEVQ QLISNLRQQQ QLYRERIISL LKDQ        714

SEQ ID NO: 565          moltype = AA  length = 688
FEATURE                 Location/Qualifiers
source                  1..688
                        mol_type = protein
                        organism = synthetic construct
SEQUENCE: 565
MGSSHHHHHH GSDYKDDDDK SGSLEVLFQG PSGMPPYWRQ KYYRRRYRPF SWRTRRIIQR  60
RHRWRYRKPR HTYWRRHLRV RHRFYHRHLH HIVLKQFQPK IIRRCTIFGT ICLFQGSPER  120
ANNNYIQTIY SYVPDKEPGG GGWTLITESL SSLWEDWEHL KNVWTQSNAG LPLVRYGGVT  180
LYFYQSAYTD YIAQVFNCYP MTDTKYTHAD SAPNRMLLKK HVIRVPSRET RKKRKPYKRV  240
RVGPPSQMQN KWYFQRDICE IPLIMIAATA VDFRYPFCAS DCASNNLTLT CLNPLLFQNQ  300
```

```
DFDHPSDTQG YFPKPGVYLY STQRSNKPSS SDCIYLGNTK DNQEGKSASS LMTLKTQKIT  360
DWGNPFWHYY IDGSKKIFSY FKPPSQLDSS DFEHMTELAE PMFIQVRYNP ERDTGQGNLI  420
YVTENFRGQH WDPPSSDNLK LDGFPLYDMC WGFIDWIEKV HETENLLTNY CFCIRSSAFN  480
EKKTVFIPVD HSFLTGFSPY ETPVKSSDQA HWHPQIRFQT KSINDICLTG PGCARSPYGN  540
YMQAKMSYKF HVKWGGCPKT YEKPYDPCSQ PNWTIPHNLN ETIQIQNPNT CPQTELQEWD  600
WRRDIVTKKA IERIRQHTEP HETLQISTGS KHNPPVHRQT SPWTDSETDS EEEKDQTQEI  660
QIQLNKLRKH QQHLKQQLKQ YLKPQNIE                                    688

SEQ ID NO: 566          moltype = AA  length = 687
FEATURE                 Location/Qualifiers
source                  1..687
                        mol_type = protein
                        organism = synthetic construct
SEQUENCE: 566
MGSSHHHHHH GSDYKDDDDK SGSLEVLFQG PSGMWGTSNC ACAKFQIRRR YARPYRRRHI  60
RRYRRRRRHF RRRRFTTNRR KRFYKRKLKK IVLKQFQPKI IRRCTIFGTI CLFQGSPERA  120
NNNYIQTIYS YVPDKEPGGG GWTLITESLS SLWEDWEHLK NVWTQSNAGL PLVRYGGVTL  180
YFYQSAYTDY IAQVFNCYPM TDTKYTHADS APNRMLLKKH VIRVPSRETR KKRKPYKRVR  240
VGPPSQMQNK WYFQRDICEI PLIMIAATAV DFRYPFCASD CASNNLTLTC LNPLLFQNQD  300
FDHPSDTQGY FPKPGVYLYS TQRSNKPSSS DCIYLGNTKD NQEGKSASSL MTLKTQKITD  360
WGNPFWHYYI DGSKKIFSYF KPPSQLDSSD FEHMTELAEP MFIQVRYNPE RDTGQGNLIY  420
VTENFRGQHW DPPSSDNLKL DGFPLYDMCW GFIDWIEKVH ETENLLTNYC FCIRSSAFNE  480
KKTVFIPVDH SFLTGFSPYE TPVKSSDQAH WHPQIRFQTK SINDICLTGP GCARSPYGNY  540
MQAKMSYKFH VKWGGCPKTY EKPYDPCSQP NWTIPHNLNE TIQIQNPNTC PQTELQEWDW  600
RRDIVTKKAI ERIRQHTEPH ETLQISTGSK HNPPVHRQTS PWTDSETDSE EEKDQTQEIQ  660
IQLNKLRKHQ QHLKQQLKQY LKPQNIE                                     687

SEQ ID NO: 567          moltype = AA  length = 688
FEATURE                 Location/Qualifiers
source                  1..688
                        mol_type = protein
                        organism = synthetic construct
SEQUENCE: 567
MGSSHHHHHH GSDYKDDDDK SGSLEVLFQG PSGMPPYWRQ KYYRRRYRPF SWRTRRIIQR  60
RKRWRYRKPR KTYWRRKLRV RKRFYKRKLK KIVLKQFQPK IIRRCTIFGT ICLFQGSPER  120
ANNNYIQTIY SYVPDKEPGG GGWTLITESL SSLWEDWEHL KNVWTQSNAG LPLVRYGGVT  180
LYFYQSAYTD YIAQVFNCYP MTDTKYTHAD SAPNRMLLKK HAKKWFSRET RKKRKPGFKR  240
LLGPPSQMQN KWYFQRDICE IPLIMIAATA VDFRYPFCAS DCASNNLTLT CLNPLLFQNQ  300
DFDHPSDTQG YFPKPGVYLY STQRSNKPSS SDCIYLGNTK DNQEGKSASS LMTLKTQKIT  360
DWGNPFWHYY IDGSKKIFSY FKPPSQLDSS DFEHMTELAE PMFIQVRYNP ERDTGQGNLI  420
YVTENFRGQH WDPPSSDNLK LDGFPLYDMC WGFIDWIEKV HETENLLTNY CFCIRSSAFN  480
EKKTVFIPVD HSFLTGFSPY ETPVKSSDQA HWHPQIRFQT KSINDICLTG PGCARSPYGN  540
YMQAKMSYKF HVKWGGCPKT YEKPYDPCSQ PNWTIPHNLN ETIQIQNPNT CPQTELQEWD  600
WRRDIVTKKA IERIRQHTEP HETLQISTGS KHNPPVHRQT SPWTDSETDS EEEKDQTQEI  660
QIQLNKLRKH QQHLKQQLKQ YLKPQNIE                                    688

SEQ ID NO: 568          moltype = AA  length = 699
FEATURE                 Location/Qualifiers
source                  1..699
                        mol_type = protein
                        organism = synthetic construct
SEQUENCE: 568
MGSSHHHHHH GSDYKDDDDK SGSLEVLFQG PSGMPYYYRR RRYNYRRPRW YGRGWIRRPF  60
RRRFRRKRRV RPTYTTIPLK QWQPPYKRRC TIFGTICLFQ GSNLRLGMNS TMYEKSIVPV  120
HWPGGGSFSV SMLTLDALYD IHKLCRNWWT STNQDLPLVR YKGCKITFYQ STFTDYIVRI  180
HTELPANSNK LTYPNTHPLM MMMSKYKHII PSRQTRRKKK PYTKIFVKPP PQFENKWYFA  240
TDLYKIPLLQ IHCTACNLQN PFVKPDKLSN NVTLWSLNTI SIQNRNMSVD QGQSWPFKIL  300
GTQSFYFYFY TGANLPGDTT QIPVADLLPL TNPRINRPGQ SLNEAKITDH ITFTEYKNKF  360
TNYWGNPFNK HIQEHLDMIL YSLKSPEAIK NEWTTENMKW NQLNNAGTMA LTPFNEPIFT  420
QIQYNPDRDT GEDTQLYLLS NATGTGWDPP GIPELILEGF PLWLIYWGFA DFQKNLKKVT  480
NIDTNYMLVA KTKFTQKPGT FYLVILNDTF VEGNSPYEKQ PLPEDNIKWY PQVQYQLEAQ  540
NKLLQTGPFT PNIQGQLSDN ISMFYKFYFK WGGSPPKAIN VENPAHQIQY PIPRNEHETT  600
SLQSPGEAPE SILYSFDYRH GNYTTTALSR ISQDWALKDT VSKITEPDRQ QLLKQALECL  660
QISEETQEKK EKEVQQLISN LRQQQQLYRE RIISLLKDQ                        699

SEQ ID NO: 569          moltype = AA  length = 699
FEATURE                 Location/Qualifiers
source                  1..699
                        mol_type = protein
                        organism = synthetic construct
SEQUENCE: 569
MGSSHHHHHH GSDYKDDDDK SGSLEVLFQG PSGMPYYYRR RRYNYRRPRW YGRGWIRRPF  60
RRRFRRKRRV RPTYTTIPLK QWQPPYKRTC YIKGQDCLIY YSPERANNNY IQTIYSYVPD  120
KEPGGGGWTL ITESLSSLWE DWEHLKNVWT QSNAGLPLVR YKGCKITFYQ STFTDYIVRI  180
HTELPANSNK LTYPNTHPLM MMMSKYKHII PSRQTRRKKK PYTKIFVKPP PQFENKWYFA  240
TDLYKIPLLQ IHCTACNLQN PFVKPDKLSN NVTLWSLNTI SIQNRNMSVD QGQSWPFKIL  300
GTQSFYFYFY TGANLPGDTT QIPVADLLPL TNPRINRPGQ SLNEAKITDH ITFTEYKNKF  360
TNYWGNPFNK HIQEHLDMIL YSLKSPEAIK NEWTTENMKW NQLNNAGTMA LTPFNEPIFT  420
QIQYNPDRDT GEDTQLYLLS NATGTGWDPP GIPELILEGF PLWLIYWGFA DFQKNLKKVT  480
```

-continued

```
NIDTNYMLVA KTKFTQKPGT FYLVILNDTF VEGNSPYEKQ PLPEDNIKWY PQVQYQLEAQ  540
NKLLQTGPFT PNIQGQLSDN ISMFYKFYFK WGGSPPKAIN VENPAHQIQY PIPRNEHETT  600
SLQSPGEAPE SILYSFDYRH GNYTTTALSR ISQDWALKDT VSKITEPDRQ QLLKQALECL  660
QISEETQEKK EKEVQQLISN LRQQQQLYRE RIISLLKDQ                        699

SEQ ID NO: 570          moltype = AA  length = 699
FEATURE                 Location/Qualifiers
source                  1..699
                        mol_type = protein
                        organism = synthetic construct
SEQUENCE: 570
MGSSHHHHHH GSDYKDDDDK SGSLEVLFQG PSGMPYYYRR RRYNYRRPRW YGRGWIRRPF  60
RRRFRRKRRV RPTYTTIPLK QWQPPYKRTC YIKGQDCLIY YSNLRLGMNS TMYEKSIVPV  120
HWPGGGSFSV SMLTLDALYD IHKLCRNWWT STNQDLPLVR YGGVTLYFYQ STFTDYIVRI  180
HTELPANSNK LTYPNTHPLM MMMSKYKHII PSRQTRRKKK PYTKIFVKPP PQFENKWYFA  240
TDLYKIPLLQ IHCTACNLQN PFVKPDKLSN NVTLWSLNTI SIQNRNMSVD QGQSWPFKIL  300
GTQSFYFYFY TGANLPGDTT QIPVADLLPL TNPRINRPGQ SLNEAKITDH ITFTEYKNKF  360
TNYWGNPFNK HIQEHLDMIL YSLKSPEAIK NEWTTENMKW NQLNNAGTMA LTPFNEPIFT  420
QIQYNPDRDT GEDTQLYLLS NATGTGWDPP GIPELILEGF PLWLIYWGFA DFQKNLKKVT  480
NIDTNYMLVA KTKFTQKPGT FYLVILNDTF VEGNSPYEKQ PLPEDNIKWY PQVQYQLEAQ  540
NKLLQTGPFT PNIQGQLSDN ISMFYKFYFK WGGSPPKAIN VENPAHQIQY PIPRNEHETT  600
SLQSPGEAPE SILYSFDYRH GNYTTTALSR ISQDWALKDT VSKITEPDRQ QLLKQALECL  660
QISEETQEKK EKEVQQLISN LRQQQQLYRE RIISLLKDQ                        699

SEQ ID NO: 571          moltype = AA  length = 699
FEATURE                 Location/Qualifiers
source                  1..699
                        mol_type = protein
                        organism = synthetic construct
SEQUENCE: 571
MGSSHHHHHH GSDYKDDDDK SGSLEVLFQG PSGMPYYYRR RRYNYRRPRW YGRGWIRRPF  60
RRRFRRKRRV RPTYTTIPLK QWQPPYKRTC YIKGQDCLIY YSNLRLGMNS TMYEKSIVPV  120
HWPGGGSFSV SMLTLDALYD IHKLCRNWWT STNQDLPLVR YKGCKITFYQ STFTDYIVRI  180
HNCYPMTDTK YTHADSAPNR MLLKKHKHII PSRQTRRKKK PYTKIFVKPP PQFENKWYFA  240
TDLYKIPLLQ IHCTACNLQN PFVKPDKLSN NVTLWSLNTI SIQNRNMSVD QGQSWPFKIL  300
GTQSFYFYFY TGANLPGDTT QIPVADLLPL TNPRINRPGQ SLNEAKITDH ITFTEYKNKF  360
TNYWGNPFNK HIQEHLDMIL YSLKSPEAIK NEWTTENMKW NQLNNAGTMA LTPFNEPIFT  420
QIQYNPDRDT GEDTQLYLLS NATGTGWDPP GIPELILEGF PLWLIYWGFA DFQKNLKKVT  480
NIDTNYMLVA KTKFTQKPGT FYLVILNDTF VEGNSPYEKQ PLPEDNIKWY PQVQYQLEAQ  540
NKLLQTGPFT PNIQGQLSDN ISMFYKFYFK WGGSPPKAIN VENPAHQIQY PIPRNEHETT  600
SLQSPGEAPE SILYSFDYRH GNYTTTALSR ISQDWALKDT VSKITEPDRQ QLLKQALECL  660
QISEETQEKK EKEVQQLISN LRQQQQLYRE RIISLLKDQ                        699

SEQ ID NO: 572          moltype = AA  length = 699
FEATURE                 Location/Qualifiers
source                  1..699
                        mol_type = protein
                        organism = synthetic construct
SEQUENCE: 572
MGSSHHHHHH GSDYKDDDDK SGSLEVLFQG PSGMPYYYRR RRYNYRRPRW YGRGWIRRPF  60
RRRFRRKRRV RPTYTTIPLK QWQPPYKRTC YIKGQDCLIY YSNLRLGMNS TMYEKSIVPV  120
HWPGGGSFSV SMLTLDALYD IHKLCRNWWT STNQDLPLVR YKGCKITFYQ STFTDYIVRI  180
HTELPANSNK LTYPNTHPLM MMMSKYKHII PSRQTRRKKK PYKRVRVKPP PQFENKWYFA  240
TDLYKIPLLQ IHCTACNLQN PFVKPDKLSN NVTLWSLNTI SIQNRNMSVD QGQSWPFKIL  300
GTQSFYFYFY TGANLPGDTT QIPVADLLPL TNPRINRPGQ SLNEAKITDH ITFTEYKNKF  360
TNYWGNPFNK HIQEHLDMIL YSLKSPEAIK NEWTTENMKW NQLNNAGTMA LTPFNEPIFT  420
QIQYNPDRDT GEDTQLYLLS NATGTGWDPP GIPELILEGF PLWLIYWGFA DFQKNLKKVT  480
NIDTNYMLVA KTKFTQKPGT FYLVILNDTF VEGNSPYEKQ PLPEDNIKWY PQVQYQLEAQ  540
NKLLQTGPFT PNIQGQLSDN ISMFYKFYFK WGGSPPKAIN VENPAHQIQY PIPRNEHETT  600
SLQSPGEAPE SILYSFDYRH GNYTTTALSR ISQDWALKDT VSKITEPDRQ QLLKQALECL  660
QISEETQEKK EKEVQQLISN LRQQQQLYRE RIISLLKDQ                        699

SEQ ID NO: 573          moltype = AA  length = 699
FEATURE                 Location/Qualifiers
source                  1..699
                        mol_type = protein
                        organism = synthetic construct
SEQUENCE: 573
MGSSHHHHHH GSDYKDDDDK SGSLEVLFQG PSGMPYYYRR RRYNYRRPRW YGRGWIRRPF  60
RRRFRRKRRV RPTYTTIPLK QWQPPYKRTC YIKGQDCLIY YSNLRLGMNS TMYEKSIVPV  120
HWPGGGSFSV SMLTLDALYD IHKLCRNWWT STNQDLPLVR YKGCKITFYQ STFTDYIVRI  180
HTELPANSNK LTYPNTHPLM MMMSKHVIRV PSRQTRRKKK PYTKIFVKPP PQFENKWYFA  240
TDLYKIPLLQ IHCTACNLQN PFVKPDKLSN NVTLWSLNTI SIQNRNMSVD QGQSWPFKIL  300
GTQSFYFYFY TGANLPGDTT QIPVADLLPL TNPRINRPGQ SLNEAKITDH ITFTEYKNKF  360
TNYWGNPFNK HIQEHLDMIL YSLKSPEAIK NEWTTENMKW NQLNNAGTMA LTPFNEPIFT  420
QIQYNPDRDT GEDTQLYLLS NATGTGWDPP GIPELILEGF PLWLIYWGFA DFQKNLKKVT  480
NIDTNYMLVA KTKFTQKPGT FYLVILNDTF VEGNSPYEKQ PLPEDNIKWY PQVQYQLEAQ  540
NKLLQTGPFT PNIQGQLSDN ISMFYKFYFK WGGSPPKAIN VENPAHQIQY PIPRNEHETT  600
SLQSPGEAPE SILYSFDYRH GNYTTTALSR ISQDWALKDT VSKITEPDRQ QLLKQALECL  660
```

-continued

```
QISEETQEKK EKEVQQLISN LRQQQQLYRE RIISLLKDQ                      699

SEQ ID NO: 574          moltype = AA  length = 673
FEATURE                 Location/Qualifiers
source                  1..673
                        mol_type = protein
                        organism = synthetic construct
SEQUENCE: 574
MGSSHHHHHH GSDYKDDDDK SGSLEVLFQG PSGMPYYYRR RRYNYRRPRW YGRGWIRRPF  60
RRRFRRKRRV RPTYTTIPLK QWQPPYKRTC YIKGQDCLIY YSNLRLGMNS TMYEKSIVPV  120
HWPGGGSFSV SMLTLDALYD IHKLCRNWWT STNQDLPLVR YKGCKITFYQ STFTDYIVRI  180
HTELPANSNK LTYPNTHPLM MMMSKYKHII PSRQTRRKKK PYTKIFVKPP PQFENKWYFA  240
TDLYKIPLIM IAATAVDFRY PFCASDCASN NLTLTCLNPL LFQNQDFDHP SDTQGYFPKP  300
GVYLYSTQRS NKPSSSDCIY LGNTKDNQEG KSASSLMTLK TQKITDWGNP FWHYYIDGSK  360
KIFSYFKPPS QLDSSDFEHM TELAEPMFIQ VRYNPERDTG QGNLIYVTEN FRGQHWDPPS  420
SDNLKLDGFP LYDMCWGFID WIEKVHETEN LLTNYCFCIR SSAFNEKKTV FIPVDHSFLT  480
GFSPYETPVK SSDQAHWHPQ IRFQTKSIND ICLTGPGCAR SPYGNYMQAK MSYKFHVKWG  540
GCPKTYEKPY DPCSQPNWTI PHNLNETIQI QNPNTCPQTE LQEWDWRRDI VTKKAIERIR  600
QHTEPHETLQ ISTGSKHNPP VHRQTSPWTD SETDSEEEKD QTQEIQIQLN KLRKHQQHLK  660
QQLKQYLKPQ NIE                                                  673

SEQ ID NO: 575          moltype = AA  length = 673
FEATURE                 Location/Qualifiers
source                  1..673
                        mol_type = protein
                        organism = synthetic construct
SEQUENCE: 575
MGSSHHHHHH GSDYKDDDDK SGSLEVLFQG PSGMPYYYRR RRYNYRRPRW YGRGWIRRPF  60
RRRFRRKRRV RPTYTTIPLK QWQPPYKRTC YIKGQDCLIY YSNLRLGMNS TMYEKSIVPV  120
HWPGGGSFSV SMLTLDALYD IHKLCRNWWT STNQDLPLVR YKGCKITFYQ STFTDYIVRI  180
HTELPANSNK LTYPNTHPLM MMMSKYKHII PSRQTRRKKK PYTKIFVKPP PQFENKWYFA  240
TDLYKIPLLQ IHCTACNLQN PFVKPDKLSN NLTLTCLNPL LFQNQDFDHP SDTQGYFPKP  300
GVYLYSTQRS NKPSSSDCIY LGNTKDNQEG KSASSLMTLK TQKITDWGNP FWHYYIDGSK  360
KIFSYFKPPS QLDSSDFEHM TELAEPMFIQ VRYNPERDTG QGNLIYVTEN FRGQHWDPPS  420
SDNLKLDGFP LYDMCWGFID WIEKVHETEN LLTNYCFCIR SSAFNEKKTV FIPVDHSFLT  480
GFSPYETPVK SSDQAHWHPQ IRFQTKSIND ICLTGPGCAR SPYGNYMQAK MSYKFHVKWG  540
GCPKTYEKPY DPCSQPNWTI PHNLNETIQI QNPNTCPQTE LQEWDWRRDI VTKKAIERIR  600
QHTEPHETLQ ISTGSKHNPP VHRQTSPWTD SETDSEEEKD QTQEIQIQLN KLRKHQQHLK  660
QQLKQYLKPQ NIE                                                  673

SEQ ID NO: 576          moltype =   length =
SEQUENCE: 576
000

SEQ ID NO: 577          moltype =   length =
SEQUENCE: 577
000

SEQ ID NO: 578          moltype =   length =
SEQUENCE: 578
000

SEQ ID NO: 579          moltype =   length =
SEQUENCE: 579
000

SEQ ID NO: 580          moltype =   length =
SEQUENCE: 580
000

SEQ ID NO: 581          moltype =   length =
SEQUENCE: 581
000

SEQ ID NO: 582          moltype =   length =
SEQUENCE: 582
000

SEQ ID NO: 583          moltype =   length =
SEQUENCE: 583
000

SEQ ID NO: 584          moltype =   length =
SEQUENCE: 584
000

SEQ ID NO: 585          moltype =   length =
SEQUENCE: 585
000
```

SEQ ID NO: 586 moltype = length =
SEQUENCE: 586
000

SEQ ID NO: 587 moltype = length =
SEQUENCE: 587
000

SEQ ID NO: 588 moltype = length =
SEQUENCE: 588
000

SEQ ID NO: 589 moltype = length =
SEQUENCE: 589
000

SEQ ID NO: 590 moltype = length =
SEQUENCE: 590
000

SEQ ID NO: 591 moltype = length =
SEQUENCE: 591
000

SEQ ID NO: 592 moltype = length =
SEQUENCE: 592
000

SEQ ID NO: 593 moltype = length =
SEQUENCE: 593
000

SEQ ID NO: 594 moltype = length =
SEQUENCE: 594
000

SEQ ID NO: 595 moltype = length =
SEQUENCE: 595
000

SEQ ID NO: 596 moltype = length =
SEQUENCE: 596
000

SEQ ID NO: 597 moltype = length =
SEQUENCE: 597
000

SEQ ID NO: 598 moltype = length =
SEQUENCE: 598
000

SEQ ID NO: 599 moltype = length =
SEQUENCE: 599
000

SEQ ID NO: 600 moltype = length =
SEQUENCE: 600
000

SEQ ID NO: 601 moltype = length =
SEQUENCE: 601
000

SEQ ID NO: 602 moltype = length =
SEQUENCE: 602
000

SEQ ID NO: 603 moltype = length =
SEQUENCE: 603
000

SEQ ID NO: 604 moltype = length =
SEQUENCE: 604
000

SEQ ID NO: 605 moltype = length =
SEQUENCE: 605

```
000

SEQ ID NO: 606         moltype =   length =
SEQUENCE: 606
000

SEQ ID NO: 607         moltype =   length =
SEQUENCE: 607
000

SEQ ID NO: 608         moltype =   length =
SEQUENCE: 608
000

SEQ ID NO: 609         moltype =   length =
SEQUENCE: 609
000

SEQ ID NO: 610         moltype =   length =
SEQUENCE: 610
000

SEQ ID NO: 611         moltype =   length =
SEQUENCE: 611
000

SEQ ID NO: 612         moltype =   length =
SEQUENCE: 612
000

SEQ ID NO: 613         moltype =   length =
SEQUENCE: 613
000

SEQ ID NO: 614         moltype =   length =
SEQUENCE: 614
000

SEQ ID NO: 615         moltype =   length =
SEQUENCE: 615
000

SEQ ID NO: 616         moltype =   length =
SEQUENCE: 616
000

SEQ ID NO: 617         moltype =   length =
SEQUENCE: 617
000

SEQ ID NO: 618         moltype =   length =
SEQUENCE: 618
000

SEQ ID NO: 619         moltype =   length =
SEQUENCE: 619
000

SEQ ID NO: 620         moltype =   length =
SEQUENCE: 620
000

SEQ ID NO: 621         moltype =   length =
SEQUENCE: 621
000

SEQ ID NO: 622         moltype =   length =
SEQUENCE: 622
000

SEQ ID NO: 623         moltype =   length =
SEQUENCE: 623
000

SEQ ID NO: 624         moltype =   length =
SEQUENCE: 624
000

SEQ ID NO: 625         moltype =   length =
```

SEQUENCE: 625
000

SEQ ID NO: 626 moltype = length =
SEQUENCE: 626
000

SEQ ID NO: 627 moltype = length =
SEQUENCE: 627
000

SEQ ID NO: 628 moltype = length =
SEQUENCE: 628
000

SEQ ID NO: 629 moltype = length =
SEQUENCE: 629
000

SEQ ID NO: 630 moltype = length =
SEQUENCE: 630
000

SEQ ID NO: 631 moltype = length =
SEQUENCE: 631
000

SEQ ID NO: 632 moltype = length =
SEQUENCE: 632
000

SEQ ID NO: 633 moltype = length =
SEQUENCE: 633
000

SEQ ID NO: 634 moltype = length =
SEQUENCE: 634
000

SEQ ID NO: 635 moltype = length =
SEQUENCE: 635
000

SEQ ID NO: 636 moltype = length =
SEQUENCE: 636
000

SEQ ID NO: 637 moltype = length =
SEQUENCE: 637
000

SEQ ID NO: 638 moltype = length =
SEQUENCE: 638
000

SEQ ID NO: 639 moltype = length =
SEQUENCE: 639
000

SEQ ID NO: 640 moltype = length =
SEQUENCE: 640
000

SEQ ID NO: 641 moltype = length =
SEQUENCE: 641
000

SEQ ID NO: 642 moltype = length =
SEQUENCE: 642
000

SEQ ID NO: 643 moltype = length =
SEQUENCE: 643
000

SEQ ID NO: 644 moltype = length =
SEQUENCE: 644
000

SEQ ID NO: 645 moltype = length =
SEQUENCE: 645
000

SEQ ID NO: 646 moltype = length =
SEQUENCE: 646
000

SEQ ID NO: 647 moltype = length =
SEQUENCE: 647
000

SEQ ID NO: 648 moltype = length =
SEQUENCE: 648
000

SEQ ID NO: 649 moltype = length =
SEQUENCE: 649
000

SEQ ID NO: 650 moltype = length =
SEQUENCE: 650
000

SEQ ID NO: 651 moltype = length =
SEQUENCE: 651
000

SEQ ID NO: 652 moltype = length =
SEQUENCE: 652
000

SEQ ID NO: 653 moltype = length =
SEQUENCE: 653
000

SEQ ID NO: 654 moltype = length =
SEQUENCE: 654
000

SEQ ID NO: 655 moltype = length =
SEQUENCE: 655
000

SEQ ID NO: 656 moltype = length =
SEQUENCE: 656
000

SEQ ID NO: 657 moltype = length =
SEQUENCE: 657
000

SEQ ID NO: 658 moltype = length =
SEQUENCE: 658
000

SEQ ID NO: 659 moltype = length =
SEQUENCE: 659
000

SEQ ID NO: 660 moltype = length =
SEQUENCE: 660
000

SEQ ID NO: 661 moltype = length =
SEQUENCE: 661
000

SEQ ID NO: 662 moltype = length =
SEQUENCE: 662
000

SEQ ID NO: 663 moltype = length =
SEQUENCE: 663
000

SEQ ID NO: 664 moltype = length =
SEQUENCE: 664
000

SEQ ID NO: 665 moltype = length =
SEQUENCE: 665
000

SEQ ID NO: 666 moltype = length =
SEQUENCE: 666
000

SEQ ID NO: 667 moltype = length =
SEQUENCE: 667
000

SEQ ID NO: 668 moltype = length =
SEQUENCE: 668
000

SEQ ID NO: 669 moltype = length =
SEQUENCE: 669
000

SEQ ID NO: 670 moltype = length =
SEQUENCE: 670
000

SEQ ID NO: 671 moltype = length =
SEQUENCE: 671
000

SEQ ID NO: 672 moltype = length =
SEQUENCE: 672
000

SEQ ID NO: 673 moltype = length =
SEQUENCE: 673
000

SEQ ID NO: 674 moltype = length =
SEQUENCE: 674
000

SEQ ID NO: 675 moltype = length =
SEQUENCE: 675
000

SEQ ID NO: 676 moltype = length =
SEQUENCE: 676
000

SEQ ID NO: 677 moltype = length =
SEQUENCE: 677
000

SEQ ID NO: 678 moltype = length =
SEQUENCE: 678
000

SEQ ID NO: 679 moltype = length =
SEQUENCE: 679
000

SEQ ID NO: 680 moltype = length =
SEQUENCE: 680
000

SEQ ID NO: 681 moltype = length =
SEQUENCE: 681
000

SEQ ID NO: 682 moltype = length =
SEQUENCE: 682
000

SEQ ID NO: 683 moltype = length =
SEQUENCE: 683
000

SEQ ID NO: 684 moltype = length =
SEQUENCE: 684

```
000

SEQ ID NO: 685         moltype =   length =
SEQUENCE: 685
000

SEQ ID NO: 686         moltype =   length =
SEQUENCE: 686
000

SEQ ID NO: 687         moltype =   length =
SEQUENCE: 687
000

SEQ ID NO: 688         moltype =   length =
SEQUENCE: 688
000

SEQ ID NO: 689         moltype =   length =
SEQUENCE: 689
000

SEQ ID NO: 690         moltype =   length =
SEQUENCE: 690
000

SEQ ID NO: 691         moltype =   length =
SEQUENCE: 691
000

SEQ ID NO: 692         moltype =   length =
SEQUENCE: 692
000

SEQ ID NO: 693         moltype =   length =
SEQUENCE: 693
000

SEQ ID NO: 694         moltype =   length =
SEQUENCE: 694
000

SEQ ID NO: 695         moltype =   length =
SEQUENCE: 695
000

SEQ ID NO: 696         moltype =   length =
SEQUENCE: 696
000

SEQ ID NO: 697         moltype = DNA  length = 20
FEATURE                Location/Qualifiers
source                 1..20
                       mol_type = other DNA
                       organism = synthetic construct
SEQUENCE: 697
gaagcccacc aaaagcaatt                                              20

SEQ ID NO: 698         moltype = DNA  length = 21
FEATURE                Location/Qualifiers
source                 1..21
                       mol_type = other DNA
                       organism = synthetic construct
SEQUENCE: 698
agttcccgtg tctatagtcg a                                            21

SEQ ID NO: 699         moltype = DNA  length = 22
FEATURE                Location/Qualifiers
source                 1..22
                       mol_type = other DNA
                       organism = synthetic construct
SEQUENCE: 699
acttcgttac agagtccagg gg                                           22

SEQ ID NO: 700         moltype = DNA  length = 20
FEATURE                Location/Qualifiers
source                 1..20
                       mol_type = other DNA
                       organism = synthetic construct
```

```
SEQUENCE: 700
agcaacaggt aatggaggac                                              20

SEQ ID NO: 701          moltype = DNA  length = 20
FEATURE                 Location/Qualifiers
source                  1..20
                        mol_type = other DNA
                        organism = synthetic construct
SEQUENCE: 701
tggaagctgg ggtctttaac                                              20

SEQ ID NO: 702          moltype = DNA  length = 22
FEATURE                 Location/Qualifiers
source                  1..22
                        mol_type = other DNA
                        organism = synthetic construct
SEQUENCE: 702
tctaccttag gtgcaaaggg cc                                           22

SEQ ID NO: 703          moltype =   length =
SEQUENCE: 703
000

SEQ ID NO: 704          moltype =   length =
SEQUENCE: 704
000

SEQ ID NO: 705          moltype =   length =
SEQUENCE: 705
000

SEQ ID NO: 706          moltype =   length =
SEQUENCE: 706
000

SEQ ID NO: 707          moltype =   length =
SEQUENCE: 707
000

SEQ ID NO: 708          moltype =   length =
SEQUENCE: 708
000

SEQ ID NO: 709          moltype =   length =
SEQUENCE: 709
000

SEQ ID NO: 710          moltype =   length =
SEQUENCE: 710
000

SEQ ID NO: 711          moltype =   length =
SEQUENCE: 711
000

SEQ ID NO: 712          moltype =   length =
SEQUENCE: 712
000

SEQ ID NO: 713          moltype =   length =
SEQUENCE: 713
000

SEQ ID NO: 714          moltype =   length =
SEQUENCE: 714
000

SEQ ID NO: 715          moltype =   length =
SEQUENCE: 715
000

SEQ ID NO: 716          moltype =   length =
SEQUENCE: 716
000

SEQ ID NO: 717          moltype =   length =
SEQUENCE: 717
000
```

SEQ ID NO: 718 moltype = length =
SEQUENCE: 718
000

SEQ ID NO: 719 moltype = length =
SEQUENCE: 719
000

SEQ ID NO: 720 moltype = length =
SEQUENCE: 720
000

SEQ ID NO: 721 moltype = length =
SEQUENCE: 721
000

SEQ ID NO: 722 moltype = length =
SEQUENCE: 722
000

SEQ ID NO: 723 moltype = length =
SEQUENCE: 723
000

SEQ ID NO: 724 moltype = length =
SEQUENCE: 724
000

SEQ ID NO: 725 moltype = length =
SEQUENCE: 725
000

SEQ ID NO: 726 moltype = length =
SEQUENCE: 726
000

SEQ ID NO: 727 moltype = length =
SEQUENCE: 727
000

SEQ ID NO: 728 moltype = length =
SEQUENCE: 728
000

SEQ ID NO: 729 moltype = length =
SEQUENCE: 729
000

SEQ ID NO: 730 moltype = length =
SEQUENCE: 730
000

SEQ ID NO: 731 moltype = length =
SEQUENCE: 731
000

SEQ ID NO: 732 moltype = length =
SEQUENCE: 732
000

SEQ ID NO: 733 moltype = length =
SEQUENCE: 733
000

SEQ ID NO: 734 moltype = length =
SEQUENCE: 734
000

SEQ ID NO: 735 moltype = length =
SEQUENCE: 735
000

SEQ ID NO: 736 moltype = length =
SEQUENCE: 736
000

SEQ ID NO: 737 moltype = length =
SEQUENCE: 737
000

SEQ ID NO: 738 moltype = length =
SEQUENCE: 738
000

SEQ ID NO: 739 moltype = length =
SEQUENCE: 739
000

SEQ ID NO: 740 moltype = length =
SEQUENCE: 740
000

SEQ ID NO: 741 moltype = length =
SEQUENCE: 741
000

SEQ ID NO: 742 moltype = length =
SEQUENCE: 742
000

SEQ ID NO: 743 moltype = length =
SEQUENCE: 743
000

SEQ ID NO: 744 moltype = length =
SEQUENCE: 744
000

SEQ ID NO: 745 moltype = length =
SEQUENCE: 745
000

SEQ ID NO: 746 moltype = length =
SEQUENCE: 746
000

SEQ ID NO: 747 moltype = length =
SEQUENCE: 747
000

SEQ ID NO: 748 moltype = length =
SEQUENCE: 748
000

SEQ ID NO: 749 moltype = length =
SEQUENCE: 749
000

SEQ ID NO: 750 moltype = length =
SEQUENCE: 750
000

SEQ ID NO: 751 moltype = length =
SEQUENCE: 751
000

SEQ ID NO: 752 moltype = length =
SEQUENCE: 752
000

SEQ ID NO: 753 moltype = length =
SEQUENCE: 753
000

SEQ ID NO: 754 moltype = length =
SEQUENCE: 754
000

SEQ ID NO: 755 moltype = length =
SEQUENCE: 755
000

SEQ ID NO: 756 moltype = length =
SEQUENCE: 756
000

SEQ ID NO: 757 moltype = length =
SEQUENCE: 757

000

SEQ ID NO: 758 moltype = length =
SEQUENCE: 758
000

SEQ ID NO: 759 moltype = length =
SEQUENCE: 759
000

SEQ ID NO: 760 moltype = length =
SEQUENCE: 760
000

SEQ ID NO: 761 moltype = length =
SEQUENCE: 761
000

SEQ ID NO: 762 moltype = length =
SEQUENCE: 762
000

SEQ ID NO: 763 moltype = length =
SEQUENCE: 763
000

SEQ ID NO: 764 moltype = length =
SEQUENCE: 764
000

SEQ ID NO: 765 moltype = length =
SEQUENCE: 765
000

SEQ ID NO: 766 moltype = length =
SEQUENCE: 766
000

SEQ ID NO: 767 moltype = length =
SEQUENCE: 767
000

SEQ ID NO: 768 moltype = length =
SEQUENCE: 768
000

SEQ ID NO: 769 moltype = length =
SEQUENCE: 769
000

SEQ ID NO: 770 moltype = length =
SEQUENCE: 770
000

SEQ ID NO: 771 moltype = length =
SEQUENCE: 771
000

SEQ ID NO: 772 moltype = length =
SEQUENCE: 772
000

SEQ ID NO: 773 moltype = length =
SEQUENCE: 773
000

SEQ ID NO: 774 moltype = length =
SEQUENCE: 774
000

SEQ ID NO: 775 moltype = length =
SEQUENCE: 775
000

SEQ ID NO: 776 moltype = length =
SEQUENCE: 776
000

SEQ ID NO: 777 moltype = length =

SEQUENCE: 777
000

SEQ ID NO: 778 moltype = length =
SEQUENCE: 778
000

SEQ ID NO: 779 moltype = length =
SEQUENCE: 779
000

SEQ ID NO: 780 moltype = length =
SEQUENCE: 780
000

SEQ ID NO: 781 moltype = length =
SEQUENCE: 781
000

SEQ ID NO: 782 moltype = length =
SEQUENCE: 782
000

SEQ ID NO: 783 moltype = length =
SEQUENCE: 783
000

SEQ ID NO: 784 moltype = length =
SEQUENCE: 784
000

SEQ ID NO: 785 moltype = length =
SEQUENCE: 785
000

SEQ ID NO: 786 moltype = length =
SEQUENCE: 786
000

SEQ ID NO: 787 moltype = length =
SEQUENCE: 787
000

SEQ ID NO: 788 moltype = length =
SEQUENCE: 788
000

SEQ ID NO: 789 moltype = length =
SEQUENCE: 789
000

SEQ ID NO: 790 moltype = length =
SEQUENCE: 790
000

SEQ ID NO: 791 moltype = length =
SEQUENCE: 791
000

SEQ ID NO: 792 moltype = length =
SEQUENCE: 792
000

SEQ ID NO: 793 moltype = length =
SEQUENCE: 793
000

SEQ ID NO: 794 moltype = length =
SEQUENCE: 794
000

SEQ ID NO: 795 moltype = length =
SEQUENCE: 795
000

SEQ ID NO: 796 moltype = length =
SEQUENCE: 796
000

```
SEQ ID NO: 797         moltype =   length =
SEQUENCE: 797
000

SEQ ID NO: 798         moltype =   length =
SEQUENCE: 798
000

SEQ ID NO: 799         moltype =   length =
SEQUENCE: 799
000

SEQ ID NO: 800         moltype =   length =
SEQUENCE: 800
000

SEQ ID NO: 801         moltype = DNA  length = 156
FEATURE                Location/Qualifiers
source                 1..156
                       mol_type = genomic DNA
                       organism = Torque teno virus
SEQUENCE: 801
gcggcggggg ggcggccgcg ttcgcgcgcc gcccaccagg gggtgctgcg cgcccccccc  60
cgcgcatgcg cggggccccc ccccgggggg gctccgcccc cccggccccc ccccgtgcta  120
aacccaccgc gcatgcgcga ccacgccccc gccgcc                            156

SEQ ID NO: 802         moltype = DNA  length = 150
FEATURE                Location/Qualifiers
source                 1..150
                       mol_type = genomic DNA
                       organism = Torque teno virus
SEQUENCE: 802
ccgagcgtta gcgaggagtg cgaccctacc ccctgggccc acttcttcgg agccgcgcgc  60
tacgccttcg gctgcgcgcg gcacctcaga cccccgctcg tgctgacacg cttgcgcgtg  120
tcagaccact tcgggctcgc gggggtcggg                                   150

SEQ ID NO: 803         moltype = DNA  length = 122
FEATURE                Location/Qualifiers
source                 1..122
                       mol_type = genomic DNA
                       organism = Torque teno virus
SEQUENCE: 803
gccgccgcgg cggcgggggg cggcgcgctg cgcgcgccgc ccagtagggg gagccatgcg  60
cccccccccg cgcatgcgcg gggccccccc ccgcgggggg ctccgccccc cggccccccc  120
cg                                                                 122

SEQ ID NO: 804         moltype = DNA  length = 111
FEATURE                Location/Qualifiers
source                 1..111
                       mol_type = genomic DNA
                       organism = Torque teno virus
SEQUENCE: 804
cggcccagcg gcggcgcgcg cgcttcgcgc gcgcgccggg gggctccgcc cccccccgcg  60
catgcgcggg gccccccccc gcggggggct ccgccccccg gtcccccccc g           111

SEQ ID NO: 805         moltype = DNA  length = 115
FEATURE                Location/Qualifiers
source                 1..115
                       mol_type = genomic DNA
                       organism = Torque teno virus
SEQUENCE: 805
cggccgtgcg gcggcgcgcg cgcttcgcgc gcgcgccggg ggctgccgcc cccccccgcg  60
catgcgcgcg gggccccccc ccgcgggggg ctccgccccc cggccccccc ccccg       115

SEQ ID NO: 806         moltype = DNA  length = 104
FEATURE                Location/Qualifiers
source                 1..104
                       mol_type = genomic DNA
                       organism = Torque teno virus
SEQUENCE: 806
cggcggcggc gcgcgcgcta cgcgcgcgcg ccgggggggct gccgcccccc ccccgcgcat  60
gcgcggggcc cccccccgcg gggggctccg ccccccggcc cccc                   104

SEQ ID NO: 807         moltype = DNA  length = 108
FEATURE                Location/Qualifiers
source                 1..108
                       mol_type = genomic DNA
                       organism = Torque teno virus
SEQUENCE: 807
```

```
ggcggcggcg cgcgcgctac gcgcgcgcgc cggggagctc tgcccccccc cgcgcatgcg  60
cgcgggtccc ccccccgcgg ggggctccgc cccccggtcc cccccccg              108

SEQ ID NO: 808         moltype =   length =
SEQUENCE: 808
000

SEQ ID NO: 809         moltype =   length =
SEQUENCE: 809
000

SEQ ID NO: 810         moltype =   length =
SEQUENCE: 810
000

SEQ ID NO: 811         moltype =   length =
SEQUENCE: 811
000

SEQ ID NO: 812         moltype =   length =
SEQUENCE: 812
000

SEQ ID NO: 813         moltype =   length =
SEQUENCE: 813
000

SEQ ID NO: 814         moltype =   length =
SEQUENCE: 814
000

SEQ ID NO: 815         moltype =   length =
SEQUENCE: 815
000

SEQ ID NO: 816         moltype =   length =
SEQUENCE: 816
000

SEQ ID NO: 817         moltype =   length =
SEQUENCE: 817
000

SEQ ID NO: 818         moltype = DNA  length = 36
FEATURE                Location/Qualifiers
source                 1..36
                       mol_type = other DNA
                       organism = synthetic construct
SEQUENCE: 818
gcgctkcgcg cgcgcgccgg ggggctgcgc cccccc                            36

SEQ ID NO: 819         moltype = DNA  length = 36
FEATURE                Location/Qualifiers
source                 1..36
                       mol_type = genomic DNA
                       organism = Torque teno virus
SEQUENCE: 819
gcgcttcgcg cgccgcccac tagggggcgt tgcgcg                            36

SEQ ID NO: 820         moltype = DNA  length = 36
FEATURE                Location/Qualifiers
source                 1..36
                       mol_type = genomic DNA
                       organism = Torque teno virus
SEQUENCE: 820
gcgctgcgcg cgccgcccag tagggggcgc aatgcg                            36

SEQ ID NO: 821         moltype = DNA  length = 36
FEATURE                Location/Qualifiers
source                 1..36
                       mol_type = genomic DNA
                       organism = Torque teno virus
SEQUENCE: 821
gcgctgcgcg cgcggccccc gggggaggca ttgcct                            36

SEQ ID NO: 822         moltype = DNA  length = 36
FEATURE                Location/Qualifiers
source                 1..36
                       mol_type = genomic DNA
```

```
                         organism = Torque teno virus
SEQUENCE: 822
gcgctgcgcg cgcgcgccgg gggggcgcca gcgccc                          36

SEQ ID NO: 823           moltype = DNA  length = 36
FEATURE                  Location/Qualifiers
source                   1..36
                         mol_type = genomic DNA
                         organism = Torque teno virus
SEQUENCE: 823
gcgcttcgcg cgcgcgccgg ggggctccgc cccccc                          36

SEQ ID NO: 824           moltype = DNA  length = 36
FEATURE                  Location/Qualifiers
source                   1..36
                         mol_type = genomic DNA
                         organism = Torque teno virus
SEQUENCE: 824
gcgcttcgcg cgcgcgccgg ggggctccgc cccccc                          36

SEQ ID NO: 825           moltype = DNA  length = 36
FEATURE                  Location/Qualifiers
source                   1..36
                         mol_type = genomic DNA
                         organism = Torque teno virus
SEQUENCE: 825
gcgcttcgcg cgcgcgccgg ggggctgcgc cccccc                          36

SEQ ID NO: 826           moltype = DNA  length = 36
FEATURE                  Location/Qualifiers
source                   1..36
                         mol_type = genomic DNA
                         organism = Torque teno virus
SEQUENCE: 826
gcgctacgcg cgcgcgccgg ggggctgcgc cccccc                          36

SEQ ID NO: 827           moltype = DNA  length = 36
FEATURE                  Location/Qualifiers
source                   1..36
                         mol_type = genomic DNA
                         organism = Torque teno virus
SEQUENCE: 827
gcgctacgcg cgcgcgccgg ggggctctgc cccccc                          36

SEQ ID NO: 828           moltype =   length =
SEQUENCE: 828
000

SEQ ID NO: 829           moltype = AA  length = 11
FEATURE                  Location/Qualifiers
source                   1..11
                         mol_type = protein
                         organism = synthetic construct
VARIANT                  4
                         note = Any amino acid
VARIANT                  5
                         note = Any amino acid
VARIANT                  7
                         note = Any amino acid
VARIANT                  9
                         note = Any amino acid
VARIANT                  10
                         note = Any amino acid
SEQUENCE: 829
YNPXXDXGXX N                                                     11

SEQ ID NO: 830           moltype = DNA  length = 3648
FEATURE                  Location/Qualifiers
source                   1..3648
                         mol_type = genomic DNA
                         organism = Alphatorquevirus sp.
SEQUENCE: 830
cgtcactaac cacgtgactc ccacaggcca accacagtgt acgtgattca cttcctggga  60
gtggtttaca ttataatata agcaactgca cttccgaatg gctgagtttt ccacgcccgt  120
ccgcagcgag aacaccacgg aggggagtcc gcgcgtcccg tgggcgggtg ccgaaggtga  180
gtttacacac cgcagtcaag gggcaattcg ggcacgggac tggccgggct atgggcaagg  240
ctcttaaaaa gctatgtttc ttggtaggcc gtaccgaaag aaaaggaaac tgctactgct  300
accactgcat tctacaccga aaactagccg ggttatgagc tggtctaggc ctgtacataa  360
tgccacaggc attgaaagaa actggtggga gtcctgtctt agatcccacg caagttcttg  420
```

```
tggctgcggt aattttgtta atcatattaa tgtactggct aatcggtatg gctttgctgg  480
ttccacggag acgccgggta atcctcggcc gaggcccccg gtactgagct ccaccaccag  540
cactcctacc gatcaatcca gaccagctct accatggcat ggggatactg gtggagaagg  600
cgcttctgga gaccccgcag gagatggaga acgtggcgcc gcagaaggag actacggccc  660
agaagatcta gacgcacttt tcgacgcact cgacgaagag taaggaggcg acggtggggg  720
aggcgtgcac gcaggcgggg atggcgacgc aggacttata ttagagccag gcgacgcagg  780
agacgaaaaa gacttgtact gactcagtgg catcccgcag ttagaagaaa atgtaaaatt  840
acaggctaca tgcctatagt atactgtgga catggcagag ctagttttaa ctatgcctgg  900
cactctgatg actgtataaa acaaccacta ccctttggag gctcactatc tacagtgtcc  960
ttcaacctaa aagtactatt tgacgaaaac caaagaggac taaacaaatg gagctaccca  1020
aatgaccaac tagacctcgc cagatacaaa ggctgtagac taacatttta cagaaaaaaa  1080
aacacagact acatagctca atatgacata tcagaacctt atcaactaga caaatatagc  1140
tgtgcaaact atcacccctc aaaaatgatg tttgcaaaaa acaaaatttt aattcctagc  1200
tatgatacaa aacctagagg cagacaaaga gttagagtta gaatagggcc ccctaaacta  1260
tttacagaca agtggtacag tcaatcagac ttatgcaagg taaaccttgt gtcacttgcg  1320
gtttctgcgg cttcctttct ccacccattc ggctcaccac aaactgccaa cttttgtgca  1380
accttccagg tgctgcaacc gttctactac caggctatag gcattagttc tacaaaacac  1440
tcagaagtta tagacatttt atataagaaa aatacatact ggcaaagcaa cattacctct  1500
tggtttttaa ctaatgttaa aaacccaaaa aatatgtcca caaaaatgtt tgaggacatt  1560
aatgttaaat caaacaaaga cagtaattat gactggtttc catttacccc atacactaca  1620
gaaaactatt caaaaattca aaatgcagct caagaatact ggaaatattt aactagtgac  1680
cacccacaag ctactaatag caatgaaggc ctagtacaac catggactaa tgccactata  1740
aaacaatatg aataccacct cggtatgttt agtcctatat ttataggacc taccagagct  1800
aaaactaaat ttaaaacagc atactttgac tgcacttata acccactact agacaaagga  1860
atgggaaaca gaatatggta tcaatacgca accaaagctg acacacaaat atcaaaaaca  1920
gggtgctact gcatgttaga agacattcca atatatgcag cattttatgg atacgtagac  1980
tttatagaaa tggaaatagg taaaggacaa gacattaaag agaacggact tatttgctgc  2040
atatgtagat acacagaccc cccaatgtac aatgaacaac atccagacat gggatttgta  2100
ttttataaca ctaactttgg aaatggaaaa tggatagatg gacggggcga catacctact  2160
tactggatgc aaagatggag acctgttgta ttatttcaaa ctgatgttat tagagactta  2220
gtagaaactg gaccttttag ttacaaagat gacctagcaa atacctcact gactatgaaa  2280
tatgaattct attttacctg gggcggaaac caggcgtacc accagacaat caaaaaccct  2340
tgtaaagacg aaggtaccgg accccataga cagcctagag acgtacaagt tacggacccg  2400
acaaccgtgg gacctgaata tgtgttccac gcgtgggact ggagacgggg cttccttagc  2460
gagcgagctc tcagacgcat gttcgaaaaa cctctcaact atgatgagta ttctaaaaaa  2520
ccaaaaagac ctagaatatt tcctccaaca gaaacagagt cccgaaacca agagctcgaa  2580
gaaagctcgc tttcagagga agaaaagtcg ctactctcca cagaagagat ccagaaagag  2640
gagatacagc gacagttcaa gcgacagctc aagcgacagc tgcgcctcgg gcagcagctc  2700
aaactcctcc aacaacaact cctcaagacg caagcgggcc tgcacctaaa ccccctttca  2760
tatttcccgc aataaataaa gtgtacctgt tcccagacag agctccaaaa cctaaaccca  2820
cctctggaga ctgggaaaca gagtatgcag cttgcagtgc ctttgacaga cccgctagaa  2880
ccaaccttag ctcacccccct tactacccag gagtacctac tccctggcaa gtaaaattca  2940
gccttaaatt tcaataaagt gcatttttac tacagctggg ccgtgggagt ttcacttgtc  3000
ggtgtctacc tcttaaggtc actaagcact ccgagcgcag cgaggagtgc gacccttaac  3060
cctgggtcaa cgccttcgga gccgcgcgct acgccttcgg ctgcgcgcgg cacctcagac  3120
ccccgctcgt gctgacgcgc ttgcgcgcgt cagaccactt cgggctcgcg ggggtcggga  3180
actttgctaa cagactccga ggtgccattg gacacagagt gggcgttcag caacgaaagt  3240
gagtggggcc agacttcgcc ataaggcctt tatcttcttg ccatttgtca gtataagggg  3300
ttgccatagg cttcggcctc aattttaggc cttccggact accaaaatgg ccgatttagt  3360
gacgtcacgg cggccatttt aagtaaggcg gaagtaactc cactatttac aaaatggcgg  3420
cggagcactt ccggcttgcc caaaatggcg gcaaaaaaca tccgggtcaa aggtcgttac  3480
cacgtcacaa gtcacgtggg agggtggtgc tgtaaacccg gaagcaatcc tctcacgtgg  3540
ctagtcacgt gactaacacg tcacacccgc catttttgttt tacaaaatgg ccgacttcct  3600
tccgcttttt taaaaataac ggctcagcgg cggcgcgcgc gctacgcg               3648
```

```
SEQ ID NO: 831          moltype = AA  length = 122
FEATURE                 Location/Qualifiers
source                  1..122
                        mol_type = protein
                        organism = Alphatorquevirus sp.
SEQUENCE: 831
MSWSRPVHNA TGIERNWWES CLRSHASSCG CGNFVNHINV LANRYGFAGS TETPGNPRPR  60
PPVLSSTTST PTDQSRPALP WHGDTGGEGA SGDPAGDGER GAAEGDYGPE DLDALFDALD  120
EE                                                                 122
```

```
SEQ ID NO: 832          moltype = AA  length = 262
FEATURE                 Location/Qualifiers
source                  1..262
                        mol_type = protein
                        organism = Alphatorquevirus sp.
SEQUENCE: 832
MSWSRPVHNA TGIERNWWES CLRSHASSCG CGNFVNHINV LANRYGFAGS TETPGNPRPR  60
PPVLSSTTST PTDQSRPALP WHGDTGGEGA SGDPAGDGER GAAEGDYGPE DLDALFDALD  120
EEQSKTLVKT KVPDPIDSLE TYKLRTRQPW DLNMCSTRGT GDGASLASEL SDACSKNLST  180
MMSILKNQKD LEYFLQQKQS PETKSSKKAR FQRKKSRYSP QKRSRKRRYS DSSSDSSSDS  240
CASGSSSNSS NNNSSRRKRA CT                                           262
```

```
SEQ ID NO: 833          moltype = AA  length = 256
FEATURE                 Location/Qualifiers
```

```
source                  1..256
                        mol_type = protein
                        organism = Alphatorquevirus sp.
SEQUENCE: 833
MSWSRPVHNA TGIERNWWES CLRSHASSCG CGNFVNHINV LANRYGFAGS TETPGNPRPR  60
PPVLSSTTST PTDQSRPALP WHGDTGGEGA SGDPAGDGER GAAEGDYGPE DLDALFDALD  120
EENRVPKPRA RRKLAFRGRK VATLHRRDPE RGDTATVQAT AQATAAPRAA AQTPPTTTPQ  180
DASGPAPKPP FIFPAINKVY LFPDRAPKPK PTSGDWETEY AACSAFDRPA RTNLSSPPYY  240
PGVPTPWQVK FSLKFQ                                                 256

SEQ ID NO: 834          moltype = AA  length = 178
FEATURE                 Location/Qualifiers
source                  1..178
                        mol_type = protein
                        organism = Alphatorquevirus sp.
SEQUENCE: 834
MSWSRPVHNA TGIERNWWES CLRSHASSCG CGNFVNHINV LANRNRVPKP RARRKLAFRG  60
RKVATLHRRD PERGDTATVQ ATAQATAAPR AAAQTPPTTT PQDASGPAPK PPFIFPAINK  120
VYLFPDRAPK PKPTSGDWET EYAACSAFDR PARTNLSSPP YYPGVPTPWQ VKFSLKFQ    178

SEQ ID NO: 835          moltype = AA  length = 733
FEATURE                 Location/Qualifiers
source                  1..733
                        mol_type = protein
                        organism = Alphatorquevirus sp.
SEQUENCE: 835
MAWGYWWRRR FWRPRRRWRT WRRRRRLRPR RSRRTFRRTR RRVRRRRWGR RARRRGWRRR  60
TYIRARRRRR RKRLVLTQWH PAVRRKCKIT GYMPIVYCGH GRASFNYAWH SDDCIKQPLP  120
FGGSLSTVSF NLKVLFDENQ RGLNKWSYPN DQLDLARYKG CRLTFYRKKN TDYIAQYDIS  180
EPYQLDKYSC ANYHPSKMMF AKNKILIPSY DTKPRGRQRV RVRIGPPKLF TDKWYSQSDL  240
CKVNLVSLAV SAASFLHPFG SPQTANFCAT FQVLQPFYYQ AIGISSTKHS EVIDILYKKN  300
TYWQSNITSW FLTNVKNPKN MSTKMFEDIN VKSNKDSNYD WFPFTPYTTE NYSKIQNAAQ  360
EYWKYLTSDH PQATNSNEGL VQPWTNATIK QYEYHLGMFS PIFIGPTRAK TKFKTAYFDC  420
TYNPLLDKGM GNRIWYQYAT KADTQISKTG CYCMLEDIPI YAAFYGYVDF IEMEIGKGQD  480
IKENGLICCI CRYTDPPMYN EQHPDMGFVF YNTNFGNGKW IDGRGDIPTY WMQRWRPVVL  540
FQTDVIRDLV ETGPFSYKDD LANTSLTMKY EFYFTWGGNQ AYHQTIKNPC KDEGTGPHRQ  600
PRDVQVTDPT TVGPEYVFHA WDWRRGFLSE RALRRMFEKP LNYDEYSKKP KRPRIFPPTE  660
TESRNQELEE SSLSEEEKSL LSTEEIQKEE IQRQFKRQLK RQLRLGQQLK LLQQQLLKTQ  720
AGLHLNPLSY FPQ                                                    733

SEQ ID NO: 836          moltype = AA  length = 191
FEATURE                 Location/Qualifiers
source                  1..191
                        mol_type = protein
                        organism = Alphatorquevirus sp.
SEQUENCE: 836
MAWGYWWRRR FWRPRRRWRT WRRRRRLRPR RSRRTFRRTR RRTIKNPCKD EGTGPHRQPR  60
DVQVTDPTTV GPEYVFHAWD WRRGFLSERA LRRMFEKPLN YDEYSKKPKR PRIFPPTETE  120
SRNQELEESS LSEEEKSLLS TEEIQKEEIQ RQFKRQLKRQ LRLGQQLKLL QQQLLKTQAG  180
LHLNPLSYFP Q                                                      191

SEQ ID NO: 837          moltype = AA  length = 107
FEATURE                 Location/Qualifiers
source                  1..107
                        mol_type = protein
                        organism = Alphatorquevirus sp.
SEQUENCE: 837
MAWGYWWRRR FWRPRRRWRT WRRRRRLRPR RSRRTFRRTR RRKQSPETKS SKKARFQRKK  60
SRYSPQKRSR KRRYSDSSSD SSSDSCASGS SSNSSNNNSS RRKRACT               107

SEQ ID NO: 838          moltype = DNA  length = 3704
FEATURE                 Location/Qualifiers
source                  1..3704
                        mol_type = genomic DNA
                        organism = Alphatorquevirus sp.
SEQUENCE: 838
ccccgaagtc cgtcactaac cacgtgactc ccacaggcca atcagatgct atgtcgtgca  60
cttcctgggc tgtgtctacg tcctcatata agtaactgca cttccgaatg gctgagtttt  120
ccacgcccgt ccgcagcggc agcaccacgg agggtgatcc ccgcgtcccg tgggcgggtg  180
ccggaggtga gtttacacac cgcagtcaag gggcaattcg ggcacgggac tggccgggct  240
atgggcaagg ctcttaaaaa gctatgttct tcggtaggtg ctggagaaag aaaaggaaag  300
tgcttctgca agatctgtca actccaccga aaaaacctgc tatgagtgtg tggcttcctc  360
ccatagacaa tgttaccgag cgtgagagga gctggctctc tagcattctt cagtctcaca  420
gagctttttg tgggtgccat gatgctatct atcatcttag cagtctggct gctcgcttta  480
atatgcaacc agggccgtcg ccgggtggtg attctaggcc gccgcgaccg ccactaagac  540
gcctgcccgc gctcccgggt cccagagacc cccctagcga caccaacaac cgcaggtcat  600
ggcctactgg ggatggtgga gacggaggcg ctggccaagg cgcaggtgga ggcgctaccg  660
ctaccgaaga agactaccgc gccgaagacc tagacgagct gtacgccgcc ctcgaaggag  720
acgagtaagg aggcgccgcg gtagggggtg gtacagaggg cgacgctact cccgcagacg  780
```

```
gtacagacgt agatatgtga ggcgaaagag aaagactcta gtttggagac agtggcagcc  840
tcaaaatatc agaaaatgca ggatcagggg cataattccc atcctgatat gcggacacgg  900
gaggggggcc agaaactatg cgctcccacag cgacgacata accccccaga acacccccctt  960
cgggggagga ctgagcacca cctcctggag cctaaaagtg ctatatgacc agcacaccag  1020
gggactcaac aggtggtctg ccagtaacga gagcctagac cttgccagat acaatggctg  1080
tagtttcact ttctacagag acaaaaagac tgactttata gtgacctatg acacctctgc  1140
tccctacaaa ctagacaaat acagctcccc cagctaccac ccagggtcca tgatgctcat  1200
gacaaaacac aaaatcctga tccccagttt tgacacaaaa cccaaaggtc ctgccaaaat  1260
tagagtcaga atcaagcccc ccaaaatgtt cttagataaa tggtacactc aagacgacct  1320
ctgttccgtt aatcttgtgt cacttgcggt tagcgcagct tcctttacac atccgttctg  1380
cccaccacta actgacactc cttgtgtaac gctgcaggtg ttgaaagact tctactacac  1440
aaccataggc tactcctcta atgcagacaa agtagagtct gtattcacta acactctcta  1500
caaacactgc tgctactatc agtcctttct caccactcaa tttatagcca aaatcactcg  1560
cacaccagat ggacaaccag tagccacatt ctctcctcct acctctttcc ctggcacaac  1620
tgtaacaaaa agttccatag aatcatttaa ccaatgggta acttccacag gtacaagtgg  1680
ctggctaaca aatgcaaacc aacactttca tttctgtaac tataaaccag atgccacaaa  1740
gctaaaatgg ctcagacagt actactttga ctgggaaaca tacaaattag cagatgtaaa  1800
gccagacggc cttacaccct cagtaaactg gtatgagtac agaataggcc tctttagtcc  1860
tattttcctg agccccttca gatctagcag tctagacttt cccagagcct accaggatgt  1920
gaactacaac cccctggtag acaaaggagt gggcaacatc atatggttcc aatacaacac  1980
aaaaccagac acacagctgt cagtacccag ctgcaagtgt gtcatagaag acaaacccct  2040
atgggcagcc ttctatggct acagtgactt tgtacaacaa gagataggag actacacaga  2100
cgcagaggcc gtgggcttcg tctgtgtcat ctgtccatac accaaacccc ctctaaaaaa  2160
cccagacaac cccatgcaag ggttcatatt ctatgacagc ctttttggca atggcaagtg  2220
gatagatggc acggggcacg tcccccttta ctggcagagc aggtggaggc cagagatgct  2280
cttccaagaa aacaccatga gagacatcac actatctggg cccttcagct acaaggacga  2340
ctataagaac tgtgtactga cttgcaaata caaatttaac tttcgattcg ggggcaatct  2400
tctccacgaa cagacgatca gaaacccatg ccccacggac ggacatccca gtaccggtag  2460
acagcctaga gacgtacaag tggttgaccc gatcaaagtg ggcccccggt tcgtgttcca  2520
ctcctgggac tggcgcagag gctaccttag cccagcagct ctcaaaagaa ttggagagca  2580
accgctcgat tatgaagctt attcgtaccg cccaaagaga cctagaatct ttcctcccac  2640
agaaggagac cagctcgccc gaagtcgaga agaagactca ttttcagagg aagaaagtcc  2700
ccatatctcg ttcgaagagg ggcaggaacc gaaagcccag gcggtacagc agcacctcct  2760
ccgacacctc agaaagcagc gagaactccg aaagcgactc cgagccctgt tccaaagcct  2820
ccaaaagacg caggcgggtc tccacgtaaa tccattatta ttcaaccagc ctgcaatcag  2880
gttctgatgt tcccagagat ggggcctaag ccagctccca ctgcccaaga ctggcagtgc  2940
gaatacgaga catgtaagca ctgggataga ccccccagaa agtttctcac agacccccct  3000
ttctatccct gggcccctac tacttacaat gtatctttca agctaaactt caaataaact  3060
aggccgtggg agtctcactt gtcggtgtct acctcttaag gtcactaagc actccgagcg  3120
tcagcgagga gtgcgaccct tccccctggt gcaacgccct cggcggccgc gcgctacgcc  3180
ttcggctgcg cgcggcacct cggacccccg ctcgtgctga cgcgctcgcg cgcgtcagac  3240
cacttcgggc tcgcgggggt cgggaaattt gctaaacaga ctccgagttg ccattggaca  3300
caggagctgt gaatcagtaa cgaaagtgag tggggccaga cttcgccata aggcctttat  3360
cttcttgcca tttgtccgtg aggaggggtc gccaagacgc ggaccccgtt ttcggacctt  3420
ccgaactacc aaaatggccg attcagtgac gtcacggcag ccattttgtg taagcaccgc  3480
ccaggacaga cgtcacagtt caaaggtcat cctcgagcgg aacttacaga aaatggcggt  3540
caattgcttc cgggtcaaag gtcacgccta cgtcataagt cacgtggtgg aggctactgc  3600
gcatacacgg aagtaggccc cgccacgtga ccgaccacgt gggtgctgcg tcacggccgc  3660
cattttgtat cacaaaatgg ccgacttcct tcctcttttt caaa                  3704
```

```
SEQ ID NO: 839          moltype = AA  length = 128
FEATURE                 Location/Qualifiers
source                  1..128
                        mol_type = protein
                        organism = Alphatorquevirus sp.
SEQUENCE: 839
MSVWLPPIDN VTERERSWLS SILQSHRAFC GCHDAIYHLS SLAARFNMQP GPSPGGDSRP  60
PRPPLRRLPA LPGPRDPPSD TNNRRSWPTG DGGDGGAGQG AGGGATATEE DYRAEDLDEL  120
YAALEGDE                                                           128
```

```
SEQ ID NO: 840          moltype = AA  length = 272
FEATURE                 Location/Qualifiers
source                  1..272
                        mol_type = protein
                        organism = Alphatorquevirus sp.
SEQUENCE: 840
MSVWLPPIDN VTERERSWLS SILQSHRAFC GCHDAIYHLS SLAARFNMQP GPSPGGDSRP  60
PRPPLRRLPA LPGPRDPPSD TNNRRSWPTG DGGDGGAGQG AGGGATATEE DYRAEDLDEL  120
YAALEGDERS ETHAPRTDIP VPVDSLETYK WLTRSKWAPG SCSTPGTGAE ATLAQQLSKE  180
LESNRSIMKL IRTAQRDLES FLPQKETSSP EVEKKTHFQR KKVPISRSKR GRNRKPRRYS  240
STSSDTSESS ENSESDSEPC SKASKRRRRV ST                                272
```

```
SEQ ID NO: 841          moltype = AA  length = 265
FEATURE                 Location/Qualifiers
source                  1..265
                        mol_type = protein
                        organism = Alphatorquevirus sp.
SEQUENCE: 841
MSVWLPPIDN VTERERSWLS SILQSHRAFC GCHDAIYHLS SLAARFNMQP GPSPGGDSRP  60
```

```
PRPPLRRLPA LPGPRDPPSD TNNRRSWPTG DGGDGGAGQG AGGGATATEE DYRAEDLDEL  120
YAALEGDERR PARPKSRRRL IFRGRKSPYL VRRGAGTESP GGTAAPPPTP QKAARTPKAT  180
PSPVPKPPKD AGGSPRKSII IQPACNQVLM FPEMGPKPAP TAQDWQCEYE TCKHWDRPPR  240
KFLTDPPFYP WAPTTYNVSF KLNFK                                        265

SEQ ID NO: 842          moltype = AA  length = 762
FEATURE                 Location/Qualifiers
source                  1..762
                        mol_type = protein
                        organism = Alphatorquevirus sp.
SEQUENCE: 842
MAYWGWWRRR RWPRRRWRRY RYRRRLPRRR PRRAVRRPRR RRVRRRRGRG WYRGRRYSRR  60
RYRRRYVRRK RKTLVWRQWQ PQNIRKCRIR GIIPILICGH GRGARNYALH SDDITPQNTP  120
FGGGLSTTSW SLKVLYDQHT RGLNRWSASN ESLDLARYNG CSFTFYRDKK TDFIVTYDTS  180
APYKLDKYSS PSYHPGSMML MTKHKILIPS FDTKPKGPAK IRVRIKPPKM FLDKWYTQDD  240
LCSVNLVSLA VSAASFTHPF CPPLTDTPCV TLQVLKDFYY TTIGYSSNAD KVESVFTNTL  300
YKHCCYYQSF LTTQFIAKIT RTPDGQPVAT FSPPTSFPGT TVTKSSIESF NQWVTSTGTS  360
GWLTNANQHF HFCNYKPDAT KLKWLRQYYF DWETYKLADV KPDGLTPSVN WYEYRIGLFS  420
PIFLSPFRSS SLDFPRAYQD VNYNPLVDKG VGNIIWFQYN TKPDTQLSVP SCKCVIEDKP  480
LWAAFYGYSD FVQQEIGDYT DAEAVGFVCV ICPYTKPPLK NPDNPMQGFI FYDSLFGNGK  540
WIDGTGHVPL YWQSRWRPEM LFQENTMRDI TLSGPFSYKD DYKNCVLTCK YKFNFRFGGN  600
LLHEQTIRNP CPTDGHPSTG RQPRDVQVVD PIKVGPRFVF HSWDWRRGYL SPAALKRIGE  660
QPLDYEAYSY RPKRPRIFPP TEGDQLARSR EEDSFSEEES PHISFEEGQE PKAQAVQQHL  720
LRHLRKQREL RKRLRALFQS LQKTQAGLHV NPLLFNQPAI RF                     762

SEQ ID NO: 843          moltype = AA  length = 199
FEATURE                 Location/Qualifiers
source                  1..199
                        mol_type = protein
                        organism = Alphatorquevirus sp.
SEQUENCE: 843
MAYWGWWRRR RWPRRRWRRY RYRRRLPRRR PRRAVRRPRR RRTIRNPCPT DGHPSTGRQP  60
RDVQVVDPIK VGPRFVFHSW DWRRGYLSPA ALKRIGEQPL DYEAYSYRPK RPRIFPPTEG  120
DQLARSREED SFSEEESPHI SFEEGQEPKA QAVQQHLLRH LRKQRELRKR LRALFQSLQK  180
TQAGLHVNPL LFNQPAIRF                                               199

SEQ ID NO: 844          moltype = AA  length = 110
FEATURE                 Location/Qualifiers
source                  1..110
                        mol_type = protein
                        organism = Alphatorquevirus sp.
SEQUENCE: 844
MAYWGWWRRR RWPRRRWRRY RYRRRLPRRR PRRAVRRPRR RRKETSSPEV EKKTHFQRKK  60
VPISRSKRGR NRKPRRYSST SSDTSESSEN SESDSEPCSK ASKRRRRVST             110

SEQ ID NO: 845          moltype = DNA  length = 3653
FEATURE                 Location/Qualifiers
source                  1..3653
                        mol_type = genomic DNA
                        organism = Alphatorquevirus sp.
misc_difference         2949
                        note = a, c, t, g, unknown or other
misc_difference         2950
                        note = a, c, t, g, unknown or other
misc_difference         2951
                        note = a, c, t, g, unknown or other
misc_difference         2952
                        note = a, c, t, g, unknown or other
misc_difference         2953
                        note = a, c, t, g, unknown or other
misc_difference         2954
                        note = a, c, t, g, unknown or other
misc_difference         2955
                        note = a, c, t, g, unknown or other
misc_difference         2956
                        note = a, c, t, g, unknown or other
misc_difference         2957
                        note = a, c, t, g, unknown or other
misc_difference         2958
                        note = a, c, t, g, unknown or other
misc_difference         2959
                        note = a, c, t, g, unknown or other
misc_difference         2960
                        note = a, c, t, g, unknown or other
misc_difference         2961
                        note = a, c, t, g, unknown or other
misc_difference         2962
                        note = a, c, t, g, unknown or other
misc_difference         2963
```

```
                          note = a, c, t, g, unknown or other
misc_difference           2964
                          note = a, c, t, g, unknown or other
misc_difference           2965
                          note = a, c, t, g, unknown or other
misc_difference           2966
                          note = a, c, t, g, unknown or other
SEQUENCE: 845
ccaaccagag tctatgtcgt gcacttcctg ggcatggtct acgtaataat ataaagcggt  60
gcacttccga atggctgagt tttccacgcc cgtccgcagc gagatcgcga cggaggagcg  120
atcgagcgtc ccgagggcgg gtgccggagg tgagtttaca caccgcagtc aaggggcaat  180
tcgggctcgg gactggccgg gctatgggca aggctcttaa aaagccatgt ttctcggtaa  240
actttacagg cagaaaagga aactgctact gcagcctgtg cgtgctccac agacgccatc  300
ttccatgagc tctacctggc gagtgccccg cggcgatgtc tccgcccgcg agctatgttg  360
gtaccgctca gttcgagaga gccacgatgc tttttgtggc tgtcgtgatc ctgtttttca  420
tctttctcgt ctggctgcac gttctaacca tcagggacct ccgacgcccc ccacggacga  480
gcgcccgtcg gcgtctaccc cagtgaggcg cctgctgccg ctgccctcct accccggcga  540
gggtccccag gctagatggc ctggtgggga tggagaaggc gctggtggcg cccgcggagg  600
cgctggagat ggcggcgccc gcgcaggcga agaagagtac cggcccgaag acctcgacga  660
gctgttcgac gctatcgaac aagaacagta aggagacgga ggcgagggtg gcggaggggc  720
tacaggcgcc gttacagact gagacgctac cgtagaaggg gcaggcgacg caaaaaaata  780
gtactgactc agtggaaccc ccagactgtc agaaagtgct ttatcagagg actgatgcca  840
gtactatggg cgggcatggg cacggggggc cacaactacg ccgtccgctc agatgacttt  900
gtggtagaca gaggcttcgg gggctccttc gccacagaaa ctttctccct gagggtcctc  960
tttgaccagt accagagagg atttaatagg tggtctcaca ccaacgaaga cctagacctg  1020
gcccgctaca cgggctgcaa atggacattt tacagacacc aagacacaga ctttatagtg  1080
tactttacaa acaatccccc catgaaaacc aaccagcaca cagcccctct cacaactcca  1140
ggcatgctca tgaggagcaa gtataaaata ctagtgccca gttttaaaac aagaccaaag  1200
ggcagaaaaa cagtgtcagt gagagttaga ccccccaaac tgtttcagga caaatggtat  1260
actcaacagg acctctgtcc agtacccctc gtccaactga acgtgaccgc agcggatttc  1320
acacatccgt tcggctcacc actaactgac acgccttgca taagattcca agttttaggg  1380
aacttataca acaagtgcct aaatatagat cttccgcaat ttgatgagga cggtgagata  1440
ctcacttcaa caccttataa cagagaaaac aaagaagatc ttaaaaagct ttataaaact  1500
ctatttgtag atgaacacgc aggcaattat tggcagacat tcttaaccaa cacaatggta  1560
aagtcacaca tagatgcaaa ccaagcaaag acatacgatc aagaaaaaac tgctgcagaa  1620
caaggtaaag accccttccc aacaaaccca ccaaaagacc aattcactac ctggaacaag  1680
aaactagtag accctagaga cagcaacttt ctctttgcca catatcaccc aaaaaacatt  1740
aaaaaagcta taaaaaccat gagagacaac aactttgctc tcaccacagg caaaaatgac  1800
atatatggag actacaccgc ggcctacacc agaaacaccc acatgctaga ctactaccta  1860
ggcttttata gccccatatt tctttccagc ggtaggtcca acacagagtt ctggaccgcc  1920
tacagagaca tagtatataa tcccctctta gacaaaggca caggcaacat gatctggttc  1980
caatatcaca caaaaacaga caatatatac aaaaaaccag agtgccactg ggagatacta  2040
gacatgcccc tgtgggccct ctgcaacggg tatgtagagt acctagagag ccaaataaag  2100
tacggggaca tcctagtaga gggcaaagtc ctcatcagat gcccctacac caaacccgca  2160
ctggtagacc ccaataacag cctagctggt tacgtggtat tcaacaccac cttcggccag  2220
ggaaaatgga tagatggcaa aggctacatc cccctacacg agaggagcaa gtggtacgtc  2280
atgctcagat accagaccga cgtactccat gacatagtga cttgtggacc ctggcagtac  2340
agagacgata acaaaaactc tcagctaata gccaagtaca gattcaagtt ctactgggga  2400
ggtaacatgg tacattctca ggtcatcaga aacccgtgca aagacaccca agtatccgga  2460
ccccgtcgac agcctcgcga agtacaagtc gttgacccgc aactcattac gccgccgtgg  2520
gtcctccact cgttcgacca gagacgagga atgtttactg caggagctat caaacgtctg  2580
ctcaagcaac caatacctgg cgagtatgct cctacaccac tcagggtccc gctcctcttt  2640
ccctcctcag agttccagcg agagggagaa gatgcagaaa gcggctcagg ttcaccaccc  2700
aagagaccgc gactctggca ggaagaggcc aaccagacgc aaacggagtc ctcggagggg  2760
ccggcggaga cgacgaggga gctcctcgag cgaaagctca gagagcagcg agtcctcaac  2820
ctccaactcc agcatgtcgc agtacaactc gccaaaaccc aagcgaacct ccacataaac  2880
cccctattat actcccagcc ttaaacaaag tgtatctatt ccccccctgac aagcccactc  2940
ccatacagnn nnnnnnnnnn nnnnnnaaca cagagttcga agcctgccag gccttcgaca  3000
gaccacctag aaaatacctc tcagacacac ctacctaccc ttggctcccc gtccccaatc  3060
ctgaaataaa ggtcagcttt aagctcggtt tcaaatctta caaggccgtg ggagtttcac  3120
tggtcggtgt ctacctctta aggtcactaa gcactccgag cgtcagcgag gagtgcgacc  3180
cttcccccctg gtgcaacgcc ctcggcggcc gcgcgctacg ccttcggctg cgcgcggcac  3240
ctcggacccc cgctcgtgct gacgcgctcg cgcgcgtcag accacttcgg gctcgcgggg  3300
gtcgggaatt ttgctaaaca gactccgagt tgccattgga cactgtagct gtgaatcagt  3360
aacgaaagtg agtggggcca gacttcgcca taaggccttt atcttcttgc cattggtccg  3420
tgtagggggt cgccataggc ttcgggttcg gttttaggcc ttccggacta caaaaatggc  3480
ggatttagtg acgtcacggc cgccatttta agtaggtgcc gtccaggact gctgttccgg  3540
gtcacagggc atcctcggcg gaacttacac aaaatggcgg tcaaaaacat ccgggtcaaa  3600
ggtcgcagct acgtcataag tcacgtgcag gggtcctgct gcgtcatatg cgg  3653

SEQ ID NO: 846            moltype = AA  length = 128
FEATURE                   Location/Qualifiers
source                    1..128
                          mol_type = protein
                          organism = Alphatorquevirus sp.
SEQUENCE: 846
MSSTWRVPRG DVSARELCWY RSVRESHDAF CGCRDPVFHL SRLAARSNHQ GPPTPPTDER  60
PSASTPVRRL LPLPSYPGEG PQARWPGGDG EGAGGARGGA GDGGARAGEE EYRPEDLDEL  120
FDAIEQEQ                                                          128
```

```
SEQ ID NO: 847          moltype = AA  length = 279
FEATURE                 Location/Qualifiers
source                  1..279
                        mol_type = protein
                        organism = Alphatorquevirus sp.
SEQUENCE: 847
MSSTWRVPRG DVSARELCWY RSVRESHDAF CGCRDPVFHL SRLAARSNHQ GPPTPPTDER  60
PSASTPVRRL LPLPSYPGEG PQARWPGGDG EGAGGARGGA GDGGARAGEE EYRPEDLDEL  120
FDAIEQEQSS ETRAKTPKYP DPVDSLAKYK SLTRNSLRRR GSSTRSTRDE ECLLQELSNV  180
CSSNQYLASM LLHHSGSRSS FPPQSSSERE KMQKAAQVHH PRDRDSGRKR PTRRKRSPRR  240
GRRRRRGSSS SESSESSESS TSNSSMSQYN SPKPKRTST                         279

SEQ ID NO: 848          moltype = AA  length = 378
FEATURE                 Location/Qualifiers
source                  1..378
                        mol_type = protein
                        organism = Alphatorquevirus sp.
VARIANT                 257
                        note = Any amino acid
VARIANT                 258
                        note = Any amino acid
VARIANT                 259
                        note = Any amino acid
VARIANT                 260
                        note = Any amino acid
VARIANT                 261
                        note = Any amino acid
VARIANT                 262
                        note = Any amino acid
SEQUENCE: 848
MSSTWRVPRG DVSARELCWY RSVRESHDAF CGCRDPVFHL SRLAARSNHQ GPPTPPTDER  60
PSASTPVRRL LPLPSYPGEG PQARWPGGDG EGAGGARGGA GDGGARAGEE EYRPEDLDEL  120
FDAIEQEQSY QTSAQATNTW RVCSYTTQGP APLSLLRVPA RGRRCRKRLR FTTQETATLA  180
GRGQPDANGV LGGAGGDDEG APRAKAQRAA SPQPPTPACR STTRQNPSEP PHKPPIILPA  240
LNKVYLFPPD KPTPIQXXXX XXNTEFEACQ AFDRPPRKYL SDTPTYPWLP VPNPEIKVSF  300
KLGFKSYKAV GVSLVGVYLL RSLSTPSVSE ECDPSPWCNA LGGRALRLRL RAAPRTPARA  360
DALARVRPLR ARGGREFC                                                378

SEQ ID NO: 849          moltype = AA  length = 269
FEATURE                 Location/Qualifiers
source                  1..269
                        mol_type = protein
                        organism = Alphatorquevirus sp.
VARIANT                 148
                        note = Any amino acid
VARIANT                 149
                        note = Any amino acid
VARIANT                 150
                        note = Any amino acid
VARIANT                 151
                        note = Any amino acid
VARIANT                 152
                        note = Any amino acid
VARIANT                 153
                        note = Any amino acid
SEQUENCE: 849
MSSTWRVPRG DVSARELCWS YQTSAQATNT WRVCSYTTQG PAPLSLLRVP ARGRRCRKRL  60
RFTTQETATL AGRGQPDANG VLGGAGGDDE GAPRAKAQRA ASPQPPTPAC RSTTRQNPSE  120
PPHKPPIILP ALNKVYLFPP DKPTPIQXXX XXXNTEFEAC QAFDRPPRKY LSDTPTYPWL  180
PVPNPEIKVS FKLGFKSYKA VGVSLVGVYL LRSLSTPSVS EECDPSPWCN ALGGRALRLR  240
LRAAPRTPAR ADALARVRPL RARGGREFC                                    269

SEQ ID NO: 850          moltype = AA  length = 782
FEATURE                 Location/Qualifiers
source                  1..782
                        mol_type = protein
                        organism = Alphatorquevirus sp.
SEQUENCE: 850
MAWWGWRRRW WRPRRRWRWR RPRRRRRVPA RRPRRAVRRY RTRTVRRRRR GWRRGYRRRY  60
RLRRYRRRGR RRKKIVLTQW NPQTVRKCFI RGLMPVLWAG MGTGGHNYAV RSDDFVVDRG  120
FGGSFATETF SLRVLFDQYQ RGFNRWSHTN EDLDLARYTG CKWTFYRHQD TDFIVYFTNN  180
PPMKTNQHTA PLTTPGMLMR SKYKILVPSF KTRPKGRKTV SVRVRPPKLF QDKWYTQQDL  240
CPVPLVQLNV TAADFTHPFG SPLTDTPCIR FQVLGNLYNK CLNIDLPQFD EDGEILTSTP  300
YNRENKEDLK KLYKTLFVDE HAGNYWQTFL TNTMVKSHID ANQAKTYDQE KTAAEQGKDP  360
FPTNPPKDQF TTWNKKLVDP RDSNFLFATY HPKNIKKAIK TMRDNNFALT TGKNDIYGDY  420
TAAYTRNTHM LDYYLGFYSP IFLSSGRSNT EFWTAYRDIV YNPLLDKGTG NMIWFQYHTK  480
TDNIYKKPEC HWEILDMPLW ALCNGYVEYL ESQIKYGDIL VEGKVLIRCP YTKPALVDPN  540
NSLAGYVVFN TTFGQGKWID GKGYIPLHER SKWYVMLRYQ TDVLHDIVTC GPWQYRDDNK  600
```

```
NSQLIAKYRF KFYWGGNMVH SQVIRNPCKD TQVSGPRRQP REVQVVDPQL ITPPWVLHSF  660
DQRRGMFTAG AIKRLLKQPI PGEYAPTPLR VPLLFPSSEF QREGEDAESG SGSPPKRPRL  720
WQEEANQTQT ESSEGPAETT RELLERKLRE QRVLNLQLQH VAVQLAKTQA NLHINPLLYS  780
QP                                                                 782

SEQ ID NO: 851         moltype =   length =
SEQUENCE: 851
000

SEQ ID NO: 852         moltype = AA  length = 204
FEATURE                Location/Qualifiers
source                 1..204
                       mol_type = protein
                       organism = Alphatorquevirus sp.
SEQUENCE: 852
MAWWGWRRRW WRPRRRWRWR RPRRRRRVPA RRPRRAVRRY RTRTVIRNPC KDTQVSGPRR  60
QPREVQVVDP QLITPPWVLH SFDQRRGMFT AGAIKRLLKQ PIPGEYAPTP LRVPLLFPSS  120
EFQREGEDAE SGSGSPPKRP RLWQEEANQT QTESSEGPAE TTRELLERKL REQRVLNLQL  180
QHVAVQLAKT QANLHINPLL YSQP                                         204

SEQ ID NO: 853         moltype = AA  length = 148
FEATURE                Location/Qualifiers
source                 1..148
                       mol_type = protein
                       organism = Alphatorquevirus sp.
SEQUENCE: 853
MAWWGWRRRW WRPRRRWRWR RPRRRRRVPA RRPRRAVRRY RTRTELSNVC SSNQYLASML  60
LHHSGSRSSF PPQSSSEREK MQKAAQVHHP RDRDSGRKRP TRRKRSPRRG RRRRRGSSSS  120
ESSESSESST SNSSMSQYNS PKPKRTST                                     148

SEQ ID NO: 854         moltype = DNA  length = 3742
FEATURE                Location/Qualifiers
source                 1..3742
                       mol_type = genomic DNA
                       organism = Alphatorquevirus sp.
SEQUENCE: 854
aaagtgctac gtcactaacc acgtgacacc cacaggccaa ccgaatgcta tgtcgtgcac  60
ttcctgggcc gggtctacgt cctcatataa ctacctgcac ttccgaatgg ctgagttttc  120
cacgcccgtc cgcagcggtg aagccacgga gggagatcag cgcgtcccga gggcgggtgc  180
cgaaggtgag tttacacacc gaagtcaagg ggcaattcgg gctcgggact ggccgggcta  240
tgggcaaggc tctgaaaaaa gcatgtttat tggcaggcat tacagaaaga aaagggcgct  300
gccactgtgt gctgtgcgat caacaaagaa ggcttgcaaa ctactaatag taatgtggac  360
cccacctcgc aatgaccaac agtaccttaa ctggcaatgg tactcaagta tacttagctc  420
ccacgctgct atgtgcgggt gtcccgacgt tgttgctcat tttaatcatc ttgcttctgt  480
gcttcgcgcc ccgcaaaatc cacccccacc cggtccccag cgaaacctgc ccctccgacg  540
gctgccggct ctcccggctg cgccagaggc gcccggagat agagcaccat ggcctatggc  600
tggtggcgcc ggaggagaag acggtggcgc aggtggagac gcagaccatg gaggcgccgc  660
tggaggacca gaagacgcag acctgttaga cgccgtggcc gccgcagaaa cgtaaggaga  720
cgccgcagag gagggaggtg gaggaggagg tacaggagat ggaaaagaaa gggcagacgc  780
agaaaaaaag ctaaaataat aataagacaa tggcaaccta actacagaag gagatgtaac  840
atagtaggct atattcctgt actgatatgt ggcgaaaata ctgtcagcag aaactatgcc  900
acacactcag acgatactaa ctacccagga ccctttgggg ggggtatgac tacagacaaa  960
tttaccttaa gaattctgta tgacgagtac aaaaggttta tgaactattg gacagcatct  1020
aatgaagacc tagacctctg tagatatcta ggagtaaacc tgtacttttt tagacaccca  1080
gaagtagact ttattataaa aataaatacc atgccccctt ttctagacac agaactaaca  1140
gctcctagca tacacccagg aatgctagcc ttagacaaaa gagcaagatg gatacctagc  1200
ttaaaatcta gaccaggaaa aaaacactat attaaaataa gagtaggggc gcctaaaatg  1260
ttcacagata aatggtaccc ccaaacagat ctttgtgaca tggtgctgct aactgtctat  1320
gcaaccgcag cggatatgca atatccgttc ggctcaccac taactgactc tgtggttgtg  1380
aacttccagg ttctgcaatc catgtatgat gaaaccatta gcatattacc agatcaaaag  1440
gagaaaagaa taacgctgct cactagtata gccttttata acaccacaca aactatagcc  1500
caattaaagc catttataga tgcaggcaat atgacttcaa ctacaacagc aacaacatgg  1560
ggatcataca taaacacaac caaatttaat acagcagcca ctacaacata cacataccca  1620
ggcagtacta caactacagt aactatgtta acttgtaatg actcctggta cagaggaaca  1680
gtatataacg accaaattaa aaatttacca aaggaagcag ctcaattata cttaaaagca  1740
acaaaaacct tactaggaaa caccttcaca aatgacgacc acacactaga ataccatgga  1800
ggactgtaca gctcaatttg gctgtccccc ggcagatctt actttgaaac accaggagca  1860
tacacagaca taaaatacaa cccatttaca gacagaggag aaggaaacat gctatggata  1920
gactggctaa gcaaaaaaaa tatgaactat gacaaactac aaagtaaatg tttaatatca  1980
gacctacctt tatgggcagc agcatatgga tatttagaat tttgtgcaaa aagtacagga  2040
gaccaaaata tacacatgaa tgccagacta ctaataagaa gtccctttac agaccccccaa  2100
ctactagtac acacaaaccc cacaaaaggc tttgttccct actctttaaa ctttggaaat  2160
ggtaaaatgc caggaggtag tagtaatgtt cctattagaa tgagagctaa atggtatcca  2220
acattgtttc accagcaaga agtactagag gccttagcac agtcaggccc ctttgcatac  2280
cactcagaca ttaaaaaagt atctctgggt atgaaatacc gttttaagtg gatctggggt  2340
ggaaaccccg ttcgccaaca ggttgttaga aatccctgca aagactccca ctcctcggtc  2400
aatagagtcc ctagaagctt acaaatcgtt gacccgaaat acaactcacc ggaactcaca  2460
ttccatacgt gggacttcag acgtggcctc tttggccaga aagctattga gagaatgcaa  2520
caacaaccaa caactactga cattttttca gcaggccgca agagacccag gagggacacc  2580
```

```
gaggtgtacc actccagcca agaaggggag caaaaagaaa gcttactttt ccccccagtc  2640
aagctcctca gacgagtccc cccgtgggaa gactcgcagc aggaggaaag cgggtcgcaa  2700
agctcagagg aagagacgca gaccgtctcc cagcagctca agcagcagct gcagcaacag  2760
cgaatcctgg gagtcaaact catactcctg ttcaaccaag tccaaaaaat ccaacaaaat  2820
caagatatca accctacctt gttaccaagg ggggggatc tagcatcctt atttcaaata  2880
gcaccataaa catgtttgga gaccccaaac cttacaaccc ttccagtaat gactggaaag  2940
aggagtatga ggcctgtaga atatgggaca gacccccaag aggcaatcta agagacaccc  3000
ccttttaccc ctgggccccc aaagaaaacc agtaccgtgt aaactttaaa cttggatttc  3060
aataaagcta ggccgtggga ctttcacttg tcggtgtctg cttataaaag taaccaagca  3120
ctccgagcga agcgaggagt gcgacccttg ggggctcaac gacttcggag ccgcgcgtta  3180
agccttcggc tgcgcgcggc acctcagacc cccgctcgtg ctgacacgct tgcgcgtgtc  3240
agaccacttc gggctcgcgg gggtcgggaa atttattaaa cagactccga gttgccattg  3300
gacacagtag tctatgaaca gcaacgaaag tgagtggggc cagacttcgc cataaggcct  3360
ttatcttctt gccatttgtc agtatagagg gtcgccatag gcttcggtct ccattttaac  3420
ctgtaaaaac taccaaaatg gccgttccag tgacgtgaca gccgccattt taagtagctg  3480
acgtcaagga ttgacgtaaa ggttaaaggt catcctcggc ggaagctaca caaaatggtg  3540
gacaacatct tccgggtcaa aggtcgtgca cacgtcaaaa gtcacgtggt ggggacccgc  3600
tgtaacccgg aagtaggccc cgtcacgtga tttgtcacgt gtgtacacgt cacagccgcc  3660
attttgtttt acaaaatggc tgacttcctt cctctttttt gaaaaaaggc gccaaaaaag  3720
gctccgcccc ccggcccccc cc                                            3742

SEQ ID NO: 855          moltype = AA  length = 120
FEATURE                 Location/Qualifiers
source                  1..120
                        mol_type = protein
                        organism = Alphatorquevirus sp.
SEQUENCE: 855
MWTPPRNDQQ YLNWQWYSSI LSSHAAMCGC PDVVAHFNHL ASVLRAPQNP PPPGPQRNLP  60
LRRLPALPAA PEAPGDRAPW PMAGGAGGED GGAGGDADHG GAAGGPEDAD LLDAVAAAET  120

SEQ ID NO: 856          moltype = AA  length = 286
FEATURE                 Location/Qualifiers
source                  1..286
                        mol_type = protein
                        organism = Alphatorquevirus sp.
SEQUENCE: 856
MWTPPRNDQQ YLNWQWYSSI LSSHAAMCGC PDVVAHFNHL ASVLRAPQNP PPPGPQRNLP  60
LRRLPALPAA PEAPGDRAPW PMAGGAGGED GGAGGDADHG GAAGGPEDAD LLDAVAAAET  120
LLEIPAKTPT PRSIESLEAY KSLTRNTTHR NSHSIRGTSD VASLARKLLR ECNNNQQLLT  180
FFQQAARDPG GTPRCTTPAK KGSKKKAYFS PQSSSSDESP RGKTRSRRKA GRKAQRKRRR  240
PSPSSSSSSC SNSESWESNS YSCSTKSKKS NKIKISTLPC YQGGGI                 286

SEQ ID NO: 857          moltype = AA  length = 289
FEATURE                 Location/Qualifiers
source                  1..289
                        mol_type = protein
                        organism = Alphatorquevirus sp.
SEQUENCE: 857
MWTPPRNDQQ YLNWQWYSSI LSSHAAMCGC PDVVAHFNHL ASVLRAPQNP PPPGPQRNLP  60
LRRLPALPAA PEAPGDRAPW PMAGGAGGED GGAGGDADHG GAAGGPEDAD LLDAVAAAET  120
PQETQEGHRG VPLQPRRGAK RKLTFPPSQA PQTSPPVGRL AAGGKRVAKL RGRDADRLPA  180
AQAAAAATAN PGSQTHTPVQ PSPKNPTKSR YQPYLVTKGG GSSILISNST INMFGDPKPY  240
NPSSNDWKEE YEACRIWDRP PRGNLRDTPF YPWAPKENQY RVNFKLGFQ              289

SEQ ID NO: 858          moltype = AA  length = 196
FEATURE                 Location/Qualifiers
source                  1..196
                        mol_type = protein
                        organism = Alphatorquevirus sp.
SEQUENCE: 858
MWTPPRNDQQ YLNWQWYSSI LSSHAAMPQE TQEGHRGVPL QPRRGAKRKL TFPPSQAPQT  60
SPPVGRLAAG GKRVAKLRGR DADRLPAAQA AAAATANPGS QTHTPVQPSP KNPTKSRYQP  120
YLVTKGGGSS ILISNSTINM FGDPKPYNPS SNDWKEEYEA CRIWDRPPRG NLRDTPFYPW  180
APKENQYRVN FKLGFQ                                                   196

SEQ ID NO: 859          moltype = AA  length = 766
FEATURE                 Location/Qualifiers
source                  1..766
                        mol_type = protein
                        organism = Alphatorquevirus sp.
SEQUENCE: 859
MAYGWWRRRR RRWRRWRRRP WRRRWRTRRR RPVRRRGRRR NVRRRRRGGR WRRRYRRWKR  60
KGRRRKKAKI IIRQWQPNYR RRCNIVGYIP VLICGENTVS RNYATHSDDT NYPGPFGGGM  120
TTDKFTLRIL YDEYKRFMNY WTASNEDLDL CRYLGVNLYF FRHPEVDFII KINTMPPFLD  180
TELTAPSIHP GMLALDKRAR WIPSLKSRPG KKHYIKIRVG APKMFTDKWY PQTDLCDMVL  240
LTVYATAADM QYPFGSPLTD SVVVNFQVLQ SMYDETISIL PDQKEKRITL LTSIAFYNTT  300
QTIAQLKPFI DAGNMTSTTT ATTWGSYINT TKFNTAATTT YTYPGSTTTT VTMLTCNDSW  360
YRGTVYNDQI KNLPKEAAQL YLKATKTLLG NTFTNDDHTL EYHGGLYSSI WLSPGRSYFE  420
TPGAYTDIKY NPFTDRGEGN MLWIDWLSKK NMNYDKLQSK CLISDLPLWA AAYGYLEFCA  480
```

```
KSTGDQNIHM NARLLIRSPF TDPQLLVHTN PTKGFVPYSL NFGNGKMPGG SSNVPIRMRA  540
KWYPTLFHQQ EVLEALAQSG PFAYHSDIKK VSLGMKYRFK WIWGGNPVRQ QVVRNPCKDS  600
HSSVNRVPRS LQIVDPKYNS PELTFHTWDF RRGLFGQKAI ERMQQQPTTT DIFSAGRKRP  660
RRDTEVYHSS QEGEQKESLL FPPVKLLRRV PPWEDSQQEE SGSQSSEEET QTVSQQLKQQ  720
LQQQRILGVK LILLFNQVQK IQQNQDINPT LLPRGGDLAS LFQIAP                 766

SEQ ID NO: 860          moltype = AA  length = 216
FEATURE                 Location/Qualifiers
source                  1..216
                        mol_type = protein
                        organism = Alphatorquevirus sp.
SEQUENCE: 860
MAYGWWRRRR RRWRRWRRRP WRRRWRTRRR RPVRRRGRRR NVVRNPCKDS HSSVNRVPRS  60
LQIVDPKYNS PELTFHTWDF RRGLFGQKAI ERMQQQPTTT DIFSAGRKRP RRDTEVYHSS  120
QEGEQKESLL FPPVKLLRRV PPWEDSQQEE SGSQSSEEET QTVSQQLKQQ LQQQRILGVK  180
LILLFNQVQK IQQNQDINPT LLPRGGDLAS LFQIAP                            216

SEQ ID NO: 861          moltype = AA  length = 143
FEATURE                 Location/Qualifiers
source                  1..143
                        mol_type = protein
                        organism = Alphatorquevirus sp.
SEQUENCE: 861
MAYGWWRRRR RRWRRWRRRP WRRRWRTRRR RPVRRRGRRR NAARDPGGTP RCTTPAKKGS  60
KKKAYFSPQS SSSDESPRGK TRSRRKAGRK AQRKRRRPSP SSSSSSCSNS ESWESNSYSC  120
STKSKKSNKI KISTLPCYQG GGI                                          143

SEQ ID NO: 862          moltype = DNA  length = 3553
FEATURE                 Location/Qualifiers
source                  1..3553
                        mol_type = genomic DNA
                        organism = Alphatorquevirus sp.
misc_difference         1842
                        note = a, c, t, g, unknown or other
misc_difference         3125
                        note = a, c, t, g, unknown or other
misc_difference         3126
                        note = a, c, t, g, unknown or other
misc_difference         3127
                        note = a, c, t, g, unknown or other
misc_difference         3128
                        note = a, c, t, g, unknown or other
misc_difference         3129
                        note = a, c, t, g, unknown or other
misc_difference         3130
                        note = a, c, t, g, unknown or other
misc_difference         3131
                        note = a, c, t, g, unknown or other
misc_difference         3132
                        note = a, c, t, g, unknown or other
misc_difference         3133
                        note = a, c, t, g, unknown or other
misc_difference         3134
                        note = a, c, t, g, unknown or other
misc_difference         3135
                        note = a, c, t, g, unknown or other
misc_difference         3136
                        note = a, c, t, g, unknown or other
misc_difference         3137
                        note = a, c, t, g, unknown or other
misc_difference         3138
                        note = a, c, t, g, unknown or other
misc_difference         3139
                        note = a, c, t, g, unknown or other
misc_difference         3140
                        note = a, c, t, g, unknown or other
misc_difference         3141
                        note = a, c, t, g, unknown or other
misc_difference         3142
                        note = a, c, t, g, unknown or other
misc_difference         3143
                        note = a, c, t, g, unknown or other
misc_difference         3144
                        note = a, c, t, g, unknown or other
misc_difference         3145
                        note = a, c, t, g, unknown or other
misc_difference         3146
                        note = a, c, t, g, unknown or other
misc_difference         3147
```

```
                        note = a, c, t, g, unknown or other
misc_difference         3148
                        note = a, c, t, g, unknown or other
misc_difference         3149
                        note = a, c, t, g, unknown or other
misc_difference         3150
                        note = a, c, t, g, unknown or other
misc_difference         3151
                        note = a, c, t, g, unknown or other
misc_difference         3152
                        note = a, c, t, g, unknown or other
misc_difference         3153
                        note = a, c, t, g, unknown or other
misc_difference         3154
                        note = a, c, t, g, unknown or other
misc_difference         3155
                        note = a, c, t, g, unknown or other
misc_difference         3156
                        note = a, c, t, g, unknown or other
misc_difference         3157
                        note = a, c, t, g, unknown or other
misc_difference         3158
                        note = a, c, t, g, unknown or other
misc_difference         3159
                        note = a, c, t, g, unknown or other
misc_difference         3160
                        note = a, c, t, g, unknown or other
misc_difference         3161
                        note = a, c, t, g, unknown or other
misc_difference         3162
                        note = a, c, t, g, unknown or other
misc_difference         3163
                        note = a, c, t, g, unknown or other
misc_difference         3164
                        note = a, c, t, g, unknown or other
misc_difference         3165
                        note = a, c, t, g, unknown or other
misc_difference         3166
                        note = a, c, t, g, unknown or other
misc_difference         3167
                        note = a, c, t, g, unknown or other
misc_difference         3168
                        note = a, c, t, g, unknown or other
misc_difference         3169
                        note = a, c, t, g, unknown or other
misc_difference         3170
                        note = a, c, t, g, unknown or other
misc_difference         3171
                        note = a, c, t, g, unknown or other
misc_difference         3172
                        note = a, c, t, g, unknown or other
misc_difference         3173
                        note = a, c, t, g, unknown or other
misc_difference         3174
                        note = a, c, t, g, unknown or other
misc_difference         3175
                        note = a, c, t, g, unknown or other
misc_difference         3176
                        note = a, c, t, g, unknown or other
SEQUENCE: 862
atacctcatc atataaagcg gcgcacttcc gaatggctga gttttccacg cccgtccgca  60
gcgagatcgc gacggaggag cgatcgagcg tcccgagggc gggtgccgga ggtgagttta  120
cacaccgcag tcaaggggca attcgggctc gggactggcc gggctatggg gcaagactct  180
taaaaaagcc atgtttctcg gtaaacttta cagaaagaaa agggcactgt cactgctacg  240
cgtgcgagct ccagaggcga aaccacctgc tatgagttgg agacccccgg tgcacaaccc  300
caatgggatc gagagaaacc tgtgggaggc attctttcgc atgcatgctt cagcttgtgg  360
ttgtggcgat cttgttggcc atcttactgt actggctggt cggtatggtg ctcctcctcg  420
tcccccggcc cccggcgctc ccagaccacc gctgatacgc cagctggccc ttccggcgcc  480
ccccgccgat cctcaacagg ctaacccaca atggcctggt ggggacggtg gagaagatgg  540
cgctggaggc cccgccgctg gcggcgccgt cgcagacgcc gagtaccaag aagacgagct  600
caacgccctg ttcgacgccg tcgagcaaga agagtaagga ggaggcgatg ggggaggcgg  660
aggtggagac gggggtacag acgcagactg agactaagac gcagacgcag acgaaagcga  720
aagatagtac taactcagtg gaatcccgcc aaagtgcgga ggtgtactat taagggagtt  780
ctgcccatga tcctgtgcgg ggccgggcgc tcggggttta actacggact gcacagcgac  840
gactacactg tacagaagcc ccttggccag aacccccacg ggggcggcat gagtacagtg  900
acttttagcc tacaggtgct ctatgaccag taccagaggt ttatgaacaa gtggtcgtac  960
tccaacgacc agctagacct cgccaggtac tttggctgca ccttctggtt ctacagacac  1020
ccagaggtgg actttgtagc tcagtttgac aacgttcccc ccatgaaaat ggacgagaac  1080
acagccccaa acactcatcc ctctttctta ctacagaaca aacacaaggt taaaattccc  1140
```

```
agctttaaaa caaagccttt tggtaaaaaa agagttagag ttacagtagg gccccccaaa  1200
ctgtttgaag ataagtggta cagccaacat gacttgtgta aggtgcccct agtcagttgg  1260
cggttaaccg cagctgactt caggtttccg ttctgctcac cacaaactga caacccttgc  1320
tacaccttcc aggtattgca tgaagagtat tacccagtaa taggcacttc tgctttagaa  1380
aacggcagta actacaatag ctcagctata acagccttag aaaaattctt atatgaaaaa  1440
tgcacacact atcaaacatt tgccacagac accagactta atcctcagcg accagtgtca  1500
tctacaaatg caaacaaaac atacaccccc tcaggctccc aagaaacaat agtgtggggg  1560
cagtcagatt ttaatttatt taaaaagcac acagacagca actatggcta ctgcacctac  1620
tgtcctacca atgacttagc tacaaaaatt aaaaagtaca gagacaaaag attcgactgg  1680
ctaacaaaca tgccagtaac aaacacctgc cacataaatg ccaccttcgc ccgaggcaaa  1740
attaaagaat gggagtacca cctagggtgg ttctcaaaca tctttatagg caacctgaga  1800
cacaacctag cattccgggc cgcatacata gacatcacct anacagacaa gggagaaggc  1860
aacattatct ggttccagta cctcactaaa cccaccacag agtacataga agcccaagca  1920
aagtgctcca tcacaaacat acccctgtat gctgcttttt atggctacga agactacctc  1980
cagagaacac taggccccta ccaagatgta gaaaccctag gtataatctg tgttaaatgt  2040
ccctacacag atccccctct agttcacaag tctacagata aaaagaactg ggctacgtg   2100
ttctacgacg tgcactttgg caacggaaag accccagagg gactgggcca ggtgcaccct  2160
tactggatgc agaggtggag accctacgta cagtttcaga aagacactat gaacaaaata  2220
gccaggacgg gaccgttcag ctacagagac gagacgcctt ccatcaccct gaccgccggg  2280
tacaagtttc attttaactg ggggggcgac tctatatttc cacagattat taaaaacccc  2340
tgcccagaca gcggggtacg accttcatcc agtagagagc gtcgctcagt acaagtcgtt  2400
agcccgctca caatggggcc agagtacata ttccaccggt gggactggcg acgggggttc  2460
tttaatcaaa aagctctcaa aagaatgctt gaaaaatcaa ttaatgatgg agagtatcca  2520
acaggcccaa aggtccctcg atggtttccc ccactcgaca accaagagca agaaggcgcc  2580
tcaggttcag aggagacaag gtcgcagtcc tcgcaagaag aagccgctca agaagccctc  2640
caagaagtcc aagaggcgtc gctacagcag cacctcctcc agcagtaccg agagcagcga  2700
cggatcggaa agcaactcca actcgtcatg ctgcagctca ccaagacgca gagcaacctg  2760
cacataaacc cccgtgttct tggccatgca taaataaagt ctacatgttt ccccccgaca  2820
agcccatgcc catacacggg taccacgggt gggagacgga gtaccaggcc tgcaaggcct  2880
tcaacaggcc ccccagaaac tacctttcag acaaacccat ctacccttgg ctccctcgcc  2940
ccgaacccga aataatagtg agctttaggt tcggtttcaa ataaacaagg ccgcaaataa  3000
acaaggccgt gggagtttca ctggtcggtg tctacctctt aaggtcacta agcactccga  3060
gcgttagcga ggagtgcgac ccttcccccct ggtgccacgc cctcggcggc cgcgcgctac  3120
gcctnnnnnn nnnnnnnnnn nnnnnnnnnn nnnnnnnnnn nnnnnnnnnn nnnnnnntgaa  3180
tcagtaacga aagtgagtgg ggccagactt cgccataagg cctttatctt cttgccattg  3240
gtccgtgtgg ggagtcgcca taggcttcgg gctcggtttt aggccttccg gactacaaaa  3300
accgccattt tagtgacgtc acggcggcca ttttaagtaa gcatggcggg cggtgacgta  3360
caagttgaaa ggtcaccgcg cttccgtgtt tactcaaaat ggtggccaac tgcttccggg  3420
tcaaaggtcg gcggccacgt cataagtcac gtgggagggc tgcgtcacaa acacggaagt  3480
ggctgtccca cgtgacttgt cacgtgattg ctacgtcacg gccgccattt tagttcacaa  3540
aatggcggac ttc                                                     3553
```

```
SEQ ID NO: 863          moltype = AA  length = 121
FEATURE                 Location/Qualifiers
source                  1..121
                        mol_type = protein
                        organism = Alphatorquevirus sp.
SEQUENCE: 863
MSWRPPVHNP NGIERNLWEA FFRMHASACG CGDLVGHLTV LAGRYGAPPR PPAPGAPRPP  60
LIRQLALPAP PADPQQANPQ WPGGDGGEDG AGGPAAGGAV ADAEYQEDEL NALFDAVEQE  120
E                                                                  121

SEQ ID NO: 864          moltype = AA  length = 267
FEATURE                 Location/Qualifiers
source                  1..267
                        mol_type = protein
                        organism = Alphatorquevirus sp.
SEQUENCE: 864
MSWRPPVHNP NGIERNLWEA FFRMHASACG CGDLVGHLTV LAGRYGAPPR PPAPGAPRPP  60
LIRQLALPAP PADPQQANPQ WPGGDGGEDG AGGPAAGGAV ADAEYQEDEL NALFDAVEQE  120
ELLKTPAQTA GYDLHPVESV AQYKSLARSQ WGQSTYSTGG TGDGGSLIKK LSKECLKNQL  180
MMESIQQAQR SLDGFPHSTT KSKKAPQVQR RQGRSPRKKK PLKKPSKKSK RRRYSSTSSS  240
STESSDGSES NSNSSCCSSP RRRATCT                                      267

SEQ ID NO: 865          moltype = AA  length = 273
FEATURE                 Location/Qualifiers
source                  1..273
                        mol_type = protein
                        organism = Alphatorquevirus sp.
SEQUENCE: 865
MSWRPPVHNP NGIERNLWEA FFRMHASACG CGDLVGHLTV LAGRYGAPPR PPAPGAPRPP  60
LIRQLALPAP PADPQQANPQ WPGGDGGEDG AGGPAAGGAV ADAEYQEDEL NALFDAVEQE  120
EPKGPSMVSP TRQPRARRRL RFRGDKVAVL ARRSRSRSPP RSPRGVATAA PPPAVPRAAT  180
DRKATPTRHA AAHQDAEQPA HKPPCSWPCI NKVYMFPPDK PMPIHGYHGW ETEYQACKAF  240
NRPPRNYLSD KPIYPWLPRP EPEIIVSFRF GFK                                273

SEQ ID NO: 866          moltype = AA  length = 196
FEATURE                 Location/Qualifiers
source                  1..196
```

```
                        mol_type = protein
                        organism = Alphatorquevirus sp.
SEQUENCE: 866
MSWRPPVHNP NGIERNLWEA FFRMHASACG CGDLVGHLTV LAGRPKGPSM VSPTRQPRAR  60
RRLRFRGDKV AVLARRSRSR SPPRSPRGVA TAAPPPAVPR AATDRKATPT RHAAAHQDAE  120
QPAHKPPCSW PCINKVYMFP PDKPMPIHGY HGWETEYQAC KAFNRPPRNY LSDKPIYPWL  180
PRPEPEIIVS FRFGFK                                                 196

SEQ ID NO: 867          moltype = AA  length = 760
FEATURE                 Location/Qualifiers
source                  1..760
                        mol_type = protein
                        organism = Alphatorquevirus sp.
VARIANT                 444
                        note = Any amino acid
SEQUENCE: 867
MAWWGRWRRW RWRPRRWRRR RRRRVPRRRA QRPVRRRRAR RVRRRRWGRR RWRRGYRRRL  60
RLRRRRRRKR KIVLTQWNPA KVRRCTIKGV LPMILCGAGR SGFNYGLHSD DYTVQKPLGQ  120
NPHGGGMSTV TFSLQVLYDQ YQRFMNKWSY SNDQLDLARY FGCTFWFYRH PEVDFVAQFD  180
NVPPMKMDEN TAPNTHPSFL LQNKHKVKIP SFKTKPFGKK RVRVTVGPPK LFEDKWYSQH  240
DLCKVPLVSW RLTAADFRFP FCSPQTDNPC YTFQVLHEEY YPVIGTSALE NGSNYNSSAI  300
TALEKFLYEK CTHYQTFATD TRLNPQRPVS STNANKTYTP SGSQETIVWG QSDFNLFKKH  360
TDSNYGYCTY CPTNDLATKI KKYRDKRFDW LTNMPVTNTC HINATFARGK IKEWEYHLGW  420
FSNIFIGNLR HNLAFRAAYI DITXTDKGEG NIIWFQYLTK PTTEYIEAQA KCSITNIPLY  480
AAFYGYEDYL QRTLGPYQDV ETLGIICVKC PYTDPPLVHK STDKKNWGYV FYDVHFGNGK  540
TPEGLGQVHP YWMQRWRPYV QFQKDTMNKI ARTGPFSYRD ETPSITLTAG YKFHFNWGGD  600
SIFPQIIKNP CPDSGVRPSS SRERRSVQVV SPLTMGPEYI FHRWDWRRGF FNQKALKRML  660
EKSINDGEYP TGPKVPRWFP PLDNQEQEGA SGSEETRSQS SQEEAAQEAL QEVQEASLQQ  720
HLLQQYREQR RIGKQLQLVM LQLTKTQSNL HINPRVLGHA                       760

SEQ ID NO: 868          moltype = AA  length = 196
FEATURE                 Location/Qualifiers
source                  1..196
                        mol_type = protein
                        organism = Alphatorquevirus sp.
SEQUENCE: 868
MAWWGRWRRW RWRPRRWRRR RRRRVPRRRA QRPVRRRRAR RIIKNPCPDS GVRPSSSRER  60
RSVQVVSPLT MGPEYIFHRW DWRRGFFNQK ALKRMLEKSI NDGEYPTGPK VPRWFPPLDN  120
QEQEGASGSE ETRSQSSQEE AAQEALQEVQ EASLQQHLLQ QYREQRRIGK QLQLVMLQLT  180
KTQSNLHINP RVLGHA                                                 196

SEQ ID NO: 869          moltype = AA  length = 121
FEATURE                 Location/Qualifiers
source                  1..121
                        mol_type = protein
                        organism = Alphatorquevirus sp.
SEQUENCE: 869
MAWWGRWRRW RWRPRRWRRR RRRRVPRRRA QRPVRRRRAR RAQRSLDGFP HSTTKSKKAP  60
QVQRRQGRSP RKKKPLKKPS KKSKRRRYSS TSSSSTESSD GSESNSNSSC CSSPRRRATC  120
T                                                                 121

SEQ ID NO: 870          moltype = DNA  length = 3896
FEATURE                 Location/Qualifiers
source                  1..3896
                        mol_type = genomic DNA
                        organism = Alphatorquevirus sp.
misc_difference         1276
                        note = a, c, t, g, unknown or other
misc_difference         3198
                        note = a, c, t, g, unknown or other
misc_difference         3199
                        note = a, c, t, g, unknown or other
misc_difference         3200
                        note = a, c, t, g, unknown or other
misc_difference         3201
                        note = a, c, t, g, unknown or other
misc_difference         3202
                        note = a, c, t, g, unknown or other
misc_difference         3203
                        note = a, c, t, g, unknown or other
misc_difference         3204
                        note = a, c, t, g, unknown or other
misc_difference         3205
                        note = a, c, t, g, unknown or other
misc_difference         3206
                        note = a, c, t, g, unknown or other
misc_difference         3207
                        note = a, c, t, g, unknown or other
misc_difference         3208
```

note = a, c, t, g, unknown or other
misc_difference 3209
note = a, c, t, g, unknown or other
misc_difference 3210
note = a, c, t, g, unknown or other
misc_difference 3211
note = a, c, t, g, unknown or other
misc_difference 3212
note = a, c, t, g, unknown or other
misc_difference 3213
note = a, c, t, g, unknown or other
misc_difference 3214
note = a, c, t, g, unknown or other
misc_difference 3215
note = a, c, t, g, unknown or other
misc_difference 3216
note = a, c, t, g, unknown or other
misc_difference 3217
note = a, c, t, g, unknown or other
misc_difference 3218
note = a, c, t, g, unknown or other
misc_difference 3219
note = a, c, t, g, unknown or other
misc_difference 3220
note = a, c, t, g, unknown or other
misc_difference 3221
note = a, c, t, g, unknown or other
misc_difference 3222
note = a, c, t, g, unknown or other
misc_difference 3223
note = a, c, t, g, unknown or other
misc_difference 3224
note = a, c, t, g, unknown or other
misc_difference 3225
note = a, c, t, g, unknown or other
misc_difference 3226
note = a, c, t, g, unknown or other
misc_difference 3227
note = a, c, t, g, unknown or other
misc_difference 3228
note = a, c, t, g, unknown or other
misc_difference 3229
note = a, c, t, g, unknown or other
misc_difference 3230
note = a, c, t, g, unknown or other
misc_difference 3231
note = a, c, t, g, unknown or other
misc_difference 3232
note = a, c, t, g, unknown or other
misc_difference 3233
note = a, c, t, g, unknown or other
misc_difference 3234
note = a, c, t, g, unknown or other
misc_difference 3235
note = a, c, t, g, unknown or other
misc_difference 3236
note = a, c, t, g, unknown or other
misc_difference 3237
note = a, c, t, g, unknown or other
misc_difference 3238
note = a, c, t, g, unknown or other
misc_difference 3239
note = a, c, t, g, unknown or other
misc_difference 3240
note = a, c, t, g, unknown or other
misc_difference 3241
note = a, c, t, g, unknown or other
misc_difference 3242
note = a, c, t, g, unknown or other
misc_difference 3243
note = a, c, t, g, unknown or other
misc_difference 3244
note = a, c, t, g, unknown or other
misc_difference 3245
note = a, c, t, g, unknown or other
misc_difference 3246
note = a, c, t, g, unknown or other
misc_difference 3247
note = a, c, t, g, unknown or other misc_difference 3248
note = a, c, t, g, unknown or other
misc_difference 3249
note = a, c, t, g, unknown or other
misc_difference 3250
note = a, c, t, g, unknown or other
misc_difference 3251
note = a, c, t, g, unknown or other
misc_difference 3252
note = a, c, t, g, unknown or other
misc_difference 3253
note = a, c, t, g, unknown or other
misc_difference 3254
note = a, c, t, g, unknown or other
misc_difference 3255
note = a, c, t, g, unknown or other
misc_difference 3256
note = a, c, t, g, unknown or other
misc_difference 3257
note = a, c, t, g, unknown or other
misc_difference 3258
note = a, c, t, g, unknown or other
misc_difference 3259
note = a, c, t, g, unknown or other
misc_difference 3260
note = a, c, t, g, unknown or other
misc_difference 3261
note = a, c, t, g, unknown or other
misc_difference 3262
note = a, c, t, g, unknown or other
misc_difference 3263
note = a, c, t, g, unknown or other
misc_difference 3264
note = a, c, t, g, unknown or other
misc_difference 3265
note = a, c, t, g, unknown or other
misc_difference 3266
note = a, c, t, g, unknown or other
misc_difference 3267
note = a, c, t, g, unknown or other
misc_difference 3268
note = a, c, t, g, unknown or other
misc_difference 3269
note = a, c, t, g, unknown or other
misc_difference 3270
note = a, c, t, g, unknown or other
misc_difference 3271
note = a, c, t, g, unknown or other
misc_difference 3272
note = a, c, t, g, unknown or other
misc_difference 3273
note = a, c, t, g, unknown or other
misc_difference 3274
note = a, c, t, g, unknown or other
misc_difference 3275
note = a, c, t, g, unknown or other
misc_difference 3276
note = a, c, t, g, unknown or other
misc_difference 3277
note = a, c, t, g, unknown or other
misc_difference 3278
note = a, c, t, g, unknown or other
misc_difference 3279
note = a, c, t, g, unknown or other
misc_difference 3280
note = a, c, t, g, unknown or other
misc_difference 3281
note = a, c, t, g, unknown or other
misc_difference 3282
note = a, c, t, g, unknown or other
misc_difference 3283
note = a, c, t, g, unknown or other
misc_difference 3284
note = a, c, t, g, unknown or other
misc_difference 3285
note = a, c, t, g, unknown or other
misc_difference 3286
note = a, c, t, g, unknown or other
misc_difference 3287 note = a, c, t, g, unknown or other
misc_difference 3288
note = a, c, t, g, unknown or other
misc_difference 3289
note = a, c, t, g, unknown or other
misc_difference 3290
note = a, c, t, g, unknown or other
misc_difference 3291
note = a, c, t, g, unknown or other
misc_difference 3292
note = a, c, t, g, unknown or other
misc_difference 3293
note = a, c, t, g, unknown or other
misc_difference 3294
note = a, c, t, g, unknown or other
misc_difference 3295
note = a, c, t, g, unknown or other
misc_difference 3296
note = a, c, t, g, unknown or other
misc_difference 3297
note = a, c, t, g, unknown or other
misc_difference 3298
note = a, c, t, g, unknown or other
misc_difference 3299
note = a, c, t, g, unknown or other
misc_difference 3300
note = a, c, t, g, unknown or other
misc_difference 3301
note = a, c, t, g, unknown or other
misc_difference 3302
note = a, c, t, g, unknown or other
misc_difference 3303
note = a, c, t, g, unknown or other
misc_difference 3304
note = a, c, t, g, unknown or other
misc_difference 3305
note = a, c, t, g, unknown or other
misc_difference 3306
note = a, c, t, g, unknown or other
misc_difference 3307
note = a, c, t, g, unknown or other
misc_difference 3308
note = a, c, t, g, unknown or other
misc_difference 3309
note = a, c, t, g, unknown or other
misc_difference 3310
note = a, c, t, g, unknown or other
misc_difference 3311
note = a, c, t, g, unknown or other
misc_difference 3312
note = a, c, t, g, unknown or other
misc_difference 3313
note = a, c, t, g, unknown or other
misc_difference 3314
note = a, c, t, g, unknown or other
misc_difference 3315
note = a, c, t, g, unknown or other
misc_difference 3316
note = a, c, t, g, unknown or other
misc_difference 3317
note = a, c, t, g, unknown or other
misc_difference 3318
note = a, c, t, g, unknown or other
misc_difference 3319
note = a, c, t, g, unknown or other
misc_difference 3320
note = a, c, t, g, unknown or other
misc_difference 3321
note = a, c, t, g, unknown or other
misc_difference 3322
note = a, c, t, g, unknown or other
misc_difference 3323
note = a, c, t, g, unknown or other
misc_difference 3324
note = a, c, t, g, unknown or other
misc_difference 3325
note = a, c, t, g, unknown or other
misc_difference 3326
note = a, c, t, g, unknown or other

```
misc_difference        3327
                       note = a, c, t, g, unknown or other
misc_difference        3328
                       note = a, c, t, g, unknown or other
misc_difference        3329
                       note = a, c, t, g, unknown or other
misc_difference        3330
                       note = a, c, t, g, unknown or other
misc_difference        3331
                       note = a, c, t, g, unknown or other
misc_difference        3332
                       note = a, c, t, g, unknown or other
misc_difference        3333
                       note = a, c, t, g, unknown or other
misc_difference        3334
                       note = a, c, t, g, unknown or other
misc_difference        3335
                       note = a, c, t, g, unknown or other
misc_difference        3336
                       note = a, c, t, g, unknown or other
misc_difference        3337
                       note = a, c, t, g, unknown or other
misc_difference        3338
                       note = a, c, t, g, unknown or other
misc_difference        3339
                       note = a, c, t, g, unknown or other
misc_difference        3340
                       note = a, c, t, g, unknown or other
misc_difference        3341
                       note = a, c, t, g, unknown or other
misc_difference        3342
                       note = a, c, t, g, unknown or other
misc_difference        3343
                       note = a, c, t, g, unknown or other
misc_difference        3344
                       note = a, c, t, g, unknown or other
misc_difference        3345
                       note = a, c, t, g, unknown or other
misc_difference        3346
                       note = a, c, t, g, unknown or other
misc_difference        3347
                       note = a, c, t, g, unknown or other
misc_difference        3348
                       note = a, c, t, g, unknown or other
misc_difference        3349
                       note = a, c, t, g, unknown or other
misc_difference        3350
                       note = a, c, t, g, unknown or other
misc_difference        3351
                       note = a, c, t, g, unknown or other
misc_difference        3352
                       note = a, c, t, g, unknown or other
misc_difference        3353
                       note = a, c, t, g, unknown or other
misc_difference        3354
                       note = a, c, t, g, unknown or other
misc_difference        3355
                       note = a, c, t, g, unknown or other
misc_difference        3356
                       note = a, c, t, g, unknown or other
misc_difference        3357
                       note = a, c, t, g, unknown or other
misc_difference        3358
                       note = a, c, t, g, unknown or other
misc_difference        3359
                       note = a, c, t, g, unknown or other
misc_difference        3360
                       note = a, c, t, g, unknown or other
misc_difference        3361
                       note = a, c, t, g, unknown or other
misc_difference        3362
                       note = a, c, t, g, unknown or other
misc_difference        3363
                       note = a, c, t, g, unknown or other
misc_difference        3364
                       note = a, c, t, g, unknown or other
misc_difference        3365
                       note = a, c, t, g, unknown or other
misc_difference        3366
```

note = a, c, t, g, unknown or other
misc_difference 3367
note = a, c, t, g, unknown or other
misc_difference 3368
note = a, c, t, g, unknown or other
misc_difference 3369
note = a, c, t, g, unknown or other
misc_difference 3370
note = a, c, t, g, unknown or other
misc_difference 3371
note = a, c, t, g, unknown or other
misc_difference 3372
note = a, c, t, g, unknown or other
misc_difference 3373
note = a, c, t, g, unknown or other
misc_difference 3374
note = a, c, t, g, unknown or other
misc_difference 3375
note = a, c, t, g, unknown or other
misc_difference 3376
note = a, c, t, g, unknown or other
misc_difference 3377
note = a, c, t, g, unknown or other
misc_difference 3378
note = a, c, t, g, unknown or other
misc_difference 3379
note = a, c, t, g, unknown or other
misc_difference 3380
note = a, c, t, g, unknown or other
misc_difference 3381
note = a, c, t, g, unknown or other
misc_difference 3382
note = a, c, t, g, unknown or other
misc_difference 3383
note = a, c, t, g, unknown or other
misc_difference 3384
note = a, c, t, g, unknown or other
misc_difference 3385
note = a, c, t, g, unknown or other
misc_difference 3386
note = a, c, t, g, unknown or other
misc_difference 3387
note = a, c, t, g, unknown or other
misc_difference 3388
note = a, c, t, g, unknown or other
misc_difference 3389
note = a, c, t, g, unknown or other
misc_difference 3390
note = a, c, t, g, unknown or other
misc_difference 3391
note = a, c, t, g, unknown or other
misc_difference 3392
note = a, c, t, g, unknown or other
misc_difference 3393
note = a, c, t, g, unknown or other
misc_difference 3394
note = a, c, t, g, unknown or other
misc_difference 3395
note = a, c, t, g, unknown or other
misc_difference 3396
note = a, c, t, g, unknown or other
misc_difference 3397
note = a, c, t, g, unknown or other
misc_difference 3398
note = a, c, t, g, unknown or other
misc_difference 3399
note = a, c, t, g, unknown or other
misc_difference 3400
note = a, c, t, g, unknown or other
misc_difference 3401
note = a, c, t, g, unknown or other
misc_difference 3402
note = a, c, t, g, unknown or other
misc_difference 3403
note = a, c, t, g, unknown or other
misc_difference 3404
note = a, c, t, g, unknown or other
misc_difference 3405
note = a, c, t, g, unknown or other misc_difference 3406
note = a, c, t, g, unknown or other
misc_difference 3407
note = a, c, t, g, unknown or other
misc_difference 3408
note = a, c, t, g, unknown or other
misc_difference 3409
note = a, c, t, g, unknown or other
misc_difference 3410
note = a, c, t, g, unknown or other
misc_difference 3411
note = a, c, t, g, unknown or other
misc_difference 3412
note = a, c, t, g, unknown or other
misc_difference 3413
note = a, c, t, g, unknown or other
misc_difference 3414
note = a, c, t, g, unknown or other
misc_difference 3415
note = a, c, t, g, unknown or other
misc_difference 3416
note = a, c, t, g, unknown or other
misc_difference 3417
note = a, c, t, g, unknown or other
misc_difference 3418
note = a, c, t, g, unknown or other
misc_difference 3419
note = a, c, t, g, unknown or other
misc_difference 3420
note = a, c, t, g, unknown or other
misc_difference 3421
note = a, c, t, g, unknown or other
misc_difference 3422
note = a, c, t, g, unknown or other
misc_difference 3423
note = a, c, t, g, unknown or other
misc_difference 3424
note = a, c, t, g, unknown or other
misc_difference 3425
note = a, c, t, g, unknown or other
misc_difference 3426
note = a, c, t, g, unknown or other
misc_difference 3427
note = a, c, t, g, unknown or other
misc_difference 3428
note = a, c, t, g, unknown or other
misc_difference 3429
note = a, c, t, g, unknown or other
misc_difference 3430
note = a, c, t, g, unknown or other
misc_difference 3431
note = a, c, t, g, unknown or other
misc_difference 3432
note = a, c, t, g, unknown or other
misc_difference 3433
note = a, c, t, g, unknown or other
misc_difference 3434
note = a, c, t, g, unknown or other
misc_difference 3435
note = a, c, t, g, unknown or other
misc_difference 3436
note = a, c, t, g, unknown or other
misc_difference 3437
note = a, c, t, g, unknown or other
misc_difference 3438
note = a, c, t, g, unknown or other
misc_difference 3439
note = a, c, t, g, unknown or other
misc_difference 3440
note = a, c, t, g, unknown or other
misc_difference 3441
note = a, c, t, g, unknown or other
misc_difference 3442
note = a, c, t, g, unknown or other
misc_difference 3443
note = a, c, t, g, unknown or other
misc_difference 3444
note = a, c, t, g, unknown or other
misc_difference 3445 note = a, c, t, g, unknown or other
misc_difference 3446
note = a, c, t, g, unknown or other
misc_difference 3447
note = a, c, t, g, unknown or other
misc_difference 3448
note = a, c, t, g, unknown or other
misc_difference 3449
note = a, c, t, g, unknown or other
misc_difference 3450
note = a, c, t, g, unknown or other
misc_difference 3451
note = a, c, t, g, unknown or other
misc_difference 3452
note = a, c, t, g, unknown or other
misc_difference 3453
note = a, c, t, g, unknown or other
misc_difference 3454
note = a, c, t, g, unknown or other
misc_difference 3455
note = a, c, t, g, unknown or other
misc_difference 3456
note = a, c, t, g, unknown or other
misc_difference 3457
note = a, c, t, g, unknown or other
misc_difference 3458
note = a, c, t, g, unknown or other
misc_difference 3459
note = a, c, t, g, unknown or other
misc_difference 3460
note = a, c, t, g, unknown or other
misc_difference 3461
note = a, c, t, g, unknown or other
misc_difference 3462
note = a, c, t, g, unknown or other
misc_difference 3463
note = a, c, t, g, unknown or other
misc_difference 3464
note = a, c, t, g, unknown or other
misc_difference 3465
note = a, c, t, g, unknown or other
misc_difference 3466
note = a, c, t, g, unknown or other
misc_difference 3467
note = a, c, t, g, unknown or other
misc_difference 3468
note = a, c, t, g, unknown or other
misc_difference 3469
note = a, c, t, g, unknown or other
misc_difference 3470
note = a, c, t, g, unknown or other
misc_difference 3471
note = a, c, t, g, unknown or other
misc_difference 3472
note = a, c, t, g, unknown or other
misc_difference 3473
note = a, c, t, g, unknown or other
misc_difference 3474
note = a, c, t, g, unknown or other
misc_difference 3475
note = a, c, t, g, unknown or other
misc_difference 3476
note = a, c, t, g, unknown or other
misc_difference 3477
note = a, c, t, g, unknown or other
misc_difference 3478
note = a, c, t, g, unknown or other
misc_difference 3479
note = a, c, t, g, unknown or other
misc_difference 3480
note = a, c, t, g, unknown or other
misc_difference 3481
note = a, c, t, g, unknown or other
misc_difference 3482
note = a, c, t, g, unknown or other
misc_difference 3483
note = a, c, t, g, unknown or other
misc_difference 3484
note = a, c, t, g, unknown or other misc_difference 3485
note = a, c, t, g, unknown or other
misc_difference 3486
note = a, c, t, g, unknown or other
misc_difference 3487
note = a, c, t, g, unknown or other
misc_difference 3488
note = a, c, t, g, unknown or other
misc_difference 3489
note = a, c, t, g, unknown or other
misc_difference 3490
note = a, c, t, g, unknown or other
misc_difference 3491
note = a, c, t, g, unknown or other
misc_difference 3492
note = a, c, t, g, unknown or other
misc_difference 3493
note = a, c, t, g, unknown or other
misc_difference 3494
note = a, c, t, g, unknown or other
misc_difference 3495
note = a, c, t, g, unknown or other
misc_difference 3496
note = a, c, t, g, unknown or other
misc_difference 3497
note = a, c, t, g, unknown or other
misc_difference 3498
note = a, c, t, g, unknown or other
misc_difference 3499
note = a, c, t, g, unknown or other
misc_difference 3500
note = a, c, t, g, unknown or other
misc_difference 3501
note = a, c, t, g, unknown or other
misc_difference 3502
note = a, c, t, g, unknown or other
misc_difference 3503
note = a, c, t, g, unknown or other
misc_difference 3504
note = a, c, t, g, unknown or other
misc_difference 3505
note = a, c, t, g, unknown or other
misc_difference 3506
note = a, c, t, g, unknown or other
misc_difference 3507
note = a, c, t, g, unknown or other
misc_difference 3508
note = a, c, t, g, unknown or other
misc_difference 3509
note = a, c, t, g, unknown or other
misc_difference 3510
note = a, c, t, g, unknown or other
misc_difference 3511
note = a, c, t, g, unknown or other
misc_difference 3512
note = a, c, t, g, unknown or other
misc_difference 3513
note = a, c, t, g, unknown or other
misc_difference 3514
note = a, c, t, g, unknown or other
misc_difference 3515
note = a, c, t, g, unknown or other
misc_difference 3516
note = a, c, t, g, unknown or other
misc_difference 3517
note = a, c, t, g, unknown or other
misc_difference 3518
note = a, c, t, g, unknown or other
misc_difference 3519
note = a, c, t, g, unknown or other
misc_difference 3520
note = a, c, t, g, unknown or other
misc_difference 3521
note = a, c, t, g, unknown or other
misc_difference 3522
note = a, c, t, g, unknown or other
misc_difference 3523
note = a, c, t, g, unknown or other
misc_difference 3524

| | | |
|---|---|---|
| | note = a, c, t, g, unknown or other |
| misc_difference | 3525 |
| | note = a, c, t, g, unknown or other |
| misc_difference | 3526 |
| | note = a, c, t, g, unknown or other |
| misc_difference | 3527 |
| | note = a, c, t, g, unknown or other |
| misc_difference | 3528 |
| | note = a, c, t, g, unknown or other |
| misc_difference | 3529 |
| | note = a, c, t, g, unknown or other |
| misc_difference | 3530 |
| | note = a, c, t, g, unknown or other |
| misc_difference | 3531 |
| | note = a, c, t, g, unknown or other |
| misc_difference | 3532 |
| | note = a, c, t, g, unknown or other |
| misc_difference | 3533 |
| | note = a, c, t, g, unknown or other |
| misc_difference | 3534 |
| | note = a, c, t, g, unknown or other |
| misc_difference | 3535 |
| | note = a, c, t, g, unknown or other |
| misc_difference | 3536 |
| | note = a, c, t, g, unknown or other |
| misc_difference | 3537 |
| | note = a, c, t, g, unknown or other |
| misc_difference | 3538 |
| | note = a, c, t, g, unknown or other |
| misc_difference | 3539 |
| | note = a, c, t, g, unknown or other |
| misc_difference | 3540 |
| | note = a, c, t, g, unknown or other |
| misc_difference | 3541 |
| | note = a, c, t, g, unknown or other |
| misc_difference | 3542 |
| | note = a, c, t, g, unknown or other |
| misc_difference | 3543 |
| | note = a, c, t, g, unknown or other |
| misc_difference | 3544 |
| | note = a, c, t, g, unknown or other |
| misc_difference | 3545 |
| | note = a, c, t, g, unknown or other |
| misc_difference | 3546 |
| | note = a, c, t, g, unknown or other |
| misc_difference | 3547 |
| | note = a, c, t, g, unknown or other |
| misc_difference | 3548 |
| | note = a, c, t, g, unknown or other |
| misc_difference | 3549 |
| | note = a, c, t, g, unknown or other |
| misc_difference | 3550 |
| | note = a, c, t, g, unknown or other |
| misc_difference | 3551 |
| | note = a, c, t, g, unknown or other |
| misc_difference | 3552 |
| | note = a, c, t, g, unknown or other |
| misc_difference | 3553 |
| | note = a, c, t, g, unknown or other |
| misc_difference | 3554 |
| | note = a, c, t, g, unknown or other |
| misc_difference | 3555 |
| | note = a, c, t, g, unknown or other |
| misc_difference | 3556 |
| | note = a, c, t, g, unknown or other |
| misc_difference | 3557 |
| | note = a, c, t, g, unknown or other |
| misc_difference | 3558 |
| | note = a, c, t, g, unknown or other |
| misc_difference | 3559 |
| | note = a, c, t, g, unknown or other |
| misc_difference | 3560 |
| | note = a, c, t, g, unknown or other |
| misc_difference | 3561 |
| | note = a, c, t, g, unknown or other |
| misc_difference | 3562 |
| | note = a, c, t, g, unknown or other |
| misc_difference | 3563 |
| | note = a, c, t, g, unknown or other |

| | | |
|---|---|---|
| misc_difference | 3564 | |
| | note = a, c, t, g, unknown or other | |
| misc_difference | 3565 | |
| | note = a, c, t, g, unknown or other | |
| misc_difference | 3566 | |
| | note = a, c, t, g, unknown or other | |
| misc_difference | 3567 | |
| | note = a, c, t, g, unknown or other | |
| misc_difference | 3568 | |
| | note = a, c, t, g, unknown or other | |
| misc_difference | 3569 | |
| | note = a, c, t, g, unknown or other | |
| misc_difference | 3570 | |
| | note = a, c, t, g, unknown or other | |
| misc_difference | 3571 | |
| | note = a, c, t, g, unknown or other | |
| misc_difference | 3572 | |
| | note = a, c, t, g, unknown or other | |
| misc_difference | 3573 | |
| | note = a, c, t, g, unknown or other | |
| misc_difference | 3574 | |
| | note = a, c, t, g, unknown or other | |
| misc_difference | 3575 | |
| | note = a, c, t, g, unknown or other | |
| misc_difference | 3576 | |
| | note = a, c, t, g, unknown or other | |
| misc_difference | 3577 | |
| | note = a, c, t, g, unknown or other | |
| misc_difference | 3578 | |
| | note = a, c, t, g, unknown or other | |
| misc_difference | 3579 | |
| | note = a, c, t, g, unknown or other | |
| misc_difference | 3580 | |
| | note = a, c, t, g, unknown or other | |
| misc_difference | 3581 | |
| | note = a, c, t, g, unknown or other | |
| misc_difference | 3582 | |
| | note = a, c, t, g, unknown or other | |
| misc_difference | 3583 | |
| | note = a, c, t, g, unknown or other | |
| misc_difference | 3584 | |
| | note = a, c, t, g, unknown or other | |
| misc_difference | 3585 | |
| | note = a, c, t, g, unknown or other | |
| misc_difference | 3586 | |
| | note = a, c, t, g, unknown or other | |
| misc_difference | 3587 | |
| | note = a, c, t, g, unknown or other | |
| misc_difference | 3588 | |
| | note = a, c, t, g, unknown or other | |
| misc_difference | 3589 | |
| | note = a, c, t, g, unknown or other | |
| misc_difference | 3590 | |
| | note = a, c, t, g, unknown or other | |
| misc_difference | 3591 | |
| | note = a, c, t, g, unknown or other | |
| misc_difference | 3592 | |
| | note = a, c, t, g, unknown or other | |
| misc_difference | 3593 | |
| | note = a, c, t, g, unknown or other | |
| misc_difference | 3594 | |
| | note = a, c, t, g, unknown or other | |
| misc_difference | 3595 | |
| | note = a, c, t, g, unknown or other | |
| misc_difference | 3596 | |
| | note = a, c, t, g, unknown or other | |
| misc_difference | 3597 | |
| | note = a, c, t, g, unknown or other | |
| misc_difference | 3598 | |
| | note = a, c, t, g, unknown or other | |
| misc_difference | 3599 | |
| | note = a, c, t, g, unknown or other | |
| misc_difference | 3600 | |
| | note = a, c, t, g, unknown or other | |
| misc_difference | 3601 | |
| | note = a, c, t, g, unknown or other | |
| misc_difference | 3602 | |
| | note = a, c, t, g, unknown or other | |
| misc_difference | 3603 | |

note = a, c, t, g, unknown or other
misc_difference 3604
note = a, c, t, g, unknown or other
misc_difference 3605
note = a, c, t, g, unknown or other
misc_difference 3606
note = a, c, t, g, unknown or other
misc_difference 3607
note = a, c, t, g, unknown or other
misc_difference 3608
note = a, c, t, g, unknown or other
misc_difference 3609
note = a, c, t, g, unknown or other
misc_difference 3610
note = a, c, t, g, unknown or other
misc_difference 3611
note = a, c, t, g, unknown or other
misc_difference 3612
note = a, c, t, g, unknown or other
misc_difference 3613
note = a, c, t, g, unknown or other
misc_difference 3614
note = a, c, t, g, unknown or other
misc_difference 3615
note = a, c, t, g, unknown or other
misc_difference 3616
note = a, c, t, g, unknown or other
misc_difference 3617
note = a, c, t, g, unknown or other
misc_difference 3618
note = a, c, t, g, unknown or other
misc_difference 3619
note = a, c, t, g, unknown or other
misc_difference 3620
note = a, c, t, g, unknown or other
misc_difference 3621
note = a, c, t, g, unknown or other
misc_difference 3622
note = a, c, t, g, unknown or other
misc_difference 3623
note = a, c, t, g, unknown or other
misc_difference 3624
note = a, c, t, g, unknown or other
misc_difference 3625
note = a, c, t, g, unknown or other
misc_difference 3626
note = a, c, t, g, unknown or other
misc_difference 3627
note = a, c, t, g, unknown or other
misc_difference 3628
note = a, c, t, g, unknown or other
misc_difference 3629
note = a, c, t, g, unknown or other
misc_difference 3630
note = a, c, t, g, unknown or other
misc_difference 3631
note = a, c, t, g, unknown or other
misc_difference 3632
note = a, c, t, g, unknown or other
misc_difference 3633
note = a, c, t, g, unknown or other
misc_difference 3634
note = a, c, t, g, unknown or other
misc_difference 3635
note = a, c, t, g, unknown or other
misc_difference 3636
note = a, c, t, g, unknown or other
misc_difference 3637
note = a, c, t, g, unknown or other
misc_difference 3638
note = a, c, t, g, unknown or other
misc_difference 3639
note = a, c, t, g, unknown or other
misc_difference 3640
note = a, c, t, g, unknown or other
misc_difference 3641
note = a, c, t, g, unknown or other
misc_difference 3642
note = a, c, t, g, unknown or other

```
misc_difference        3643
                       note = a, c, t, g, unknown or other
misc_difference        3644
                       note = a, c, t, g, unknown or other
misc_difference        3645
                       note = a, c, t, g, unknown or other
misc_difference        3646
                       note = a, c, t, g, unknown or other
misc_difference        3647
                       note = a, c, t, g, unknown or other
misc_difference        3648
                       note = a, c, t, g, unknown or other
misc_difference        3649
                       note = a, c, t, g, unknown or other
misc_difference        3650
                       note = a, c, t, g, unknown or other
misc_difference        3651
                       note = a, c, t, g, unknown or other
misc_difference        3652
                       note = a, c, t, g, unknown or other
misc_difference        3653
                       note = a, c, t, g, unknown or other
misc_difference        3654
                       note = a, c, t, g, unknown or other
misc_difference        3655
                       note = a, c, t, g, unknown or other
SEQUENCE: 870
taaacttcct cttttaatag gaaaccacaa aatttgcatt gccgaccaca aacgcatatg  60
caaatttact tccccaaaaa ctcaaccaca aaatttgcat tgccgcccac aaacgtctac  120
tttaaccaca tcctctaaca tgttagaaac tccacccaac tacttcatta gtatacagca  180
tcacaaggga ggagccaaac aactatataa ccaagtgtac ttccgaatgg ctgagtttat  240
gccgccagac ggagacggga tcgcgacgga ggagcgatcg agcgtcccga gggcgggtgc  300
cggaggtgag tttacacacc gcagtcaagg ggcaattcgg gctcgggact ggccgggcta  360
tgggcaaggc tcttaaaaaa gccatgtttc tcggtcgacc ttacagaaag aaaagggcac  420
tgtcactgct acgcgtgcga gctccagagg cgaaaccacc tgctatgagc tggaggcccc  480
cggtgcacaa ccctaatggg atccagagaa acctgtggga ggcattcttt cgcatgcatg  540
ctgcagcttg tggttgtggc gatcttgttg gccatattac tgtactggct ggtcggtatg  600
gtgctcctcc tcgtccccg gcccccgggg ctcccagacc accgctgata cgccagctgg  660
cccttccggc gccccccgcc gatcctcaac aggctaaccc acaatggcct ggtggggacg  720
gtggagaaga tggcgctgga ggccccgccg ctggcggcgc cgtcgcagac gccgagtacc  780
aagaagacga gctcaacgcc ctgttcgacg ccgtcgagca agaagagtaa ggaggaggcg  840
atgggggagg cggaggtgga gacgggggta cagacgcaga ctaagactga gacgcagacg  900
cagacgaaag aaaataagac tgactcagtg gaacccagcc aaagtcagga gatgtactat  960
taagggggtg ctacccatga tcttatgcgg cgccggccgc tcggggttta actatggact  1020
gcacagcgac gactacacgg tgcagaaacc cctggggcag aacccccacg ggggcggcat  1080
gagcacagta actttagcc tacaagtact atttgaccag taccagaggt ttatgaaccg  1140
gtggtcgtac tccaacgacc agctagacct cgccaggtac tttggctgca ccttctactt  1200
ttacagacac cctgaaattg actttgtagc tcagtatgac aatgtacccc caatgaaaat  1260
ggacgagaac acggcncta acactcaccc ctcttttcta ctacaaaaca aacgcaaaat  1320
taaaatcccc agctttaaaa ccaagccatt tggcagaaaa agagtaaaag taacagtggg  1380
gccccccaaa ctgtttgaag ataaatggta cagccagcat gacttgtgta aggtgcccct  1440
agtcagttgg cggttaaccg catgtgactt caggtttccg ttctgctcac cactaactga  1500
caacccttgc tacaccttcc aggtattgca tgaaaactat tacccagtca taggcacttc  1560
ctctttagaa aacggtacaa actacaataa cactgctata actacccttg agacatggct  1620
atatggaaaa tgcacacact atcaaacatt tgccacagac accagactta atccacagag  1680
acctgtatct tcaagtaatg caaatgaaac ttatactcct agtggttcta aagaatcaat  1740
aatatgggga cagtctgact gggcaaactt taaaaagaac acagacagca actatggcta  1800
ctgttcctac tgcccctcaa atggcactaa cggaacagta gataaaatta aaaaatacag  1860
agaccaaaga tttagatggc ttacagaaat gccagtacct aacacctgtc acatacatgc  1920
caccttcgcc cgaggcacta ttaaatactg ggagtaccac ctaggctggt actcaaacat  1980
atttattggc aacctcagac acaacttagc cttcagacca gcctacatag acattaccta  2040
caatcccatc actgacaaag gagagggcaa cattatctgg ttccagtacc tcactaagcc  2100
caccacagaa tacatagaaa cccaggcaaa atgcaccatt actaacattc ccctttatgc  2160
tgctttctat ggctacgaag actacctcca gagaacacta ggcccctacc aagatgtaga  2220
aaccctaggc ataatctgtg ttaaatgtcc ctacacagat ccccctctag ttcacaaaga  2280
caaaagtaaa accaactggg gctacgtatt ctacgacgcc cactttggca acggaaagac  2340
cccagaggga ctaggccaag tacaccctta ctggatgcag agatggagac cctatgtaca  2400
gtttcaaaaa gacaccatgc acaaaatatc cagaacggga cccttcagct acagagacga  2460
cacgccttcc atcaccctca ctgccgaata caagtttcgt tttaactggg ggggcgactc  2520
tatatttcca cagattatta aaaacccctg cccagacacc ggggttcgac cttcaaccgg  2580
tagagaccgt cgctcagtac aagtcgttag cccgctcaca atgggacccc agtttatatt  2640
ccactcatgg gactggagac gggggttctt taatcaaaaa actctcaaaa gaatgcttga  2700
aaaaccagtt aatgatggag aatatccaac aggcccaaag gtgcctcgat ggtttccccc  2760
actcgacaac caagagcaag aaggcgtctc agatacagag acgacaacct cgcagtcctc  2820
gcaagaagaa gccgctcaag aagccctcca agaagtccaa gaggcgtcgc tacagcagca  2880
cctcctccag cagtaccgag agcagcgaag aatcggaaag caactccaac tcgtcatgct  2940
ccaactcacc aagacgcaga gcaacctgca cataaatccc cgtgtccttg gccatgcata  3000
aataaagtgt acatgtttcc ccccgaaaag ccaatgccca tacacggcta ccacgggtgg  3060
gagacagagt atcaggcctg caaggccttt gacaggcccc ctagaaacta cctatcagac  3120
```

-continued

```
aaacccatct acccctggct tccccgctcc caaccagaat ttaaagtgag ttttaagctt  3180
ggctgtcaat aaacaagnnn nnnnnnnnnn nnnnnnnnnn nnnnnnnnnn nnnnnnnnnn  3240
nnnnnnnnnn nnnnnnnnnn nnnnnnnnnn nnnnnnnnnn nnnnnnnnnn nnnnnnnnnn  3300
nnnnnnnnnn nnnnnnnnnn nnnnnnnnnn nnnnnnnnnn nnnnnnnnnn nnnnnnnnnn  3360
nnnnnnnnnn nnnnnnnnnn nnnnnnnnnn nnnnnnnnnn nnnnnnnnnn nnnnnnnnnn  3420
nnnnnnnnnn nnnnnnnnnn nnnnnnnnnn nnnnnnnnnn nnnnnnnnnn nnnnnnnnnn  3480
nnnnnnnnnn nnnnnnnnnn nnnnnnnnnn nnnnnnnnnn nnnnnnnnnn nnnnnnnnnn  3540
nnnnnnnnnn nnnnnnnnnn nnnnnnnnnn nnnnnnnnnn nnnnnnnnnn nnnnnnnnnn  3600
nnnnnnnnnn nnnnnnnnnn nnnnnnnnnn nnnnnnnnnn nnnnnnnnnn nnnnngttta  3660
cacaaaatgg tggccaagtc cttccgggtg aaaggtcggc gcctacgtca taagtcacgt  3720
ggggagggct gcgtcacaac caggaagcaa tcctcaccac gtgatttgtc acgtgatcgc  3780
tacgtcacgg ccgccatttt agtttacaaa atggcggact tccttcctct ttttcaaaaa  3840
taacggccct gcggcggcgc gcgcgctgcg cgcgcgcgcc gggggctgcc gcccca      3896

SEQ ID NO: 871          moltype = AA  length = 121
FEATURE                 Location/Qualifiers
source                  1..121
                        mol_type = protein
                        organism = Alphatorquevirus sp.
SEQUENCE: 871
MSWRPPVHNP NGIQRNLWEA FFRMHAAACG CGDLVGHITV LAGRYGAPPR PPAPGAPRPP  60
LIRQLALPAP PADPQQANPQ WPGGDGGEDG AGGPAAGGAV ADAEYQEDEL NALFDAVEQE  120
E                                                                  121

SEQ ID NO: 872          moltype = AA  length = 267
FEATURE                 Location/Qualifiers
source                  1..267
                        mol_type = protein
                        organism = Alphatorquevirus sp.
SEQUENCE: 872
MSWRPPVHNP NGIQRNLWEA FFRMHAAACG CGDLVGHITV LAGRYGAPPR PPAPGAPRPP  60
LIRQLALPAP PADPQQANPQ WPGGDGGEDG AGGPAAGGAV ADAEYQEDEL NALFDAVEQE  120
ELLKTPAQTP GFDLQPVETV AQYKSLARSQ WDPSLYSTHG TGDGGSLIKK LSKECLKNQL  180
MMENIQQAQR CLDGFPHSTT KSKKASQIQR RQPRSPRKKK PLKKPSKKSK RRRYSSTSSS  240
STESSEESES NSNSSCSNSP RRRATCT                                      267

SEQ ID NO: 873          moltype = AA  length = 277
FEATURE                 Location/Qualifiers
source                  1..277
                        mol_type = protein
                        organism = Alphatorquevirus sp.
SEQUENCE: 873
MSWRPPVHNP NGIQRNLWEA FFRMHAAACG CGDLVGHITV LAGRYGAPPR PPAPGAPRPP  60
LIRQLALPAP PADPQQANPQ WPGGDGGEDG AGGPAAGGAV ADAEYQEDEL NALFDAVEQE  120
EISNRPKGAS MVSPTRQPRA RRRLRYRDDN LAVLARRSRS RSPPRSPRGV ATAAPPPAVP  180
RAAKNRKATP TRHAPTHQDA EQPAHKSPCP WPCINKVYMF PPEKPMPIHG YHGWETEYQA  240
CKAFDRPPRN YLSDKPIYPW LPRSQPEFKV SFKLGCQ                           277

SEQ ID NO: 874          moltype = AA  length = 200
FEATURE                 Location/Qualifiers
source                  1..200
                        mol_type = protein
                        organism = Alphatorquevirus sp.
SEQUENCE: 874
MSWRPPVHNP NGIQRNLWEA FFRMHAAACG CGDLVGHITV LAGRISNRPK GASMVSPTRQ  60
PRARRRLRYR DDNLAVLARR SRSRSPPRSP RGVATAAPPP AVPRAAKNRK ATPTRHAPTH  120
QDAEQPAHKS PCPWPCINKV YMFPPEKPMP IHGYHGWETE YQACKAFDRP PRNYLSDKPI  180
YPWLPRSQPE FKVSFKLGCQ                                              200

SEQ ID NO: 875          moltype = AA  length = 765
FEATURE                 Location/Qualifiers
source                  1..765
                        mol_type = protein
                        organism = Alphatorquevirus sp.
SEQUENCE: 875
MAWWGRWRRW RWRPRRWRRR RRRRVPRRRA QRPVRRRRAR RVRRRRWGRR RWRRGYRRRL  60
RLRRRRRRKK IRLTQWNPAK VRRCTIKGVL PMILCGAGRS GFNYGLHSDD YTVQKPLGQN  120
PHGGGMSTVT FSLQVLFDQY QRFMNRWSYS NDQLDLARYF GCTFYFYRHP EIDFVAQYDN  180
VPPMKMDENT APNTHPSFLL QNKRKIKIPS FKTKPFGRKR VKVTVGPPKL FEDKWYSQHD  240
LCKVPLVSWR LTACDFRFPF CSPLTDNPCY TFQVLHENYY PVIGTSSLEN GTNYNNTAIT  300
TLETWLYGKC THYQTFATDT RLNPQRPVSS SNANETYTPS GSKESIIWGQ SDWANFKKNT  360
DSNYGYCSYC PSNGTNGTVD KIKKYRDQRF RWLTEMPVPN TCHIHATFAR GTIKYWEYHL  420
GWYSNIFIGN LRHNLAFRPA YIDITYNPIT DKGEGNIIWF QYLTKPTTEY IETQAKCTIT  480
NIPLYAAFYG YEDYLQRTLG PYQDVETLGI ICVKCPYTDP PLVHKDKSKT NWGYVFYDAH  540
FGNGKTPEGL GQVHPYWMQR WRPYVQFQKD TMHKISRTGP FSYRDDTPSI TLTAEYKFRF  600
NWGGDSIFPQ IIKNPCPDTG VRPSTGRDRR SVQVVSPLTM GPQFIFHSWD WRRGFFNQKT  660
LKRMLEKPVN DGEYPTGPKV PRWFPPLDNQ EQEGVSDTET TTSQSSQEEA AQEALQEVQE  720
ASLQQHLLQQ YREQRRIGKQ LQLVMLQLTK TQSNLHINPR VLGHA                  765
```

```
SEQ ID NO: 876          moltype = AA  length = 196
FEATURE                 Location/Qualifiers
source                  1..196
                        mol_type = protein
                        organism = Alphatorquevirus sp.
SEQUENCE: 876
MAWWGRWRRW RWRPRRWRRR RRRRVPRRRA QRPVRRRRAR RIIKNPCPDT GVRPSTGRDR  60
RSVQVVSPLT MGPQFIFHSW DWRRGFFNQK TLKRMLEKPV NDGEYPTGPK VPRWFPPLDN  120
QEQEGVSDTE TTTSQSSQEE AAQEALQEVQ EASLQQHLLQ QYREQRRIGK QLQLVMLQLT  180
KTQSNLHINP RVLGHA                                                  196

SEQ ID NO: 877          moltype = AA  length = 125
FEATURE                 Location/Qualifiers
source                  1..125
                        mol_type = protein
                        organism = Alphatorquevirus sp.
SEQUENCE: 877
MAWWGRWRRW RWRPRRWRRR RRRRVPRRRA QRPVRRRRAR RNIQQAQRCL DGFPHSTTKS  60
KKASQIQRRQ PRSPRKKKPL KKPSKKSKRR RYSSTSSSST ESSEESESNS NSSCSNSPRR  120
RATCT                                                              125

SEQ ID NO: 878          moltype = DNA  length = 3264
FEATURE                 Location/Qualifiers
source                  1..3264
                        mol_type = genomic DNA
                        organism = Gammatorquevirus sp.
SEQUENCE: 878
taaaatggcg gcaaccaatc attttatact ttcactttcc aattacaagc cgccacgtca  60
cagaacaggg gtggagactt taaaactata taaccaagtg atgtgacgaa tggctgagtt  120
taccccgcta gacggtgcag ggaccggatc gagcgcagcg aggaggtccc cggctgcccg  180
tgggcgggag cccgaggtga gtgaaaccac cgaggtctag gggcaattcg ggctagggca  240
gtctagcgga acgggcaaga aacttaaaat atgttttgtt tcagatgcag acacctgctt  300
cacagataag ctcagacgac ttctttgtac acactccatt taatgcagta actaaacagc  360
aaatatggat gtctcaaatt gctgatggac atgacaacat ttgtcactgc caccgtcctt  420
ttgctcacct gcttgctaat atttttcctc ctggtcataa agacagggat cttaccatta  480
atcaaatact tgctagagat cttacagaaa catgccattc tggtggagac gaaggaacaa  540
gcggtggtgg ggtcgccgct tccgctaccg ccgctacaac aaatataaaa ccagaaggag  600
acgcagaata cccagaagac gaaatagaag atttactaag acacgcagga gaagaaaaag  660
aaagaaggta agaagaaaac ttaaaaaaat tactattaaa caatggcagc cagattcagt  720
gaaaaaatgt aaaattaaag gatatagtac tttagttatg ggtgcacaag gaaaacaata  780
caactgttac acaaaccaag caagtgacta tgttcagcct aaagcaccac aaggtggggg  840
ctttggctgt gaagtattta atttaaaatg gctataccaa gaatatactg cacacagaaa  900
tatttggaca aaaacaaatg aatatacaga cctttgtaga tacactggag ctcaaataat  960
tttatacagg cacccagatg ttgattttat agtcagctgg gacaatcagc cacctttttt  1020
acttaacaaa tatacatatc cagaactgca accacaaaac cttttactag ctagaaggaa  1080
aagaattatt cttagtcaaa aatcaaaccc caaaggaaaa ctaagaatta aactaagaat  1140
accaccacca aaacaaatga taacaaaatg gtttttttcaa agagactttt gtgatgtgaa  1200
tctgtttaaa ctatgtgctt ctgctgcttc tttccgctac ccaggtatca gtcatggagc  1260
tcaaagtact attttttctg catatgcttt aaacactgac ttttatcaat gcagtgactg  1320
gtgccaaact aacacagaaa ctggctacct aaacattaaa acacaacaaa tgccactatg  1380
gtttcattac agagagggtg gcaaagagaa atggtataaa tacaccaaca aagaacacag  1440
accatataca aatacatatc ttaaaagtat tagctataat gatggattgt tttctcctaa  1500
agccatgttt gcatttgaag taaaagcggg gggtgaagga acaacagaac caccacaagg  1560
cgcccaatta attgctaacc ttccactcat tgcactaaga tataatccac atgaagacac  1620
aggccatggc aatgaaattt accttacatc aacttttaaa ggtacatatg acaaacctaa  1680
agttactgat gctctatact ttaacaatgt accccctgtgg atgggatttt atggctactg  1740
ggactttata ttacaagaaa caaaaaaacaa aggtgtcttt gatcaacata tgtttgttgt  1800
taaatgtcct gccttaaggc ccatatcaca agtcacaaaa caagtatact acccacttgt  1860
agacatggac ttttgttcag ggagactgcc atttgatgaa tatttatcca aagacattaa  1920
aagtcattgg tatcccactg cagaaaagaca aacagttaca ataaataatt ttgttacagc  1980
aggtccatac atgcctaaat ttgaacccac agacaaagac agtacatggc aattaaacta  2040
tcactataaa ttttttttta agtggggtgg tccacaagtc acagacccaa ctgttgaaga  2100
cccatgcagc agaaacaaat atcctgtccc cgatacaatg caacaaacaa tacaaattaa  2160
aaaccctgaa aagctgcacc cagcaaccct cttccatgac tgggacctta gaaggggctt  2220
cattacacaa gcagctatta aaagaatgtc agaaaacctc caaattgatt catctttcga  2280
atctgatggc acagaatcac ccaaaaaaaa gaaaagatgc accaaagaaa tcccaacaca  2340
aaaccaaaag caagaagaga tccaagaatg tctcctctca ctctgcgaag agcctacatg  2400
ccaagaagaa acagaggacc tccagctctt catccagcag cagcagcagc agcagtacaa  2460
gctcagaaaa aacctcttca aactcctcac tcacctgaaa aaaggacaga gaataagtca  2520
actacaaacg ggactttttag agtaatacca tttaaaccag gttttgaaca agaaacagaa  2580
aaagaacttg ccatagcttt ctgcagacca cctagaaaat ataaaaatga tcccccctttt  2640
tatccctggt taccatggac accccttgta cactttaacc ttaattacaa aggctaggcc  2700
aacactgttc acttagtggt gtatgtttaa taaagtttca cccccaaaaa aaaaaaaaaa  2760
aaaaaaaaaa aaaaaaaaaa taaaaaattg caaaaattcg gcgctcgcgc gcgctgcgcg  2820
cgcgcgagcg ccgtcacgcg ccggcgctcg cgcgccgcgc gtatgtgcta acacaccacg  2880
cacctagatt ggggtgcgcg cgctagcgcg cgcaccccaa tgcgccccgc cctcgttccg  2940
acccgcttgc gcgggtcgga ccacttcggg ctcgggggggg cgcgcctgcg gcgcttttttt  3000
actaaacaga ctccgagccg ccatttggcc cccccctaagc tccgcccccc tcatgaatat  3060
tcataaagga aaccacataa ttagaattgc cgaccacaaa ctgccatatg ctaattagtt  3120
```

```
ccccttttac acagtaaaaa ggggaagtgg gggggcatag cccccccaca ccccccgcgg  3180
ggggggcaga gccccccccc gcaccccccc cctacgtcac aatccacgcc cccgccgcca  3240
tcttgggtgc ggcagggcgg gggc                                         3264

SEQ ID NO: 879          moltype = AA  length = 128
FEATURE                 Location/Qualifiers
source                  1..128
                        mol_type = protein
                        organism = Gammatorquevirus sp.
SEQUENCE: 879
MQTPASQISS DDFFVHTPFN AVTKQQIWMS QIADGHDNIC HCHRPFAHLL ANIFPPGHKD  60
RDLTINQILA RDLTETCHSG GDEGTSGGGV AASATAATTN IKPEGDAEYP EDEIEDLLRH  120
AGEEKERR                                                           128

SEQ ID NO: 880          moltype = AA  length = 272
FEATURE                 Location/Qualifiers
source                  1..272
                        mol_type = protein
                        organism = Gammatorquevirus sp.
SEQUENCE: 880
MQTPASQISS DDFFVHTPFN AVTKQQIWMS QIADGHDNIC HCHRPFAHLL ANIFPPGHKD  60
RDLTINQILA RDLTETCHSG GDEGTSGGGV AASATAATTN IKPEGDAEYP EDEIEDLLRH  120
AGEEKERSGV VHKSQTQLLK THAAETNILS PIQCNKQYKL KTLKSCTQQP SSMTGTLEGA  180
SLHKQLLKEC QKTSKLIHLS NLMAQNHPKK RKDAPKKSQH KTKSKKRSKN VSSHSAKSLH  240
AKKKQRTSSS SSSSSSSSST SSEKTSSNSS LT                                272

SEQ ID NO: 881          moltype = AA  length = 261
FEATURE                 Location/Qualifiers
source                  1..261
                        mol_type = protein
                        organism = Gammatorquevirus sp.
SEQUENCE: 881
MQTPASQISS DDFFVHTPFN AVTKQQIWMS QIADGHDNIC HCHRPFAHLL ANIFPPGHKD  60
RDLTINQILA RDLTETCHSG GDEGTSGGGV AASATAATTN IKPEGDAEYP EDEIEDLLRH  120
AGEEKERRIT QKKEKMHQRN PNTKPKARRD PRMSPLTLRR AYMPRRNRGP PALHPAAAAA  180
AVQAQKKPLQ TPHSPEKRTE NKSTTNGTFR VIPFKPGFEQ ETEKELAIAF CRPPRKYKND  240
PPFYPWLPWT PLVHFNLNYK G                                            261

SEQ ID NO: 882          moltype = AA  length = 67
FEATURE                 Location/Qualifiers
source                  1..67
                        mol_type = protein
                        organism = Gammatorquevirus sp.
SEQUENCE: 882
MDMTTFVTAT VLLLTCLLIF FLLVIKTGIL PLIKYLLEIL QKHAILVETK EQAVVGSPLP  60
LPPLQQI                                                            67

SEQ ID NO: 883          moltype = AA  length = 677
FEATURE                 Location/Qualifiers
source                  1..677
                        mol_type = protein
                        organism = Gammatorquevirus sp.
SEQUENCE: 883
MPFWWRRRNK RWWGRRFRYR RYNKYKTRRR RRIPRRRNRR FTKTRRRRKR KKVRRKLKKI  60
TIKQWQPDSV KKCKIKGYST LVMGAQGKQY NCYTNQASDY VQPKAPQGGG FGCEVFNLKW  120
LYQEYTAHRN IWTKTNEYTD LCRYTGAQII LYRHPDVDFI VSWDNQPPFL LNKYTYPELQ  180
PQNLLLARRK RIILSQKSNP KGKLRIKLRI PPPKQMITKW FFQRDFCDVN LFKLCASAAS  240
FRYPGISHGA QSTIFSAYAL NTDFYQCSDW CQTNTETGYL NIKTQQMPLW FHYREGGKEK  300
WYKYTNKEHR PYTNTYLKSI SYNDGLFSPK AMFAFEVKAG GEGTTEPPQG AQLIANLPLI  360
ALRYNPHEDT GHGNEIYLTS TFKGTYDKPK VTDALYFNNV PLWMGFYGYW DFILQETKNK  420
GVFDQHMFVV KCPALRPISQ VTKQVYYPLV DMDFCSGRLP FDEYLSKDIK SHWYPTAERQ  480
TVTINNFVTA GPYMPKFEPT DKDSTWQLNY HYKFFFKWGG PQVTDPTVED PCSRNKYPVP  540
DTMQQTIQIK NPEKLHPATL FHDWDLRRGF ITQAAIKRMS ENLQIDSSFE SDGTESPKKK  600
KRCTKEIPTQ NQKQEEIQEC LLSLCEEPTC QEETEDLQLF IQQQQQQQYK LRKNLFKLLT  660
HLKKGQRISQ LQTGLLE                                                 677

SEQ ID NO: 884          moltype = AA  length = 212
FEATURE                 Location/Qualifiers
source                  1..212
                        mol_type = protein
                        organism = Gammatorquevirus sp.
SEQUENCE: 884
MPFWWRRRNK RWWGRRFRYR RYNKYKTRRR RRIPRRRNRR FTKTRRRRKR KKWGGPQVTD  60
PTVEDPCSRN KYPVPDTMQQ TIQIKNPEKL HPATLFHDWD LRRGFITQAA IKRMSENLQI  120
DSSFESDGTE SPKKKKRCTK EIPTQNQKQE EIQECLLSLC EEPTCQEETE DLQLFIQQQQ  180
QQQYKLRKNL FKLLTHLKKG QRISQLQTGL LE                                212

SEQ ID NO: 885          moltype = AA  length = 119
FEATURE                 Location/Qualifiers
```

```
source                 1..119
                       mol_type = protein
                       organism = Gammatorquevirus sp.
SEQUENCE: 885
MPFWWRRRNK RWWGRRFRYR RYNKYKTRRR RRIPRRRNRR FTKTRRRRKR KKNHPKKRKD  60
APKKSQHKTK SKKRSKNVSS HSAKSLHAKK KQRTSSSSSS SSSSSSTSSE KTSSNSSLT   119

SEQ ID NO: 886         moltype = DNA  length = 3176
FEATURE                Location/Qualifiers
source                 1..3176
                       mol_type = genomic DNA
                       organism = Gammatorquevirus sp.
SEQUENCE: 886
taaaatggcg ggagccaatc attttatact ttcactttcc aattaaaaat ggccacgtca  60
caaacaaggg gtggagccat ttaaactata taactaagtg gggtggcgaa tggctgagtt  120
taccccgcta gacggtgcag ggaccggatc gagcgcagcg aggaggtccc cggctgccca  180
tgggcgggag ccgaggtgag tgaaaccacc gaggtctagg ggcaattcgg gctagggcag  240
tctagcggaa cgggcaagaa acttaaaaca atatttgttt tacagatggt tagtatatcc  300
tcaagtgatt tttttaagaa aacgaaattt aatgaggaga cgcagaacca agtatggatg  360
tctcaaattg ctgactctca tgataatatc tgcagttgct ggcatccatt tgctcacctt  420
cttgcttcca tatttcctcc tggccacaaa gatcgtgatc ttactattaa ccaaattctt  480
ctaagagatt ataaagaaaa atgccattct ggtggagaag aaggagaaaa ttctggacca  540
acaacaggtt taattacacc aaaagaagaa gatatagaaa aagatggccc agaaggcgcc  600
gcagaagaag accatacaga cgccctgttc gccgccgccg tagaaaactt cgaaaggtaa  660
agagaaaaaa aaaatcttta attgttagac aatggcaacc agacagtata agaacttgta  720
aaattatagg acagtcagct atagttgttg gggctgaagg aaagcaaatg tactgttata  780
ctgtcaataa gttaattaat gtgcccccaa aaacaccata tgggggaggc tttggagtag  840
accaatacac actgaaatac ttatatgaag aatacagatt tgcacaaaac atttggacac  900
aatctaatgt actgaaagac ttatgcagat acataaatgt taagctaata ttctacagag  960
acaacaaaac agactttgtc ctttcctatg acagaaaccc accttttcaa ctaacaaaat  1020
ttacataccc aggagcacac ccacaacaaa tcatgcttca aaaacaccac aaattcatac  1080
tatcacaaat gacaaagcct aatggaagac taacaaaaaa actcaaaatt aaacctccta  1140
aacaaatgct ttctaaatgg ttcttttcaa aacaattctg taaataccct ttactatctc  1200
ttaaagcttc tgcactagac cttaggcact cttacctagg ctgctgtaat gaaaatccac  1260
aggtattttt ttattattta aaccatggat actacacaat aacaaactgg ggagcacaat  1320
cctcaacagc atacagacct aactccaagg tgacagacac aacatactac agatacaaaa  1380
atgacagaaa aaatattaac attaaaagcc atgaatacga aaaaagtata tcatatgaaa  1440
acggttattt tcaatctagt ttcttacaaa cacagtgcat atataccagt gagcgtggtg  1500
aagcctgtat agcagaaaaa ccactaggaa tagctattta caatccagta aaagacaatg  1560
gagatggtaa tatgatatac cttgtaagca ctctagcaaa cacttgggac cagcctccaa  1620
aagacagtgc tattttaata caaggagtac ccatatggct aggcttattt ggatatttag  1680
actactgtag acaaattaaa gctgacaaaa catggctaga cagtcatgta ctagtaattc  1740
aaagtcctgc tatttttact tacccaaatc caggagcagg caaatggtat tgtccactat  1800
cacaaagttt tataaatggc aatggtccgt ttaatcaacc acctacactg ctacaaaaag  1860
caaagtggtt tccacaaata caataccaac aagaaattat taatagcttt gtagaatcag  1920
gaccatttgt tcccaaatat gcaaatcaaa ctgaaagcaa ctgggaacta aaatataaat  1980
atgtttttac atttaagtgg ggtggaccac aattccatga accagaaatt gctgacccta  2040
gcaaacaaga gcagtatgat gtccccgata ctttctacca aacaatacaa attgaagatc  2100
cagaaggaca agaccccaga tctctcatcc atgattggga ctacagacga ggctttatta  2160
aagaaagatc tcttaaaaga atgtcaactt acttctcaac tcatacagat cagcaagcaa  2220
cttcagagga agacattccc aaaaagaaaa agagaattgg accccaactc acagtcccac  2280
aacaaaaaga agaggagaca ctgtcatgtc tcctctctct ctgcaaaaaa gataccttcc  2340
aagaaacaga gacacaagaa gacctccagc agctcatcaa gcagcagcag gagcagcagc  2400
tcctcctcaa gagaaacatc ctccagctca tccacaaact aaaagagaat caacaaatgc  2460
ttcagcttca cacaggcatg ttaccttaac cagatttaaa cctggatttg aagagcaaac  2520
agagagagaa ttagcaatta tatttcatag gcccccctaga acctacaaag aggaccttcc  2580
attctatccc tggctaccac ctgcacccct tgtacaattt aaccttaact tcaaaggcta  2640
ggccaacaat gtacacttag taaagcatgt ttattaaagc acaaccccca aaataaatgt  2700
aaaaataaaa aaaaaaaaaa aaaaataaaa aattgcaaaa attcggcgct cgcgcgcatg  2760
tgcgcctctg gcgcaaatca cgcaacgctc gcgcgcccgc gtatgtctct ttaccacgca  2820
cctagattgg ggtgcgcgcg ctagcgcgcg caccccaatg cgccccgccc tcgttccgac  2880
ccgcttgcgc gggtcggacc acttcgggct cggggggcg cgcctgcggc gctttttttac  2940
taaacagact ccgagccgcc atttggcccc ctaagctccg cccccctcat gaatattcat  3000
aaaggaaacc acataattag aattgccgac cacaaactgc catatgctaa ttagttcccc  3060
ttttacaaag taaaagggga agtgaacata gccccacacc cgcaggggca aggccccgca  3120
cccctacgtc actaaccacg cccccgccgc catcttgggt gcggcagggc gggggc      3176

SEQ ID NO: 887         moltype = AA  length = 124
FEATURE                Location/Qualifiers
source                 1..124
                       mol_type = protein
                       organism = Gammatorquevirus sp.
SEQUENCE: 887
MVSISSSDFF KKTKFNEETQ NQVWMSQIAD SHDNICSCWH PFAHLLASIF PPGHKDRDLT  60
INQILLRDYK EKCHSGGEEG ENSGPTTGLI TPKEEDIEKD GPEGAAEEDH TDALFAAAVE  120
NFER                                                              124

SEQ ID NO: 888         moltype = AA  length = 271
FEATURE                Location/Qualifiers
```

```
source                  1..271
                        mol_type = protein
                        organism = Gammatorquevirus sp.
SEQUENCE: 888
MVSISSSDFF KKTKFNEETQ NQVWMSQIAD SHDNICSCWH PFAHLLASIF PPGHKDRDLT  60
INQILLRDYK EKCHSGGEEG ENSGPTTGLI TPKEEDIEKD GPEGAAEEDH TDALFAAAVE  120
NFESGVDHNS MNQKLLTLAN KSSMMSPILS TKQYKLKIQK DKTPDLSSMI GTTDEALLKK  180
DLLKECQLTS QLIQISKQLQ RKTFPKRKRE LDPNSQSHNK KKRRHCHVSS LSAKKIPSKK  240
QRHKKTSSSS SSSSRSSSSS SRETSSSSST N                                271

SEQ ID NO: 889          moltype = AA  length = 267
FEATURE                 Location/Qualifiers
source                  1..267
                        mol_type = protein
                        organism = Gammatorquevirus sp.
SEQUENCE: 889
MVSISSSDFF KKTKFNEETQ NQVWMSQIAD SHDNICSCWH PFAHLLASIF PPGHKDRDLT  60
INQILLRDYK EKCHSGGEEG ENSGPTTGLI TPKEEDIEKD GPEGAAEEDH TDALFAAAVE  120
NFERSASNFR GRHSQKEKEN WTPTHSPTTK RRGDTVMSPL SLQKRYLPRN RDTRRPPAAH  180
QAAAGAAAPP QEKHPPAHPQ TKRESTNASA SHRHVTLTRF KPGFEEQTER ELAIIFHRPP  240
RTYKEDLPFY PWLPPAPLVQ FNLNFKG                                     267

SEQ ID NO: 890          moltype = AA  length = 50
FEATURE                 Location/Qualifiers
source                  1..50
                        mol_type = protein
                        organism = Gammatorquevirus sp.
SEQUENCE: 890
MRRRRTKYGC LKLLTLMIIS AVAGIHLLTF LLPYFLLATK IVILLLTKFF            50

SEQ ID NO: 891          moltype = AA  length = 662
FEATURE                 Location/Qualifiers
source                  1..662
                        mol_type = protein
                        organism = Gammatorquevirus sp.
SEQUENCE: 891
MPFWWRRRRK FWTNNRFNYT KRRRYRKRWP RRRRRRRPYR RPVRRRRRKL RKVKRKKKSL  60
IVRQWQPDSI RTCKIIGQSA IVVGAEGKQM YCYTVNKLIN VPPKTPYGGG FGVDQYTLKY  120
LYEEYRFAQN IWTQSNVLKD LCRYINVKLI FYRDNKTDFV LSYDRNPPFQ LTKFTYPGAH  180
PQQIMLQKHH KFILSQMTKP NGRLTKKLKI KPPKQMLSKW FFSKQFCKYP LLSLKASALD  240
LRHSYLGCCN ENPQVFFYYL NHGYYTITNW GAQSSTAYRP NSKVTDTTYY RYKNDRKNIN  300
IKSHEYEKSI SYENGYFQSS FLQTQCIYTS ERGEACIAEK PLGIAIYNPV KDNGDGNMIY  360
LVSTLANTWD QPPKDSAILI QGVPIWLGLF GYLDYCRQIK ADKTWLDSHV LVIQSPAIFT  420
YPNPGAGKWY CPLSQSFING NGPFNQPPTL LQKAKWFPQI QYQQEIINSF VESGPFVPKY  480
ANQTESNWEL KYKYVFTFKW GGPQFHEPEI ADPSKQEQYD VPDTFYQTIQ IEDPEGQDPR  540
SLIHDWDYRR GFIKERSLKR MSTYFSTHTD QQATSEEDIP KKKKRIGPQL TVPQQKEEET  600
LSCLLSLCKK DTFQETETQE DLQQLIKQQQ EQQLLLKRNI LQLIHKLKEN QQMLQLHTGM  660
LP                                                                662

SEQ ID NO: 892          moltype = AA  length = 215
FEATURE                 Location/Qualifiers
source                  1..215
                        mol_type = protein
                        organism = Gammatorquevirus sp.
SEQUENCE: 892
MPFWWRRRRK FWTNNRFNYT KRRRYRKRWP RRRRRRRPYR RPVRRRRRKL RKWGGPQFHE  60
PEIADPSKQE QYDVPDTFYQ TIQIEDPEGQ DPRSLIHDWD YRRGFIKERS LKRMSTYFST  120
HTDQQATSEE DIPKKKKRIG PQLTVPQQKE EETLSCLLSL CKKDTFQETE TQEDLQQLIK  180
QQQEQQLLLK RNILQLIHKL KENQQMLQLH TGMLP                            215

SEQ ID NO: 893          moltype = AA  length = 129
FEATURE                 Location/Qualifiers
source                  1..129
                        mol_type = protein
                        organism = Gammatorquevirus sp.
SEQUENCE: 893
MPFWWRRRRK FWTNNRFNYT KRRRYRKRWP RRRRRRRPYR RPVRRRRRKL RKISKQLQRK  60
TFPKRKRELD PNSQSHNKKK RRHCHVSSLS AKKIPSKKQR HKKTSSSSSS SSRSSSSSSR  120
ETSSSSSTN                                                         129

SEQ ID NO: 894          moltype = DNA  length = 3696
FEATURE                 Location/Qualifiers
source                  1..3696
                        mol_type = genomic DNA
                        organism = Alphatorquevirus sp.
SEQUENCE: 894
atttgttca gcccgccaat ttctctttca aacaggccaa tcagctacta cttcgtgcac  60
ttcctggggc gtgtcctgcc gctctatata agcagaggcg gtgacgaatg gtagagtttt  120
tcttggcccg tccgcggcga gagcgcgagc gaagcgagcg atcgagcgtc ccgagggcgg  180
```

```
gtgccggagg tgagtttaca caccgcagtc aaggggcaat tcgggctcgg gactggccgg  240
gctatgggca agattcttaa aaaattcccc cgatcccttt gccgccagga cataaaaaca  300
tgccgtggag accgccggtc catagtgtcc aggggcgaga ggatcagtgg ttcgcaagct  360
tttttcacgg ccacgattcg ttttgcggct gcggtgaccc tcttggccat attaatagca  420
ttgctcatcg ctttcctcgc gccggtccac caaggccccc tccggggcta gatcagccta  480
acccccggga gcagggcccg gccggacccg gagggccgcc cgccatcttg gccctgccgg  540
ctccgcccgc ggagcctgac gacccgcagc cacggcgtgg tggtggggac ggtggcgccg  600
ccgctggcgc cgcagacgac catacacaac gagactacga cgaagaagag ctagacgagc  660
ttttccgcgc cgccgccgaa gacgatttgt aagtaggaga tggcgccggc cttacaggcg  720
caggaggaga cgcgggcgac gcagacgcag acgcagacgc agacataagc ccaccctaat  780
actcagacag tggcaacctg actgtatcag acactgtaaa ataacaggat ggatgcccct  840
cattatctgt ggaaaggggt ccacccagtt caactacatc acccacgcgg acgatatcac  900
ccccaggggga gcctcctacg gaggcaattt cacaaacatg actttctccc tggaggccat  960
atatgaacag ttcctatacc acagaaacag gtggtcggcc tctaaccacg acctagaact  1020
gtgcagatac aaggggacca ccttaaaact ctacagacac ccagaagtag actacatagt  1080
tacctacagc agaacaggac cctttgaaat cagccacatg acctacctca gcactcaccc  1140
catgctaatg ctgctaaaca agcaccacat tgtggtgccc agcttaaaga ctaagcccag  1200
aggcagaaag gccataaaag tcaggataag gcccccaaaa ctcatgaaca acaagtggta  1260
cttcaccaga gacttctgta acataggcct cttccagctc tgggccacag gcttagaact  1320
cagaaacccc tggctcagaa tgagcaccct gagcccctgc ataggcttta atgtcctcaa  1380
aaacagcatt tacacaaacc tcagcaacct gccacaatac aaaaacgaaa gactaaacat  1440
cattaacaac atacttcacc cacaagaaat tacaggtaca aacaacaaaa agtggcagta  1500
cacatacacc aaactcatgg cccctattta ctattcagca aacagggcca gcacctatga  1560
ctgggaaaat tacagcaaag aaacaaacta caataataca tatgttaaat ttacccagaa  1620
aagacaggaa aaactaacta aaattagaaa agagtggcag atgctttatc cacaacaacc  1680
cacagcactg ccagactcct atgacctcct acaagagtat ggcctctaca gtccatacta  1740
cctaaacccc acaagaataa acctagactg gatgacccca tacacacacg tcagatacaa  1800
tcccctagta gacaagggct ttggaaacag aatatacatc cagtggtgct cagaagcaga  1860
tgttagctac aacaggacaa aatccaagtg tctgctacaa gacatgcccc tgtttttcat  1920
gtgctatggc tacatagact gggcaataaa aaacactgga gtgtcatctc tagtgaagga  1980
cgccagaatc tgcatcaggt gtccctacac agagccacaa ctagttggct ccacagaaga  2040
cataggcttt gtacccatct cagaaacctt catgaggggc gacatgccgg tacttgcacc  2100
atacataccg ttaagctggt tttgcaagtg gtatcccaac atagctcacc aaaaggaagt  2160
ccttgagtca atcatttcct gcagcccctt catgccccgt gaccaagaca tgaacggttg  2220
ggatatcaca atcggttaca aaatggactt cttatggggc ggttcccctc tcccctcaca  2280
gccaatcgac gacccctgcc agcagggaac ccaccccgatt cccgaccccg ataaacaccc  2340
tcgcctccta caagtctcga acccgaaact actcggaccg aggacagtgt tccacaagtg  2400
ggacatcaga cgtgggcagt ttagcaaaag aagtattaag agagtgtcag aatactcaag  2460
cgatgatgaa tctcttgcgc caggtctccc atcaaagcga aacaagctcg actcggcgtt  2520
ccgaggagaa aatcgagagc aaaaagaatg ctattctctc ctcaaagcgc tcgaggaaga  2580
agagacccca gaagaagaag aaccagcacc ccaagaaaaa gcccagaaag aggagctact  2640
ccaccagctc cagctccaga gacgccacca gcgagtcctc agacgagggc tcaagctcgt  2700
ctttacagac atcctccgac tccgccaggg agtccactgg aacccggagc tcacatagcg  2760
cccccacctt acataccaga cctgcttttt cccaatactg gtaaaaaaaa aaaattctct  2820
cccttcgatt gggagacaga ggcgcaaata gcggggtgga tgcggcggcc catgcgcttc  2880
tatccctcag acacccctca ctacccgtgg ctaccccccg agcgagatat cccgaaaata  2940
tgtaacataa acttcaaaat aaagcttcaa gagtgagtga ttcgaggccc tcctctgttc  3000
acttagcggt gtctacctct taaggtcact aagcactccg agcgtaagcg aggagtgcga  3060
ccctctacca aggggcaact tcctcggggt ccggcgctac gcgcttcgcg ctgcgccgga  3120
catctcggac ccctcgaccc gaatcgcttg cgcgattcgg acctgcggcc tcggggggt  3180
cgggggcttt actaaacaga ctccgaggtg ccattggaca ctgtaggggg tgaacagcaa  3240
cgaaagtgag tggggccaga cttcgccata aggcctttat cttcttgcca ttggatagtg  3300
acttccgggt ccgcctgggg gccgccattt tagcttcggc cgccatttta ggccctcgcg  3360
ggcctccgta ggcgcgcttt agtgacgtca cggcagccat tttgtcgtga cgtttgagac  3420
acgtgatggg ggcgtgccta aacccggaag catccctggt cacgtgactc tgacgtcacg  3480
gcggccatct tgtgctgtcc gccatcttgt aacttccttc cgctttttca aaaaaaaaga  3540
ggaagtgtga cgtagcggcg ggggggcggc gcgcttcgcg cgccgcccac caggggggcgc  3600
tgcgcgcccc ccgcgcatgc gcaggggcct ctcgaggggc tccgcccccc ccccgtgcta  3660
aatttaccgc gcatgcgcga ccacgccccc gccgcc                            3696
```

```
SEQ ID NO: 895         moltype = AA  length = 130
FEATURE                Location/Qualifiers
source                 1..130
                       mol_type = protein
                       organism = Alphatorquevirus sp.
SEQUENCE: 895
MPWRPPVHSV QGREDQWFAS FFHGHDSFCG CGDPLGHINS IAHRFPRAGP PRPPPGLDQP  60
NPREQGPAGP GGPPAILALP APPAEPDDPQ PRRGGGDGGA AAGAADDHTQ RDYDEEELDE  120
LFRAAAEDDL                                                        130
```

```
SEQ ID NO: 896         moltype = AA  length = 303
FEATURE                Location/Qualifiers
source                 1..303
                       mol_type = protein
                       organism = Alphatorquevirus sp.
SEQUENCE: 896
MPWRPPVHSV QGREDQWFAS FFHGHDSFCG CGDPLGHINS IAHRFPRAGP PRPPPGLDQP  60
NPREQGPAGP GGPPAILALP APPAEPDDPQ PRRGGGDGGA AAGAADDHTQ RDYDEEELDE  120
LFRAAAEDDF QSTTPASREP TRFPTPINTL ASYKSRTRNY SDRGQCSTSG TSDVGSLAKE  180
```

```
VLRECQNTQA MMNLLRQVSH QSETSSTRRS EEKIESKKNA ILSSKRSRKK RPQKKKNQHP  240
KKKPRKRSYS TSSSSRDATS ESSDEGSSSS LQTSSDSARE STGTRSSHSA PTLHTRPAFS  300
QYW                                                               303

SEQ ID NO: 897         moltype = AA  length = 292
FEATURE                Location/Qualifiers
source                 1..292
                       mol_type = protein
                       organism = Alphatorquevirus sp.
SEQUENCE: 897
MPWRPPVHSV QGREDQWFAS FFHGHDSFCG CGDPLGHINS IAHRFPRAGP PRPPPGLDQP  60
NPREQGPAGP GGPPAILALP APPAEPDDPQ PRRGGGDGGA AAGAADDHTQ RDYDEEELDE  120
LFRAAAEDDL SPIKAKQARL GVPRRKSRAK RMLFSPQSAR GRRDPRRRRT STPRKSPERG  180
ATPPAPAPET PPASPQTRAQ ARLYRHPPTP PGSPLEPGAH IAPPPYIPDL LFPNTGKKKK  240
FSPFDWETEA QIAGWMRRPM RFYPSDTPHY PWLPPERDIP KICNINFKIK LQ          292

SEQ ID NO: 898         moltype = AA  length = 180
FEATURE                Location/Qualifiers
source                 1..180
                       mol_type = protein
                       organism = Alphatorquevirus sp.
SEQUENCE: 898
MPWRPPVHSV QGREDQWSPI KAKQARLGVP RRKSRAKRML FSPQSARGRR DPRRRRTSTP  60
RKSPERGATP PAPAPETPPA SPQTRAQARL YRHPPTPPGS PLEPGAHIAP PPYIPDLLFP  120
NTGKKKKFSP FDWETEAQIA GWMRRPMRFY PSDTPHYPWL PPERDIPKIC NINFKIKLQE  180

SEQ ID NO: 899         moltype = AA  length = 49
FEATURE                Location/Qualifiers
source                 1..49
                       mol_type = protein
                       organism = Alphatorquevirus sp.
SEQUENCE: 899
IVSRGERISG SQAFFTATIR FAAAVTLLAI LIALLIAFLA PVHQGPLRG             49

SEQ ID NO: 900         moltype = AA  length = 728
FEATURE                Location/Qualifiers
source                 1..728
                       mol_type = protein
                       organism = Alphatorquevirus sp.
SEQUENCE: 900
TAWWWGRWRR RWRRRRPYTT RLRRRRARRA FPRRRRRRFV SRRWRRPYRR RRRRGRRRRR  60
RRRRHKPTLI LRQWQPDCIR HCKITGWMPL IICGKGSTQF NYITHADDIT PRGASYGGNF  120
TNMTFSLEAI YEQFLYHRNR WSASNHDLEL CRYKGTTLKL YRHPEVDYIV TYSRTGPFEI  180
SHMTYLSTHP MLMLLNKHHI VVPSLKTKPR GRKAIKVRIR PPKLMNNKWY FTRDFCNIGL  240
FQLWATGLEL RNPWLRMSTL SPCIGFNVLK NSIYTNLSNL PQYKNERLNI INNILHPQEI  300
TGTNNKKWQY TYTKLMAPIY YSANRASTYD WENYSKETNY NNTYVKFTQK RQEKLTKIRK  360
EWQMLYPQQP TALPDSYDLL QEYGLYSPYY LNPTRINLDW MTPYTHVRYN PLVDKGFGNR  420
IYIQWCSEAD VSYNRTKSKC LLQDMPLFFM CYGYIDWAIK NTGVSSLVKD ARICIRCPYT  480
EPQLVGSTED IGFVPISETF MRGDMPVLAP YIPLSWFCKW YPNIAHQKEV LESIISCSPF  540
MPRDQDMNGW DITIGYKMDF LWGGSPLPSQ PIDDPCQQGT HPIPDPDKHP RLLQVSNPKL  600
LGPRTVFHKW DIRRGQFSKR SIKRVSEYSS DDESLAPGLP SKRNKLDSAF RGENREQKEC  660
YSLLKALEEE ETPEEEEPAP QEKAQKEELL HQLQLQRRHQ RVLRRGLKLV FTDILRLRQG  720
VHWNPELT                                                          728

SEQ ID NO: 901         moltype = AA  length = 197
FEATURE                Location/Qualifiers
source                 1..197
                       mol_type = protein
                       organism = Alphatorquevirus sp.
SEQUENCE: 901
TAWWWGRWRR RWRRRRPYTT RLRRRRARRA FPRRRRRRFP IDDPCQQGTH PIPDPDKHPR  60
LLQVSNPKLL GPRTVFHKWD IRRGQFSKRS IKRVSEYSSD DESLAPGLPS KRNKLDSAFR  120
GENREQKECY SLLKALEEEE TPEEEEPAPQ EKAQKEELLH QLQLQRRHQR VLRRGLKLVF  180
TDILRLRQGV HWNPELT                                                197

SEQ ID NO: 902         moltype = AA  length = 145
FEATURE                Location/Qualifiers
source                 1..145
                       mol_type = protein
                       organism = Alphatorquevirus sp.
SEQUENCE: 902
TAWWWGRWRR RWRRRRPYTT RLRRRRARRA FPRRRRRRFV SHQSETSSTR RSEEKIESKK  60
NAILSSKRSR KKRPQKKKNQ HPKKKPRKRS YSTSSSSRDA TSESSDEGSS SSLQTSSDSA  120
RESTGTRSSH SAPTLHTRPA FSQYW                                       145

SEQ ID NO: 903         moltype = DNA  length = 3828
FEATURE                Location/Qualifiers
source                 1..3828
                       mol_type = genomic DNA
```

```
                         organism = Alphatorquevirus sp.
SEQUENCE: 903
gtgctacgtc actaacctac gtgtccgtct cccataggcc ggacaccgta tacgtcatac  60
acttcctggg catggtctac gtgataatat aagtggctgc acttccgaat ggctgagttt  120
tccacgcccg tccgcagcga ggacgccacg gagggggatc cgcgcgtccc gagggcgggt  180
gccggaggtg agtttacaca ccgcagtcaa ggggcaattc gggctcggga ctggccgggc  240
tatgggcaag gctcttaaaa atgcactttt ctaggtgcag tagaaagaaa aggacattgt  300
cactgctacc actgtaccat tcacagaaag ctaggccatc tgtgacaggt atgtggagac  360
ccccgactcg aaatgcgttc aatattcaac gtgactggtt ctacagttgc tttcactccc  420
acgcttctat gtgcggctgt gctgatttta ttggtcattt caatcatatc gctgctatgc  480
tcggccgtcc ggaagaccag aaccctcctc cgccacccgg ggctctgaga cccctacccg  540
ctctcccggc ctcttccgag gcacccggtg atcgagcgcc atggcctatg ggtggtggcg  600
gaggcgacgg aggcgcccgt ggtggaggag gagatggcgc cgctggagac gccgtcggag  660
accccgcaga cgccgacctc gtcgccgcta tcgacgccgc agaacagtaa ggaggcgcgg  720
cagggggagg tggactagag cacacaggag atggcgccgc aagggaaaac gcagtcgcaa  780
aaaaaagatt attataagac aatggcagcc caactacact cgcagatgca acatagtggg  840
ctacatgcct ctactaatat gtggggaaaa tactgttgct acaaactatg ccacccactc  900
agacgacagc tactaccccg gaccctttgg ggggggaatg actacagaca aatttactct  960
aagaatactg tatgatgagt acaaaaggtt catgaactac tggacctctt caaacgagga  1020
cctagaccta tgtagatacc tgggatgcac tctatatgtg tttagacacc cagaagtaga  1080
ctttataatc attataaata cctctcctcc attcctagac acagaaataa cagggcctag  1140
catacaccca ggtatgatgg cccttaacaa aagaagcaga tggataccta gcataaaaaa  1200
cagaccaggc agaaagcact atataaagat taaagtagga gccccccgaa tgttcacaga  1260
taagtggtac ccccaaacag acctctgtga catgacactc ctaacgatct ttgccagtgc  1320
ggcggatatg caatatccgt tcggctcacc actaactgac accatagttg tgtcattcca  1380
agttctgcaa tccatgtaca acgactgcct gagtgtactt cctgataatt ttgcagagac  1440
atcaggcaaa ggcacccaac tacatgagaa cataatacaa catctgccct actacaacac  1500
cacacaaaca caagcacaat ttaaaagatt tatagaaaac atgaatgcaa caaatggaga  1560
caatatatgg gcaagctaca taaacacaac caagttctca tccgcaaaca ctccaaagaa  1620
tgacacaggc ataggaggcc cttacactac atattcagac tcatggtaca aaggcacagt  1680
atacaatgac aaaattaaaa ccataccaat aaaagcaagc aagttatact acgagcaaac  1740
caaaaacctc attggcatta cattcactgg atccacacac agactccatt actgtggagg  1800
cctatactcc tccgtatggc tatcagcagg tagatcctac tttgaaacca aaggcccata  1860
cacagacata acttacaacc ccttttcaga cagaggagag ggtaacatgc tatggataga  1920
ctggctaact aaaaatgact cagtgtactc aaaaacaagt agcaagtgtc ttatagaaaa  1980
cctgcccctg tgggcctcag tatacggata taaagaatac tgcagcaagg taacaggaga  2040
cacaaacata gaacacaact gtagatgtgt tatcagaagc ccctacacag taccacaact  2100
gttagaccac aacaatccct tcagaggata cgtgccttat agcttcaact ttggaaatgg  2160
taaaatgcca ggcggtagca gcctagtgcc cattagaatg agagccaagt ggtaccccac  2220
tctgttccac caaaaagaag ttctagaagc catagcacag gcgggcccct tcgcatacca  2280
ctcagatatt aaaaaagtgt ccctgggcat aaagtacaga tttaagtggg tgtggggtgg  2340
caaccccgtg tcccaacagg ttgttagaaa cccctgcaag accacccaag gttcctcggg  2400
caatagagtg cctcgatcaa tacaagtcgt tgacccgcgg tacaacacgc cagaactcac  2460
catacacgcg tgggacttca gacatgggtt ctttggcaga aaagctatta agagaatgca  2520
agaacaacca atacctcatg acactttttc agcagggttc aagcgcagtc gccgagatac  2580
agaagcactc caatgcagcc aagaagagca acaaaaagaa aacttacttt tcccagtcca  2640
gcagctcaag cgagtccccc cgtgggagac ctcgcaagag agccaaagcg aggaagaaaa  2700
ctcgcaaaaa caggagaccc tctcccagca actcagagac cagctgcaca agcagcggct  2760
catgggagag caactccgat cgctcctcta ccaaatgcag agggtccaac aaaatcaaca  2820
cataaaccct atgttattgc caaagggtct ggcattaact tctatttctc acaatgtaat  2880
atagatatgt ttggtgaccc caaaccctac aagccctcct ccaatgactg gaaggaggag  2940
tacgaggccg caaagtactg ggacagaccc cccagacgcg acctgaggag cacccccttc  3000
tacccctggg cccccacccc caaaccatac aatgtcaact ttgccctcaa ctacaaataa  3060
acggtggccg tgggagtttc acttgtcggt gtctacctct taaggtcact aagcactccg  3120
agcgtaagcg aggagtgcga cccttcacca agggcaactc cctcgaagtc cggcgctacg  3180
cgcttcgcgc tgcgccggac atctcggacc ccccctcgac ccgaatcgct tgcgcgattc  3240
ggacctgcgg cctcgggggg gtcgggggct ttactaaaca gactccgagg tgccattgga  3300
cactgagggg gtgaacagca acgaaagtga gtggggccag acttcgccat aaggccttta  3360
tcttcttgcc atttgtccgc gaccgggggt cgctcctagg cgcggacccc gtttcggggt  3420
ccttccgggt tcatcggcgc cgttccagtg acgtcacggg cgccatgtta agtggctgtc  3480
gccgaggatt gacgtcacag ttcaaaggtc atcctcggcg gtaaccgcaa acatggcggt  3540
caatctcttc cgggtcaaag gtcgtgcata cgtcataagt cacatgacag ggtccactt   3600
aaacacggaa gtaggccccg acatgtgact cgtcacgtgt gtacacgtca cggccgccat  3660
tttgttttac aaaatggccg acttccttcc tgttttttaa aaaaaggcgc gaaaaaaccg  3720
tcggcggggg ccgcgcgctg cgcgcgcggg aggcaatgcc tccccccccc cgcgcgcatg  3780
cgcgcgggtc ccccccctc cgggggctc cgccccccgg cccccccc                 3828

SEQ ID NO: 904           moltype = AA  length = 119
FEATURE                  Location/Qualifiers
source                   1..119
                         mol_type = protein
                         organism = Alphatorquevirus sp.
SEQUENCE: 904
MWRPPTRNAF NIQRDWFYSC FHSHASMCGC ADFIGHFNHI AAMLGRPEDQ NPPPPPGALR  60
PLPALPASSE APGDRAPWPM GGGGGDGGAR GGGGDGAAGD AVGDPADADL VAAIDAAEQ   119

SEQ ID NO: 905           moltype = AA  length = 273
FEATURE                  Location/Qualifiers
source                   1..273
```

```
                        mol_type = protein
                        organism = Alphatorquevirus sp.
SEQUENCE: 905
MWRPPTRNAF NIQRDWFYSC FHSHASMCGC ADFIGHFNHI AAMLGRPEDQ NPPPPPGALR  60
PLPALPASSE APGDRAPWPM GGGGGDGGAR GGGGDGAAGD AVGDPADADL VAAIDAAEQL  120
LETPARPPKV PRAIECLDQY KSLTRGTTRQ NSPYTRGTSD MGSLAEKLLR ECKNNQYLMT  180
LFQQGSSAVA EIQKHSNAAK KSNKKKTYFS QSSSSESPR GRPRKRAKAR KKTRKNRRPS  240
PSNSETSCTS SGSWESNSDR SSTKCRGSNK INT                             273

SEQ ID NO: 906          moltype = AA  length = 286
FEATURE                 Location/Qualifiers
source                  1..286
                        mol_type = protein
                        organism = Alphatorquevirus sp.
SEQUENCE: 906
MWRPPTRNAF NIQRDWFYSC FHSHASMCGC ADFIGHFNHI AAMLGRPEDQ NPPPPPGALR  60
PLPALPASSE APGDRAPWPM GGGGGDGGAR GGGGDGAAGD AVGDPADADL VAAIDAAEQV  120
QAQSPRYRST PMQPRRATKR KLTFPSPAAQ ASPPVGDLAR EPKRGRKLAK TGDPLPATQR  180
PAAQAAAHGR ATPIAPLPNA EGPTKSTHKP YVIAKGSGIN FYFSQCNIDM FGDPKPYKPS  240
SNDWKEEYEA AKYWDRPPRR DLRSTPFYPW APTPKPYNVN FALNYK                 286

SEQ ID NO: 907          moltype = AA  length = 51
FEATURE                 Location/Qualifiers
source                  1..51
                        mol_type = protein
                        organism = Alphatorquevirus sp.
SEQUENCE: 907
MRSIFNVTGS TVAFTPTLLC AAVLILLVIS IISLLCSAVR KTRTLLRHPG L           51

SEQ ID NO: 908          moltype = AA  length = 767
FEATURE                 Location/Qualifiers
source                  1..767
                        mol_type = protein
                        organism = Alphatorquevirus sp.
SEQUENCE: 908
MAYGWWRRRR RRPWWRRRWR RWRRRRRPRR RRPRRRYRRR RTVRRRGRGR WTRAHRRWRR  60
KGKRSRKKKI IIRQWQPNYT RRCNIVGYMP LLICGENTVA TNYATHSDDS YYPGPFGGGM  120
TTDKFTLRIL YDEYKRFMNY WTSSNEDLDL CRYLGCTLYV FRHPEVDFII IINTSPPFLD  180
TEITGPSIHP GMMALNKKRSR WIPSIKNRPG RKHYIKIKVG APRMFTDKWY PQTDLCDMTL  240
LTIFASAADM QYPFGSPLTD TIVVSFQVLQ SMYNDCLSVL PDNFAETSGK GTQLHENIIQ  300
HLPYYNTTQT QAQFKRFIEN MNATNGDNIW ASYINTTKFS SANTPKNDTG IGGPYTTYSD  360
SWYKGTVYND KIKTIPIKAS KLYYEQTKNL IGITFTGSTH RLHYCGGLYS SVWLSAGRSY  420
FETKGPYTDI TYNPFSDRGE GNMLWIDWLT KNDSVYSKTS SKCLIENLPL WASVYGYKEY  480
CSKVTGDTNI EHNCRCVIRS PYTVPQLLDH NNPFRGYVPY SFNFGNGKMP GGSSLVPIRM  540
RAKWYPTLFH QKEVLEAIAQ AGPFAYHSDI KKVSLGIKYR FKWVWGGNPV SQQVVRNPCK  600
TTQGSSGNRV PRSIQVVDPR YNTPELTIHA WDFRHGFFGR KAIKRMQEQP IPHDTFSAGF  660
KRSRRDTEAL QCSQEEQQKE NLLFPVQQLK RVPPWETSQE SQSEEENSQK QETLSQQLRD  720
QLHKQRLMGE QLRSLLYQMQ RVQQNQHINP MLLPKGLALT SISHNVI                767

SEQ ID NO: 909          moltype = AA  length = 216
FEATURE                 Location/Qualifiers
source                  1..216
                        mol_type = protein
                        organism = Alphatorquevirus sp.
SEQUENCE: 909
MAYGWWRRRR RRPWWRRRWR RWRRRRRPRR RRPRRRYRRR RTVVRNPCKT TQGSSGNRVP  60
RSIQVVDPRY NTPELTIHAW DFRHGFFGRK AIKRMQEQPI PHDTFSAGFK RSRRDTEALQ  120
CSQEEQQKEN LLFPVQQLKR VPPWETSQES QSEEENSQKQ ETLSQQLRDQ LHKQRLMGEQ  180
LRSLLYQMQR VQQNQHINPM LLPKGLALTS ISHNVI                            216

SEQ ID NO: 910          moltype = AA  length = 131
FEATURE                 Location/Qualifiers
source                  1..131
                        mol_type = protein
                        organism = Alphatorquevirus sp.
SEQUENCE: 910
MAYGWWRRRR RRPWWRRRWR RWRRRRRPRR RRPRRRYRRR RTGSSAVAEI QKHSNAAKKS  60
NKKKTYFSQS SSSSESPRGR PRKRAKARKK TRKNRRPSPS NSETSCTSSG SWESNSDRSS  120
TKCRGSNKIN T                                                       131

SEQ ID NO: 911          moltype = DNA  length = 3815
FEATURE                 Location/Qualifiers
source                  1..3815
                        mol_type = genomic DNA
                        organism = Alphatorquevirus sp.
SEQUENCE: 911
aagatcgtca ctaaccacgt gactcctctc gcccaatcag tgtctacgtc gtccatttcc  60
tgggcatggt ctacatcctg atataaagcg atgcacttcc gaatggctga gttttccacg  120
cccgtccgcg gcgagatcgc gacggaggag cgatcgagcg tcccgagggc gggtgccgga  180
```

```
ggtgagttta cacaccgcag tcaaggggca attcgggctc gggactggcc gggctatggg  240
caaggctctt aaagcgtacg tcccccgcta tgtttctcgg cagggtgtgg aggaaacaga  300
aaaggaaagt gcttctgctg gctgtgcgag ctacacagaa aacatcttcc atgagtatct  360
ggcgtccccc ccttgggaat gtctcctaca gggagagaaa ttggcttcag gccgtcgaaa  420
catcccacag ttctttttgt ggctgtggtg attttattct tcatcttact aatttggctg  480
cacgctttgc tctccagggg cccccgccag agggtggtcc acctcggccg aggccgccgc  540
tcctgagagc gctgccggcc cccgaggtcc gcagggagac gcgcacagag aaccggggcg  600
cctccggtga gccatggcct ggcgatggtg gtggcagaga cgatggcgcc gccgccggtg  660
gccccgcaga cggtggagac gcctacgacg ccggagacct agacgacctg ttcgccgccg  720
tcgaagaaga acaacagtaa ggaggcggag gtggaggggc agacgtgggc gacgcacata  780
cacccgacgc gcggtcagac gcagacgcag acccagaaag agacttgtac tgactcagtg  840
gagcccccag acagtcagaa actgctcaat aaggggcata gtgcccatgg taatatgcgg  900
acacacaaaa gcaggtagaa actatgctat tcatagcgag gacttcacca cacagataca  960
acccttcggg ggcagtttca gcacgaccac ctggtcccta aaagtgctgt gggacgagca  1020
ccagaaattc cagaacagat ggtcctaccc aaacacacaa ctagacctgg ccagatacag  1080
aggggtcacc ttctggttct acagagacca gaaaacagac tatatagtac agtggagtag  1140
gaatccccct tttaaactca ataaatacag cagtgccatg taccacccgg gcatgatgat  1200
gcaggccaaa aggaaactag ttgtacctag tttccagacc agacccaaag gcaagaagag  1260
atacagagtc acaataaaac cccctaacat gtttgctgac aagtggtaca ctcaagagga  1320
cctgtgtccg gtacctcttg tgcaaattgt ggtttctgcg gcgagcctgc tacatccgtt  1380
ctgcccacca caaacgaaca acccttgcat caccttccag gttttgaaag acatatatga  1440
tgaatgcata ggagttaacg aaactatgaa agataagtat aagaaattac aaacaacact  1500
atacaccact tgcacatact atcaaacaac acaagtactg gcacagctat ctcctgcctt  1560
tcaacctgct atgaaaccta ctactacaca atcagcagct acagcgacaa cactaggaaa  1620
ctatgtacca gagttaaagt acaacaatgg ctcttttcac acaggacaaa acgcagtatt  1680
cggcatgtgc tcatacaaac caacagacag cataatgaca aaagctaatg gctggttttg  1740
gcaaaaccta atggtagaca acaacctaca tagttcttat ggcaaggcaa cattagaatg  1800
catggagtat cacacaggca tatacagctc tatatttcta agtccacaaa gatctttaga  1860
attcccagca gcataccaag acgttacata caaccctaac tgtgatagag cagttggaaa  1920
cgtagtttgg tttcagtaca gcactaaaat ggatacaaat tttgatgaaa caaaatgtaa  1980
atgtgtcctt aaaaacattc cactgtgggc ggccttcaat ggctactcag actttataat  2040
gcaagaactc agcataagta cagaaatcca caactttggc atagtgtgct ttcagtgccc  2100
gtacactttt cccccctgtt tcaataaaaa caaaccccta aaggggtacg tgttctatga  2160
caccaccttt ggtaatggaa aaatgccaga cggatcgggg cacgtaccca tctactggca  2220
gcagagatgg tggatcagac tagccttcca ggtccaggtc atgcatgact ttgtactaac  2280
aggccccttt agctacaaag atgacctagc aaacaccaca ctcacagcca gatacaaatt  2340
taaattcaaa tggggcggca atatcatccc tgaacagatt atcaagaacc cgtgtcacag  2400
agagcagtcc ctcgcttcct atcccgatag acaacgtcgc gacctacaag ttgttgaccc  2460
atcaaccatg ggcccgatct acaccttcca cacatgggac tggcgacggg ggcttttttgg  2520
tgcagatgct atccagagag tgtcacaaaa accgggagat gctctccgct ttacaaaccc  2580
tttcaagaga cccagatatc ttcccccgac agacagagaa gactaccgac aagaagaaga  2640
cttcgcttta caggaaaaaa gacggcgcac atccacagaa gaagcccagg acgaggagag  2700
ccccccggaa agcgcgccgc tcctacagca gcagcagcag cagcggcagc tctcagtcca  2760
cctcgcggag cagcagcgac tcggagtcca actccgatac atcctccaag aagtcctcaa  2820
aacgcaagcg ggtctccacc taaaccccct attattaggc ccgccacaaa caaggtctat  2880
ctctttgagc cctccaaagg cctactcccc atagtaggaa aagaggcctg ggaggacgag  2940
tactgcacct gcaagtactg ggatcgccct cccagaacca accacctaga catccccact  3000
tatccctgga tgcccacaaa cttcaaagtc agcttcaaac ttggatttaa accctaaata  3060
aaaatacaag gccgtacact gttcacttgt cggtgtctac ctctataagt cactaagcac  3120
tccgagcgca gcgaggagtg cgaccctcag cggtgggtgc aacgccctcg gcggccgcgc  3180
gctacgcctt cggctgcgcg cggcacctcg gacccccgct cgtgctgaca cgctcgcgcg  3240
tgtcagacca cttcgggctc gcgggggtcg ggaattttgc taaacagact ccgagttgct  3300
cttggacact gtagctgtga atcagtaacg aaagtgagtg gggccagact tcgccataag  3360
gcctttatct tcttgccatt ggtccgtctc gggggtcgcc ataggcttcg ggctcggttt  3420
taggccttcc ggactaccaa aatggcggat tccgtgacgt catggccgcc attttaagta  3480
aggcggaaca ggctgtcacc ccgtgtcaaa gttcaggggt cagccttccg ctttacacaa  3540
aatggaggtc aatatcttcc gggtcaaagg tcgctaccgc gtcataagtc acgtggggaa  3600
ggctgctgtg aatccggaag tagctgaccc acgtgacttg tcacgtgact agcacgtcac  3660
ggcagccatt ttgaatcaca aaatggccga cttccttcct cttttttaaa aataacggcc  3720
cggcggcggc gcgcgcgctt cgcgccgctc cgcccccccc gcgcatgcgc gggacccccc  3780
cccgcggggg gctccgcccc ccggtccccc ccccg                            3815
```

```
SEQ ID NO: 912         moltype = AA  length = 129
FEATURE                Location/Qualifiers
source                 1..129
                       mol_type = protein
                       organism = Alphatorquevirus sp.
SEQUENCE: 912
MSIWRPPLGN VSYRERNWLQ AVETSHSSFC GCGDFILHLT NLAARFALQG PPPEGGPPRP  60
RPPLLRALPA PEVRRETRTE NRGASGEPWP GDGGGRDDGA AAGGPADGGD AYDAGDLDDL  120
FAAVEEEQQ                                                         129
```

```
SEQ ID NO: 913         moltype = AA  length = 283
FEATURE                Location/Qualifiers
source                 1..283
                       mol_type = protein
                       organism = Alphatorquevirus sp.
SEQUENCE: 913
MSIWRPPLGN VSYRERNWLQ AVETSHSSFC GCGDFILHLT NLAARFALQG PPPEGGPPRP  60
```

```
RPPLLRALPA PEVRRETRTE NRGASGEPWP GDGGGRDDGA AAGGPADGGD AYDAGDLDDL  120
FAAVEEEQQL SRTRVTESSP SLPIPIDNVA TYKLLTHQPW ARSTPSTHGT GDGGFLVQML  180
SRECHKNREM LSALQTLSRD PDIFPRQTEK TTDKKKTSLY RKKDGAHPQK KPRTRRAPRK  240
ARRSYSSSSS SGSSQSTSRS SSDSESNSDT SSKKSSKRKR VST                    283

SEQ ID NO: 914         moltype = AA  length = 305
FEATURE                Location/Qualifiers
source                 1..305
                       mol_type = protein
                       organism = Alphatorquevirus sp.
SEQUENCE: 914
MSIWRPPLGN VSYRERNWLQ AVETSHSSFC GCGDFILHLT NLAARFALQG PPPEGGPPRP  60
RPPLLRALPA PEVRRETRTE NRGASGEPWP GDGGGRDDGA AAGGPADGGD AYDAGDLDDL  120
FAAVEEEQQC YPESVTKTGR CSPLYKPFQE TQISSPDRQR RLPTRRRLRF TGKKTAHIHR  180
RSPGRGEPPG KRAAPTAAAA AAAALSPPRG AAATRSPTPI HPPRSPQNAS GSPPKPPIIR  240
PATNKVYLFE PSKGLLPIVG KEAWEDEYCT CKYWDRPPRT NHLDIPTYPW MPTNFKVSFK  300
LGFKP                                                             305

SEQ ID NO: 915         moltype = AA  length = 55
FEATURE                Location/Qualifiers
source                 1..55
                       mol_type = protein
                       organism = Alphatorquevirus sp.
SEQUENCE: 915
MSPTGREIGF RPSKHPTVLF VAVVILFFIL LIWLHALLSR GPRQRVVHLG RGRRS       55

SEQ ID NO: 916         moltype = AA  length = 766
FEATURE                Location/Qualifiers
source                 1..766
                       mol_type = protein
                       organism = Alphatorquevirus sp.
SEQUENCE: 916
MAWRWWWQRR WRRRRWPRRR WRRLRRRRPR RPVRRRRRRT TVRRRRWRGR RGRRTYTRRA  60
VRRRRRPRKR LVLTQWSPQT VRNCSIRGIV PMVICGHTKA GRNYAIHSED FTTQIQPFGG  120
SFSTTTWSLK VLWDEHQKFQ NRWSYPNTQL DLARYRGVTF WFYRDQKTDY IVQWSRNPPF  180
KLNKYSSAMY HPGMMMQAKR KLVVPSFQTR PKGKKRYRVT IKPPNMFADK WYTQEDLCPV  240
PLVQIVVSAA SLLHPFCPPQ TNNPCITFQV LKDIYDECIG VNETMKDKYK KLQTTLYTTC  300
TYYQTTQVLA QLSPAFQPAM KPTTTQSAAT ATTLGNYVPE LKYNNGSFHT GQNAVFGMCS  360
YKPTDSIMTK ANGWFWQNLM VDNNLHSSYG KATLECMEYH TGIYSSIFLS PQRSLEFPAA  420
YQDVTYNPNC DRAVGNVVWF QYSTKMDTNF DETKCKCVLK NIPLWAAFNG YSDFIMQELS  480
ISTEIHNFGI VCFQCPYTFP PCFNKNKPLK GYVFYDTTFG NGKMPDGSGH VPIYWQQRWW  540
IRLAFQVQVM HDFVLTGPFS YKDDLANTTL TARYKFKFKW GGNIIPEQII KNPCHREQSL  600
ASYPDRQRRD LQVVDPSTMG PIYTFHTWDW RRGLFGADAI QRVSQKPGDA LRFTNPFKRP  660
RYLPPTDRED YRQEEDFALQ EKRRRTSTEE AQDEESPPES APLLQQQQQQ RQLSVHLAEQ  720
QRLGVQLRYI LQEVLKTQAG LHLNPLLLGP PQTRSISLSP PKAYSP                766

SEQ ID NO: 917         moltype = AA  length = 219
FEATURE                Location/Qualifiers
source                 1..219
                       mol_type = protein
                       organism = Alphatorquevirus sp.
SEQUENCE: 917
MAWRWWWQRR WRRRRWPRRR WRRLRRRRPR RPVRRRRRRT TIIKNPCHRE QSLASYPDRQ  60
RRDLQVVDPS TMGPIYTFHT WDWRRGLFGA DAIQRVSQKP GDALRFTNPF KRPRYLPPTD  120
REDYRQEEDF ALQEKRRRTS TEEAQDEESP PESAPLLQQQ QQQRQLSVHL AEQQRLGVQL  180
RYILQEVLKT QAGLHLNPLL LGPPQTRSIS LSPPKAYSP                        219

SEQ ID NO: 918         moltype = AA  length = 146
FEATURE                Location/Qualifiers
source                 1..146
                       mol_type = protein
                       organism = Alphatorquevirus sp.
SEQUENCE: 918
MAWRWWWQRR WRRRRWPRRR WRRLRRRRPR RPVRRRRRRT TMLSRECHKN REMLSALQTL  60
SRDPDIFPRQ TEKTTDKKKT SLYRKKDGAH PQKKPRTRRA PRKARRSYSS SSSSGSSQST  120
SRSSSDSESN SDTSSKKSSK RKRVST                                      146

SEQ ID NO: 919         moltype = AA  length = 677
FEATURE                Location/Qualifiers
source                 1..677
                       mol_type = protein
                       organism = Gammatorquevirus sp.
SEQUENCE: 919
MPFWWRRRNK RWWGRRFRYR RYNKYKTRRR RRIPRRRNRR FTKTRRRRKR KKVRRKLKKI  60
TIKQWQPDSV KKCKIKGYST LVMGAQGKQY NCYTNQASDY VQPKAPQGGG FGCEVFNLKW  120
LYQEYTAHRN IWTKTNEYTD LCRYTGAQII LYRHPDVDFI VSWDNQPPFL LNKYTYPELQ  180
PQNLLLARRK RIILSQKSNP KGKLRIKLRI PPPKQMITKW FFQRDFCDVN LFKLCASAAS  240
FRYPGISHGA QSTIFSAYAL NTDFYQCSDW CQTNTETGYL NIKTQQMPLW FHYREGGKEK  300
WYKYTNKEHR PYTNTYLKSI SYNDGLFSPK AMFAFEVKAG GEGTTEPPQG AQLIANLPLI  360
```

```
ALRYNPHEDT GHGNEIYLTS TFKGTYDKPK VTDALYFNNV PLWMGFYGYW DFILQETKNK  420
GVFDQHMFVV KCPALRPISQ VTKQVYYPLV DMDFCSGRLP FDEYLSKDIK SHWYPTAERQ  480
TVTINNFVTA GPYMPKFEPT DKDSTWQLNY HYKFFFKWGG PQVTDPTVED PCSRNKYPVP  540
DTMQQTIQIK NPEKLHPATL FHDWDLRRGF ITQAAIKRMS ENLQIDSSFE SDGTESPKKK  600
KRCTKEIPTQ NQKQEEIQEC LLSLCEEPTC QEETEDLQLF IQQQQQQQYK LRKNLFKLLT  660
HLKKGQRISQ LQTGLLE                                                 677

SEQ ID NO: 920         moltype = AA  length = 59
FEATURE                Location/Qualifiers
source                 1..59
                       mol_type = protein
                       organism = Gammatorquevirus sp.
SEQUENCE: 920
MPFWWRRRNK RWWGRRFRYR RYNKYKTRRR RRIPRRRNRR FTKTRRRRKR KKVRRKLKK   59

SEQ ID NO: 921         moltype = AA  length = 201
FEATURE                Location/Qualifiers
source                 1..201
                       mol_type = protein
                       organism = Gammatorquevirus sp.
SEQUENCE: 921
ITIKQWQPDS VKKCKIKGYS TLVMGAQGKQ YNCYTNQASD YVQPKAPQGG GFGCEVFNLK  60
WLYQEYTAHR NIWTKTNEYT DLCRYTGAQI ILYRHPDVDF IVSWDNQPPF LLNKYTYPEL  120
QPQNLLLARR KRIILSQKSN PKGKLRIKLR IPPPKQMITK WFFQRDFCDV NLFKLCASAA  180
SFRYPGISHG AQSTIFSAYA L                                            201

SEQ ID NO: 922         moltype = AA  length = 96
FEATURE                Location/Qualifiers
source                 1..96
                       mol_type = protein
                       organism = Gammatorquevirus sp.
SEQUENCE: 922
NTDFYQCSDW CQTNTETGYL NIKTQQMPLW FHYREGGKEK WYKYTNKEHR PYTNTYLKSI  60
SYNDGLFSPK AMFAFEVKAG GEGTTEPPQG AQLIAN                            96

SEQ ID NO: 923         moltype = AA  length = 161
FEATURE                Location/Qualifiers
source                 1..161
                       mol_type = protein
                       organism = Gammatorquevirus sp.
SEQUENCE: 923
LPLIALRYNP HEDTGHGNEI YLTSTFKGTY DKPKVTDALY FNNVPLWMGF YGYWDFILQE  60
TKNKGVFDQH MFVVKCPALR PISQVTKQVY YPLVDMDFCS GRLPFDEYLS KDIKSHWYPT  120
AERQTVTINN FVTAGPYMPK FEPTDKDSTW QLNYHYKFFF K                      161

SEQ ID NO: 924         moltype = AA  length = 160
FEATURE                Location/Qualifiers
source                 1..160
                       mol_type = protein
                       organism = Gammatorquevirus sp.
SEQUENCE: 924
WGGPQVTDPT VEDPCSRNKY PVPDTMQQTI QIKNPEKLHP ATLFHDWDLR RGFITQAAIK  60
RMSENLQIDS SFESDGTESP KKKKRCTKEI PTQNQKQEEI QECLLSLCEE PTCQEETEDL  120
QLFIQQQQQQ QYKLRKNLFK LLTHLKKGQR ISQLQTGLLE                        160

SEQ ID NO: 925         moltype = AA  length = 662
FEATURE                Location/Qualifiers
source                 1..662
                       mol_type = protein
                       organism = Gammatorquevirus sp.
SEQUENCE: 925
MPFWWRRRRK FWTNNRFNYT KRRRYRKRWP RRRRRRRPYR RPVRRRRRKL RKVKRKKKSL  60
IVRQWQPDSI RTCKIIGQSA IVVGAEGKQM YCYTVNKLIN VPPKTPYGGG FGVDQYTLKY  120
LYEEYRFAQN IWTQSNVLKD LCRYINVKLI FYRDNKTDFV LSYDRNPPFQ LTKFTYPGAH  180
PQQIMLQKHH KFILSQMTKP NGRLTKKLKI KPPKQMLSKW FFSKQFCKYP LLSLKASALD  240
LRHSYLGCCN ENPQVFFYYL NHGYYTITNW GAQSSTAYRP NSKVTDTTYY RYKNDRKNIN  300
IKSHEYEKSI SYENGYFQSS FLQTQCIYTS ERGEACIAEK PLGIAIYNPV KDNGDGNMIY  360
LVSTLANTWD QPPKDSAILI QGVPIWLGLF GYLDYCRQIK ADKTWLDSHV LVIQSPAIFT  420
YPNPGAGKWY CPLSQSFING NGPFNQPPTL LQKAKWFPQI QYQQEIINSF VESGPFVPKY  480
ANQTESNWEL KYKYVFTFKW GGPQFHEPEI ADPSKQEQYD VPDTFYQTIQ IEDPEGQDPR  540
SLIHDWDYRR GFIKERSLKR MSTYFSTHTD QQATSEEDIP KKKKRIGPQL TVPQQKEEET  600
LSCLLSLCKK DTFQETETQE DLQQLIKQQQ EQQLLLKRNI LQLIHKLKEN QQMLQLHTGM  660
LP                                                                 662

SEQ ID NO: 926         moltype = AA  length = 58
FEATURE                Location/Qualifiers
source                 1..58
                       mol_type = protein
                       organism = Gammatorquevirus sp.
```

```
SEQUENCE: 926
MPFWWRRRRK FWTNNRFNYT KRRRYRKRWP RRRRRRRPYR RPVRRRRRKL RKVKRKKK    58

SEQ ID NO: 927         moltype = AA  length = 202
FEATURE                Location/Qualifiers
source                 1..202
                       mol_type = protein
                       organism = Gammatorquevirus sp.
SEQUENCE: 927
SLIVRQWQPD SIRTCKIIGQ SAIVVGAEGK QMYCYTVNKL INVPPKTPYG GGFGVDQYTL  60
KYLYEEYRFA QNIWTQSNVL KDLCRYINVK LIFYRDNKTD FVLSYDRNPP FQLTKFTYPG  120
AHPQQIMLQK HHKFILSQMT KPNGRLTKKL KIKPPKQMLS KWFFSKQFCK YPLLSLKASA  180
LDLRHSYLGC CNENPQVFFY YL                                           202

SEQ ID NO: 928         moltype = AA  length = 79
FEATURE                Location/Qualifiers
source                 1..79
                       mol_type = protein
                       organism = Gammatorquevirus sp.
SEQUENCE: 928
NHGYYTITNW GAQSSTAYRP NSKVTDTTYY RYKNDRKNIN IKSHEYEKSI SYENGYFQSS  60
FLQTQCIYTS ERGEACIAE                                               79

SEQ ID NO: 929         moltype = AA  length = 160
FEATURE                Location/Qualifiers
source                 1..160
                       mol_type = protein
                       organism = Gammatorquevirus sp.
SEQUENCE: 929
KPLGIAIYNP VKDNGDGNMI YLVSTLANTW DQPPKDSAIL IQGVPIWLGL FGYLDYCRQI  60
KADKTWLDSH VLVIQSPAIF TYPNPGAGKW YCPLSQSFIN GNGPFNQPPT LLQKAKWFPQ  120
IQYQQEIINS FVESGPFVPK YANQTESNWE LKYKYVFTFK                        160

SEQ ID NO: 930         moltype = AA  length = 163
FEATURE                Location/Qualifiers
source                 1..163
                       mol_type = protein
                       organism = Gammatorquevirus sp.
SEQUENCE: 930
WGGPQFHEPE IADPSKQEQY DVPDTFYQTI QIEDPEGQDP RSLIHDWDYR RGFIKERSLK  60
RMSTYFSTHT DQQATSEEDI PKKKKRIGPQ LTVPQQKEEE TLSCLLSLCK KDTFQETETQ  120
EDLQQLIKQQ QEQQLLLKRN ILQLIHKLKE NQQMLQLHTG MLP                    163

SEQ ID NO: 931         moltype = AA  length = 728
FEATURE                Location/Qualifiers
source                 1..728
                       mol_type = protein
                       organism = Alphatorquevirus sp.
SEQUENCE: 931
TAWWWGRWRR RWRRRRPYTT RLRRRRARRA FPRRRRRRFV SRRWRRPYRR RRRRGRRRRR  60
RRRRHKPTLI LRQWQPDCIR HCKITGWMPL IICGKGSTQF NYITHADDIT PRGASYGGNF  120
TNMTFSLEAI YEQFLYHRNR WSASNHDLEL CRYKGTTLKL YRHPEVDYIV TYSRTGPFEI  180
SHMTYLSTHP MLMLLNKHHI VVPSLKTKPR GRKAIKVRIR PPKLMNNKWY FTRDFCNIGL  240
FQLWATGLEL RNPWLRMSTL SPCIGFNVLK NSIYTNLSNL PQYKNERLNI INNILHPQEI  300
TGTNNKKWQY TYTKLMAPIY YSANRASTYD WENYSKETNY NNTYVKFTQK RQEKLTKIRK  360
EWQMLYPQQP TALPDSYDLL QEYGLYSPYY LNPTRINLDW MTPYTHVRYN PLVDKGFGNR  420
IYIQWCSEAD VSYNRTKSKC LLQDMPLFFM CYGYIDWAIK NTGVSSLVKD ARICIRCPYT  480
EPQLVGSTED IGFVPISETF MRGDMPVLAP YIPLSWFCKW YPNIAHQKEV LESIISCSPF  540
MPRDQDMNGW DITIGYKMDF LWGGSPLPSQ PIDDPCQQGT HPIPDPDKHP RLLQVSNPKL  600
LGPRTVFHKW DIRRGQFSKR SIKRVSEYSS DDESLAPGLP SKRNKLDSAF RGENREQKEC  660
YSLLKALEEE ETPEEEEPAP QEKAQKEELL HQLQLQRRHQ RVLRRGLKLV FTDILRLRQG  720
VHWNPELT                                                           728

SEQ ID NO: 932         moltype = AA  length = 66
FEATURE                Location/Qualifiers
source                 1..66
                       mol_type = protein
                       organism = Alphatorquevirus sp.
SEQUENCE: 932
TAWWWGRWRR RWRRRRPYTT RLRRRRARRA FPRRRRRRFV SRRWRRPYRR RRRRGRRRRR  60
RRRRHK                                                             66

SEQ ID NO: 933         moltype = AA  length = 211
FEATURE                Location/Qualifiers
source                 1..211
                       mol_type = protein
                       organism = Alphatorquevirus sp.
SEQUENCE: 933
PTLILRQWQP DCIRHCKITG WMPLIICGKG STQFNYITHA DDITPRGASY GGNFTNMTFS  60
```

```
LEAIYEQFLY HRNRWSASNH DLELCRYKGT TLKLYRHPEV DYIVTYSRTG PFEISHMTYL  120
STHPMLMLLN KHHIVVPSLK TKPRGRKAIK VRIRPPKLMN NKWYFTRDFC NIGLFQLWAT  180
GLELRNPWLR MSTLSPCIGF NVLKNSIYTN L                                211

SEQ ID NO: 934         moltype = AA  length = 118
FEATURE                Location/Qualifiers
source                 1..118
                       mol_type = protein
                       organism = Alphatorquevirus sp.
SEQUENCE: 934
SNLPQYKNER LNIINNILHP QEITGTNNKK WQYTYTKLMA PIYYSANRAS TYDWENYSKE  60
TNYNNTYVKF TQKRQEKLTK IRKEWQMLYP QQPTALPDSY DLLQEYGLYS PYYLNPTR    118

SEQ ID NO: 935         moltype = AA  length = 166
FEATURE                Location/Qualifiers
source                 1..166
                       mol_type = protein
                       organism = Alphatorquevirus sp.
SEQUENCE: 935
INLDWMTPYT HVRYNPLVDK GFGNRIYIQW CSEADVSYNR TKSKCLLQDM PLFFMCYGYI  60
DWAIKNTGVS SLVKDARICI RCPYTEPQLV GSTEDIGFVP ISETFMRGDM PVLAPYIPLS  120
WFCKWYPNIA HQKEVLESII SCSPFMPRDQ DMNGWDITIG YKMDFL                166

SEQ ID NO: 936         moltype = AA  length = 167
FEATURE                Location/Qualifiers
source                 1..167
                       mol_type = protein
                       organism = Alphatorquevirus sp.
SEQUENCE: 936
WGGSPLPSQP IDDPCQQGTH PIPDPDKHPR LLQVSNPKLL GPRTVFHKWD IRRGQFSKRS  60
IKRVSEYSSD DESLAPGLPS KRNKLDSAFR GENREQKECY SLLKALEEEE TPEEEEPAPQ  120
EKAQKEELLH QLQLQRRHQR VLRRGLKLVF TDILRLRQGV HWNPELT               167

SEQ ID NO: 937         moltype = AA  length = 767
FEATURE                Location/Qualifiers
source                 1..767
                       mol_type = protein
                       organism = Alphatorquevirus sp.
SEQUENCE: 937
MAYGWWRRRR RRPWWRRRWR RWRRRRRPRR RRPRRRYRRR RTVRRRGRGR WTRAHRRWRR  60
KGKRSRKKKI IIRQWQPNYT RRCNIVGYMP LLICGENTVA TNYATHSDDS YYPGPFGGGM  120
TTDKFTLRIL YDEYKRFMNY WTSSNEDLDL CRYLGCTLYV FRHPEVDFII IINTSPPFLD  180
TEITGPSIHP GMMALNKRSR WIPSIKNRPG RKHYIKIKVG APRMFTDKWY PQTDLCDMTL  240
LTIFASAADM QYPFGSPLTD TIVVSFQVLQ SMYNDCLSVL PDNFAETSGK GTQLHENIIQ  300
HLPYYNTTQT QAQFKRFIEN MNATNGDNIW ASYINTTKFS SANTPKNDTG IGGPYTTYSD  360
SWYKGTVYND KIKTIPIKAS KLYYEQTKNL IGITFTGSTH RLHYCGGLYS SVWLSAGRSY  420
FETKGPYTDI TYNPFSDRGE GNMLWIDWLT KNDSVYSKTS SKCLIENLPL WASVYGYKEY  480
CSKVTGDTNI EHNCRCVIRS PYTVPQLLDH NNPFRGYVPY SFNFGNGKMP GGSSLVPIRM  540
RAKWYPTLFH QKEVLEAIAQ AGPFAYHSDI KKVSLGIKYR FKWVWGGNPV SQQVVRNPCK  600
TTQGSSGNRV PRSIQVVDPR YNTPELTIHA WDFRHGFFGR KAIKRMQEQP IPHDTFSAGF  660
KRSRRDTEAL QCSQEEQQKE NLLFPVQQLK RVPPWETSQE SQSEEENSQK QETLSQQLRD  720
QLHKQRLMGE QLRSLLYQMQ RVQQNQHINP MLLPKGLALT SISHNVI                767

SEQ ID NO: 938         moltype = AA  length = 69
FEATURE                Location/Qualifiers
source                 1..69
                       mol_type = protein
                       organism = Alphatorquevirus sp.
SEQUENCE: 938
MAYGWWRRRR RRPWWRRRWR RWRRRRRPRR RRPRRRYRRR RTVRRRGRGR WTRAHRRWRR  60
KGKRSRKKK                                                         69

SEQ ID NO: 939         moltype = AA  length = 200
FEATURE                Location/Qualifiers
source                 1..200
                       mol_type = protein
                       organism = Alphatorquevirus sp.
SEQUENCE: 939
IIIRQWQPNY TRRCNIVGYM PLLICGENTV ATNYATHSDD SYYPGPFGGG MTTDKFTLRI  60
LYDEYKRFMN YWTSSNEDLD LCRYLGCTLY VFRHPEVDFI IIINTSPPFL DTEITGPSIH  120
PGMMALNKRS RWIPSIKNRP GRKHYIKIKV GAPRMFTDKW YPQTDLCDMT LLTIFASAAD  180
MQYPFGSPLT DTIVVSFQVL                                             200

SEQ ID NO: 940         moltype = AA  length = 155
FEATURE                Location/Qualifiers
source                 1..155
                       mol_type = protein
                       organism = Alphatorquevirus sp.
SEQUENCE: 940
```

```
QSMYNDCLSV LPDNFAETSG KGTQLHENII QHLPYYNTTQ TQAQFKRFIE NMNATNGDNI  60
WASYINTTKF SSANTPKNDT GIGGPYTTYS DSWYKGTVYN DKIKTIPIKA SKLYYEQTKN  120
LIGITFTGST HRLHYCGGLY SSVWLSAGRS YFETK                            155

SEQ ID NO: 941         moltype = AA  length = 160
FEATURE                Location/Qualifiers
source                 1..160
                       mol_type = protein
                       organism = Alphatorquevirus sp.
SEQUENCE: 941
GPYTDITYNP FSDRGEGNML WIDWLTKNDS VYSKTSSKCL IENLPLWASV YGYKEYCSKV  60
TGDTNIEHNC RCVIRSPYTV PQLLDHNNPF RGYVPYSFNF GNGKMPGGSS LVPIRMRAKW  120
YPTLFHQKEV LEAIAQAGPF AYHSDIKKVS LGIKYRFKWV                       160

SEQ ID NO: 942         moltype = AA  length = 183
FEATURE                Location/Qualifiers
source                 1..183
                       mol_type = protein
                       organism = Alphatorquevirus sp.
SEQUENCE: 942
WGGNPVSQQV VRNPCKTTQG SSGNRVPRSI QVVDPRYNTP ELTIHAWDFR HGFFGRKAIK  60
RMQEQPIPHD TFSAGFKRSR RDTEALQCSQ EEQQKENLLF PVQQLKRVPP WETSQESQSE  120
EENSQKQETL SQQLRDQLHK QRLMGEQLRS LLYQMQRVQQ NQHINPMLLP KGLALTSISH  180
NVI                                                               183

SEQ ID NO: 943         moltype = AA  length = 766
FEATURE                Location/Qualifiers
source                 1..766
                       mol_type = protein
                       organism = Alphatorquevirus sp.
SEQUENCE: 943
MAWRWWWQRR WRRRRWPRRR WRRLRRRRPR RPVRRRRRRT TVRRRRWRGR RGRRTYTRRA  60
VRRRRRPRKR LVLTQWSPQT VRNCSIRGIV PMVICGHTKA GRNYAIHSED FTTQIQPFGG  120
SFSTTTWSLK VLWDEHQKFQ NRWSYPNTQL DLARYRGVTF WFYRDQKTDY IVQWSRNPPF  180
KLNKYSSAMY HPGMMMQAKR KLVVPSFQTR PKGKKRYRVT IKPPNMFADK WYTQEDLCPV  240
PLVQIVVSAA SLLHPFCPPQ TNNPCITFQV LKDIYDECIG VNETMKDKYK KLQTTLYTTC  300
TYYQTTQVLA QLSPAFQPAM KPTTTQSAAT ATTLGNYVPE LKYNNGSFHT GQNAVFGMCS  360
YKPTDSIMTK ANGWFWQNLM VDNNLHSSYG KATLECMEYH TGIYSSIFLS PQRSLEFPAA  420
YQDVTYNPNC DRAVGNVVWF QYSTKMDTNF DETKCKCVLK NIPLWAAFNG YSDFIMQELS  480
ISTEIHNFGI VCFQCPYTFP PCFNKNKPLK GYVFYDTTFG NGKMPDGSGH VPIYWQQRWW  540
IRLAFQVQVM HDFVLTGPFS YKDDLANTTL TARYKFKFKW GGNIIPEQII KNPCHREQSL  600
ASYPDRQRRD LQVVDPSTMG PIYTFHTWDW RRGLFGADAI QRVSQKPGDA LRFTNPFKRP  660
RYLPPTDRED YRQEEDFALQ EKRRRTSTEE AQDEESPPES APLLQQQQQQ RQLSVHLAEQ  720
QRLGVQLRYI LQEVLKTQAG LHLNPLLLGP PQTRSISLSP PKAYSP                 766

SEQ ID NO: 944         moltype = AA  length = 70
FEATURE                Location/Qualifiers
source                 1..70
                       mol_type = protein
                       organism = Alphatorquevirus sp.
SEQUENCE: 944
MAWRWWWQRR WRRRRWPRRR WRRLRRRRPR RPVRRRRRRT TVRRRRWRGR RGRRTYTRRA  60
VRRRRRPRKR                                                        70

SEQ ID NO: 945         moltype = AA  length = 201
FEATURE                Location/Qualifiers
source                 1..201
                       mol_type = protein
                       organism = Alphatorquevirus sp.
SEQUENCE: 945
LVLTQWSPQT VRNCSIRGIV PMVICGHTKA GRNYAIHSED FTTQIQPFGG SFSTTTWSLK  60
VLWDEHQKFQ NRWSYPNTQL DLARYRGVTF WFYRDQKTDY IVQWSRNPPF KLNKYSSAMY  120
HPGMMMQAKR KLVVPSFQTR PKGKKRYRVT IKPPNMFADK WYTQEDLCPV PLVQIVVSAA  180
SLLHPFCPPQ TNNPCITFQV L                                           201

SEQ ID NO: 946         moltype = AA  length = 147
FEATURE                Location/Qualifiers
source                 1..147
                       mol_type = protein
                       organism = Alphatorquevirus sp.
SEQUENCE: 946
KDIYDECIGV NETMKDKYKK LQTTLYTTCT YYQTTQVLAQ LSPAFQPAMK PTTTQSAATA  60
TTLGNYVPEL KYNNGSFHTG QNAVFGMCSY KPTDSIMTKA NGWFWQNLMV DNNLHSSYGK  120
ATLECMEYHT GIYSSIFLSP QRSLEFP                                     147

SEQ ID NO: 947         moltype = AA  length = 161
FEATURE                Location/Qualifiers
source                 1..161
                       mol_type = protein
```

```
                        organism = Alphatorquevirus sp.
SEQUENCE: 947
AAYQDVTYNP NCDRAVGNVV WFQYSTKMDT NFDETKCKCV LKNIPLWAAF NGYSDFIMQE  60
LSISTEIHNF GIVCFQCPYT FPPCFNKNKP LKGYVFYDTT FGNGKMPDGS GHVPIYWQQR  120
WWIRLAFQVQ VMHDFVLTGP FSYKDDLANT TLTARYKFKF K                      161

SEQ ID NO: 948          moltype = AA  length = 187
FEATURE                 Location/Qualifiers
source                  1..187
                        mol_type = protein
                        organism = Alphatorquevirus sp.
SEQUENCE: 948
WGGNIIPEQI IKNPCHREQS LASYPDRQRR DLQVVDPSTM GPIYTFHTWD WRRGLFGADA  60
IQRVSQKPGD ALRFTNPFKR PRYLPPTDRE DYRQEEDFAL QEKRRRTSTE EAQDEESPPE  120
SAPLLQQQQQ QRQLSVHLAE QQRLGVQLRY ILQEVLKTQA GLHLNPLLLG PPQTRSISLS  180
PPKAYSP                                                            187

SEQ ID NO: 949          moltype = AA  length = 21
FEATURE                 Location/Qualifiers
source                  1..21
                        mol_type = protein
                        organism = synthetic construct
VARIANT                 1
                        note = W or F
VARIANT                 2
                        note = Any amino acid
VARIANT                 3
                        note = Any amino acid
VARIANT                 4
                        note = Any amino acid
VARIANT                 5
                        note = Any amino acid
VARIANT                 6
                        note = Any amino acid
VARIANT                 7
                        note = Any amino acid
VARIANT                 8
                        note = Any amino acid
VARIANT                 10
                        note = Any amino acid
VARIANT                 11
                        note = Any amino acid
VARIANT                 12
                        note = Any amino acid
VARIANT                 14
                        note = Any amino acid
VARIANT                 16
                        note = Any amino acid
VARIANT                 17
                        note = Any amino acid
VARIANT                 18
                        note = Any amino acid
VARIANT                 19
                        note = Any amino acid
VARIANT                 20
                        note = Any amino acid
SEQUENCE: 949
XXXXXXXXHX XXCXCXXXXX H                                            21

SEQ ID NO: 950          moltype =   length =
SEQUENCE: 950
000

SEQ ID NO: 951          moltype =   length =
SEQUENCE: 951
000

SEQ ID NO: 952          moltype =   length =
SEQUENCE: 952
000

SEQ ID NO: 953          moltype =   length =
SEQUENCE: 953
000

SEQ ID NO: 954          moltype =   length =
SEQUENCE: 954
000
```

SEQ ID NO: 955 moltype = length =
SEQUENCE: 955
000

SEQ ID NO: 956 moltype = length =
SEQUENCE: 956
000

SEQ ID NO: 957 moltype = length =
SEQUENCE: 957
000

SEQ ID NO: 958 moltype = length =
SEQUENCE: 958
000

SEQ ID NO: 959 moltype = length =
SEQUENCE: 959
000

SEQ ID NO: 960 moltype = length =
SEQUENCE: 960
000

SEQ ID NO: 961 moltype = length =
SEQUENCE: 961
000

SEQ ID NO: 962 moltype = length =
SEQUENCE: 962
000

SEQ ID NO: 963 moltype = length =
SEQUENCE: 963
000

SEQ ID NO: 964 moltype = length =
SEQUENCE: 964
000

SEQ ID NO: 965 moltype = length =
SEQUENCE: 965
000

SEQ ID NO: 966 moltype = length =
SEQUENCE: 966
000

SEQ ID NO: 967 moltype = length =
SEQUENCE: 967
000

SEQ ID NO: 968 moltype = length =
SEQUENCE: 968
000

SEQ ID NO: 969 moltype = length =
SEQUENCE: 969
000

SEQ ID NO: 970 moltype = length =
SEQUENCE: 970
000

SEQ ID NO: 971 moltype = length =
SEQUENCE: 971
000

SEQ ID NO: 972 moltype = length =
SEQUENCE: 972
000

SEQ ID NO: 973 moltype = length =
SEQUENCE: 973
000

SEQ ID NO: 974 moltype = length =
SEQUENCE: 974
000

SEQ ID NO: 975 moltype = length =
SEQUENCE: 975
000

SEQ ID NO: 976 moltype = length =
SEQUENCE: 976
000

SEQ ID NO: 977 moltype = length =
SEQUENCE: 977
000

SEQ ID NO: 978 moltype = length =
SEQUENCE: 978
000

SEQ ID NO: 979 moltype = length =
SEQUENCE: 979
000

SEQ ID NO: 980 moltype = length =
SEQUENCE: 980
000

SEQ ID NO: 981 moltype = length =
SEQUENCE: 981
000

SEQ ID NO: 982 moltype = length =
SEQUENCE: 982
000

SEQ ID NO: 983 moltype = length =
SEQUENCE: 983
000

SEQ ID NO: 984 moltype = length =
SEQUENCE: 984
000

SEQ ID NO: 985 moltype = length =
SEQUENCE: 985
000

SEQ ID NO: 986 moltype = length =
SEQUENCE: 986
000

SEQ ID NO: 987 moltype = length =
SEQUENCE: 987
000

SEQ ID NO: 988 moltype = length =
SEQUENCE: 988
000

SEQ ID NO: 989 moltype = length =
SEQUENCE: 989
000

SEQ ID NO: 990 moltype = length =
SEQUENCE: 990
000

SEQ ID NO: 991 moltype = length =
SEQUENCE: 991
000

SEQ ID NO: 992 moltype = length =
SEQUENCE: 992
000

SEQ ID NO: 993 moltype = length =
SEQUENCE: 993
000

SEQ ID NO: 994 moltype = length =
SEQUENCE: 994

000

SEQ ID NO: 995 moltype = length =
SEQUENCE: 995
000

SEQ ID NO: 996 moltype = length =
SEQUENCE: 996
000

SEQ ID NO: 997 moltype = length =
SEQUENCE: 997
000

SEQ ID NO: 998 moltype = length =
SEQUENCE: 998
000

SEQ ID NO: 999 moltype = length =
SEQUENCE: 999
000

SEQ ID NO: 1000 moltype = length =
SEQUENCE: 1000
000

SEQ ID NO: 1001 moltype = DNA length = 2845
FEATURE Location/Qualifiers
source 1..2845
mol_type = genomic DNA
organism = Betatorquevirus sp.
SEQUENCE: 1001

```
ttattaatat tcaacaggaa aaccacctaa tttaaattgc cgaccacaaa ccgtcactaa  60
cttccttatt taacattact tcccttttaa ccaatgaata ttcatacaac acatcacact  120
tcctgggagg agacataaaa ctatataact aactacacag acgaatggct gagtttatgc  180
cgctagacgg aggacgcaca gctactgctg cgacctgaac ttgggcgggt gccgaaggtg  240
agtgtaacca ccgtagtcaa ggggcaattc gggctagttc agtctagcgg aacgggcaag  300
attattaata caaacttatt tttacagatg agcaaacaac taaaaccaac tttatacaaa  360
gacaaatcat tggaattaca atggctaaac aacattttta gctctcacga cctgtgctgc  420
ggctgcaacg atccagtttt acatttactg attttaatta acaaaaccgg agaagcacct  480
aaaccagaag aagacattaa aaatataaaa tgcctcctta ctggcgccaa aaatactacc  540
gaagaagata tagacctttc tcctggagaa ctagaagaat tattcaaaga agaaaaagat  600
ggagataccg caaaccaaga aaaacatact ggagaagaaa actgcgggta agaaaacgtt  660
tttataaaag aaagttaaaa aaaattgtac ttaaacagtt tcaaccaaaa attattagaa  720
gatgtacaat atttggaaca atctgcctat ttcaaggctc tccagaaaga gccaacaata  780
attatattca aacaatctac tcctacgtac cagataaaga accaggagga gggggatgga  840
ctttaataac tgaaagctta agtagtttat gggaagactg ggaacattta aaaaatgtat  900
ggactcaaag taacgctggt ttaccacttg taagatacgg gggagtaaca ttatactttt  960
atcaatctgc ctatactgac tatattgctc aagttttcaa ctgttatcct atgacagaca  1020
caaaatacac acatgcagac tcagcaccaa acagaatgtt attaaaaaaa catgtaataa  1080
gagtacctag cagagaaaca cgcaaaaaaa gaaagccata caaaagagtt agagtaggac  1140
ctccttctca aatgcaaaac aaatggtact ttcaaagaga catatgtgaa ataccattaa  1200
taatgattgc agccacagcc gttgacttta gatatccctt ttgtgcaagc gactgtgcta  1260
gtaacaactt aactctaaca tgtttaaacc cactattgtt tcaaaaccaa gactttgacc  1320
acccatccga tacacaaggc tactttccaa aacctggagt atatctatac tcaacacaaa  1380
gaagtaacaa gccaagttct tcagactgta tatacttagg aaacacaaaa gacaatcaag  1440
aaggtaaatc tgcaagtagt ctaatgactc taaaaacaca aaaaataaca gattggggaa  1500
atccattttg gcattattat atagacggtt ctaaaaaaat attttcttac tttaaacccc  1560
catcacaatt agacagcagc gactttgaac acatgacaga attagcagaa ccaatgttta  1620
tacaagttag atacaaccca gaaagagaca caggacaagg aaacttaata tacgtaacag  1680
aaaactttag aggacaacac tggaccctc catctagtga caacctaaaa ttagatggat  1740
ttcccttata tgacatgtgc tggggtttca tagactggat agaaaaagtt catgaaacag  1800
aaaacttact taccaactac tgcttctgta ttagaagcag cgctttcaat gaaaaaaaaa  1860
cagtttttat acctgtagat cattcatttt taacaggttt tagcccatat gaaactccag  1920
ttaaatcatc agaccaagct cactggcacc cacaaataag atttcaaaca aaatcaataa  1980
atgacatttg tttaacaggc cccggttgtg ctaggtcccc atatggcaat tacatgcagg  2040
caaaaatgag ttataaattt catgtaaaat ggggaggatg tccaaaaact tatgaaaaac  2100
catatgatcc ttgttcacag cccaattgga ctattcccca taacctcaat gaaacaatac  2160
aaatccagaa tccaaacaca tgcccacaaa cagaactcca agaatgggac tggcgacgtg  2220
atattgttac aaaaaaagct atcgaaagaa ttagacaaca cacggaacct catgaaactt  2280
tgcaaatctc tacaggttcc aaacacaacc caccagtaca cagacaaaca tcaccgtgga  2340
cggactcaga aacggactcg gaagaggaaa aagaccaaac acaagagatc cagatccagc  2400
tcaacaagct cagaaagcat caacagcatc tcaagcagca gctcaagcag tacctgaaac  2460
cccaaaatat agaatagttg caagcaacat aaaagttgaa ctttttccta ctaaaaaacc  2520
ttttaaaaac agacgcttta ctccttctga aagagaaaca gaaagacaat gtgctaaagc  2580
tttttgtaga ccagaaagac atttctttta tgatcctcct ttttaccctt actgtgtacc  2640
tgaacctatt gtaaactttg ctttgggata taaaatttaa ggccaacaaa tttcacttag  2700
tggtgtctgt ttattaaagt ttaaccttaa taagcatact ccgcctccct acattaaggc  2760
gccaaaaggg ggctccgccc ccttaaaccc caagggggct ccgccccctt aaaccccaa  2820
```

```
gggggctccg cccccttaca ccccc                                          2845

SEQ ID NO: 1002          moltype = AA  length = 107
FEATURE                  Location/Qualifiers
source                   1..107
                         mol_type = protein
                         organism = Betatorquevirus sp.
SEQUENCE: 1002
MSKQLKPTLY KDKSLELQWL NNIFSSHDLC CGCNDPVLHL LILINKTGEA PKPEEDIKNI  60
KCLLTGAKNT TEEDIDLSPG ELEELFKEEK DGDTANQEKH TGEENCG                107

SEQ ID NO: 1003          moltype = AA  length = 218
FEATURE                  Location/Qualifiers
source                   1..218
                         mol_type = protein
                         organism = Betatorquevirus sp.
SEQUENCE: 1003
MSKQLKPTLY KDKSLELQWL NNIFSSHDLC CGCNDPVLHL LILINKTGEA PKPEEDIKNI  60
KCLLTGAKNT TEEDIDLSPG ELEELFKEEK DGDTANQEKH TGEENCGPIG LFPITSMKQY  120
KSRIQTHAHK QNSKNGTGDV ILLQKKLSKE LDNTRNLMKL CKSLQVPNTT HQYTDKHHRG  180
RTQKRTRKRK KTKHKRSRSS STSSESINSI SSSSSSST                          218

SEQ ID NO: 1004          moltype = AA  length = 234
FEATURE                  Location/Qualifiers
source                   1..234
                         mol_type = protein
                         organism = Betatorquevirus sp.
SEQUENCE: 1004
MSKQLKPTLY KDKSLELQWL NNIFSSHDLC CGCNDPVLHL LILINKTGEA PKPEEDIKNI  60
KCLLTGAKNT TEEDIDLSPG ELEELFKEEK DGDTANQEKH TGEENCGFQT QPTSTQTNIT  120
VDGLRNGLGR GKRPNTRDPD PAQQAQKAST ASQAAAQAVP ETPKYRIVAS NIKVELFPTK  180
KPFKNRRFTP SERETERQCA KAFCRPERHF FYDPPFYPYC VPEPIVNFAL GYKI        234

SEQ ID NO: 1005          moltype = AA  length = 655
FEATURE                  Location/Qualifiers
source                   1..655
                         mol_type = protein
                         organism = Betatorquevirus sp.
SEQUENCE: 1005
MPPYWRQKYY RRRYRPFSWR TRRIIQRRKR WRYRKPRKTY WRRKLRVRKR FYKRKLKKIV  60
LKQFQPKIIR RCTIFGTICL FQGSPERANN NYIQTIYSYV PDKEPGGGGW TLITESLSSL  120
WEDWEHLKNV WTQSNAGLPL VRYGGVTLYF YQSAYTDYIA QVFNCYPMTD TKYTHADSAP  180
NRMLLKKHVI RVPSRETRKK RKPYKRVRVG PPSQMQNKWY FQRDICEIPL IMIAATAVDF  240
RYPFCASDCA SNNLTLTCLN PLLFQNQDFD HPSDTQGYFP KPGVYLYSTQ RSNKPSSSDC  300
IYLGNTKDNQ EGKSASSLMT LKTQKITDWG NPFWHYYIDG SKKIFSYFKP PSQLDSSDFE  360
HMTELAEPMF IQVRYNPERD TGQGNLIYVT ENFRGQHWDP PSSDNLKLDG FPLYDMCWGF  420
IDWIEKVHET ENLLTNYCFC IRSSAFNEKK TVFIPVDHSF LTGFSPYETP VKSSDQAHWH  480
PQIRFQTKSI NDICLTGPGC ARSPYGNYMQ AKMSYKFHVK WGGCPKTYEK PYDPCSQPNW  540
TIPHNLNETI QIQNPNTCPQ TELQEWDWRR DIVTKKAIER IRQHTEPHET LQISTGSKHN  600
PPVHRQTSPW TDSETDSEEE KDQTQEIQIQ LNKLRKHQQH LKQQLKQYLK PQNIE        655

SEQ ID NO: 1006          moltype = AA  length = 164
FEATURE                  Location/Qualifiers
source                   1..164
                         mol_type = protein
                         organism = Betatorquevirus sp.
SEQUENCE: 1006
MPPYWRQKYY RRRYRPFSWR TRRIIQRRKR WRYRKPRKTY WRRKLRPNWT IPHNLNETIQ  60
IQNPNTCPQT ELQEWDWRRD IVTKKAIERI RQHTEPHETL QISTGSKHNP PVHRQTSPWT  120
DSETDSEEEK DQTQEIQIQL NKLRKHQQHL KQQLKQYLKP QNIE                  164

SEQ ID NO: 1007          moltype = AA  length = 99
FEATURE                  Location/Qualifiers
source                   1..99
                         mol_type = protein
                         organism = Betatorquevirus sp.
SEQUENCE: 1007
MPPYWRQKYY RRRYRPFSWR TRRIIQRRKR WRYRKPRKTY WRRKLRVPNT THQYTDKHHR  60
GRTQKRTRKR KKTKHKRSRS SSTSSESINS ISSSSSSST                         99

SEQ ID NO: 1008          moltype = DNA  length = 2912
FEATURE                  Location/Qualifiers
source                   1..2912
                         mol_type = genomic DNA
                         organism = Betatorquevirus sp.
SEQUENCE: 1008
taataaatat tcaacaggaa aaccacctaa tttaaattgc cgaccacaaa ccgtcactta  60
gttcctcttt ttccacaact tcctctttta ctaatgaata ttcatgtaat taattaataa  120
tcaccgtaat tccggggagg agcctttaaa ctataaaact aactacacat tcgaatggct  180
```

```
gagtttatgc cgccagacgg agacgggatc acttcagtga ctccaggctg atcaagggcg  240
ggtgccgaag gtgagtgaaa ccaccgtagt caaggggcaa ttcgggctag atcagtctgg  300
cggaacgggc aagaaactta aaatgtactt tattttacag aaatgttcaa atctccaaca  360
tacttaacaa ctaaaggcaa aaacaatgcc ttaatcaact gcttcgttgg agaccacgat  420
cttctgtgca gctgtaacaa tcctgcctac cattgcctcc aaatacttgc aactacctta  480
gcacctcaac taaaacaaga agaaaaacaa caaataatac aatgccttgg tggtacagac  540
gccgtagcta caacccgtgg agacgaagaa attggtttag aagacctaga aaaactattt  600
acagaagata cagaagaaga cgccgctggg taagaagaaa accttttac aaacgtaaaa  660
ttaagagact aaatatagta gaatggcaac ctaaatcaat tagaaaatgt agaataaaag  720
gaatgctatg cttgtttcaa acgacagaag acagactgtc atataacttt gatatgtatg  780
aagagtctat tataccagaa aaactgccgg gaggggggg atttagcatt aagaatataa  840
gcttatatgc cttataccaa gaacacatac atgcacacaa catatttaca cacacaaaca  900
cagacagacc actagcaaga tacacaggct gttctttaaa attctaccaa agcaaagaca  960
tagactacgt agtaacatat tctacatcac tcccactaag aagctcaatg ggaatgtaca  1020
actccatgca accatccata catctaatgc aacaaaacaa actaattgta ccaagcaaac  1080
aaacacaaaa aagaagaaaa ccatatatta aaaaacatat atcaccacca acacaaatga  1140
aatctcaatg gtactttcaa cataacattg caaacatacc gctactaatg ataagaacca  1200
cagcattaac attagataat tactatatag gaagcagaca attaagtaca aatgtcacta  1260
tacatacact taacacaaca tacatccaaa acagagactg gggagacaga aataaaactt  1320
actactgcca aacattagga acacaaagat acttcctata tggaacacat tcaactgcac  1380
aaaatattaa tgacataaag ctacaagaac taataccttt aacaaacaca caagactatg  1440
tacaaggctt tgattggaca gaaaaagaca aacataacat aacaacctac aaagaattct  1500
taactaaagg agcaggaaat ccatttcacg cagaatggat aacagcacaa aacccagtaa  1560
tacacacagc aaacagtcct acacaaatag aacaaatata caccgcttca acaacaacat  1620
tccaaaacaa aaaactaaca gacctaccaa cgccaggata tatatttata actccaacag  1680
taagcttaag atacaaccca tacaaagacc tagcagaaag aaacaaatgc tactttgtaa  1740
gaagcaaaat aaatgcacac gggtgggacc cagaacaaca ccaagaatta ataaacagtg  1800
acctaccaca atggttacta ttatttggct acccagacta cataaaaaga acacaaaact  1860
ttgcattagt agacacaaat tacatactag tagaccactg cccatacaca aatccagaaa  1920
aaacaccatt tataccttta agcacatcat ttatagaagg tagaagccca tacagtcctt  1980
cagacacaca tgaaccagat gaagaagacc aaaacaggtg gtacccatgc taccaatatc  2040
aacaagaatc aataaattca atatgtctta gcggtccagg cacaccaaaa ataccaaaag  2100
gaataacagc agaagcaaaa gtaaaatatt cctttaattt taagtggggt ggtgacctac  2160
caccaatgtc tacaattaca aacccgacag accagccaac atatgttgtt cccaataact  2220
tcaatgaaac aacttcgtta cagaatccaa ccaccagacc agagcacttc ttgtactcct  2280
ttgacgaaag gaggggacaa cttacagaaa aagctacaaa acgcttgctt aaagactggg  2340
aaactaaaga aacttcttta ttgtctacag aatacagatt cgcggagcca acacaaacac  2400
aagcccccaca agaggacccg tcctcggaag aagaagaaga gagcaacctc ttcgagcgac  2460
tcctccgaca gcgaaccaag cagctccagc tcaagcgcag aataatacaa acattgaaag  2520
acctacaaaa attagaataa ctaacagcaa aaacaccgtt tacctatttc cacctgaaca  2580
aaagaacaga agactaacac catgggaaat acaagaagac aaagaaatag ccaatttatt  2640
tggcagacca catagatact ttttaaaaga cattcctttc tattgggata tacccccaga  2700
gcctaaagta aactttgatt taaattttca ataaagaaat aaagggcaag gccccattaa  2760
ctcaaagtcg gtgtctacct ctttaagttt aactttacta aacggactcc gcctccctaa  2820
atttgggcgc caaaaggggg ctccgccccc ttaaaccccca gggggctccg ccccctaaaa  2880
cccccaaggg ggctacgccc ccttacaccc cc                                2912

SEQ ID NO: 1009        moltype = AA  length = 96
FEATURE                Location/Qualifiers
source                 1..96
                       mol_type = protein
                       organism = Betatorquevirus sp.
SEQUENCE: 1009
MFKSPTYLTT KGKNNALINC FVGDHDLLCS CNNPAYHCLQ ILATTLAPQL KQEEKQQIIQ  60
CLGGTDAVAT TRGDEEIGLE DLEKLFTEDT EEDAAG                            96

SEQ ID NO: 1010        moltype = AA  length = 198
FEATURE                Location/Qualifiers
source                 1..198
                       mol_type = protein
                       organism = Betatorquevirus sp.
SEQUENCE: 1010
MFKSPTYLTT KGKNNALINC FVGDHDLLCS CNNPAYHCLQ ILATTLAPQL KQEEKQQIIQ  60
CLGGTDAVAT TRGDEEIGLE DLEKLFTEDT EEDAAGQHML FPITSMKQLR YRIQPPDQST  120
SCTPLTKGGD NLQKKLQNAC LKTGKLKKLL YCLQNTDSRS QHKHKPHKRT RPRKKKKRAT  180
SSSDSSDSEP SSSSSSAE                                                198

SEQ ID NO: 1011        moltype = AA  length = 216
FEATURE                Location/Qualifiers
source                 1..216
                       mol_type = protein
                       organism = Betatorquevirus sp.
SEQUENCE: 1011
MFKSPTYLTT KGKNNALINC FVGDHDLLCS CNNPAYHCLQ ILATTLAPQL KQEEKQQIIQ  60
CLGGTDAVAT TRGDEEIGLE DLEKLFTEDT EEDAAGIQIR GANTNTSPTR GPVLGRRRRE  120
QPLRATPPTA NQAAPAQAQN NTNIERPTKI RITNSKNTVY LFPPEQKNRR LTPWEIQEDK  180
EIANLFGRPH RYFLKDIPFY WDIPPEPKVN FDLNFQ                            216

SEQ ID NO: 1012        moltype = AA  length = 672
```

```
FEATURE                Location/Qualifiers
source                 1..672
                       mol_type = protein
                       organism = Betatorquevirus sp.
SEQUENCE: 1012
MPWWYRRRSY NPWRRRNWFR RPRKTIYRRY RRRRRWVRRK PFYKRKIKRL NIVEWQPKSI  60
RKCRIKGMLC LFQTTEDRLS YNFDMYEESI IPEKLPGGGG FSIKNISLYA LYQEHIHAHN  120
IFTHTNTDRP LARYTGCSLK FYQSKDIDYV VTYSTSLPLR SSMGMYNSMQ PSIHLMQQNK  180
LIVPSKQTQK RRKPYIKKHI SPPTQMKSQW YFQHNIANIP LLMIRTTALT LDNYYIGSRQ  240
LSTNVTIHTL NTTYIQNRDW GDRNKTYYCQ TLGTQRYFLY GTHSTAQNIN DIKLQELIPL  300
TNTQDYVQGF DWTEKDKHNI TTYKEFLTKG AGNPFHAEWI TAQNPVIHTA NSPTQIEQIY  360
TASTTTFQNK KLTDLPTPGY IFITPTVSLR YNPYKDLAER NKCYFVRSKI NAHGWDPEQH  420
QELINSDLPQ WLLLFGYPDY IKRTQNFALV DTNYILVDHC PYTNPEKTPF IPLSTSFIEG  480
RSPYSPSDTH EPDEEDQNRW YPCYQYQQES INSICLSGPG TPKIPKGITA EAKVKYSFNF  540
KWGGDLPPMS TITNPTDQPT YVVPNNFNET TSLQNPTTRP EHFLYSFDER RGQLTEKATK  600
RLLKDWETKE TSLLSTEYRF AEPTQTQAPQ EDPSSEEEEE SNLFERLLRQ RTKQLQLKRR  660
IIQTLKDLQK LE                                                    672

SEQ ID NO: 1013        moltype = AA  length = 80
FEATURE                Location/Qualifiers
source                 1..80
                       mol_type = protein
                       organism = Betatorquevirus sp.
SEQUENCE: 1013
MPWWYRRRSY NPWRRRNWFR RPRKTIYRRY RRRRRWNTDS RSQHKHKPHK RTRPRKKKKR  60
ATSSSDSSDS EPSSSSSSAE                                            80

SEQ ID NO: 1014        moltype = DNA  length = 3853
FEATURE                Location/Qualifiers
source                 1..3853
                       mol_type = genomic DNA
                       organism = Alphatorquevirus sp.
SEQUENCE: 1014
ggcttagtgc gtcaccaccc acgtgacccg cctccgccaa ttaacaggta cttcgtacac  60
ttcctgggcg ggcttataag actaatataa gtagctgcac ttccgaatgg ctgagttttc  120
cacgcccgtc cgcagcggtg aagccacgga gggagctcag cgcgtcccga gggcgggtgc  180
cggaggtgag tttacacacc gcagtcaagg ggcaattcgg gctcgggact ggccgggctt  240
tgggcaaggc tcttaaaaaa gctatgttta ttggcaggca ctaccgaaag aaaagggcgc  300
tgctactgct atctgtgcat tctacaaaga caaaagggaa acttctaata gctatgtgga  360
ctcccccacg caatgatcaa caatacctta actggcaatg gtacacttct gtacttagct  420
cccactctgc tatgtgcggg tgttccgacg ctatcgctca tcttaatcat cttgctaatc  480
tgcttcgtgc cccgcaaaat ccgccccccgc ctgataatcc aagaccccta cccgtgcgag  540
cactgcctgc tcccccggct gcccacgagg cagccggtga tcgagcacca tggcctatgg  600
gtggtggagg agacgccgga ggcgctggcg caggtggaga cgccgaccat ggaggcgccg  660
ctggaggacc cgcagacgca gacctgctag acgccgtggc cgccgcagaa acgtaaggag  720
acggcgcaga gggaggtgga gaaggaggta caggaggtgg aaaagaaagg gcagacgtag  780
aagaaaagca aaaataataa taagacagtg gcagccaaac tacagaagaa gatgtaatat  840
agtgggctac ctccctatac ttatctgtgg tggaaatact gtttctagaa actatgccac  900
acactcagac gatactaact atccaggacc ctttgggggga ggcatgacca cagacaaatt  960
cagccttaga atactatatg atgaatacaa aagatttatg aactactgga cagcctcaaa  1020
tgaggaccta gatctctgta gatatctagg atgcactttt tacttcttta gacaccctga  1080
agtagacttt attataaaaa taaacaccat gcccccattc ttagatacaa ccataacagc  1140
acctagcata cacccaggcc tcatggccct agacaaaaga gccagatgga ttccttctct  1200
taaaaataga ccaggtaaaa aacactatat aaaaattaga gtaggggctc ctaaaatgtt  1260
cacagataaa tggtaccctc aaacagacct ctgtgacatg acactgctaa ctatctatgc  1320
aaccgcagcg gatatgcaat atccgttcgg ctcaccacta actgacactg tggttgttaa  1380
ctcccaagtt ctgcaatcca tgtatgatga aacaattagc atattacctg atgaaaaaac  1440
taaaagaaat agccttctta cttctataag aagctacata cctttttata atactacaca  1500
aacaatagct caattaaaac catttgtaga tgcaggagga cacacaacag gctcaacaac  1560
aactacatgg ggacaactat taaacacaac taaatttacc actaccacaa caaccacata  1620
cacataccct ggcaccacaa atacagcagt aacatttata acagccaatg atacctggta  1680
caggggaaca gcatataaag ataacattaa agatgtacca caaaaagcag cacaattata  1740
ctttcaaaca acacaaaaac tactaggaaa cacattccat ggctcagatg aaacacttga  1800
ataccatgca ggcctataca gctctatctg gctatcacca ggtagatcct actttgaaac  1860
accaggtgca tacacagaca ttaaatataa ccctttttaca gacagaggag aaggcaacat  1920
gctgtggata gactggctaa gtaaaaaaaa catgaaatat gacaaagtgc aaagtaagtg  1980
cctagtagca gacctaccac tgtgggcagc agcatatggt tatgtagaat tctgctctaa  2040
aagcacagga gacacaaaca tacacatgaa tgccagacta ctaataagaa gtcctttttac  2100
agacccccag ctaatagtac acacagaccc cactaaaggc tttgtaccct attctttaaa  2160
ctttggaaat ggtaaaatgc caggaggtag cagcaatgtt cccataagaa tgagagctaa  2220
gtggtacccc actttatccc accaacaaga agttctagag gccttagcac agtcaggacc  2280
ctttgcttat cactcagaca ttaaaaaagt atctctaggc ataaaatacc gttttaagtg  2340
gatctggggt ggaaaccccg ttcgccaaca ggttgttaga aatccctgca aggaacccca  2400
ctcctcgggc aatagagtcc ctagaagcat acaaatcgtt gacccgagat acaactcacc  2460
ggaacttacc atccatgcct gggacttcag acgtggcttc tttggcccga aagctattca  2520
aagaatgcaa caacaaccaa ctgctactga atttttttca gcaggccgca agagacccag  2580
aagggacaca gaagtgtatc agtccgacca agaaaaggag caaaaagaaa gctcgctttt  2640
ccccccagtc aagctcctcc gaagagtccc cccgtgggag gactcggaac aggagcaaag  2700
cgggtcgcaa agctcagagg aagagacggc gaccctctcc cagcagctca aacagcagct  2760
```

```
gcagcagcag cgagtcttgg gagtcaaact cagactcctg ttcaaccaag tccaaaaaat  2820
ccaacaaaat caagatatca accctacctt gttaccaagg ggggggggatc tagtatcctt  2880
ctttcaggct gtaccataaa tatgtttcca gaccctaaac cttactgccc ctccagcaat  2940
gactggaaag aagagtatga ggcctgtaaa tattgggata gacctcccag acacaacctt  3000
agagaccccc ccttttaccc ctgggcccct aaaaacaatc cttgcaatgt aagctttaaa  3060
cttggcttca aataaactag gccgtgggag tttcacttgt cggtgtctac ctctataagt  3120
cactaagcac tccgagcgca gcgaggagtg cgacccttcc ccctggtgca acgccctcgg  3180
cggccgcgcg ctacgccttc ggctgcgcgc ggcacctcgg acccccgctc gtgctgacac  3240
gcttgcgcgt gtcagaccac ttcgggctcg cgggggtcgg gaaatttgct aaacagactc  3300
cgagttgcca ttggacactg tagctatgaa tcagtaacga aagtgagtgg ggccagactt  3360
cgccataagg cctttatctt cttgccattt gtcagtattg gggtcgcca taaactttgg  3420
gctccatttt aggccttccg gactacaaaa atcgccatat ttgtgacgtc agagccgcca  3480
ttttaagtca gctctgggga ggcgtgactt ccagttcaaa ggtcatcctc accataactg  3540
gcacaaaatg gccgccaact tcttccgggt caaaggtcac tgctacgtca taggtgacgt  3600
gggggggac ctacttaaac acggaagtag gccccgacac gtcactgtca cgtgacagta  3660
cgtcacagcc gccattttgt tttacaaaat agccgacttc cttcctcttt tttaaaaaaa  3720
ggcgccaaaa aaccgtcggc gggggggccg cgcgctgcgc gcgcggcccc cgggggaggc  3780
acagcctccc ccccccgcgc gcatgcgcgc gggtcccccc ccctccgggg ggctccgccc  3840
cccggccccc ccc                                                     3853
```

```
SEQ ID NO: 1015        moltype = AA  length = 120
FEATURE                Location/Qualifiers
source                 1..120
                       mol_type = protein
                       organism = Alphatorquevirus sp.
SEQUENCE: 1015
MWTPPRNDQQ YLNWQWYTSV LSSHSAMCGC SDAIAHLNHL ANLLRAPQNP PPPDNPRPLP  60
VRALPAPPAA HEAAGDRAPW PMGGGGDAGG AGAGGDADHG GAAGGPADAD LLDAVAAAET  120

SEQ ID NO: 1016        moltype = AA  length = 286
FEATURE                Location/Qualifiers
source                 1..286
                       mol_type = protein
                       organism = Alphatorquevirus sp.
SEQUENCE: 1016
MWTPPRNDQQ YLNWQWYTSV LSSHSAMCGC SDAIAHLNHL ANLLRAPQNP PPPDNPRPLP  60
VRALPAPPAA HEAAGDRAPW PMGGGGDAGG AGAGGDADHG GAAGGPADAD LLDAVAAAET  120
LLEIPARNPT PRAIESLEAY KSLTRDTTHR NLPSMPGTSD VASLARKLFK ECNNNQLLLN  180
FFQQAARDPE GTQKCISPTK KRSKKKARFS PQSSSSEESP RGRTRNRSKA GRKAQRKRRR  240
PSPSSSNSSC SSSESWESNS DSCSTKSKKS NKIKISTLPC YQGGGI                 286

SEQ ID NO: 1017        moltype = AA  length = 289
FEATURE                Location/Qualifiers
source                 1..289
                       mol_type = protein
                       organism = Alphatorquevirus sp.
SEQUENCE: 1017
MWTPPRNDQQ YLNWQWYTSV LSSHSAMCGC SDAIAHLNHL ANLLRAPQNP PPPDNPRPLP  60
VRALPAPPAA HEAAGDRAPW PMGGGGDAGG AGAGGDADHG GAAGGPADAD LLDAVAAAET  120
PQETQKGHRS VSVRPRKGAK RKLAFPPSQA PPKSPPVGGL GTGAKRVAKL RGRDGDPLPA  180
AQTAAAAAAS LGSQTQTPVQ PSPKNPTKSR YQPYLVTKGG GSSILLSGCT INMFPDPKPY  240
CPSSNDWKEE YEACKYWDRP PRHNLRDPPF YPWAPKNNPC NVSFKLGFK              289

SEQ ID NO: 1018        moltype = AA  length = 185
FEATURE                Location/Qualifiers
source                 1..185
                       mol_type = protein
                       organism = Alphatorquevirus sp.
SEQUENCE: 1018
MWTPPRNDQQ YLNWQWPQET QKGHRSVSVR PRKGAKRKLA FPPSQAPPKS PPVGGLGTGA  60
KRVAKLRGRD GDPLPAAQTA AAAAASLGSQ TQTPVQPSPK NPTKSRYQPY LVTKGGGSSI  120
LLSGCTINMF PDPKPYCPSS NDWKEEYEAC KYWDRPPRHN LRDPPFYPWA PKNNPCNVSF  180
KLGFK                                                              185

SEQ ID NO: 1019        moltype = AA  length = 105
FEATURE                Location/Qualifiers
source                 1..105
                       mol_type = protein
                       organism = Alphatorquevirus sp.
SEQUENCE: 1019
MINNTLTGNG TLLYLAPTLL CAGVPTLSLI LIILLICFVP RKIRPRLIIQ DPYPCEHCLL  60
PRLPTRQPVI EHHGLWVVEE TPEALAQVET PTMEAPLEDP QTQTC                  105

SEQ ID NO: 1020        moltype = AA  length = 769
FEATURE                Location/Qualifiers
source                 1..769
                       mol_type = protein
                       organism = Alphatorquevirus sp.
SEQUENCE: 1020
```

```
MAYGWWRRRR RRWRRWRRRP WRRRWRTRRR RPARRRGRRR NVRRRRRGRW RRRYRRWKRK  60
GRRRRKAKII IRQWQPNYRR RCNIVGYLPI LICGGNTVSR NYATHSDDTN YPGPFGGGMT  120
TDKFSLRILY DEYKRFMNYW TASNEDLDLC RYLGCTFYFF RHPEVDFIIK INTMPPFLDT  180
TITAPSIHPG LMALDKRARW IPSLKNRPGK KHYIKIRVGA PKMFTDKWYP QTDLCDMTLL  240
TIYATAADMQ YPFGSPLTDT VVVNSQVLQS MYDETISILP DEKTKRNSLL TSIRSYIPFY  300
NTTQTIAQLK PFVDAGGHTT GSTTTTWGQL LNTTKFTTTT TTTYTYPGTT NTAVTFITAN  360
DTWYRGTAYK DNIKDVPQKA AQLYFQTTQK LLGNTFHGSD ETLEYHAGLY SSIWLSPGRS  420
YFETPGAYTD IKYNPFTDRG EGNMLWIDWL SKKNMKYDKV QSKCLVADLP LWAAAYGYVE  480
FCSKSTGDTN IHMNARLLIR SPFTDPQLIV HTDPTKGFVP YSLNFGNGKM PGGSSNVPIR  540
MRAKWYPTLS HQQEVLEALA QSGPFAYHSD IKKVSLGIKY RFKWIWGGNP VRQQVVRNPC  600
KEPHSSGNRV PRSIQIVDPR YNSPELTIHA WDFRRGFFGP KAIQRMQQQP TATEFFSAGR  660
KRPRRDTEVY QSDQEKEQKE SSLFPPVKLL RRVPPWEDSE QEQSGSQSSE EETATLSQQL  720
KQQLQQQRVL GVKLRLLFNQ VQKIQQNQDI NPTLLPRGGD LVSFFQAVP              769

SEQ ID NO: 1021        moltype = AA  length = 216
FEATURE                Location/Qualifiers
source                 1..216
                       mol_type = protein
                       organism = Alphatorquevirus sp.
SEQUENCE: 1021
MAYGWWRRRR RRWRRWRRRP WRRRWRTRRR RPARRRGRRR NVVRNPCKEP HSSGNRVPRS  60
IQIVDPRYNS PELTIHAWDF RRGFFGPKAI QRMQQQPTAT EFFSAGRKRP RRDTEVYQSD  120
QEKEQKESSL FPPVKLLRRV PPWEDSEQEQ SGSQSSEEET ATLSQQLKQQ LQQQRVLGVK  180
LRLLFNQVQK IQQNQDINPT LLPRGGDLVS FFQAVP                            216

SEQ ID NO: 1022        moltype = AA  length = 143
FEATURE                Location/Qualifiers
source                 1..143
                       mol_type = protein
                       organism = Alphatorquevirus sp.
SEQUENCE: 1022
MAYGWWRRRR RRWRRWRRRP WRRRWRTRRR RPARRRGRRR NAARDPEGTQ KCISPTKKRS  60
KKKARFSPQS SSSEESPRGR TRNRSKAGRK AQRKRRRPSP SSSNSSCSSS ESWESNSDSC  120
STKSKKSNKI KISTLPCYQG GGI                                          143

SEQ ID NO: 1023        moltype = AA  length = 228
FEATURE                Location/Qualifiers
source                 1..228
                       mol_type = protein
                       organism = Betatorquevirus sp.
SEQUENCE: 1023
MPWWYRRRSY NPWRRRNWFR RPRKTIYRRY RRRRRWVRRK PFYKRKIKRL NIVEWQPKSI  60
RKCRIKGMLC LFQTTEDRLS YNFDMYEESI IPEKLPGGGG FSIKNISLYA LYQEHIHAHN  120
IFTHTNTDRP LARYTGCSLK FYQSKDIDYV VTYSTSLPLR SSMGMYNSMQ PSIHLMQQNK  180
LIVPSKQTQK RRKPYIKKHI SPPTQMKSQW YFQHNIANIP LLMIRTTA                228

SEQ ID NO: 1024        moltype = AA  length = 222
FEATURE                Location/Qualifiers
source                 1..222
                       mol_type = protein
                       organism = Betatorquevirus sp.
SEQUENCE: 1024
MPYYYRRRRY NYRRPRWYGR GWIRRPFRRR FRRKRRVRPT YTTIPLKQWQ PPYKRTCYIK  60
GQDCLIYYSN LRLGMNSTMY EKSIVPVHWP GGGSFSVSML TLDALYDIHK LCRNWWTSTN  120
QDLPLVRYKG CKITFYQSTF TDYIVRIHTE LPANSNKLTY PNTHPLMMMM SKYKHIIPSR  180
QTRRKKKPYT KIFVKPPPQF ENKWYFATDL YKIPLLQIHC TA                      222

SEQ ID NO: 1025        moltype = AA  length = 238
FEATURE                Location/Qualifiers
source                 1..238
                       mol_type = protein
                       organism = Gammatorquevirus sp.
SEQUENCE: 1025
MPFWWRRRRK FWTNNRFNYT KRRRYRKRWP RRRRRRRPYR RPIRRRRRKL RKVKRKKKSL  60
IVRQWQPDSI RTCKIIGQSA IVVGAEGKQM YCYTVNKLIN VPPKTPYGGG FGVDQYTLKY  120
LYEEYRFAQN IWTQSNVLKD LCRYINVKLI FYRDNKTDFV LSYDRNPPFQ LTKFTYPGAH  180
PQQIMLQKHH KFILSQMTKP NGRLTKKLKI KPPKQMLSKW FFSKQFCKYP LLSLKASA    238

SEQ ID NO: 1026        moltype = AA  length = 246
FEATURE                Location/Qualifiers
source                 1..246
                       mol_type = protein
                       organism = Alphatorquevirus sp.
SEQUENCE: 1026
MAYGWWRRRR RRWRRWRRRP WRRRWRTRRR RPARRRGRRR NVRRRRRGRW RRRYRRWKRK  60
GRRRRKAKII IRQWQPNYRR RCNIVGYLPI LICGGNTVSR NYATHSDDTN YPGPFGGGMT  120
TDKFSLRILY DEYKRFMNYW TASNEDLDLC RYLGCTFYFF RHPEVDFIIK INTMPPFLDT  180
TITAPSIHPG LMALDKRARW IPSLKNRPGK KHYIKIRVGA PKMFTDKWYP QTDLCDMTLL  240
TIYATA                                                              246
```

```
SEQ ID NO: 1027        moltype = AA  length = 142
FEATURE                Location/Qualifiers
source                 1..142
                       mol_type = protein
                       organism = Betatorquevirus sp.
SEQUENCE: 1027
EAKVKYSFNF KWGGDLPPMS TITNPTDQPT YVVPNNFNET TSLQNPTTRP EHFLYSFDER  60
RGQLTEKATK RLLKDWETKE TSLLSTEYRF AEPTQTQAPQ EDPSSEEEEE SNLFERLLRQ  120
RTKQLQLKRR IIQTLKDLQK LE                                           142

SEQ ID NO: 1028        moltype = AA  length = 140
FEATURE                Location/Qualifiers
source                 1..140
                       mol_type = protein
                       organism = Betatorquevirus sp.
SEQUENCE: 1028
NISMFYKFYF KWGGSPPKAI NVENPAHQIQ YPIPRNEHET TSLQSPGEAP ESILYSFDYR  60
HGNYTTTALS RISQDWALKD TVSKITEPDR QQLLKQALEC LQISEETQEK KEKEVQQLIS  120
NLRQQQQLYR ERIISLLKDQ                                              140

SEQ ID NO: 1029        moltype = AA  length = 176
FEATURE                Location/Qualifiers
source                 1..176
                       mol_type = protein
                       organism = Gammatorquevirus sp.
SEQUENCE: 1029
NWELKYKYIF TFKWGGPQFH EPEIADPSKQ EQYDVPDTFY QTIQIEDPEG QDPRSLIHDW  60
DYRRGFVKER SLKRMSTYFS THTDQQATSE EDIPKKKKRI GPQLTVPQQK EEETLSCLLS  120
LCKKDTFQET ETQEDLQQLI KQQQEQQLLL KRNILQLIHK LKENQQMLQL HTGMLP      176

SEQ ID NO: 1030        moltype = AA  length = 195
FEATURE                Location/Qualifiers
source                 1..195
                       mol_type = protein
                       organism = Alphatorquevirus sp.
SEQUENCE: 1030
SLGIKYRFKW IWGGNPVRQQ VVRNPCKEPH SSGNRVPRSI QIVDPRYNSP ELTIHAWDFR  60
RGFFGPKAIQ RMQQQPTATE FFSAGRKRPR RDTEVYQSDQ EKEQKESSLF PPVKLLRRVP  120
PWEDSEQEQS GSQSSEEETA TLSQQLKQQL QQQRVLGVKL RLLFNQVQKI QQNQDINPTL  180
LPRGGDLVSF FQAVP                                                   195

SEQ ID NO: 1031        moltype = AA  length = 301
FEATURE                Location/Qualifiers
source                 1..301
                       mol_type = protein
                       organism = Betatorquevirus sp.
SEQUENCE: 1031
TLDNYYIGSR QLSTNVTIHT LNTTYIQNRD WGDRNKTYYC QTLGTQRYFL YGTHSTAQNI  60
NDIKLQELIP LTNTQDYVQG FDWTEKDKHN ITTYKEFLTK GAGNPFHAEW ITAQNPVIHT  120
ANSPTQIEQI YTASTTTFQN KKLTDLPTPG YIFITPTVSL RYNPYKDLAE RNKCYFVRSK  180
INAHGWDPEQ HQELINSDLP QWLLLFGYPD YIKRTQNFAL VDTNYILVDH CPYTNPEKTP  240
FIPLSTSFIE GRSPYSPSDT HEPDEEDQNR WYPCYQYQQE SINSICLSGP GTPKIPKGIT  300
A                                                                  301

SEQ ID NO: 1032        moltype = AA  length = 303
FEATURE                Location/Qualifiers
source                 1..303
                       mol_type = protein
                       organism = Betatorquevirus sp.
SEQUENCE: 1032
NLQNPFVKPD KLSNNVTLWS LNTISIQNRN MSVDQGQSWP FKILGTQSFY FYFYTGANLP  60
GDTTQIPVAD LLPLTNPRIN RPGQSLNEAK ITDHITFTEY KNKFTNYWGN PFNKHIQEHL  120
DMILYSLKSP EAIKNEWTIE NMKWNQLNNA GTMALTPFNE PIFTQIQYNP DRDTGEDTQL  180
YLLSNATGTG WDPPGIPELI LEGFPLWLIY WGFADFQKNL KKVTNIDTNY MLVAKTKFTQ  240
KPGTFYLVIL NDTFVEGNSP YEKQPLPEDN IKWYPQVQYQ LEAQNKLLQT GPFTPNIQGQ  300
LSD                                                                303

SEQ ID NO: 1033        moltype = AA  length = 247
FEATURE                Location/Qualifiers
source                 1..247
                       mol_type = protein
                       organism = Gammatorquevirus sp.
SEQUENCE: 1033
DLRHSYLGCC NENPQVFFYY LNHGYYIQTN WGAQSTTAYR PNSSVTETTY YKYKNEKKNI  60
NIKSSEYSES ISYDKGYFQS SFLQTQCIYT SAAGDTCAAE KPLGIAIYNP VKDNGDGNMI  120
YLVSTLANTW DQPPKDSAIL IQGVPIWLGL FGYLDYCRQI KADKTWLDSH ILVMQSPAIF  180
TYPNPGAGKW YCPLSQSFIN GNGPFNQPPT LLQKAKWFPQ IQYQQEIINS FVESGPFVPK  240
YANQTES                                                            247
```

```
SEQ ID NO: 1034        moltype = AA  length = 327
FEATURE                Location/Qualifiers
source                 1..327
                       mol_type = protein
                       organism = Alphatorquevirus sp.
SEQUENCE: 1034
DMQYPFGSPL TDTVVVNSQV LQSMYDETIS ILPDEKTKRN SLLTSIRSYI PFYNTTQTIA  60
QLKPFVDAGG HTTGSTTTTW GQLLNTTKFT TTTTTYTYP GTTNTAVTFI TANDTWYRGT  120
AYKDNIKDVP QKAAQLYFQT TQKLLGNTFH GSDETLEYHA GLYSSIWLSP GRSYFETPGA  180
YTDIKYNPFT DRGEGNMLWI DWLSKKNMKY DKVQSKCLVA DLPLWAAAYG YVEFCSKSTG  240
DTNIHMNARL LIRSPFTDPQ LIVHTDPTKG FVPYSLNFGN GKMPGGSSNV PIRMRAKWYP  300
TLSHQQEVLE ALAQSGPFAY HSDIKKV                                    327

SEQ ID NO: 1035        moltype = AA  length = 664
FEATURE                Location/Qualifiers
source                 1..664
                       mol_type = protein
                       organism = Betatorquevirus sp.
SEQUENCE: 1035
MPPFRRNWWS NYYKPKWRRR RFPARRRRFT TTFRKRRRRT KKVKRHFYSK KYKRKLKKII  60
LRQWQPSTIK RCKIEGYLCL FQAGKGRFSF NYASYKESFC PEHEPGGGGW GLQQLSLSNL  120
YSQNCDLMNW WTKSNNHLNL CRYMGCEITL FRQDTVDYVF TYFDEQPKNV SKYYYATFHP  180
TKLMLYNRKI VVPSFASQPH KRKPYKRKFI RAPKLMKNQW YFQQQLAPYP LLQFAATAVS  240
LNKMFGSSKA LNNNCTVYCL NTDFFRHPHF QYSAQPFTPD GGNQPTYIYT IQRGEPPITA  300
YKYFNLTFLG QTMTNDPGIP LSNNNNYTKN EWGNVFFYKY LNNDELTYVS KETIDQVKQK  360
KNQQITSGFT LKDQPYYYTL KYNPYKDKGK GNQAYWVSNI EATKQNWEPP NDPDLIISDF  420
PFWIMLWGWE DMTKRIGKCR NLDNDWILVL RTQYFSDKMT AYVPLSEAFI HGQGPYFVDR  480
SEIKGQDYAH WYPRYRYQRE AIENILMTGP MVCRADNINN IQSLIKYKFF FKWGGTPATM  540
ENVYDPMSQP ITPSPNNLIS TNEIINPETS IDNYIYKWDT RRDILTQKAT DRITKSSTYD  600
SNVFTDGRET STDIPLFQTT QKAPQEETPE TQAETLLLQL HQLQQFNLQL QQRFNNLKQL  660
MQNI                                                             664

SEQ ID NO: 1036        moltype = AA  length = 656
FEATURE                Location/Qualifiers
source                 1..656
                       mol_type = protein
                       organism = Betatorquevirus sp.
SEQUENCE: 1036
MPWYNYWPRR RRLRRYWRRP RKTLRRRYWR RPRWVRRPYK RKLRKIVLTQ FQPKTIRKSK  60
IKGPICLFQT TNKRLVNNFD MYETSEVPEH QPGGGGWGIK VFTLEGLYSE HIYGRNIWTV  120
TNQDLPLVRY LGCSIRFYQS EYTDYVATYS NQLPLQSSLG MYNAMQPNIH LLLKNKITMP  180
GLKTYKRRVP YKKVFVPPPT QLENKWYFQQ NIAKTPLLMT RVTACSLNKF YIDPDHINTN  240
LTITSLNVSL FSNRQFQDAT DYHPKTVGTI NYYLYSTTQN PPYNGPLKLK MLIPLTDTMI  300
YKPGINYEEY KRNNTTKGWN DWKTEYTIYS GNPFHANYLS VGEPVFLIGK KPSDLFSSEE  360
GETSDYTTAE LTKTIRYNPY NDQGQTNICY FKANFKSETT WQPPDNPDLT NENLPFWLLL  420
WGFSDWHKKI KKHLHIDSSY ILVMRHIPLA LNTEYIVPLS DSFLQGKSPF SPEEQPIGAD  480
RTTWHPQFQH QAEAINTICS SGPGTTKIPD NYSVQGLMKY SFYFKWGGSP PPMSTIEDPI  540
QQPTYPVPHN FNLTTSLQNP ETDPASILWS FDQRRHTLTK KAIERLQKDT GIKTITVTGG  600
SHFDPTPTIS QEETSEESSE EEKETSLLEK LQQQQRQQRR LKLRIMKTLL KIQQLE    656

SEQ ID NO: 1037        moltype = AA  length = 672
FEATURE                Location/Qualifiers
source                 1..672
                       mol_type = protein
                       organism = Betatorquevirus sp.
SEQUENCE: 1037
MPWRRRRYFR RYRYRPRRWR PRKTFRTRYY RRRHWVRKKR LRKKLKKLHI TEYQPSSIRK  60
CKVKGILCLF QTSIERICYN FDMYEESIVP DRLPGGGGFS IKNLSLQSLY LEHTHGHNIF  120
TSTNEPYPLM RYTGCTIRLY RSADVDYIVS YDNQWPLKST MKMYNSMQPQ IHYLLRHRII  180
VTSKKTNPNK RKLYKKVFIP PPTQMKNQWY FQSTLANIPL FMLRTSATSL DHWFIGTRDK  240
STNITILTLN TSVIFHRNWD KGTQPYYANV VGTQKVWLYA TDQSASPIFN EIKLKNLIFL  300
GNTQHNTQGY SYAEYLTHYH KTHSSTTVEE WQKSANWGNP FYKDYLTNPS NDHQVFASYT  360
DILQFANKLK TSQDTTIKES TFSFTPIEMT KRLRYNPYKD NGVNNLCYFL NCKEVNGLSW  420
DQPHNPDLTN ENLPLWILLF GFSDFQKKLA KLKRIDTDYT FVIKSTYTEP THLYIVPINI  480
SMSEGHSPYE DQANFVDDDK WFPSFQFQQE AYTDICLSGP GTARIPKGDT AEAKMHYTFH  540
FKWGGELPDM EQIADPSEKP TYPIPNNFLS TTSLQNPTQA PETYLYKFDQ RGDYITKTAA  600
KRIRKDWSTK TDSLSITAPR FAEAAQTQDT STETTSEEEE EEDLFQQLNQ QRLKQQRLKQ  660
RIKLILQKLQ TT                                                    672

SEQ ID NO: 1038        moltype = AA  length = 756
FEATURE                Location/Qualifiers
source                 1..756
                       mol_type = protein
                       organism = Alphatorquevirus sp.
SEQUENCE: 1038
MPWWRWRRGW RWPRRRWRTY RRRRRLPRRR PRRAVRRPRR RRVRRRRGRG WYRGRRYSRR  60
LYRRRYVRRK RKTLIWRQWQ PQNIRKCRIR GIIPMIICGH LRSNRNYALH SDDIVEQNTP  120
FGGALSTTSW SLKVLYDQHQ RGLNRWSSSN EMLDLARYNG CRFTFYRDKV TDFIVTYDIS  180
```

```
APYKLDKYSS PSYHPGMMML KTKNKILIPS FNTKPKGRST VSVKIKPPKL FLDKWYTQED  240
LCTVNLVTFA VSAASFTHPF CPPQTDNPCC TFQVLKDFYY PIIGYSAAET KVSSVFSNIL  300
YKHCTYYQSF LTQQFIGKIV KLPDGTLVSS LASGPSSYPE GSNINKNSIE QYNTWLSQFN  360
TGANQHYNFC NYKPDYSKLE WLRKYYFEWE TYKKASIPPD HLTPSVNWYE YHIGLFSPIF  420
LSPFRSSSLE FPRAYQDVTY NPLVDKGVGN VIWFQYNTKA DTQLTLPSCK CVIEDIPLWA  480
AFYGYSDFVQ QEIGPYTDAE SVGLVCVICP YTKPPMKNPD NPMMGYVFYD SNFGAGKWID  540
GSGFVPLYWQ TRWRPETLFQ ESTMRDITMT GPFSYKDELK NTVLTAKYKF NFRWGGNLLH  600
EQTIRNPCPT NAHPSTGRQP RDVQVVDPIT VGPRFVFHSW DWRRGFLSEA AIKRIRDQPL  660
DYEAYSFMPK RPRFFPPTTG GEQLPGEQEE SSSSAEENNL ISFEEGQEPK AQAVHKQLLK  720
HLRKQRVLGQ RLRALYQNLQ KTQAGLHINP LLFSQA                           756

SEQ ID NO: 1039        moltype = AA  length = 748
FEATURE                Location/Qualifiers
source                 1..748
                       mol_type = protein
                       organism = Alphatorquevirus sp.
SEQUENCE: 1039
MAWRWWWRRR RPWPYRRRRW RTIRTRRPRR PVRRRRRRRR VRRRRWGRRR GRRTYYRRRF  60
RKKKRKRKKL VLKQWNPSTI RRCTITGMIP LIVCGHTSAG RNYALRSDDF IPQSQPFGGS  120
FSTTTWNLNV LYDEHLKFHN KWSYPNTQLD LARYLGAYFY FYRDPKTDFI VTYNTVPPFK  180
IDKYSSPMLH PGMLMQRKKR ILIPSFETRP KGKRRIRVKI KPPTLFEDKW YTQSDLCSVN  240
LLSLAVSAAS FKHPFCPPQT ENICITFQVL RDFYYTQMNV TDTKGTDISD KDKAIFDNHL  300
YKFANYYQTV HTLGQLNPTQ QPALFSDRQN QGIPEKDSYL SGIGPNKLQT GNNSIYGQPN  360
YNPDIEKLHK IRKWFFKQET TANTIHGQYG HPQNDAVDYH IGKYSPIFLS PYRTNLQFPT  420
AYVDVTYNPL VDKGLGNKMW IQSVTKSDTQ FNELNCKCVL QDIPIWAMAT GYAEFIESEL  480
GLQEEVYSVY IICVICPYTQ PKMYSDTNVN TGYVFYDSLF GDGKMPSGTG LVPFYYQSRW  540
YPRLRFQLQV LHDMYICGPF SYKDDLKSTV LTAEYKFRFL WGGNMIPEQV IRNPCKAEGA  600
GSGYTYPDRL PRDLQIADPQ TMGPEWAFHT WDWRHGLFGK GALKRVSEKP DYDADYYVLP  660
KKPRFFPPTD GSQGQEKDSD LQEISLPFPF EETLSKSQEE VQTQQQQRDL HLRLAQQQRL  720
GQQLKHLYTQ ILKTQAGLHI NPLLYNHV                                    748

SEQ ID NO: 1040        moltype = AA  length = 742
FEATURE                Location/Qualifiers
source                 1..742
                       mol_type = protein
                       organism = Alphatorquevirus sp.
SEQUENCE: 1040
MAWRWWWNRR PRRRWTRRRW RRLRTRRPRR PVRRRRRRRR VRRRRWGRRR GRRTFYRRRF  60
KKRRRRRRKL TLKQWNPSTI RKCSIRGTVA LVMCGHTKAG RNYALHSEDY VPSLISMGGS  120
FSTTTWSLKA LYDEFQKFHN RWSYPNTQLD LARFKGSKWT FYRDPKVDYI VTYYTVPPFK  180
LNKLSSPFLH PGMMMQYKKK ILVPSYQTKP KGKGKVSIWI KPPVLFEDKW YTQQDLCPVN  240
LLSLAVSAAS FLHPFCPPES DNMCITFQVL QDFYYTQMGV TQMTGTTLTE ADNNIFKNHL  300
YKQASYYQSL HTTGQLNATQ KPANYSTNDK IPQETWLSTT GPAGFKTGNN SIYGVPNYKP  360
DYTKLEEIRK WFFKQETTDN AIHGSYGKPV YNAVDYHIGK YSPIFLSPYR TNTQFSTAYR  420
DITYNPNTDK GKGNHIWIQS VTKTNTTLNS QCRCHIQDIP IWAAVTGYAE FCESELNSEV  480
HNLYICCIIC PYTKPKLYNN TDPTQGYVFY DTLFGDGKMP TGTGLVPVWL QSRWYPRLIF  540
QAQVLHDLYL TGPFSYKDDL KSFTISAKYN FKFLWGGTII PEQVIKNPCK EQDSPFTFTG  600
RQPRDLQVTD PQTMGPEWVF HTWDWRRGLF GENAIKRVSE QPSHDADYYA PPKKPRLFPP  660
TDLQEQESAF DFTPQELKIL SEAPQQSEEE ENQEEEQQLQ QRELQLRLQE QFRIRHQLQH  720
LFVQVLKTQA GLHINPLFLN PV                                          742

SEQ ID NO: 1041        moltype = AA  length = 735
FEATURE                Location/Qualifiers
source                 1..735
                       mol_type = protein
                       organism = Alphatorquevirus sp.
SEQUENCE: 1041
MAYWWWRRRR RRPWRRRRRW RLRRPRRRRA TYRRRRGRRR VRKRRGRWRR TYRRWRRRKG  60
RRRHKKKIIM KQWQPNFIRH CFIVGFMPLI FCGENTTSQN FATHSDDLVA KGPYGGGMTT  120
TKFTLRILYD EHLRFMNFWT VSNEDLDLCR YLGVKLTFYR HPTVDFMVQI HTQPPFLDTE  180
LTGPSIHPGM MILNKKKIFV PSLKTRPNRK HKVRVKIGPP RLYEDKWYPQ SELCDTTLLT  240
VYATACDLQF PFGSPLTDNP CVNFQVLGSA YKKHLSILST NDSKNLTHYE TALFSKTAYY  300
NTFETIAQLK PTGQTTGVTP TWQDVQNTTN LDSSGTNQAT SNDTWYYGNT YKDNIKDLTK  360
KARDRYLAAT QKAFPAYATL QSPLYEYHGG CYSSIFLSAG RAYFETLGAY SDIIYNPFVD  420
KGIGNMVWID YLSKEDAVYT PRTSKCLIRD QPLWASFNGY SEFCSKSTGD GAVNINTRVV  480
IKCPYTTPML ADNSNENQGF VPYSLNFGKG KMKGGSSQVP LSWRCKWYVM MYHQQEFMEA  540
IVQSGPWAYK GDEKSAVLAM KYVFNWKWGG NPISGQVVRN PCKTSSSSRE PRSIQAVDPK  600
RVAPPLVFHS WDYRRGLFGH ASIKRMSEES ATPTLFTGPA GKRPRRDTSV QQAEEDQQKE  660
SSSFRVQRQL QPWIHSSQET QSSQEEMQAQ GTVQEQLIQQ LGEQRALRKQ LEFLASQVLK  720
VQAGQHIHPL LSSQA                                                  735

SEQ ID NO: 1042        moltype = AA  length = 662
FEATURE                Location/Qualifiers
source                 1..662
                       mol_type = protein
                       organism = Gammatorquevirus sp.
SEQUENCE: 1042
MPFWWRRRRK FWTNNRFNYT KRRRYRKRWP RRRRRRRPYR RPIRRRRRKL RKVKRKKKSL  60
IVRQWQPDSI RTCKIIGQSA IVVGAEGKQM YCYTVNKLIN VPPKTPYGGG FGVDQYTLKY  120
```

```
LYEEYRFAQN IWTQSNVLKD LCRYINVKLI FYRDNKTDFV LSYDRNPPFQ LTKFTYPGAH  180
PQQIMLQKHH KFILSQMTKP NGRLTKKLKI KPPKQMLSKW FFSKQFCKYP LLSLKASALD  240
LRHSYLGCCN ENPQVFFYYL NHGYYIQTNW GAQSTTAYRP NSSVTETTYY KYKNEKKNIH  300
IKSSEYSESI SYDKGYFQSS FLQTQCIYTS AAGDTCAAEK PLGIAIYNPV KDNGDGNMIY  360
LVSTLANTWD QPPKDSAILI QGVPIWLGLF GYLDYCRQIK ADKTWLDSHI LVMQSPAIFT  420
YPNPGAGKWY CPLSQSFING NGPFNQPPTL LQKAKWFPQI QYQQEIINSF VESGPFVPKY  480
ANQTESNWEL KYKYIFTFKW GGPQFHEPEI ADPSKQEQYD VPDTFYQTIQ IEDPEGQDPR  540
SLIHDWDYRR GFVKERSLKR MSTYFSTHTD QQATSEEDIP KKKKRIGPQL TVPQQKEEET  600
LSCLLSLCKK DTFQETETQE DLQQLIKQQQ EQQLLLKRNI LQLIHKLKEN QQMLQLHTGM  660
LP                                                                662

SEQ ID NO: 1043        moltype = AA  length = 660
FEATURE                Location/Qualifiers
source                 1..660
                       mol_type = protein
                       organism = Gammatorquevirus sp.
SEQUENCE: 1043
MPFWWGRRNR FWYKNNYRRR AYRRKRKRWP KRRRRNFRRP TRRRRRRRRK QKVRKKKQTL  60
TLKVWQPDTI RKCKIKGTGI HIVGGNGTQY RCFTANRFDW TPPLMPGGGG FGVEKFTLQH  120
LYNEHLLSNN IWTQSNKMLD LVRYTGCRIK FYRHETIDFI ASYNRNLPFN LEKYTYADSH  180
PNSLLHSRHK KLIPSLKTRR SGKRYITMKI KPPKPVSNKW FFQETFSSTP LFKLTTSIID  240
LRYPHISQIG SNELVSLFCL NTDFYANAGW GNVHPPGTHS KWYVPYHNIA AITTVVIKGR  300
DTQITVDGSD YKKSVSYETG YFQPKLLQAE KIKNTAMENI PIQASRYNPT KDDGVGNKLW  360
LVNVLNYSFA PPKTDADLYI ENLPLWQLVW GFTDFVKQTK KDSTFLNTYY AAFESKYLEP  420
AVSTSKIYIP IDMSFIQGKG PYDSYVSNYR KQNWYPTLNA QLKTLNAIAQ AGPFVPKLDN  480
IFLSSWELYS NYTFYFKFGG SELPEPDTVN PQDQGTYVIP TNIQKAIQVS NPQKQSPYTT  540
LHSWDYRRGL ITSSAFKRMC ENQTTDTEFE PDTETIPKKK KKIQHGNQLQ RAEEETQEIQ  600
NCLLSLCEEN TFQETPQTSL LELIQQQQQQ QQQLKHNLLK LLSDLKLKQR SLQLQTGLIH  660

SEQ ID NO: 1044        moltype = AA  length = 663
FEATURE                Location/Qualifiers
source                 1..663
                       mol_type = protein
                       organism = Gammatorquevirus sp.
SEQUENCE: 1044
MPFWWRRRRK PWYGKWRFRR RRRYNAPRRK RKFYQRRRYR RTNRRRRKYK VRRKKRKTIA  60
IRQWQPESIT KCKIIGFSNL VLGAEGTQYL CWTSQQEDYT QPKAPGGGGF GCELINLDWL  120
YSEWVKHNNI WTKTNTNKDL VRYTGAYIYF LRHPTIDFVI AYSLQPPFEL TKFTYPDIQP  180
QNLLLRKRKR IILSLASKPH GKRFVKVKIR PPKQMITKWF FQHQFSGYGL VQLSAAAATF  240
RHPNIGPKSQ NQMVTIYFLD TTIFNRPNWA QAQEDAWTPA GTHRTWTFEY QVKGQTQPKT  300
VQMPPSTPQD PYKTKYATSI SRDYGWWQKA ILNSTKVTID GTMYSNRTVY SARYNPNEDT  360
GQGNAVYLVS LLQSKWTAPS DDRLVIVGQP LWMCMYGLYS YYQDLLKDKN FNTHYMFVVR  420
SPAIKPITVS RQDFYPFIDW DFINGVLPWE EYLSEKIKAT WYPQATFQTT TINALVESGP  480
FVPRLTNIPD STWELVYKYK FFFKWGGPQT HDDHVQDPKH QPDYDTPDTL HQTIQIGDPK  540
KQTPESIIHE WDYRRGFITQ TALKRMSENI QTDTDFQSDD SASPRKKRKV TKKMPITSQK  600
EENIKKCLLS LCQEETQETP ENLQDLIQQQ QQQQHLLKRN LLQLLTHLKQ QQRYLSLQTG  660
ILD                                                               663

SEQ ID NO: 1045        moltype = AA  length = 662
FEATURE                Location/Qualifiers
source                 1..662
                       mol_type = protein
                       organism = Gammatorquevirus sp.
SEQUENCE: 1045
MPFWWPRRRR WWATTRFKRR KPRYPKRRRR RRYKRKYRRA PRRRRRRRRK VRRKKPNLIV  60
RQWQPDSIVL CKIKLFGSLV LGAEGTQYLC YTNEKGAWTP PQQPGGGGFG IETYSLSYLY  120
DQYLLRRCIW TKSNDYKDLC RYLRCKITFF RHPKIDFVVN YARQPPFLLE KPTYMNCHPI  180
ALLLSQHKRV ILSKRSDPKA KNRVTLIIKP PKQMITKWFF TKQFALFDLL QIQAAACTLN  240
YPKLGCCNEN LIISIFYLNP QFFQDSQWAQ YTTSPYKPYQ TIDTQLTYHY KIGNQTGQYK  300
PEFLNKTGQQ AYYESISLDK GWFSPKIMNT QYITQSGSET HLAAIPVGAA RYNPEIDDGK  360
GNEIYLVSVT TGHYTKPSED NLVFRGLPLW LMFFGLYSFI KKIKTASFLP LHMFVVKSEY  420
ILPKPKDPQK QYFPFVDLNF INGKNPYNSY ISSTQRQTWY PTCEHQVETI NAFVKCGPFV  480
PKLDNDRDST WELPFKSTFY FKWGGPQMPN QNVSDPKDKT SYIVPDTVQE GLQITNPLKQ  540
KAESLLHEWD YRRGLIKTKA FKRMLENLSI ESDVYPSAET PRKRQRVENS LHYQEEENQE  600
IKTCLLSLCE SSSSEKEEEE KNLLHLIQQQ QQQQKQLKLQ LLTLIKDLKE KQNALQLQTG  660
VI                                                                662

SEQ ID NO: 1046        moltype = AA  length = 672
FEATURE                Location/Qualifiers
source                 1..672
                       mol_type = protein
                       organism = Gammatorquevirus sp.
SEQUENCE: 1046
MPFWWRRRRK FWRGRRRPFY KRTTKRRRRR VRYRQRFRRP YRRRRRRRKH KVRRKRQKLP  60
IYQWQPDSIR KCKIKGVGTL ILGAHGKQFV CYTDVQKKAP PPKAPGGGGF ACEQFSLGGL  120
YEQYKFRNNI WTASNINMDL CRYLGVRMIF YRHPDIDFIL NYDRQPPFVL DQLTYPLCHP  180
QNLLLGKHKI LLLSKATKPN GKLRKKVFIK PPKQMLNKWF FQEQFQSAPL LSIRASICSL  240
QYPHIGCCMP NRTVTFFALN PGFYQQGNWA YDGGETNPYK PWPHIPKKLY FWDVATIPAS  300
WMEQEKAKHR VEIDLSTYSQ SIDYQKGYFT SKVLQAKLVT QDSTGTSTIA NTPLNIARYN  360
```

```
PAIDTGKGNT IWLHSNLTTA YTKPAVDKTV ILEGLPLWMM LFGWLSWVQH VKGAPDFYLS  420
YTLCVESPAI EIATKGETIN PVIPLDASFI NGNAPYNQTI SQKDLTHWYP DIYNQTEIIN  480
SIVTSGPYIP KLDNIKNSTW ELHYYYQFFF KWGGPEITDQ PVADPSKQPV YDALDKQQQG  540
IQVRNPAKQK YATLMHPWDI RRGIITNKAL KRMQQNLSID STFEAGSTPA KKPRITGPCF  600
TALQEIHQEE RSCLQTLCKE STSQEAQEET DIQLLIAQQQ QKQRELKYNL LKLISYMKEQ  660
QNMLKLHTGM LN                                                     672

SEQ ID NO: 1047        moltype = AA  length = 39
FEATURE                Location/Qualifiers
source                 1..39
                       mol_type = protein
                       organism = Torque teno midi virus
SEQUENCE: 1047
CSEEEEESNL FERLLRQRTK QLQLKRRIIQ TLKDLQKLE                        39

SEQ ID NO: 1048        moltype = AA  length = 150
FEATURE                Location/Qualifiers
source                 1..150
                       mol_type = protein
                       organism = Betatorquevirus sp.
SEQUENCE: 1048
MPWWYRRRSY NPWRRRNWFR RPRKTIYRRY RRRRRWPTYV VPNNFNETTS LQNPTTRPEH  60
FLYSFDERRG QLTEKATKRL LKDWETKETS LLSTEYRFAE PTQTQAPQED PSSEEEEESN  120
LFERLLRQRT KQLQLKRRII QTLKDLQKLE                                  150

SEQ ID NO: 1049        moltype = AA  length = 45
FEATURE                Location/Qualifiers
source                 1..45
                       mol_type = protein
                       organism = Betatorquevirus sp.
SEQUENCE: 1049
MPWWYRRRSY NPWRRRNWFR RPRKTIYRRY RRRRRWVRRK PFYKR                 45

SEQ ID NO: 1050        moltype = AA  length = 184
FEATURE                Location/Qualifiers
source                 1..184
                       mol_type = protein
                       organism = Betatorquevirus sp.
SEQUENCE: 1050
KIKRLNIVEW QPKSIRKCRI KGMLCLFQTT EDRLSYNFDM YEESIIPEKL PGGGGFSIKN  60
ISLYALYQEH IHAHNIFTHT NTDRPLARYT GCSLKFYQSK DIDYVVTYST SLPLRSSMGM  120
YNSMQPSIHL MQQNKLIVPS KQTQKRRKPY IKKHISPPTQ MKSQWYFQHN IANIPLLMIR  180
TTAL                                                              184

SEQ ID NO: 1051        moltype = AA  length = 156
FEATURE                Location/Qualifiers
source                 1..156
                       mol_type = protein
                       organism = Betatorquevirus sp.
SEQUENCE: 1051
TLDNYYIGSR QLSTNVTIHT LNTTYIQNRD WGDRNKTYYC QTLGTQRYFL YGTHSTAQNI  60
NDIKLQELIP LTNTQDYVQG FDWTEKDKHN ITTYKEFLTK GAGNPFHAEW ITAQNPVIHT  120
ANSPTQIEQI YTASTTTFQN KKLTDLPTPG YIFITP                           156

SEQ ID NO: 1052        moltype = AA  length = 158
FEATURE                Location/Qualifiers
source                 1..158
                       mol_type = protein
                       organism = Betatorquevirus sp.
SEQUENCE: 1052
TVSLRYNPYK DLAERNKCYF VRSKINAHGW DPEQHQELIN SDLPQWLLLF GYPDYIKRTQ  60
NFALVDTNYI LVDHCPYTNP EKTPFIPLST SFIEGRSPYS PSDTHEPDEE DQNRWYPCYQ  120
YQQESINSIC LSGPGTPKIP KGITAEAKVK YSFNFKWG                         158

SEQ ID NO: 1053        moltype = AA  length = 129
FEATURE                Location/Qualifiers
source                 1..129
                       mol_type = protein
                       organism = Betatorquevirus sp.
SEQUENCE: 1053
GDLPPMSTIT NPTDQPTYVV PNNFNETTSL QNPTTRPEHF LYSFDERRGQ LTEKATKRLL  60
KDWETKETSL LSTEYRFAEP TQTQAPQEDP SSEEEEESNL FERLLRQRTK QLQLKRRIIQ  120
TLKDLQKLE                                                         129

SEQ ID NO: 1054        moltype = AA  length = 4
FEATURE                Location/Qualifiers
source                 1..4
                       mol_type = protein
                       organism = synthetic construct
```

```
SEQUENCE: 1054
NANP                                                          4

SEQ ID NO: 1055         moltype = AA  length = 409
FEATURE                 Location/Qualifiers
source                  1..409
                        mol_type = protein
                        organism = synthetic construct
SEQUENCE: 1055
ANPNANPNAN PNANPNANPN ANPNANPNAN PNANPNANPN ANPNANPNAN PNANPNANPN  60
KNNQGNGQGH NMPNDPNRNV DENANANSAV KNNNNEEPSD KHIKEYLNKI QNSLSTEWSP  120
CSVTCGNGIQ VRIKPGSANK PKDELDYAND IEKKICKMEK CSSVFNVVNS SIGLIMVLSF  180
LFLNENTTSG FLGPLLVLQA GFFLLTRILT IPQSLDSWWT SLNFQGGAPT CPGQNSQSPT  240
SNHSPTSCPP ICPGYRWMCL RRFIIFLFIL LLCLIFLLVL LDYQGMLPVC PLLPGTSTTG  300
TGPCRTCTIP AQGTSMFPSC CCTKPSDGNC TCIPIPSSWA FARFLWEWAS VRFSWLSLLV  360
PFVQWFAGLS PTVWLSVIWM MWYRGPSLYN TLSPFLPLLP ISFCLWVYI             409

SEQ ID NO: 1056         moltype = AA  length = 410
FEATURE                 Location/Qualifiers
source                  1..410
                        mol_type = protein
                        organism = synthetic construct
SEQUENCE: 1056
ANPNANPNAN PNANPNANPN ANPNANPNAN PNANPNANPN ANPNANPNAN PNANPNANPN  60
KNNQGNGQGH NMPNDPNRNV DENANANSAV KNNNNEEPSD KHIKEYLNKI QNSLSTEWSP  120
CSVTCGNGIQ VRIKPGSANK PKDELDYAND IEKKICKMEK CSSVFNVVNS SIGLIMVLSF  180
LFLNENTTSG FLGPLLVLQA GFFLLTRILT IPQSLDSWWT SLNFQGGAPT CPGQNSQSPT  240
SNHSPTSCPP ICPGYRWMCL RRFIIFLFIL LLCLIFLLVL LDYQGMLPVC PLLPGTSTTG  300
TGPCRTCTIP AQGTSMFPSC CCTKPSDGNC TCIPIPSSWA FARFLWEWAS VRFSWLSLLV  360
PFVQWFAGLS PTVWLSVIWM MWYRGPSLYN TLSPFLPLLP ISFCLWVYIC            410

SEQ ID NO: 1057         moltype = AA  length = 218
FEATURE                 Location/Qualifiers
source                  1..218
                        mol_type = protein
                        organism = synthetic construct
SEQUENCE: 1057
MKIKTGARIL ALSALTTMMF SASALAANPN ANPNANPNAN PNANPNANPN ANPNANPNAN  60
PNANPNANPN ANPNANPNAN PNANPNKNNQ GNGQGHNMPN DPNRNVDENA NANSAVKNNN  120
NEEPSDKHIK EYLNKIQNSL STEWSPCSVT CGNGIQVRIK PGSANKPKDE LDYANDIEKK  180
ICKMEKCSSV FNVVNSSIGL IMVLSFLFLN PHHHHHHA                          218

SEQ ID NO: 1058         moltype = AA  length = 219
FEATURE                 Location/Qualifiers
source                  1..219
                        mol_type = protein
                        organism = synthetic construct
SEQUENCE: 1058
MKIKTGARIL ALSALTTMMF SASALAANPN ANPNANPNAN PNANPNANPN ANPNANPNAN  60
PNANPNANPN ANPNANPNAN PNANPNKNNQ GNGQGHNMPN DPNRNVDENA NANSAVKNNN  120
NEEPSDKHIK EYLNKIQNSL STEWSPCSVT CGNGIQVRIK PGSANKPKDE LDYANDIEKK  180
ICKMEKCSSV FNVVNSSIGL IMVLSFLFLN PHHHHHHAC                         219

SEQ ID NO: 1059         moltype = AA  length = 24
FEATURE                 Location/Qualifiers
source                  1..24
                        mol_type = protein
                        organism = synthetic construct
SEQUENCE: 1059
NPNANPNANP NANPNANPNA NPNA                                    24

SEQ ID NO: 1060         moltype = AA  length = 40
FEATURE                 Location/Qualifiers
source                  1..40
                        mol_type = protein
                        organism = synthetic construct
SEQUENCE: 1060
ANPNKNNQGN GQGHNMPNDP NRNVDENANA NSAVKNNNNE                       40

SEQ ID NO: 1061         moltype = AA  length = 66
FEATURE                 Location/Qualifiers
source                  1..66
                        mol_type = protein
                        organism = synthetic construct
SEQUENCE: 1061
EPSDKHIKEY LNKIQNSLST EWSPSSVTSG NGIQVRIKPG SANKPKDELD YANDIEKKIS  60
KMEKSS                                                        66

SEQ ID NO: 1062         moltype = AA  length = 266
```

```
FEATURE                 Location/Qualifiers
source                  1..266
                        mol_type = protein
                        organism = synthetic construct
SEQUENCE: 1062
MRGTPKTHLL AFSLLCLLSK VRTQLCPTPC TCPWPPPRCP LGVPLVLDGC GCCRVCARRL  60
GEPCDQLHVC DASQGLVCQP GAGPGGRGAL CLLAEDDSSC EVNGRLYREG ETFQPHCSIR  120
CRCEDGGFTC VPLCSEDVRL PSWDCPHPRR VEVLGKCCPE WVCGQGGGLG TQPLPAQGPQ  180
FSGLVSSLPP GVPCPEWSTA WGPCSTTCGL GMATRVSNQN RFCRLETQRR LCLSRPCPPS  240
RGRSPQNSAF GGGGSGGGGS GGGGSC                                      266

SEQ ID NO: 1063         moltype = AA  length = 477
FEATURE                 Location/Qualifiers
source                  1..477
                        mol_type = protein
                        organism = synthetic construct
SEQUENCE: 1063
MKIKTGARIL ALSALTTMMF SASALASDTG RPFVEMYSEI PEIIHMTEGR ELVIPCRVTS  60
PNITVTLKKF PLDTLIPDGK RIIWDSRKGF IISNATYKEI GLLTCEATVN GHLYKTNYLT  120
HRQTNTIIDV VLSPSHGIEL SVGEKLVLNC TARTELNVGI DFNWEYPSSK HQHKKLVNRD  180
LKTQSGSEMK KFLSTLTIDG VTRSDQGLYT CAASSGLMTK KNSTFVRVHE KDKTHTCPPC  240
PAPELLGGPS VFLFPPKPKD TLMISRTPEV TCVVVDVSHE DPEVKFNWYV DGVEVHNAKT  300
KPREEQYNST YRVVSVLTVL HQDWLNGKEY KCKVSNKALP APIEKTISKA KGQPREPQVY  360
TLPPSRDELT KNQVSLTCLV KGFYPSDIAV EWESNGQPEN NYKTTPPVLD SDGSFFLYSK  420
LTVDKSRWQQ GNVFSCSVMH EALHNHYTQK SLSLSPGGGG SGGGGSGGGG SGGGGSC     477

SEQ ID NO: 1064         moltype = AA  length = 247
FEATURE                 Location/Qualifiers
source                  1..247
                        mol_type = protein
                        organism = synthetic construct
SEQUENCE: 1064
MKIKTGARIL ALSALTTMMF SASALASDTG RPFVEMYSEI PEIIHMTEGR ELVIPCRVTS  60
PNITVTLKKF PLDTLIPDGK RIIWDSRKGF IISNATYKEI GLLTCEATVN GHLYKTNYLT  120
HRQTNTIIDV VLSPSHGIEL SVGEKLVLNC TARTELNVGI DFNWEYPSSK HQHKKLVNRD  180
LKTQSGSEMK KFLSTLTIDG VTRSDQGLYT CAASSGLMTK KNSTFVRVHE KGGGGSGGGG  240
SGGGGSC                                                           247

SEQ ID NO: 1065         moltype = AA  length = 273
FEATURE                 Location/Qualifiers
source                  1..273
                        mol_type = protein
                        organism = synthetic construct
SEQUENCE: 1065
MKIKTGARIL ALSALTTMMF SASALAEVQL VESGGGLVQP GGSLRLSCAA SGYDFTHYGM  60
NWVRQAPGKG LEWVGWINTY TGEPTYAADF KRRFTFSLDT SKSTAYLQMN SLRAEDTAVY  120
YCAKYPYYYG TSHWYFDVWG QGTLVTVSSA STKGPSVFPL APSSKSTSGG TAALGCLVKD  180
YFPEPVTVSW NSGALTSGVH TFPAVLQSSG LYSLSSVVTV PSSSLGTQTY ICNVNHKPSN  240
TKVDKKVEPK SCDKTHLGGG GSGGGGSGGG GSC                              273

SEQ ID NO: 1066         moltype = AA  length = 499
FEATURE                 Location/Qualifiers
source                  1..499
                        mol_type = protein
                        organism = synthetic construct
SEQUENCE: 1066
MKIKTGARIL ALSALTTMMF SASALAEVQL VESGGGLVQP GGSLRLSCAA SGYTFTNYGM  60
NWVRQAPGKG LEWVGWINTY TGEPTYAADF KRRFTFSLDT SKSTAYLQMN SLRAEDTAVY  120
YCAKYPHYYG SSHWYFDVWG QGTLVTVSSA STKGPSVFPL APSSKSTSGG TAALGCLVKD  180
YFPEPVTVSW NSGALTSGVH TFPAVLQSSG LYSLSSVVTV PSSSLGTQTY ICNVNHKPSN  240
TKVDKKVEPK SCDKTHTCPP CPAPELLGGP SVFLFPPKPK DTLMISRTPE VTCVVVDVSH  300
EDPEVKFNWY VDGVEVHNAK TKPREEQYNS TYRVVSVLTV LHQDWLNGKE YKCKVSNKAL  360
PAPIEKTISK AKGQPREPQV YTLPPSREEM TKNQVSLTCL VKGFYPSDIA VEWESNGQPE  420
NNYKTTPPVL DSDGSFFLYS KLTVDKSRWQ QGNVFSCSVM HEALHNHYTQ KSLSLSPGKK  480
DELGGGGSGG GGSGGGGSC                                              499

SEQ ID NO: 1067         moltype = AA  length = 537
FEATURE                 Location/Qualifiers
source                  1..537
                        mol_type = protein
                        organism = synthetic construct
SEQUENCE: 1067
MKIKTGARIL ALSALTTMMF SASALAEVQL VESGGGLVQP GGSLRLSCAA SGYDFTHYGM  60
NWVRQAPGKG LEWVGWINTY TGEPTYAADF KRRFTFSLDT SKSTAYLQMN SLRAEDTAVY  120
YCAKYPYYYG TSHWYFDVWG QGTLVTVSSA STKGPSVFPL APSSKSTSGG TAALGCLVKD  180
YFPEPVTVSW NSGALTSGVH TFPAVLQSSG LYSLSSVVTV PSSSLGTQTY ICNVNHKPSN  240
TKVDKKVEPK SCDKTHLGGS SGSGSGSTGT SSSGTGTSAG TTGTSASTSG SGSGGGGGSG  300
GGGSAGGDIQ LTQSPSSLSA SVGDRVTITC SASQDISNYL NWYQQKPGKA PKVLIYFTSS  360
LHSGVPSRFS GSGSGTDFTL TISSLQPEDF ATYYCQQYST VPWTFGQGTK VEIKRTVAAP  420
```

```
SVFIFPPSDE QLKSGTASVV CLLNNFYPRE AKVQWKVDNA LQSGNSQESV TEQDSKDSTY  480
SLSSTLTLSK ADYEKHKVYA CEVTHQGLSS PVTKSFNRGE CGGGGSGGGG SGGGGSC     537

SEQ ID NO: 1068        moltype = AA  length = 24
FEATURE                Location/Qualifiers
source                 1..24
                       mol_type = protein
                       organism = synthetic construct
SEQUENCE: 1068
NANPNANPNA NPNANPNANP NANP                                         24

SEQ ID NO: 1069        moltype = AA  length = 6
FEATURE                Location/Qualifiers
source                 1..6
                       mol_type = protein
                       organism = synthetic construct
SEQUENCE: 1069
HHHHHH                                                             6

SEQ ID NO: 1070        moltype = DNA  length = 19
FEATURE                Location/Qualifiers
source                 1..19
                       mol_type = other DNA
                       organism = synthetic construct
SEQUENCE: 1070
tgaagctggg gtctttaac                                               19

SEQ ID NO: 1071        moltype = DNA  length = 21
FEATURE                Location/Qualifiers
source                 1..21
                       mol_type = other DNA
                       organism = synthetic construct
SEQUENCE: 1071
tctacctagg tgcaaagggc c                                            21

SEQ ID NO: 1072        moltype = AA  length = 13
FEATURE                Location/Qualifiers
source                 1..13
                       mol_type = protein
                       organism = synthetic construct
SEQUENCE: 1072
KIKRLNIVEW QPK                                                     13

SEQ ID NO: 1073        moltype = AA  length = 18
FEATURE                Location/Qualifiers
source                 1..18
                       mol_type = protein
                       organism = synthetic construct
SEQUENCE: 1073
SPSDTHEPDE EDQNRWYP                                                18

SEQ ID NO: 1074        moltype = AA  length = 38
FEATURE                Location/Qualifiers
source                 1..38
                       mol_type = protein
                       organism = synthetic construct
SEQUENCE: 1074
SEEEEESNLF ERLLRQRTKQ LQLKRRIIQT LKDLQKLE                          38

SEQ ID NO: 1075        moltype = AA  length = 4
FEATURE                Location/Qualifiers
source                 1..4
                       mol_type = protein
                       organism = synthetic construct
SITE                   4
                       note = Proline N-hydroxysuccinimide
SEQUENCE: 1075
NANP                                                               4
```

What is claimed is:

1. A mixture comprising:

a plurality of Anellovirus ORF1 molecules, and a chaotropic agent;

wherein at least 75% of the plurality of Anellovirus ORF1 molecules in the mixture are comprised in a plurality of pentameric or decameric capsomers.

2. The mixture of claim 1, wherein the mixture comprises a plurality of pentamers comprising the Anellovirus ORF1 molecules.

3. The mixture of claim 1, wherein the mixture comprises a plurality of decamers comprising the Anellovirus ORF1 molecules.

4. The mixture of claim 1, which does not comprise a proteinaceous exterior comprising about 40-80 copies of an Anellovirus ORF1 molecule.

5. The mixture of claim 1, wherein the Anellovirus ORF1 molecules comprise an arginine-rich region.

6. The mixture of claim 1, wherein the Anellovirus ORF1 molecules do not comprise a C-terminal domain.

7. The mixture of claim 1, which is a cell-free system.

8. The mixture of claim 1, wherein the Anellovirus ORF1 molecules each comprise a tagging moiety.

9. The mixture of claim 8, wherein the tagging moiety comprises chitin binding protein (CBP), maltose binding protein (MBP), glutathione-S-transferase (GST), and poly (His) tag.

10. The mixture of claim 9, wherein the mixture comprises a plurality of pentamers comprising the Anellovirus ORF1 molecules.

11. The mixture of claim 9, wherein the mixture comprises a plurality of decamers comprising the Anellovirus ORF1 molecules.

12. The mixture of claim 1, wherein the mixture comprises host cell DNA that is dissociated from the plurality of Anellovirus ORF1 molecules.

* * * * *